US012577325B2

(12) United States Patent
Zhu et al.

(10) Patent No.: US 12,577,325 B2
(45) Date of Patent: Mar. 17, 2026

(54) BISPECIFIC ANTIBODY-CAMPTOTHECIN DRUG CONJUGATE AND PHARMACEUTICAL USE THEREOF

(71) Applicant: SYSTIMMUNE, INC., Redmond, WA (US)

(72) Inventors: Yi Zhu, Chengdu (CN); Weili Wan, Chengdu (CN); Tianzi Yu, Chengdu (CN); Guili Zhu, Chengdu (CN); Yiying Zhang, Chengdu (CN); Shi Zhuo, Chengdu (CN); Yong Zhang, Chengdu (CN); Gangrui Li, Chengdu (CN)

(73) Assignee: SYSTIMMUNE, INC., Redmond, WA (US)

( * ) Notice: Subject to any disclaimer, the term of this patent is extended or adjusted under 35 U.S.C. 154(b) by 0 days.

(21) Appl. No.: 18/957,324

(22) Filed: Nov. 22, 2024

(65) Prior Publication Data

US 2025/0115679 A1 Apr. 10, 2025

Related U.S. Application Data

(63) Continuation of application No. 18/710,044, filed as application No. PCT/CN2022/132027 on Nov. 15, 2022, now abandoned.

(30) Foreign Application Priority Data

Nov. 15, 2021 (CN) ........................ 202111351599.X

(51) Int. Cl.

*C07K 16/32* (2006.01)
*A61K 47/68* (2017.01)

(Continued)

(52) U.S. Cl.

CPC ........ *C07K 16/32* (2013.01); *A61K 47/68037* (2023.08); *A61K 47/6851* (2017.08);

(Continued)

(58) Field of Classification Search

None

See application file for complete search history.

(56) References Cited

U.S. PATENT DOCUMENTS 6,512,118 B1 1/2003 Tsujihara et al.
8,586,714 B2 11/2013 Ghayur et al.

(Continued)

FOREIGN PATENT DOCUMENTS

CN 108220244 A 6/2018
CN 109106951 A 1/2019

(Continued)

OTHER PUBLICATIONS

International Searching Authority, International Search Report and Written Opinion for International Patent Application No. PT/CN2022/132027 (Pub No. WO/2023/083381) mailed Feb. 9, 2023 (28 pages).

(Continued)

*Primary Examiner* — Karl J Puttlitz
(74) *Attorney, Agent, or Firm* — Jones Day

(57) ABSTRACT

A bispecific antibody simultaneously targeting two different epitopes or targets is coupled with a camptothecin drug to form a bispecific antibody-toxin conjugate that is stable in treatment and excellent in uniformity, and a drug-to-antibody ratio (DAR) thereof is 6.0-8.0. The antibody-toxin conjugate has a structure as represented by general formula (I), wherein Ab represents the bispecific antibody simultaneously targeting two different epitopes or targets, which is coupled with a linker-camptothecin drug. In addition, the (Continued)

present invention further relates to a preparation and purification method for the antibody-toxin conjugate, and an application thereof in tumor treatment. Furthermore, the present invention further relates to a linker-drug compound capable of being coupled with Ab to form the antibody-toxin conjugate.

I

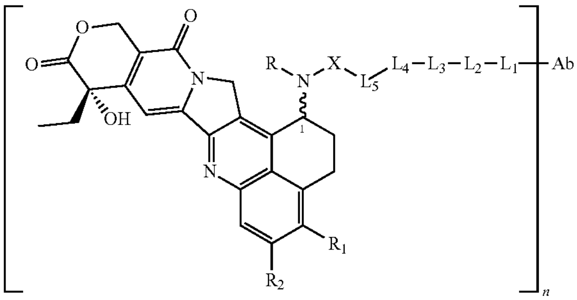

46 Claims, 32 Drawing Sheets

Specification includes a Sequence Listing.

(51) Int. Cl.
*A61P 35/00* (2006.01)
*C07K 16/28* (2006.01)

(52) U.S. Cl.
CPC .......... *A61P 35/00* (2018.01); *C07K 16/2863* (2013.01); *C07K 2317/24* (2013.01); *C07K 2317/31* (2013.01)

(56) References Cited

U.S. PATENT DOCUMENTS 8,623,592 B2 1/2014 Schoeberl et al.
8,658,175 B2 2/2014 Dubridge et al.
8,927,694 B2 1/2015 McDonagh et al.
9,051,370 B2 6/2015 Goletz et al.
9,345,766 B2 5/2016 Zhang et al.
9,493,563 B2 11/2016 Blein et al.
9,683,044 B2 6/2017 Block et al.
9,850,312 B2 12/2017 Agatsuma et al.
9,879,081 B2 1/2018 Suh et al.
9,988,456 B2 6/2018 Govindappa et al.
10,118,966 B2 11/2018 Qian
10,239,951 B2 3/2019 Ng et al.
10,273,303 B2 4/2019 Ng et al.
10,709,799 B2 7/2020 Lowman et al.
10,759,860 B2 9/2020 Tsao
10,766,963 B2 9/2020 Govindappa et al.
10,822,419 B2 11/2020 Wang et al.
10,835,606 B2 11/2020 Leppanen et al.
10,836,833 B2 11/2020 Jang et al.
10,919,977 B2 2/2021 Gao et al.
10,994,021 B1 5/2021 Zhou et al.
11,046,954 B2 6/2021 Bradner et al.
11,053,303 B2 7/2021 Lebert et al.
11,161,906 B2 11/2021 Lowman et al.
11,180,562 B2 11/2021 Lowman et al.
11,357,826 B2 6/2022 Xu et al.
2005/0142133 A1 6/2005 Lazar et al.
2011/0044980 A1 2/2011 Ghayur et al.
2012/0195900 A1 8/2012 Ghayur et al.
2012/0263722 A1 10/2012 Ghayur et al.
2014/0056898 A1 2/2014 Zhang et al.
2014/0170159 A9 6/2014 Wei et al.
2014/0242077 A1 8/2014 Choi et al.
2015/0071923 A1 3/2015 Wei et al.
2015/0139936 A1 5/2015 Frye et al.
2015/0231238 A1 8/2015 Garcia et al.
2015/0239977 A1 8/2015 Trout et al.
2015/0352224 A1 12/2015 Naito et al.
2016/0009824 A1 1/2016 Lo et al.
2016/0046730 A1 2/2016 Ghayur et al.
2016/0280791 A1 9/2016 Ghayur et al.
2016/0319026 A1 11/2016 Ghayur et al.
2016/0333112 A1 11/2016 Naito et al.
2017/0021031 A1 1/2017 Hettmann et al.
2017/0035906 A1 2/2017 Naito et al.
2017/0145101 A1 5/2017 Kim et al.
2017/0247458 A1 8/2017 Cao et al.
2018/0055944 A1 3/2018 Lu et al.
2018/0154014 A1 6/2018 Reznik et al.
2019/0008981 A1 1/2019 Masuda et al.
2019/0077752 A1 3/2019 Lerchen et al.
2019/0153104 A1 5/2019 Zhukovsky et al.
2019/0314362 A1 10/2019 Iwata et al.
2019/0351066 A1 11/2019 Lerchen et al.
2020/0140547 A1 5/2020 Bedi et al.
2020/0147236 A1 5/2020 Westby et al.
2020/0317792 A1 10/2020 Griswold et al.
2020/0325208 A1 10/2020 Wu et al.
2020/0354478 A1 11/2020 Xu et al.
2020/0384121 A1 12/2020 Nishi et al.
2021/0024638 A1 1/2021 Yong et al.
2021/0100912 A1 4/2021 Zhu et al.
2021/0139553 A1 5/2021 Li et al.
2021/0198370 A1 7/2021 Fan et al.
2021/0261649 A1 8/2021 Parry et al.
2021/0261668 A1 8/2021 Chang et al.
2021/0346514 A1 11/2021 Glossop
2021/0347894 A1 11/2021 Ying et al.
2021/0353764 A1 11/2021 Xu et al.
2021/0353765 A1 11/2021 Westby et al.
2021/0371526 A1 12/2021 Li et al.
2022/0017635 A1 1/2022 Mitamura et al.
2022/0073635 A1 3/2022 Sall et al.
2022/0098262 A1 3/2022 Cai et al.
2022/0098329 A1 3/2022 Santich et al.
2022/0204582 A1 6/2022 Chaudhary
2022/0259330 A1 8/2022 Zhao et al.
2022/0372142 A1 11/2022 Baliga et al.
2022/0378928 A1 12/2022 Zhu et al.
2022/0411436 A1 12/2022 Zhu et al.
2023/0054458 A1 2/2023 Yang et al.
2023/0055408 A1 2/2023 Ying et al.
2023/0072897 A1 3/2023 Hua et al.
2023/0101735 A1 3/2023 Yang et al.
2023/0140397 A1 5/2023 Ying et al.
2023/0165969 A1 6/2023 Yue et al.
2023/0183377 A1 6/2023 Zhang et al.
2023/0226207 A1* 7/2023 Zhu .................... A61K 47/6835
424/181.1
2023/0241242 A1 8/2023 Liang et al.
2023/0257465 A1 8/2023 Zhu et al.
2023/0381332 A1* 11/2023 Zhu .................... A61K 47/6849
2023/0405138 A1 12/2023 Ren et al.
2024/0024498 A1 1/2024 Wang et al.
2024/0026028 A1 1/2024 Yang et al.
2024/0158410 A1 5/2024 Tian et al.
2024/0269307 A1 8/2024 Yang et al.
2024/0358843 A1 10/2024 Huang et al.
2024/0390509 A1 11/2024 Mao et al.

FOREIGN PATENT DOCUMENTS

CN 110669132 A 1/2020
CN 111689980 A 9/2020
CN 112125915 A 12/2020
CN 113816969 A 12/2021
CN 113827736 A 12/2021
CN 113943310 A 1/2022
CN 108948195 B 5/2022

(56) References Cited

FOREIGN PATENT DOCUMENTS

| | | | | | |
|---|---|---|---|---|---|
| CN | 110256583 | B | | 5/2022 | |
| CN | 111848806 | B | | 6/2022 | |
| CN | 114569739 | A | | 6/2022 | |
| CN | 109306010 | B | | 7/2022 | |
| CN | 108948206 | B | | 8/2022 | |
| CN | 113388631 | B | | 8/2022 | |
| CN | 115192732 | A | | 10/2022 | |
| CN | 111196855 | B | | 11/2022 | |
| CN | 115850291 | A | | 3/2023 | |
| EP | 4227310 | A1 | | 8/2023 | |
| EP | 4434549 | A1 | | 9/2024 | |
| EP | 4442283 | A1 | | 10/2024 | |
| EP | 4450506 | A1 | | 10/2024 | |
| WO | WO 2009126920 | A2 | | 10/2009 | |
| WO | WO 2015123679 | A1 | | 8/2015 | |
| WO | WO-2016106157 | A1 | * | 6/2016 | ......... A61K 39/3955 |
| WO | WO 2016106158 | A1 | | 6/2016 | |
| WO | WO 2019034176 | A1 | | 2/2019 | |
| WO | WO 2020063676 | A1 | | 4/2020 | |
| WO | WO 2021190480 | A1 | | 9/2021 | |
| WO | WO 2021190564 | A1 | | 9/2021 | |
| WO | WO 2021190586 | A1 | | 9/2021 | |
| WO | WO-2021249228 | A1 | * | 12/2021 | ......... A61K 31/4745 |
| WO | WO-2022078259 | A1 | * | 4/2022 | ......... A61K 31/4745 |
| WO | WO-2022078260 | A1 | * | 4/2022 | ............. A61K 47/64 |
| WO | WO 2022099762 | A1 | | 5/2022 | |
| WO | WO 2022166719 | A1 | | 8/2022 | |
| WO | WO 2022194257 | A1 | | 9/2022 | |
| WO | WO 2022236136 | A1 | | 11/2022 | |
| WO | WO 2023004266 | A1 | | 1/2023 | |
| WO | WO 2023088235 | A1 | | 5/2023 | |
| WO | WO 2023125530 | A1 | | 7/2023 | |

OTHER PUBLICATIONS

Xue et al., 2020, "Prediction of Human Pharmacokinetics and Clinical Effective Dose of SI-B001, an EGFR/HER3 Bi-specific Monoclonal Antibody," J. Pharm Sci. 109(10):3172-3180 (9 pages).

Ogitani et al., 2016, ""DS-8201a, a novel her2-targeting ADC with a novel DNA topoisomerase I inhibitor, demonstrates a promising antitumor efficacy with differentiation from T-DM1,"" Clin Cancer Res. 22(20):5097-5108 (12 pages).

* cited by examiner

BISPECIFIC ANTIBODY-CAMPTOTHECIN DRUG CONJUGATE AND PHARMACEUTICAL USE THEREOF

CROSS-REFERENCE TO RELATED APPLICATIONS

This application is a continuation application of U.S. application Ser. No. 18/710,044, which is a U.S. National Stage Application under 35 U.S.C. § 371 of International Patent Application No. PCT/CN2022/132027, filed Nov. 15, 2022, which claims priority to CN 202111351599.X, filed Nov. 15, 2021, each of which is incorporated by reference herein in its entirety.

SEQUENCE LISTING

This application contains a computer readable Sequence Listing which has been submitted in XML file format via Patent Center, the entire content of which is incorporated by reference herein in its entirety. The Sequence Listing XML file submitted via Patent Center is entitled "14247-846-999_SEQLISTING.xml", was created on May 13, 2024, and is 71,054 bytes in size.

TECHNICAL FIELD

The present invention relates to the field of biopharmaceuticals, and specifically to an antibody-drug conjugate formed by a bispecific antibody and a camptothecin drug, and to a method of preparation and application of the antibody-drug conjugate. The present invention also relates to linker-drug compounds that can be coupled with Ab to form an antibody-toxin conjugate.

TECHNICAL BACKGROUND

Epidermal Growth Factor Receptor (EGFR) and human epidermal growth factor receptor 3 (also known as HER3 and ErbB3) are receptor protein tyrosine kinases and belong to the epidermal growth factor receptor (EGFR) subfamily of receptor protein tyrosine kinases, which includes EGFR (ErbB-1), HER2/c-neu (ErbB-2), HER3 (ErbB-3) and HER4 (ErbB-4).

The epidermal growth factor receptor is a glycoprotein with a molecular weight of 170 kDa that crosses cell membranes and is activated by binding to ligands. Upon activation, EGFR is converted from a monomer to an auto-dimer or forms a heterodimer with other HER family members. Dimer formation activates intracellular kinase pathways that direct the phosphorylation of downstream pathways, including the MAPK, Akt, and JNK pathways, to induce cell proliferation. Studies have shown that high expression of EGFR is associated with tumor cell proliferation, angiogenesis, tumor invasion, etc. EGFR-related signaling pathways play a very important role in the maintenance and growth of epidermal tissues. Especially in breast cancer, malignant glioma and lung cancer, EGFR can promote tumorigenesis. In lung cancer tissues, the EGFR signaling pathway shows a stimulated state, and there is a positive correlation between the expression level of EGFR and the stage of cancer development. Meanwhile, more and more studies are using EGFR as a biomarker of tumor drug resistance due to the finding of secondary mutations of EGFR under drug stress.

Epidermal growth factor receptor 3 (HER3 or ErbB3) also has the structure of a typical epidermal growth factor receptor, but HER3 lacks the structural domain of the intracellular protein tyrosine kinase and thus cannot autophosphorylate. HER3 can bind to ligand proteins and promote their heterodimerization with other human epidermal growth factor receptor family members to activate receptor-mediated signaling pathways, which not only acts as a signal diversification means, but also plays a role of signal amplification and accelerates tumor progression. Heregulins (glial cell growth factor, neu differentiation factor) can activate intracellular kinase-dependent multistep signaling pathway responses upon binding to the transmembrane receptors HER3 and HER4. Down-regulation of this signaling pathway often leads to Alzheimer's disease, heart failure, atherosclerosis, and cancer, etc. Up-regulation of HER3 expression level can promote tumorigenesis and growth by interacting with receptor tyrosine kinases (RTKs). Also, since HER3 is a heterodimeric molecular chaperone for other EGFR family members, it has the potential to modulate EGFR/HER2 signaling pathway-mediated drug resistance in cancer cells. Studies have also shown that HER3 defeats cancer therapy by activating the PI3K/AKT, MAPK/ERK and JAK/STAT signaling pathways.

Overexpression/dysregulation of EGFR and HER3 has been closely associated with the development of a variety of tumors. EGFR and HER3 have been shown to drive tumor progression in solid tumors such as breast, lung, gastric, and pancreatic cancers. Several studies have shown that high expression of HER3 is associated with clinical failure of EGFR antibodies and inhibitors. Several combination drug therapies targeting EGFR and HER3 are already underway in clinical settings.

Monoclonal antibodies have been widely used in anti-tumor therapy in recent years, but their efficacy leaves much to be desired. A large number of tumor patients have poor clinical responses, and some patients with clinical responses develop drug resistance after a sustained period of monoclonal antibody therapy, leading to tumor recurrence. A bispecific monoclonal antibody is a monoclonal antibody molecule with two different antigen recognition sequences, which can bind protein molecules of two antigenic epitopes, and thus can achieve, for example, a variety of new and unique anti-tumor mechanisms, such as mediating the killing of tumor cells by immune cells, mediating the killing of tumor cells by toxic small molecules, or blocking the signaling pathways that promote the growth of tumors. The development of bispecific monoclonal antibodies is mainly in consideration of the fact that multiple mediators participate in the pathogenesis of tumors through specific or overlapping mechanisms, and if multiple targets are blocked at the same time, this will produce better therapeutic effects than inhibition of a single target, and at the same time, the action of multiple targets greatly reduces the probability of developing drug resistance. Currently, two bispecific antibodies, Catumaxomab and Blinatumomab, have been approved for marketing in the U.S., and more than fifty bispecific antibody molecules are in clinical trials.

Antibody-Drug Conjugates (ADCs) are molecules with specifically targeted killing effects, obtained by attaching small molecule toxins with cell-killing effects to antibodies, and are mainly used in the treatment of tumors and other diseases. Antibody-drug coupled drugs use antibodies that can specifically bind to proteins on the surface of tumor cells, and therefore have tumor specificity and potential unachievable by conventional drugs. Currently, 12 ADC drugs have received marketing approval worldwide and hundreds of programs are in clinical trials. However, most ADC programs currently on the market or in clinical settings are directed at a single target and cannot achieve the synergistic benefits of dual-target therapy.

SUMMARY OF THE INVENTION

The inventors, based on a comprehensive understanding of the ADC class of drugs, disclose a bispecific antibody-drug conjugate and a method of preparing the same, a pharmaceutical composition comprising said conjugate and a use of said conjugate or pharmaceutical composition. The present invention also relates to linker-drug compounds that can be coupled to a bispecific antibody to form an antibody-toxin conjugate.

A first aspect of the present invention discloses a ligand-camptothecin derivative conjugate as shown in general formula I or a pharmaceutically acceptable salt or solvate thereof;

I

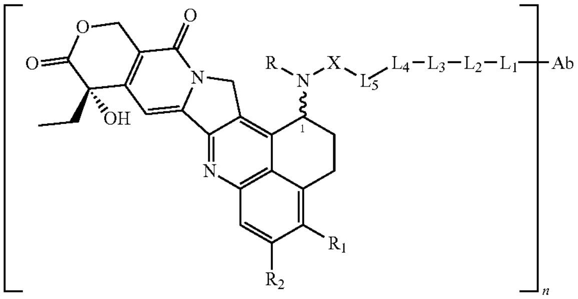

wherein:

Ab is a bispecific antibody or antigen-binding fragment thereof that simultaneously targets two different epitopes or targets;

$L_1$ is selected without limitation from the group:

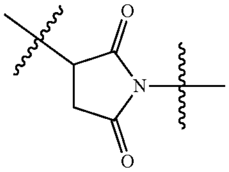 , 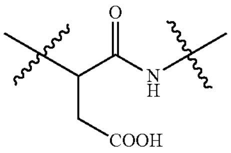 ,

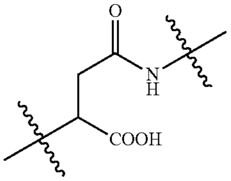 , 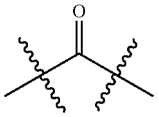 ,

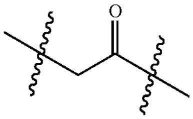 , 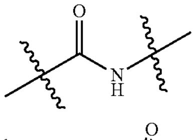 ,

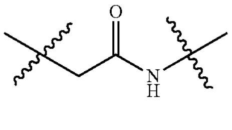 , 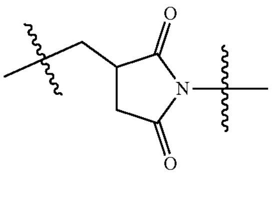 ,

-continued

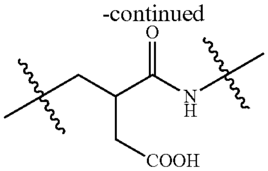 or

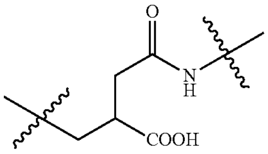 ;

preferably $L_1$ is

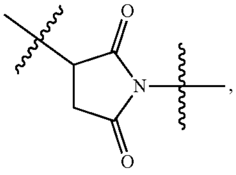 , 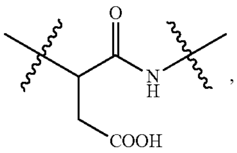 ,

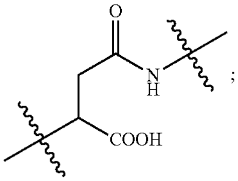 ;

preferably $L_1$ is

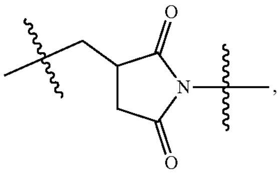 ,

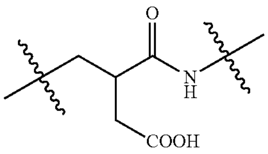 or

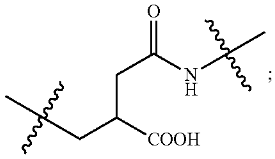 ;

$L_2$ has the structure shown in formula A below, formula A

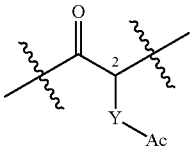

wherein Y is a scaffold selected from C1-C6 alkyl, substituted C1-C6 alkyl, or C3-C8 cycloalkyl; preferably Y is C1-C6 alkyl; Ac is a hydrophilic structural unit; and the carbon No. 2 attached to Y has absolute chirality in the R configuration or the S configuration;

$L_3$ is present or absent, and when present, $L_3$ is selected from PEG hydrophilic units:

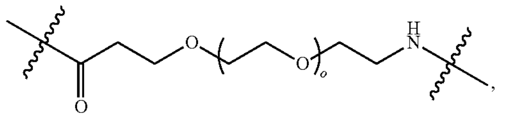

o is selected from an integer in the range of 1-10 (e.g., 1, 2, 3, 4, 5, 6, 7, 8, 9, or 10), preferably an integer in the range of 2-8;

$L_4$ is an enzymatic cutting unit;

$L_5$ is a linking unit;

in formula I, the No. 1 chiral carbon atom attached to N has absolute chirality in the R configuration or the S configuration;

R is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, C6-C10 aryl, substituted C6-C10 aryl, 5-10-membered heteroaryl, substituted 5-10-membered heteroaryl;

preferably R is selected from a hydrogen atom or a C1-C6 alkyl group;

$R_1$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered-heteroaryl, or substituted 5-10-membered heteroaryl;

preferably $R_1$ is selected from a hydrogen atom or a C1-C6 alkyl group;

more preferably $R_1$ is selected from C1-C6 alkyl;

$R_2$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably $R_2$ is selected from a hydrogen atom, a halogen or a C1-C6 alkyl group;

more preferably $R_2$ is selected from halogen;

X is selected from $-C(O)-CR_aR_b-(CR_3R_4)_m-O-$, $-C(O)-CR_aR_b-(CR_3R_4)_m-NH-$ or $-C(O)-CR_aR_b-(CR_3R_4)_m-S-$;

preferably X is selected from $-C(O)-CR_aR_b-(CR_3R_4)_m-O-$;

$R_a$ and $R_b$ are each independently selected from a hydrogen atom, a deuterium atom, a halogen, a C1-C6 alkyl, a deuterated C1-C6 alkyl, a halogenated C1-C6 alkyl, a C3-C8 cycloalkyl, a C3-C8 cycloalkyl C1-C6 alkyl, a C6-C10 aryl C1-C6 alkyl, a C1-C6 alkoxy C1-C6 alkyl, a 3-7-membered heterocyclic group, a substituted 3-7-membered heterocyclic group, a C6-C10 aryl, substituted C6-C10 aryl, 5-10-membered heteroaryl, substituted 5-10-membered heteroaryl;

preferably, $R_a$ and $R_b$ are each independently selected from a hydrogen atom, a C1-C6 alkyl, a halo-C1-C6 alkyl, a C3-C8 cycloalkyl C1-C6 alkyl or a C6-C10 aryl C1-C6 alkyl;

alternatively, $R_a$, $R_b$ and the carbon atoms to which they are attached constitute a C3-C8 cycloalkyl group, a C3-C8 cycloalkyl C1-C6 alkyl group, a 3-7-membered heterocyclyl group, a substituted 3-7-membered heterocyclyl group; preferably $R_a$, $R_b$ and the carbon atoms to which they are attached constitute a C3-C8 cycloalkyl group;

$R_3$, $R_4$ are identical or different and are each independently a hydrogen atom, deuterium atom, halogen, C1-C6 alkyl, halogenated C1-C6 alkyl, deuterated C1-C6 alkyl, C1-C6 alkoxy, hydroxyl, amino, cyano, nitro, hydroxy C1-C6 alkyl, C3-C8 cycloalkyl, 3-7-membered heterocyclyl, or substituted 3-7-membered heterocyclyl;

preferably, $R_3$, $R_4$ are each independently a hydrogen atom or C1-C6 alkyl group;

alternatively, $R_3$, $R_4$ and the carbon atoms attached thereto constitute a C3-C8 cycloalkyl group, a C3-C8 cycloalkyl C1-C6 alkyl group, a 3-7-membered heterocyclic group, or a substituted 3-7-membered heterocyclic group;

m is selected from integers 0-4 (e.g., 0, 1, 2, 3, or 4), preferably 0, 1; n is selected from integers 1-10 (e.g., 1, 2, 3, 4, 5, 6, 7, 8, 9, or 10).

In some embodiments of the first aspect of the present invention, ligand-camptothecin derivative conjugates as shown in general formula I or pharmaceutically acceptable salts or solvates thereof are disclosed, characterized in that Ab is a bispecific antibody or antigen-binding fragment thereof that simultaneously targets two different epitopes or targets, preferably a bispecific antibody or antigen-binding fragment thereof that simultaneously targets EGFR and HER3.

In some embodiments of the first aspect of the present invention, the disclosure of a ligand-camptothecin derivative conjugate as shown in general formula I, or a pharmaceutically acceptable salt or solvate thereof, is characterized in that the Ab antibody comprises: an IgG1 heavy chain, a κ light chain, and a single-chain Fv (scFv) structural domain; wherein said single-chain Fv (scFv) structural domain forms a construct with the IgG1 heavy chain or the κ light chain; wherein said IgG1 heavy chain and κ light chain form an IgG portion with binding specificity for EGFR; said scFv structural domain has binding specificity for HER3, and the scFv structural domain is connected by a linker (e.g., having an amino acid sequence of (gly-gly-gly-gly-ser)n, wherein n is an integer of at least 1, preferably n is an integer of 1 to 10) to the C-terminus or N-terminus of said IgG1 heavy chain or C-terminus or N-terminus of said κ light chain; and wherein the single-chain Fv structural domain has a structural order of N-terminus-heavy chain variable region-joint-light chain variable region-C-terminus or N-terminus-light chain variable region-joint-heavy chain variable region-C-terminus (e.g., said joint consists of an amino acid sequence of $(gly-gly-gly-gly-ser)_m$, wherein m is an integer of at least 3, preferably m is 3, 4, 5, or 6).

In some embodiments of the first aspect of the present invention, the disclosure of a ligand-camptothecin derivative conjugate as shown in general formula I, or a pharmaceutically acceptable salt or solvate thereof, is characterized in that the κ light chain of the Ab antibody comprises CDRs as shown in SEQ ID NO: 25, SEQ ID NO: 26, and SEQ ID NO: 27, and the IgG1 heavy chain comprises CDRs as shown in SEQ ID NO: 29, SEQ ID NO: 30, and SEQ ID NO: 31, and the single-chain Fv (scFv) structural domain comprises the heavy chain variable region CDRs as shown in SEQ ID NO: 32, SEQ ID NO: 33, and SEQ ID NO: 34, and light chain variable region CDRs as shown in SE) ID NO: 35, SEQ ID NO: 36, and SEQ ID NO: 37.

In some embodiments of the first aspect of the present invention, the ligand-camptothecin derivative conjugate shown in general formula I, or a pharmaceutically acceptable salt or solvate thereof, is disclosed, characterized in that the light chain of the Ab antibody comprises a variable region as shown in SEQ ID NO: 28, the IgG1 heavy chain comprises a variable region as shown in SEQ ID NO: 38, and the single chain Fv (scFv) structural domain comprises a heavy chain variable region as shown in SEQ ID NO: 39 and a light chain variable region as shown in SEQ ID NO: 40.

In some embodiments of the first aspect of the present invention, a ligand-camptothecin derivative conjugate shown in general formula I, or a pharmaceutically acceptable salt or solvate thereof, is disclosed, characterized in that the light chain amino acid sequence of the Ab antibody is SEQ ID NO: 2, and the amino acid sequence of the construct of the antibody heavy chain and the single-chain Fv (scFv) structural domain is SEQ ID NO: 4.

In some embodiments of the first aspect of the present invention, the ligand-camptothecin derivative conjugate shown in general formula I, or a pharmaceutically acceptable salt or solvate thereof, is disclosed, characterized in that the light chain nucleic acid coding sequence of the Ab antibody is SEQ ID NO: 1, and the nucleic acid coding sequence of the construct of the antibody heavy chain and the single-chain Fv (scFv) structural domain is SEQ ID NO: 3.

In some embodiments of the first aspect of the present invention, a ligand-camptothecin derivative conjugate shown in general formula I, or a pharmaceutically acceptable salt or solvate thereof, is disclosed, characterized in that the κ light chain of the Ab antibody comprises CDRs as shown in SEQ ID NO: 41, SEQ ID NO: 42, and SEQ ID NO: 43, the IgG1 heavy chain comprises CDRs as shown in SEQ ID NO: 45, SEQ ID NO: 46, and SEQ ID NO: 47, and the single-chain Fv (scFv) structural domain comprises heavy chain variable region CDRs as shown in SEQ ID NO: 32, SEQ ID NO: 33, and SEQ ID NO: 34, and light chain variable region CDRs as shown in SEQ ID NO: 35, SEQ ID NO: 36, and SEQ ID NO: 37.

In some embodiments of the first aspect of the present invention, the ligand-camptothecin derivative conjugate shown in general formula I, or a pharmaceutically acceptable salt or solvate thereof, is disclosed, characterized in that the light chain of the Ab antibody comprises a variable region as shown in SEQ ID NO: 44, the IgG11 heavy chain comprises a variable region as shown in SEQ ID NO: 48, and the single-chain Fv (scFv) structural domain comprises a heavy chain variable region as shown in SEQ ID NO: 39 and a light chain variable region as shown in SEQ ID NO: 40.

In some embodiments of the first aspect of the present invention, a ligand-camptothecin derivative conjugate shown in general formula I, or a pharmaceutically acceptable salt or solvate thereof, is disclosed, characterized in that the light chain amino acid sequence of the Ab antibody is SEQ ID NO: 6, and the amino acid sequence of the construct of the heavy chain of the antibody and the single-chain Fv (scFv) structural domain is SEQ ID NO: 8.

In some embodiments of the first aspect of the present invention, the ligand-camptothecin derivative conjugate shown in general formula I, or a pharmaceutically acceptable salt or solvate thereof, is disclosed, characterized in that the light chain nucleic acid coding sequence of the Ab antibody is SEQ ID NO: 5, and the nucleic acid coding sequence of the construct of the antibody heavy chain and the single-chain Fv (scFv) structural domain is SEQ ID NO: 7.

In some embodiments of the first aspect of the present invention, the ligand-camptothecin derivative conjugate shown in general formula I, or a pharmaceutically acceptable salt or solvate thereof, is disclosed, characterized in that the light chain of the Ab antibody comprises a variable region as shown in SEQ ID NO: 49, the IgG1 heavy chain comprises a variable region as shown in SEQ ID NO: 52, and a single-chain Fv (scFv) structural domain comprises a heavy chain variable region as shown in SEQ ID NO: 50 and a light chain variable region as shown in SEQ ID NO: 51.

In some embodiments of the first aspect of the present invention, a ligand-camptothecin derivative conjugate shown in general formula I, or a pharmaceutically acceptable salt or solvate thereof, is disclosed, characterized in that an Ab antibody has a heavy chain amino acid sequence of SEQ ID NO: 12, and a construct of the antibody light chain and a single-chain Fv (scFv) structural domain has an amino acid sequence of SEQ ID NO: 10.

In some embodiments of the first aspect of the present invention, a ligand-camptothecin derivative conjugate shown in general formula I, or a pharmaceutically acceptable salt or solvate thereof, is disclosed, characterized in that the Ab antibody has a heavy chain nucleic acid coding sequence of SEQ ID NO: 11, and a construct of the light chain of the antibody and a single-chain Fv (scFv) structural domain has a nucleic acid coding sequence of SEQ ID NO: 9.

In some embodiments of the first aspect of the present invention, the ligand-camptothecin derivative conjugate shown in general formula I, or a pharmaceutically acceptable salt or solvate thereof, is disclosed, characterized in that the Ab antibody has a light chain amino acid sequence of SEQ ID NO: 14, and a construct of the antibody heavy chain and a single-chain Fv (scFv) structural domain has an amino acid sequence of SEQ ID NO: 16.

In some embodiments of the first aspect of the present invention, the ligand-camptothecin derivative conjugate shown in general formula I, or a pharmaceutically acceptable salt or solvate thereof, is disclosed, characterized in that the Ab antibody has a light chain nucleic acid coding sequence of SEQ ID NO: 13, and a construct of the antibody heavy chain and a single-chain Fv (scFv) structural domain has a nucleic acid coding sequence of SEQ ID NO: 15.

In some embodiments of the first aspect of the present invention, the ligand-camptothecin derivative conjugate shown in general formula I, or a pharmaceutically acceptable salt or solvate thereof, is disclosed, characterized in that the Ab antibody has a heavy chain amino acid sequence of SEQ ID NO: 20, and a construct of the antibody light chain and a single-chain Fv (scFv) structural domain has an amino acid sequence of SEQ ID NO: 18.

In some embodiments of the first aspect of the present invention, the ligand-camptothecin derivative conjugate shown in general formula I, or a pharmaceutically acceptable salt or solvate thereof, is disclosed, characterized in that the Ab antibody has a heavy chain nucleic acid coding sequence of SEQ ID NO: 19, and a construct of the light chain of the antibody and a single-chain Fv (scFv) structural domain has a nucleic acid coding sequence of SEQ ID NO: 17.

In some embodiments of the first aspect of the present invention, the ligand-camptothecin derivative conjugate shown in general formula I, or a pharmaceutically acceptable salt or solvate thereof, is disclosed, characterized in that the light chain of the Ab antibody comprises a variable region as shown in SEQ ID NO: 53, an IgG1 heavy chain comprises a variable region as shown in SEQ ID NO: 54, and a single-chain Fv (scFv) structural domain comprises a heavy chain variable region as shown in SEQ ID NO: 50 and a light chain variable region as shown in SEQ ID NO: 51.

In some embodiments of the first aspect of the present invention, the ligand-camptothecin derivative conjugate shown in general formula I, or a pharmaceutically acceptable salt or solvate thereof, is disclosed, characterized in that the Ab antibody has a heavy chain amino acid sequence of SEQ ID NO: 24, and the amino acid sequence of a construct of the light chain of the antibody and a single-chain Fv (scFv) structural domain is SEQ ID NO: 22.

In some embodiments of the first aspect of the present invention, the ligand-camptothecin derivative conjugate shown in general formula I, or a pharmaceutically acceptable salt or solvate thereof, is disclosed, characterized in that the Ab antibody has a heavy chain nucleic acid coding sequence of SEQ ID NO: 23, and a construct of the antibody light chain and a single-chain Fv (scFv) structural domain has a nucleic acid coding sequence of SEQ ID NO: 21.

In some embodiments of the first aspect of the present invention, a ligand-camptothecin derivative conjugate shown in general formula I, or a pharmaceutically acceptable salt or solvate thereof, is disclosed, characterized in that the Ab antibody comprises: two IgG1 heavy chains; two κ light chains; and two single-chain Fv (scFv) structural domains In some embodiments of the first aspect of the present invention, ligand-camptothecin derivative conjugates as shown in general formula I or pharmaceutically acceptable salts or solvates thereof are disclosed, characterized in that said X is selected without limitation from the following structures or isomers thereof:

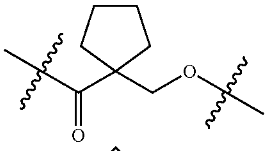
,
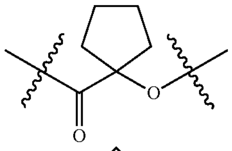
,
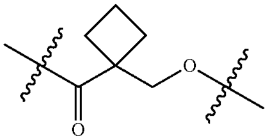
,
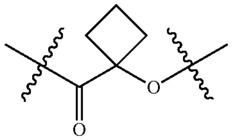
,
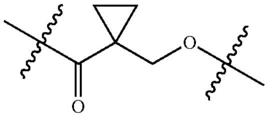
,
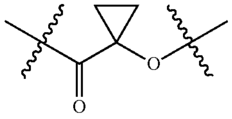
,
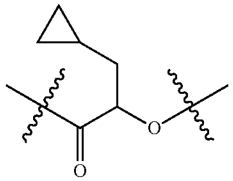
,
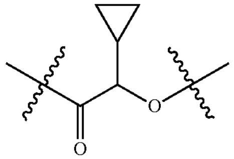
, -continued

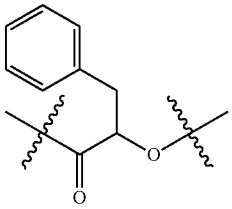
,
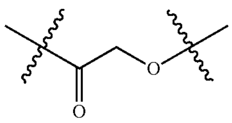
,
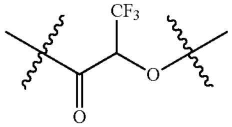
,
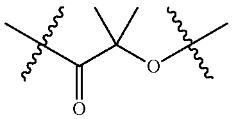
,
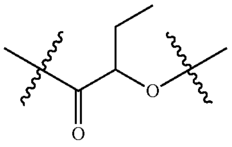
or
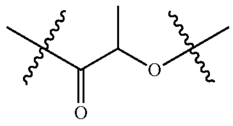
, where the left wavy line is linked to a camptothecin derivative portion and the right wavy line is linked to $L_5$.

In some embodiments of the first aspect of the present invention, ligand-camptothecin derivative conjugates as shown in general formula I or pharmaceutically acceptable salts or solvates thereof are disclosed, characterized in that $L_4$ is selected without limitation from peptide residues formed of amino acids;

wherein optionally, said amino acid is further substituted with one or more substituents selected from deuterium atoms, halogens, hydroxyl, cyano, amino, nitro, carboxyl, C1-C6 alkyl, substituted C1-C6 alkyl, C1-C6 alkoxy and C3-C8 cycloalkyl or substituted C3-C8 cycloalkyl;

preferably, said peptide residue is a peptide residue formed from one, two or more amino acids selected from phenylalanine (F), glycine (G), valine (V), lysine (K), citrulline (C), serine (S), glutamic acid (E) or aspartic acid (D);

more preferably, said peptide residue is a tetrapeptide residue consisting of glycine (G)-glycine (G)-phenylalanine (F)-glycine (G).

Particularly preferably, said peptide residue is -GGFG-.

In some embodiments of the first aspect of the present invention, ligand-camptothecin derivative conjugates as shown in general formula I or pharmaceutically acceptable salts or solvates thereof are disclosed, characterized as follows:

$L_5$ is non-limitatively selected from $—NR_5(CR_6R_7)_q—$ or a chemical bond, q is selected from an integer from 0-6 (e.g., 0, 1, 2, 3, 4, 5, or 6);

$R_5$, $R_6$ and $R_7$ are identical or different and are each independently selected from a hydrogen atom, a deuterium atom, a halogen, a C1-C6 alkyl group, a substituted C1-C6 alkyl group, a deuterated C1-C6 alkyl group, a C3-C8 cycloalkyl group, a C3-C8 cycloalkyl C1-C6 alkyl group, a C1-C6 alkoxy C1-C6 alkyl group, a 3-7-membered heterocyclyl group, a substituted 3-7-membered heterocyclyl group, a C6-C10 aryl group, a substituted C6-C10 aryl, 5-10-membered heteroaryl, substituted 5-10-membered heteroaryl;

preferably, $R_5$, $R_6$ and $R_7$ are each independently selected from a hydrogen atom or a C1-C6 alkyl group;

more preferably, $R_5$, $R_6$ and $R_7$ are each independently selected from a hydrogen atom.

In certain embodiments, $L_1$ is selected without limitation from:

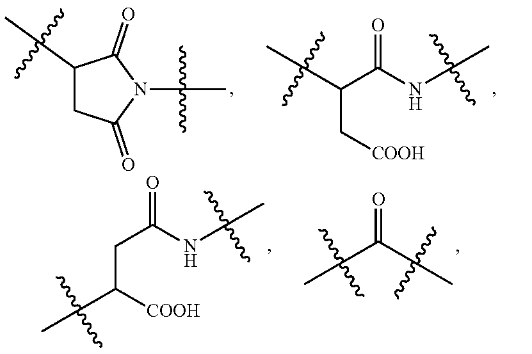

-continued

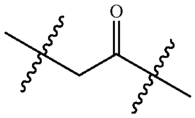

or

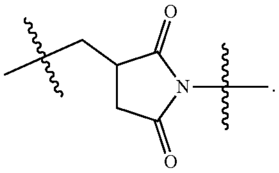

In some embodiments of the first aspect of the present invention, ligand-camptothecin derivative conjugates as shown in general formula I or pharmaceutically acceptable salts or solvates thereof are disclosed, characterized in that said linking unit $-L_1-L_2-L_3-L_4-L_5-$ is selected without limitation from the following structures;

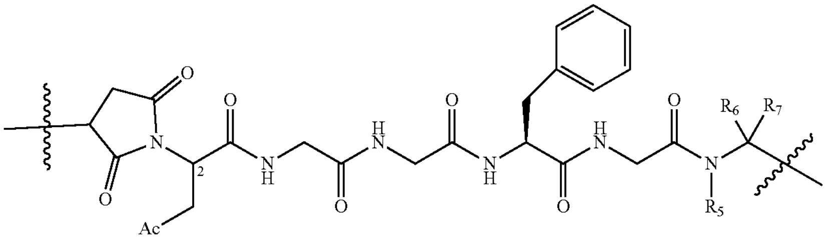

,

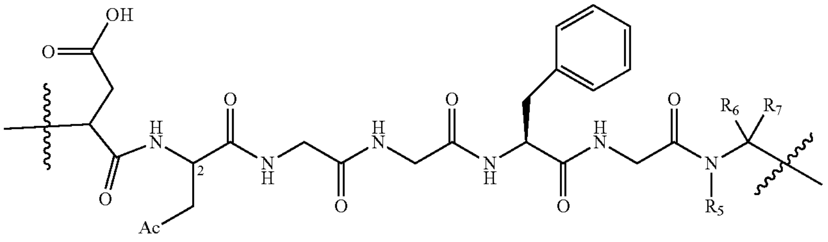

,

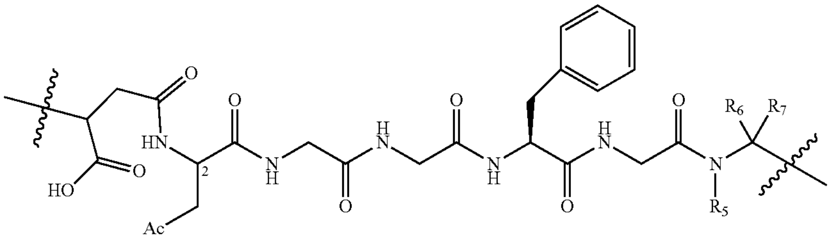

,

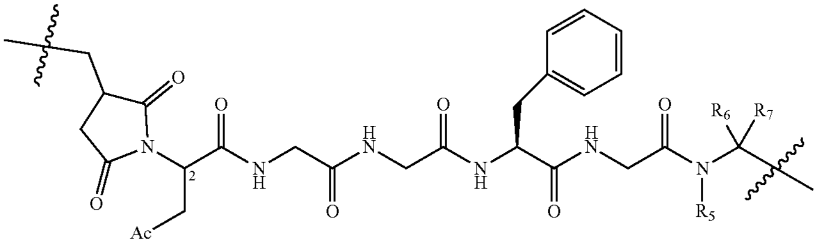

,

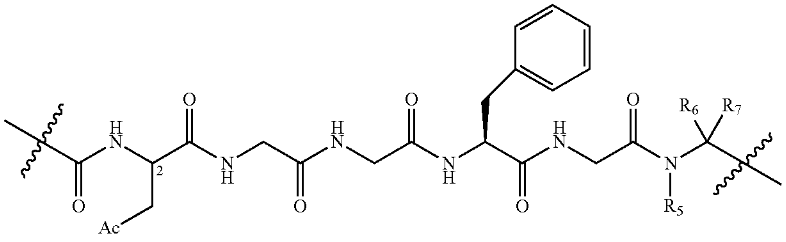

-continued
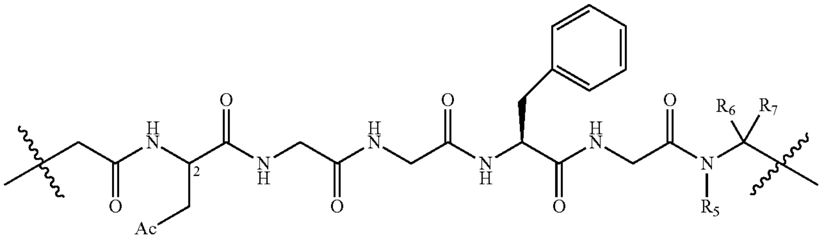
,
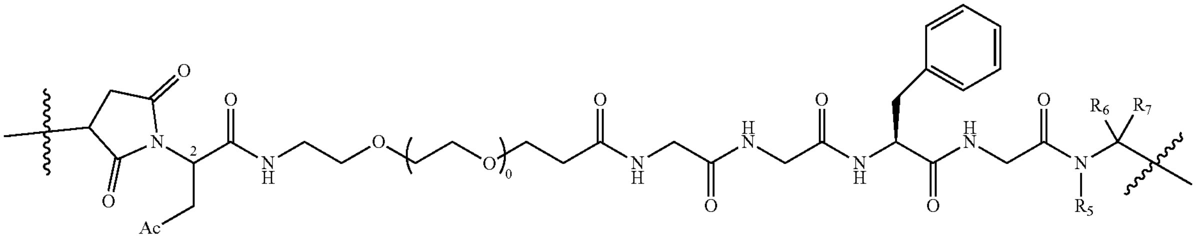
,
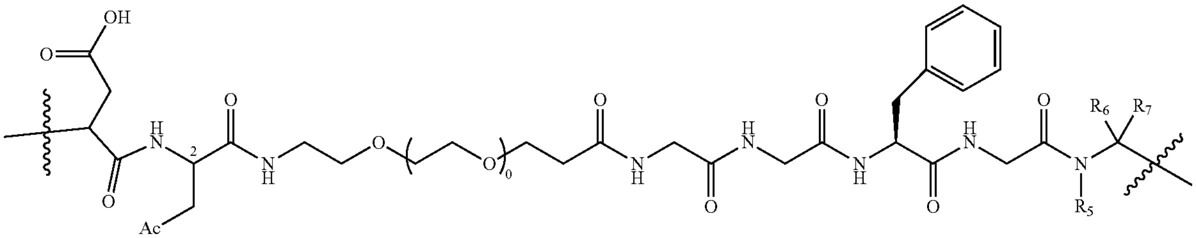
,
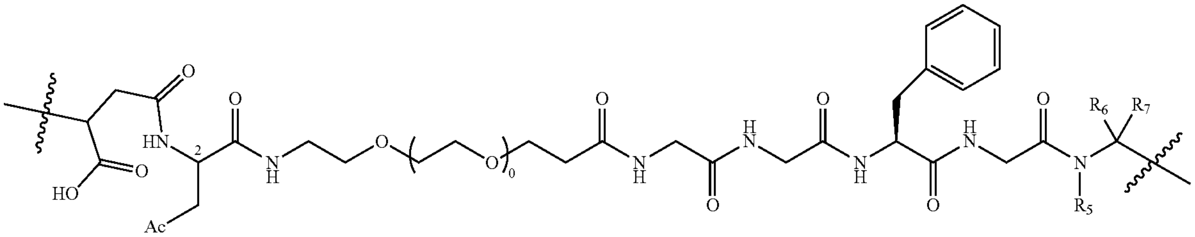
,
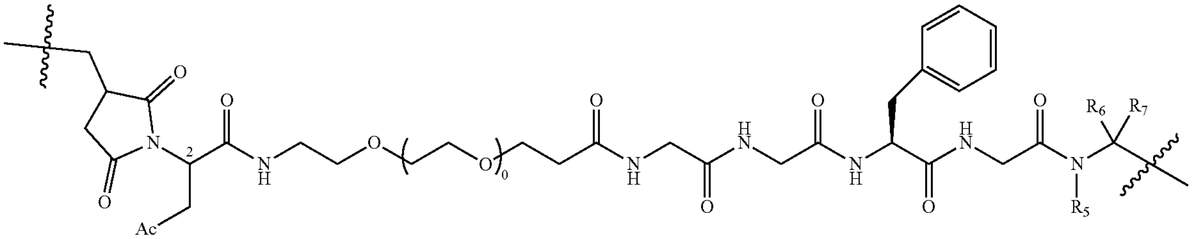
,
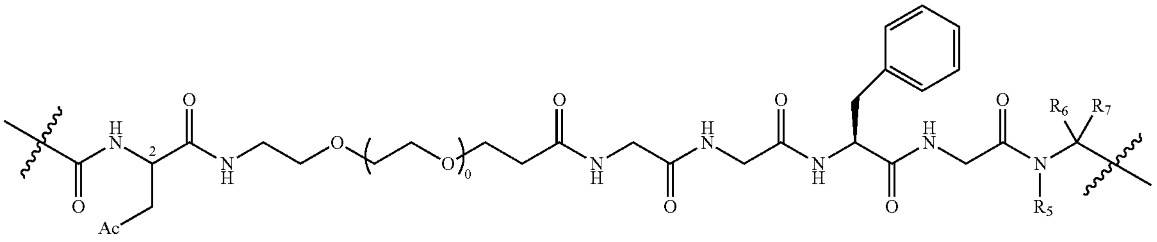
or
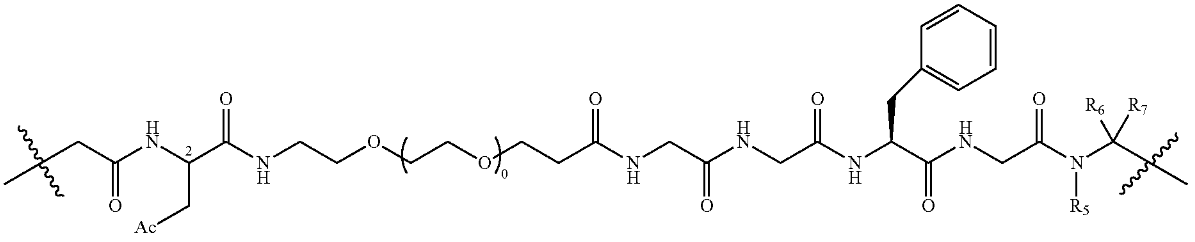
.

preferably

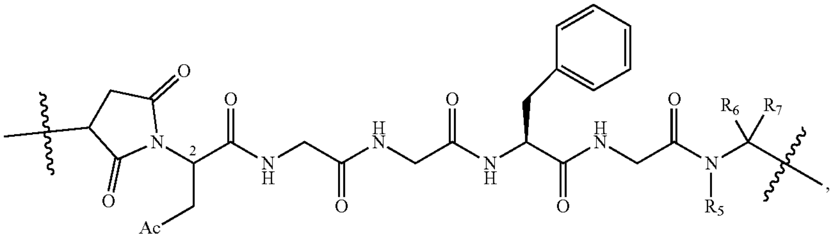

,

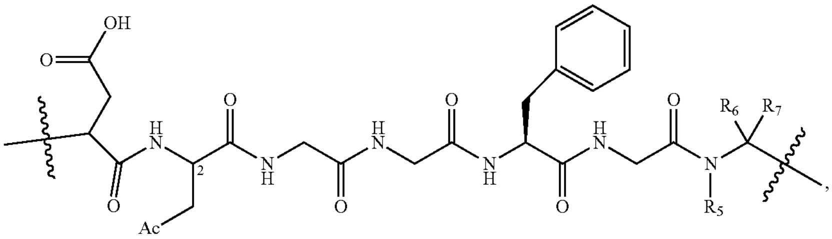

,

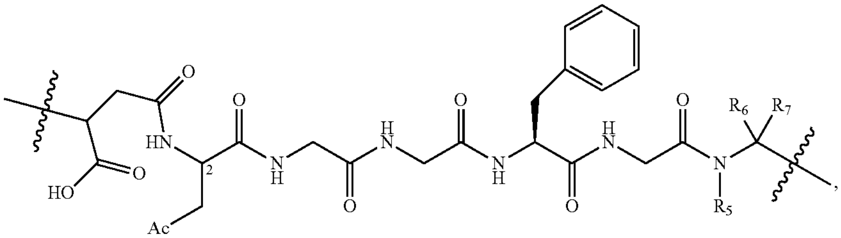

,

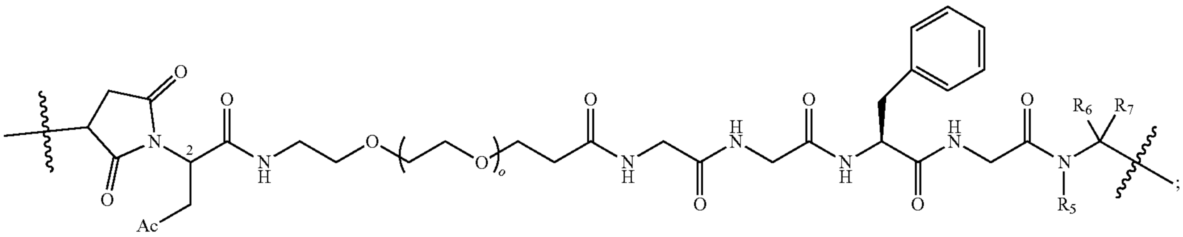

;

wherein:

Ac is a hydrophilic structural unit;

$R_5$, $R_6$ and $R_7$ are identical or different and are each independently selected from hydrogen atom, deuterium atom, halogen, C1-C6 alkyl, substituted C1-C6 alkyl, deuterated C1-C6 alkyl, C3-C8 cycloalkyl, C3-C8 cycloalkyl C1-C6 alkyl, C1-C6 alkoxy C1-C6 alkyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably, $R_5$, $R_6$ and $R_7$ are each independently selected from a hydrogen atom or a C1-C6 alkyl group;

more preferably, $R_5$, $R_6$ and $R_7$ are each independently selected from a hydrogen atom;

the carbon atom No. 2 attached to N has absolute chirality in the R configuration or the S configuration;

the left wavy line is linked to the antibody or its antigen-binding fragment portion, and the right wavy line is connected to the X;

o is selected from integers 1-10 (i.e., 1, 2, 3, 4, 5, 6, 7, 8, 9, or 10).

The second aspect of the present invention discloses a ligand-camptothecin derivative conjugate as shown in general formula II, or a pharmaceutically acceptable salt or solvate thereof;

II
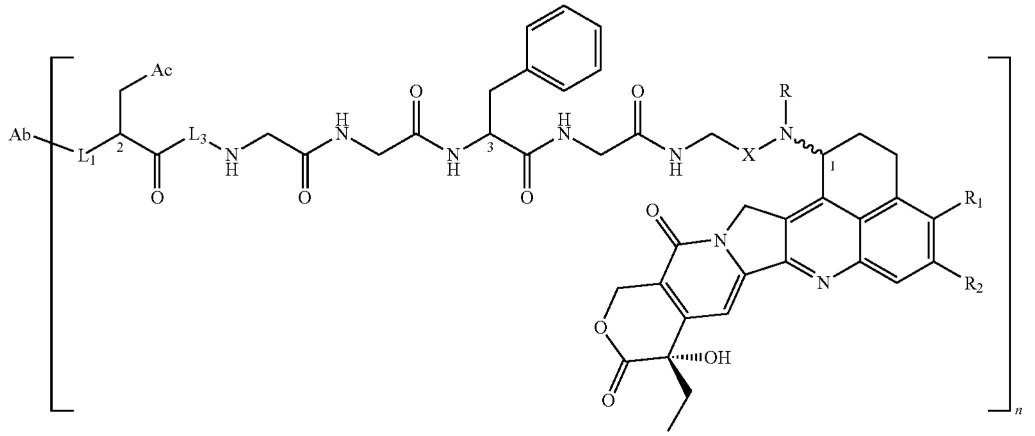
wherein:
Ab is a bispecific antibody or antigen-binding fragment thereof that simultaneously targets EGFR and HER3;
$L_1$ is a linking unit that is connected to Ab, selected without limitation from:
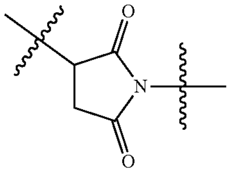
,
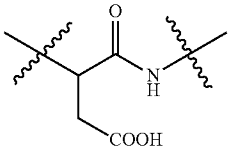
,
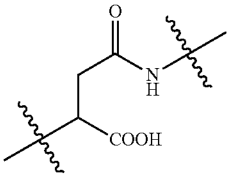
,
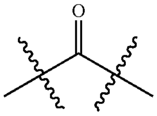
,
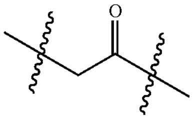
,
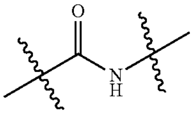
,
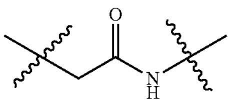
,
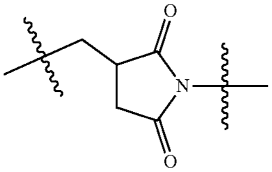
,
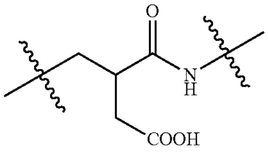
or
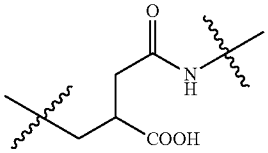
;
preferably, $L_1$ is:
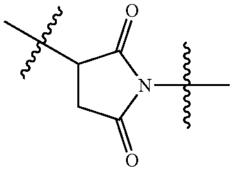
,
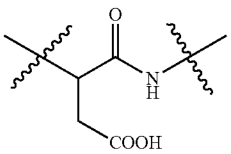
,
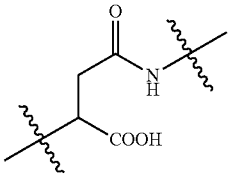
;
preferably, $L_1$ is:
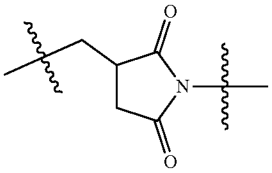
,
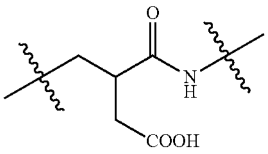
,
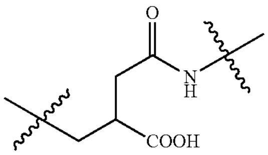
;
$L_3$ is present or absent, and when $L_3$ is present, $L_3$ is selected from
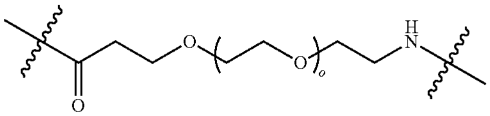
,
o is selected from integers 1-10 (e.g., 1, 2, 3, 4, 5, 6, 7, 8, 9, or 10), preferably integers 2-8;

Ac is a hydrophilic structural unit;

the chiral carbon atoms at position 1, position 2 and position 3 have two chiral configurations, namely the R absolute configuration or the S absolute configuration;

R is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, C6-C10 aryl, substituted C6-C10 aryl, 5-10-membered heteroaryl, and substituted 5-10-membered heteroaryl;

preferably R is selected from a hydrogen atom or a C1-C6 alkyl group;

$R_1$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably $R_1$ is selected from a hydrogen atom or a C1-C6 alkyl group;

more preferably, $R_1$ is selected from C1-C6 alkyl;

$R_2$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably $R_2$ is selected from a hydrogen atom, a halogen or a C1-C6 alkyl group;

more preferably $R_2$ is selected from halogen;

X is selected from $—C(O)—CR_aR_b—(CR_3R_4)_m—O—$, $—C(O)—CR_aR_b—(CR_3R_4)_m—NH—$ or $—C(O)—CR_aR_b—(CR_3R_4)_m—S—$;

preferably X is selected from $—C(O)—CR_aR_b—(CR_3R_4)_m—O—$;

$R_a$ and $R_b$ are each independently selected from a hydrogen atom, a deuterium atom, a halogen, a C1-C6 alkyl group, a deuterated C1-C6 alkyl group, a halogenated C1-C6 alkyl group, a C3-C8 cycloalkyl group, a C3-C8 cycloalkyl C1-C6 alkyl group, a C1-C6 alkoxy C1-C6 alkyl group, a 3-7-membered heterocyclic group, a substituted 3-7-membered heterocyclic group, a C6-C10 aryl group, a substituted C6-C10 aryl group, a 5-10-membered heteroaryl, a substituted 5-10-membered heteroaryl;

preferably, $R_a$ and $R_b$ are each independently selected from a hydrogen atom, a C1-C6 alkyl, a halo-C1-C6 alkyl, a C3-C8 cycloalkyl C1-C6 alkyl or a C6-C10 aryl C1-C6 alkyl;

alternatively, $R_a$, $R_b$ and the carbon atoms to which they are attached constitute a C3-C8 cycloalkyl group, a C3-C8 cycloalkyl C1-C6 alkyl group, a 3-7-membered heterocyclyl group, a substituted 3-7-membered heterocyclyl group; preferably $R_a$, $R_b$ and the carbon atoms to which they are attached constitute a C3-C8 cycloalkyl group;

$R_3$, $R_4$ are identical or different and are independently hydrogen atoms, deuterium atoms, halogens, C1-C6 alkyl, halogenated C1-C6 alkyl, deuterated C1-C6 alkyl, C1-C6 alkoxy, hydroxyl, amino, cyano, nitro, hydroxy C1-C6 alkyl, C3-C8 cycloalkyl, 3-7-membered heterocyclyl, substituted 3-7-membered heterocyclyl, respectively;

preferably, $R_3$, $R_4$ are independently hydrogen atoms or C1-C6 alkyl groups, respectively;

alternatively, $R_3$, $R_4$ and the carbon atoms attached thereto constitute a C3-C8 cycloalkyl group, a C3-C8 cycloalkyl C1-C6 alkyl group, a 3-7-membered heterocyclic group, a substituted 3-7-membered heterocyclic group;

m is selected from integers 0-4 (i.e., 0, 1, 2, 3 or 4), preferably 0, 1;

n is selected from the integers 1-10 (e.g., 1, 2, 3, 4, 5, 6, 7, 8, 9, or 10).

In some embodiments of the first and second aspects of the present invention, it is disclosed that said ligand-camptothecin derivative conjugate, or a pharmaceutically acceptable salt or solvate thereof, is characterized in that: said Ac has the structure shown in formula B, as follows,

B

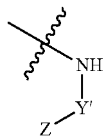

wherein:

Z is selected without limitation from the group consisting of one or more of a hydrophilic structural carboxyl group, phosphoric acid, polyphosphoric acid, phosphorous acid, sulfonic acid, sulfinic acid, or polyethylene glycol (PEG);

preferably Z is selected from a hydrophilic structural carboxyl group, phosphoric acid or polyethylene glycol (PEG);

Y' is optionally a scaffold connecting the amino group to Z; preferably Y' is a C1-C6 alkylene group (e.g. methylene);

Ac is connected to the 2-position carbon that has been labeled in structural formula I by means of a scaffold Y.

In some embodiments of the first aspect and the second aspect of the present invention, it is disclosed that said ligand-camptothecin derivative conjugate, or a pharmaceutically acceptable salt or solvate thereof, is characterized in that: said Ac is selected without limitation from glycine, (D/L) alanine, (D/L) leucine, (D/L) isoleucine, (D/L) valine, (D/L) phenylalanine, (D/L) proline, (D/L) tryptophan, (D/L) serine, (D/L) tyrosine, (D/L) cysteine, (D/L) cystine, (D/L) arginine, (D/L) histidine, (D/L) methionine, (D/L) asparagine, (D/L) glutamine, (D/L) threonine, (D/L) aspartic acid, (D/L) glutamic acid, natural or unnatural amino acid derivatives or the following structures or isomers thereof,

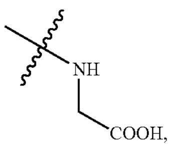

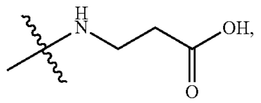

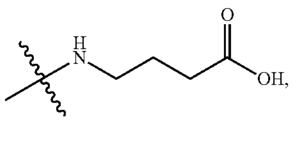

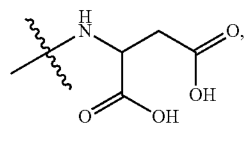

-continued

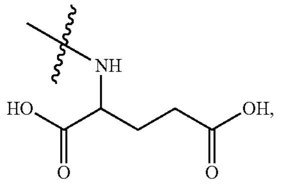

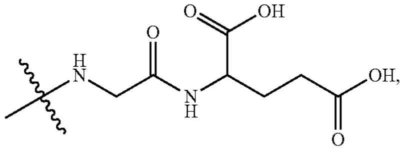

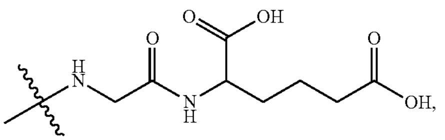

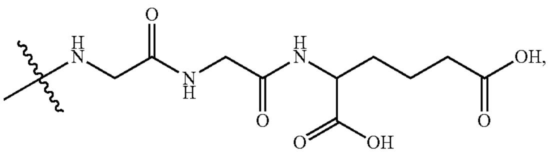

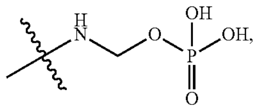

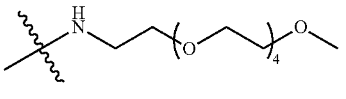

or

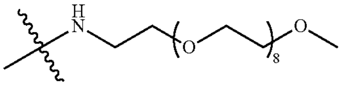

;

preferably

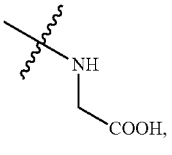

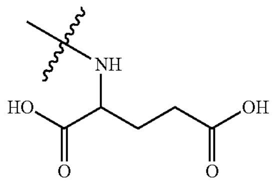

or

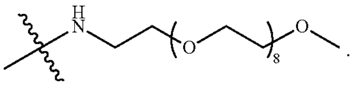

In some embodiments of the first and second aspects of the present invention, the disclosure of said ligand-camptothecin derivative conjugates or pharmaceutically acceptable salts or solvates thereof is characterized in that: said Ac is selected without limitation from a glycine, phosphoric acid, (D/L) glutamic acid, or polyethylene glycol hydrophilic structure.

In some embodiments of the first and second aspects of the present invention, the disclosure of said ligand-camptothecin derivative conjugates or pharmaceutically acceptable salts or solvates thereof is characterized in that said

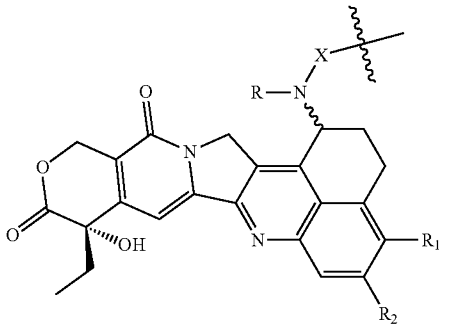

has the structure shown in formula d below;

d

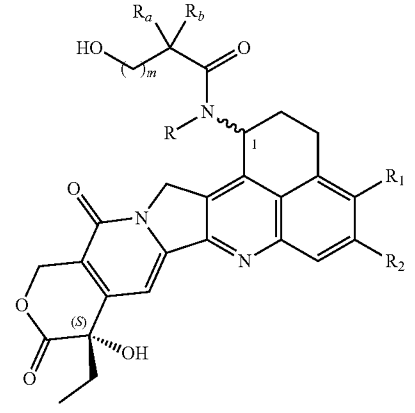

wherein:

R is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, C6-C10 aryl, substituted C6-C10 aryl, 5-10-membered heteroaryl, substituted 5-10-membered heteroaryl;

preferably R is selected from a hydrogen atom or a C1-C6 alkyl group;

$R_1$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably $R_1$ is selected from a hydrogen atom or a C1-C6 alkyl group;

more preferably $R_1$ is selected from C1-C6 alkyl;

$R_2$ is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, carboxyl, 3-7-membered heterocyclyl, substituted 3-7-membered heterocyclyl, C6-C10 aryl, substituted C6-C10 aryl, 5-10-membered heteroaryl, substituted 5-10-membered heteroaryl;

preferably $R_2$ is selected from a hydrogen atom, a halogen or a C1-C6 alkyl group;

more preferably $R_2$ is selected from halogen;

$R_a$ and $R_b$ are each independently selected from a hydrogen atom, a deuterium atom, a halogen, a C1-C6 alkyl, a deuterated C1-C6 alkyl, a halogenated C1-C6 alkyl, a C3-C8 cycloalkyl, a C3-C8 cycloalkyl C1-C6 alkyl, a C1-C6 alkoxy C1-C6 alkyl, a 3-7-membered heterocyclic group, a substituted 3-7-membered heterocyclic group, a C6-C10 aryl, a substituted C6-C10 aryl, a 5-10-membered heteroaryl, a substituted 5-10-membered heteroaryl;

preferably, $R_a$ and $R_b$ are each independently selected from a hydrogen atom, a C1-C6 alkyl, a halo-C1-C6 alkyl, a C3-C8 cycloalkyl C1-C6 alkyl or a C6-C10 aryl C1-C6 alkyl;

preferably $R_a$ and $R_b$ are each independently selected from a hydrogen atom, a C1-C6 alkyl, a halo-C1-C6 alkyl, a C3-C8 cycloalkyl C1-C6 alkyl, a C6-C10 aryl; preferably $R_a$ and $R_b$ are each independently selected from a hydrogen atom, a methyl group, an ethyl group, a trifluoromethyl group, a cyclopropylmethyl group, a phenyl group;

alternatively, $R_a$, $R_b$ and the carbon atoms to which they are attached constitute a C3-C8 cycloalkyl group, a C3-C8 cycloalkyl C1-C6 alkyl group, a 3-7-membered heterocyclyl group, a substituted 3-7-membered heterocyclyl group; preferably, $R_a$, $R_b$ and the carbon atoms to which they are attached constitute a C3-C8 cycloalkyl group (e.g., a C3-C5 cycloalkyl group);

the 1-position chiral carbon atom has two chiral configurations, namely the R absolute configuration or the S absolute configuration;

m is selected from 0 or 1.

In some embodiments of the first and second aspects of the present invention, the disclosure of said ligand-camptothecin derivative conjugate or a pharmaceutically acceptable salt or solvate thereof is characterized in that: said structural formula d is selected without limitation from the following compounds:

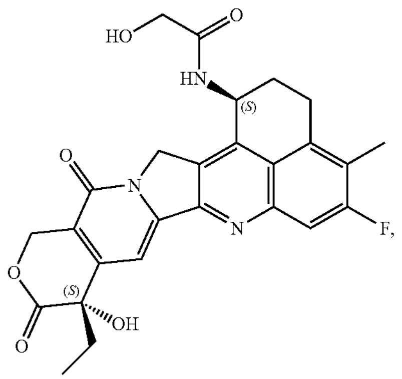

$d_1$

-continued

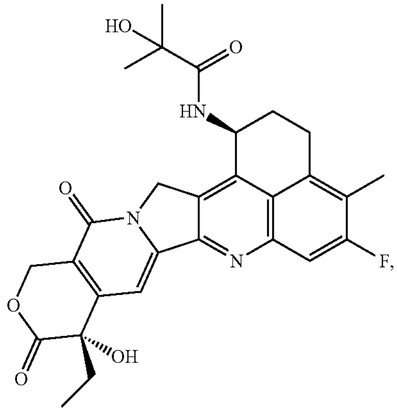

$d_2$

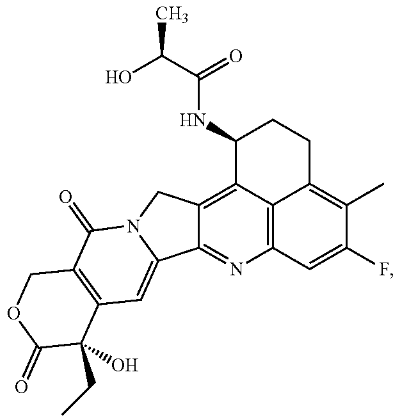

$d_3$

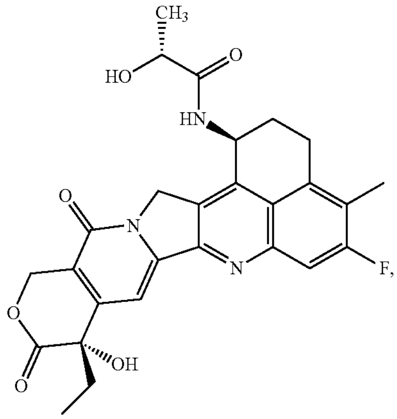

$d_4$

-continued
d5
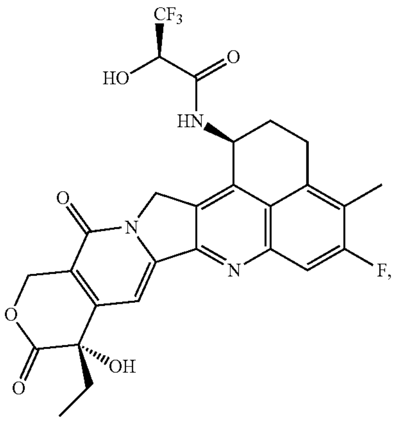
d6
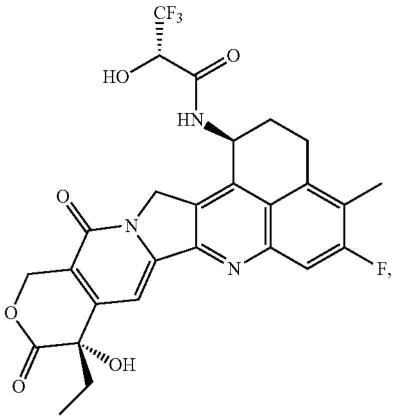
d7
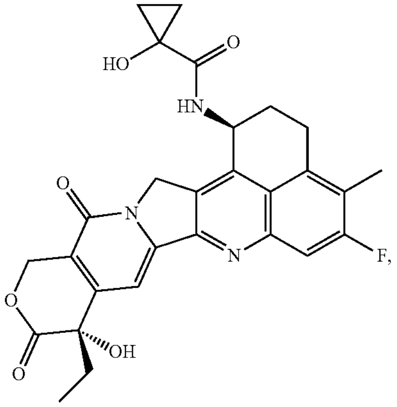
-continued
d8
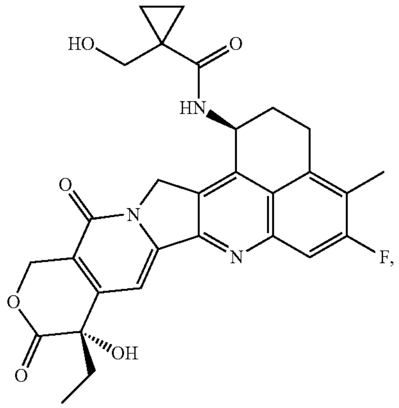
d9
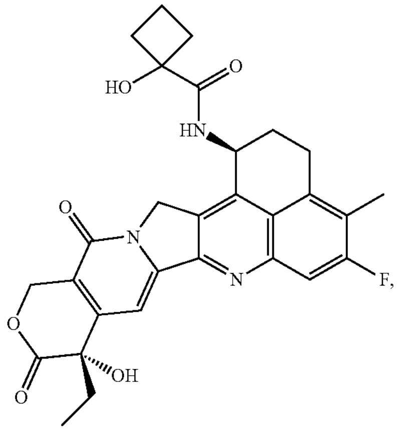
d10
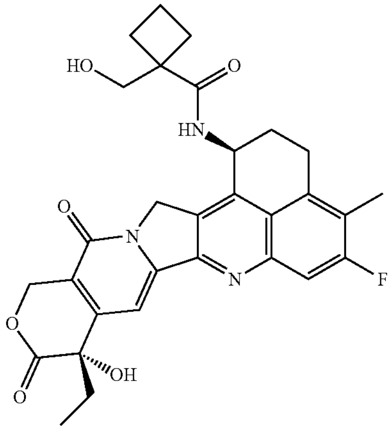

-continued
d11
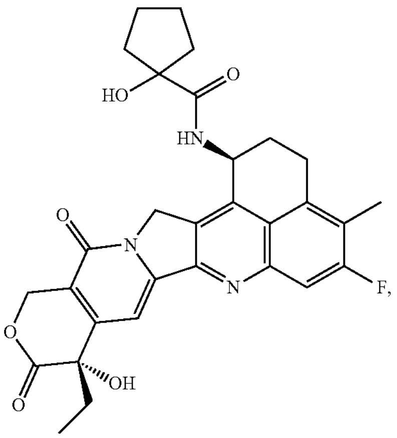
d12
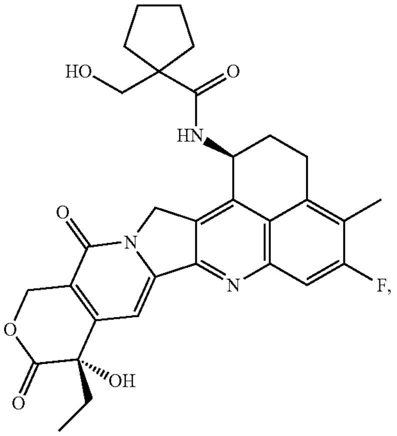
d13
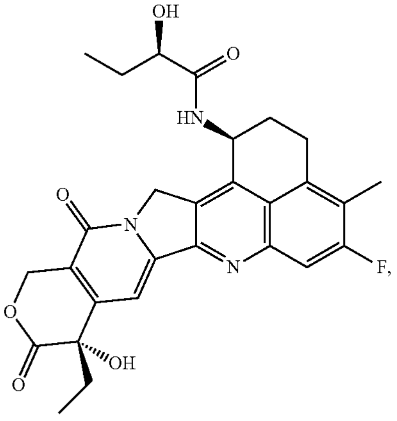
-continued
d14
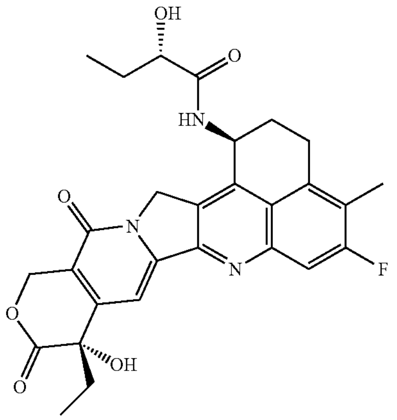
d15
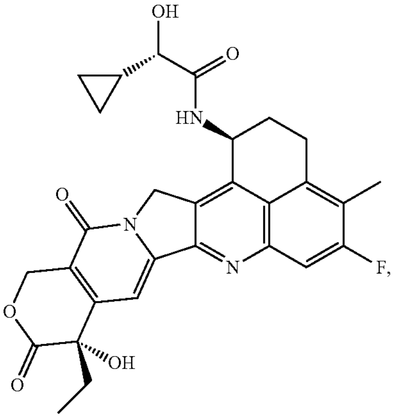
d16
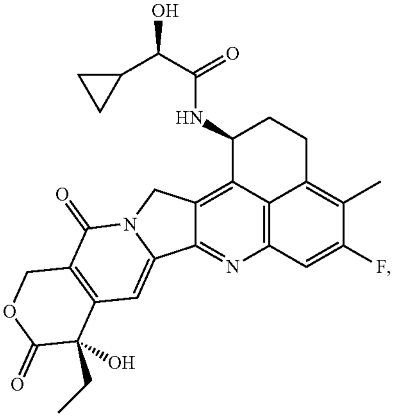

-continued
d17
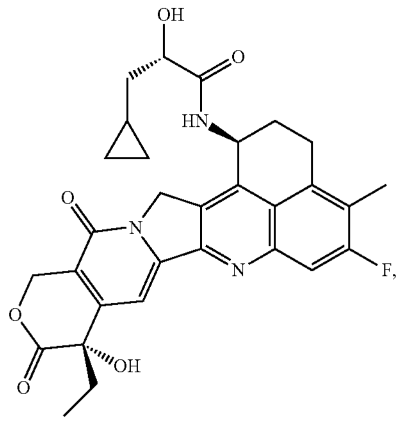
d18
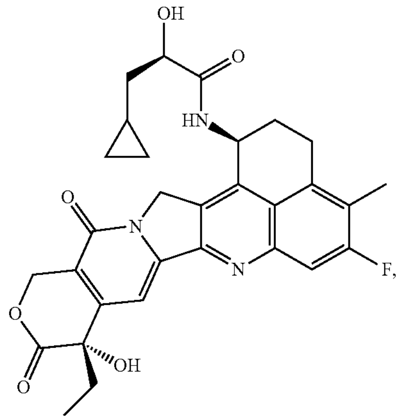
d19
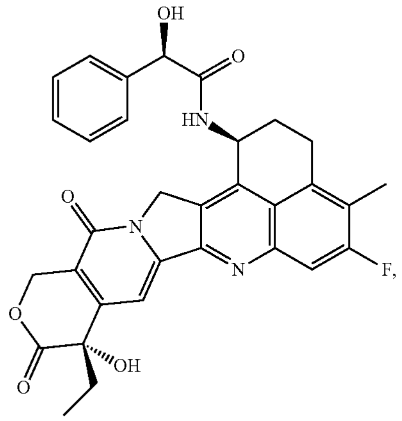
-continued
d20
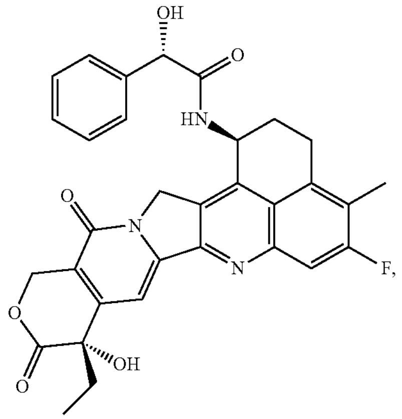
d21
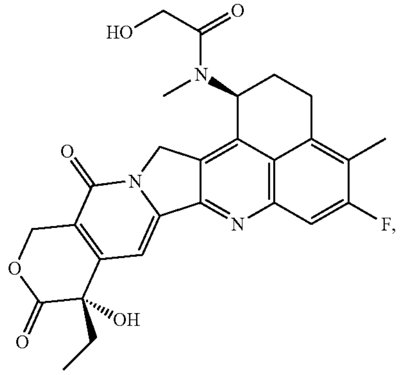
d22
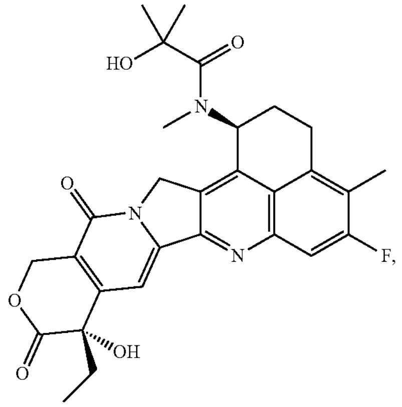
d23
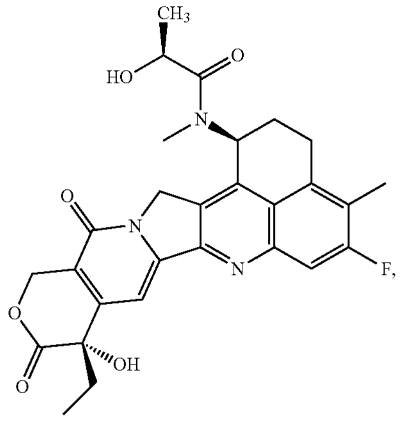

-continued
d24
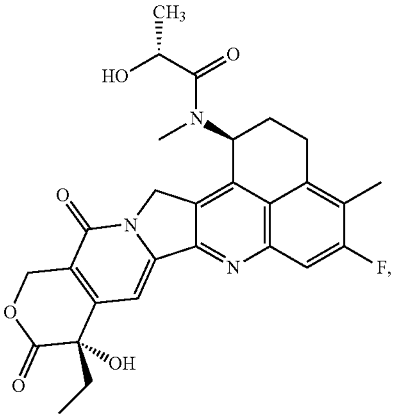
d25
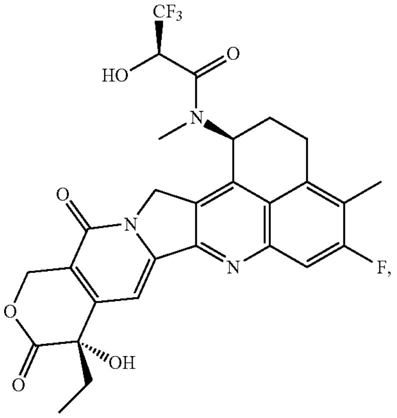
d26
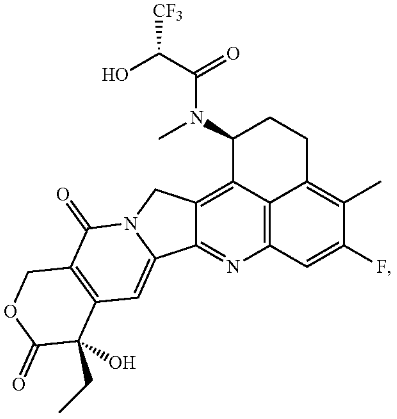
-continued
d27
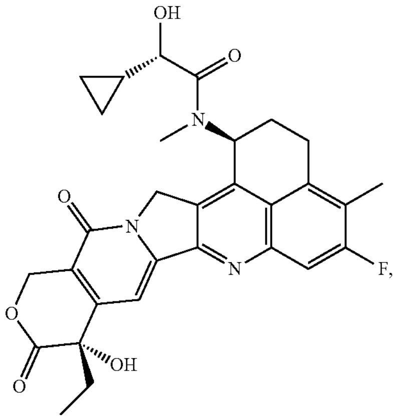
d28
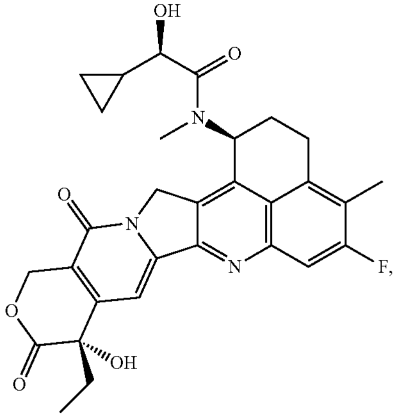
d29
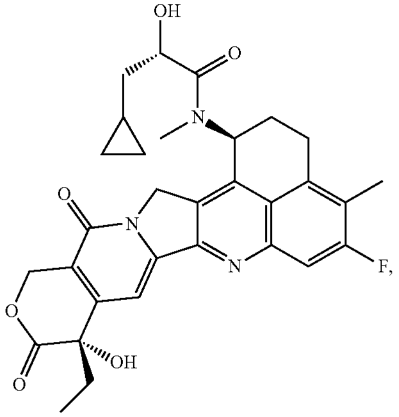

-continued
d30
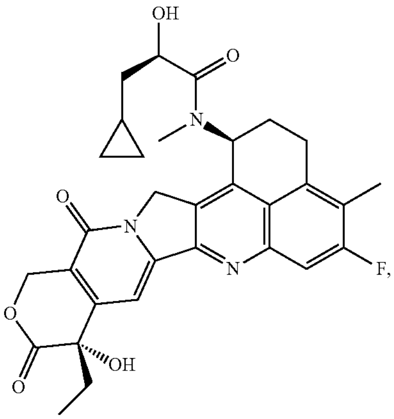
d31
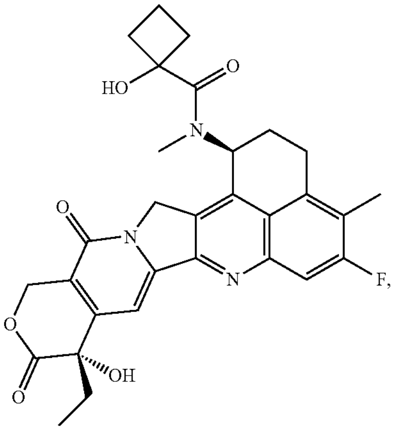
d32
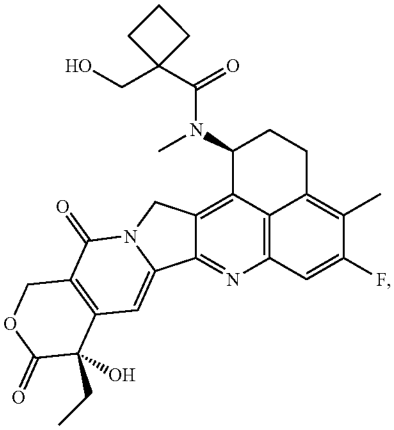
-continued
d33
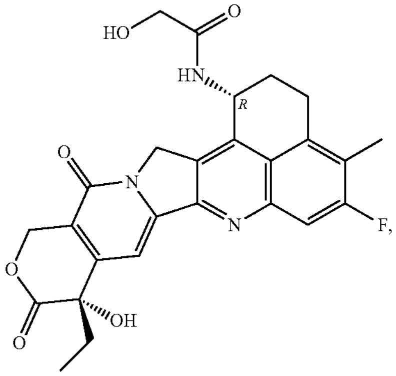
d34
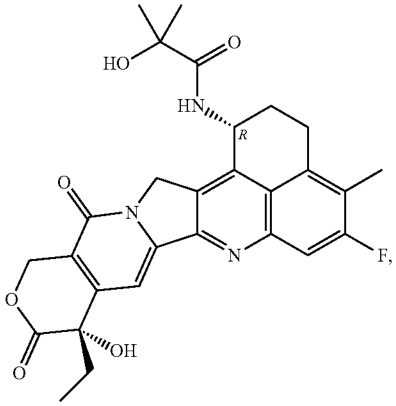
d35
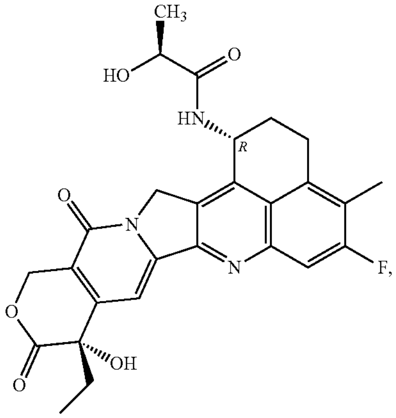
d36
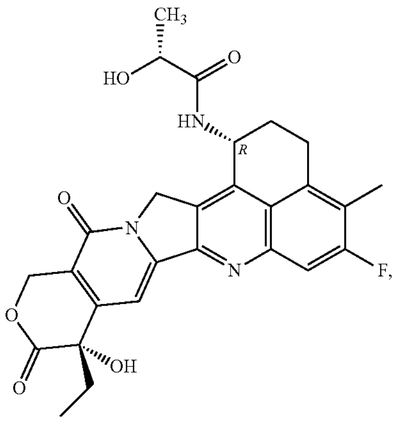

-continued
d37
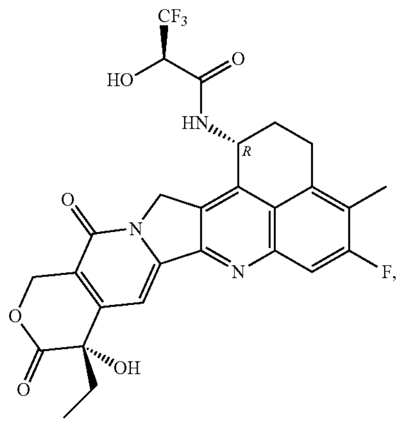
d38
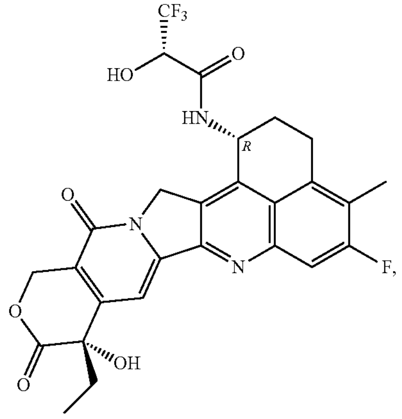
d39
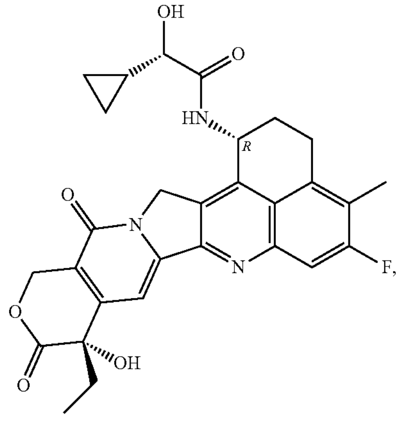
-continued
d40
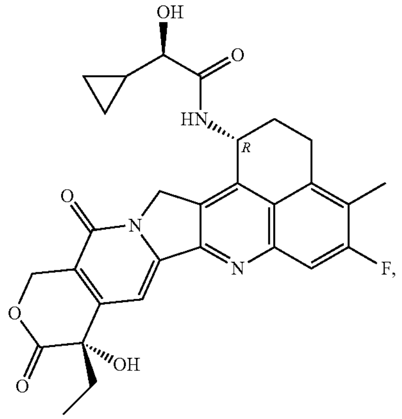
d41
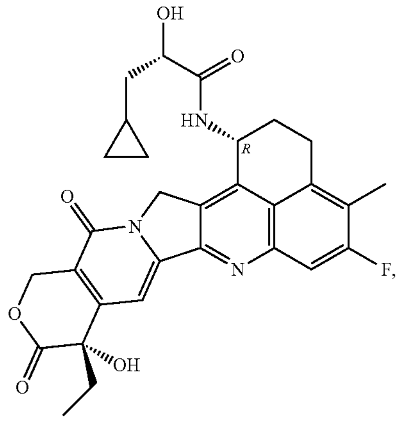
d42
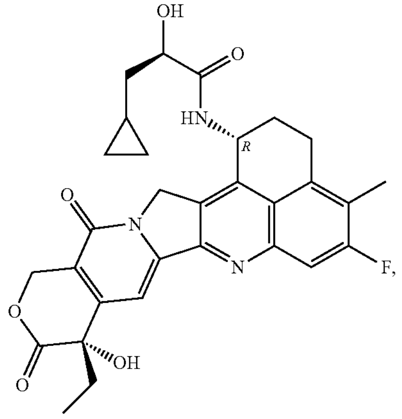

-continued d43

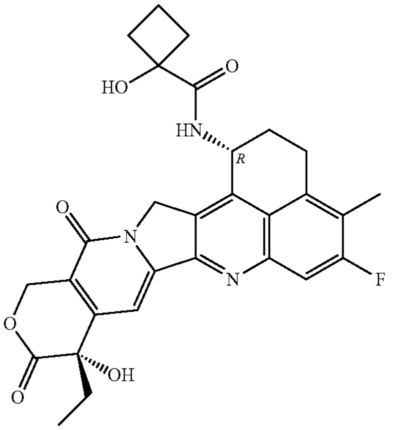

or d44

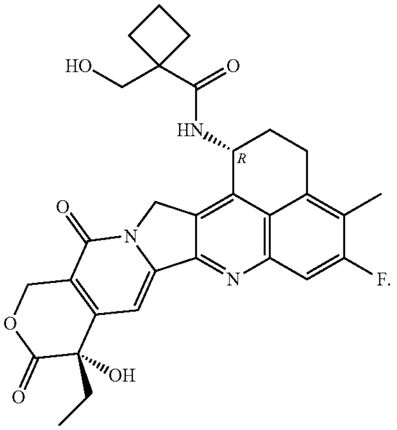

In some embodiments of the present invention, $L_1$ can comprise a succinimide group. In these embodiments, the ligand-drug conjugate can undergo hydrolysis under readily hydrolyzable conditions, with the site of hydrolysis being the succinimide group of the linker unit. When the ligand contains multiple linker-drugs, the following scenarios can occur with varying degrees of hydrolysis:

the succinimide groups are completely non-hydrolyzed, i.e., the succinimide groups are all in a closed ring form

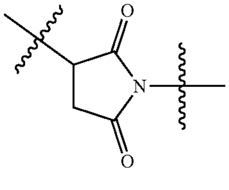 or 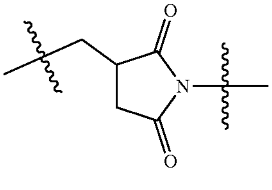 ;

incomplete hydrolysis of the succinimide groups, i.e., some of the succinimide groups are in a closed ring form

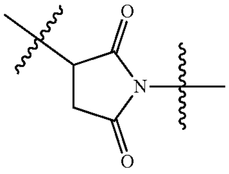 or 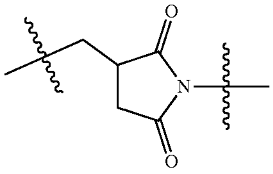 , and some of the succinimide groups are in an open ring form

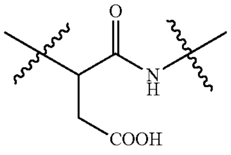 , 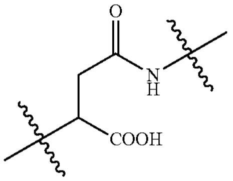 , or

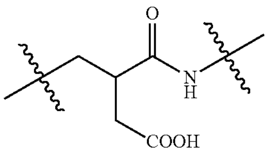 , 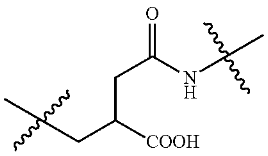 ;

complete hydrolysis of the succinimide groups, i.e., the succinimide groups are all in an open ring form

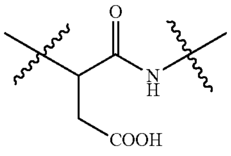 , 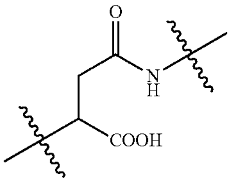 , or

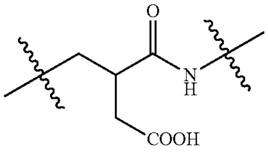 , 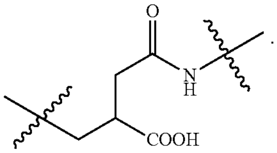 .

Thus, when multiple $L_1$ containing succinimide groups are present in the ADC at the same time (i.e., Ab is connected to multiple drug-linkers containing succinimide groups), these succinimide groups may be all in a closed ring form, partially in an open ring form, or all in an open ring form.

It will be appreciated that the present application, even though the succinimide group appearing in the chemical structural formula of the ADC is in the closed ring form, actually covers the three scenarios of the succinimide being all in a closed ring form, partially in an open ring form, and all in an open ring form. A third aspect of the present invention discloses a linker-drug compound or a pharmaceutically acceptable salt or solvate thereof, characterized by having the structure shown in formula III below,

III

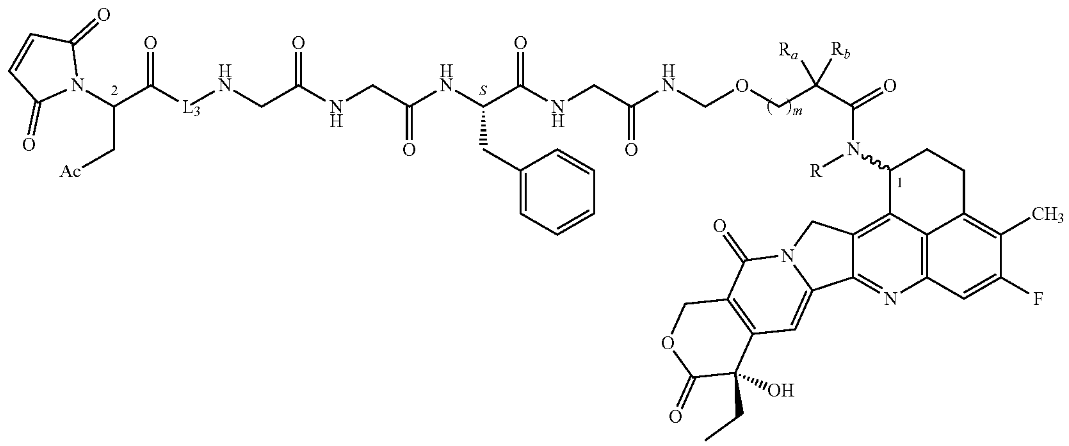

wherein:

R is selected from hydrogen atom, deuterium atom, halogen, C1-C6 alkyl, substituted C1-C6 alkyl, deuterated C1-C6 alkyl, C3-C8 cycloalkyl C1-C6 alkyl, C1-C6 alkoxy C1-C6 alkyl, C6-C10 aryl, substituted C6-C10 aryl, 5-10-membered heteroaryl, substituted 5-10-membered heteroaryl;

$R_a$ is selected from hydrogen atom, deuterium atom, halogen, C1-C6 alkyl, deuterated C1-C6 alkyl, halogenated C1-C6 alkyl, C3-C8 cycloalkyl, C3-C8 cycloalkyl C1-C6 alkyl, C1-C6 alkoxy C1-C6 alkyl, 3-7-membered heterocyclic group, substituted 3-7 membered heterocyclic group, C6-C10 aryl, substituted C6-C10 aryl, 5-10 membered heteroaryl, substituted 5-10-membered heteroaryl;

$R_b$ is selected from hydrogen atom, deuterium atom, halogen, C1-C6 alkyl, deuterated C1-C6 alkyl, halogenated C1-C6 alkyl, C3-C8 cycloalkyl, C3-C8 cycloalkyl C1-C6 alkyl, C1-C6 alkoxy C1-C6 alkyl, 3-7 membered heterocyclic group, substituted 3-7 membered heterocyclic group, C6-C10 aryl, substituted C6-C10 aryl, 5-10 membered heteroaryl, substituted 5-10-membered heteroaryl;

alternatively, $R_a$, $R_b$ and the carbon atoms attached thereto constitute a C3-C8 cycloalkyl group, a C3-C8 cycloalkyl C1-C6 alkyl group, a 3-7-membered heterocyclic group, a substituted 3-7-membered heterocyclic group;

preferably $R_a$ and $R_b$ are each independently selected from a hydrogen atom, a C1-C6 alkyl, a halo-C1-C6 alkyl, a C3-C8 cycloalkyl C1-C6 alkyl, a C6-C10 aryl; preferably $R_a$ and $R_b$ are each independently selected from a hydrogen atom, a methyl group, an ethyl group, a trifluoromethyl group, a cyclopropylmethyl group, a phenyl group;

alternatively, $R_a$, $R_b$ and the carbon atoms to which they are attached constitute a C3-C8 cycloalkyl group, a C3-C8 cycloalkyl C1-C6 alkyl group, a 3-7-membered heterocyclyl group, a substituted 3-7-membered heterocyclyl group; preferably, $R_a$, $R_b$ and the carbon atoms to which they are attached constitute a C3-C8 cycloalkyl group (e.g., a C3-C5 cycloalkyl group);

$L_3$ is present or absent, and when L3 is present, it is selected from

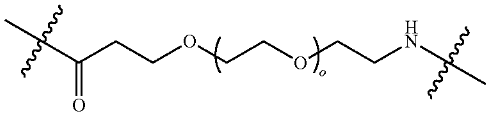

, o is selected from an integer from 1 to 10 (e.g., 1, 2, 3, 4, 5, 6, 7, 8, 9, or 10);

the 1-position or 2-position chiral carbon atom has two chiralities, namely the R absolute configuration or S absolute configuration;

Ac is a hydrophilic structural unit;

m is selected from 0 or 1.

In some embodiments of the third aspect of the present invention, it is disclosed that said linker-drug compounds or pharmaceutically acceptable salts or solvates thereof are characterized in that: said Ac has the structure shown in formula B below,

B

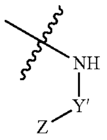

wherein:

Z is selected without limitation from the group consisting of one or more of a hydrophilic structural carboxyl group, a phosphoric acid, a polyphosphoric acid, a phosphorous acid, a sulfonic acid, a sulfinic acid, or a polyethylene glycol (PEG);

Y' is an optional scaffold connecting the amino group to Z; preferably Y' is a C1-C6 alkylene group (e.g. methylene);

Ac is connected to the 2-position carbon that has been labeled in structural formula I by means of scaffold Y.

In some embodiments of the third aspect of the present invention, disclosed are the linker-drug compounds or pharmaceutically acceptable salts or solvates thereof, characterized in that said Ac is selected without limitation from glycine, (D/L) alanine, (D/L) leucine, (D/L) isoleucine, (D/L) valine, (D/L) phenylalanine, (D/L) proline, (D/L) tryptophan, (D/L) serine, (D/L) tyrosine, (D/L) cysteine, (D/L) cystine, (D/L) arginine, (D/L) histidine, (D/L) methionine, (D/L) asparagine, (D/L) glutamine, (D/L) threonine, (D/L) aspartic acid, (D/L) glutamic acid, natural or unnatural amino acid derivatives or the following structures

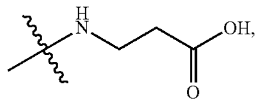

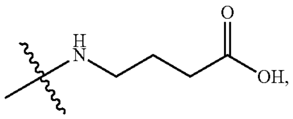

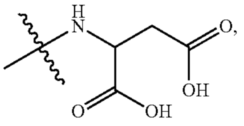

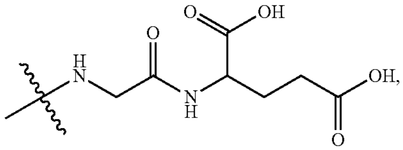

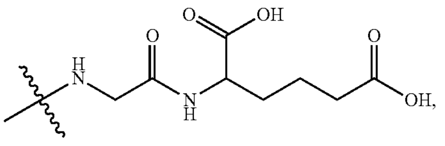

-continued

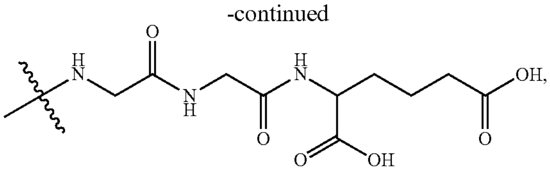

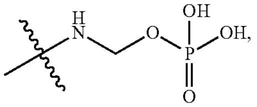

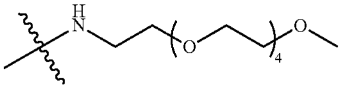

or

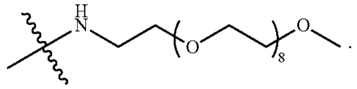

In some embodiments of the third aspect of the present invention, disclosed are the linker-drug compounds or pharmaceutically acceptable salts or solvates thereof, characterized in that: the Ac is selected without limitation from a glycine, phosphoric acid, (D/L) glutamic acid, or polyethylene glycol hydrophilic structure.

In some embodiments of the third aspect of the present invention, disclosed are the linker-drug compounds or pharmaceutically acceptable salts or solvates thereof, characterized in that said linker-drug compounds are selected without limitation from the following structures or isomers thereof,

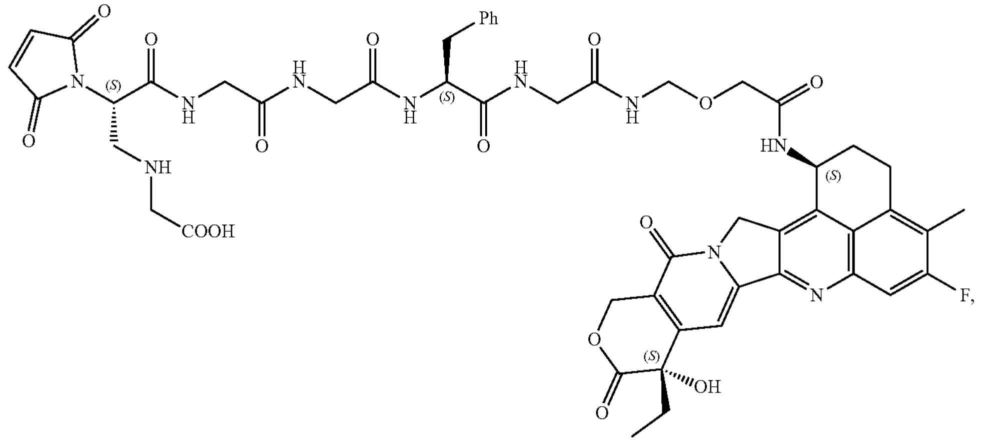

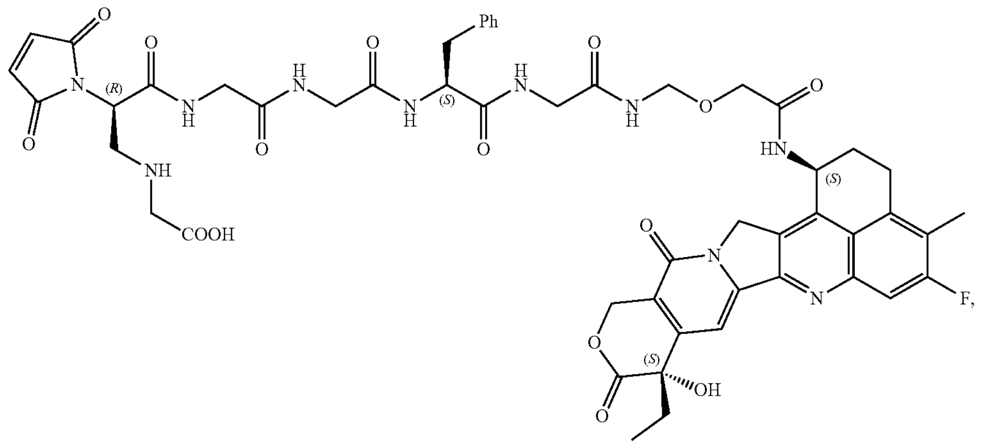

-continued
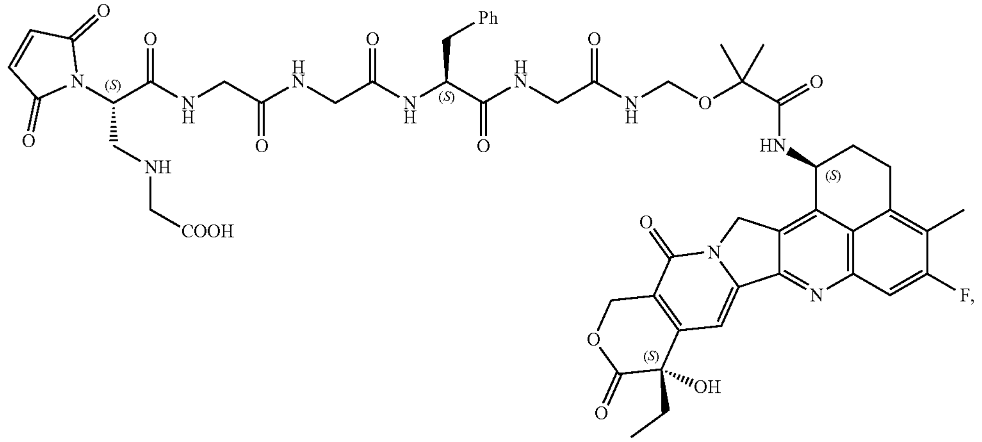
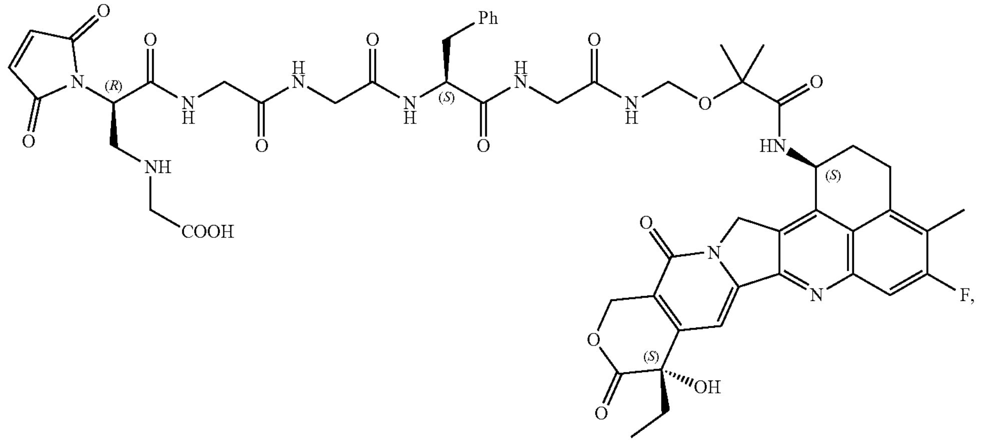
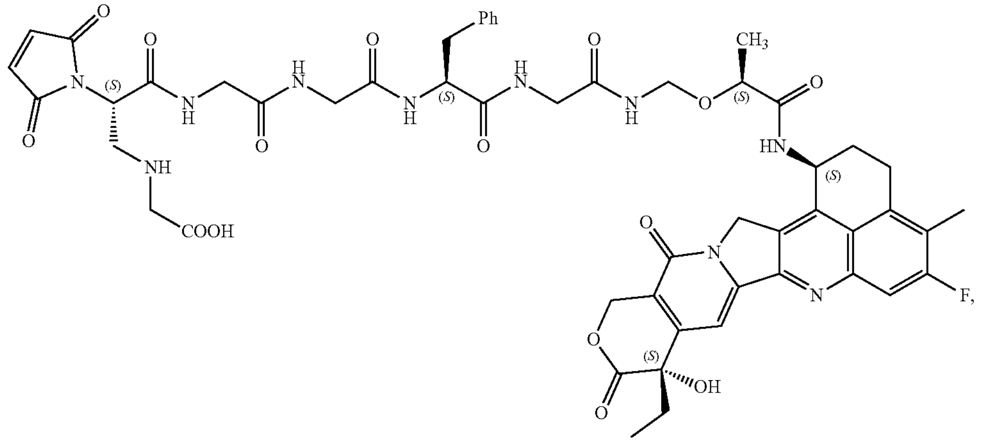

-continued
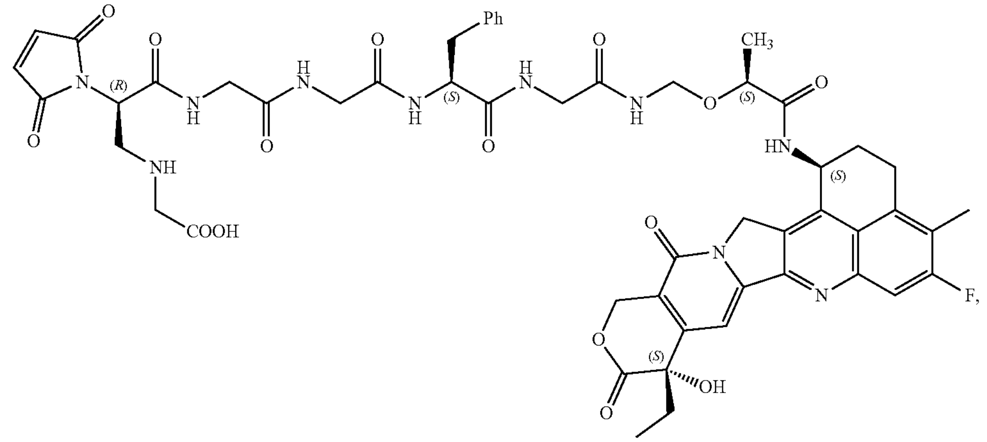
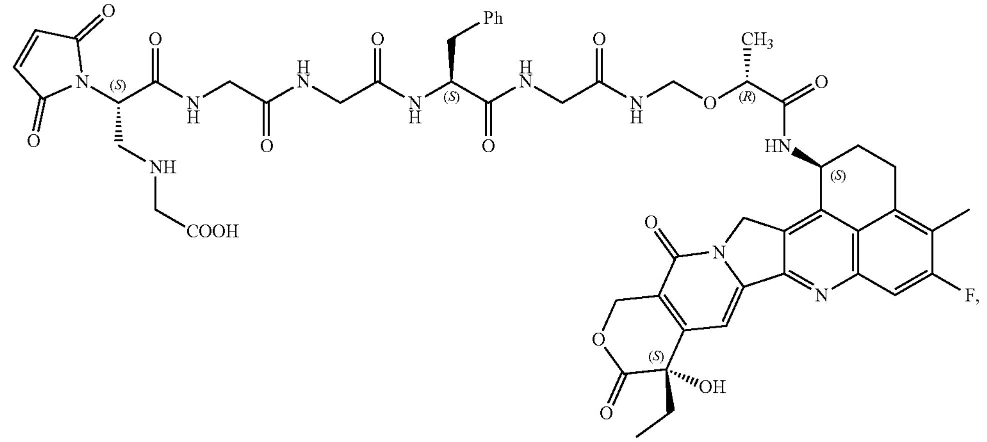
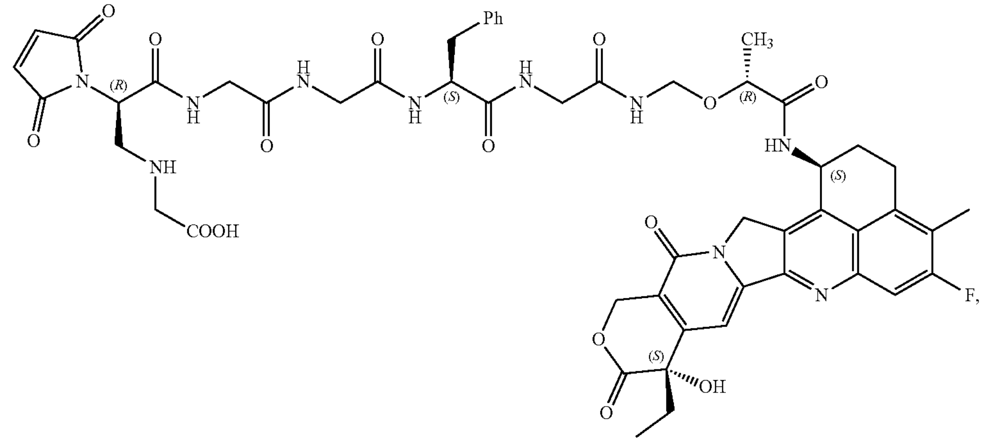

-continued
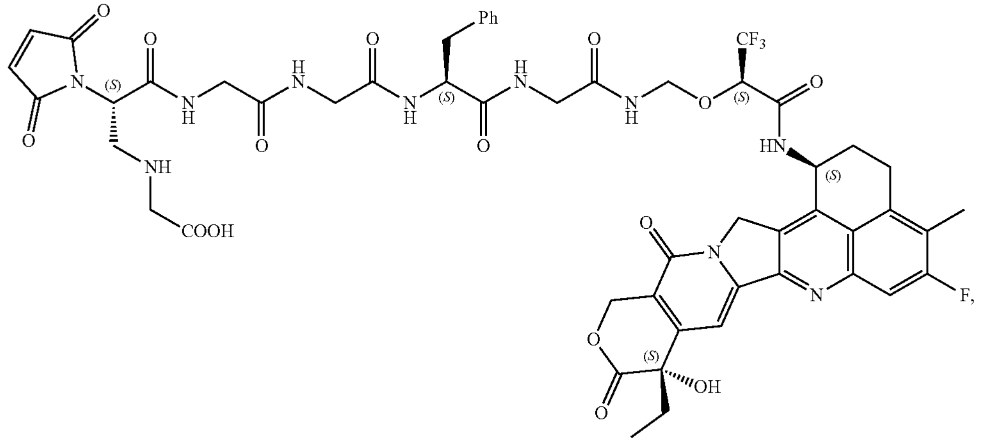
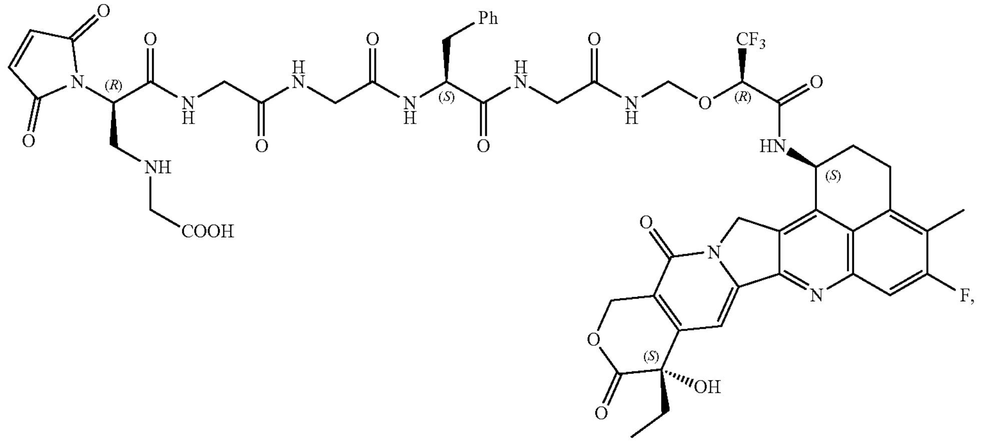
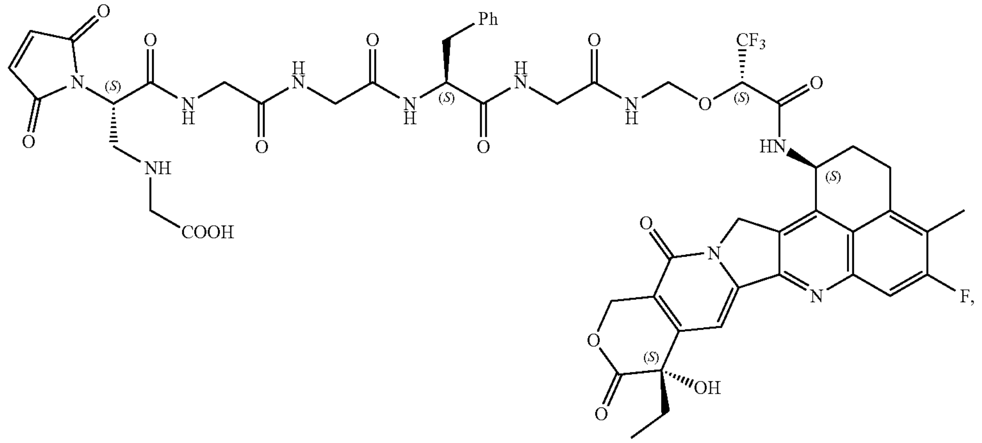

-continued
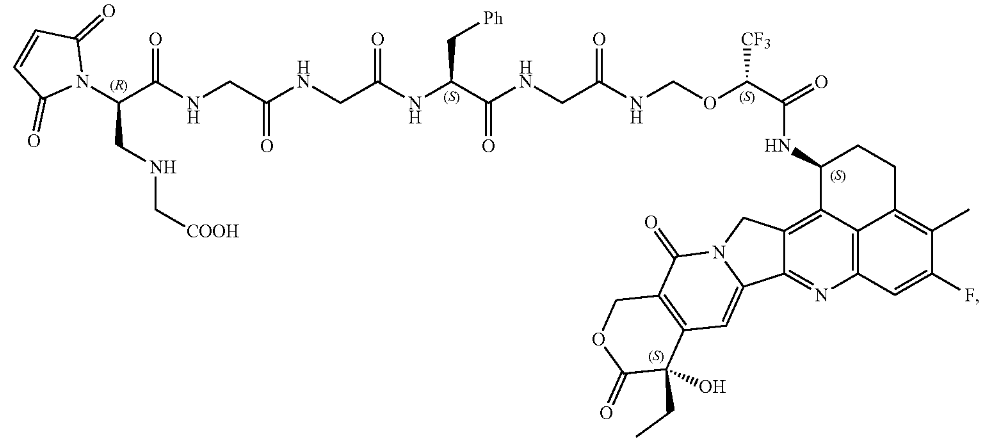
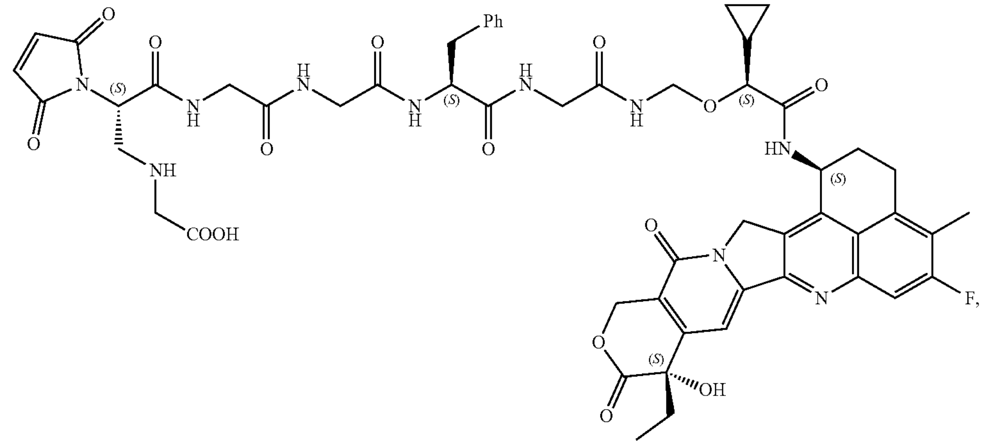
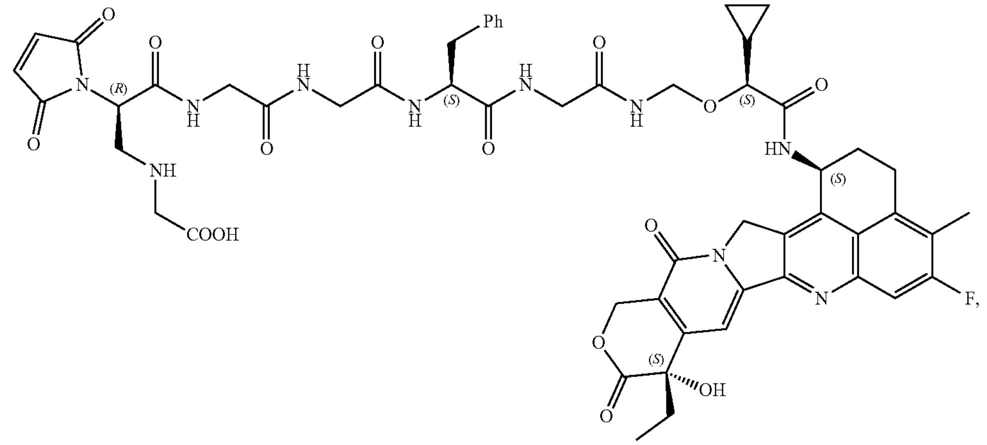

-continued
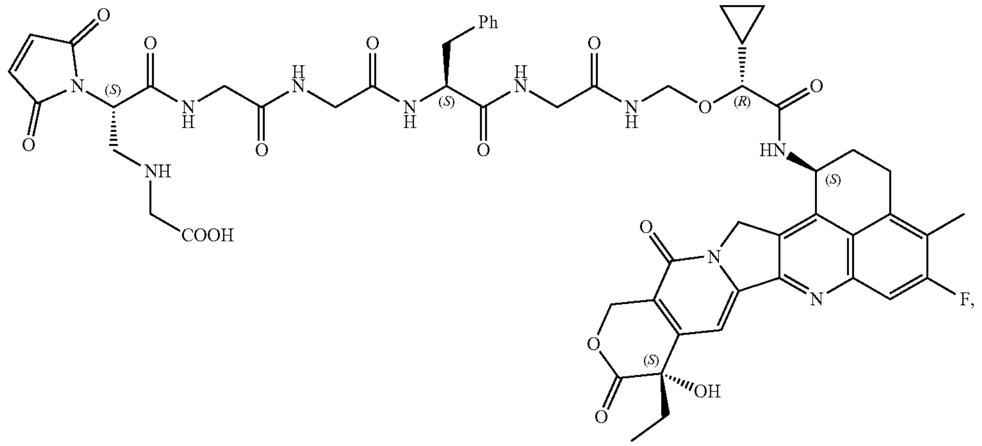
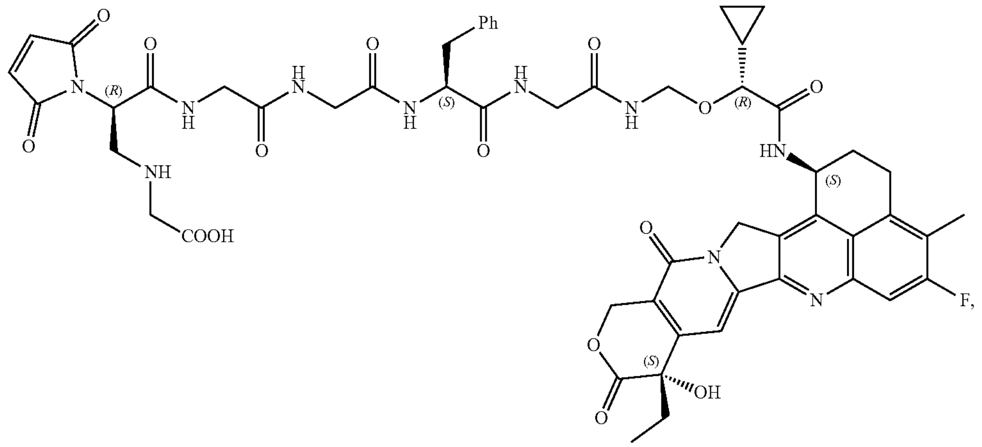
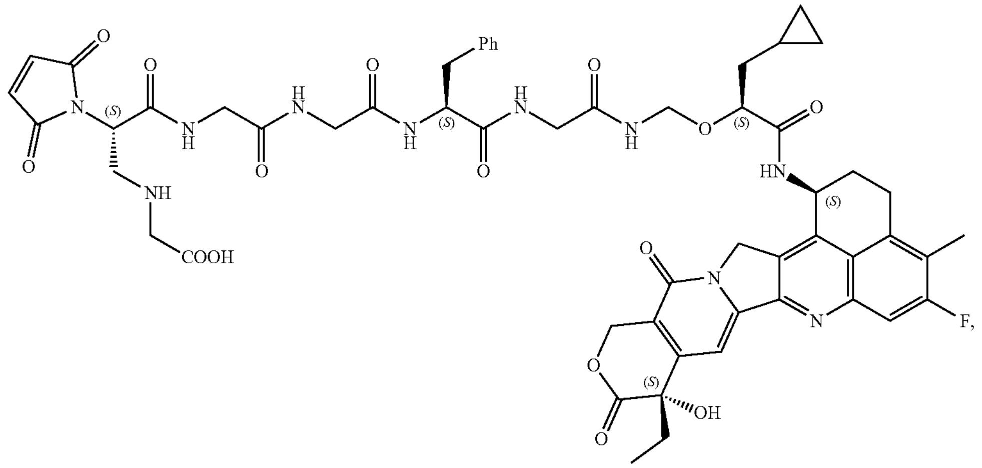

-continued
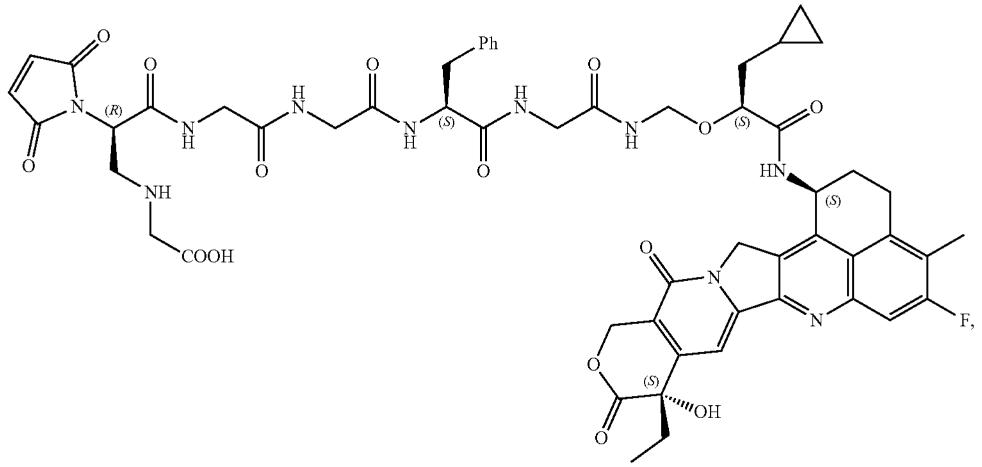
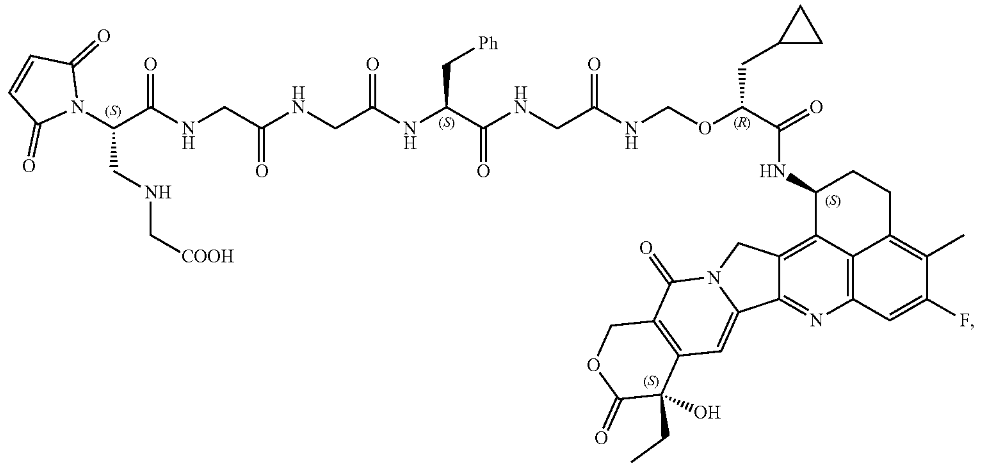
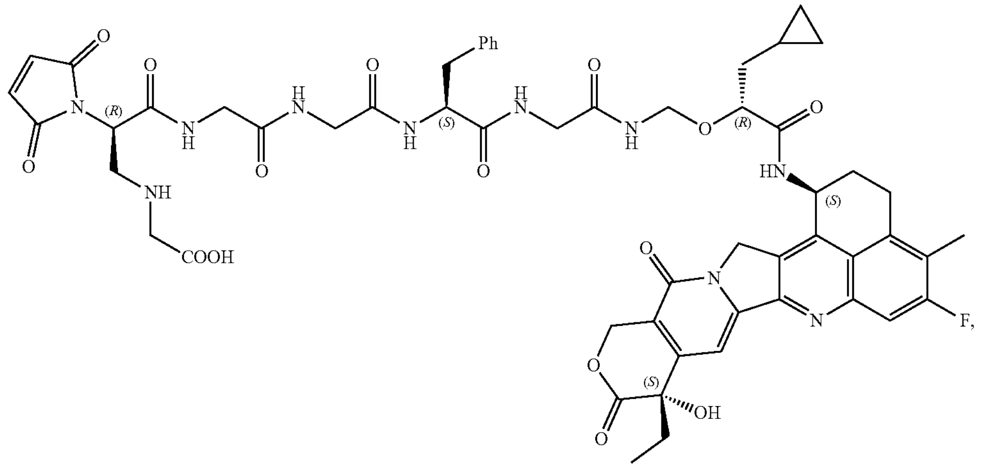

-continued
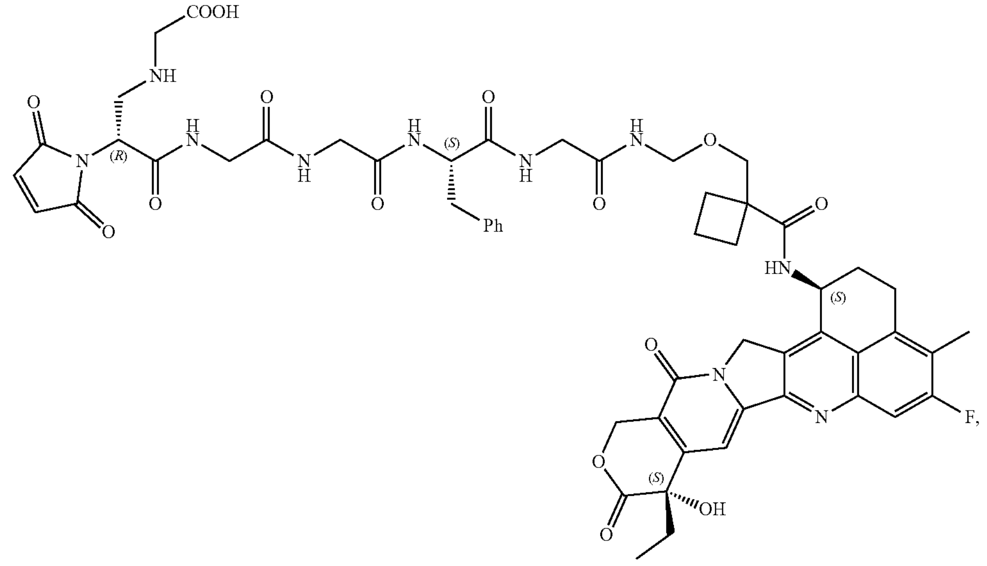
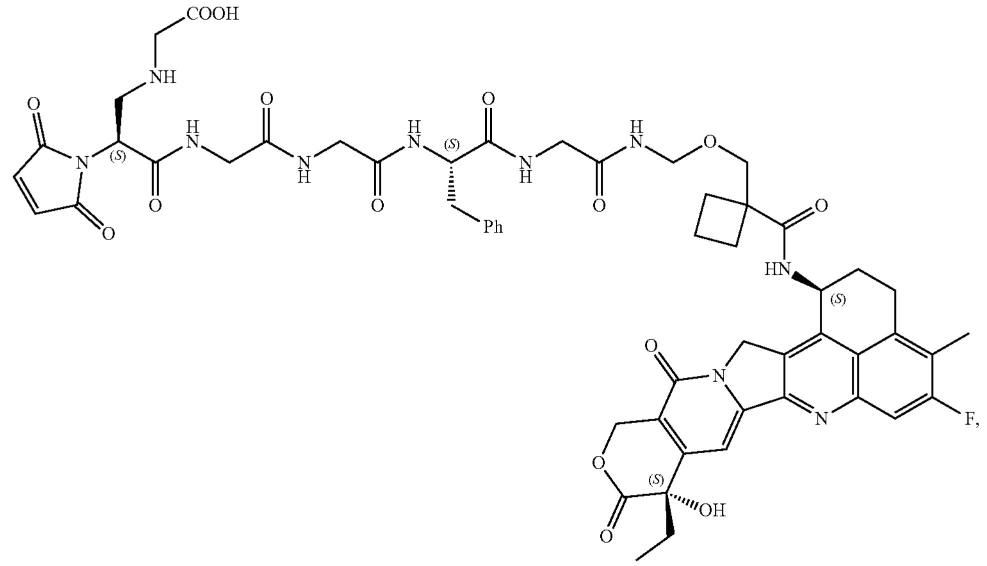
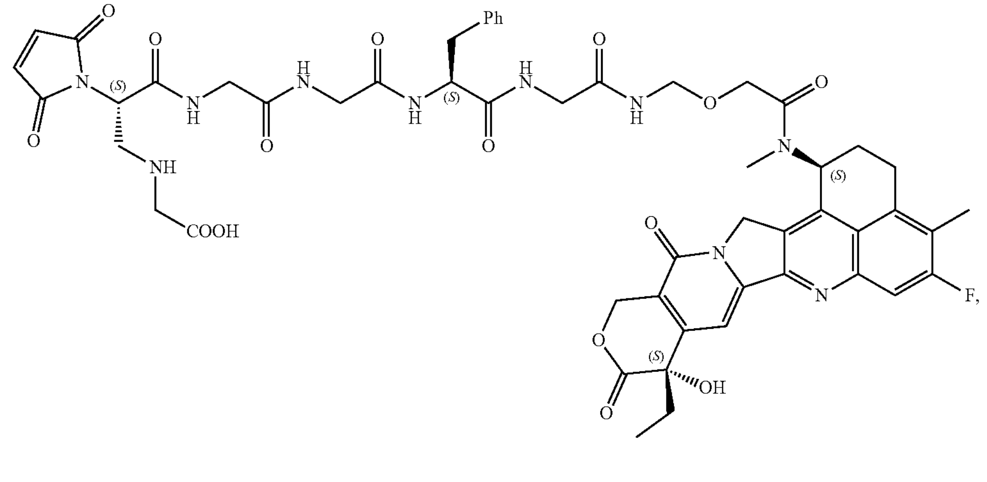

-continued
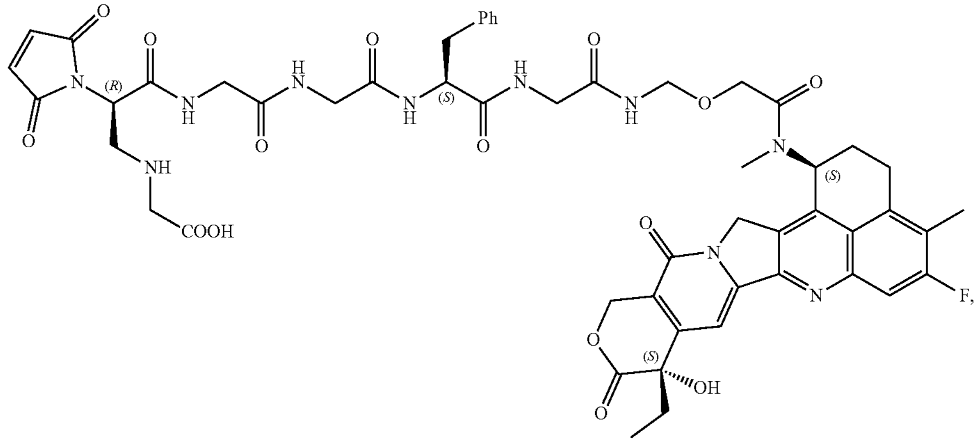
,
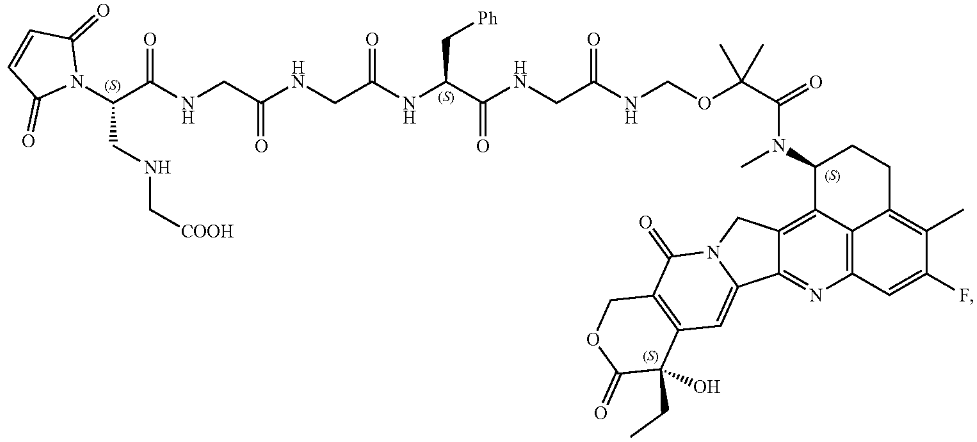
,
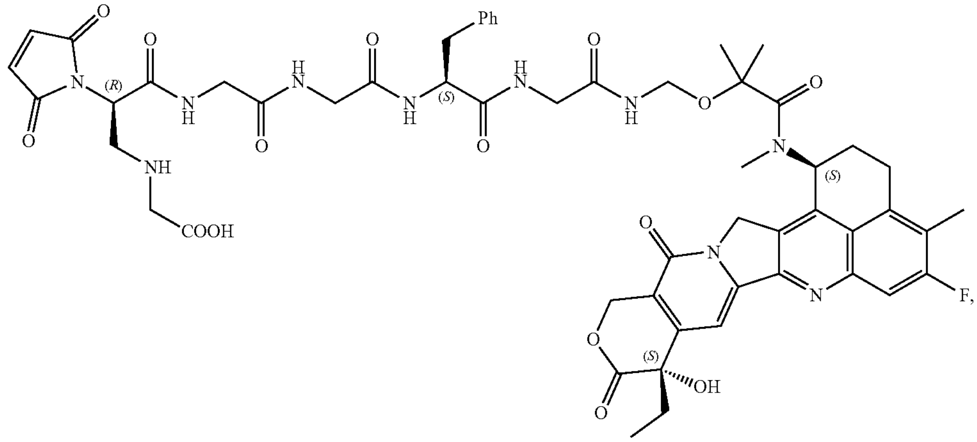
,

-continued
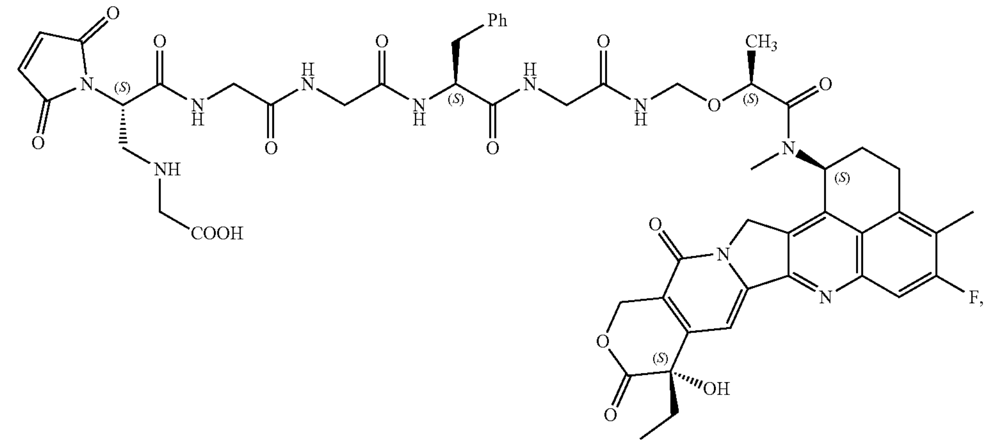
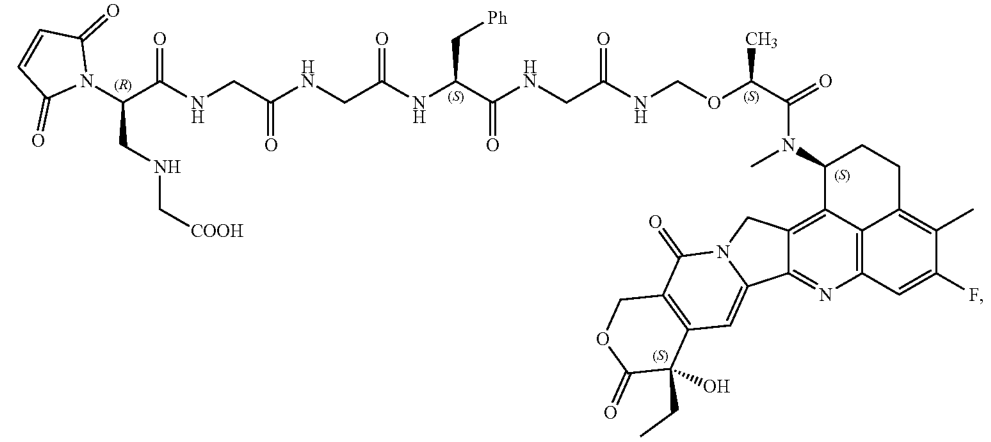
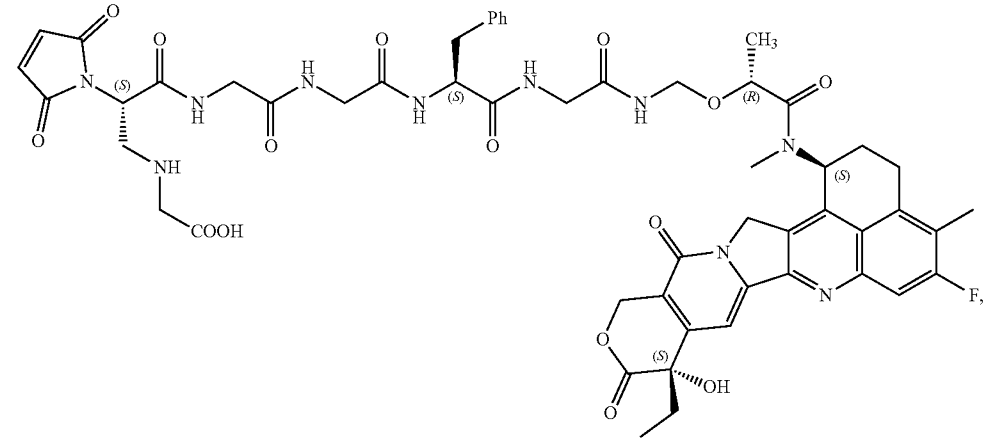

-continued
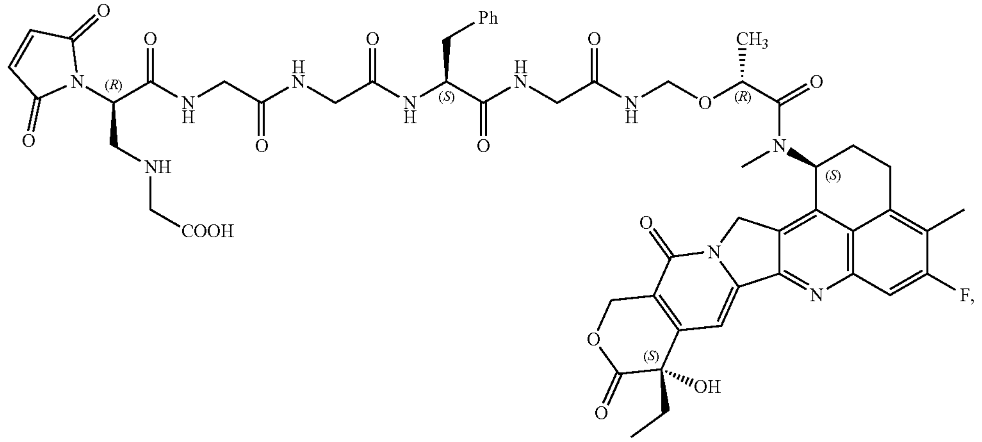
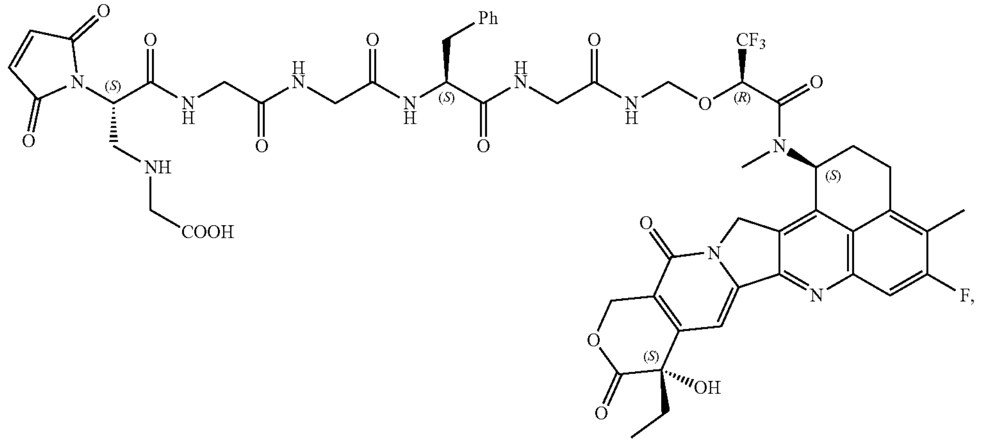
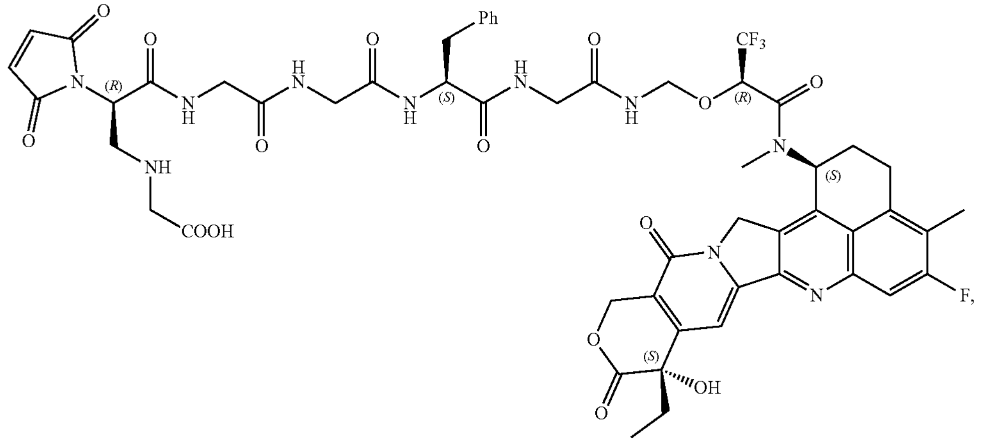

-continued
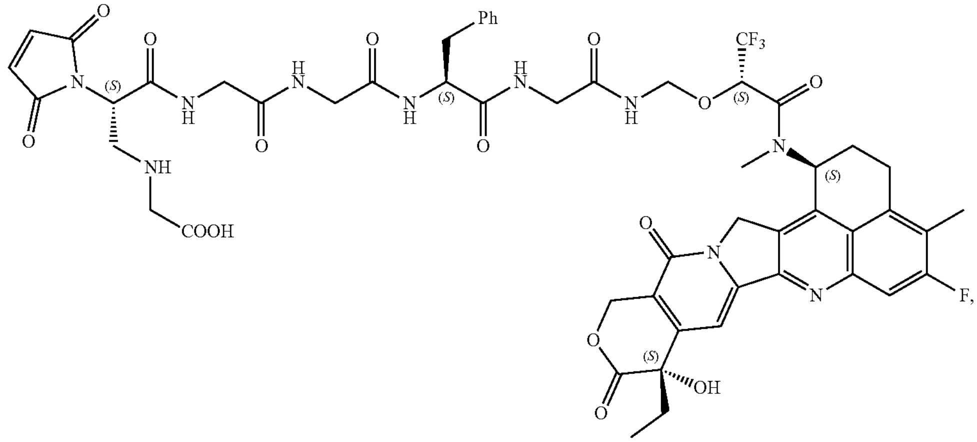
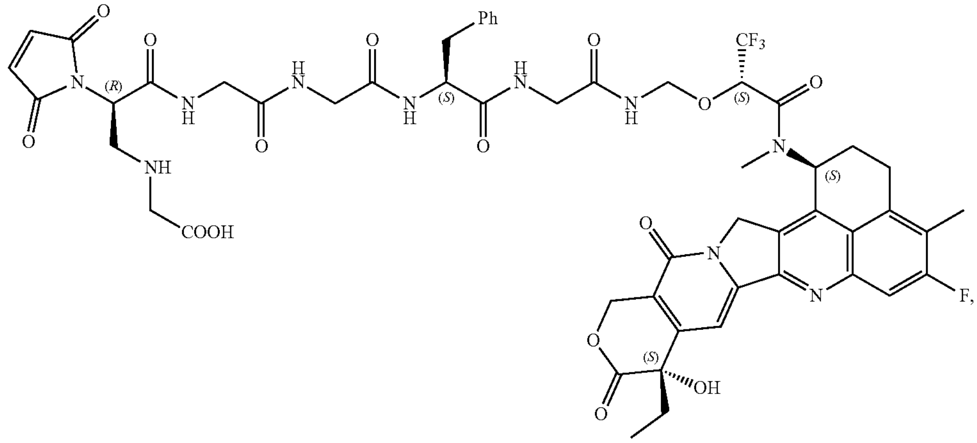
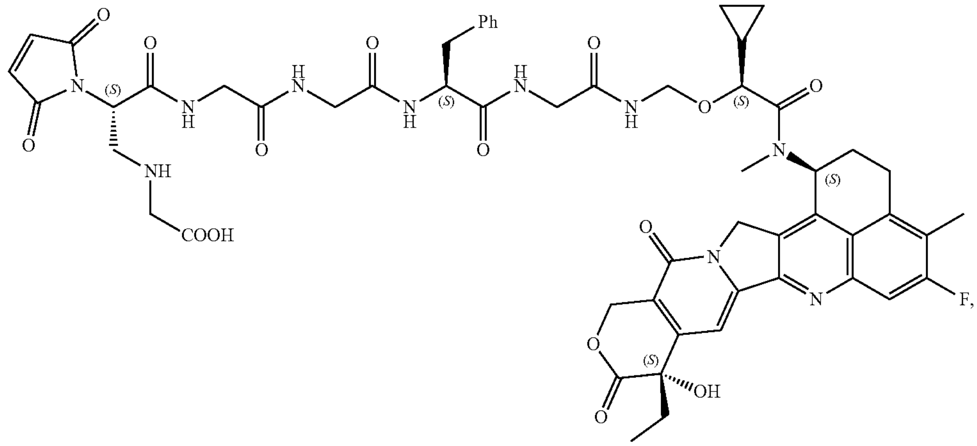

-continued
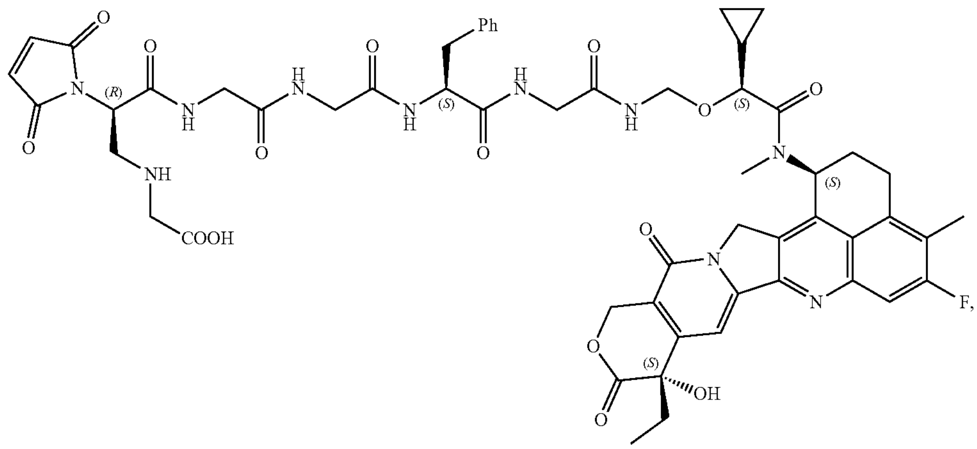
F,
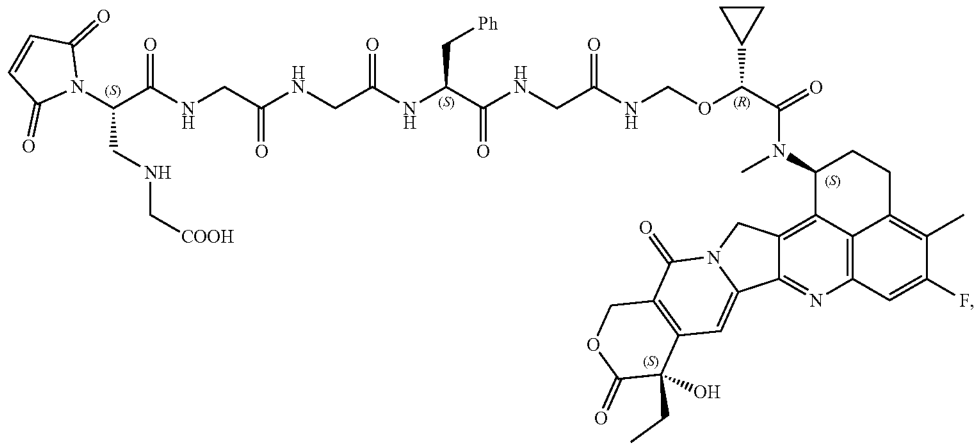
F,
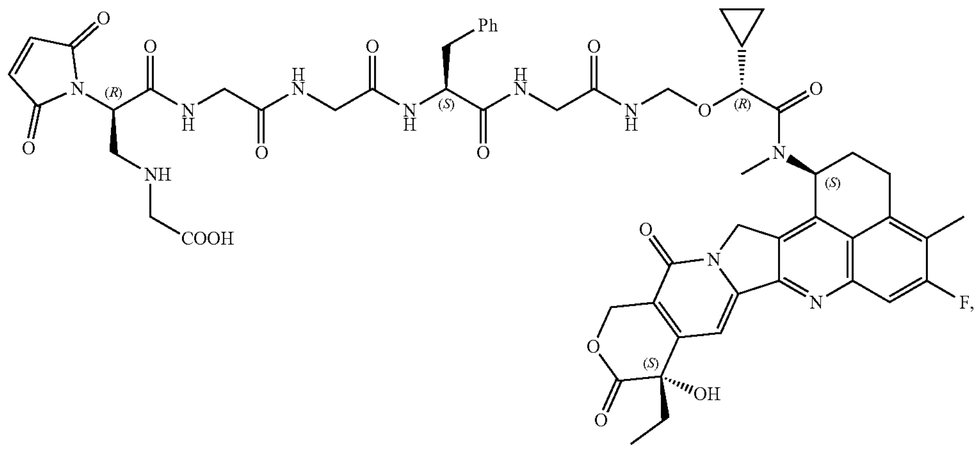
F,

-continued
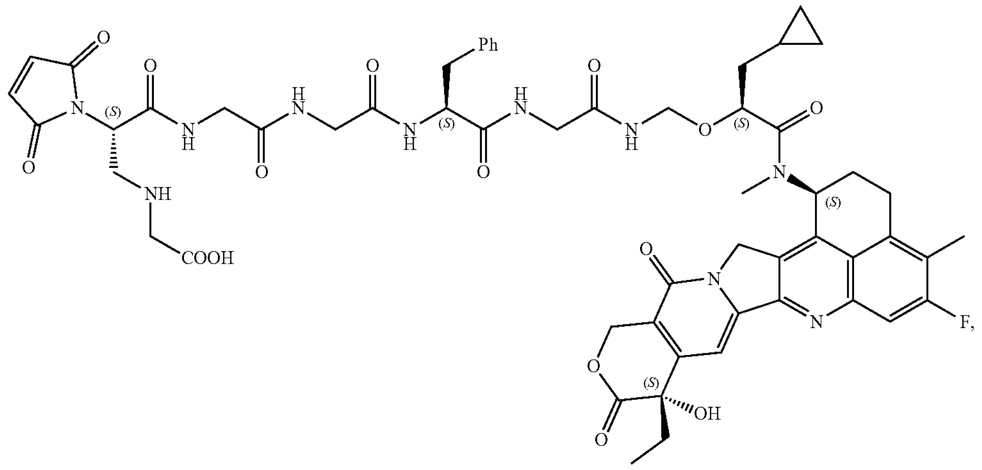
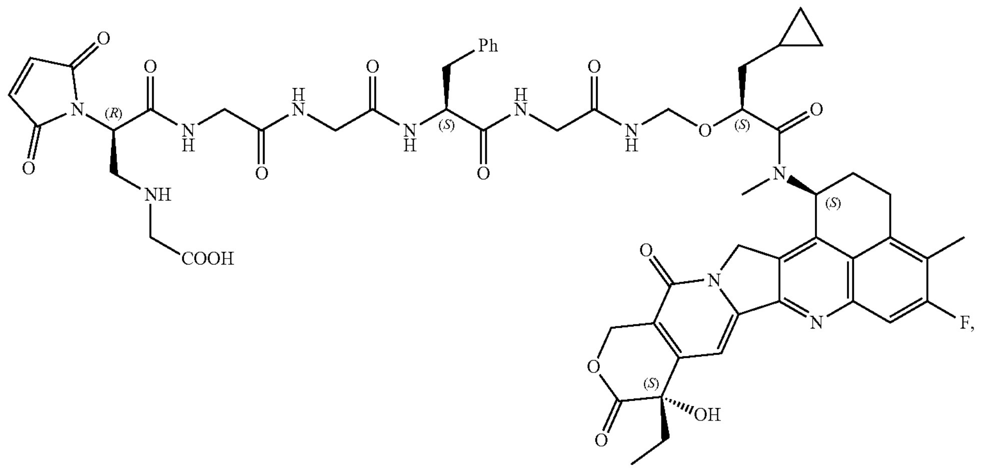
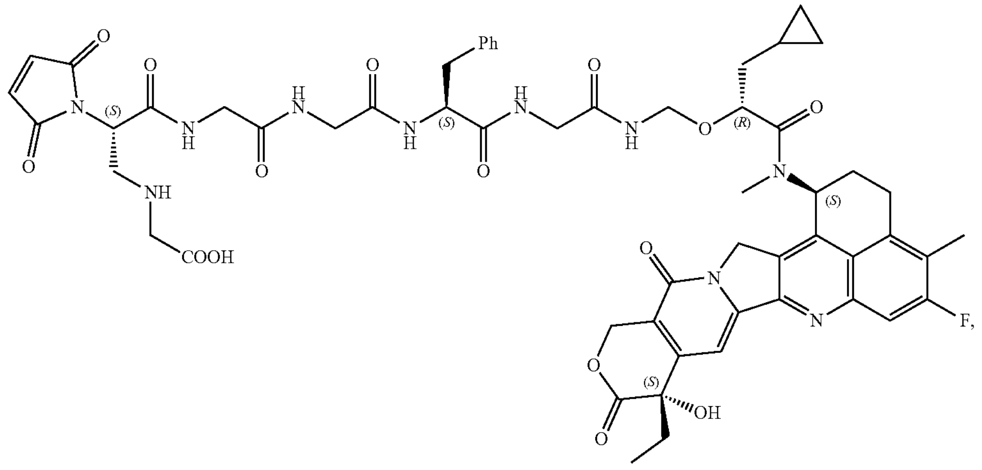

-continued
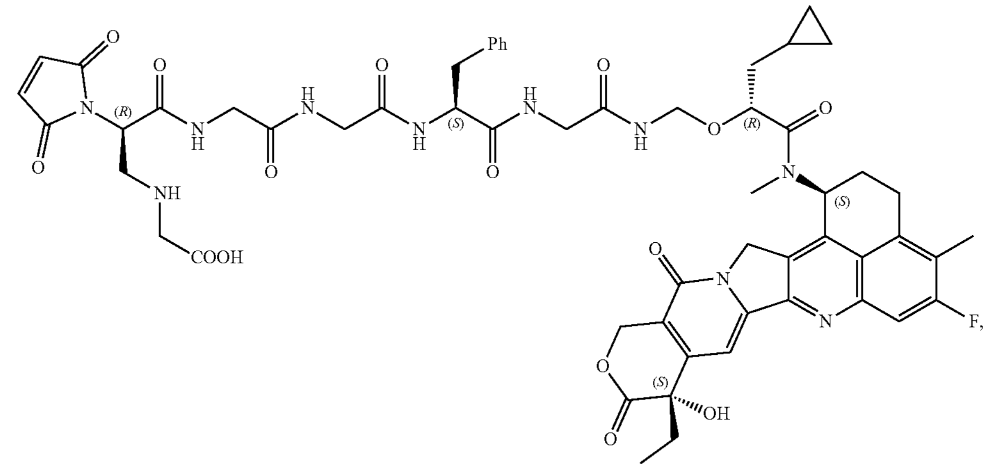
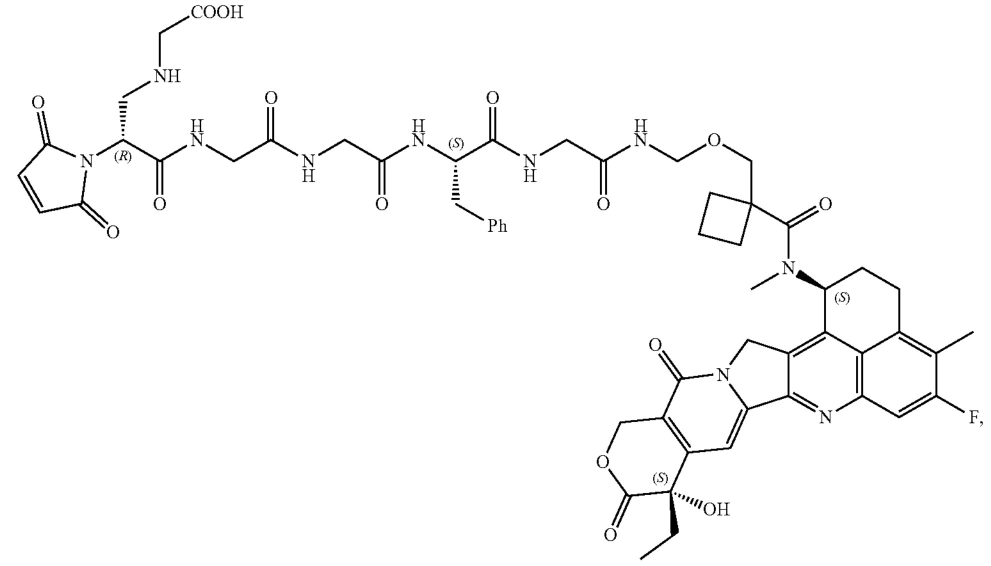
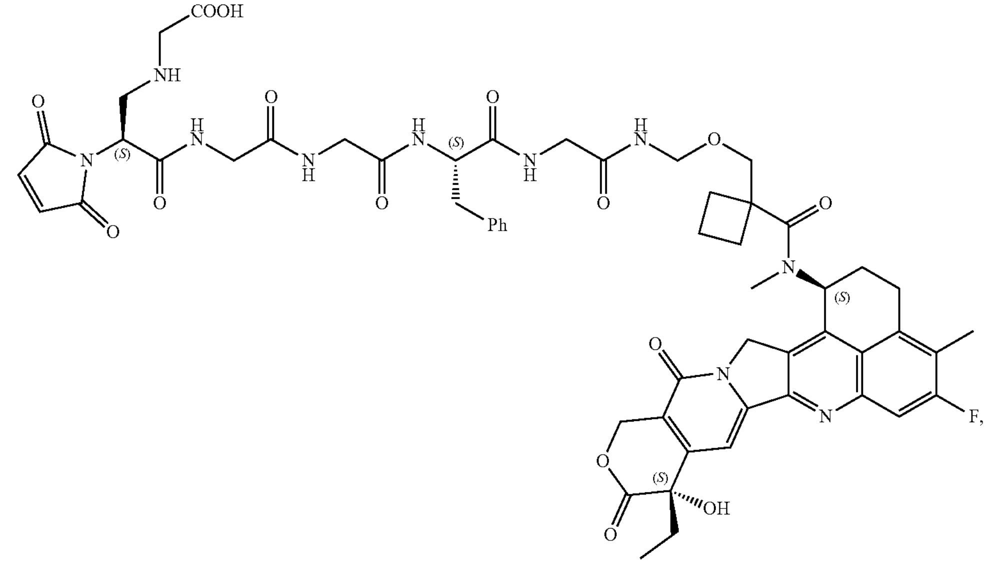

-continued
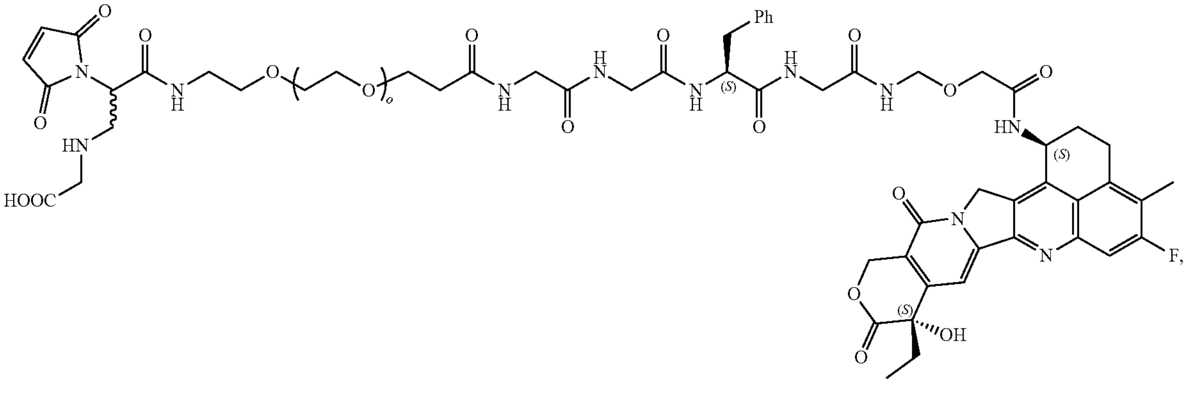
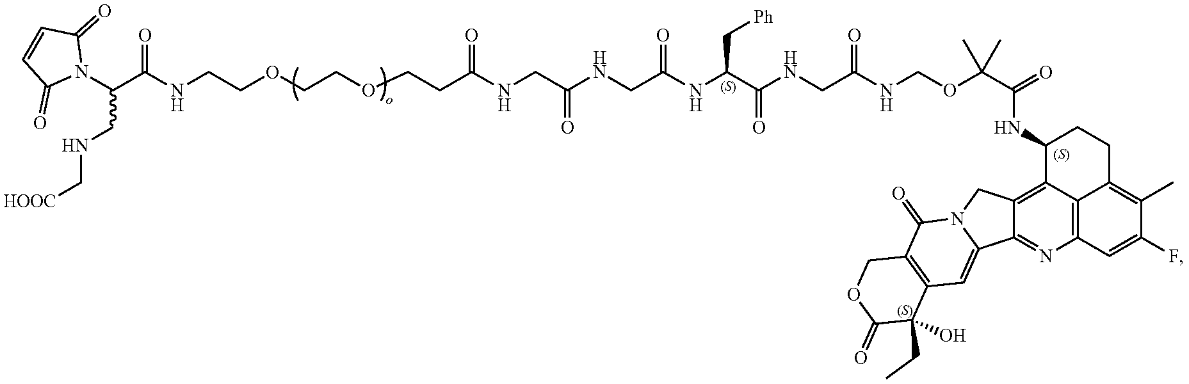
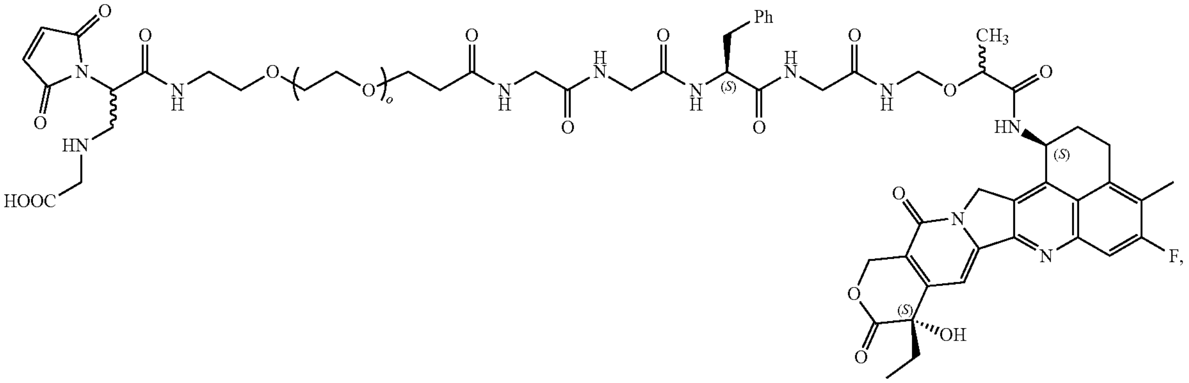
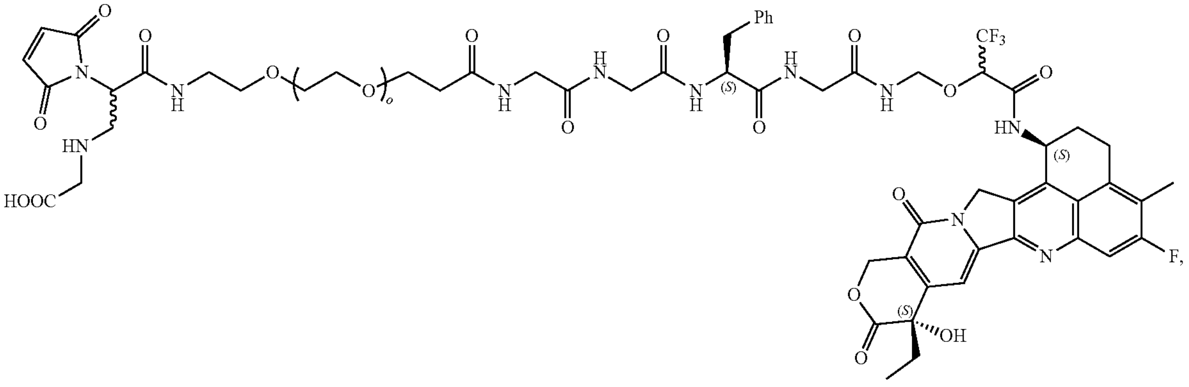

-continued

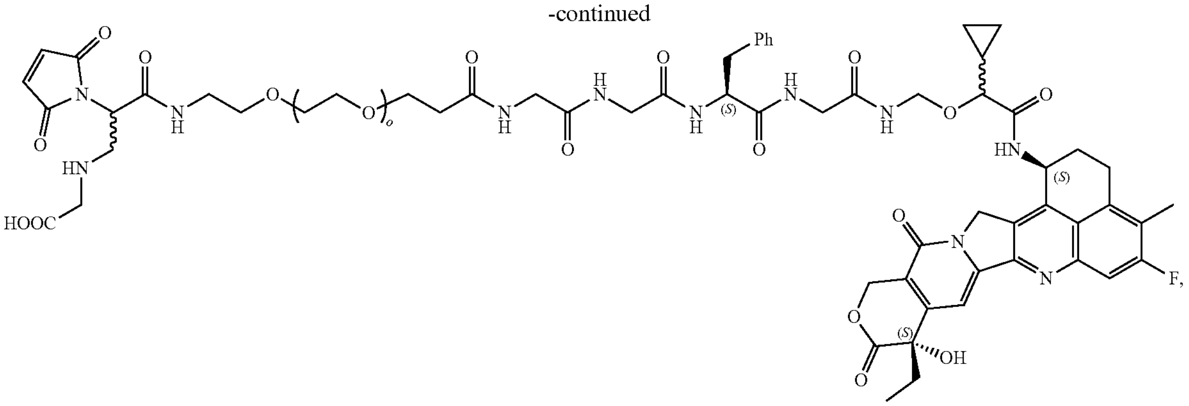

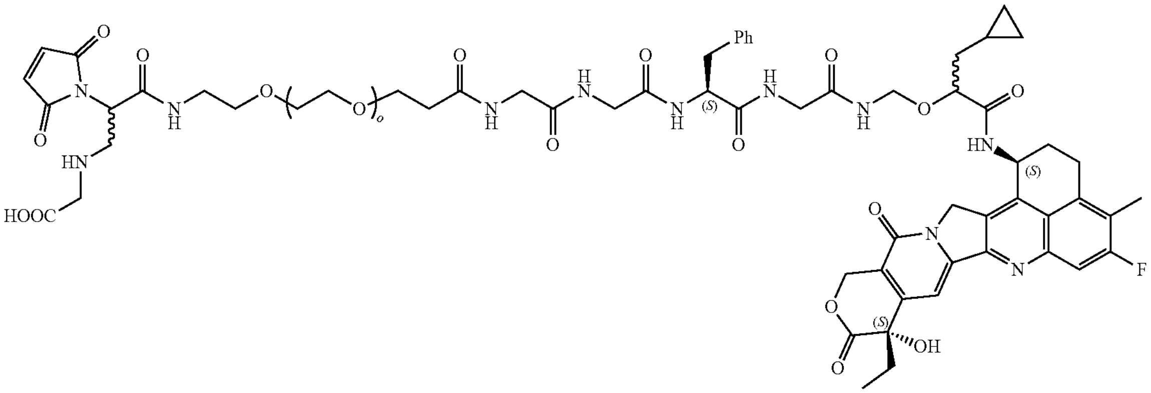

or

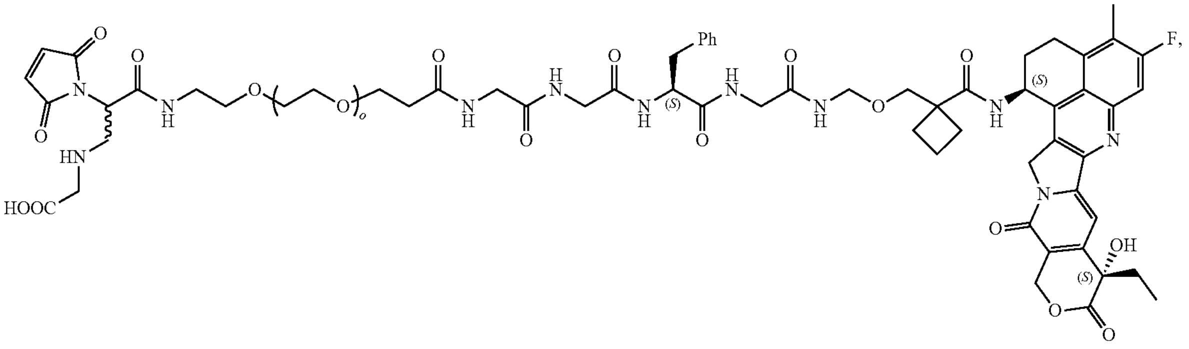

where: o is selected from the integers 1-10 (e.g., 1, 2, 3, 4, 5, 6, 7, 8, 9, or 10).

Said linker-drug compounds or pharmaceutically acceptable salts or solvates thereof disclosed in the third aspect of the present invention can be used as intermediates for coupling with the ligand Ab to form ligand-camptothecin derivative conjugates of formula I or formula II described in the first aspect and the second aspect.

A fourth aspect of the present invention discloses a method of preparing a ligand-camptothecin derivative conjugate or a pharmaceutically acceptable salt or solvate thereof as shown in general formula I or general formula II as described in the first and second aspects, characterized in that the method comprises the following steps,

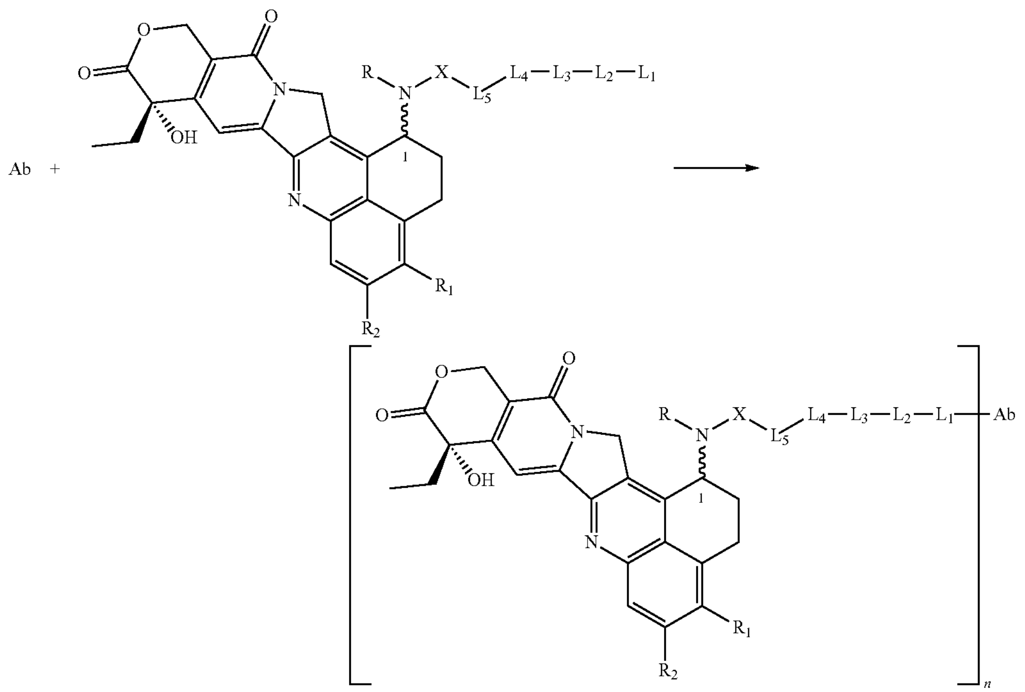
I
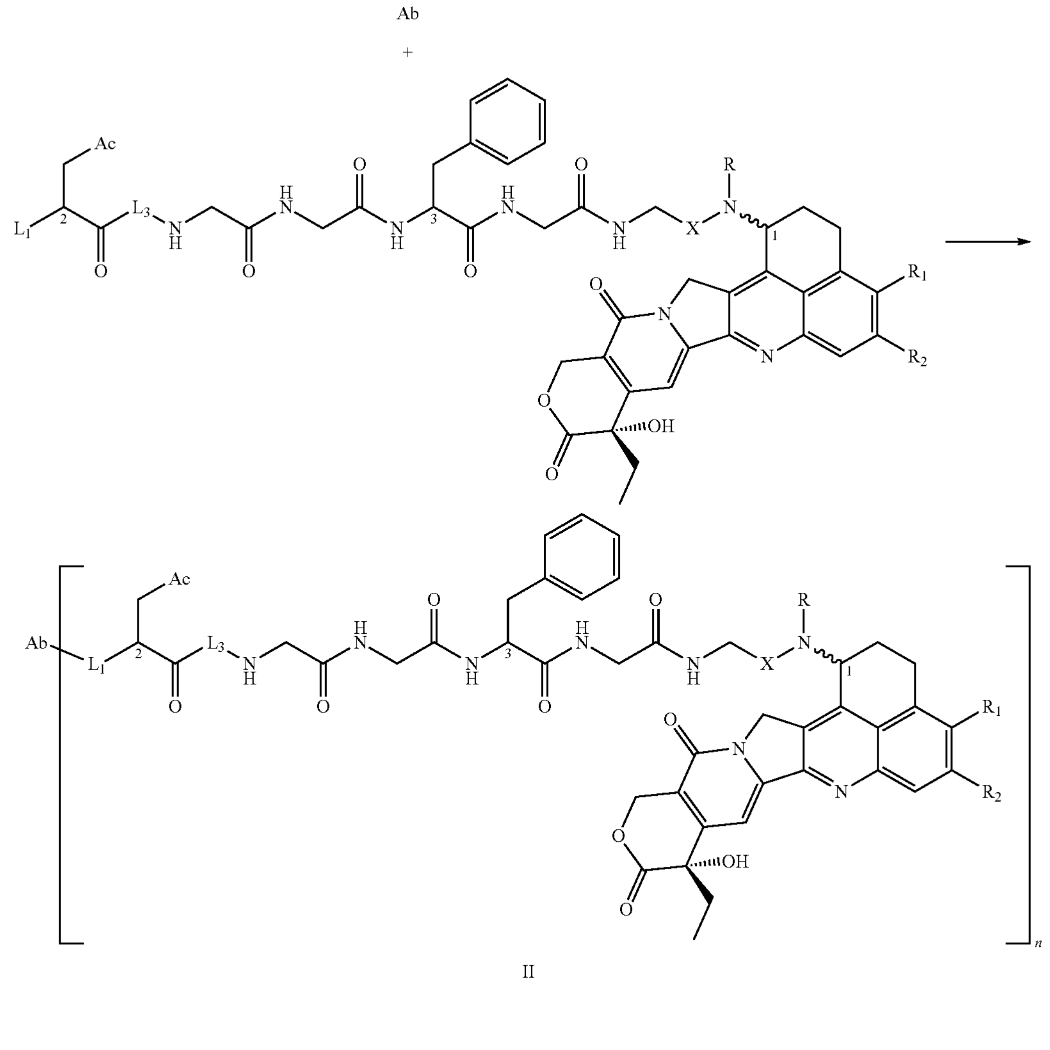
II a ligand-camptothecin derivative conjugate as shown in general formula I or general formula II is obtained by a coupling reaction of a reduced antibody or antigen-binding fragment thereof with a linker-drug compound;

the chiral carbon atom at position 1, position 2, or position 3 has absolute chirality in the R configuration or S configuration;

Ab, $L_1$, $L_2$, $L_3$, $L_4$, $L_5$, X, R, $R_1$, $R_2$ and n are as previously described.

The present application also relates to the use of the linker-drug compounds or pharmaceutically acceptable salts or solvates thereof, disclosed and described in the third aspect, as intermediates in the preparation of ligand-camptothecin derivative conjugates or pharmaceutically acceptable salts or solvates thereof. In certain embodiments, said ligand-camptothecin derivative conjugates or pharmaceutically acceptable salts or solvates thereof are the ligand-camptothecin derivative conjugates or pharmaceutically acceptable salts or solvates thereof disclosed in the first, second and fourth aspects of the present invention. In certain embodiments, said preparation is carried out according to the method of preparation disclosed in the fourth aspect.

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures, or succinimide open-ring structures thereof, or isomers thereof,

ADC-1

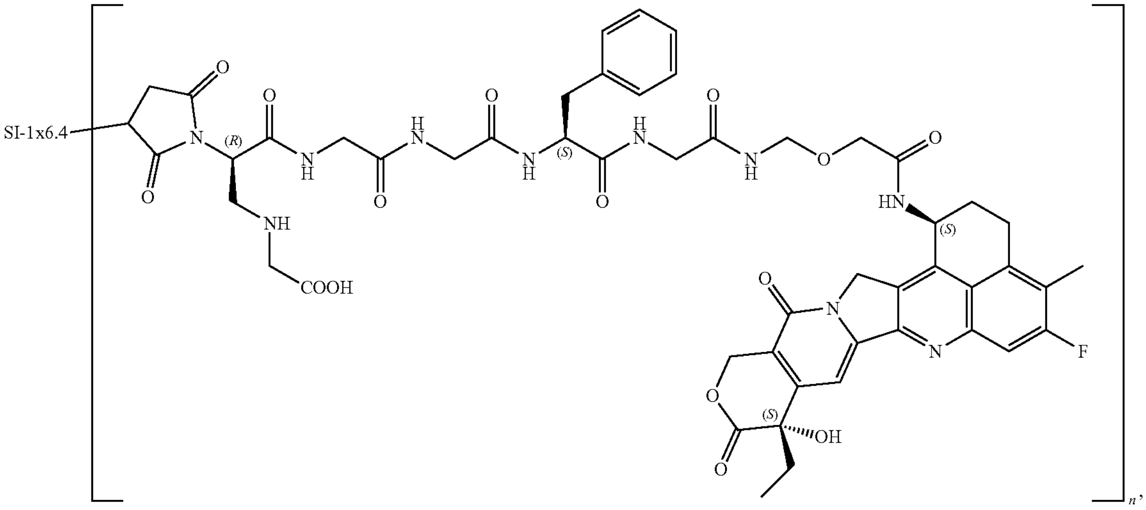

ADC-2

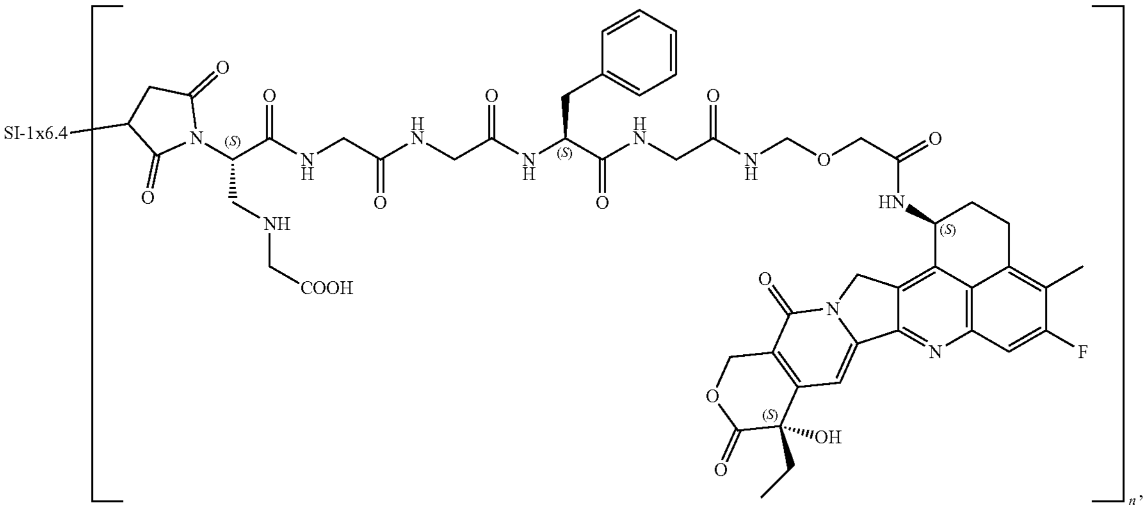

-continued
ADC-3
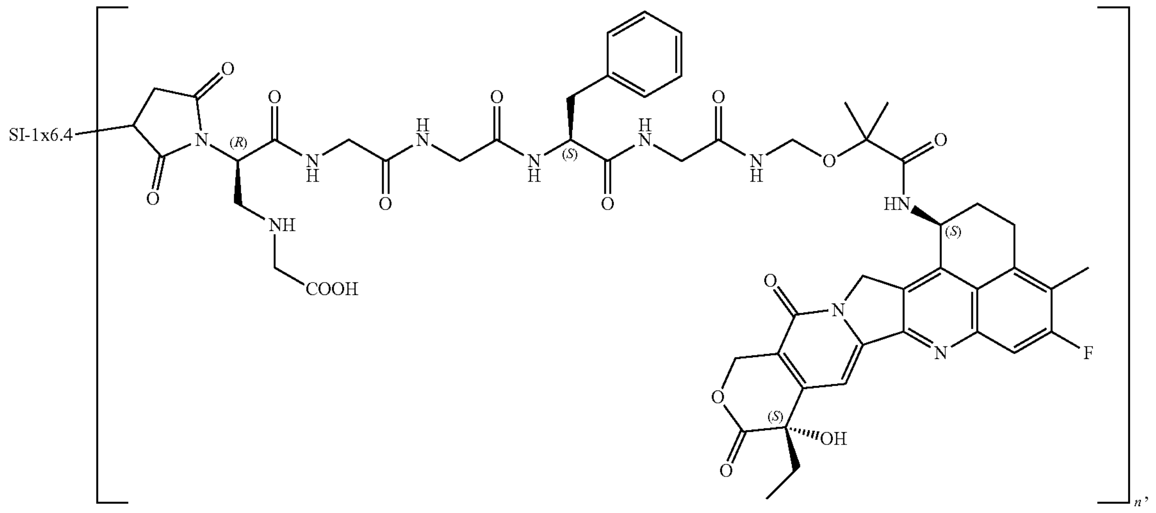
ADC-4
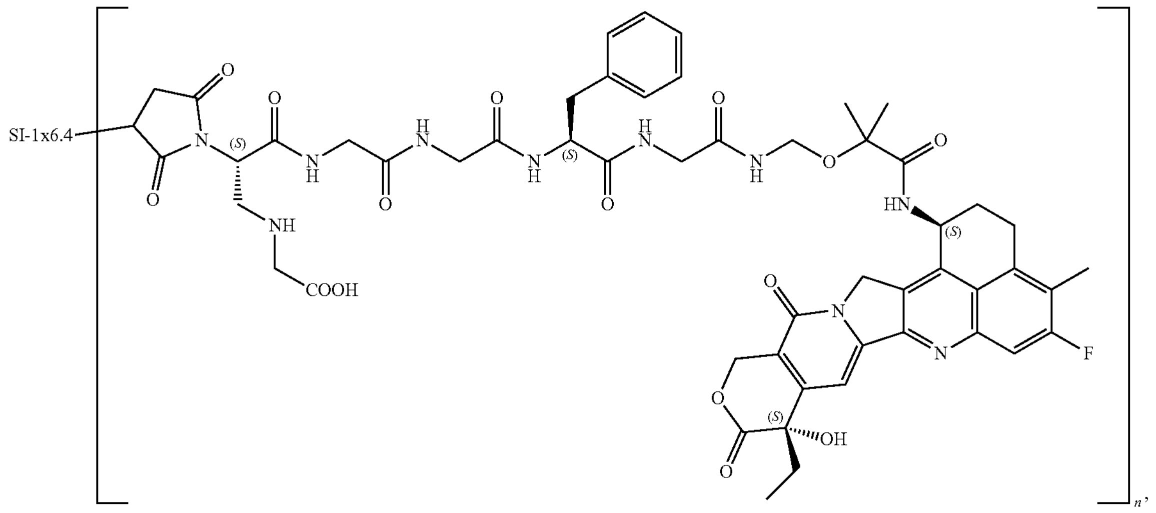
ADC-5
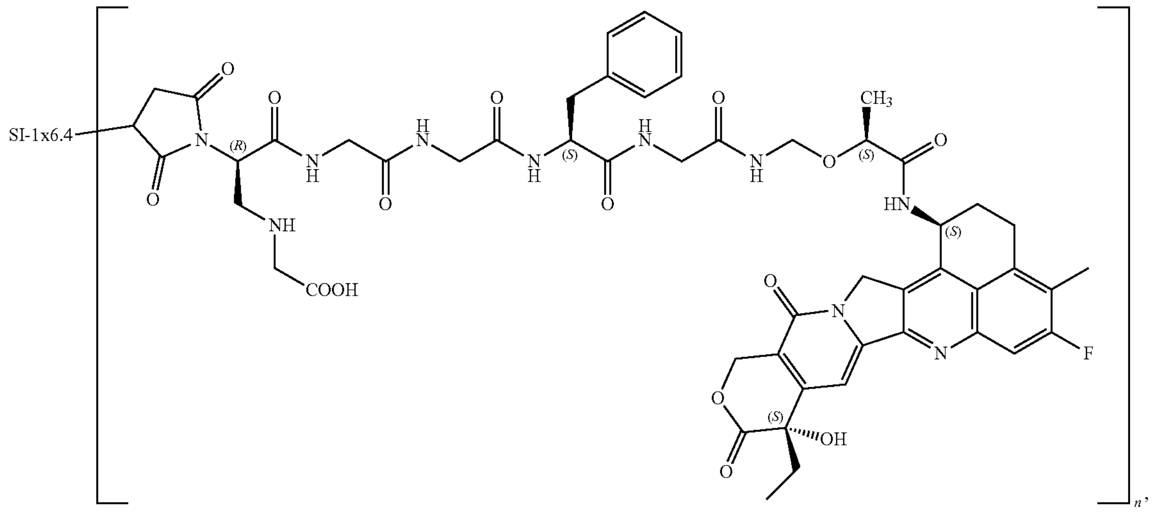

-continued
ADC-5a
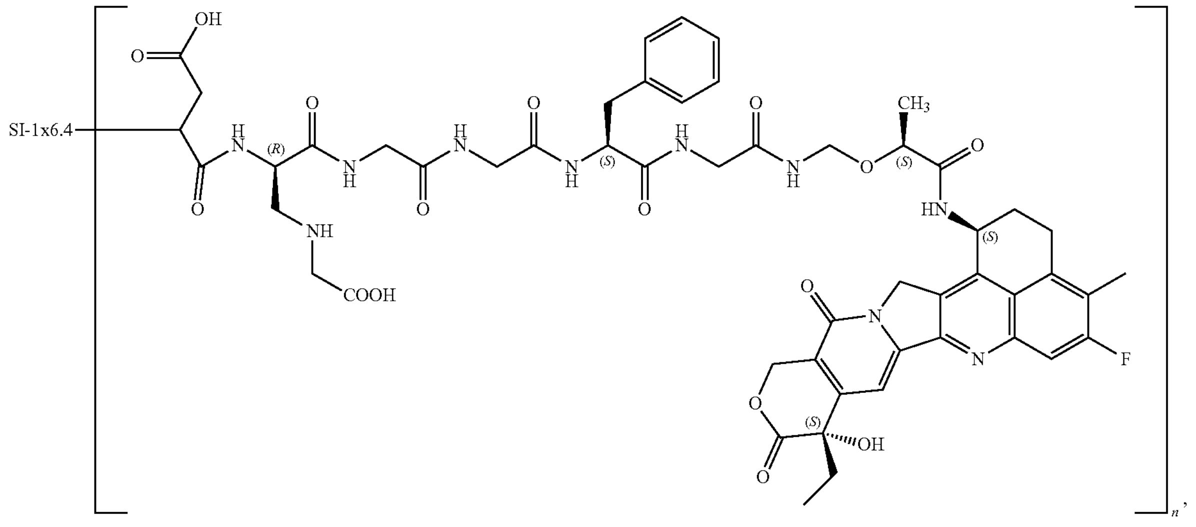
ADC-5b
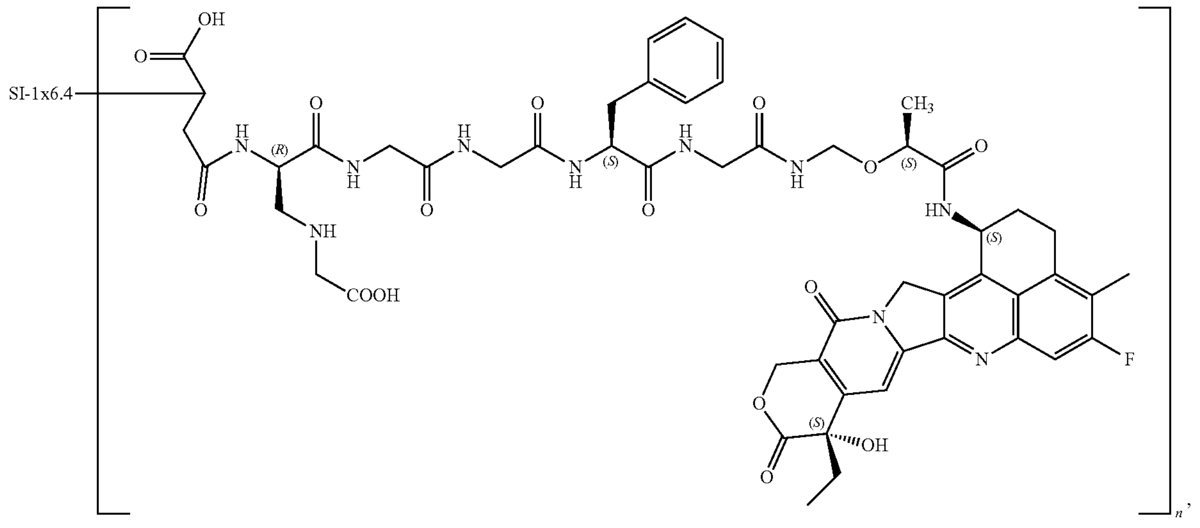
ADC-6
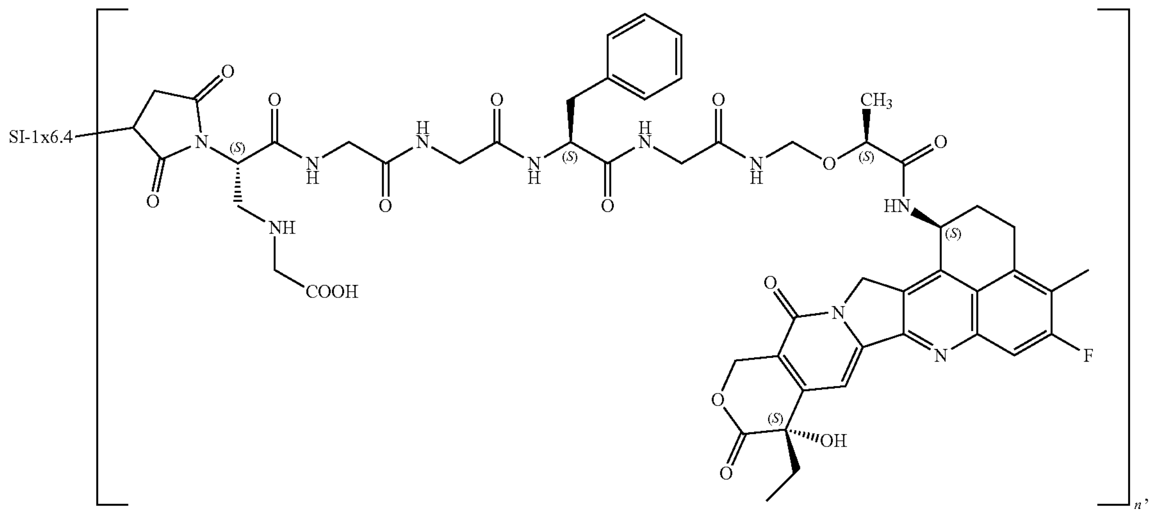

-continued
ADC-6a
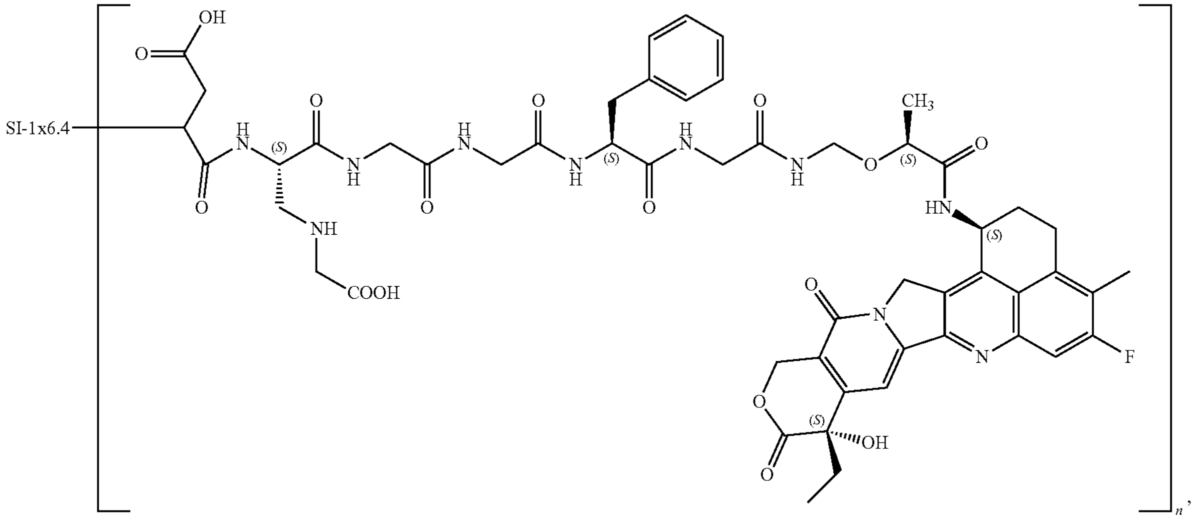
ADC-6b
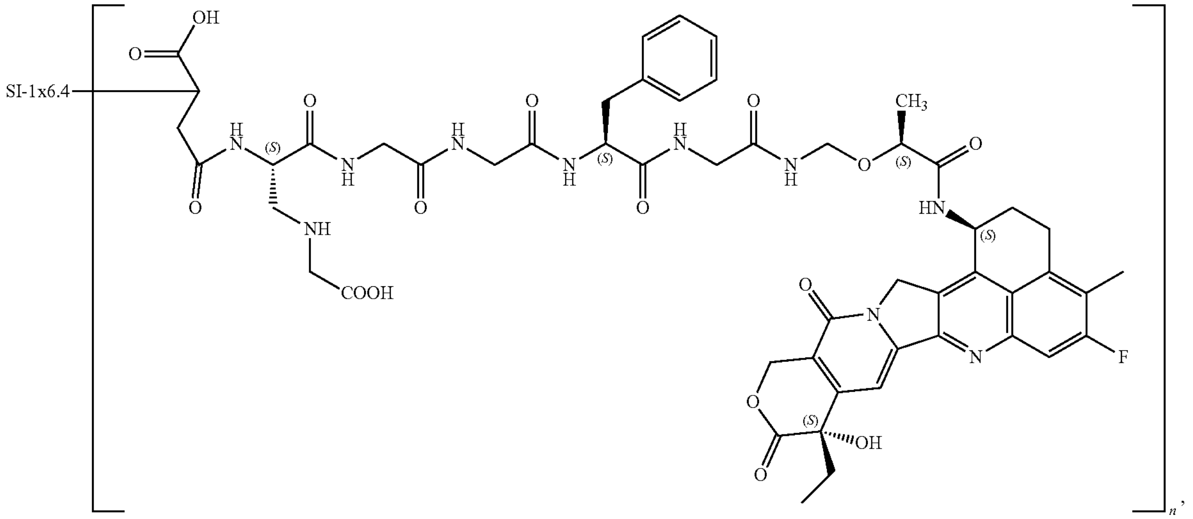
ADC-7
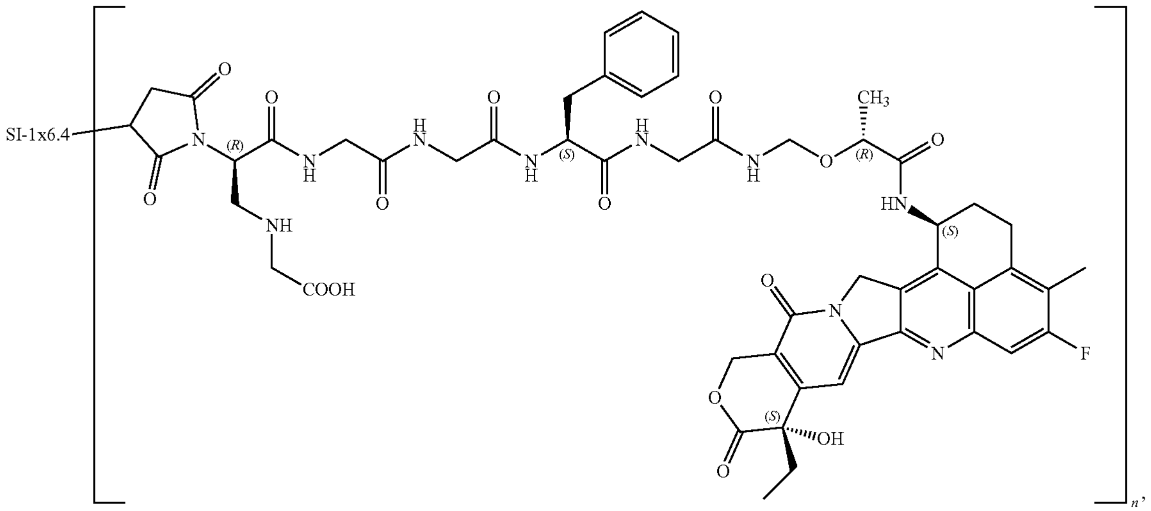

-continued
ADC-7a
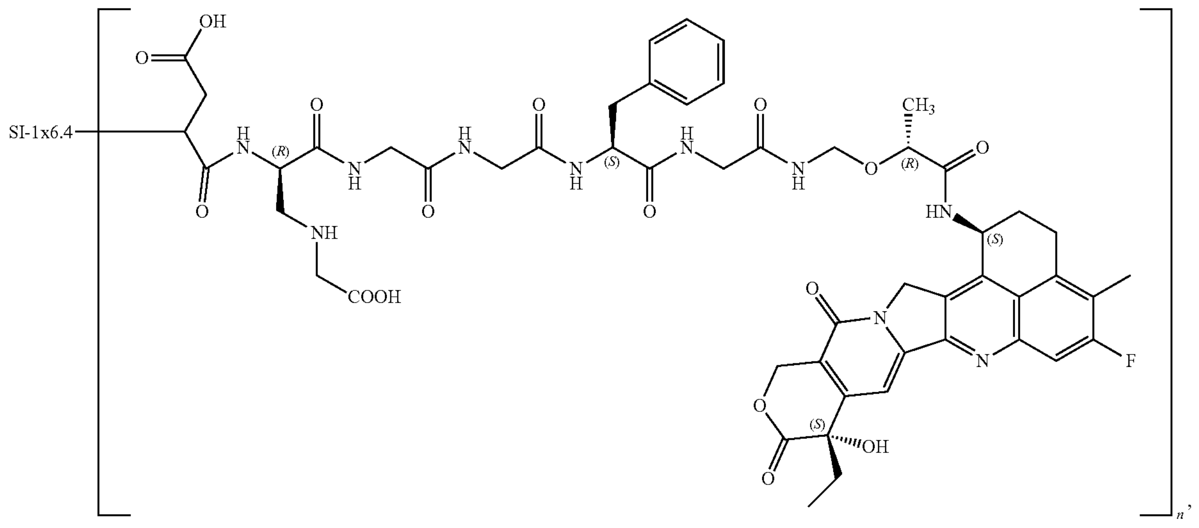
ADC-7b
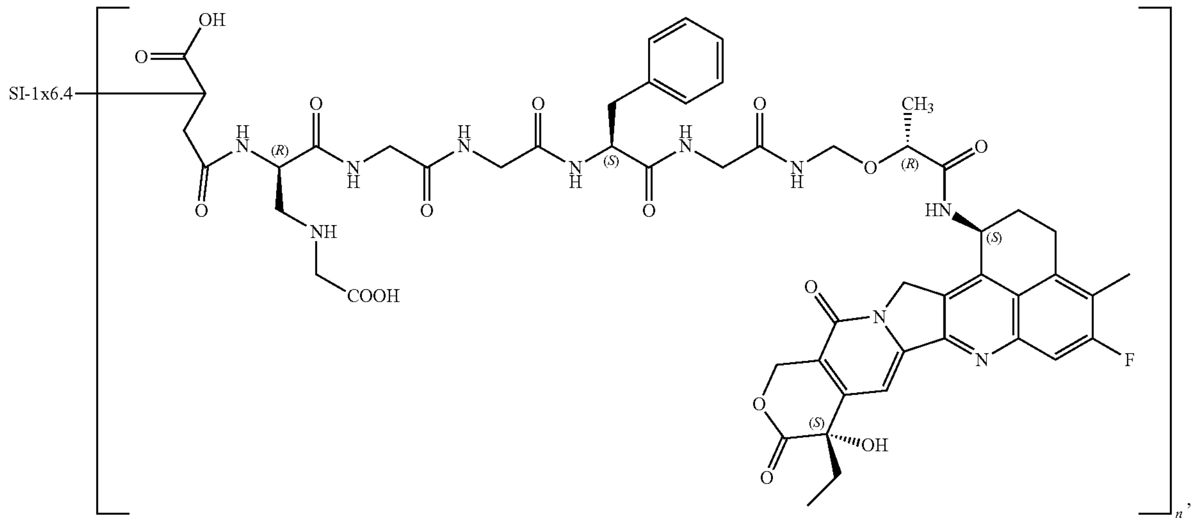
ADC-8
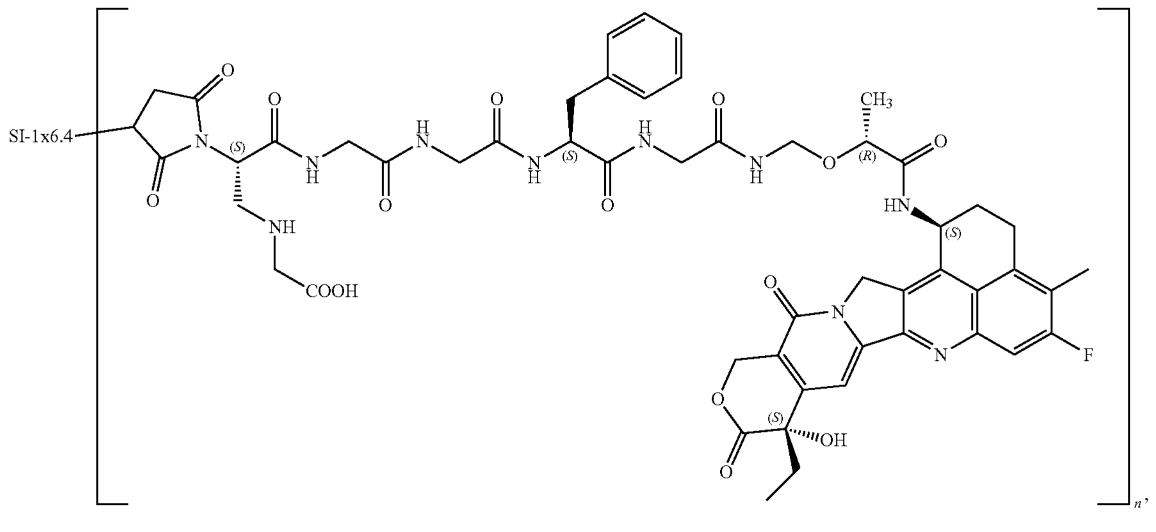

-continued
ADC-8a
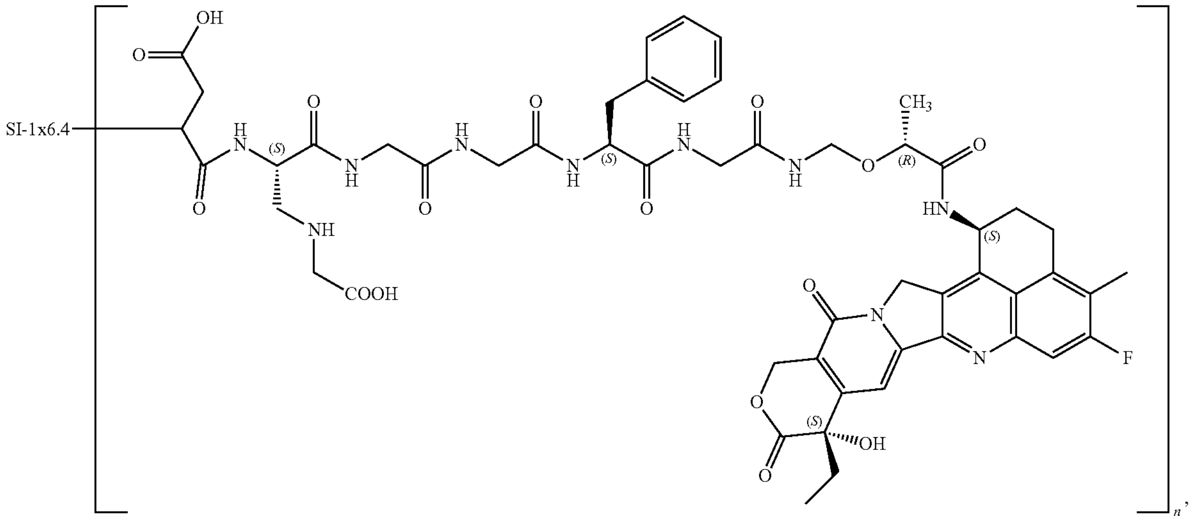
ADC-8b
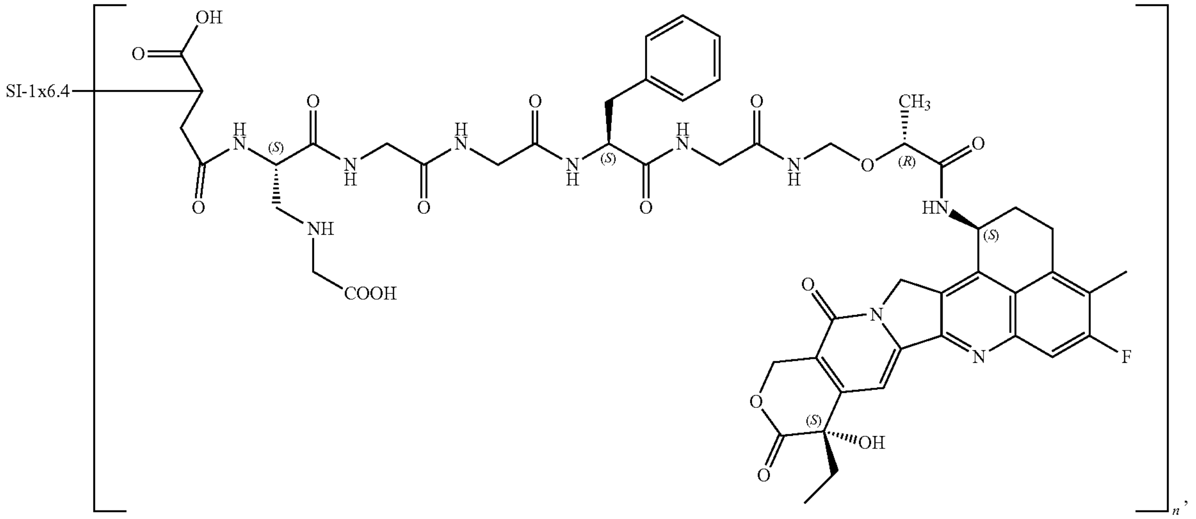
ADC-9
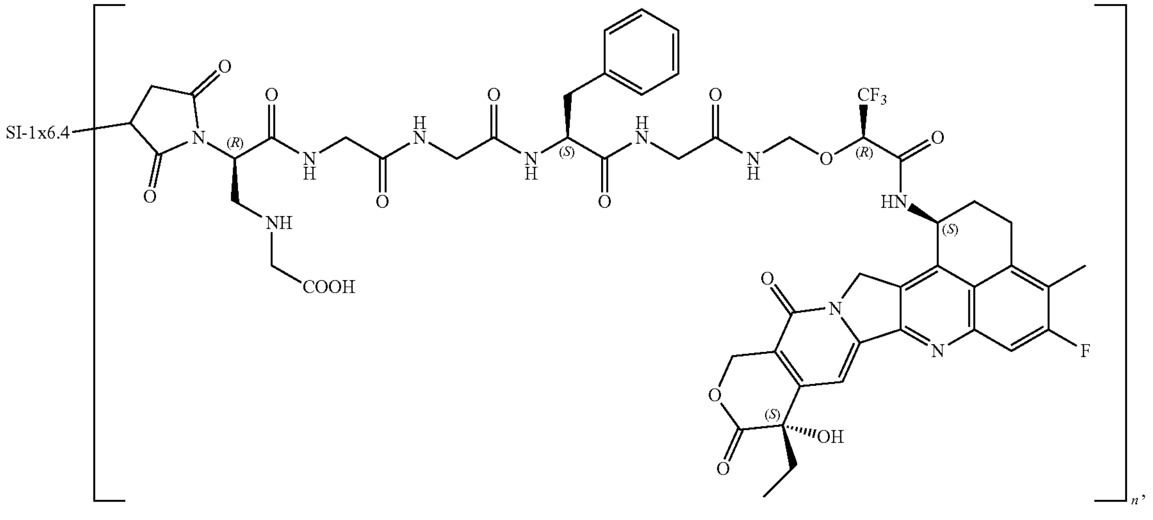

-continued
ADC-10
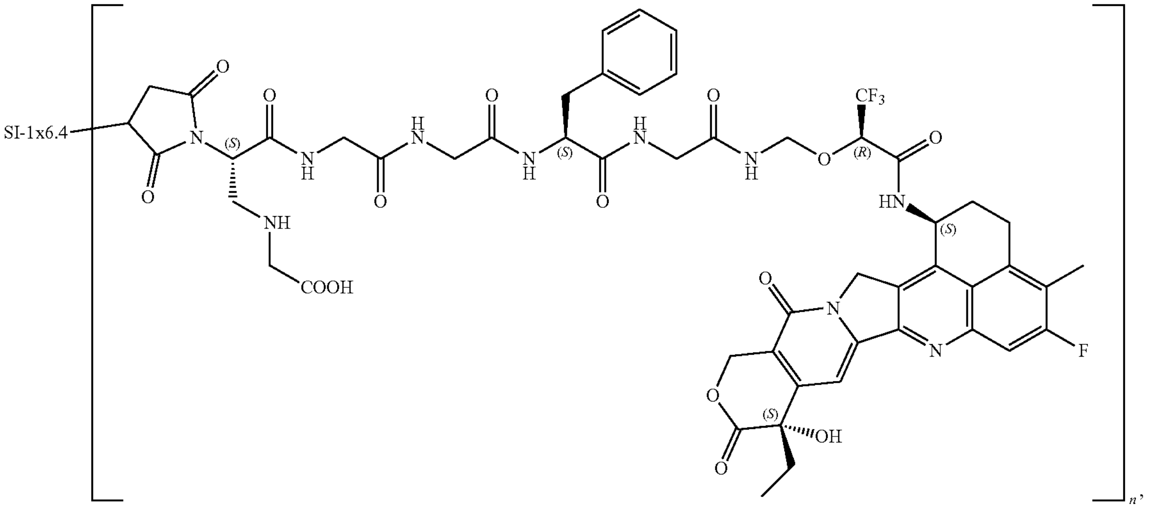
ADC-11
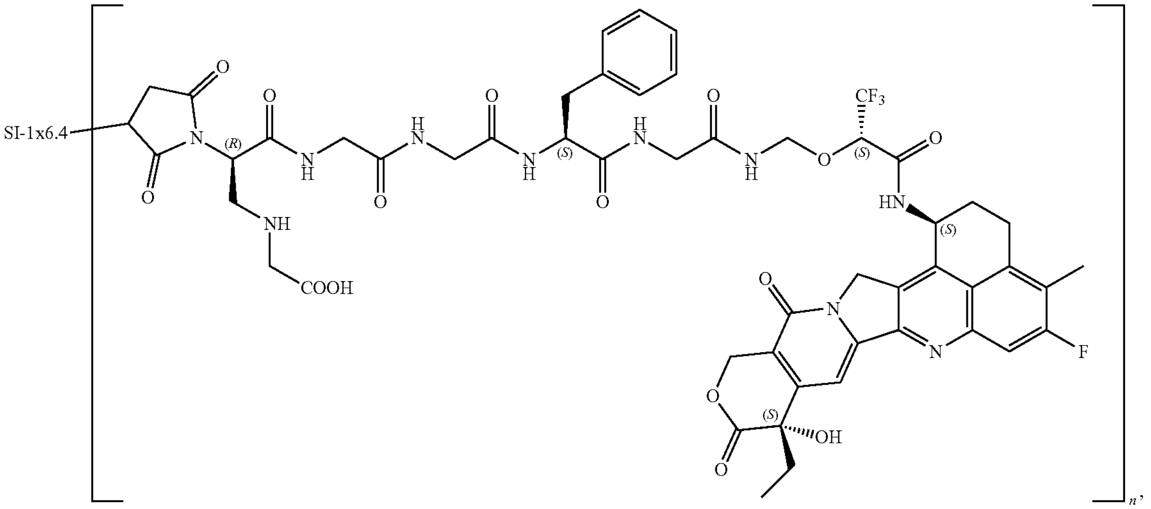
ADC-12
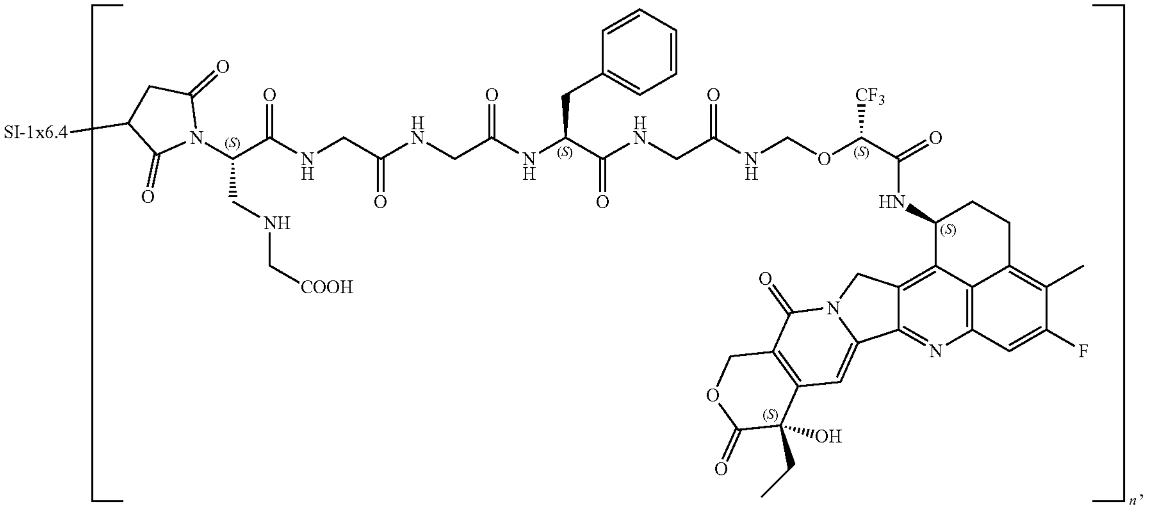

-continued
ADC-13
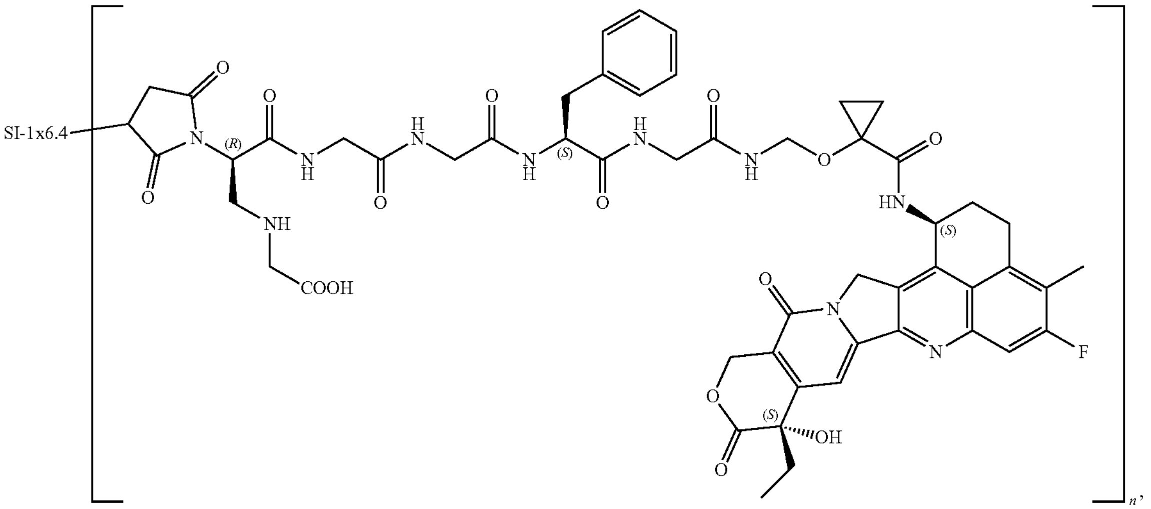
ADC-14
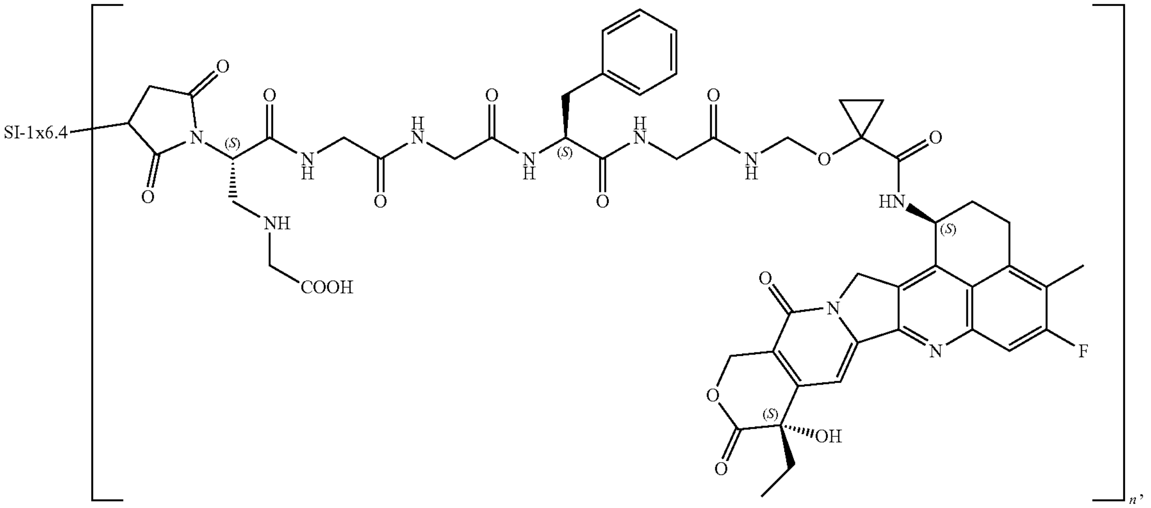
ADC-15
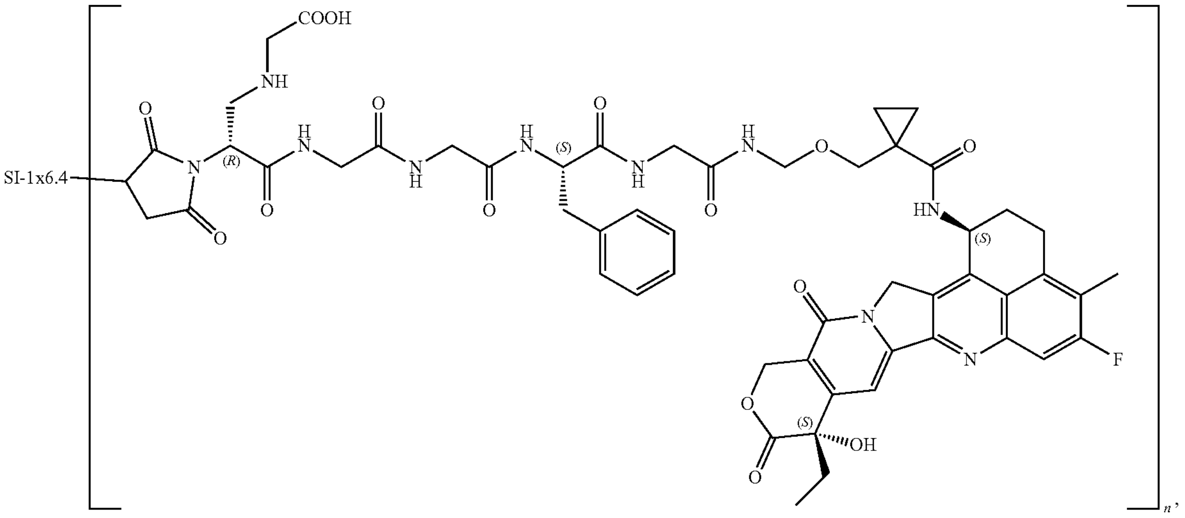

-continued
ADC-16
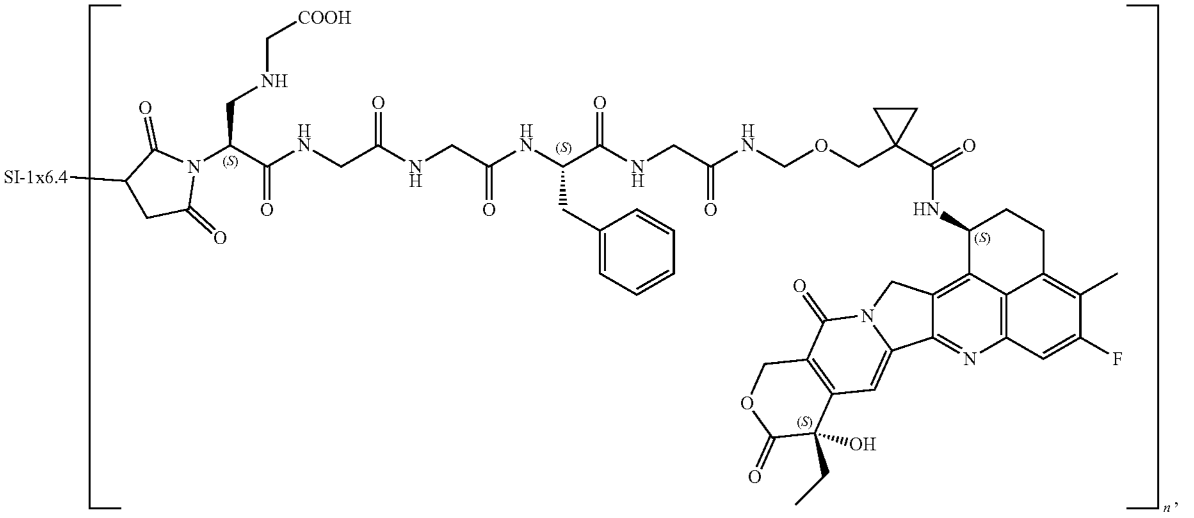
ADC-17
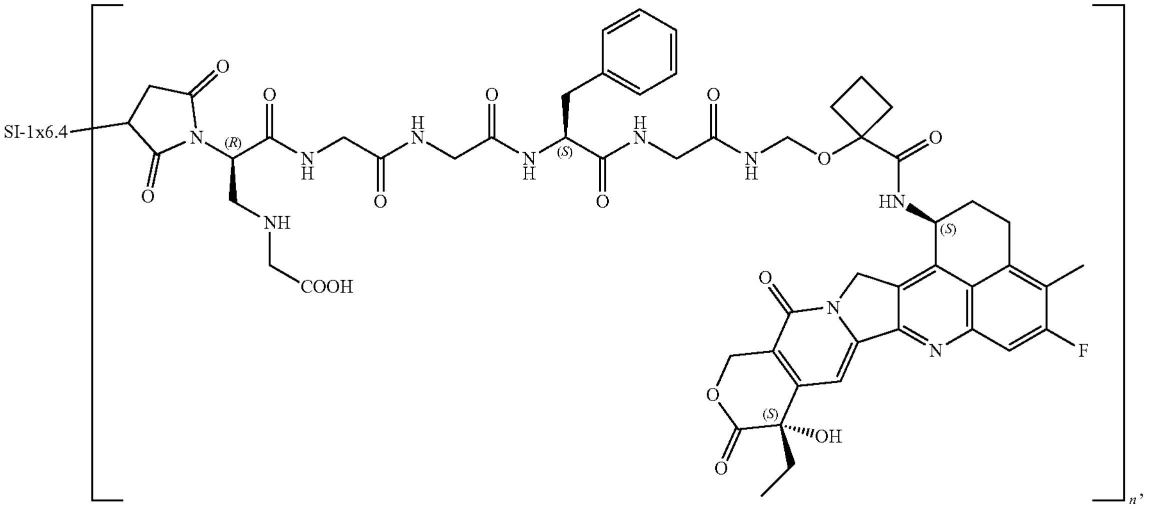
ADC-18
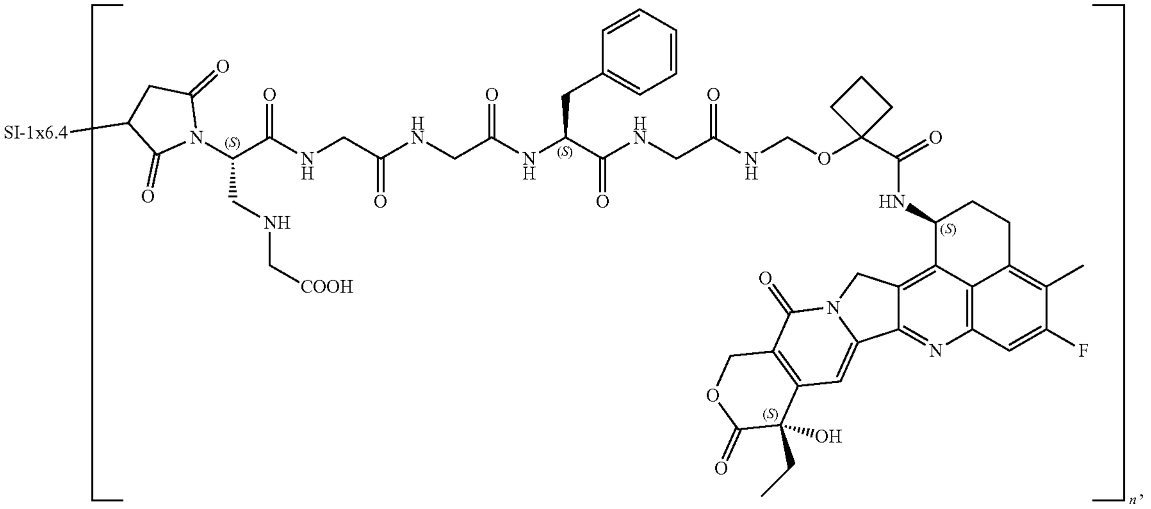

-continued
ADC-19
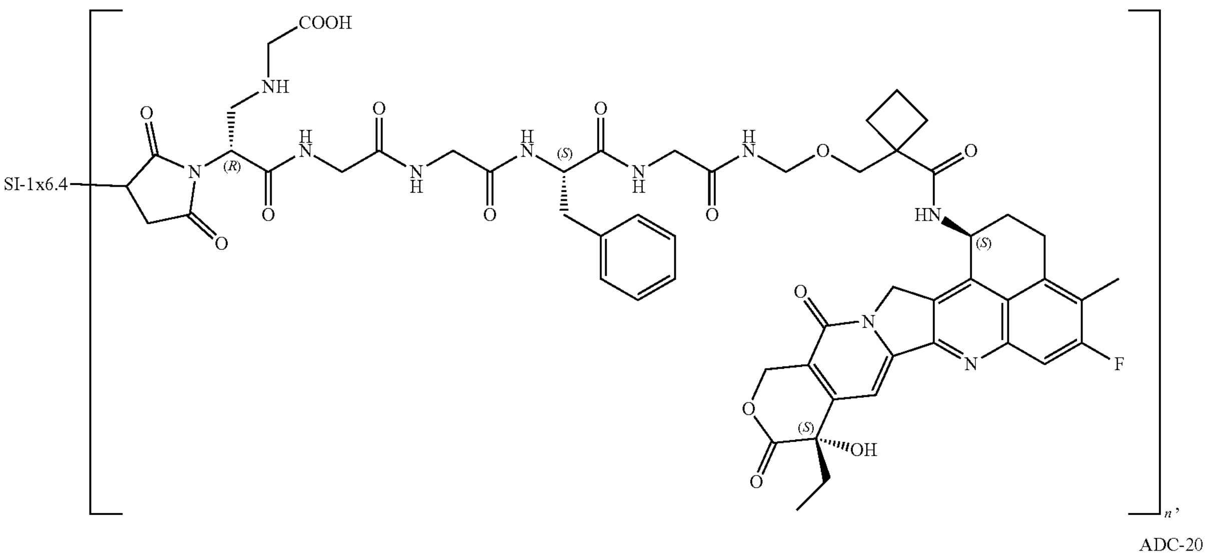
ADC-20
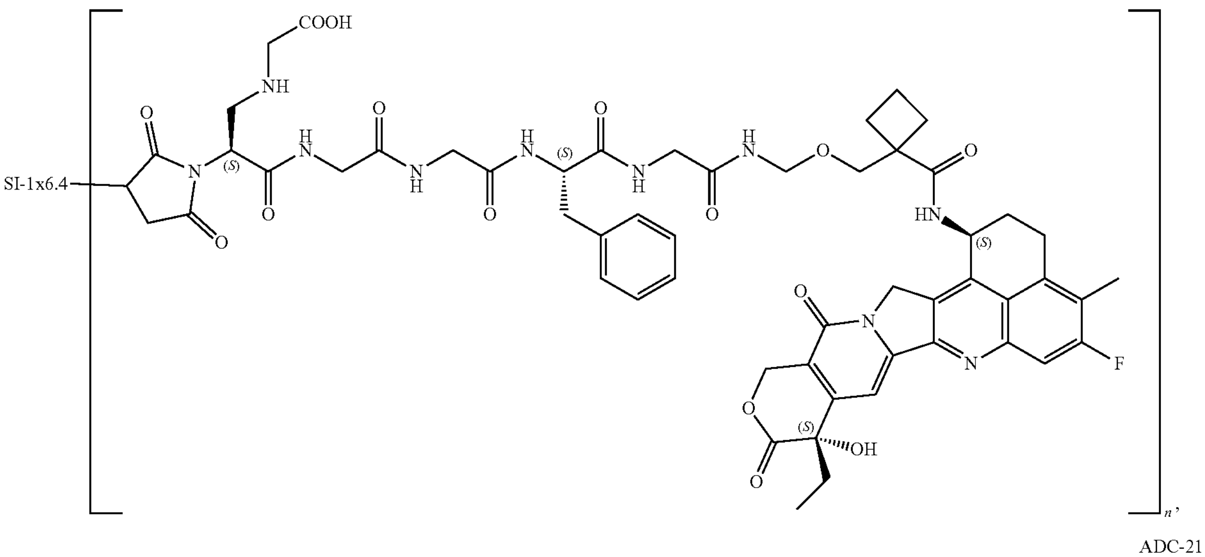
ADC-21
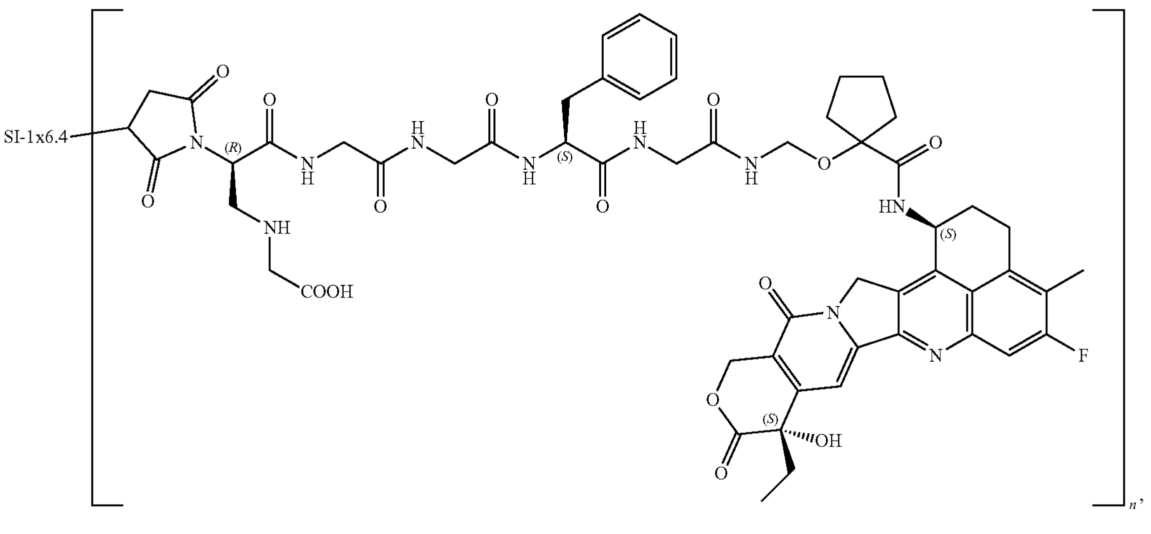

-continued
ADC-22
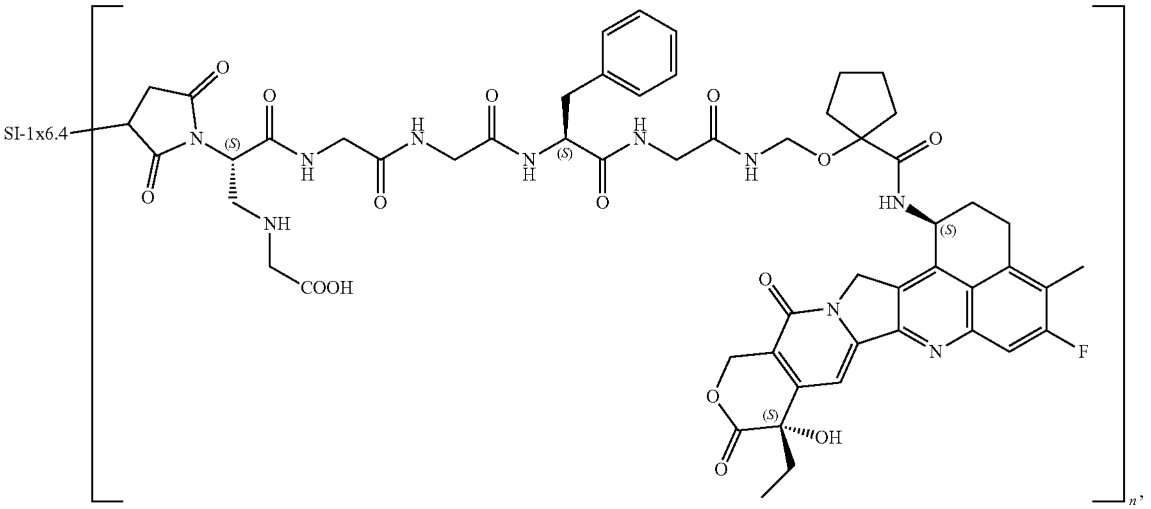
ADC-23
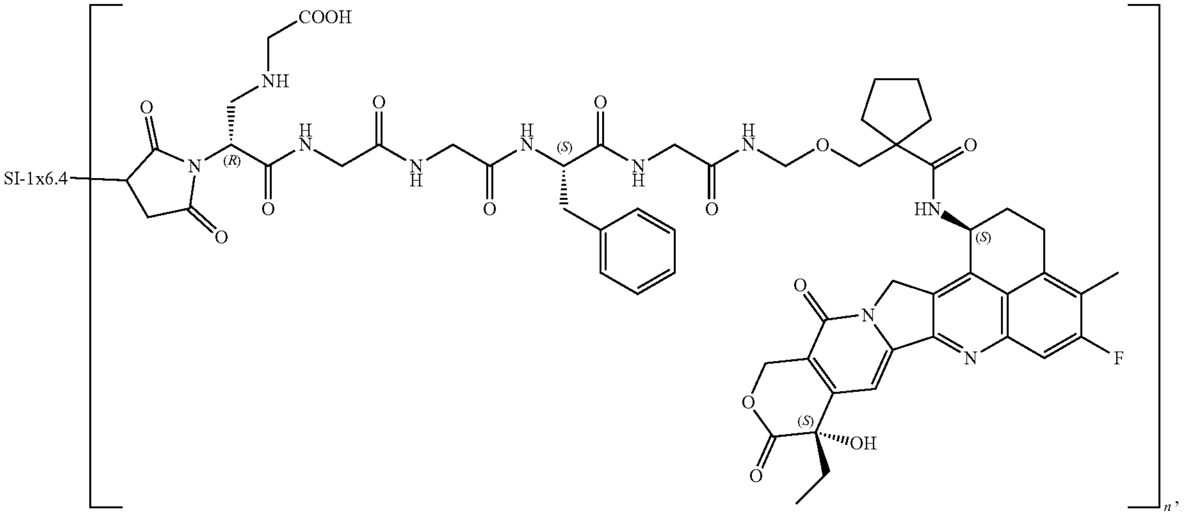
ADC-24
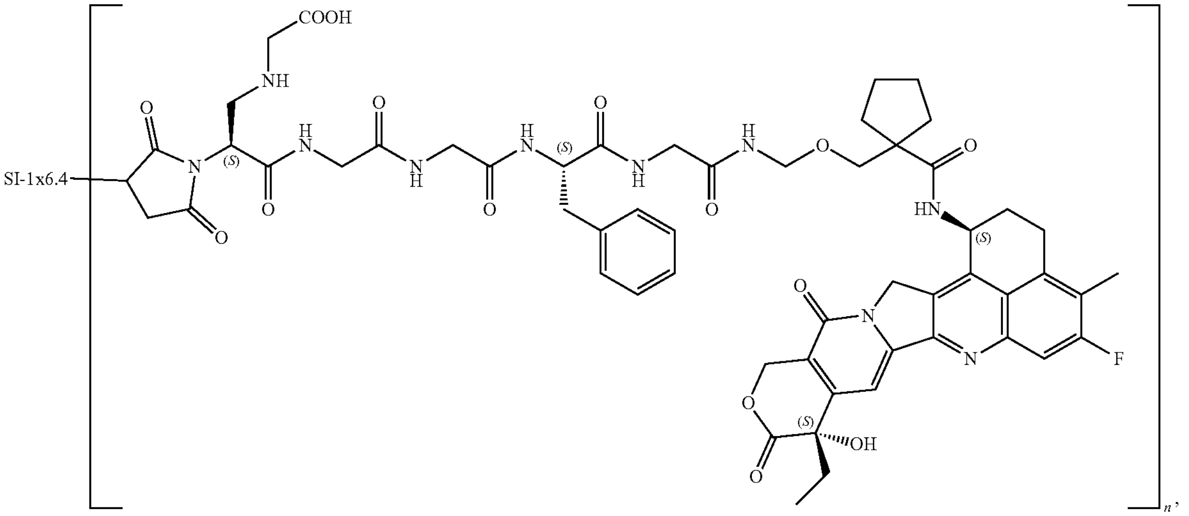

-continued
ADC-25
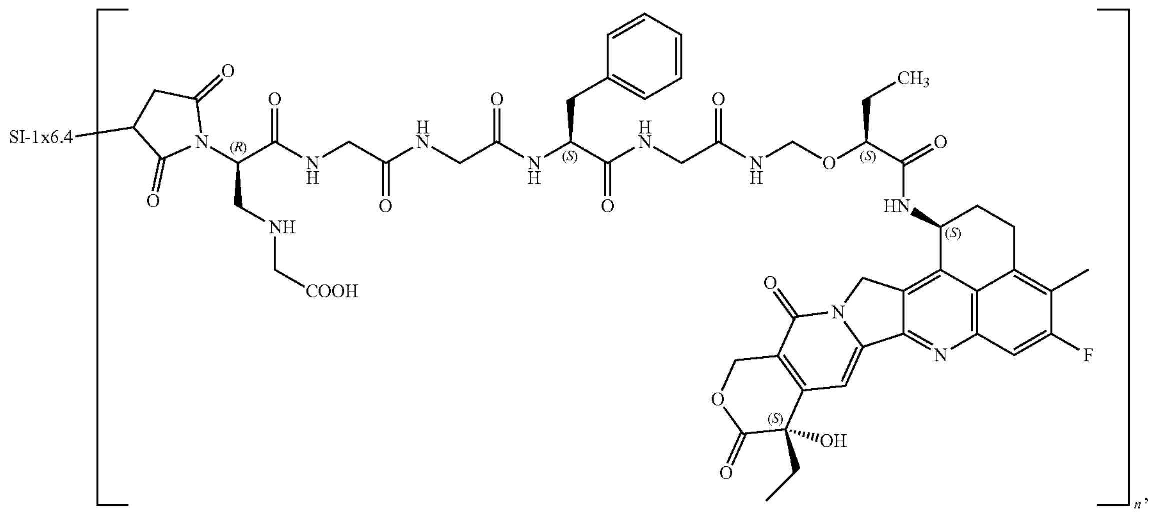
ADC-26
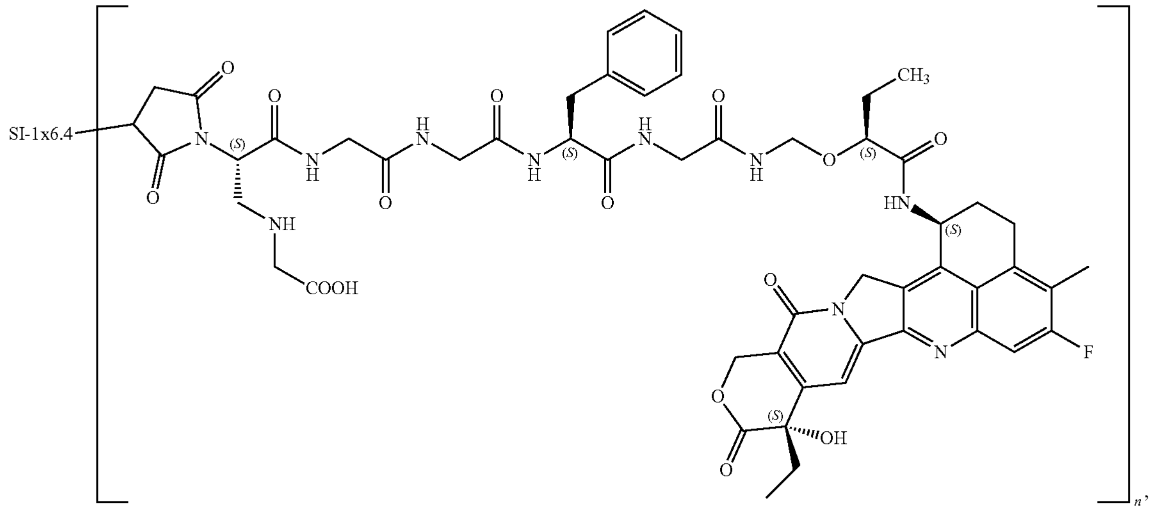
ADC-27
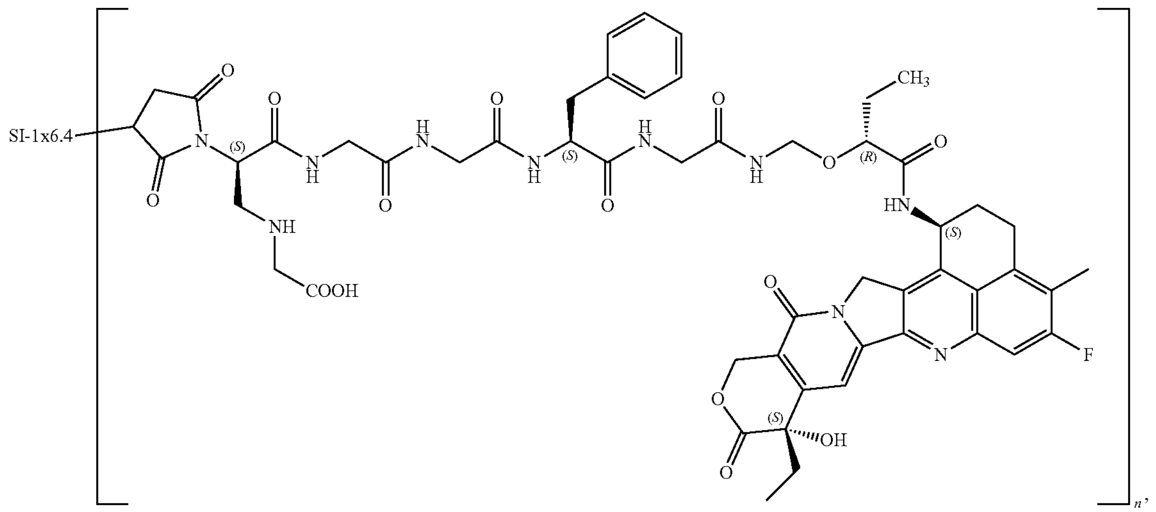

-continued
ADC-28
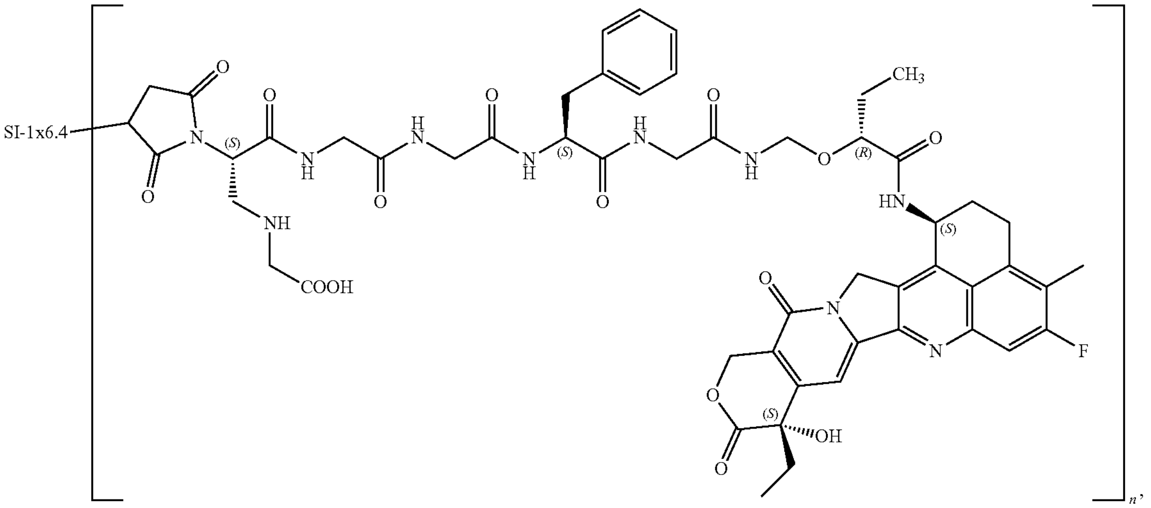
ADC-29
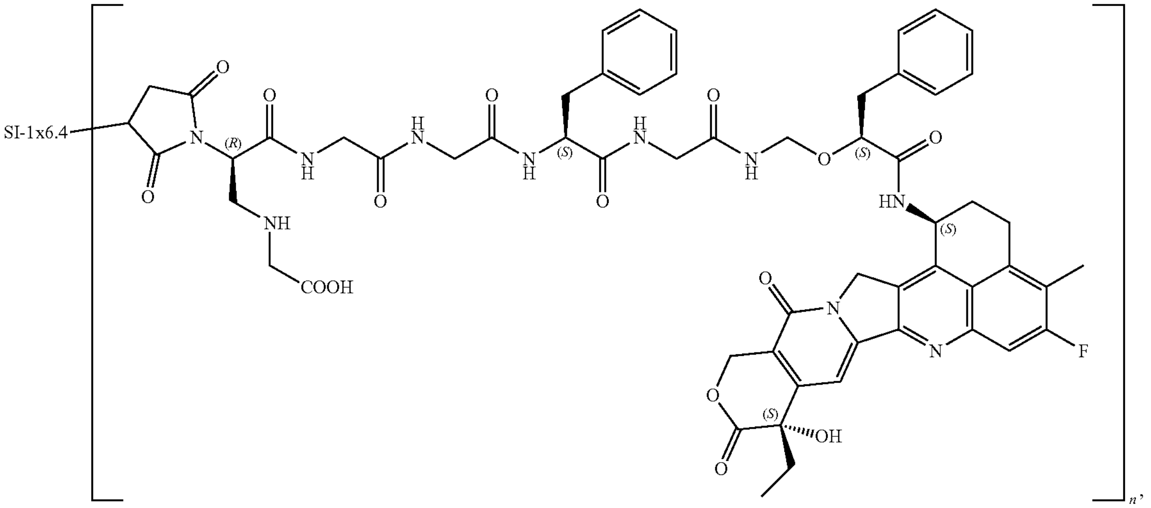
ADC-30
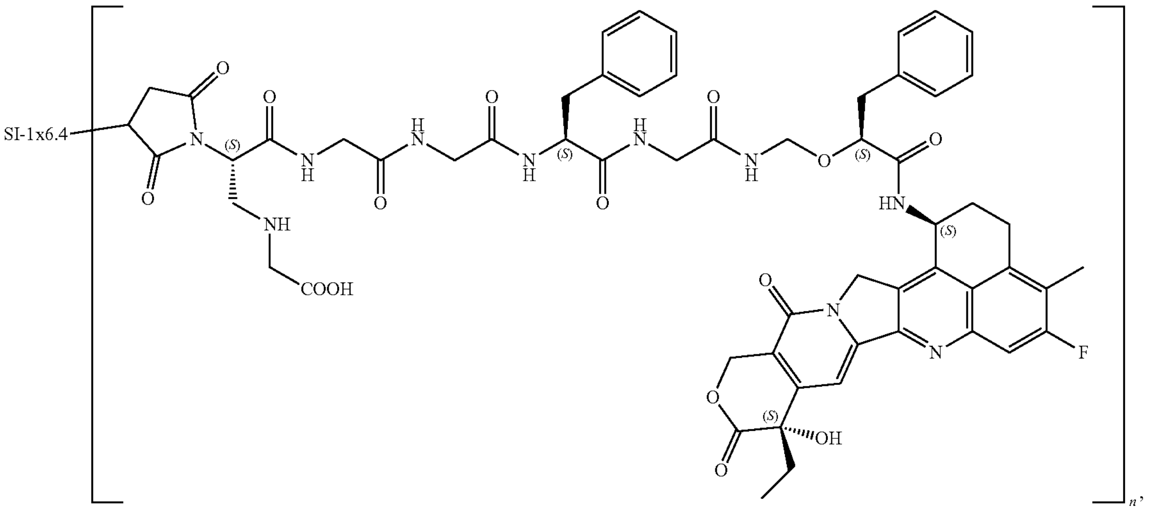

-continued
ADC-31
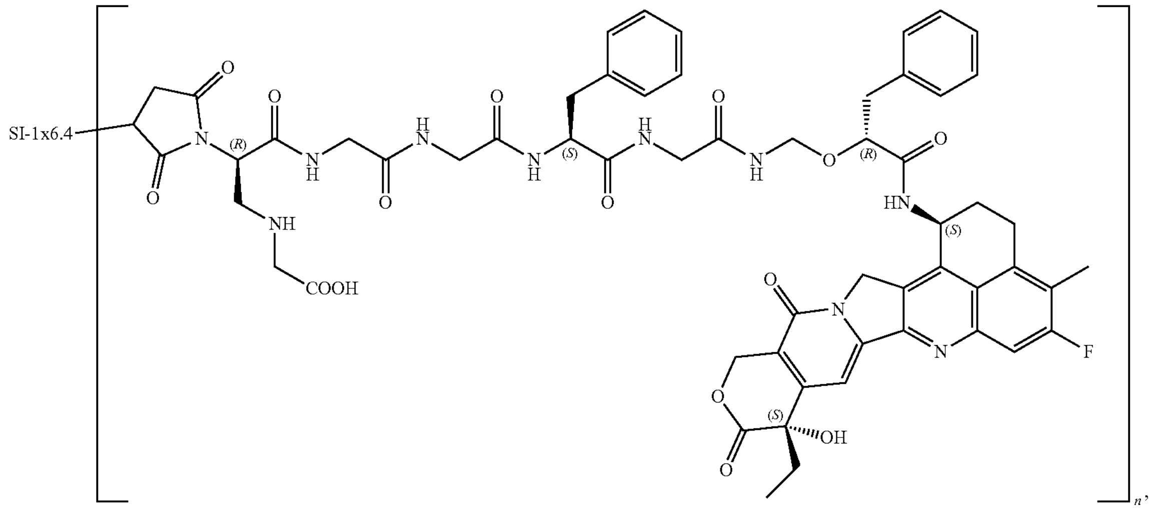
ADC-32
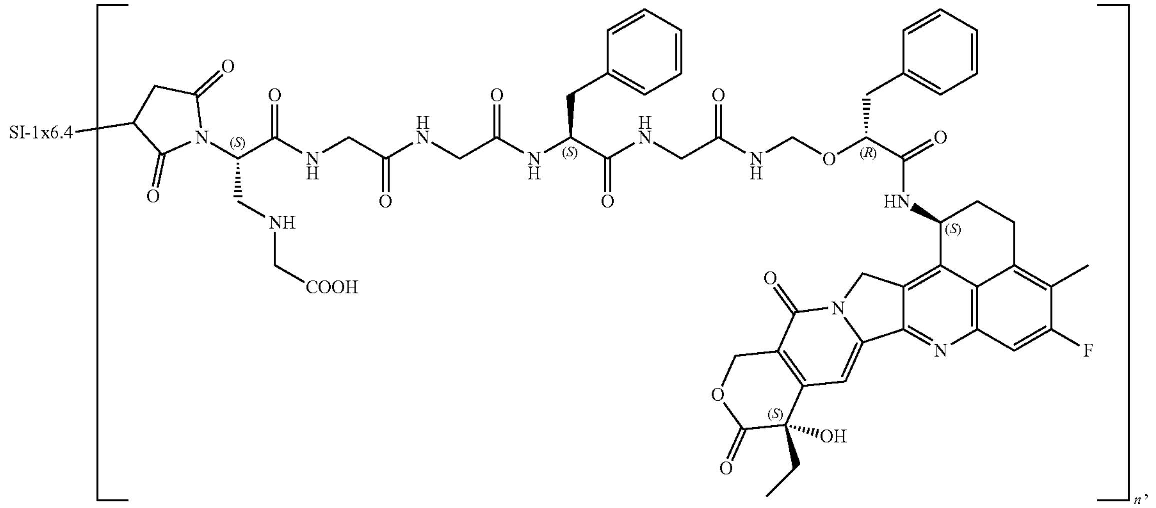
ADC-33
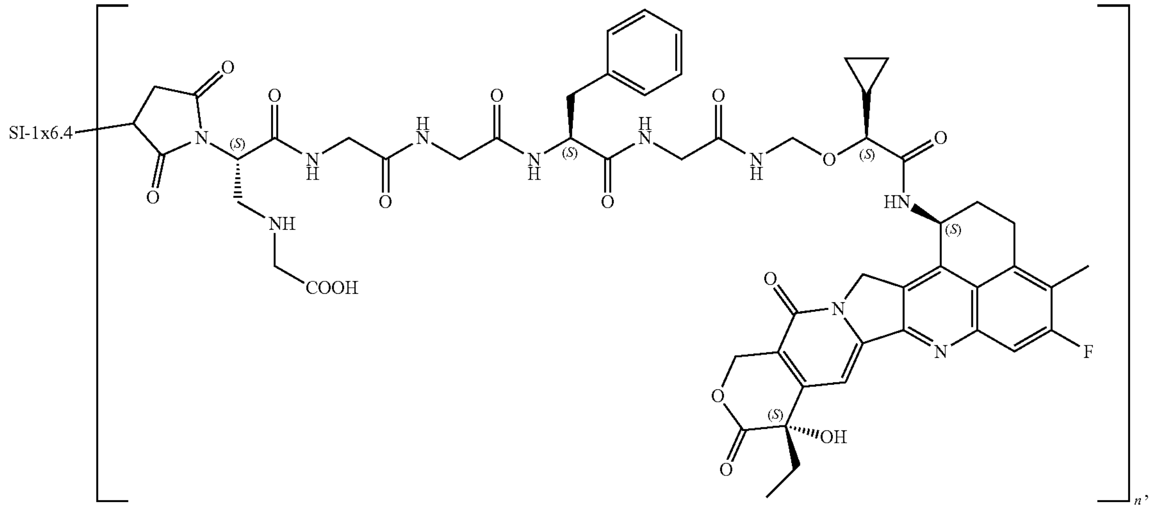

-continued
ADC-34
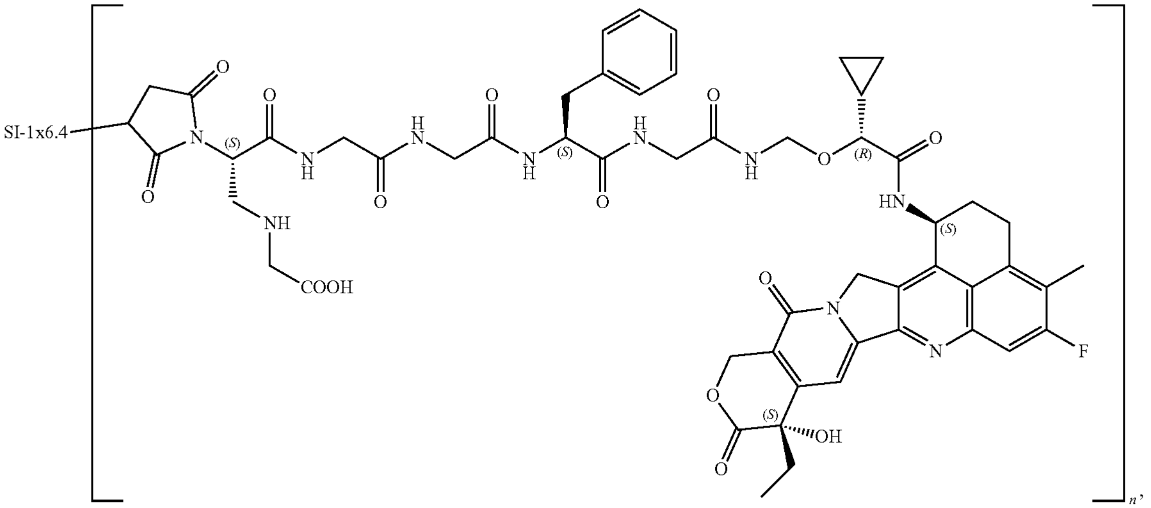
ADC-35
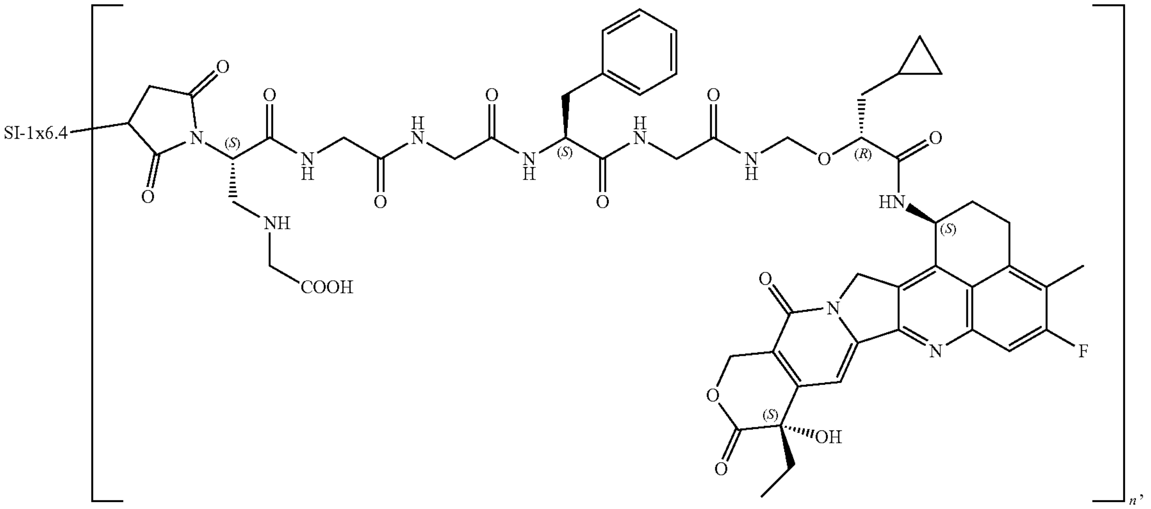
ADC-36
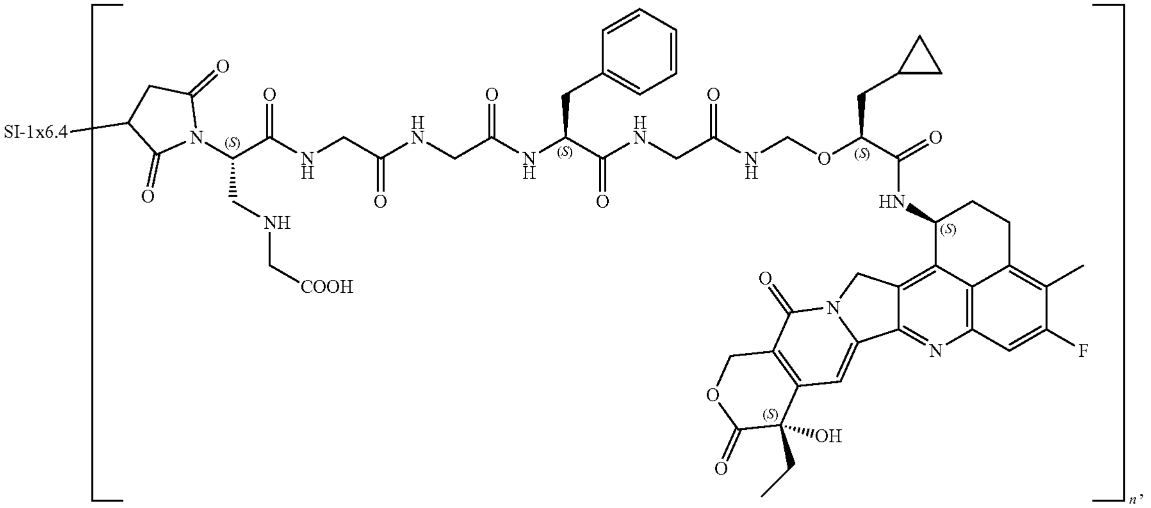

-continued
ADC-37
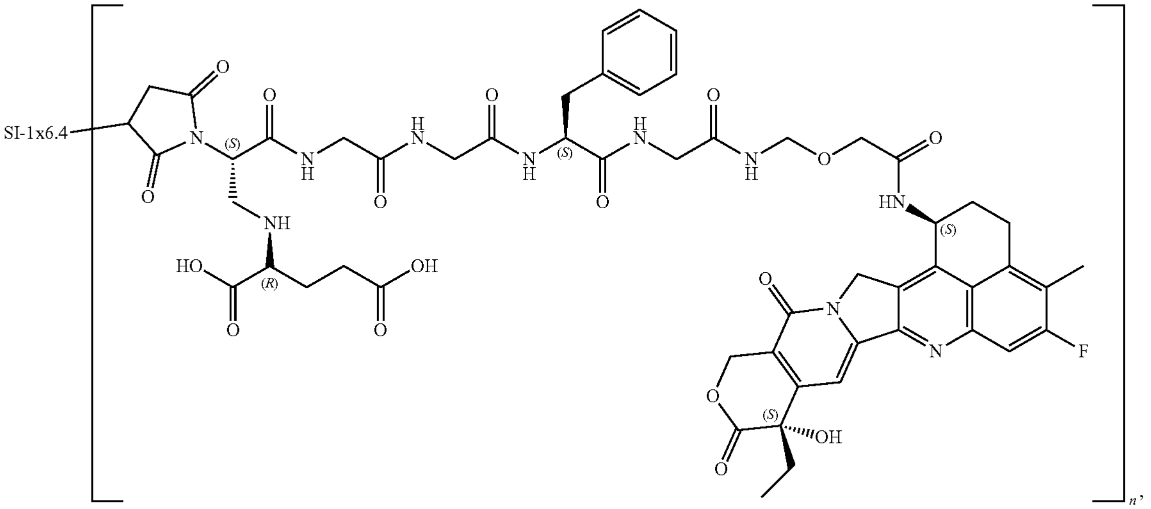
ADC-38
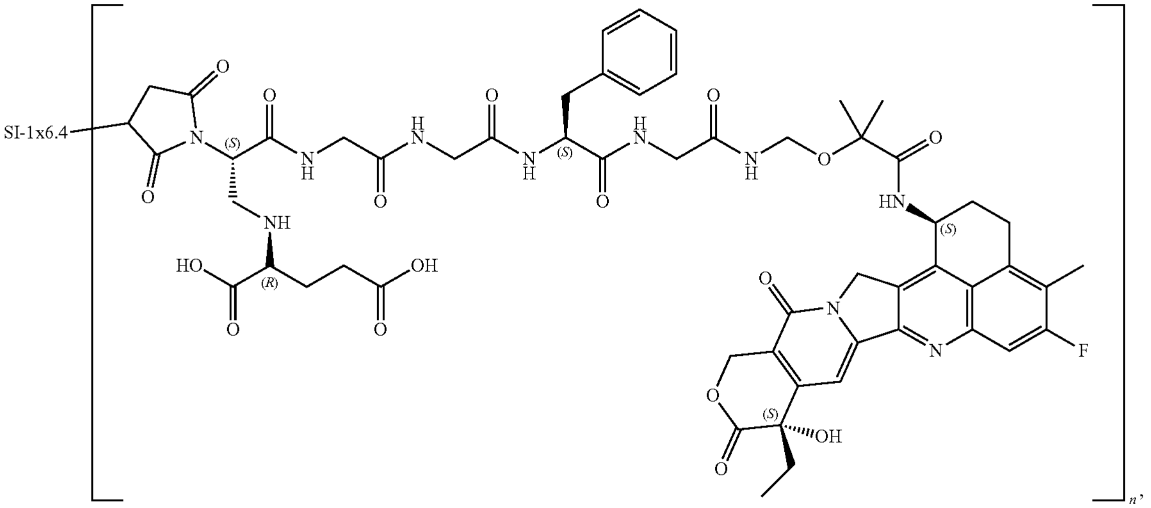
ADC-39
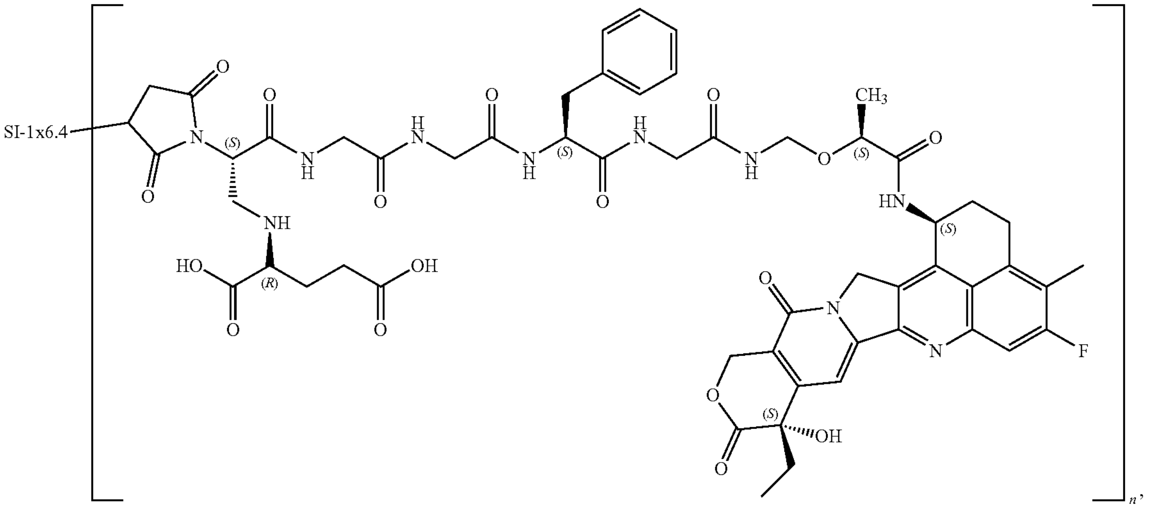

-continued
ADC-40
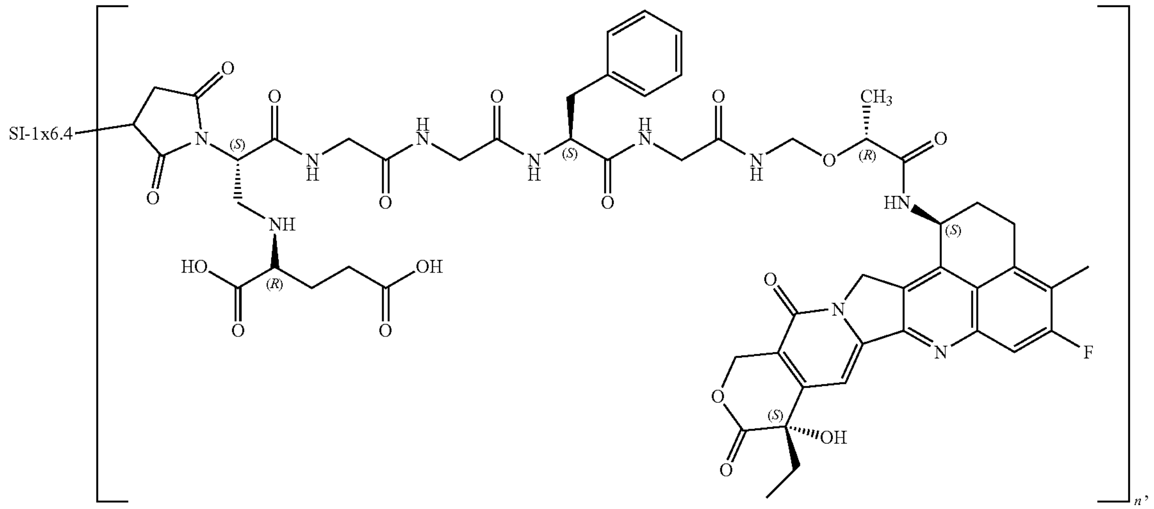
ADC-41
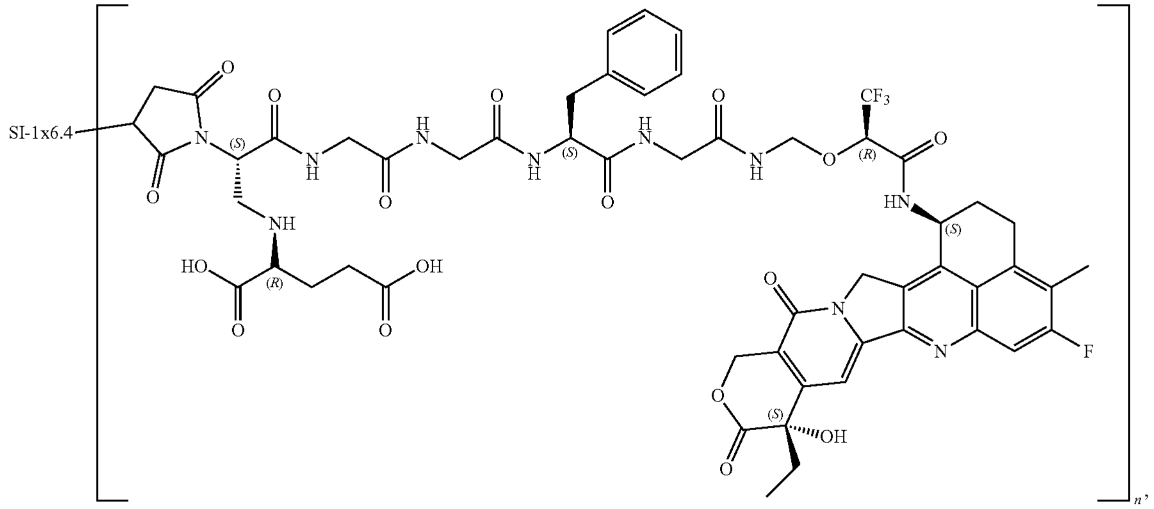
ADC-42
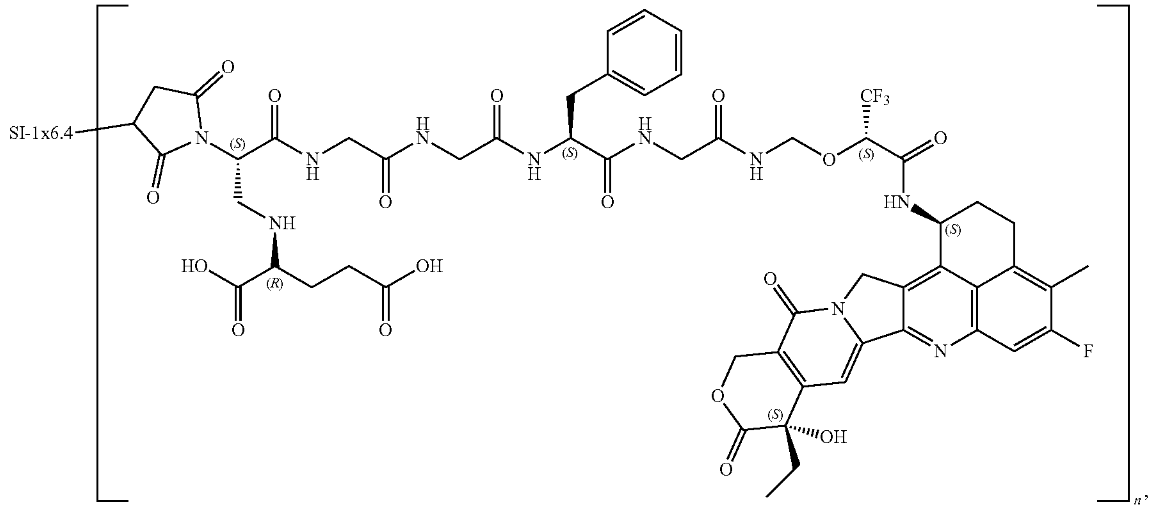

-continued
ADC-43
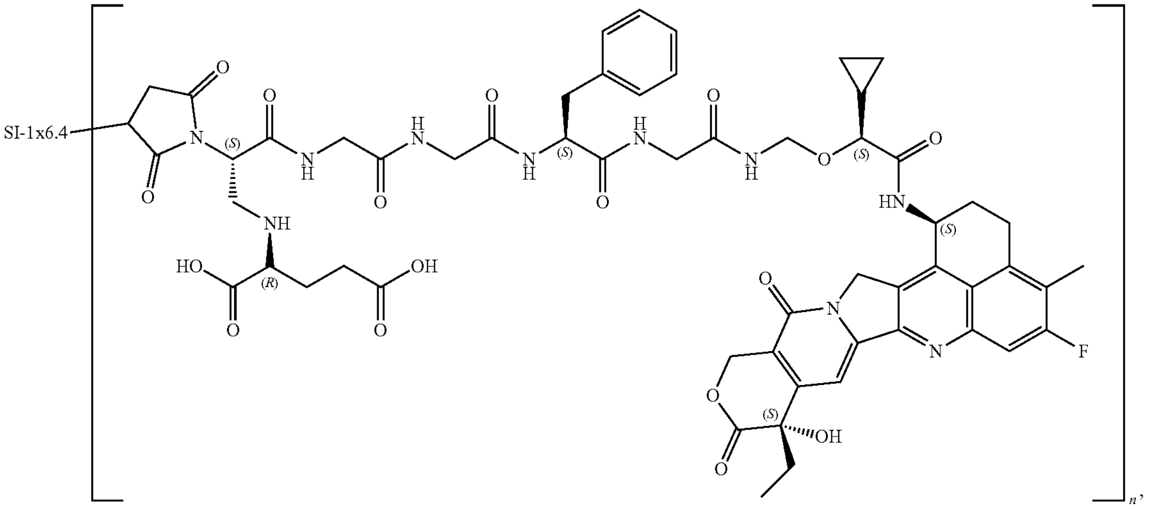
ADC-44
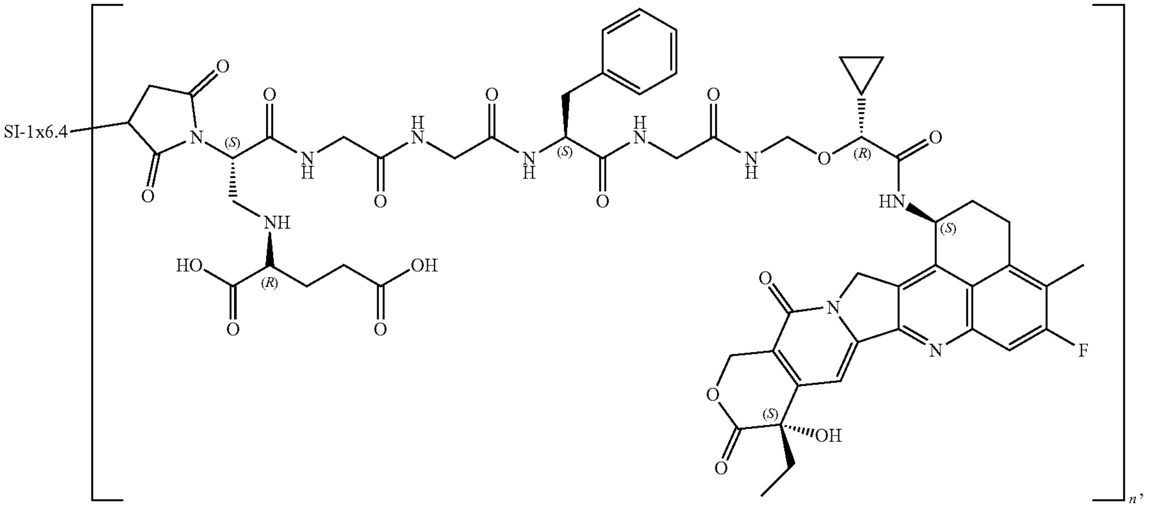
ADC-45
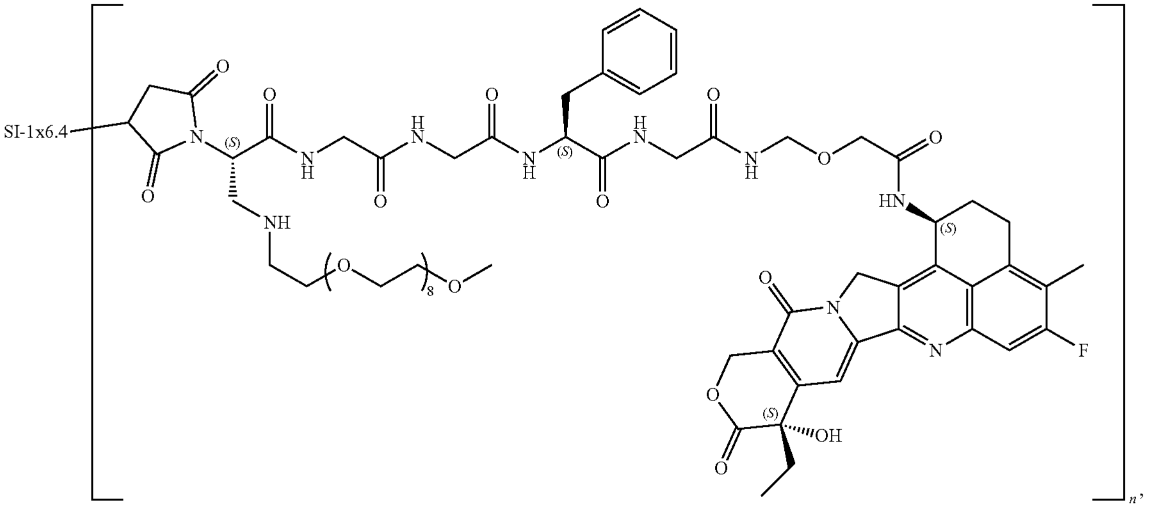

-continued
ADC-46
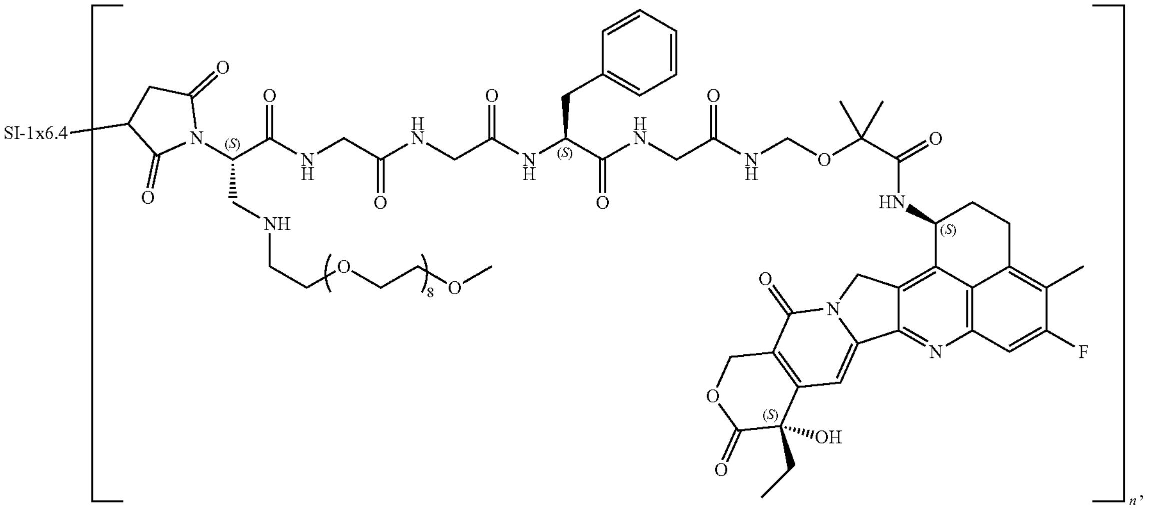
ADC-47
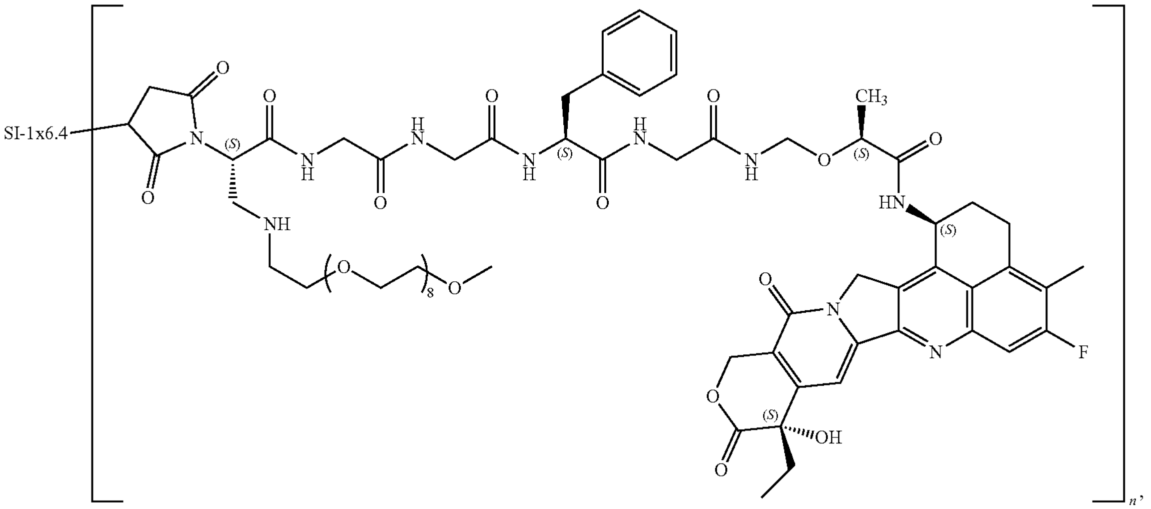
ADC-48
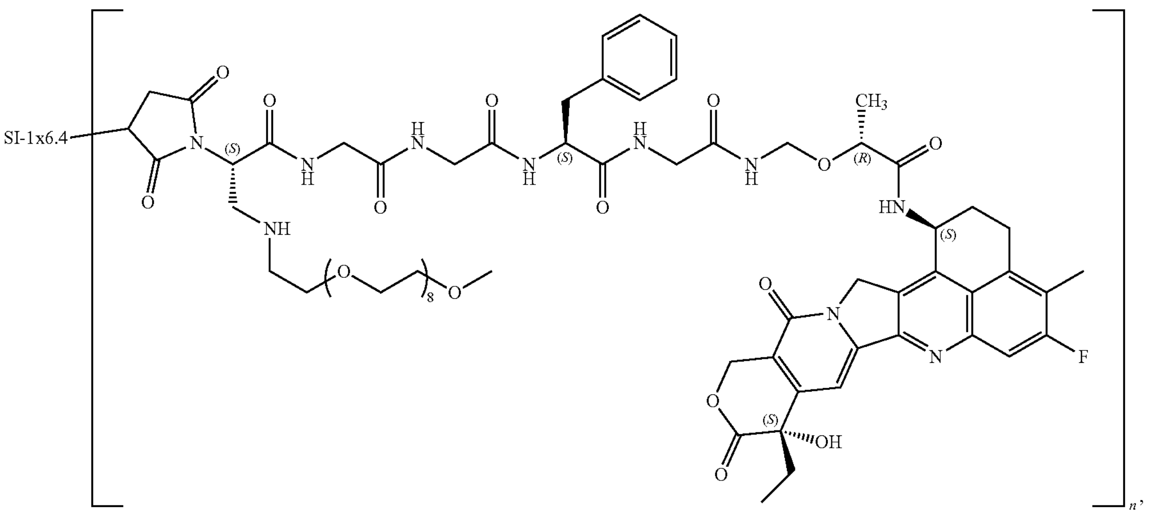

-continued
ADC-49
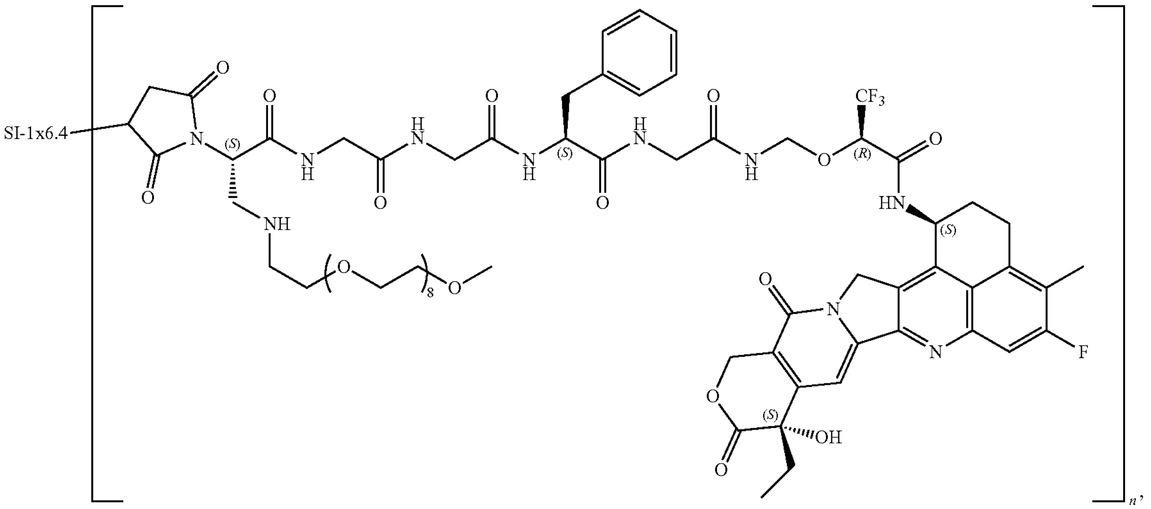
ADC-50
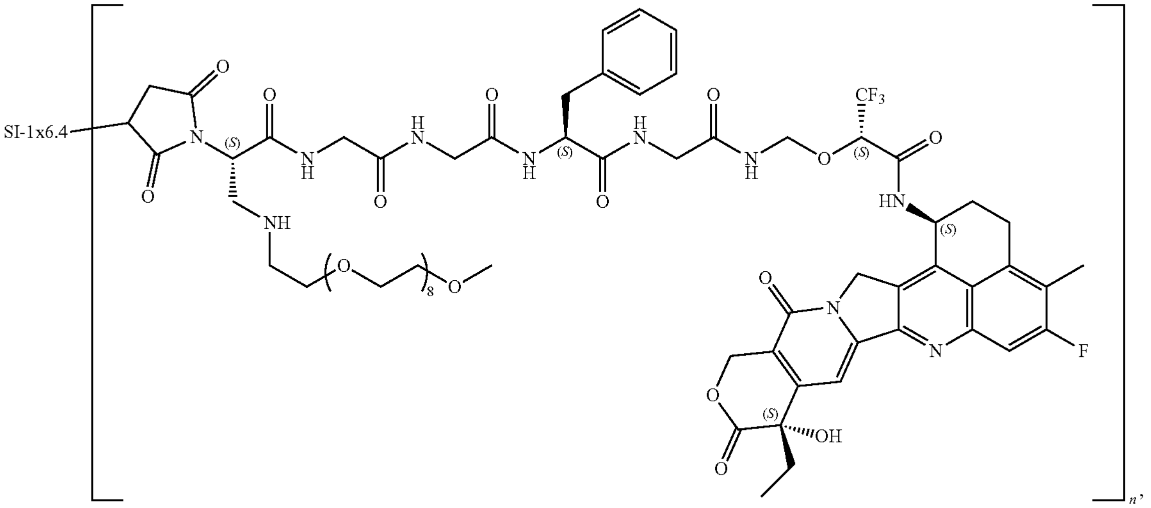
ADC-51
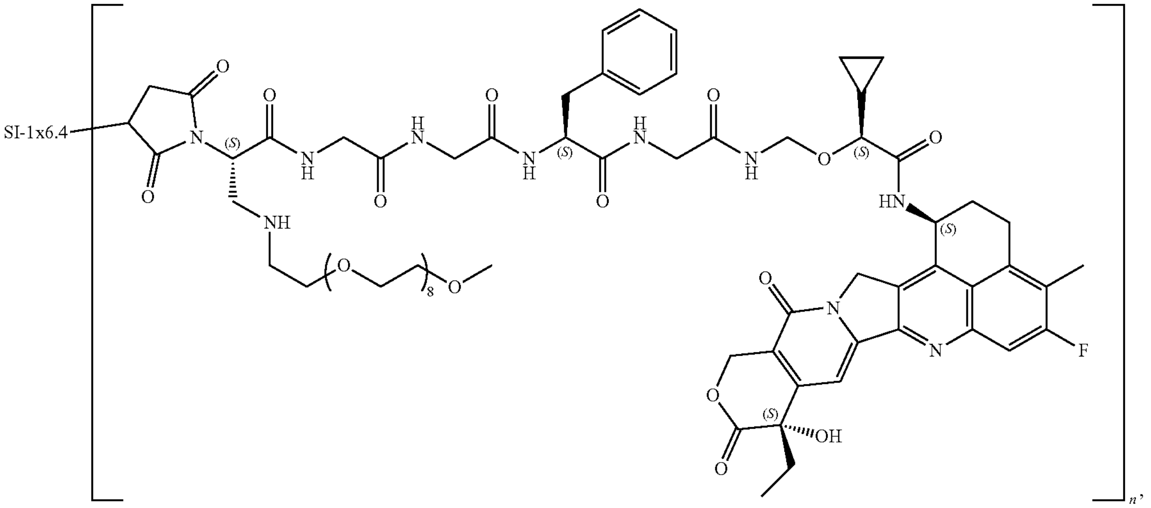

-continued
ADC-52
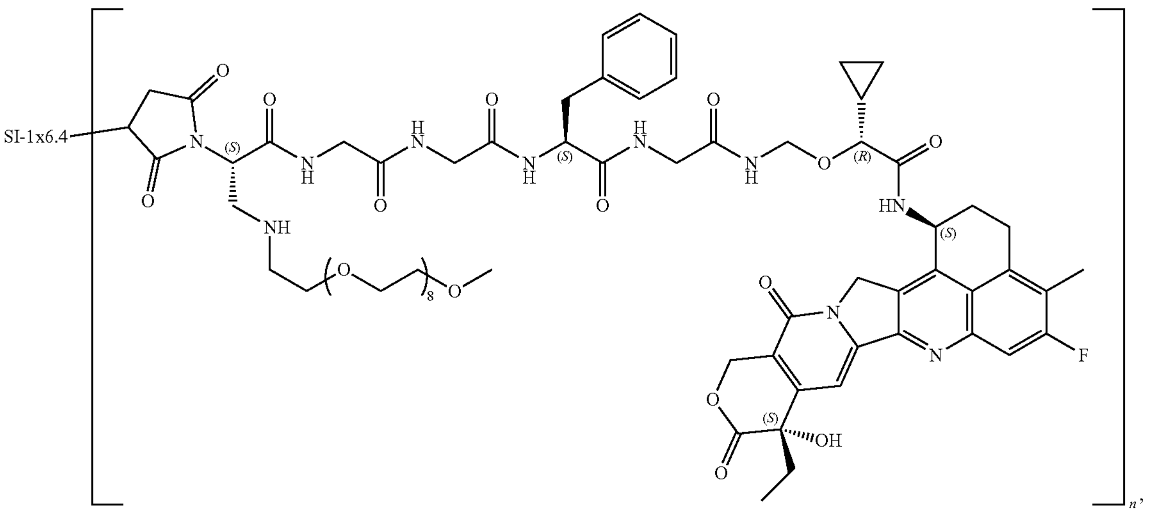
ADC-53
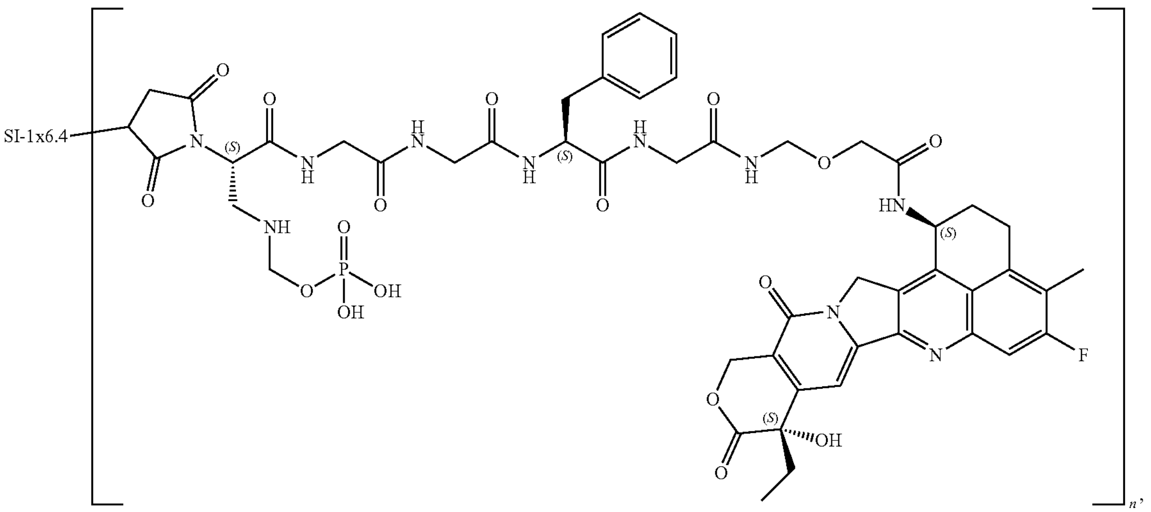
ADC-54
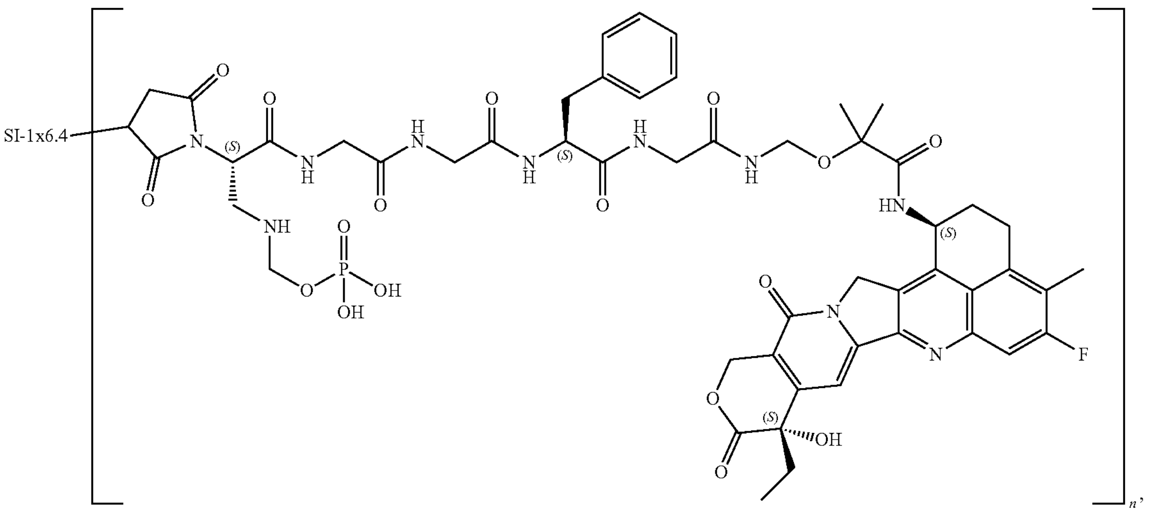

-continued
ADC-55
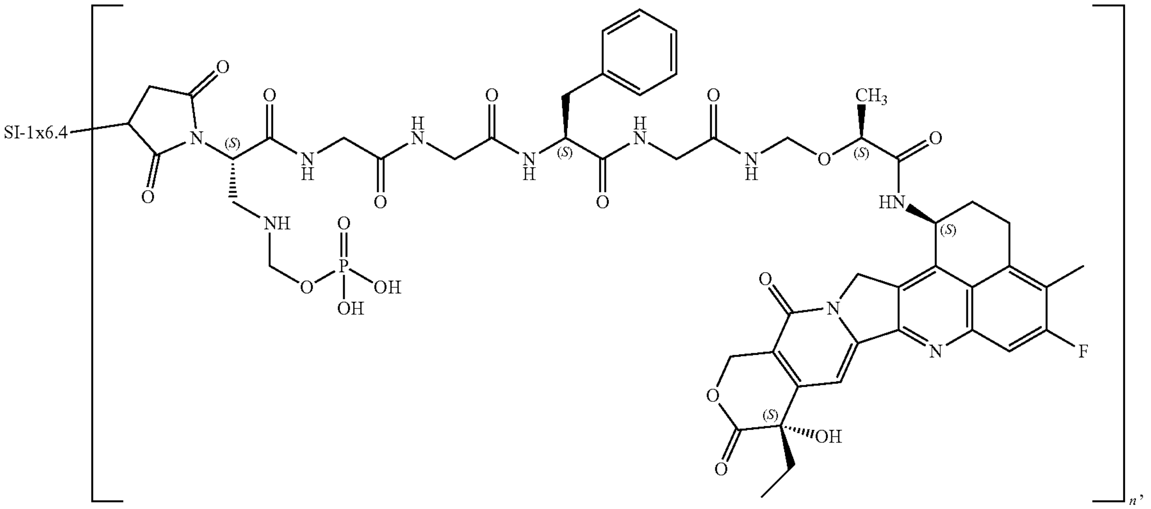
ADC-56
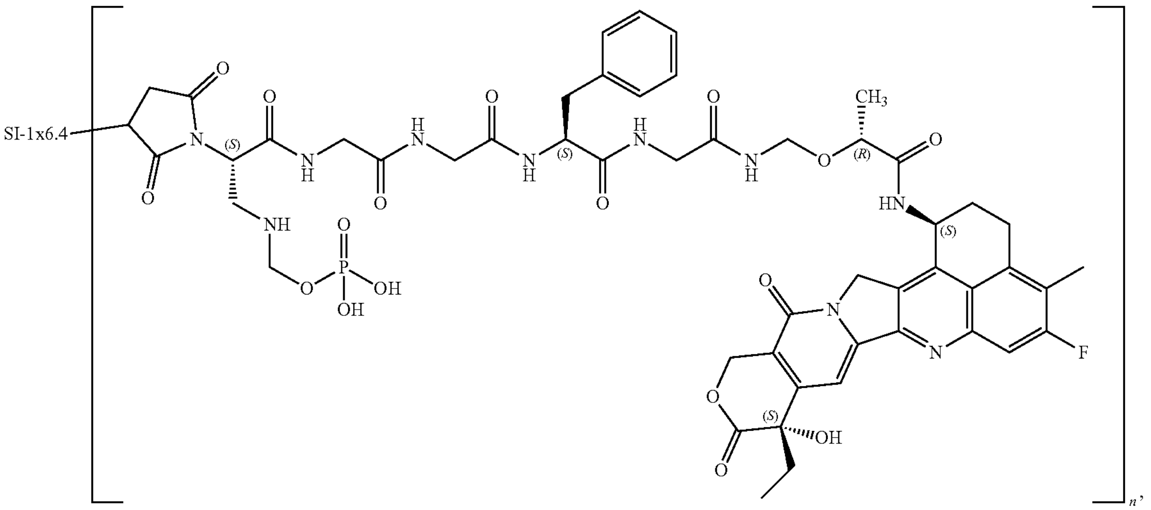
ADC-57
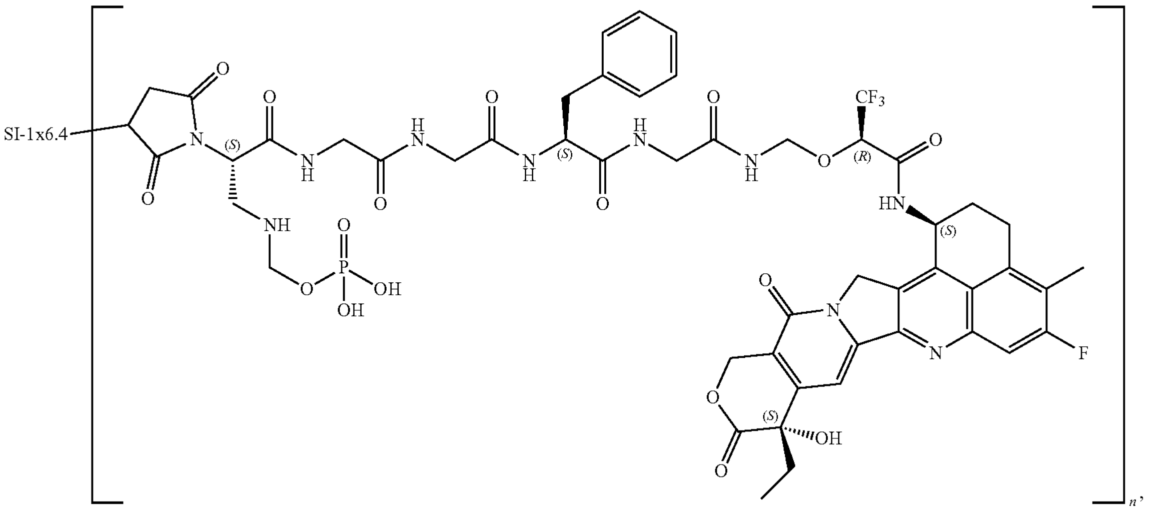

-continued
ADC-58
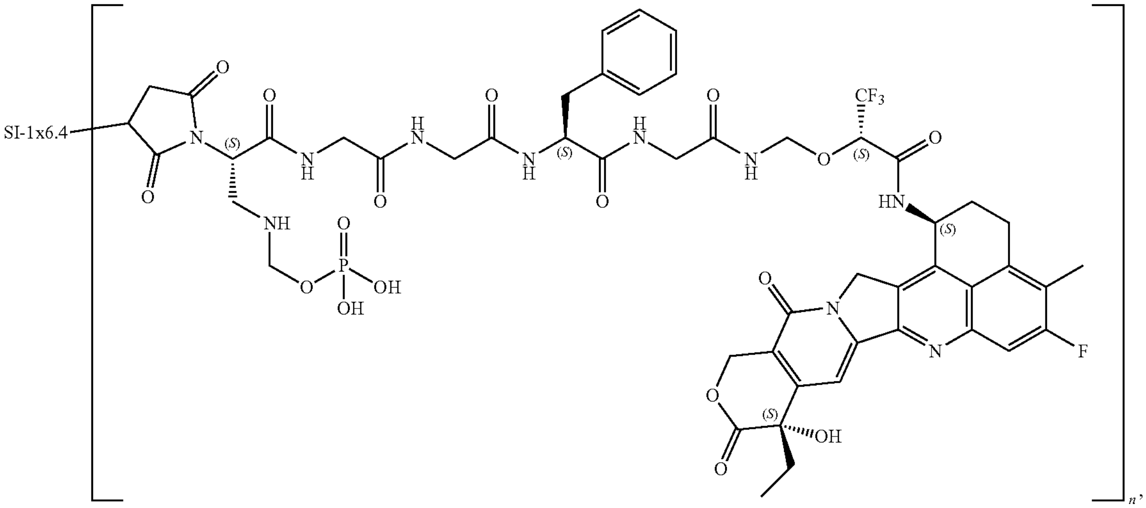
ADC-59
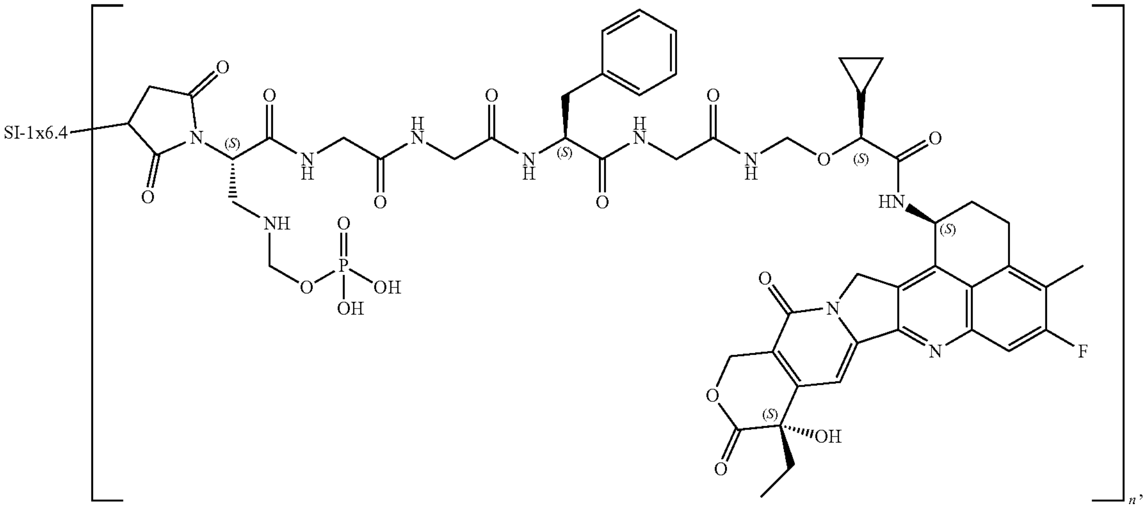
ADC-60
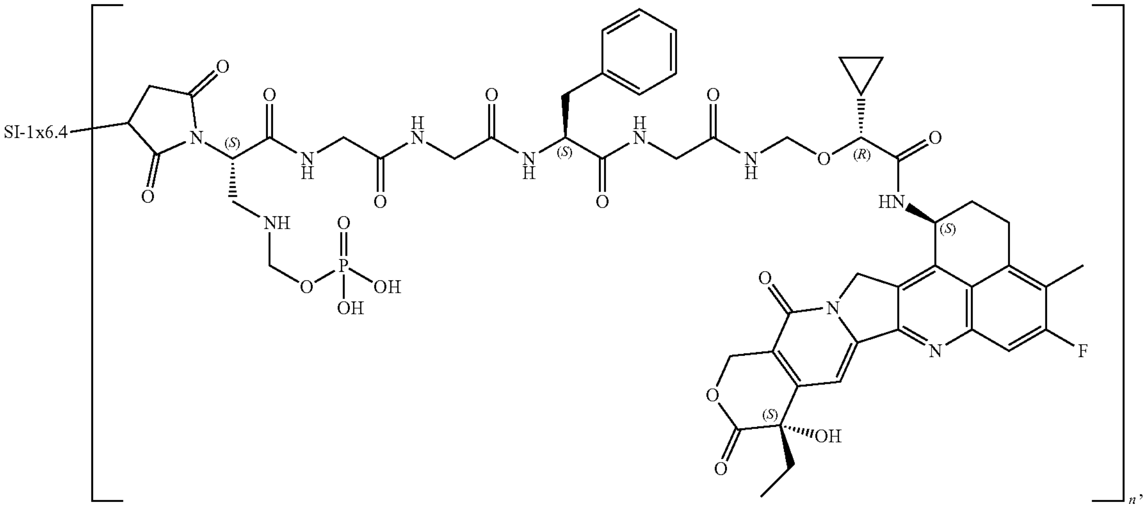

-continued
ADC-61
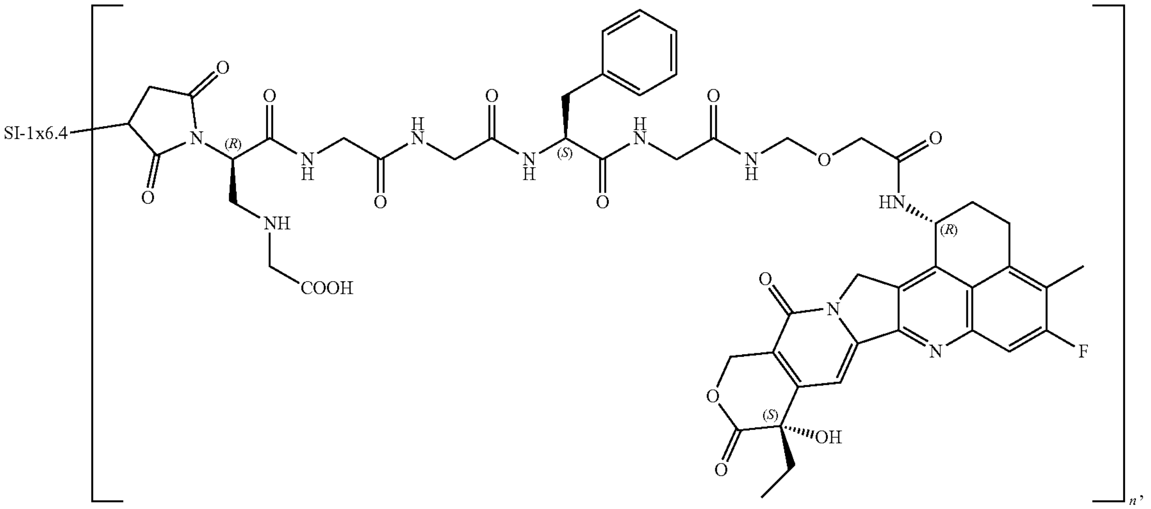
ADC-62
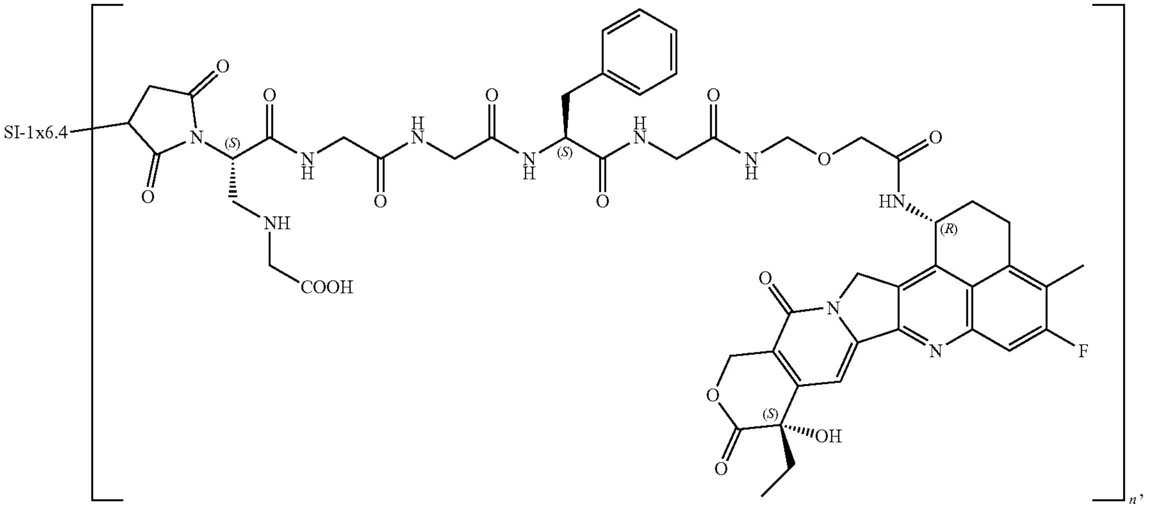
ADC-63
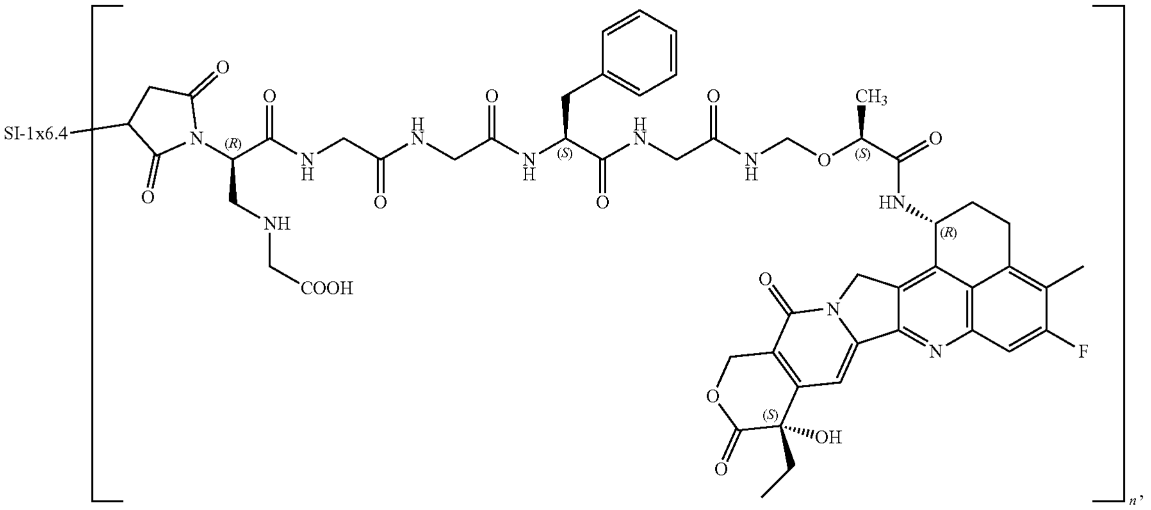

-continued
ADC-64
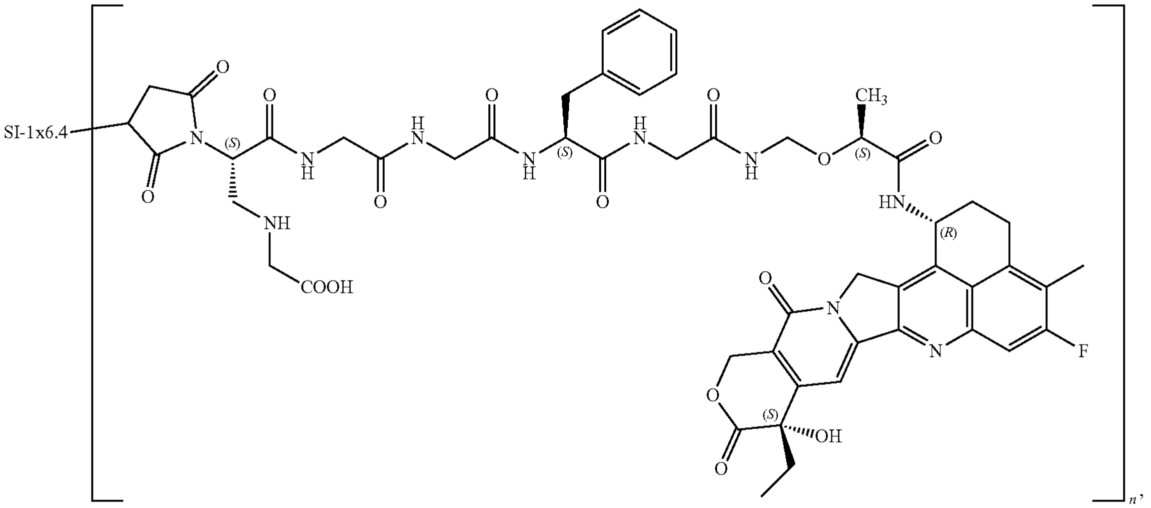
ADC-65
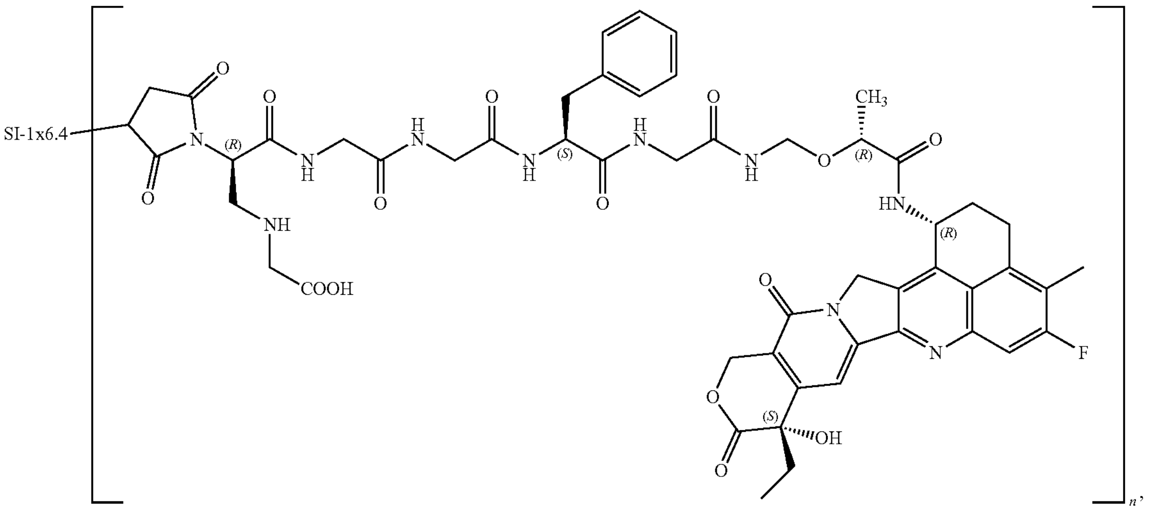
ADC-66
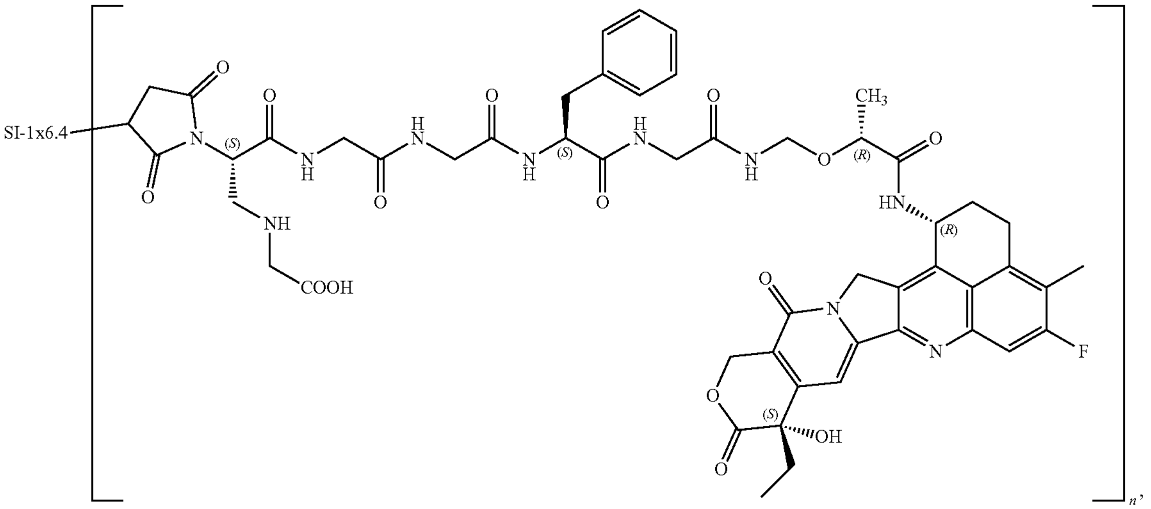

-continued
ADC-67
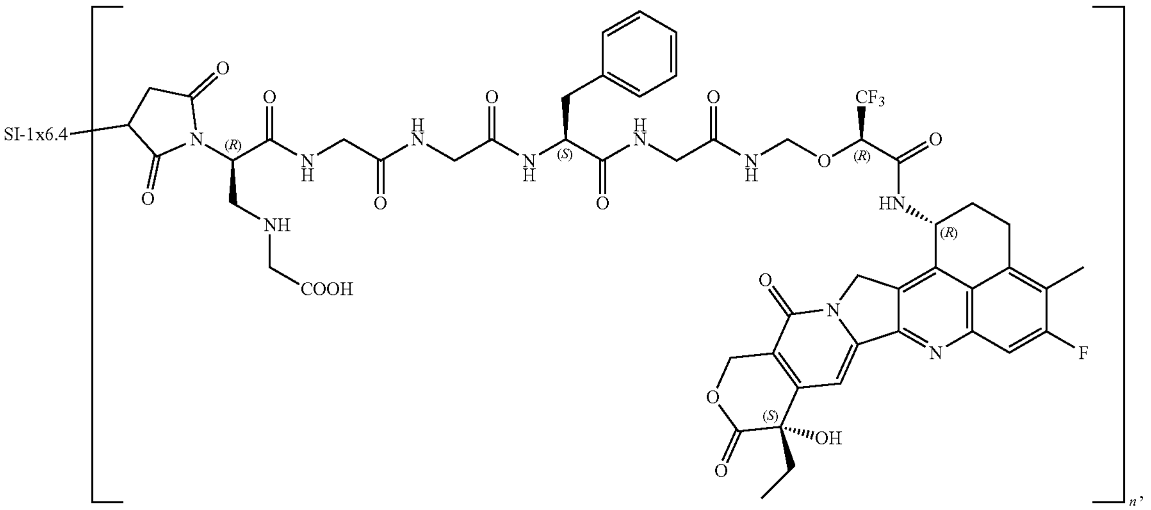
ADC-68
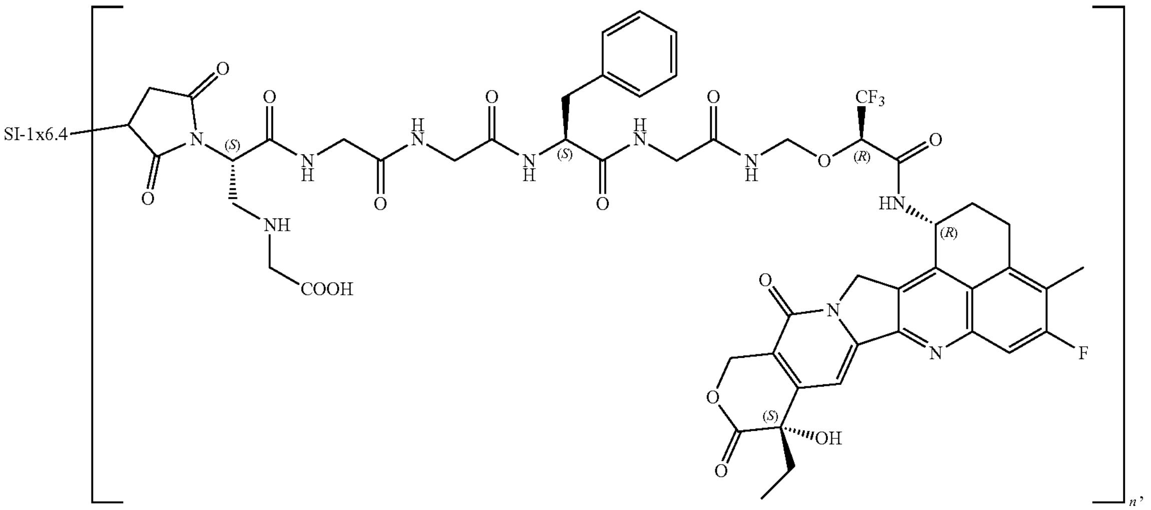
ADC-69
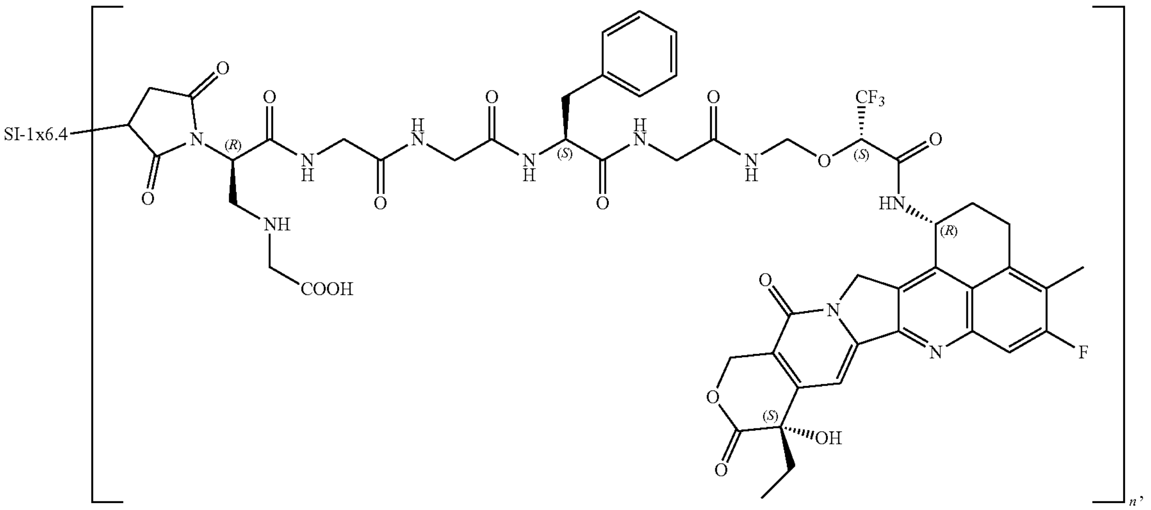

-continued
ADC-70
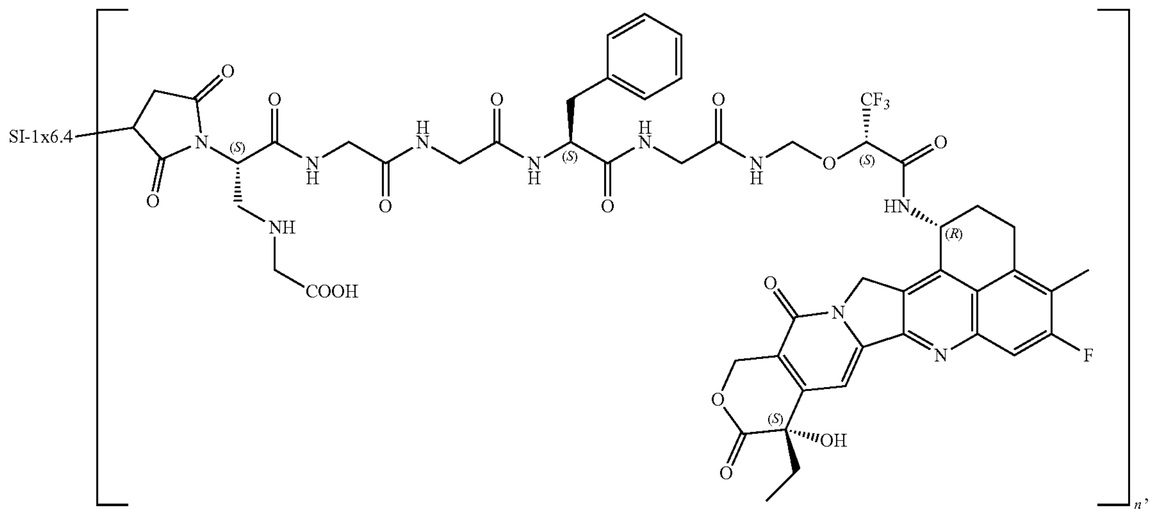
ADC-71
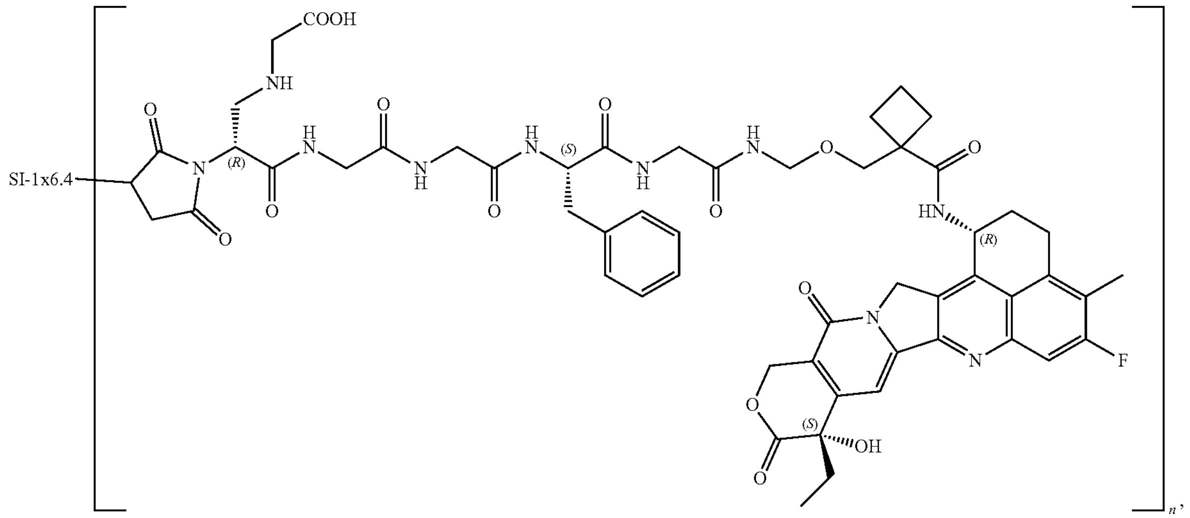
ADC-72
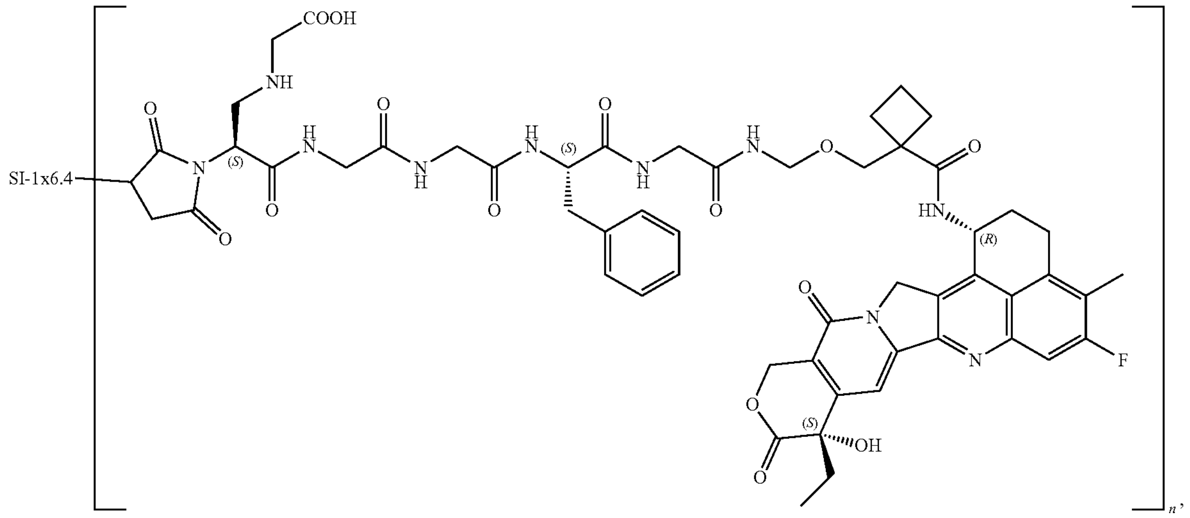

ADC-73
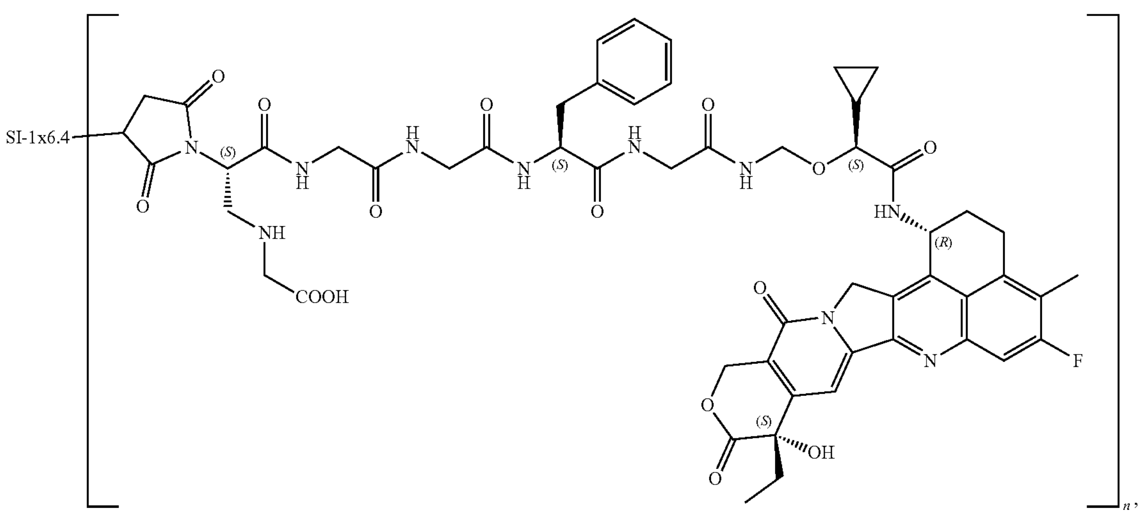
ADC-74
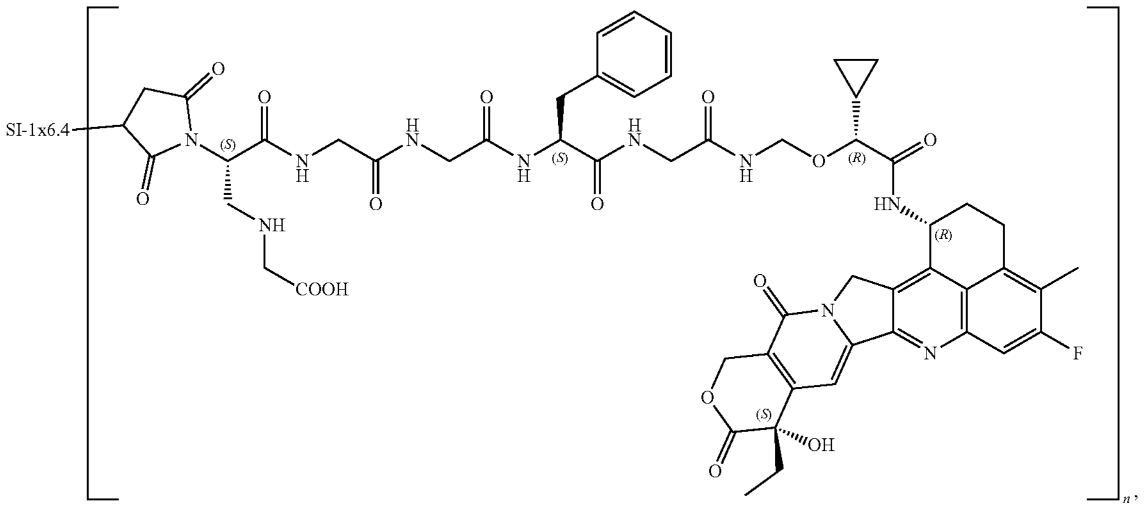
ADC-75
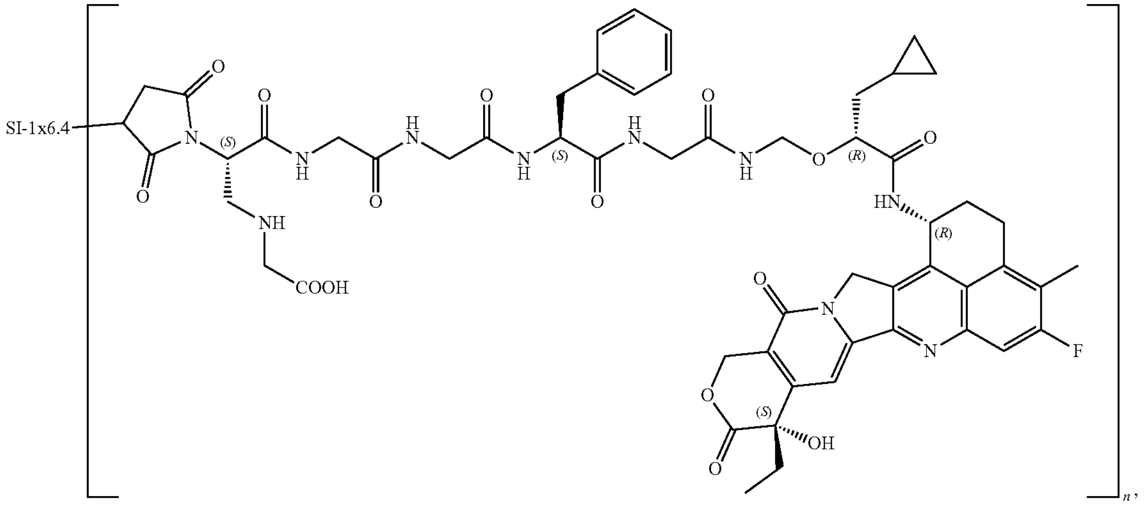

-continued
ADC-76
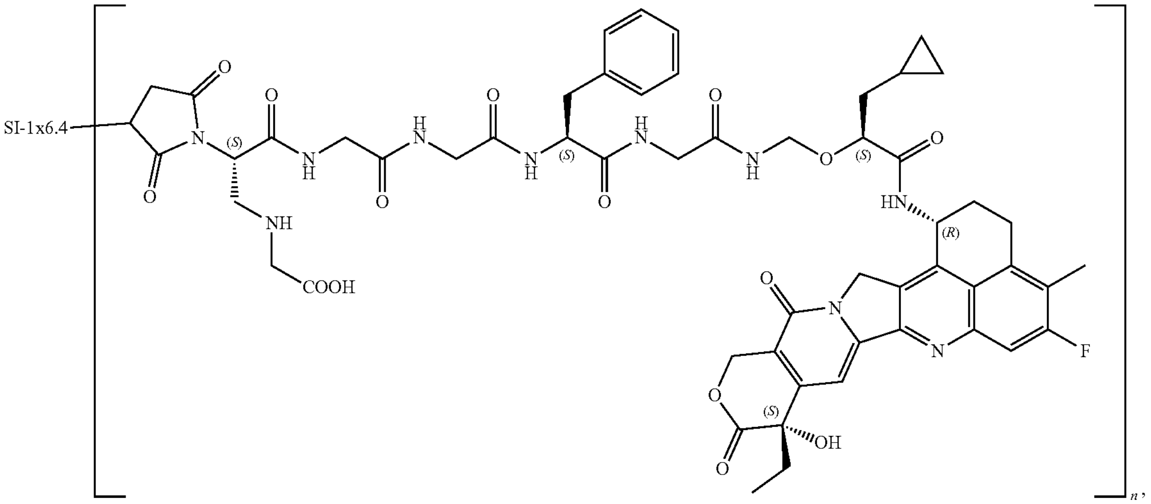
ADC-77
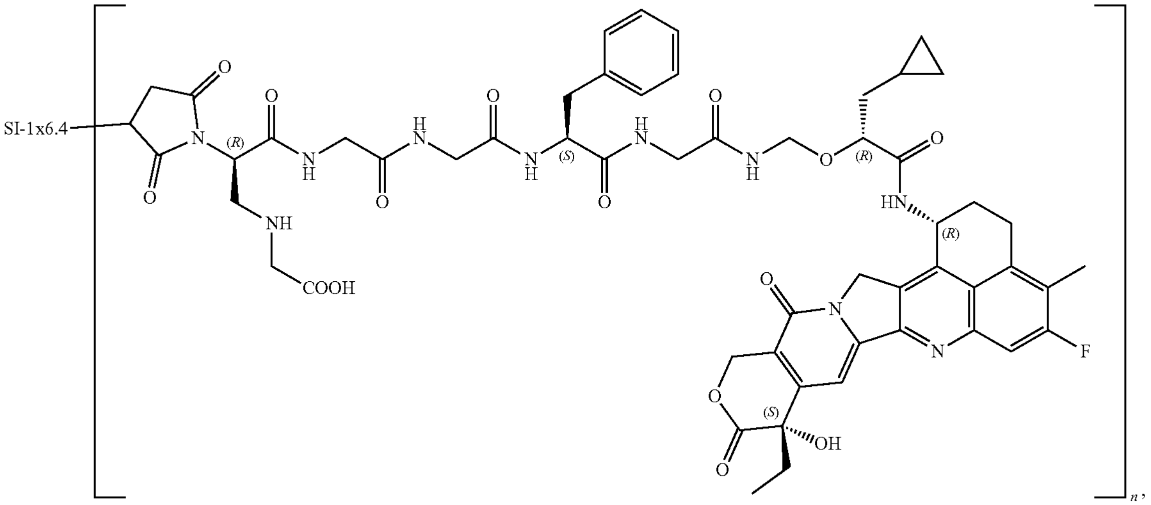
ADC-78
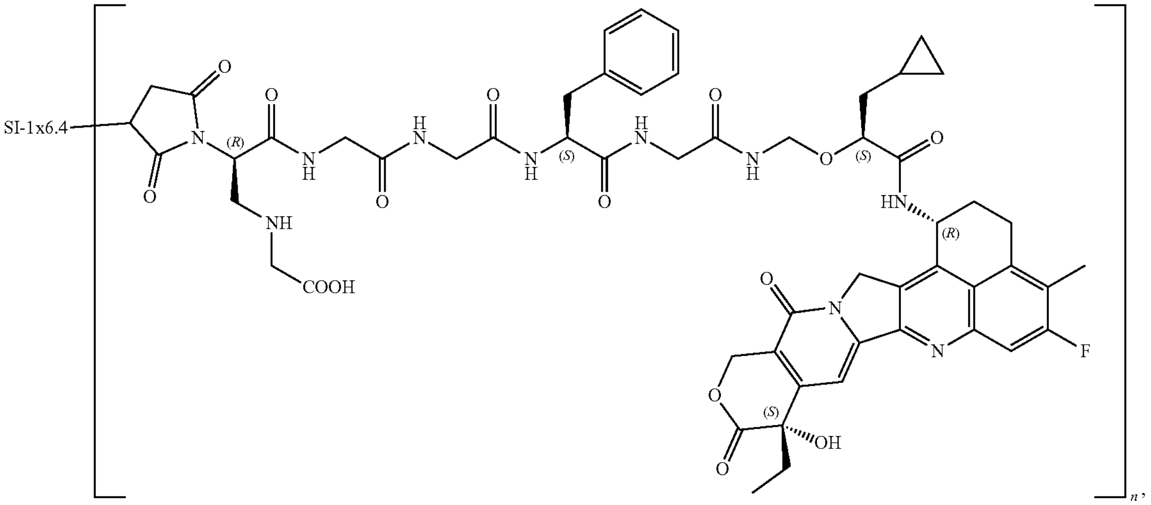

-continued
ADC-79
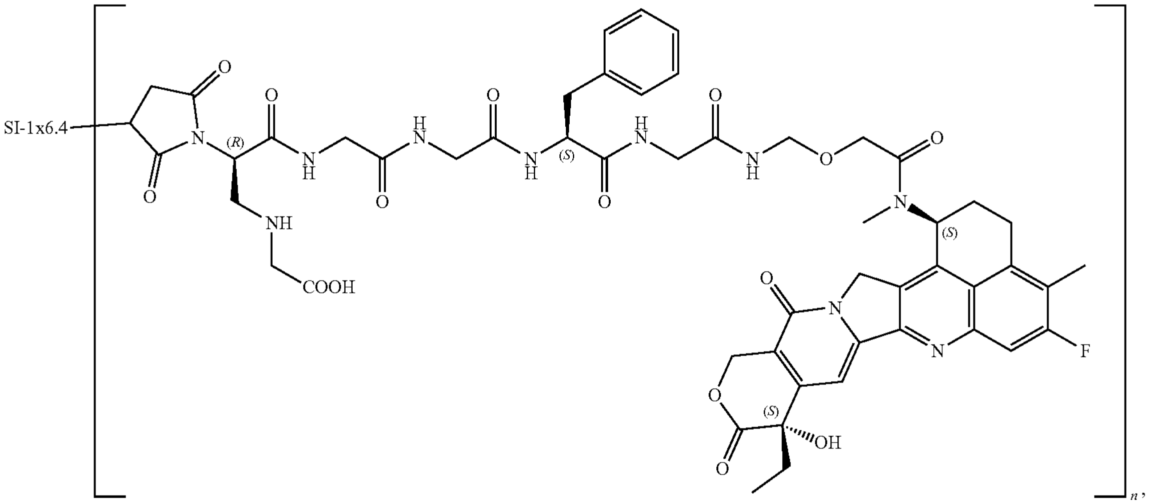
ADC-80
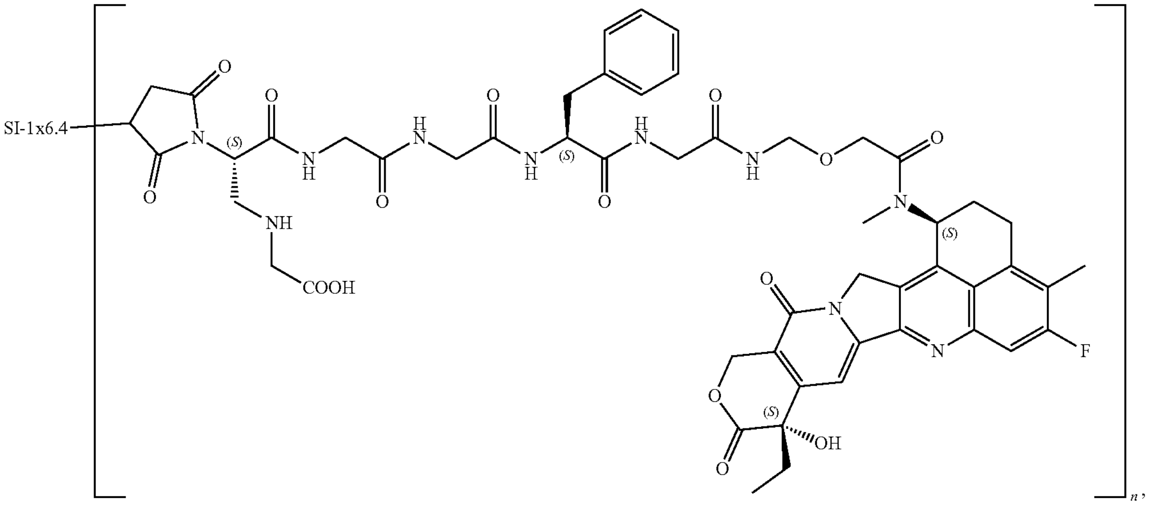
ADC-81
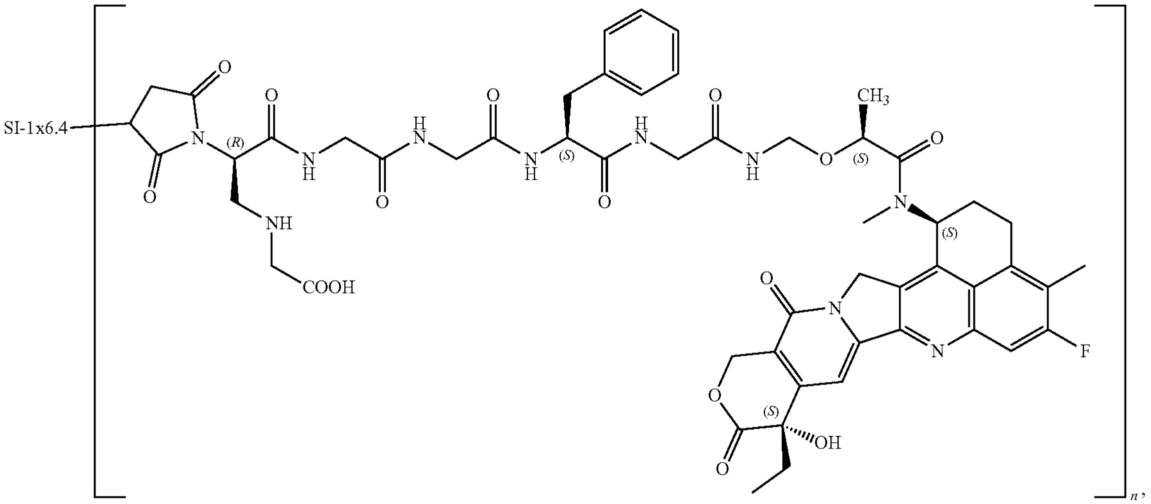

-continued
ADC-82
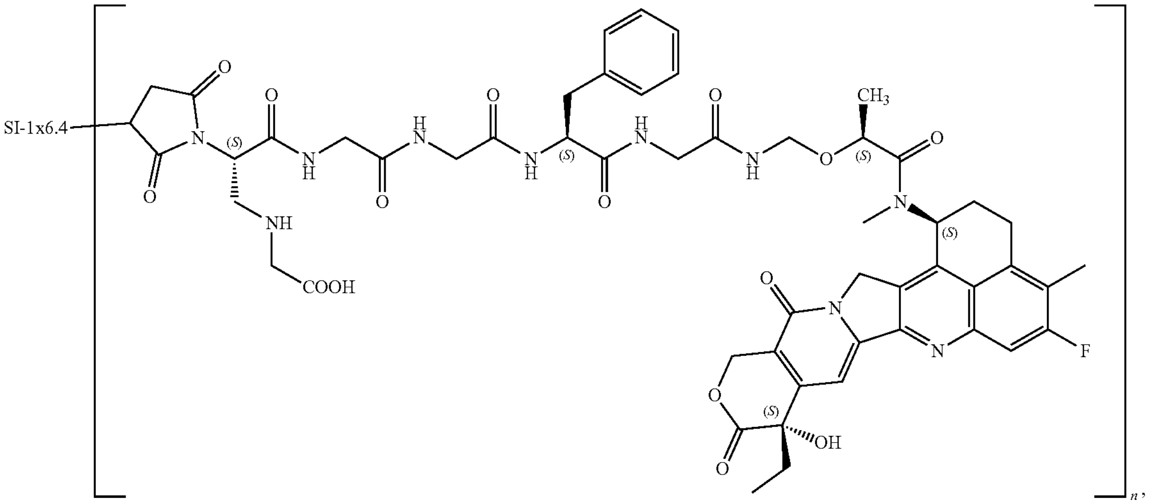
ADC-83
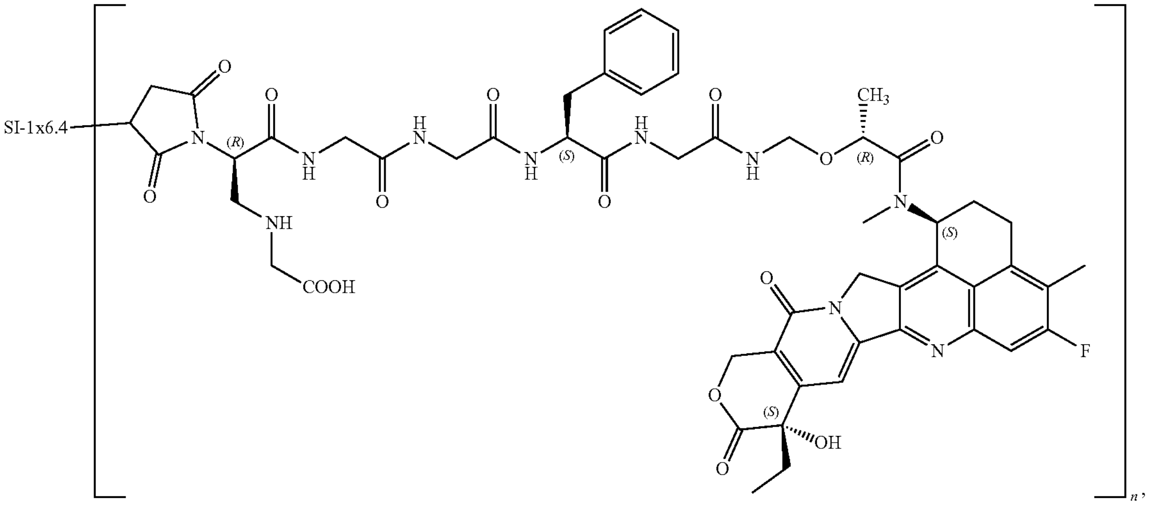
ADC-84
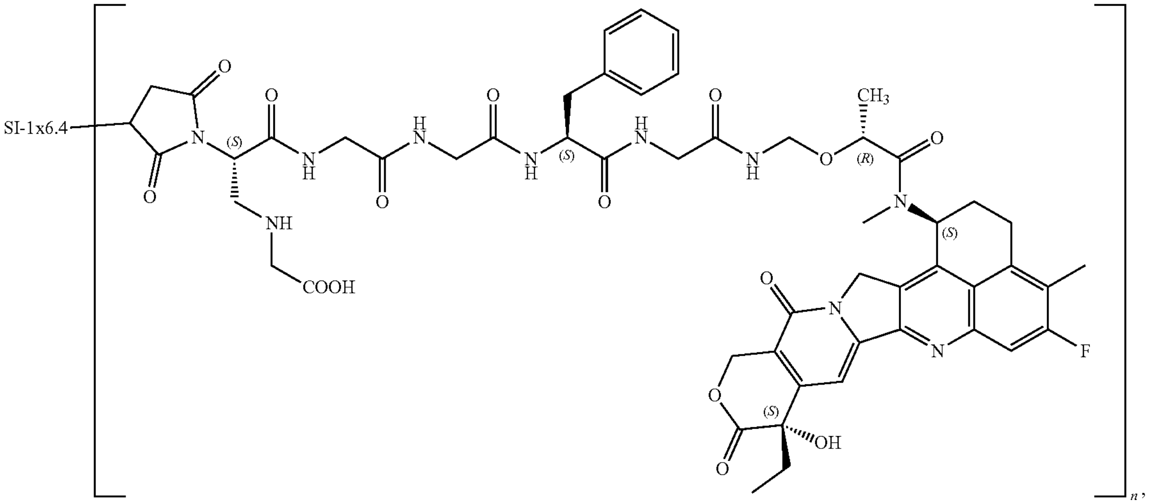

-continued
ADC-85
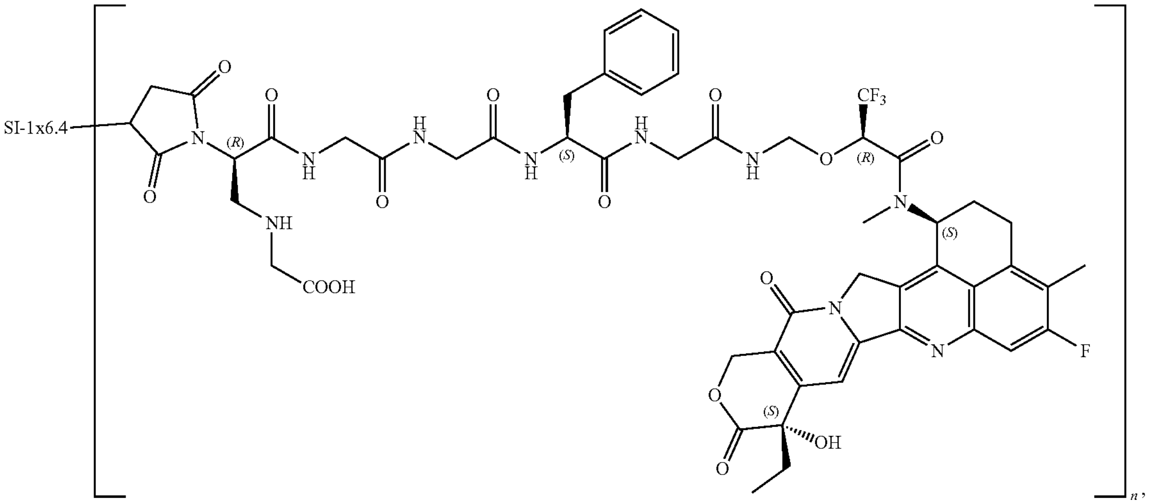
ADC-86
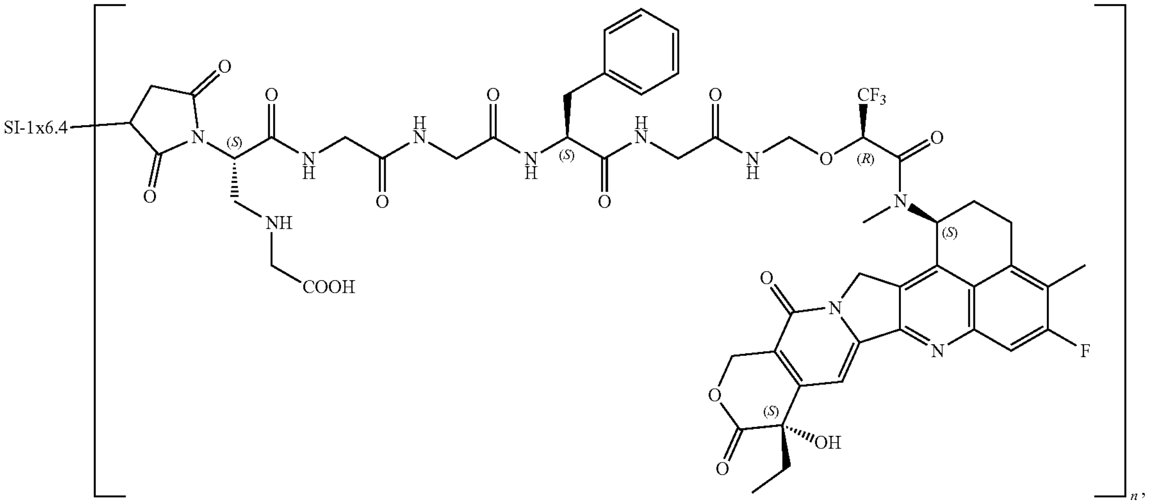
ADC-87
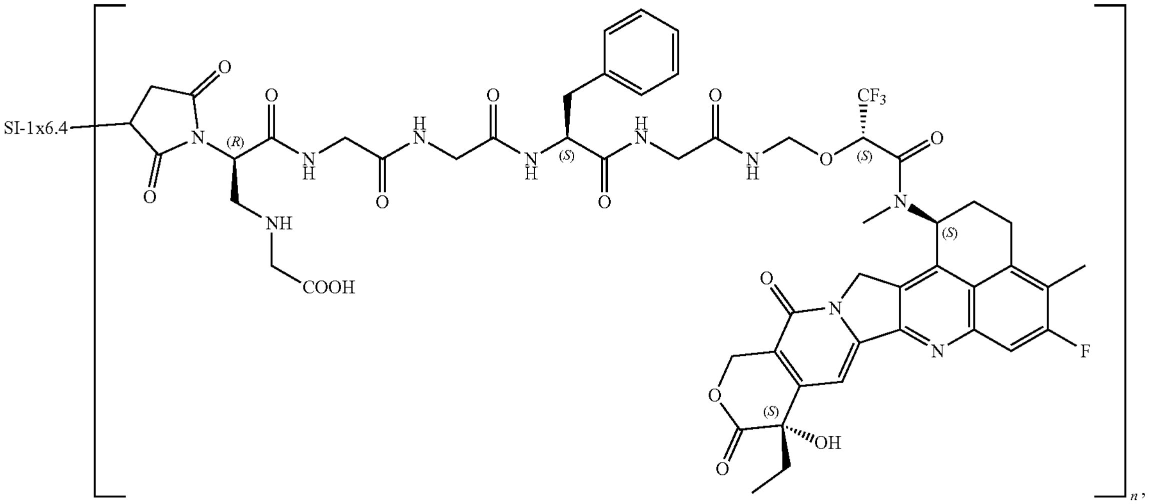

-continued
ADC-88
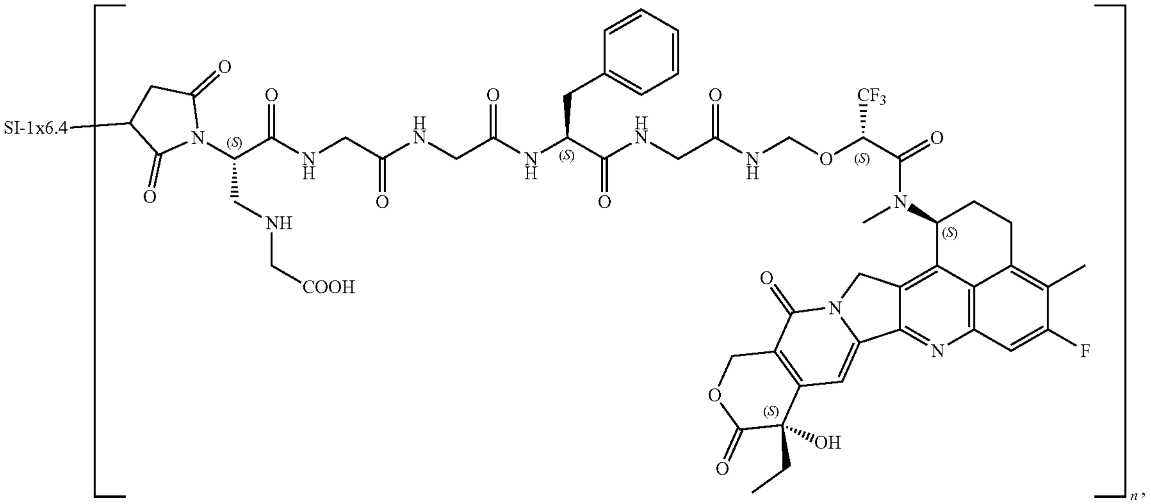
ADC-89
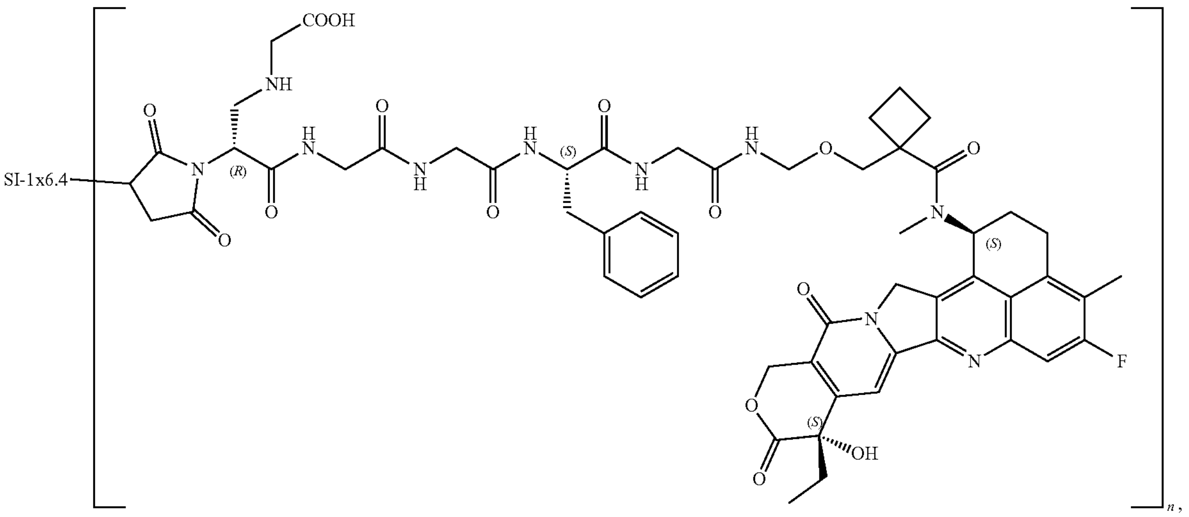
ADC-90
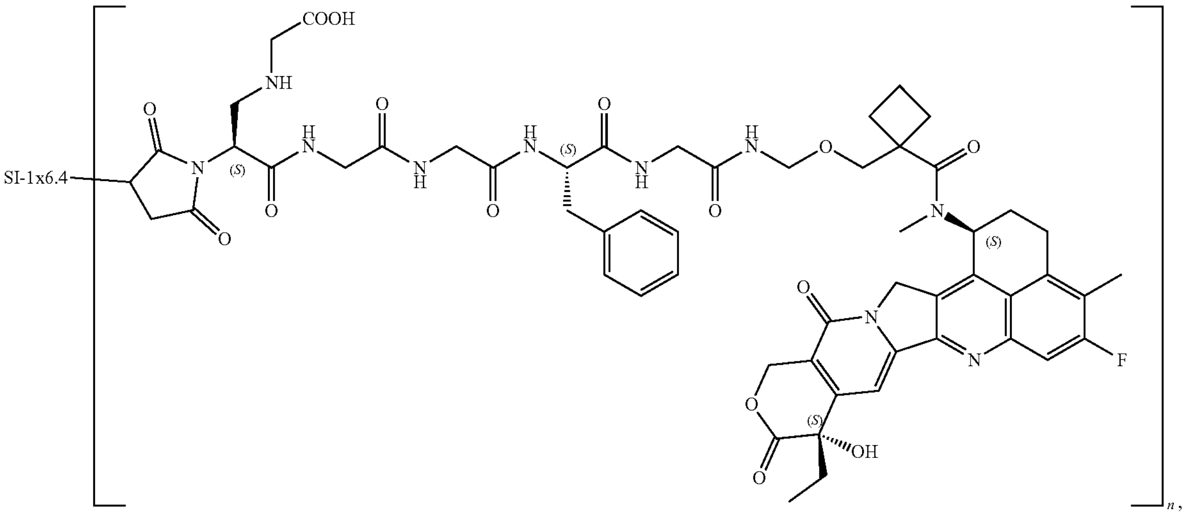

-continued
ADC-91
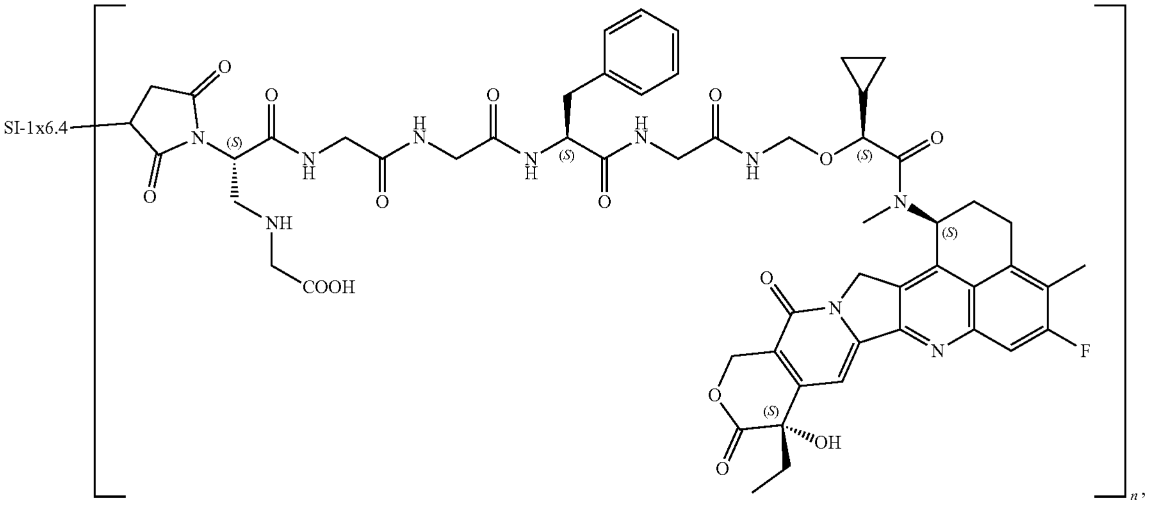
ADC-92
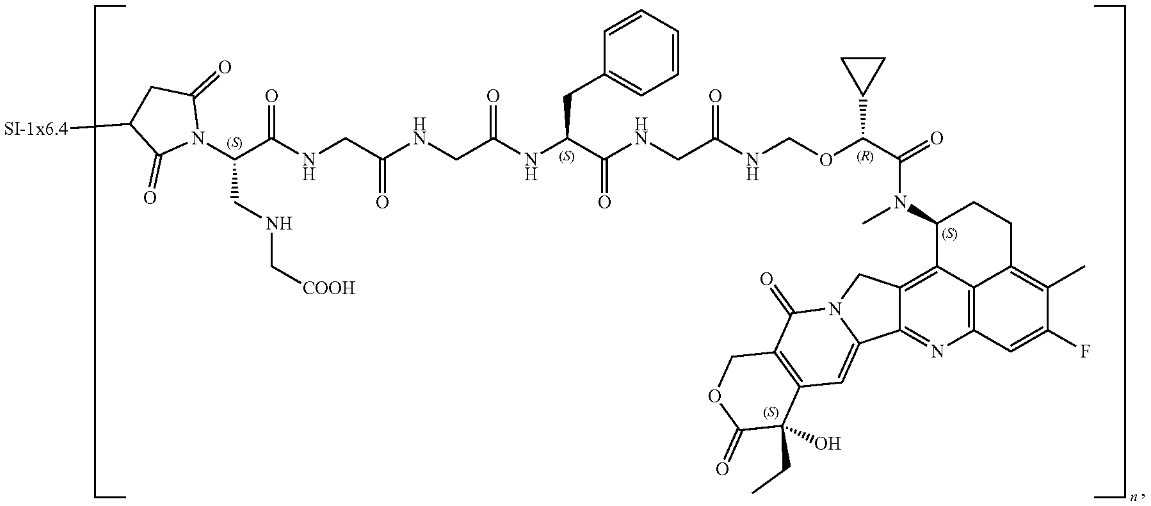
ADC-93
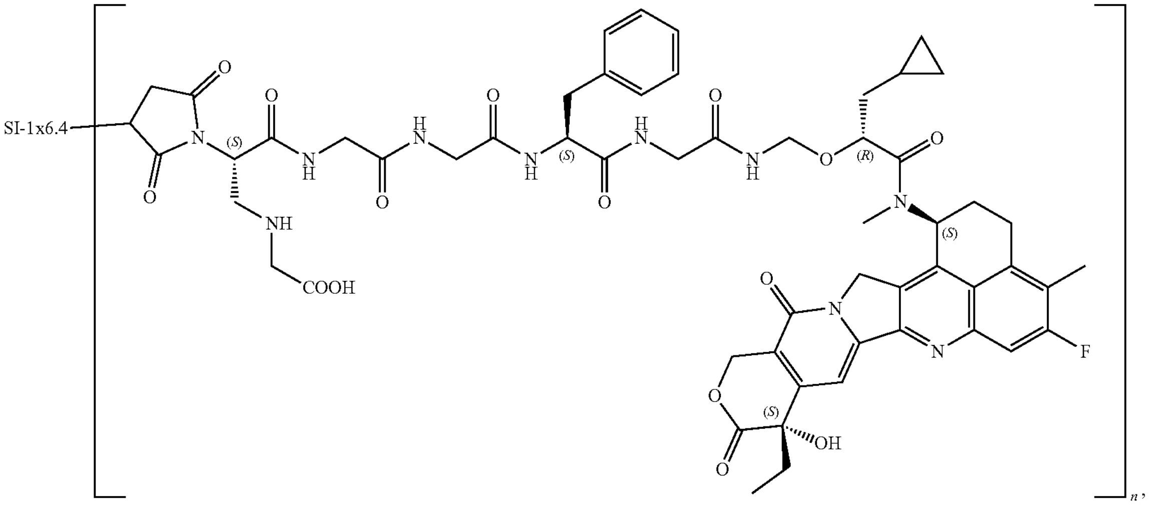

-continued
ADC-94
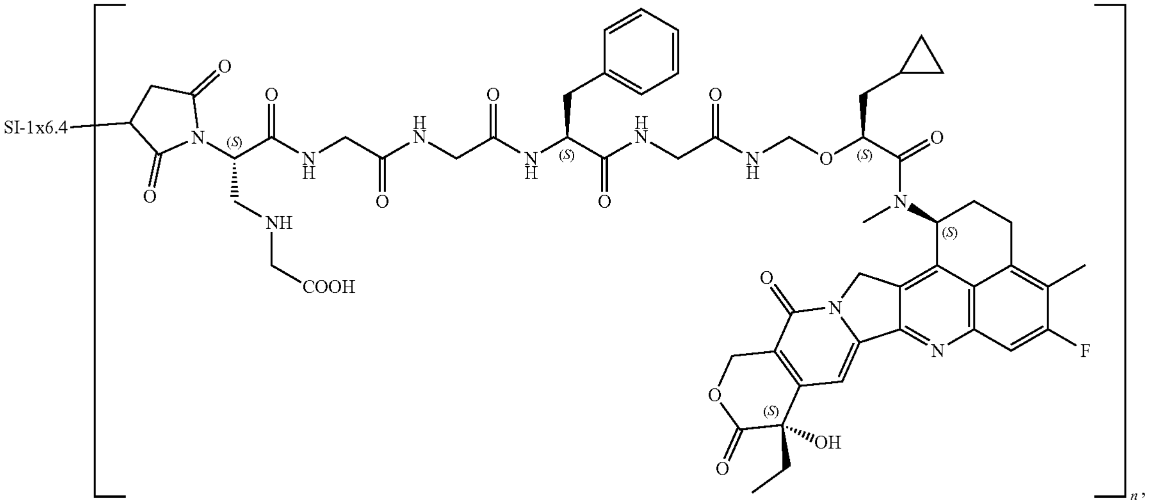
ADC-95
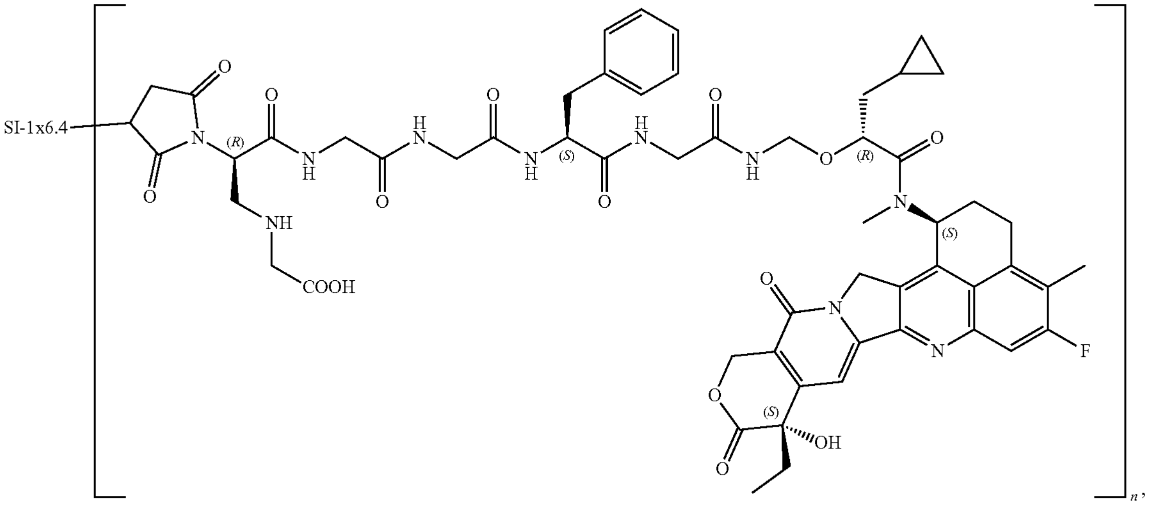
ADC-96
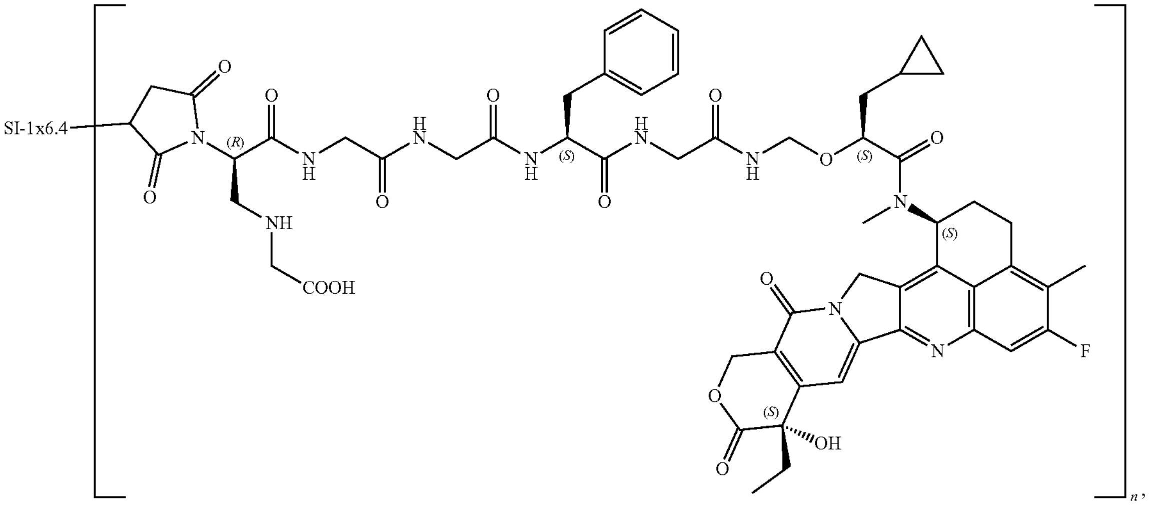

-continued
ADC-97
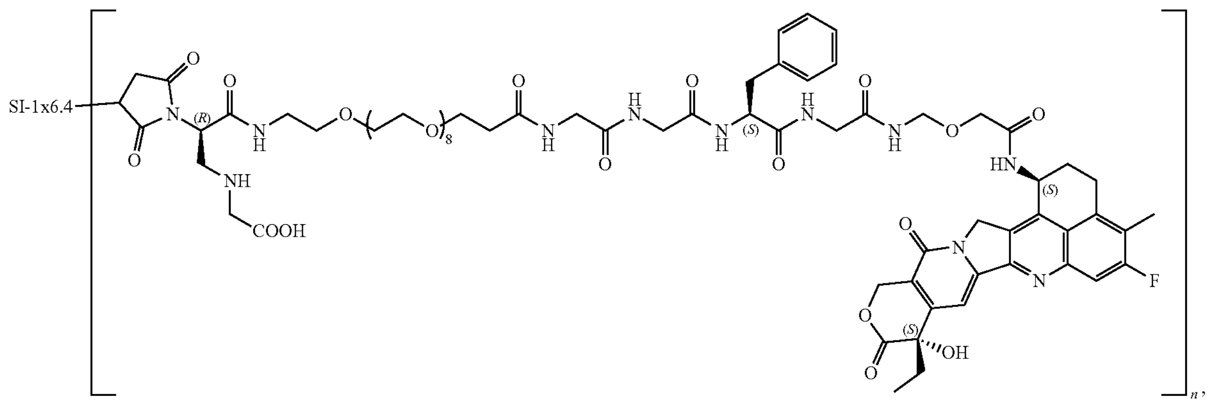
ADC-98
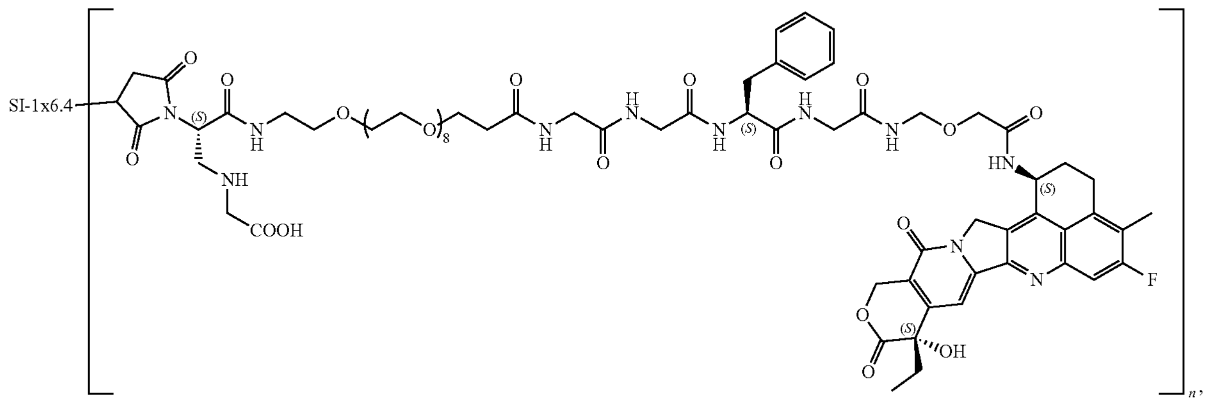
ADC-99
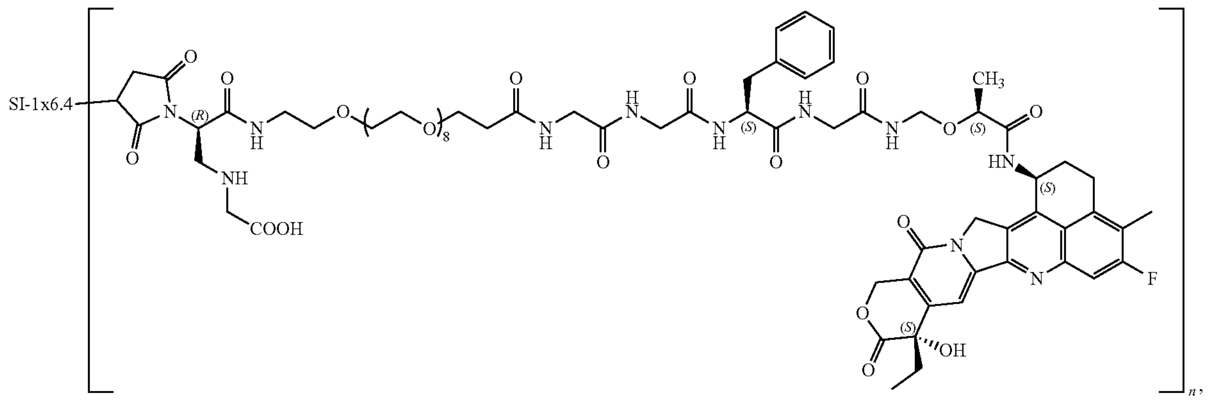

-continued
ADC-100
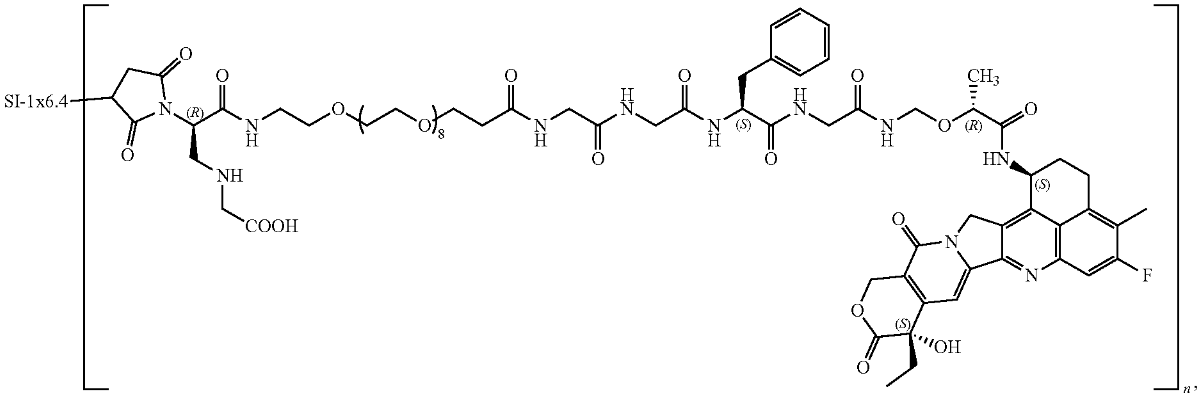
ADC-101
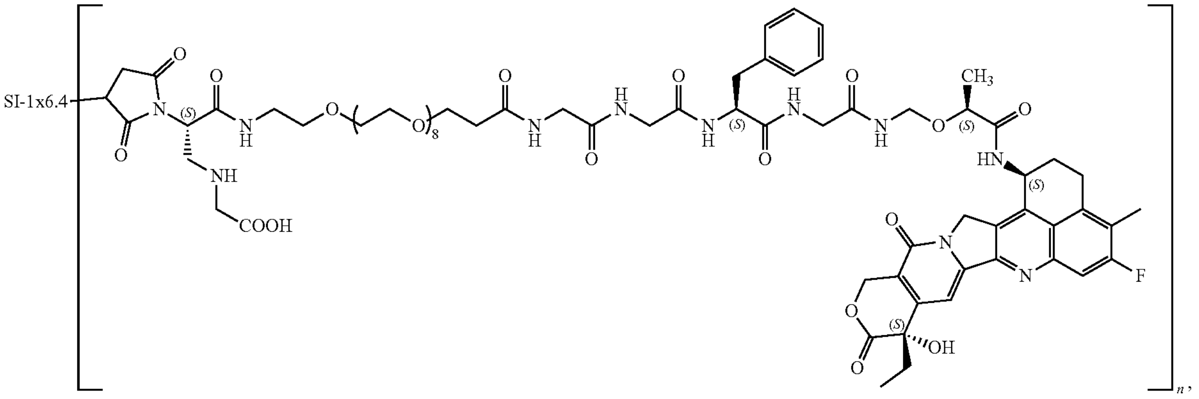
ADC-102
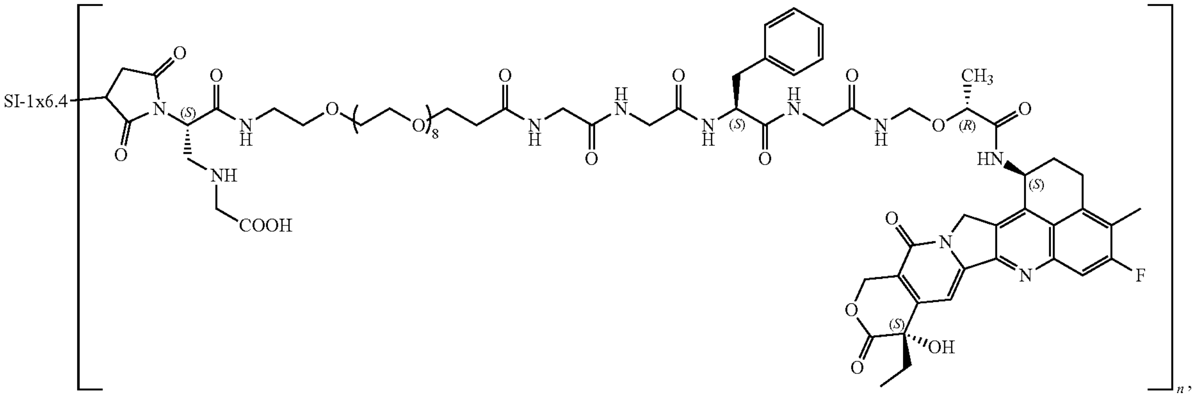

-continued
ADC-103
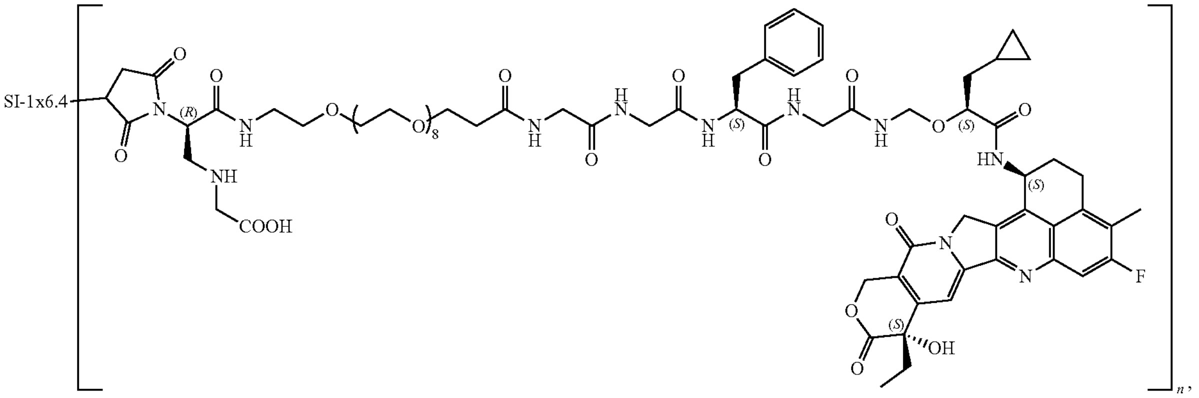
ADC-104
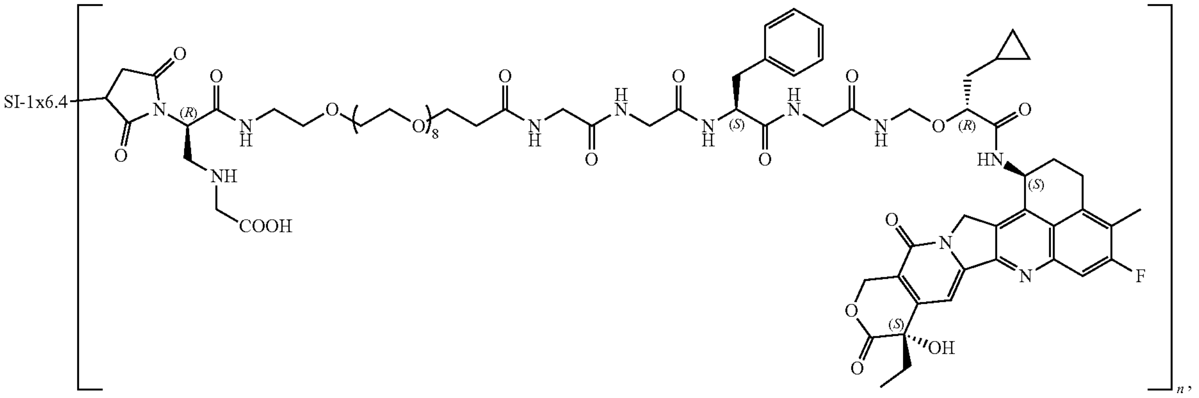
ADC-105
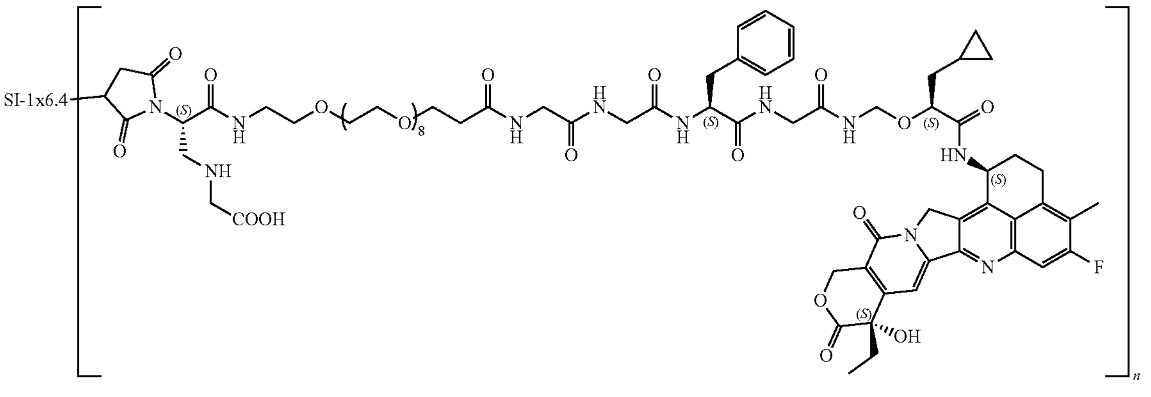
or

-continued

ADC-106

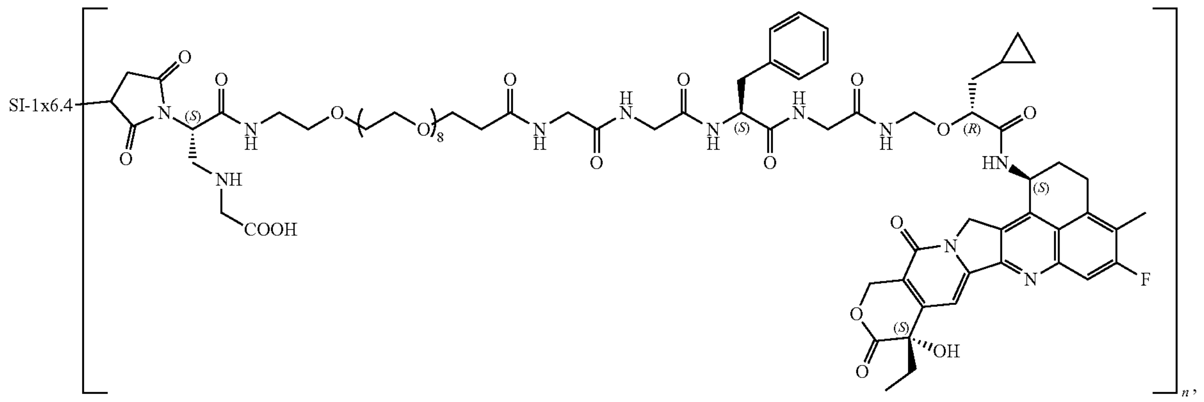

wherein:

SI-1×6.4 is a bispecific antibody or its antigen-binding fragment simultaneously targeting EGFR and HER3;

n is selected from the integers 1-10 (i.e., 1, 2, 3, 4, 5, 6, 7, 8, 9, or 10).

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures or succinimide open-ring structures thereof or isomers thereof,

ADC-107

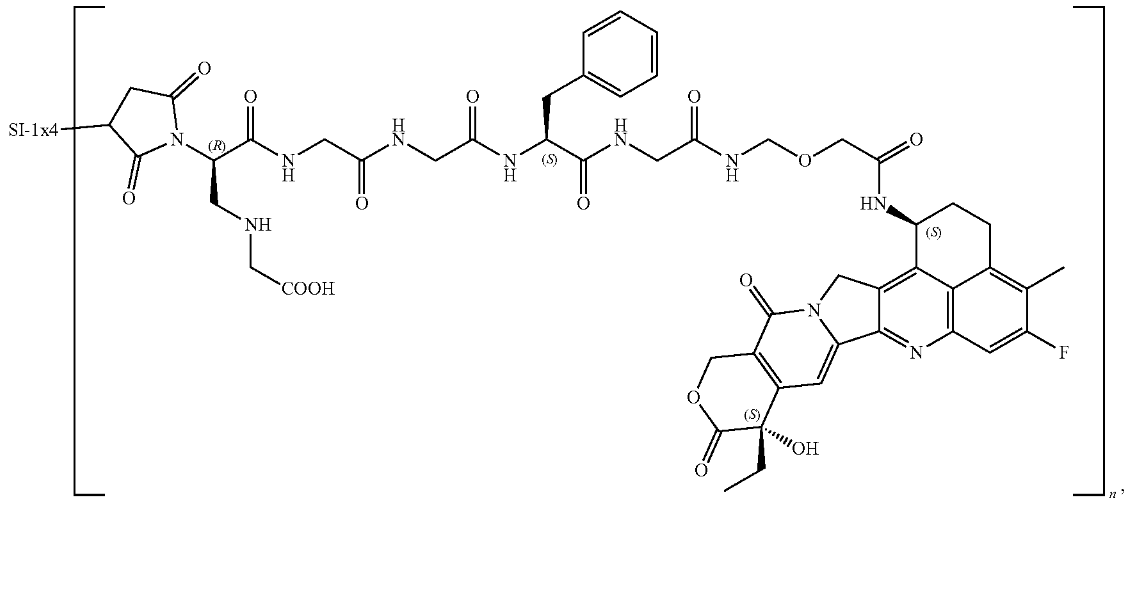

-continued
ADC-108
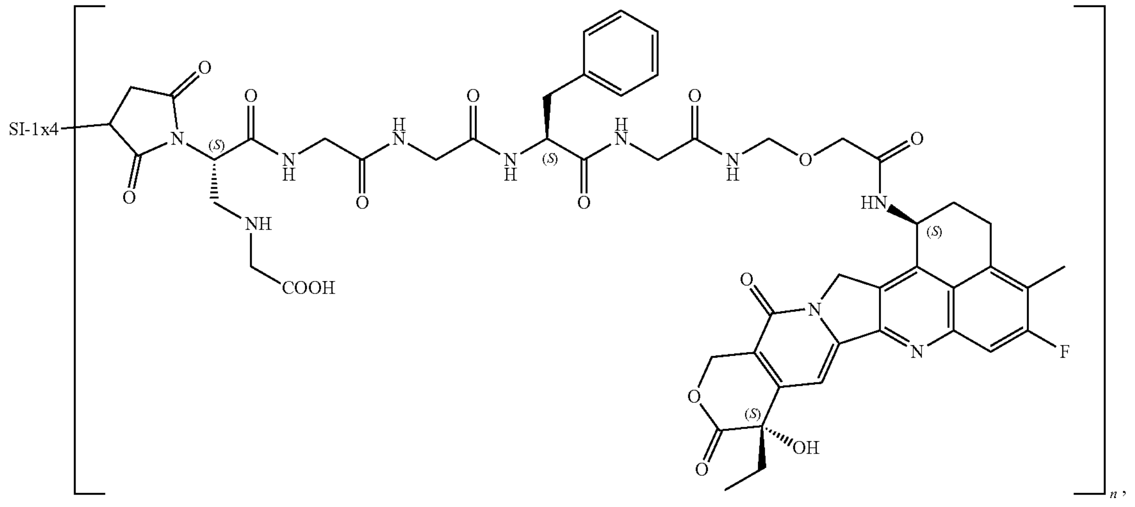
ADC-109
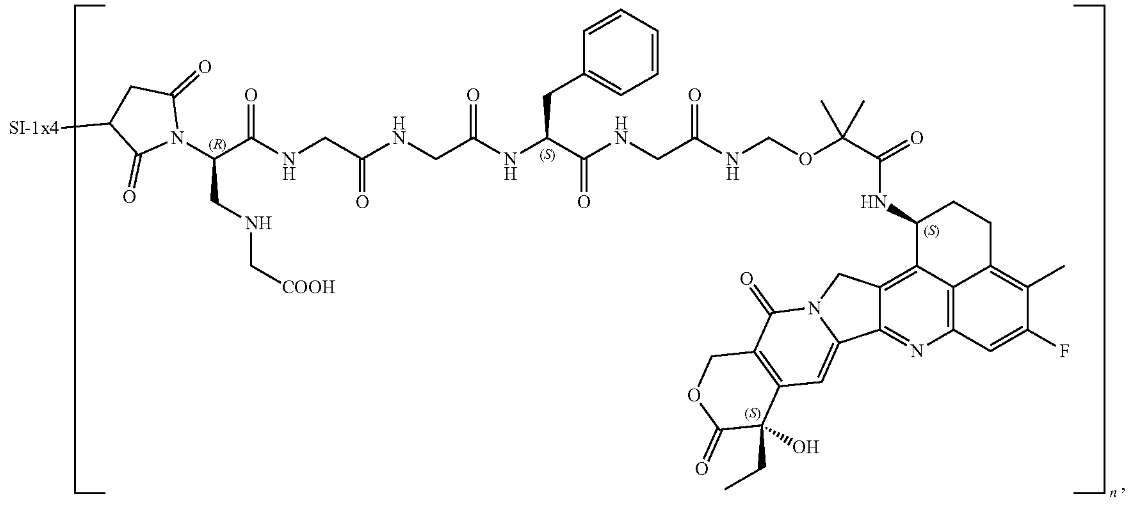
ADC-110
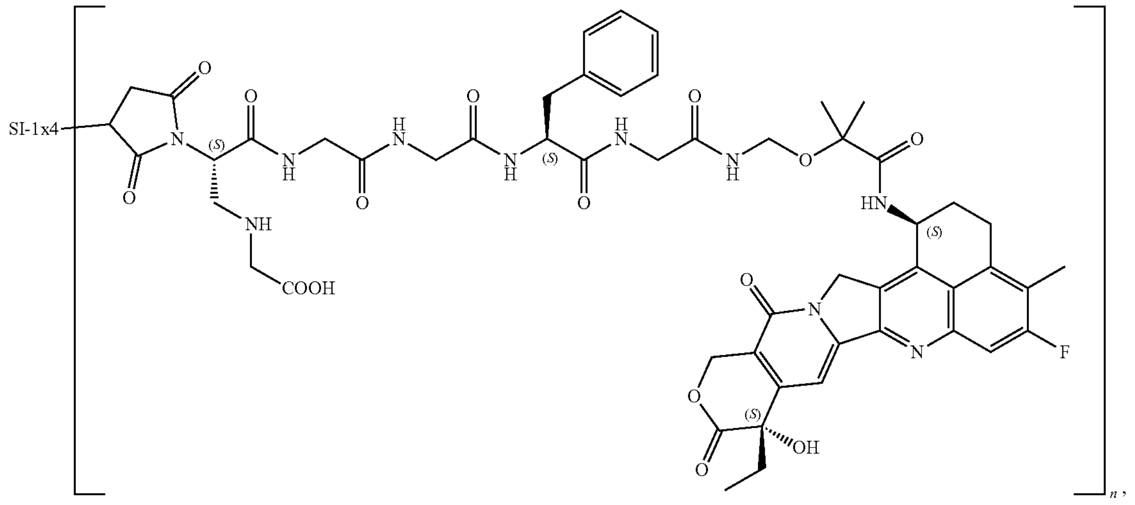

-continued
ADC-111
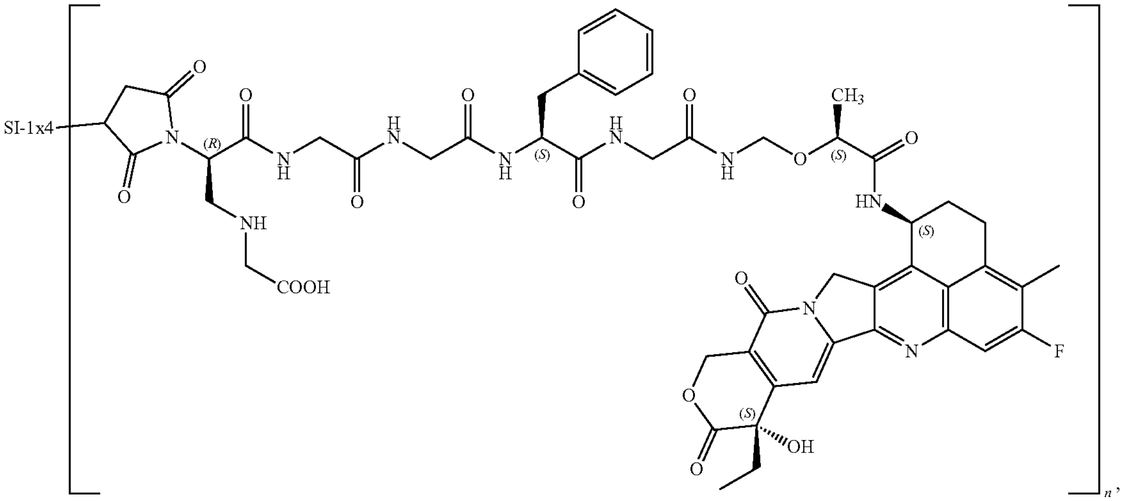
ADC-111a
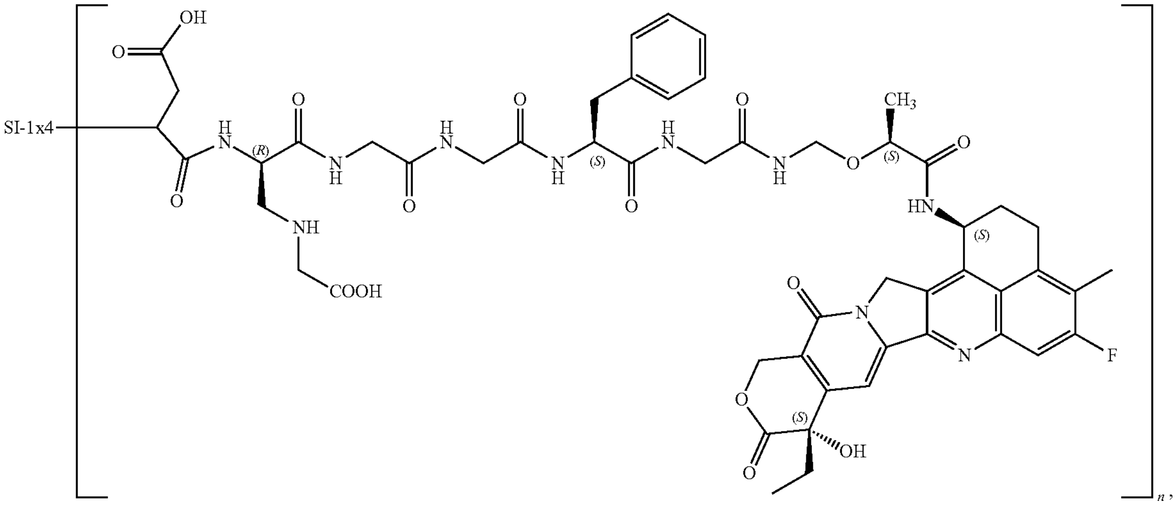
ADC-111b
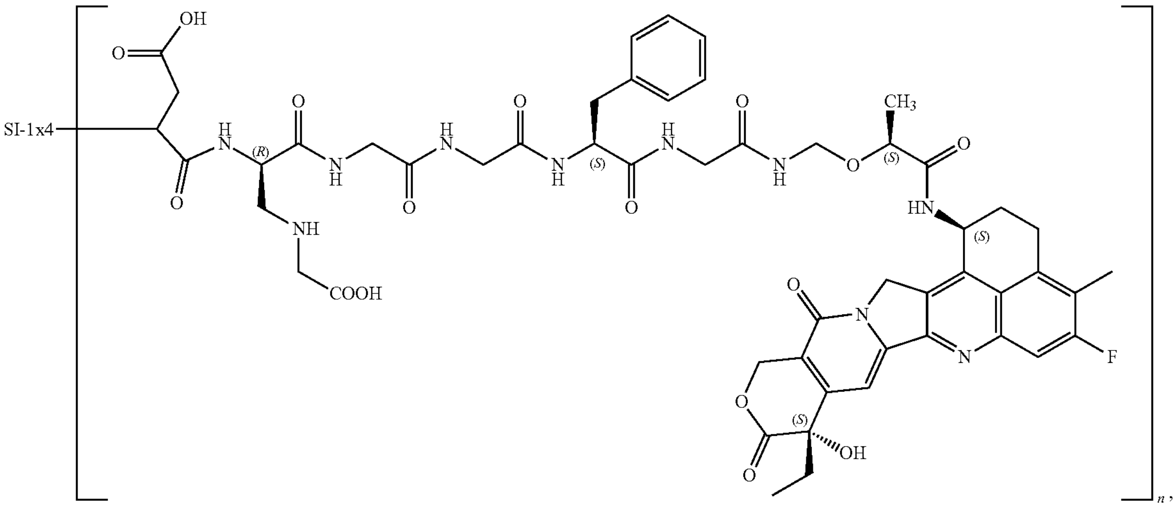

-continued
ADC-112
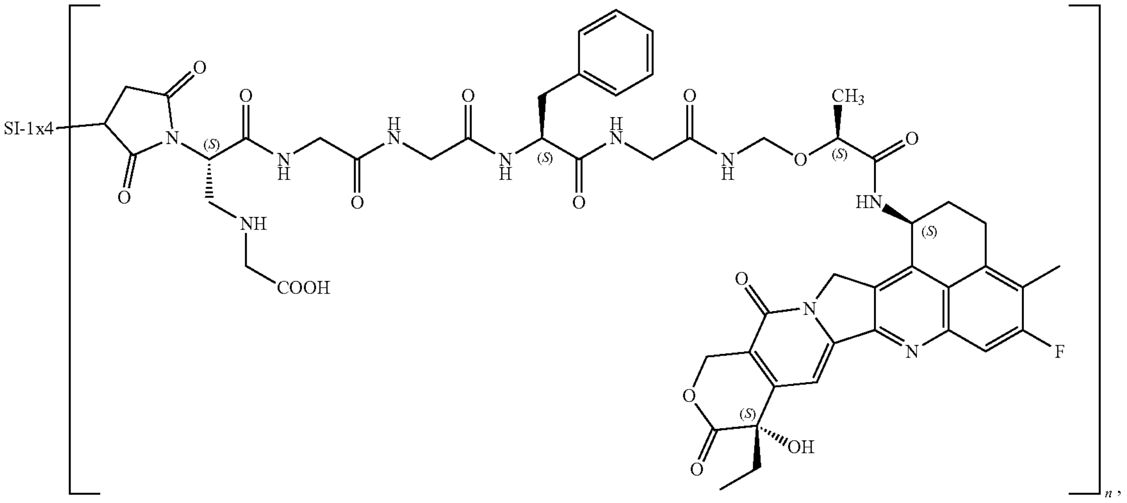
ADC-112a
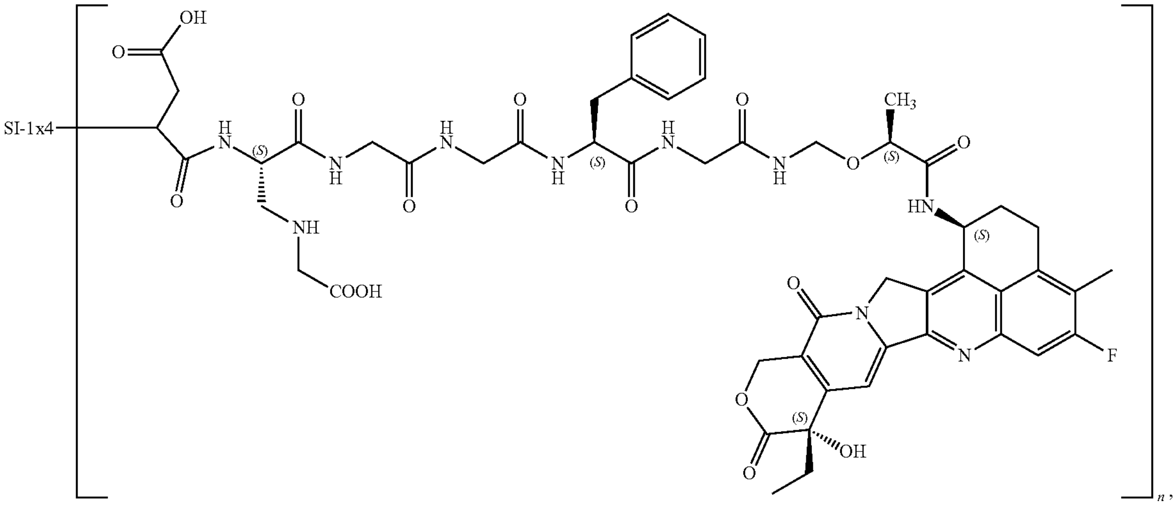
ADC-112b
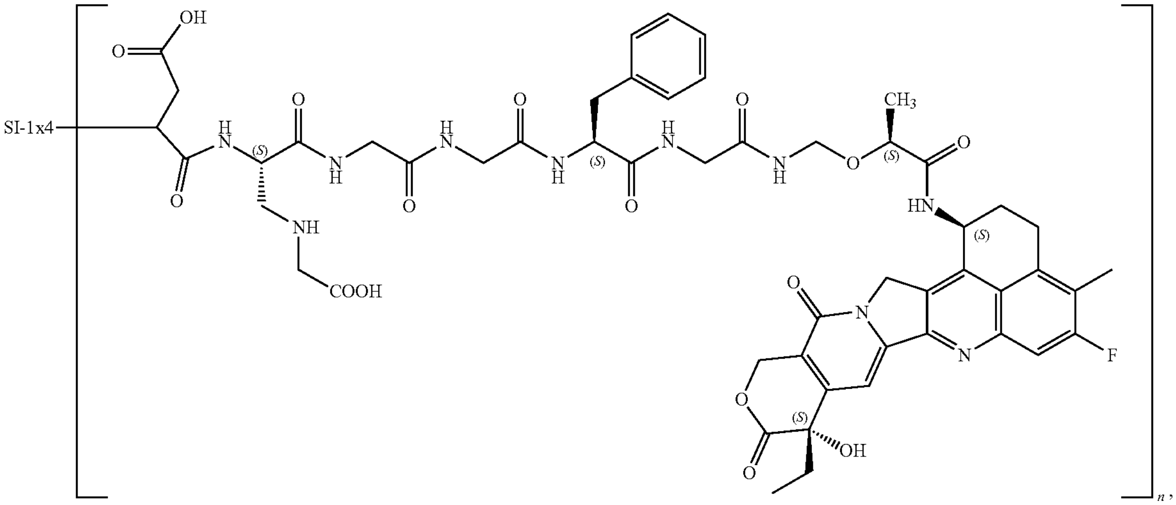

-continued
ADC-113
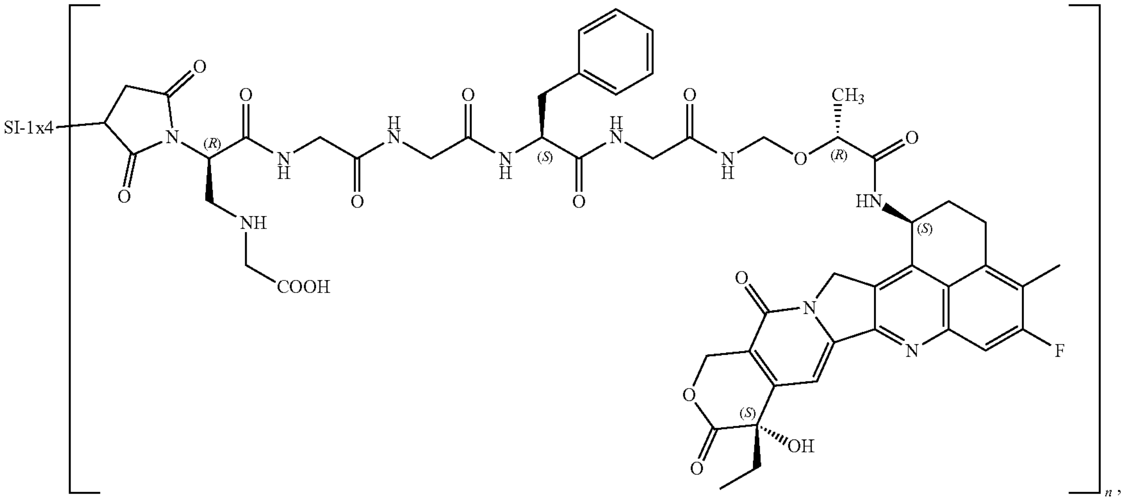
ADC-113a
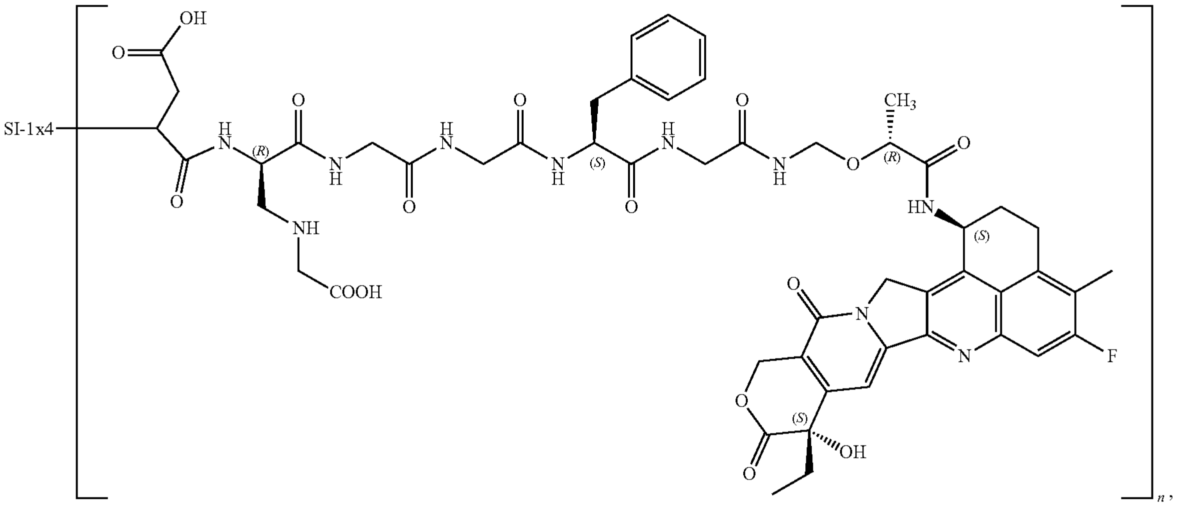
ADC-113b
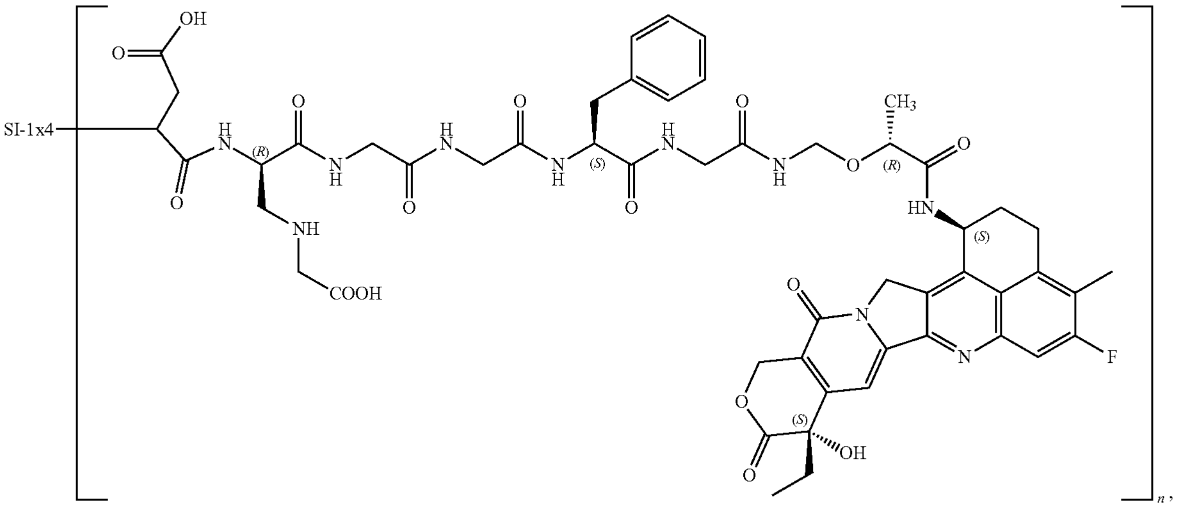

-continued
ADC-114
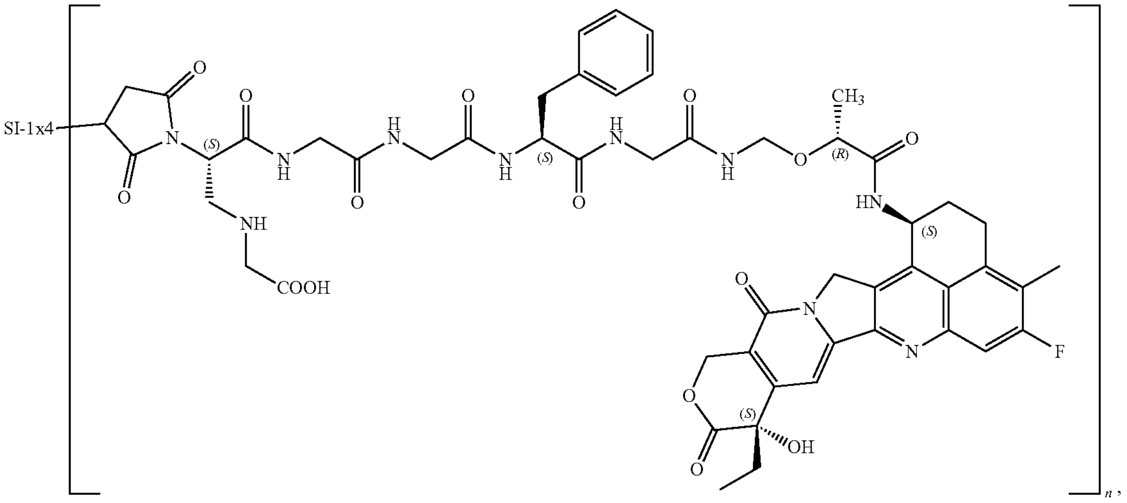
ADC-114a
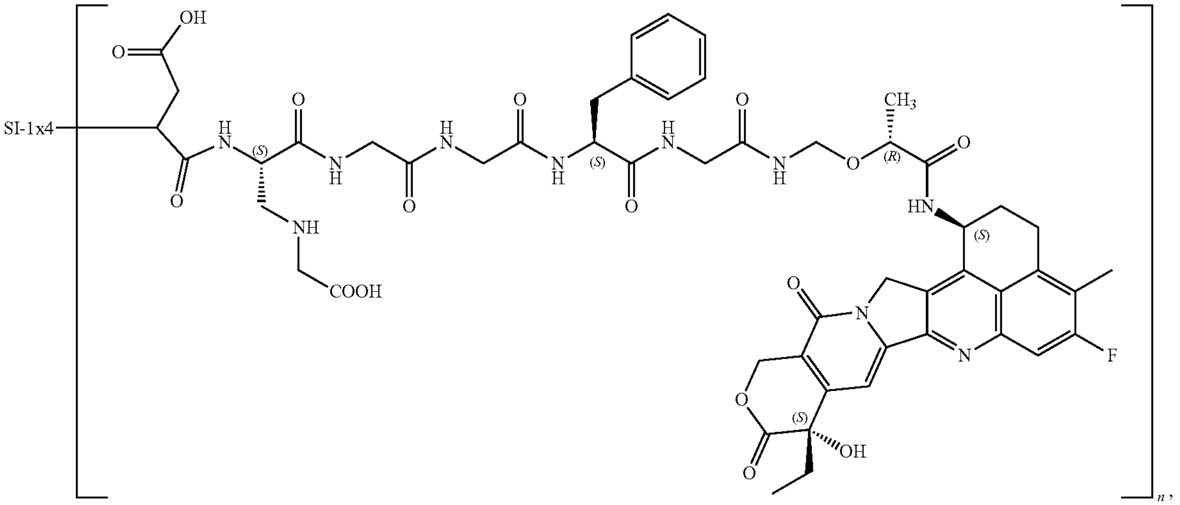
ADC-114b
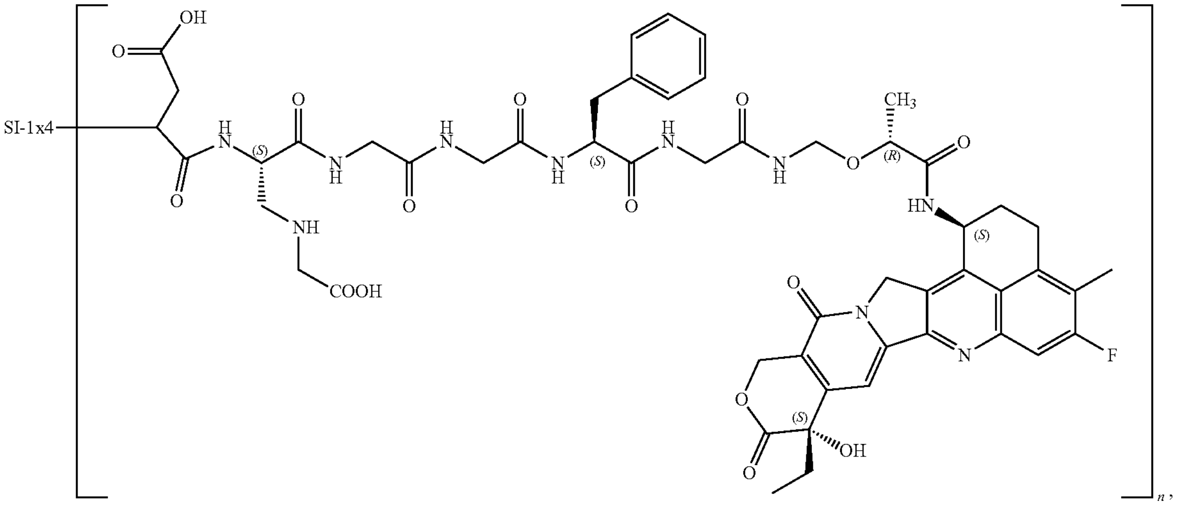

-continued
ADC-115
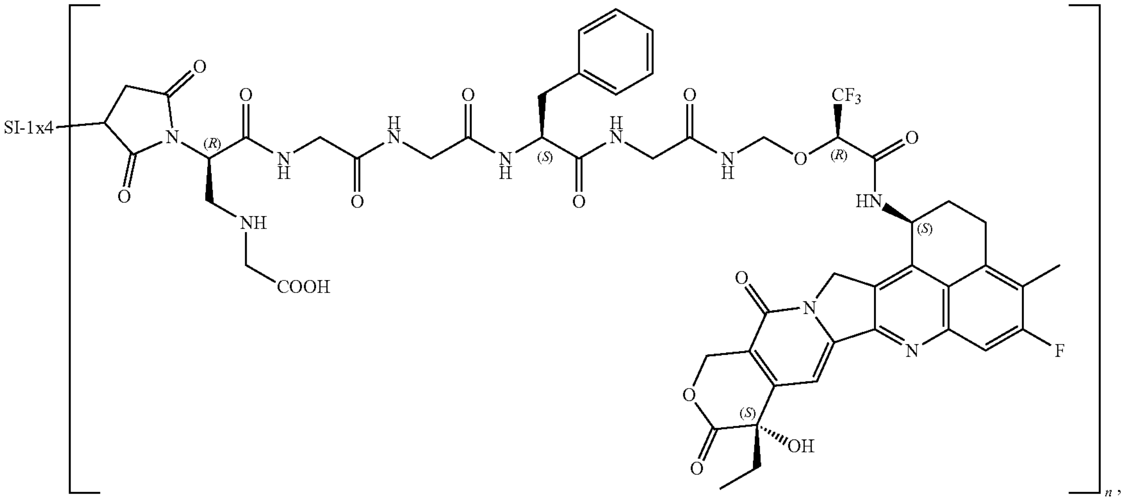
ADC-116
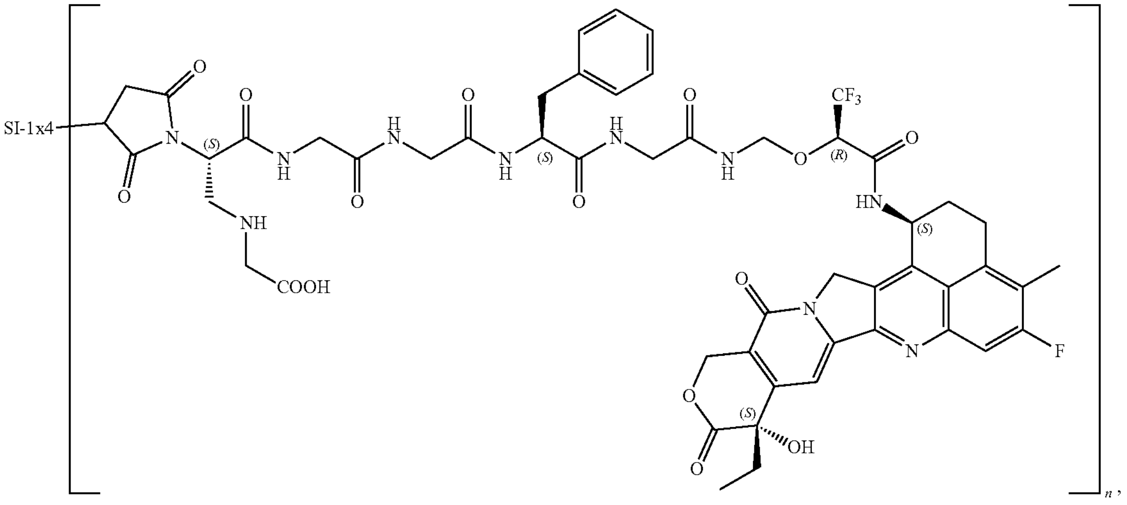
ADC-117
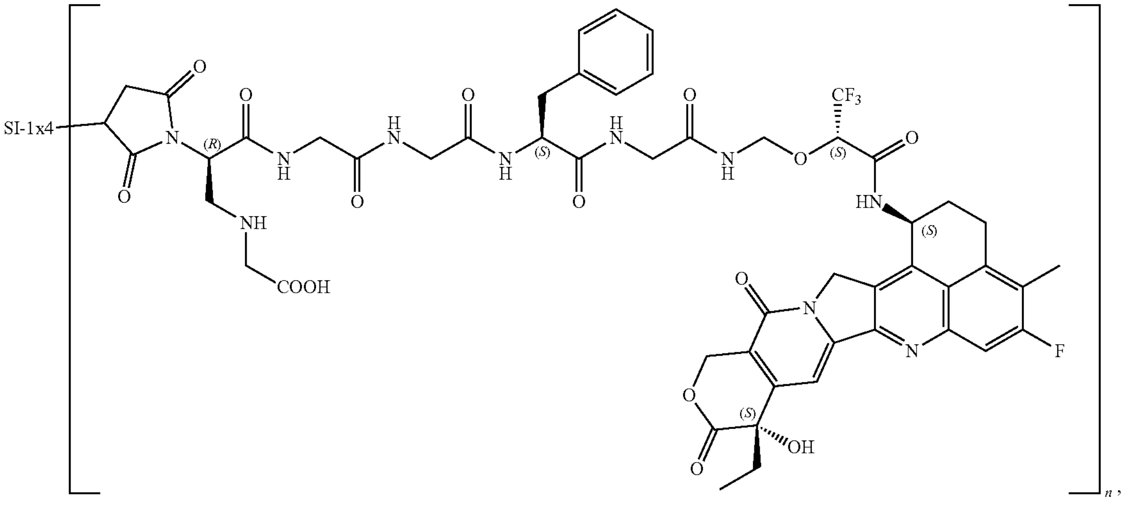

-continued
ADC-118
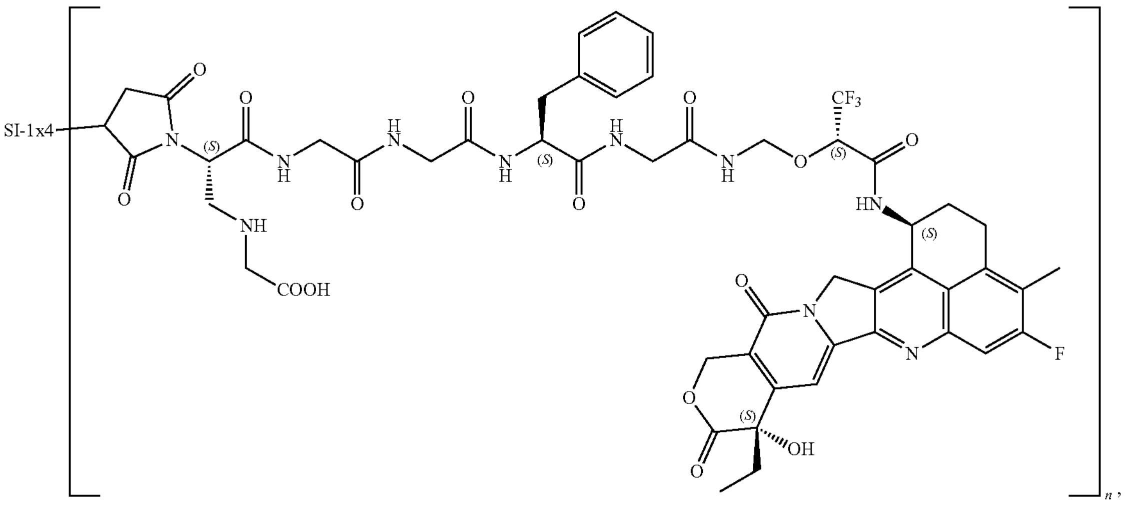
ADC-119
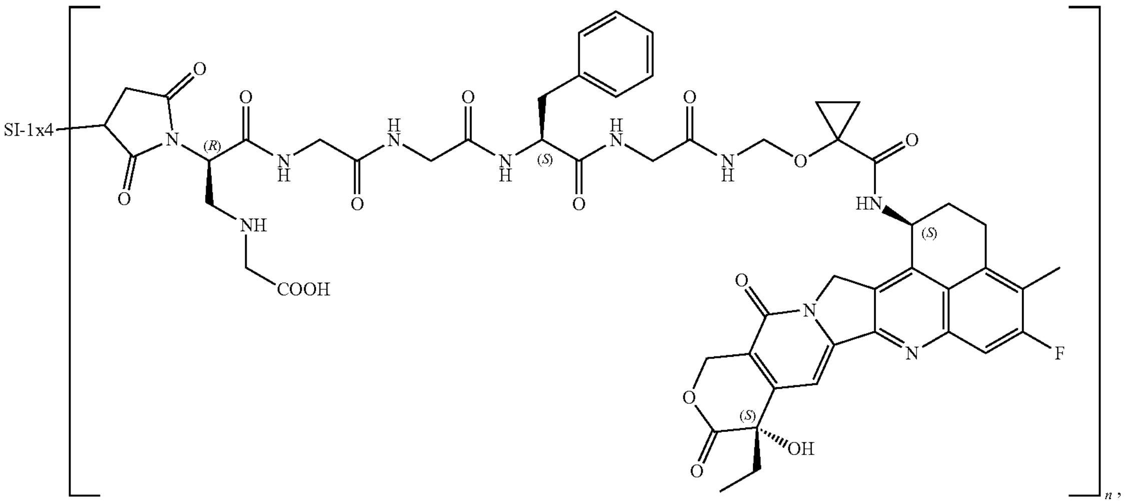
ADC-120
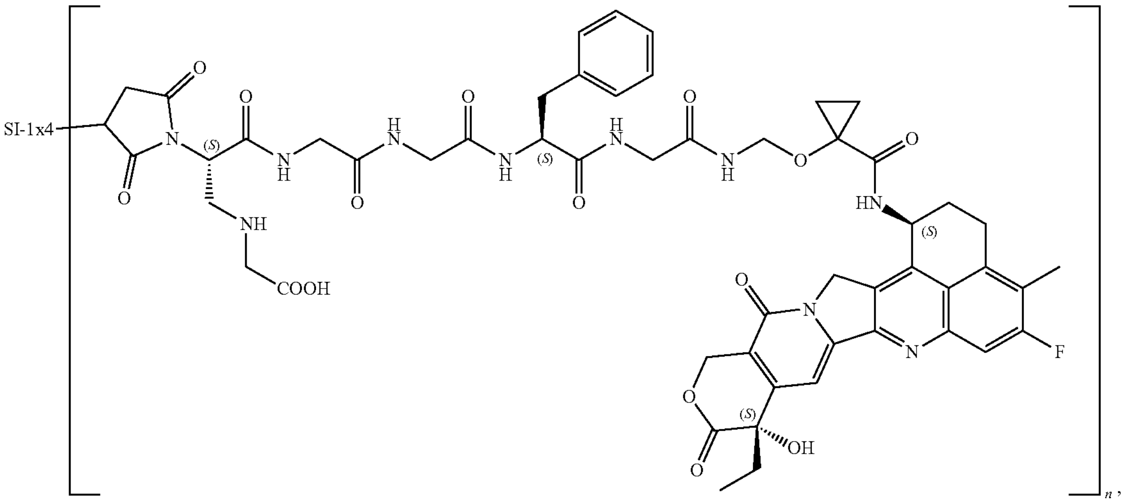

-continued
ADC-121
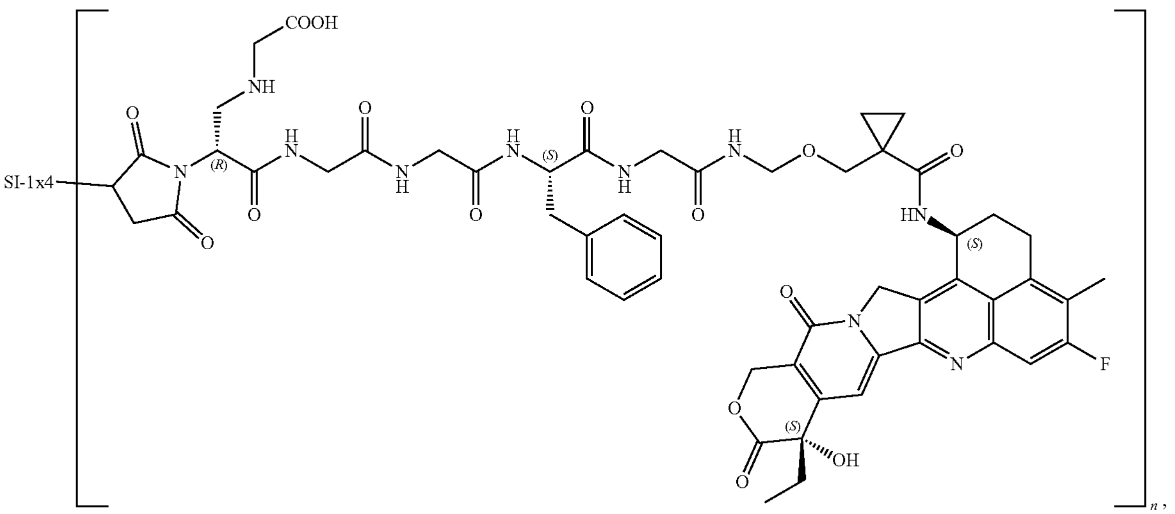
ADC-122
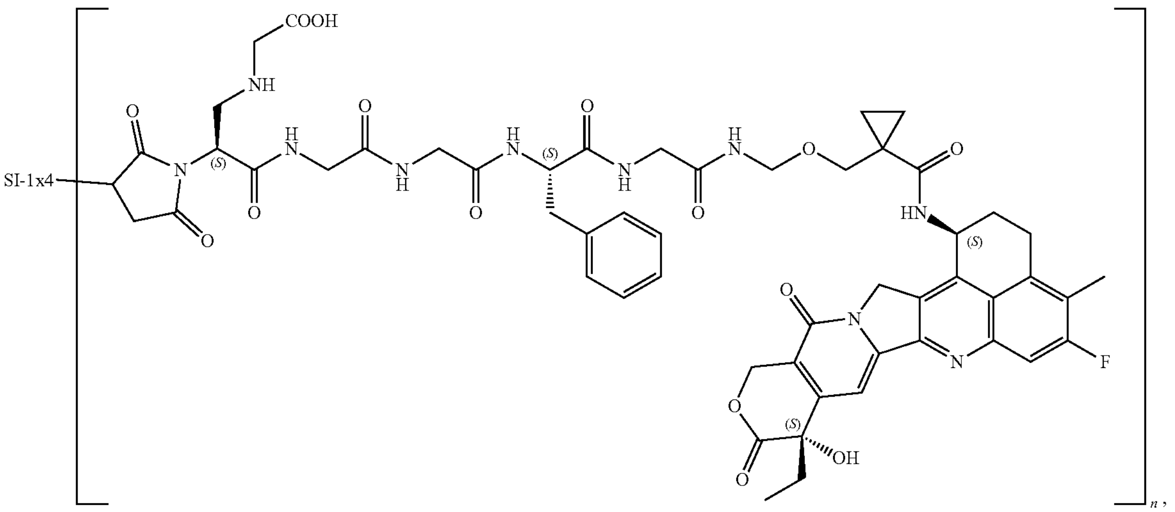
ADC-123
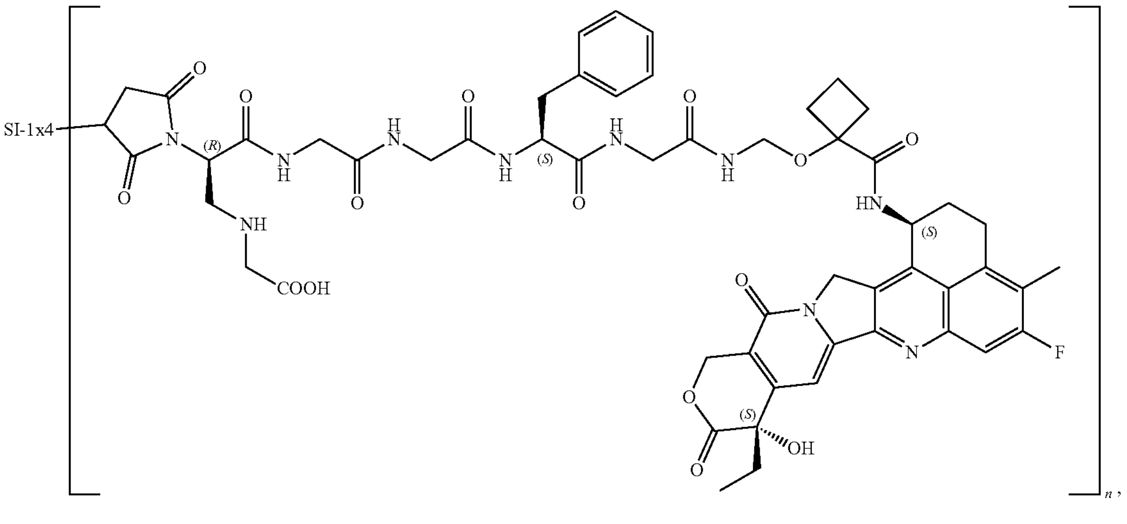

-continued
ADC-124
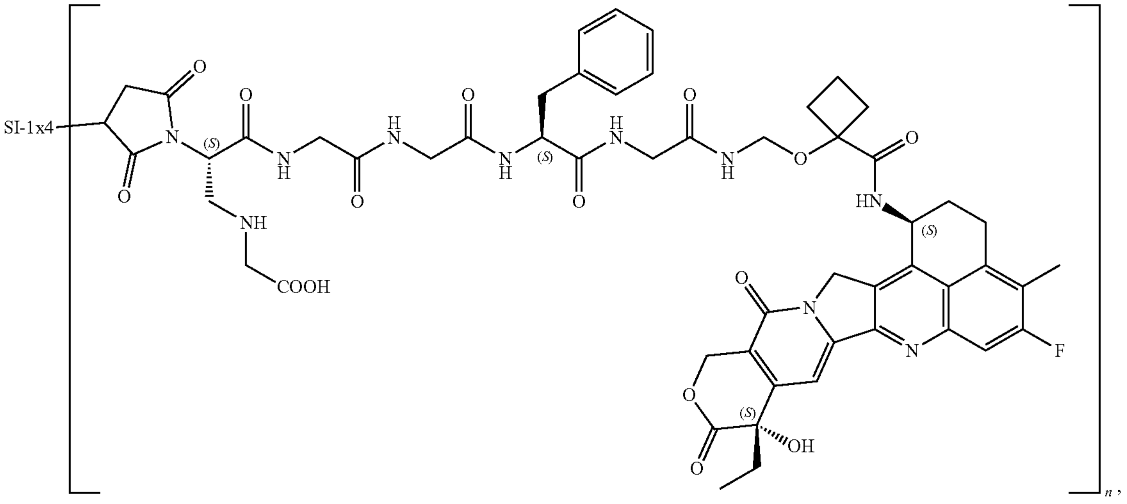
ADC-125
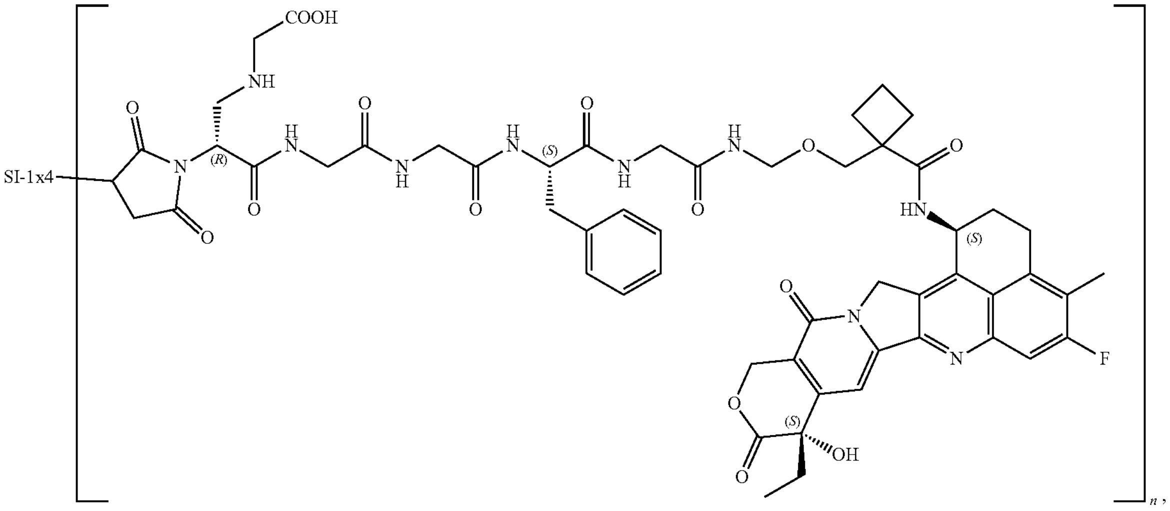
ADC-126
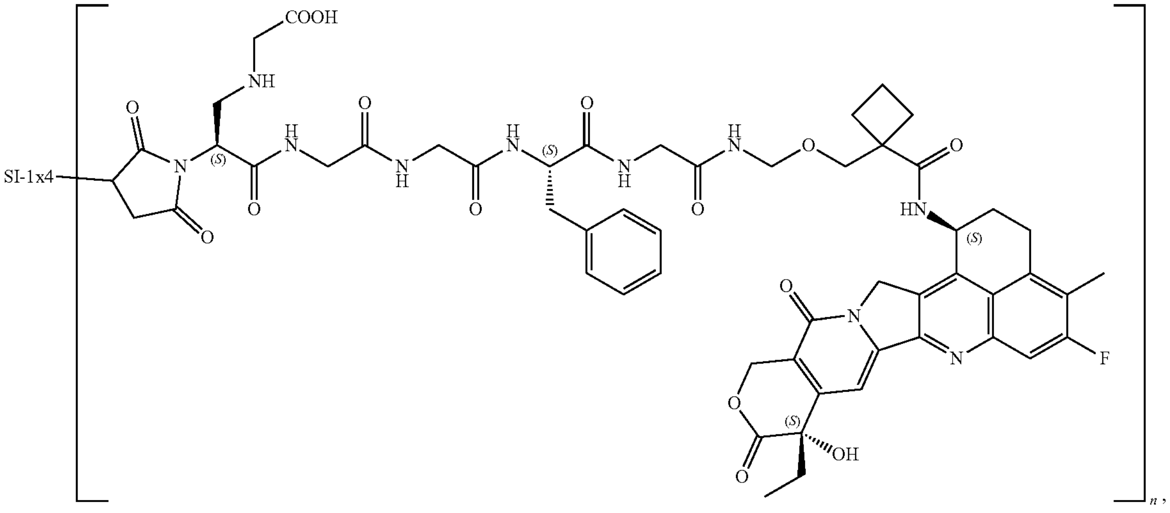

-continued
ADC-127
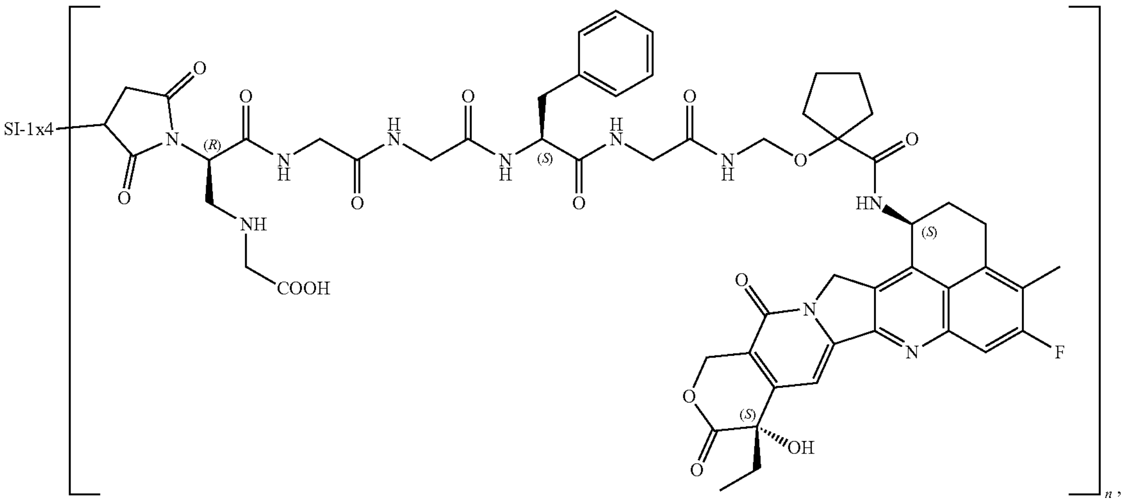
ADC-128
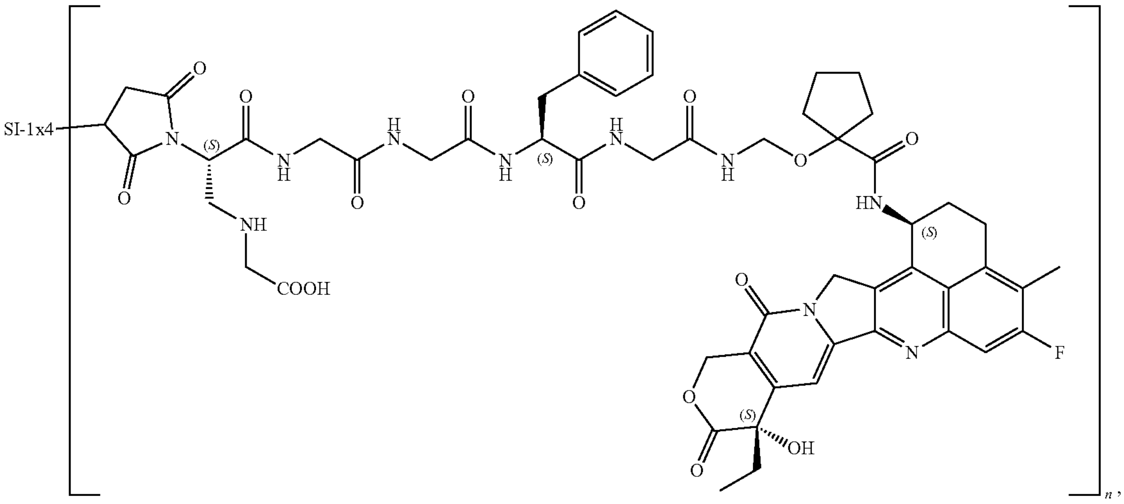
ADC-129
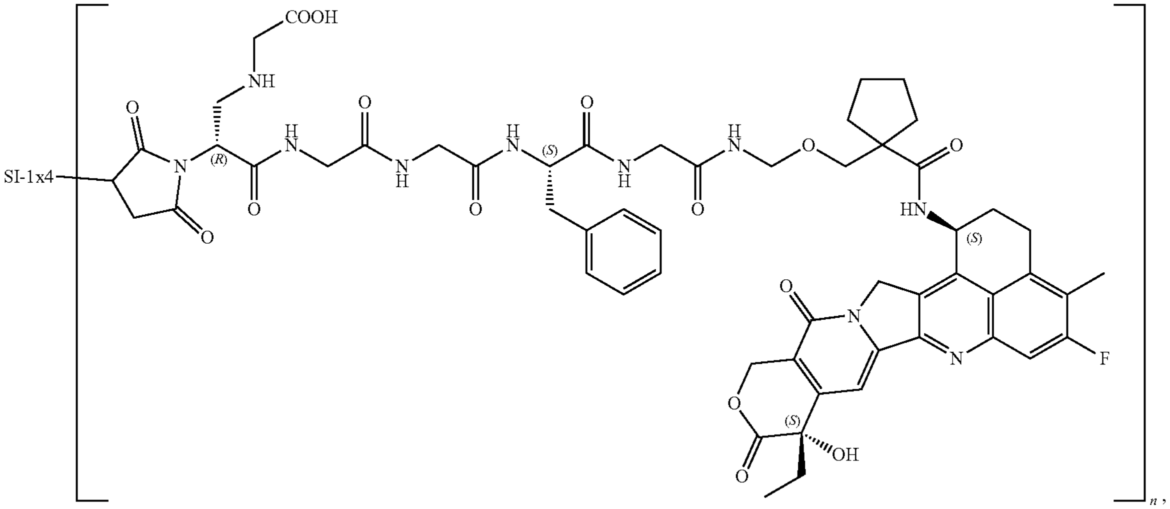

-continued
ADC-130
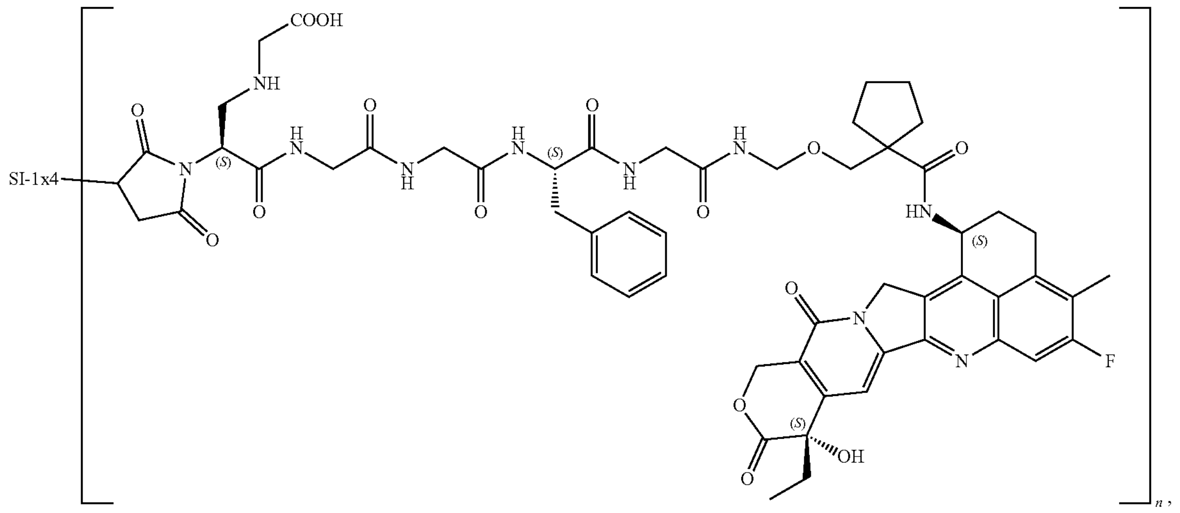
ADC-131
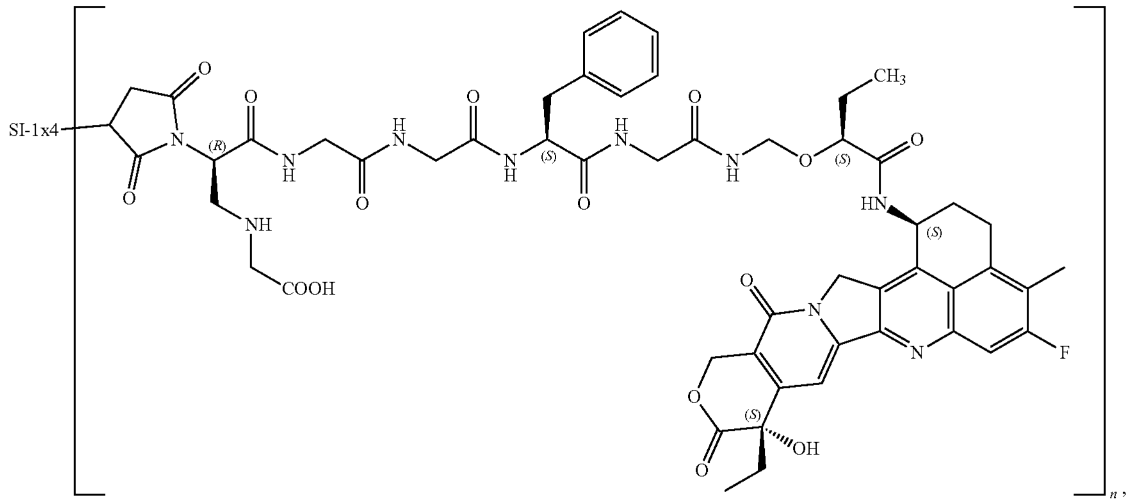
ADC-132
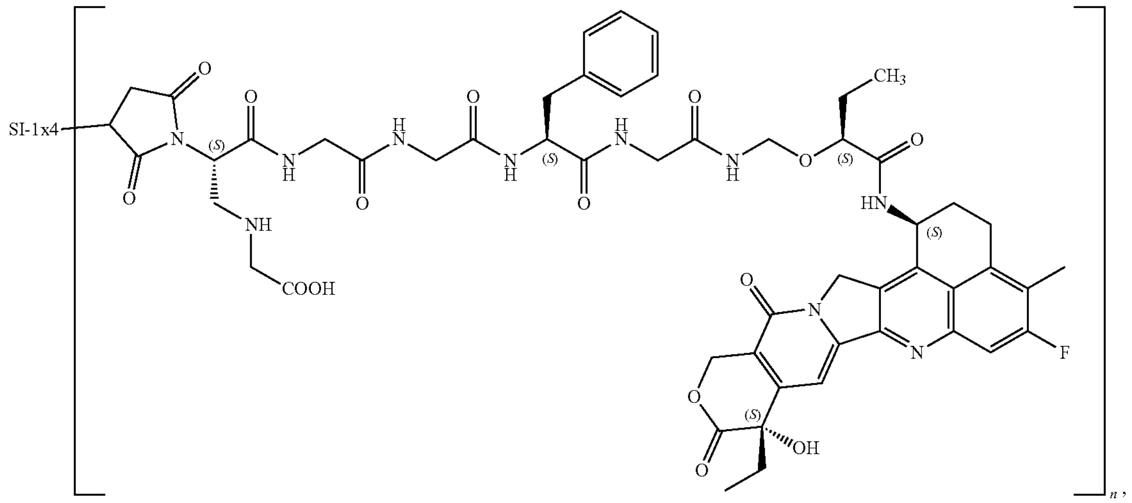

-continued
ADC-133
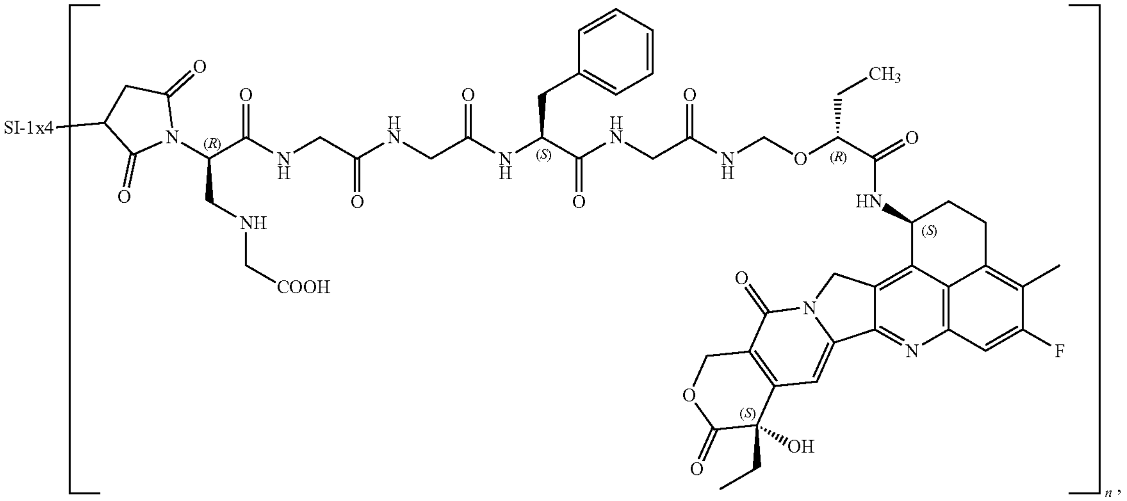
ADC-134
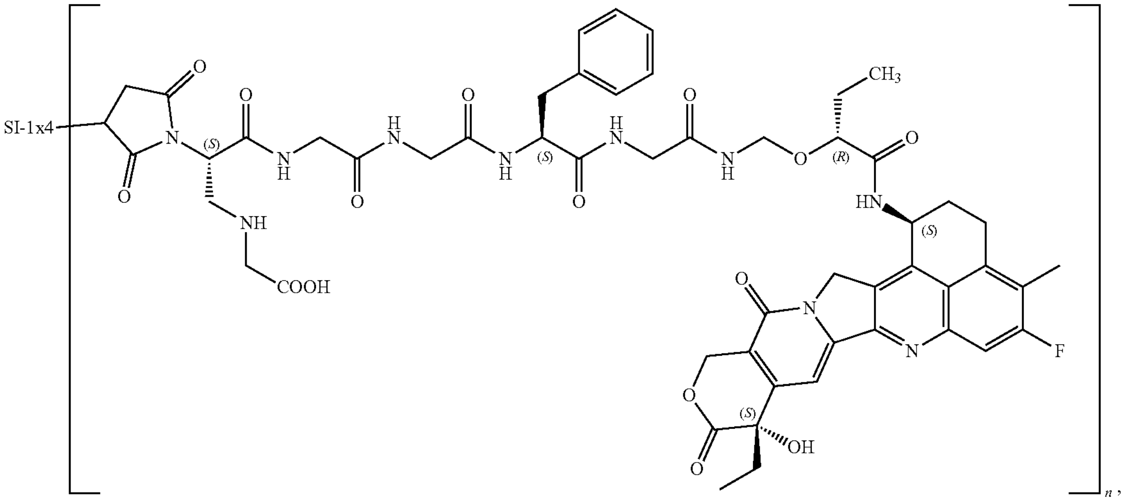
ADC-135
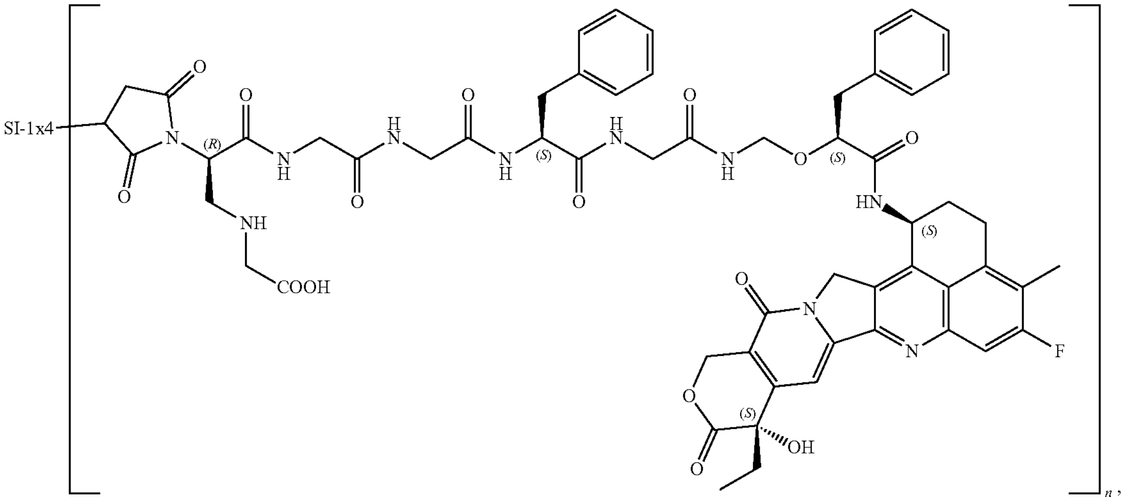

-continued
ADC-136
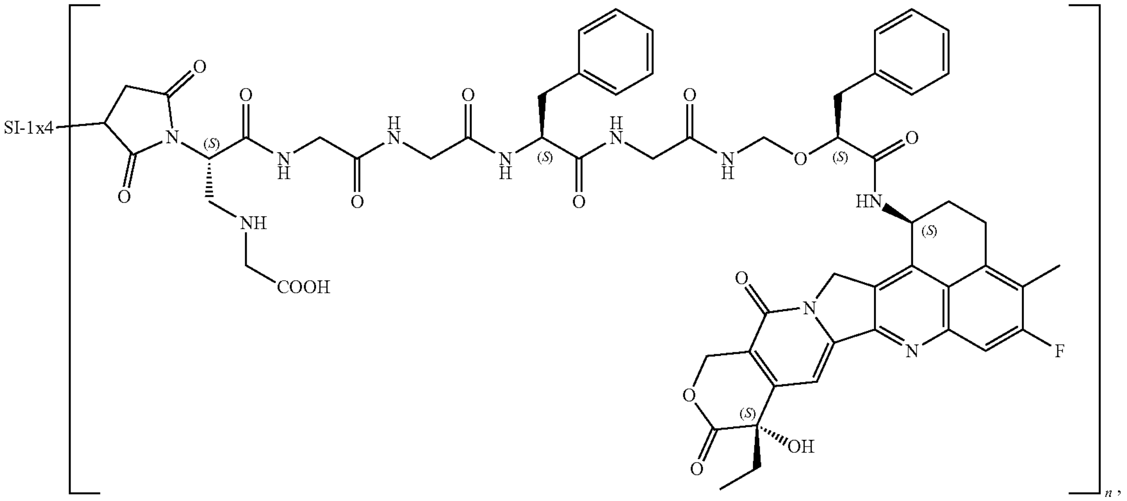
ADC-137
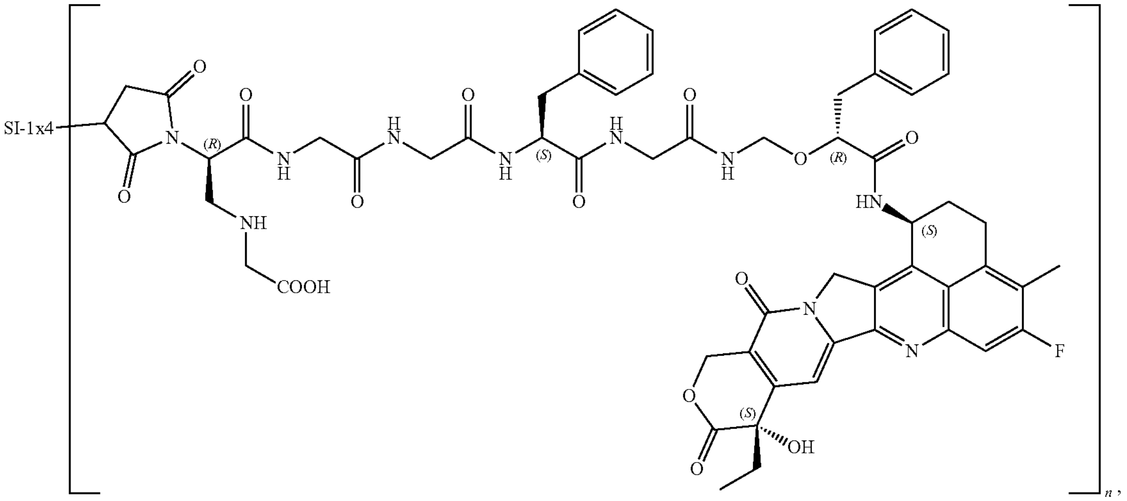
ADC-138
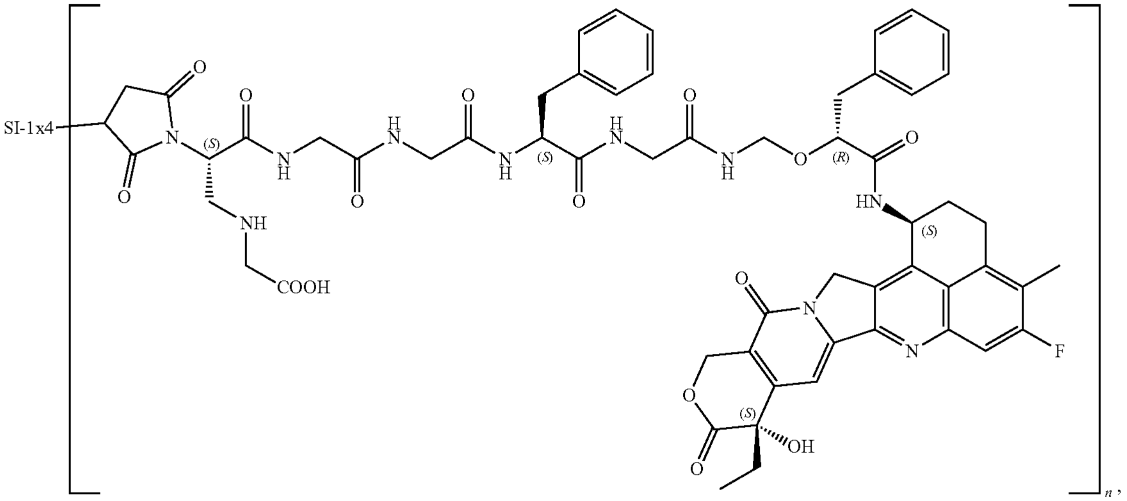

-continued
ADC-139
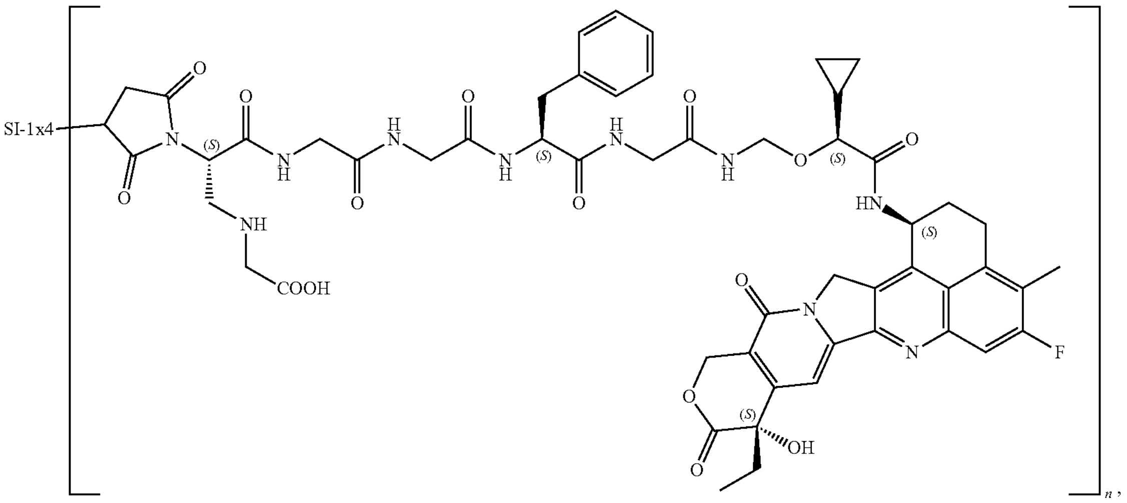
ADC-140
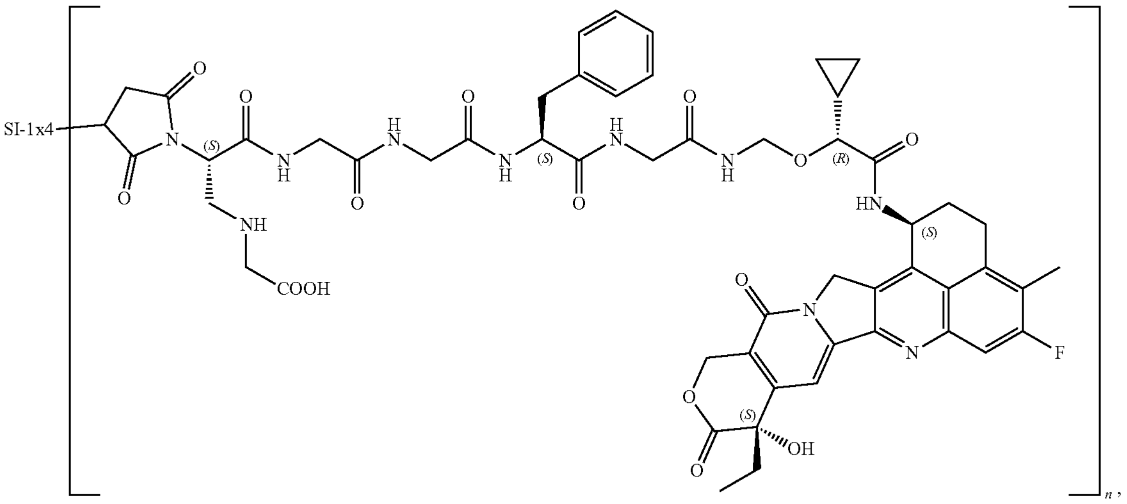
ADC-141
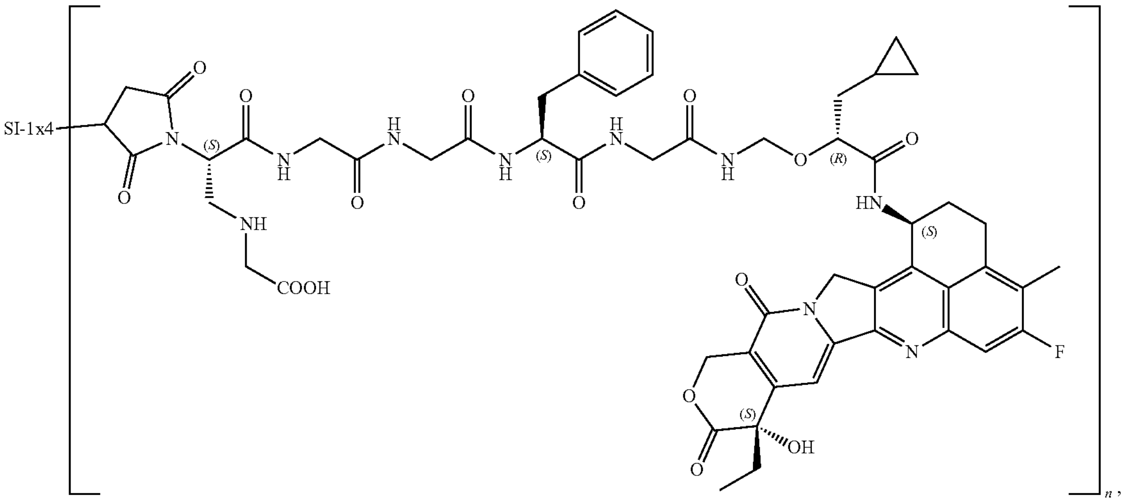

-continued
ADC-142
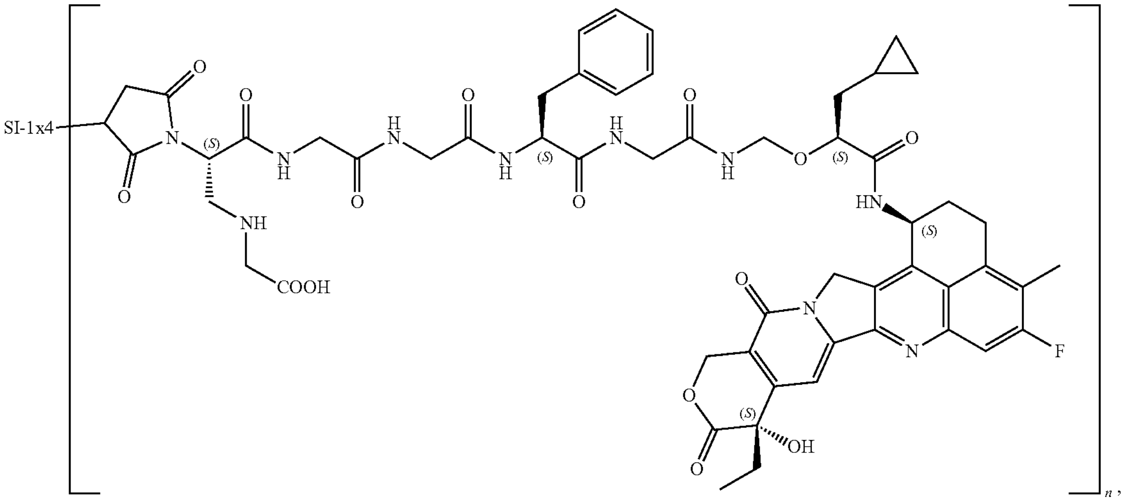
ADC-143
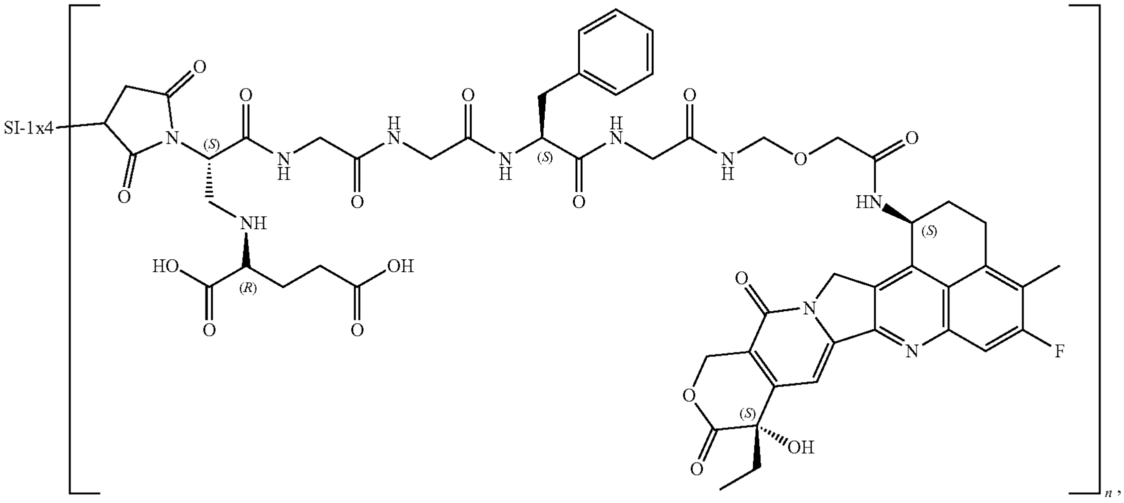
ADC-144
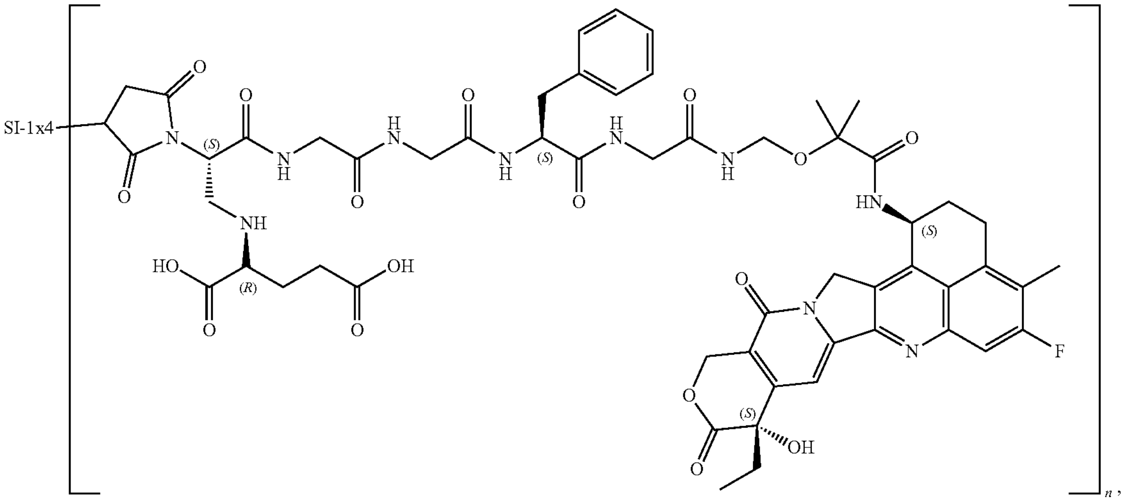

-continued
ADC-145
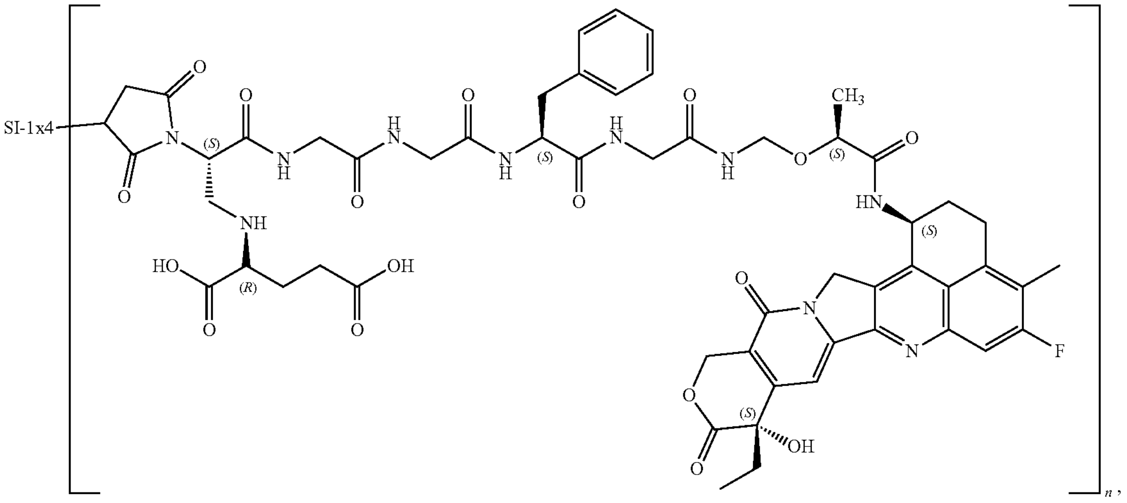
ADC-146
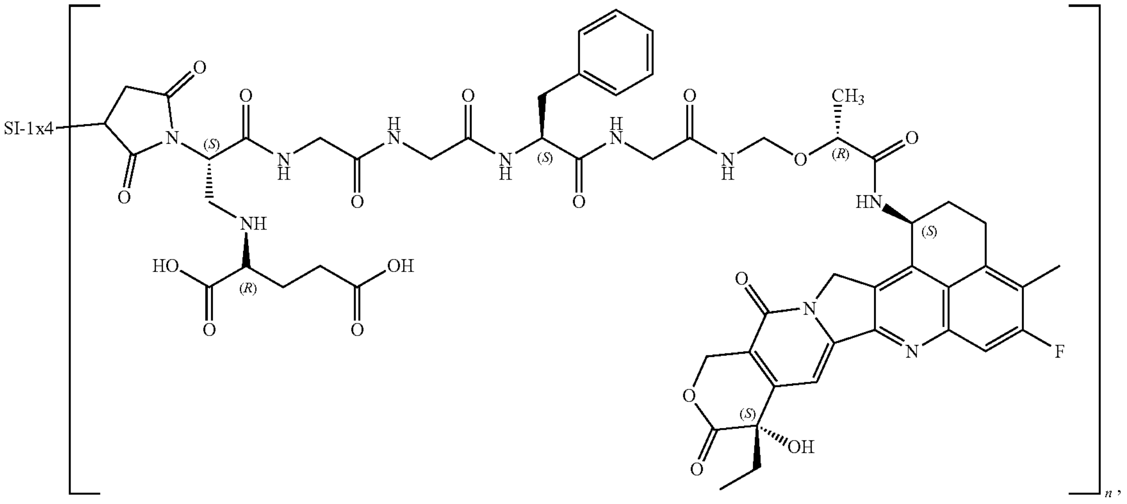
ADC-147
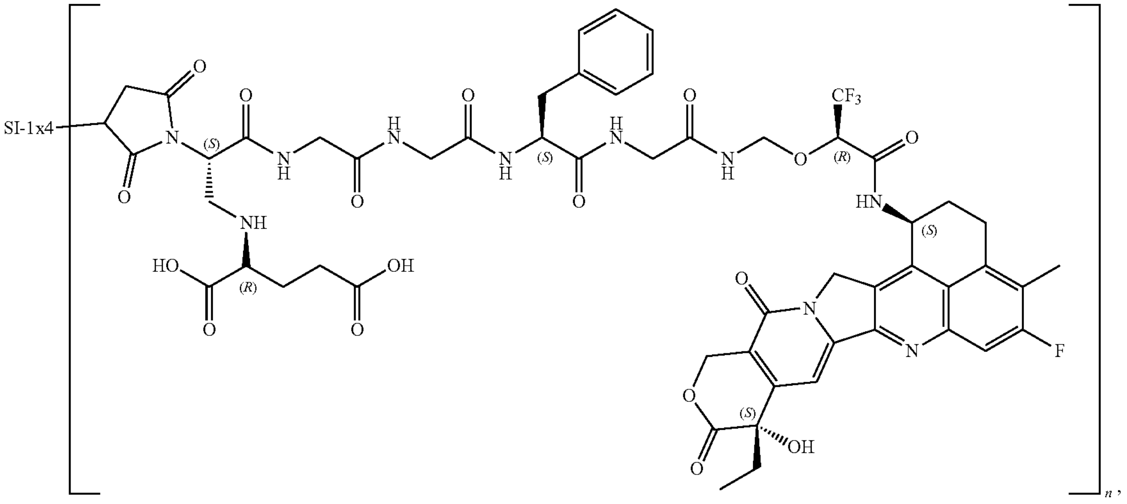

-continued
ADC-148
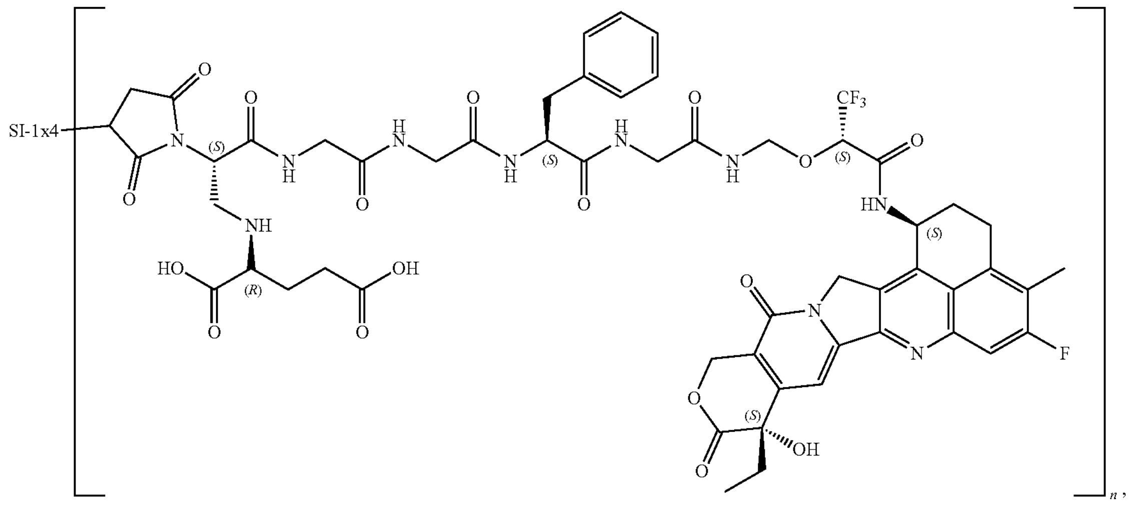
ADC-149
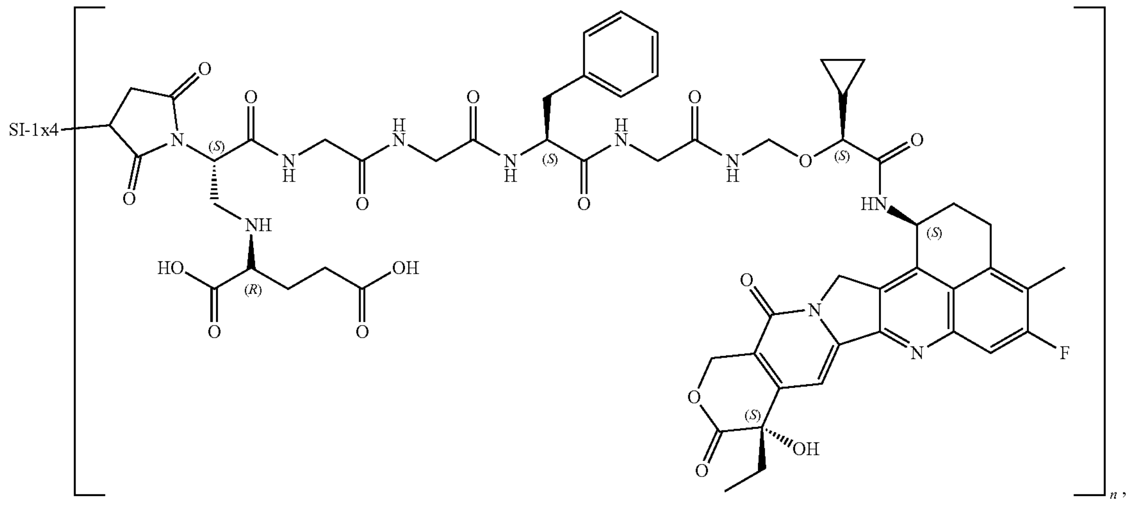
ADC-150
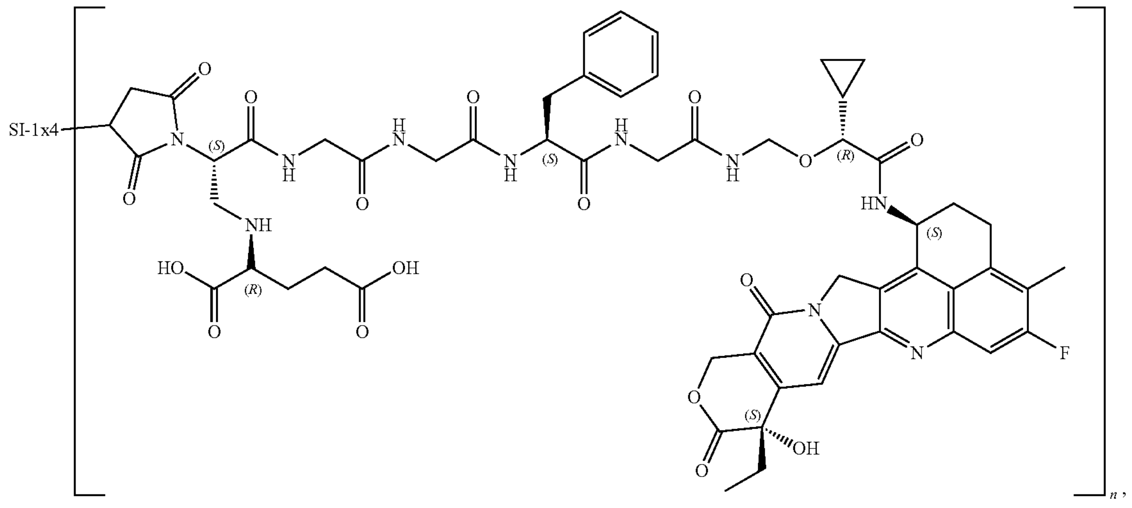

-continued
ADC-151
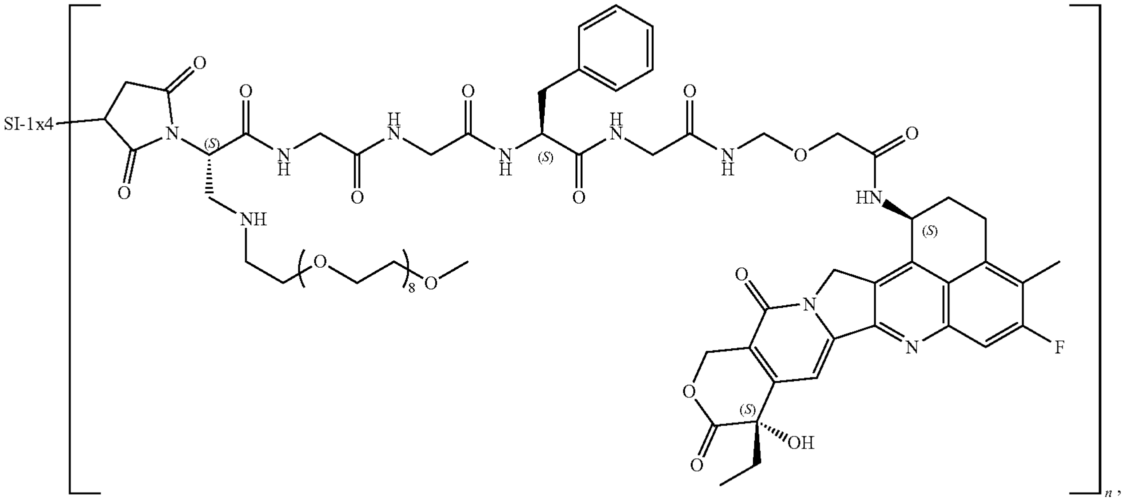
ADC-152
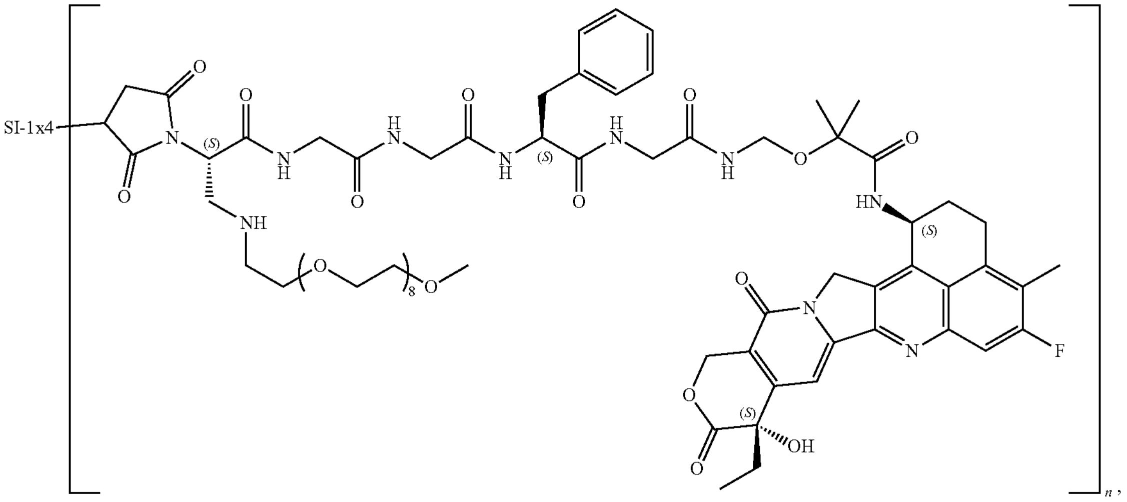
ADC-153
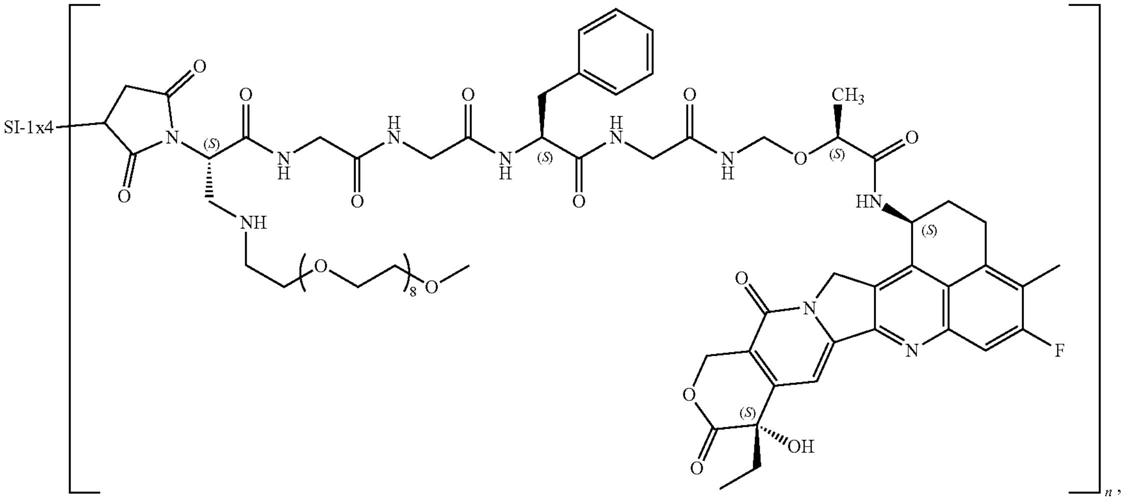

-continued
ADC-154
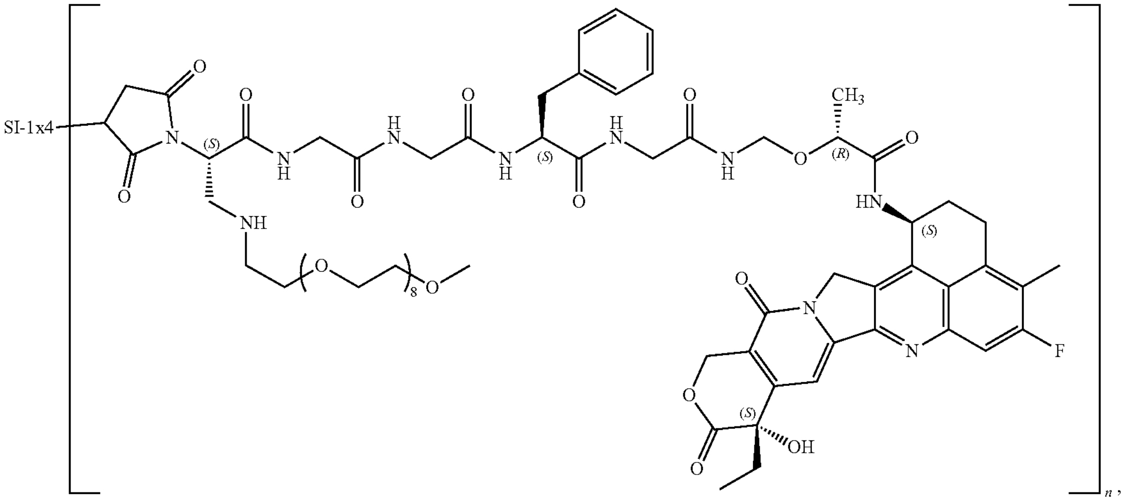
ADC-155
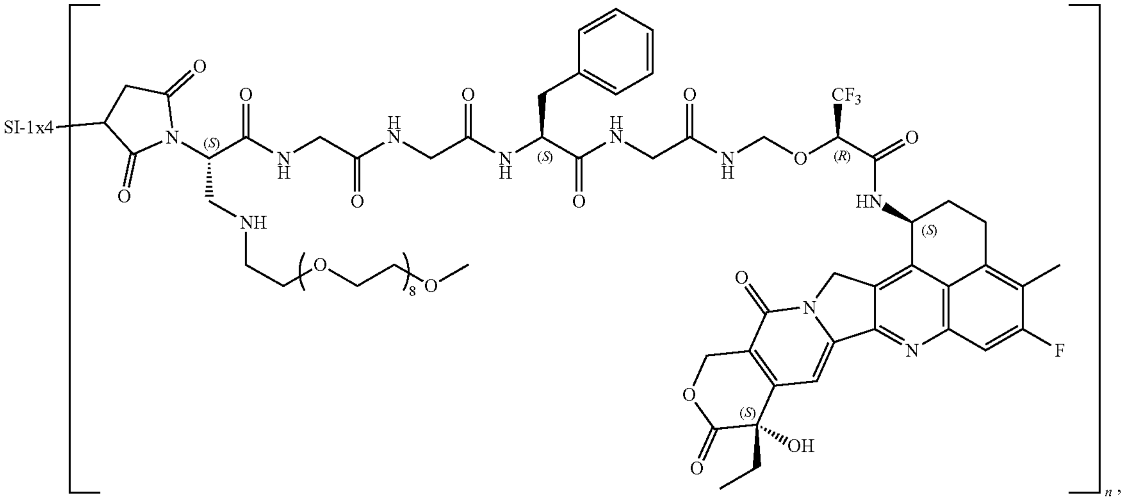
ADC-156
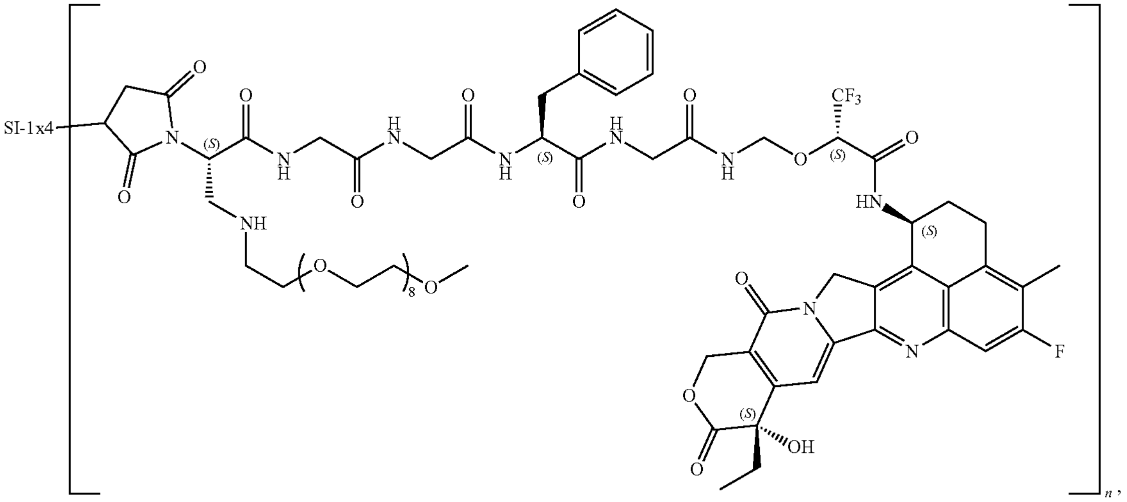

-continued
ADC-157
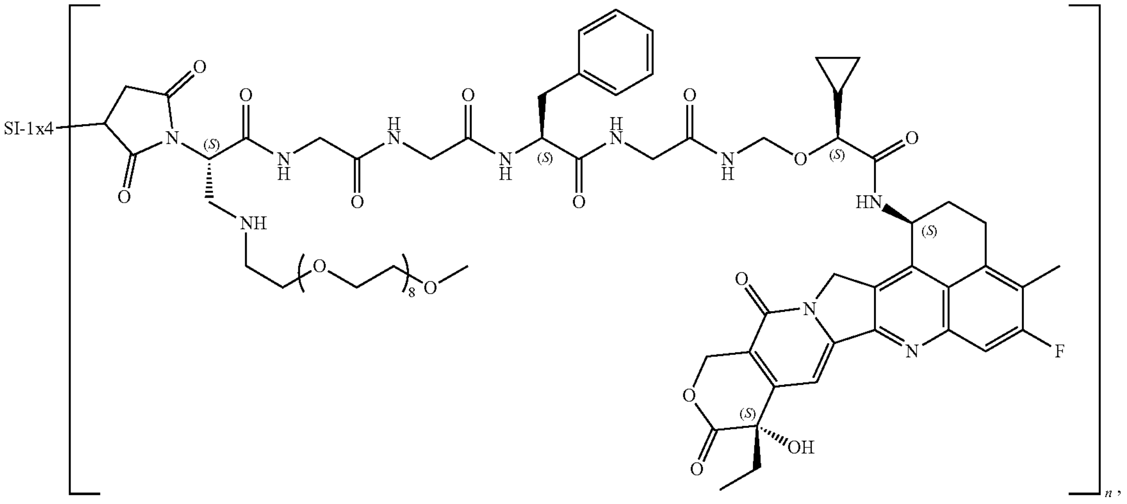
ADC-158
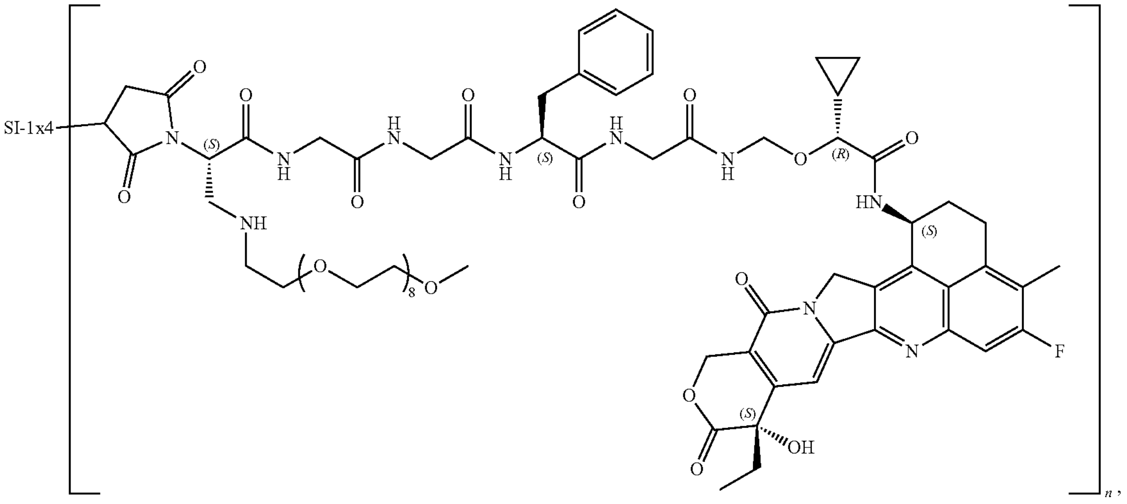
ADC-159
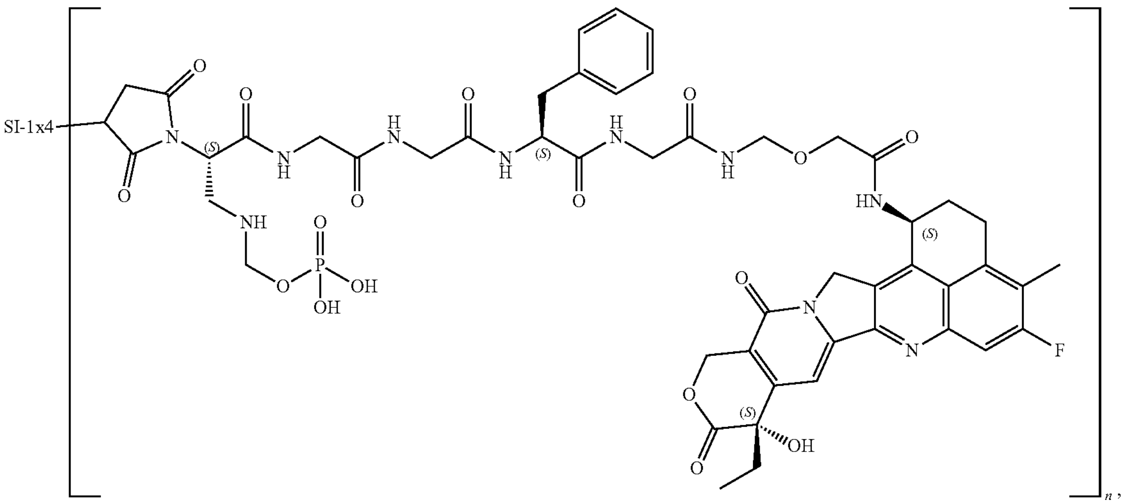

-continued
ADC-160
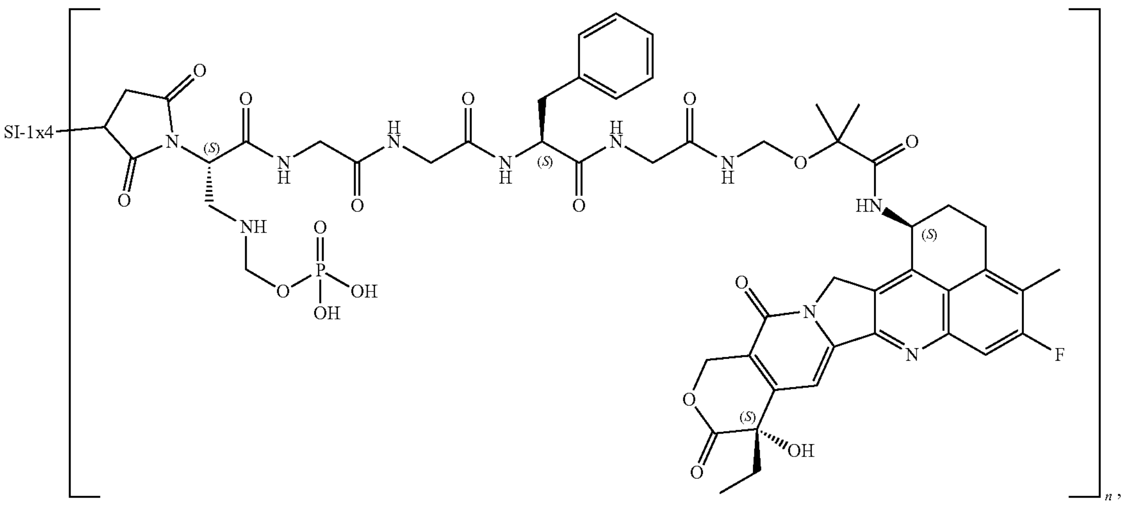
ADC-161
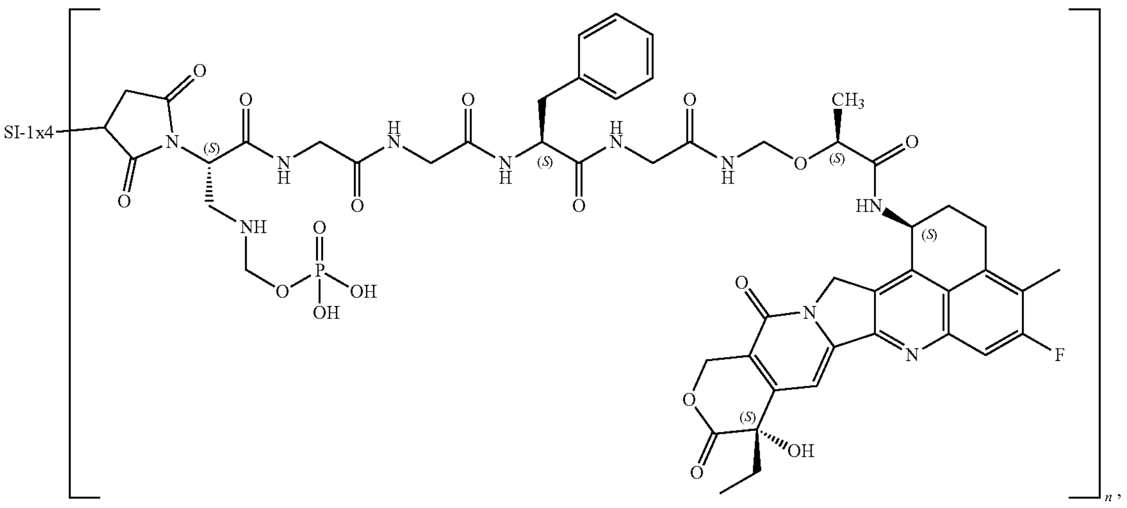
ADC-162
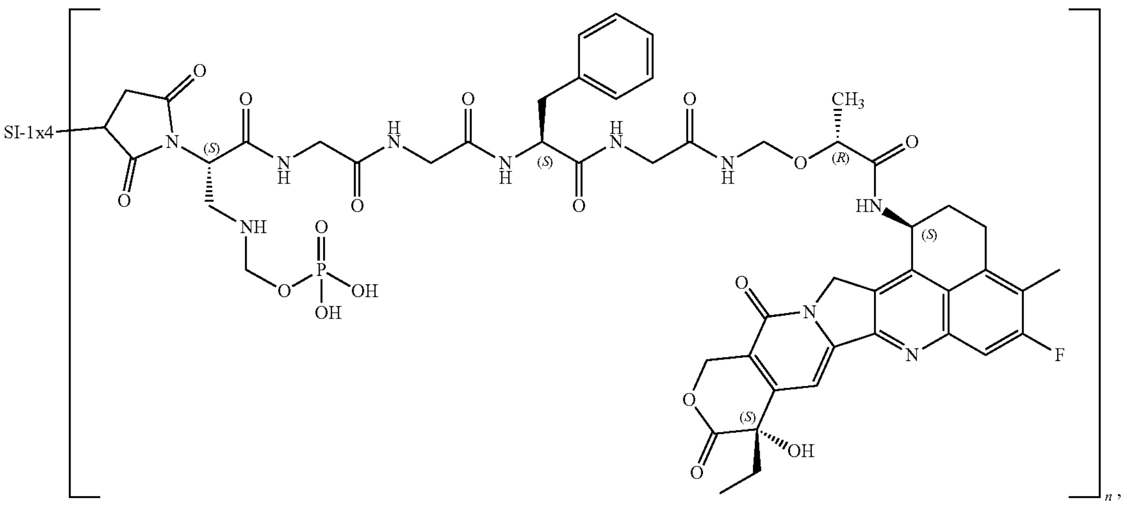

-continued
ADC-163
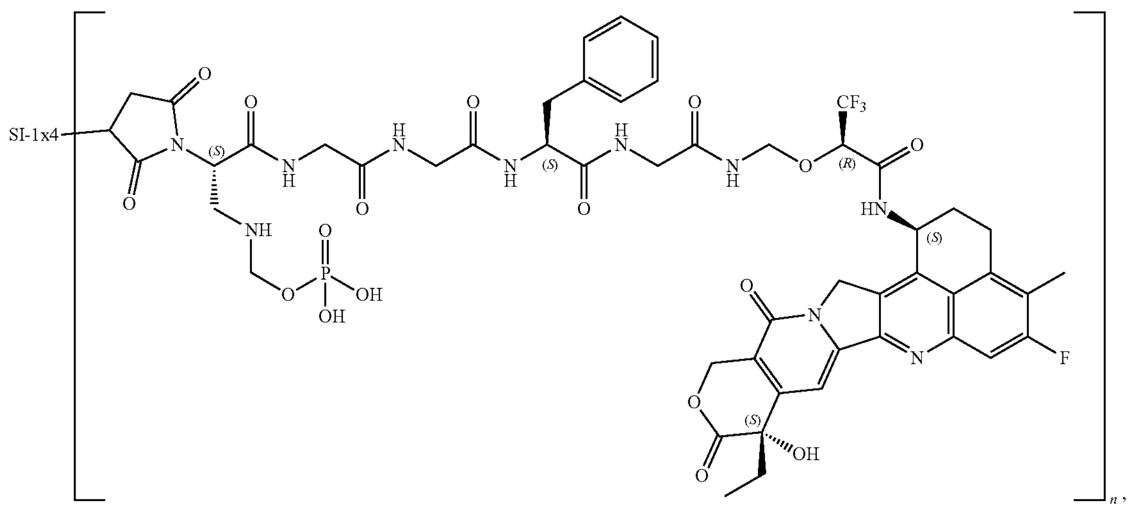
ADC-164
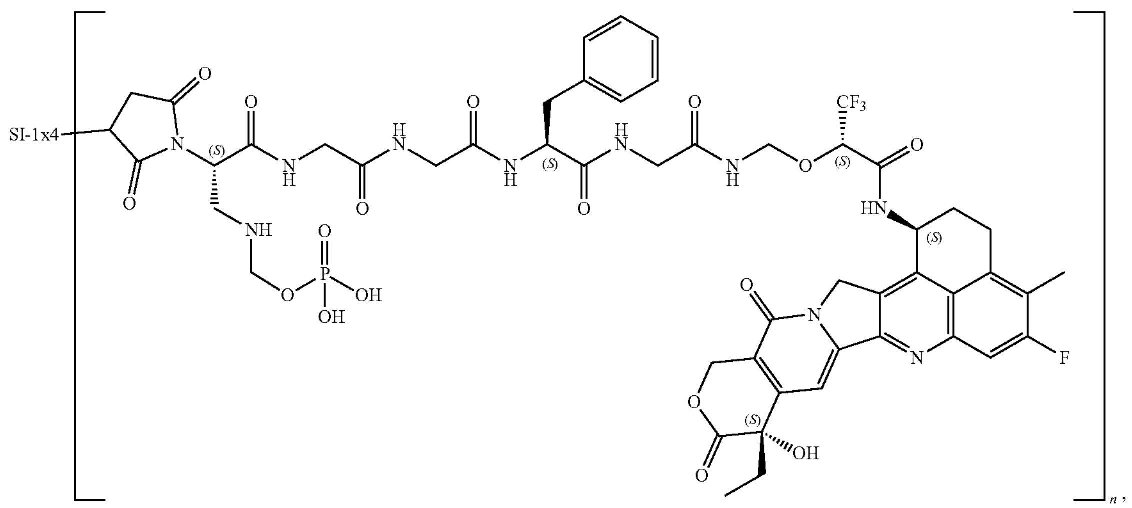
ADC-165
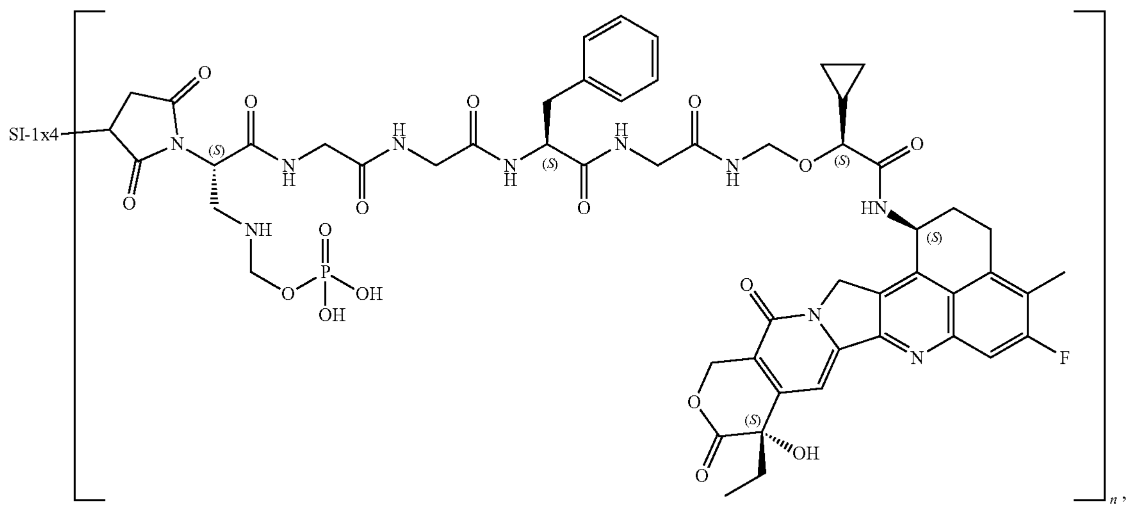

-continued
ADC-166
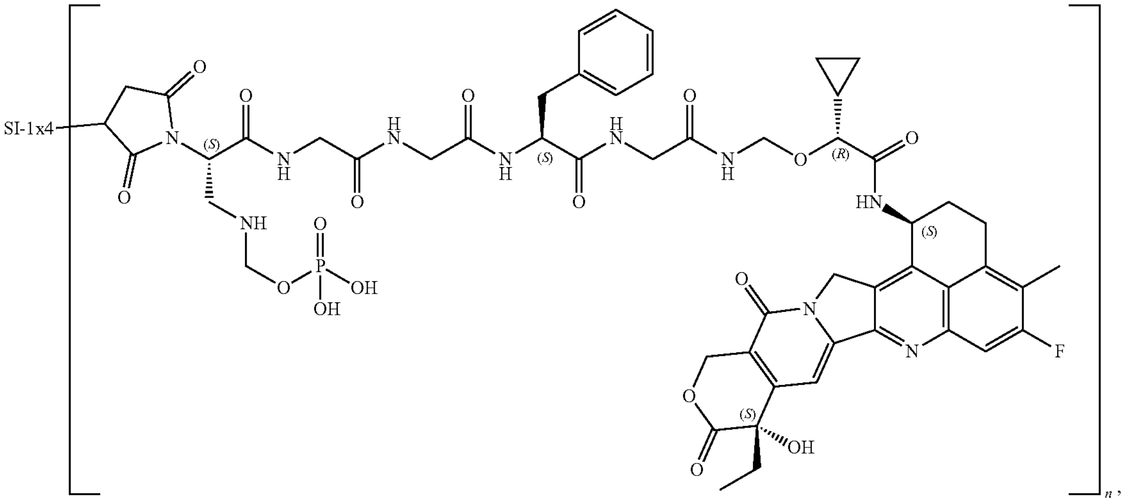
ADC-167
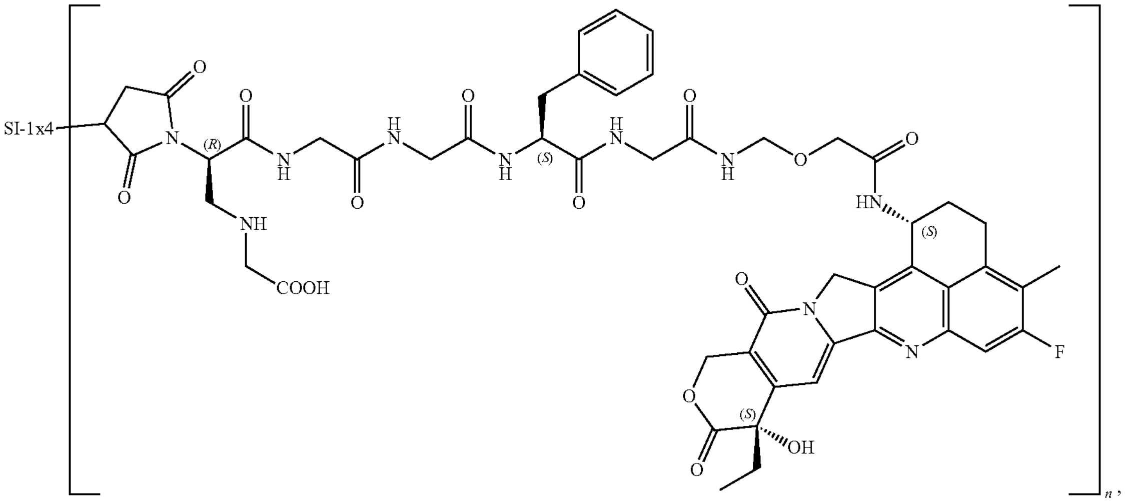
ADC-168
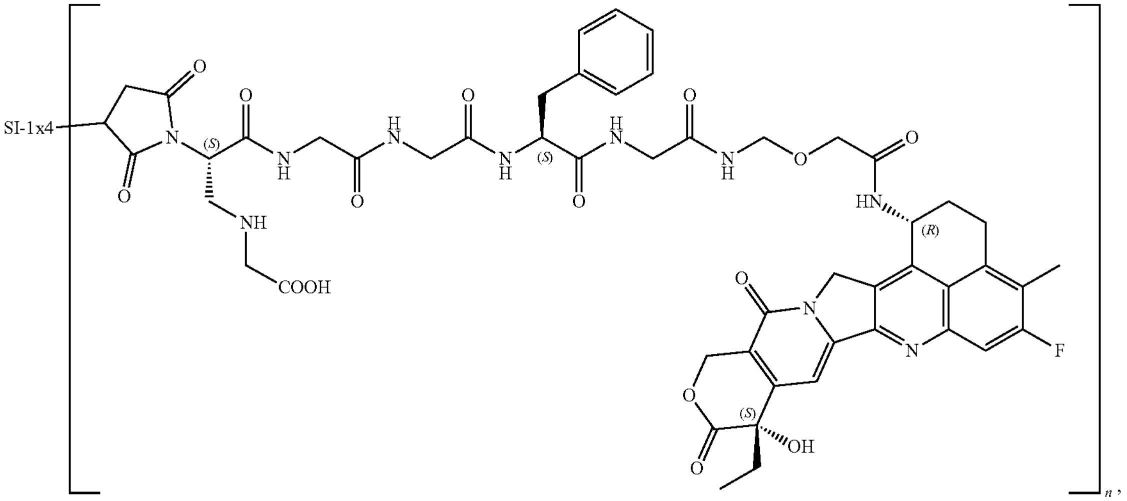

-continued
ADC-169
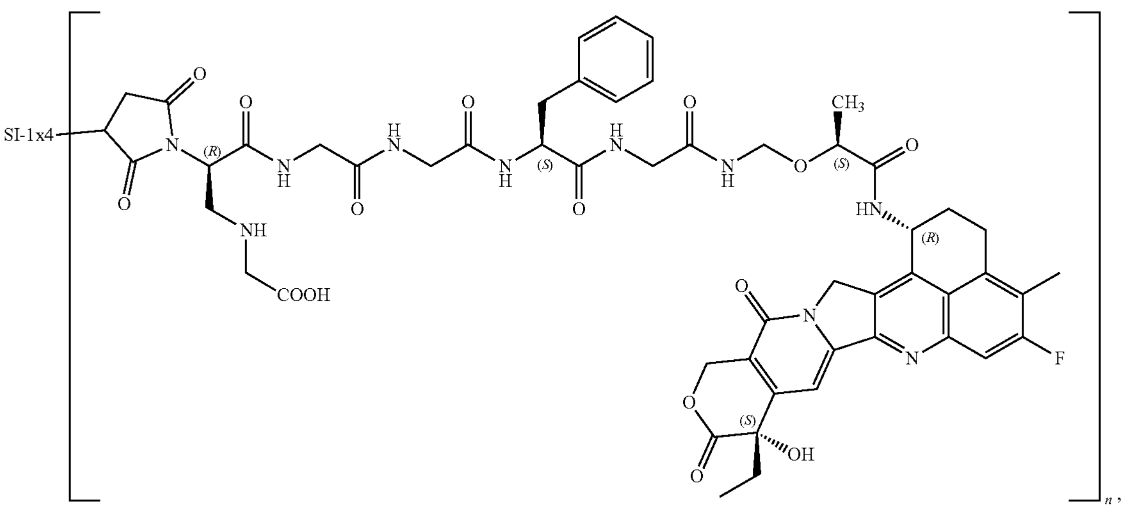
ADC-170
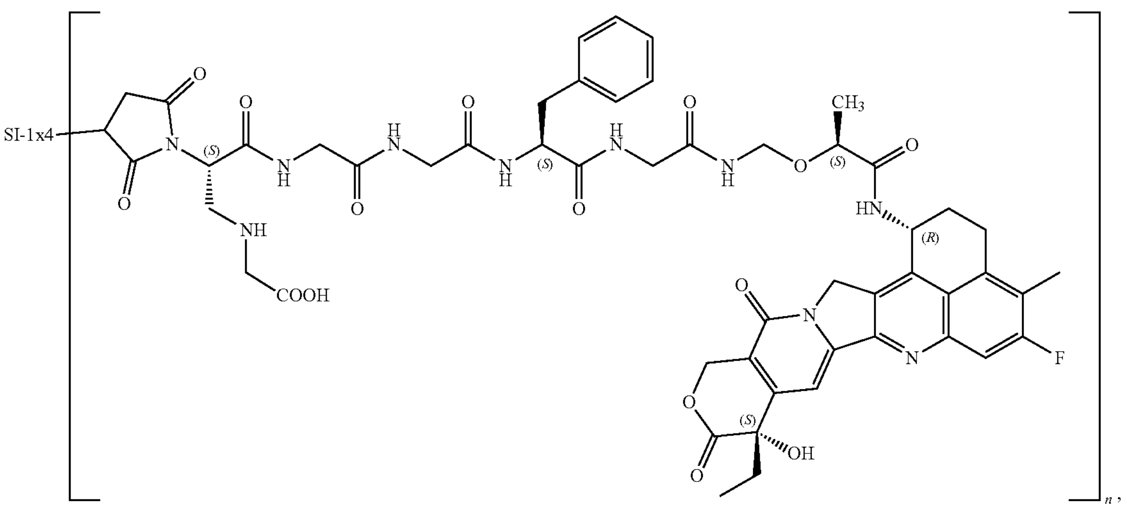
ADC-171
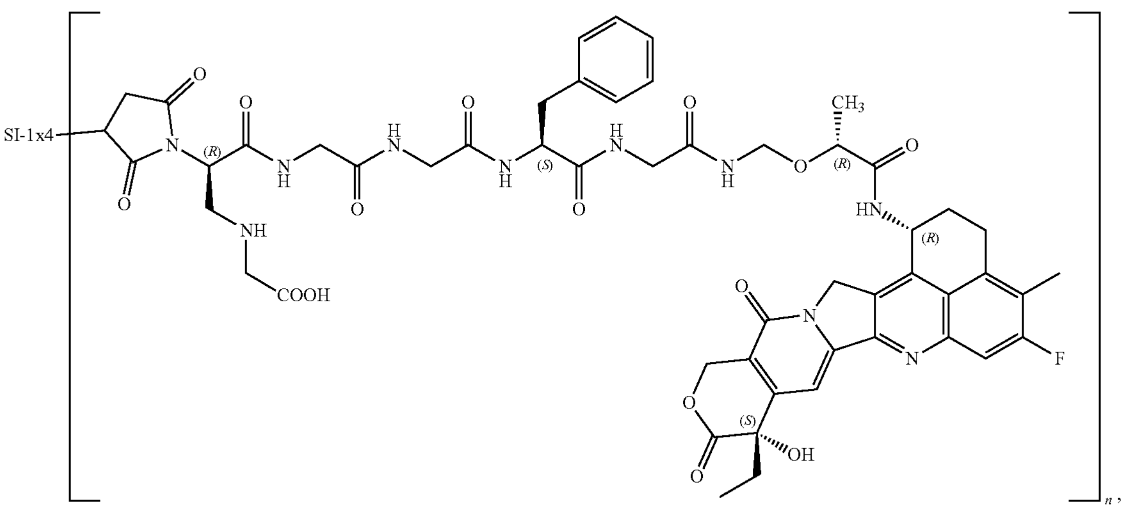

-continued
ADC-172
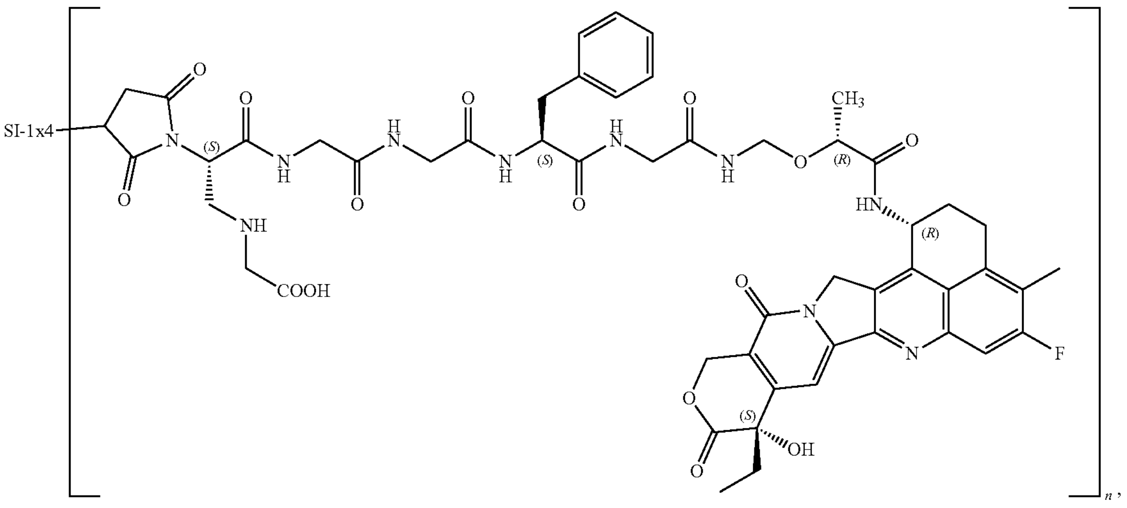
ADC-173
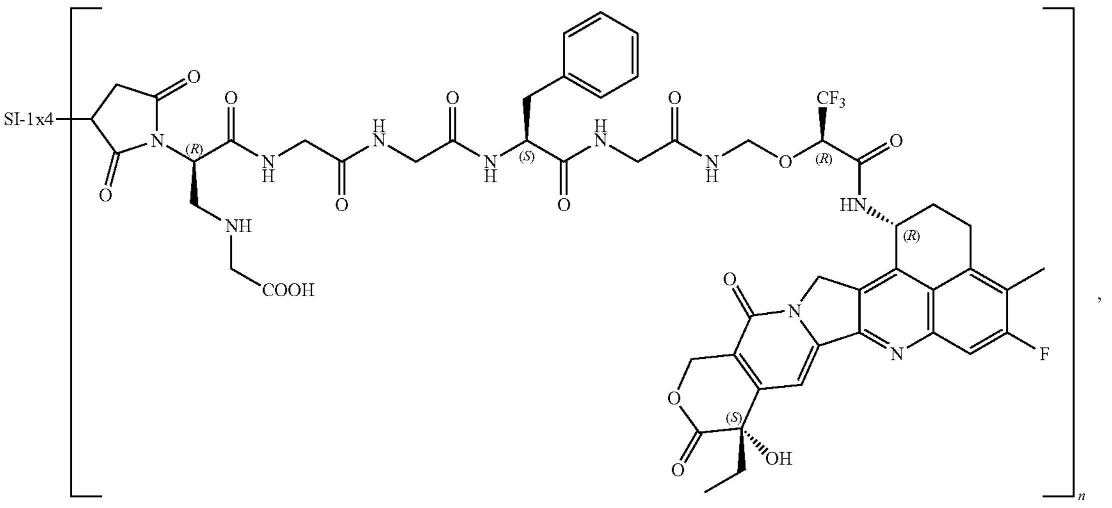
ADC-174
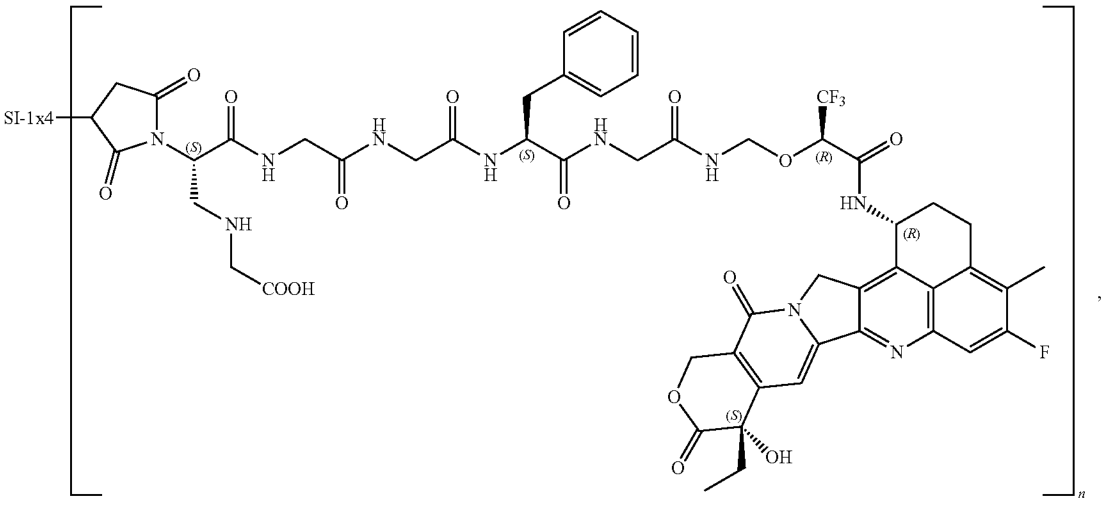

-continued
ADC-175
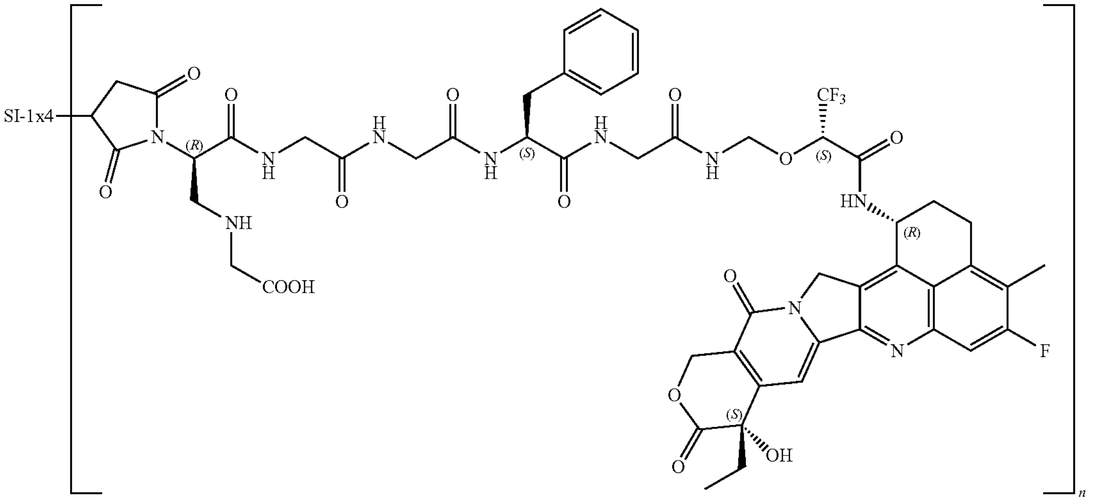
,
ADC-176
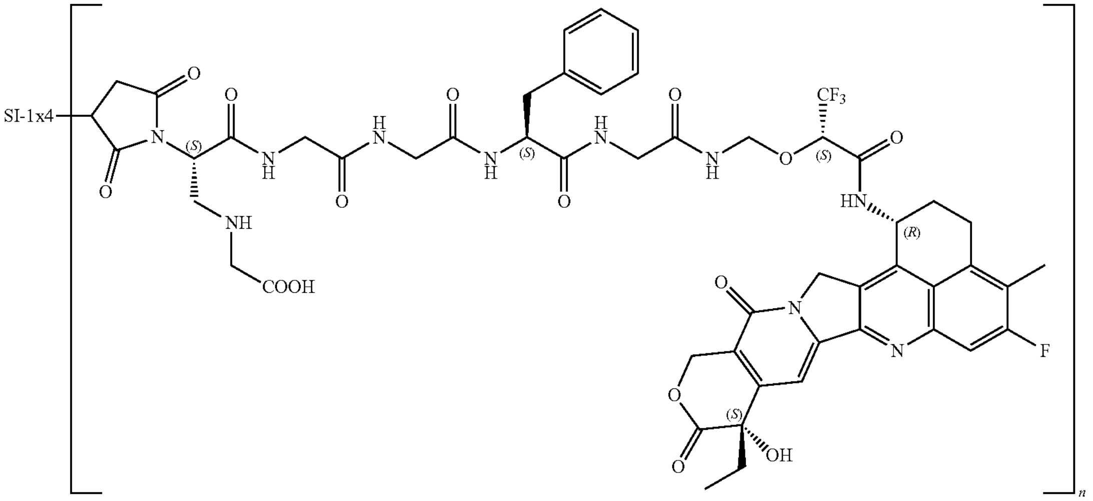
,
ADC-177
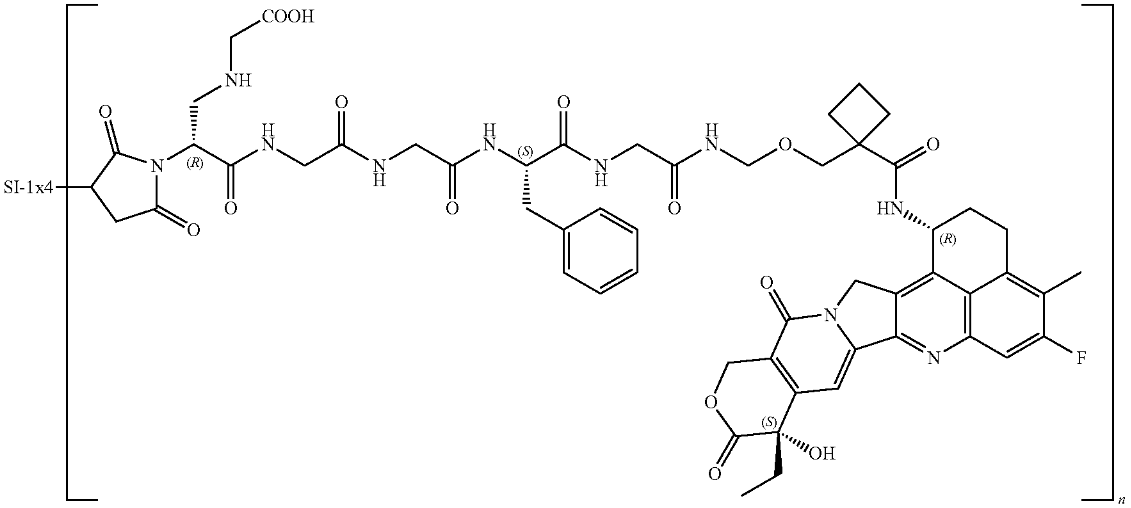
,

-continued
ADC-178
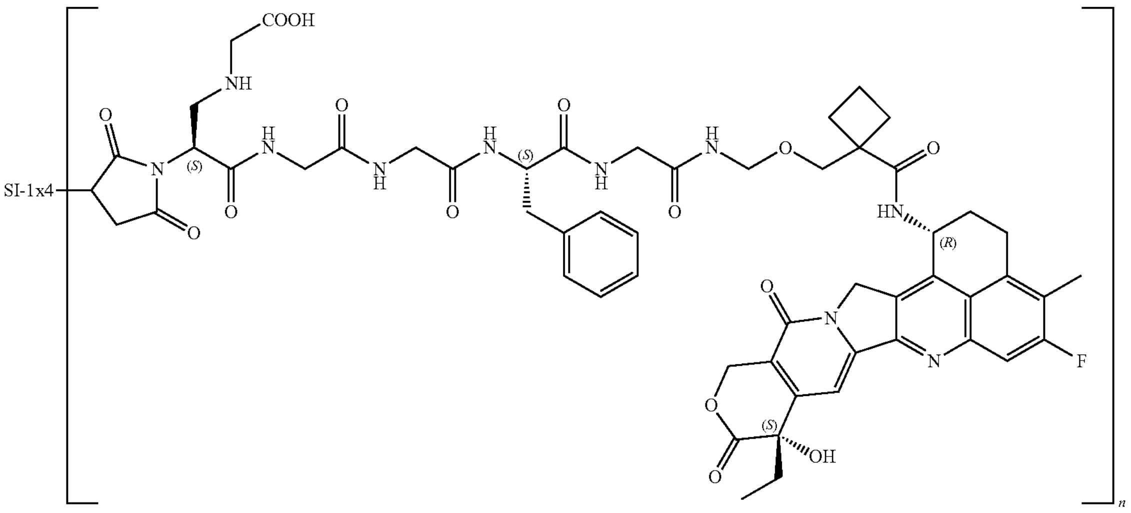
,
ADC-179
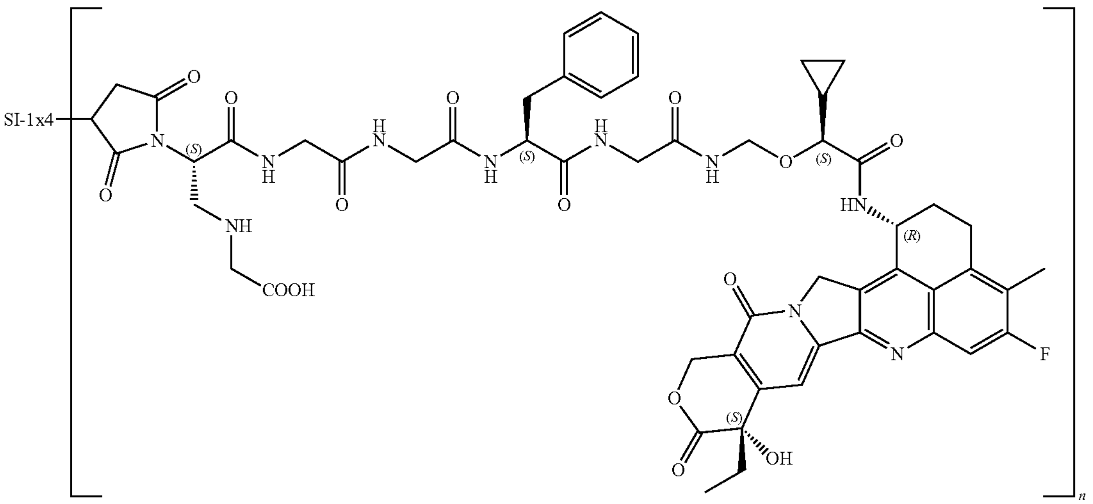
,
ADC-180
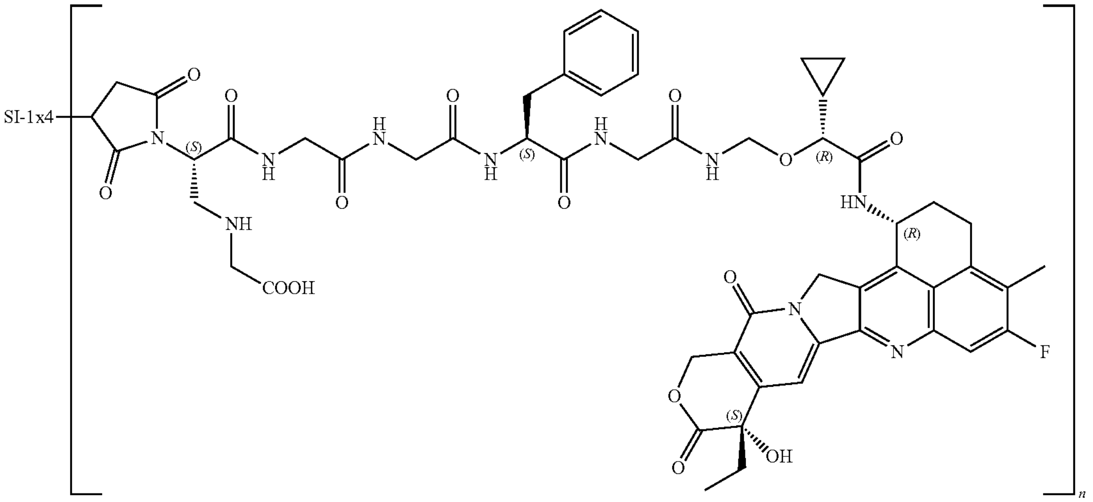
,

-continued
ADC-181
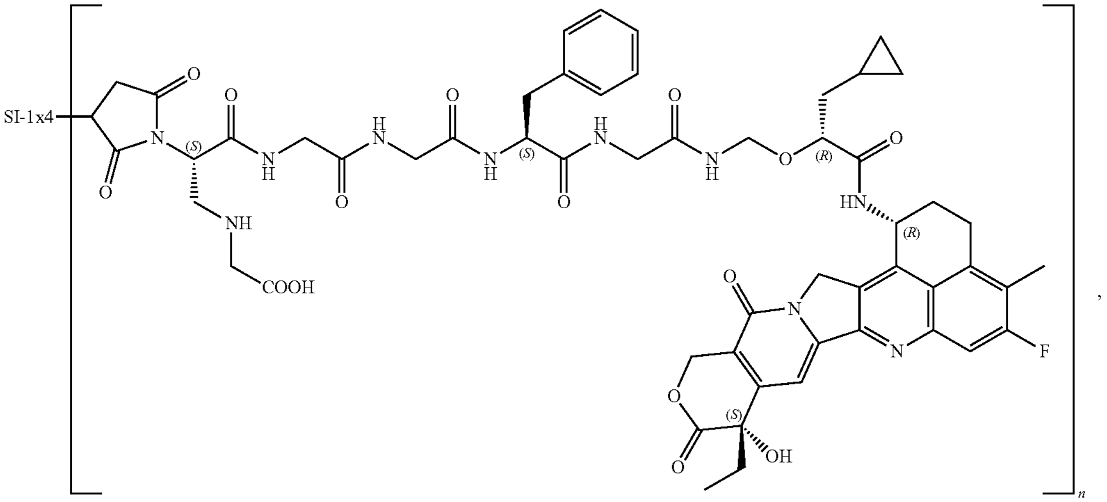
ADC-182
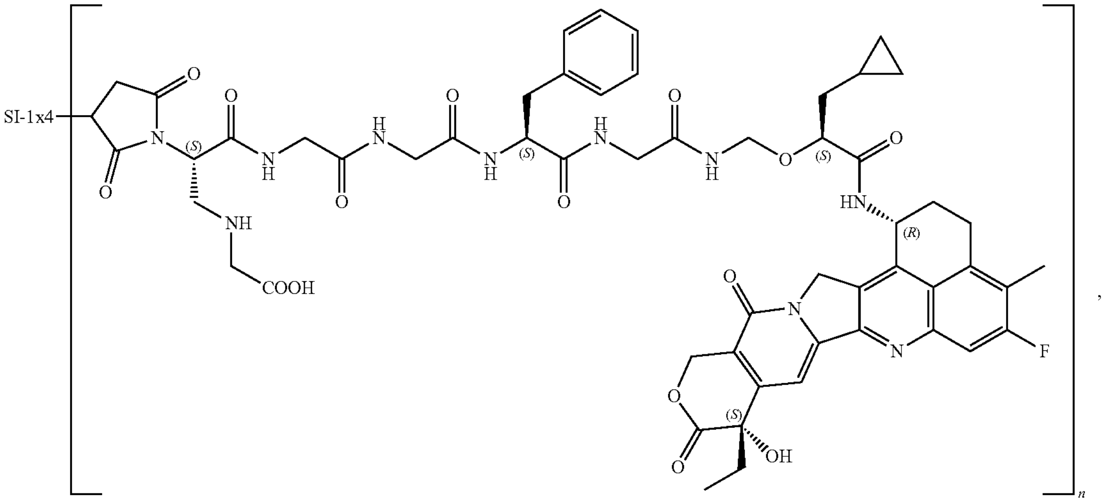
ADC-183
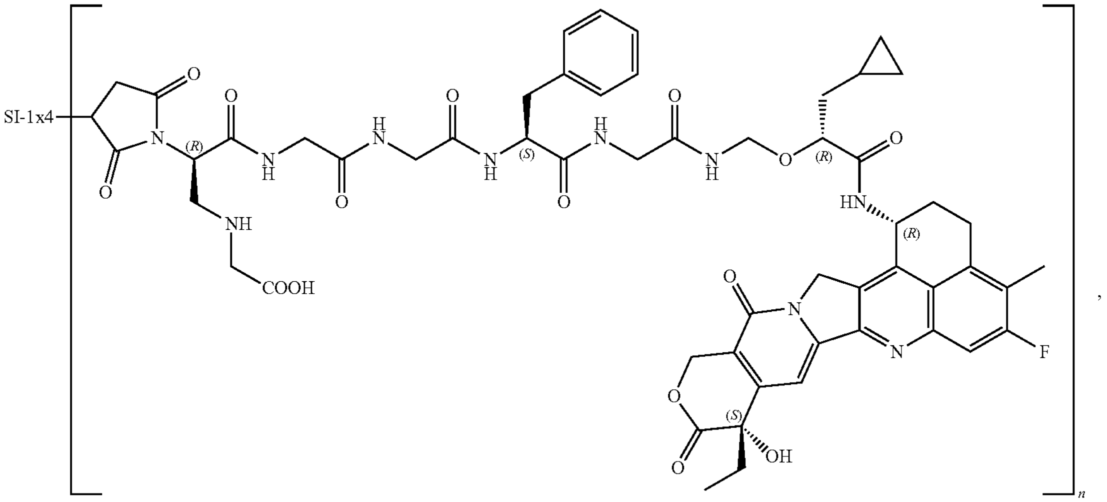

-continued
ADC-184
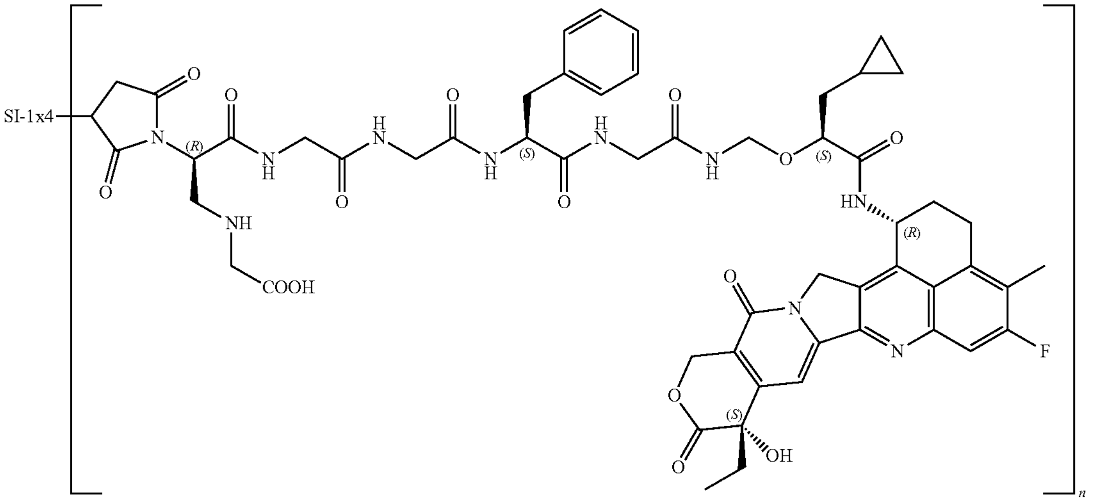
,
ADC-185
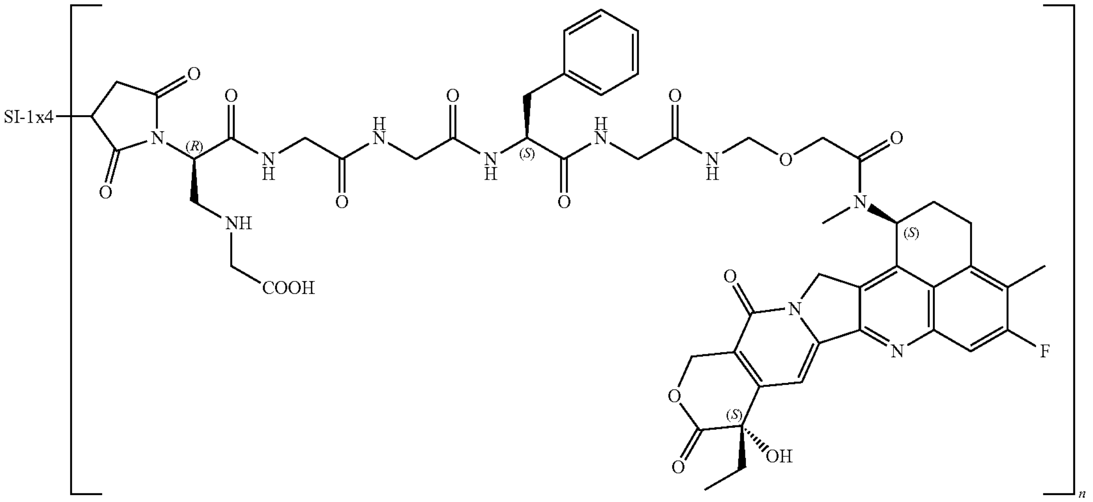
,
ADC-186
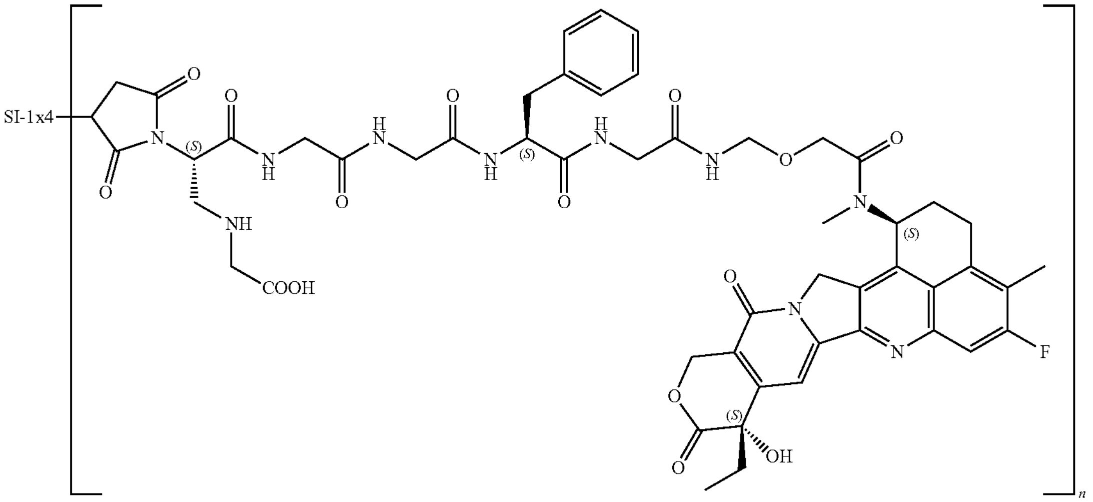
,

-continued
ADC-187
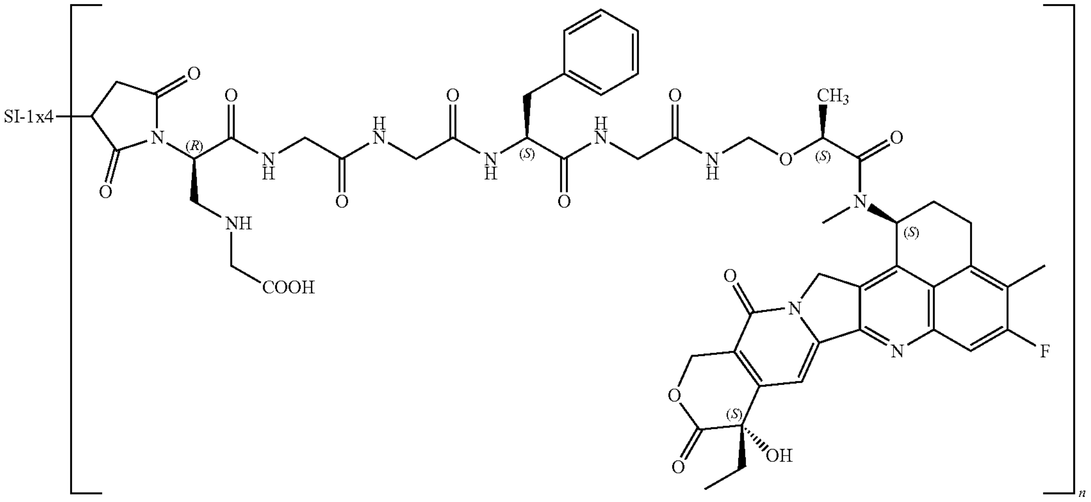
,
ADC-188
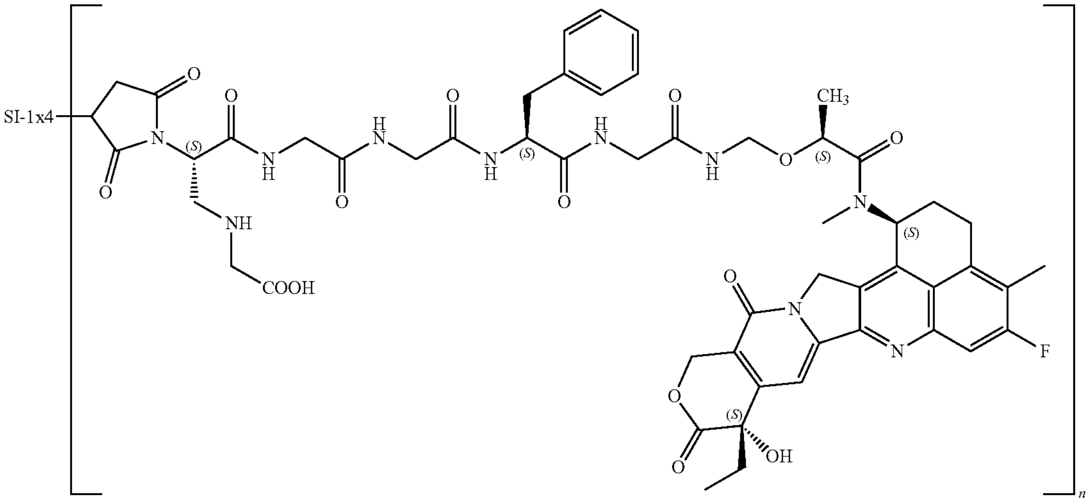
,
ADC-189
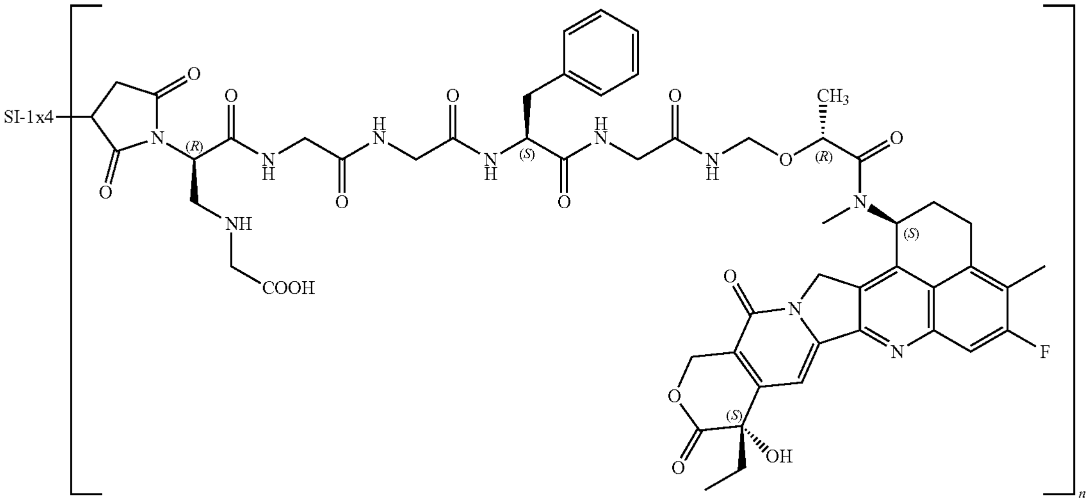
,

-continued
ADC-190
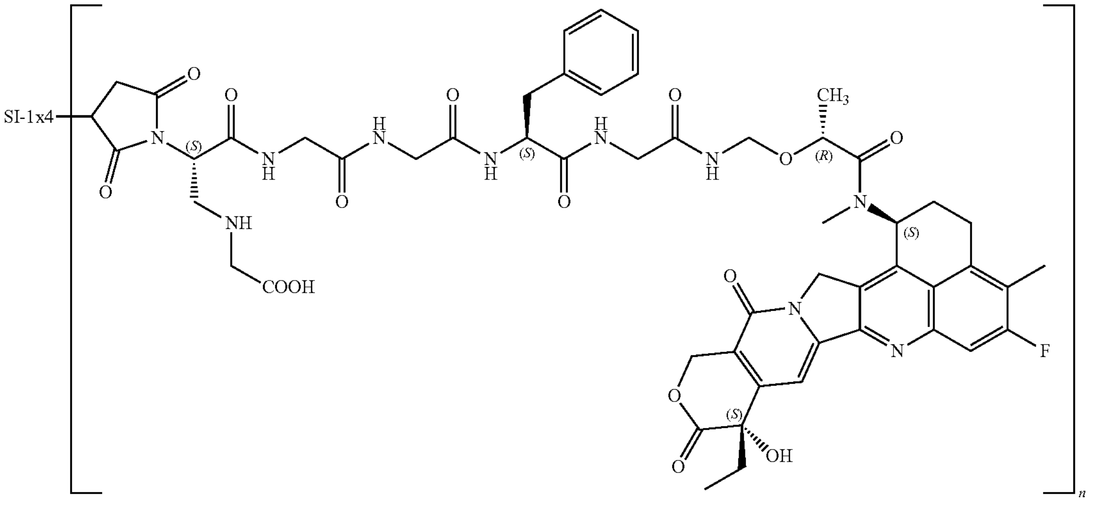
,
ADC-191
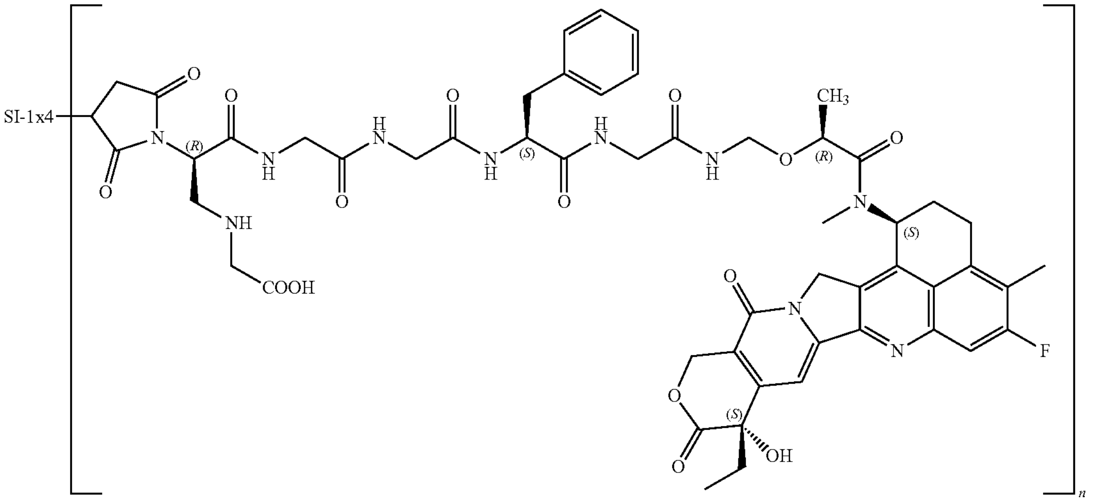
,
ADC-192
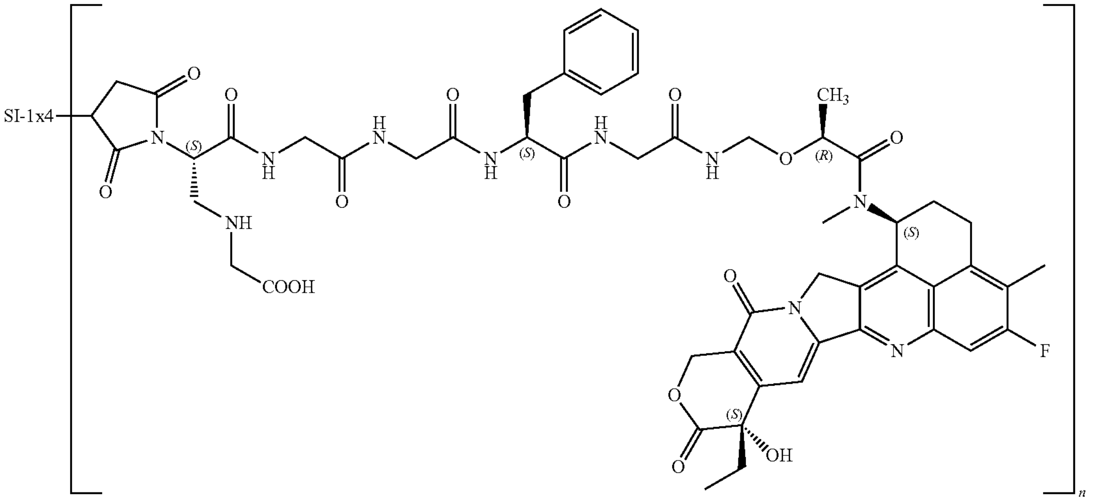
,

-continued
ADC-193
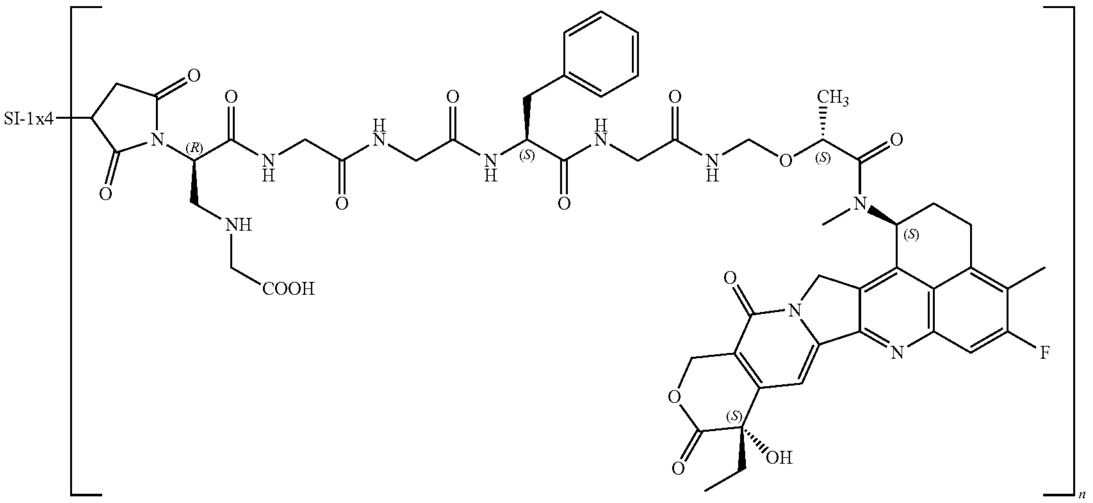
,
ADC-194
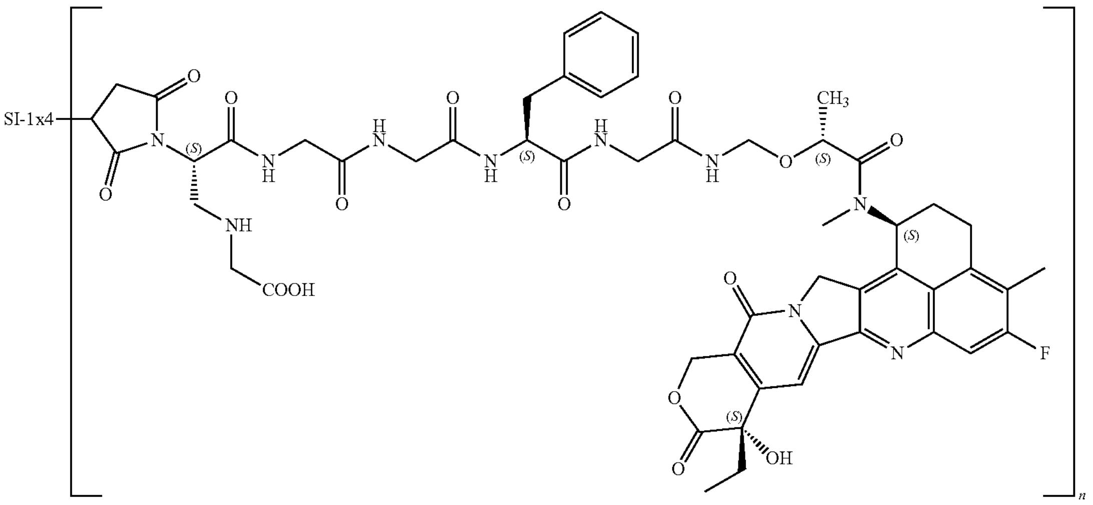
,
ADC-195
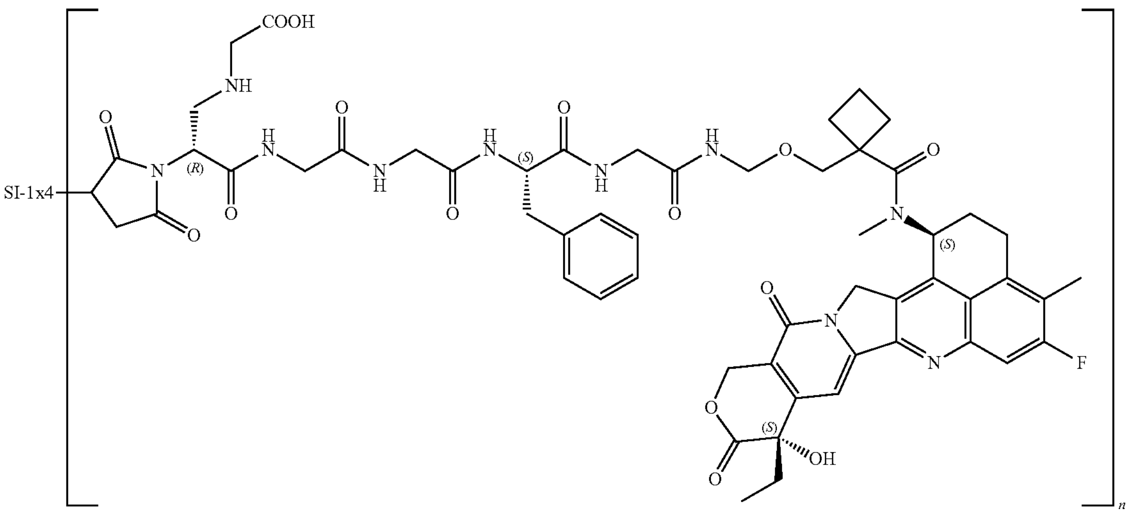
,

-continued
ADC-196
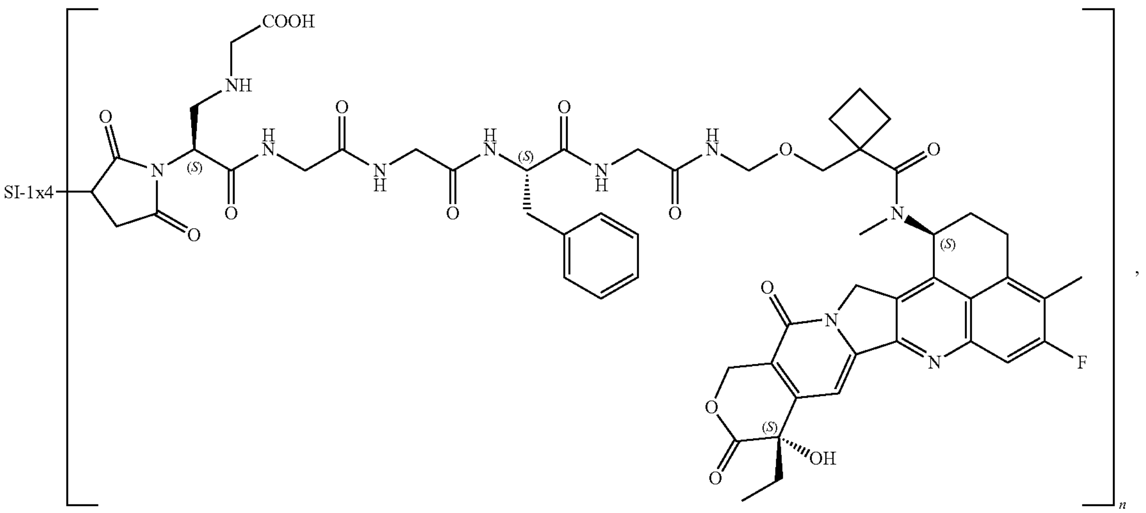
ADC-197
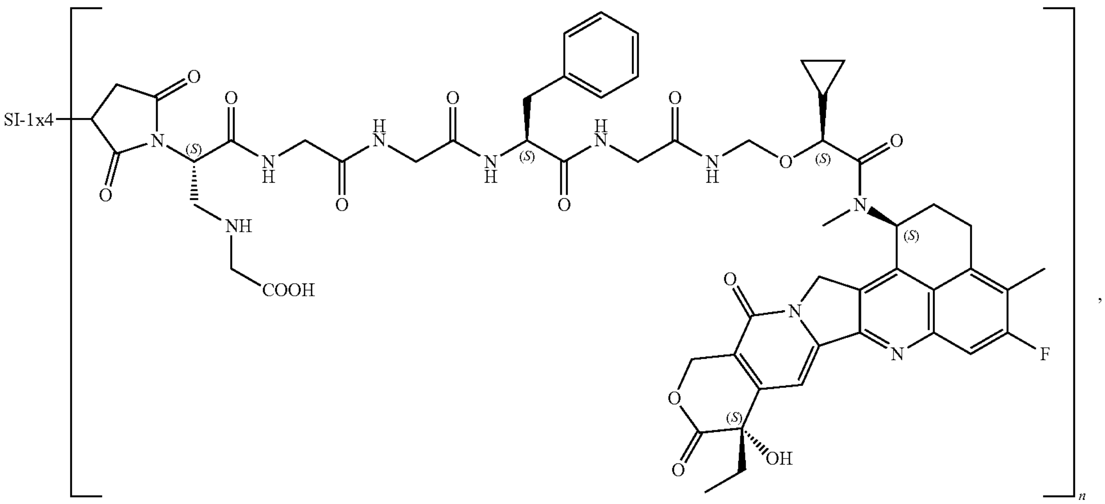
ADC-198
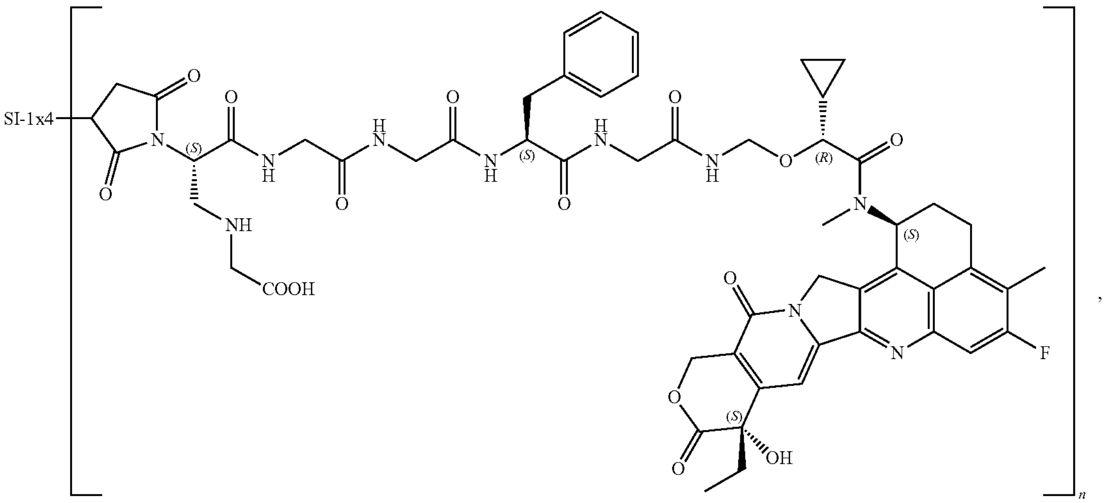

-continued
ADC-199
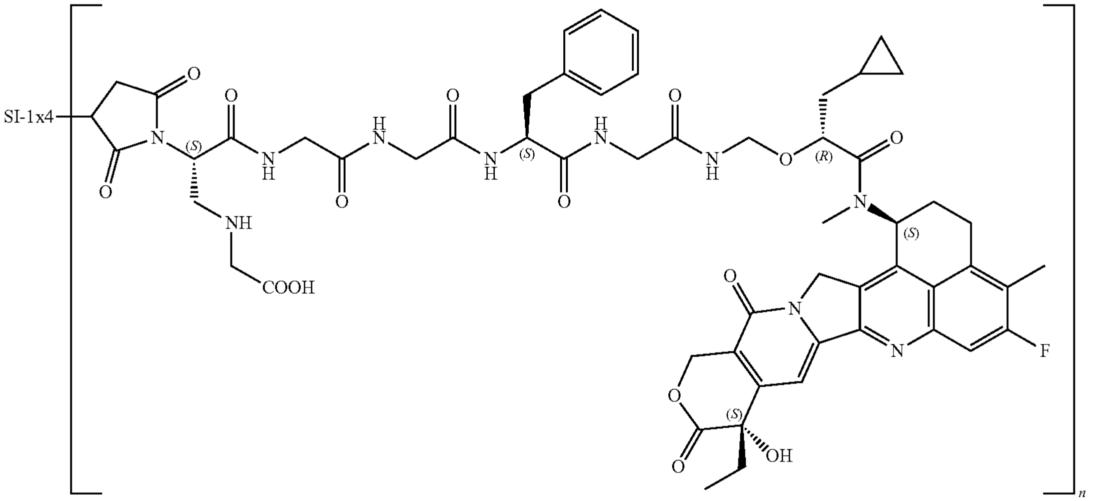
,
ADC-200
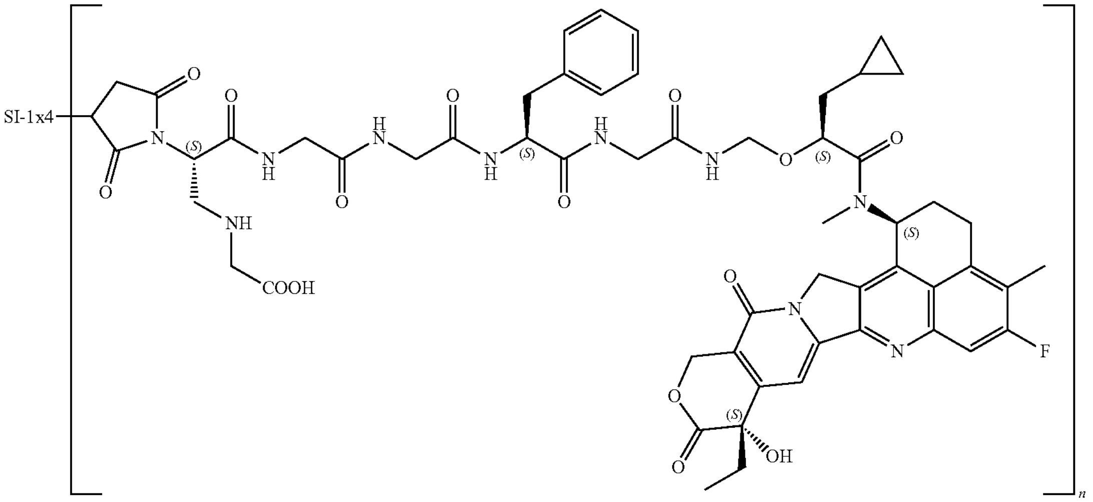
,
ADC-201
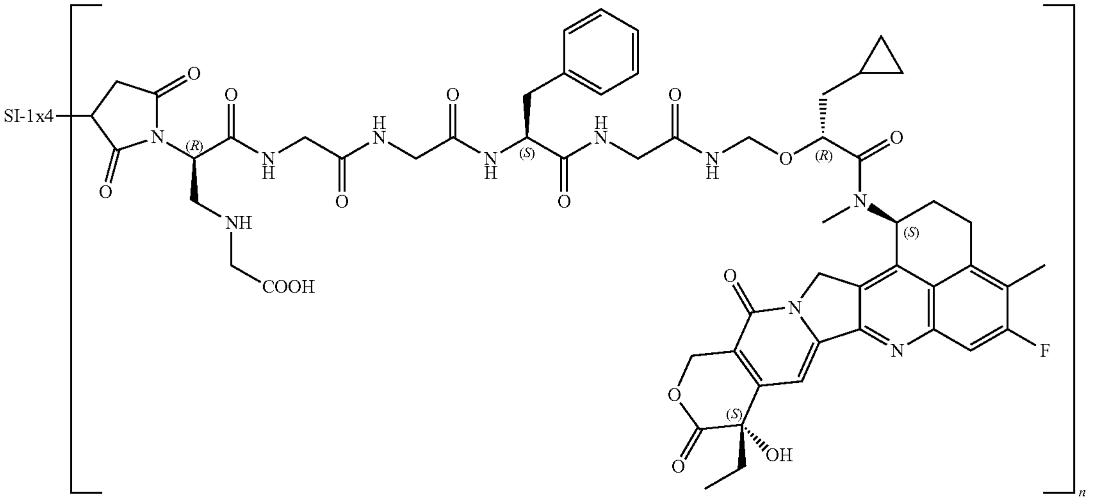
,

-continued
ADC-202
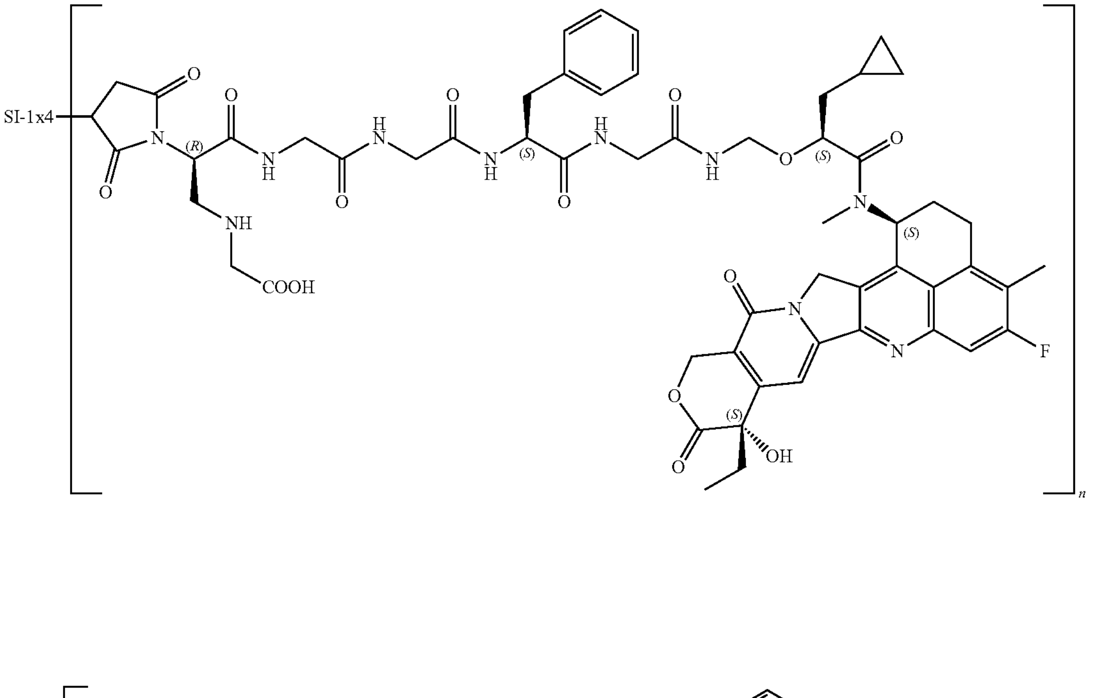
,
ADC-203
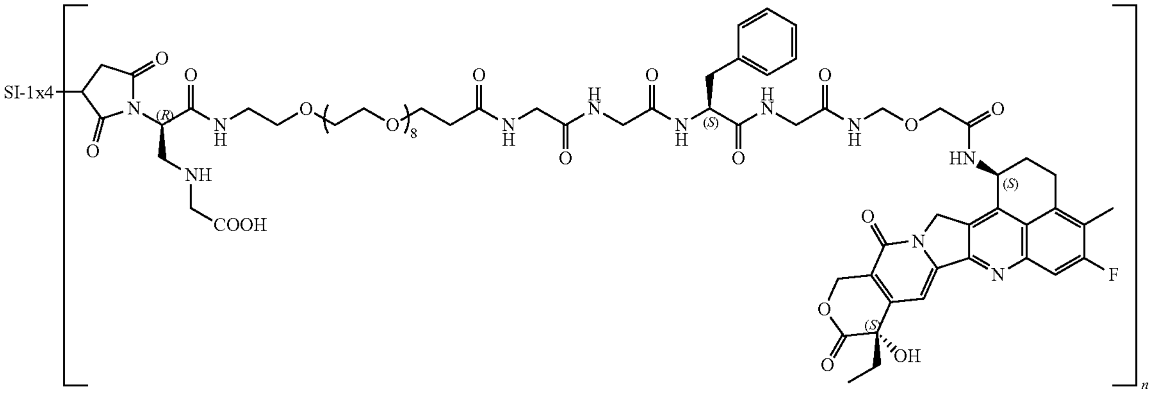
,
ADC-204
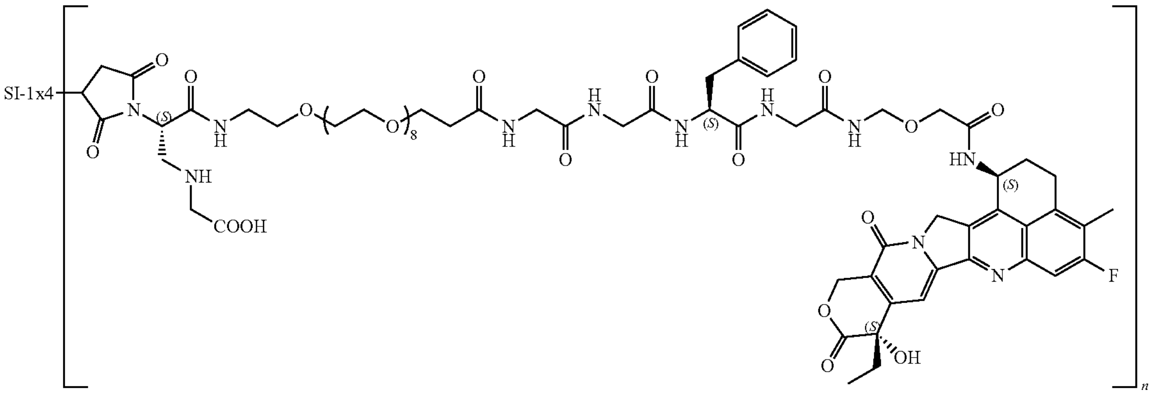
,

-continued
ADC-205
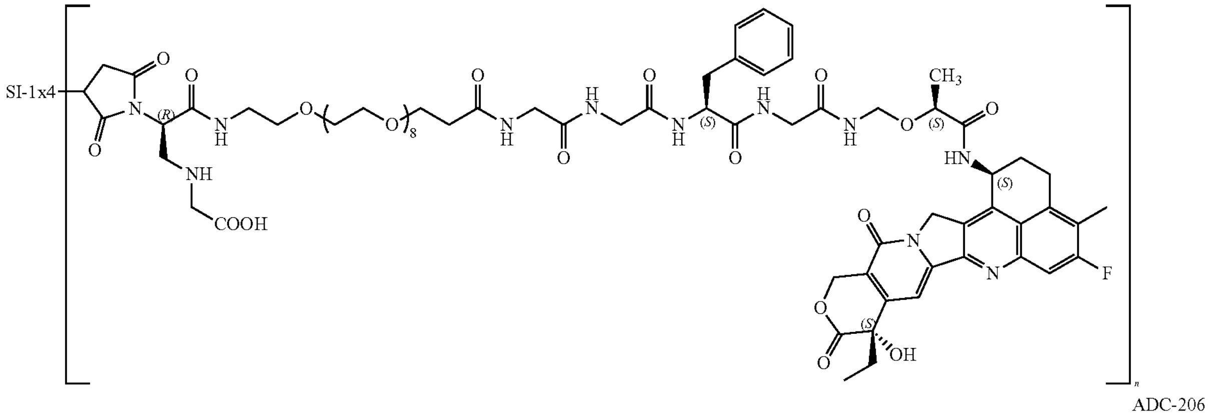
ADC-206
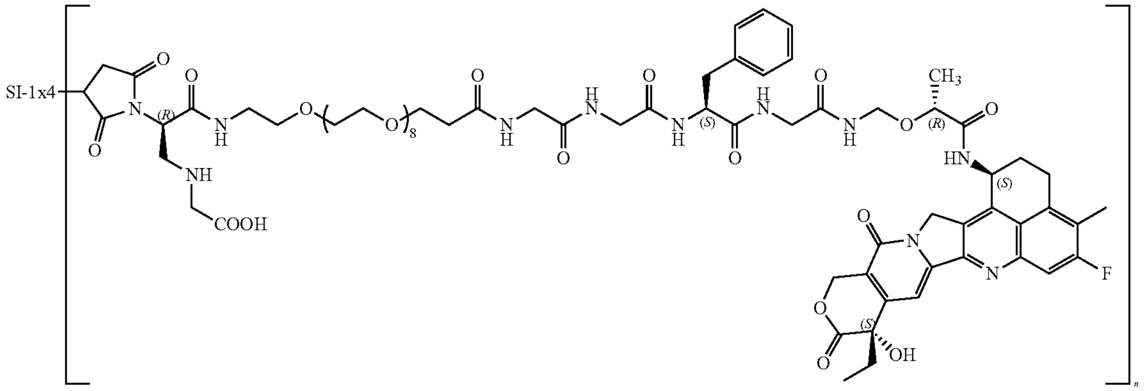
ADC-207
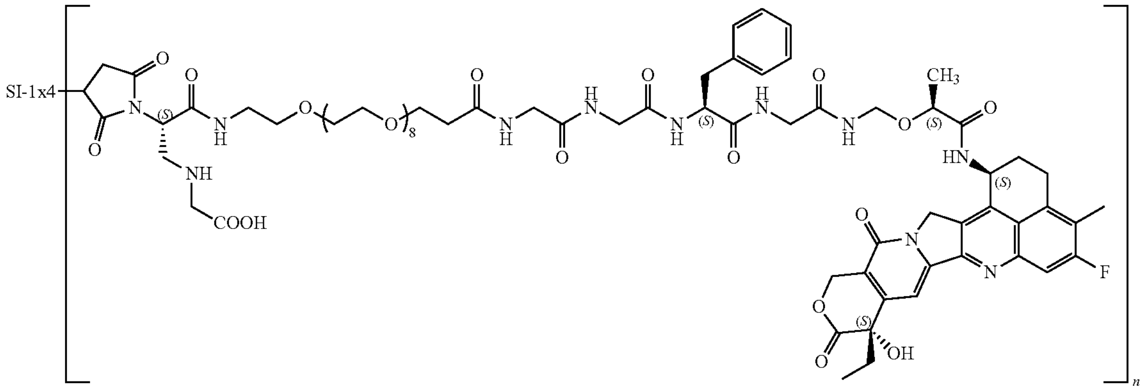
,
ADC-208
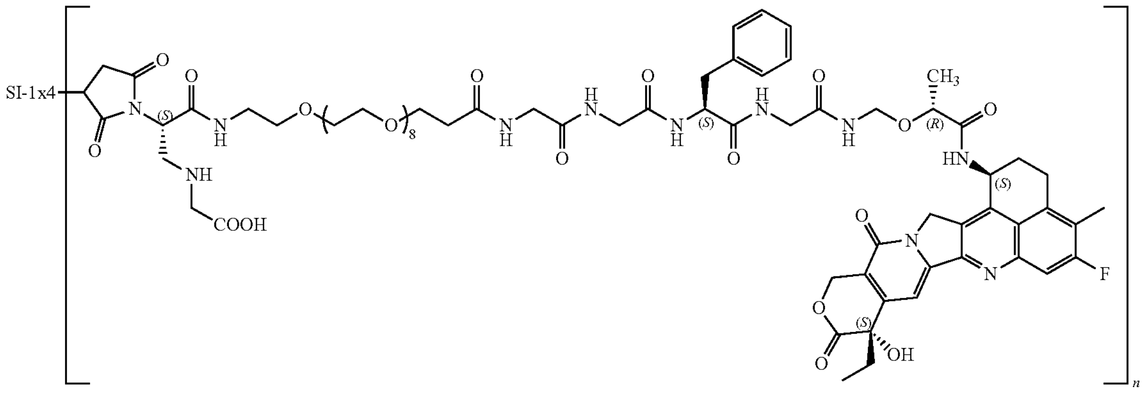
, -continued
ADC-209
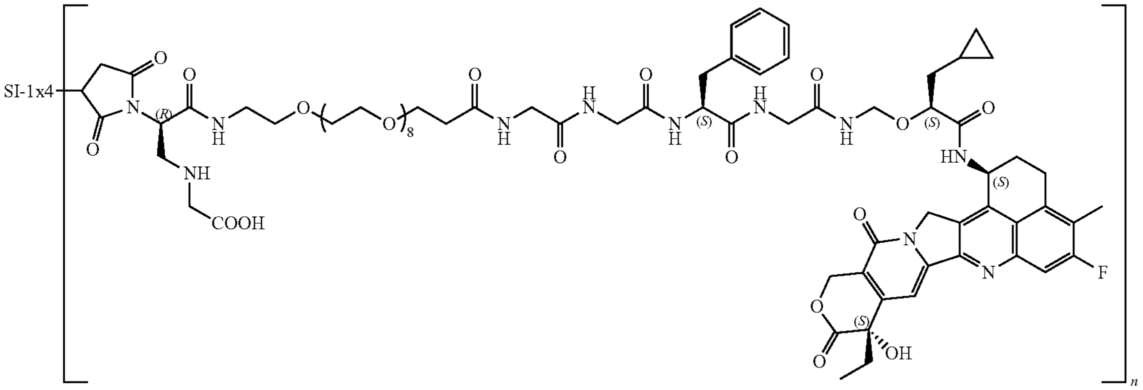
,
ADC-210
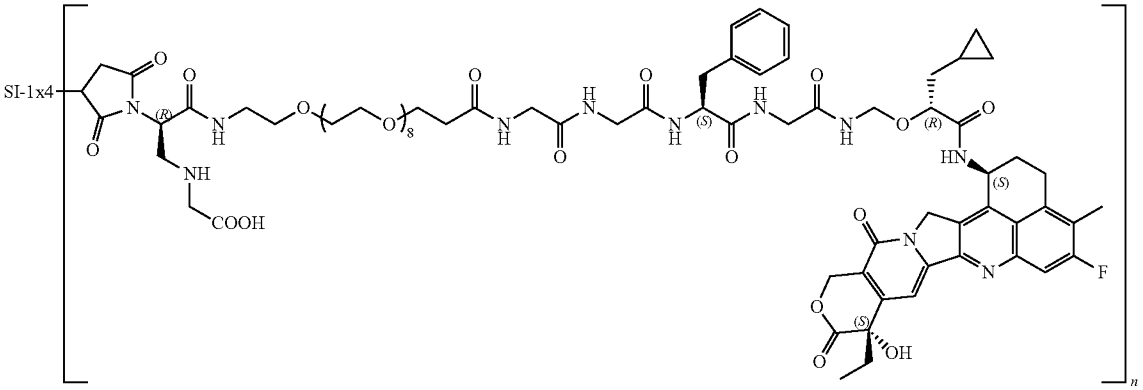
,
ADC-211
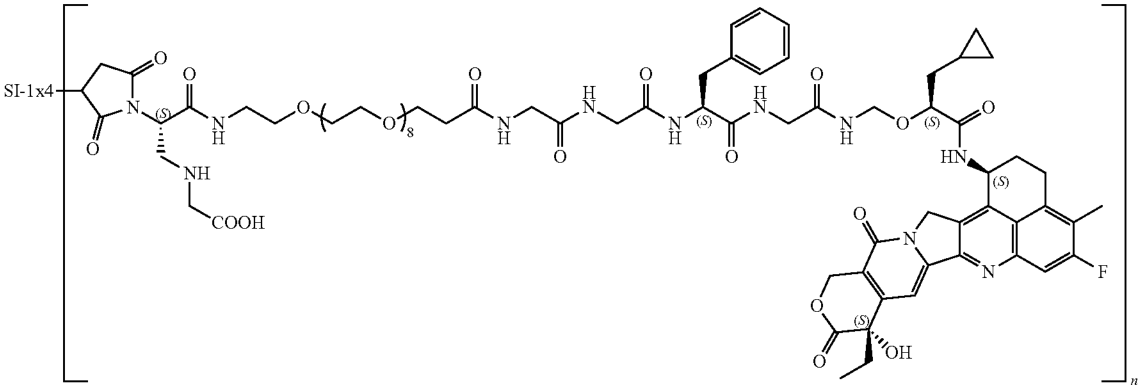
, or -continued

ADC-212

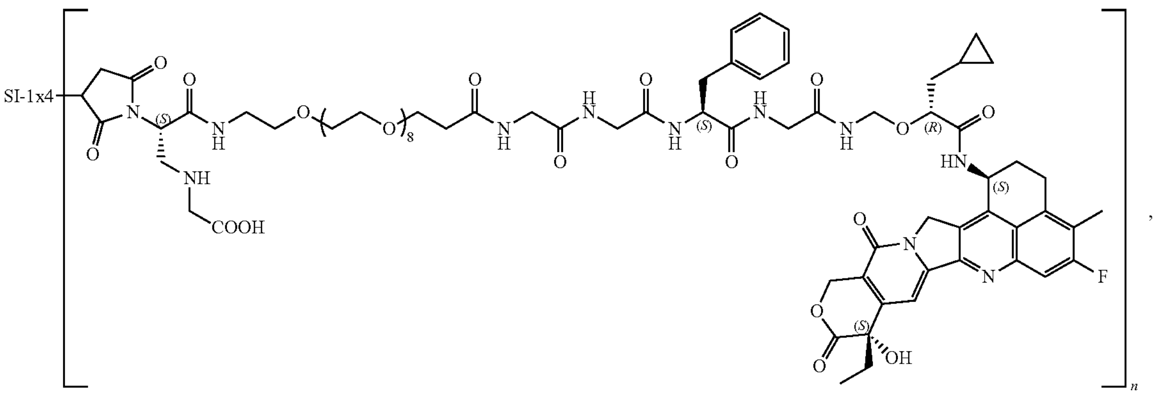

wherein:

SI-1×4 is a bispecific antibody or its antigen-binding fragment simultaneously targeting EGFR and HER3;

n is selected from the integers 1-10 (i.e., 1, 2, 3, 4, 5, 6, 7, 8, 9, or 10).

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures or succinimide open-ring structures thereof or isomers thereof,

ADC-216

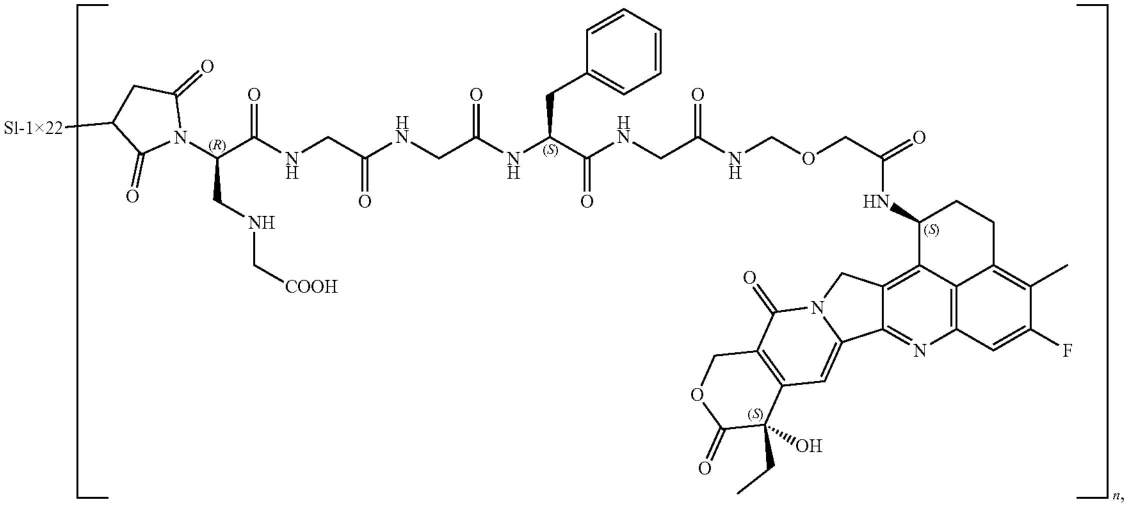

-continued
ADC-217
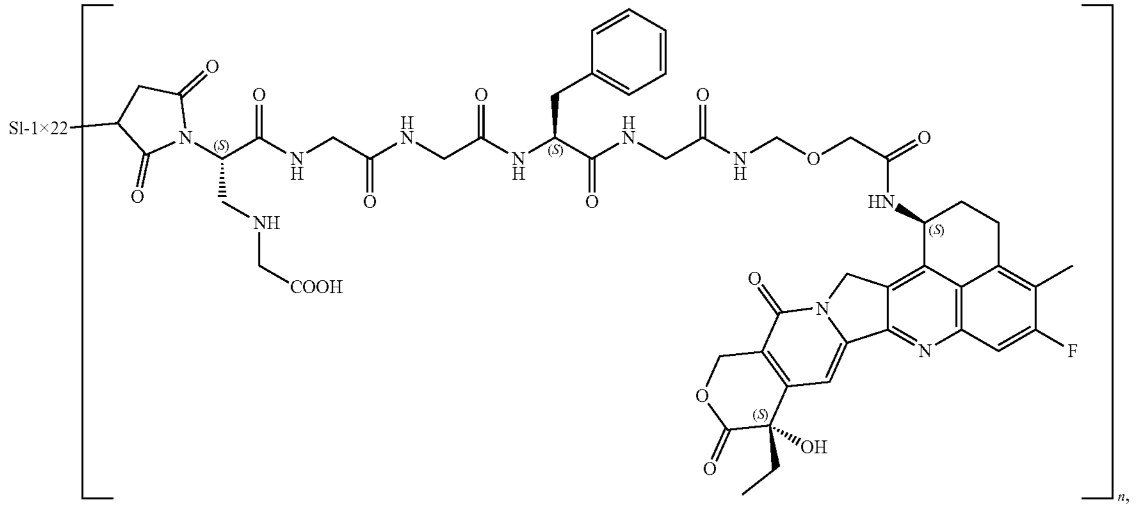
ADC-218
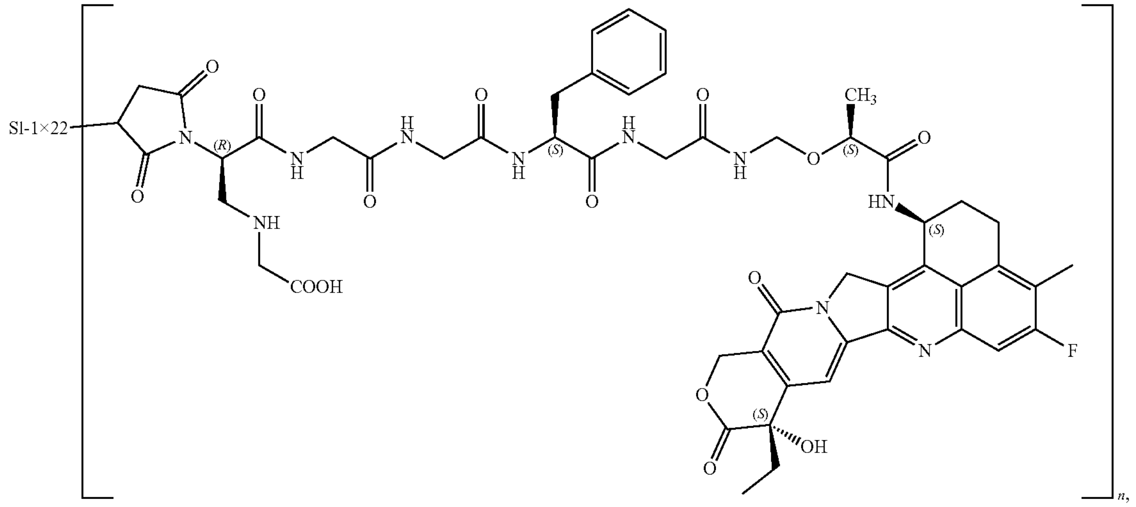
ADC-219
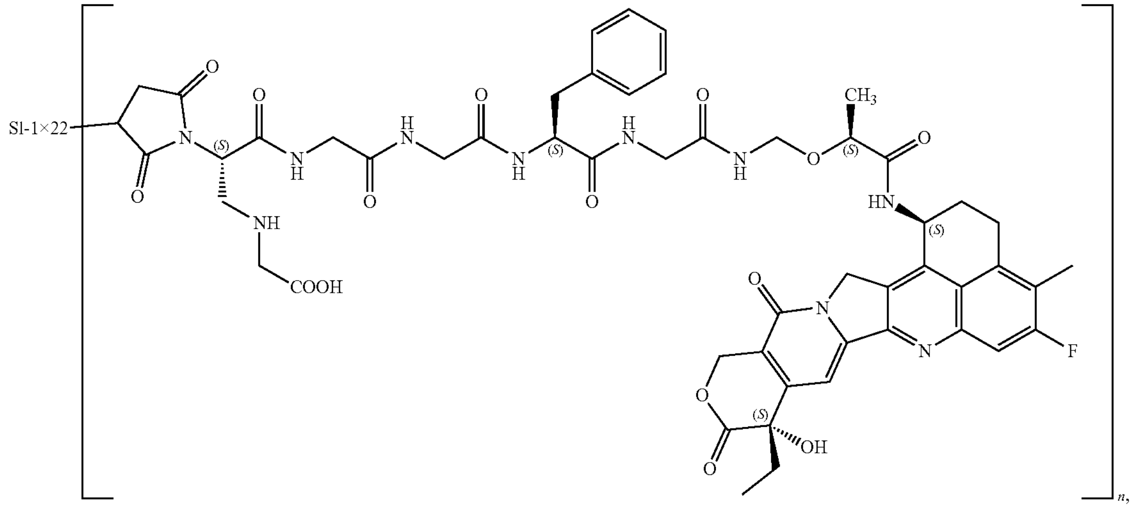

-continued
ADC-219a
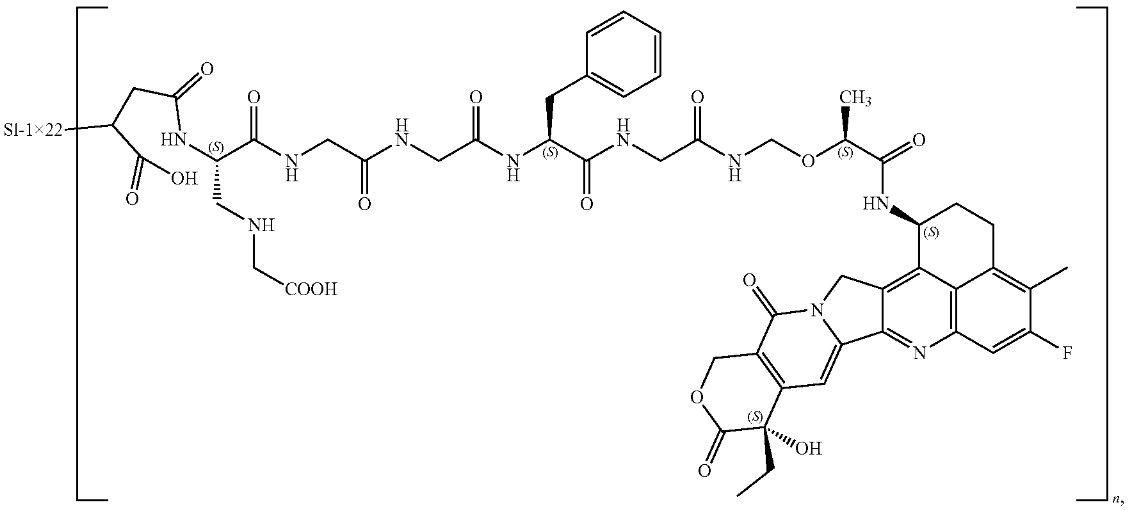
ADC-219b
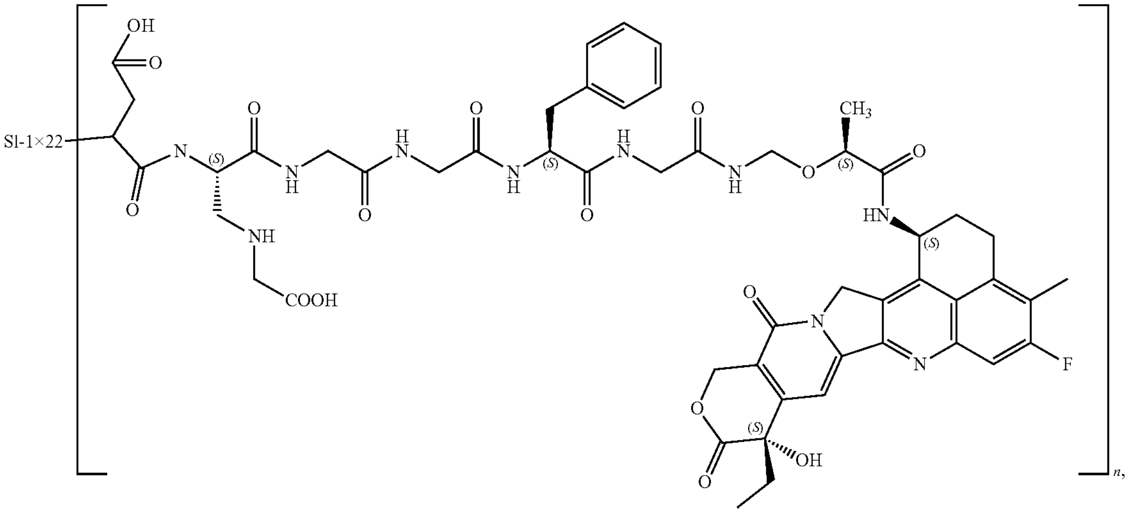
ADC-220
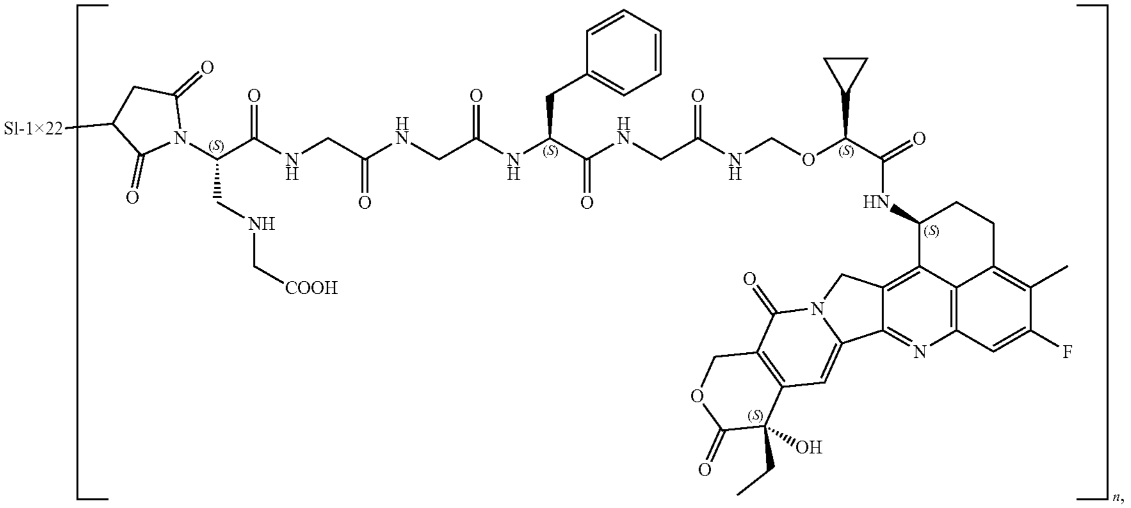

-continued
ADC-221
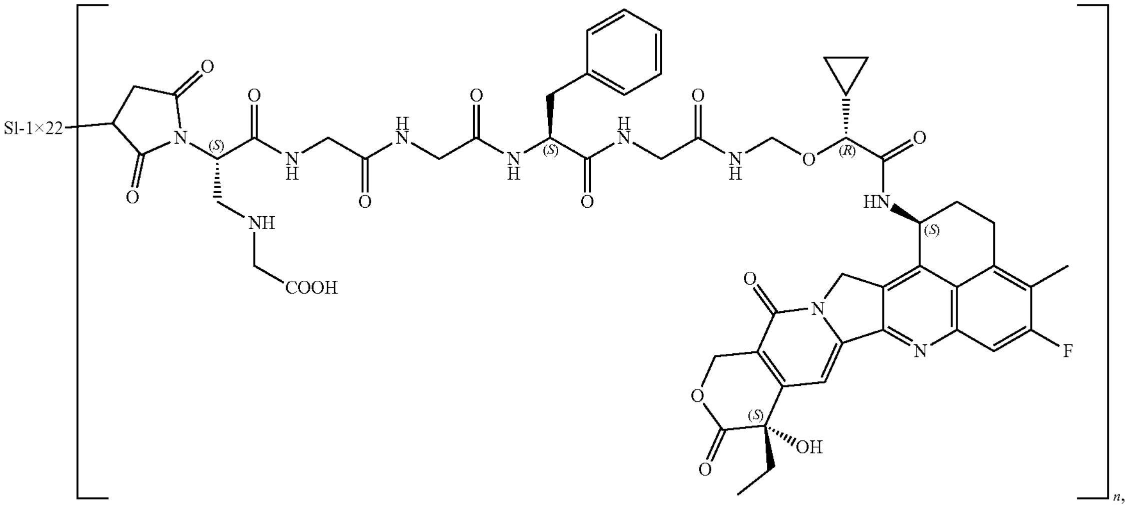
n,
ADC-222
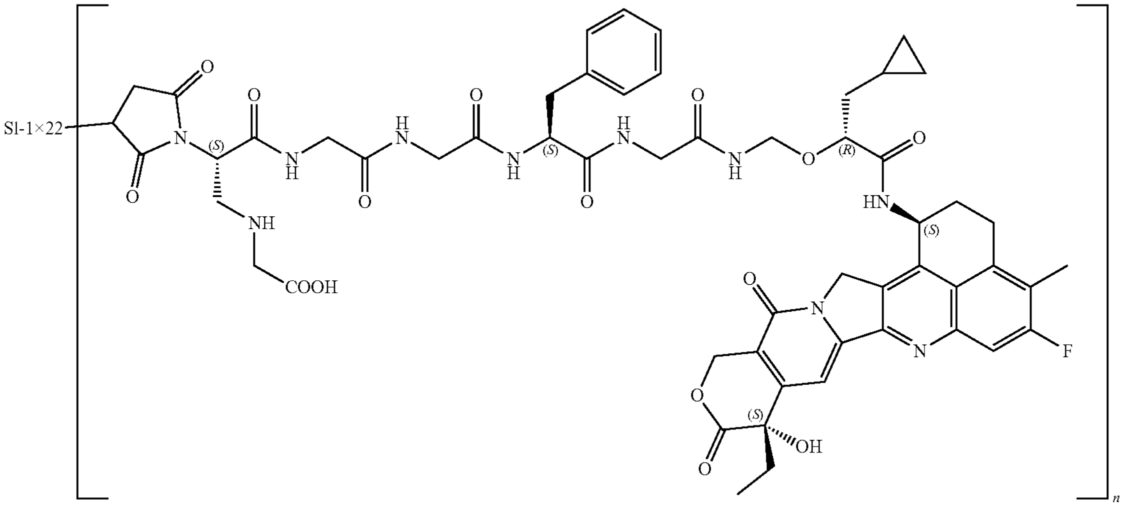
n or
ADC-223
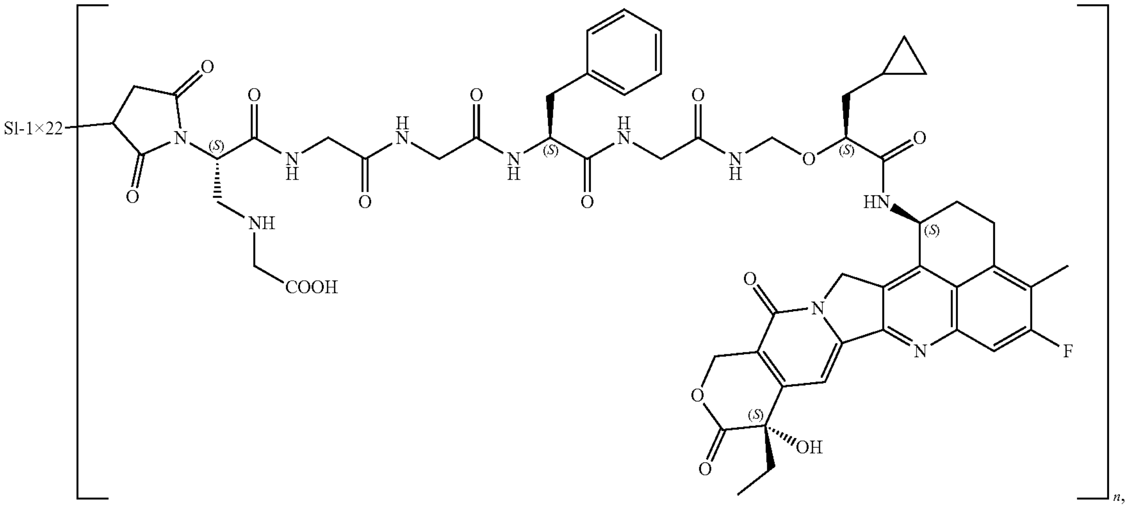
n, wherein:

SI-1×22 is a bispecific antibody or an antigen-binding fragment thereof simultaneously targeting EGFR and HER3;

n is selected from the integers 1-10 (e.g., 1, 2, 3, 4, 5, 6, 7, 8, 9, or 10).

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures or succinimide open-ring structures thereof or isomers thereof,

ADC-224

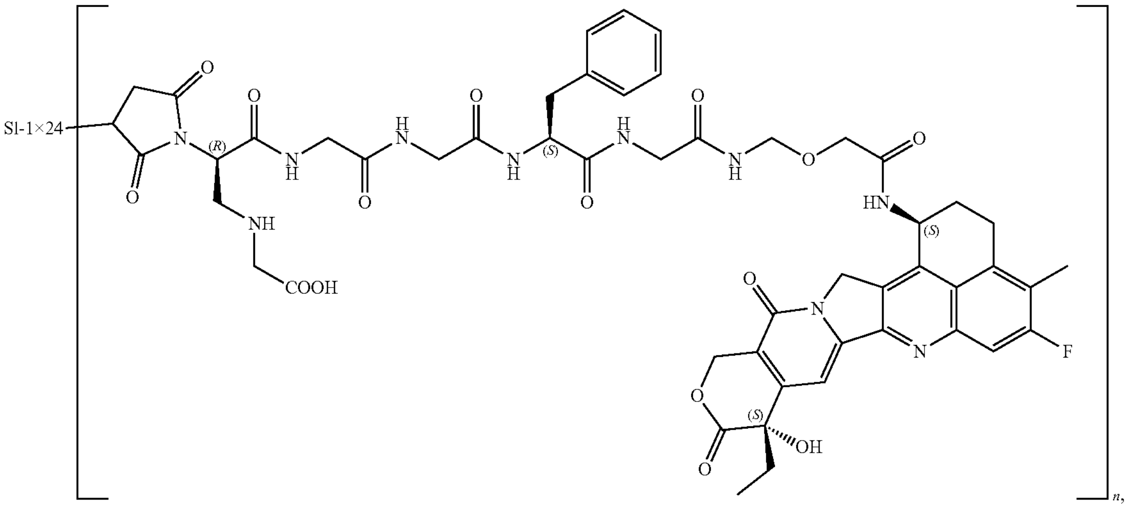

ADC-225

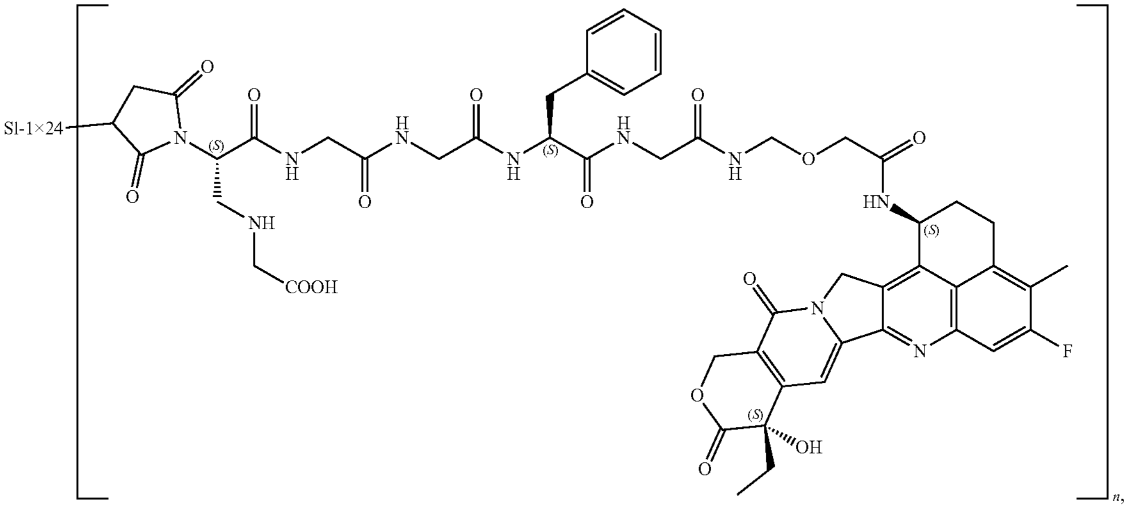

-continued
ADC-226
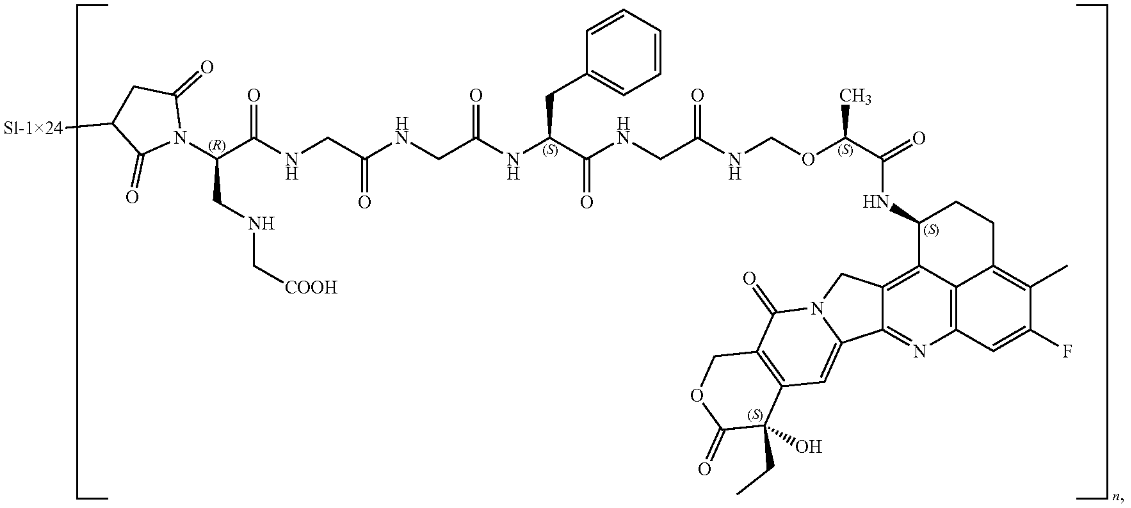
ADC-227
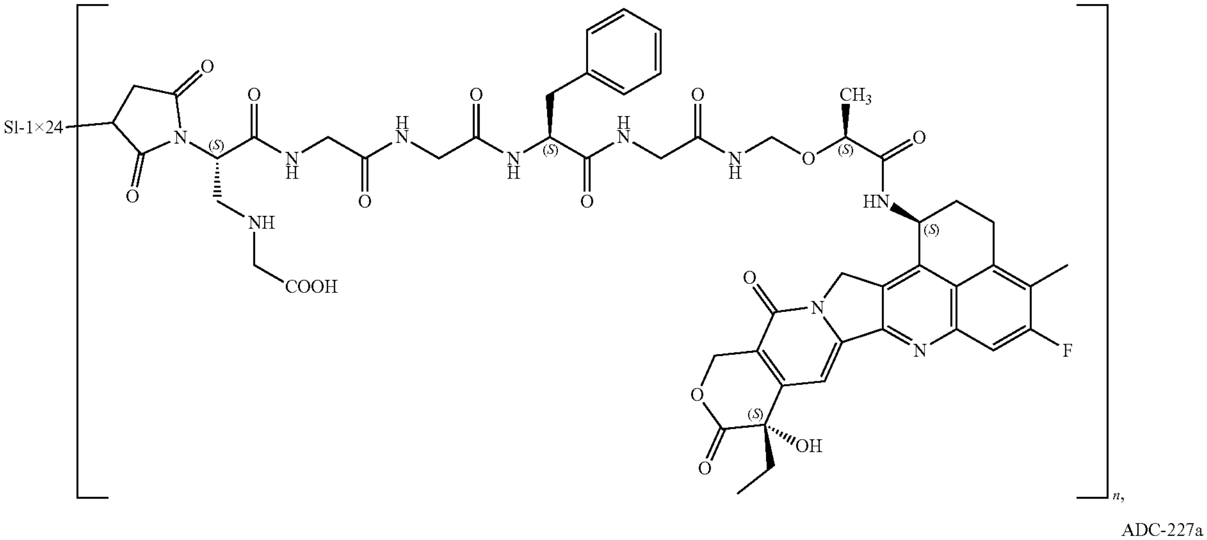
ADC-227a
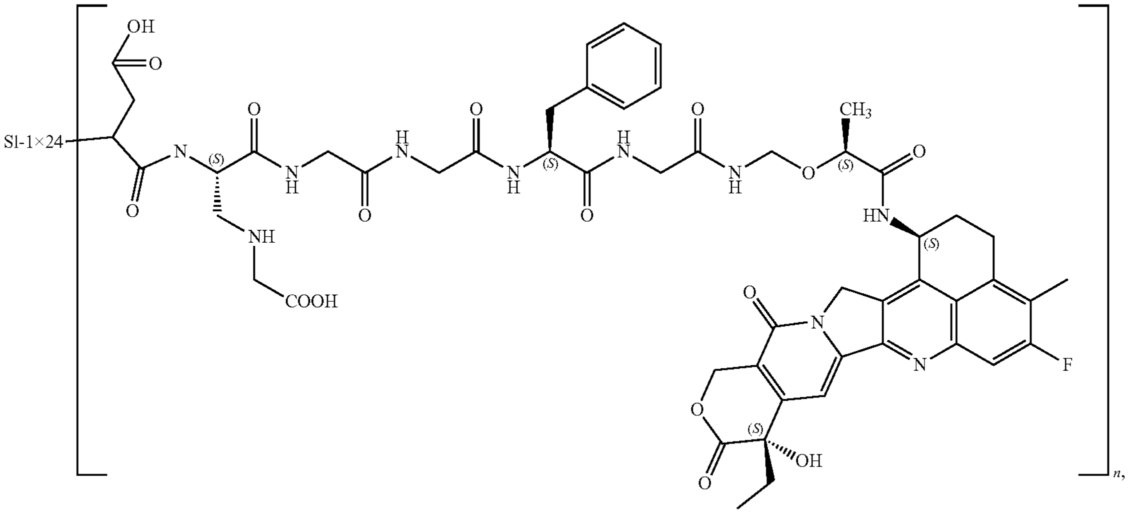

-continued
ADC-227b
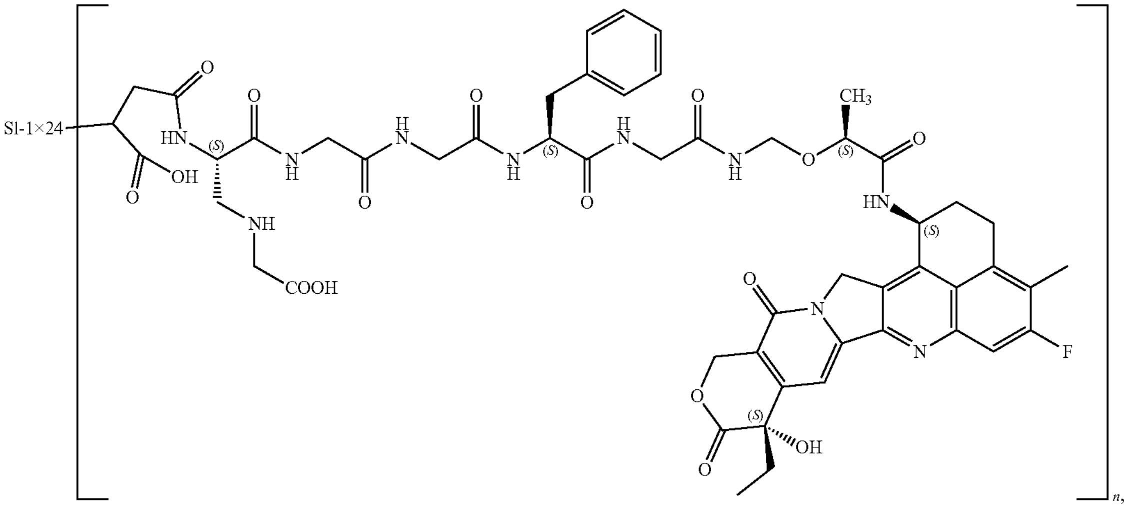
ADC-228
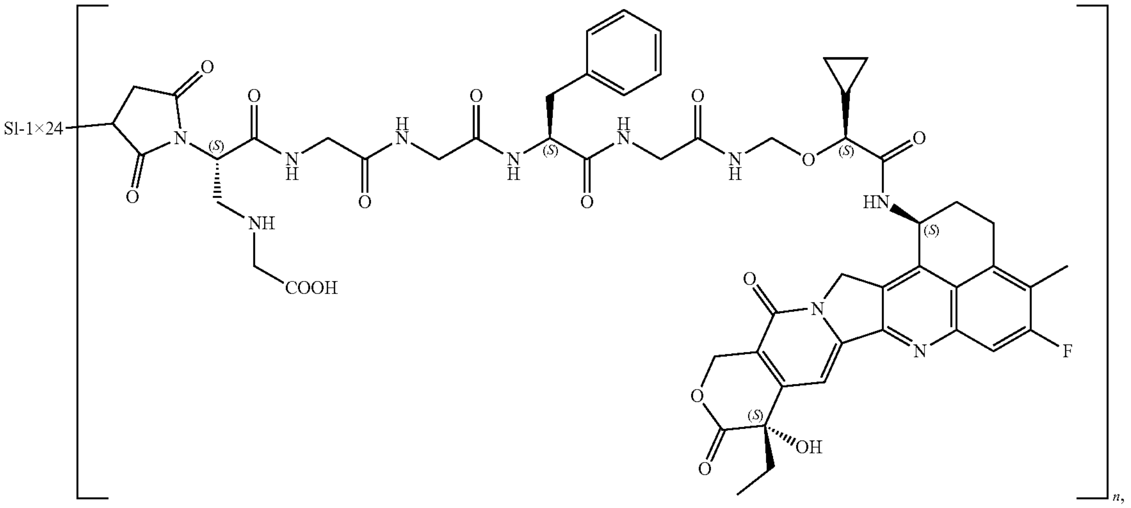
ADC-229
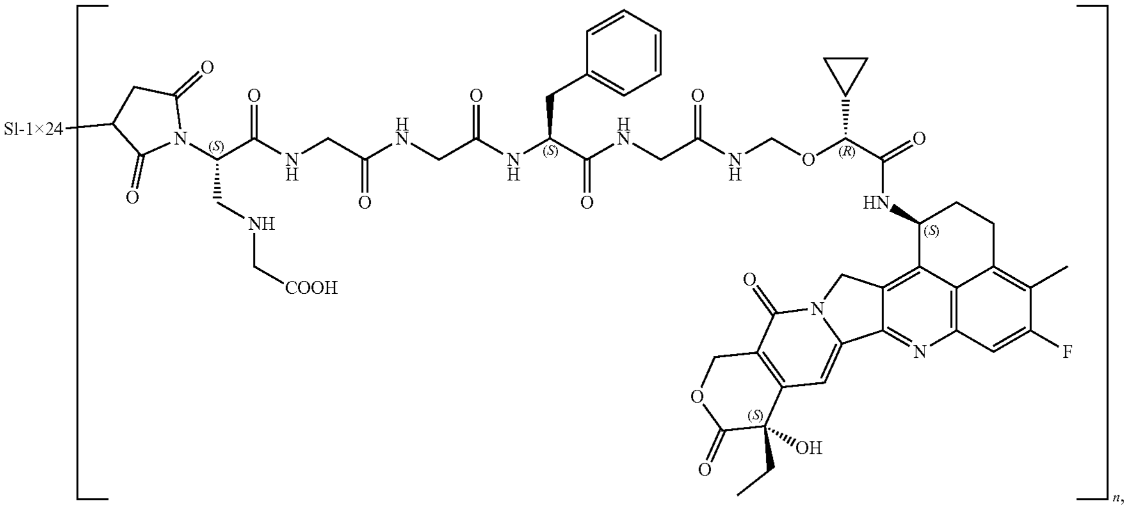

-continued

ADC-230

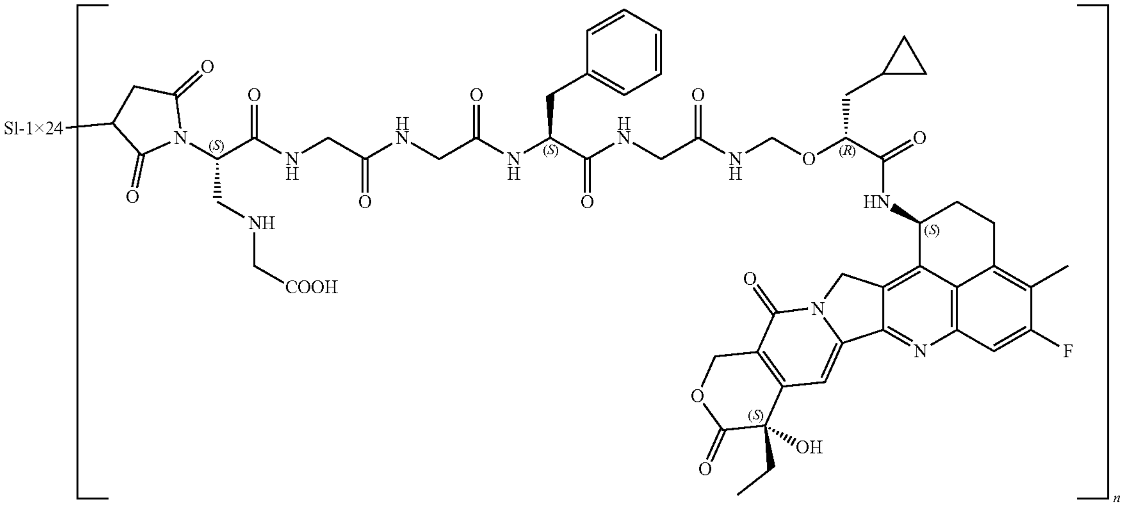

or

ADC-231

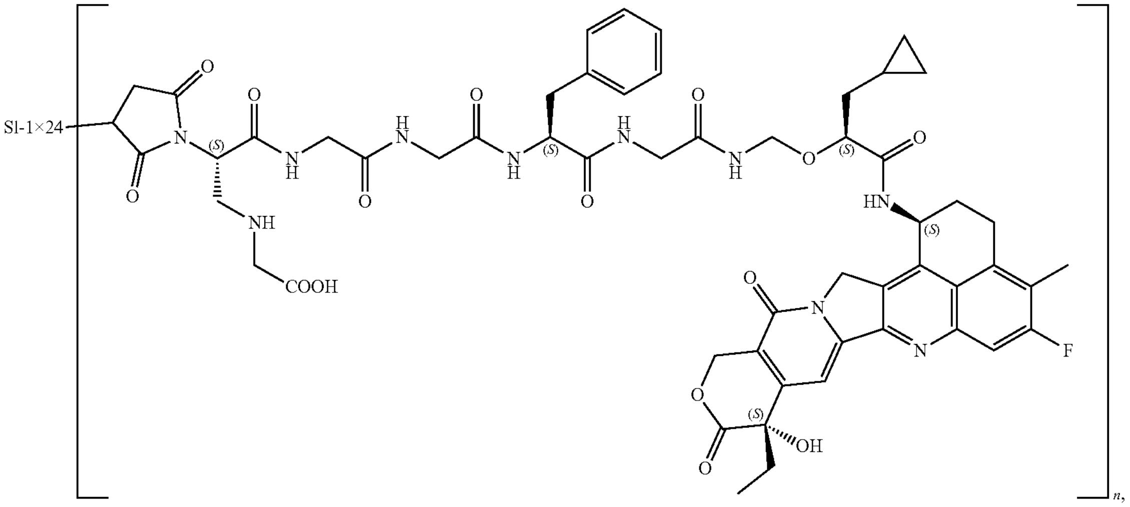

wherein:

SI-1×24 is a bispecific antibody or its antigen-binding fragment simultaneously targeting EGFR and HER3;

n is selected from the integers 1-10 (i.e., 1, 2, 3, 4, 5, 6, 7, 8, 9, or 10).

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures or succinimide open-ring structures thereof or isomers thereof, ADC-232
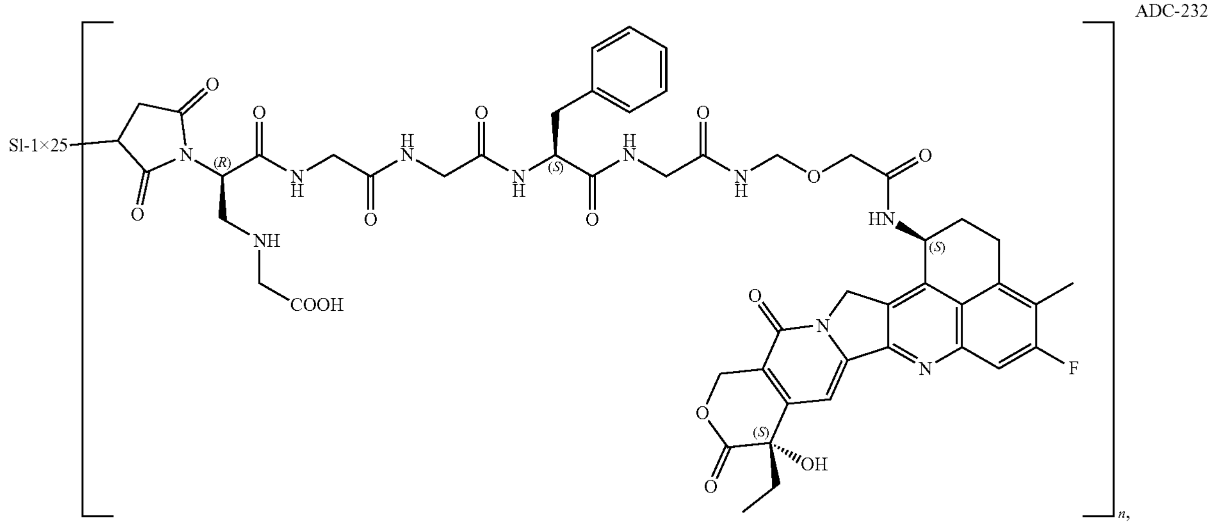
ADC-233
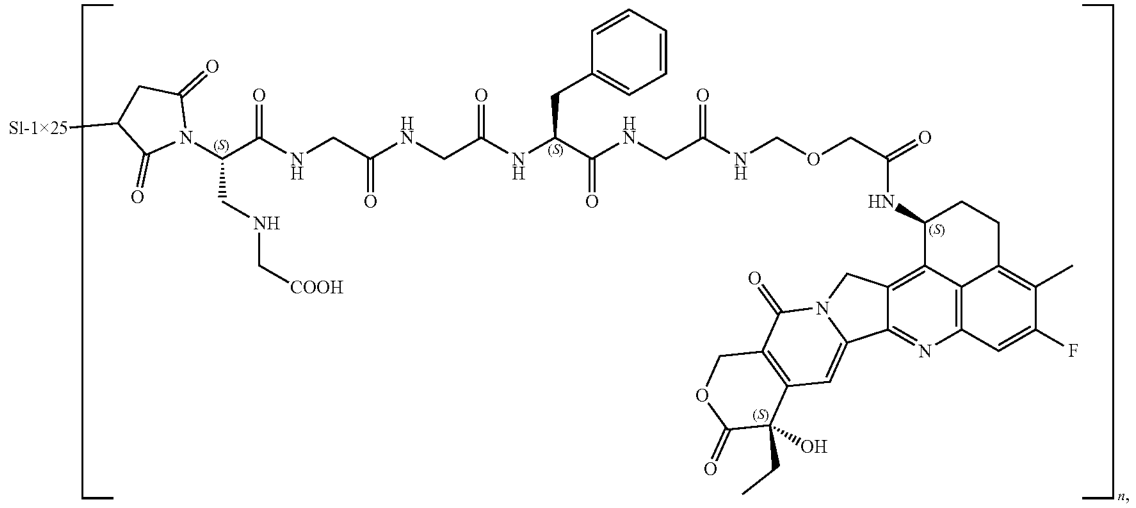
ADC-234
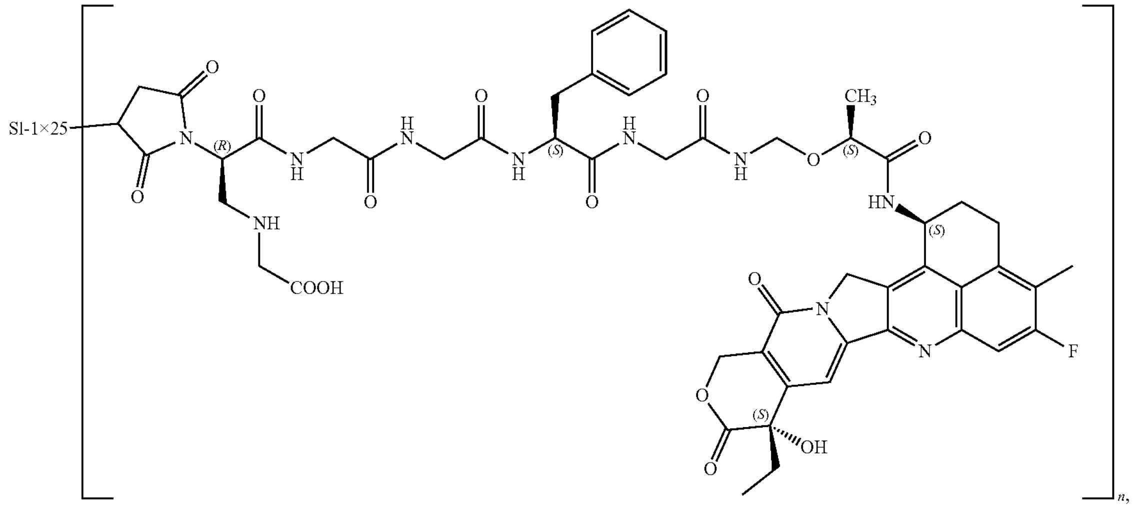

-continued
ADC-235
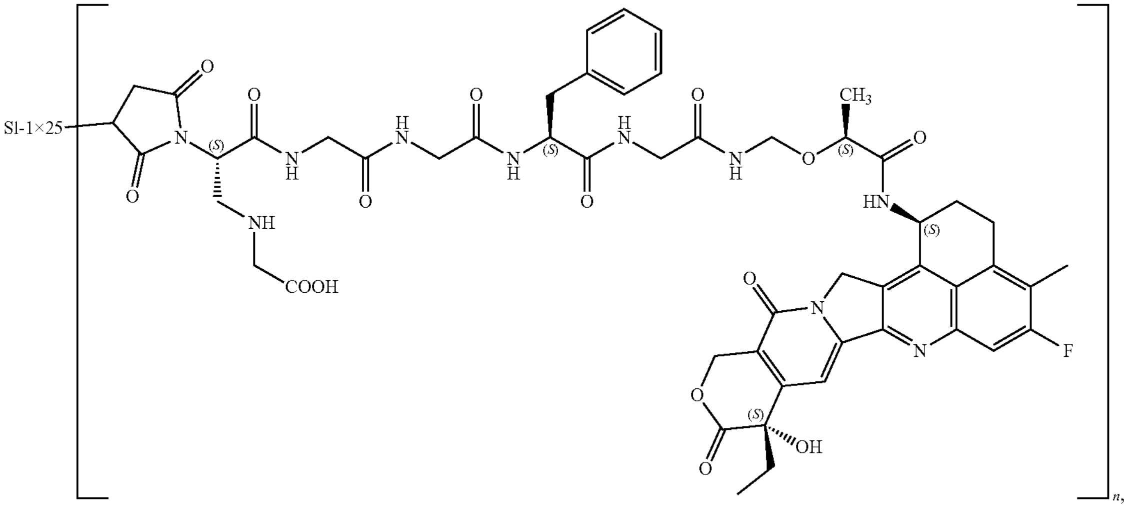
ADC-235a
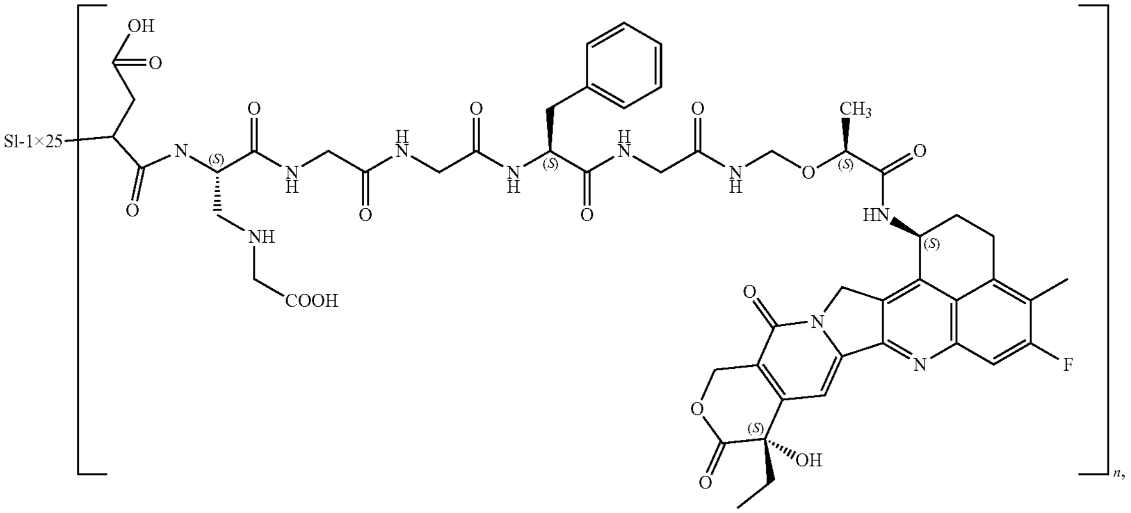
ADC-235b
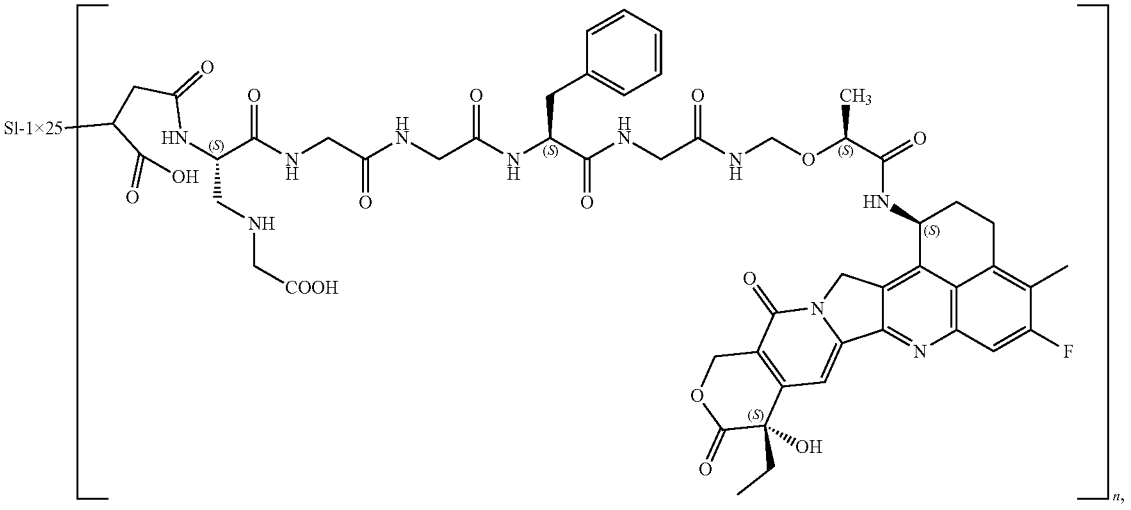

-continued
ADC-236
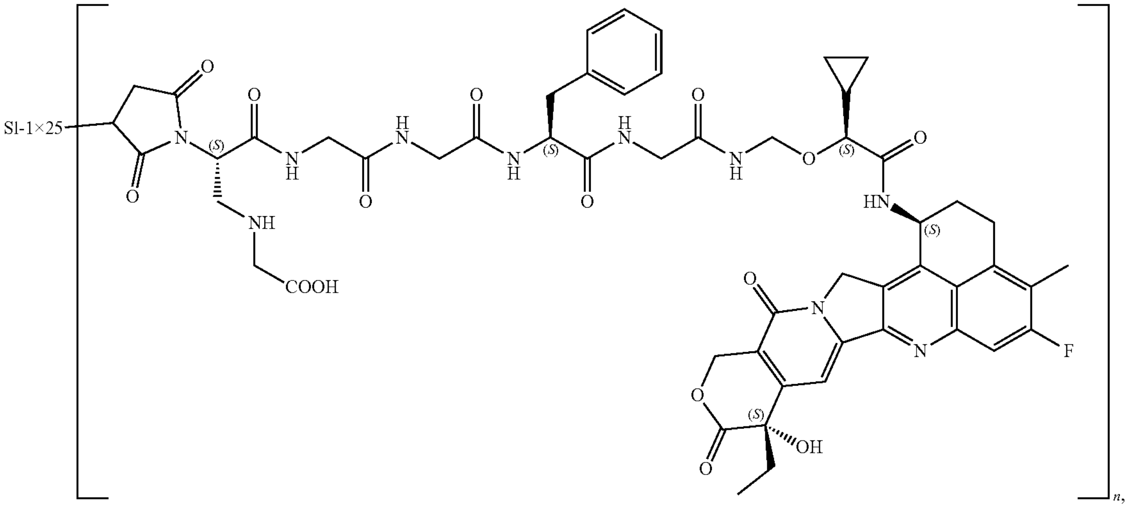
ADC-237
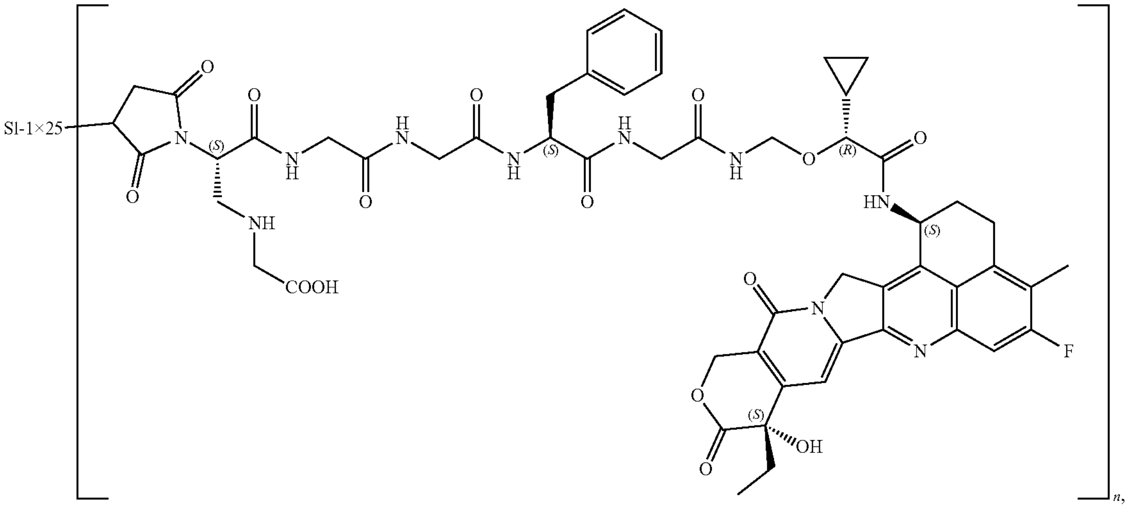
ADC-238
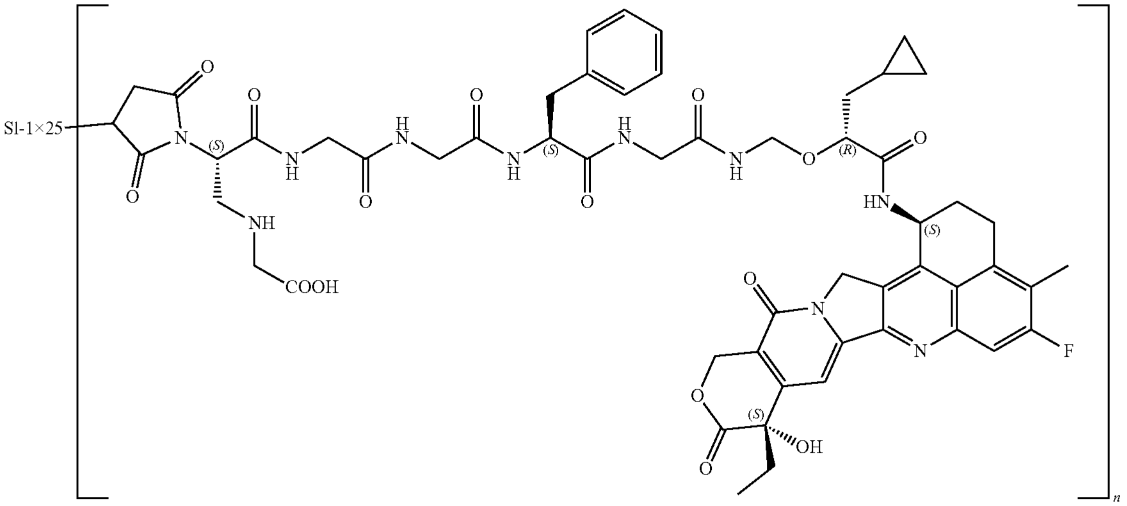
or

-continued

ADC-239

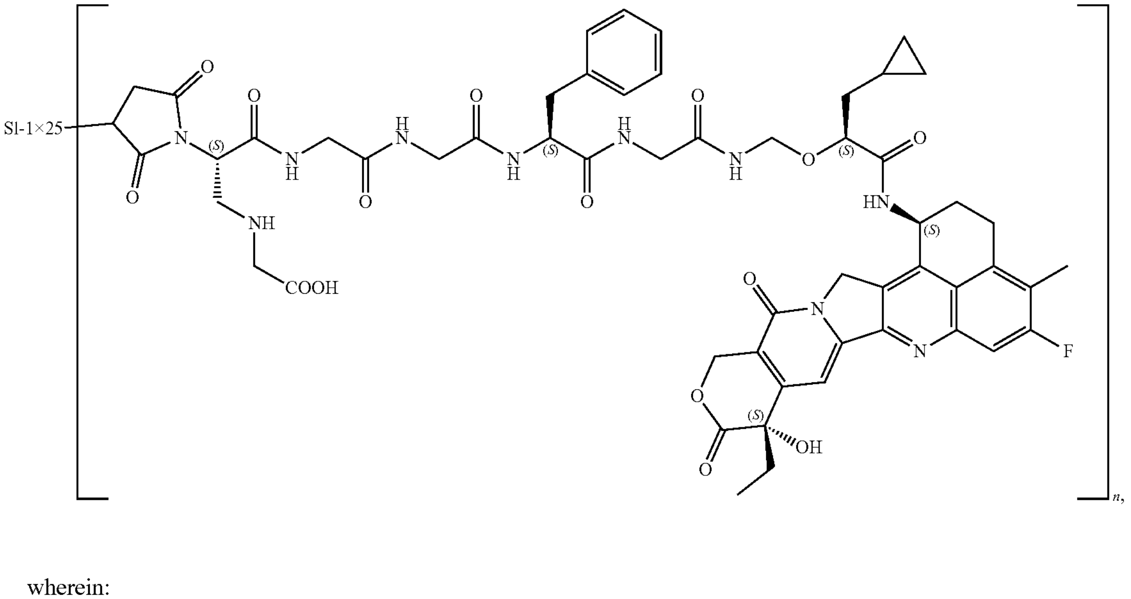

wherein:

SI-1×25 is a bispecific antibody or an antigen-binding fragment thereof simultaneously targeting EGFR and HER3;

n is selected from the integers 1-10 (i.e., 1, 2, 3, 4, 5, 6, 7, 8, 9, or 10).

In some embodiments of the first aspect, the second aspect and the fourth aspect of the present invention, the disclosure of said ligand-camptothecin derivative conjugate, or a pharmaceutically acceptable salt or solvate thereof, is characterized in that said ligand-camptothecin derivative conjugate, or a pharmaceutically acceptable salt or solvate thereof, is selected without limitation from the following structures or succinimide open-ring structures thereof or isomers thereof,

ADC-240

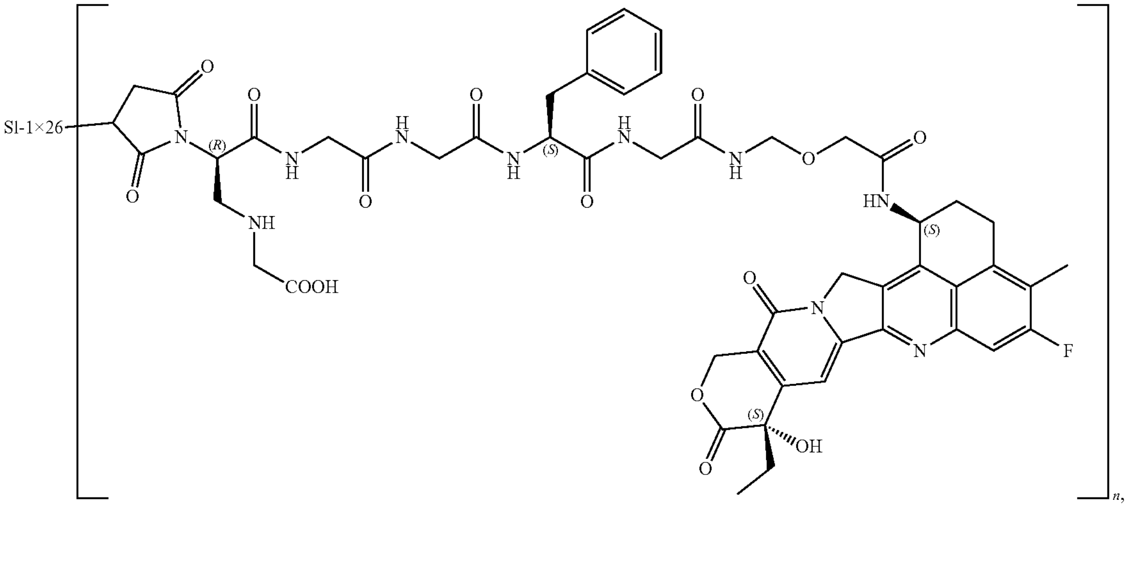

-continued
ADC-241
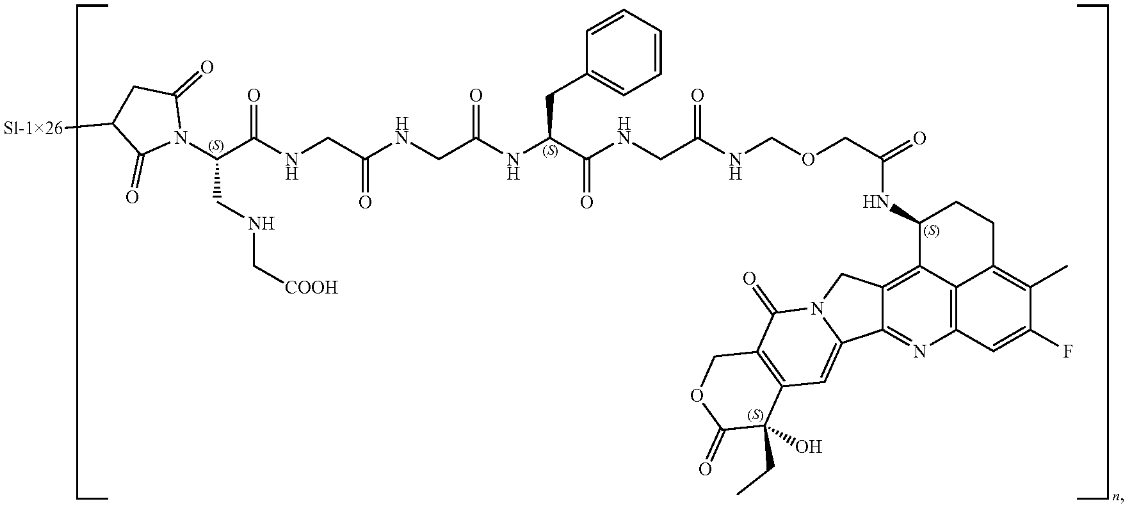
ADC-242
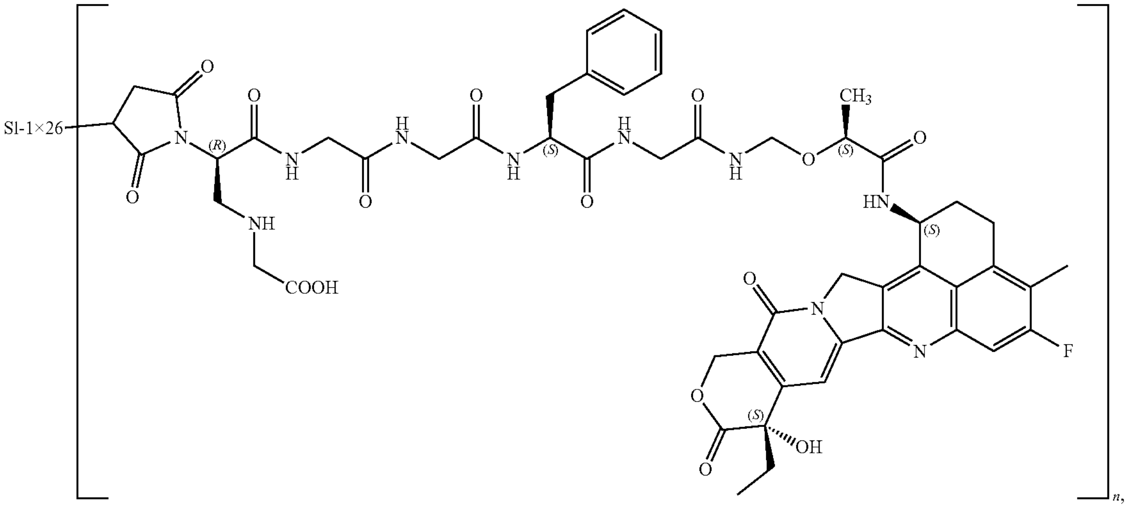
ADC-243
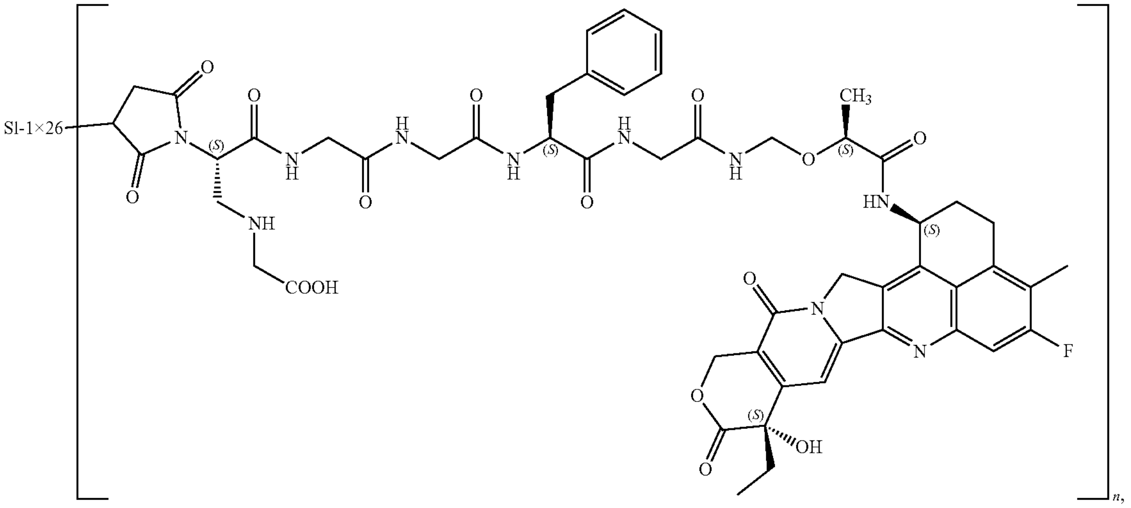

-continued
ADC-243a
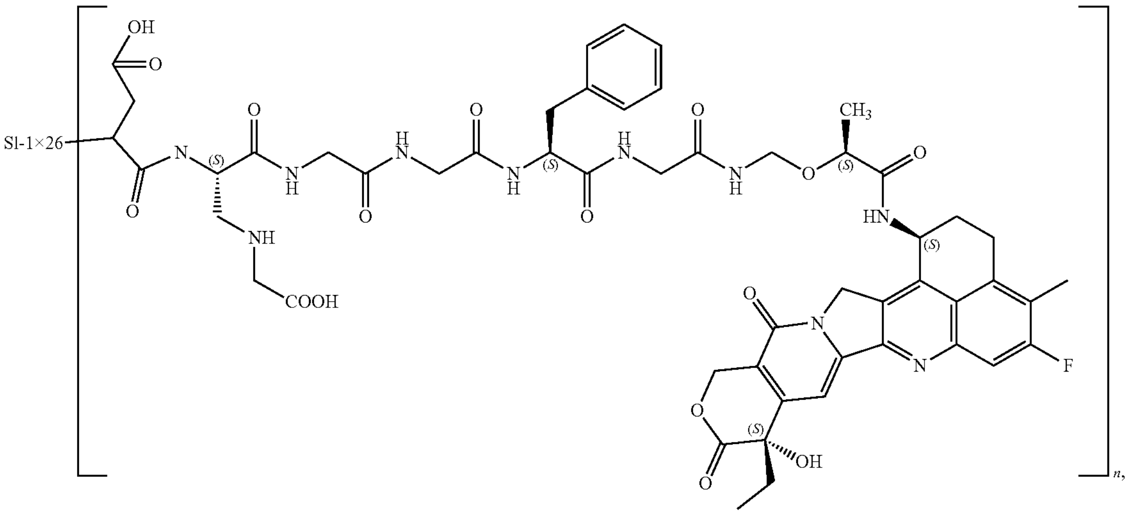
ADC-243b
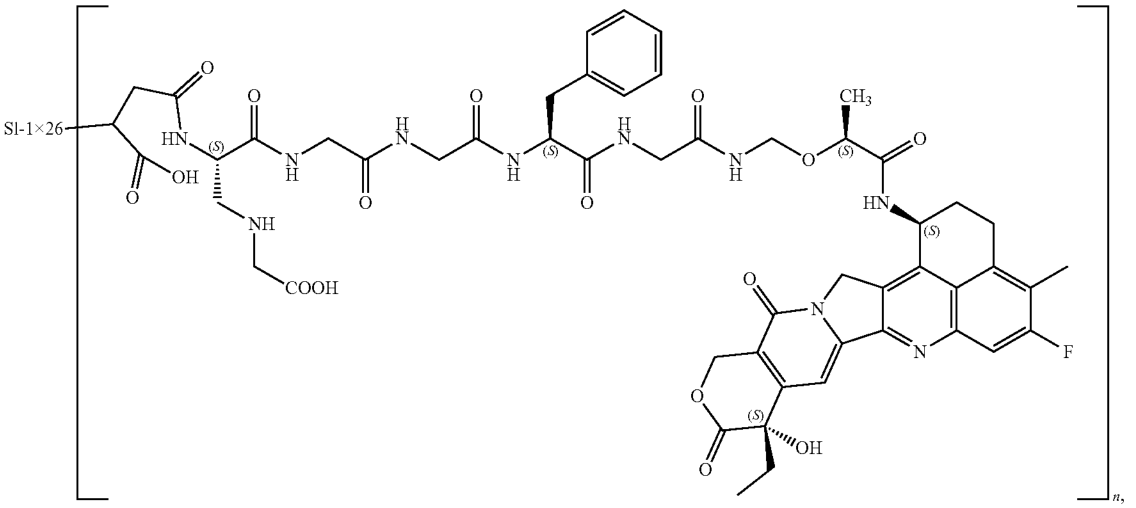
ADC-244
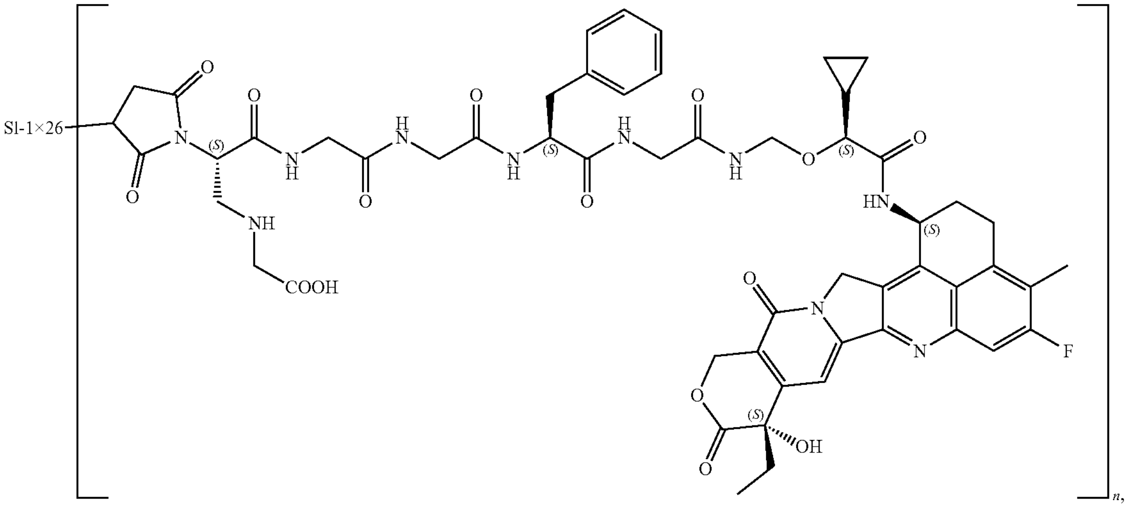

-continued
ADC-245
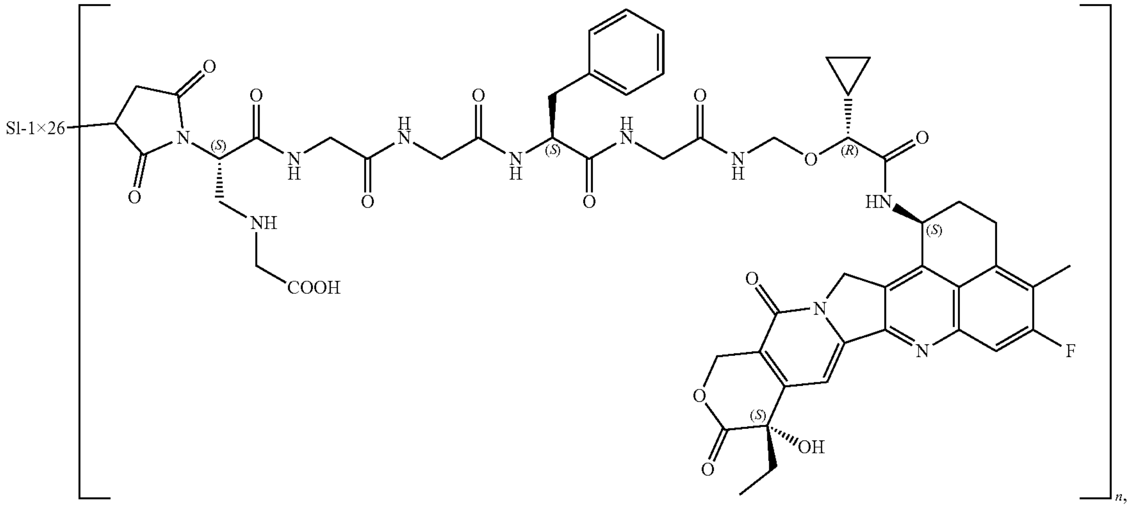
,
ADC-246
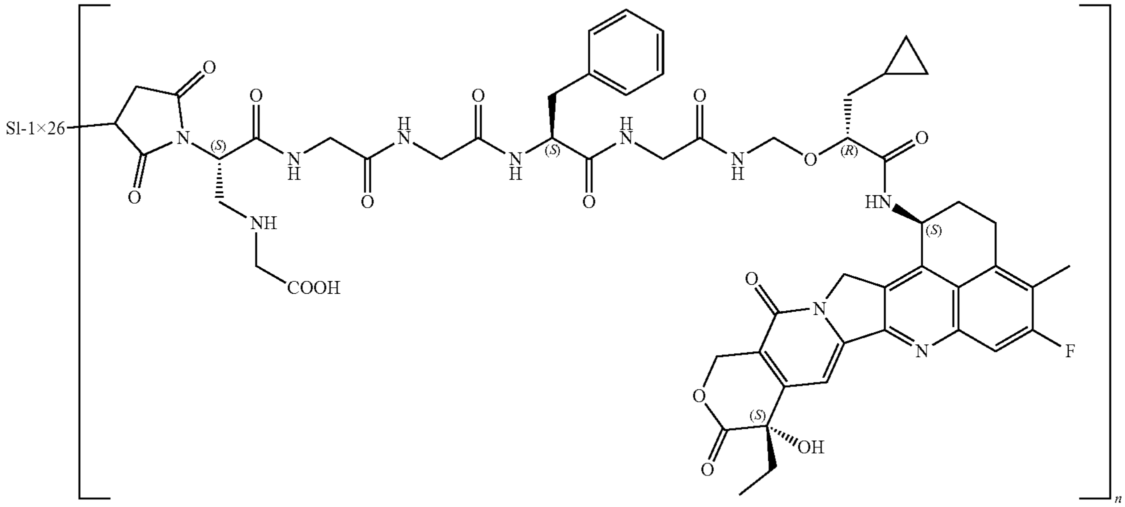
or
ADC-247
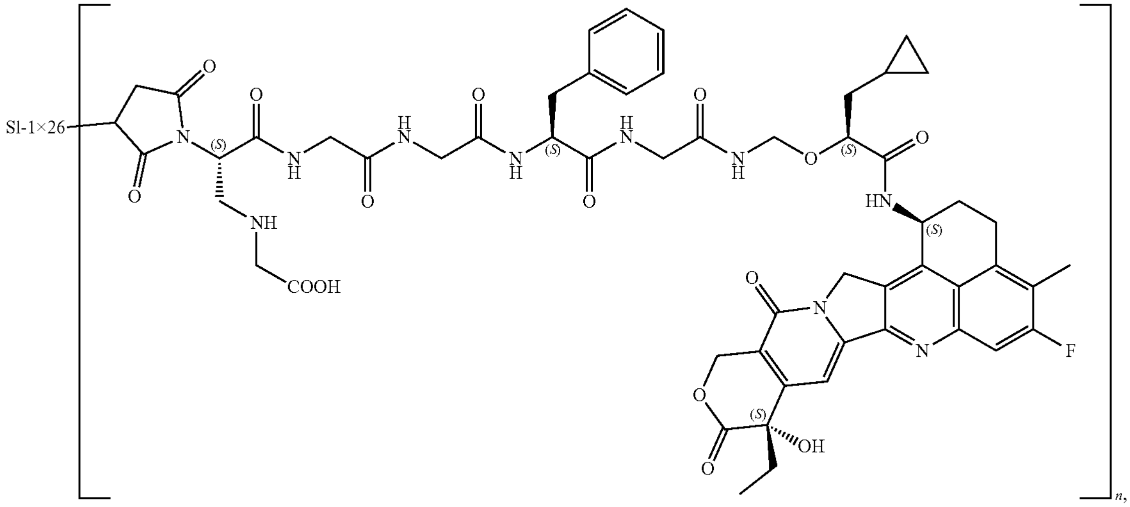
, wherein:

SI-1×26 is a bispecific antibody or its antigen-binding fragment simultaneously targeting EGFR and HER3;

n is selected from the integers 1-10 (i.e., 1, 2, 3, 4, 5, 6, 7, 8, 9, or 10).

In some embodiments of the first aspect, the second aspect and the third aspect of the present invention, the disclosure of said ligand-camptothecin derivative conjugate or pharmaceutically acceptable salt or solvate thereof or linker-drug compound or pharmaceutically acceptable salt or solvate thereof is characterized in that said pharmaceutically acceptable salt comprises a sodium salt, a potassium salt, a calcium salt or a magnesium salt formed with an acidic functional group in the structural formula, and acetate, trifluoroacetate, citrate, oxalate, tartrate, malate, nitrate, chloride, bromide, iodide, sulfate, bisulfate, phosphate, lactate, oleate, ascorbate, salicylate, formate, glutamate, methanesulfonate, ethanesulfonate, benzenesulfonate or p-toluenesulfonate formed with a basic functional group in the structure.

A fifth aspect of the present invention discloses a pharmaceutical composition comprising a ligand-camptothecin derivative conjugate described in the first aspect and the second aspect or a pharmaceutically acceptable salt or solvate thereof or a linker-drug compound described in the third aspect or a pharmaceutically acceptable salt or solvate thereof, and optionally a pharmaceutically acceptable carrier.

A sixth aspect of the present invention discloses a pharmaceutical preparation comprising a ligand-camptothecin derivative conjugate described in the first aspect and the second aspect, or a pharmaceutically acceptable salt or solvate thereof, or a linker-drug compound described in the third aspect, or a pharmaceutically acceptable salt or solvate thereof.

A seventh aspect of the present invention discloses the use of the following in the preparation of drugs for the treatment or prevention of cancers or tumors: the ligand-camptothecin derivative conjugates described in the first aspect and the second aspect or pharmaceutically acceptable salts or solvates thereof, or the linker-drug compounds described in the third aspect or pharmaceutically acceptable salts or solvates thereof, or the pharmaceutical compositions described in the fifth aspect and/or the pharmaceutical preparations described in the sixth aspect;

alternatively, the use of the following in the treatment or prevention of cancer or tumors: the ligand-camptothecin derivative conjugates described in the first aspect and the second aspect or pharmaceutically acceptable salts or solvates thereof, or the linker-drug compounds described in the third aspect or pharmaceutically acceptable salts or solvates thereof, or the pharmaceutical compositions described in the fifth aspect and/or the pharmaceutical preparations described in the sixth aspect;

preferably, the cancer or tumor expresses EGFR and/or HER3;

more preferably, the cancer or tumor is selected from adenocarcinoma, ovarian cancer, cervical cancer, uterine cancer, prostate cancer, renal cancer, urethral cancer, bladder cancer, liver cancer, gastric cancer, endometrial cancer, salivary gland cancer, esophageal cancer, lung cancer, colon cancer, rectal cancer, colorectal cancer, bone cancer, skin cancer, thyroid cancer, pancreatic cancer, melanoma, glioma, neuroblastoma, glioblastoma multiforme, sarcoma, lymphoma and leukemia, and other solid tumors or blood tumors.

An eighth aspect of the present invention discloses a method of treating or preventing cancer or tumors, the method comprising administering to a subject in need thereof a prophylactically or therapeutically effective amount of a ligand-camptothecin derivative conjugate described in the first or second aspect or a pharmaceutically acceptable salt or solvate thereof or a linker-drug compound described in the third aspect or a pharmaceutically acceptable salt or solvate thereof, or a pharmaceutical composition as described in the fifth aspect and/or a pharmaceutical preparation described in the sixth aspect;

preferably, the cancer or tumor expresses EGFR and/or HER3;

more preferably, the cancer or tumor is selected from adenocarcinoma, ovarian cancer, cervical cancer, uterine cancer, prostate cancer, renal cancer, urethral cancer, bladder cancer, liver cancer, gastric cancer, endometrial cancer, salivary gland cancer, esophageal cancer, lung cancer, colon cancer, rectal cancer, colorectal cancer, bone cancer, skin cancer, thyroid cancer, pancreatic cancer, melanoma, glioma, neuroblastoma, glioblastoma multiforme, sarcoma, lymphoma and leukemia, and other solid tumors or blood tumors.

In the above aspects of the present invention and its embodiments,

"C1-C6 alkyl" and "C1-C6 alkyl" in various composite groups involving "C1-C6 alkyl" (e.g., "substituted C1-C6 alkyl", "deuterated C1-C6 alkyl") may be replaced with "C1-C20 alkyl", "C1-C12 alkyl" or "C1-C10 alkyl";

"C3-C8 cycloalkyl" and "C3-C8 cycloalkyl" in various composite groups involving "C3-C8 cycloalkyl" may be replaced by "C3-C20 cycloalkyl" or "C3-C10 cycloalkyl"; "C1-C6 alkoxy" and "C1-C6 alkoxy" in various composite groups involving same can be replaced with "C1-C20 alkoxy", "C1-C12 alkoxy" or "C1-C10 alkoxy";

"C6-C10 aryl" and "C6-C10 aryl" in various composite groups involving same can be replaced with "C6-C12 aryl";

"3-7-membered heterocyclic group" and "3-7-membered heterocyclic group" in various composite groups involving same may be replaced with "3-20-membered heterocyclic group", "3-12-membered heterocyclic group" or "3-10-membered heterocyclic group".

Beneficial Effects

The EGFR/HER3 bispecific antibody-drug conjugate provided by the present invention is a bispecific antibody ADC directed against both EGFR/HER3 targets, with good molecular stability and good preclinical efficacy, and is expected to have excellent clinical therapeutic effects.

ABBREVIATIONS AND DEFINITIONS

Figure 1A:
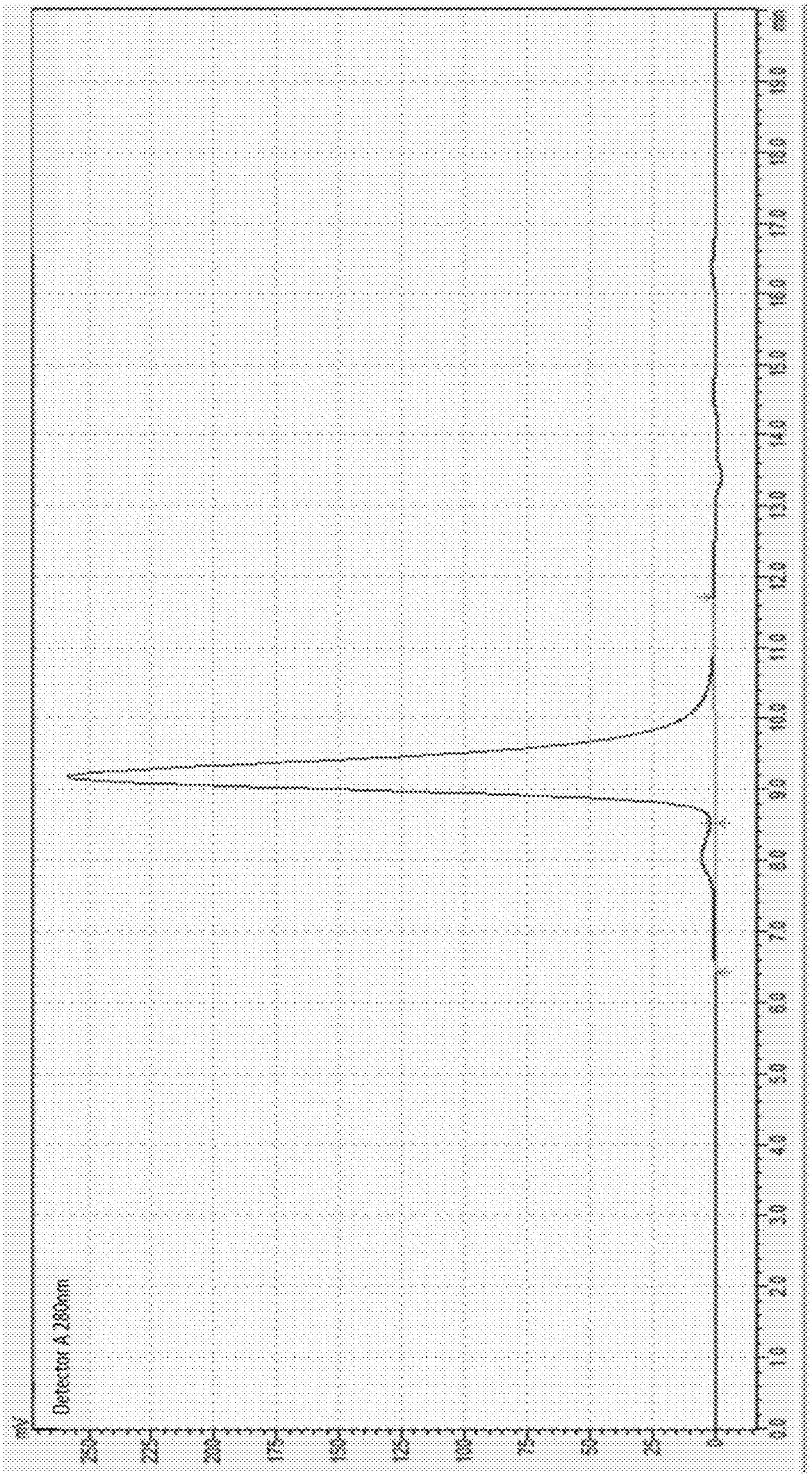
FIG. 1A illustrates SEC-HPLC detection/measurement of ADC-5 aggregation.
Figure 1B:
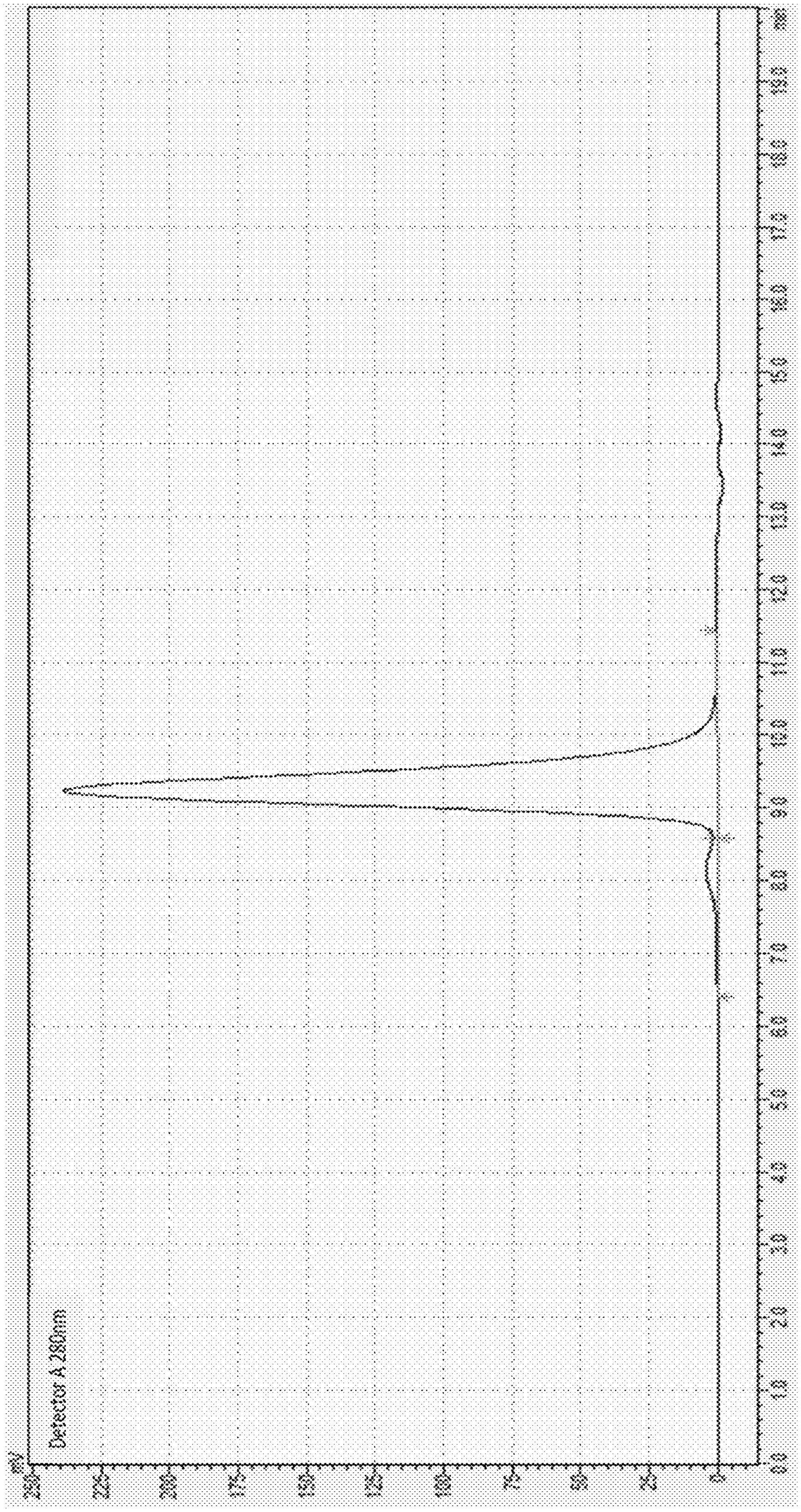
FIG. 1B illustrates SEC-HPLC detection/measurement of ADC-6 aggregation.
Figure 1C:
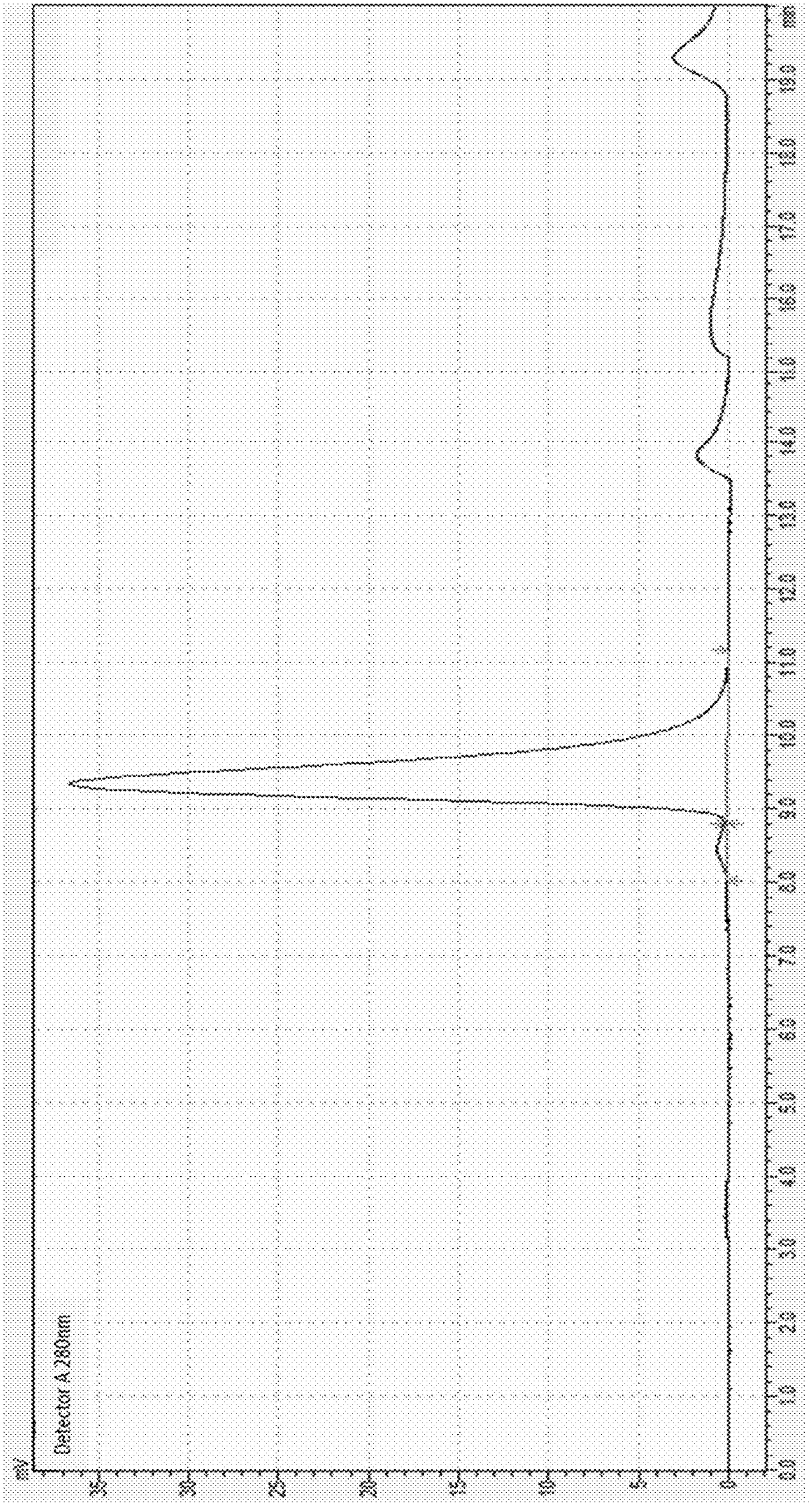
FIG. 1C illustrates SEC-HPLC detection/measurement of ADC-64 aggregation.
Figure 1D:
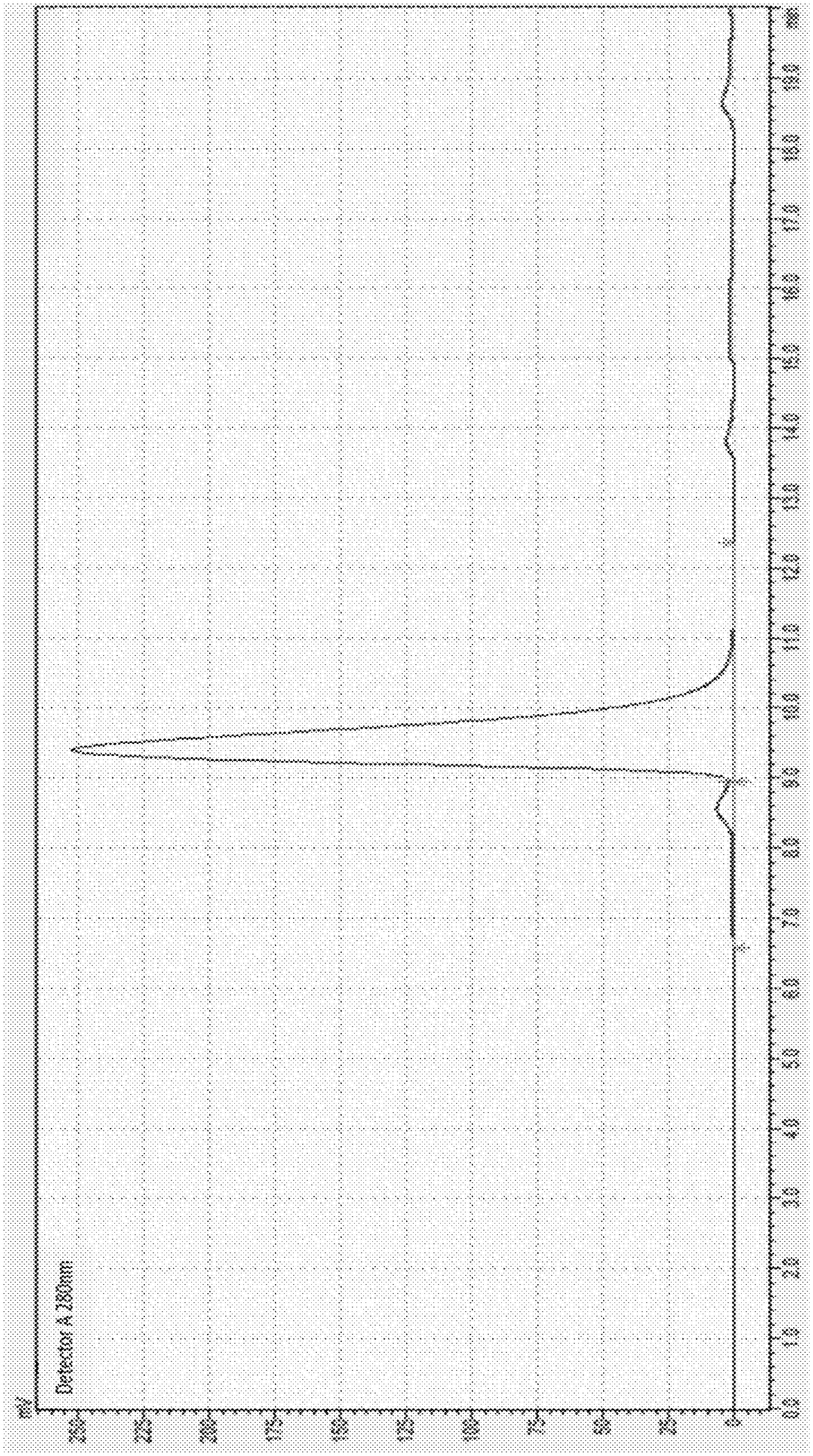
FIG. 1D illustrates SEC-HPLC detection/measurement of ADC-DS aggregation.
Figure 1E:
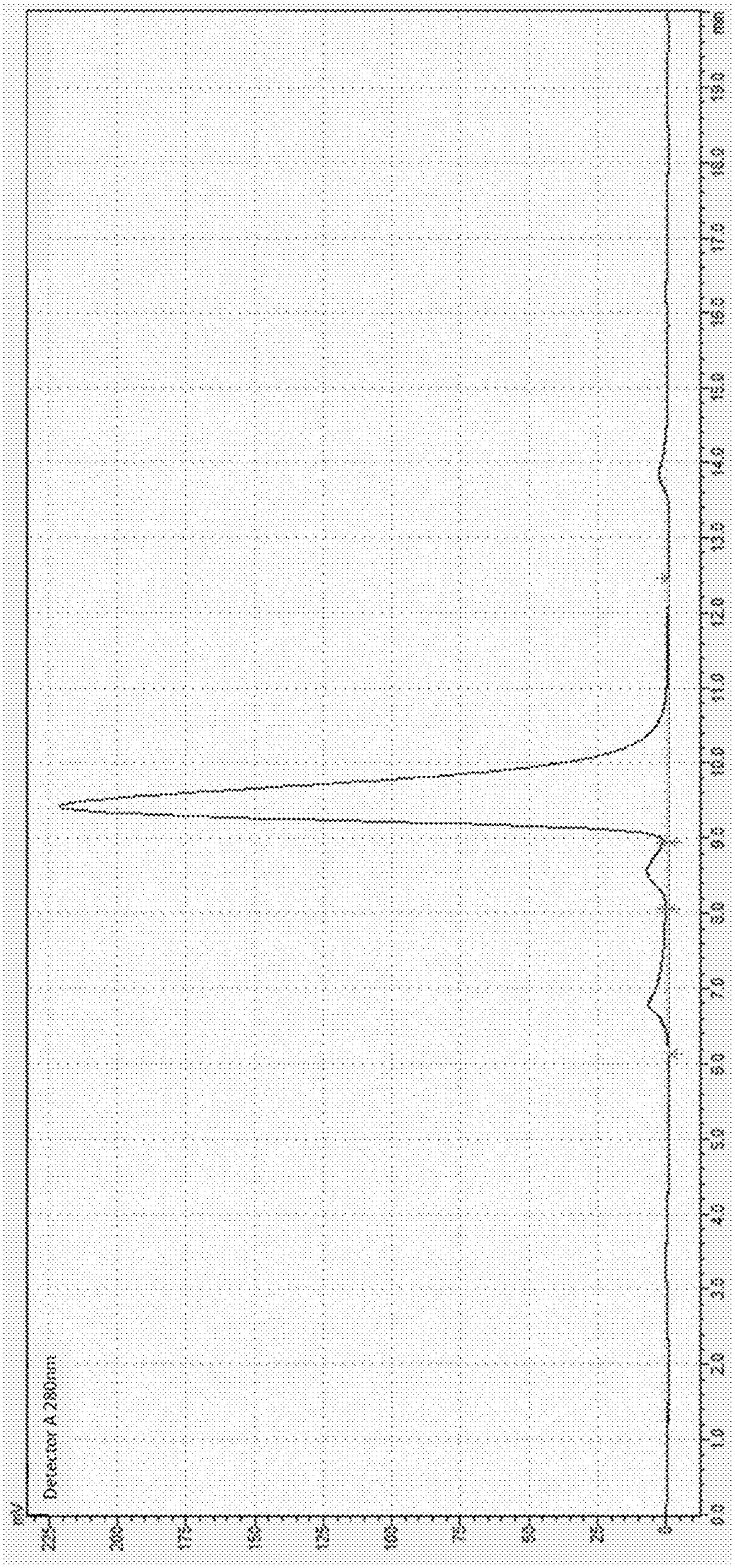
FIG. 1E illustrates SEC-HPLC detection/measurement of ADC-108 aggregation.
Figure 1F:
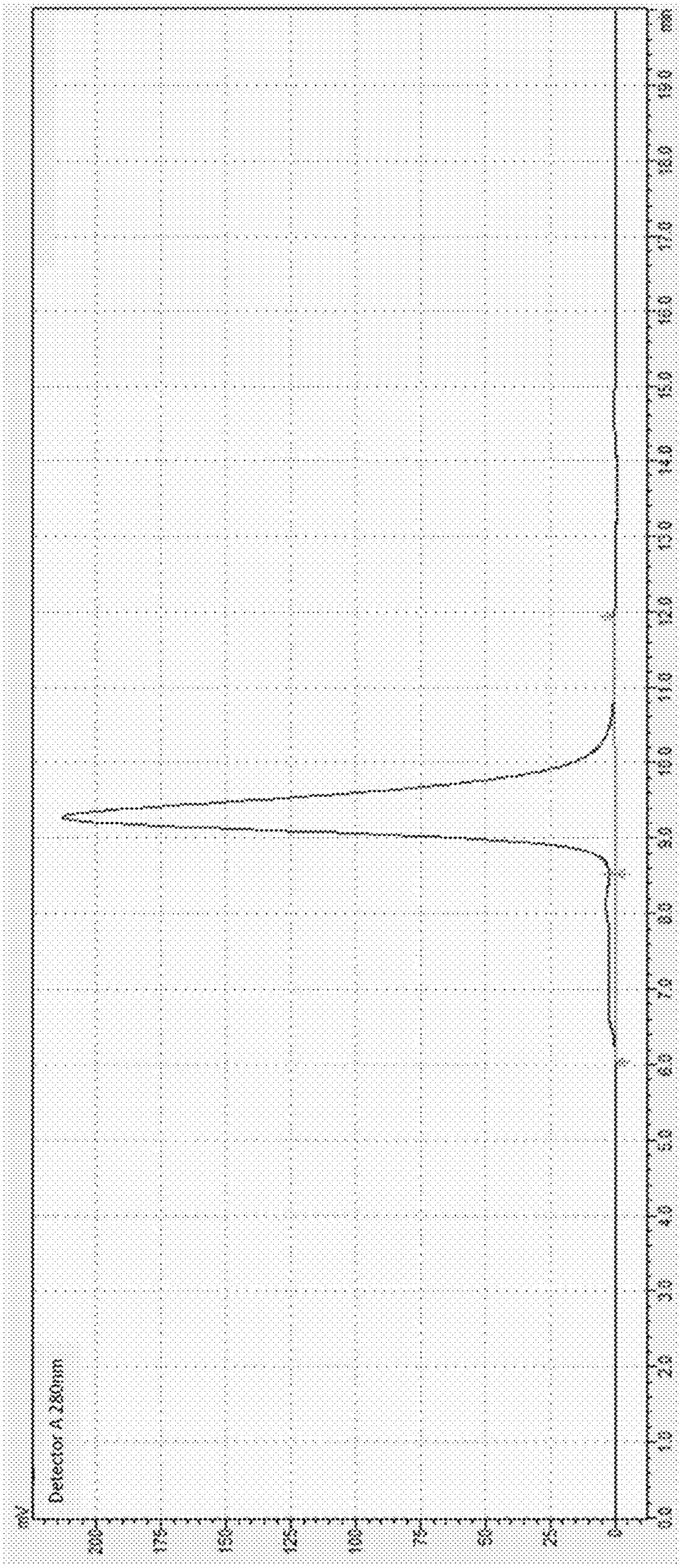
FIG. 1F illustrates SEC-HPLC detection/measurement of ADC-112 aggregation.
Figure 1G:
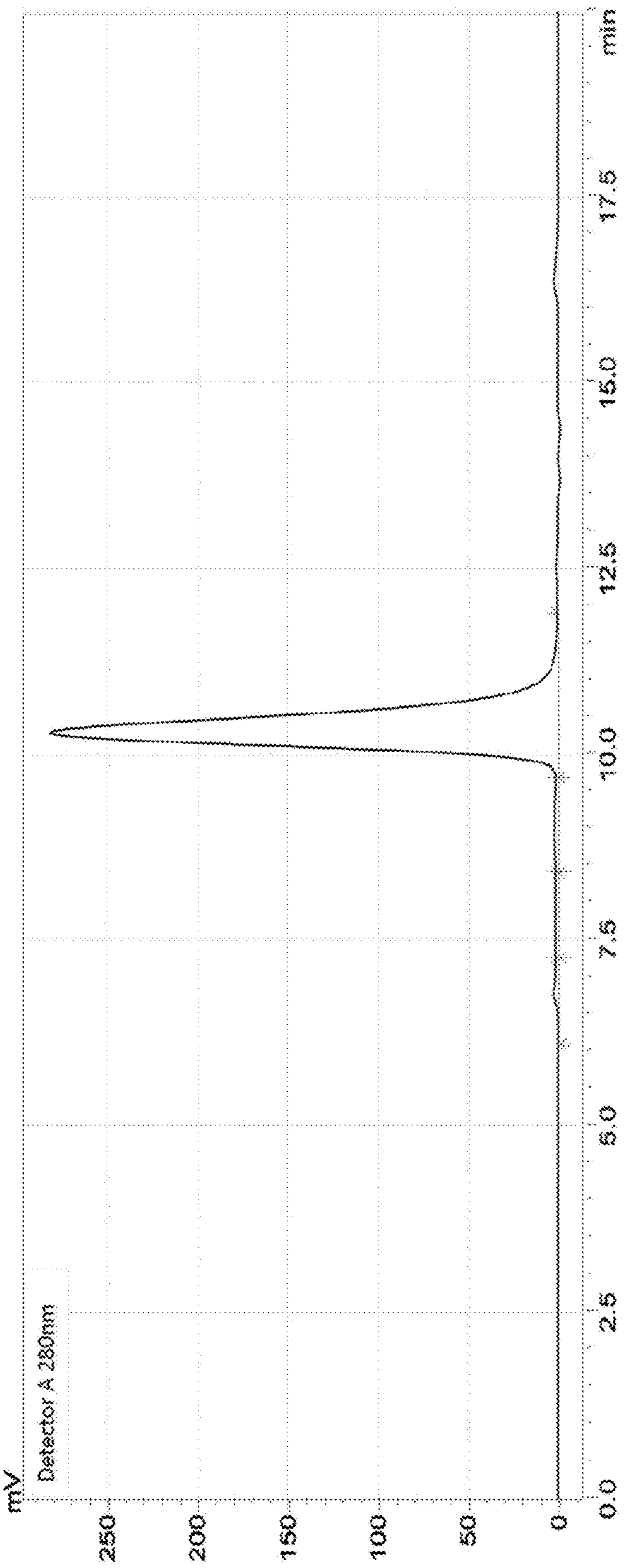
FIG. 1G illustrates SEC-HPLC detection/measurement of ADC-215 aggregation.
Figure 1H:
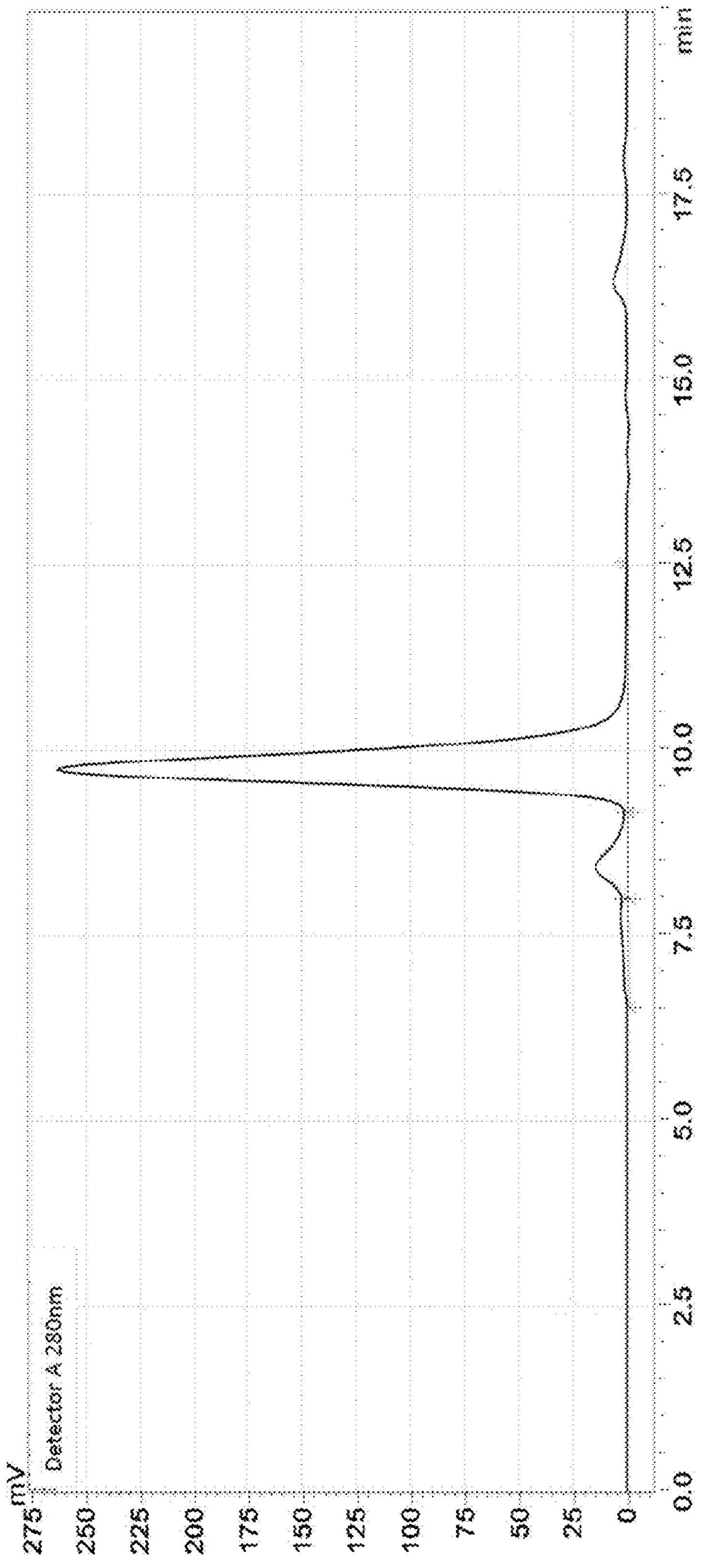
FIG. 1H illustrates SEC-HPLC detection/measurement of ADC-219 aggregation.
Figure 1I:
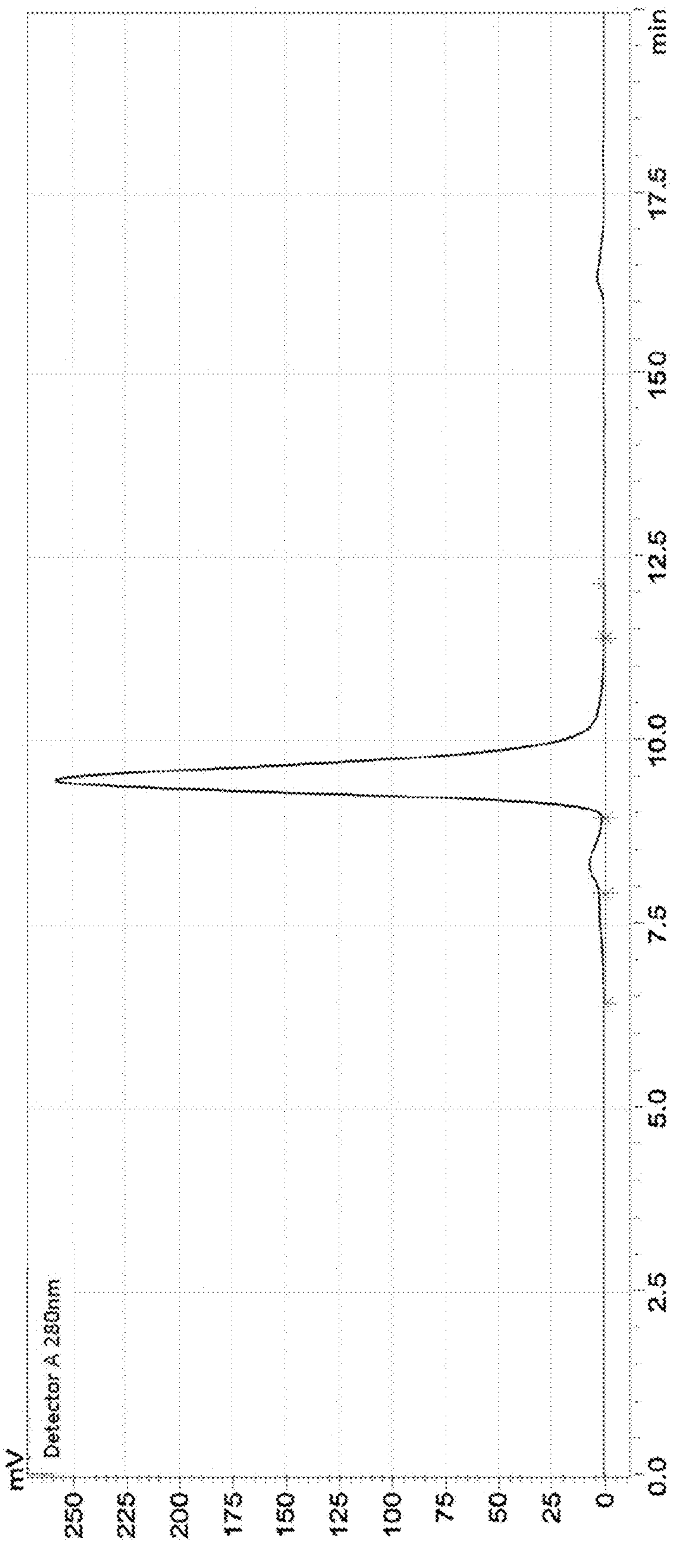
FIG. 1I illustrates SEC-HPLC detection/measurement of ADC-227 aggregation.
Figure 1J:
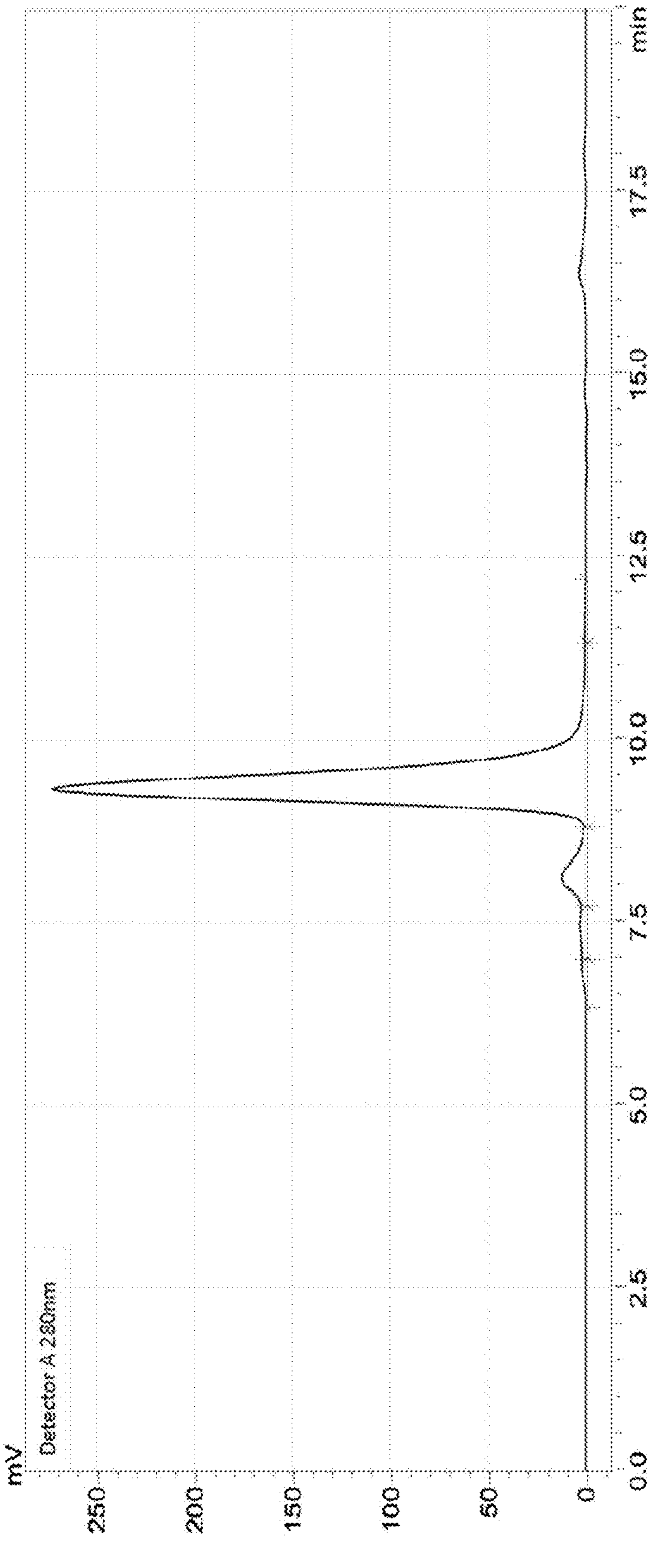
FIG. 1J illustrates SEC-HPLC detection/measurement of ADC-235 aggregation.
Figure 2A:
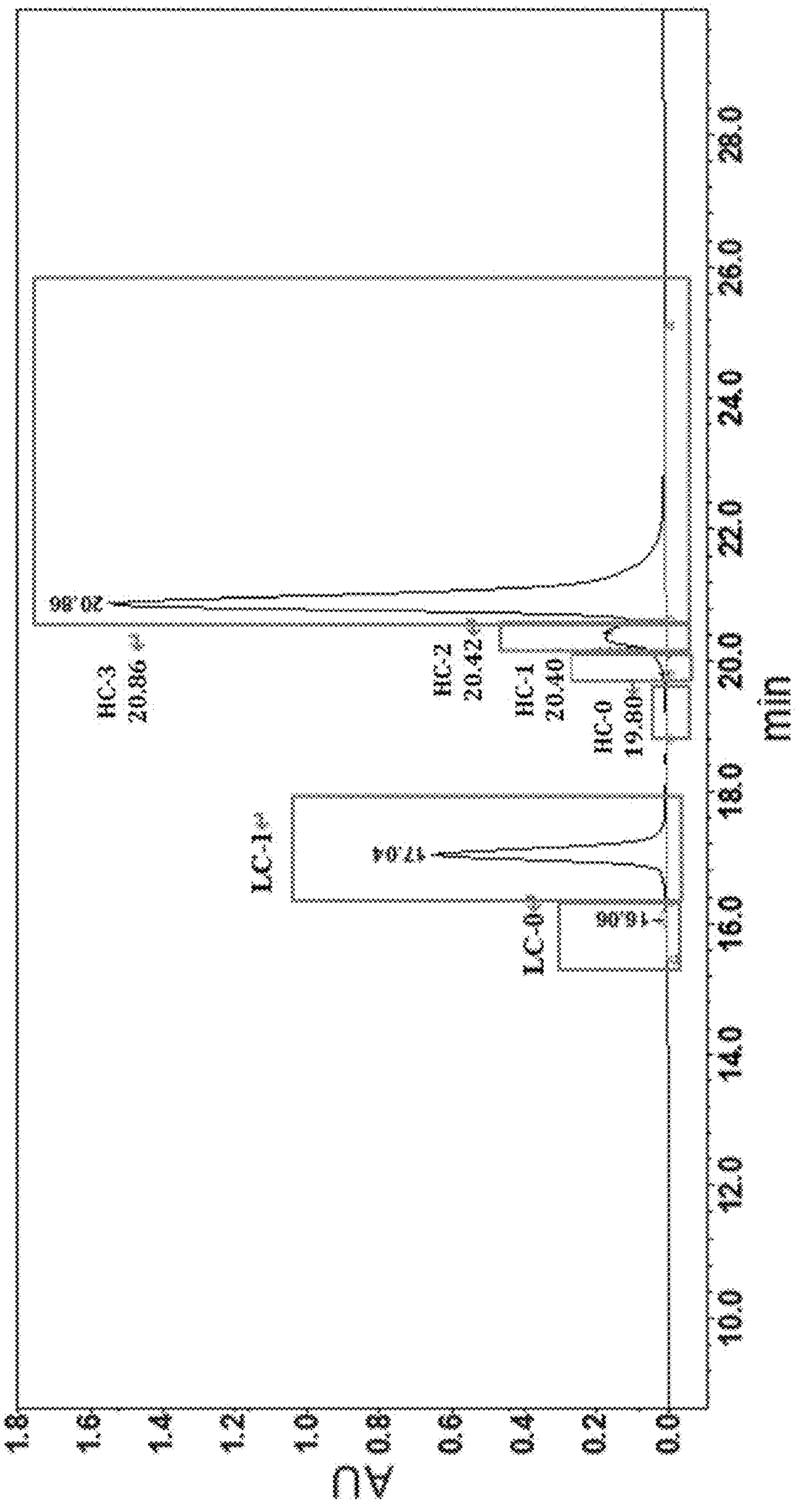
FIG. 2A illustrates RP-HPLC detection/measurement of ADC-5 drug-antibody coupling ratio (DAR).
Figure 2B:
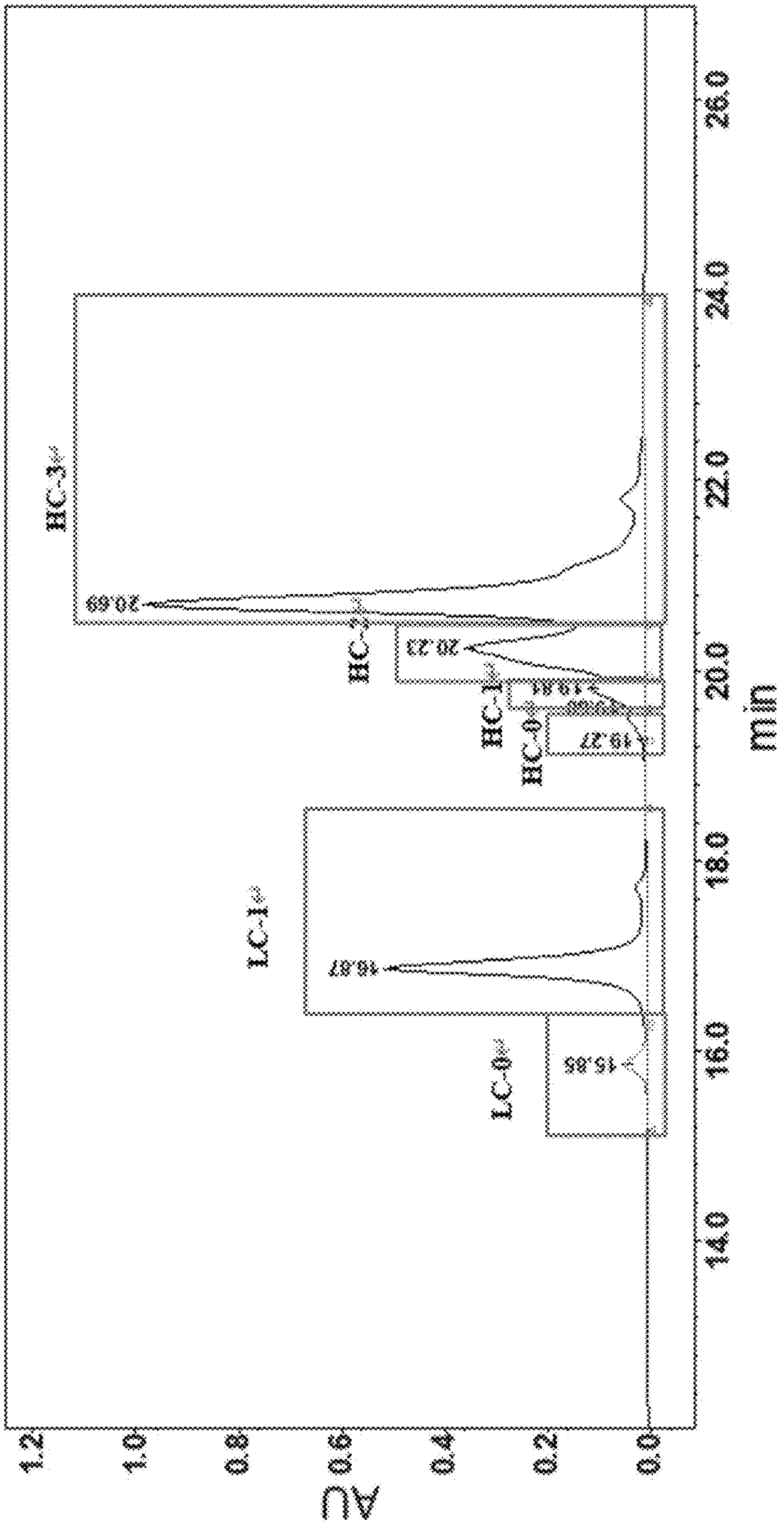
FIG. 2B illustrates RP-HPLC detection/measurement of ADC-6 drug-antibody coupling ratio (DAR).
Figure 2C:
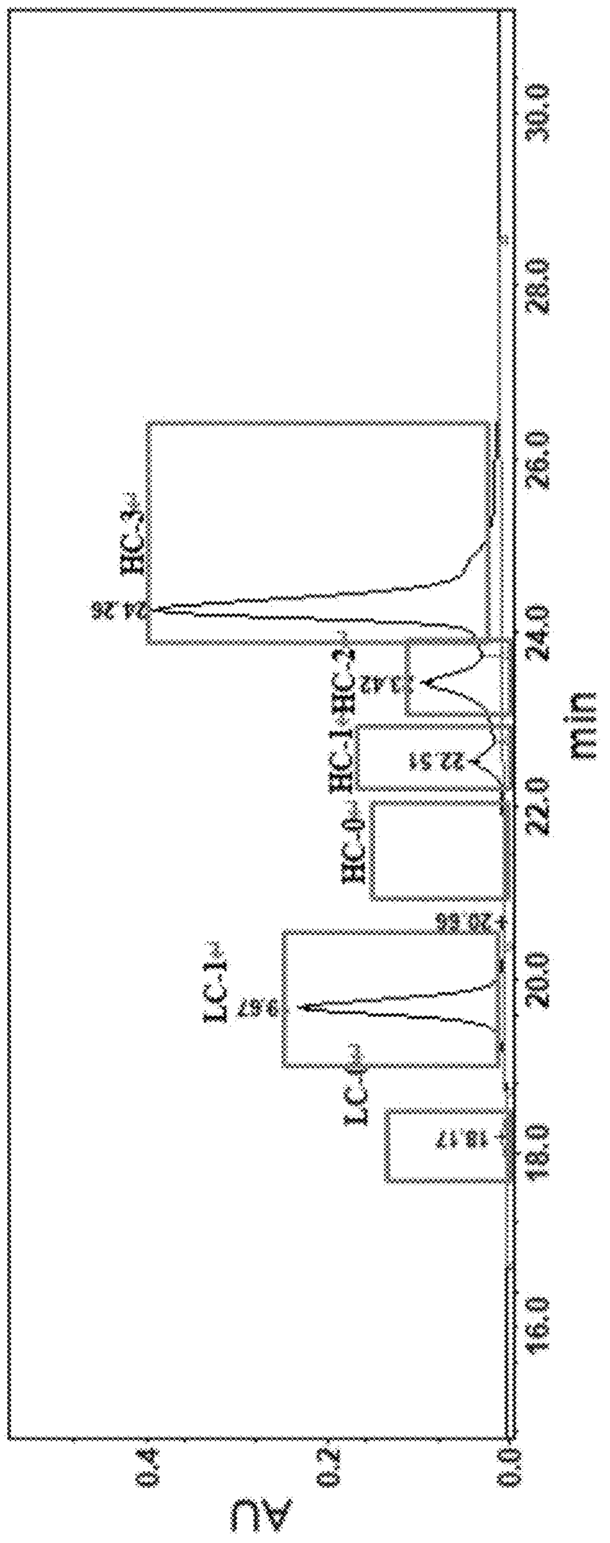
FIG. 2C illustrates RP-HPLC detection/measurement of ADC-10 drug-antibody coupling ratio (DAR).
Figure 2D:
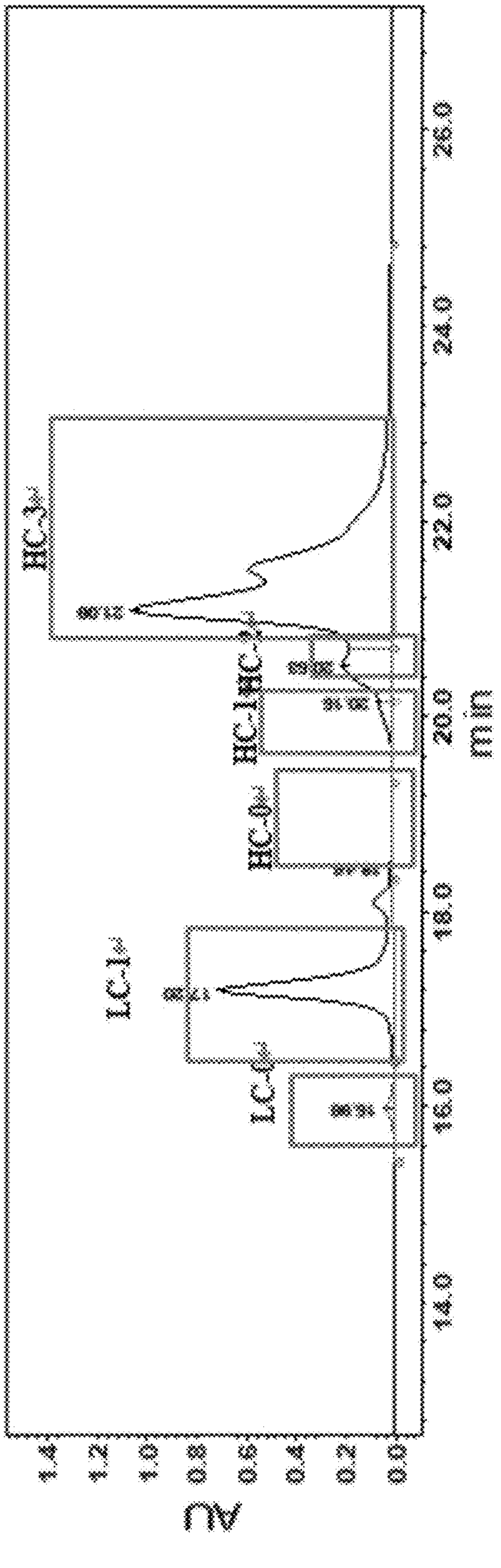
FIG. 2D illustrates RP-HPLC detection/measurement of ADC-12 drug-antibody coupling ratio (DAR).
Figure 2E:
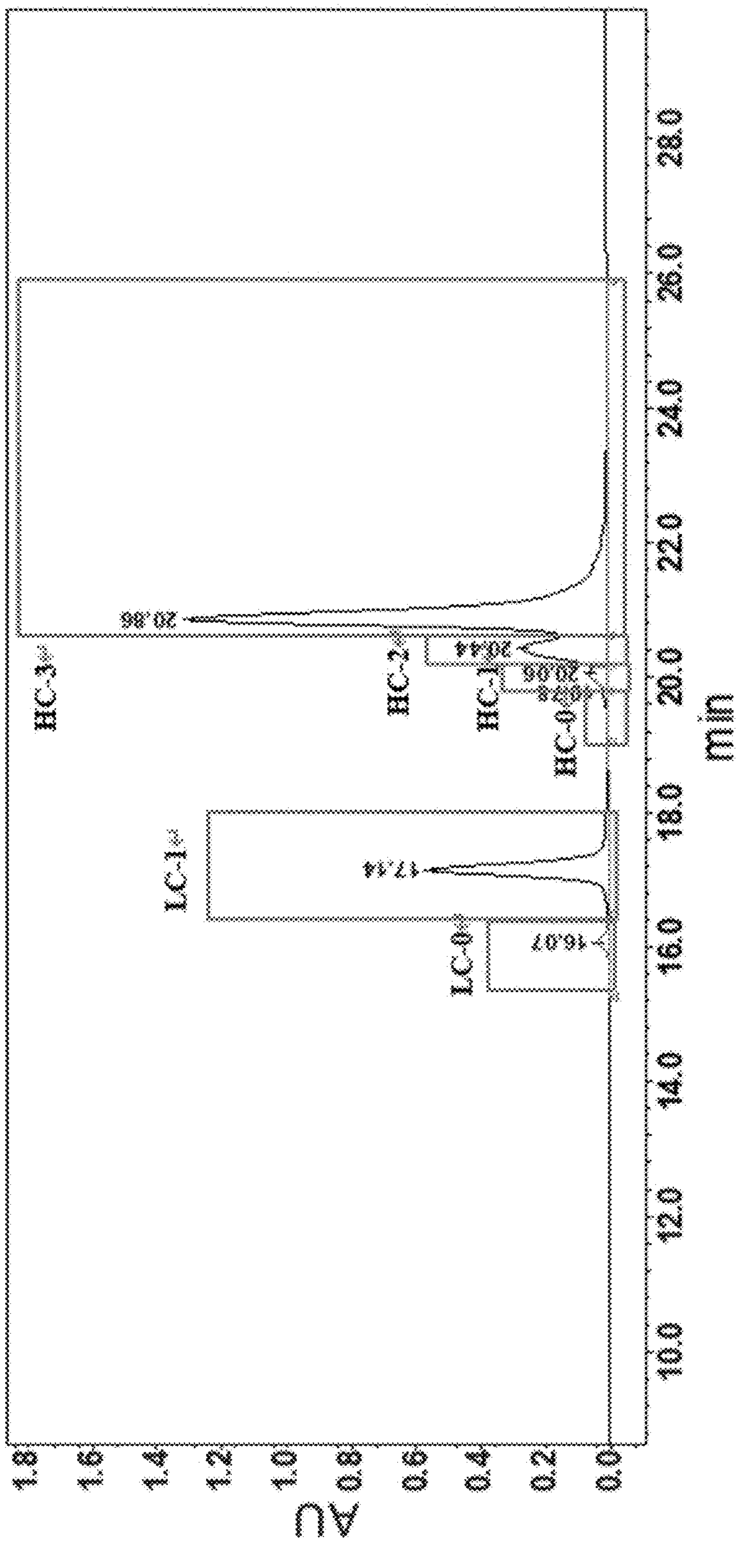
FIG. 2E illustrates RP-HPLC detection/measurement of ADC-64 drug-antibody coupling ratio (DAR).
Figure 2F:
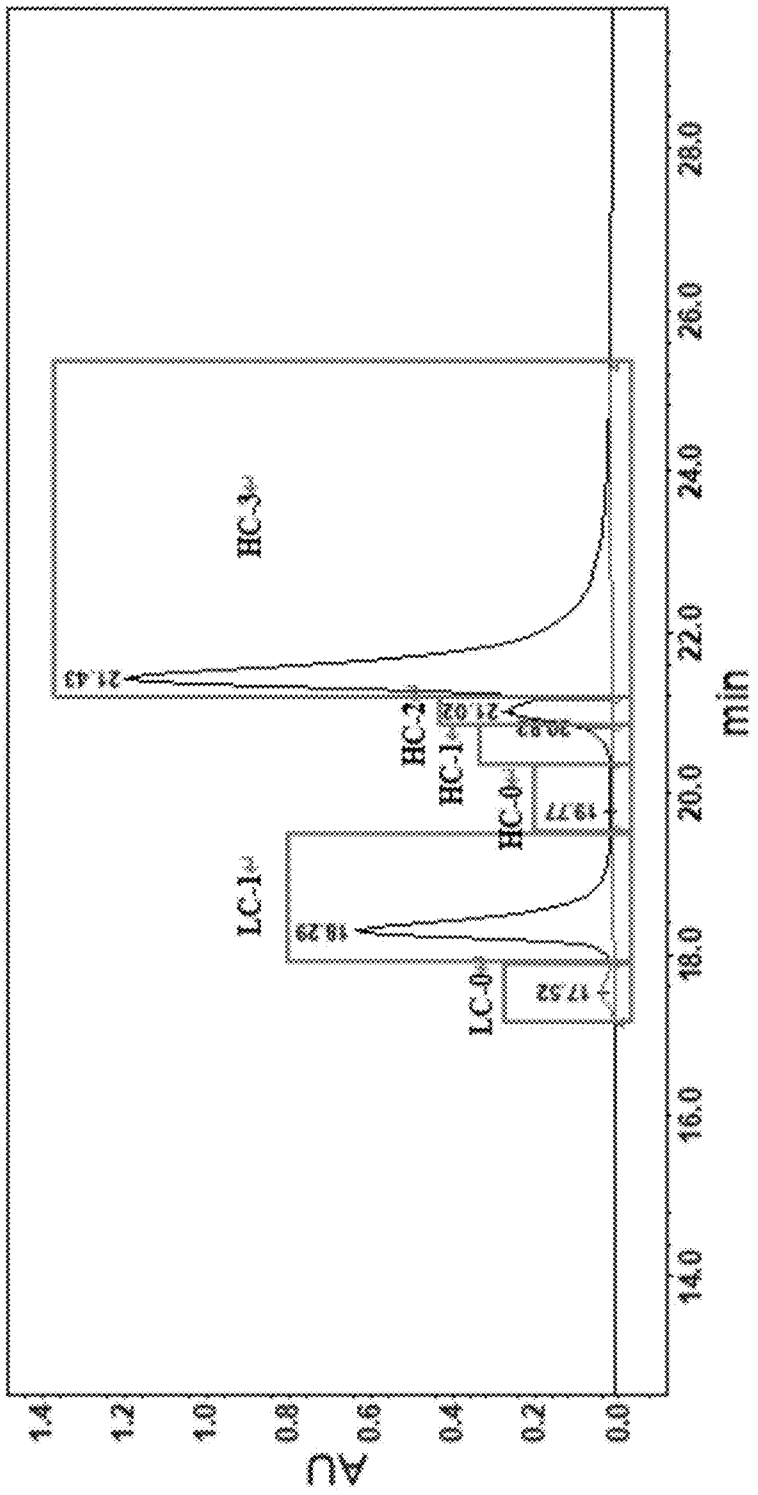
FIG. 2F illustrates RP-HPLC detection/measurement of ADC-108 drug-antibody coupling ratio (DAR).
Figure 2G:
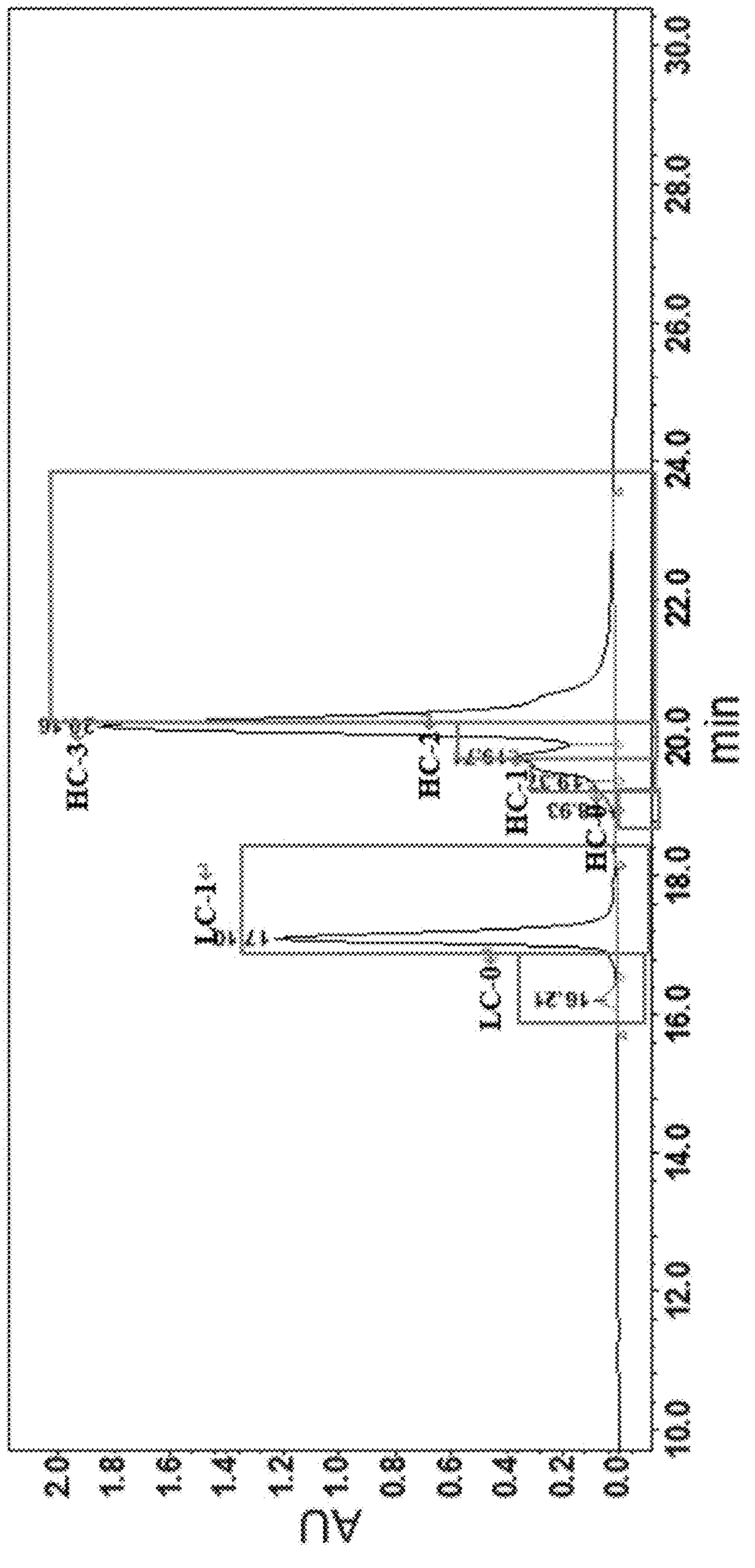
FIG. 2G illustrates RP-HPLC detection/measurement of ADC-112 drug-antibody coupling ratio (DAR).
Figure 2H:
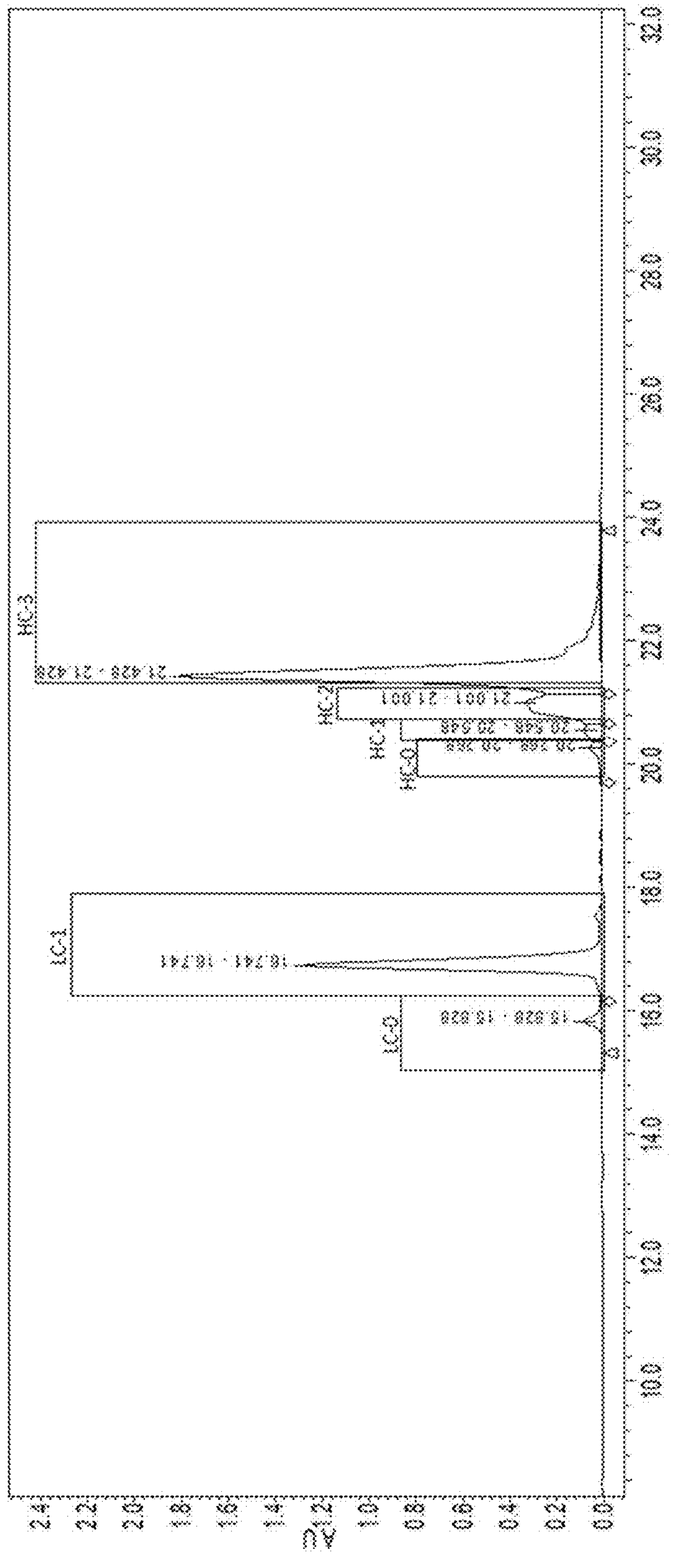
FIG. 2H illustrates RP-HPLC detection/measurement of ADC-215 drug-antibody coupling ratio (DAR).
Figure 2I:
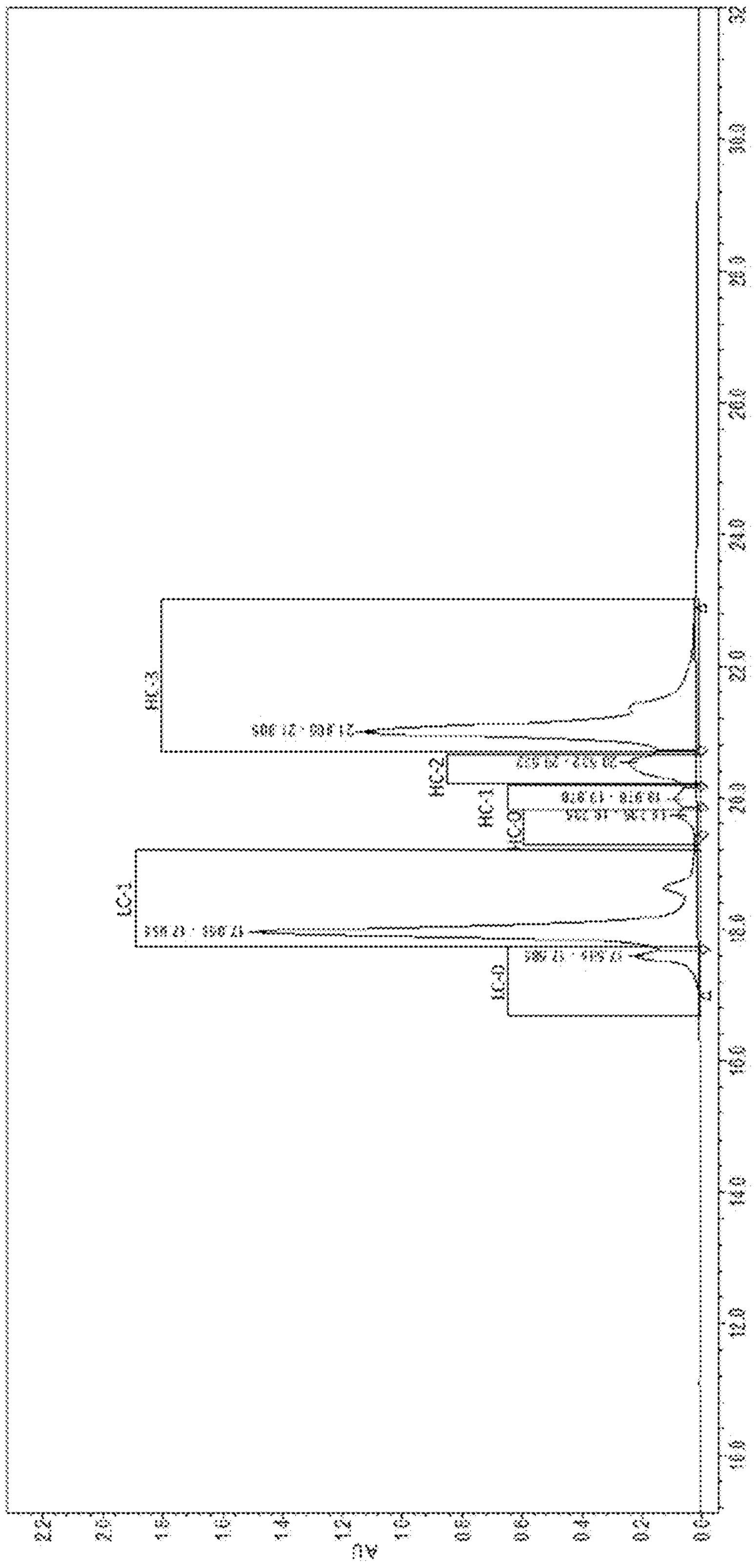
FIG. 2I illustrates RP-HPLC detection/measurement of ADC-219 drug-antibody coupling ratio (DAR).
Figure 2J:
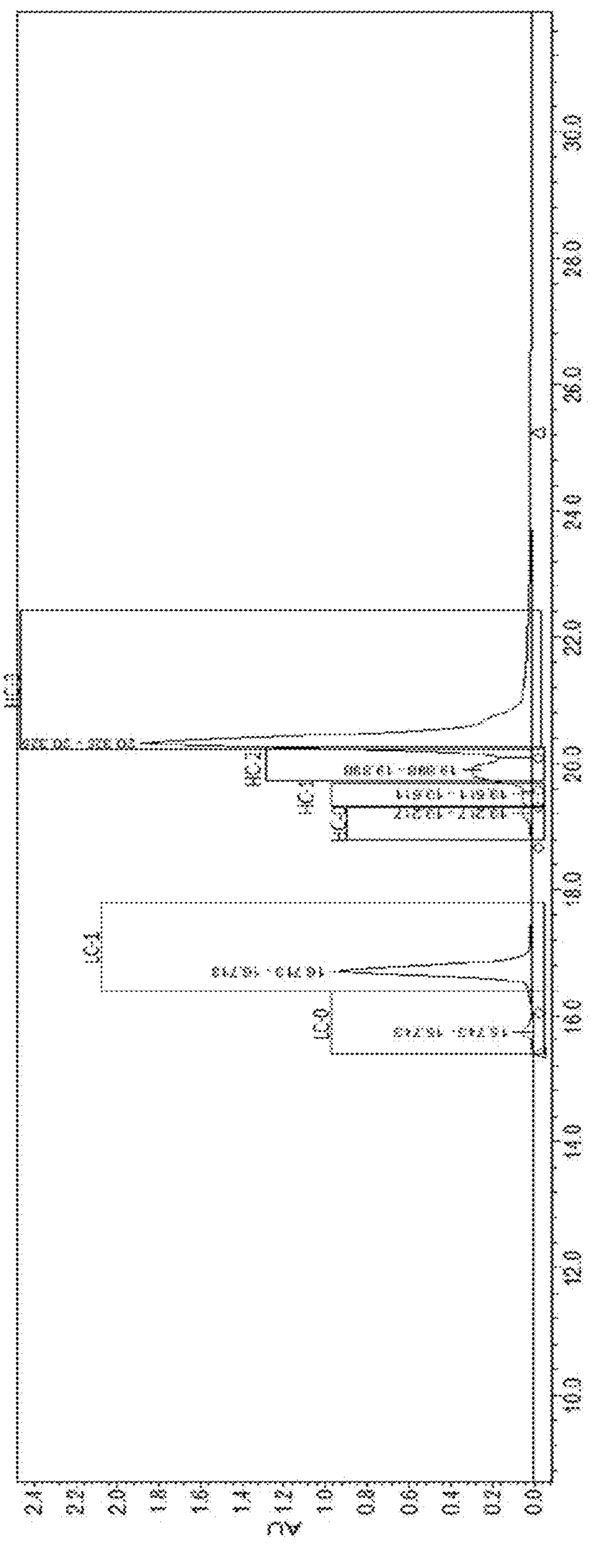
FIG. 2J illustrates RP-HPLC detection/measurement of ADC-227 drug-antibody coupling ratio (DAR).
Figure 2K:
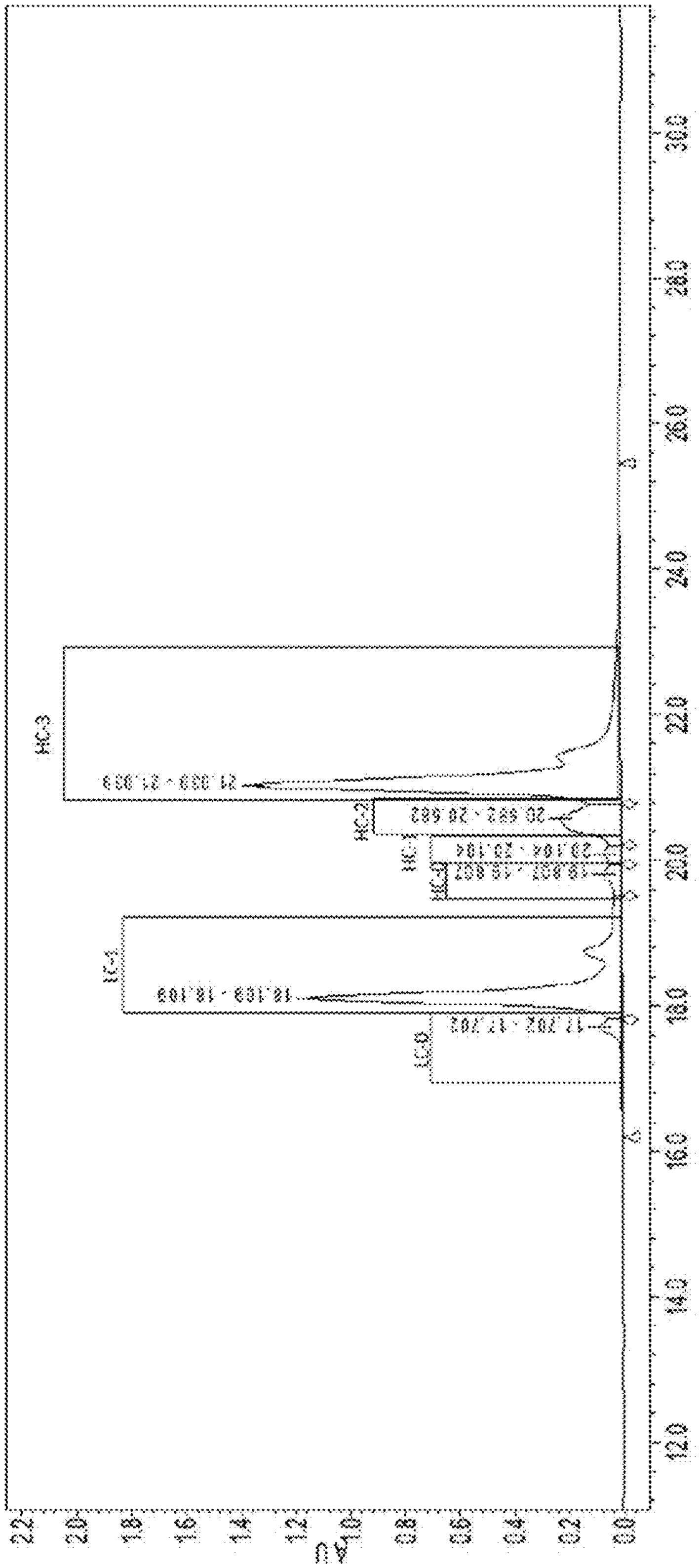
FIG. 2K illustrates RP-HPLC detection/measurement of ADC-235 drug-antibody coupling ratio (DAR).
Figure 2L:
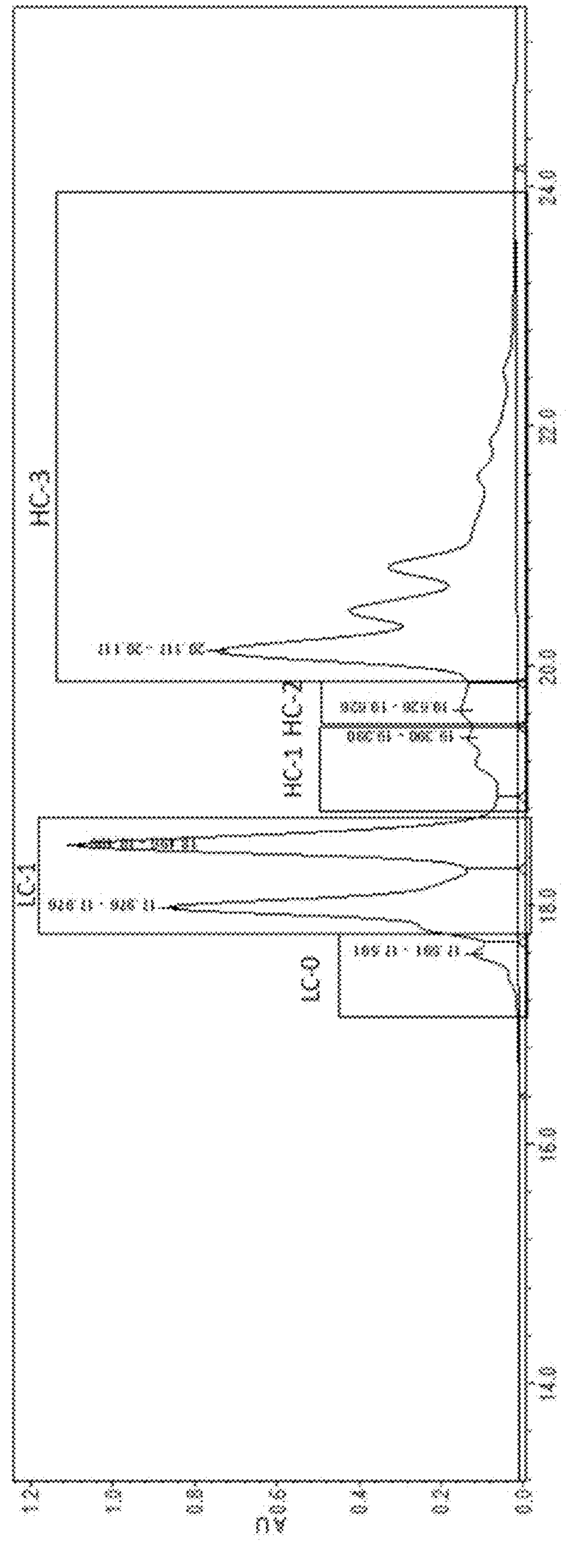
FIG. 2L illustrates RP-HPLC detection/measurement of ADC-243 drug-antibody coupling ratio (DAR).

Unless otherwise indicated, the following terms and phrases, as used herein, are intended to have the meanings set forth below. When a trade name is used herein, unless otherwise indicated in the context, the trade name includes the product formula, generic drug and active ingredient of said trade name product.

Unless stated to the contrary, terms used in the claims and specification herein have the meanings set forth below.

The term "ligand" refers to a macromolecular compound that is able to recognize and bind to an antigen or receptor associated with a target cell. The ligand serves to present the drug to a target cell population bound to the ligand; these ligands include, but are not limited to, protein-like hormones, lectins, growth factors, antibodies, or other molecules capable of binding to cells. In embodiments of the present invention, the ligand is denoted as Ab, and the ligand may form a linkage bond with a linkage unit via a heteroatom on the ligand, and is preferably an antibody or an antigen-binding fragment thereof, said antibody being selected from chimeric, humanized, fully human, or murine antibodies; preferably monoclonal antibodies.

A ligand unit is a targeting agent that binds specifically to a target part. Said ligand is capable of specifically binding to a cellular component or binding to a cellular component or binding to other target molecules of interest. The target part or target is typically on the surface of the cell. In some aspects, the ligand unit serves to deliver the drug unit to a specific target cell population with which the ligand unit interacts. Ligands include, but are not limited to, proteins, polypeptides and peptides, and non-proteins such as sugars. Suitable ligand units include, for example, antibodies, such as full-length (intact) antibodies and antigen-binding fragments thereof. In embodiments where the ligand unit is a non-antibody targeting reagent, it may be a peptide or polypeptide, or a non-protein molecule. Examples of such targeting reagents include interferons, lymphokines, hormones, growth factors and colony stimulating factors, vitamins, nutrient transporter molecules, or any other cell-binding molecule or substance. In some embodiments, the linker is covalently attached to the sulfur atom of the ligand. In some aspects, the sulfur atom is a sulfur atom of a cysteine residue, and forms an interchain disulfide bond of the antibody. In another aspect, the sulfur atom is a sulfur atom of a cysteine residue that has been introduced into the ligand unit, and forms an interchain disulfide bond of the antibody. In another aspect, the sulfur atom is a sulfur atom of a cysteine residue that has been introduced into the ligand unit (e.g., by site-directed mutagenesis or chemical reaction). In other aspects, the linker-bound sulfur atom is selected from a cysteine residue that forms the interchain disulfide bond of the antibody or a cysteine residue that has been introduced into the ligand unit (e.g., by site-directed mutagenesis or chemical reaction). In some embodiments, the system is numbered according to the EU index in Kabat {[Kabat E. A et al, (1991)]"Sequences of proteins of Immunological Interest", Fifth Edition, NIH Publication 91-3242}.

As used herein, "antibody" or "antibody unit" includes, to the extent thereof, any part of an antibody structure. This unit may bind, reactively associate, or complex with a receptor, antigen, or other receptor unit possessed by the target cell population. The antibody may be any protein or protein-like molecule, and can bind, complex, or react with a portion of the cell population to be treated or biologically modified. The antibodies forming the antibody-drug conjugates in the present invention maintain their original antigen-binding capacity from the wild state. Thus, the antibodies of the present invention are capable of binding exclusively to antigens. Antigens involved include, for example, tumor-associated antigens (TAA), cell surface receptor proteins and other cell surface molecules, cell survival regulators, cell proliferation regulators, molecules associated with tissue growth and differentiation (such as are known or foreseen to be functional), lymphokines, cytokines, molecules participating in the regulation of the cell cycle, molecules participating in angiogenesis, and molecules associated with angiogenesis (such as are known or foreseen to be functional). Tumor-associated factors may be cluster differentiation factors (e.g., CD proteins).

Antibodies applied in antibody drug conjugates include, but are not limited to, antibodies directed against cell surface receptors and tumor-associated antigens. Such tumor-associated antigens are well known in the industry and can be prepared by methods and information for antibody preparation well known in the industry. To develop effective cellular level targets that can be used in cancer diagnosis and therapy, researchers seek to find transmembrane or other tumor-associated peptides. These targets can be specifically expressed on the surface of one or more cancer cells with little or no expression on the surface of one or more non-cancer cells. Typically, such tumor-associated polypeptides are more overexpressed on the surface of cancer cells than on the surface of non-cancer cells. Confirmation of such tumor-associated factors can greatly enhance the specific targeting properties of antibody-based cancer therapies. For convenience, information related to antigens known to the industry is labeled below, including name, other names, and gene bank accession number. Nucleic acid and protein sequences corresponding to the tumor-associated antigens can be found in publicly available databases, such as Genbank. The tumor-associated antigens corresponding to antibody targeting include all amino acid sequence variants and isoforms having at least 70%, 80%, 85%, 90%, or 95% homology with the sequences confirmed in the references, or possessing biological properties and characteristics that are identical to those of the tumor-associated antigen sequences in the cited literature.

The term "inhibit" or "inhibition" means that a detectable amount is reduced or completely prevented.

The term "cancer" refers to a physiological condition or disease characterized by dysregulated cell growth. "Tumor" includes cancer cells.

The term "autoimmune disease" refers to diseases or disorders that originate in tissues or proteins that target an individual's own body.

The term "drug" refers to cytotoxic drugs, denoted by d, which are chemical molecules that have a strong ability to disrupt normal growth in tumor cells. Cytotoxic drugs can in principle kill tumor cells at sufficiently high concentrations, but due to a lack of specificity, they will also cause apoptosis of normal cells while killing tumor cells, leading to serious side effects. The term includes toxins, such as small molecule toxins or enzymatically active toxins of bacterial, fungal, plant or animal origin, radioisotopes (e.g., radioisotopes of $At^{211}$, $I^{131}$, $I^{125}$, $Y^{90}$, $Re^{186}$, $Re^{188}$, $Sm^{153}$, $Bi^{212}$, $P^{32}$ and $Lu^{176}$), toxic drugs, chemotherapeutic drugs, antibiotics and nucleolytic enzymes, preferably toxic drugs.

The term "linker" or "linker fragment" or "linker unit" refers to a fragment or bond of a chemical structure that is attached to a ligand at one end and to the drug at the other end, or may be attached to other connectors and then to the drug.

Connectors, including extensions, spacers, and amino acid units, can be synthesized by methods known in the art, such as those described in US2005-0238649A1. The connectors can be "cleavable connectors" that facilitate the release of the drug in the cell. For example, acid-unstable connectors (e.g., hydrazone), protease-sensitive (e.g., peptidase-sensitive) connectors, photo-unstable connectors, dimethyl connectors, or disulfide-containing connectors can be used (Chari et al. Cancer Research 52:127-131, 1992); U.S. Pat. No. 5,208,020.

According to the mechanism of intracellular drug release, as used herein, "linkers" or "linkers of antibody-drug conjugates" can be categorized into two types: unbreakable linkers and breakable linkers. For antibody-drug conjugates containing an unbreakable linker, the mechanism of drug release is as follows: after the conjugate binds to the antigen and is endocytosed by the cell, the antibody is cleaved enzymatically in lysosomes, releasing an active molecule consisting of the small-molecule drug, the linker, and amino acid residues of the antibody. The resulting change in the structure of the drug molecule does not diminish its cytotoxicity, but because the active molecule is electrically charged (amino acid residues), it cannot penetrate neighboring cells. Therefore, such active drugs cannot kill neighboring tumor cells that do not express the targeted antigen (antigen-negative cells) (bystander effect) (Ducry et al., 2010, Bioconjugate Chem. 21: 5-13). For antibody-drug conjugates containing a breakable linker, the mechanism of drug release is that after the conjugate binds to the antigen and is endocytosed by the cell, the conjugate breaks and releases the active ingredient (the small-molecule drug itself) in the target cell. Breakable linkers are mainly categorized into: chemical-sensitive linkers and enzyme-sensitive linkers. Chemically sensitive linkers can be selectively broken due to differences in the properties of the plasma and cytoplasm or tumor microenvironment. Such properties include pH, glutathione concentration, etc. pH-sensitive linkers, which are relatively stable in the neutral or weakly alkaline environment of blood (pH 7.3-7.5), will however be hydrolyzed within the weakly acidic tumor microenvironment (pH 5.0-6.5) and lysosomes (pH 4.5-5.0), e.g., hydrazones, carbonates, acetals, and ketals. Due to the limited plasma stability of acid-breakable linkers, antibody-drug conjugates based on such linkers typically have a short half-life (2-3 days). This short half-life has somewhat limited the use of pH-sensitive linkers in the new generation of antibody-drug conjugates. Glutathione-sensitive linkers are also known as disulfide-bond linkers. Drug release is based on the difference between the high intracellular glutathione concentration (millimolar range) and the relatively low glutathione concentration in the blood (micromolar range). This is particularly true for tumor cells, whose low oxygen content leads to enhanced reductase activity and thus to higher glutathione concentrations. Disulfide bonds are thermodynamically stable and therefore have better stability in plasma. Enzyme-unstable linkers, such as peptide linkers, provide better control of drug release. Peptide linkers can be effectively severed by lysosomal proteases such as cathepsins (Cathepsin B). This peptide linkage is thought to be very stable in the plasma circulation due to the unfavorable extracellular pH and serum protease inhibitors resulting in proteases that are normally inactive outside the cell. In view of the high plasma stability and good intracellular break selectivity and effectiveness, enzyme-unstable linkers are widely used as breakable linkers for antibody-drug conjugates.

The term "antibody-drug conjugate" refers to the attachment of an antibody to a biologically active drug by means of a stable linkage unit. In the context of the present invention, "ligand-drug conjugate", preferably antibody-drug conjugate (ADC), refers to the attachment of a monoclonal antibody or antibody fragment to a biologically active toxic drug by means of a stable linkage unit.

The three-letter codes and single-letter codes for amino acids used in this disclosure are as described in *J. boil. Chem.* 1968, 243, 3558.

The term "alkyl" refers to a saturated aliphatic hydrocarbon group, which is a straight or branched chain group containing 1 to 20 carbon atoms (i.e., "C1-C20 alkyl"), preferably an alkyl group containing 1 to 12 carbon atoms (i.e., "C1-C12 alkyl"), more preferably an alkyl group containing 1 to 10 carbon atoms (i.e., "C1-C10 alkyl"), and most preferably an alkyl group containing 1 to 6 carbon atoms (i.e., "C1-C6 alkyl"). Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and their various branched isomers, and the like. More preferred are lower alkyl groups containing 1 to 6 carbon atoms, and non-limiting embodiments include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group may be substituted or non-substituted, and when substituted, the substituent group may be substituted at any available point of attachment, said substituent group preferably being one or more of the following groups, independently selected from alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio, oxo.

The term "substituted alkyl" means that a hydrogen in the alkyl group has been replaced by a substituent group. Unless otherwise indicated in the text, the substituent group of the alkyl group may be a variety of groups selected from the following group: -halogen, —OR', —NR'R", —SR', —SiR'R"R"', —OC(O)R', —C(O)R', —$CO_2$R', —CONR'R", —OC(O)NR'R", —NR"C(O)R', —NR', —C(O)NR"R"', —NR"C(O)$_2$R', —NH—C($NH_2$)═NH, —NR'C($NH_2$)═NH, —NH—C($NH_2$)═NR', —S(O)R', —S(O)$_2$R', —S(O)$_2$NR'R", —NR'S(O)$_2$R", —CN and —$NO_2$, the number of substituents is from 0 to (2m'+1), where m' is the total number of carbon atoms in the group. R', R" and R"' each independently refer to hydrogen, unsubstituted $C_{1-8}$ alkyl, unsubstituted C6-C12 aryl (or C6-C10 aryl), C6-C12 aryl (or C6-C10 aryl) substituted by 1-3 halogens, unsubstituted $C_{1-8}$ alkyl, $C_{1-8}$ alkoxy or $C_{1-8}$ thioalkoxy, or unsubstituted C6-C12 aryl (or C6-C10 aryl)-$C_{1-4}$ alkyl. When R' and R" are attached to the same nitrogen atom, they may form a 3-, 4-, 5-, 6-, or 7-membered ring together with that nitrogen atom. For example, —NR'R" includes 1-pyrrolidinyl and 4-morpholinyl.

The term "alkylene" means a saturated straight or branched aliphatic hydrocarbon group, having two residues derived by removing two hydrogen atoms from the same carbon atom or two different carbon atoms of a parent alkane, and is a straight or branched group comprising 1 to 20 carbon atoms, preferably an alkylene group containing 1 to 12 carbon atoms, more preferably 1 to 6 carbon atoms. Non-limiting examples of alkylene groups include, but are not limited to, methylene (—$CH_2$—, 1,1-ethylidene (—CH($CH_3$)—), 1,2-ethylidene (—$CH_2CH_2$)—, 1,1-propylidene (—CH($CH_2CH_3$)—), 1,2-propylidene (—$CH_2$CH($CH_3$)—), 1,3-propylidene (—$CH_2CH_2CH_2$—), 1,4-butylidene (—$CH_2CH_2CH_2CH_2$), and 1,5-butylidene (—$CH_2CH_2CH_2CH_2CH_2$—), among others. The alkylene group may be substituted or non-substituted, and when substituted, the substituent may be substituted at any available point of attachment, said substituent preferably being independently and optionally substituted with one or more substituents selected from alkyl, alkenyl, alkynyl, alkoxy, alkylthio, alkylamino, halo, mercapto, hydroxyl, nitro, cyano, cycloalkyl, heterocyclo, aryl, heteroaryl, cycloalkoxy, heterocycloalkoxy, cycloalkylthio, heterocycloalkylthio and oxo.

The term "alkoxy" refers to —O-(alkyl) and —O-(cycloalkyl), wherein alkyl or cycloalkyl is defined as above. Non-limiting examples of C1-C6 alkoxy include: methoxy, ethoxy, propoxy, butoxy, cyclopropoxy, cyclobutoxy, cyclopentyloxy, cyclohexyloxy. The alkoxy group may be optionally substituted or non-substituted, and when substituted, the substituent is preferably one or more of the following groups independently selected from alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio.

The term "cycloalkyl" refers to a saturated or partially unsaturated monocyclic or polycyclic cyclic hydrocarbon substituent, wherein the cycloalkyl ring comprises from 3 to 20 carbon atoms (i.e. "C3-C20 cycloalkyl"), preferably comprising from 3 to 12 carbon atoms (i.e. "C3-C12 cycloalkyl"), more preferably comprising 3 to 10 carbon atoms (i.e., "C3-C10 cycloalkyl"), most preferably comprising 3 to 8 carbon atoms (i.e., "C3-C8 cycloalkyl"). Non-limiting examples of monocyclic cycloalkyl groups (e.g., "C3-C8 cycloalkyl") include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like; and polycyclic cycloalkyl groups include cycloalkyl groups of spirocycles, fused rings, and bridged rings.

The term "heterocyclyl" means a saturated or partially unsaturated monocyclic or polycyclic cyclic hydrocarbon substituent comprising from 3 to 20 ring atoms (i.e., a "3-20-membered heterocyclyl"), wherein one or more of the ring atoms is a heteroatom selected from nitrogen, oxygen or $S(O)_m$ (wherein $_m$ is an integer from 0 to 2), but excluding ring portions of —O—O—, —O—S— or —S—S—), with the remaining ring atom(s) being carbon. Preferably, it comprises 3 to 12 ring atoms (i.e., a "3-12 membered heterocyclic group"), 1 to 4 of which are heteroatoms; more preferably, the cycloalkyl ring comprises 3 to 10 ring atoms (i.e., a "3-10 membered heterocyclic group"). Non-limiting examples of monocyclic heterocyclic groups (e.g., 3-7-membered heterocyclic groups) include pyrrolidinyl, piperidinyl, piperazinyl, morpholinyl, thiomorpholinyl, homopiperazinyl, and the like. Polycyclic heterocyclic groups include spiro, fused and bridged heterocyclic groups.

The term "cycloalkylalkyl" means that the alkyl group is substituted with one or more cycloalkyl groups, preferably with one cycloalkyl group, wherein alkyl is defined as above and wherein cycloalkyl is defined as above, for example, C3-C8 cycloalkyl C1-C6 alkyl.

The term "haloalkyl" means an alkyl group substituted with one or more halogens, wherein the alkyl group is as defined above, for example, halo C1-C6 alkyl.

The term "deuteroalkyl" means an alkyl group substituted with one or more deuterium atoms, wherein the alkyl group is as defined above, for example, deutero C1-C6 alkyl.

The term "C6-C12 aryl" refers to carbocyclic aromatic system groups having 6-12 carbon atoms.

The term "C6-C10 aryl" refers to carbocyclic aromatic system groups having 6-10 carbon atoms, such as phenyl, naphthyl, etc.

The term "5-10-membered heteroaryl" refers to aromatic heterocyclic rings, typically 5-, 6-, 7-, 8-, 9- and 10-membered heterocyclic rings having 1 to 3 heteroatoms selected from N, O, or S; the heteroaryl ring can optionally be further fused or attached to aromatic and non-aromatic carbon rings and heterocyclic rings. Non-limiting examples of said 5- to 10-membered heteroaryl rings are, for example, pyridinyl, pyrazinyl, pyrimidinyl, pyridazinyl, indolyl, imidazolyl, thiazolyl, isothiazolyl, thioxazolyl, pyrrolyl, phenyl-pyrrolyl, furanyl, phenyl-furanyl, oxazolyl, isoxazolyl, pyrazolyl, thiophenyl, benzofuranyl, benzothiophenyl, benzo 1,3-dioxolane (benzodioxole), isodihydroindolyl, benzimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl, and others.

The term "substituted C6-C10 aryl" or "substituted 5-10 membered heteroaryl" or "substituted 3-7 membered heterocyclyl" means that a hydrogen in the aryl or heteroaryl or heterocyclic group is replaced by a substituent group. Unless otherwise stated in the text, the substituent of the aryl or heteroaryl or heterocyclyl group may be a variety of groups selected from the following group: -halogen, —OR', —NR'R", —SR', —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, $—NH—C(NH_2)=NH$, $—NR'C(NH_2)=NH$, $—NH—C(NH_2)=NR'$, —S(O)R', $—S(O)_2R'$, $—S(O)_2NR'R"$, $—NR'S(O)_2R"$, —CN and $—NO_2$, with substituent numbers from 0 to (2m'+1), where m' is the total number of carbon atoms in the group. R', R" and R'" each independently refer to hydrogen, unsubstituted $C_{1-8}$ alkyl, unsubstituted C6-C12 aryl (or C6-C10 aryl), C6-C12 aryl (or C6-C10 aryl) substituted by 1-3 halogens, unsubstituted $C_{1-8}$ alkyl, $C_{1-8}$ alkoxy or $C_{1-8}$ thioalkoxy, or unsubstituted C6-C12 aryl (or C6-C10 aryl)-$C_{1-4}$alkyl. When R' and R" are attached to the same nitrogen atom, they may form a 3-, 4-, 5-, 6-, or 7-membered ring with that nitrogen atom. For example, —NR'R" includes 1-pyrrolidinyl and 4-morpholinyl.

The term "hydroxyl" refers to the —OH group.

The term "halogen" means fluorine, chlorine, bromine, or iodine.

The term "amino" means $—NH_2$. The term "nitro" means $—NO_2$.

The term "amide group" means —C(O)N(alkyl) or (cycloalkyl), wherein alkyl and cycloalkyl are as defined above.

The term "carboxylate group" means —C(O)O(alkyl) or (cycloalkyl), wherein alkyl and cycloalkyl are as defined above.

The present invention also includes various deuterated forms of formula I. Each of the available hydrogen atoms attached to the carbon atoms may be independently replaced by a deuterium atom. A person skilled in the art can synthesize the deuterated form of formula I with reference to the relevant literature. Commercially available deuterated starting materials may be used in the preparation of deuterated forms of formula I, or they may be synthesized by conventional techniques using deuterated reagents, non-limiting examples of deuterated reagents including: deuteroborane, trideuteroborane tetrahydrofuran solution, deuterated lithium-aluminum hydride, deuterated ethyl iodide, and deuterated methyl iodide, and the like.

The term "antibody" refers to immunoglobulins, which are tetrapeptide chain structures consisting of two identical heavy chains and two identical light chains linked by interchain disulfide bonds. Immunoglobulins differ in the composition and order of amino acids in the constant region of the heavy chain, and therefore differ in their antigenicity. Accordingly, immunoglobulins can be categorized into five classes, or isoforms of immunoglobulins, i.e., IgM, IgD, IgG, IgA, and IgE, whose corresponding heavy chains are μ, δ, γ, α, and ε chains, respectively. The same class of Ig can be further divided into different subclasses according to differences in the amino acid composition of its hinge region and the number and positions of disulfide bonds of the heavy chain, e.g. IgG can be divided into IgG1, IgG2, IgG3 and IgG4. The light chains are divided into κ-chains or λ-chains by the differences in the constant region. Each of the five classes of Ig may have a κ chain or a λ chain. The antibodies described in the present invention are preferably specific antibodies against cell surface antigens on target cells, and non-limiting embodiments are the following antibodies: one or more of anti-EGFRvIII antibody, anti-DLL-3 antibody, anti-PSMA antibody, anti-CD70 antibody, anti-MUC16 antibody, anti-ENPP3 antibody, anti-TDGF1 antibody, anti-ETBR antibody, anti-MSLN antibody, anti-TIM-1 antibody, anti-LRRC15 antibody, anti-LIV-1 antibody, anti-CanAg/AFP antibody, anti-cladin 18.2 antibody, anti-Mesothelin antibody, anti-HER2 (ErbB2) antibody, anti-EGFR antibody, anti-c-MET antibody, anti-SLITRK6 antibody, anti- KIT/CD117 antibody, anti-STEAP1 antibody, anti-SLAMF7/CS1 antibody, anti-NaPi2B/SLC34A2 antibody, anti-GPNMB antibody, anti-HER3(ErbB3) antibody, anti-MUC1/CD227 antibody, anti-AXL antibody, anti-CD166 antibody, anti-B7-H3(CD276) antibody, anti-PTK7/CCK4 antibody, anti-PRLR antibody, anti-EFNA4 antibody, anti-5T4 antibody, anti-NOTCH3 antibody, anti-Nectin 4 antibody, anti-TROP-2 antibody, anti-CD142 antibody, anti-CA6 antibody, anti-GPR20 antibody, anti-CD174 antibody, anti-CD71 antibody, anti-EphA2 antibody, anti-LYPD3 antibody, anti-FGFR2 antibody, anti-FGFR3 antibody, anti-FRα antibody, anti-CEACAMs antibody, anti-GCC antibody, anti-Integrin Av antibody, anti-CAIX antibody, anti-P-cadherin antibody, anti-GD3 antibody, anti-Cadherin 6 antibody, anti-LAMP1 antibody, anti-FLT3 antibody, anti-BCMA antibody, anti-CD79b antibody, anti-CD19 antibody, anti-CD33 antibody, anti-CD56 antibody, anti-CD74 antibody, anti-CD22 antibody, anti-CD30 antibody, anti-CD37 antibody, anti-CD138 antibody, anti-CD352 antibody, anti-CD25 antibody or anti-CD123 antibody.

The term "solvate" or "solvent compound" refers to the formation of a pharmaceutically usable solvate from the ligand-drug conjugate of the present invention with one or more solvent molecules, non-limiting examples of solvent molecules including water, ethanol, acetonitrile, isopropanol, DMSO and ethyl acetate.

The term "drug load" refers to the average number of cytotoxic drugs loaded on each antibody in formula I. It can also be expressed as the ratio of drug amount to antibody amount, and the drug load can range from 0-12, preferably 1-10 cytotoxic drugs (D) connected to each antibody (Ab). In embodiments of the invention, the drug load is denoted as n, which exemplarily may be the mean value of 1, 2, 3, 4, 5, 6, 7, 8, 9, 10. The average number of drugs per ADC molecule after the coupling reaction can be identified by conventional methods such as UV/visible spectroscopy, mass spectrometry, ELISA tests and HPLC characteristics.

In one embodiment of the present invention, the cytotoxic drug is coupled to the open cysteine sulfhydryl-SH and/or the sulfhydryl-SH of the site-directed mutagenesis cysteine residue between the antibody chains by a linker unit, and generally the number of drug molecules that can be coupled to the antibody in the coupling reaction will be less than or equal to a theoretical maximum.

The loading of ligand cytotoxic drug conjugates can be controlled by the following non-limiting methods, including:

(1) controlling the molar ratio of the linking reagent to the monoclonal antibody;
(2) control of reaction time and temperature;
(3) selection of different reaction reagents.

For the preparation of conventional pharmaceutical compositions, see the Chinese Pharmacopoeia.

The term "pharmaceutically acceptable salt" or "pharmaceutically usable salt" means a salt of a ligand-drug conjugate of the present invention, or a salt of a compound described in the present invention; salts of this kind are safe and efficacious when used in a mammal, and are biologically active as desired. The ligand-drug conjugates of the present invention contain at least one carboxyl group, so they can form salts with bases, and non-limiting examples of pharmaceutically acceptable salts include sodium, potassium, calcium, or magnesium salts, etc.

The term "pharmaceutically acceptable salt" or "pharmaceutically usable salt" means a salt of an antibody-drug conjugate of the present invention, or a salt of a compound described herein; salts of this kind are safe and efficacious when used in a mammal, and are biologically active as desired.

The ligand-drug conjugates of the present invention contain at least one amino group and can therefore form salts with acids, non-limiting examples of pharmaceutically acceptable salts including: hydrochloride, hydrobromide, hydriodate, sulfate, bisulfate, citrate, acetate, succinate, ascorbate, oxalate, nitrate, phosphate, hydrogen phosphate, dihydrogen phosphate, salicylate, hydrogen citrate, tartrate, maleate, fumarate, formate, benzoate, methanesulfonate, ethanesulfonate, benzenesulfonate, p-toluenesulfonate.

"Acidic amino acid" refers to amino acids with an isoelectric point of less than 7. Acidic amino acid molecules tend to have one or more acidic groups, such as carboxyl groups, which can be effectively ionized into negative ionic forms in the structure to increase hydrophilicity. Acidic amino acids can be natural or unnatural.

The term "natural amino acids" refers to biologically synthesized amino acids. Natural amino acids are generally of the L-type, but there are a few exceptions, such as glycine, including natural and synthesized by organisms.

"Unnatural amino acids" means amino acids obtained by synthetic means.

The invention is further elaborated below in connection with specific embodiments which, it should be understood, are intended only to illustrate the invention, and are not intended to limit the scope of the invention. Test methods for which specific conditions are not indicated in the following embodiments are generally in accordance with conventional conditions or in accordance with conditions recommended by the manufacturer. All percentages, proportions, ratios or parts are by weight unless otherwise indicated.

Example 1

Synthesis of Compound M1:

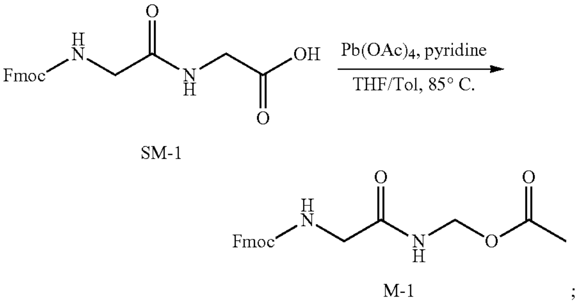

SM-1

M-1 ;

In a 5000 mL single-necked flask, N-fluorenylmethoxycarbonyl-glycine-glycine (100 g, 282 mmol, 1.0 eq), lead tetraacetate (175 g, 395 mmol, 1.4 eq), 2000 mL of dry tetrahydrofuran and 670 mL of toluene were added, stirred uniformly, protected by nitrogen, heated to 85° C. and reacted for 2.5 h. The reaction was monitored by TLC, and after the starting materials had finished reacting, cooling to room temperature and filtration were performed, the filtrate was concentrated under reduced pressure, and the residue was purified by column chromatography to obtain compound M1 (87 g); LC-MS: $[M+NH_4]^+$=386.0.

Example 2

Synthesis of Compound M3:

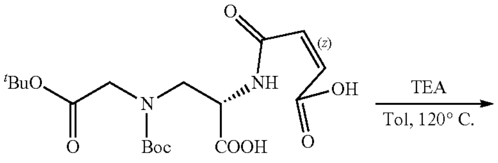

SM-2

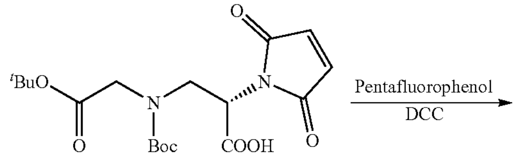

M2

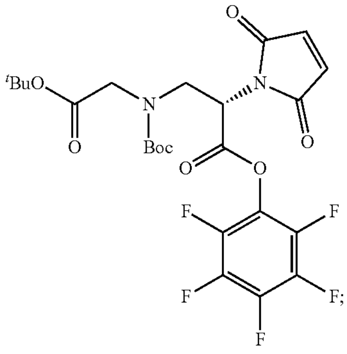

M3

In a 1000 mL single-necked flask, compound SM-2 (synthesized according to the method published in patent CN108452321A) (40 g, 96 mmol, 1.0 eq), triethylamine (26.7 mL, 2.0 eq), and toluene (400 mL) were added, heated to 120° C., and a reaction was carried out by refluxing for 2 h. When TLC monitoring indicated that the reaction was essentially complete, cooling to 50° C. was performed, and solvent was removed by spinning under reduced pressure. Dissolution with ethyl acetate (150 mL) and water (40 mL) was performed, the pH was adjusted to 2-3 with 1M HCl under ice bath stirring, and liquid separation was performed. The aqueous layer was extracted once more with ethyl acetate, the organic layers were combined, and drying was performed by adding anhydrous sodium sulfate. After filtration, a light yellow oily crude product was obtained by concentration, and the crude product was purified by column chromatography (DCM:MeOH=40:1) to obtain compound M2 (26.6 g); LC-MS: $[M+H]^+=399.3$.

In a 1000 mL single-necked flask, compound M2 (26.5 g, 60.5 mmol, 1.0 eq), pentafluorophenol (12.2 g, 66.5 mmol, 1.1 eq), DCC (13.7 g, 66.5 mmol, 1.1 eq), and THF (300 mL) were added, and a reaction was carried out at room temperature for 30 min (monitored by TLC). The insoluble material was filtered out. The reaction solution was purified directly by preparative LC, and the prepared solution was concentrated at 35° C. in a water bath under reduced pressure by pumping water to remove acetonitrile, and lyophilized to obtain compound M3 (31.5 g) with 64% yield; LC-MS: $[M+H]^+=565.1$.

Example 3

Synthesis of the Compound Ent-M3:

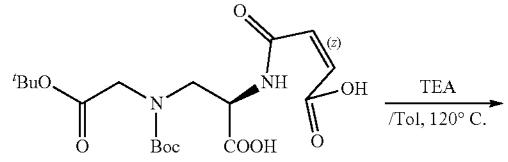

ent-SM-2

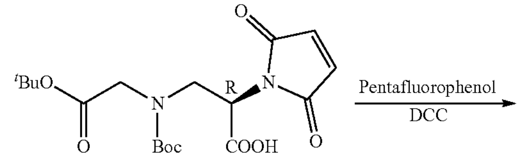

ent-M2

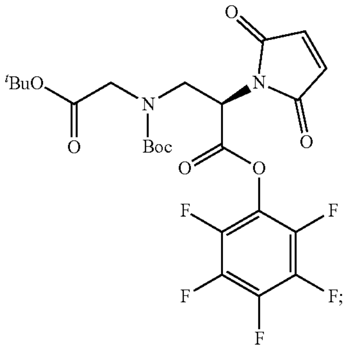

ent-M3

Referring to the synthetic route of Example 2, compound ent-M3 (27.8 g) was obtained; LC-MS: $[M+H]^+=565.2$.

Example 4

Synthesis of Compound 1:

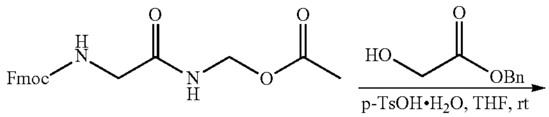

M1

-continued
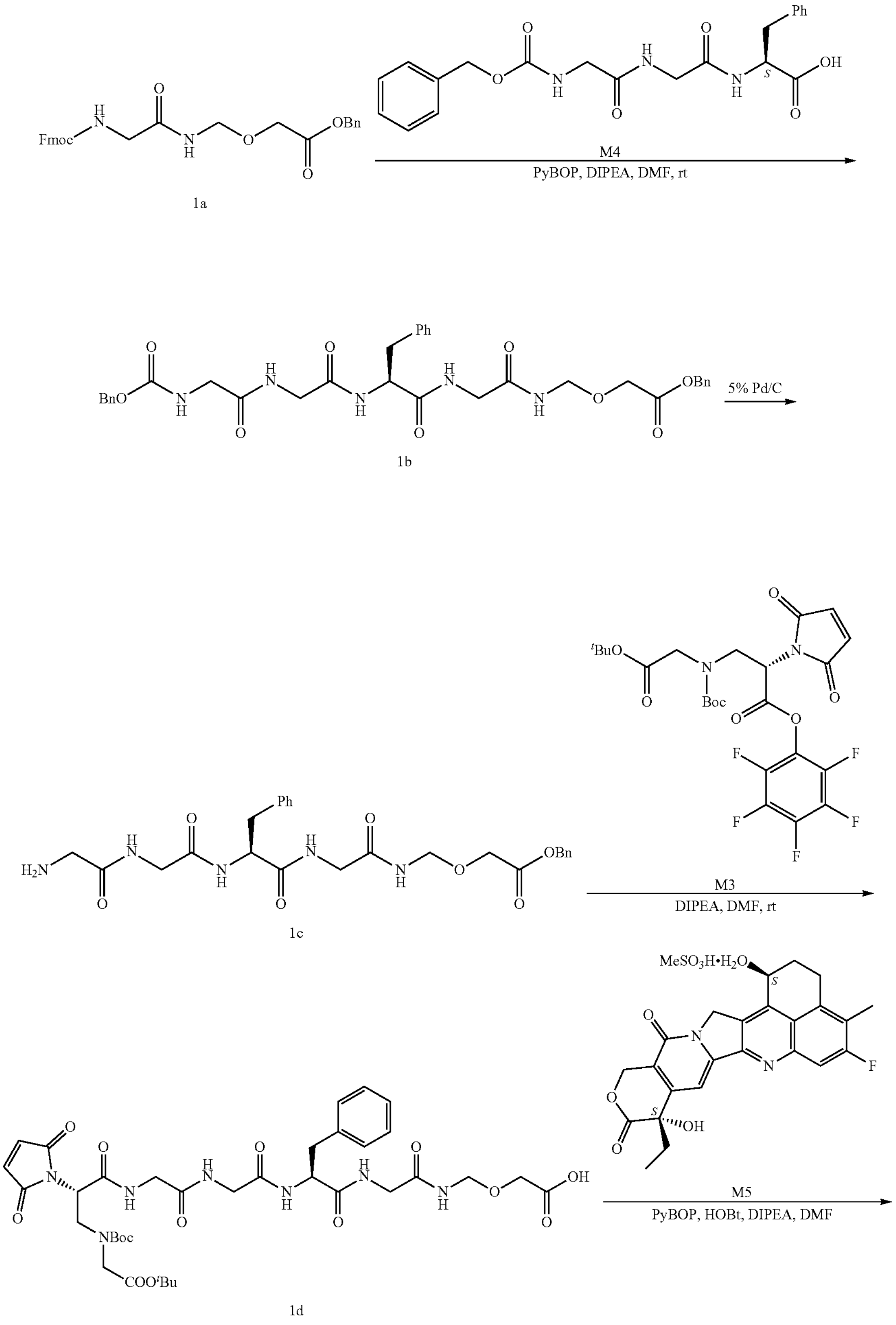

-continued

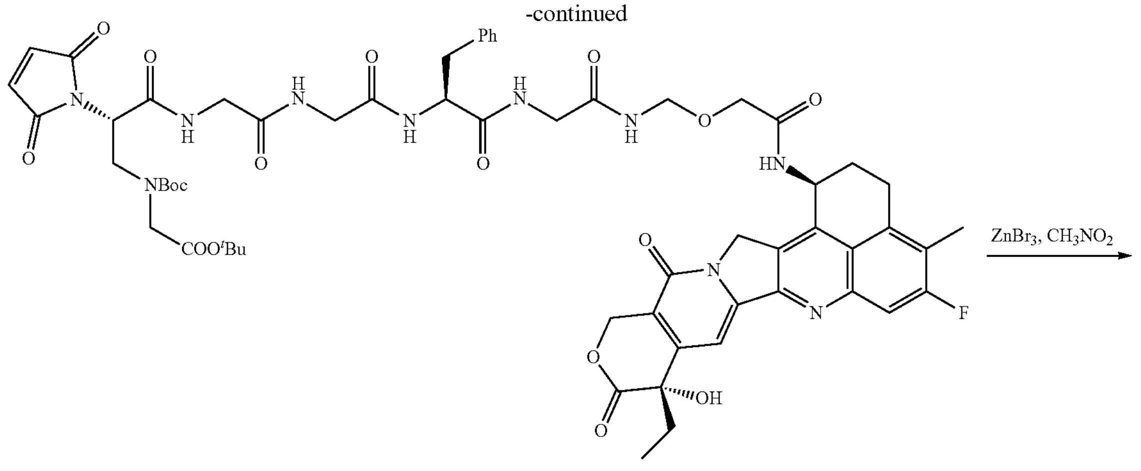

1e

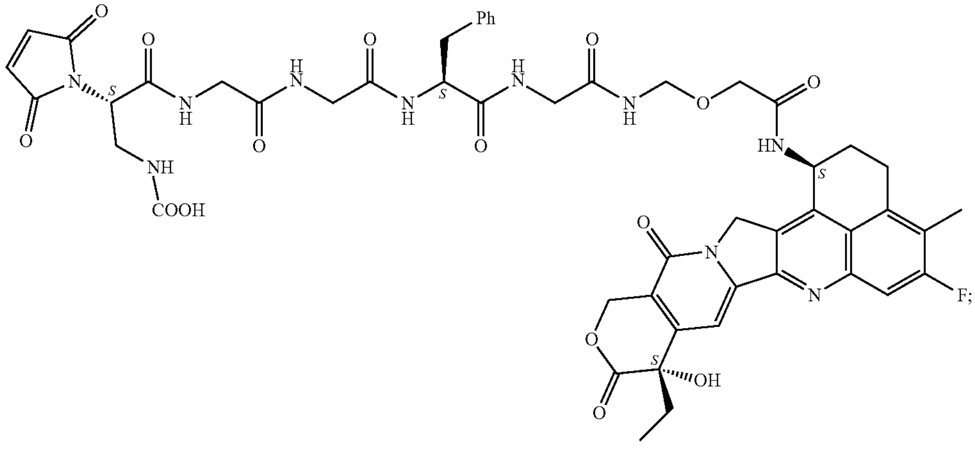

compound 1

Step 1: Compound 1a

In a 250 mL single-necked flask, add M1 (6 g, 16.3 mmol), 100 mL THF, p-toluenesulfonic acid monohydrate (0.31 g, 1.63 mmol), stir and cool to 0° C., perform dropwise addition of benzyl hydroxyacetate (5.4 g, 32.6 mmol), then naturally warm to room temperature for a reaction (the reaction lasts for about 2-4 h), with TLC monitoring. At the end of the reaction, saturated $NaHCO_3$ solution was added, extracted with ethyl acetate, washed with saturated sodium chloride solution, dried with anhydrous sodium sulfate, filtered, concentrated, and the residue was purified by silica gel column (PE:EA=10:1-5:1-1:1) to obtain 1a (4 g) at 52% yield; LC-MS: $[M+H]^+$=475.18.

Step 2: Compound 1b

In a 25 mL single-necked flask, add 1a (2 g, 4.2 mmol), 10 mL DMF, stir at 0° C., add DBU (766 mg, 5.04 mmol), and react for 1 h. After the completion of Fmoc deprotection as detected by TLC, the reaction solution was set aside ready for use.

M4 (prepared according to the method published in patent CN111051330 A) (1.73 g, 4.2 mmol), PyBOP (2.61 g, 5.04 mmol), HOBt (680 mg, 5.04 mmol) and 10 mL of DMF were added to another 25 mL single-necked flask, DIPEA (830 uL, 5.04 mmol) was added in an ice-water bath, stirring was continued for 30 min, the above reaction solution was added to the reaction flask, and the temperature was raised to room temperature for a reaction. When HPLC monitoring indicated the end of the reaction, the reaction solution was purified by preparative LC to obtain a product preparation liquid, the preparation liquid was extracted by dichloromethane, washed with saturated sodium chloride solution, dried with anhydrous sodium sulfate, filtered, and the filtrate was concentrated under reduced pressure to obtain solid 1b (1.7 g) at 63% yield; LCMS: $[M+H]^+$=648.26.

Step 3: Compound 1c 1b (900 mg, 1.39 mmol) was added to a 25 mL single-necked flask, and after dissolution with 15 mL of DMF, 900 mg of 5% Pd/C was added, and a hydrogenation reaction took place for 2 h. After the completion of the reaction, filtering was performed to obtain the filtrate, which was used directly for the next step of the reaction without purification.

Step 4: Compound 1d

The crude product 1c was placed in an ice-water bath, DIPEA (235 uL, 1.39 mmol) was added, and compound M3 (784 mg, 1.39 mmol) was added, then the temperature was raised to room temperature to react for 1 h. When the reaction was complete as indicated by HPLC monitoring, the reaction solution was purified by HPLC to obtain a preparation liquid, which was lyophilized to obtain 1d (504 mg); LC-MS: $[M+H]^+$=804.4.

Step 5: Compound 1e

Add 1d (500 mg, 0.62 mmol), M5 (310 mg, 0.62 mmol), PyBOP (448 mg, 0.86 mmol), HOBt (116 mg, 0.86 mmol) and 15 mL DMF into a 50 mL single-necked flask, add DIPEA (378 uL, 2.29 mmol) in an ice-water bath, raise to room temperature and react for 2 h. After completion of the reaction was indicated by monitoring by HPLC, the reaction solution was purified by HPLC to obtain a preparation liquid of compound 1e, which was lyophilized to obtain 1e (210 mg); LC-MS: [M+H]+=1221.6.

Step 6: Compound 1

1e (100 mg, 0.081 mmol), zinc bromide (368 mg, 1.63 mmol) and 5 mL of nitromethane were added to a 25 mL single-necked flask and the reaction was carried out at 40° C. for 1 h. After the completion of the reaction was indicated by monitoring by HPLC, concentration under reduced pressure was performed to remove the solvent, and a crude product was obtained. The crude product was purified by HPLC to obtain a product preparation liquid, and the preparation liquid was lyophilized to obtain the solid compound 1 (60 mg); LC-MS: $[M+H]^+$=1065.3.

Example 5

Synthesis of Compound 2:

compound 2

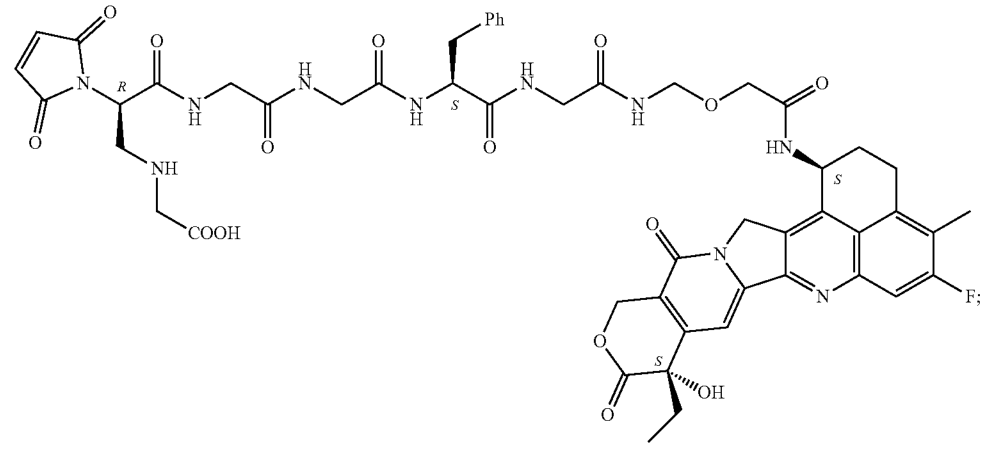

Referring to the synthetic route of Example 4, compound 2 (51 mg) was obtained; LC-MS: $[M+H]^+$=1065.3.

Example 6

Synthesis of Compound 3:

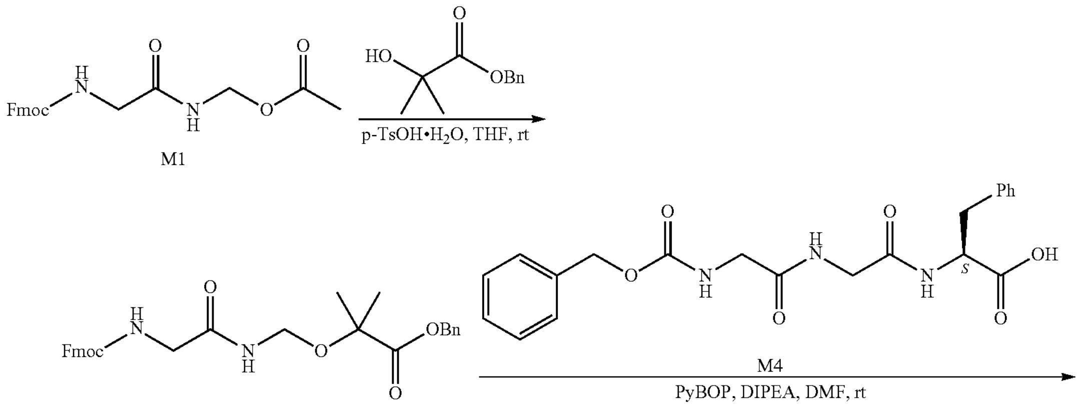

M1

3a

-continued
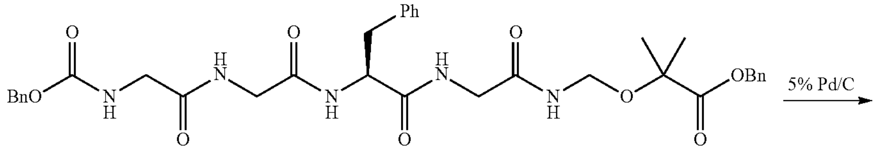
3b
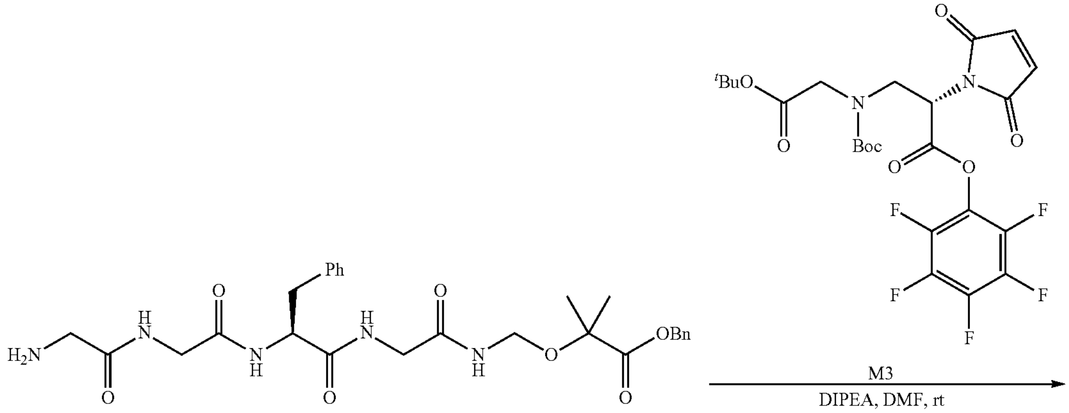
3c
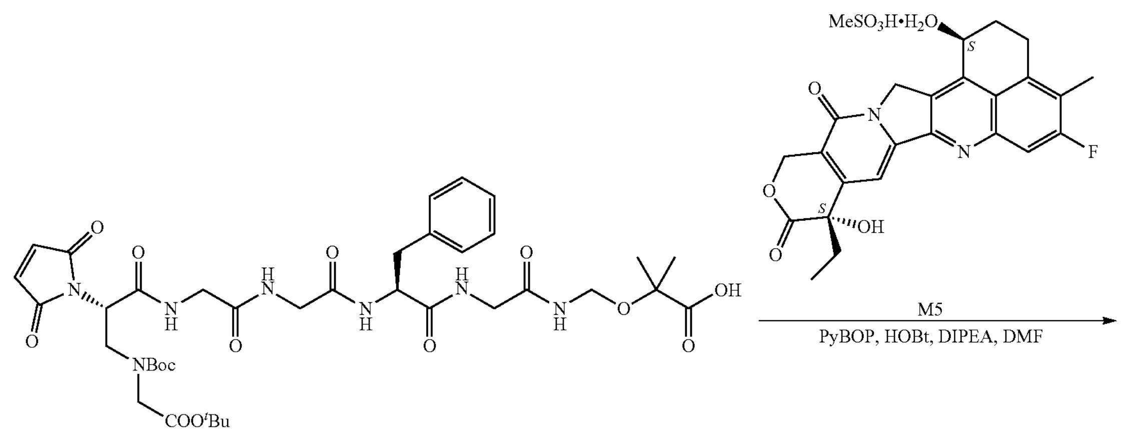
3d
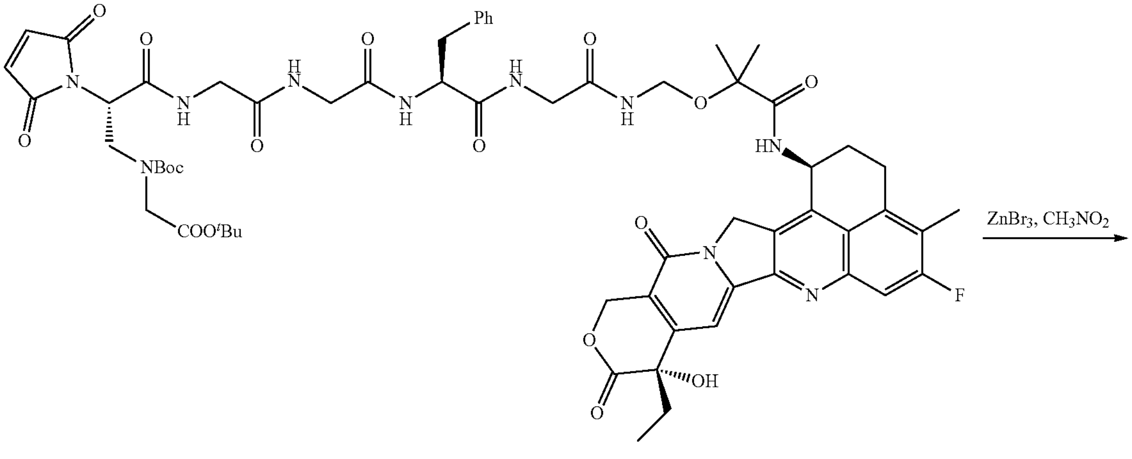
3e

-continued

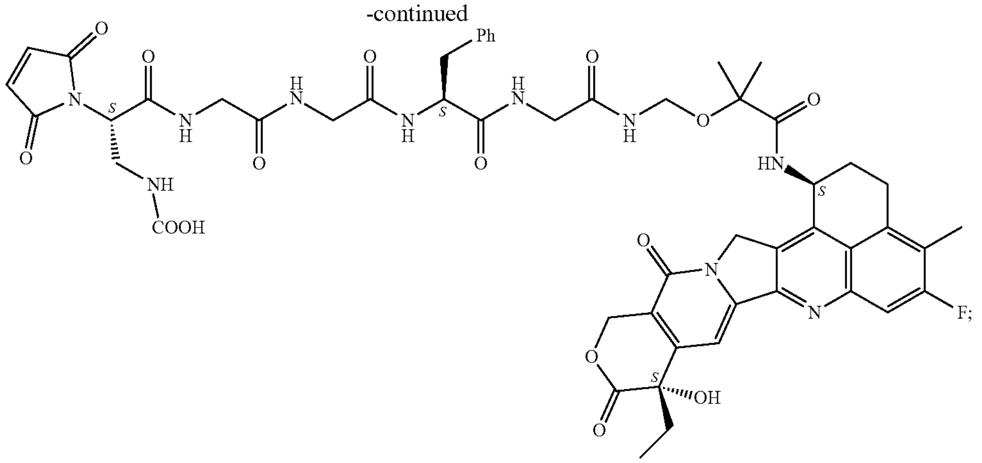

compound 3

Step 1: Compound 3a

In a 250 mL single-necked flask, add M1 (6 g, 16.3 mmol), 100 mL THF, p-toluenesulfonic acid monohydrate (0.31 g, 1.63 mmol), stir and cool to 0° C., perform dropwise addition of benzyl 2-hydroxy-2-methylpropionate (6.3 g, 32.6 mmol), then perform natural warming to room temperature for a reaction (the reaction lasts for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to obtain 3a (4.2 g) at 52% yield; LC-MS: $[M+H]^+$=503.3.

Step 2: Compound 3b

In a 25 mL single-necked flask, add 3a (2 g, 4.0 mmol) and 10 mL DMF, stir at 0° C., add DBU (760 mg, 5.0 mmol), and react for 1 h. After the completion of Fmoc deprotection as detected by TLC, the reaction solution was set aside ready for use.

Add M4 (1.65 g, 4.0 mmol), PyBOP (2.59 g, 5.0 mmol), HOBt (675 mg, 5.0 mmol) and 10 mL of DMF into another 25 mL single-necked flask, and add DIPEA (823 uL, 5.04 mmol) in an ice-water bath, continue stirring for 30 min, and then add the above reaction solution to the reaction flask and raise to room temperature for a reaction. After the completion of the reaction as indicated by monitoring by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain the solid 3b (1.4 g) at 53% yield; LC-MS: $[M+H]^+$=676.2.

Step 3: Compound 3c

Add 3b (700 mg, 1.04 mmol) to a 25 mL single-necked flask, dissolve in 10 mL of DMF, add 700 mg of 5% Pd/C, and perform a hydrogenation reaction for 1.5 h. After the completion of the reaction, filtering was performed to obtain a filtrate, which was used directly for the next step of the reaction without purification.

Step 4: Compound 3d

Place the crude product 3c in an ice-water bath, add DIPEA (210 uL, 1.25 mmol) and then compound M3 (704 mg, 1.25 mmol), then raise to room temperature and react for 1 h. After the completion of the reaction as indicated by HPLC monitoring, the reaction solution was purified by HPLC to obtain a preparation liquid, which was lyophilized to give 3d (486 mg); LC-MS: $[M-H]^-$=830.5.

Step 5: Compound 3e

Add 3d (300 mg, 0.36 mmol), M5 (180 mg, 0.36 mmol), PyBOP (260 mg, 0.5 mmol), HOBt (67 mg, 0.5 mmol) and 10 mL of DMF to a 50 mL single-necked flask, add DIPEA (219.5 uL, 1.33 mmol) in an ice-water bath, raise to room temperature and react for 3 h. After the completion of the reaction as detected by HPLC, the reaction solution was purified by HPLC to give the preparation liquid of compound 3e, which was lyophilized to obtain 3e (157 mg); LC-MS: $[M+H]^+$=1249.6.

Step 6: Compound 3

Add 3e (100 mg, 0.08 mmol), zinc bromide (360 mg, 1.6 mmol) and 5 mL of nitromethane to a 25 mL single-necked flask, and react at 40° C. for 1 h. After the completion of the reaction as detected by HPLC, perform concentration under reduced pressure to remove the solvent, to obtain a crude product. The crude product was purified by high performance liquid chromatography to obtain a product preparation liquid, and the preparation liquid was lyophilized to obtain the solid compound 3 (64 mg); LC-MS: $[M+H]^+$=1093.1.

Example 7
Synthesis of Compound 4:
compound 4
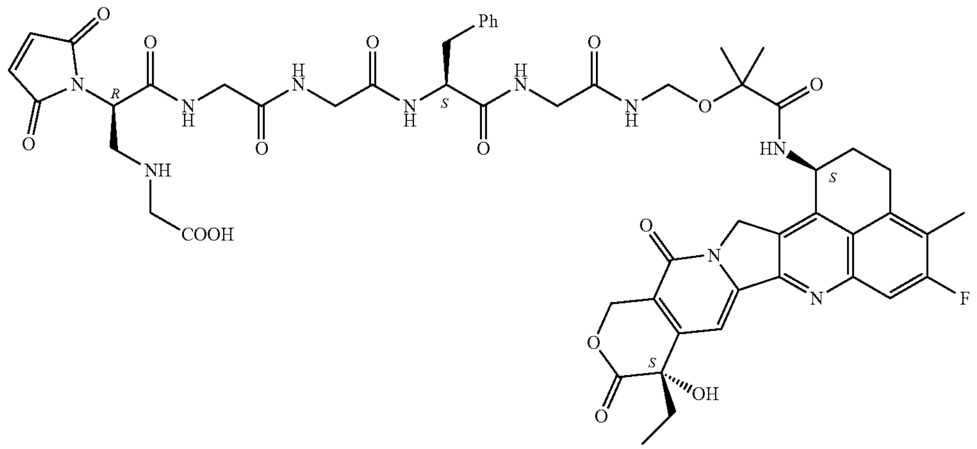
Referring to the synthetic route of Example 6, compound 4 (60 mg) was obtained; LC-MS: $[M+H]^+$=1093.2.
Example 8
Synthesis of Compound 5A:
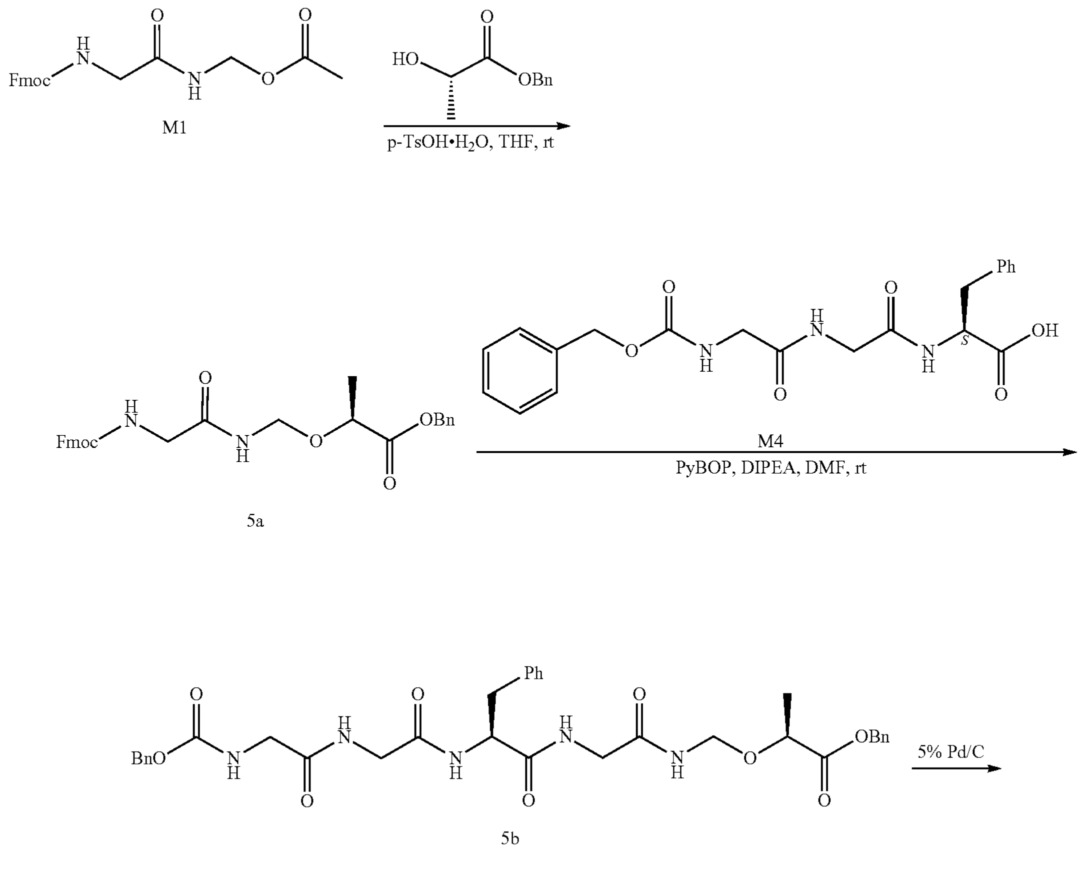

-continued
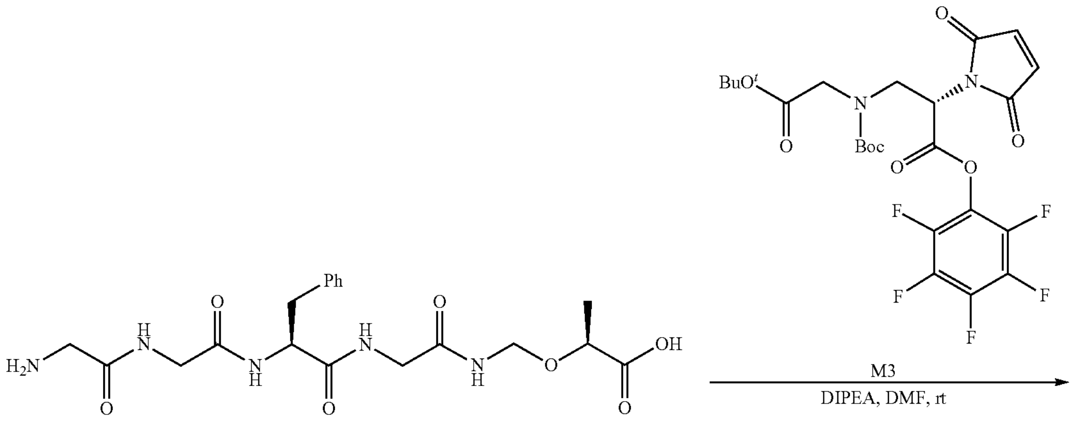
5c
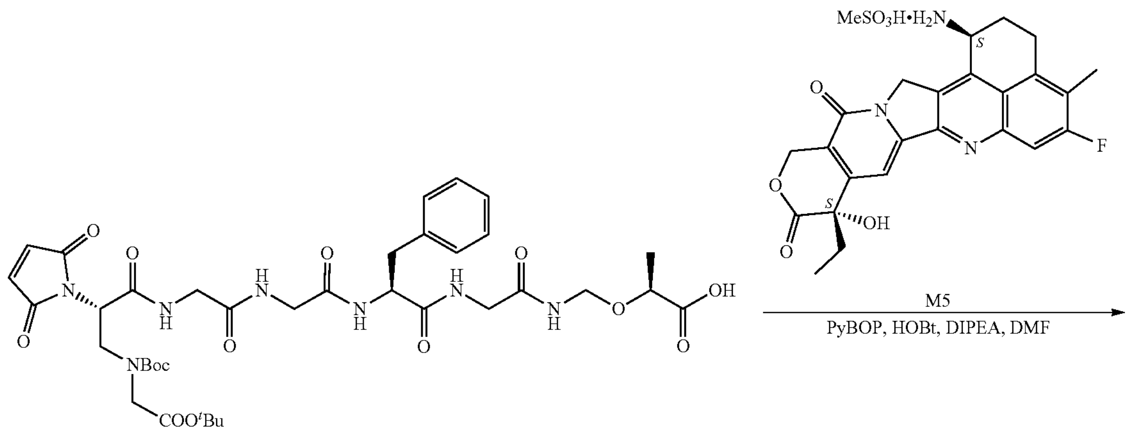
5d
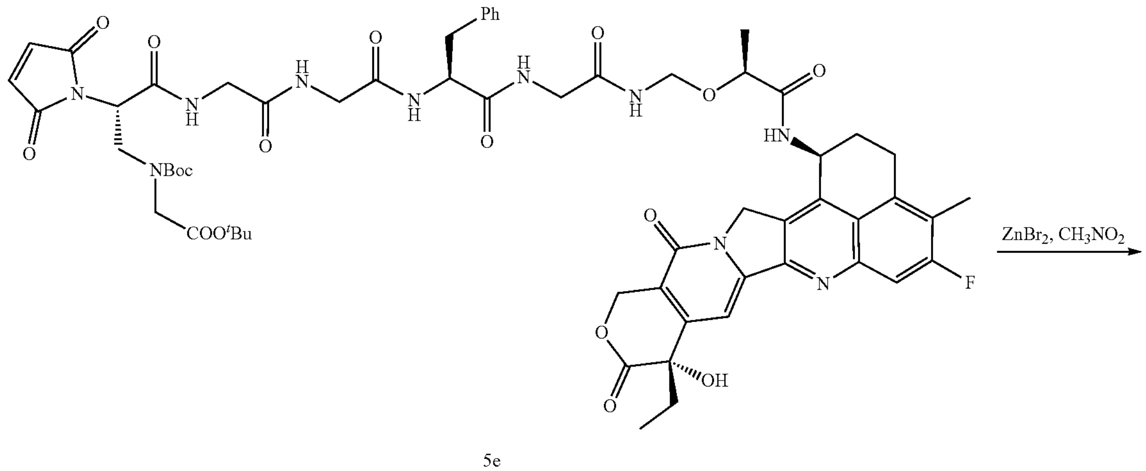
5e

-continued

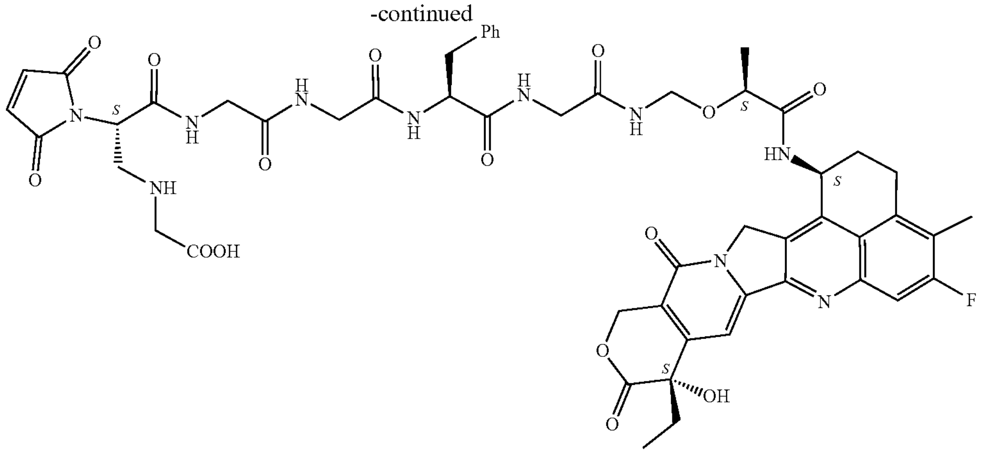

compound 5A

Step 1: Compound 5a

Add M1 (500 mg, 1.4 mmol, 1.0 eq), p-toluenesulfonic acid monohydrate (26 mg, 0.1 mmol, 0.1 eq) and 10 mL of THF in a 25 mL single-necked flask, stir well, then lower to 0° C., and then slowly add L-lactic acid benzyl ester (1.2 g, 7.0 mmol, 5 eq), and then raise to room temperature for a reaction. TLC monitoring was performed, and at the end of the reaction, saturated $NaHCO_3$ solution was added, followed by extraction with ethyl acetate, drying over anhydrous sodium sulfate, filtering and concentration, and the residue was purified by reverse-phase column to give 5a (400 mg);

LC-MS: $[M+NH_4]^+$=506.2.

$^1$H NMR (400 Mz, $CDCl_3/CD_3OD$): 1.39 (3H, d, J=6.8 Hz), 3.78 (2H, t, J=4.0 Hz), 4.17-4.27 (2H, m), 4.42 (2H, d, J=4.0 Hz), 4.72-4.85 (2H, m), 5.11-5.58 (2H, m), 5.43 (1H, s), 7.06 (1H, t, J=8.0 Hz), 7.25-7.33 (6H, m), 7.38 (2H, t, J=8.0 Hz), 7.57 (2H, d, J=8.0 Hz), 7.75 (2H, d, J=8.0 Hz).

Step 2: Compound 5b

Add Compound 5a (400 mg, 0.8 mmol, 1.0 eq) and 4 mL of DMF to a 25 mL single-necked flask, stir well, and then lower to 0° C. before slowly adding DBU (137 mg, 0.9 mmol, 1.1 eq). After the completion of the addition, raise to room temperature for a reaction. The reaction was monitored by TLC, and at the end of the reaction, the reaction solution was recorded as reaction solution①;

To another 25 mL single-necked flask, add M4 (372 mg, 0.9 mmol, 1.1 eq), PyBOP (852 mg, 1.6 mmol, 2.0 eq) and 3 mL of DMF, stir at room temperature for 5 min, and add reaction solution①. The reaction was carried out at room temperature and monitored by HPLC. When the reaction was completed, the reaction solution was purified through HPLC to yield compound 5b (326 mg); LC-MS: $[M+NH_4]^+$ =679.2.

Step 3: Compound 5c

Add 5b (4.0 g, 6.05 mmol, 1.0 eq) to a 100 mL single-necked flask, dissolve in DMF (60 mL), then add 5% Pd/C (4 g), and perform a hydrogenation reaction at room temperature for 4 h (HPLC was used to monitor the progress of the reaction). The Pd/C was filtered, and the filtrate was placed directly in an ice-water bath (about 0° C.) without being concentrated, ready for use.

Step 4: Compound 5d

Place the crude product 5c in an ice-water bath, add DIPEA (1.1 mL, 1.1 eq) and then compound M3 (3.4 g, 6.05 mmol), and then raise to room temperature and react for 2 h. After the completion of the reaction as detected by HPLC, the reaction solution was purified by HPLC to obtain a preparative liquid, which was lyophilized to obtain 5d (3.15 g); LC-MS: $[M-H]^-$=816.3.

Step 5: Compound 5e

Add 5d (2.07 g, 2.53 mmol, 1.0 eq), M5 (1.35 g, 2.53 mmol, 1.0 eq), PyBOP (1.98 g, 3.79 mmol, 1.5 eq), HOBt (0.51 g, 3.79 mmol, 1.5 eq) and DMF (40 mL) to a 100 mL single-necked flask, add DIPEA (1.05 mL, 1.5 eq) in an ice-water bath, raise to room temperature and react for 2 h (monitored by HPLC). The reaction solution was directly purified by preparative LC, and the preparation liquid was concentrated in a water bath under reduced pressure by a water pump at 35° C. to remove acetonitrile and freeze-dried to obtain compound 5e (1.92 g), with a yield of 61%; LC-MS: $[M+H]^+$=1235.4.

Step 6: Compound 5A

To a 100 mL single-necked flask, add compound 5e (1.0 g, 0.8 mmol, 1.0 eq) and 35 mL nitromethane, and after dissolution, add zinc bromide (3.64 g, 16 mmol, 20.0 eq), react for 30 min in an oil bath at 40° C. (stabilized in advance by preheating), and concentrate at 45° C. in a water bath under reduced pressure by a water pump to remove the nitromethane, yielding a yellow residue solid (monitored by HPLC). After acid preparation, the preparation liquid of compound 5A was obtained, and was concentrated at 35° C. in a water bath under reduced pressure by a water pump to remove acetonitrile by spinning, and lyophilized to obtain compound 5A (786 mg) at a yield of 90%.

LC-MS: $[M+H]^+$=1079.4;

$^1$H NMR (400 MHz, DMSO-d6) δ 9.39-9.02 (m, 1H), 8.70 (t, J=6.5 Hz, 1H), 8.64 (t, J=5.7 Hz, 1H), 8.56 (d, J=8.8 Hz, 1H), 8.34 (t, J=5.7 Hz, 1H), 8.16 (d, J=8.2 Hz, 1H), 8.01 (t, J=5.5 Hz, 1H), 7.71 (d, J=10.9 Hz, 1H), 7.30 (s, 1H), 7.28-7.15 (m, 4H), 7.14 (s, 2H), 5.53 (dd, J=14.5, 6.4 Hz, 1H), 5.49-5.34 (m, 2H), 5.22 (d, J=18.8 Hz, 1H), 5.09 (d, J=18.7 Hz, 1H), 5.03 (dd, J=9.6, 3.9 Hz, 1H), 4.73 (dd, J=9.9, 6.9 Hz, 1H), 4.59 (dd, J=10.1, 6.5 Hz, 1H), 4.49 (ddd, J=13.2, 8.6, 4.4 Hz, 1H), 4.14 (dd, J=13.3, 6.6 Hz, 2H), 3.93 (s, 2H), 3.84 (dd, J=16.5, 6.3 Hz, 1H), 3.76 (dd, J=16.9, 5.7 Hz, 2H), 3.70 (dd, J=5.2 Hz, 2H), 3.60 (dd, J=16.7, 5.4 Hz, 1H), 3.52 (dd, J=16.4, 5.1 Hz, 1H), 3.45 (dd, J=12.8, 10.1 Hz, 1H), 3.25-3.15 (m, 1H), 3.14-3.05 (m, 1H), 3.01 (dd, J=13.7, 4.1 Hz, 1H), 2.73 (dd, J=13.5, 9.8 Hz, 1H), 2.54-2.47 (m, 1H), 2.33 (s, 2H), 2.17 (d, J=5.5 Hz, 2H), 1.91-1.79 (m, 2H), 1.33 (d, J=6.6 Hz, 2H), 0.87 (t, J=7.3 Hz, 2H).
Example 9
Synthesis of Compound 5B:
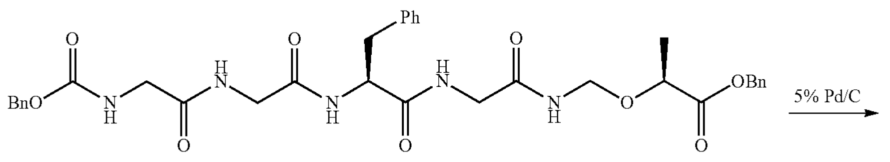
5b
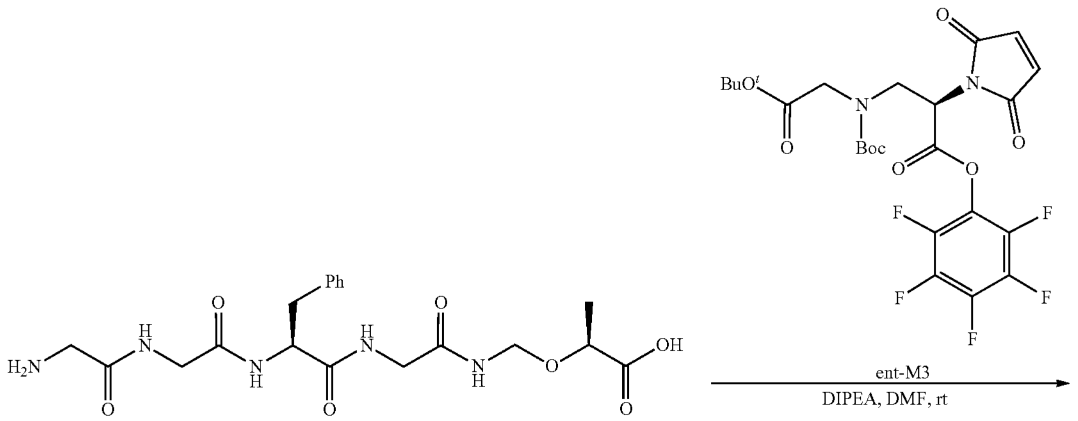
5c
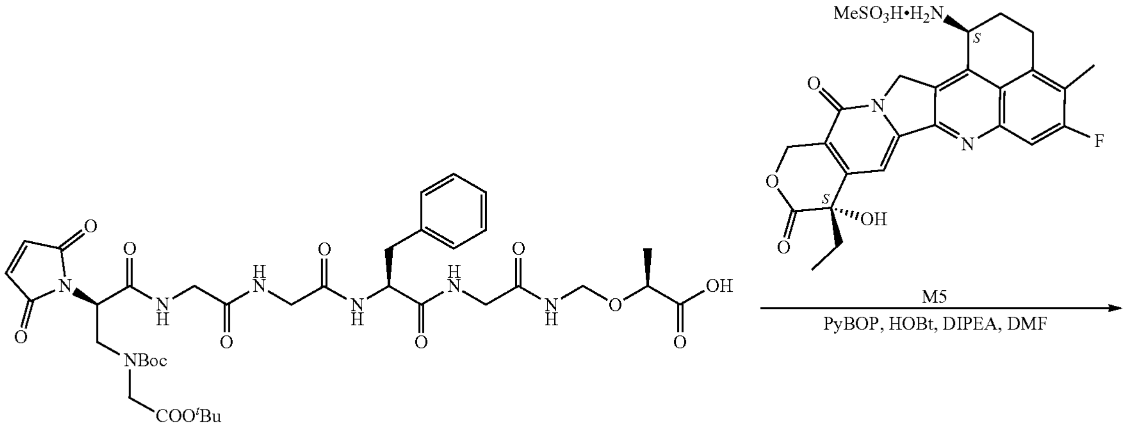
5d-1

-continued

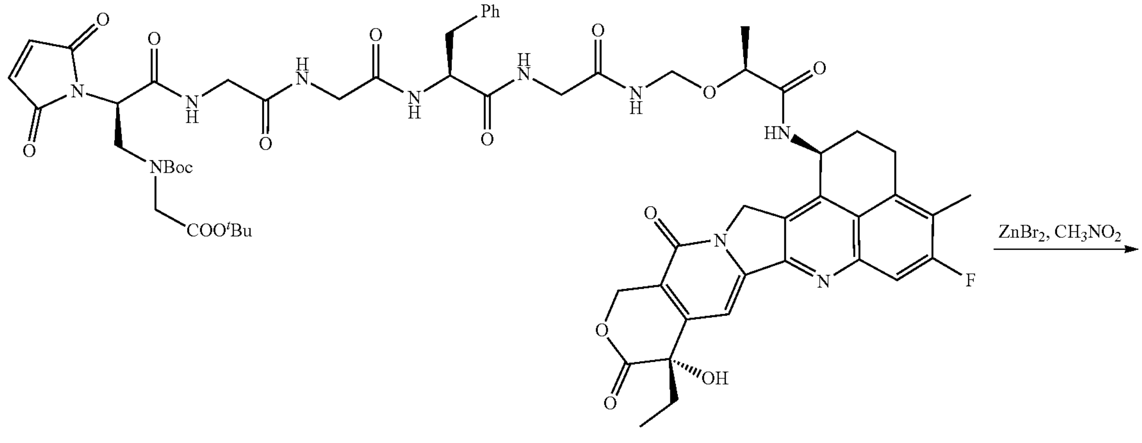

5e-1

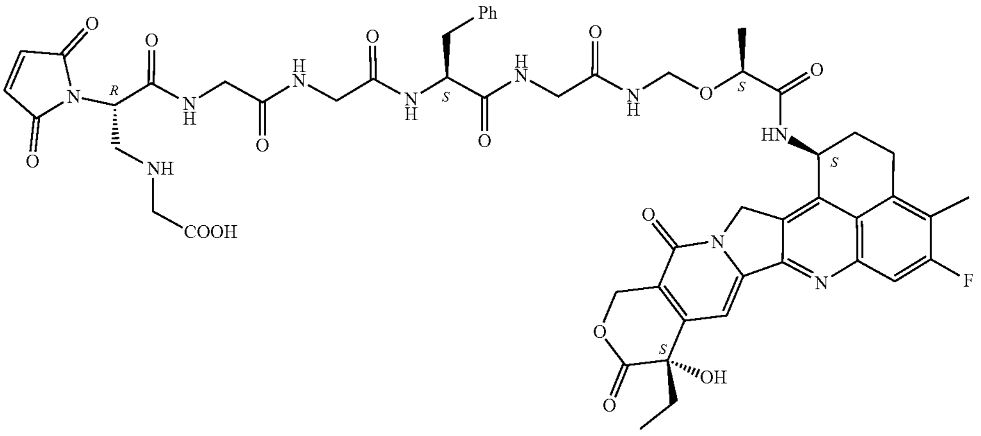

compound 5B

Step 1: Compound 5d-1

Add compound 5b (300 mg, 0.45 mmol, 1.0 eq) and DMF (3 mL) to a 25 mL single-necked flask, stir to dissolve, add 5% Pd/C (300 mg), perform hydrogen replacement three times, perform a hydrogenation reaction for 2 h, and monitor for the end of the reaction by HPLC. After the reaction is over, remove Pd/C by filtration, cool the filtrate to 0-5° C., add DIPEA (65 mg, 0.5 mmol, 1.1 eq), then add ent-M3 (255 mg, 0.45 mmol) to the filtrate, then raise to 20±5° C. and react for 1 h, and monitor for the end of the reaction by HPLC. After the completion of the reaction, preparative purification was performed by HPLC, and the product preparation liquid was collected and lyophilized to obtain compound 5d-1 (200 mg), with a yield of 54%; LC-MS: $[M-H]^-$=816.3.

Step 2: Compound 5e-1

Add compound 5d-1 (200 mg, 0.24 mmol, 1.0 eq), M5 (127 mg, 0.24 mmol, 1.0 eq), PyBOP (187 mg, 0.36 mmol, 1.2 eq), HOBt (48 mg, 0.36 mmol, 1.2 eq) and DMF (6 mL) into a 25 mL single-necked flask, lower the temperature in an ice-water bath to 0-5° C., and add DIPEA (62 mg, 0.48 mmol, 2.0 eq). After the addition is completed, raise to 20±5° C. and react for 2 h, and use HPLC to monitor for the completion of the reaction. The reaction solution underwent preparative purification by HPLC, and the product preparation liquid was collected and lyophilized to obtain compound 5e-1 (162.8 mg); LC-MS: $[M+H]^+$=1235.4.

Step 3: Compound 5B

Sequentially add compound 5e-1 (110 mg, 0.089 mmol, 1.0 eq), ZnBr2 (400 mg, 1.78 mmol, 20.0 eq) and $CH_3NO_2$ (10 mL) into a 25 mL single-necked flask. After the addition, raise to 40° C. and react for 0.5 h, and then stop the reaction. The reaction solution was dried directly at 45° C. by spin-drying under reduced pressure to obtain a yellow solid. Samples were taken and the reaction was monitored by HPLC. The spin-dried solid was directly purified by HPLC preparation, and the product preparation liquid was collected and lyophilized to obtain compound 5B (73.4 mg) at 76.5% yield; LC-MS: $[M+H]^+$=1079.4.

Example 10
Preparation of Compound 6A:
compound 6A
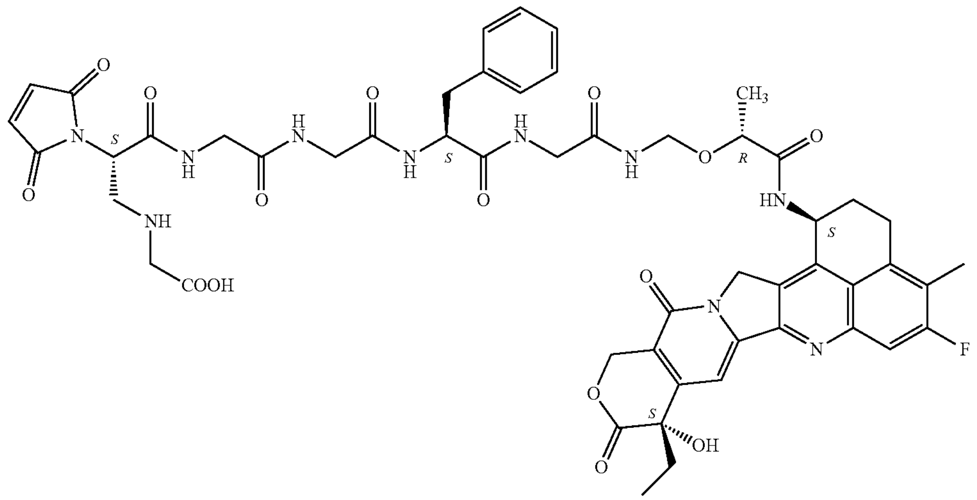
Referring to the synthetic route of Example 8, compound 6A (71 mg) was obtained; LC-MS: $[M+H]^+$=1079.4.
Example 11
Preparation of Compound 6B:
compound 6B
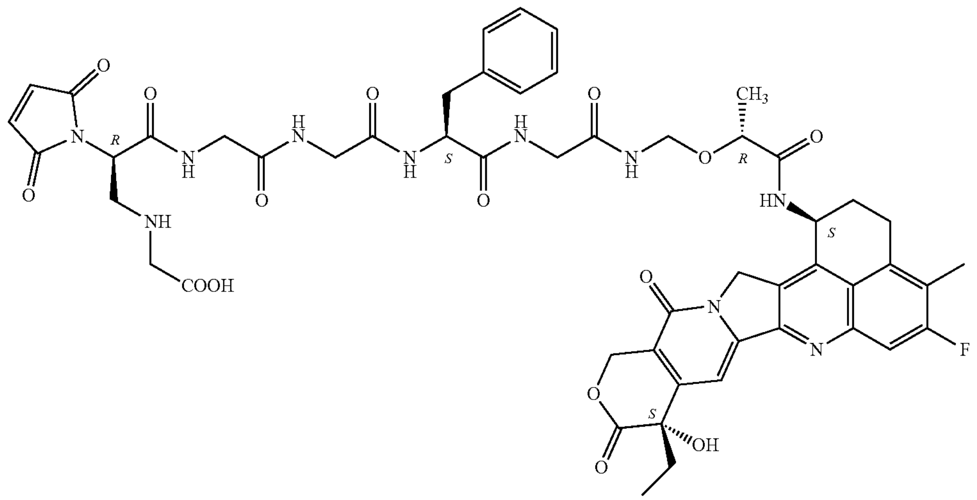
Referring to the synthetic route of Example 9, compound 6B (59 mg) was obtained; LC-MS: $[M+H]^+$=1079.4.

Example 12
Preparation of Compounds 7A and 7B:
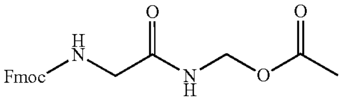
M1
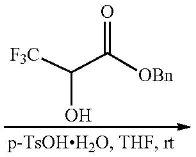
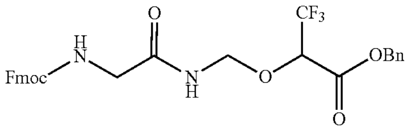
7a
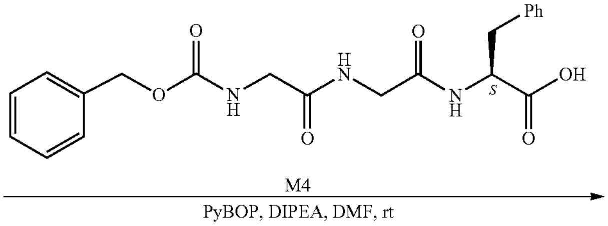
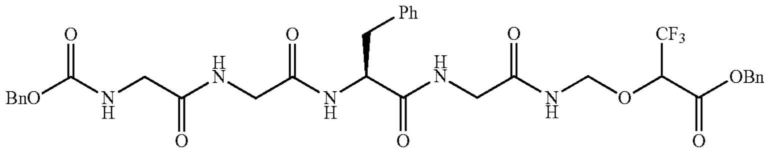
7b
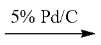
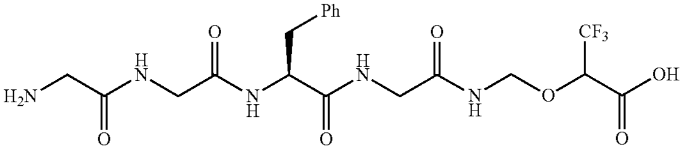
7c
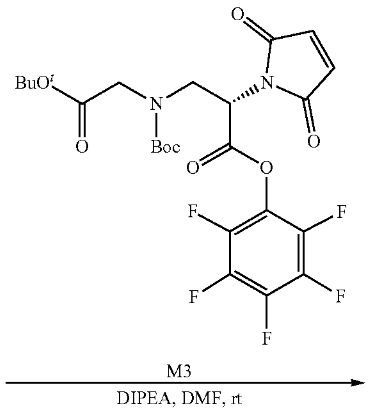
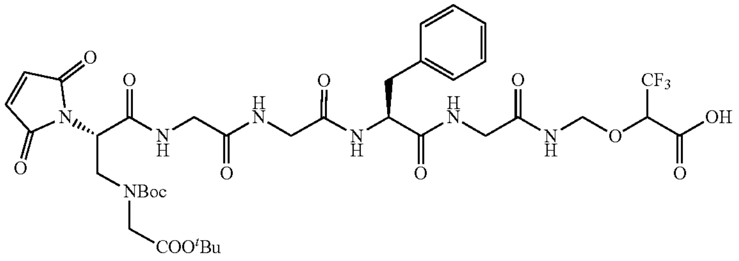
7d
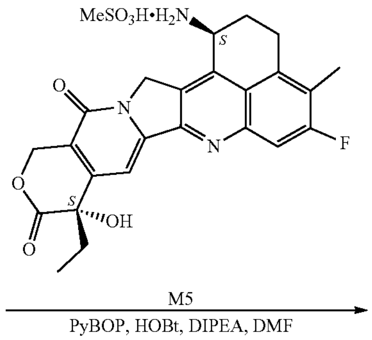

-continued

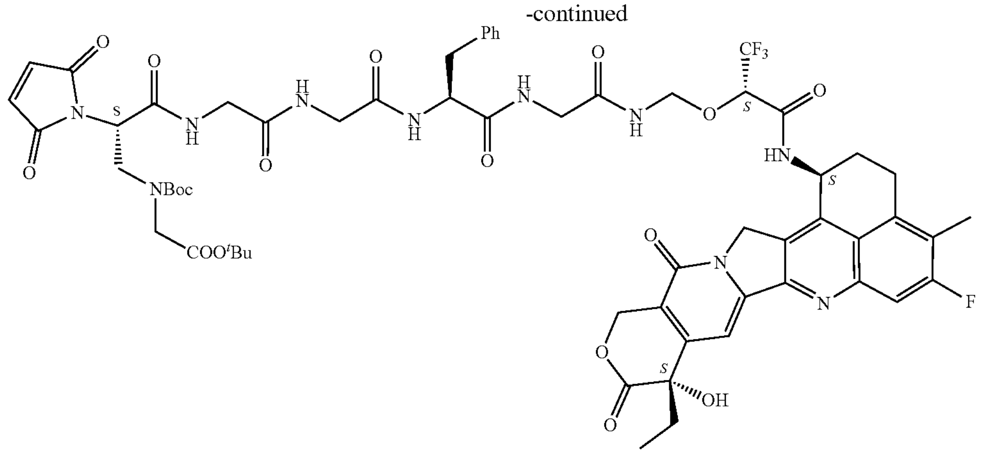

7e-1

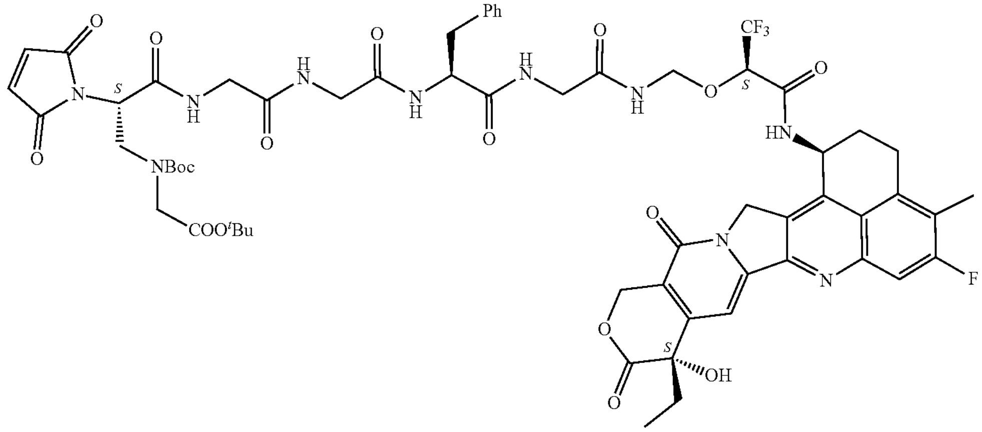

7e-2

Step 1: Compound 7a

In a 250 mL single-necked flask, add M1 (10 g, 27.1 mmol), benzyl 3,3,3-trifluorolactate (prepared according to the method published in patent WO2020063673A1) (12.7 g, 54.3 mmol), zinc acetate (9.96 g, 54.3 mmol) and 100 mL of toluene, heat to 100° C. and react for 4 h. When the reaction is completed, reduce to room temperature, filter to remove insoluble material, and concentrate the filtrate to obtain a crude product. The crude product was purified by silica gel column chromatography (PE:EA=10:1-5:1-2:1) to obtain 5.15 g of the target material, yield 35.1%; LC-MS: $[M+H]^+$=543.17.

Step 2: Compound 7b

Add 7a (5 g, 9.2 mmol) and 15 mL of DMF in a 50 mL single-necked flask, dissolve until clear, and then add DBU (1.68 g, 11 mmol) in an ice-water bath and react for 1 h, and record the reaction solution as reaction solution ①.

Take another 50 mL single-necked flask, add M4 (3.8 g, 9.2 mmol), PyBOP (5.75 g, 11 mmol), HOBt (1.49 g, 11 mmol) and 10 mL DMF. When dissolved, add DIPEA (1.82 mL, 11 mmol) in an ice-water bath, and continue the reaction for 30 min, then add reaction solution ①, and raise to room temperature and react for 2 h. The reaction progress was monitored by HPLC. After the completion of the reaction, the reaction solution was purified by high performance liquid chromatography to obtain a preparation liquid. The preparation liquid was extracted with dichloromethane, washed with saturated sodium chloride solution, dried with anhydrous sodium sulfate, filtered, and concentrated to obtain 4.1 g of solid, with a yield of 62.3%; LC-MS: $[M+H]^+$=716.25.

Step 3: Compound 7d

Add 7b (900 mg, 1.26 mmol) in a 25 mL single-necked flask, and after dissolution with 15 mL of DMF, add 900 mg of 5% Pd/C, and perform a hydrogenation reaction for 2 h. After the completion of the reaction, perform filtration, place the filtrate in an ice-water bath, add DIPEA (228 uL, 1.38 mmol), and then add M3 (712 mg, 1.26 mmol), and then raise to room temperature and react for 1 h. When the reaction was completed as detected by HPLC, the reaction solution was purified by high performance liquid chromatography to obtain a preparation liquid, which was lyophilized to obtain 525 mg of a product at 47.9% yield; LC-MS: $[M-H]^-$=870.33.

Step 4: Compound 7e

Add 7d (500 mg, 0.57 mmol), M5 (305 mg, 0.57 mmol), PyBOP (448 mg, 0.86 mmol), HOBt (116 mg, 0.86 mmol) and 15 mL of DMF to a 50 mL single-necked flask, add DIPEA (378 uL, 2.29 mmol) in an ice-water bath, raise to room temperature and react for 2 h. After the completion of the reaction as detected by HPLC, the reaction solution was purified by high performance liquid chromatography to obtain the preparation liquids of compound 7e-1 and compound 7e-2, and the preparation liquids were lyophilized to obtain 150 mg of compound 7e-1, LC-MS: $[M+H]^+$=1289.46, and 220 mg of compound 7e-2, LC-MS: $[M+H]^+$=1289.46, respectively.

Step 5: Compound 7A

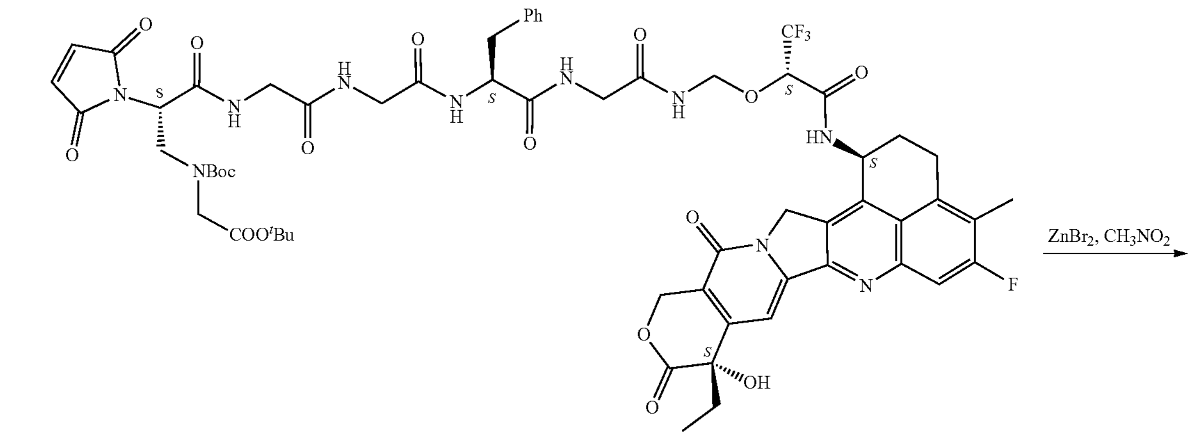

7e-1

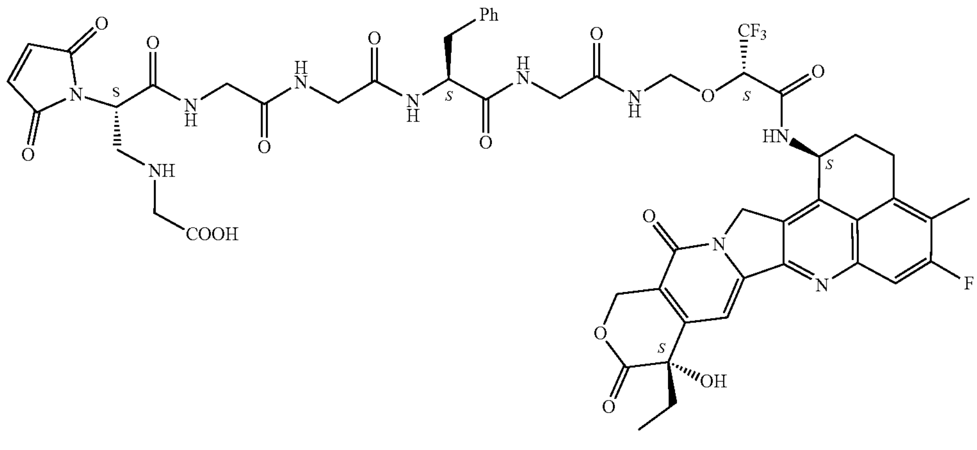

7A

Add 7e-1 (100 mg, 0.077 mmol), zinc bromide (349 mg, 1.55 mmol) and 5 mL of nitromethane to a 25 mL single-necked flask, and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 52 mg of solid; TOF result: 1133.3613.

Step 6: Compound 7B

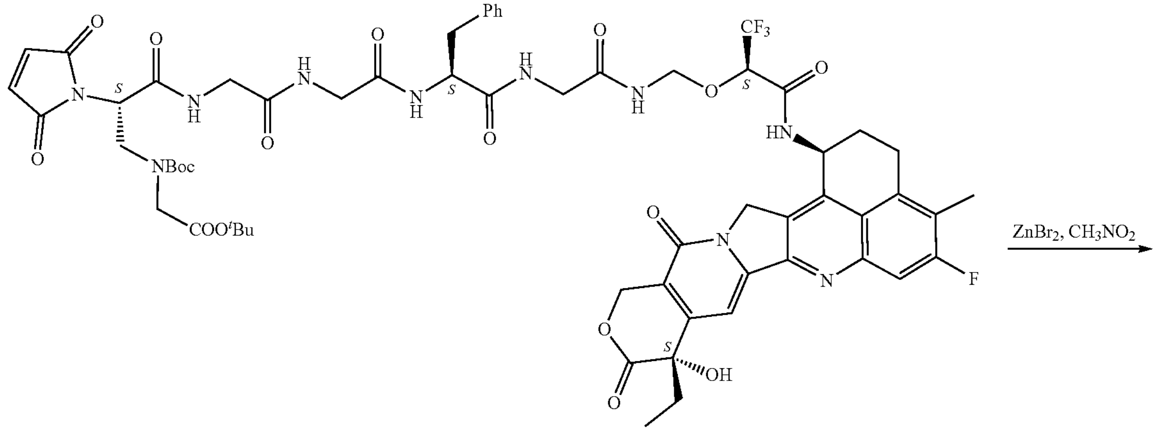

7e-2

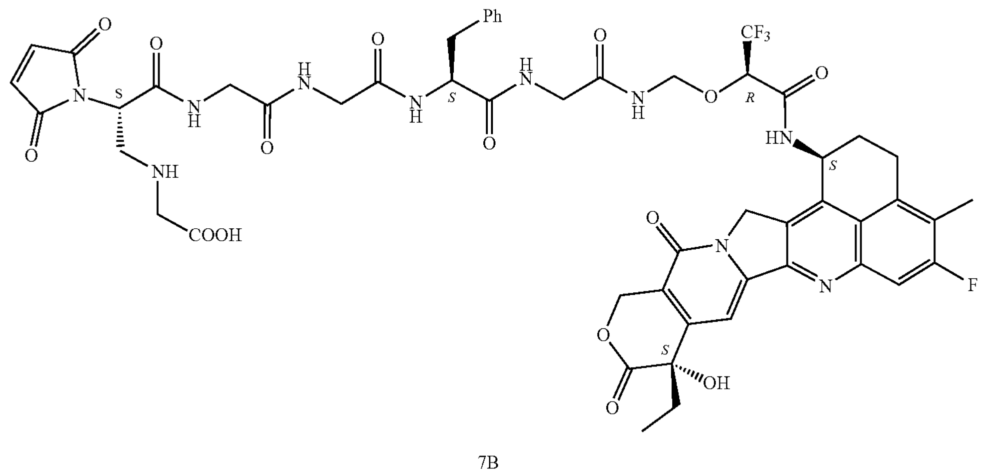

7B

Add 7e-2 (100 mg, 0.077 mmol), zinc bromide (349 mg, 1.55 mmol) and 5 mL of nitromethane to a 25 mL single-necked flask and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 63 mg of solid; TOF result: 1133.3668.

Example 13

Synthesis of Compounds 8A and 8B:

7c

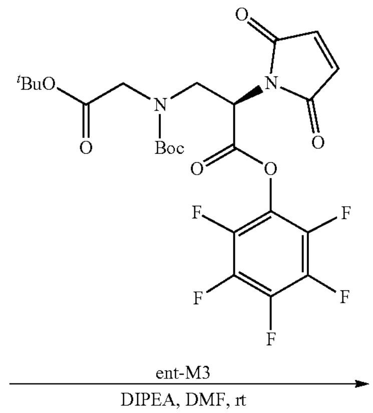

-continued

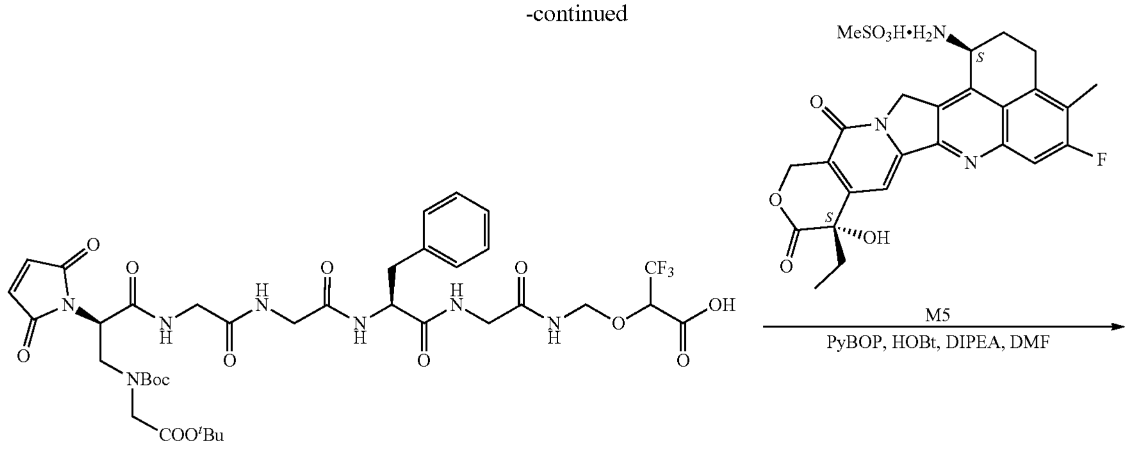

8d

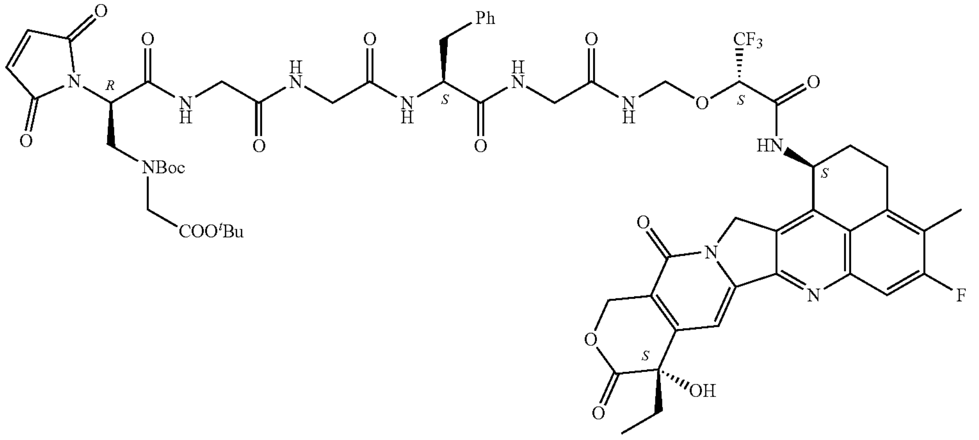

8e-1

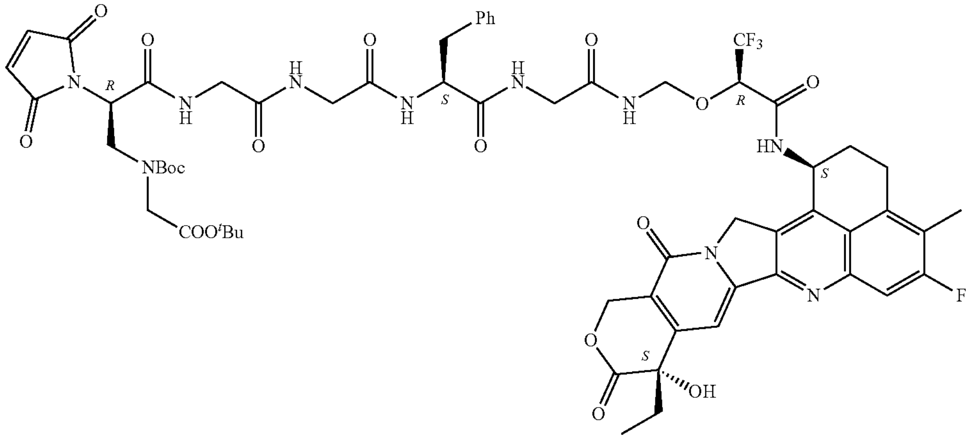

8e-2

Step 1: Compound 8d

In a 25 mL single-necked flask, 7c (900 mg, 1.83 mmol) was added, 20 mL of DMF was used to dissolve, then DIPEA (303 uL, 1.83 mmol) was added, and ent-M3 (1034 mg, 1.83 mmol) was added, and then the temperature was raised to room temperature to react for 1 h. After the completion of the reaction as detected by HPLC, the reaction solution was purified by high-performance liquid chromatography to obtain a preparation liquid, which was lyophilized to give 613 mg of a product at 38.5% yield; LC-MS: $[M-H]^-$=870.32.

Step 2: Compound 8e-1 and Compound 8e-2

Add 8d (500 mg, 0.57 mmol), M5 (305 mg, 0.57 mmol), PyBOP (448 mg, 0.86 mmol), HOBt (116 mg, 0.86 mmol) and 15 mL of DMF into a 50 mL single-necked flask, add DIPEA (378 uL, 2.29 mmol) in an ice-water bath, and raise to room temperature to react for 2 h. After the completion of the reaction as detected by HPLC, the reaction solution was purified by high performance liquid chromatography to obtain the preparation liquids of compound 8e-1 and compound 8e-2, and the preparation liquids were lyophilized to obtain 140 mg of compound 8e-1 and 210 mg of compound 8e-2, respectively. LC-MS of compound 8e-1: $[M+H]^+$=1289.47; LC-MS of compound 8e-2: $[M+H]^+$=1289.47.

Step 3: Compound 8A

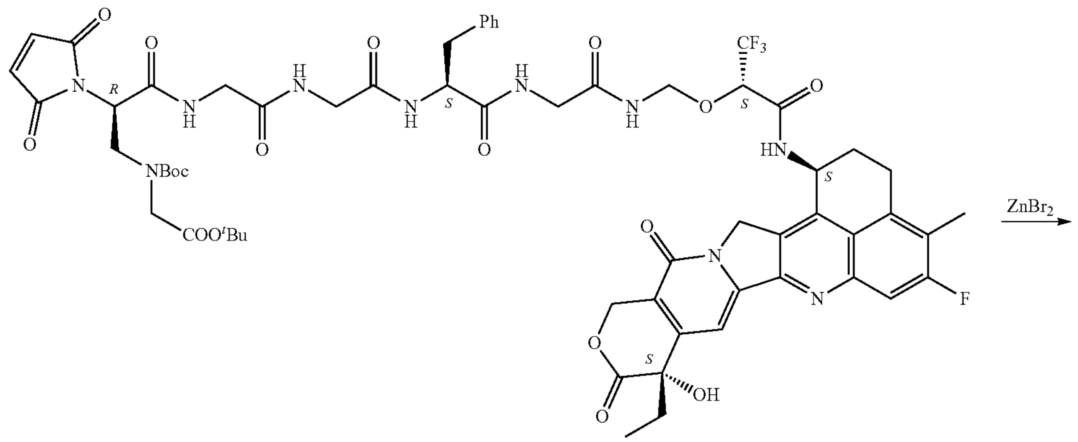

8e-1

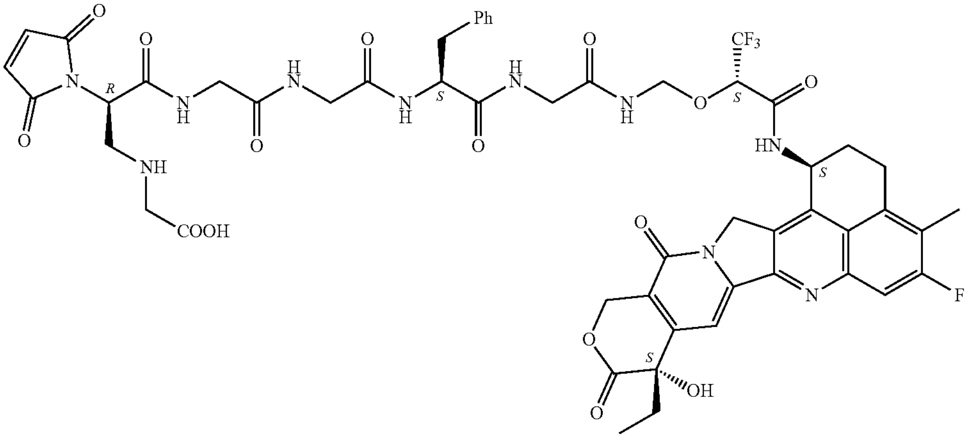

8A

Add Compound 8e-1 (100 mg, 0.077 mmol), zinc bromide (349 mg, 1.55 mmol) and 5 mL of nitromethane into a 25 mL single-necked flask, and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 50 mg of solid; TOF result: 1133.3623.

Step 4: Compound 8B

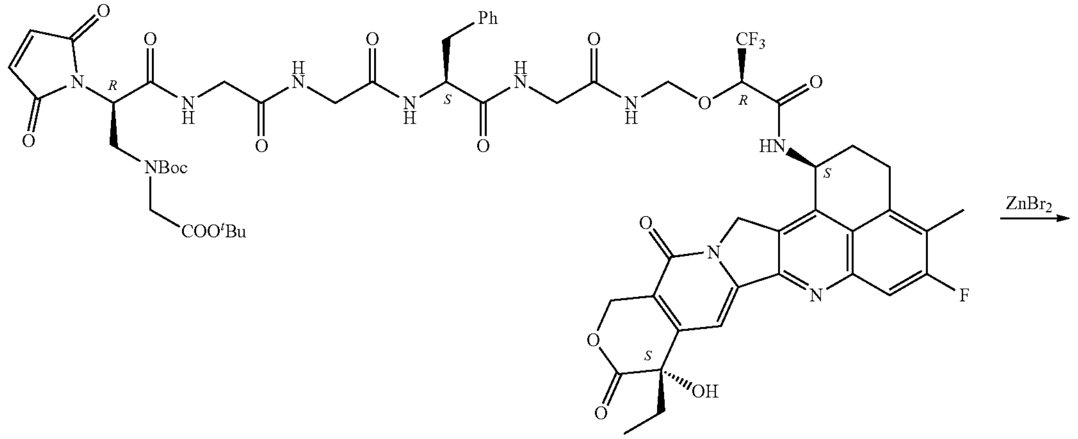

8e-2

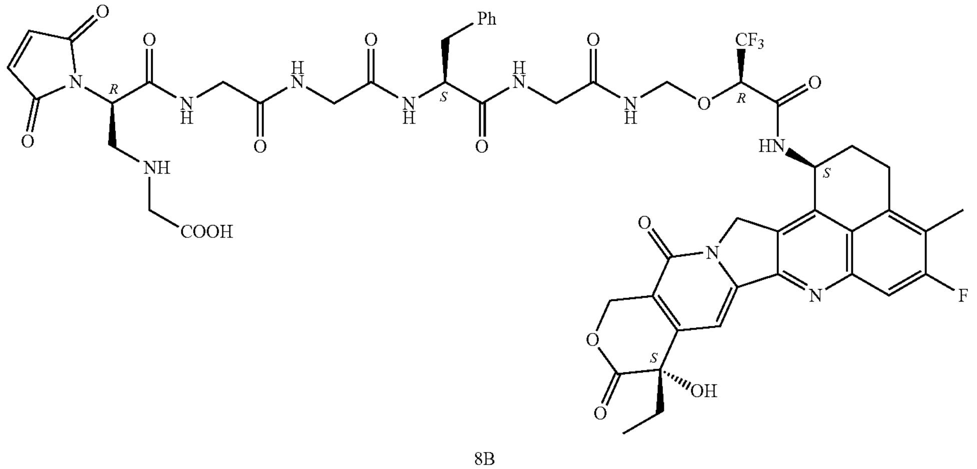

8B

Add Compound 8e-2 (100 mg, 0.077 mmol), zinc bromide (349 mg, 1.55 mmol) and 5 mL of nitromethane into a 25 mL single-necked flask and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 58 mg of a solid; TOF result: 1133.3653.

Example 14

Synthesis of Compound 9A:

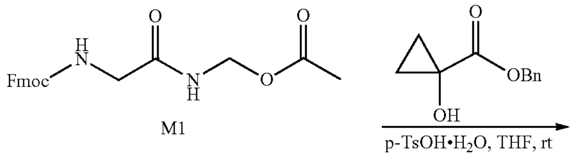

M1

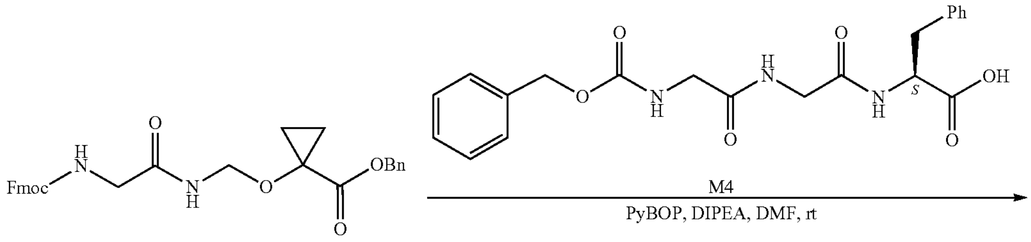

M4

9a

-continued
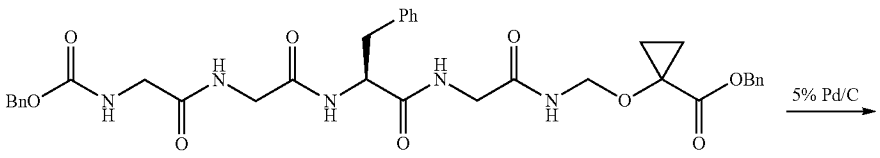
9b
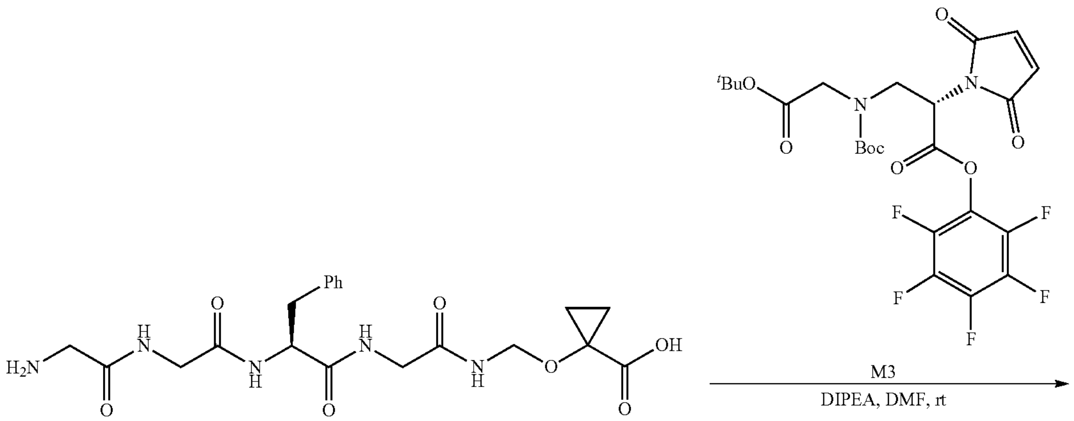
9c
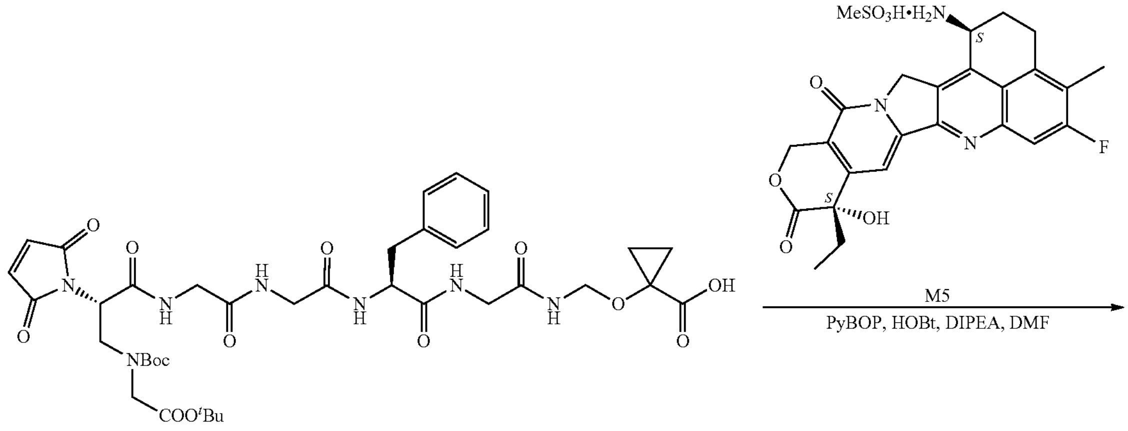
9d
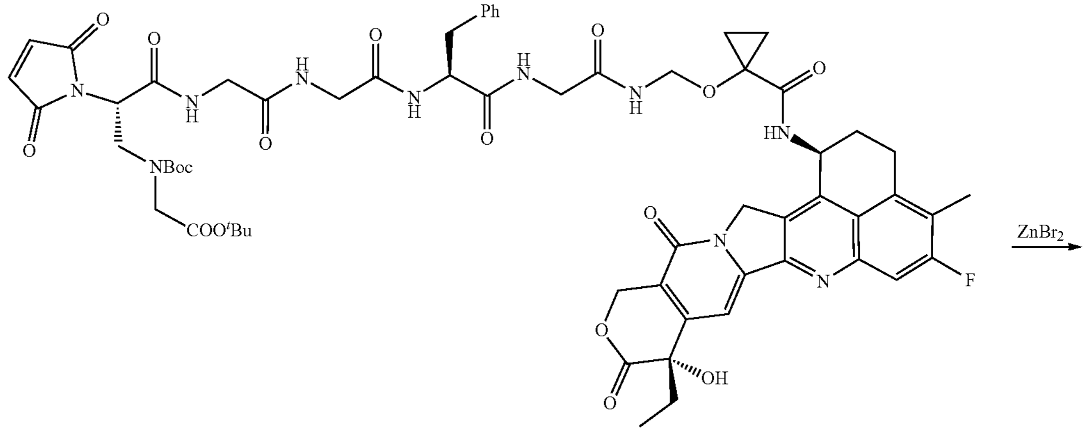
9e

-continued

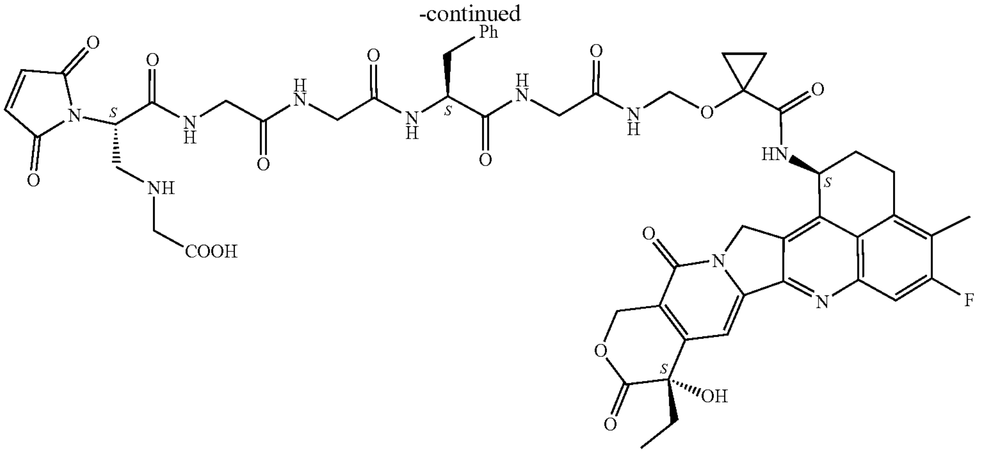

9A

Step 1: Compound 9a

In a 250 mL single-necked flask, add M1 (6 g, 16.3 mmol), 100 mL THF and p-toluenesulfonic acid monohydrate (0.31 g, 1.63 mmol), stir and cool to 0° C., add benzyl 2-hydroxy-2-cyclopropyl acetate dropwise (prepared according to the method published in patent US20050020645 A1) (6.3 g, 32.6 mmol), then naturally warm up to room temperature to react (the reaction lasts for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 9a (3.7 g) at 45% yield; LC-MS: $[M+H]^+$=501.5.

Step 2: Compound 9b

In a 25 mL single-necked flask, add 9a (2 g, 4.0 mmol) and 10 mL DMF, stir at 0° C., add DBU (760 mg, 5.0 mmol), and react for 1 h. After the completion of TLC-monitored Fmoc deprotection, the reaction solution was set aside, ready for use.

Add M4 (1.65 g, 4.0 mmol), PyBOP (2.59 g, 5.0 mmol), HOBt (675 mg, 5.0 mmol) and 10 mL of DMF into another 25 mL single-necked flask, add DIPEA (823 uL, 5.04 mmol) in an ice-water bath, continue stirring for 30 min, and then add the above reaction solution to the reaction flask and raise to room temperature to react. After completion of the reaction as detected by HPLC, the reaction solution was purified by preparative LC to obtain a product preparation liquid, which was extracted by dichloromethane, washed with saturated sodium chloride solution, dried with anhydrous sodium sulfate, and filtered, and the filtrate was concentrated under reduced pressure to obtain 1.5 g of a solid at 56% yield; LC-MS: $[M+H]^+$=674.7.

Step 3: Compound 9c 9b (900 mg, 1.3 mmol) was added into a 25 mL single-necked flask, and after dissolution with 10 mL of DMF, 900 mg of 5% Pd/C was added, and a hydrogenation reaction was carried out for 1.5 h. After the completion of the reaction, filtration was performed to obtain the filtrate, which was used directly for the next step of the reaction without purification.

Step 4: Compound 9d

Place the crude product 9c in an ice-water bath, add DIPEA (223 uL, 1.3 mmol) and then compound M3 (750 mg, 1.3 mmol), then raise to room temperature and react for 1 h. After the completion of the reaction as detected by HPLC, the reaction solution was purified by HPLC to give a preparation liquid, which was lyophilized to give 9d (529 mg); LC-MS: $[M-H]^-$=828.4.

Step 5: Compound 9e

Add 9d (500 mg, 0.6 mmol), M5 (300 mg, 0.6 mmol), PyBOP (416 mg, 0.8 mmol), HOBt (108 mg, 0.5 mmol) and 15 mL of DMF into a 50 mL single-necked flask, add DIPEA (351 uL, 2.13 mmol) in an ice-water bath, raise to room temperature and react for 3 h. After the completion of the reaction as detected by HPLC, the reaction solution was purified by high performance liquid chromatography to obtain the preparative liquid of compound 9e, which was lyophilized to obtain 9e (257 mg); LC-MS: $[M+H]^+$=1247.5.

Step 6: Compound 9A

Add 9e (100 mg, 0.08 mmol), zinc bromide (360 mg, 1.6 mmol) and 5 mL of nitromethane to a 25 mL single-necked flask and carry out a reaction at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 9A (55 mg); LC-MS: $[M+H]^+$=1091.3.

Example 15
Synthesis of Compound 9B:
9B
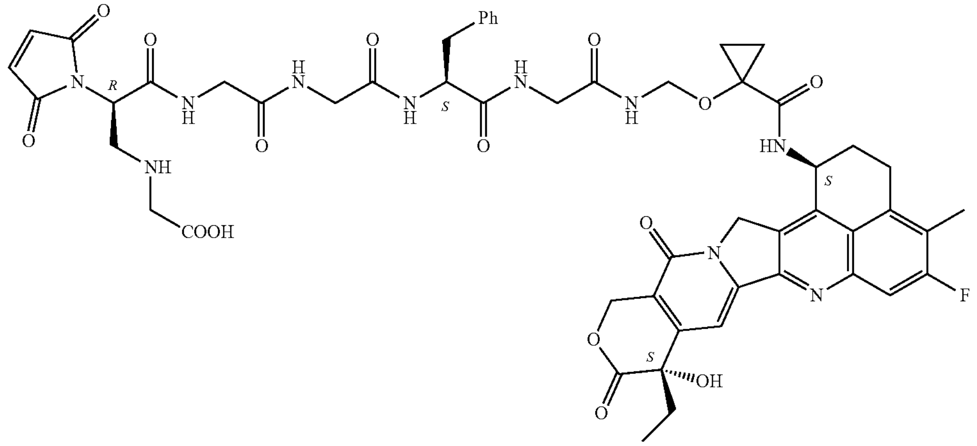
Referring to the synthetic route of Example 14, compound 9B (44 mg) was obtained; LC-MS: $[M+H]^+$=1091.3.
Example 16
Synthesis of Compound 10A:
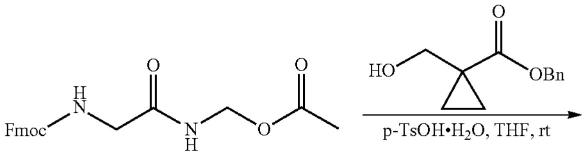
M1
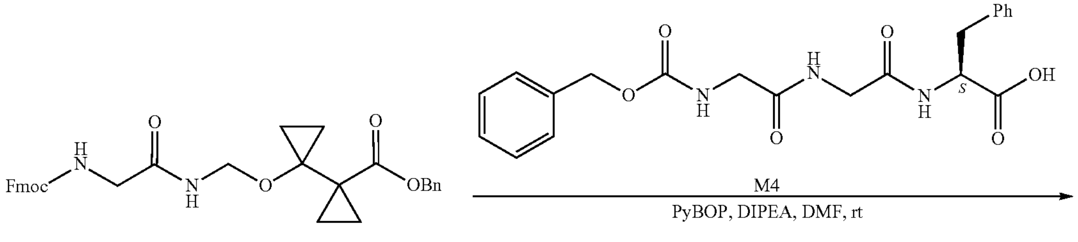
10a
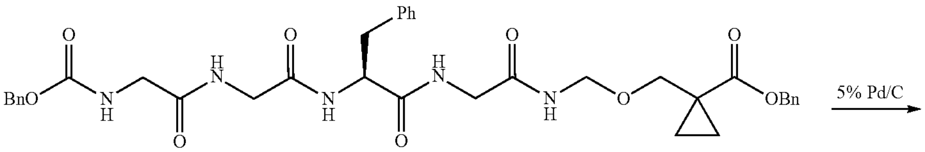
10b -continued
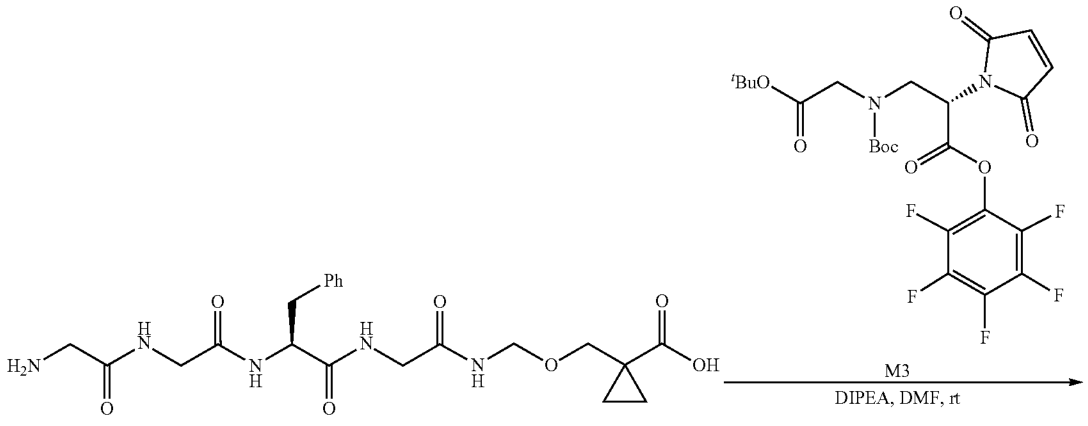
10c
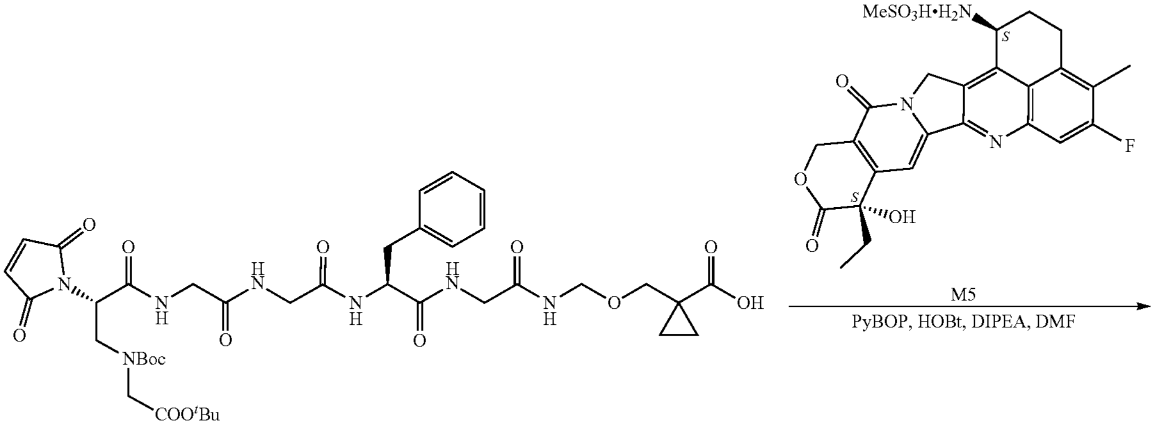
10d
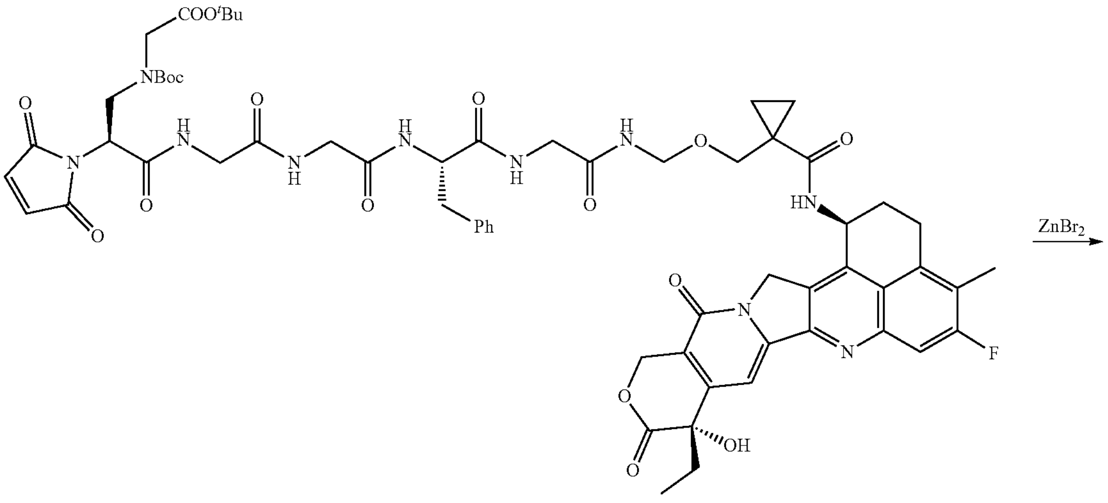
10e -continued

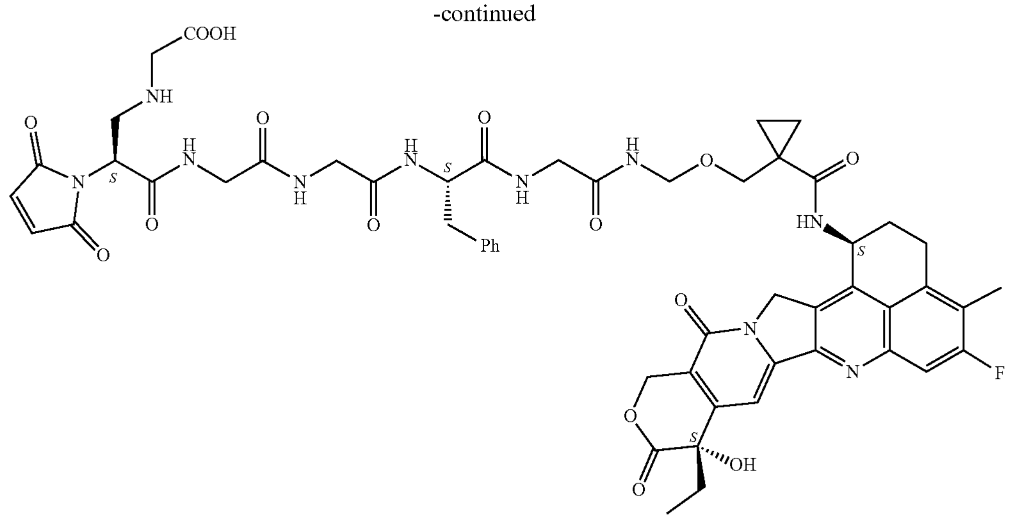

10A

Step 1: Compound 10a

In a 250 mL single-necked flask, add M1 (6 g, 16.3 mmol), 100 mL THF and p-toluenesulfonic acid monohydrate (0.31 g, 1.63 mmol), stir and cool to 0° C., add benzyl 3-hydroxy-2-cyclopropylpropionate dropwise (prepared with reference to the method published in patent WO2013187496A1) (6.7 g, 32.6 mmol), then naturally warm up to room temperature to react (react for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 10a (4.9 g) at 58% yield; LC-MS: $[M+H]^+$=515.4.

Step 2: Compound 10b

In a 25 mL single-necked flask, add 10a (4 g, 7.8 mmol) and 10 mL DMF, stir at 0° C., add DBU (1.2 g, 8.0 mmol), and react for 1 h. After the completion of TLC-monitored Fmoc deprotection, set aside the reaction solution, ready for use.

Add M4 (3.3 g, 8.0 mmol), PyBOP (5.2 g, 10.0 mmol), HOBt (1.35 g, 10.0 mmol) and 10 mL of DMF into another 25 mL single-necked flask, and add DIPEA (1.65 mL, 10.1 mmol) in an ice-water bath, continue stirring for 50 min, and then add the above reaction solution to the reaction flask, raise to room temperature and react. After the completion of the reaction as detected by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain 2.3 g of a solid at 42% yield; LC-MS: $[M+H]^+$=688.8.

Step 3: Compound 10c

Add 10b (1.0 g, 1.45 mmol) into a 25 mL single-necked flask, dissolve in 15 mL of DMF until clear, then add 1.0 g of 5% Pd/C, and perform a hydrogenation reaction for 1.5 h. After the completion of the reaction, filtration was performed to obtain a filtrate, which was used directly for the next step of the reaction without purification.

Step 4: Compound 10d

The crude product 10c was placed in an ice-water bath, DIPEA (258 uL, 1.5 mmol) was added, and compound M3 (837 mg, 1.45 mmol) was then added, and then the temperature was raised to room temperature to react for 1 h. Upon completion of the reaction as detected by HPLC, the reaction solution was purified by HPLC to obtain a preparation liquid, which was lyophilized to obtain 10d (499 mg); LC-MS: $[M-H]^-$=842.4.

Step 5: Compound 10e 10d (400 mg, 0.48 mmol), M5 (240 mg, 0.48 mmol), PyBOP (250 mg, 0.48 mmol), HOBt (104 mg, 0.48 mmol) and 15 mL of DMF were added into a 50 mL single-necked flask, DIPEA (330 uL, 2.0 mmol) was added in an ice-water bath, and the temperature was raised to room temperature to react for 3 h. After the completion of the reaction as detected by HPLC, the reaction solution was purified by HPLC to give the preparation liquid of compound 10e, which was lyophilized to obtain 10e (188 mg); LC-MS: $[M+H]^+$=1261.5.

Step 6: Compound 10A 10e (100 mg, 0.08 mmol), zinc bromide (360 mg, 1.6 mmol) and 5 mL of nitromethane were added to a 25 mL single-necked flask and a reaction was carried out at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 10A (61 mg); LC-MS: $[M+H]^+$=1105.4.

Example 17
Synthesis of Compound 10B:
compound 10B
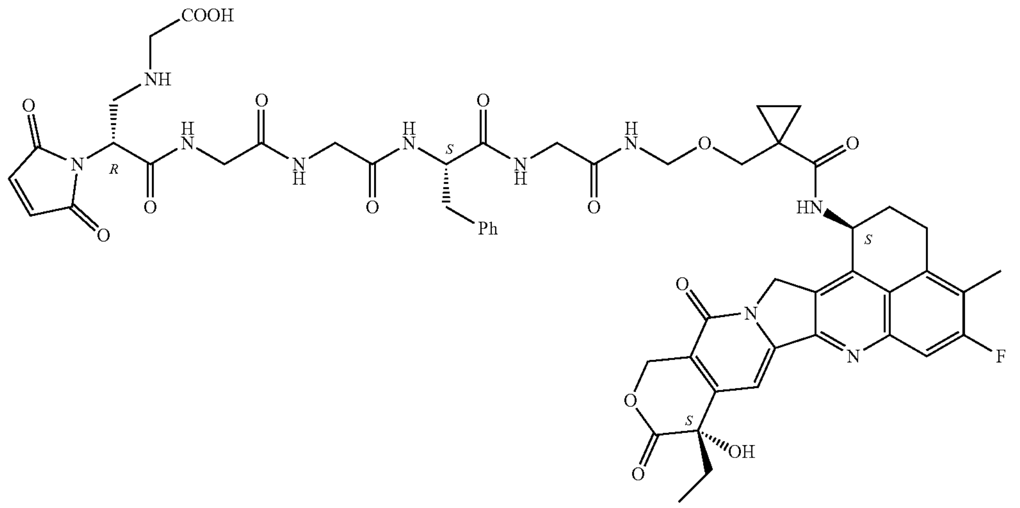
Referring to the synthetic route of Example 16, compound 10B (75 mg) was obtained; LC-MS: $[M+H]^+=1105.4$.
Example 18
Synthesis of Compound 11A:
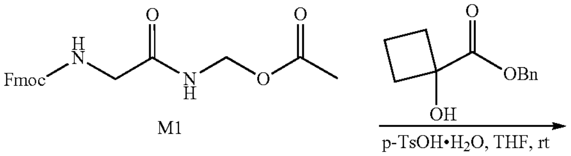
M1
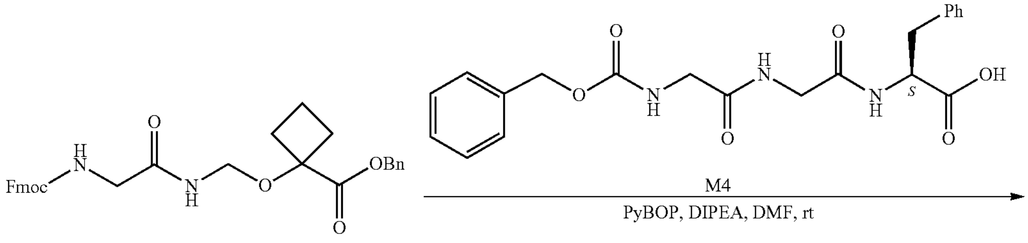
11a
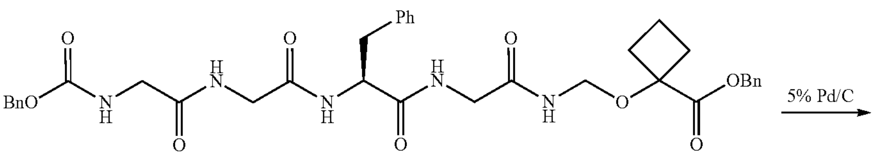
11b -continued
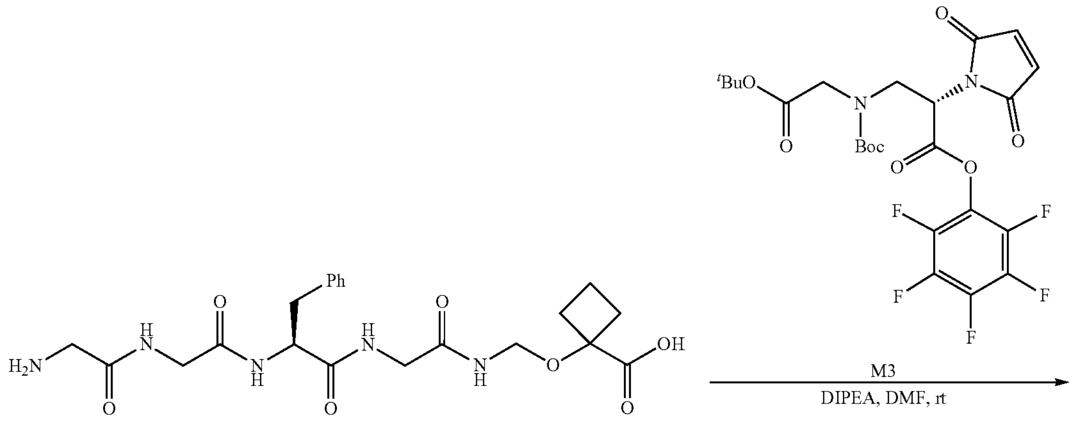
11c
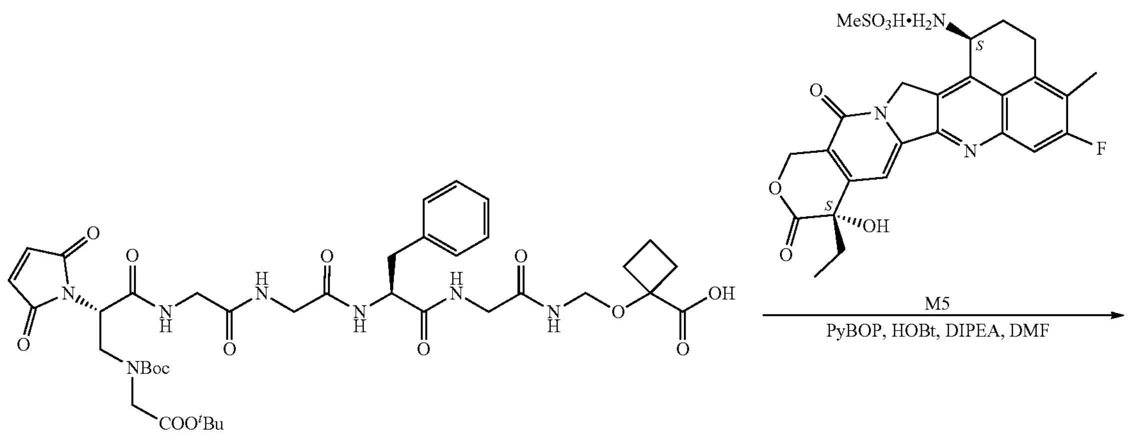
11d
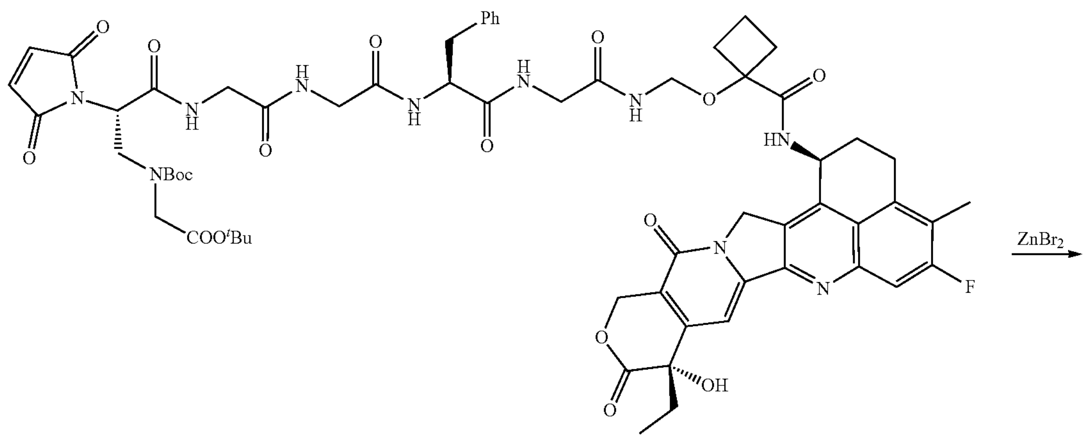
11e -continued

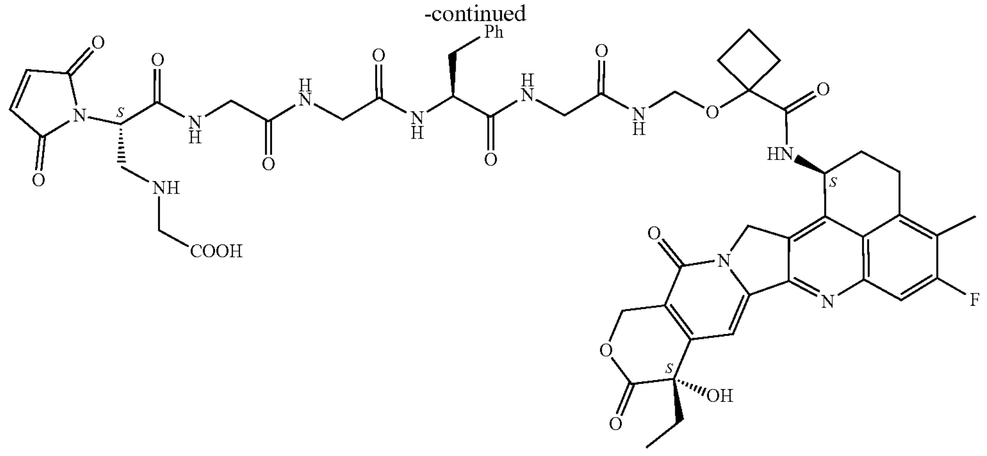

11A

Step 1: Compound 11a

In a 250 mL single-necked flask, add M1 (6 g, 16.3 mmol), 100 mL TIFF and p-toluenesulfonic acid monohydrate (0.31 g, 1.63 mmol), stir and cool to 0° C., add benzyl 2-hydroxy-2-cyclobutylacetate dropwise (synthesized by the method published in the literature *Journal of Medicinal Chemistry,* 2013, 56(13), 5541-5552) (6.7 g, 32.6 mmol), then naturally warm up to room temperature and react (react for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 11a (5.1 g) at 62% yield; LC-MS: $[M+H]^+$=515.7.

Step 2: Compound 11b

In a 25 mL single-necked flask, add 11a (4 g, 7.8 mmol) and 10 mL DMF, stir at 0° C., add DBU (1.2 g, 8.0 mmol), and react for 1 h. After the completion of TLC-monitored Fmoc deprotection, set aside the reaction solution, ready for use.

Add M4 (3.3 g, 8.0 mmol), PyBOP (5.2 g, 10.0 mmol), HOBt (1.35 g, 10.0 mmol) and 10 mL of DMF into another 25 mL single-necked flask, and add DIPEA (1.63 mL, 10.0 mmol) in an ice-water bath, continue stirring for 40 min, and then add the above reaction solution to the reaction flask, and raise to room temperature to react. After the completion of the reaction as detected by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain 2.3 g of a solid at 42% yield; LC-MS: $[M+H]^+$=688.3.

Step 3: Compound 11c

Add 11b (2.0 g, 2.9 mmol) into a 25 mL single-necked flask, and after dissolution with 25 mL of DMF, add 2.0 g of 5% Pd/C, and carry out a hydrogenation reaction for 3 h. After the completion of the reaction, it was filtered to obtain a filtrate, which was used directly for the next step of the reaction without purification.

Step 4: Compound 11d

The crude product 11c was placed in an ice-water bath, DIPEA (516 uL, 3.0 mmol) was added, and then compound M3 (1.7 g, 2.9 mmol) was added, and then the temperature was raised to room temperature to react for 2 h. After the completion of the reaction as detected by HPLC, the reaction solution was purified by HPLC to obtain a preparation liquid, which was lyophilized to give 11d (934 mg); LC-MS: $[M-H]^-$=842.4.

Step 5: Compound 11e

Add 11d (800 mg, 0.96 mmol), M5 (480 mg, 0.96 mmol), PyBOP (500 mg, 0.96 mmol), HOBt (208 mg, 0.96 mmol) and 30 mL of DMF into a 50 mL single-necked flask, add DIPEA (660 uL, 4.0 mmol) in an ice-water bath, raise to room temperature and react for 4 h. After the completion of the reaction as detected by HPLC, the reaction solution was purified by HPLC to give the preparation liquid of compound 11e, which was lyophilized to obtain 11e (401 mg); LC-MS: $[M+H]^+$=1261.4.

Step 6: Compound 11A 11e (150 mg, 0.12 mmol), zinc bromide (532 mg, 2.4 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 11A (86 mg); LC-MS: $[M+H]^+$=1105.4.

Example 19
Synthesis of Compound 11B
11B
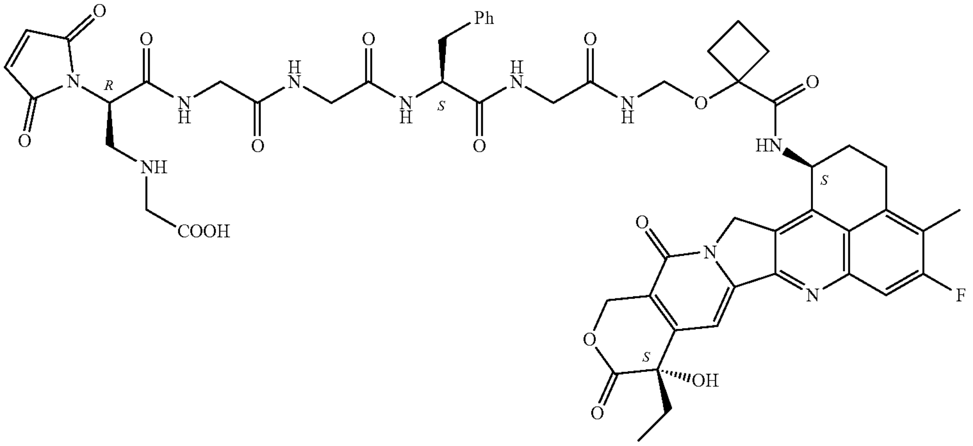
Referring to the synthetic route of Example 18, compound 11B (50 mg) was obtained. LC-MS: $[M+H]^+$=1105.4.
Example 20
Synthesis of Compound 12A:
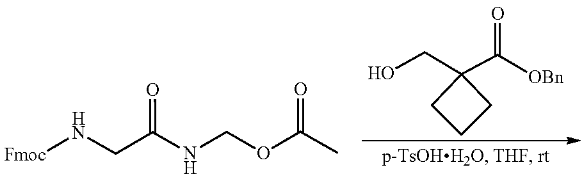
M1
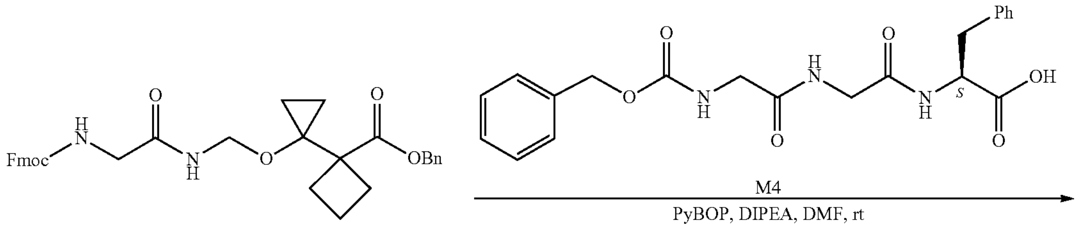
12a
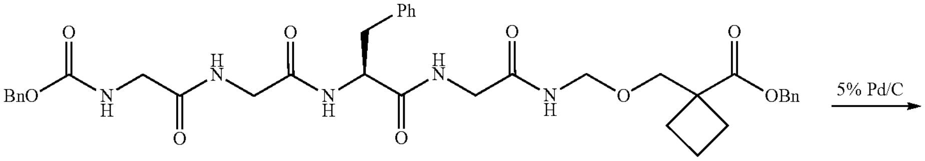
12b -continued
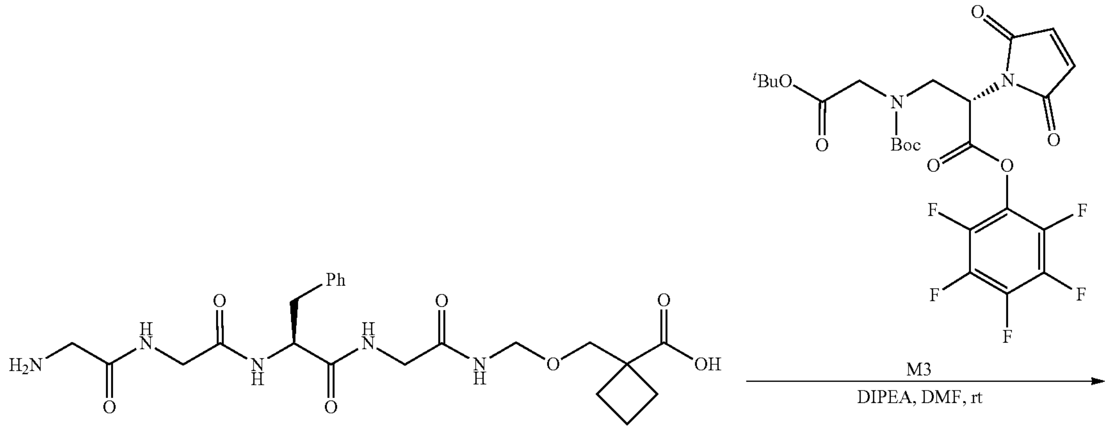
12c
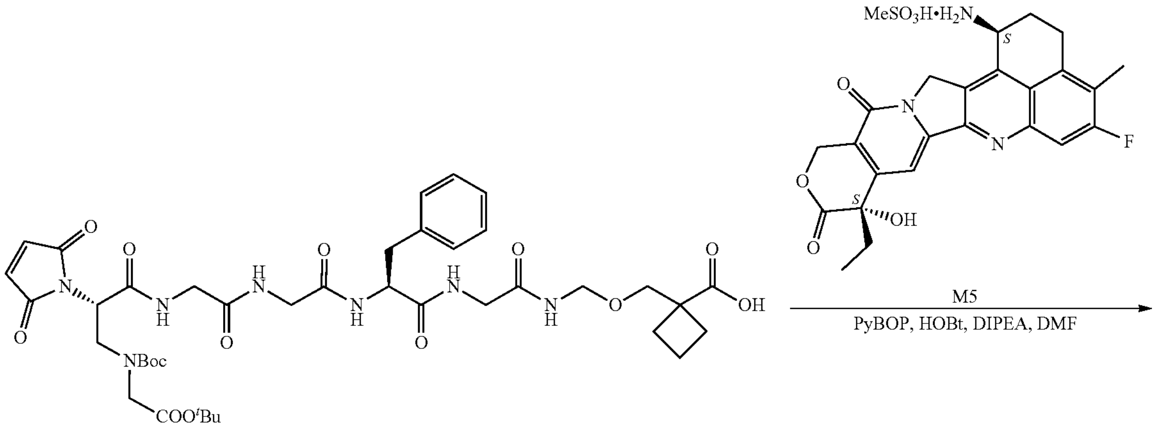
12d
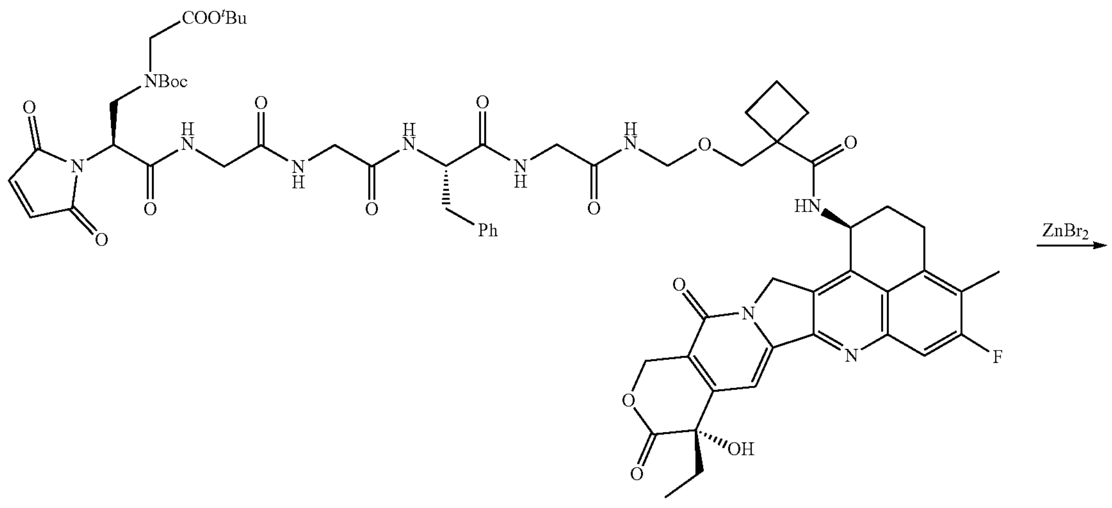
12e -continued

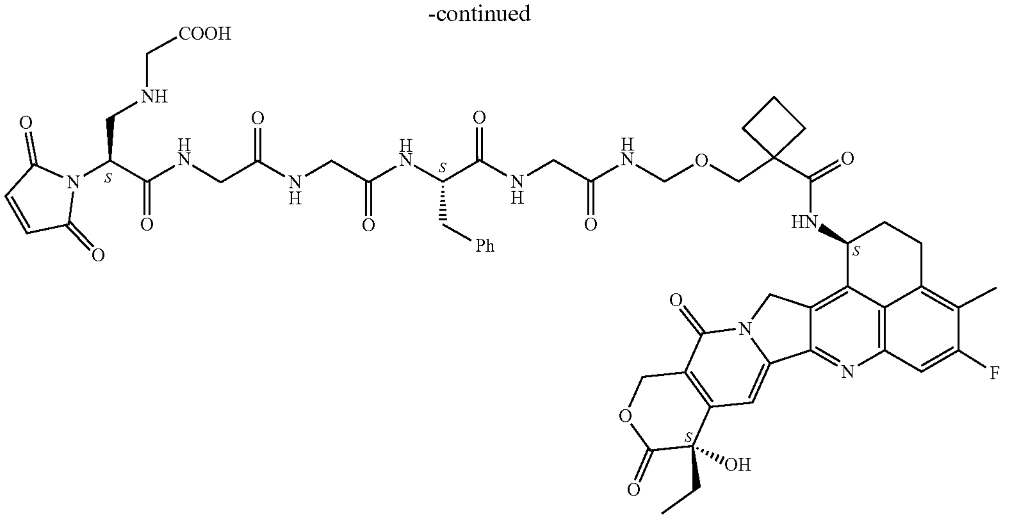

12A

Step 1: Compound 12a

In a 250 mL single-necked flask, add M1 (6 g, 16.3 mmol), 100 mL THF and p-toluenesulfonic acid monohydrate (0.31 g, 1.63 mmol), stir and cool to 0° C., add benzyl 3-hydroxy-2-cyclobutylpropionate dropwise (prepared according to the method published in patent WO2009011285A1) (7.2 g, 32.6 mmol). Then warm up to room temperature naturally to react (react for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 12a (4.5 g) at 52% yield; LC-MS: $[M+H]^+$=529.4.

Step 2: Compound 12b

In a 25 mL single-necked flask, add 12a (4 g, 7.6 mmol) and 10 mL DMF, stir at 0° C., add DBU (1.2 g, 8.0 mmol), and react for 1 h. After the completion of TLC-monitored Fmoc deprotection, set aside the reaction solution, ready for use.

Add M4 (3.2 g, 7.6 mmol), PyBOP (4.7 g, 9.0 mmol), HOBt (1.22 g, 9.0 mmol) and 10 mL of DMF in another 25 mL single-necked flask, add DIPEA (1.49 mL, 0.9 mmol) in an ice-water bath, and continue stirring for 30 min, then add the above reaction solution to the reaction flask and raise the temperature to room temperature to react. After the completion of the reaction as detected by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain 2.0 g of a solid at 37% yield; LC-MS: $[M+H]^+$=702.8.

Step 3: Compound 12c

Add 12b (1.0 g, 1.43 mmol) into a 25 mL single-necked flask, and dissolve in 15 mL of DMF until clear, add 1.0 g of 5% Pd/C, and carry out a hydrogenation reaction for 1.5 h. After the completion of the reaction, it was filtered to obtain a filtrate, which was used directly for the next step of the reaction without purification.

Step 4: Compound 12d

Place the crude product 12c in an ice-water bath, add DIPEA (258 uL, 1.5 mmol) and then compound M3 (825 mg, 1.43 mmol), the raise to room temperature and react for 1 h. After the completion of the reaction as detected by HPLC, the reaction solution was purified by HPLC to obtain a preparation liquid, which was lyophilized to obtain 12d (522 mg); LC-MS: $[M-H]^-$=856.4.

Step 5: Compound 12e

Add 12d (400 mg, 0.47 mmol), M5 (240 mg, 0.47 mmol), PyBOP (250 mg, 0.47 mmol), HOBt (101 mg, 0.47 mmol) and 15 mL of DMF into a 50 mL single-necked flask, add DIPEA (330 uL, 2.0 mmol) in an ice-water bath, raise to room temperature and react for 3 h. After the completion of the reaction as detected by HPLC, the reaction solution was purified by HPLC to give a preparation liquid of compound 12e, which was lyophilized to obtain 12e (198 mg); LC-MS: $[M+H]^+$=1275.4.

Step 6: Compound 12A

Add 12e (100 mg, 0.08 mmol), zinc bromide (360 mg, 1.6 mmol) and 5 mL of nitromethane to a 25 mL single-necked flask and carry out a reaction at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 12A (55 mg); LC-MS: $[M+H]^+$=1119.4.

Example 21
Synthesis of Compound 12B:
12B
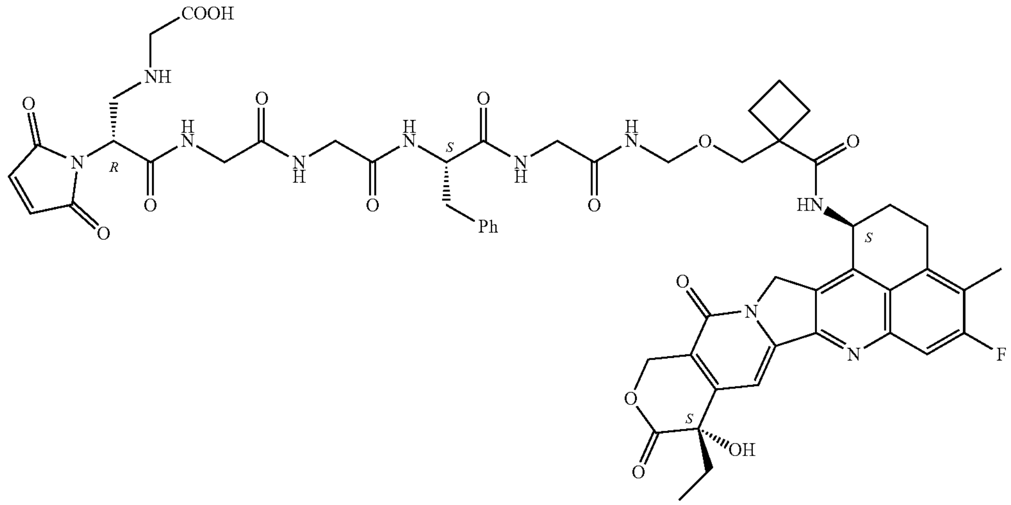
Referring to the synthetic route of Example 20, compound 12B (50 mg) was obtained; LC-MS: $[M+H]^+=1119.4$.
Example 22
Synthesis of Compound 13A:
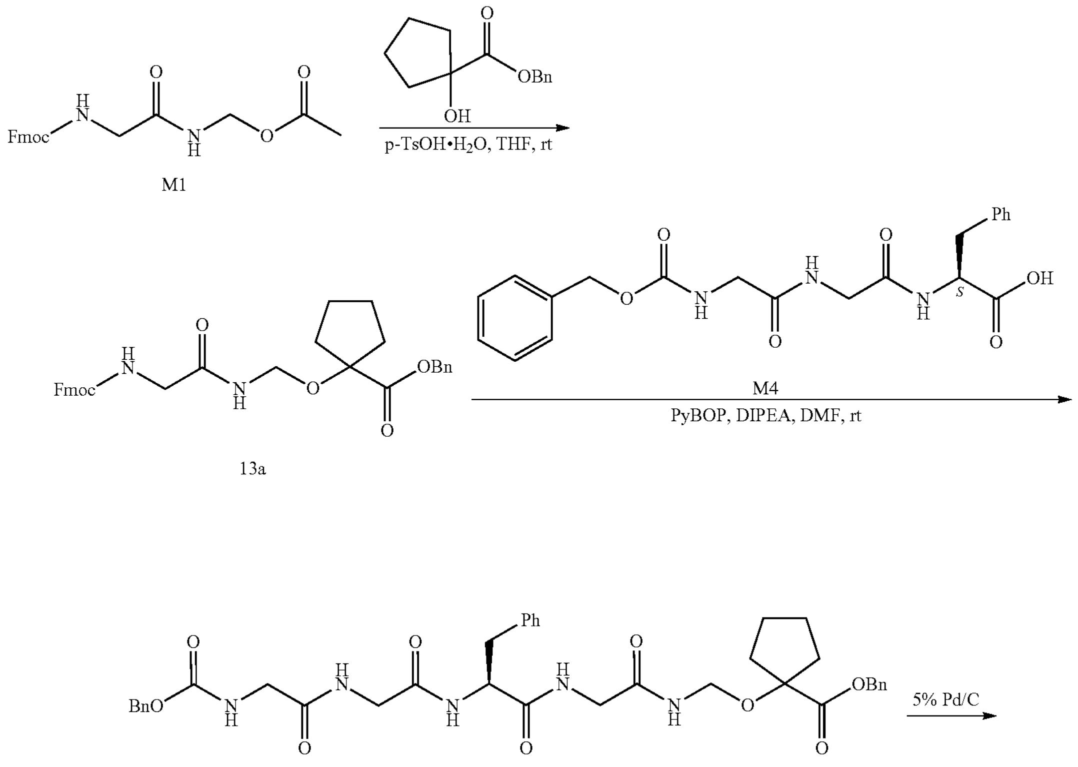
13b -continued
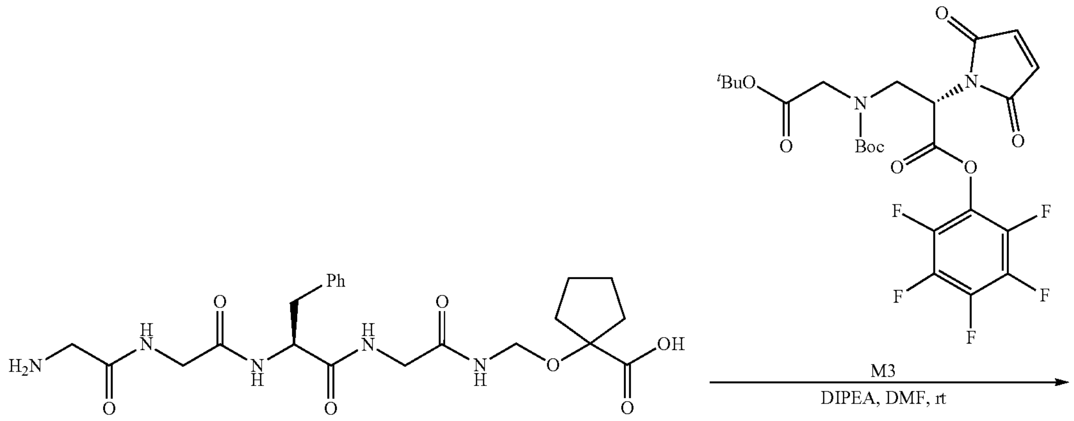
13c
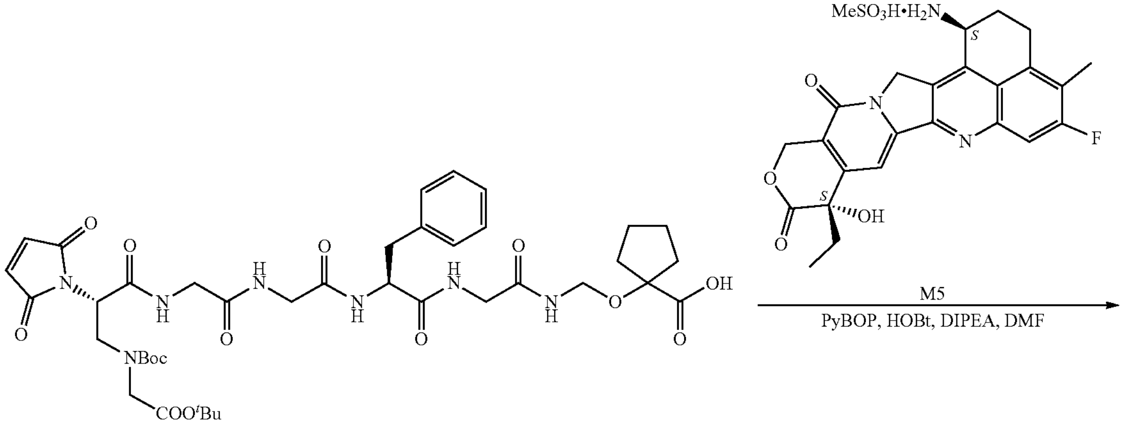
13d
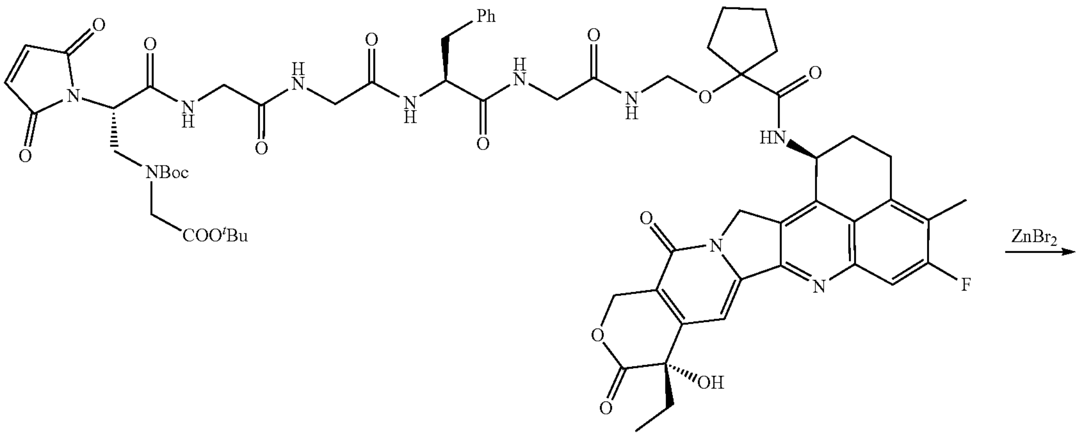
13e -continued

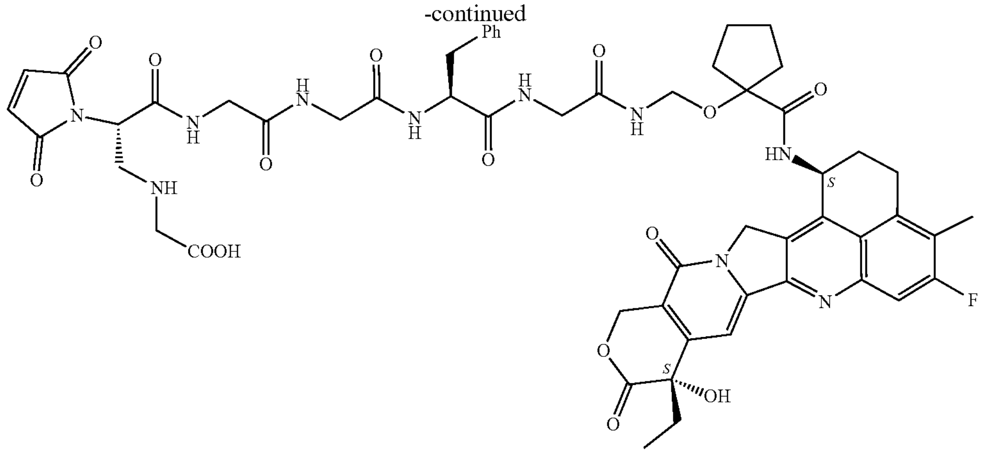

13A

Step 1: Compound 13a

In a 250 mL single-necked flask, add M1 (6 g, 16.3 mmol), 100 mL THF and p-toluenesulfonic acid monohydrate (0.31 g, 1.63 mmol), stir and cool to 0° C., add benzyl 2-hydroxy-2-cyclopentylacetate dropwise (synthesized by the method published in the literature, *Journal of Medicinal Chemistry,* 2013, 56(13), 5541-5552) (7.2 g, 32.6 mmol), then naturally warm up to room temperature to react (react for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 13a (4.6 g) at 53% yield; LC-MS: $[M+H]^+$=529.5.

Step 2: Compound 13b

In a 25 mL single-necked flask, add 13a (4 g, 7.6 mmol) and 10 mL DMF, stir at 0° C., add DBU (1.17 g, 7.8 mmol), and react for 1 h. After the completion of TLC-monitored Fmoc deprotection, set aside the reaction solution, ready for use.

Add M4 (3.14 g, 7.6 mmol), PyBOP (4.42 g, 8.5 mmol), HOBt (1.15 g, 8.5 mmol) and 10 mL of DMF into another 25 mL single-necked flask, add DIPEA (1.39 mL, 0.85 mmol) in an ice-water bath, continue stirring for 30 min, and then add the above reaction solution to the reaction flask, and raise to room temperature to react. After the completion of the reaction as detected by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain 2.1 g of a solid at 39% yield; LC-MS: $[M+H]^+$=702.8.

Step 3: Compound 13c 13b (1.5 g, 1.87 mmol) was added to a 25 mL single-necked flask, and after dissolution with 25 mL of DMF, 1.5 g of 5% Pd/C was added, and a hydrogenation reaction was carried out for 3 h. After completion of the reaction, filtration was performed, and a filtrate was obtained, and used directly for the next step of the reaction without purification.

Step 4: Compound 13d

The crude product 13c was placed in an ice-water bath, DIPEA (333 uL, 1.93 mmol) was added, and compound M3 (1.1 g, 1.87 mmol) was then added, before raising to room temperature to react for 1 h. Upon completion of the reaction as detected by HPLC, the reaction solution was purified by HPLC to obtain a preparation liquid, which was lyophilized to give 13d (519 mg); LC-MS: $[M-H]^-$=856.6.

Step 5: Compound 13e

Add 13d (400 mg, 0.47 mmol), M5 (240 mg, 0.48 mmol), PyBOP (250 mg, 0.48 mmol), HOBt (103 mg, 48 mmol) and 15 mL of DMF to a 50 mL single-necked flask, add DIPEA (330 uL, 2.0 mmol) in an ice-water bath, and raise to room temperature to react for 4 h. Upon completion of the reaction as detected by HPLC, the reaction solution was purified by HPLC to obtain the preparation liquid of compound 13e, which was lyophilized to obtain 13e (187 mg); LC-MS: $[M+H]^+$=1275.5.

Step 6: Compound 13A

Add 13e (100 mg, 0.08 mmol), zinc bromide (355 mg, 0.16 mmol) and 5 mL of nitromethane into a 25 mL single-necked flask and carry out a reaction at 40° C. for 1 h. Upon completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 13A (60 mg); LC-MS: $[M+H]^+$=1119.6.

Example 23
Synthesis of Compound 13B:
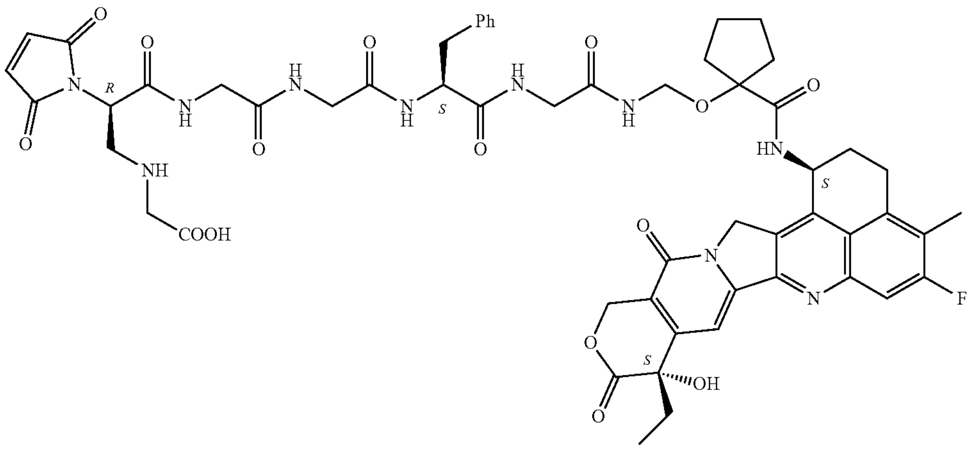
13B
Referring to the synthetic route of Example 22, compound 13B (51 mg) was obtained; LC-MS: $[M+H]^+$=1119.6.
Example 24
Synthesis of Compound 14A:
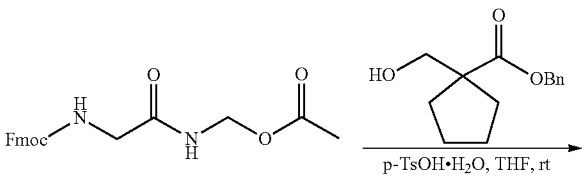
M1
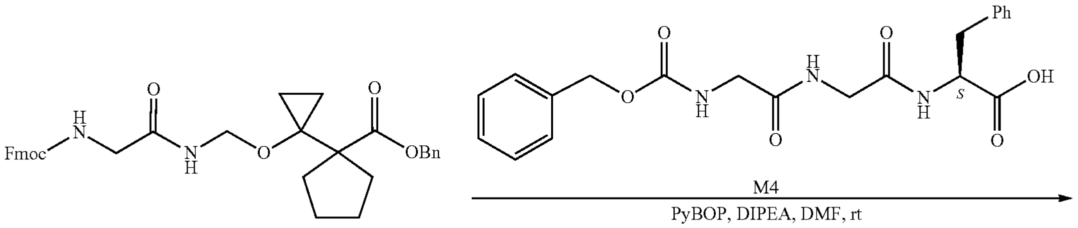
14a
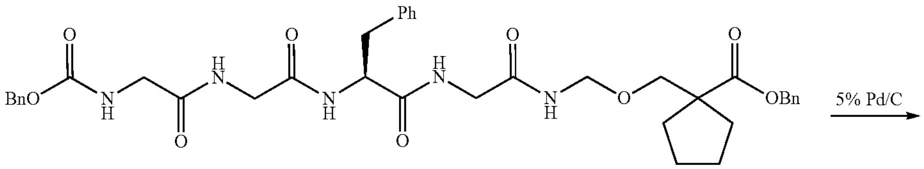
14b -continued
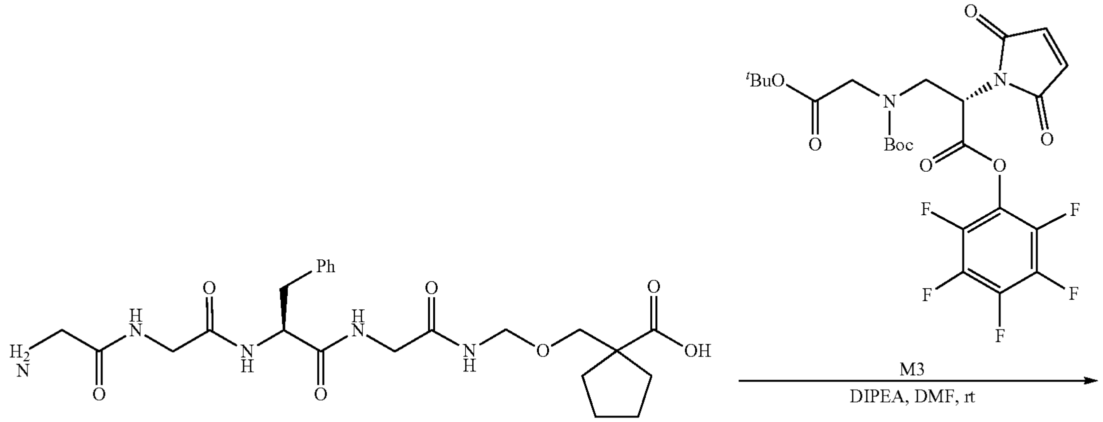
14c
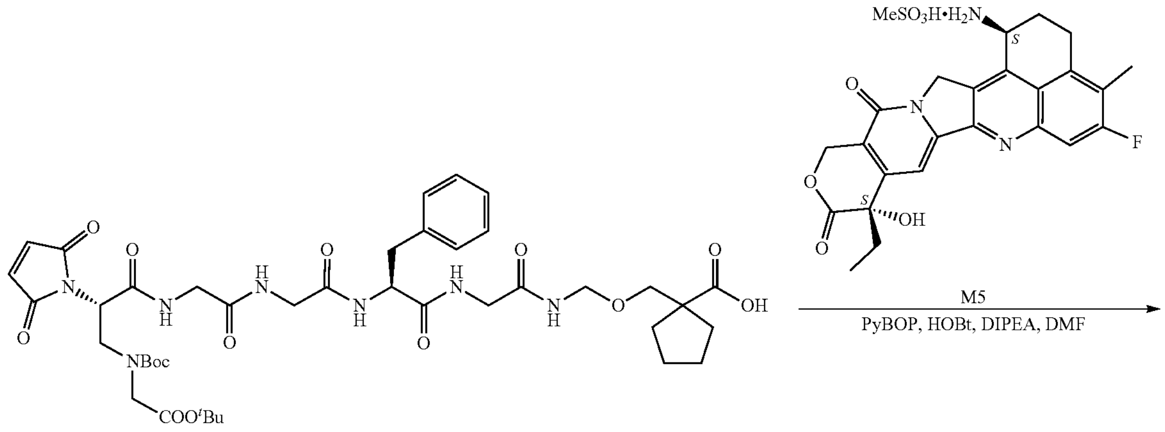
14d
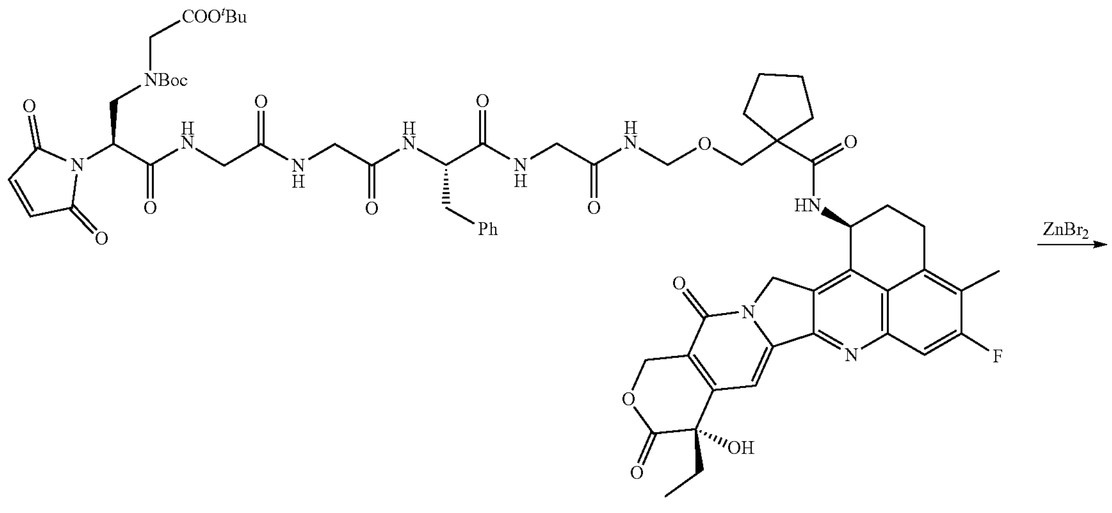
14e -continued

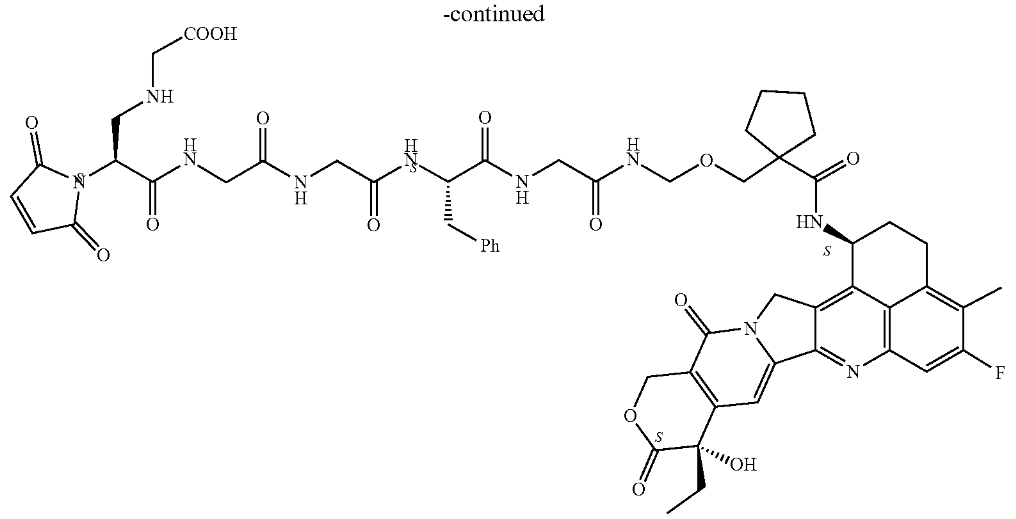

14A

Step 1: Compound 14a

In a 250 mL single-necked flask, add M1 (6 g, 16.3 mmol), 100 mL THF and p-toluenesulfonic acid monohydrate (0.31 g, 1.63 mmol), stir and cool to 0° C., add benzyl 3-hydroxy-2-cyclopentylpropionate dropwise (synthesized by the method published in patent WO2009011285A1) (7.6 g, 32.6 mmol), then naturally warm up to room temperature and react (react for about 2-4 h), with TLC monitoring. At the end of the reaction, saturated $NaHCO_3$ solution was added, followed by extraction with ethyl acetate, washing with saturated sodium chloride solution, drying with anhydrous sodium sulfate, filtering and concentration, and the residue was purified by silica gel column (PE:EA=10:1-5:1-2:1) to give 14a (4.4 g) at 49% yield; LC-MS: $[M+H]^+$ =543.6.

Step 2: Compound 14b

In a 25 mL single-necked flask, add 14a (4 g, 7.4 mmol) and 10 mL DMF, stir at 0° C., add DBU (1.2 g, 8.0 mmol), and react for 1 h. After the completion of Fmoc deprotection as detected by TLC, set aside the reaction solution, ready for use.

Add M4 (3.1 g, 7.4 mmol), PyBOP (4.6 g, 8.8 mmol), HOBt (1.19 g, 8.8 mmol) and 10 mL of DMF into another 25 mL single-necked flask, add DIPEA (1.49 mL, 9.0 mmol) in an ice-water bath, and continue stirring for 30 min, then add the above reaction solution to the reaction flask and raise the temperature to room temperature to react. After the completion of the reaction as detected by HPLC, the reaction solution was purified by preparative LC to obtain a product preparation liquid, which was extracted by dichloromethane, washed with saturated sodium chloride solution, dried with anhydrous sodium sulfate and filtered, and the filtrate was concentrated under reduced pressure to obtain 2.6 g of a solid at 49% yield; LC-MS: $[M+H]^+$=716.4.

Step 3: Compound 14c

In a 25 mL single-necked flask, 14b (1.0 g, 1.4 mmol) was added, and after dissolution with 15 mL of DMF, 1.0 g of 5% Pd/C was added, and a hydrogenation reaction was carried out for 1.5 h. After completion of the reaction, filtration was performed, and a filtrate was obtained, and used directly for the next step of the reaction without purification.

Step 4: Compound 14d

The crude product 14c was placed in an ice-water bath, DIPEA (248 uL, 1.5 mmol) was added, then compound M3 (808 mg, 1.4 mmol) was added, then the temperature was raised to room temperature to react for 1 h. When the reaction was completed as detected by HPLC, the reaction solution was purified by HPLC to obtain a preparation liquid, which was lyophilized to obtain 14d (500 mg); LC-MS: $[M-H]^+$=870.5.

Step 5: Compound 14e

Add 14d (400 mg, 0.46 mmol), M5 (235 mg, 0.46 mmol), PyBOP (245 mg, 0.46 mmol), HOBt (99 mg, 0.46 mmol) and 15 mL of DMF into a 50 mL single-necked flask, add DIPEA (331 uL, 2.0 mmol) in an ice-water bath, raise to room temperature and react for 3 h. After the completion of the reaction as detected by HPLC, the reaction solution was purified by HPLC to give the preparation liquid of compound 14e, which was lyophilized to obtain 14e (146 mg); LC-MS: $[M+H]^+$=1289.5.

Step 6: Compound 14A 14e (100 mg, 0.08 mmol), zinc bromide (360 mg, 1.6 mmol) and 5 mL of nitromethane were added to a 25 mL single-necked flask and a reaction was carried out at 40° C. for 1 h. After completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 14A (52 mg); LC-MS: $[M+H]^+$=1133.4.

Example 25
Synthesis of Compound 14B:
compound 14B
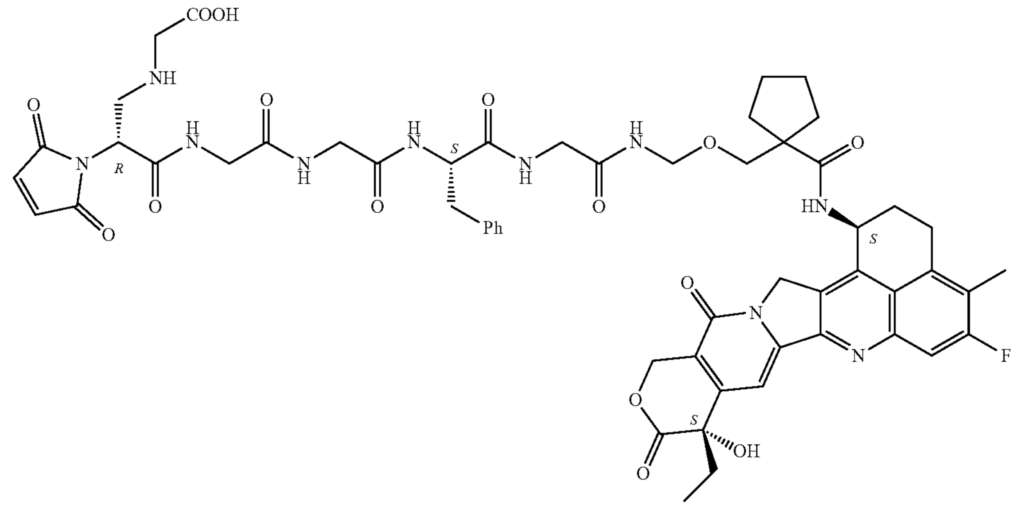
Referring to the synthetic route of Example 24, compound 14B (48 mg) was obtained; LC-MS: $[M+H]^+$=1133.4.
Example 26
Synthesis of Compounds 15A and 15B:
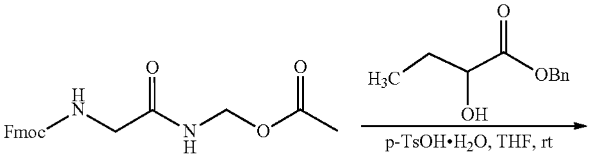
M1
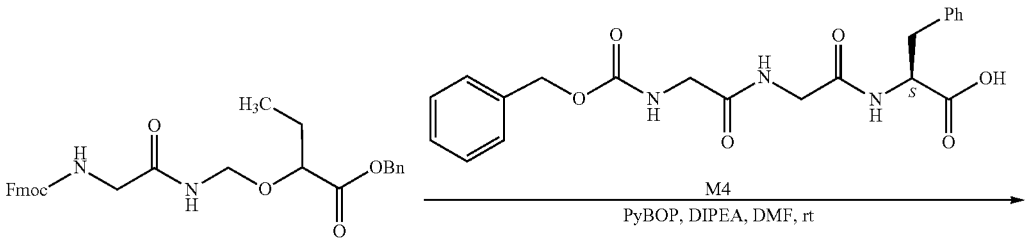
15a
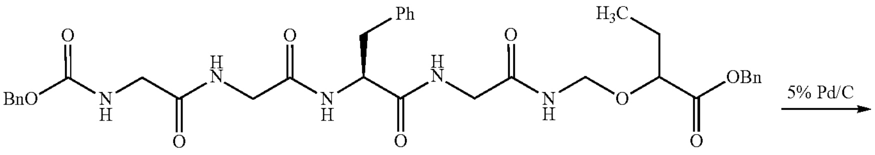
15b -continued
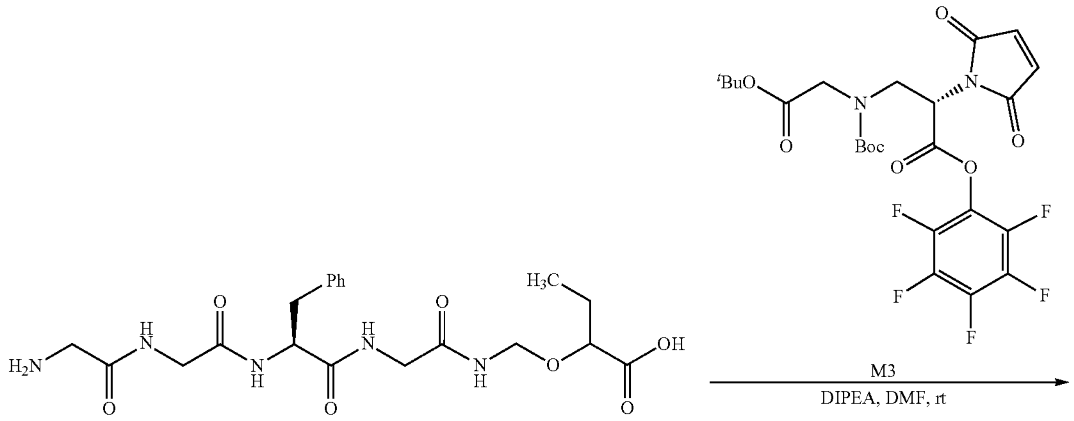
15c
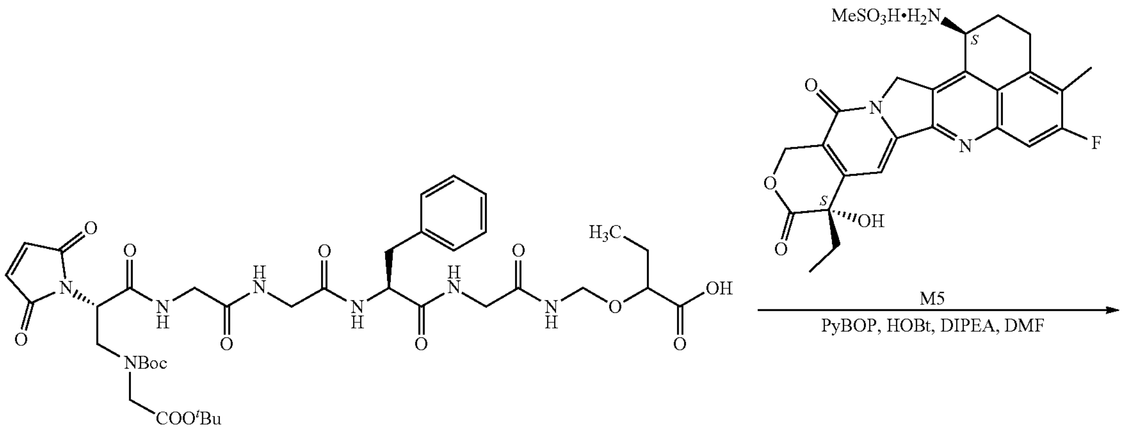
15d
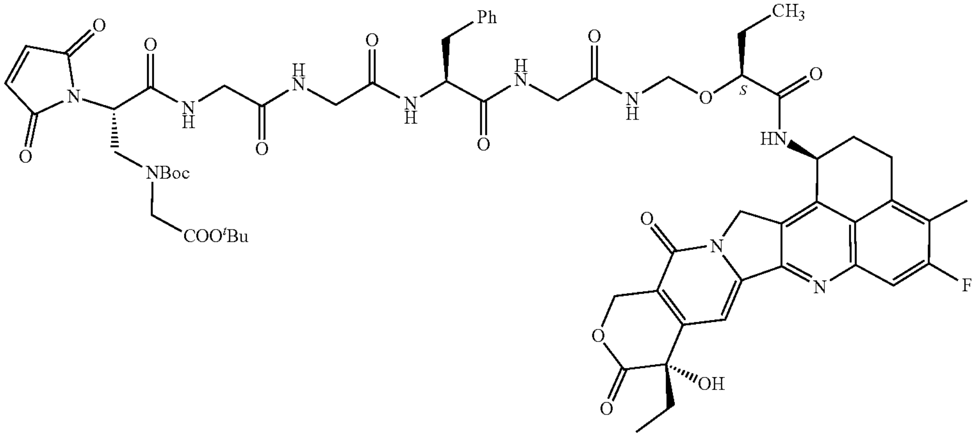
15e-1

-continued

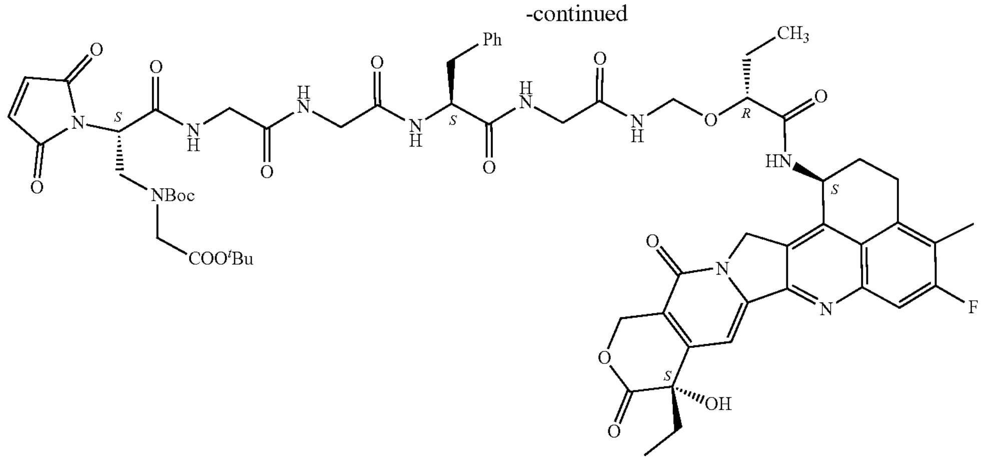

15e-2

Step 1: Compound 15a

In a 250 mL single-necked flask, M1 (10 g, 27.1 mmol), benzyl 2-hydroxy-butyrate (prepared by the method published in the literature *Chemical Communications,* 2019, 55(53), 7699-7702) (10.5 g, 54.3 mmol), zinc acetate (9.96 g, 54.3 mmol) and 100 mL of toluene were added, heated to 100° C. and reacted for 4 h. After the reaction was completed, the temperature was reduced to room temperature, filtration was performed to remove insoluble material, and the filtrate was concentrated to obtain a crude product. The crude product was purified by silica gel column chromatography (PE:EA=10:1-5:1-2:1) to obtain 5.67 g of the target material at 42% yield; LC-MS: $[M+H]^+$=503.5.

Step 2: Compound 15b

Add 15a (5 g, 9.95 mmol) and 15 mL of DMF in a 50 mL single-necked flask, and after dissolution, add DBU (1.68 g, 11 mmol) in an ice-water bath and react for 1 h. The reaction solution was recorded as reaction solution ①.

In another 50 mL single-necked flask, M4 (4.1 g, 10.0 mmol), PyBOP (5.75 g, 11 mmol), HOBt (1.49 g, 11 mmol) and 10 mL DMF were added, and after dissolution, DIPEA (1.82 mL, 11 mmol) was added in an ice-water bath, and a reaction was continued for 40 min, then reaction solution ① was added, and the temperature was raised to room temperature to react for 2 h. The reaction progress was monitored by HPLC. After completion of the reaction, the reaction solution was purified by high performance liquid chromatography to obtain a preparation liquid. The preparation liquid was extracted with dichloromethane, washed with saturated sodium chloride solution, dried with anhydrous sodium sulfate, filtered, and concentrated to obtain 4.6 g of solid, at a yield of 68%; LC-MS: $[M+H]^+$=676.7.

Step 3: Compound 15d

Add 15b (2.0 g, 2.96 mmol) in a 25 mL single-necked flask, dissolve in 15 mL of DMF, then add 2.0 g of 5% Pd/C, and perform a hydrogenation reaction for 2 h. After the completion of the reaction, filtration was carried out, and the filtrate was placed in a bath of ice-water, and DIPEA (496 uL, 3.0 mmol) was added, followed by M3 (1.7 g, 2.96 mmol), and then the temperature was raised to room temperature to react for 1 h. When the reaction was complete as detected by HPLC, the reaction solution was purified by high performance liquid chromatography to obtain a preparation liquid, which was lyophilized to give 1120.0 mg of a product at 45% yield; LC-MS: $[M-H]^-$=830.3.

Step 4: Compound 15e

Add 15d (500 mg, 0.60 mmol), M5 (321 mg, 0.60 mmol), PyBOP (469 mg, 0.90 mmol), HOBt (121 mg, 0.90 mmol) and 15 mL of DMF into a 50 mL single-necked flask, add DIPEA (446 uL, 2.7 mmol) in an ice-water bath, raise to room temperature and react for 2 h. After the completion of the reaction as detected by HPLC, the reaction solution was purified by HPLC to obtain the preparation liquids of compound 15e-1 and compound 15e-2, and the preparation liquids were lyophilized to obtain 138 mg of compound 15e-1, LC-MS: $[M+H]^+$=1249.5, and 140 mg of compound 15e-2, LC-MS: $[M+H]^+$=1249.5, respectively.

Step 5: Compound 15A

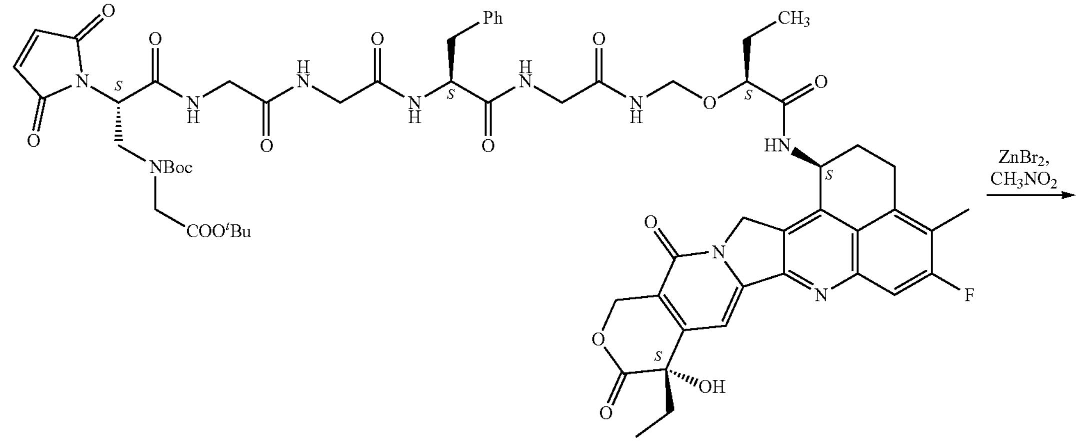

15e-1

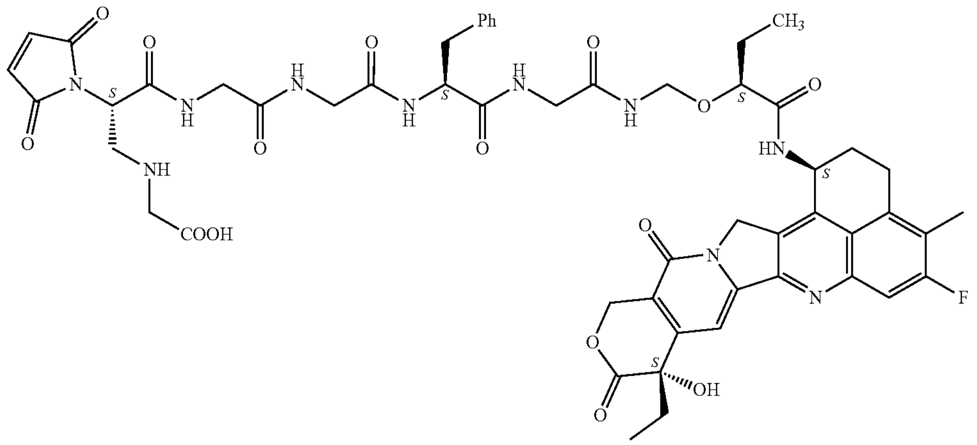

15A

Add 15e-1 (100 mg, 0.08 mmol), zinc bromide (360 mg, 1.6 mmol) and 5 mL of nitromethane into a 25 mL single-necked flask and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 59 mg of a solid; LC-MS: $[M+H]^+$= 1093.4.

Step 6: Compound 15B

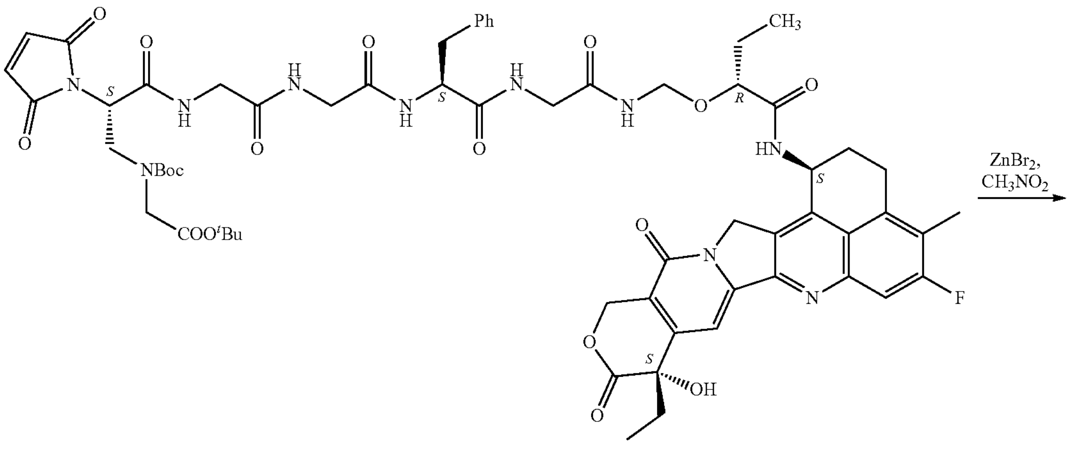

15e-2

-continued

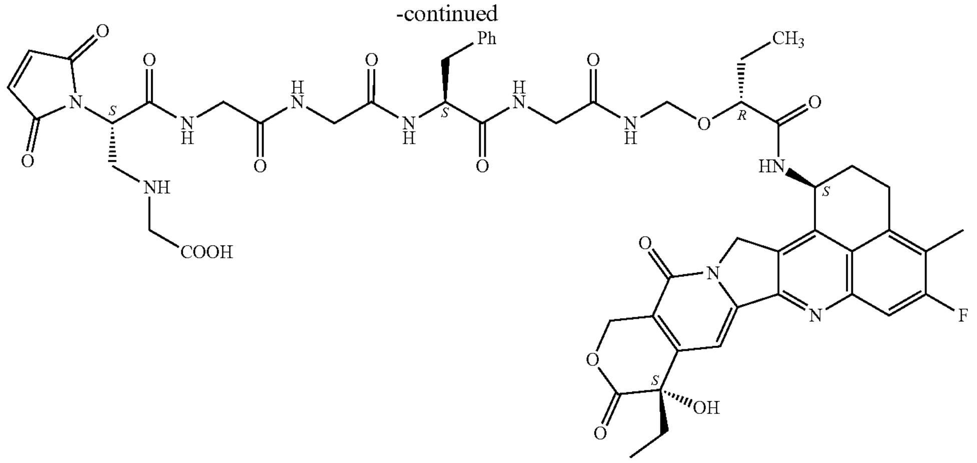

15B

Add 15e-2 (100 mg, 0.08 mmol), zinc bromide (360 mg, 1.6 mmol) and 5 mL of nitromethane into a 25 mL single-necked flask and react at 40° C. for 1 h. After the completion of the reaction as detected by HPLC, the solvent was removed by concentration under reduced pressure, and a crude product was obtained. The crude product was purified by high performance liquid chromatography to obtain a product preparation liquid, and the preparation liquid was lyophilized to obtain 60 mg of solid; LC-MS: $[M+H]^+$ =1093.4.

Example 27

Synthesis of Compounds 16A and 16B:

compound 16A

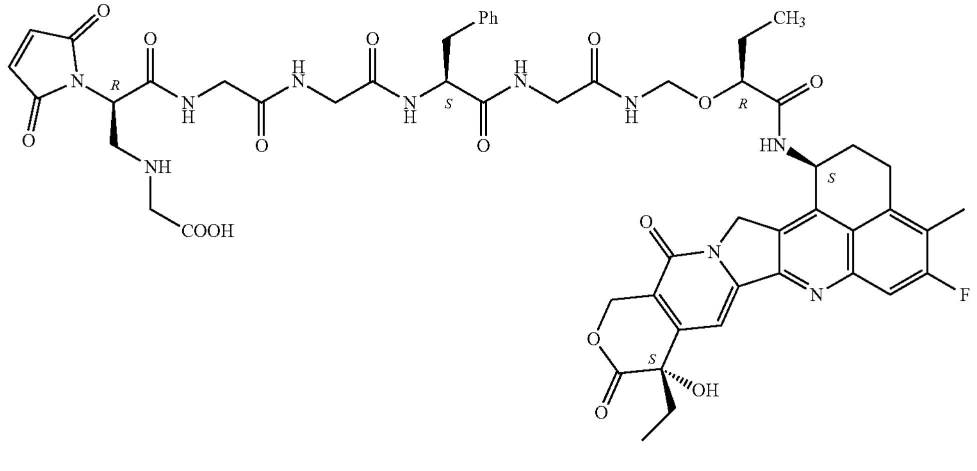

Referring to the synthetic route of Example 26, compound 16A (55 mg) was obtained; LC-MS: $[M+H]^+$=1093.4.

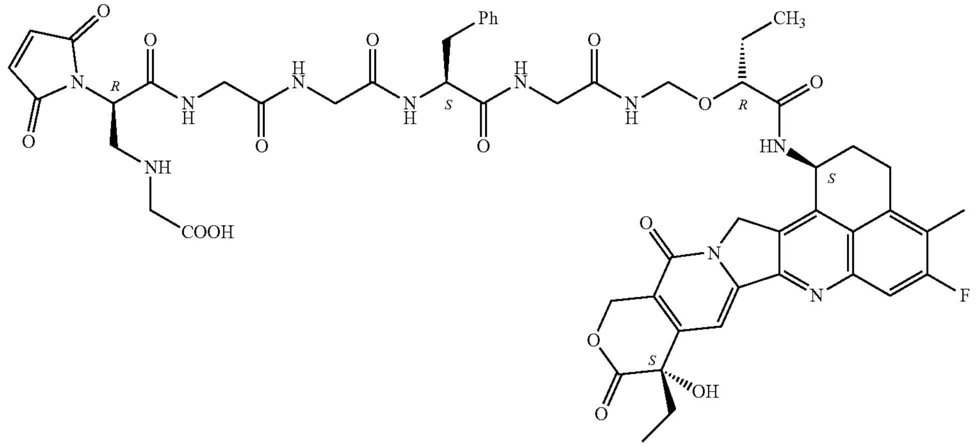
compound 16B
Referring to the synthetic route of Example 26, compound 16B (54 mg) was obtained; LC-MS: $[M+H]^+=1093.4$.
Example 28
Synthesis of Compounds 17A and 17B:
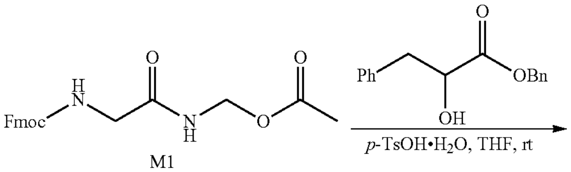
M1
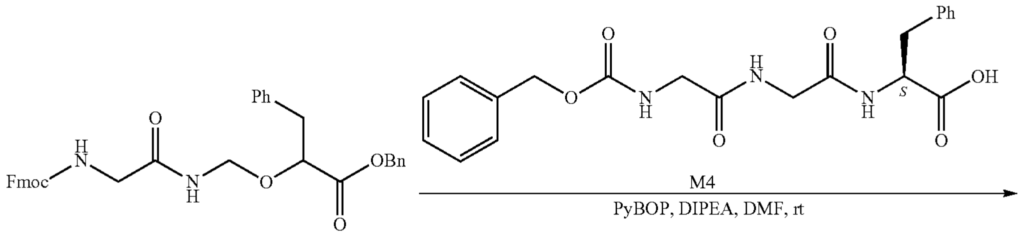
17a
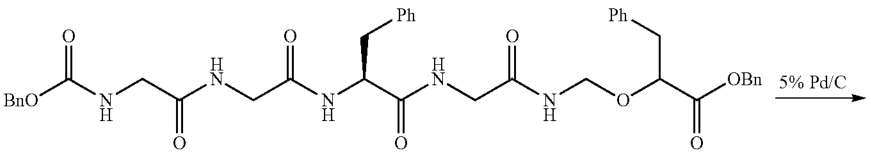
17b -continued
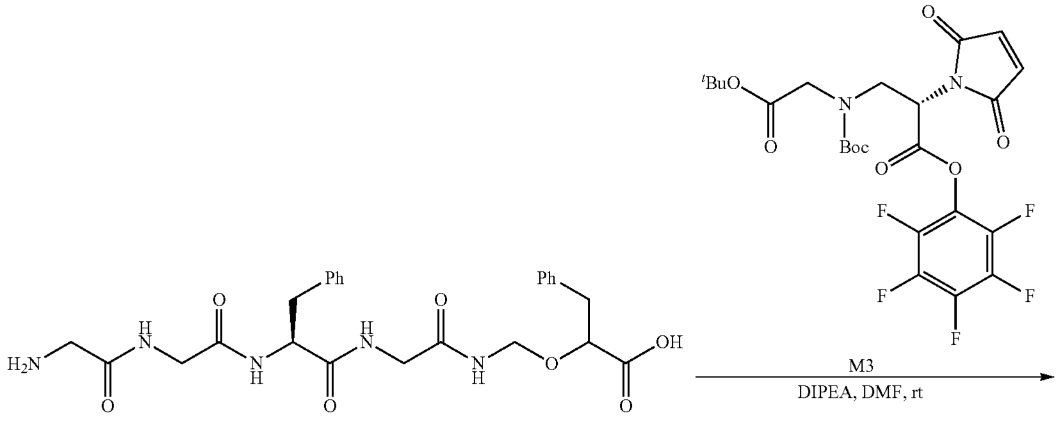
17c
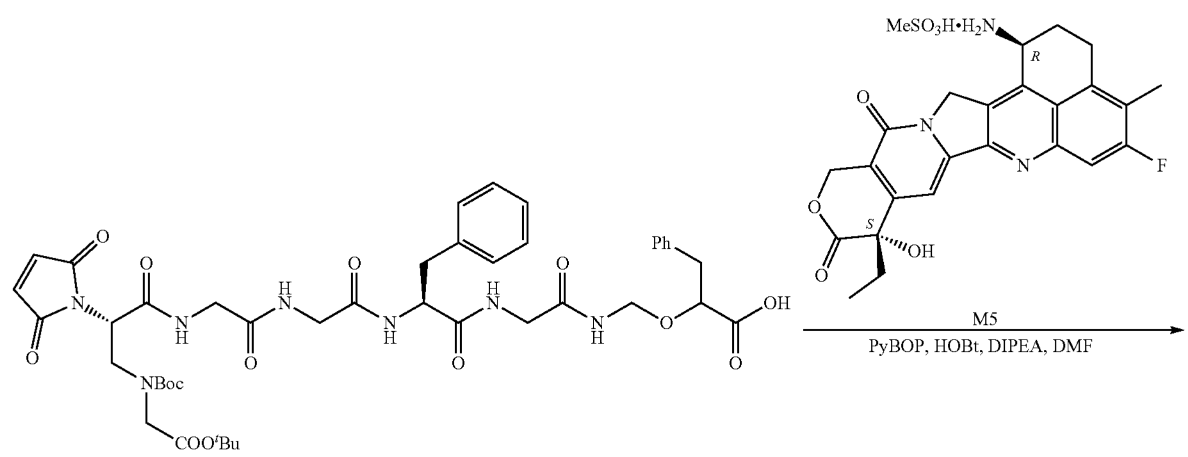
17d
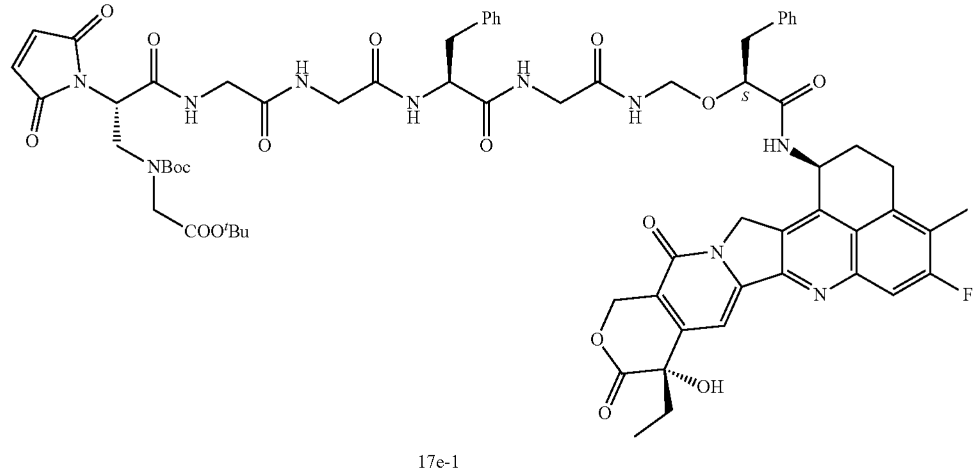
17e-1

-continued

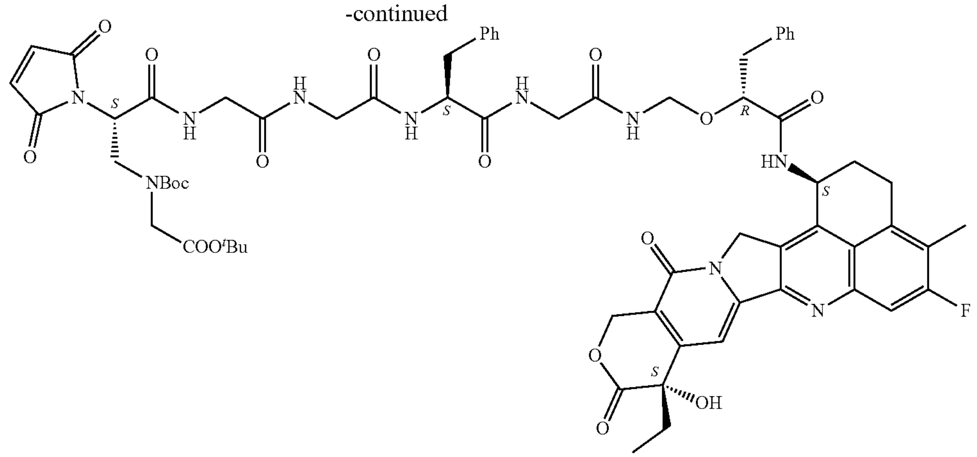

17e-2

Step 1: Compound 17a

Add M1 (10 g, 27.1 mmol), benzyl 2-hydroxy-phenylpropionate (synthesized by the method published in the literature *Nature Communications,* 2020. 11(1), 56.) (14.7 g, 54.3 mmol), zinc acetate (9.96 g, 54.3 mmol) and 100 mL of toluene into a 250 mL single-necked flask, heat to 100° C. and react for 4 h. After the reaction was completed, the temperature was lowered to room temperature, filtration was performed to remove insoluble material, and the filtrate was concentrated to obtain a crude product. The crude product was purified by silica gel column chromatography (PE: EA=10:1-5:1-2:1) to obtain 6.13 g of the target material at 40% yield; LC-MS: $[M+H]^+$=565.6.

Step 2: Compound 17b

In a 50 mL single-necked flask, add 17a (5 g, 8.86 mmol) and 15 mL of DMF, and after dissolution, add DBU (1.53 g, 10 mmol) in an ice-water bath and react for 1 h, and record the reaction solution as reaction solution ①.

In another 50 mL single-necked flask, add M4 (3.6 g, 8.86 mmol), PyBOP (5.23 g, 10 mmol), HOBt (1.36 g, 10 mmol) and 10 mL of DMF, and after dissolution, add DIPEA (1.65 mL, 10 mmol) in an ice-water bath, and continue reacting for 30 min, then add reaction solution ①, raise to room temperature and react for 2 h. The reaction progress was monitored by HPLC. After completion of the reaction, the reaction solution was purified by high performance liquid chromatography to obtain a preparation liquid. The preparation liquid was extracted with dichloromethane, washed with saturated sodium chloride solution, dried with anhydrous sodium sulfate, filtered, and concentrated to obtain 5.0 g of solid at 77% yield; LC-MS: $[M+H]^+$=738.3.

Step 3: Compound 17d

Add 17b (3.0 g, 4.07 mmol) in a 25 mL single-necked flask, and after dissolution with 15 mL of DMF, add 3.0 g of 5% Pd/C, and perform a hydrogenation reaction for 2 h. When the reaction was completed, filtration was performed, the filtrate was placed in an ice-water bath, and DIPEA (744 uL, 4.5 mmol) was added, followed by M3 (2.34 g, 4.07 mmol), and then the temperature was raised to room temperature to react for 1 h. When the reaction was complete as detected by HPLC, the reaction solution was purified by HPLC to obtain a preparation liquid, which was lyophilized to give 1.2 g of a product at 33% yield; LC-MS: $[M-H]^-$=892.4.

Step 4: Compound 17e 17d (500 mg, 0.56 mmol), M5 (300 mg, 0.56 mmol), PyBOP (438 mg, 0.84 mmol), HOBt (113 mg, 0.84 mmol) and 15 mL of DMF were added to a 50 mL single-necked flask, DIPEA (330 uL, 2.0 mmol) was added in an ice-water bath, and the temperature was raised to room temperature to react for 2 h. After the reaction was complete as detected by HPLC, the reaction solution was purified by HPLC to obtain the preparation liquids of compound 17e-1 and compound 17e-2, and the preparation liquids were lyophilized to obtain 156 mg of compound 17e-1, LC-MS: $[M+H]^+$=1311.4, and 150 mg of compound 17e-2, LC-MS: $[M+H]^+$=1311.7, respectively.

Step 5: Compound 17A

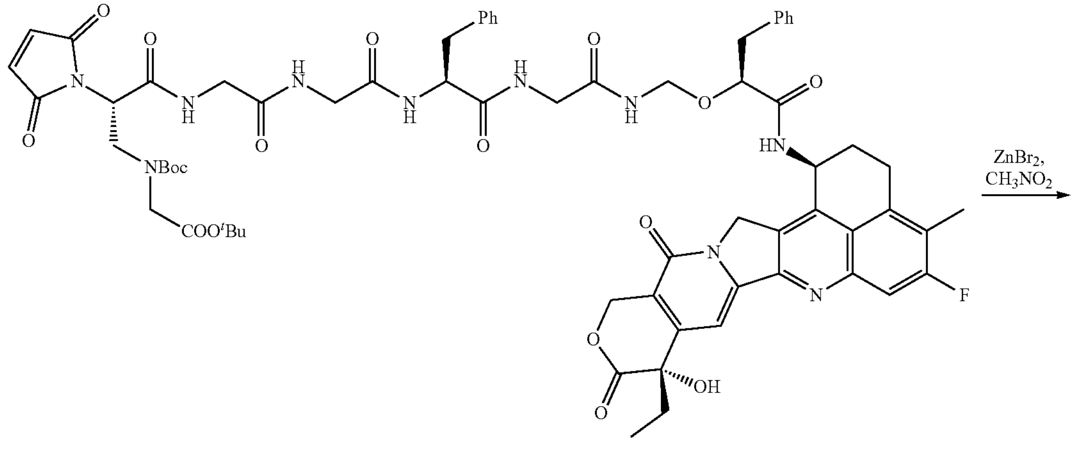

17e-1

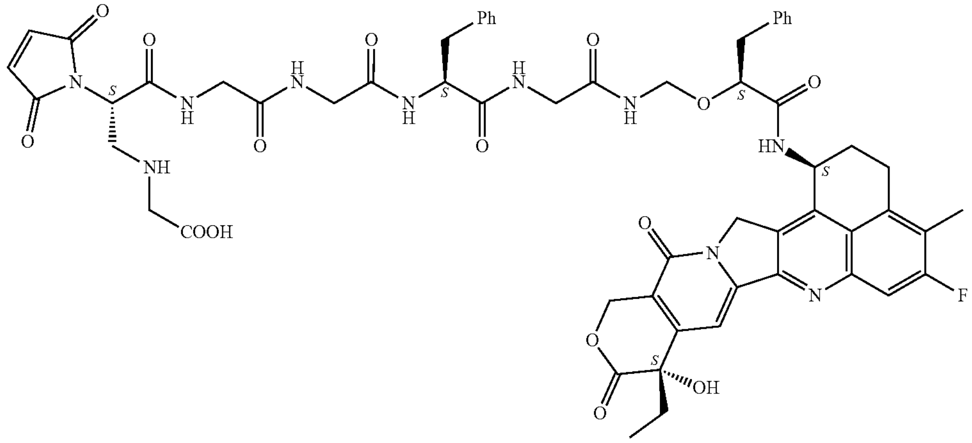

17A 17e-1 (100 mg, 0.08 mmol), zinc bromide (360 mg, 1.6 mmol) and 5 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain a product preparation liquid, and the preparation liquid was lyophilized to obtain 43 mg of solid; LC-MS: $[M+H]^+=1155.4$.

Step 6: Compound 17B

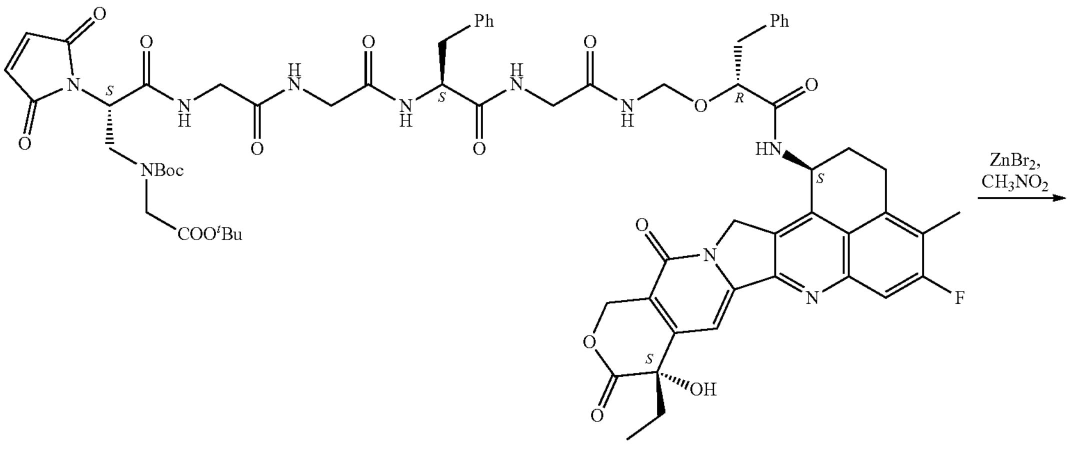

17e-2

-continued

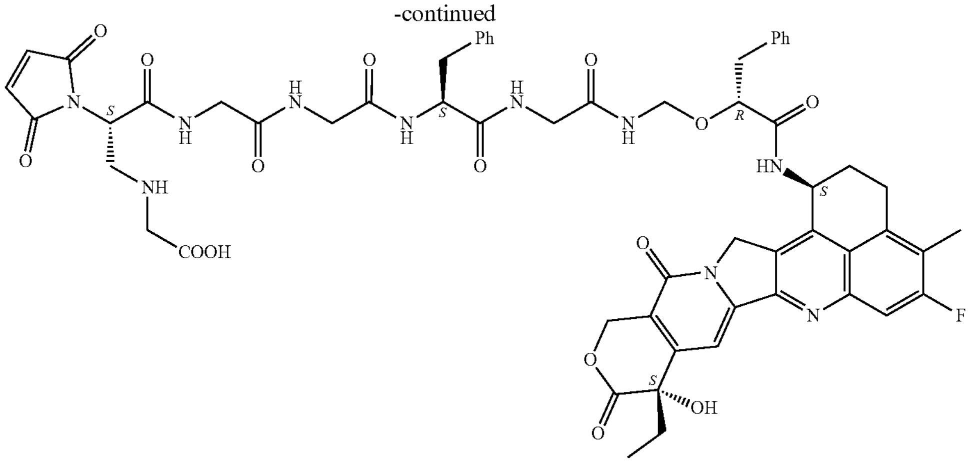

17B 17e-2 (100 mg, 0.08 mmol), zinc bromide (360 mg, 1.6 mmol) and 5 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain a product preparation liquid, and the preparation liquid was lyophilized to obtain 40 mg of solid; LC-MS: $[M+H]^+=1155.4$.

Example 29

Synthesis of Compounds 18A and 18B:

compound 18A

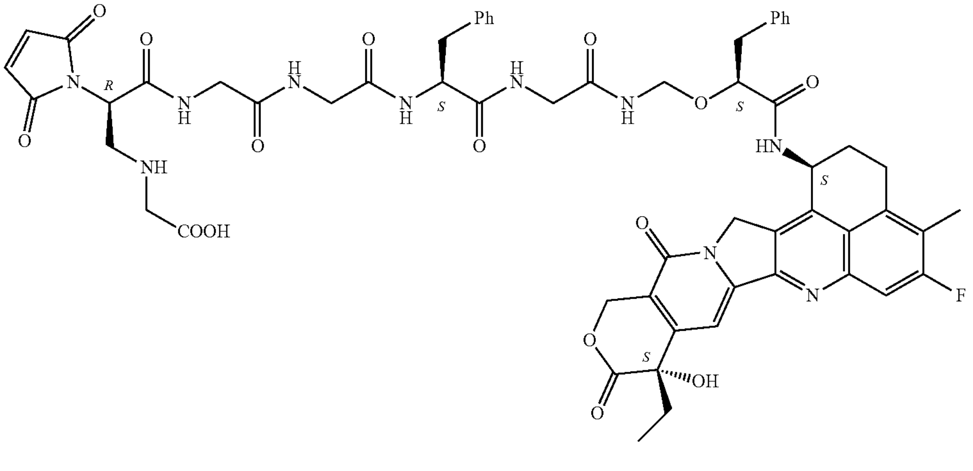

Referring to the synthetic route of Example 28, compound 18A (54 mg) was obtained; LC-MS: $[M+H]^+=1155.4$.

compound 18B
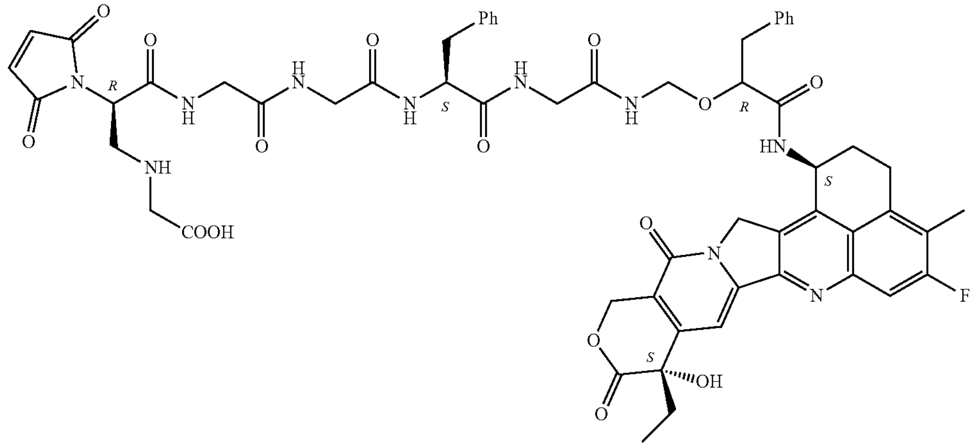
Referring to the synthetic route of Example 28, compound 18B (55 mg) was obtained; LC-MS: $[M+H]^+=1155.4$.
Example 30
Synthesis of Compounds 19A and 19B:
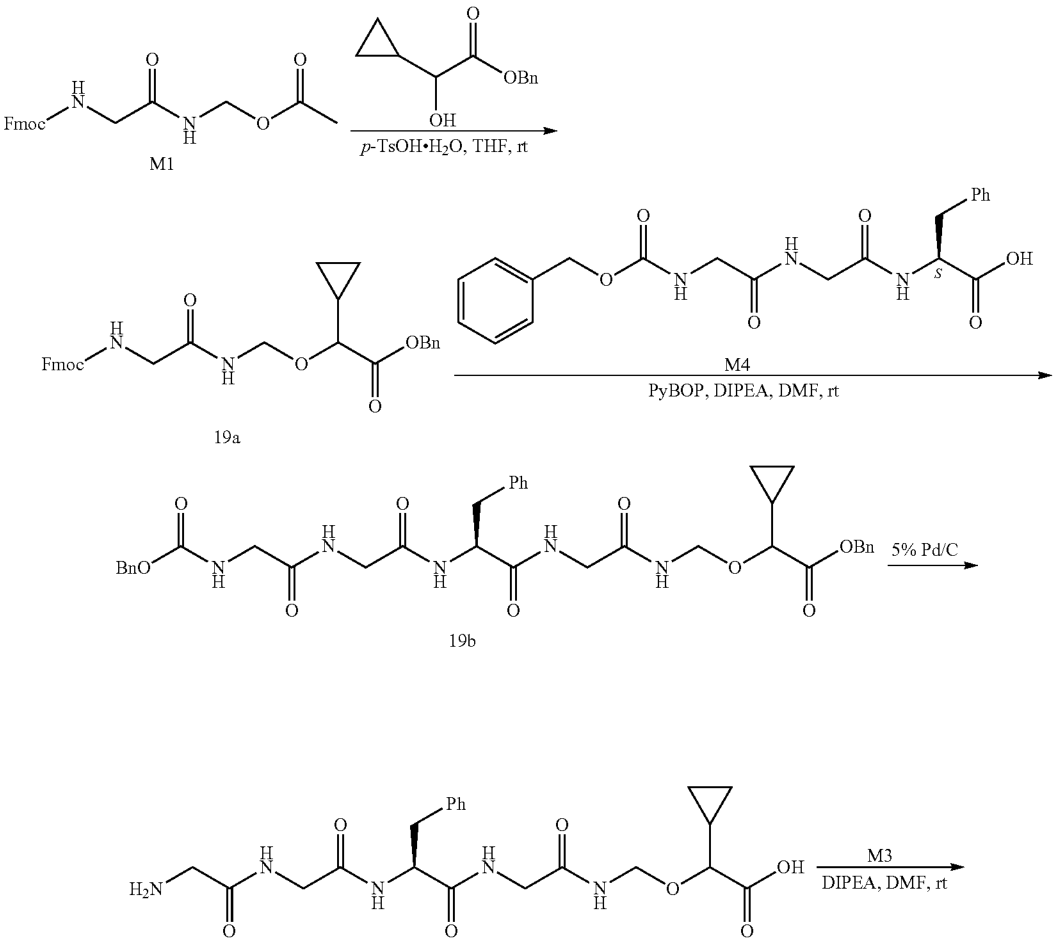

-continued

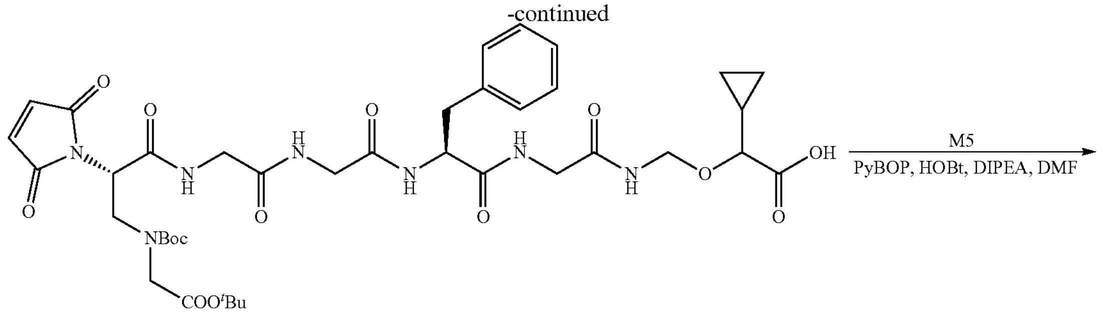

19d

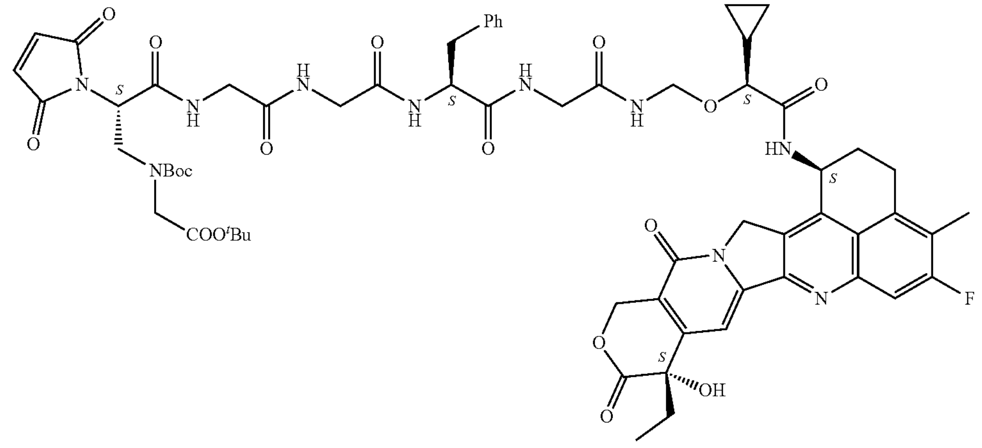

19e-1

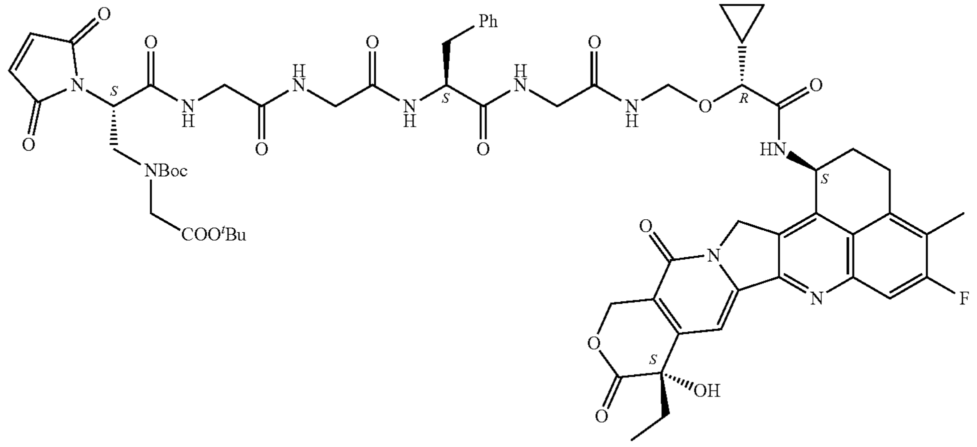

19e-2

Step 1: Compound 19a

Add M1 (10 g, 27.1 mmol), benzyl 2-cyclopropyl-2-hydroxyacetate (prepared according to the method published in patent WO2020244657A1) (11.2 g, 54.3 mmol), zinc acetate (9.96 g, 54.3 mmol) and 100 mL of toluene in a 250 mL single-necked flask, heat to 100° C. and react for 4 h. When the reaction was completed, the temperature was reduced to room temperature, filtering was performed to remove insoluble material, and the filtrate was concentrated to obtain a crude product. The crude product was purified by silica gel column chromatography (PE:EA=10:1-5:1-2:1) to obtain 4.97 g of the target material at 36% yield; LC-MS: $[M+H]^+$=515.2.

Step 2: Compound 19b

Add 19a (4 g, 7.8 mmol) and 10 mL of DMF in a 50 mL single-necked flask, and after dissolution, add DBU (1.42 g, 9.3 mmol) in an ice-water bath and react for 1 h. The reaction solution was recorded as reaction solution ①.

In another 50 mL single-necked flask, M4 (3.2 g, 7.8 mmol), PyBOP (4.5 g, 8.6 mmol), HOBt (1.16 g, 8.6 mmol) and 10 mL of DMF were added, and after dissolution, DIPEA (1.65 mL, 10 mmol) was added in an ice-water bath, and the reaction was continued for 30 min, then reaction solution ① was added, and the temperature was raised to room temperature to react for 2 h. The reaction process was monitored by HPLC, and after completion of the reaction, the reaction solution was purified by high performance liquid chromatography to obtain a preparation liquid. The preparation liquid was extracted with dichloromethane, washed with saturated sodium chloride solution, dried with anhydrous sodium sulfate, filtered, and concentrated to obtain 4.2 g of solid, with a yield of 78%; LC-MS: $[M+H]^+$ =688.3.

Step 3: Compound 19d

In a 25 mL single-necked flask, 19b (1000 mg, 1.45 mmol) was added, and after dissolution with 15 mL of DMF, 1000 mg of 5% Pd/C was added, and a hydrogenation reaction was performed for 2 h. When the reaction was completed, filtering was performed, the filtrate was placed in an ice-water bath, and DIPEA (248 uL, 1.5 mmol) was added, followed by M3 (720 mg, 1.45 mmol), and then the temperature was raised to room temperature to react for 1 h. When the reaction was complete as detected by HPLC, the reaction solution was purified by HPLC to obtain a preparation liquid, and the preparation liquid was lyophilized to obtain 503 mg of product at 41% yield; LC-MS: $[M-H]^-$= 842.3.

Step 4: Compounds 19e-1 and 19e-2

19d (500 mg, 0.59 mmol), M5 (317 mg, 0.59 mmol), PyBOP (339 mg, 0.65 mmol), HOBt (88 mg, 0.86 mmol) and 10 mL of DMF were added to a 50 mL single-necked flask, and DIPEA (292 uL, 1.77 mmol) was added in an ice-water bath, and the temperature was raised to room temperature to react for 2 h. After the reaction was complete as detected by HPLC, the reaction solution was purified by HPLC to obtain the preparation liquids of compound 19e-1 and compound 19e-2, and the preparation liquids were lyophilized to obtain 112 mg of compound 19e-1, LC-MS: $[M+H]^+$=1261.5, and 131 mg of compound 19e-2, LC-MS: $[M+H]^+$=1261.5, respectively.

Step 5: Compound 19A

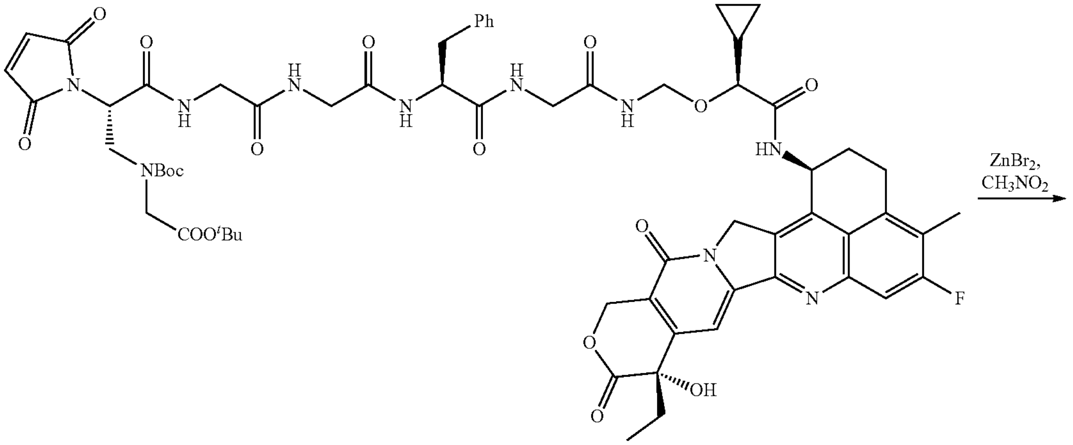

19e-1

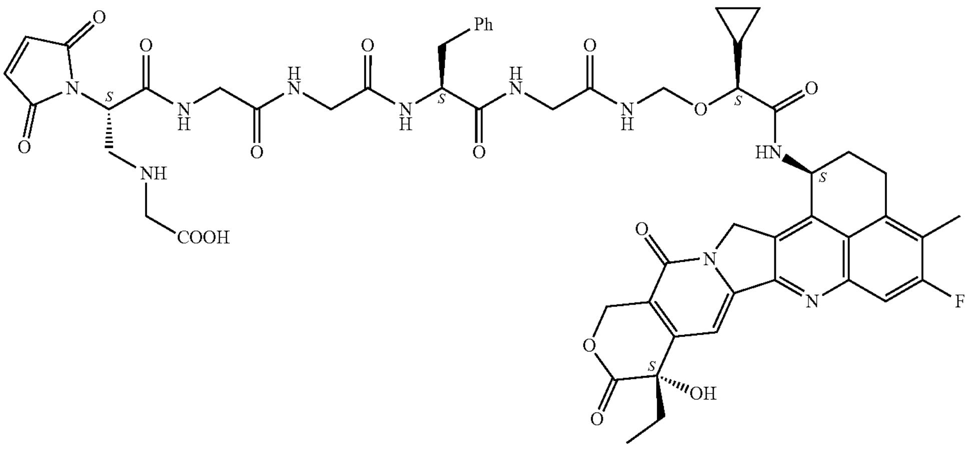

19A 19e-1 (100 mg, 0.079 mmol), zinc bromide (357 mg, 1.59 mmol) and 5 mL of nitromethane were added to a 25 mL single-necked flask and a reaction was carried out at 40° C. for 1 h. After the completion of the reaction as detected by HPLC, the solvent was removed by concentration under reduced pressure, to obtain a crude product. The crude product was purified by high performance liquid chromatography to obtain a product preparation liquid, and the preparation liquid was lyophilized to obtain 55 mg of solid; LC-MS: $[M+H]^+$=1105.4.

Step 6: Compound 19B

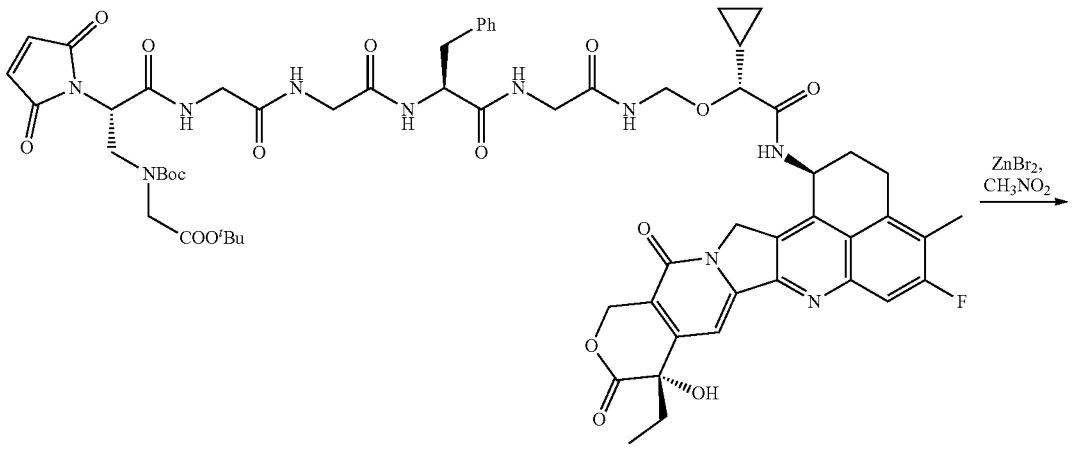

19e-2

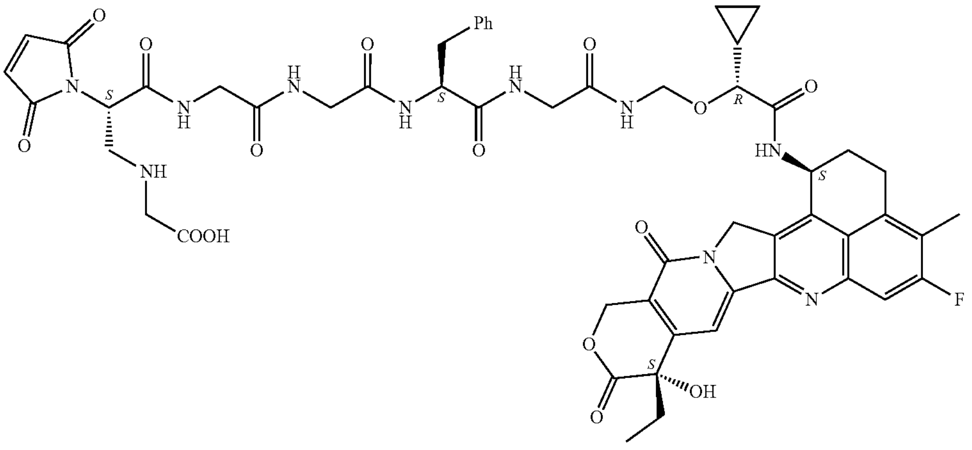

19B 19e-2 (100 mg, 0.079 mmol), zinc bromide (357 mg, 1.59 mmol) and 5 mL of nitromethane were added to a 25 mL single-necked flask and a reaction was carried out at 40° C. for 1 h. After the reaction was completed as detected by HPLC, the solvent was removed by concentration under reduced pressure, and a crude product was obtained. The crude product was purified by high performance liquid chromatography to obtain a product preparation liquid, and the preparation liquid was lyophilized to obtain 58 mg of a solid; LC-MS: $[M+H]^+$=1105.4.

Example 31

Synthesis of Compounds 20A and 20B:

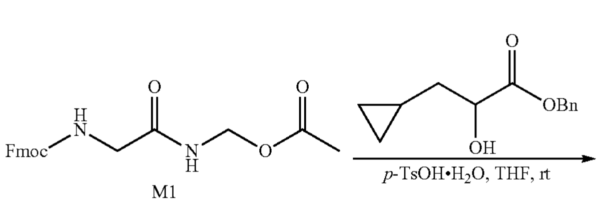

M1

-continued
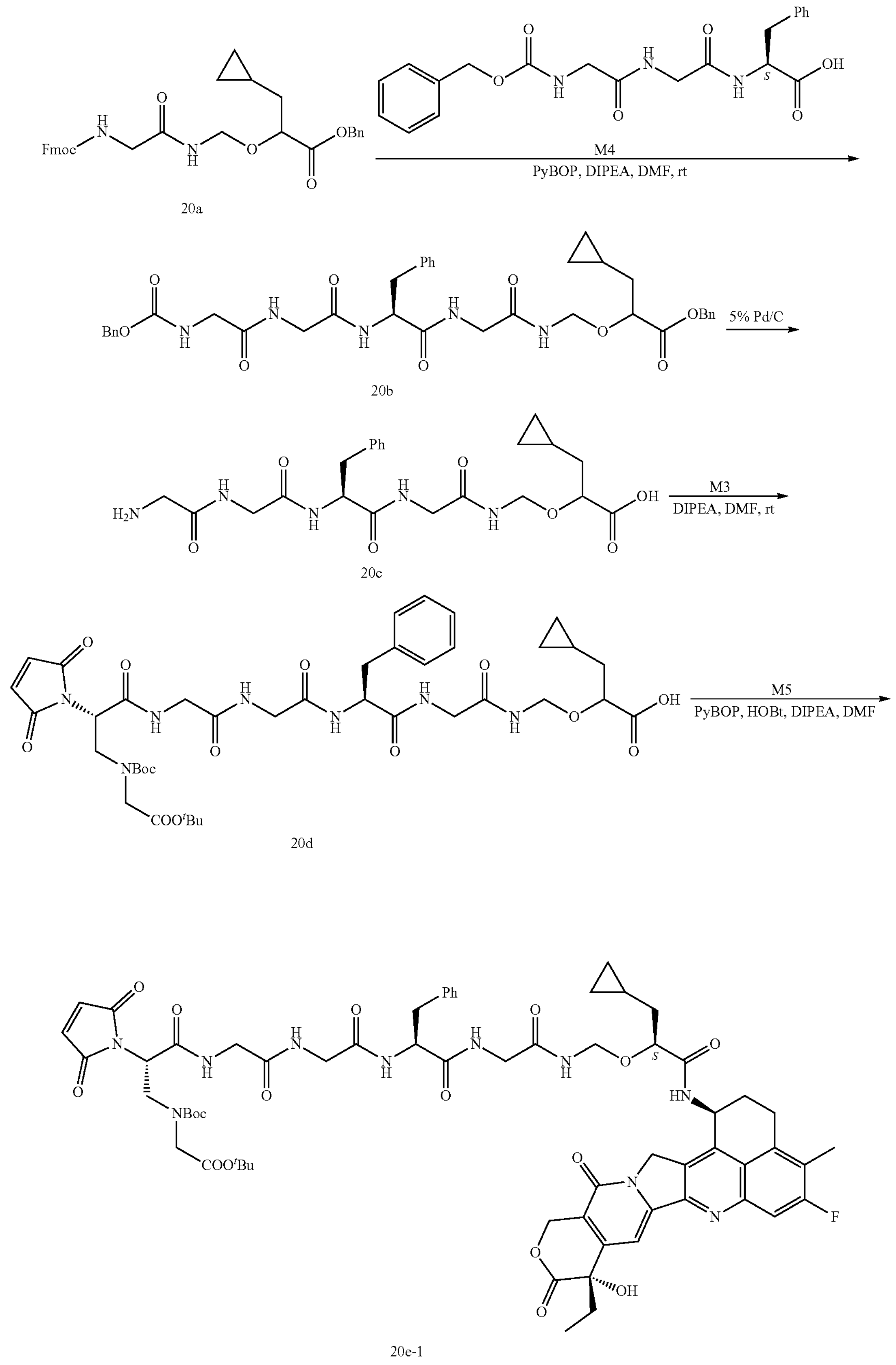
20a
20b
20c
20d
20e-1

-continued

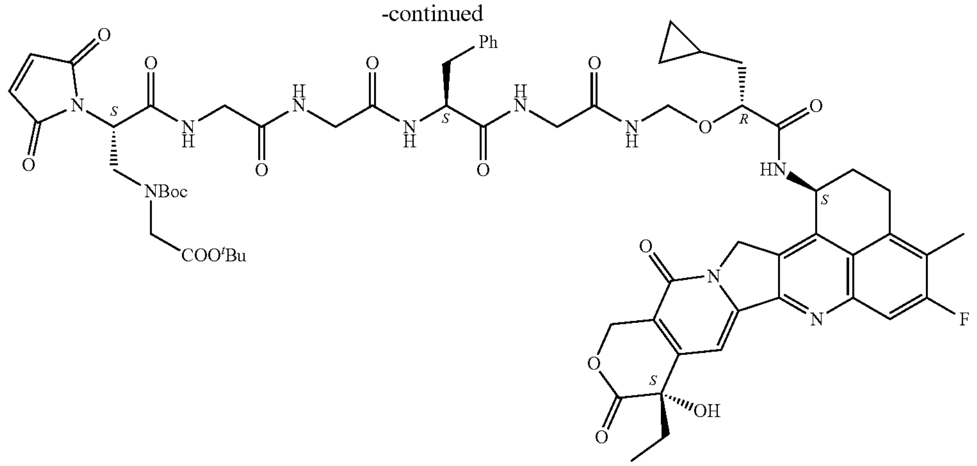

20e-2

Step 1: Compound 20a

Add M1 (10 g, 27.1 mmol), benzyl 2-hydroxy-cyclopropylpropionate (synthesized by the method published in patent WO2020063676A) (12.0 g, 54.3 mmol), zinc acetate (9.96 g, 54.3 mmol) and 100 mL of toluene in a 250 mL single-necked flask, heat to 100° C. and react for 4 h. When the reaction is completed, reduce to room temperature. Filter to remove insoluble material, and the filtrate is concentrated to obtain a crude product. The crude product was purified by silica gel column chromatography (PE:EA=10:1-5:1-2:1) to obtain 5.09 g of the target material; LC-MS: $[M+H]^+$=529.2.

Step 2: Compound 20b 20a (4 g, 7.6 mmol) and 10 mL of DMF were added to a 50 mL single-necked flask, and after dissolution, DBU (1.39 g, 9.1 mmol) was added in an ice-water bath and a reaction was carried out for 1 h, and the reaction solution was recorded as reaction solution ①.

In another 50 mL single-necked flask, M4 (3.12 g, 7.6 mmol), PyBOP (4.5 g, 8.6 mmol), HOBt (1.16 g, 8.6 mmol) and 10 mL of DMF were added, and after dissolution, DIPEA (1.65 mL, 10 mmol) was added in an ice-water bath and a reaction was continued for 30 min, and then the reaction solution ① was added, and the temperature was raised to room temperature to react for 2 h. HPLC was performed to monitor the reaction progress, and when the reaction was complete, the reaction solution was purified by high performance liquid chromatography to obtain a preparation liquid. The preparation liquid was extracted with dichloromethane, washed with saturated sodium chloride solution, dried with anhydrous sodium sulfate, filtered, and concentrated to obtain 4.5 g of solid, with a yield of 84%; LC-MS: $[M+H]^+$=702.3.

Step 3: Compound 20d

Add 20b (1000 mg, 1.42 mmol) in a 25 mL single-necked flask, and after dissolution with 15 mL of DMF, add 1000 mg of 5% Pd/C, and perform a hydrogenation reaction for 2 h. After the reaction was completed, filtration was performed, the filtrate was placed in an ice-water bath, and then DIPEA (248 uL, 1.5 mmol) was added, followed by M5 (708 mg, 1.42 mmol), and the temperature was raised to room temperature to react for 1 h. When the reaction was complete as detected by HPLC, the reaction solution was purified by HPLC to obtain a preparation liquid, which was lyophilized to obtain 443 mg of product at 36% yield; LC-MS: $[M-H]^-$= 856.4.

Step 4: Compounds 20e-1 and 20e-2

20d (400 mg, 0.47 mmol), exatecan mesylate (250 mg, 0.47 mmol), PyBOP (223 mg, 0.56 mmol), HOBt (83 mg, 0.56 mmol) and 10 mL of DMF were added to a 50 mL single-necked flask, DIPEA (248 uL, 1.5 mmol) was added in an ice-water bath, and the temperature was raised to room temperature to react for 2 h. After the reaction was complete as detected by HPLC, the reaction solution was purified by HPLC to obtain the preparation liquids of compound 20e-1 and compound 20e-2, which were lyophilized to obtain 103 mg of compound 20e-1, LC-MS: $[M+H]^+$=1275.5, and 103 mg of compound 20e-2, LC-MS: $[M+H]^+$=1275.5, respectively.

Step 5: Compound 20A

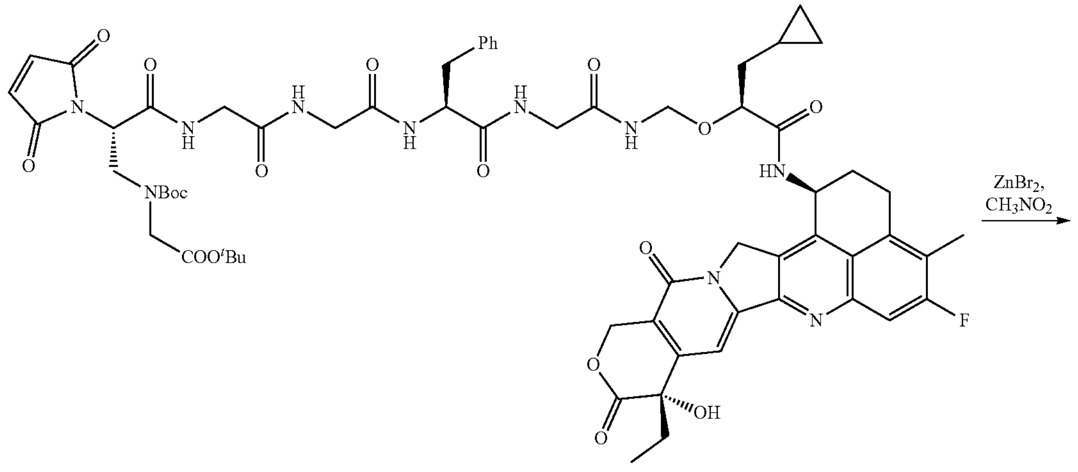

20e-1

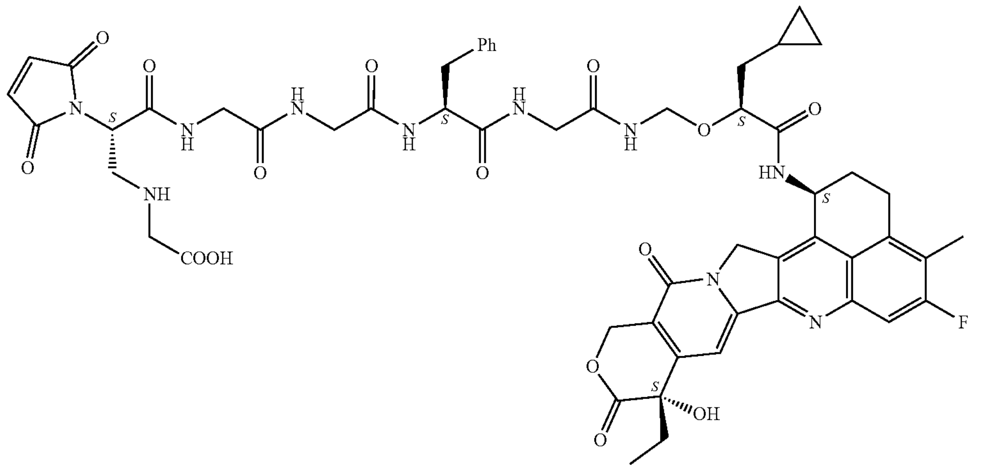

20A

In a 25 mL single-necked flask, 8A (100 mg, 0.078 mmol), zinc bromide (352 mg, 1.57 mmol) and 5 mL of nitromethane were added, and a reaction was carried out at 40° C. for 1 h. After the completion of the reaction as detected by HPLC, the solvent was removed by concentration under reduced pressure and a crude product was obtained. The crude product was purified by high performance liquid chromatography to obtain a product preparation liquid, and the preparation liquid was lyophilized to obtain 51 mg of solid; LC-MS: $[M+H]^+=1119.4$.

Step 6: Compound 20B

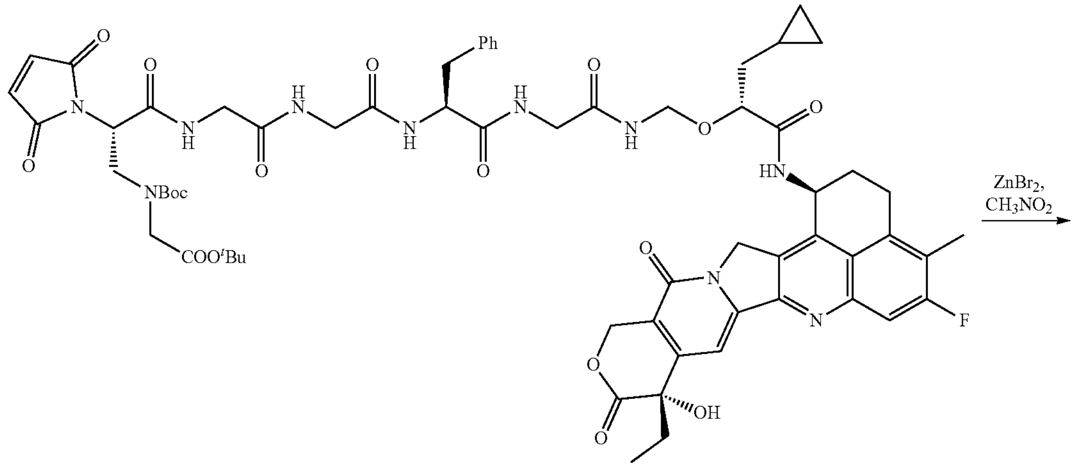

20e-2

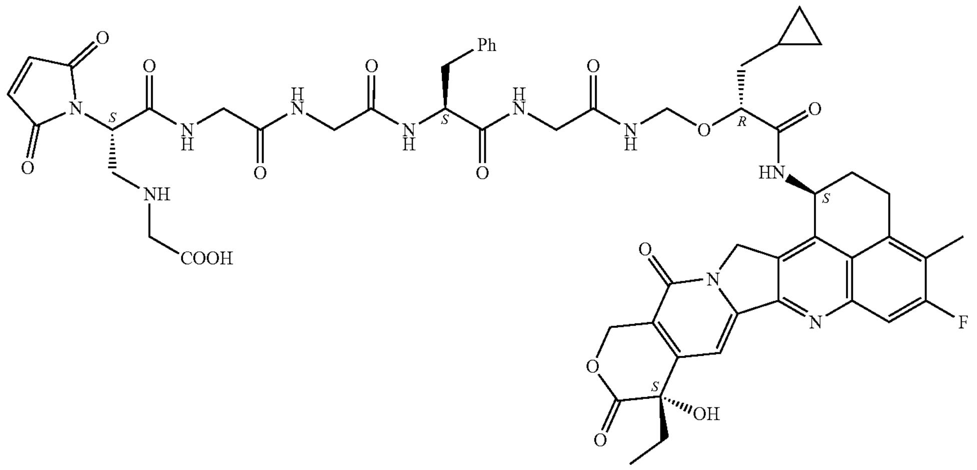

20B 20e-2 (100 mg, 0.079 mmol), zinc bromide (357 mg, 1.59 mmol) and 5 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain a product preparation liquid, and the preparation liquid was lyophilized to obtain 47 mg of a solid; LC-MS: $[M+H]^+$=1119.4.

Example 32
Synthesis of Compound 21:
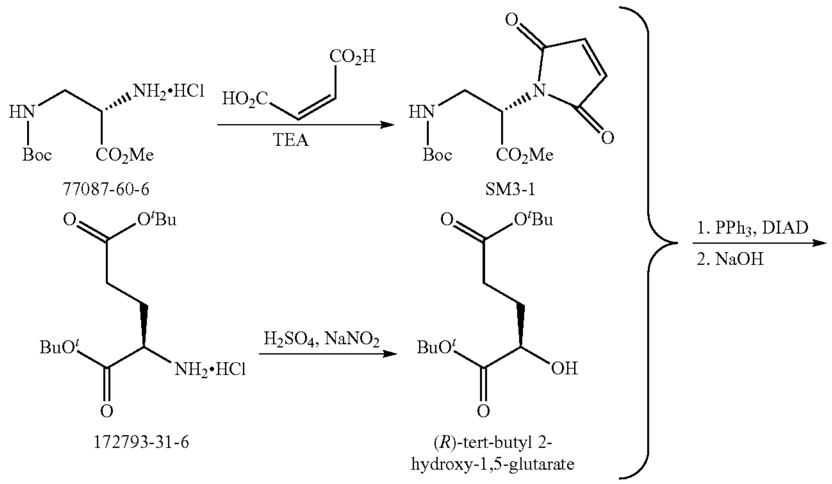
77087-60-6
SM3-1
172793-31-6
(*R*)-tert-butyl 2-hydroxy-1,5-glutarate
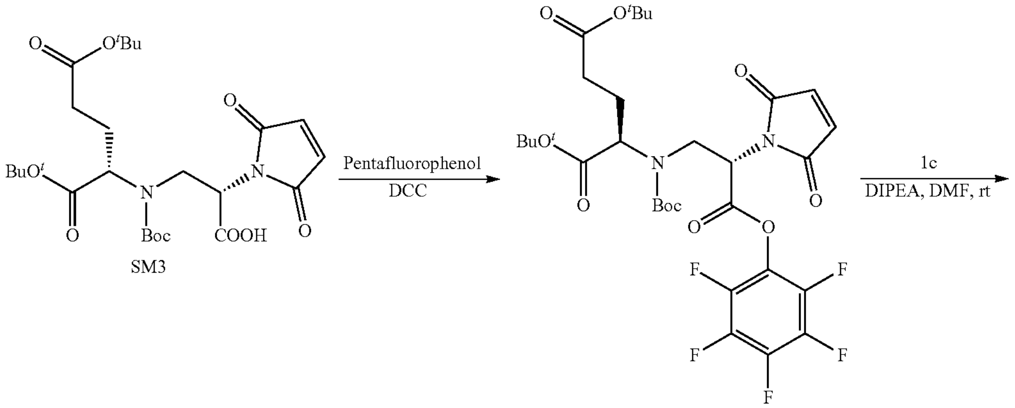
SM3
M6
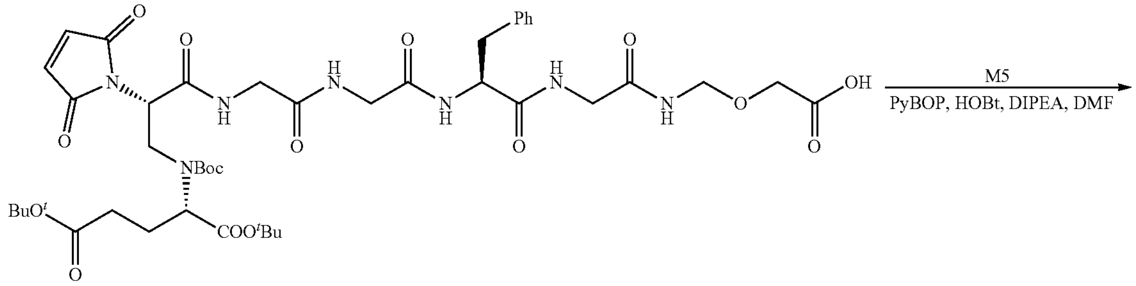
21a -continued

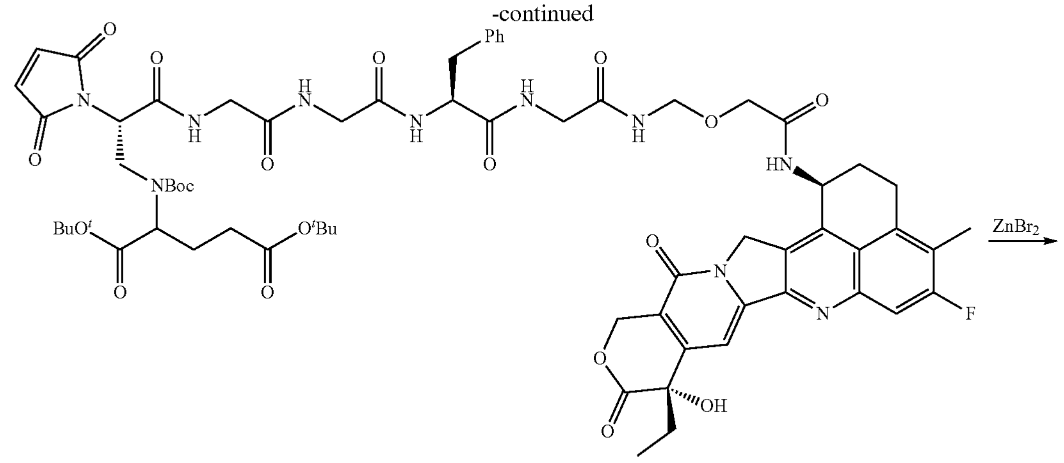

21b

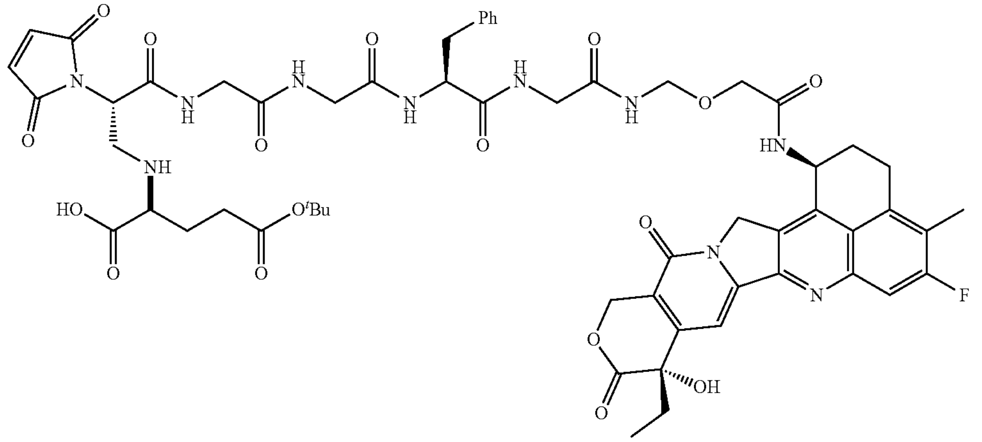

21

Step 1: Compound SM3-1

Add 77087-60-6 (100 g, 458 mmol), maleic acid (53.4 g, 460 mmol), TEA (64 mL, 460 mmol) and 1000 mL toluene in a 2000 mL single-necked flask and heat to 100° C. to react for 5 h. After the reaction was completed, the temperature was lowered to room temperature, and then filtering was performed to remove insoluble material, and the filtrate was concentrated to obtain a crude product. The crude product was purified by silica gel column chromatography (PE:EA=100:1-50:1-20:1) to obtain 75.6 g of the target material; LC-MS: $[M+H]^+$=299.1.

Step 2: Compound (R)-tert-butyl 2-hydroxy-1,5-glutarate

Add 172793-31-6 (100 g, 338 mmol) and 1000 mL water in a 2000 mL single-necked flask, then sequentially add sodium nitrite (35 g, 507 mmol) and concentrated sulfuric acid (32 mL, 35 mmol), and slowly raise the temperature to room temperature to react for 24 h. After the reaction was completed, extraction was performed with 500 mL of ethyl acetate three times, and the organic phase was dried with anhydrous sodium sulfate, filtered, and concentrated under reduced pressure to remove the solvent, and a crude product was obtained. The crude product was purified by silica gel column chromatography (PE:EA=50:1-30:1-2:1) to obtain 91.2 g of the target material; LC-MS: $[M+H]^+$=261.4.

Step 3: Compound SM3

Add (R)-tert-butyl 2-hydroxy-1,5-glutarate (50 g, 192 mmol) and 1000 mL of anhydrous tetrahydrofuran into a 2000 mL single-necked flask, cool down the temperature to 0° C. in an ice-water bath, then add $PPh_3$ (87.7 g, 288 mmol), DEAD (50.2 g, 288 mmol) and SM3-1 (57.3, 192 mmol) in sequence. The temperature was slowly raised to room temperature to react for 13 h. After completion of the reaction, the insoluble material was removed by filtration and the filtrate was concentrated to obtain a crude product. The crude product was purified by silica gel column chromatography (PE:EA=50:1-30:1-1:1) to obtain 68.6 g of product.

The above product was dissolved in 500 mL of methanol, cooled to 0° C. in an ice-water bath, NaOH (64 mL, 190 mmol, 3M/L) was added dropwise at this temperature, and a reaction was performed for 12 h while maintaining this temperature. Next, the pH was adjusted to 3 by the addition of HCl (6 M/L), extraction was performed five times with 500 mL of dichloromethane, drying was performed with anhydrous sodium sulfate, followed by filtering, the filtrate was concentrated under reduced pressure, and the crude product obtained was purified by column chromatography (DCM/MeOH=50/1-20/1-2/1), to obtain 50.4 g of SM3; LC-MS: $[M-H]^-$=525.5.

Step 4: Compound M6

In a 2000 mL single-necked flask, compound SM3 (50 g, 95 mmol, 1.0 eq), pentafluorophenol (19.2 g, 104.5 mmol, 1.1 eq), DCC (21.5 g, 104.5 mmol, 1.1 eq) and THF (600 mL) were added, and a reaction was carried out at room temperature for 1 h (monitored by TLC), and insoluble material was filtered off. The reaction solution was purified directly by preparative LC, and the preparation liquid was concentrated at 35° C. in a water bath under reduced pressure by water pump to remove acetonitrile, and lyophilized to obtain compound M6 (51.9 g) at 79% yield; LC-MS: $[M+H]^+$=693.3.

Step 5: Compound 21a

In a 25 mL single-necked flask, 1c (1 g, 2.36 mmol) was added, and after dissolution with 25 mL DMF, DIPEA (430 uL, 2.6 mmol) was added, then M6 (1177 mg, 2.36 mmol) was added, and then the temperature was raised to room temperature to react for 1 h. The completion of the reaction was detected by HPLC, and the reaction solution was purified by high performance liquid chromatography to obtain a preparation liquid, which was lyophilized to yield 555 mg of product; LC-MS: $[M-H]^-$=931.0.

Step 6: Compound 21b

In a 100 mL single-necked flask, 21a (500 mg, 0.54 mmol), exatecan mesylate M5 (285 mg, 0.54 mmol), PyBOP (239 mg, 0.6 mmol), HOBt (239 mg, 0.6 mmol) and 10 mL of DMF were added, DIPEA (248 uL, 1.5 mmol) was added in an ice-water bath, and the temperature was raised to room temperature to react for 2 h. After the completion of the reaction as detected by HPLC, the reaction solution was purified by HPLC to obtain the preparation liquid of compound 21b, which was lyophilized to give 231 mg of the compound; LC-MS: $[M+H]^+$=1349.5.

Step 7: Compound 21

Compound 21b (200 mg, 0.1488 mmol), zinc bromide (665 mg, 2.96 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain the product preparation liquid, and the preparation liquid was lyophilized to obtain 103 mg of solid; LC-MS: $[M+H]^+$=1137.5.

Example 33

Synthesis of Compound 22:

22

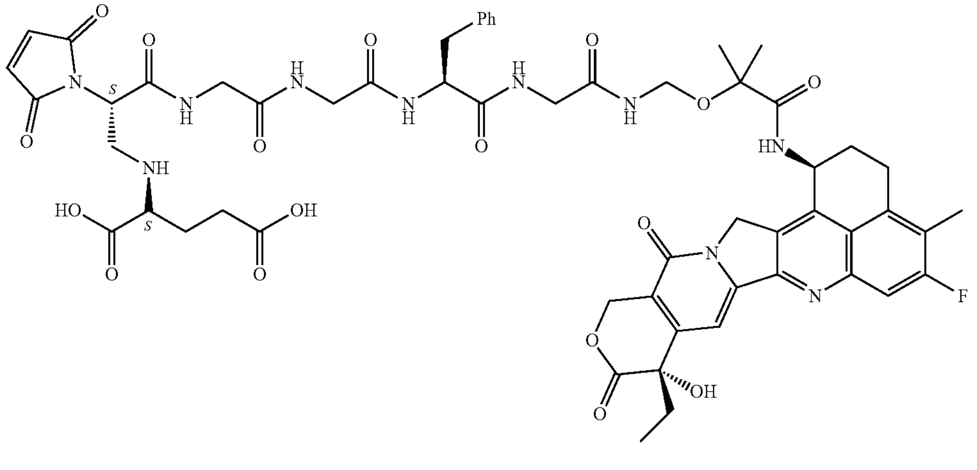

Using compounds M6 and 3c as starting materials and referring to the synthetic route of Example 32, compound 22 (91 mg) was obtained; LC-MS: $[M+H]^+$=1165.5.

Example 34
Synthesis of Compounds 23 and 24:
23
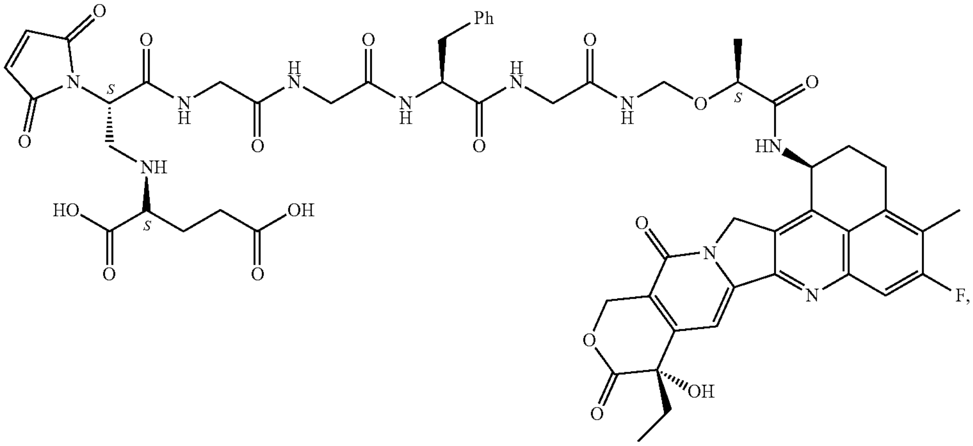
24
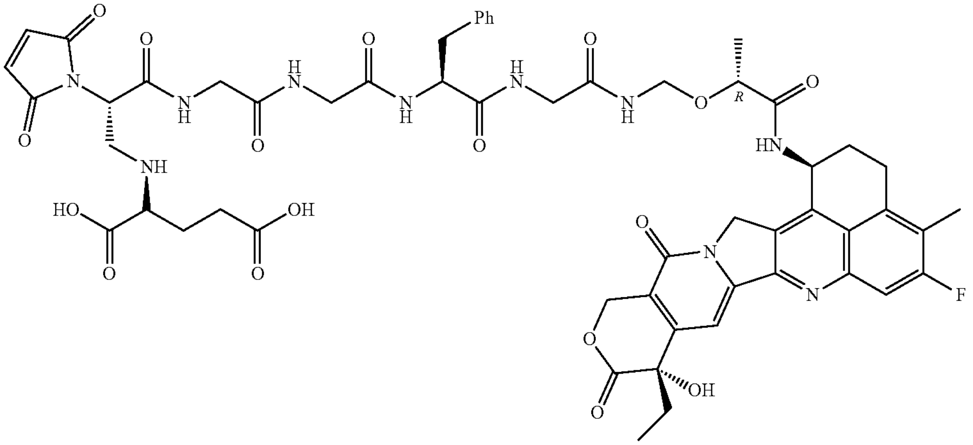
Using compounds M6 and 5c as starting materials and referring to the synthetic route of Example 32, 102 mg of compound 23 was obtained, LC-MS: $[M+H]^+=1151.4$; 99 mg of compound 24 was obtained, LC-MS: $[M+H]^+=1151.4$.
Example 35
Synthesis of Compounds 25 and 26:
25
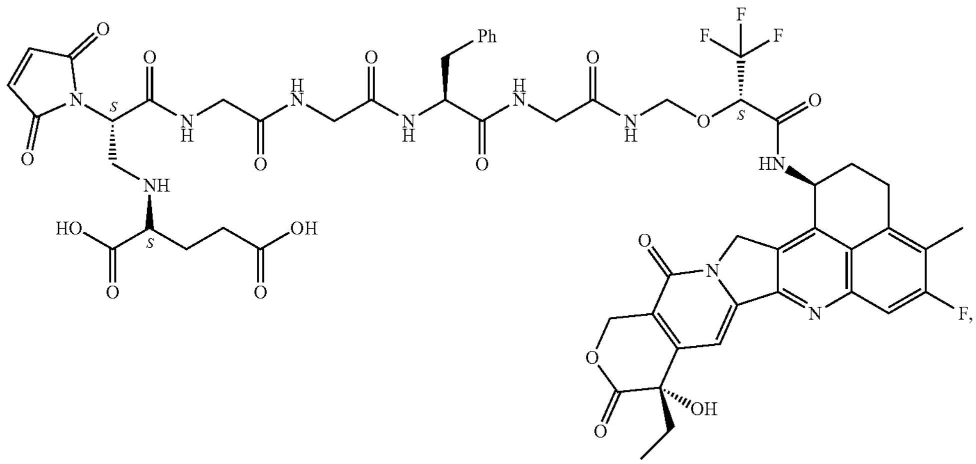

-continued
26
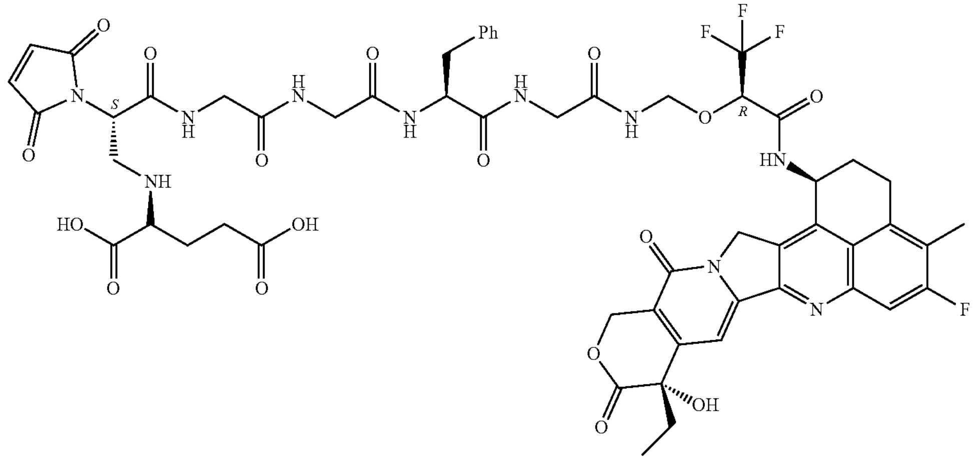
Using compounds M6 and 7c as starting materials and referring to the synthetic route of Example 32, 83 mg of compound 25 was obtained, LC-MS: $[M+H]^+$=1205.7; 80 mg of compound 26 was obtained, LC-MS: $[M+H]^+$=1205.7.
Example 36
Synthesis of Compounds 27 and 28:
27
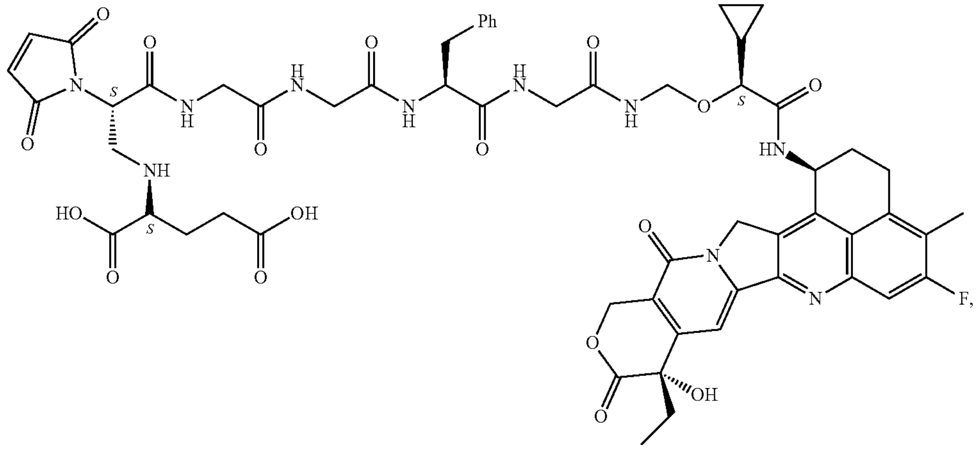
28
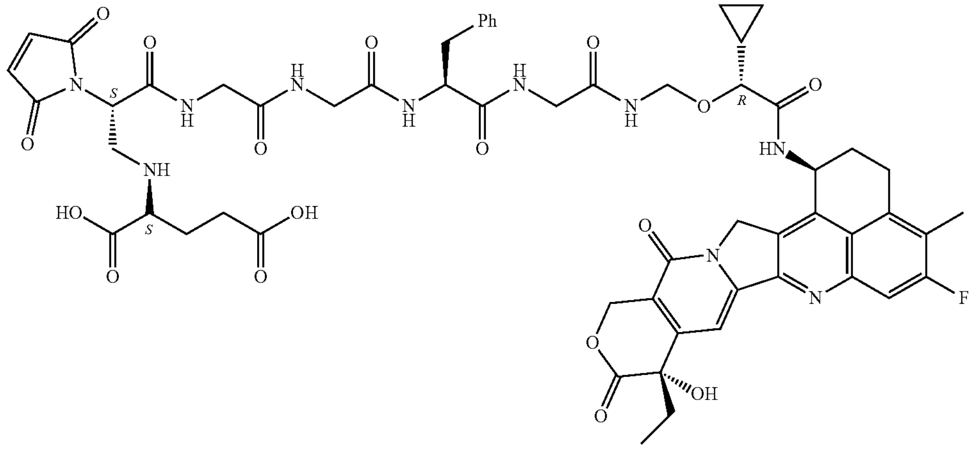

Using compounds M6 and 19c as starting materials and referring to the synthetic route of Example 32, 100 mg of compound 27 was obtained, LC-MS: $[M+H]^+$=1177.5; 101 mg of compound 28 was obtained, LC-MS: $[M+H]^+$=1177.5.
Example 37
Synthesis of Compound 29:
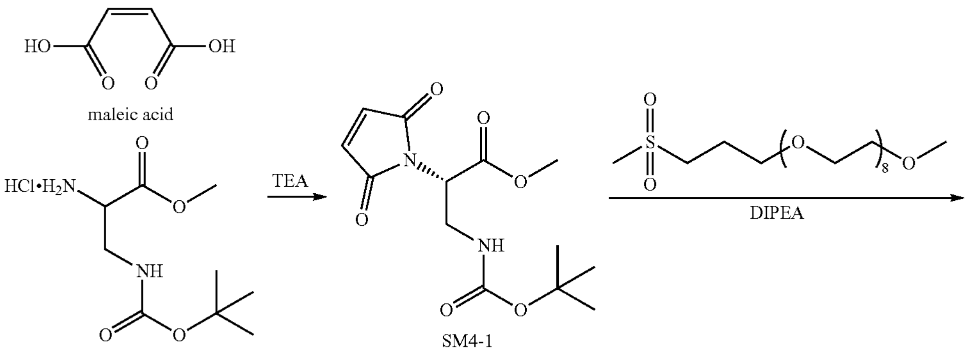
maleic acid
114559-25-0
SM4-1
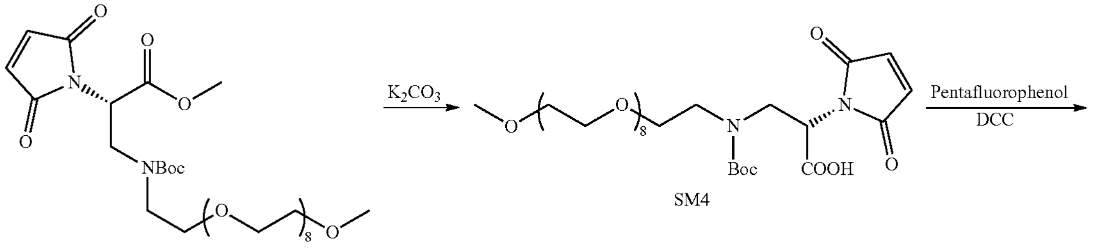
SM4-2
SM4
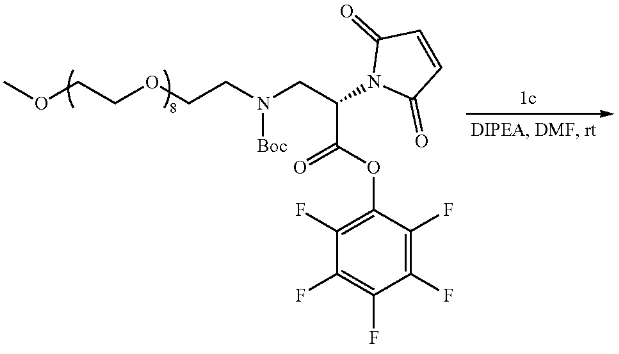
M7
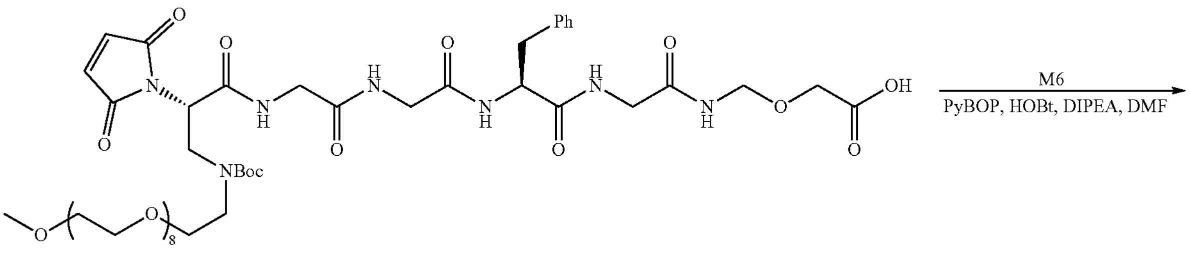
29a -continued

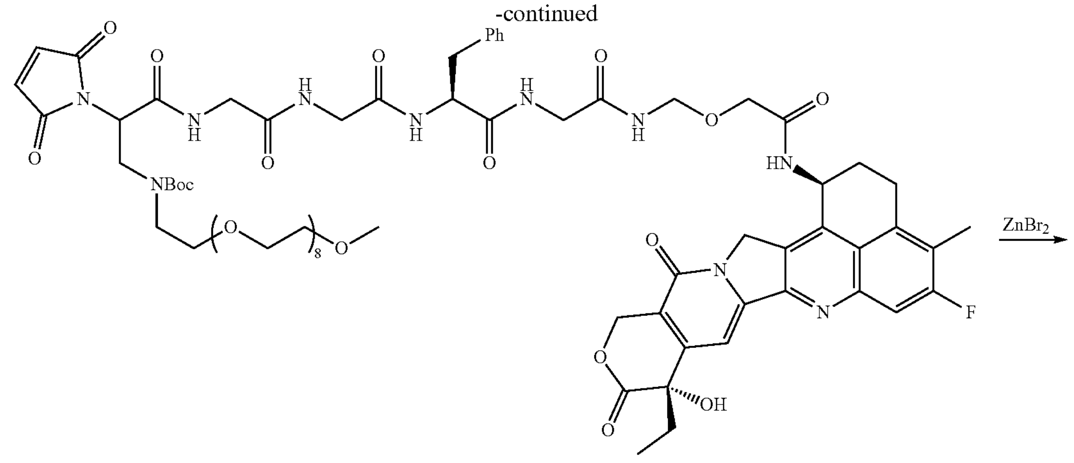

29b

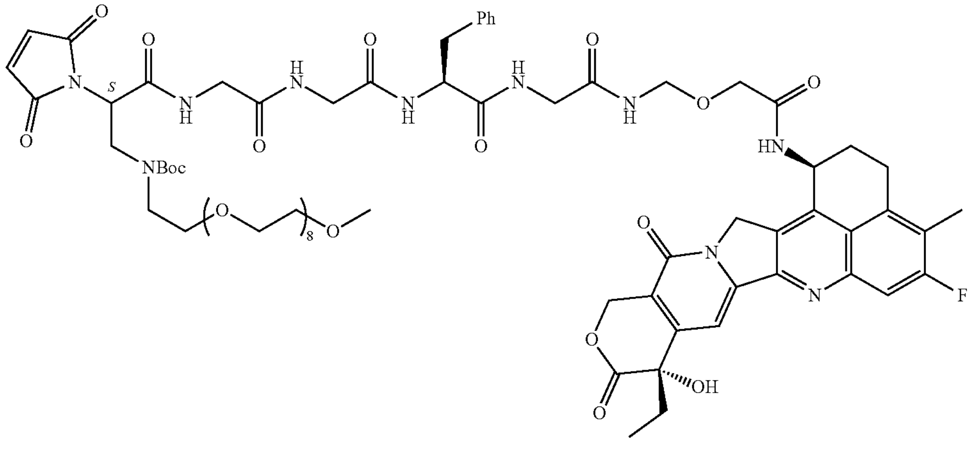

29

Step 1: Compound SM4-1

In a 5000 mL single-necked flask, maleic acid (50 g, 431 mmol, 1.0 eq), 114559-25-0 (110 g, 431 mmol, 1 eq), TEA (263 g, 2.16 mol, 5 eq) and toluene (2000 mL) were added, heating was performed to react under reflux for 5 h (monitored by TLC), and insoluble material was filtered off. The reaction solution was directly subjected to rotary distillation under reduced pressure to remove solvent, and the residue was subjected to silica gel column chromatography (PE/EA=50/1-20/1-1/1) to obtain SM4-1 (64.7 g) at 50% yield; LC-MS: $[M+H]^+$=299.2.

Step 2: Compound SM4-2

SM4-1 (64 g, 215 mmol) was added into a 2000 mL single-necked flask, and after dissolution with 1000 mL of DMF, DIPEA (71 mL, 430 mmol) was added, and then nonaethylene glycol monomethyl ether methanesulfonate (111.5 g, 220 mmol) was added, and then the temperature was raised to room temperature to react for 2 h. The completion of the reaction was detected by HPLC, and the reaction solution was purified by silica gel column chromatography (PE/EA=50/1-20/1-1/1) to obtain 59.9 g of product; LC-MS: $[M+H]^+$=709.4.

Step 3: Compound SM4

SM4-2 (59 g, 83 mmol) was added into a 2000 mL single-necked flask, and after dissolution with 1000 mL MeOH, $K_2CO_3$ (11.75 g, 85 mmol) was added, and then a reaction was carried out at room temperature for 4 h. When the reaction was complete as detected by HPLC, insoluble materials were removed by filtration, and the reaction solution was purified directly by preparative LC, and the preparation liquid was concentrated at 35° C. in a water bath under reduced pressure by water pump to remove acetonitrile, and then lyophilized to obtain compound SM4 (27 g); LC-MS: $[M-H]^-$=693.5.

Step 4: Compound M7

In a 500 mL single-necked flask, compound SM4 (25 g, 36 mmol, 1.0 eq), pentafluorophenol (7.3 g, 40 mmol, 1.1 eq), DCC (8.2 g, 40 mmol, 1.1 eq) and THF (200 mL) were added, a reaction was carried out at room temperature for 1 h (monitored by TLC), and insoluble material was filtered off. The reaction solution was purified directly by preparative LC, and the preparation liquid was concentrated at 35° C. in a water bath under reduced pressure by water pump to remove acetonitrile, and lyophilized to obtain compound M7 (23.3 g) at 93% yield; LC-MS: $[M+H]^+$=695.8.

Step 5: Compound 29a

In a 25 mL single-necked flask, 1c (1 g, 2.36 mmol) was added, and after dissolution with 25 mL DMF, DIPEA (430 uL, 2.6 mmol) was added, then M7 (1640 mg, 2.36 mmol)

was added, and then the temperature was raised to room temperature to react for 1 h. The completion of the reaction was detected by HPLC, and the reaction solution was purified by high performance liquid chromatography to obtain a preparation liquid, which was lyophilized to obtain 609 mg of product; LC-MS: $[M-H]^-$=1098.5.

Step 6: Compound 29b 29a (500 mg, 0.45 mmol), exatecan mesylate M5 (240 mg, 0.45 mmol), PyBOP (215 mg, 0.54 mmol), HOBt (215 mg, 0.54 mmol) and 10 mL of DMF were added to a 100 mL single-necked flask, DIPEA (248 uL, 1.5 mmol) was added in an ice-water bath, and the temperature was raised to room temperature to react for 2 h. After the completion of the reaction as detected by HPLC, the reaction solution was purified by HPLC to obtain the preparation liquid of compound 29b, and the preparation liquid was lyophilized to obtain 187 mg of the compound; LC-MS: $[M+H]^+$=1517.6.

Step 7: Compound 29

Compound 29b (150 mg, 0.988 mmol), zinc bromide (223 mg, 0.988 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain the product preparation liquid, and the preparation liquid was lyophilized to obtain 114 mg of solid; LC-MS: $[M+H]^+$=1517.9.

Example 38

Synthesis of Compound 30:

30

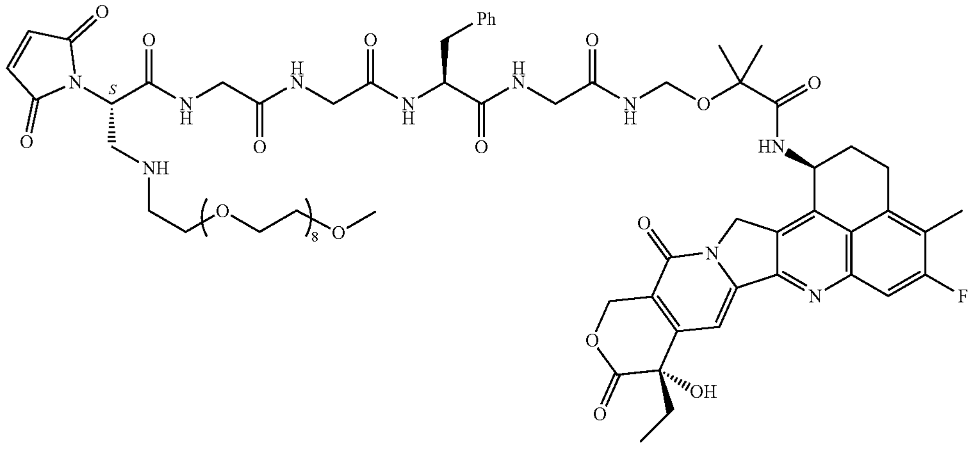

Using compounds M7 and 3c as starting materials and referring to the synthetic route of Example 37, compound 30 (125 mg) was obtained; LC-MS: $[M+H]^+$=1445.6.

Example 39

Synthesis of Compounds 31 and 32:

31

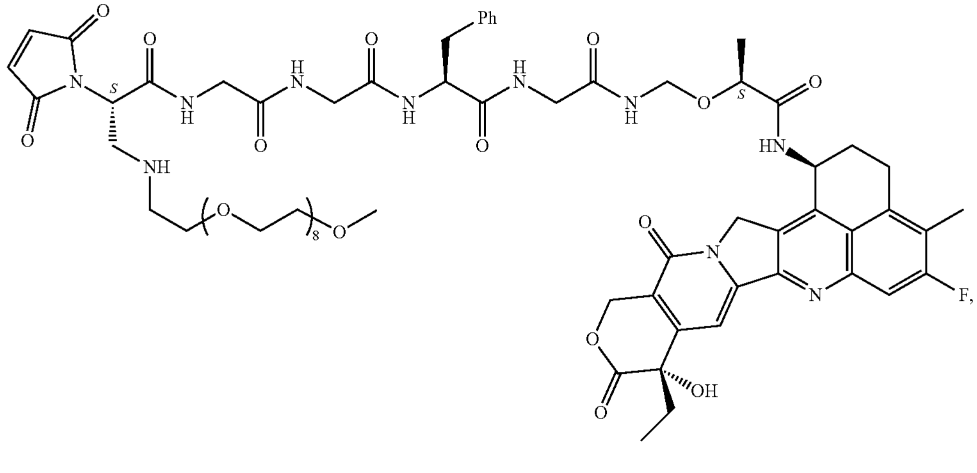

-continued
32
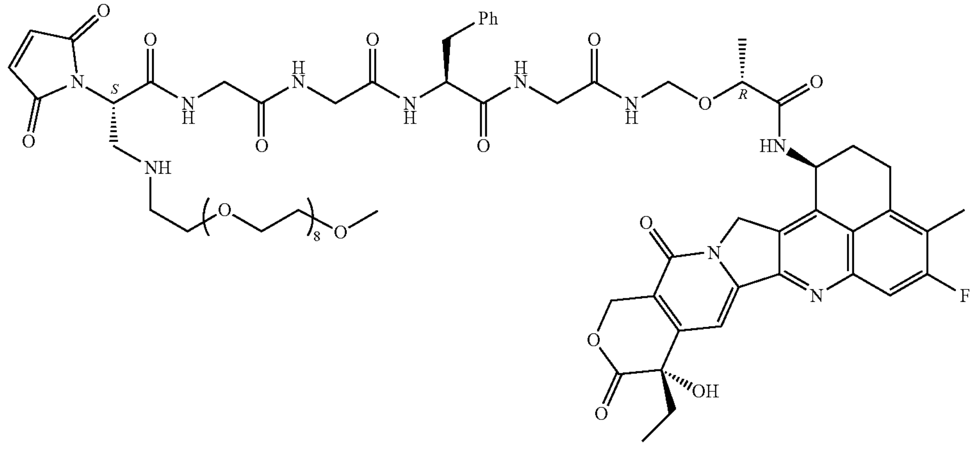
Using compounds M7 and 5c as starting materials and referring to the synthetic route of Example 37, 61 mg of compound 31 was obtained, LC-MS: $[M+H]^+$=1431.7; 63 mg of compound 32 was obtained, LC-MS: $[M+H]^+$=1431.7.
Example 40
Synthesis of Compounds 33 and 34:
33
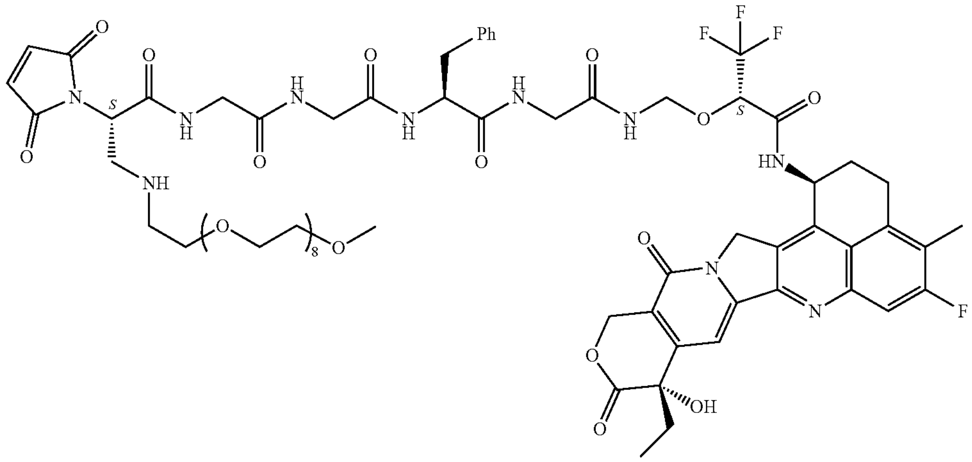
34
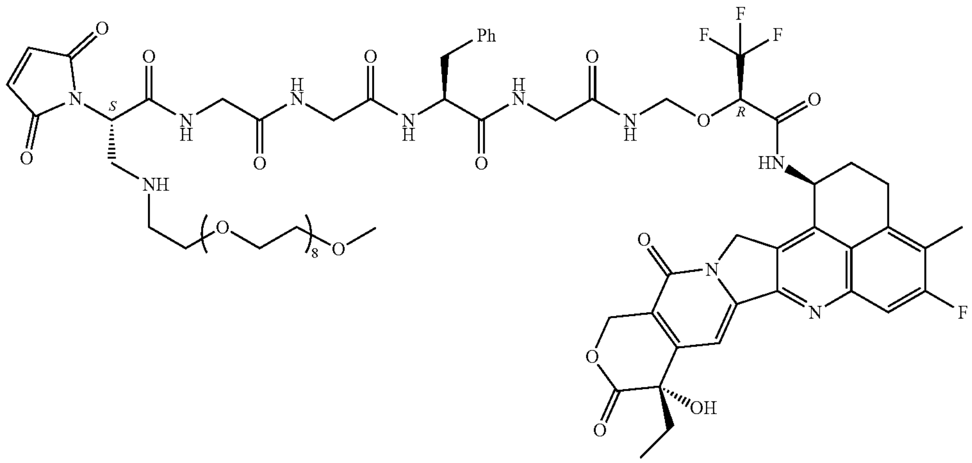

Using compounds M7 and 7c as starting materials, referring to the synthetic route of Example 37, 60 mg of compound 33 was obtained, LC-MS: $[M+H]^+$=1485.6; 58 mg of compound 34 was obtained, LC-MS: $[M+H]^+$=1485.6.

Example 41

Synthesis of Compounds 35 and 36:

35

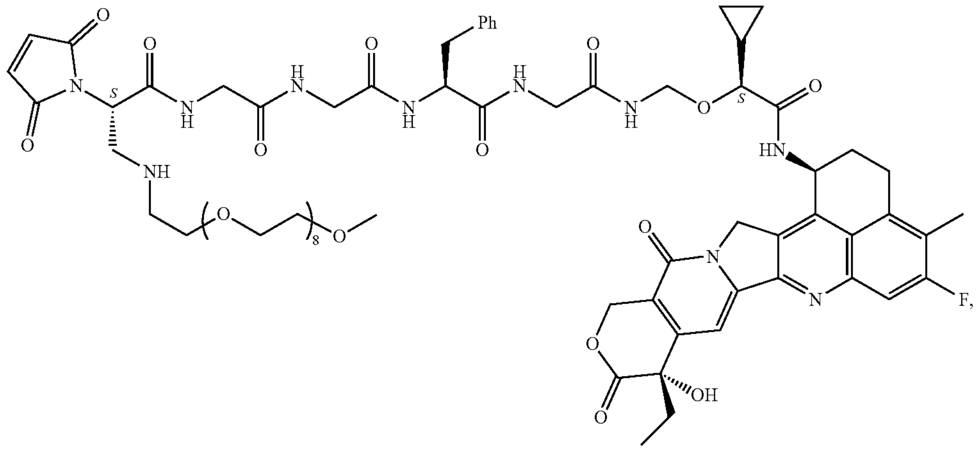

36

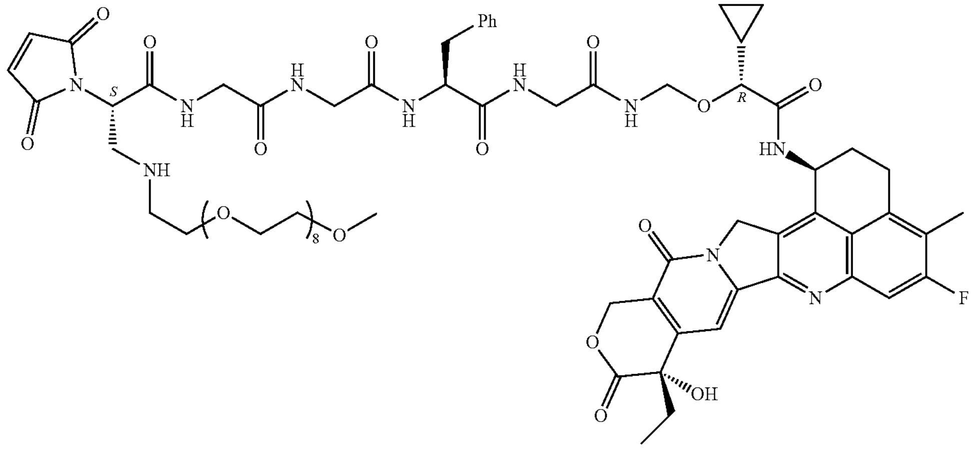

Using compounds M7 and 19c as starting materials and referring to the synthetic route of Example 37, 102 mg of compound 35 was obtained, LC-MS: $[M+H]^+$=1457.8; 102 mg of compound 36 was obtained, LC-MS: $[M+H]^+$=1457.8.

Example 42

Synthesis of Compound 37:

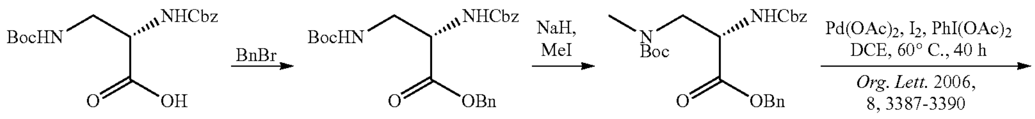

16947-84-5 SM5-1 SM5-2

-continued
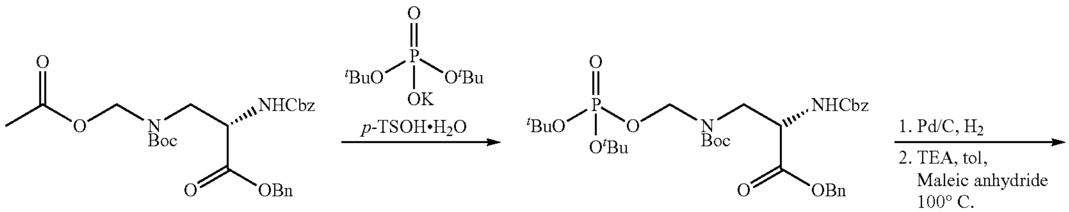
SM5 SM6
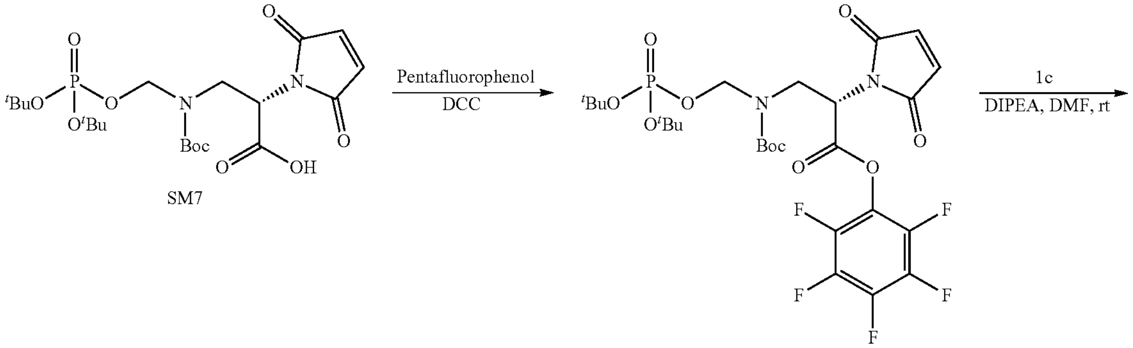
SM7 M8
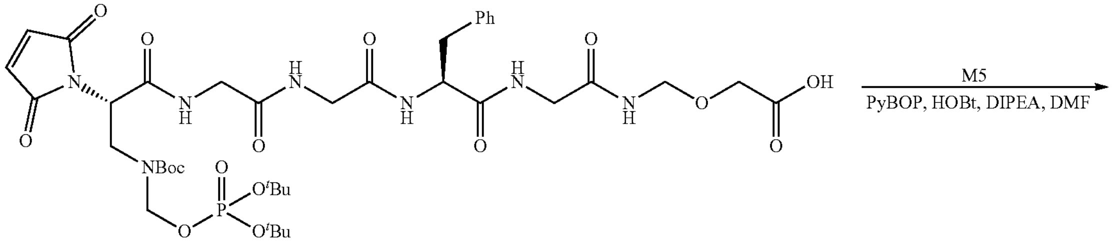
37a
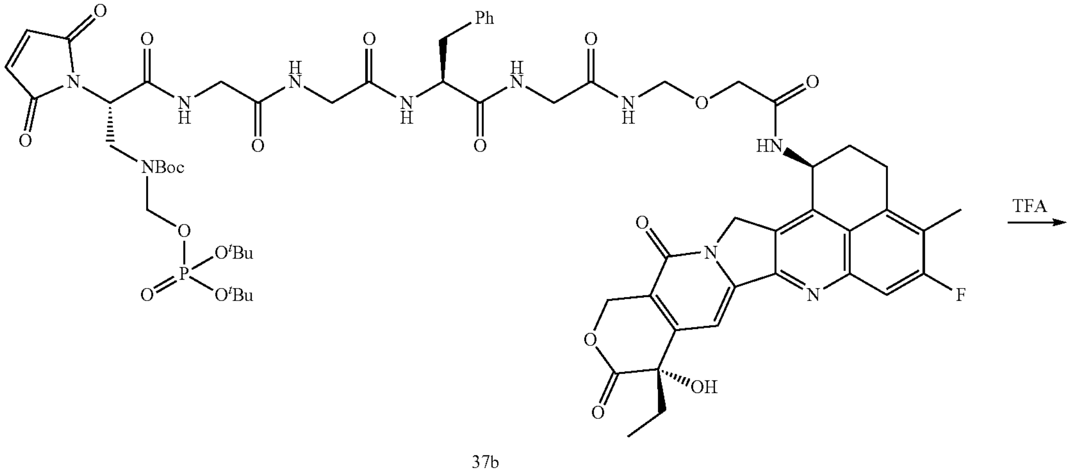
37b -continued

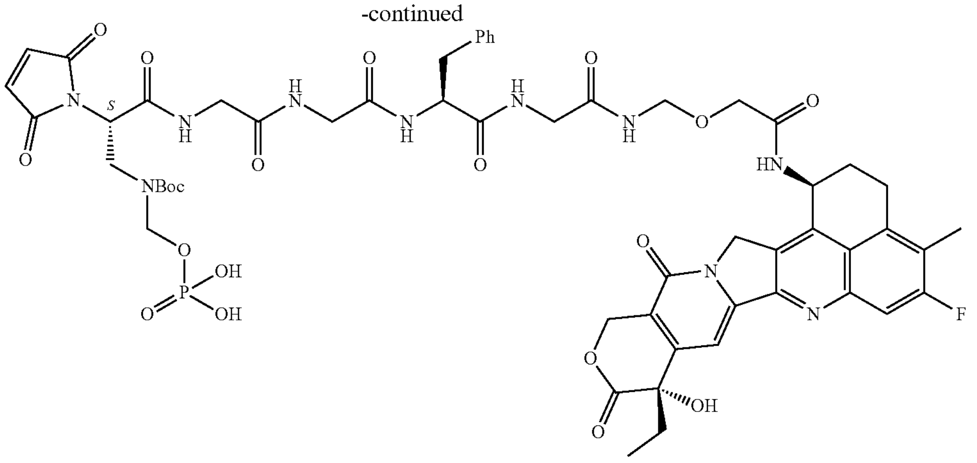

37

Step 1: Compound SM5-1

In a 2000 mL single-necked flask, compound 16947-84-5 (100 g, 295 mmol, 1.0 eq), DIPEA (50 mL, 300 mmol), benzyl bromide (51.3 g, 300 mmol) and T3 (1000 mL) were added, and reacted at room temperature for 12 h (monitored by TLC), and the insoluble material was filtered off. The solvent was directly removed from the reaction solution by rotary distillation under reduced pressure, and the residue was subjected to silica gel column chromatography (PE/EA=50/1-20/1-2/1) to obtain SM5-1 (110.1 g) at 87% yield; LC-MS: $[M+H]^+$=429.2.

Step 2: Compound SM5-2

In a 2000 mL single-necked flask, compound SM5-1 (100 g, 233.4 mmol, 1.0 eq) and THF (1000 mL) were added, cooled to 0° C. in an ice-water bath, NaH (37.4 g, 933.5 mmol) and MeI (132.5 g, 933.5 mmol) were added in batches, and a reaction was maintained at 0° C. for 24 h (monitored by TLC). The reaction was quenched by adding 500 mL of saturated $NH_4Cl$ aqueous solution, extraction was performed three times with 500 mL of ethyl acetate, followed by drying of the organic phase with anhydrous sodium sulfate, and filtering. The solvent was directly removed from the filtrate by rotary distillation under reduced pressure, and the residue was subjected to silica gel column chromatography (PE/EA=100/1-50/1-10/1) to obtain SM5-2 (37.1 g); LC-MS: $[M+H]^+$=443.3.

Step 3: Compound SM5 (cf. *Org. Lett.,* 2006, 8, 3387-3390.)

In a 1000 mL single-necked flask, compound SM5-2 (35 g, 79 mmol, 1.0 eq) and DCE (500 mL) were added, palladium diacetate (180 mg, 0.8 mmol), I2 (20 g, 79 mmol) and iodobenzene diacetate (40.8 g, 126.4 mmol) were added sequentially, and the temperature was raised to 60° C. to react for 40 h (monitored by TLC). The reaction was quenched by adding 500 mL of saturated aqueous sodium thiosulfate solution, extraction was performed three times with 500 mL of dichloromethane, followed by drying of the organic phase with anhydrous sodium sulfate, and filtering. The solvent was directly removed from the filtrate by rotary distillation under reduced pressure, and the residue was subjected to silica gel column chromatography (PE/EA=100/1-50/1-10/1) to obtain SM5 (28 g); LC-MS: $[M+H]^+$=501.3.

Step 4: Compound SM6

In a 500 mL single-necked flask, compound SM5 (25 g, 50 mmol, 1.0 eq), di-tert-butyl potassium phosphate (13.66 g, 55 mmol, 1.1 eq), p-toluenesulfonic acid monohydrate (951 mg, 5 mmol, 0.1 eq) and THF (200 mL) were added, and the reaction was carried out at room temperature for 1 h (monitored by TLC), and insoluble material was filtered off. The reaction solution was purified directly by preparative LC, and the preparation liquid was concentrated at 35° C. in a water bath under reduced pressure by water pump to remove acetonitrile, and lyophilized to obtain compound SM6 (15.1 g) at 46% yield; LC-MS: $[M+H]^+$=651.4.

Step 5: Compound SM7

SM6 (15 g, 23 mmol) and 100 mL of DMF were added into a 250 mL single-necked flask, and after dissolving, 15 g of 5% Pd/C was added in an ice-water bath, the atmosphere in the system was replaced by hydrogen three times, and a reaction was carried out at room temperature for 12 h. The Pd/C was removed by filtration, and then the solvent was removed by rotary distillation under reduced pressure with an oil pump, leaving a crude product ready for use.

In another 250 mL single-necked flask, add the above crude product and 100 mL of toluene, triethylamine (6.4 mL, 46 mmol) and maleic anhydride (2.4 g, 24 mmol), and after dissolution, raise to 100° C. to react for 2 h. Use HPLC to monitor the progress of the reaction, and when the reaction is completed, purify the reaction solution by HPLC, to obtain a preparation liquid. The preparation liquid was extracted with dichloromethane, washed with saturated sodium chloride solution, dried with anhydrous sodium sulfate, filtered, and concentrated to obtain 4.2 g of a solid at 36% yield; LC-MS: $[M+H]^+$=507.3.

Step 6: Compound M8

In a 100 mL single-necked flask, compound SM7 (4 g, 7.9 mmol, 1.0 eq), pentafluorophenol (1.6 g, 8.7 mmol, 1.1 eq), DCC (1.8 g, 8.7 mmol, 1.1 eq) and THF (60 mL) were added, and the reaction was carried out at room temperature for 1 h (monitored by TLC), and insoluble material was filtered off. The reaction solution was purified directly by preparative LC, and the preparation liquid was concentrated at 35° C. in a water bath under reduced pressure by water pump to remove acetonitrile, and lyophilized to obtain compound M8 (3.7 g) at 70% yield; LC-MS: $[M+H]^+$ =673.2.

Step 7: Compound 37a

In a 25 mL single-necked flask, 1c (1 g, 2.36 mmol) was added, and after dissolution with 25 mL of DMF, DIPEA (430 uL, 2.6 mmol) was added, then M8 (1.2 g, 2.36 mmol) was added, and then the temperature was raised to room temperature to react for 1 h. The completion of the reaction was detected by HPLC, and the reaction solution was purified by high performance liquid chromatography to obtain a preparation liquid, which was lyophilized to obtain 488 mg of product; LC-MS: $[M-H]^-$=911.0.

Step 8: Compound 37b 37a (400 mg, 0.44 mmol), exatecan mesylate M5 (235 mg, 0.44 mmol), PyBOP (199 mg, 0.5 mmol), HOBt (69 mg, 0.5 mmol) and 10 mL of DMF were added to a 100 mL single-necked flask, DIPEA (218 uL, 1.32 mmol) was added in an ice-water bath, and the temperature was raised to room temperature to react for 2 h. After the reaction was complete as detected by HPLC, the reaction solution was purified by HPLC to obtain the preparation liquid of compound 37b, which was lyophilized to give 201 mg of the compound; LC-MS: $[M+H]^+$=1329.6.

Step 9: Compound 37

Compound 37b (130 mg, 0.098 mmol), zinc bromide (221 mg, 0.98 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain the product preparation liquid, and the preparation liquid was lyophilized to obtain 96 mg of solid; LC-MS: $[M+H]^+$=1117.4.

Example 43

Synthesis of Compound 38:

38

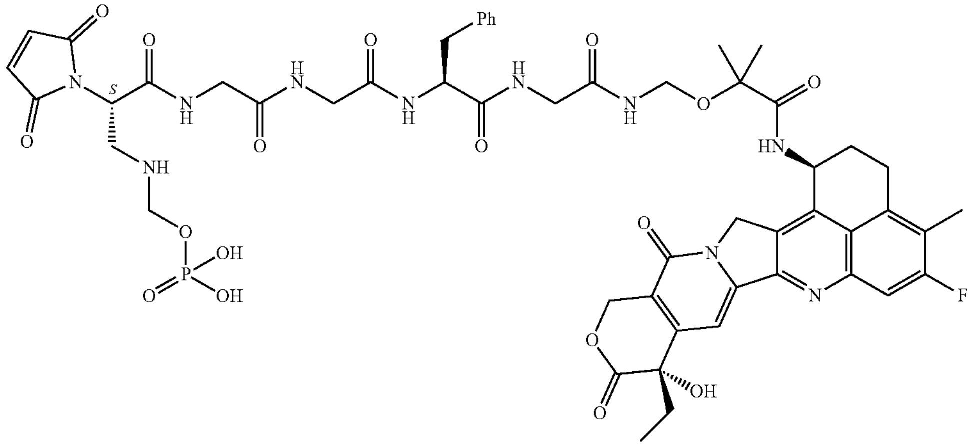

Using compounds M8 and 3c as starting materials and referring to the synthetic route of Example 42, compound 38 (51 mg) was obtained; LC-MS: $[M+H]^+$=1145.6.

Example 44
Synthesis of Compounds 39 and 40:
39
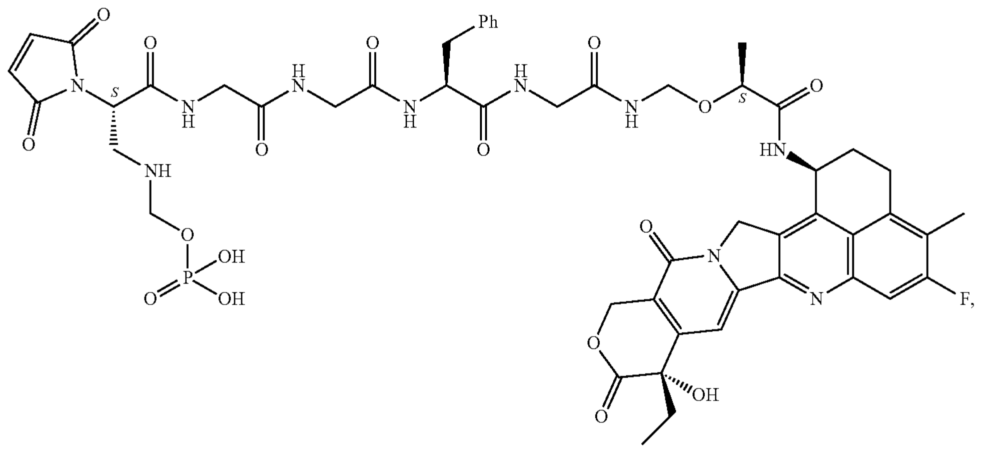
40
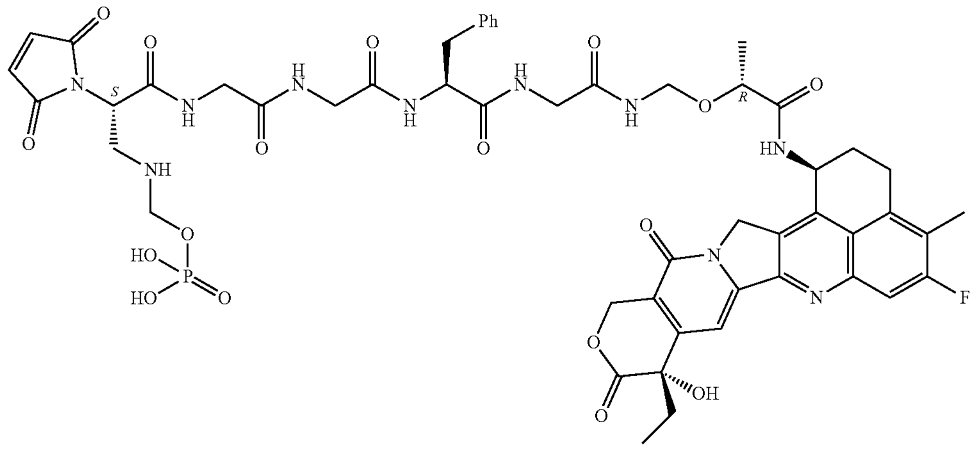
Using compounds M8 and 5c as starting materials and referring to the synthetic route of Example 42, 57 mg of compound 39 was obtained, LC-MS: $[M+H]^+$=1131.4; 60 mg of compound 40 was obtained, LC-MS: $[M+H]^+$= 1131.4.
Example 45
Synthesis of Compounds 41 and 42:
41
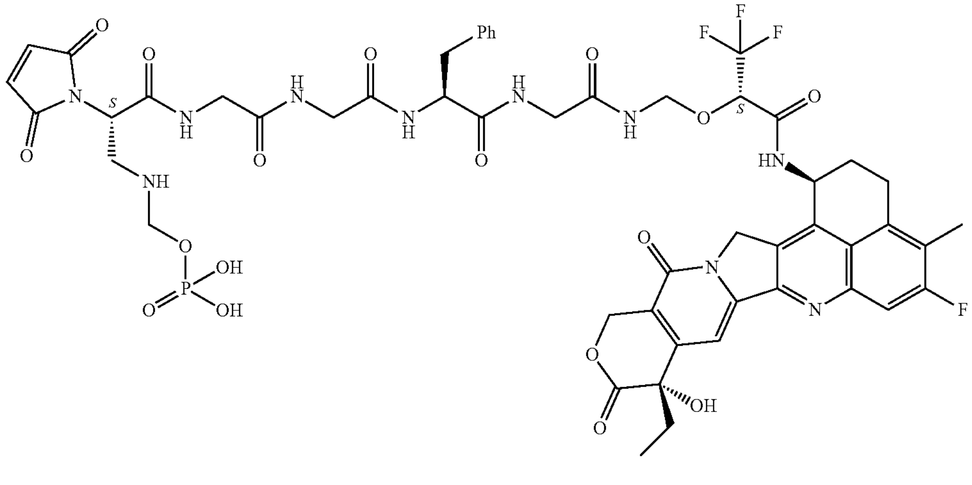

-continued
42
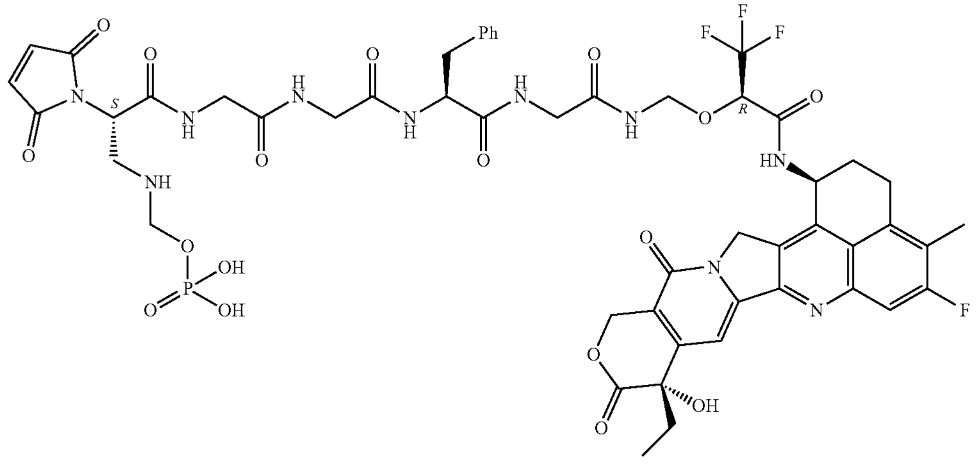
Using compounds M7 and 7c as starting materials, referring to the synthetic route of Example 42, 44 mg of compound 41 was obtained, LC-MS: $[M+H]^+$=1185.3; 44 mg of compound 42 was obtained, LC-MS: $[M+H]^+$=1185.3.
Example 46
Synthesis of Compounds 43 and 44:
43
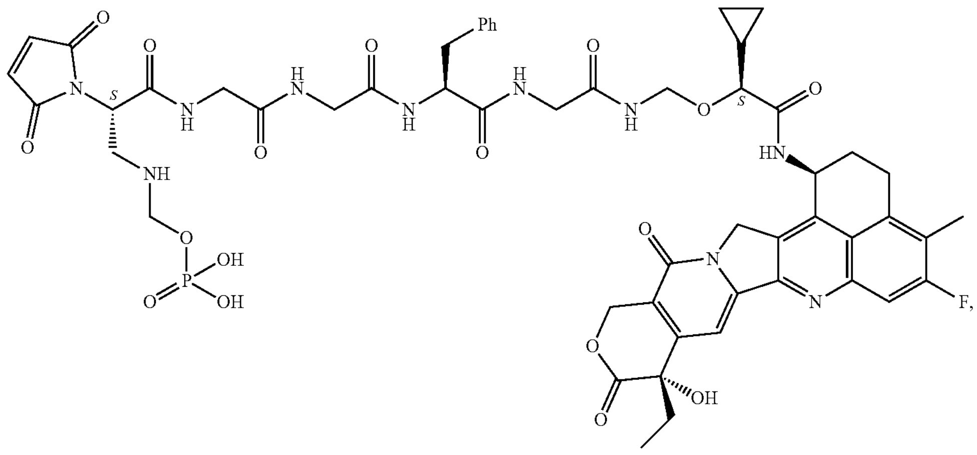
44
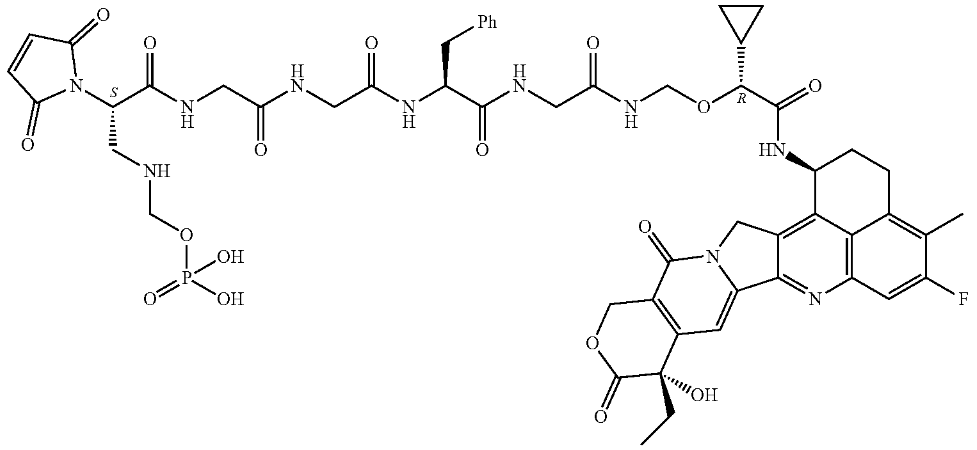

Using compounds M8 and 19c as starting materials and referring to the synthetic route of Example 42, 62 mg of compound 43 was obtained, LC-MS: $[M+H]^+$=1157.4; 59 mg of compound 44 was obtained, LC-MS: $[M+H]^+$= 1157.4.
Example 47 (Comparative Example)
Synthesis of Compound 45:
45
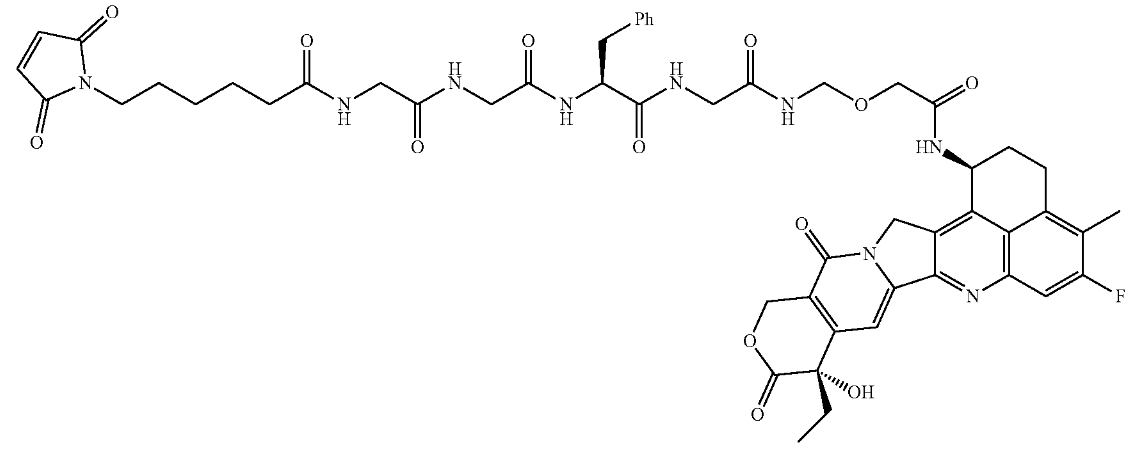
Compound 45 was synthesized by the method provided in Example 58 of patent "CN104755494A".
Example 48
Synthesis of Compound 46:
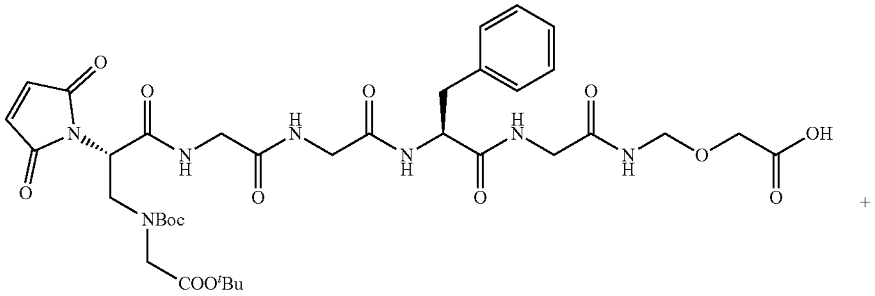
1d
+
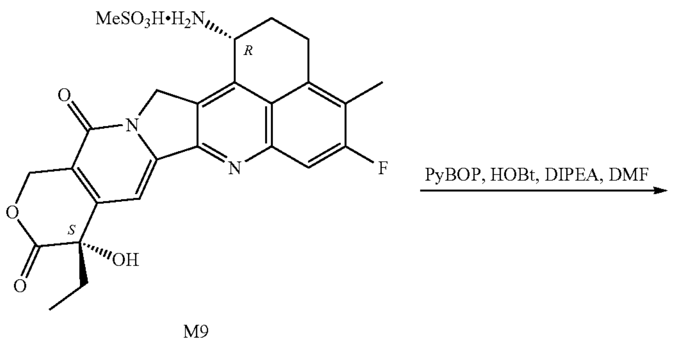
M9

-continued

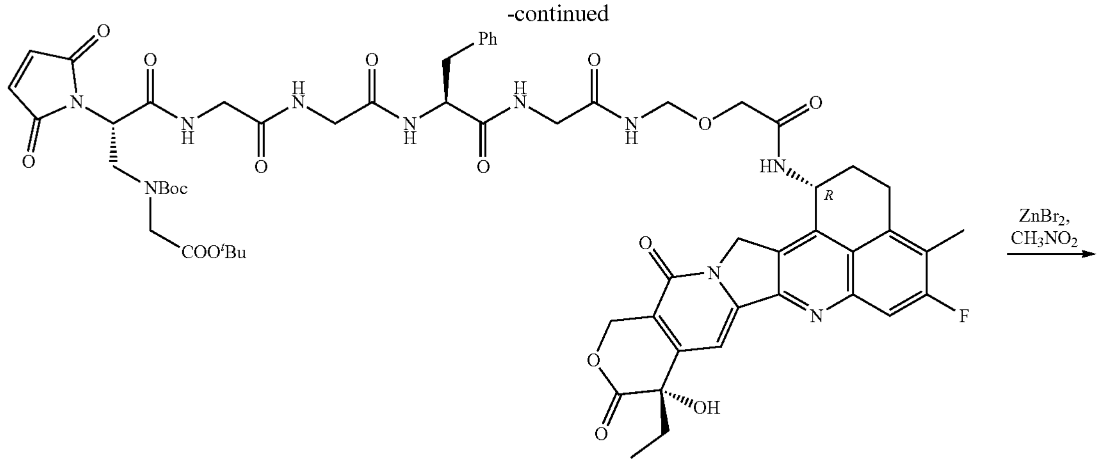

46a

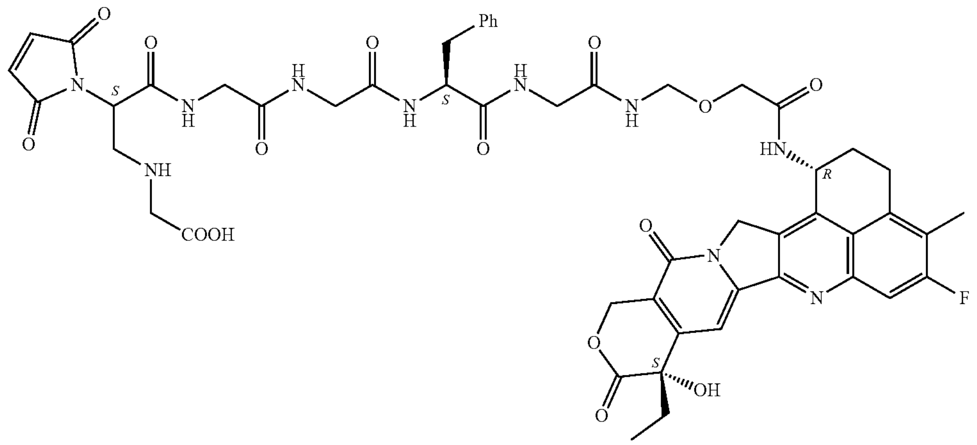

compound 46

Step 1: Compound 46a 1d (500 mg, 0.62 mmol), M9 (310 mg, 0.62 mmol), PyBOP (448 mg, 0.86 mmol), HOBt (116 mg, 0.86 mmol) and 15 mL of DMF were added to a 50 mL single-necked flask, DIPEA (378 uL, 2.29 mmol) was added in an ice-water bath, and the temperature was raised to room temperature to react for 2 h. After the completion of the reaction as detected by HPLC, the reaction solution was purified by high performance liquid chromatography to obtain a preparation liquid, which was lyophilized to give 46a (210 mg); LC-MS: $[M+H]^+$=1221.6.

Step 2: Compound 46

46a (200 mg, 0.162 mmol), zinc bromide (736 mg, 3.26 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain the product preparation liquid, and the preparation liquid was lyophilized to obtain solid compound 46 (120 mg); LC-MS: $[M+H]^+$=1065.3.

Example 49
Synthesis of Compound 47:
compound 47
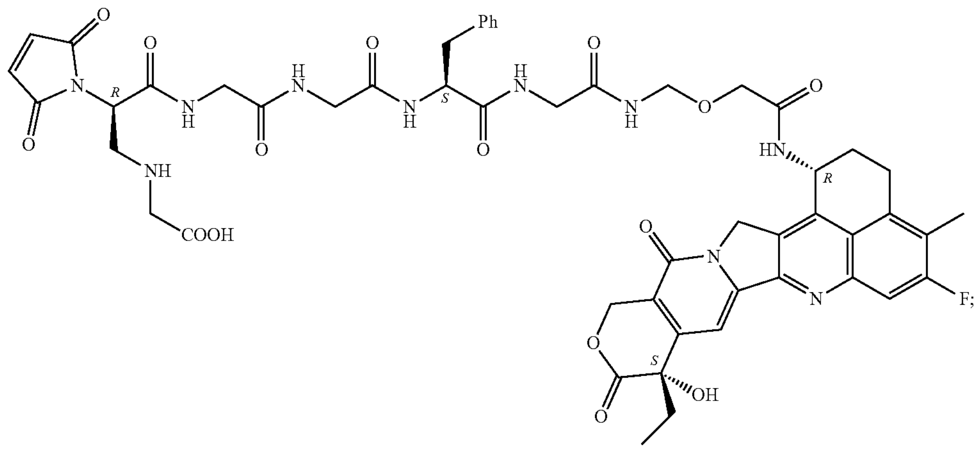
Referring to the synthetic route of Example 48, compound 47 (81 mg) was obtained; LC-MS: $[M+H]^+$=1065.3.
Example 50
Synthesis of Compound 48A:
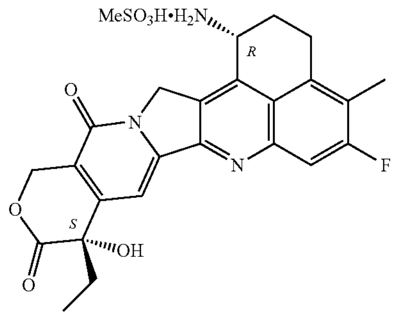
+
M9
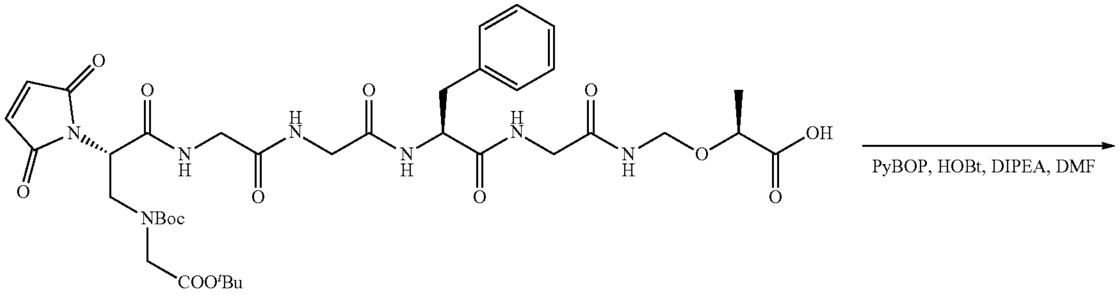
5d -continued

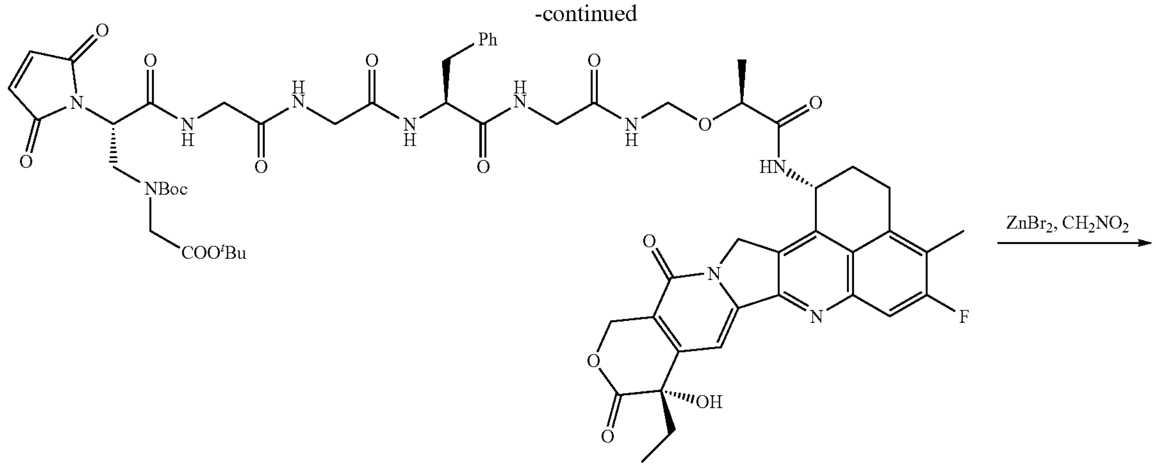

48a

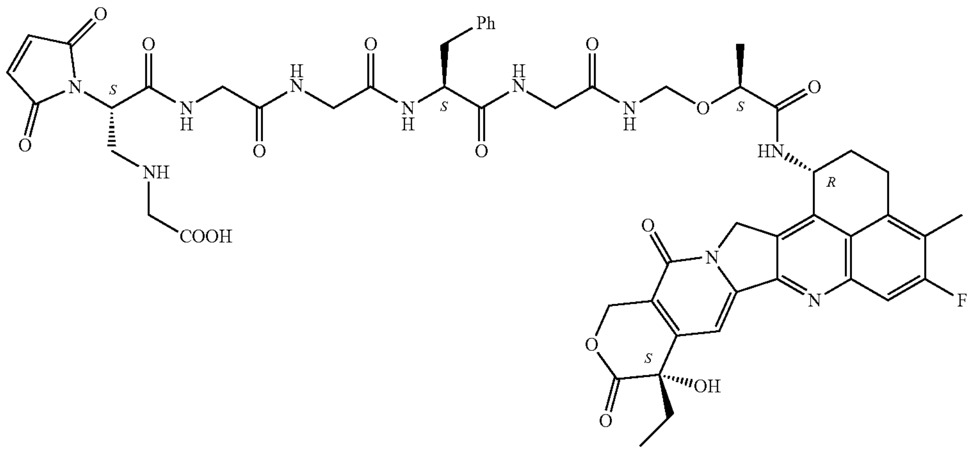

compound 48A

Step 1: Compound 48a

Add 5d (1.66 g, 2.02 mmol, 1.0 eq), M9 (1.08 g, 2.02 mmol, 1.0 eq), PyBOP (1.58 g, 3.03 mmol, 1.5 eq), HOBt (0.41 g, 3.03 mmol, 1.5 eq) and DMF (40 mL) to a 100 mL single-necked flask. DIPEA (0.84 mL, 1.5 eq) was added in an ice-water bath, and the temperature was raised to room temperature to react for 2 h (monitored by HPLC). The reaction solution was directly purified by preparative LC, and the preparation liquid was concentrated at 35° C. in a water bath under reduced pressure by water pump to remove acetonitrile, and freeze-dried to obtain compound 48a (1.54 g), with a yield of 61%; LC-MS: $[M+H]^+=1235.4$.

Step 6: Compound 48A

Add compound 48a (1.0 g, 0.8 mmol, 1.0 eq) and 35 mL nitromethane into a 100 mL single-necked flask, and after dissolving, add zinc bromide (3.64 g, 16 mmol, 20.0 eq), react in an oil bath at 40° C. (preheated to stabilize) for 30 min, and perform concentration in a water bath at 45° C. under reduced pressure with a water pump to remove nitromethane, to obtain a yellow residue solid (monitored by HPLC). A preparation liquid was obtained by acid preparation. The preparation liquid was concentrated at 35° C. in a water bath under reduced pressure by a water pump to remove acetonitrile by spinning, and was lyophilized to obtain compound 48A (786 mg) with a yield of 90%.

Example 51
Synthesis of Compound 48B:
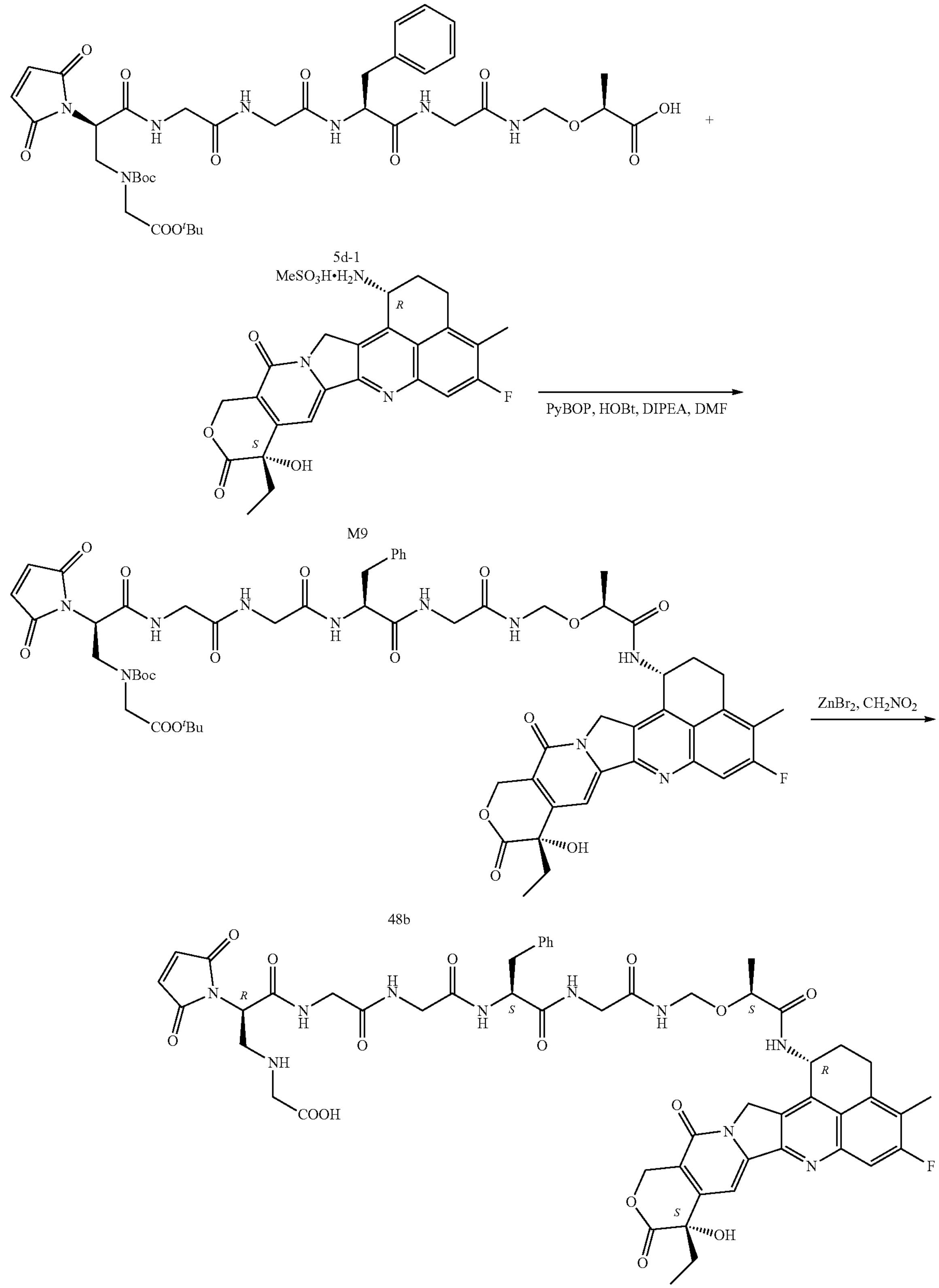
5d-1
M9
48b
compound 48B

Step 1: Compound 48b

Compound 5d-1 (200 mg, 0.24 mmol, 1.0 eq), M9 (127 mg, 0.24 mmol, 1.0 eq), PyBOP (187 mg, 0.36 mmol, 1.2 eq), HOBt (48 mg, 0.36 mmol, 1.2 eq), and DMF (6 mL) were added to a 25 mL single-necked flask. The temperature was lowered to 0-5° C. in an ice-water bath, DIPEA (62 mg, 0.48 mmol, 2.0 eq) was added, and then the temperature was raised to 20±5° C. to react for 2 h. The end of the reaction was detected by HPLC. The reaction solution was purified directly by HPLC preparation, and the product preparation liquid was collected and lyophilized to obtain compound 48b (150.2 mg); LC-MS: $[M+H]^+$=1235.4.

Step 2: Compound 48B

Compound 48b (100 mg, 0.081 mmol, 1.0 eq), ZnBr2 (364 mg, 1.62 mmol, 20.0 eq) and $CH_3NO_2$ (10 mL) were added to a 25 mL single-necked flask in sequence, and then the temperature was raised to 40° C. to react for 0.5 h. The reaction was stopped, and the reaction solution was directly spin-dried at 45° C. under reduced pressure to obtain a yellow solid, taking samples to monitor the reaction by HPLC. The spin-dried solid was directly purified by HPLC preparation, and the product preparation liquid was collected and lyophilized to obtain compound 48B (70.0 mg); LC-MS: $[M+H]^+$=1079.4.

Example 52

Synthesis of Compound 49A:

compound 49A

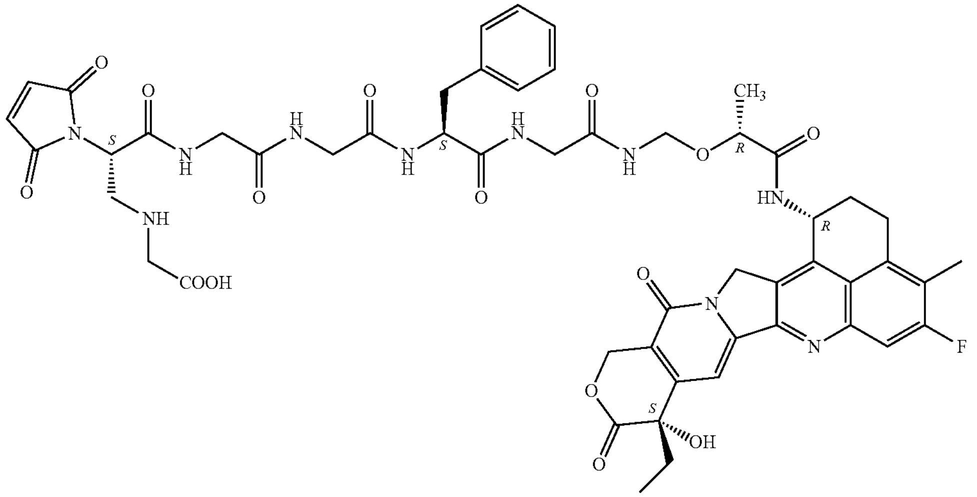

Referring to the route of Example 50, compound 49A (71 mg) was obtained; LC-MS: $[M+H]^+$=1079.4.

Example 53

Preparation of Compound 49B:

compound 49B

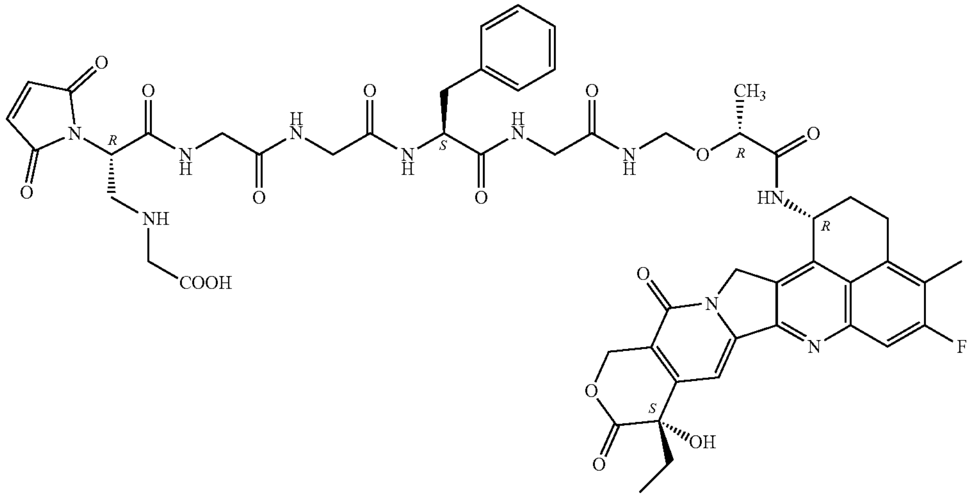

Referring to the synthetic route of Example 51, compound 49B (65 mg) was obtained; LC-MS: $[M+H]^+=1079.4$.
Example 54
Synthesis of Compounds 50A and 50B:
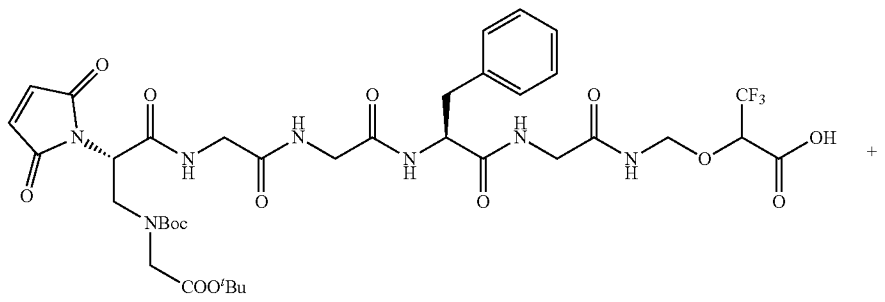
7d
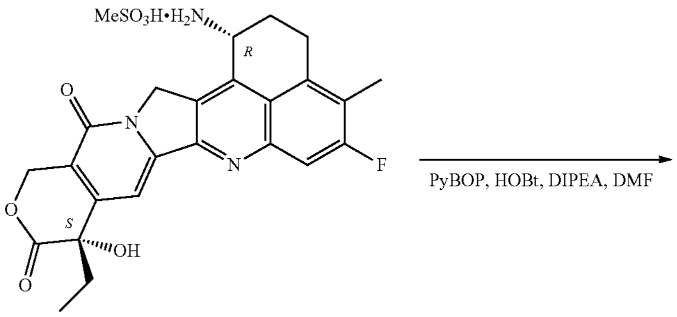
M9
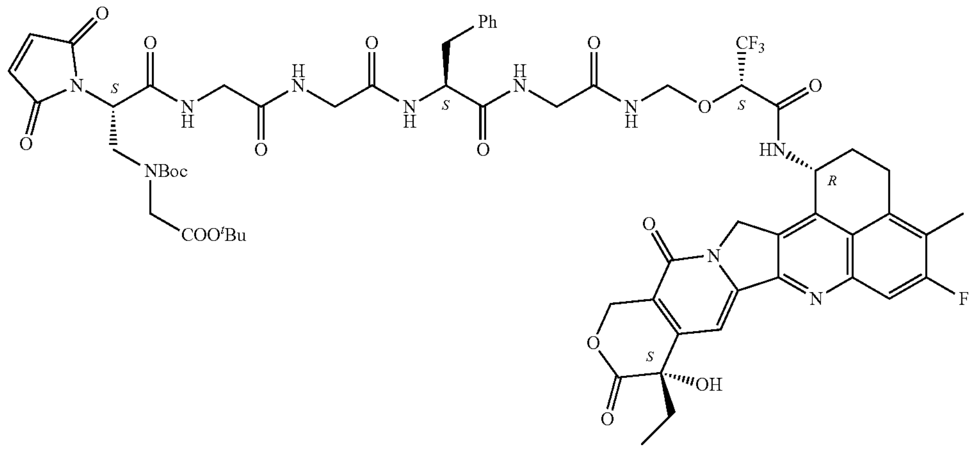
50a -continued

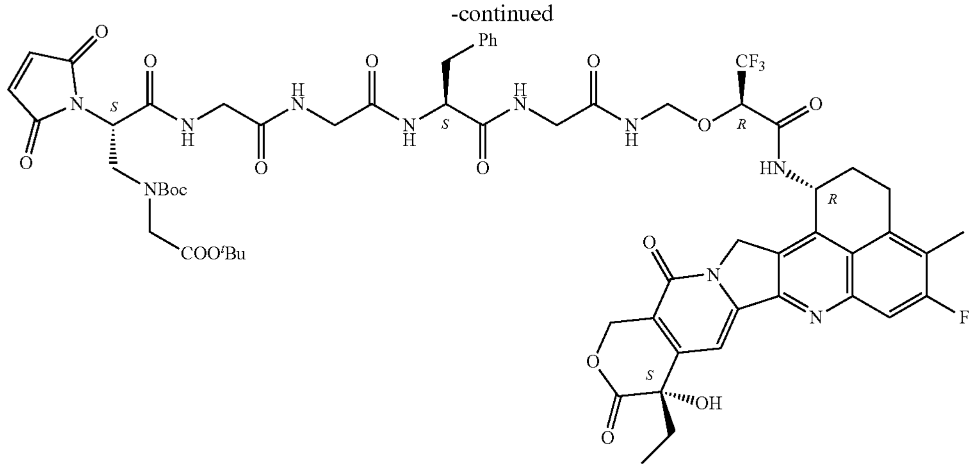

50b

Step Compounds 50a and 50b

Add 7d (500 mg, 0.57 mmol), M9 (305 mg, 0.57 mmol), PyBOP (448 mg, 0.86 mmol), HOBt (116 mg, 0.86 mmol) and 15 mL DMF into a 50 mL single-necked flask, add DIPEA (378 uL, 2.29 mmol) in an ice-water bath, raise to room temperature and react for 2 h. After the completion of the reaction as detected by HPLC, the reaction solution was purified by HPLC to obtain the preparation liquids of compound 50a and compound 50b, and the preparation liquids were freeze-dried respectively to obtain 170 mg of compound 50a, LC-MS: $[M+H]^+$=1289.46, and 202 mg of compound 50b, LC-MS: $[M+H]^+$=1289.46.

Step 2: Compound 50A

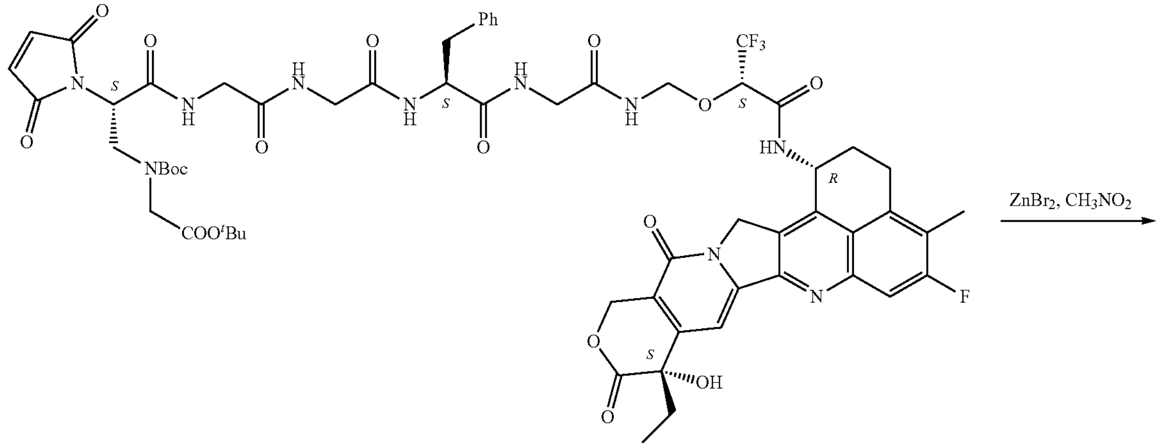

50a

-continued

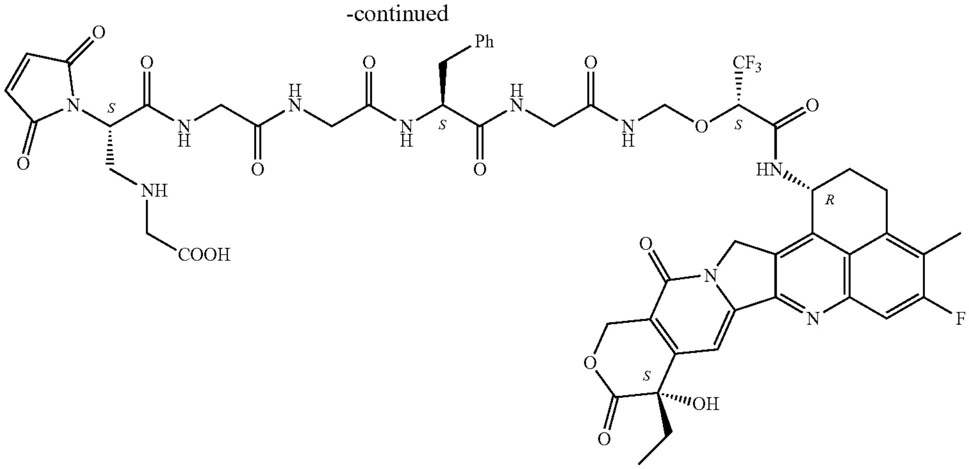

50A

Add 50a (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was freeze-dried to obtain 44 mg of solid.

Step 3: Compound 50B

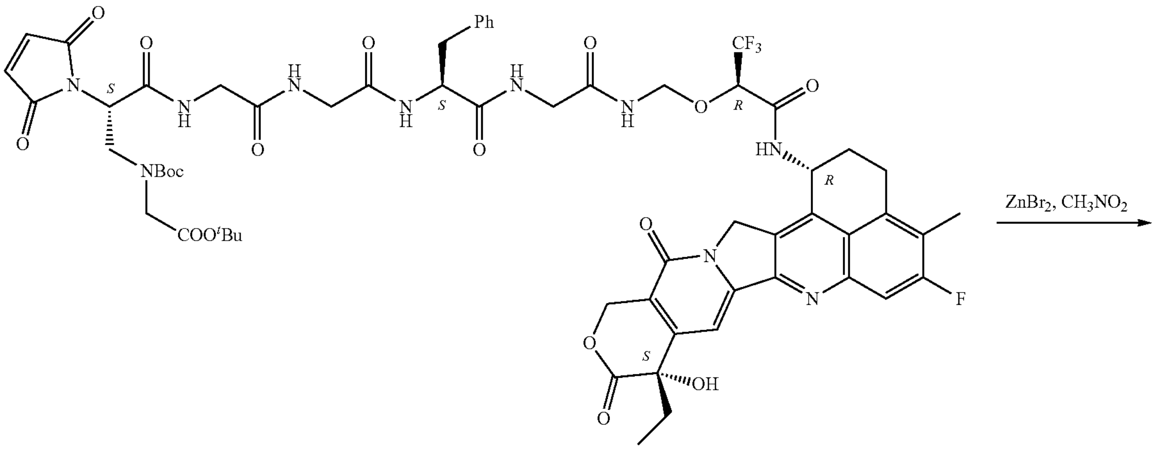

50b

-continued

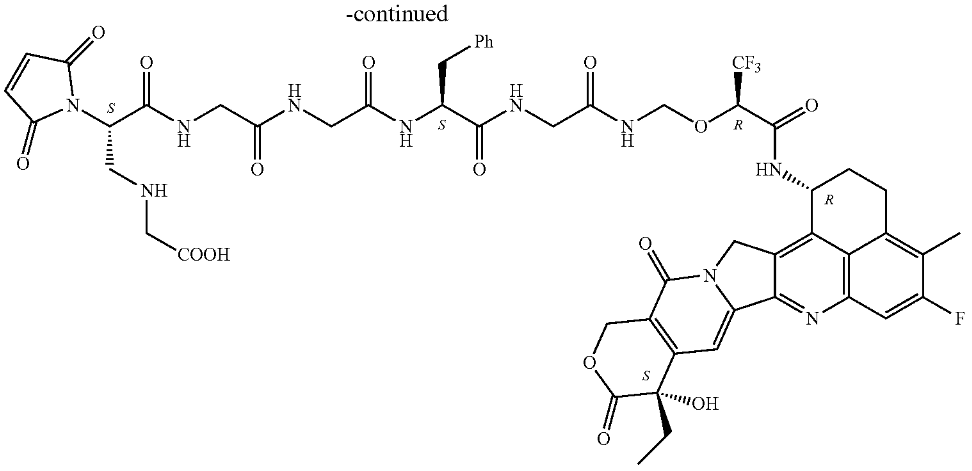

50B

Add 50b (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was freeze-dried to obtain 45 mg of solid.

Example 55

Synthesis of Compounds 51A and 51B:

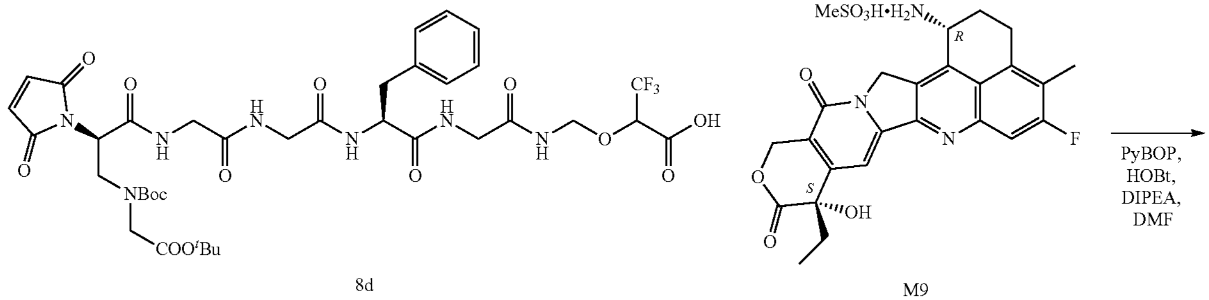

8d

M9

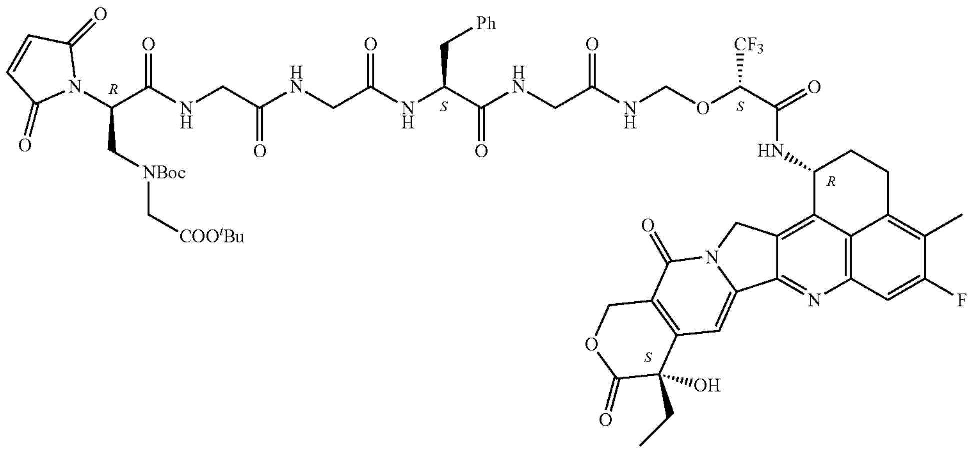

51a

-continued

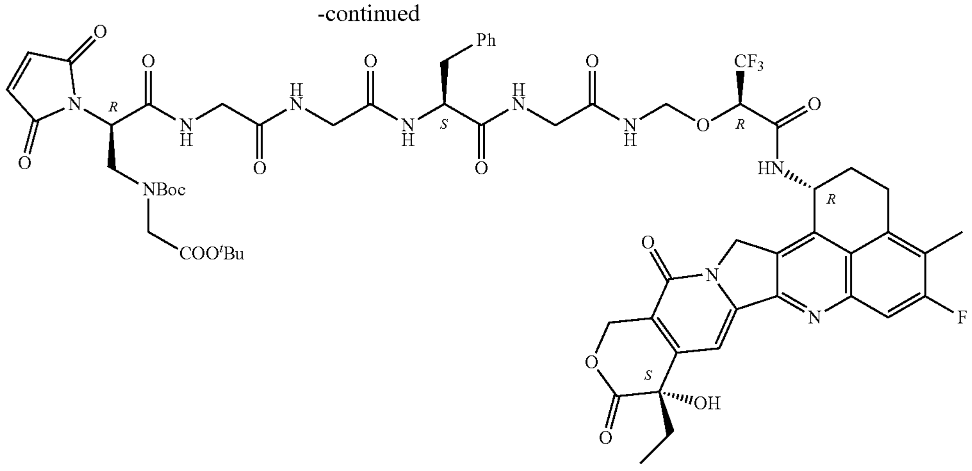

51b

Step 1: Compound 51a and Compound 51b

Add 8d (500 mg, 0.57 mmol), M9 (305 mg, 0.57 mmol), PyBOP (448 mg, 0.86 mmol), HOBt (116 mg, 0.86 mmol) and 15 mL DMF into a 50 mL single-necked flask, add DIPEA (378 uL, 2.29 mmol) in an ice-water bath, raise to room temperature and react for 2 h. After the reaction was complete as detected by HPLC, the reaction solution was purified by HPLC to obtain preparation liquids of compound 51a and compound 51b, which were respectively lyophilized to obtain 190 mg of compound 51a and 186 mg of compound 51b. LC-MS of compound 51a: $[M+H]^+$=1289.47; LC-MS of compound 51b: $[M+H]^+$=1289.47.

Step 2: Compound 51A

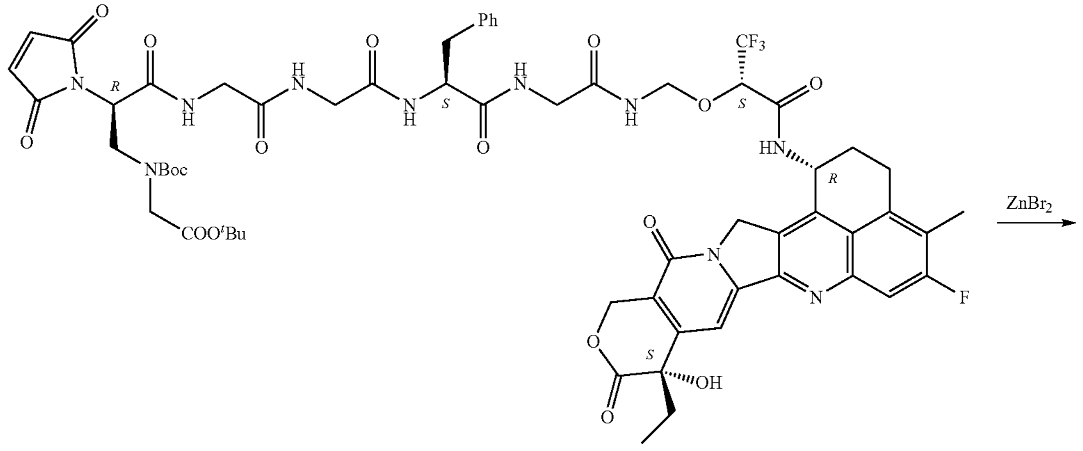

51a

-continued

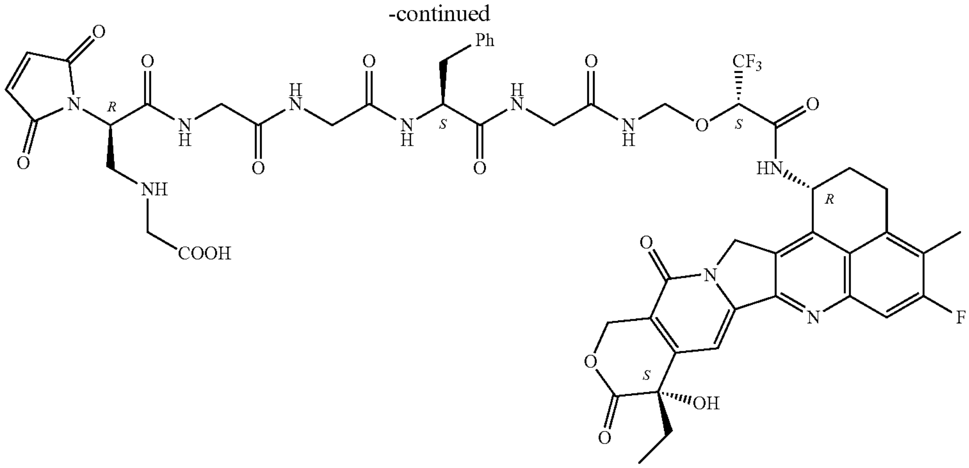

51A

Add compound 51a (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 39 mg of solid.

Step 3: Compound 51B

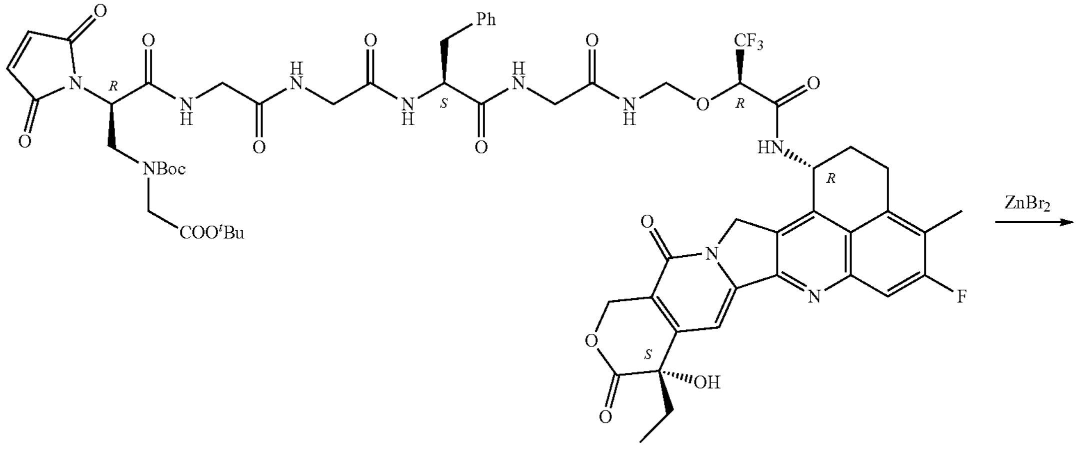

51b

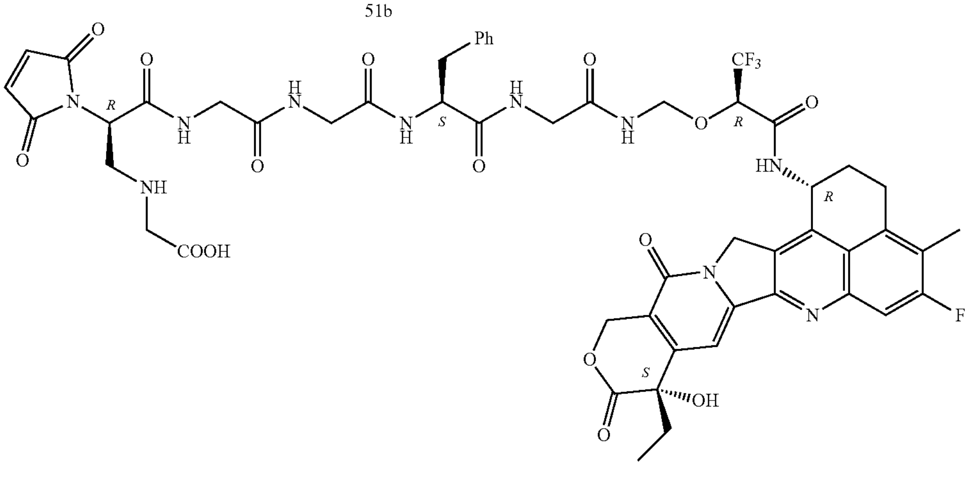

51B

Add compound 51b (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was freeze-dried to obtain 60 mg of solid.

Example 56

Synthesis of Compound 52A:

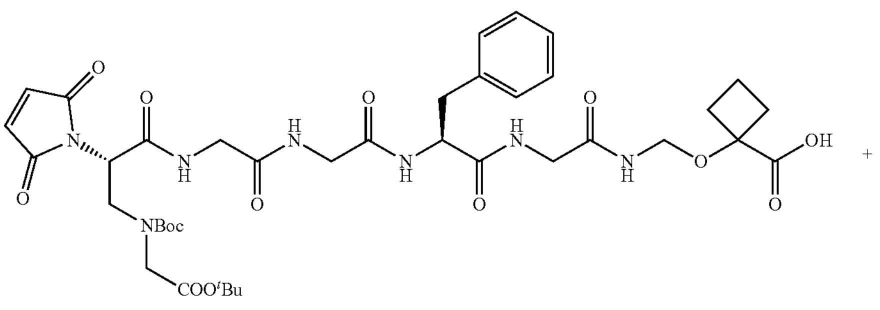

11d

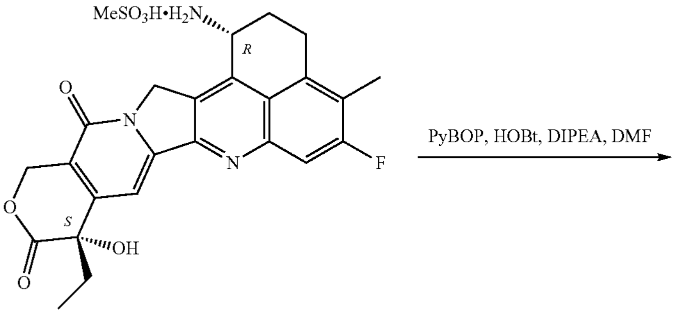

M9

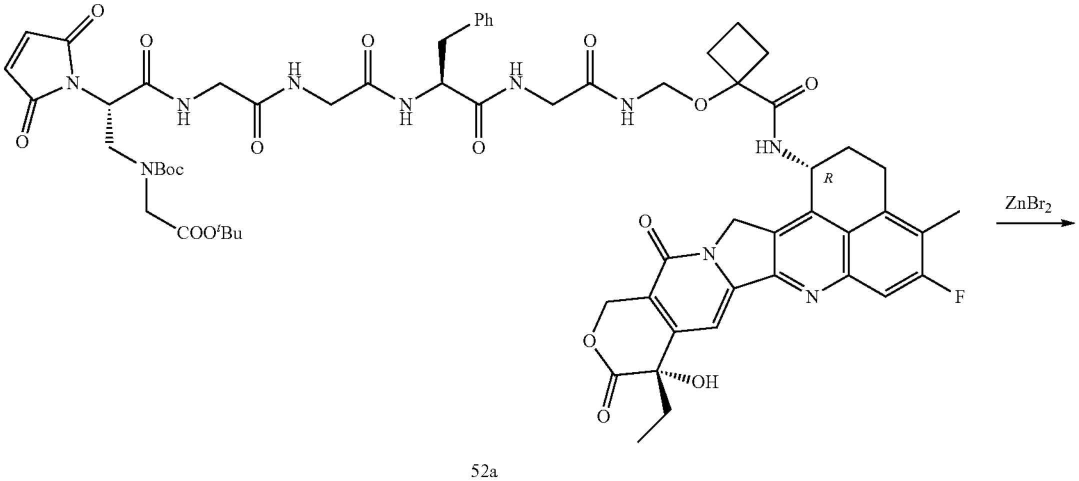

52a

-continued

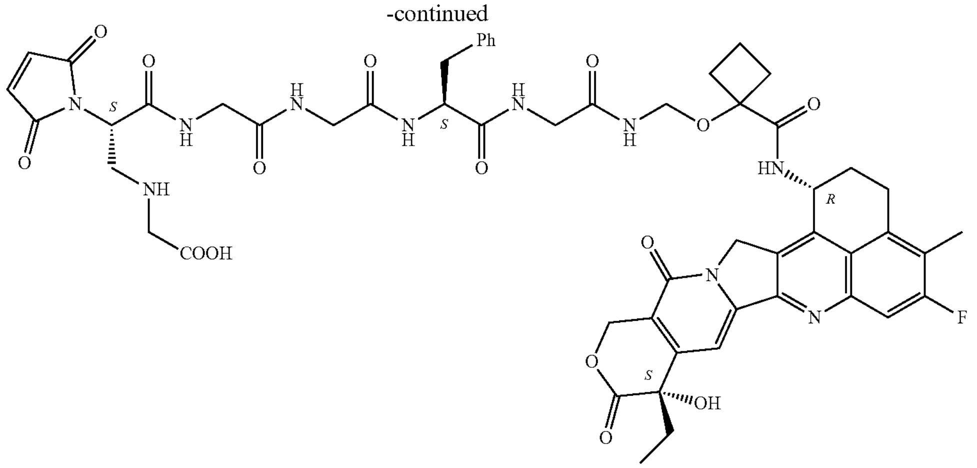

52A

Step 1: Compound 52a

Add 11d (800 mg, 0.96 mmol), M9 (480 mg, 0.96 mmol), PyBOP (500 mg, 0.96 mmol), HOBt (208 mg, 0.96 mmol) and 30 mL DMF into a 50 mL single-necked flask, add DIPEA (660 uL, 4.0 mmol) in an ice-water bath, raise to room temperature and react for 4 h. After the completion of the reaction as detected by HPLC, the reaction solution was purified by HPLC to obtain a preparation liquid of compound 52a, which was lyophilized to obtain 52a (388 mg); LC-MS: $[M+H]^+$=1261.4.

Step 2: Compound 52A

Add 52a (150 mg, 0.12 mmol), zinc bromide (532 mg, 2.4 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 52A (79 mg); LC-MS: $[M+H]^+$=1105.4.

Example 57

Synthesis of Compound 52B

52B

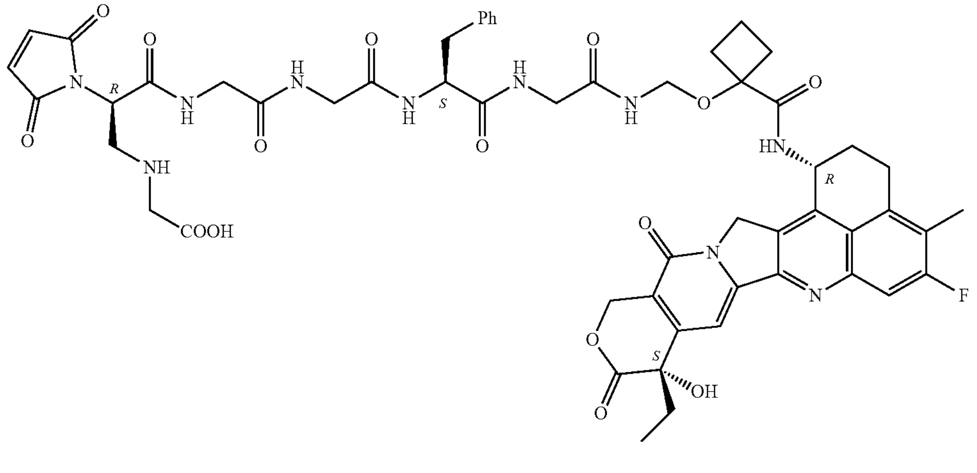

Referring to the synthetic route of Example 56, compound 52B (50 mg) was obtained. LC-MS: $[M+H]^+$=1105.4.

Example 58

Synthesis of Compound 53A:

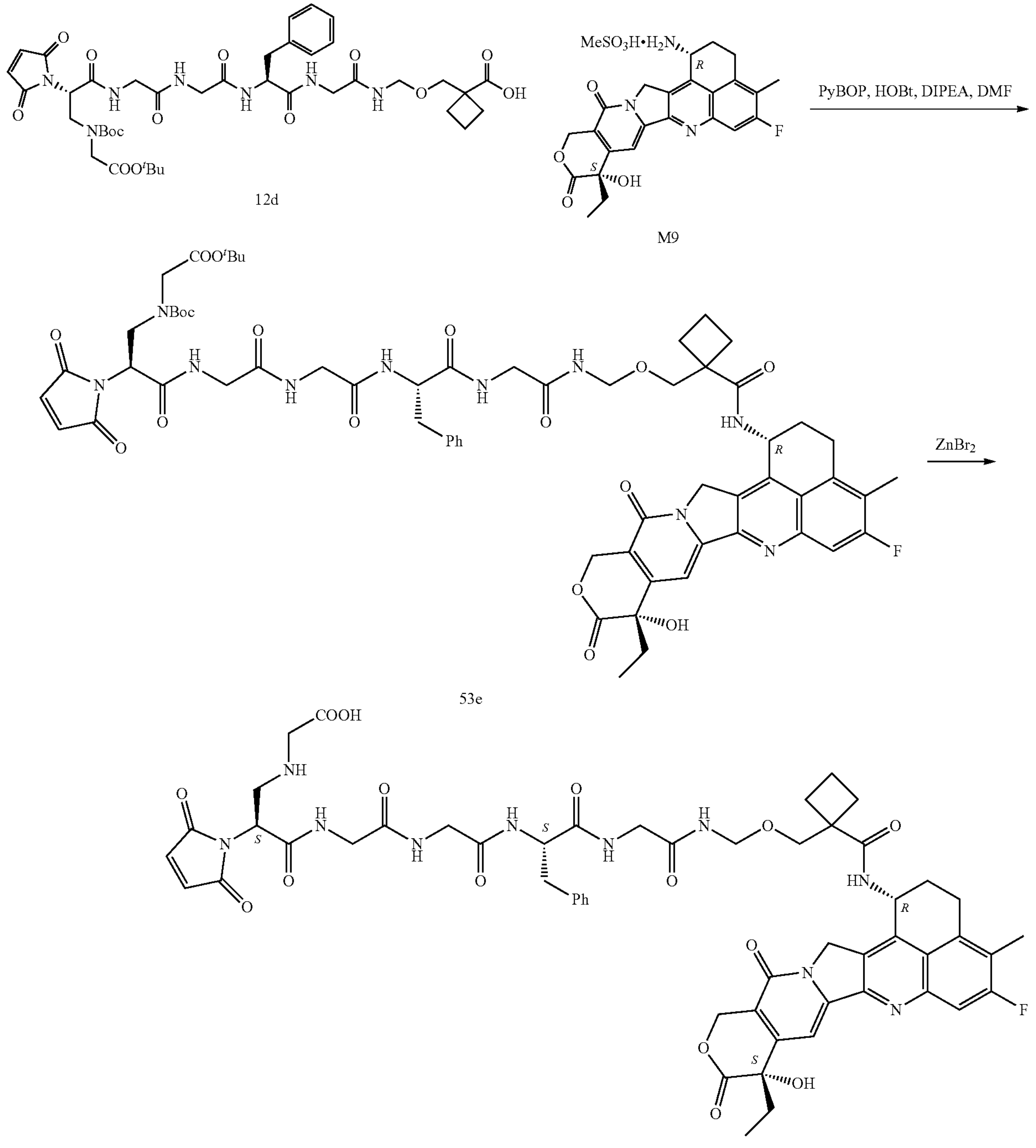

12d

M9

53e

53A

Step 1: Compound 53a

Add 12d (400 mg, 0.47 mmol), M9 (240 mg, 0.47 mmol), PyBOP (250 mg, 0.47 mmol), HOBt (101 mg, 0.47 mmol) and 15 mL DMF into a 50 mL single-necked flask, add DIPEA (330 uL, 2.0 mmol) in an ice-water bath, raise to room temperature and react for 3 h. After the completion of the reaction as detected by HPLC, the reaction solution was purified by HPLC to obtain a preparation liquid of compound 53a, which was lyophilized to obtain 53a (200 mg); LC-MS: $[M+H]^+$=1275.4.

Step 2: Compound 53A

Add 53a (100 mg, 0.08 mmol), zinc bromide (360 mg, 1.6 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 53A (51 mg); LC-MS: $[M+H]^+$ =1119.4.

Example 59

Synthesis of Compound 53B:

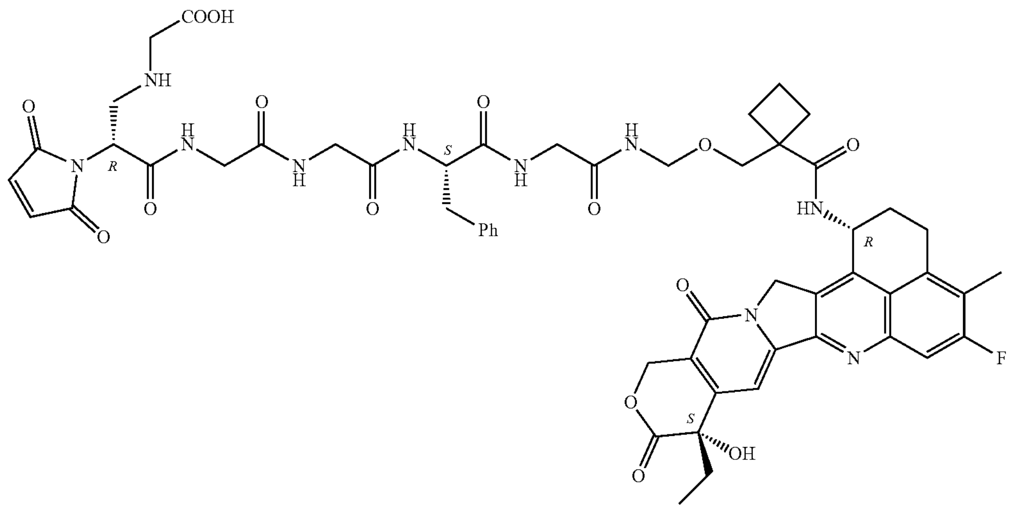

53B

Referring to the synthetic route of Example 58, compound 53B (50 mg) was obtained; LC-MS: $[M+H]^+$=1119.4.

Example 60

Synthesis of Compounds 54A and 54B:

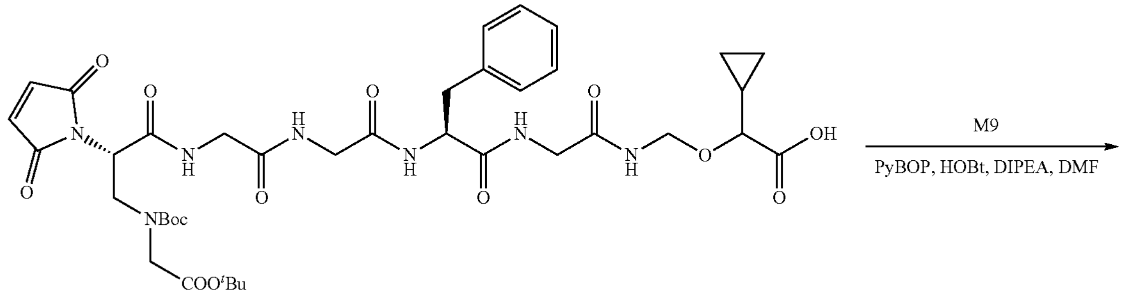

19d

-continued

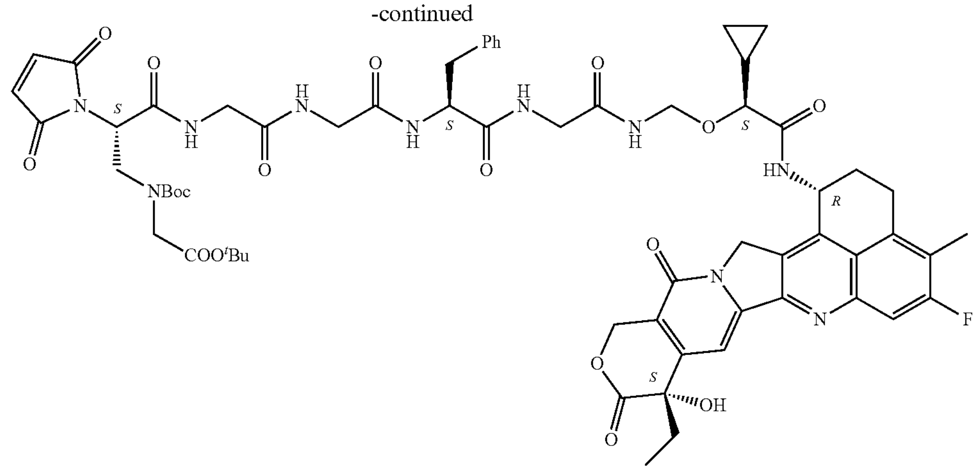

54a

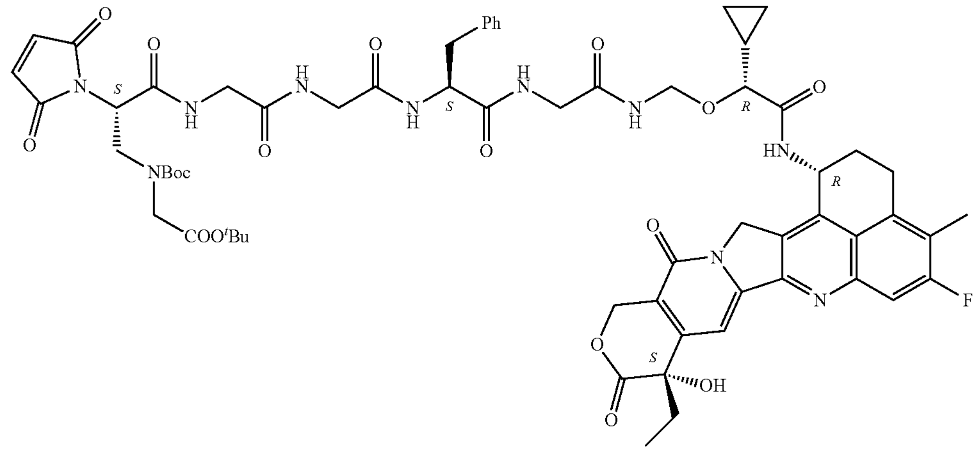

54b

Step 1: Compounds 54a and 54b

Add 19d (500 mg, 0.59 mmol), M9 (317 mg, 0.59 mmol), PyBOP (339 mg, 0.65 mmol), HOBt (88 mg, 0.86 mmol) and 10 mL DMF into a 50 mL single-necked flask, add DIPEA (292 uL, 1.77 mmol) in an ice-water bath, raise to room temperature and react for 2 h. After the completion of reaction as detected by HPLC, the reaction solution was purified by HPLC to obtain the preparation liquids of compounds 54a and 54b. The preparation solutions were lyophilized separately to obtain 103 mg of compound 54a, LC-MS: $[M+H]^+$=1261.5, and 111 mg of compound 54b, LC-MS: $[M+H]^+$=1261.5.

Step 2: Compound 54A

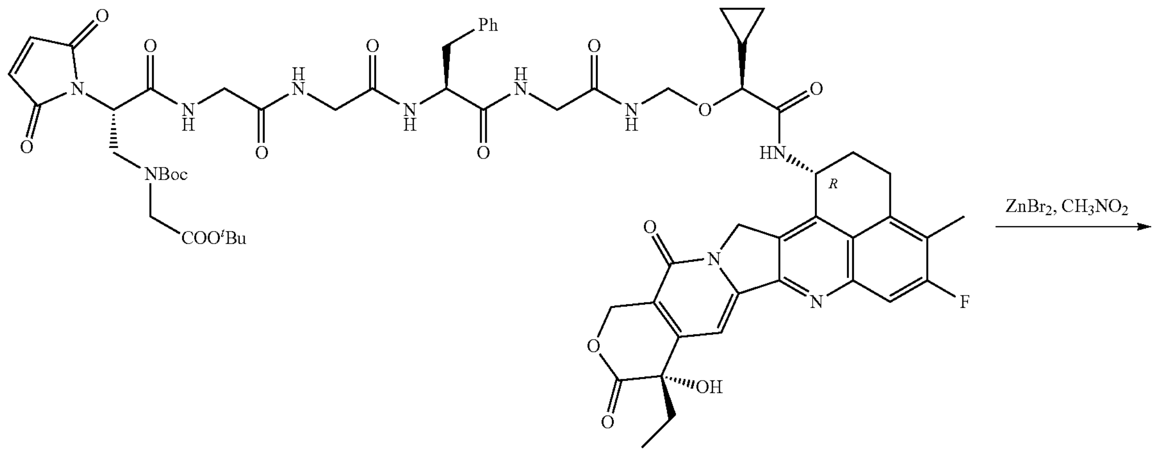

54a

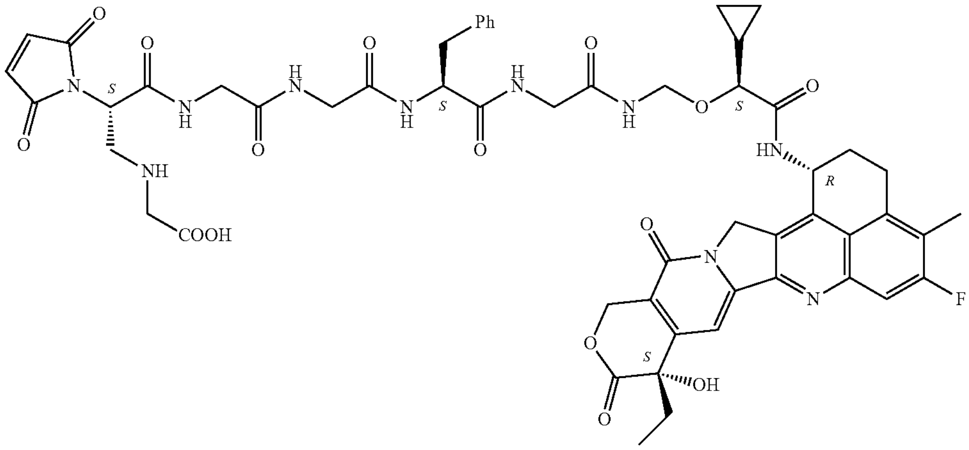

54A

Add 54a (100 mg, 0.079 mmol), zinc bromide (357 mg, 1.59 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 61 mg of solid; LC-MS: $[M+H]^+$=1105.4.

Step 3: Compound 54B

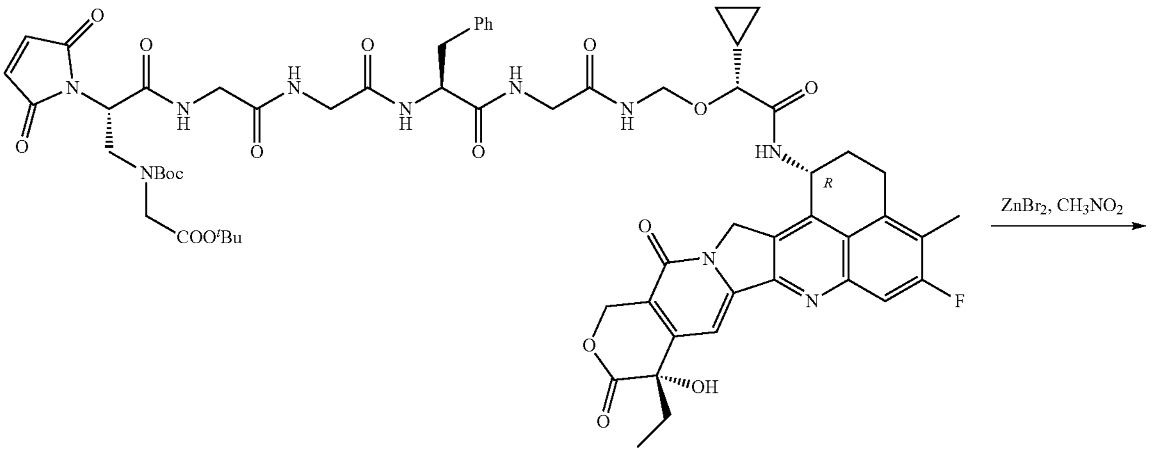

54b

-continued

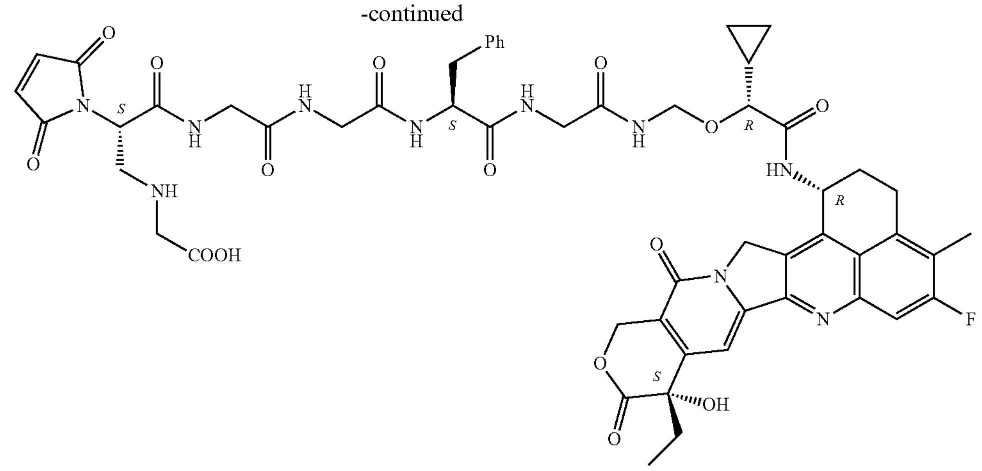

54B

Add 54b (100 mg, 0.079 mmol), zinc bromide (357 mg, 1.59 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 57 mg of solid; LC-MS: $[M+H]^+$=1105.4.

Example 61

Synthesis of Compounds 55A and 55B:

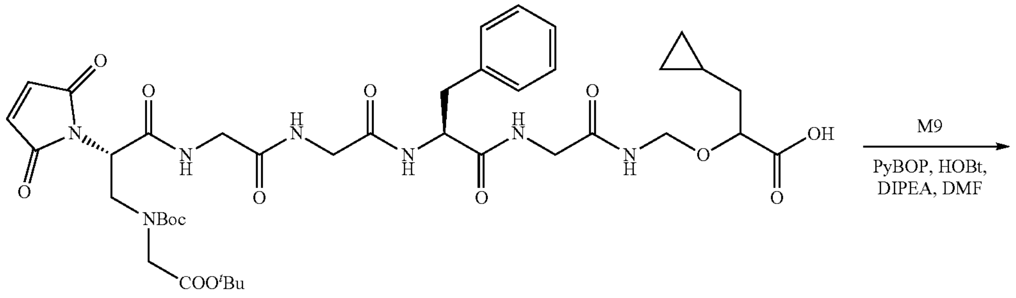

20d

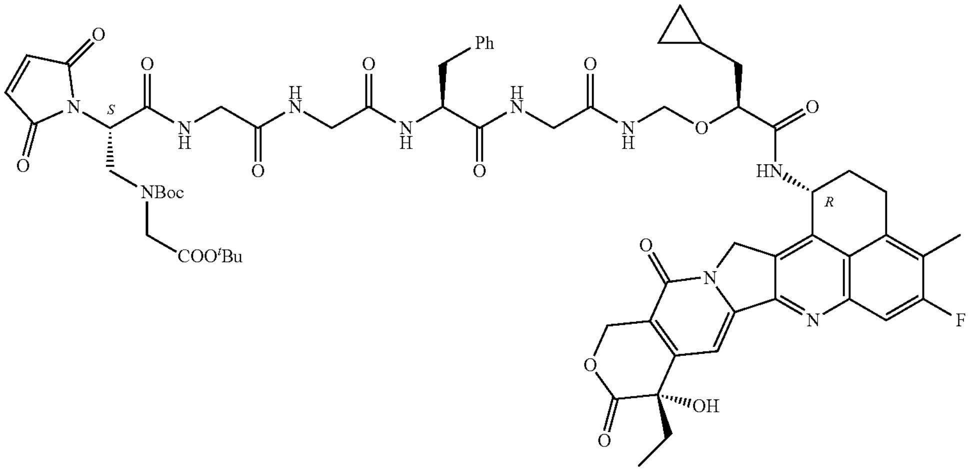

55a

-continued

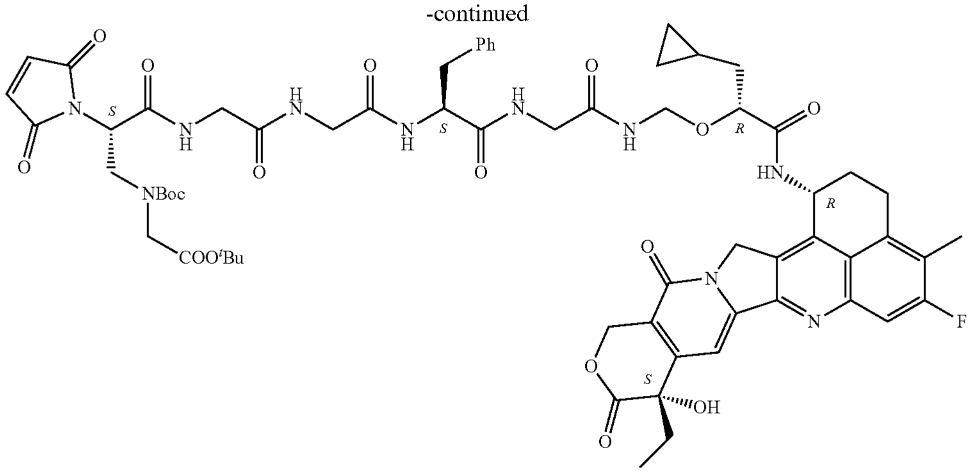

55b

Step 1: Compounds 55a and 55b

Add 20d (400 mg, 0.47 mmol), M9 (250 mg, 0.47 mmol), PyBOP (223 mg, 0.56 mmol), HOBt (83 mg, 0.56 mmol) and 10 mL DMF into a 50 mL single-necked flask, add DIPEA (248 uL, 1.5 mmol) in an ice-water bath, raise to room temperature and react for 2 h. After the reaction was complete as detected by HPLC, the reaction solution was purified by HPLC to obtain the preparation liquids of compounds 55a and 55b. The preparation liquids were separately freeze-dried to obtain 100 mg of compound 55a, LC-MS: $[M+H]^+=1275.5$, and 101 mg of compound 55b, LC-MS: $[M+H]^+=1275.5$.

Step 2: Compound 55A

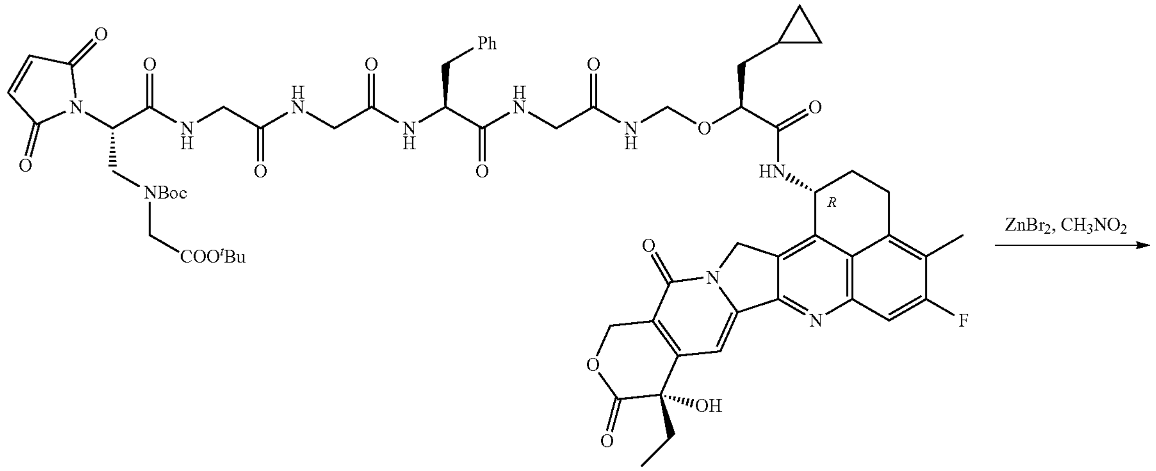

55a

-continued

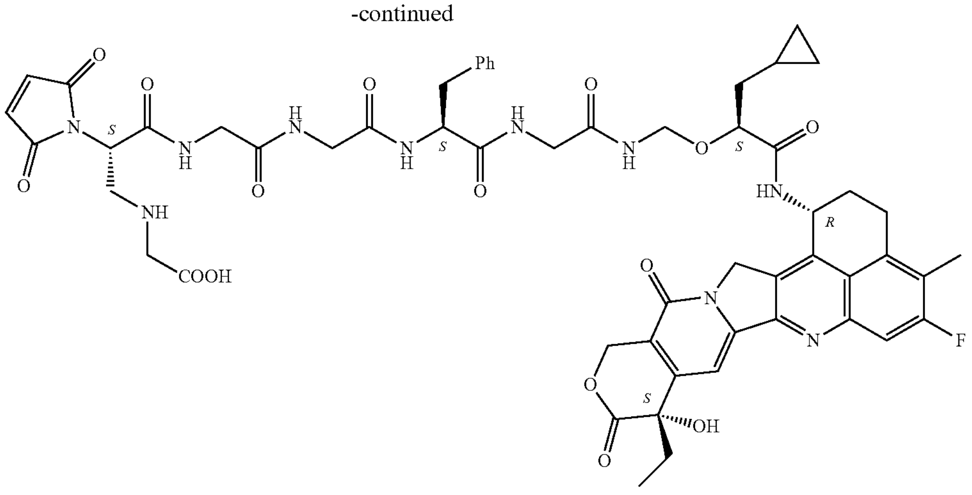

55A

Add 55a (100 mg, 0.078 mmol), zinc bromide (352 mg, 1.57 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 42 mg of solid; LC-MS: $[M+H]^+=1119.4$.

Step 3: Compound 55B

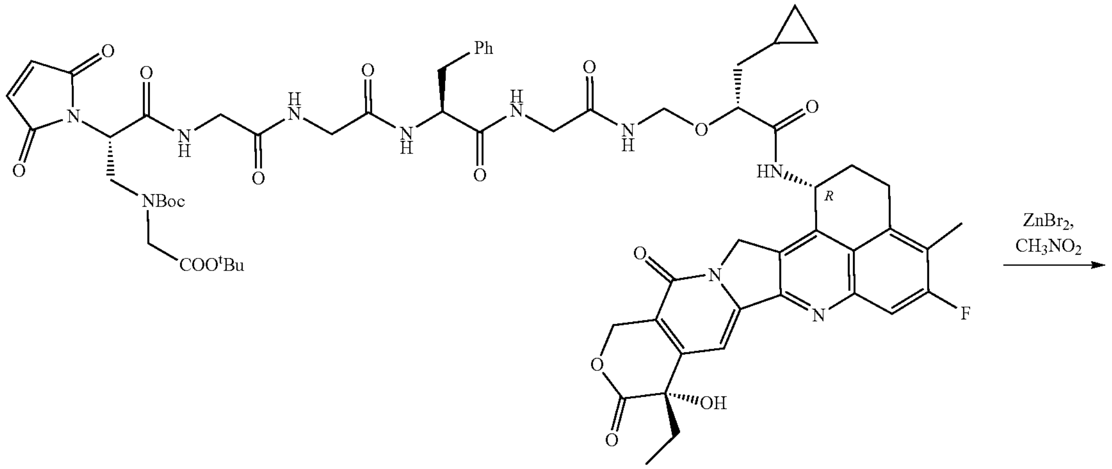

55b

-continued

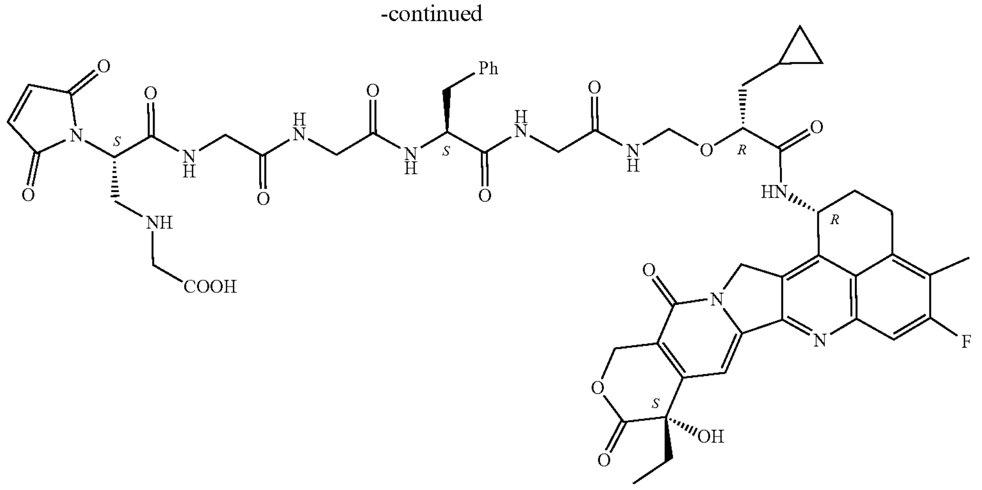

55B

Add 55b (100 mg, 0.079 mmol), zinc bromide (357 mg, 1.59 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 45 mg of solid; LC-MS: $[M+H]^+$=1119.4.

Example 62

Synthesis of Compound 56:

56

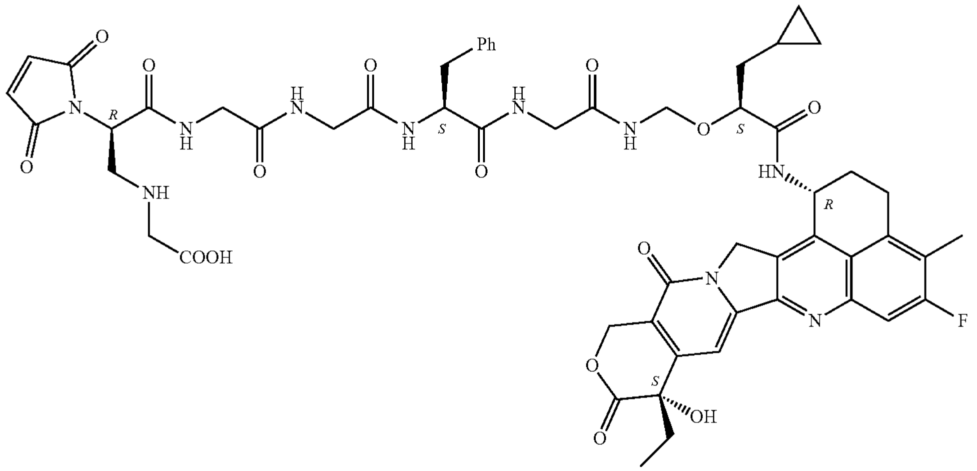

Referring to the synthetic route of Example 60, compound 56 (50 mg) was obtained; LC-MS: $[M+H]^+$=1119.3.

Example 63

Synthesis of Compound 57:

57

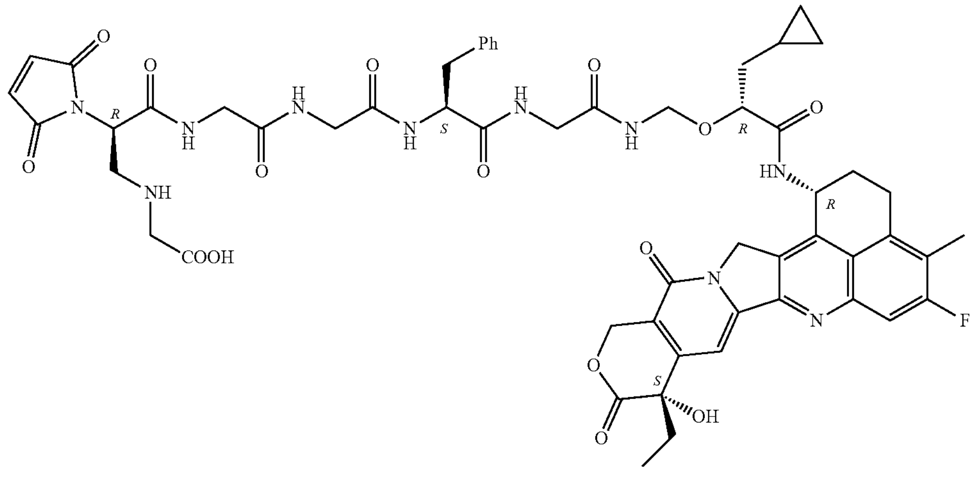

Referring to the synthetic route of Example 61, compound 57 (50 mg) was obtained; LC-MS: $[M+H]^+=1119.4$.

Example 64

Synthesis of Compound 58:

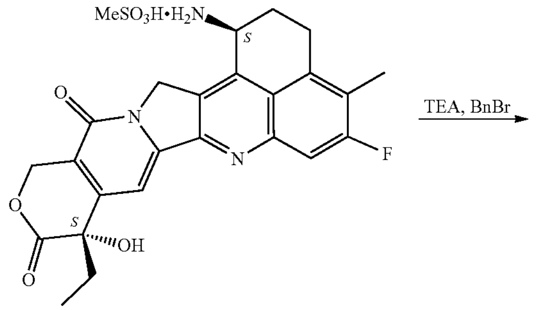

M5

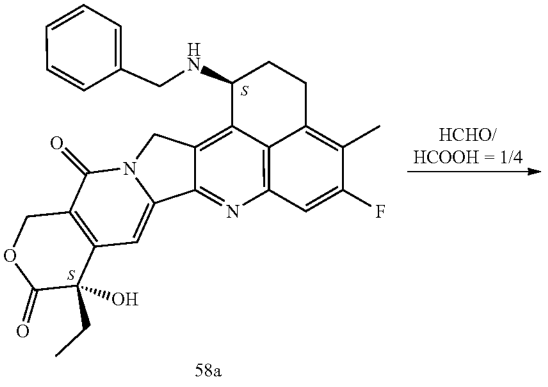

58a

-continued

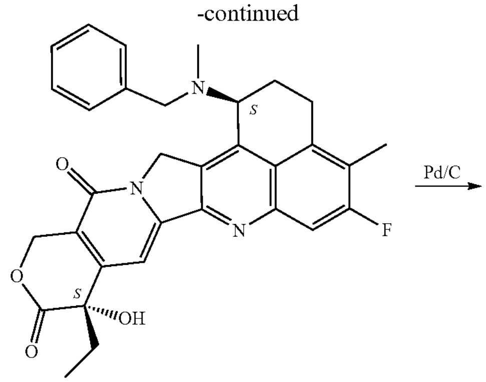

58b

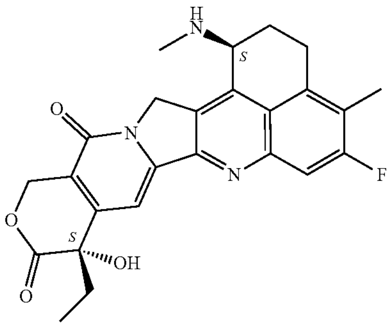

58

Step 1: Synthesis of Compound 58a

Add 400 mL of DMF to exatecan mesylate M5 (15 g, 28 mol, prepared by the method disclosed in patent application "EP0737683A1"), cool in an ice-water bath to 0° C., add triethylamine dropwise, and adjust the pH to 7-8. Benzyl bromide (9.6 g, 56 mmol) was added dropwise in an ice-water bath, the temperature was raised to room temperature (25° C.) to react for 1 hour, completion of the reaction was detected by TLC, the reaction solution was concentrated under reduced pressure, the crude product obtained was purified by preparative high-performance liquid chromatography (acetonitrile/purified water system), the target peak was collected, the acetonitrile was removed under reduced pressure, then lyophilization was performed, to obtain about 11 g of compound 58a, a yellow solid, with a yield of about 74%, MS m/z: $[M+H]^+$ 526.3.

Step 2: Synthesis of Compound 58b

At room temperature, compound 58a (11 g, 21 mol) and 120 mL of formic acid for dissolution were sequentially added in a 250 mL single-necked flask, 30 mL of formaldehyde (40% aqueous solution) was added to the resulting bright yellow solution, and the temperature was raised to 50° C. to react for 1 h. When the reaction was complete as detected by TLC, the temperature was cooled down to room temperature, and the reaction solution was purified by preparative high-performance liquid chromatography (acetonitrile/purified water system), and the target peak was collected. After removing acetonitrile under reduced pressure, lyophilization was performed to give about 4.5 g of compound 58b, a yellow powdery solid, yield about 40%, MS m/z: $[M+H]^+$ 540.6.

Step 3: Synthesis of Compound 58

At room temperature, add compound 58b (2.3 g, 4.3 mol) in a 250 mL single-necked flask, add 100 mL of DMF to dissolve, add 2.3 g of 5% Pd/C to the resulting bright yellow solution, use a hydrogen balloon to replace the atmosphere in the system, and maintain the reaction at room temperature for 1.5 hours. Completion of the reaction was then detected by HPLC, Pd/C was removed by filtration, and the resulting reaction solution was concentrated, and then purified by preparative high-performance liquid chromatography (acetonitrile/purified water system). The target peak was collected, and after removing acetonitrile under reduced pressure, lyophilization was performed to obtain about 1.0 g of compound 58, a yellow powdery solid with about 52% yield, MS m/z: $[M+H]^+$ 450.5.

Example 65

Synthesis of Compound 59:

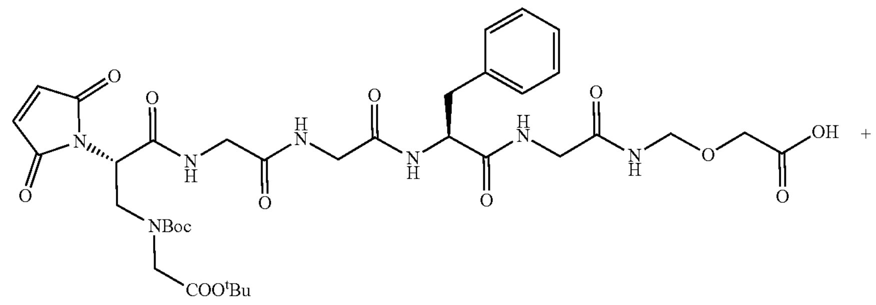

1d

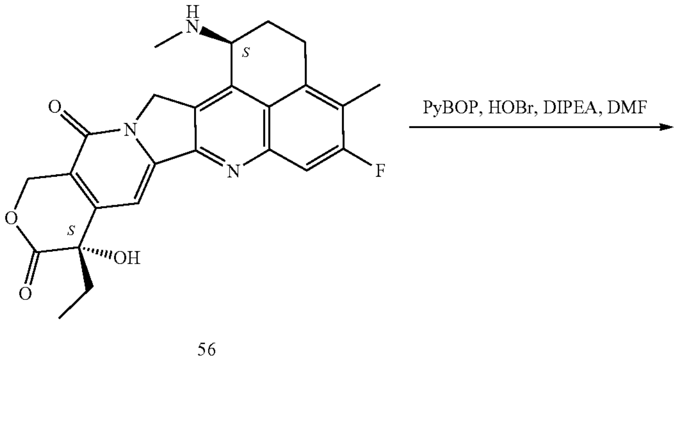

56

-continued

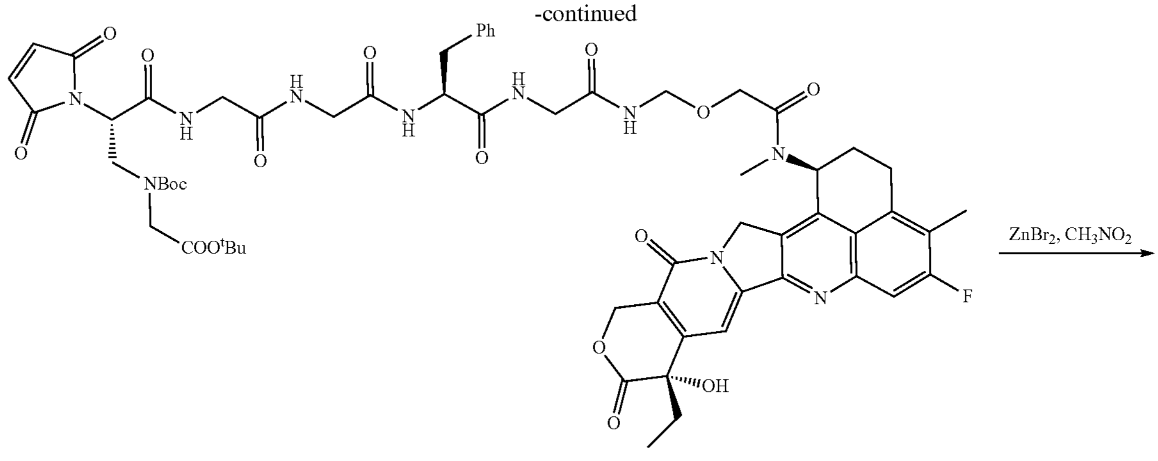

59a

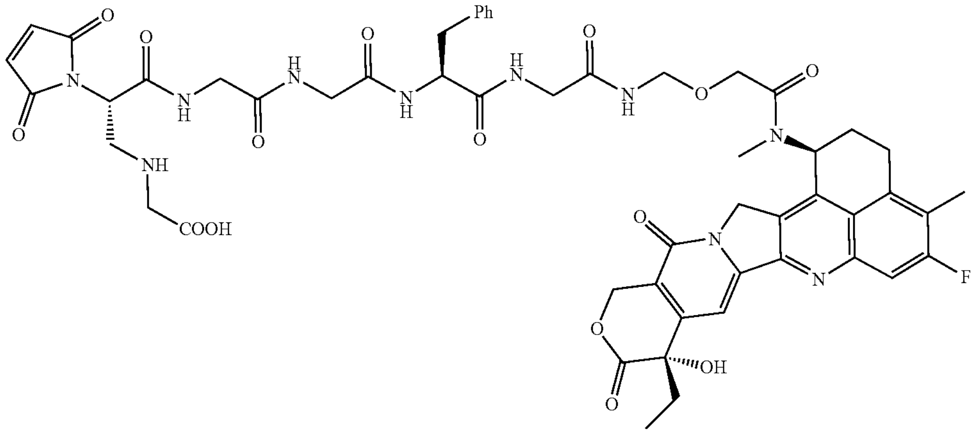

compound 59

Step 1: Compound 59a

Add 1d (500 mg, 0.62 mmol), 58 (279 mg, 0.62 mmol), PyBOP (448 mg, 0.86 mmol), HOBt (116 mg, 0.86 mmol) and 15 mL of DMF into a 50 mL single-necked flask, add DIPEA (378 uL, 2.29 mmol) in an ice-water bath, raise to room temperature and react for 2 h. After the completion of the reaction as detected by HPLC, the reaction solution was purified by HPLC to obtain a preparation liquid, which was lyophilized to obtain 59a (166 mg); LC-MS: $[M+H]^+$= 1235.6.

Step 2: Compound 59

59a (100 mg, 0.081 mmol), zinc bromide (368 mg, 1.63 mmol) and 10 mL of nitromethane were added to a 25 mL single-necked flask and a reaction was carried out at 40° C. for 1 h. After the reaction was complete as detected by HPLC, the solvent was removed by concentration under reduced pressure, and a crude product was obtained. The crude product was purified by high performance liquid chromatography to obtain a product preparation liquid, and the preparation liquid was lyophilized to obtain the solid compound 59 (43 mg); LC-MS: $[M+H]^+$=1079.3.

Example 66
Synthesis of Compound 60:
compound 60
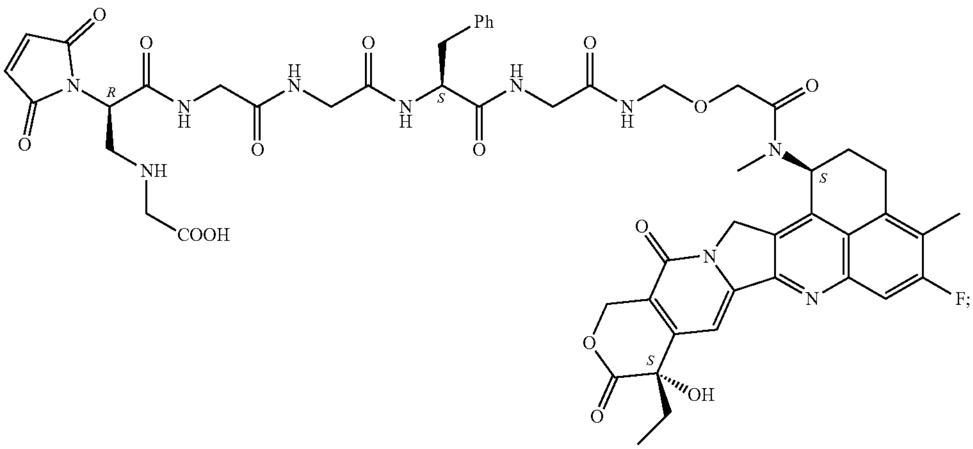
Referring to the synthetic route of Example 65, compound 60 (40 mg) was obtained; LC-MS: $[M+H]^+$=1079.3.
Example 67
Synthesis of Compound 61:
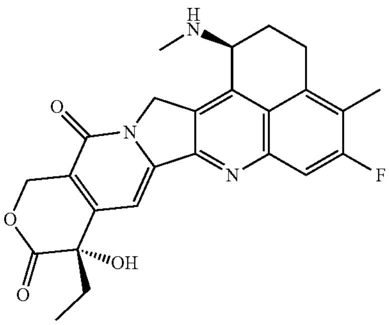
58
+
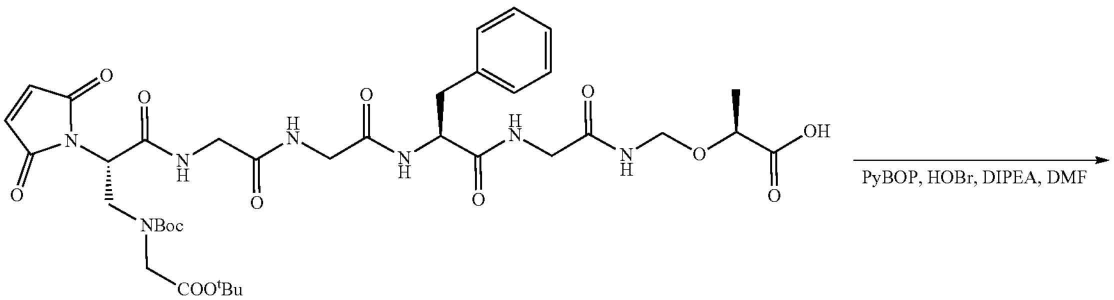
5d -continued

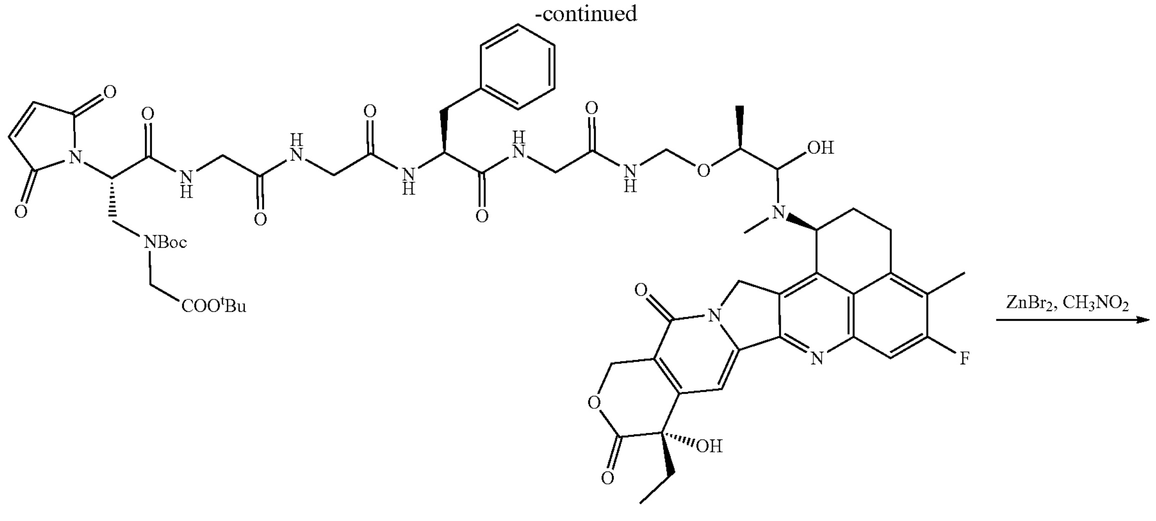

61a

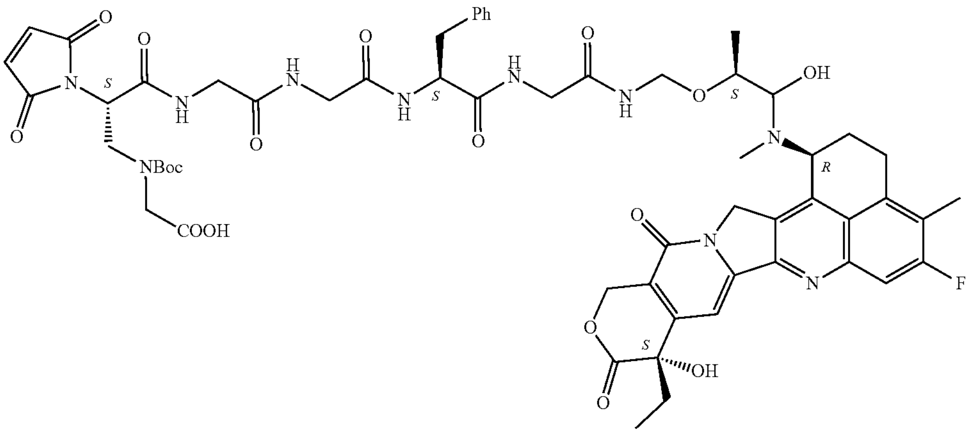

compound 61

Step 1: Compound 61a

Add 5d (1.66 g, 2.02 mmol, 1.0 eq), 58 (0.91 g, 2.02 mmol, 1.0 eq), PyBOP (1.58 g, 3.03 mmol, 1.5 eq), HOBt (0.41 g, 3.03 mmol, 1.5 eq), and DMF (40 mL) in a 100 mL single-necked flask, add DIPEA (0.84 mL, 1.5 eq) in an ice-water bath, and raise the temperature to room temperature to react for 2 h (monitored by HPLC). The reaction solution was purified directly by preparative LC, the preparation liquid was concentrated at 35° C. in a water bath under reduced pressure with a water pump to remove acetonitrile, and lyophilized to obtain compound 61a (1.21 g); LC-MS: $[M+H]^+$=1249.4.

Step 2: Compound 61

Add compound 61a (1.0 g, 0.8 mmol, 1.0 eq) and 35 mL nitromethane into a 100 mL single-necked flask, and after dissolving, add zinc bromide (3.64 g, 16 mmol, 20.0 eq), react in an oil bath at 40° C. (preheated to stabilize) for 30 min, and concentrate at 45° C. in a water bath under reduced pressure with a water pump to remove nitromethane, to obtain a yellow residue solid (monitored by HPLC). After acid preparation, a preparation liquid was obtained. The preparation liquid was concentrated at 35° C. in a water bath under reduced pressure with a water pump to remove acetonitrile by spinning, and freeze-dried to obtain compound 61 (786 mg). LC-MS: $[M+H]^+$=1093.6.

Example 68
Synthesis of Compound 62:
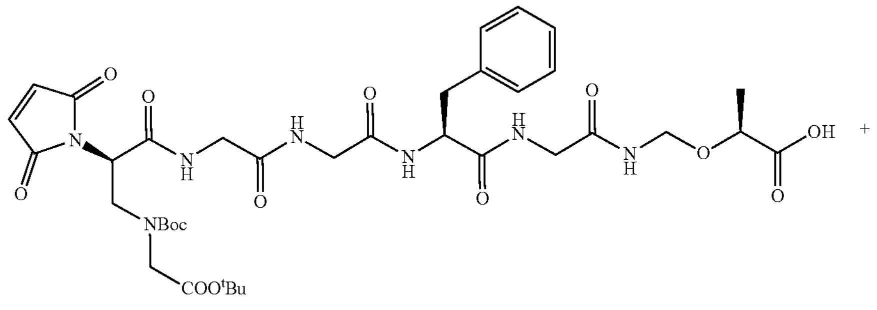
5d-1
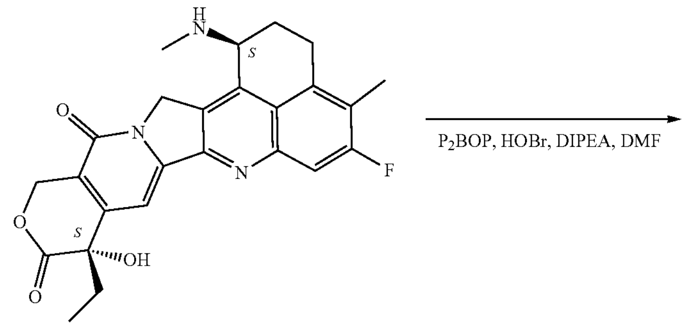
58
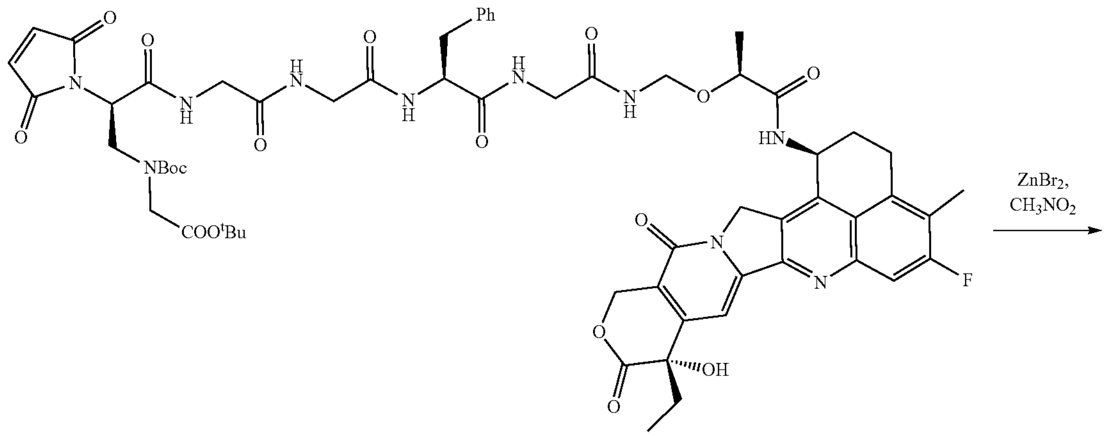
62a -continued

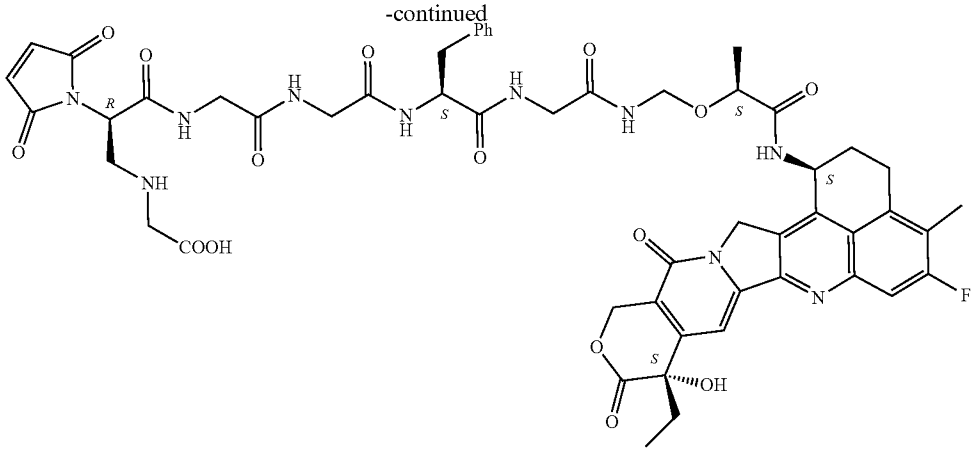

compound 62

Step 1: Compound 62a

Add compound 5d-1 (200 mg, 0.24 mmol, 1.0 eq), 58 (110.3 mg, 0.24 mmol, 1.0 eq), PyBOP (187 mg, 0.36 mmol, 1.2 eq), HOBt (48 mg, 0.36 mmol, 1.2 eq) and DMF (6 mL) to a 25 mL single-necked flask, lower to 0-5° C. in an ice-water bath, and add DIPEA (62 mg, 0.48 mmol, 2.0 eq). Then raise to 20±5° C. to react for 2 h, and use HPLC to monitor for the end of the reaction. The reaction solution was directly purified by HPLC preparation, and the product preparation liquid was collected and freeze-dried to obtain compound 62a (120.9 mg); LC-MS: $[M+H]^+$=1249.4.

Step 2: Compound 62

Add compound 62a (100 mg, 0.081 mmol, 1.0 eq), ZnBr2 (364 mg, 1.62 mmol, 20.0 eq) and $CH_3NO_2$ (10 mL) sequentially into a 25 mL single-necked flask. After the addition is complete, raise the temperature to 40° C. and react for 0.5 h. The reaction was stopped, and the reaction solution was directly spin-dried under reduced pressure at 45° C. to obtain a yellow solid, which was sampled to monitor the reaction by HPLC. The spin-dried solid was directly purified by HPLC preparation, and the product preparation liquid was collected and lyophilized to obtain compound 62 (61 mg); LC-MS: $[M+H]^+$=1093.4.

Example 69

Preparation of Compound 63:

compound 63

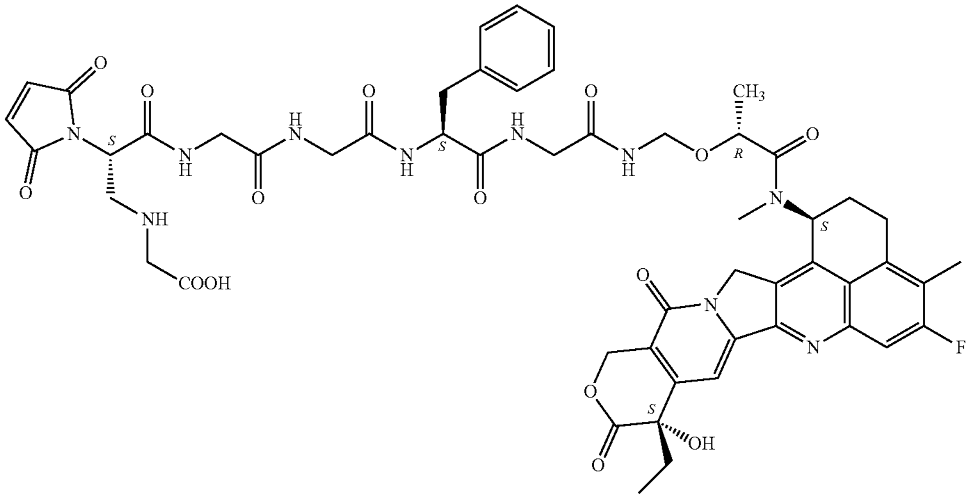

Referring to the route of Example 67, compound 63 (60 mg) was obtained; LC-MS: $[M+H]^+$=1093.4.

Example 70
Preparation of Compound 64:
compound 64
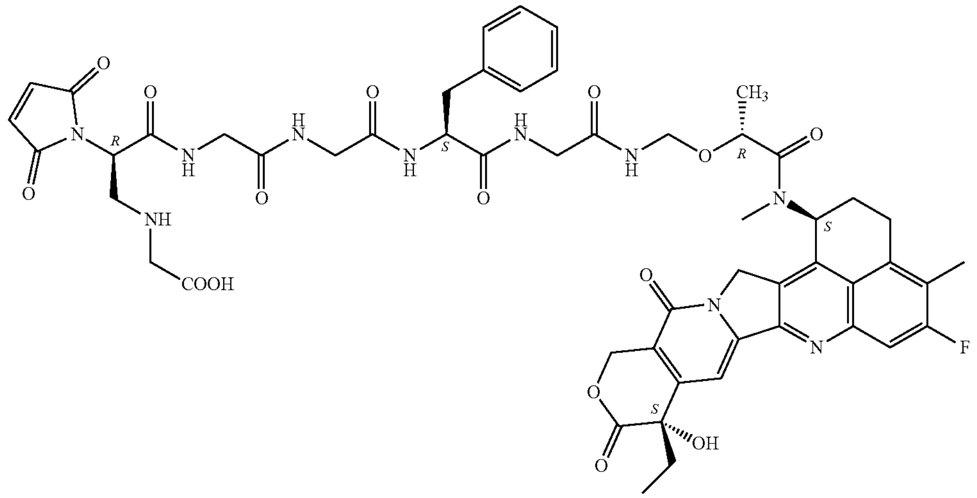
Referring to the synthetic route of Example 68, compound 64 (65 mg) was obtained; LC-MS: $[M+H]^+$=1093.4.
Example 71
Preparation of Compounds 65A and 65B:
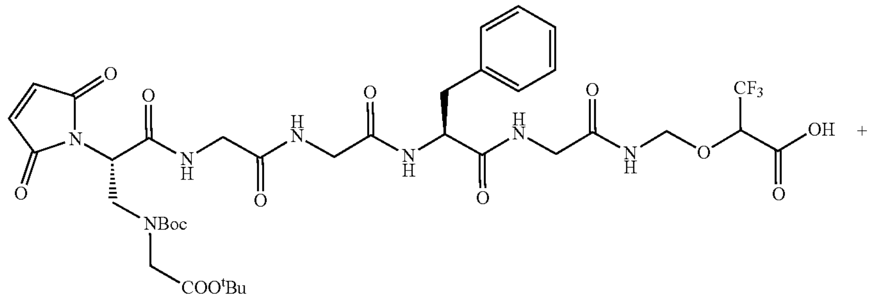
7d
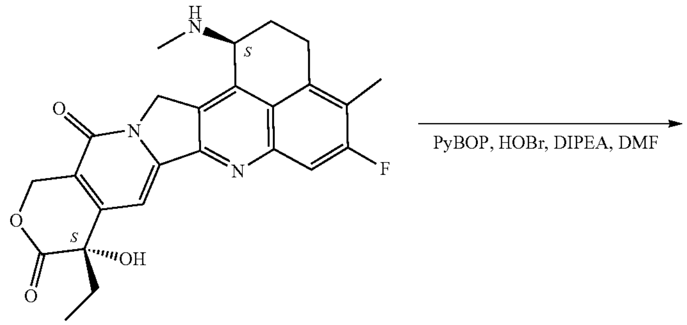
58

-continued

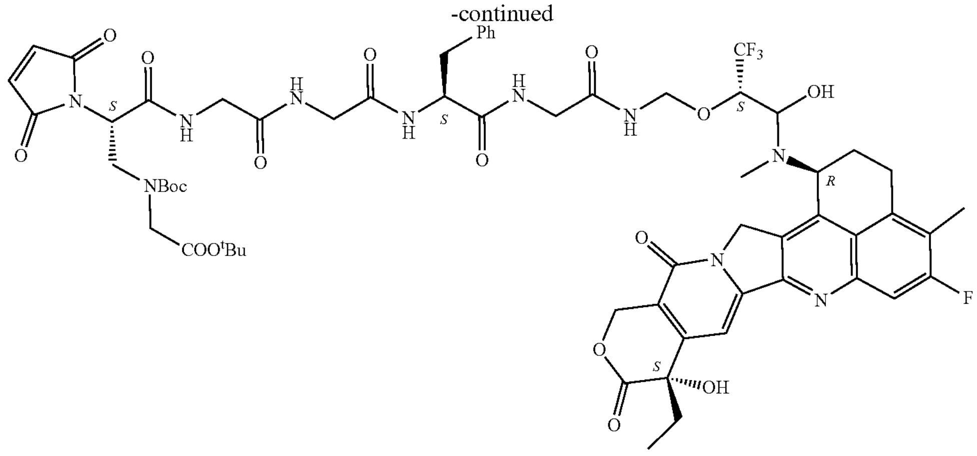

65a

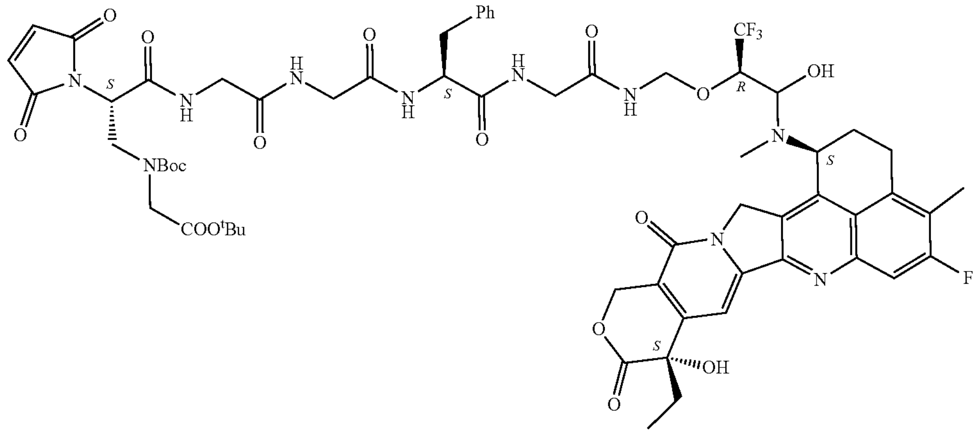

65b

Step 1: Compounds 65a and 65b

Add 7d (500 mg, 0.57 mmol), 58 (256.8 mg, 0.57 mmol), PyBOP (448 mg, 0.86 mmol), HOBt (116 mg, 0.86 mmol) and 15 mL DMF into a 50 mL one-necked flask, add DIPEA (378 uL, 2.29 mmol) in an ice-water bath, raise to room temperature and react for 2 h. After the completion of the reaction as detected by HPLC, the reaction solution was purified by HPLC to obtain the preparation liquids of compounds 65a and 65b. The preparation liquids were lyophilized separately to obtain 155 mg of compound 65a, LC-MS: $[M+H]^+$=1303.4, and 158 mg of compound 65b, LC-MS: $[M+H]^+$=1303.6.

Step 2: Compound 65A

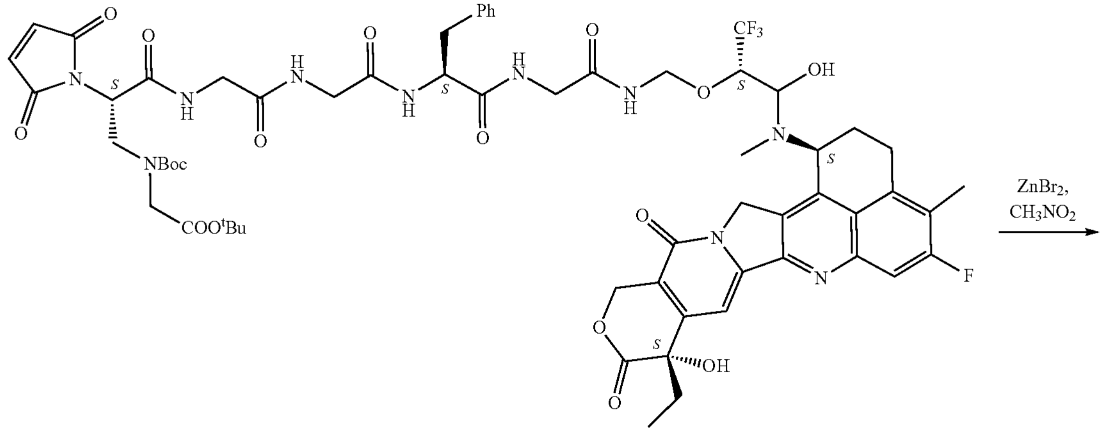

65a

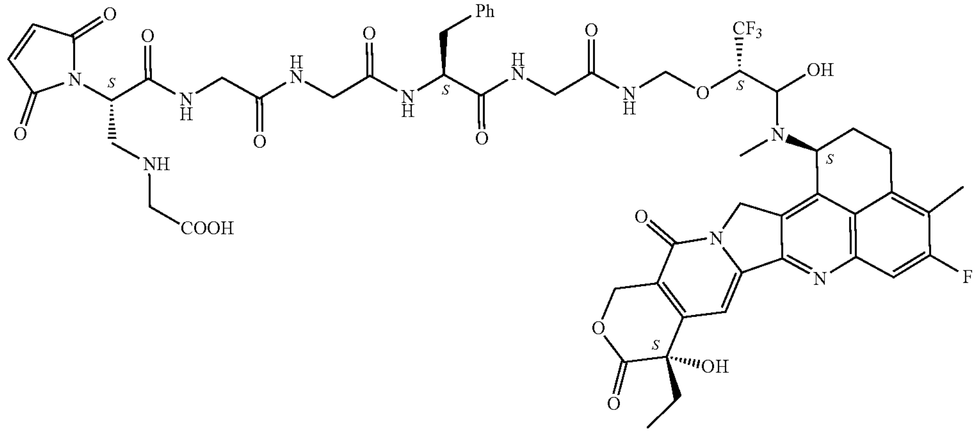

65A

Add 50a (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a preparation liquid, which was lyophilized to obtain 49 mg of solid.

Step 3: Compound 65B

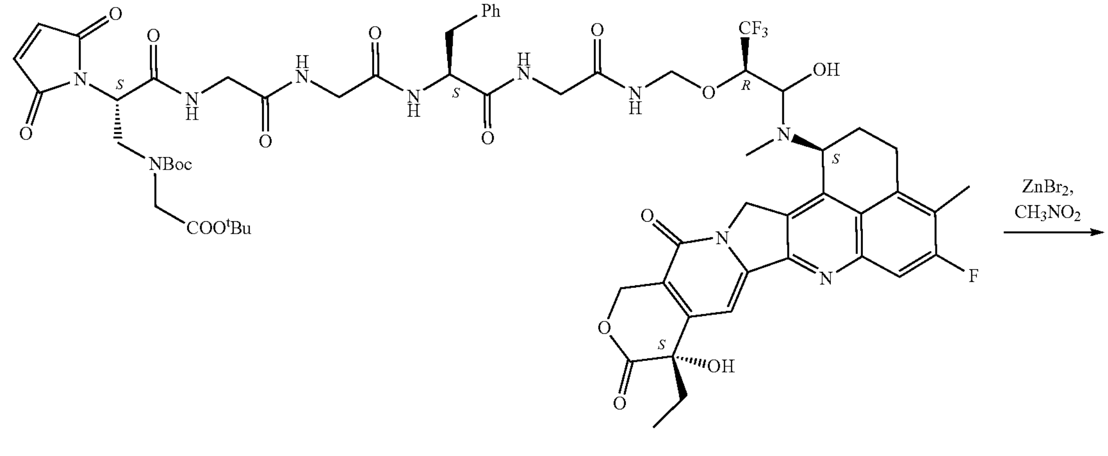

65b

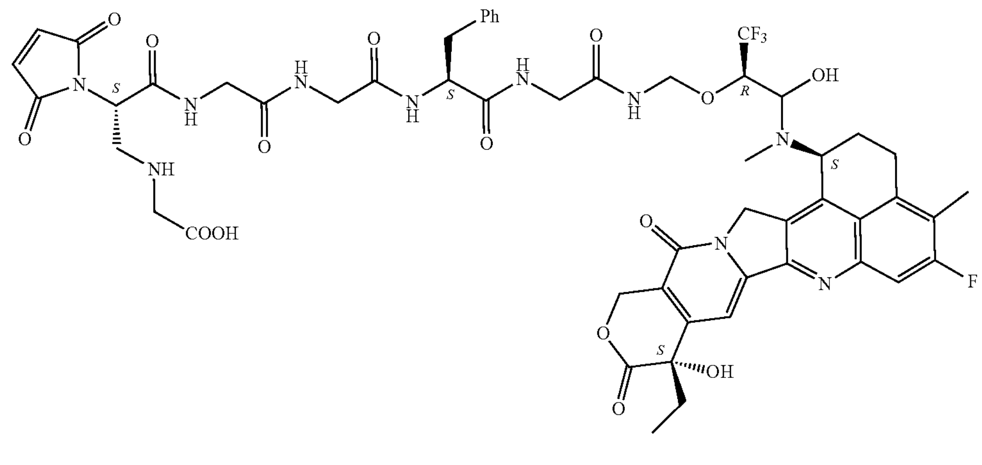

65B

Add 65b (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a preparation liquid, which was lyophilized to obtain 47 mg of solid.

Example 72

Synthesis of Compounds 66A and 66B:

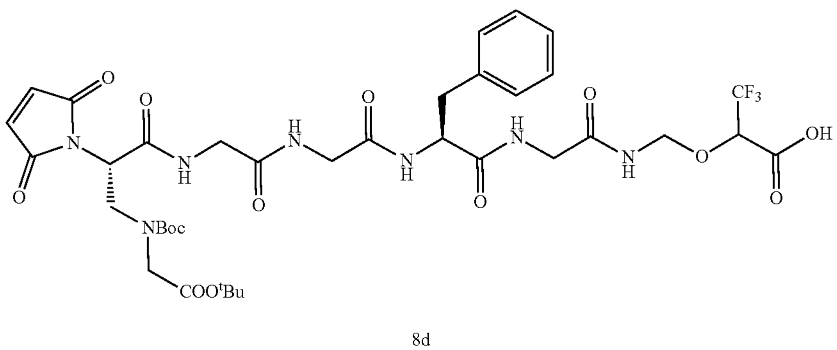

8d

-continued

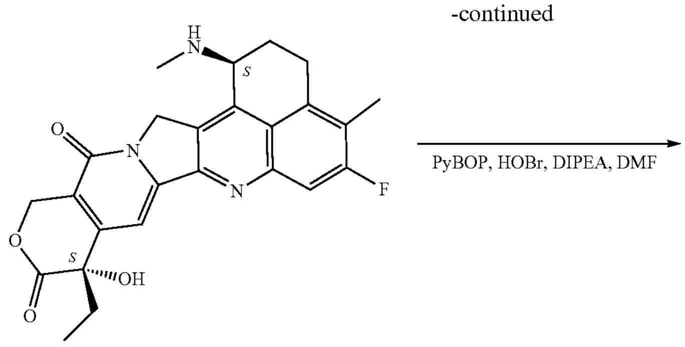

58

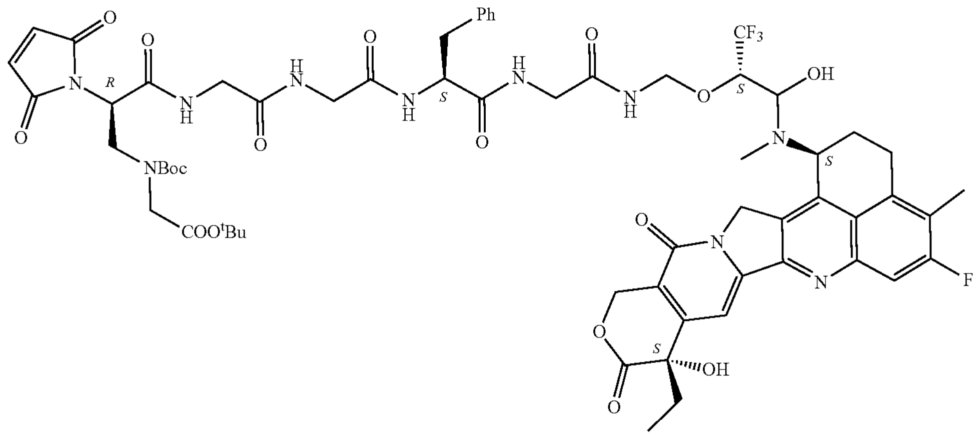

65a

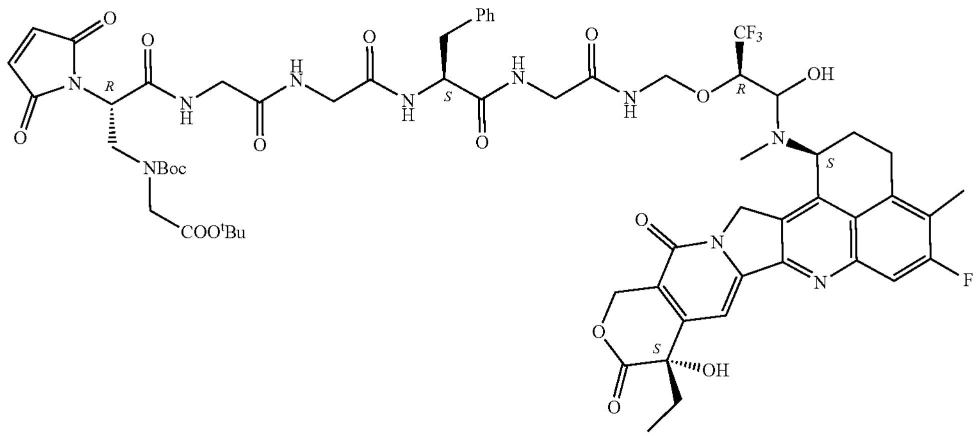

65b

Step 1: Compound 66a and Compound 66b

Add 8d (500 mg, 0.57 mmol), 58 (256.8 mg, 0.57 mmol), PyBOP (448 mg, 0.86 mmol), HOBt (116 mg, 0.86 mmol) and 15 mL DMF into a 50 mL one-necked flask, add DIPEA (378 uL, 2.29 mmol) in an ice-water bath, raise to room temperature and react for 2 h. After the completion of the reaction as detected by HPLC, the reaction solution was purified by HPLC to obtain the preparation liquids of compound 66a and compound 66b, and the preparation liquids were separately lyophilized to obtain 160 mg of compound 66a and 160 mg of compound 66b. LC-MS of compound 66a: $[M+H]^+=1303.7$; LC-MS of compound 66b: $[M+H]^+=1303.6$.

Step 2: Compound 66A

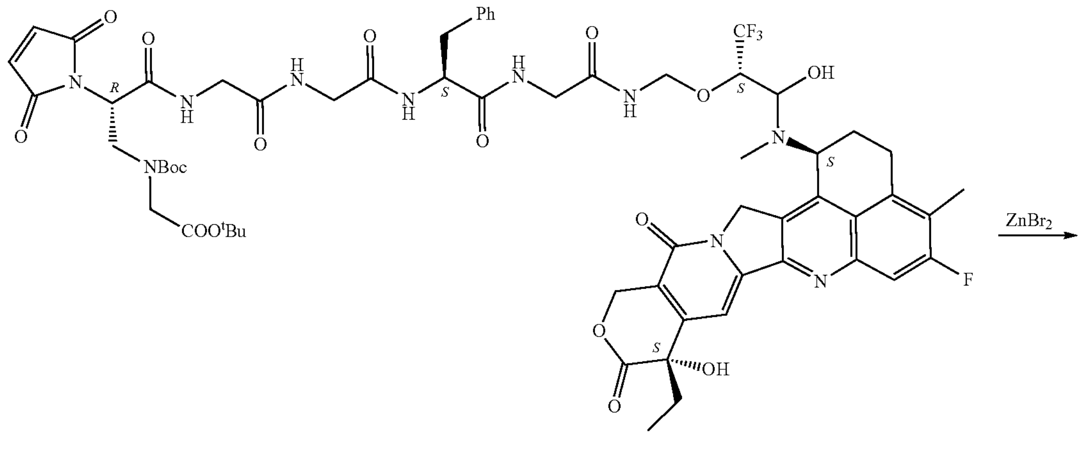

66a

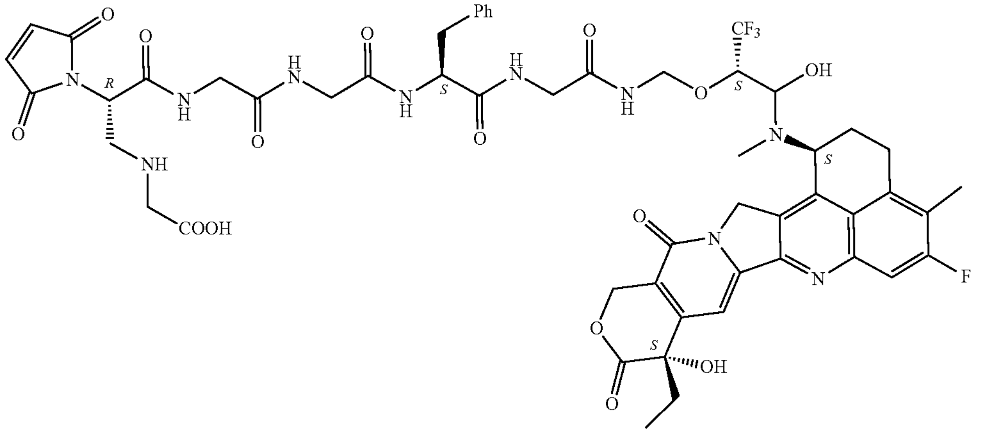

66A

Add compound 66a (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 57 mg of solid, LC-MS: $[M+H]^+$= 1147.5.

Step 3: Compound 66B

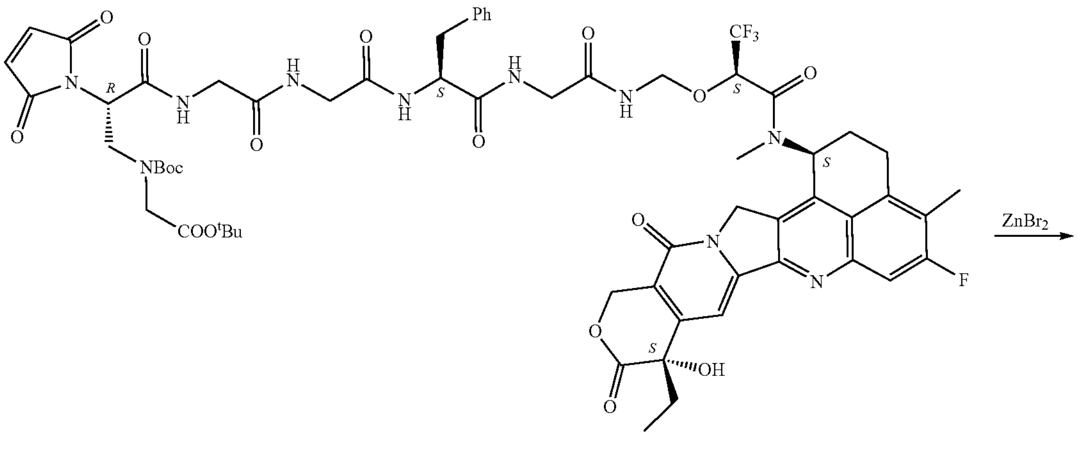

66b

-continued

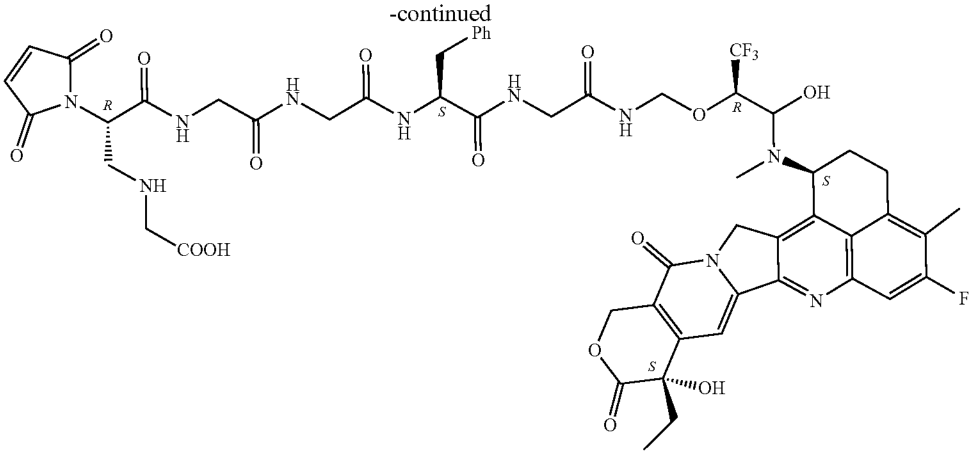

66B

Add compound 66b (100 mg, 0.077 mmol), zinc bromide (349 mg, 1.55 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 57 mg of solid, LC-MS: $[M+H]^+$=1147.5.

Example 73

Synthesis of Compound 67A:

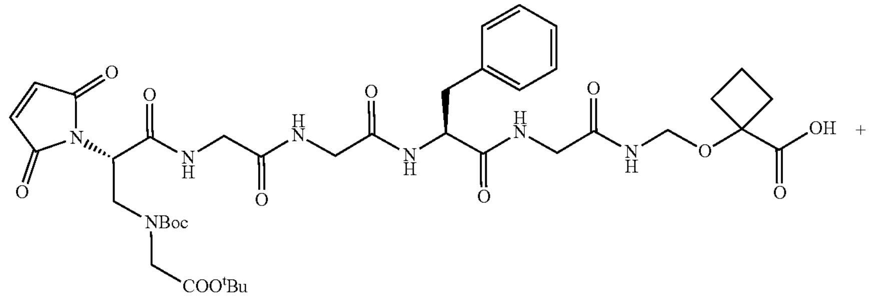

11d

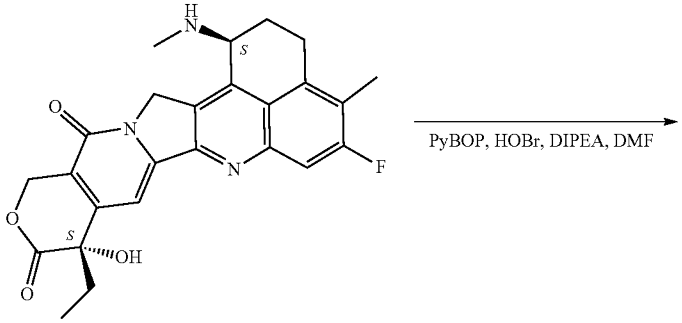

58

-continued

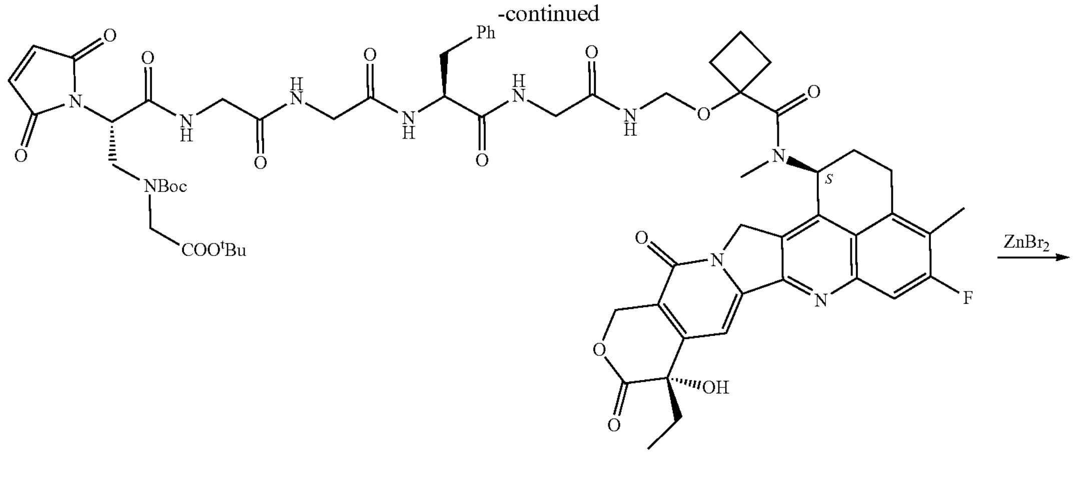

67a

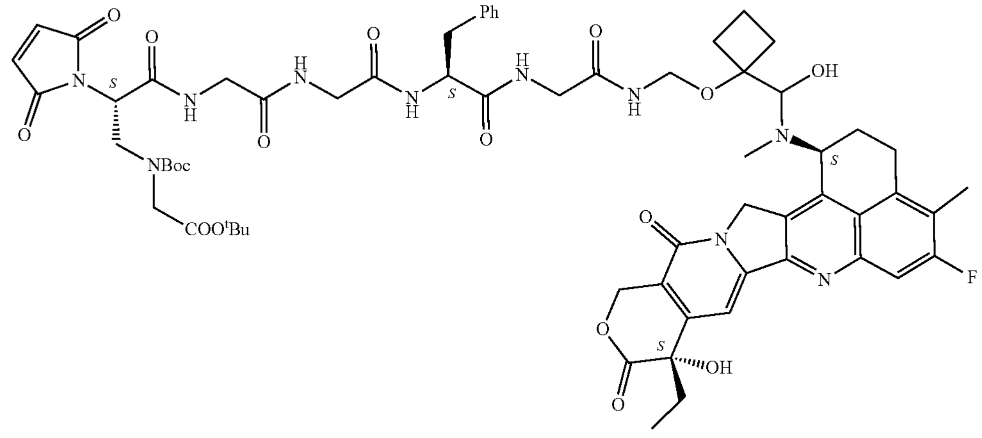

67A

Step 1: Compound 67a

Add 11d (800 mg, 0.96 mmol), 58 (432.5 mg, 0.96 mmol), PyBOP (500 mg, 0.96 mmol), HOBt (208 mg, 0.96 mmol) and 30 mL DMF into a 50 mL single-necked flask, add DIPEA (660 uL, 4.0 mmol) in an ice-water bath, raise to room temperature and react for 4 h. After the completion of the reaction as detected by HPLC, the reaction solution was purified by HPLC to obtain a preparation liquid of compound 67a, which was lyophilized to obtain 67a (402 mg); LC-MS: $[M+H]^+$=1275.4.

Step 2: Compound 67A

Add 67a (100 mg, 0.78 mmol), zinc bromide (356 mg, 1.57 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 67A (47 mg); LC-MS: $[M+H]^+$=1119.5.

Example 74
Synthesis of Compound 67B:
67B
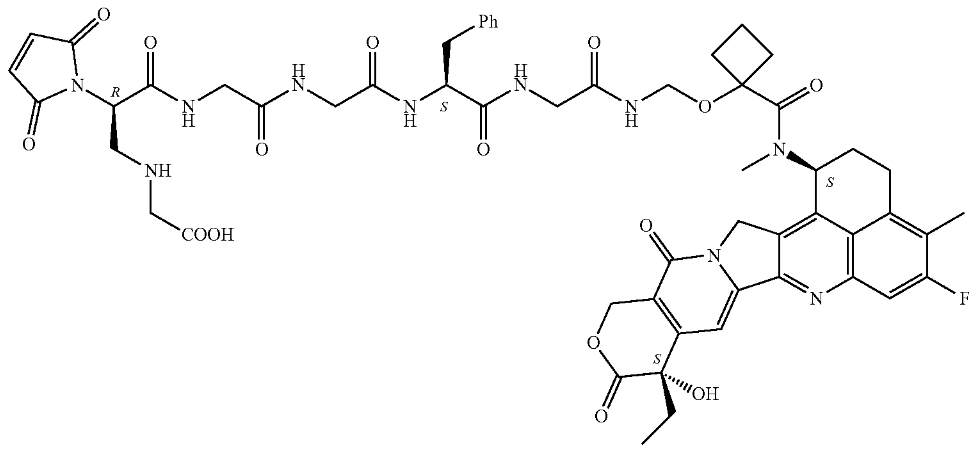
Referring to the synthetic route of Example 73, compound 67B (50 mg) was obtained. LC-MS: $[M+H]^+$ 1119.4.
Example 75
Synthesis of Compound 68A:
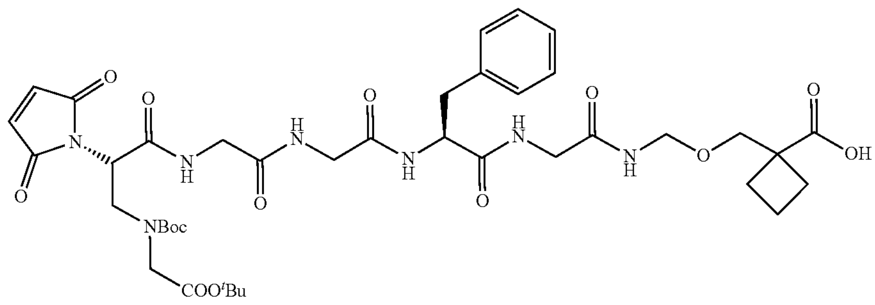
12d
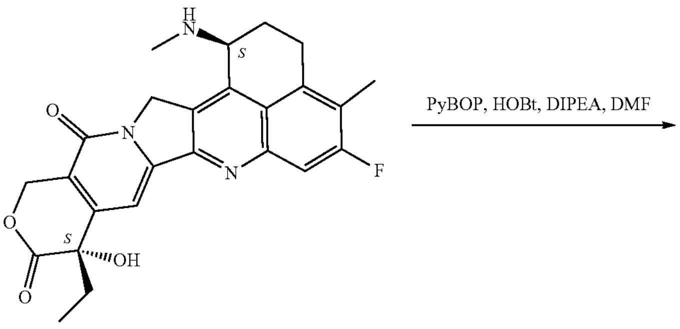
58

-continued

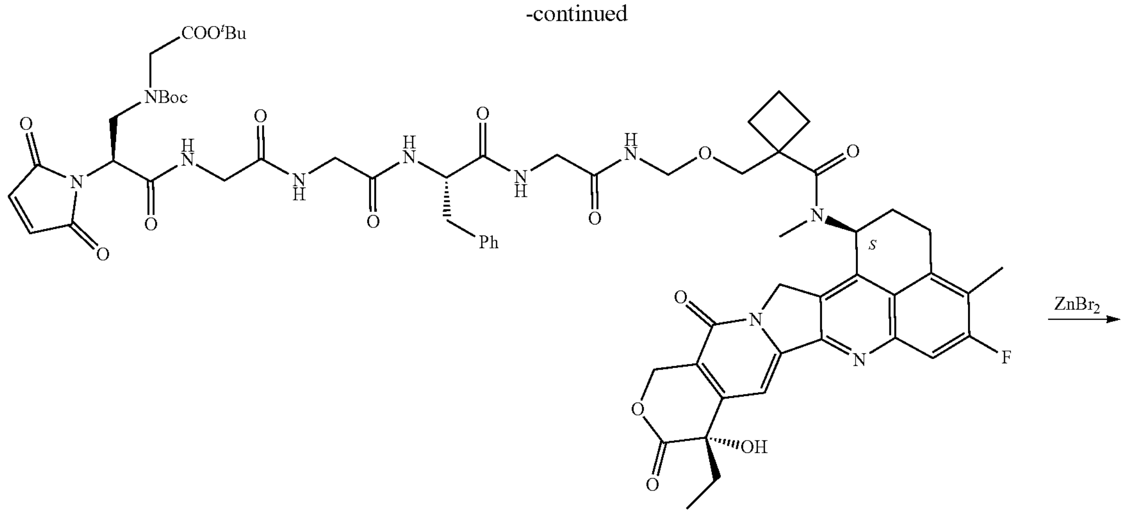

68e

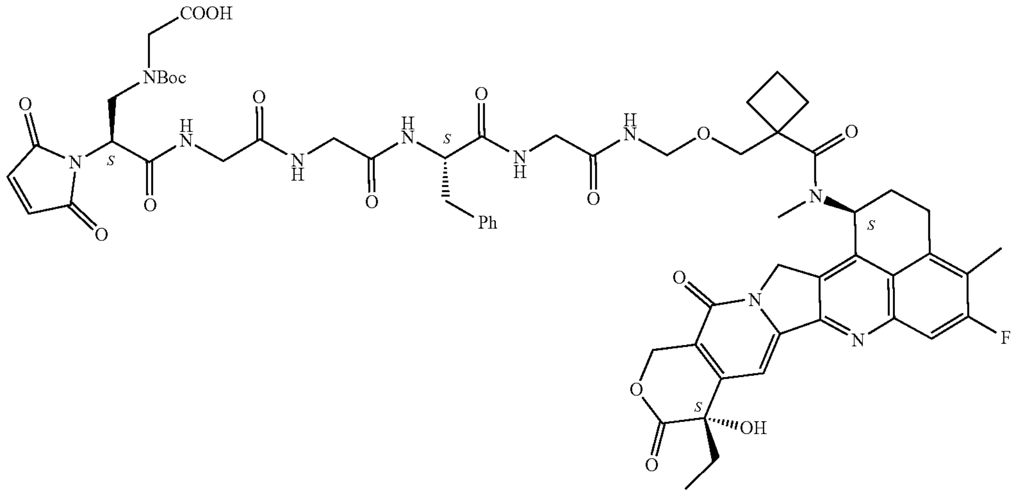

68A

Add 12d (400 mg, 0.47 mmol), 58 (211.7 mg, 0.47 mmol), PyBOP (250 mg, 0.47 mmol), HOBt (101 mg, 0.47 mmol) and 15 mL DMF into a 50 mL single-necked flask, add DIPEA (330 uL, 2.0 mmol) in an ice-water bath, and raise to room temperature and react for 3 h. After the completion of the reaction as detected by HPLC, the reaction solution was purified by HPLC to obtain a preparation liquid of compound 68a, which was lyophilized to obtain 68a (177 mg); LC-MS: $[M+H]^+$=1289.4.

Step 2: Compound 68A

Add 68a (100 mg, 0.08 mmol), zinc bromide (360 mg, 1.6 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 68A (45 mg); LC-MS: $[M+H]^+$= 1133.4.

Example 76
Synthesis of Compound 68B:
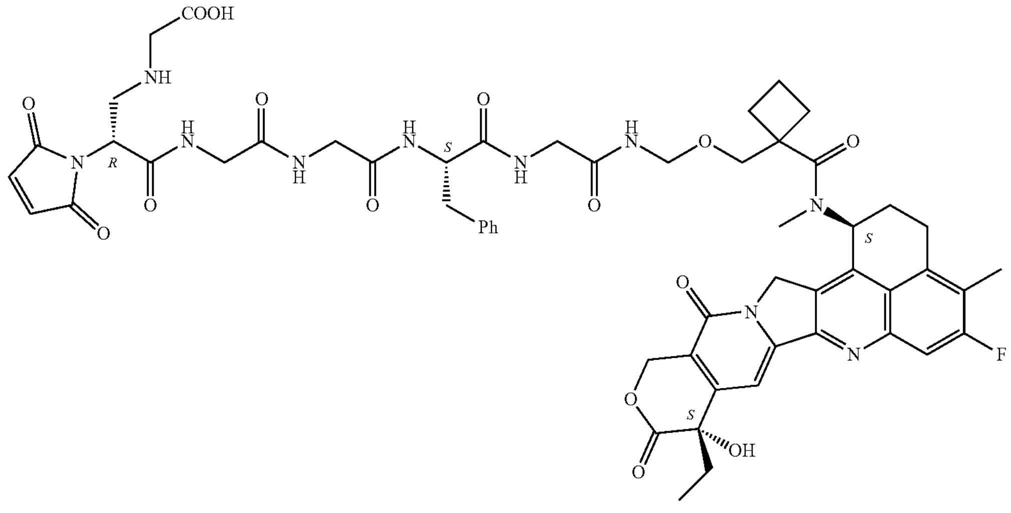
68B
Referring to the synthetic route of Example 75, compound 68B (50 mg) was obtained; LC-MS: $[M+H]^+$=1133.4.
Example 77
Synthesis of Compounds 69A and 68B:
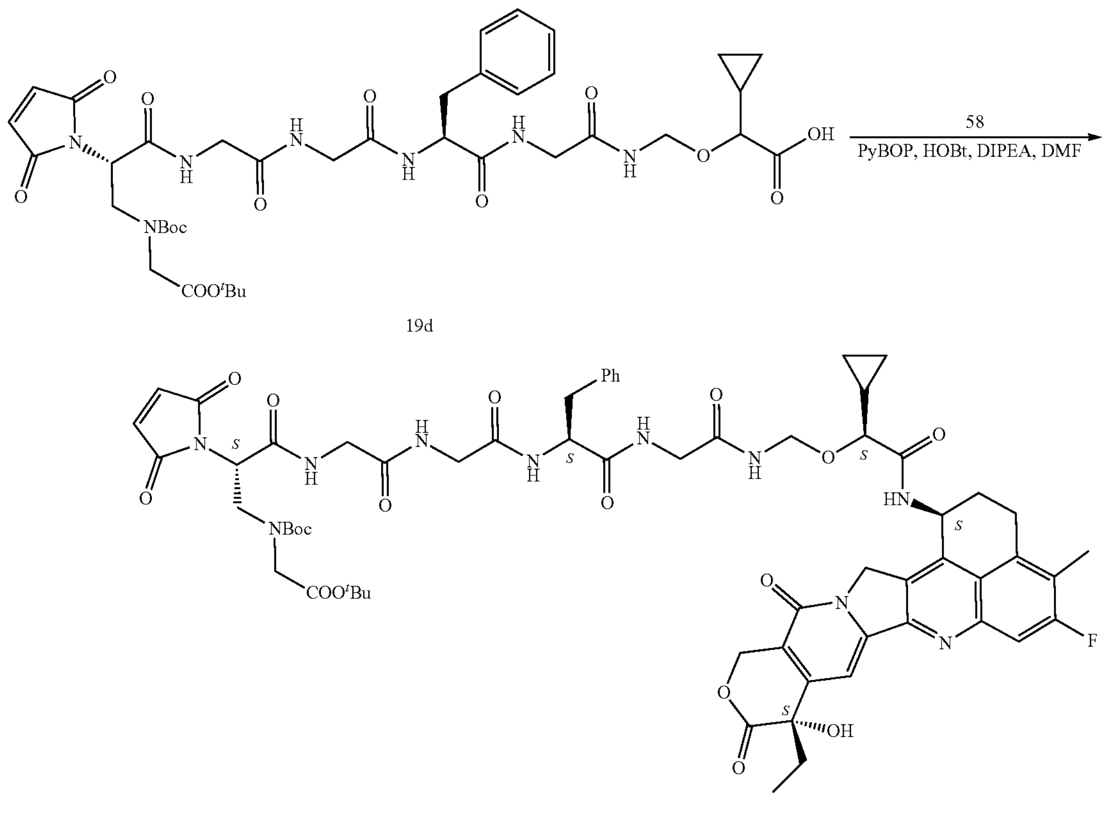
19d
69a -continued

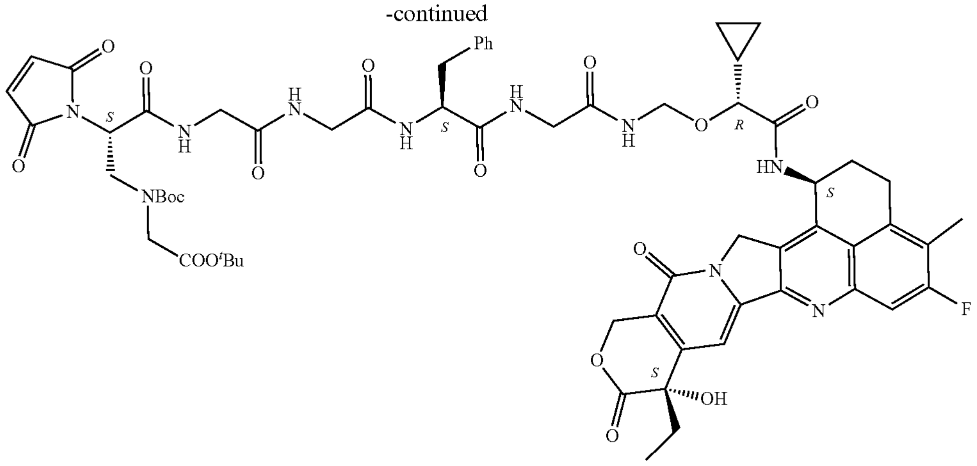

69b

Step 1: Compounds 69a and 69b

Add 19d (500 mg, 0.59 mmol), 58 (266 mg, 0.59 mmol), PyBOP (339 mg, 0.65 mmol), HOBt (88 mg, 0.86 mmol) and 10 mL DMF into a 50 mL single-necked flask, add DIPEA (292 uL, 1.77 mmol) in an ice-water bath, raise to room temperature and react for 2 h. After the completion of the reaction as detected by HPLC, the reaction solution was purified by HPLC to obtain the preparation liquids of compounds 69a and 69b. The preparation solutions were freeze-dried separately to obtain 109 mg of compound 69a, LC-MS: $[M+H]^+$=1275.5, and 111 mg of compound 69b, LC-MS: $[M+H]^+$=1275.7.

Step 2: Compound 69A

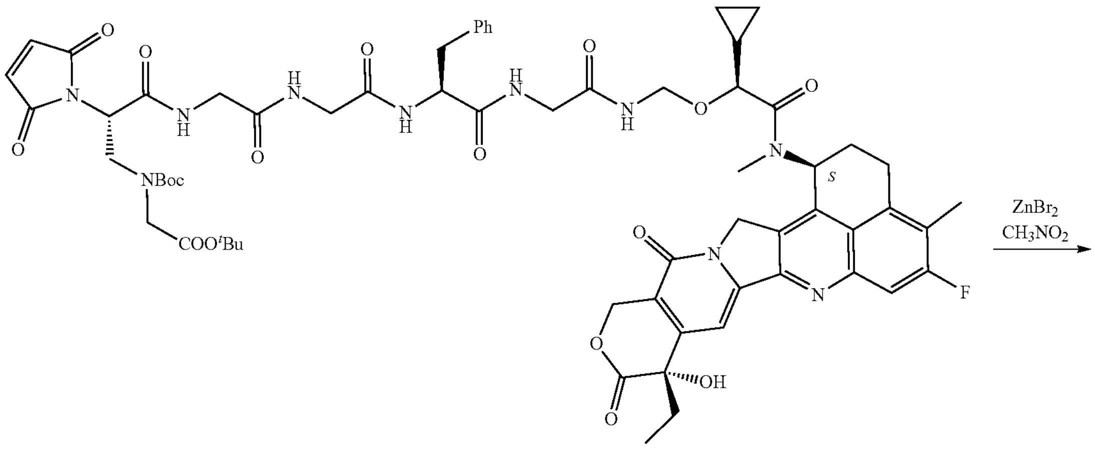

69a

-continued

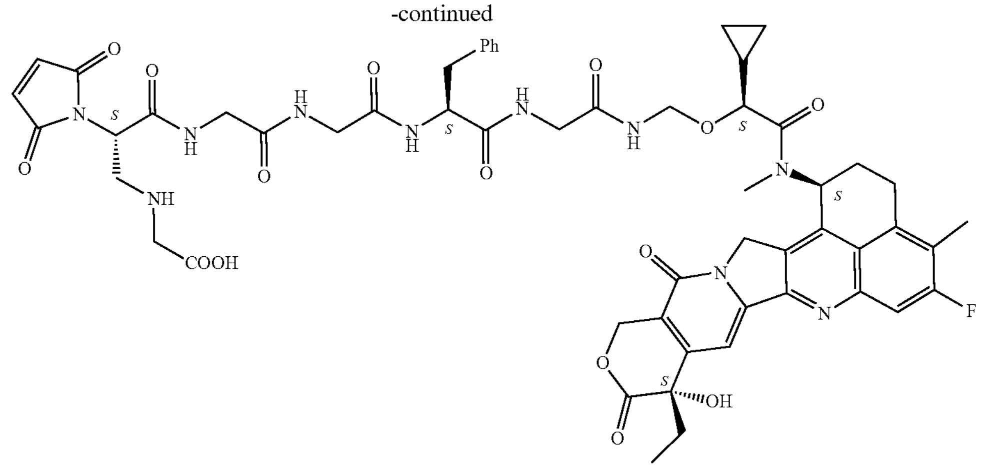

69A

Add 69a (100 mg, 0.078 mmol), zinc bromide (352 mg, 1.56 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 53 mg of solid; LC-MS: $[M+H]^+=1119.4$.

Step 3: Compound 69B

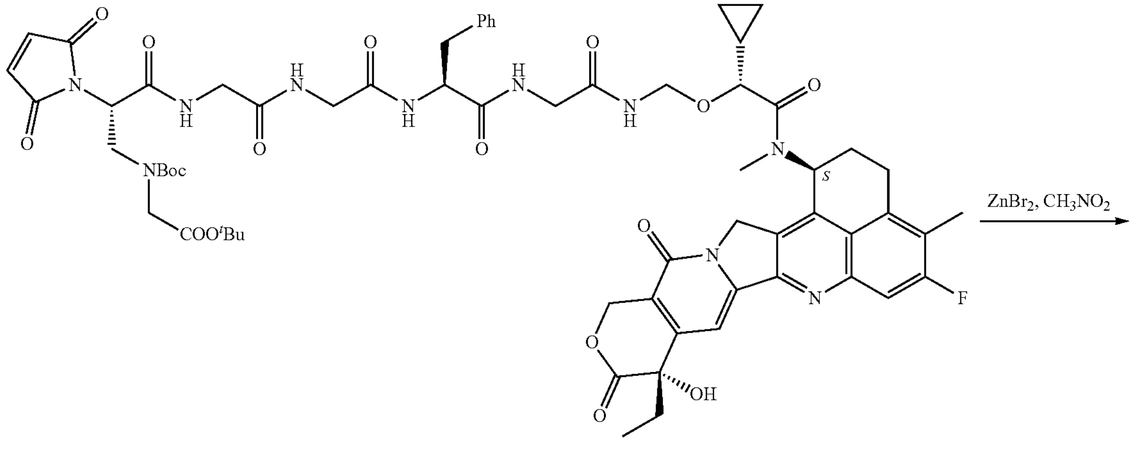

69b

-continued

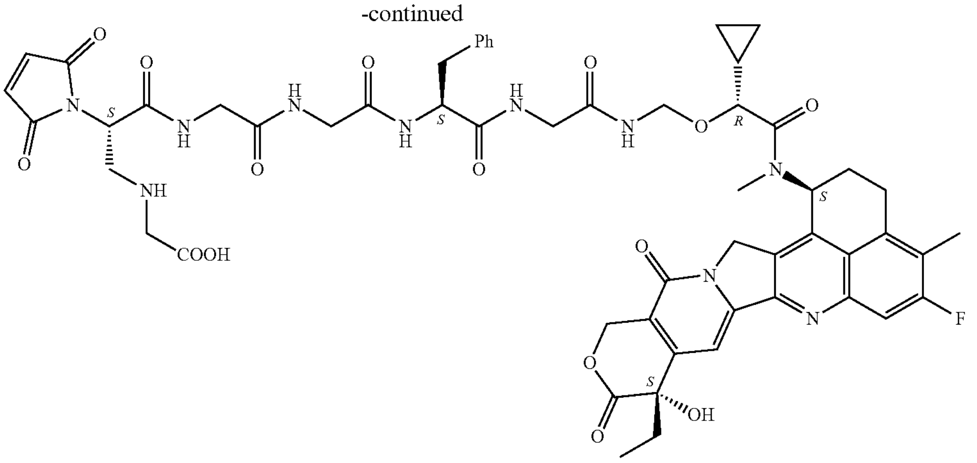

69B

Add 69b (100 mg, 0.078 mmol), zinc bromide (352 mg, 1.56 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 54 mg of solid; LC-MS: $[M+H]^+=1119.4$.

Example 78

Synthesis of Compounds 70A and 70B:

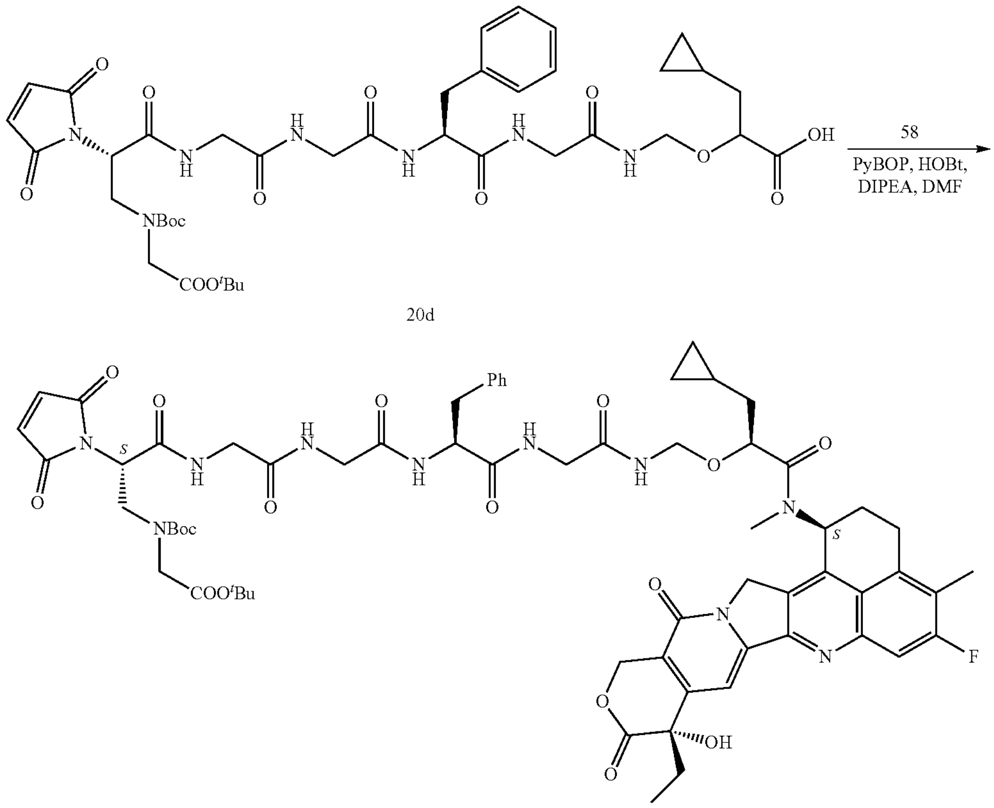

20d

70a

-continued

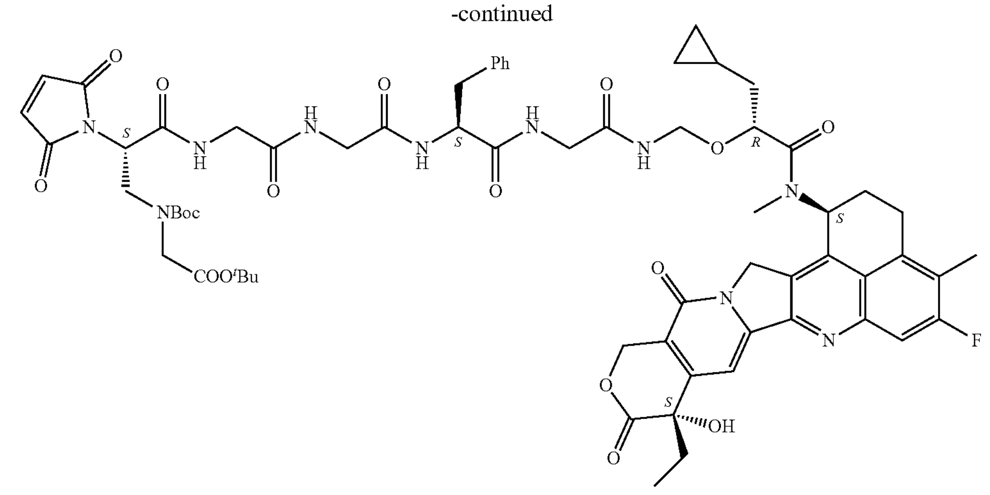

70b

Step 1: Compounds 70a and 70b

Add 20d (400 mg, 0.47 mmol), 58 (211.7 mg, 0.47 mmol), PyBOP (223 mg, 0.56 mmol), HOBt (83 mg, 0.56 mmol) and 10 mL DMF into a 50 mL single-necked flask, add DIPEA (248 uL, 1.5 mmol) in an ice-water bath, raise to room temperature and react for 2 h. After the completion of the reaction as detected by HPLC, the reaction solution was purified by HPLC to obtain the preparation liquids of compounds 70a and 70b. The preparation liquids were freeze-dried separately to obtain 106 mg of compound 70a, LC-MS: $[M+H]^+$=1289.5, and 101 mg of compound 70b, LC-MS: $[M+H]^+$=1289.4.

Step 2: Compound 70A

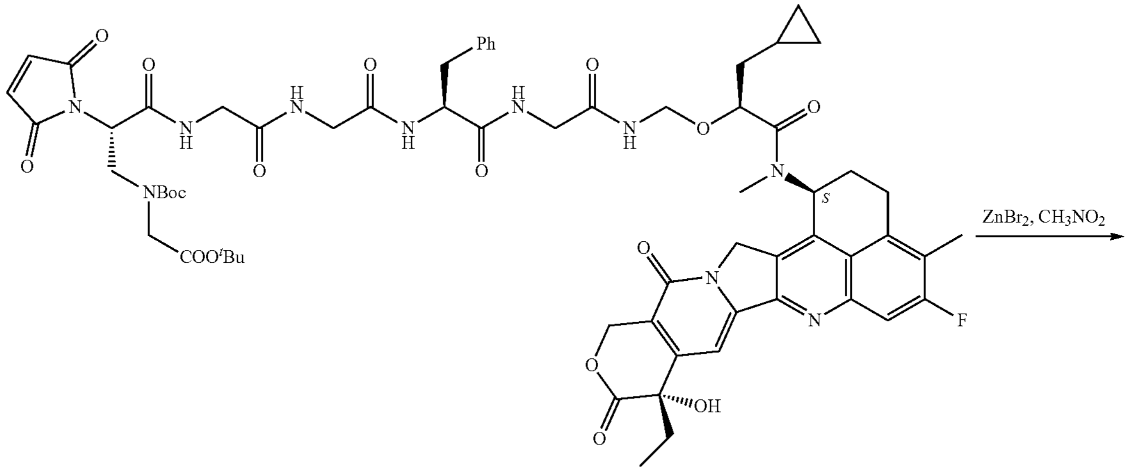

70a

-continued

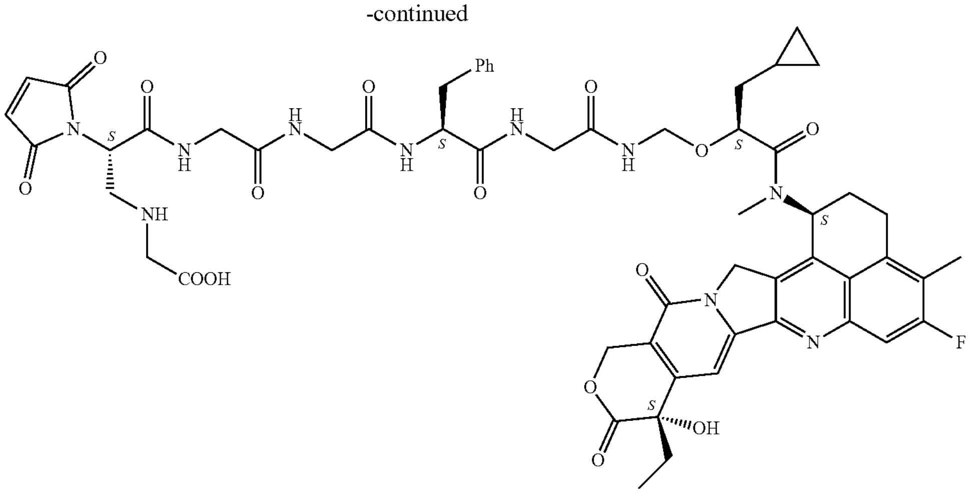

70A

Add 70a (100 mg, 0.078 mmol), zinc bromide (352 mg, 1.57 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 39 mg of solid; LC-MS: $[M+H]^+=1133.4$.

Step 3: Compound 70B

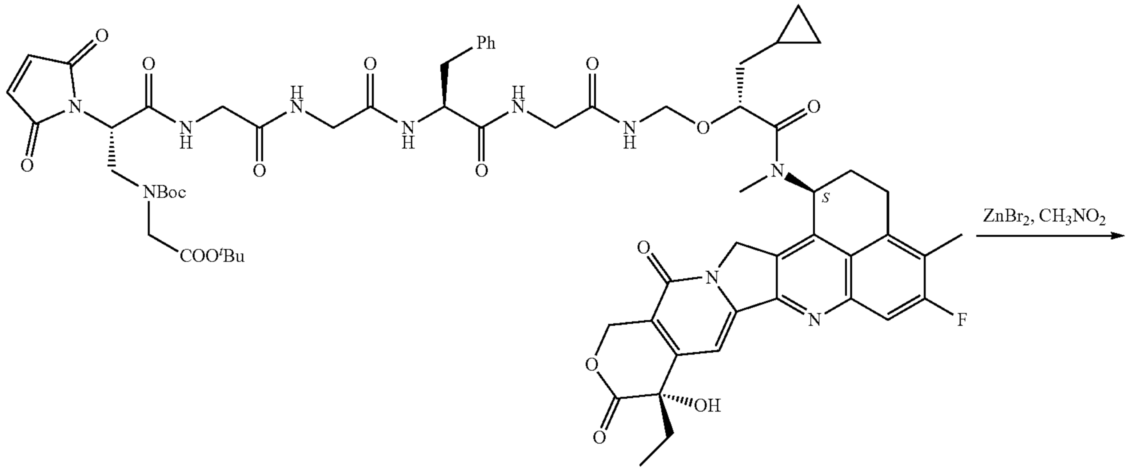

70b

-continued

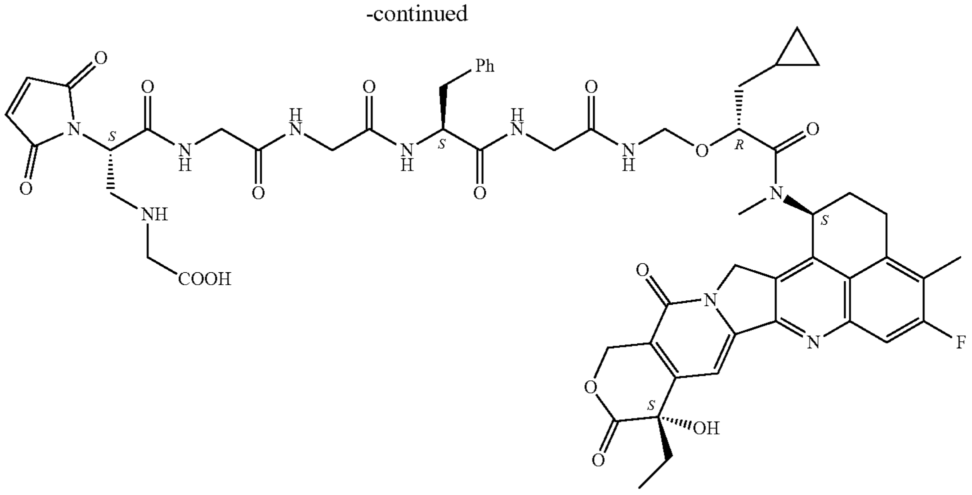

70B

Add 70b (100 mg, 0.078 mmol), zinc bromide (352 mg, 1.56 mmol) and 5 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain 35 mg of solid; LC-MS: $[M+H]^+=1133.4$.

Example 79

Synthesis of Compound 71:

71

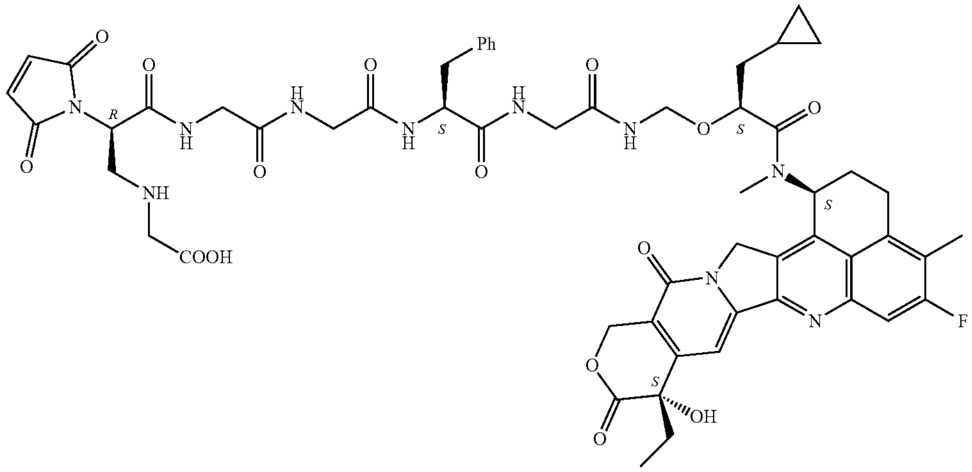

Referring to the synthetic route of Example 78, compound 71 (30 mg) was obtained; LC-MS: $[M+H]^+=1133.3$.

Example 80
Synthesis of Compound 72:
72
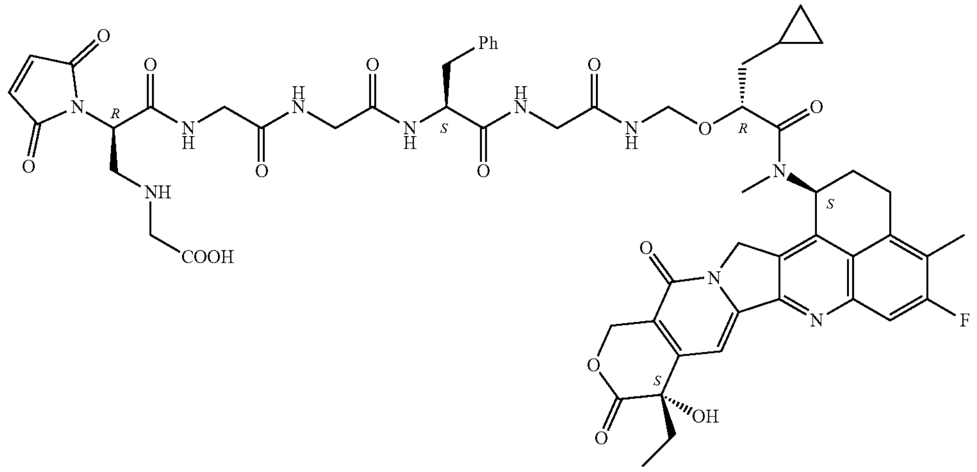
Referring to the synthetic route of Example 78, compound 72 (33 mg) was obtained; LC-MS: $[M+H]^+$=1133.4.
Example 81
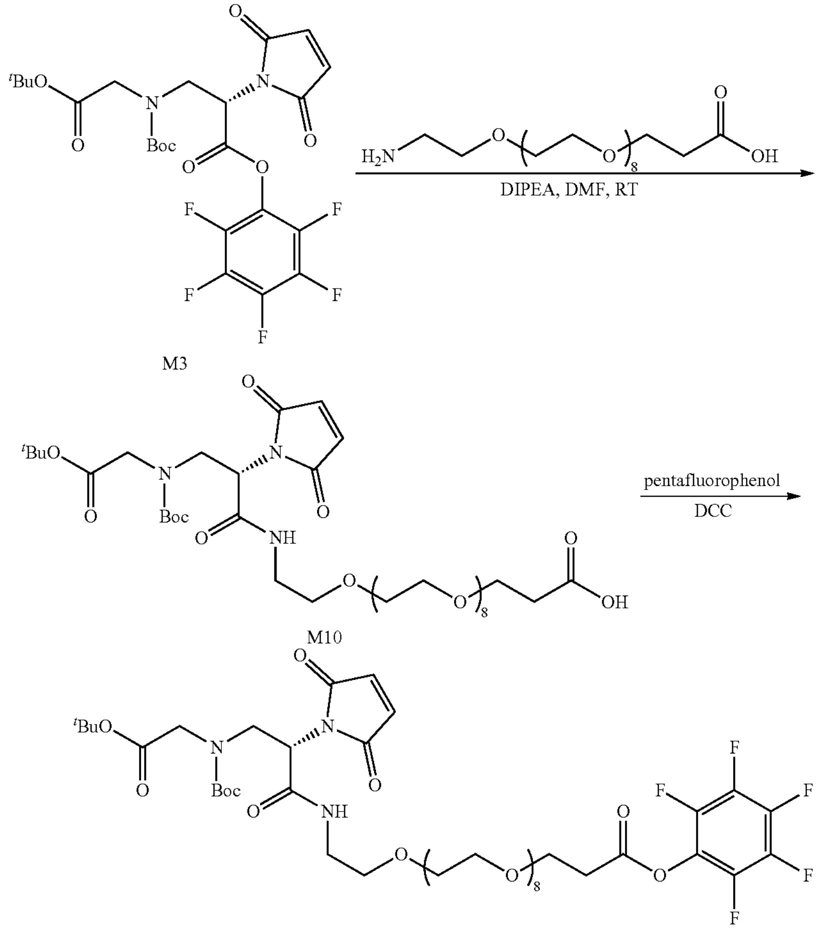
M3
M10
M11

Synthesis of Compound M11:

In a 100 mL single-necked flask, add compound M3 (11.0 g, 19.5 mmol, 1.0 eq), DIPEA (2.8 g, 21.4 mmol, 1.1 eq), 27-amino-4,7,10,13,16,19,22,25-octaoxaheptacosanoic acid (9.7 g, 20.5 mmol, 1.05 eq) and DMF (60 mL), and react at room temperature (monitored by TLC) for 20 minutes. The reaction solution was purified directly by preparative LC, and the preparation liquid was concentrated at 35° C. in a water bath under reduced pressure with a water pump to remove acetonitrile, and lyophilized to obtain compound M10 (13.2 g) in a yield of 78%; LC-MS: $[M+H]^+=866.5$.

Add compound M10 (13.0 g, 15 mmol, 1.0 eq), pentafluorophenol (3 g, 16.5 mmol, 1.1 eq), DCC (3.4 g, 16.5 mmol, 1.1 eq) and THF (30 mL) in a 100 mL single-necked flask, react at room temperature for 30 min (monitored by TLC), and filter off the insoluble material. The reaction solution was directly purified by preparative LC, and the preparation liquid was concentrated at 35° C. in a water bath under reduced pressure with a water pump to remove acetonitrile, and lyophilized to obtain compound M11 (14.2 g) in 92% yield; LC-MS: $[M+H]^+=1032.5$.

Example 82

Synthesis of Compound 73:

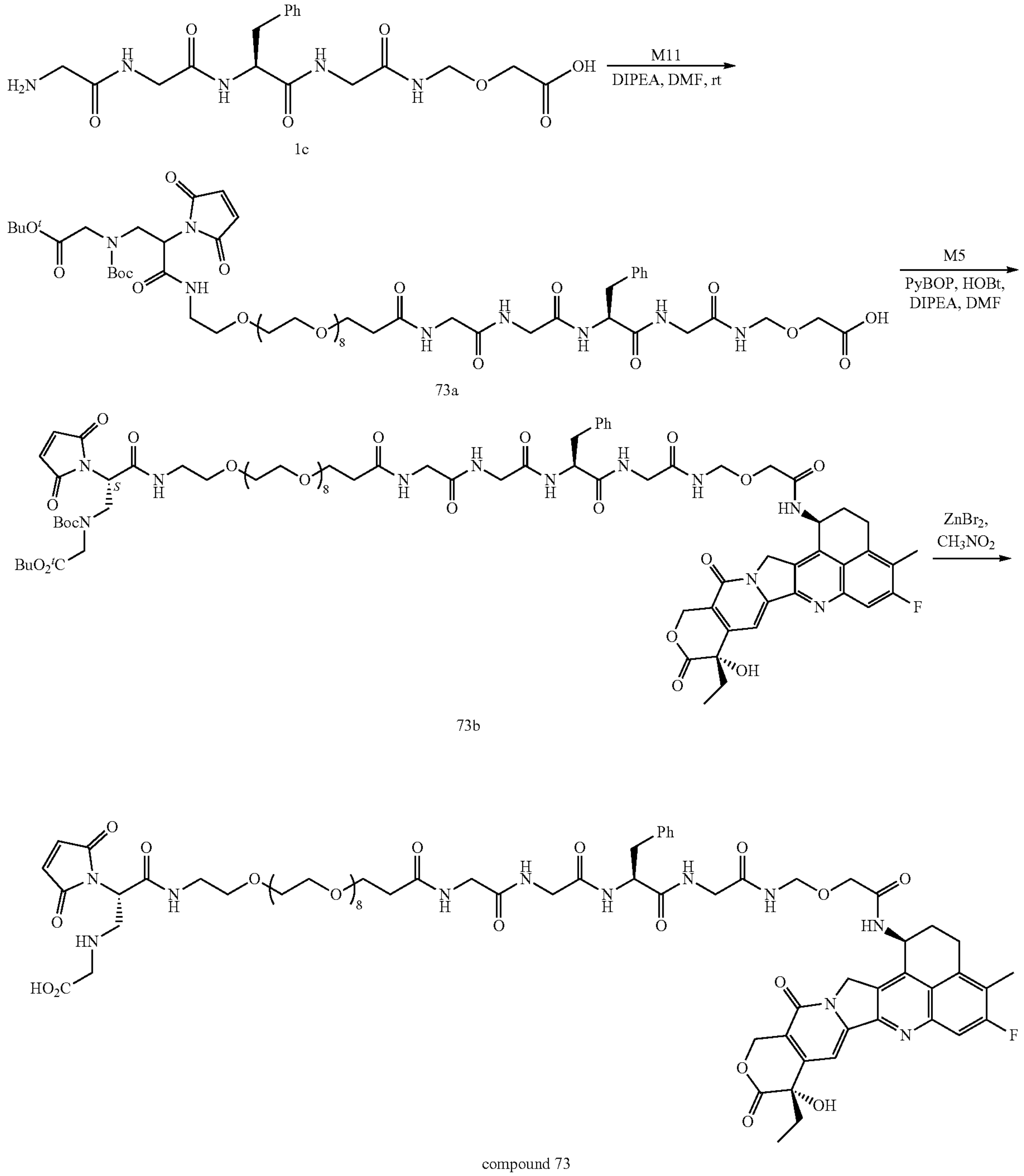

1c

73a

73b compound 73

Step 1: Synthesis of Compound 73a

Add 10 mL of DMF to M11 (1 g, 0.79 mol), cool in an ice-water bath to 0° C., add compound 1c (334 mg, 0.79 mol) and DIPEA (154 mg, 1.19 mol), and maintain the conditions to react for 1 h. TLC monitors for the completion of the reaction. The reaction solution was purified by preparative high-performance liquid chromatography (acetonitrile/purified water system), and the target peak was collected. After removing acetonitrile under reduced pressure, freeze-drying was performed to obtain about 1.2 g of compound 73a, MS m/z: $[M+H]^+$=1271.9.

Step 2: Synthesis of Compound 73b

Add 73a (1.2 g, 0.94 mmol), M5 (500 mg, 0.94 mmol), PyBOP (625 mg, 1.2 mmol), HOBt (162 mg, 1.2 mmol) and 15 mL DMF into a 25 mL single-necked flask, add DIPEA (310 mg, 2.4 mmol) in an ice-water bath, raise to room temperature and react for 2 h. After the completion of the reaction as detected by HPLC, the reaction solution was purified by HPLC to obtain a preparation liquid, which was lyophilized to obtain 73b (709 mg); LC-MS: $[M+H]^+$=1720.8.

Step 3: Synthesis of Compound 73

Add 73b (200 mg, 0.116 mmol), zinc bromide (523 mg, 2.32 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 73 (88 mg); LC-MS: $[M+H]^+$=1532.6.

Example 83

Synthesis of Compound 74:

compound 74

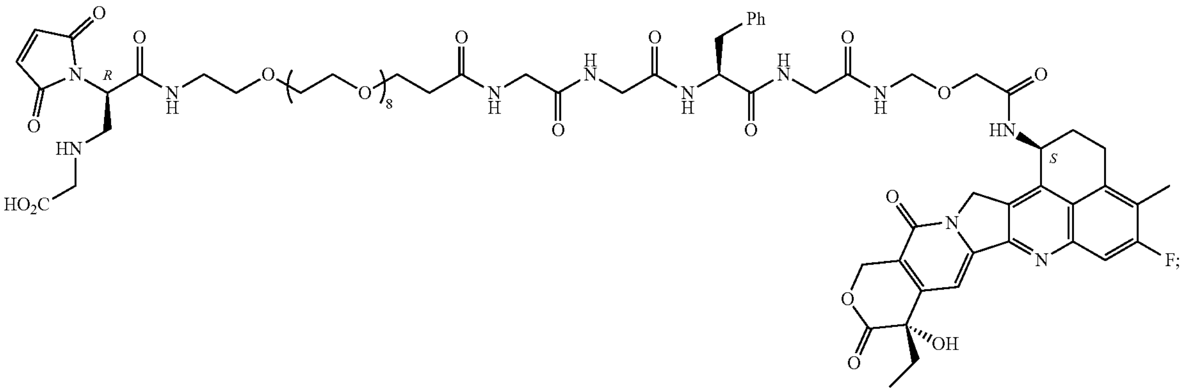

Referring to the synthetic route of Example 82, compound 74 (90 mg) was obtained; LC-MS: $[M+H]^+$=1532.6.

Example 84

Synthesis of Compound 75:

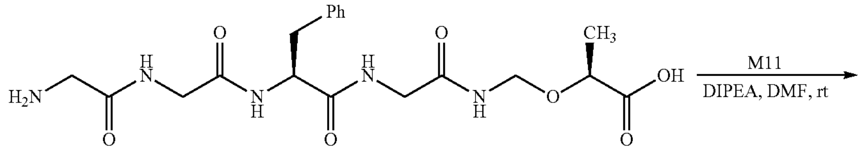

5c

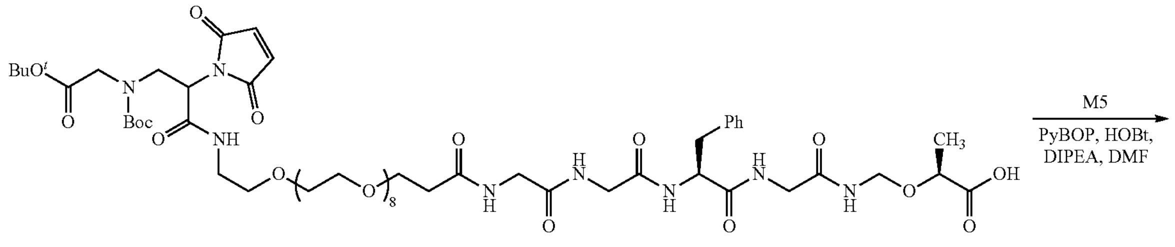

75a

-continued

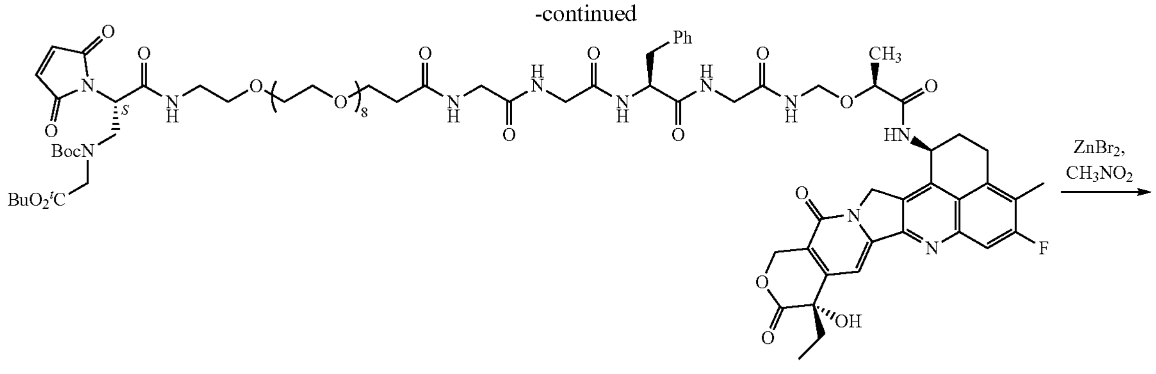

75b

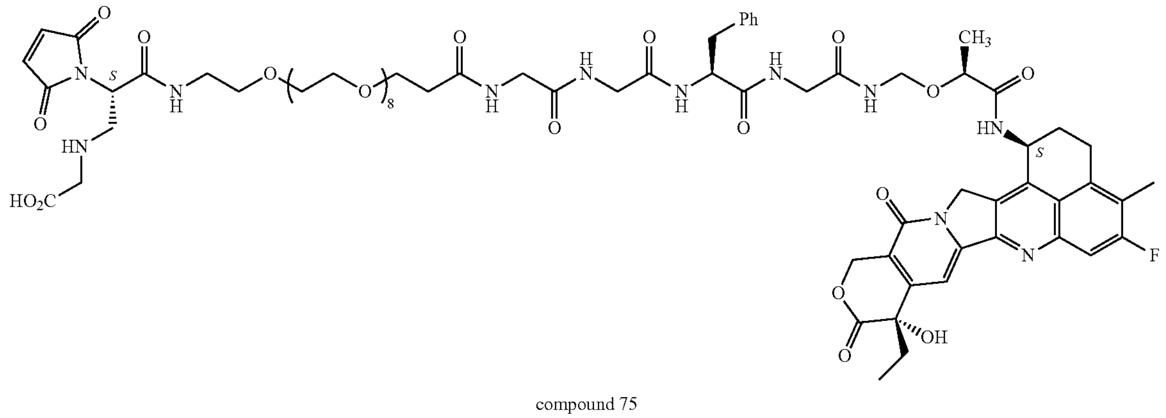

compound 75

Step 1: Synthesis of Compound 75a

Add 10 mL of DMF to M11 (1 g, 0.79 mol), cool in an ice-water bath to 0° C., add compound 5c (345 mg, 0.79 mol) and DIPEA (154 mg, 1.19 mol), and maintain the conditions to react for 1 h. TLC monitors for completion of the reaction. The reaction solution was purified by preparative high-performance liquid chromatography (acetonitrile/purified water system), and the target peak was collected. After removing acetonitrile under reduced pressure, lyophilization was performed to obtain 0.9 g of compound 75a, MS m/z: $[M+H]^+$=1285.6.

Step 2: Synthesis of Compound 75b

Add 75a (700 mg, 0.54 mmol), M5 (289 mg, 0.54 mmol), PyBOP (313 mg, 0.6 mmol), HOBt (81 mg, 0.6 mmol) and 10 mL DMF into a 25 mL single-necked flask, add DIPEA (155 mg, 1.2 mmol) in an ice-water bath, raise to room temperature and react for 2 h. After completion of the reaction as detected by HPLC, the reaction solution was purified by HPLC to obtain a preparation liquid, which was lyophilized to obtain 75b (304 mg); LC-MS: $[M+H]^+$= 1734.8.

Step 3: Synthesis of Compound 75

Add 75b (200 mg, 0.116 mmol), zinc bromide (523 mg, 2.32 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 75 (96 mg); LC-MS: $[M+H]^+$= 1546.6.

Example 85
Synthesis of Compound 76:
compound 76
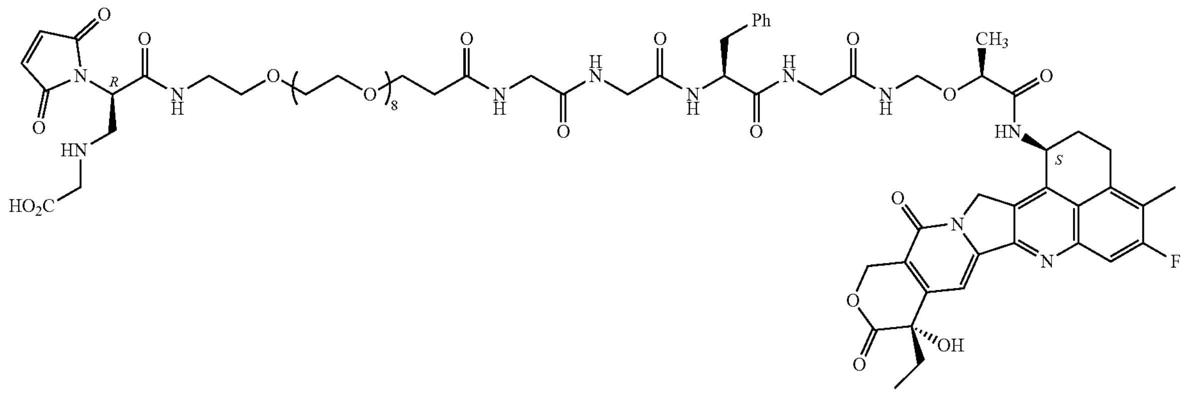
Referring to the synthetic route of Example 84, compound 76 (92 mg) was obtained; LC-MS: $[M+H]^+=1546.5$.
Example 86
Synthesis of Compound 77:
compound 77
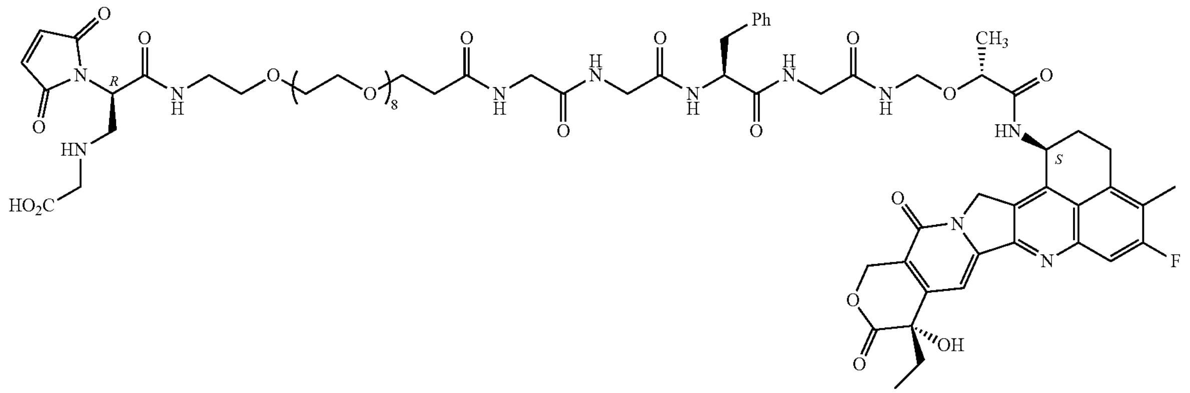
Referring to the synthetic route of Example 84, compound 77 (87 mg) was obtained; LC-MS: $[M+H]^+=1546.5$.

Example 87
Synthesis of Compound 78:
compound 78
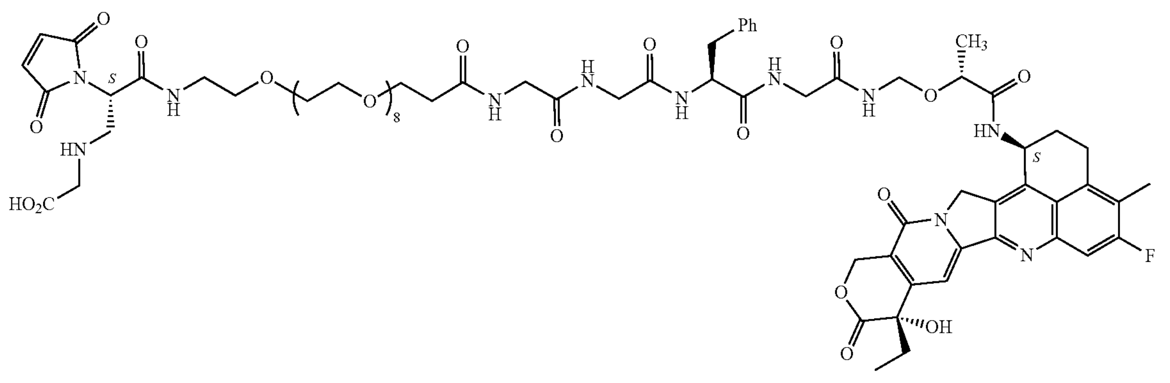
Referring to the synthetic route of Example 84, compound 78 (94 mg) was obtained; LC-MS: $[M+H]^+=1546.7$.
Example 88
Synthesis of Compounds 79 and 80:
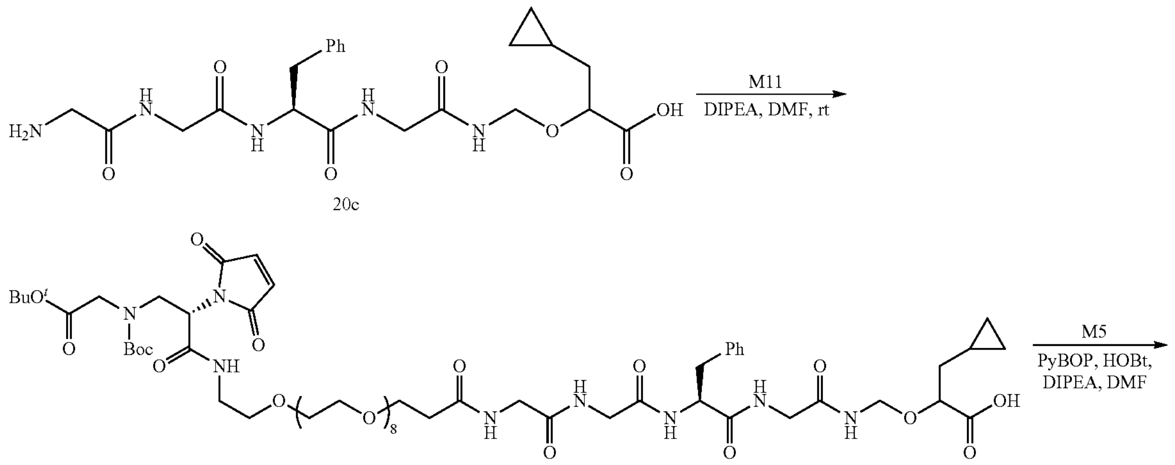
20c
79a
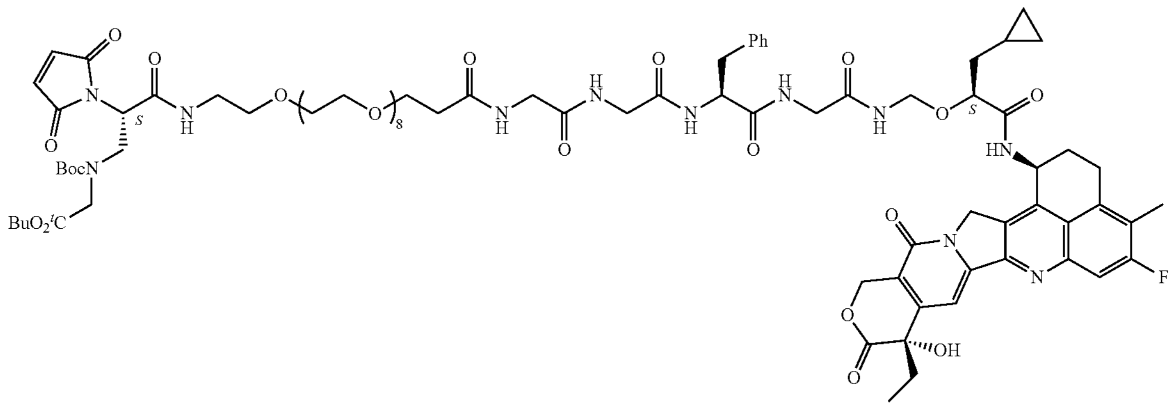
79b-1

-continued

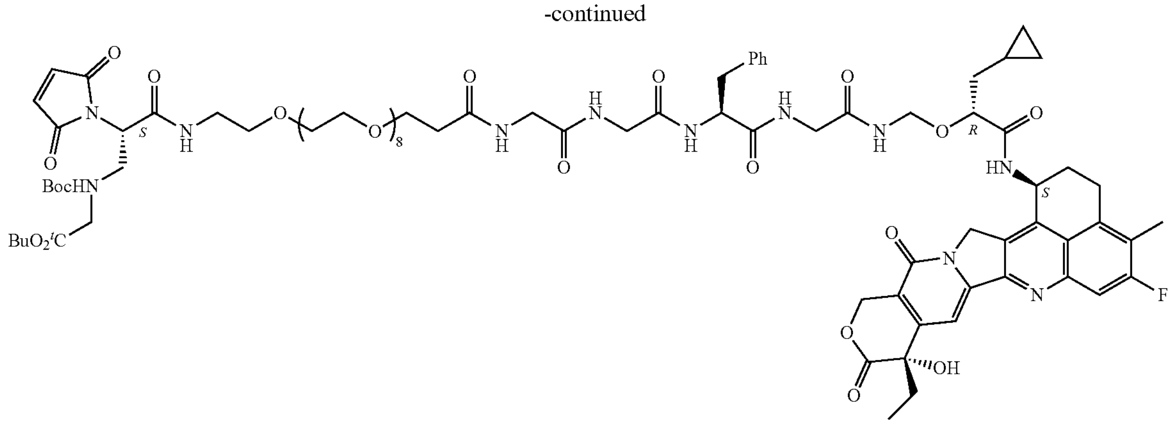

79b-2

Step 1: Synthesis of Compound 79a

Add 10 mL of DMF to M11 (1 g, 0.79 mol), cool to 0° C. in an ice-water bath, add compound 20c (377 mg, 0.79 mol) and DIPEA (154 mg, 1.19 mol), and maintain the conditions to react for 1 h. TLC monitors for completion of the reaction. The reaction solution was purified by preparative high-performance liquid chromatography (acetonitrile/purified water system), and the target peak was collected. After removing acetonitrile under reduced pressure, lyophilization was performed to obtain 783 mg of compound 79a, MS m/z: $[M+H]^+$=1325.8.

Step 2: Synthesis of Compounds 79b-1 and 79b-2

Add 79a (600 mg, 0.45 mmol), M5 (240 mg, 0.45 mmol), PyBOP (261 mg, 0.5 mmol), HOBt (68 mg, 0.5 mmol) and 10 mL of DMF to a 25 mL single-necked flask, add DIPEA (130 mg, 1 mmol) in an ice-water bath, and raise to room temperature to react for 2 h. After the completion of the reaction as detected by HPLC, the reaction solution was purified by HPLC to obtain the preparation liquids of compounds 79b-1 and 79b-2, and the preparation liquids were lyophilized to obtain 79b-1 (124 mg); LC-MS: $[M+H]^+$= 1743.0; and obtain 79b-1 (122 mg); LC-MS: $[M+H]^+$= 1743.0.

Step 3: Synthesis of Compound 79

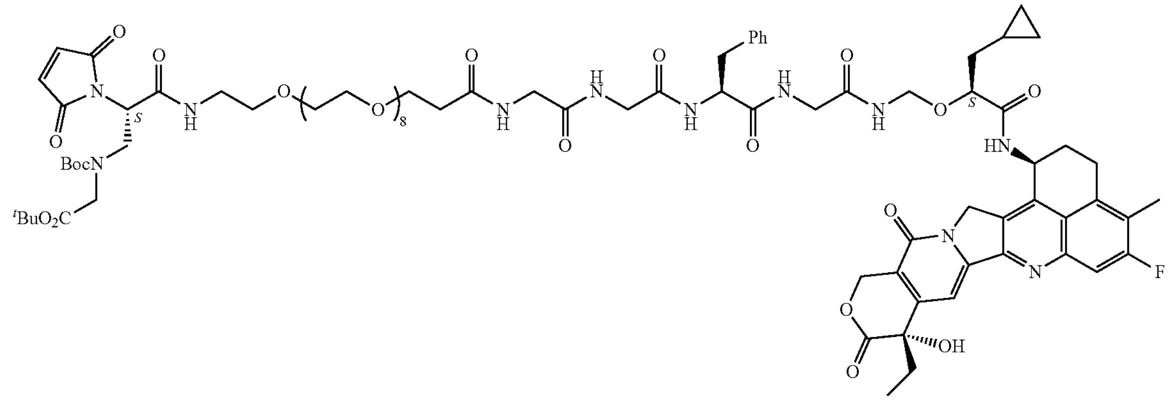

79b-1

ZnBr$_2$

-continued

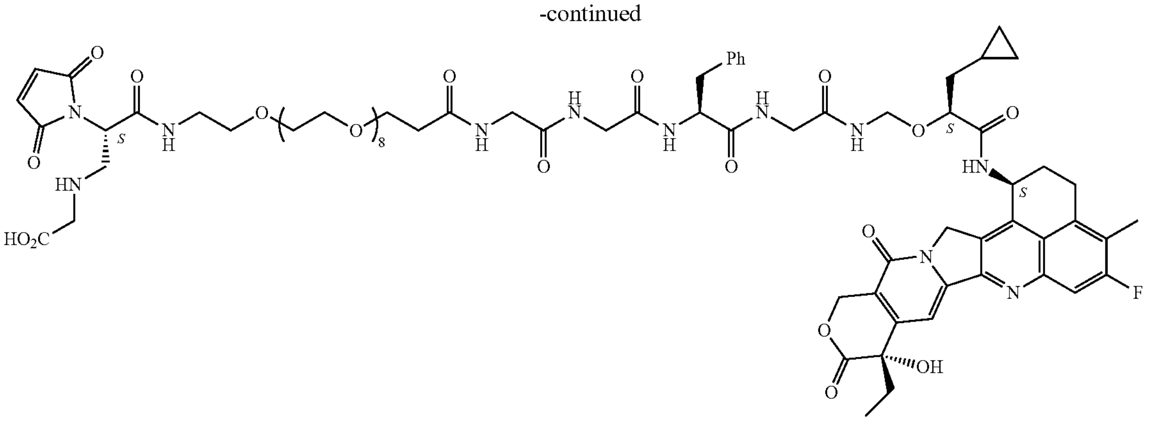

79

Add 79b-1 (100 mg, 0.057 mmol), zinc bromide (258 mg, 1.15 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 79 (30 mg); LC-MS: $[M+H]^+=$ 1586.9.

Step 4: Synthesis of Compound 80

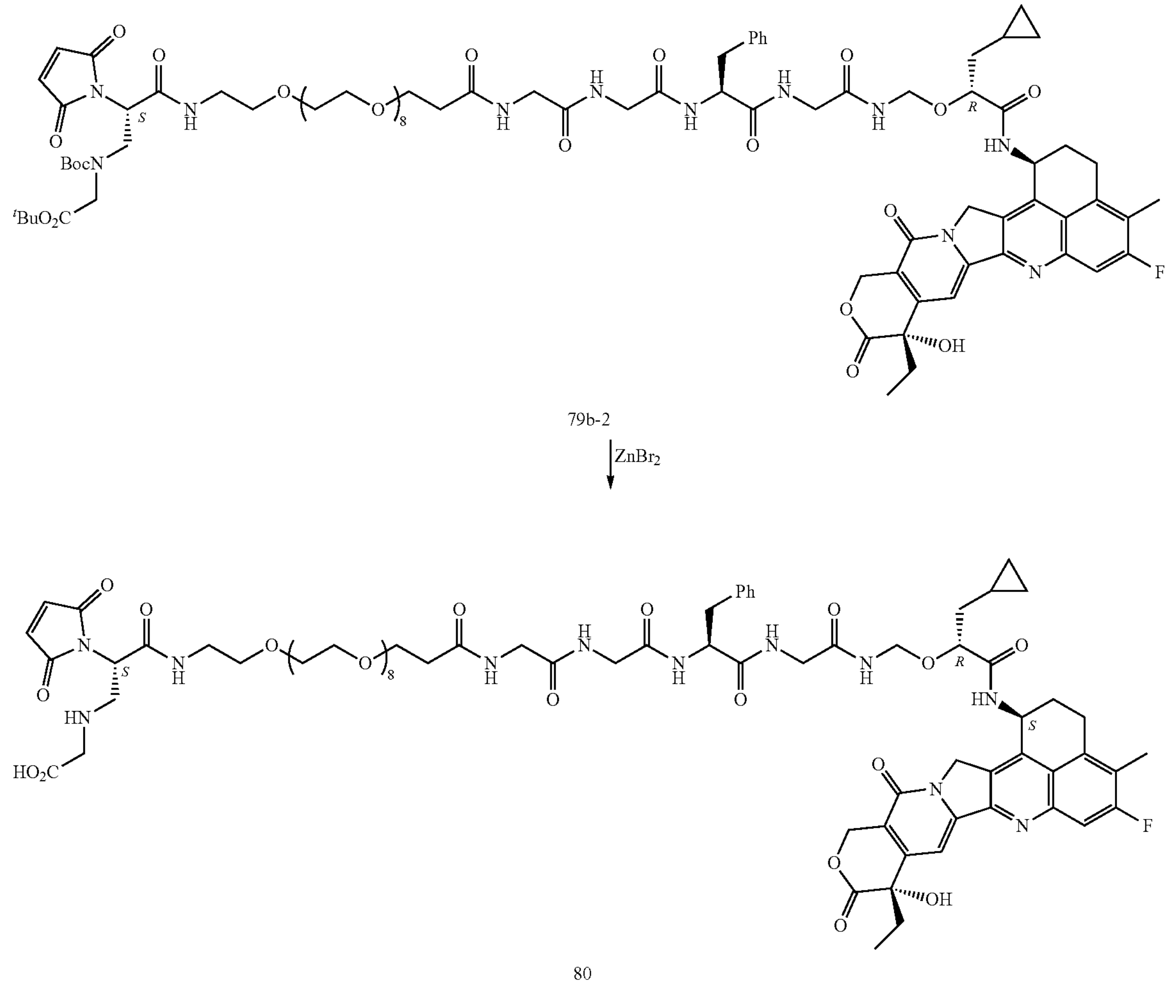

79b-2

80

Add 79b-2 (100 mg, 0.057 mmol), zinc bromide (258 mg, 1.15 mmol) and 10 mL nitromethane into a 25 mL single-necked flask and react at 40° C. for 1 h. After the completion of the reaction as detected by HPLC, the solvent was removed by concentration under reduced pressure to obtain a crude product. The crude product was purified by HPLC to obtain a product preparation liquid, which was lyophilized to obtain solid compound 80 (33 mg); LC-MS: $[M+H]^+$= 1587.0.

Example 89

Synthesis of Compound 81:

81

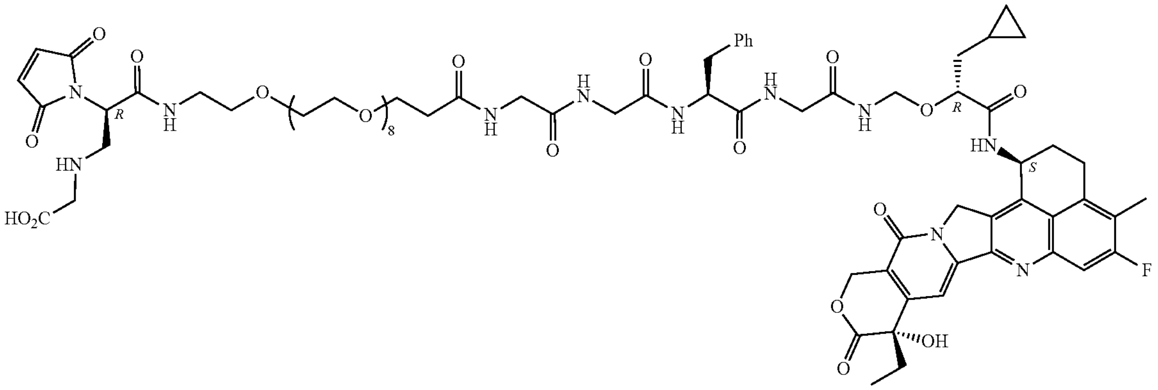

Referring to the synthetic route of Example 88, compound 81 (24 mg) was obtained; LC-MS: $[M+H]^+$=1586.9.

Example 90

Synthesis of Compound 82:

82

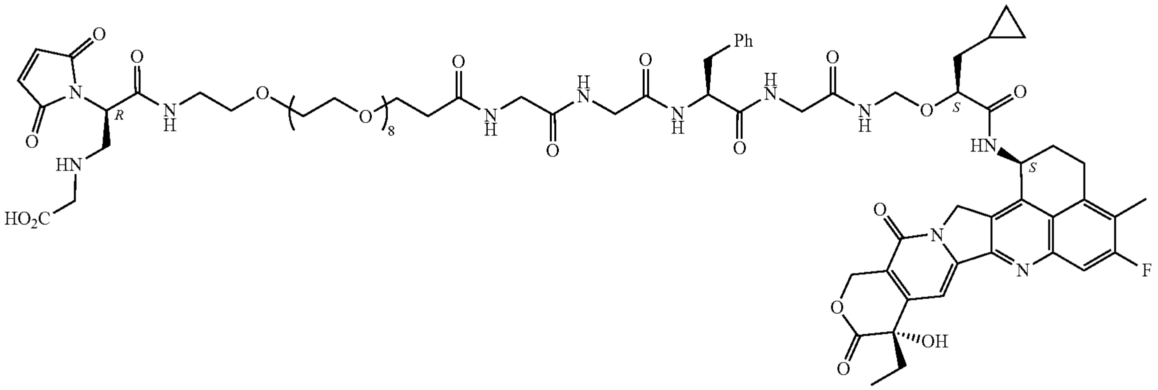

Referring to the synthetic route of Example 88, compound 82 (29 mg) was obtained; LC-MS: $[M+H]^+$=1586.9.

Example 91

1) Expression and Purification of SI-1x6.4 Antibody:

Expi293 (Shanghai OPM Biosciences Co., Ltd.) suspension cells were used to express SI-1x6.4 antibody. The day before transfection, cells were inoculated at a density of $0.9\times10^6$ cells/mL in a 1 L shake flask containing 300 mL of OPM-293 CD05 Medium (81075-001, Shanghai OPM Biosciences Co., Ltd.), culturing was performed overnight at 37° C., 5% C02, and 120 rpm in a cell culture shaker. On the next day, the antibody expression plasmid was transfected with PEI-MAX, wherein the mass ratio of plasmid:PEI-MAX was 1:3. OPM-293 ProFeed supplement was added at 5% (v/v) on the first day after transfection, and then again at 5% (v/v) on the third day after transfection, and centrifugation was performed to collect the supernatant on the sixth day after transfection.

The collected cell expression supernatant was eluted with 0.05 M sodium acetate (pH 3.6) in a Protein A affinity chromatography column (UniMab 50, Suzhou Nanomicro Technology Co., Ltd.), and the captured antibody was adjusted to pH 7.0 with 1 M Tris-HCl (pH 8.8) at 0.7/10 (v/v), and then passed through a gel filtration chromatography column SEC (Superdex 200, GE) to remove impurities such as polymers, while the antibody buffer was replaced with 20 mM PB (pH 6.5).

Antibody SI-1×6.4:

Light chain nucleic acid coding sequence

SEQ ID NO: 1

```
GACATCTTGCTGACTCAGTCTCCAGTCATCCTGTCTGTGAGTCCAGGAGA
AAGAGTCAGTTTCTCCTGCAGGGCCAGTCAGAGTATTGGCACAAACATAC
ACTGGTATCAGCAAAGAACAAATGGTTCTCCAAGGCTTCTCATAAAGTAT
GCTTCTGAGTCTATCTCTGGGATTCCTTCCAGGTTTAGTGGCAGTGGATC
AGGGACAGATTTTACTCTTAGCATCAACAGTGTGGAGTCTGAAGATATTG
CAGATTATTACTGTCAACAAAATAATAACTGGCCAACCACGTTCGGTGCT
GGGACCAAGCTGGAGCTGAAACGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGTTAG
```

Light chain amino acid sequence

SEQ ID NO: 2

```
DILLTQSPVILSVSPGERVSFSCRASQSIGTNIHWYQQRTNGSPRLLIKY
ASESISGIPSRFSGSGSGTDFILSINSVESEDIADYYCQQNNNEPTIFGA
GIKLELKRTVAAPSVFIFPPSDEQLKSGTASVVCLLNNFYPREAKVQWKV
DNALQSGNSQESVTEQDSKDSTYSLSSTLILSKADYEKHKVYACEVTHQG
LSSPVTKSENRGEC
```

wherein the variable region is:

SEQ ID NO: 28

```
DILLTQSPVILSESPGERESFSCRASQSIGTNIHWYQQRTNGSPRLLIKY
ASESISGIPSRESGSGSGIDFTLSINSVESEDIADYYCQQNNNWPTTFGA
GTKLELK
```

where the underlined portions are, from left to right, CDR1 (SEQ ID NO: 25), CDR2 (SEQ ID NO: 26), and CDR3 (SEQ ID NO: 27), respectively.

Nucleic acid coding sequence for the construct of the heavy chain and single-chain Fv (scFv) structural domain

SEQ ID NO: 3

```
CAGGTGCAGCTGAAGCAGTCAGGACCTGGCCTAGTGCAGCCCTCACAGA
GCCTGTCCATCACCTGCACAGTCTCTGGTTTCTCATTAACTAACTATGG
```

-continued

```
TGTACACTGGGTTCGCCAGTCTCCAGGAAAGGGTCTGGAGTGGCTGGGA
GTGATATGGAGTGGTGGAAACACAGACTATAATACACCTTTCACATCCA
GACTGAGCATCAACAAGGACAATTCCAAGAGCCAAGTTTTCTTTAAAAT
GAACAGTCTGCAATCTAATGACACAGCCATATATTACTGTGCCAGAGCC
CTCACCTACTATGATTACGAGTTTGCTTACTGGGGCCAAGGGACTCTGG
TCACTGTCTCTAGCGCTAGCACCAAGGGCCCATCGGTCTTCCCCCTGGC
ACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCG
CCCTGACCAGCGGCGTGCACACCTTCCCGGCTGTCCTACAGTCCTCAGG
ACTCTACTCCCTCAGCAGCGTGGTGACCGTGCCCTCCAGCAGCTTGGGC
ACCCAGACCTACATCTGCAACGTGAATCACAAGCCCAGCAACACCAAGG
TGGACAAGAGAGTTGAGCCCAAATCTTGTGACAAAACTCACACATGCCC
ACCGTGCCCAGCACCTGAACTCCTGGGGGGACCGTCAGTCTTCCTCTTC
CCCCCAAAACCCAAGGACACCCTCATGATCTCCCGGACCCCTGAGGTCA
CATGCGTGGTGGTGGACGTGAGCCACGAAGACCCTGAGGTCAAGTTCAA
CTGGTACGTGGACGGCGTGGAGGTGCATAATGCCAAGACAAAGCCGCGG
GAGGAGCAGTACAACAGCACGTACCGTGTGGTCAGCGTCCTCACCGTCC
TGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGG
CAGCCCCGAGAACCACAGGTGTACACCCTGCCCCCATCCCGGGATGAGC
TGACCAAGAACCAGGTCAGCCTGACCTGCCTGGTCAAAGGCTTCTATCC
CAGCGACATCGCCGTGGAGTGGGAGAGCAATGGGCAGCCGGAGAACAAC
TACAAGACCACGCCTCCCGTGCTGGACTCCGACGGCTCCTTCTTCCTCT
ATAGCAAGCTCACCGTGGACAAGAGCAGGTGGCAGCAGGGGAACGTCTT
CTCATGCTCCGTGATGCATGAGGCTCTGCACAACCACTACACGCAGAAG
AGCCTCTCCCTGTCTCCGGGTGGCGGTGGAGGGTCCGGCGGTGGTGGAT
CACAGGTGCAATTGCAGGAGTCGGGGGGAGGCCTGGTCAAGCCTGGAGG
GTCCCTGAGACTCTCCTGTGCAGCCTCTGGATTCACCTTTAGTAGTTAT
TGGATGAGCTGGGTCCGCCAGGCTCCAGGGAAGGGGCTGGAGTGGGTGG
CCAACATAAACCGCGATGGAAGTTGCGAGTTACTATGTGGACTCTGTGA
AGGGCCGATTCACCATCTCCAGAGACGACGCCAAGAACTCACTGTATCT
GCAAATGAACAGCCTGAGAGCTGAGGACACGGCTGTGTATTACTGTGCG
AGAGATCGTGGGGTGGGCTACTTCGATCTCTGGGGCCGTGGCACCCTGG
TCACCGTCTCGAGCGGTGGAGGCGGTTCAGGCGGAGGTGGTTCCGGCGG
TGGCGGCTCCCAGTCTGCCCTGACTCAGCCTGCCTCCGTGTCTGGGTCT
CCTGGACAGTCGATCACCATCTCCTGCACTGGAACCAGCAGTGACGTTG
GTGGTTATAACTTTGTCTCCTGGTACCAACAACACCCAGGCAAAGCCCC
CAAACTCATGATCTATGATGTCAGTGATCGGCCCTCAGGGGTGTCTGAT
CGCTTCTCCGGCTCCAAGTCTGGCAACACGGCCTCCCTGATCATCTCTG
GCCTCCAGGCTGACGACGAGGCTGATTATTACTGCAGCTCATATGGGAG
```

-continued

CAGCAGCACTCATGTGATTTTCGGCGGAGGGACCAAGGTGACCGTCCTA

TAA

Amino acid sequence for the construct of heavy chain and single-chain Fv (scFv) structural domain

SEQ ID NO: 4

QVQLKQSGPGLVQPSQSLSTTCTVSGFSLTNYGTHWVRQSPGKGLEWLGT

TWSGGNTDYNTPFTSRLSINKDNSKSQVFFKMNSLQSNDTAIYYCARALT

YYDYFFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGGG

GGSGGGGSQVQLQESGGGLVKPGGSLRLSCAASGFTFSSYWMSWVRQAPG

KGLEWVANINRDGSASYYYDSVKGRFTISRDDAKNSLYLQMNSLRAEDTA

VYYCARDRGVGYFDLWGRGTLVTVSSGGGGSGGGGSGGGGSQSALTQPAS

VSGSPGQSITISCTGTSSDVGGYNFVSWYQQHPGKAPKLMIYDVSDRPSG

VSDRFSGSKSGNTASLIISGLQADDEADYYCSSYGSSSTHVIFGGGTKVT

VL where the variable region of the heavy chain is:

SEQ ID NO: 38

QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCAR

ALTYYDYEFAYWGQGTLVTVSS where the underlined portions are, from left to right, CDR1 (SEQ ID NO: 29), CDR2 (SEQ ID NO: 30), and CDR3 (SEQ ID NO: 31), respectively.

The variable region of the heavy chain in the structural domain of the single chain Fv (scFv) is:

SEQ ID NO: 39

QVQLQESGGGLVKPGGSLRLSCAASGFTFSSYWMSWVRQAPGKGLEWVAN-INR

DGSASYYVDSVKGRFTISRDDAKNSLYLQMNSLRAEDTAVYY-CARDRGVGYFD

LWGRGTLVTVSS where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

SEQ ID NO: 40

QSALTQPASVSGSPGQSITISCTGTSSDVGGY-NFVSWYQQHPGKAPKLMIYDV

-continued

SDRPSGVSDRFSGSKSGNTASLIISGLQADDEADYYCSSYGSSSTHV-IFGGGT

KVTVL where the underlined portions are, from left to right, CDR1 (SEQ ID NO: 35), CDR2 (SEQ ID NO: 36), and CDR3 (SEQ ID NO: 37), respectively.

2) Expression and purification of SI-1×22 antibody: a similar method was followed for the expression and purification of SI-1×22 antibody.

Antibody SI-1×22:

Nucleic acid coding sequence for the construct of light chain and single-chain Fv (scFv) structural domain

SEQ ID NO: 9

GACATCTTGCTGACTCAGTCTCCAGTCATCCTGTCTGTGAGTCCAGGAG

AAAGAGTCAGTTTCTCCTGCAGGGCCAGTCAGAGTATTGGCACAAACAT

ACACTGGTATCAGCAAAGAACAAATGGTTCTCCAAGGCTTCTCATAAAG

TATGCTTCTGAGTCTATCTCTGGGATTCCTTCCAGGTTTAGTGGCAGTG

GATCAGGGACAGATTTTACTCTTAGCATCAACAGTGTGGAGTCTGAAGA

TATTGCAGATTATTACTGTCAACAAAATAATAACTGGCCAACCACGTTC

GGTTGTGGGACCAAGCTGGAGCTGAAACGTACGGTGGCTGCACCATCTG

TCTTCATCTTCCCGCCATCTGATGAGCAGTTGAAATCTGGAACTGCCTC

TGTTGTGTGCCTGCTGAATAACTTCTATCCCAGAGAGGCCAAAGTACAG

TGGAAGGTGGATAACGCCCTCCAATCGGGTAACTCCCAGGAGAGTGTCA

CAGAGCAGGACAGCAAGGACAGCACCTACAGCCTCAGCAGCACCCTGAC

GCTGAGCAAAGCAGACTACGAGAAACACAAAGTCTACGCCTGCGAAGTC

ACCCATCAGGGCCTGAGCTCGCCCGTCACAAAGAGCTTCAACAGGGGAG

AGTGTGGTGGCGGCGGAAGTGGCGGTGGAGGATCCGGCGGTGGTGGATC

ACAGGTGCAGCTGCAGGAGTCGGGGGGAGGCCTGGTCAAGCCTGGAGGG

TCCCTGAGTCTCTCCTGTGCAGCCTCTGGATTCACCTTTAGTAGTTATT

GGATGAGCTGGGTCCGCCAGGCTCCAGGGAAGGGGCTGGAGTGGGTGGC

CAACATAAACCGCCATGGAAGTGCGAGTTACTATGTGGACTCTGTGAAG

GGCCGATTCACCATCTCCAGAGACGACGCCAAGAACTCACTGTATCTGC

AAATGAACAGCCTGAGAGCTGAGGACACGGCTGTGTATTACTGTGCGAG

AGATCGTGGGGTGGGCTACTTCGATCTCTGGGGCCGTGGCACCCTGGTC

ACCGTCTGAGCGGTGGAGGCGGTTCAGGCGGAGGTGGTTCCGGCGGTGG

CGGCTCCCAGTCTGCCCTGACTCAGCCTGCCTCCGTGTCTGGGTCTCCT

GGACAGTCGATCACCATCTCCTGCACTGGAACCAGCAGTGACGTTGGTG

GTTATAACTTTGTCTCCTGGTACCAACAACACCCAGGCAAAGCCCCCAA

ACTCATGATCTATGATGTCAGTGATCGGCCCTCAGGGGTGTCTGATCGC

TTCTCCGGCTCCAAGTCTGGCAACACGGCCTCCCTGATCATCTCTGGCC

TCCAGGCTGACGACGAGGCTGATTATTACTGCAGCTCATATGGGAGCAG

CAGCACTCATGTGATTTTCGGCGGAGGGACCAAGGTGACCGTCCTATAA

Amino acid sequence of construct of light chain and single-chain Fv (scFv) structural domain SEQ ID NO: 10
DLLTQSPVILSVSPGERVSFSCRASQSIGTNIHWYQQRTNGSPRLLIKYA
SESISGIPSRFSGSGSGTDFTLSINSVESEDIADYYCQQNNNWPTTFGCG
TKLELKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGECGGGGSGGGGSGGGGSQVQLQESGGGLVKPGGSLSLSC
AASGFTFSSYWMSWVRQAPGKGLEWVANINRDGSASYYVDSVKGRFTISR
DDAKNSLYLQMNSLRAEDTAVYYCARDRGVGYFDLWGRGTLVTVSSGGGG
SGGGGSGGGGSQSALTQPASVSGSPGQSITISCTGTSSDVGGYNFVSWYQ
QHPGKAPKLMIYDVSDRPSGVSDRFSGSKSGNTASLIISGLQADDEADYY
CSSYGSSSTHVTFGGGTKVTVL where the variable region of the light chain is:

SEQ ID NO: 49
DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGCGT
KLELK where the underlined portions are, from left to right, CDR1 (SEQ ID NO: 25), CDR2 (SEQ ID NO: 26), and CDR3 (SEQ ID NO: 27), respectively.

The variable region of the heavy chain in the structural domain of the single-chain Fv (scFv) is:

SEQ ID NO: 50
QVQLQESGGGLVKPGGSLSLSCAASGFTFSSYWMSWVRQAPGKGLEWVANI
NRDGSASYYVDSVKGRFTISRDDAKNSLYLQMNSLRAEDTAVYYCARDRGV
GYFDLWGRGTLVTVSS where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

SEQ ID NO: 51
QSALTQPASVSGSPGQSITISCTGTSSDVGGYNFVSWYQQHPGKAPKLMIY
DVSDRPSGVSDRFSGSKSGNTASLIISGLQADDEADYYCSSYGSSSTHVIF
GGGTKVTVL where the underlined portions are, from left to right, CDR1 (SEQ ID NO: 35), CDR2 (SEQ ID NO: 36), and CDR3 (SEQ ID NO: 37), respectively.

Nucleic acid coding sequence for heavy chains

SEQ ID NO: 11
CAGGTGCAGCTGAAGCAGTCAGGACCTGGCCTAGTGCAGCCCTCACAGA
GCCTGTCCATCACCTGCACAGTCTCTGGTTTCTCATTAACTAACTATGG
TGTACACTGGGTTCGCCAGTCTCCAGGAAAGTGCCTGGAGTGGCTGGGA
GTGATATGGAGTGGTGGAAACACAGACTATAATACACCTTTCACATCCA
GACTGAGCATCAACAAGGACAATTCCAAGAGCCAAGTTTTCTTTAAAAT

-continued

GAACAGTCTGCAATCTAATGACACAGCCATATATTACTGTGCCAGAGCC
CTCACCTACTATGATTACGAGTTTGCTTACTGGGGCCAAGGGACTCTGG
TCACTGTCTCTGCTGCTAGCACCAAGGGCCCATCGGTCTTCCCCCTGGC
ACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCG
CCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCA
CCCAGACCTACATCTGCAACGTGAATCACAAGCCCAGCAACACCAGGTG
GACAAGAGAGTTGAGCCCAAATCTTGTGACAAAACTCACACATGCCCAC
CGTGCCCAGCACCTGAACTCCTGGGGGGACCGTCAGTCTTCCTCTTCCC
CCCAAAACCCAAGGACACCCTCATGATCTCCCGGACCCCTGAGGTCACA
TGCGTGGTGGTGGACGTGAGCCACGAAGACCCTGAGGTCAAGTTCAACT
GGTACGTGGACGGCGTGGAGGTGCATAATGCCAAGACAAAGCCGCGGGA
GGAGCAGTACAACAGCACGTACCGTGTGGTCAGCGTCCTCACCGTCCTG
CACCAGGACTGGCTGAATGGCAAGGAGTACAAGTGCAAGGTCTCCAACA
AAGCCCTCCCAGCCCCCATCGAGAAAACCATCTCCAAAGCCAAAGGGCA
GCCCCGAGAACCACAGGTGTACACCCTGCCCCCATCCCGGGATGAGCTG
ACCAAGAACCAGGTCAGCCTGACCTGCCTGGTCAAAGGCTTCTATCCCA
GCGACATCGCCGTGGAGTGGGAGAGCAATGGGCAGCCGGAGAACAACTA
CAAGACCACGCCTCCCGTGCTGGACTCCGACGGCTCCTTCTTCCTCTAT
AGCAAGCTCACCGTGGACAAGAGCAGGTGGCAGCAGGGGAACGTCTTCT
CATGCTCCGTGATGCATGAGGCTCTGCACAACCACTACACGCAGAAGAG
CCTCTCCCTGTCTCCGGGTTAA

Amino acid sequence of the heavy chain

SEQ ID NO: 12
QVQLKQSGPGLVQPSQSLSITCTVSGFSLTNYGVHWVRQSPGKCLEWLGV
IWSGGNTDYNTPFTSRLSINKDNSKSQVFFKMNSLQSNDTAIYYCARALT
YYDYEFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG where the variable region of the heavy chain is:

SEQ ID NO: 52
QVQLKQSGPGLVQPSQSLSITCTVSGFSLTNYGVHWVRQSPGKCLEWLGVI
WSGGNTDYNTPFTSRLSINKDNSKSQVFFKNMSLQSNDTAIYYCARALTYY
DYEFAYWGQGTLVTVSA where the underlined portions are, from left to right, CDR1 (SEQ ID NO: 29), CDR2 (SEQ ID NO: 30), and CDR3 (SEQ ID NO: 31), respectively.

(3) Expression and purification of SI-1×24 antibody: a similar method was followed for the expression and purification of SI-1×24 antibody.

Antibody SI-1×24:

Light chain nucleic acid coding sequence

SEQ ID NO: 13

GACATCTTGCTGACTCAGTCTCCAGTCATCCTGTCTGTGAGTCCAGGAG
AAAGAGTCAGTTTCTCCTGCAGGGCCAGTCAGAGTATTGGCACAAACAT
ACACTGGTATCAGCAAAGAACAAATGGTTCTCCAAGGCTTCTCATAAAG
TATGCTTCTGAGTCTATCTCTGGGATTCCTTCCAGGTTTAGTGGCAGTG
GATCAGGGACAGATTTTACTCTTAGCATCAACAGTGTGGAGTCTGAAGA
TATTGCAGATTATTACTGTCAACAAAATAATAACTGGCCAACCACGTTC
GGTGCTGGGACCAAGCTGGAGCTGAAACGTACGGTGGCTGCACCATCTG
TCTTCATCTTCCCGCCATCTGATGAGCAGTTGAAATCTGGAACTGCCTC
TGTTGTGTGCCTGCTGAATAACTTCTATCCCAGAGAGGCCAAAGTACAG
TGGAAGGTGGATAACGCCCTCCAATCGGGTAACTCCCAGGAGAGTGTCA
CAGAGCAGGACAGCAAGGACAGCACCTACAGCCTCAGCAGCACCCTGAC
GCTGAGCAAAGCAGACTACGAGAAACACAAAGTCTACGCCTGCGAAGTC
ACCCATCAGGGCCTGAGCTCGCCCGTCACAAAGAGCTTCAACAGGGGAG
AGTGTTAG

Light chain amino acid sequence

SEQ ID NO: 14

*DILLTQSPVILSVSPGERVSFSCRASQSIGTNIHWYQQRTNGSPRLLIKY*
*ASESISGIPSRFSGSGSGTDFTLSINSVESEDIADYYCQQNNNWPTTTFG*
*AGTKLELK*RTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC wherein the variable region is:

SEQ ID NO: 28

*DILLTQSPVILSVSPGERVSFSCRASQSIGTNIHWYQQTRNGSPRLLIKYA*
*SESISGIPSRFSGSGSGTDFTLSINSVESEDIADYYCQQNNNWPTTFGAGT*
*KLELK* where the underlined portions are, from left to right, CDR1 (SEQ ID NO: 25), CDR2 (SEQ ID NO: 26), and CDR3 (SEQ ID NO: 27), respectively.

Nucleic acid coding sequence for the construct of heavy chain and single-chain Fv (scFv) structural domain

SEQ ID NO: 15

CAGGTGCAGCTGCAGGAGTCGGGGGGAGGCCTGGTCAAGCCTGGAGGGTC
CCTGAGACTCTCCTGTGCAGCCTCTGGATTCACCTTTAGTAGTTATTGGA
TGAGCTGGGTCCGCCAGGCTCCAGGGAAGGGGCTGGAGTGGGTGGCCAAC
ATAAACCGCGATGGAAGTGCGAGTTACTATGTGGACTCTGTGAAGGGCCG
ATTCACCATCTCCAGAGACGACGCCAAGAACTCACTGTATCTGCAAATGA

-continued

ACAGCCTGAGAGCTGAGGACACGGCTGTGTATTACTGTGCGAGAGATCGT
GGGGTGGGCTACTTCGATCTCTGGGGCCGTGGCACCCTGGTCACCGTCTC
GAGCGGTGGAGGCGGTTCAGGCGGAGGTGGTTCCGGCGGTGGCGGCTCCC
AGTCTGCCCTGACTCAGCCTGCCTCCGTGTCTGGGTCTCCTGGACAGTCG
ATCACCATCTCCTGCACTGGAACCAGCAGTGACGTTGGTGGTTATAACTT
TGTCTCCTGGTACCAACAACACCCAGGCAAAGCCCCCAAACTCATGATCT
ATGATGTCAGTGATGGGCCCTCAGGGGTGTCTGATCGCTTCTCCGGCTCC
AAGTCTGGCAACACGGCCTCCCTGATCATCTCTGGCCTCCAGGCTGACGA
CGAGGCTGATTATTACTGCAGCTCATATGGGAGCAGCAGCACTCATGTGA
TTTTCGGCGGAGGGACCAAGGTGACCGTCCTAGGCGGTGGAGGATCCGGC
GGTGGTGGATCACAGGTGCAGCTGAAGCAGTCAGGACCTGGCCTAGTGCA
GCCCTCACAGAGCCTGTCCATCACCTGCACAGTCTCTGGTTTCTCATTAA
CTAACTATGGTGTACACTGGGTTCGCCAGTCTCCAGGAAAGGGTCTGGAG
TGGCTGGGAGTGATATGGAGTGGTGGAAACACAGACTATAATACACCTTT
CACATCCAGACTGAGCATCAACAAGGACAATTCCAAGAGCCAAGTTTTCT
TTAAAATGAACAGTCTGCAATCTAATGACACAGCCATATATTACTGTGCC
AGAGCCCTCACCTACTATGATTACGAGTTTGCTTACTGGGGCCAAGGGAC
TCTGGTCACTGTCTCTAGCGCTAGCACCAAGGGCCCATCGGTCTTCCCCC
TGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGC
ACCCAGACCTACATCTGCAACGTGAATCACAAGCCCAGCAACACCAAGGT
GGACAAGAGAGTTGAGCCCAAATCTTGTGACAAAACTCACACATGCCCAC
CGTGCCCAGCACCTGAACTCCTGGGGGGACCGTCAGTCTTCCTCTTCCCC
CCAAAACCCAAGGACACCCTCATGATCTCCCGGACCCCTGAGGTCACATG
CGTGGTGGTGGACGTGAGCCACGAAGACCCTGAGGTCAAGTTCAACTGGT
ACGTGGACGGCGTGGAGGTGCATAATGCCAAGACAAAGCGGCGGGAGGAG
CAGTACAACAGCACGTACCGTGTGGTCAGCGTCCTCACCGTCCTGCACCA
GGACTGGCTGAATGGCAAGGAGTACAAGTGCAAGGTCTCCAACAAAGCCC
TGCCAGCCCCCATCGAGAAAACCATCTCCAAAGCCAAAGGGCAGCCCCGA
GAACCACAGGTGTACACCCTGCCCCCATCCCGGGATGAGCTGACCAAGAA
CCAGGTCAGCCTGACCTGCCTGGTCAAAGGCTTCTATCCCAGCGACATCG
CCGTGGAGTGGGAGAGCAATGGGCAGCCGGAGAACAACTACAAGACCACG
CCTCCCGTGCTGGACTCCGACGGCTCCTTCTTCCTCTATAGCAAGCTCAC
CGTGGACAAGAGCAGGTGGCAGCAGGGGAACGTCTTCTCATGCTCCGTGA
TGCATGAGGCTCTGCACAACCACTACACGCAGAAGAGCCTCTCCCTGTCT
CCGGGTTAA

Amino acid sequence of the construct of the heavy chain and single-chain Fv (scFv) structural domain

SEQ ID NO: 16
*QVQLQESGGGLVKPGGSLRLSCAASGFTFSSYWMSWVRQAPGKGLEWVAN*

*INRDGSASYYVDSVKGRFTISRDDAKNSLYLQMNSLRAEDTAVYYCARDR*

*GVGYFDLWGRGTLVTVSS*GGGGSGGGGSGGGGS*QSALTQPASVSGSPGQS*

*ITISCTGTSSDVGGYNFVSWYQQHPGKAPKLMIYDVSDRPSGVSDRFSG*

*SKSGNTASLIISGLQADDEADYYCSSYGSSSTHVIFGGGTKVTVL*GGGGS

GGGGS*QVQLKQSGPGLVQPSQSLSITCTVSGFSLTNYGVHWVRQSPGKGL*

*EWLGVIWSGGNTDYNTPFTSRLSINKDNSKSQVFFKMNSLQSNDTAIYYC*

*ARALTYYDYEFAYWGQGTLVTVSS*ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPFPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPG where the variable region of the heavy chain is:

SEQ ID NO: 38
*QVQLKQSGPGLVQPSQSLSITCTVSGFSLTNYGVHWVRQSPGKGLEWLGVI*

*WSGGNTDYNTPFTSRLSINKDNSKSQVFFKMNSLQSNDTAIYYCARALTYY*

*DYEFAYWGQGTLVTVSS* where the underlined portions are, from left to right, CDR1 (SEQ ID NO: 29), CDR2 (SEQ ID NO: 30), and CDR3 (SEQ ID NO: 31), respectively.

The variable region of the heavy chain in the structural domain of the single-chain Fv (scFv) is:

SEQ ID NO: 39
*QVQLQESGGGLVKPGGSLRLSCAASGFTFSSYWMSWVRQAPGKGLEWVANI*

*NRDGSASYYVDSVKGRFTISRDDAKNSLYLQMNSLRAEDTAVYYCARDRGV*

*GYFDLWGRGTLVTVSS* where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

SEQ ID NO: 40
*QSALTQPASVSGSPGQSITISCTGTSSDVGGYNFVSWYQQHPGKAPKLMIY*

*DVSDRPSGVSDRFSGSKSGNTASLIISGLQADDEADYYCSSYGSSSTHVIF*

*GGGTKVTVL* where the underlined portions are, from left to right, CDR1 (SEQ ID NO: 35), CDR2 (SEQ ID NO: 36), and CDR3 (SEQ ID NO: 37), respectively.

Example 92

1) Expression and purification of SI-1×4 antibody:

(Shanghai OPM Biosciences Co., Ltd.) suspension cells were used to express SI-1×4 antibody. The day before transfection, cells were inoculated at a density of $0.9\times10^6$ cells/mL in a 1 L shake flask containing 300 mL of OPM-293 CD05 Medium (81075-001, Shanghai OPM Biosciences Co., Ltd.), and cultured overnight at 37° C., 5% $CO_2$, and 120 rpm in a cell culture shaker. On the next day, the antibody expression plasmid was transfected with PEI-MAX, wherein the mass ratio of plasmid:PEI-MAX was 1:3. OPM-293 ProFeed supplement was added at 5% (v/v) on the first day after transfection, and then again at 5% (v/v) on the third day after transfection, and then centrifugation was performed to collect the supernatant on the sixth day after transfection.

The collected cell expression supernatant was collected and eluted with 0.05 M sodium acetate (pH 3.6) in a Protein A affinity chromatography column (UniMab 50, Suzhou Nanomicro Technology Co., Ltd.), and the captured antibody was adjusted to pH 7.0 with 1 M Tris-HCl (pH 8.8) at 0.7/10 (v/v), and then passed through a gel filtration chromatography column SEC (Superdex 200, GE) to remove impurities such as polymers, while the antibody buffer was replaced with 20 mM PB (pH 6.5).

Antibody SI-1×4:

Light chain nucleic acid coding sequence

SEQ ID NO: 5
GATATTCAAATGACTCAATCTCCTTCTTCTCTTTCTGCTTCTGTTGGTGA

TCGTGTTACTATTACTTGTCGTTCTTCTCAAAATATTGTTCATTCTAATG

GTAATACTTATCTTGATTGGTATCAACAAACTCCTGGTAAAGCTCCTAAA

CTTCTTATTTATAAAGTTTCTAATCGTTTTTCTGGTGTTCCTTCTCGGTT

TTTCTGGTTCTGGTTTCTGGTACTGATTTTACTTTTACTATTTCTTCTCT

TCAACCTGAAGATATTGCTACTTATTATTGTTTTCAATATTCTCATGTTC

CTTGGACTTTTGGTCAAGGTACTAAACTTCAAATTACTCGTACGGTGGCT

GCACCATCTGTCTTCATCTTCCCGCCATCTGATGAGCAGTTGAAATCTGG

AACTGCCTCTGTTGTGTGCCTGCTGAATAACTTCTATCGCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTAG

Light chain amino acid sequence

SEQ ID NO: 6
*DIQMTQSPSSLSASVGDRVTITCRSSQNIVHSNGNTYLDWYQQTPGKAPK*

*LLIYKVSNRFSGVPSRFSGSGSGTDFTFTISSLQPEDIATYYCFQYSHVP*

*WTFGQGTKLQIT*RTVAAPSVIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC wherein the variable region is:

SEQ ID NO: 44
*DIQMTQSPSSLSASVGDRVTITCRSSQNIVHSNGNTYLDWYQQTPGKAPKL*

*LIYKVSNRFSGVPSRFSGSGSGTDFTFTISSLQPEDIATYYCFQYSHVPWT*

*FGQGTKLQIT* where the underlined portions are, from left to right, CDR1 (SEQ ID NO: 41), CDR2 (SEQ ID NO: 42), and CDR3 (SEQ ID NO: 43), respectively.

Nucleic acid coding sequence for the construct of the heavy chain and single-chain Fv (scFv) structural domain

SEQ ID NO: 7

```
CAGGTGCAGCTGCAGCAGAGCGGCGCCGAGGTGAAGAAGCCCGGCAGCAG
CGTGAAGGTGAGCTGCAAGGCCAGCGGCTACACCTTCACCAACTACTACA
TCTACTGGGTGCGGCAGGCCCCCGGCCAGGGCCTGGAGTGGATCGGCGGC
ATCAACCCCACCAGCGGCGGCAGCAACTTCAACGAGAAGTTCAAGACCCG
GGTGACCATCACCGCCGACGAGAGCAGCACCACCGCCTACATGGAGCTGA
GCAGCCTGCGGAGCGAGGACACCGCCTTCTACTTCTGCACCCGGCAGGGC
CTGTGGTTCGACAGCGACGGCCGGGGCTTCGACTTCTGGGGCCAGGGCAC
CACCGTGACCGTGAGCAGCGCTAGCACCAAGGGCCCATCGGTCTTCCCCC
TGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAG
GACTCTACTGCCTCAGCAGCGTGGTGACCGTGCCCTCCAGCAGCTTGGGC
ACCCAGACCTACATCTGCAACGTGAATCACAAGCCCAGCAACACCAAGGT
GGACAAGAGAGTTGAGCCCAAATCTTGTGACAAAACTCACACATGCCCAC
CGTGCCCAGCACCTGAACTCCTGGGGGGACCGTCAGTCTTCCTCTTCCCC
CCAAAACCCAAGGACACCCTCATGATCTCCCGGACCCCTGAGGTCACATG
CGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAG
CAGTACAACAGCACGTACCGTGTGGTCAGCGTCCTCACCGTCCTGCACCA
GGACTGGCTGAATGGCAAGGAGTACAAGTGCAAGGTCTCCAACAAAGCCC
TCCCAGCCCCCATCGAGAAAACCATCTCCAAAGCCAAAGGGCAGCCCCGA
GAACCACAGGTGTACACCCTGCCCCCATCCCGGGATGAGCTGACCAAGAA
CCAGGTCAGCCTGACCTGCCTGGTCAAAGGCTTCTATCCCAGCGACATCG
CCGTGGAGTGGGAGAGCAATGGGCAGCCGGAGAACAACTACAAGACCACG
CCTCCCGTGCTGGACTCCGACGGCTCCTTCTTCCTCTATAGCAAGCTCAC
CGTGGACAAGAGCAGGTGGCAGCAGGGGAACGTCTTCTCATGCTCCGTGA
TGCATGAGGCTCTGCACAACCACTACACGCAGAAGAGCCTCTCCCTGTCT
CCGGGTGGCGGTGGAGGGTCCGGCGGTGGTGGATCACAGGTGCAATTGCA
GGAGTCGGGGGGAGGCCTGGTCAAGCCTGGAGGGTCCCTGAGACTCTCCT
GTGCAGCCTCTGGATTCACCTTTAGTAGTTATTGGATGAGCTGGGTCCGC
CAGGCTCCAGGGAAGGGGCTGGAGTGGGTGGCCAACATAAACCGCGATGG
AAGTGCGAGTTACTATGTGGACTCTGTGAAGGGCCGATTCACCATCTCCA
GAGACGACGCCAAGAACTCACTGTATCTGCAAATGAACAGCCTGAGAGCT
GAGGACACGGCTGTGTATTACTGTGCGAGAGATCGTGGGGTGGGCTACTT
CGATCTCTGGGGCCGTGGCACCCTGGTCACCGTCTCGAGCGGTGGAGGCG
GTTCAGGCGGAGGTGGTTCCGGCGGTGGGGGCTCCCAGTCTGCCCTGACT
CAGCCTGCCTCCGTGTCTGGGTCTCCTGGACAGTCGATCACCATCTCCTG
```

-continued

```
CACTGGAACCAGCAGTGACGTTGGTGGTTATAACTTTGTCTCCTGGTACC
AACAACACCCAGGCAAAGCCCCCAAACTCATGATCTATGATGTCAGTGAT
CGGCCCTCAGGGGTGTCTGATCGCTTCTCCGGCTCCAAGTCTGGCAACAC
GGCCTCCCTGATCATCTCTGGCCTCCAGGCTGACGACGAGGCTGATTATT
ACTGCAGCTCATATGGGAGCAGCAGCACTCATGTGATTTTCGGCGGAGGG
ACCAAGGTGACCGTCCTATAA
```

Amino acid sequence of the construct of heavy chain and single chain Fv (scFv) structural domain

SEQ ID NO: 8

*QVQLQQSGAEVKKPGSSVKVSCKASGYTFTNYYIYWVRQAPGQGLEWIGG*
*INPTSGGSNENEKFKTRVTITADESSTTAYMELSSLRSEDTAFYFCTRQG*
*LWFDSDGRGFDFWGQGTTVTVSS*ASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKBYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGGGGGSGGGGS*QVQLQESGGGLVKPGGSLRLSCAASGFTFSSYWMSWVR*
*QAPGKGLEWVANINRDGSASYYVDSVKGRFTISRDDAKNSLYLQMNSLRA*
*EDTAVYYCARDRGVGYFDLWGRGTLVTVSS*GGGGSGGGGSGGGGS*QSALT*
*QPASVSGSPGQSITISCTGTSSDVGGYNFVSWYQQHPGKAPKLMIYDVSD*
*RPSGVSDRFSGSKSGNTASLIISGLQADDEADYYCSSYGSSSTHVIFGGG*
*TKVTVL* where the variable region of the heavy chain is:

SEQ ID NO: 48

*QVQLQQSGAVKKPGSSVKVSKASGYTFTNYYIYWVRQAPGQGLEWIGGINP*
*TSGGSNFNEKFKTRVTTTADESTTAYMELSSLRSEDTAFYFCTRQGLWFDS*
*DGRGFDFWGQGTTVTVSS* where the underlined portions are, from left to right, CDR1 (SEQ ID NO: 45), CDR2 (SEQ ID NO: 46), and CDR3 (SEQ ID NO: 47), respectively.

The variable region of the heavy chain in the structural domain of the single-chain Fv (scFv) is:

SEQ ID NO: 39

*QVQLQESGGGLVKPGGSLRLSCAASGFTFSSYWMSWVRQAPGKGLEWVAN*
*INRDGSASYYVDSVKGRFTISRDDAKNSLYLQMNSLRAEDTAVYYCARDR*
*GVGYFDLWGRGTLVTVSS* where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

SEQ ID NO: 40
QSALTQPASVGSGSPGQSITISCTGTSSDVGGYNFVSWYQQHPGKAPKLMI

YDVSDRPSGVSDRFSGSKSGNTASLIISGLQADDEADYYCSSYGSSSTYVI

FGGGTKVTVL where the underlined portions are, from left to right, CDR1 (SEQ ID NO: 35), CDR2 (SEQ ID NO: 36), and CDR3 (SEQ ID NO: 37), respectively.

2) Expression and purification of SI-1×25 antibody: a similar method was followed for the expression and purification of SI-1×25 antibody.

Antibody SI-1×25:

Nucleic acid coding sequence for the construct of light chain and single-chain Fv (scFv) structural domain

SEQ ID NO: 17
CAGGTGCAGCTGCAGGAGTCGGGGGGAGGCCTGGTCAAGCCTG-
GAGGGTCCC

TGAGTCTCTCCTGTGCAGCCTCTGGATTCACCTTTAGTAGTTATTGGAT-
GAG

CTGGGTCCGCCAGGCTCCAGGGAAGGGGCTGGAGTGGGTGGCCAACAT-
AAAC

CGCGATGGAAGTGCGAGTTACTATGTGGACTCTGTGAAGGGCCGATTCAC-
CAT

CTCCAGAGACGACGCCAAGAACTCACTGTATCTGCAAATGAACAGCCT-
GAGAG

CTGAGGACCGGCTGTGTATTACTGTGCGAGAGATCGTGGGGTGGGC-
TACTTCG

ATCTCTGGGGCCGTGGCACCCTGGTCACCGTCTCGAGCGGTG-
GAGGCGGTTCA

GGCG-
GAGGTGGTTCCGGCGGTGGCGGCTCCCAGTCTGCCCTGACTCAGCCTGC

CTCCGTGTCTGGGTCTCCTGGACAGTCGATCACCATCTCCTGCACTG-
GAACCA

GCAGTGACGTTGGTGGTTATAACTTTGTCTCCTGGTAC-
CAACAACACCCAGGC

AAAGCCCCCAAACTCATGATCTATGATGTCAGT-
GATCGGCCCTCAGGGGTGT

CTGATCGCTTCTCCGGCTCCAAGTCTGGCAACACGGCCTCCCTGAT-
CATCTCT

GGCCTCCAGGCTGACGACGAGGCTGATTATTACTGCAGCTCATATGG-
GAGCAG

CAGCACTCATGTGATTTTCGGCGGAGGGAC-
CAAGGTGACCGTCCTAGGCGGTG

GAGGATCCGGCGGTGGTGGATCAGACATCTTGCTGACTCAGTCTCCAGT-
CATC

CTGTCTGTGAGTCCAG-
GAGAAAGAGTCAGTTTCTCCTGCAGGGCCAGTCAGAG

TATTGGCACAAACATACACTGGTATCAGCAAAGAACAAATGGTTCTC-
CAAGGC

TTCTCATAAAGTATGCTTCTGAGTCTATCTCTGGGATTCCTTCCAGGTT-
TAGT

GGCAGTGGATCAGGGACAGATTTTACTCTTAGCATCAACAGTGTG-
GAGTCTG

AAGATATTGCAGATTATTACTGTCAACAAAATAATAACTGGCCAAC-
CACGTT

CGGTTGTGGGACCAAGCTGGAGCTGAAACGTACGGTGGCTGCAC-
CATCTGTC

-continued

TTCATCTTCCCGCCATCTGATGAGCAGTTGAAATCTG-
GAACTGCCTCTGTTG

TGTGCCTGCTGAATAACTTCTATCCCAGAGAGGCCAAAGTACAGTG-
GAAGGT

GGATAACGCCCTCCAATCGGGTAACTCCCAGGAGAGTGT-
CACAGAGCAGGAC

AGCAAGGACAGCACCTACAGCCTCAGCAGCACCCTGACGCT-
GAGCAAAGCAG

ACTACGAGAAACACAAAGTCTACGCCTGCGAAGTCACCCATCAGGGCCT-
GAG

CTCGCCCGTCACAAAGAGCTTCAACAGGGGAGAGTGTTAG

Amino acid sequence of construct of light chain and single-chain Fv (scFv) structural domain

SEQ ID NO: 18
QVQLQESGGGLVKPGGSLSLSCAASGFTFSSYWMSWVRQAPGKGLEWVAN

INRDGSASYYVDSVKGRFTISRDDAKNSLYLQMNSLRAEDTAVYYCARDR

GVGYFDLWGRGTLVTVSSGGGGSGGGGSGGGGSQSALTQPASVSGSPGQS

ITISCTGTSSDVGGYNFVSWYQQHPGKAPKLMIYDVSDRPSGVSDRFSGS

KSGNTASLIISGLQADDEADYYCSSYGSSSTHVIFGGGTKVTVLGGGGSG

GGGSDILLTQSPVILSVSPGERVSFSCRASQSIGTNIHWYQQRTNGSPRL

LIKYASESISGIPSRFSGSGSGTDFTLSINSVESEDIADYYCQQNNNWPT

TFGCGTKLELKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC where the variable region of the light chain is:

SEQ ID NO: 49
DILLTQSPVILSVSPGERVSFSCRASQSIGTNIHWYQQRTNGSPRLLIKYA

SESISGIPSRFSGSGSGTDFTLSINSVESEDIADYYCQQNNNWPITFGCGT

KLELK where the underlined portions are, from left to right, CDR1 (SEQ ID NO: 25), CDR2 (SEQ ID NO: 26), and CDR3 (SEQ ID NO: 27), respectively.

The variable region of the heavy chain in the structural domain of the single-chain Fv (scFv) is:

SEQ ID NO: 50
QVQLQESGGGLVKPGGSLSLSCAASGFTFSSYWMSWVRQAPGKGLEWVANI

NRDGSASYYVISVRGRFTISRDDAKNSLYLQMNSLRAEDTAVYYCARDRGV

GYFDLWGRGTLVTVSS where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

SEQ ID NO: 51
QSALTQPASVSGSPGQSITISCTGTSSDYGGYNFVSWYQQHPGKAPKLMIY

DVSDRPSGVSDRFSGSKSGNTASLHSGLQADDEADYYCSSYGSSSTHVIFG

GGTKVTVL where the underlined portions are, from left to right, CDR1 (SEQ ID NO: 35), CDR2 (SEQ ID NO: 36), and CDR3 (SEQ ID NO: 37), respectively.

Nucleic acid coding sequence for the heavy chain

SEQ ID NO: 19

CAGGTGCAGCTGAAGCAGTCAGGACCTGGCCTAGTGCAGCCCTCACAGAGC
CTGTCCATCACCTGCACAGTCTCTGGTTTCTCATTAACTAACTATGGTGTA
CACTGGGTTCGCCAGTCTCCAGGAAAGTGCCTGGAGTGGCTGGGAGTGATA
TGGAGTGGTGGAAACACAGACTATAATACACCTTTCACATCCAGACTGAGC
ATCAACAAGGACAATTCCAAGAGCCAAGTTTTCTTTAAAATGAACAGTCTG
CAATCTAATGACACAGCCATATATTACTGTGCCAGAGCCCTCACCTACTAT
GATTACGAGTTTGCTTACTGGGGCCAAGGGACTCTGGTCACTGTCTCTGCT
GCTAGCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGT
GGTGACCGTGCCCTCCAGCAGCTTGGGCACCCAGACCTACATCTGCAACG
TGAATCACAAGCCCAGCAACACCAAGGTGGACAAGAGAGTTGAGCCCAAA
TCTTGTGACAAAACTCACACATGCCCACCGTGCCCAGCACCTGAACTCCT
GGGGGGACCGTCAGTCTTCCTCTTCCCCCCAAAACCCAAGGACACCCTCA
TGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCA
TAATGCCAAGACAAAGCCGCGGGAGGAGCAGTACAACAGCACGTACCGTG
TGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGC
CCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGG
GCAGCCGGAGAACAACTACAAGACCACGCCTCCCGTGCTGGACTCCGACG
GCTCCTTCTTCCTCTATAGCAAGCTCACCGTGGACAAGAGCAGGTGGCAG
CAGGGGAACGTCTTCTCATGCTCCGTGATGCATGAGGCTCTGCACAACCA
CTACACGCAGAAGAGCCTCTCCCTGTCTCCGGGTTAA

Amino acid sequence of the heavy chain

SEQ ID NO: 20

*QVQLKQSGPGLVQPSQSLSITCTVSGFSLTNYGVHWVRQSPGKCLEWLGV*
*TWSGGNTDYNTPFTSRLSINKDNSKSQVFFKMNSLQSNDTAIYYCARALT*
*YYDYEFAYWGQGTLVTVSA*ASTKGPSVFPLAPSSKSTSGGTAALGCLVDK
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV

-continued

YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG where the variable region of the heavy chain is:

SEQ ID NO: 52

*QVQLKQSGPGLVQPSQSLSITCTVSGFLSTNYGVHWVRQSPGKCLEWLGVI*
*WSGGNTDYNTPFTSRLSINKDNSKSQVFFKMNSLQSNDTAIYYCARALTYY*
*DYEFAYWGQGTLVTVSA* where the underlined portions are, from left to right, CDR1 (SEQ ID NO: 29), CDR2 (SEQ ID NO: 30), and CDR3 (SEQ ID NO: 31), respectively.

(3) Expression and purification of SI-1×26 antibody: a similar method was followed for the expression and purification of SI-1×26 antibody.

Antibody SI-1×26:

Nucleic acid coding sequence for the construct of light chain and single-chain Fv (scFv) structural domain

SEQ ID NO: 21

GATATTCAAATGACTCAATCTCCTTCTTCTCTTTCTGCTTCTGTTGGTGA
TCGTGTTACTATTACTTGTCGTTCTTCTCAAAATATTGTTCATTCTAATG
GTAATACTTATCTTGATTGGTATCAACAAACTCCTGGTAAAGCTCCTAAA
CTTCTTATTTATAAAGTTTCTAATCGTTTTTCTGGTGTTCCTTCTCGTTT
TTCTGGTTCTGGTTCTGGTACTGATTTTACTTTTACTATTTCTTCTCTTC
AACCTGAAGATATTGCTACTTATTATTGTTTTCAATATTCTCATGTTCCT
TGGACTTTTGGTTGCGGTACTAAACTTCAAATTACTCGTACGGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACCC
TGACGCTGAGCAAAGCAGACTACGAGAAACACAAAGTCTACGCCTGCGAA
GTCACCCATCAGGGCCTGAGCTCGCCCGTCACAAAGAGCTTCAACAGGGG
AGAGTGTGGTGGCGGCGGAAGTGGCGGTGGAGGATCCGGCGGTGGTGGAT
CACAGGTGCAGCTGCAGGAGTCGGGGGGAGGCCTGGTCAAGCCTGGAGGG
TCCCTGAGTCTCTCCTGTGCAGCCTCTGGATTCACCTTTAGTAGTTATTG
GATGAGCTGGGTCCCCCAGGCTCCAGGGAAGGGGCTGGAGTGGGTGGCCA
ACATAAACCGCGATGGAAGTGCGAGTTACTATGTGGACTCTGTGAAGGGC
CGATTCACCATCTCCAGAGACGACGCCAAGAACTCACTGTATCTGCAAAT
GAACAGCCTGAGAGCTGAGGACACGGCTGTGTATTACTGTGCGAGAGATC
GTGGGGTGGGCTACTTCGATCTCTGGGGCCGTGGCACCCTGGTCACCGTC
TCGAGCGGTGGAGGCGGTTCAGGCGGAGGTGGTTCCGGCGGTGGCGGCTC
CCAGTCTGCCCTGACTCAGCCTGCCTCCGTGTCTGGGTCTCCTGGACAGT
CGATCACCATCTCCTGCACTGGAACCAGCAGTGACGTTGGTGGTTATAAC
TTTGTCTCCTGGTACCAACAACACCCAGGCAAAGCCCCCAAACTCATGAT
CTATGATGTCAGTGATCGGCCCTCAGGGGTGTCTGATCGCTTCTCCGGCT

-continued

```
CCAAGTCTGGCAACACGGCCTCCCTGATCATCTCTGGCCTCCAGGCTGAC

GACGAGGCTGATTATTACTGCAGCTCATATGGGAGCAGCAGCACTCATGT

GATTTTCGGCGGAGGGACCAAGGTGACCGTCCTATAA
```

Amino acid sequence of the construct of light chain and single-chain Fv (scFv) structural domain

```
                                          SEQ ID NO: 22
DIQMTQSPSSLSASVGDRVTITCRSSQNIVHSNGNTYLDWYQQTPGKAPK

LLIYKVSNRFSGVPSRFSGSGSGTDFTFTISSLQPEDIATYYCFQYSHVP

WTFGCGTKLQITRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGECGGGGSGGGGSGGGGSQVQESGGGLVKPGGS

LSLSCAASGFTFSSYWMSWVRQAPGKGLEWVANINRDGSASYVVDSVKG

RFTISRDDAKNSLYLQMSLRAEDTAVYYCARDRGVGYFDLWGRGTLVTV

SSGGGGSGGGGSGGGGSQSALTQPASVSGSPGQSITISCTGTSSDVGGY

NFVSWYQQHPGKAPKLMIYDVSDRPSGVSDRFSGSKSGNTASLHSGLQA

DDEADYYCSSYGSSSTHVIFGGGTKVTVL
```

where the variable region of the light chain is:

```
                                          SEQ ID NO: 53
DIQMTQSPSSLSASVGDDRVITTCRSSQNIVHSNGNTYLDWYQQTPGKA

PKLLIYKVSNRFSGCPSRGSGSGSGTDFTFTISSLQPEDIATYYCFQYS

HVPWTFGCGTKLQIT
```

where the underlined portions are, from left to right, CDR1 (SEQ ID NO: 41), CDR2 (SEQ ID NO: 42), and CDR3 (SEQ ID NO: 43), respectively.

The variable region of the heavy chain in the structural domain of the single-chain Fv (scFv) is:

```
                                          SEQ ID NO: 50
QVQLQESGGGLVKPGGSLSLSCAASGFTFSSYWMSWVRQAPGKGLEWVA

NINRDGSASYYVDSVGRFTISRDDAKNSLYLQMNSLRAEDTAVYYCARD

RGVGYFDLWGRGTKVTVSS
```

where the underlined portions are, from left to right, CDR1 (SEQ ID NO: 32), CDR2 (SEQ ID NO: 33), and CDR3 (SEQ ID NO: 34), respectively.

The variable region of the light chain in the single-chain Fv (scFv) structural domain is:

```
                                          SEQ ID NO: 51
QSALTTQPASVSGSPGQSITISCTGTSSDVGGYNFVSWYQQHPGKAPK

LMIYDVSDRFSGVSDRFSGSKSGNTASLHSGLQADDEADYYCSSYGSS

STHVIFGGGTKVTVL
```

where the underlined portions are, from left to right, CDR1 (SEQ ID NO: 35), CDR2 (SEQ ID NO: 36), and CDR3 (SEQ ID NO: 37), respectively.

Nucleic acid coding sequence for the heavy chain

```
                                          SEQ ID NO: 23
CAGGTGCAGCTGCAGCAGAGCGGCGCCGAGGTGAAGAAGCCCGGCAGC

AGCGTGAAGGTGAGCTGCAAGGCCAGCGGCTACACCTTCACCAACTAC

TACATCTACTGGGTGCGGCAGGCCCCCGGCCAGTGTCTGGAGTGGATC

GGCGGCATCAACCCCACCAGCGGCGGCAGCAACTTCAACGAGAAGTTC

AAGACCCGGGTGACCATCACCGCCGACGAGAGCAGCACCACCGCCTAC

ATGGAGCTGAGCAGCCTGCGGAGCGAGGACACCGCCTTCTACTTCTGC

ACCCGGCAGGGCCTGTGGTTCGACAGCGACGGCCGGGGCTTCGACTTC

TGGGGCCAGGGCACCACCGTGACCGTGAGCAGCGCTAGCACCAAGGGC

CCATCGGTCTTCCCCCTGGCACCCTCCTCCAAGAGCACCTCTGGGGGC

ACAGCGGCCCTGGGCTGCCTGGTCAAGGACTACTTCCCCGAACCGGTG

ACGGTGTCGTGGAACTCAGGGGCCCTGACCAGCGGCGTGCACACCTTC

CCGGCTGTCCTACAGTCCTCAGGACTCTACTCCCTCAGCAGCGTGGTG

ACCGTGCCCTCCAGCAGCTTGGGCACCCAGACCTACATCTGCAACGTG

GACAAAACTCACACATGCAATCACAAGCCCAGCAACACCAAGGTGGAC

AAGAGAGTTGAGCCCAAATCTTGTCCACCGTGCCCAGCACCTGAACTC

CTGGGGGGACCGTCAGTCTTCCTCTTCCCCCCAAAACCCAAGGACACC

CTCATGATCTCCCGGACCCCTGAGGTCACATGCGTGGTGGTGGACGTG

AGCCACGAAGACCCTGAGGTCAAGTTCAACTGGTACGTGGACGGCGTG

GAGGTGCATAATGCCAAGACAAAGCCGCGGGAGGAGCAGTACAACAGC

ACGTACCGTGTGGTCAGCGTCCTCACCGTCCTGCACCAGGACTGGCTG

AATGGCAAGGAGTACAAGTGCAAGGTCTCCAACAAAGCCCTCCCAGCC

CCCATCGAGAAAACCATCTCCAAAGCCAAAGGGCAGCCCCGAGAACCA

CAGGTGTACACGCTGCCCCCATCCCGGGATGAGCTGACCAAGAACCAG

GTCAGCCTGACCTGCCTGGTCAAAGGCTTCTATCCCAGCGACATCGCC

GTGGAGTGGGÅGAGCAATGGGCAGCCGGAGAACAACTACAAGACCACG

CCTCCCGTGCTGGACTCCGACGGCTCCTTCTTCCTCTATAGCAAGCTC

ACCGTGGACAAGAGCAGGTGGCAGCAGGGGAACGTCTTCTCATGCTCC

GTGATGCATGAGGCTCTGCACAACCACTACACGCAGAAGAGCCTCTCC

CTGTCTCCGGGTTAA
```

Amino acid sequence of the heavy chain

```
                                          SEQ ID NO: 24
QVQLQQSGAEVKKPGSSVKVSCKASGYTFTNYYIYWVRQAPGQCLEWIGG

INPTSGGSNFNEKFKTRVTITADESSTTAYMELSSLRSEDTAFYFCTRQG

LWFDSDGRGFDFWGQGTTVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKIKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT
```

-continued

PPVLDSDGSFFLYSKLTVDKSRWQQGNVFSCSVMHEALHNHYTQKSLSLS

PG where the variable region of the heavy chain is:

SEQ ID NO: 54

*QVQLQQSGAEVKKPGSSVKVSCKASGYTFTNYYIYWVRQAPGQCL*

*EWIGGINPTSGGSNFNEKFKTRVTITADESSTTAYMELSSLRSED*

*TAFYFCTRQGLWFDSDGRGFDFWGQTTVTVSS* where the underlined portions are, from left to right, CDR1 (SEQ ID NO: 45), CDR2 (SEQ ID NO: 46), and CDR3 (SEQ ID NO: 47), respectively.

Example 93

1) A sample of SI-1×6.4 antibody-drug conjugate was prepared by coupling SI-1×6.4 antibody with payload:

After cellular expression and purification by Protein A affinity chromatography and molecular sieve chromatography, the SI-1×6.4 antibody was replaced in 20 mM PB, pH 6.5 buffer, and the SI-1×6.4 antibody was concentrated or diluted to a protein concentration of 3 mg/mL. The payload was a white powder, which was dissolved to 20 mg/mL using DMA and set aside. To open the interchain disulfide bonds of SI-1×6.4 antibody, 20-fold TECP was first added according to the molecular ratio and a reaction was performed at room temperature for 3 h. Then 20-fold payload solution was added according to the molecular ratio and a reaction was performed at room temperature for 1 h. After the reaction was completed, the payload that was not coupled to SI-1×6.4 was removed by ultrafiltration using a 30 KDa ultrafiltration centrifuge tube, and the SI-1×6.4 antibody-drug conjugate sample was thus obtained.

2) A sample of SI-1×22 antibody-drug conjugate was prepared by coupling SI-1×22 antibody with payload following a similar method.

3) A sample of SI-1×24 antibody-drug conjugate was prepared by coupling SI-1×24 antibody with payload following a similar method.

Example 94

1) A sample of SI-1×4 antibody-drug conjugate was prepared by coupling SI-1×4 antibody with payload:

After cellular expression and purification by Protein A affinity chromatography and molecular sieve chromatography, the SI-1×4 antibody was replaced in 20 mM PB, pH 6.5 buffer, and the SI-1×4 antibody was concentrated or diluted to a protein concentration of 3 mg/mL. The payload was a white powder, which was dissolved to 20 mg/mL using DMA and set aside. To open the interchain disulfide bonds of SI-1×4 antibody, 20-fold TECP was first added according to the molecular ratio and a reaction was carried out at room temperature for 3 h. Then, 20-fold payload solution was added according to the molecular ratio and a reaction was carried out at room temperature for 1 h. At the end of the reaction, the payload that was not coupled with SI-1×4 was removed by ultrafiltration using a 30 KDa ultrafiltration centrifuge tube to obtain a sample of SI-1×4 antibody-drug conjugate.

2) A sample of SI-1×25 antibody-drug conjugate was prepared by coupling SI-1×25 antibody with payload following a similar method.

3) A sample of SI-1×26 antibody-drug conjugate was prepared by coupling SI-1×26 antibody with payload following a similar method.

Example 95

ADC-1 was prepared according to the general-purpose coupling method of Example 93,

ADC-1

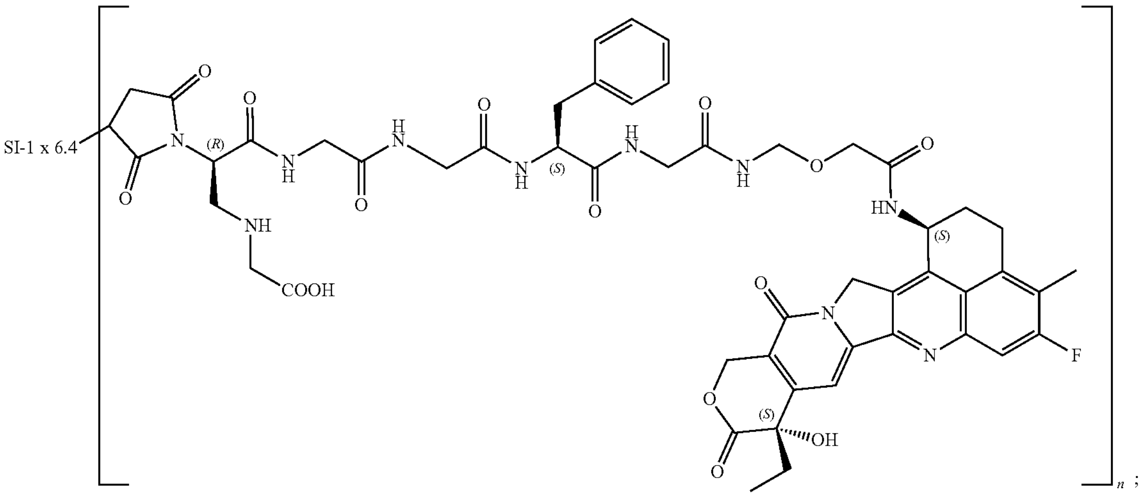

Example 96

ADC-2 was prepared according to the general-purpose coupling method of Example 93, ADC-2
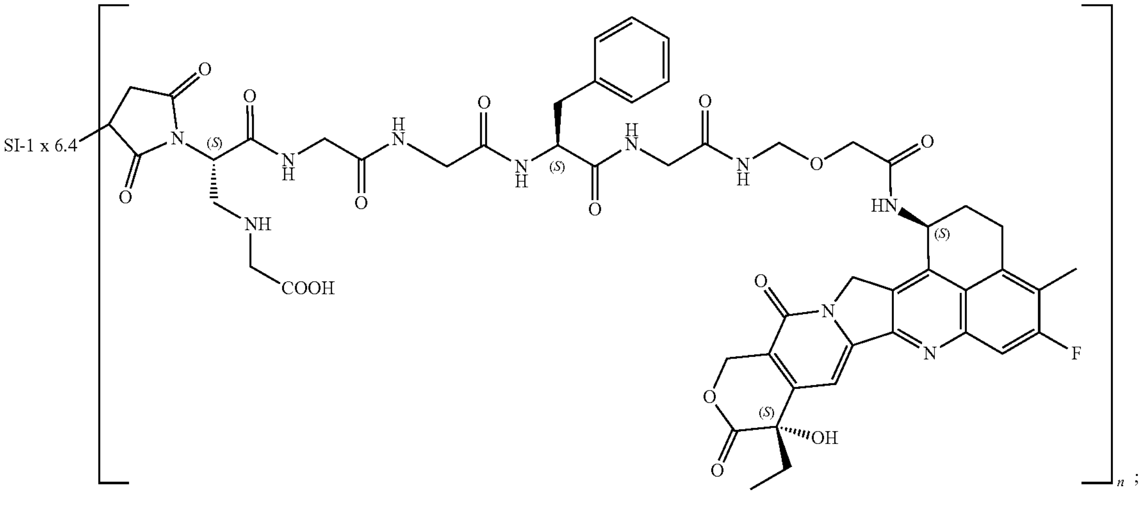
Example 97
ADC-3 was prepared according to the general-purpose coupling method of Example 93,
ADC-3
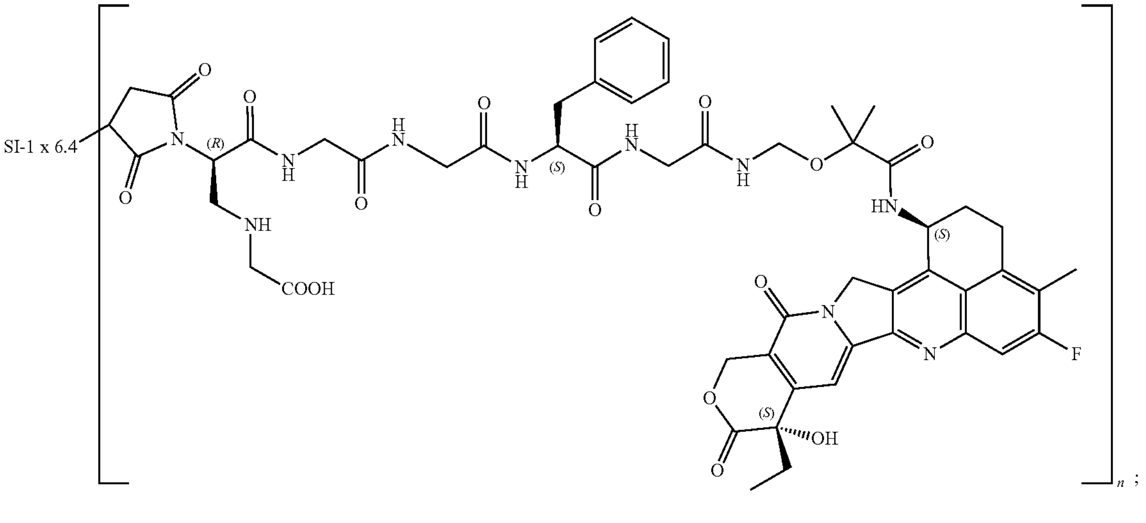
Example 98
ADC-4 was prepared according to the general-purpose coupling method of Example 93, ADC-4
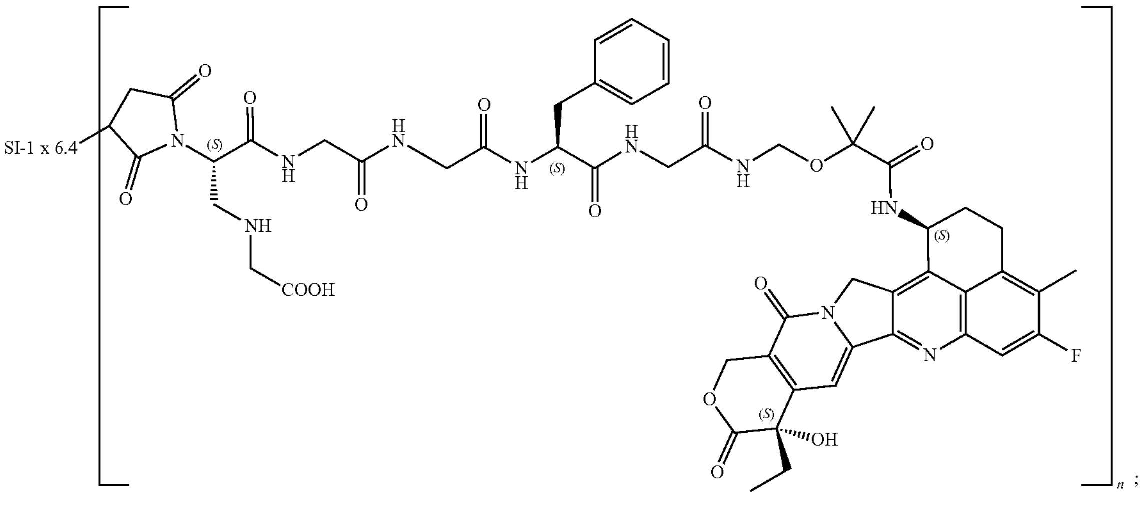
Example 99
ADC-5 was prepared according to the general-purpose coupling method of Example 93,
ADC-5
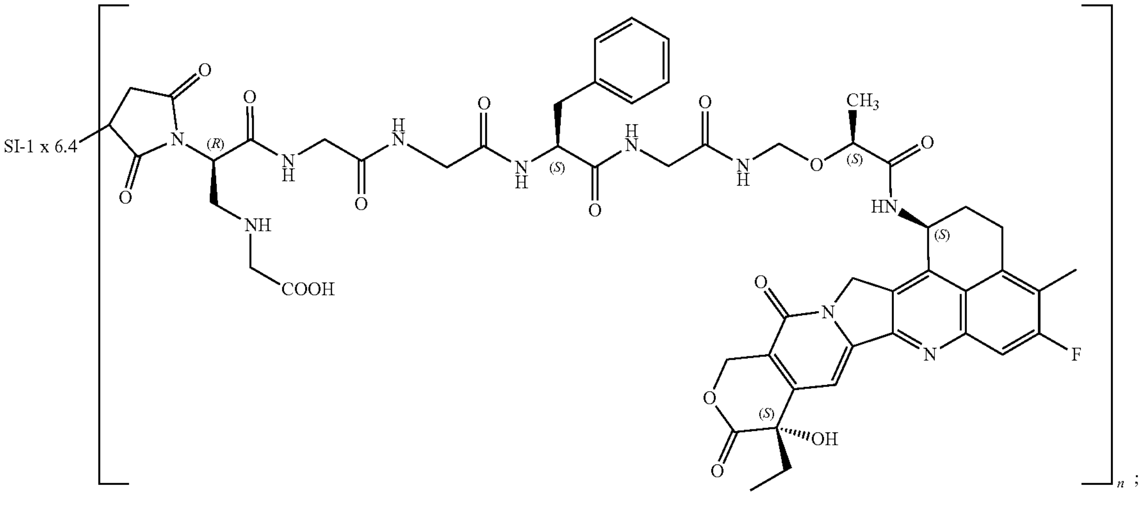
Example 100
ADC-6 was prepared according to the general-purpose coupling method of Example 93, ADC-6
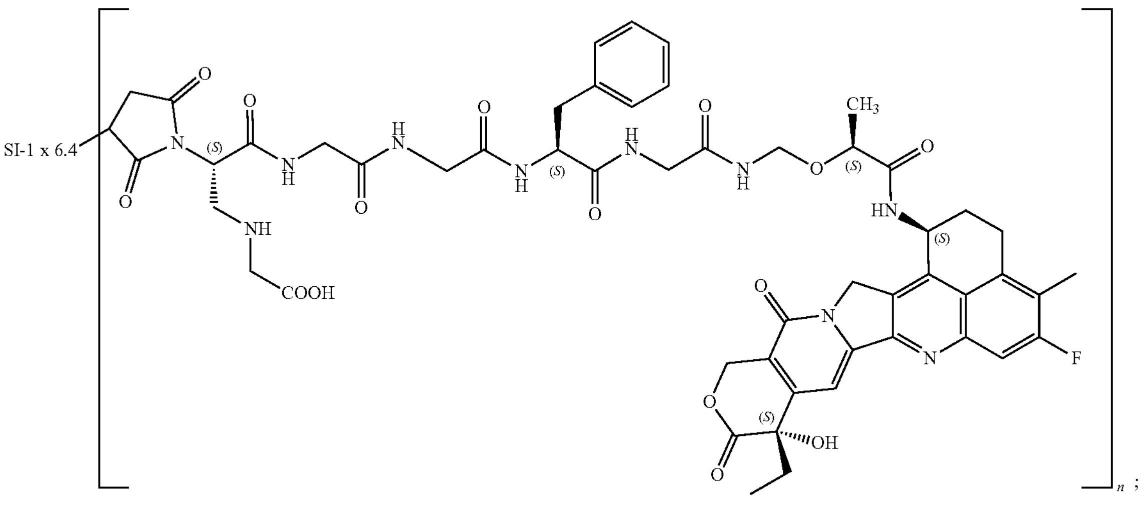
Example 101
ADC-7 was prepared according to the general-purpose coupling method of Example 93,
ADC-7
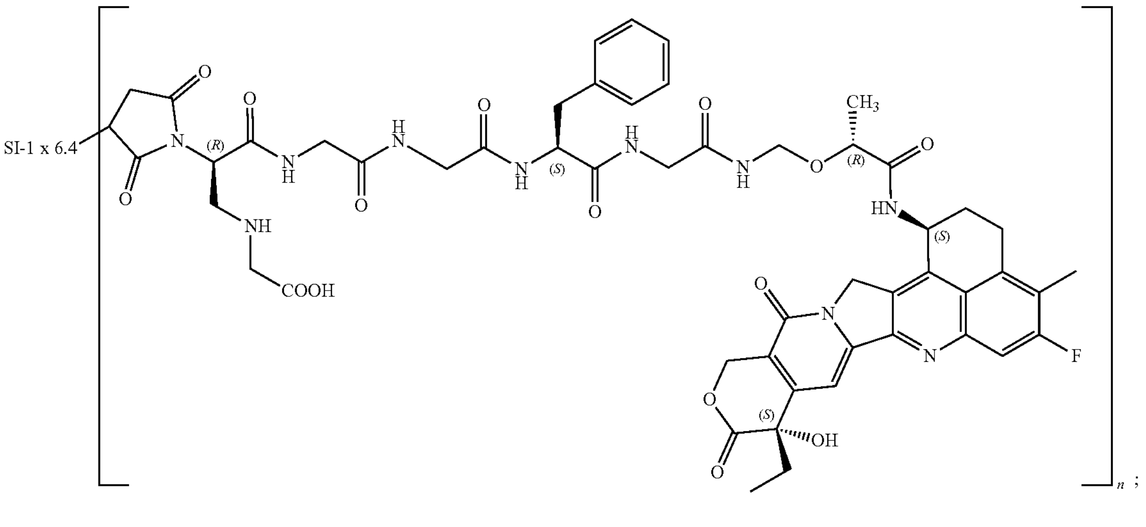
Example 102
ADC-8 was prepared according to the general-purpose coupling method of Example 93, ADC-8
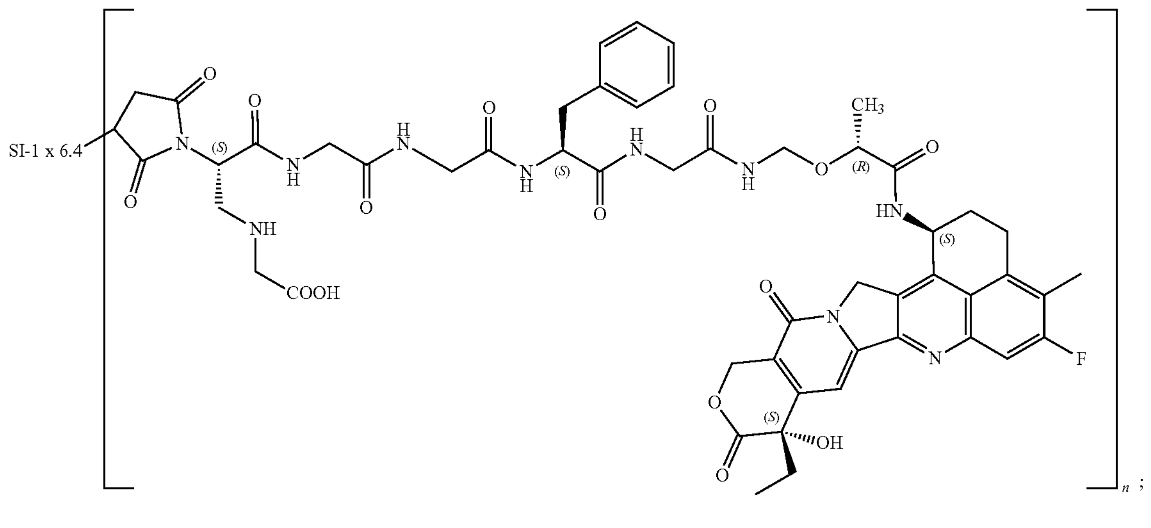
Example 103
ADC-9 was prepared according to the general-purpose coupling method of Example 93,
ADC-9
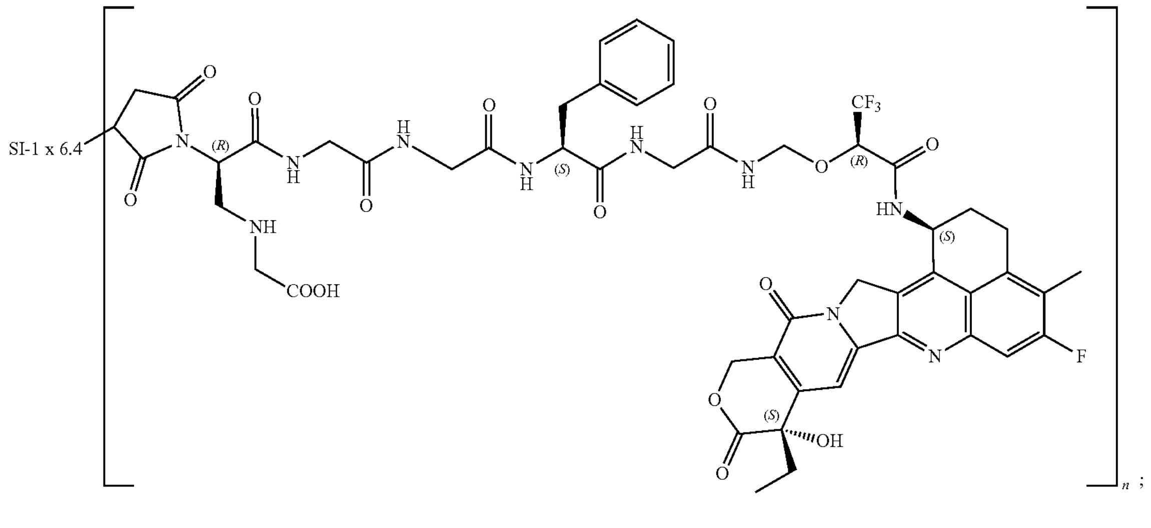
Example 104
ADC-10 was prepared according to the general-purpose coupling method of Example 93, ADC-10
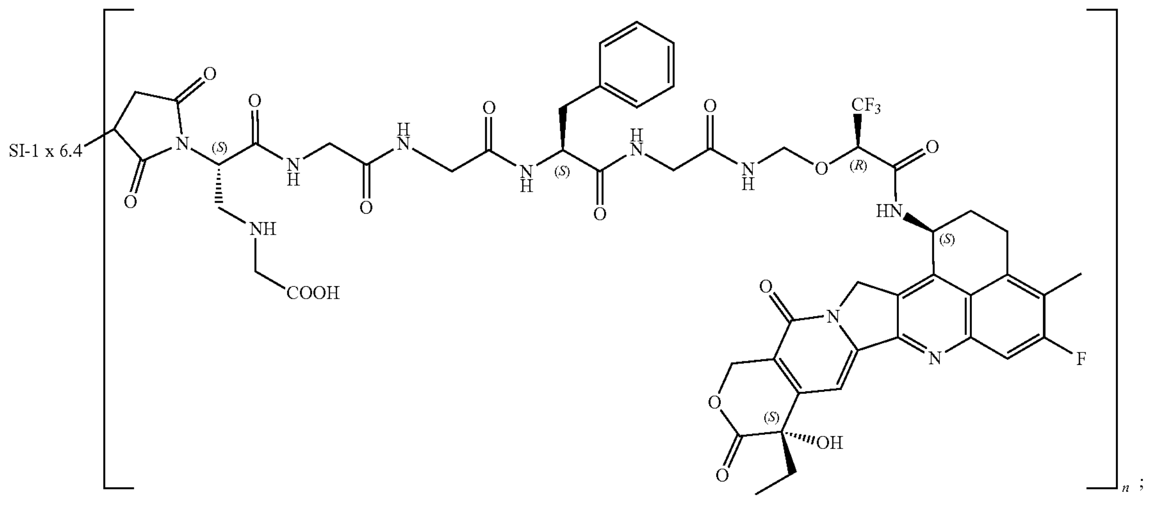
Example 105
ADC-11 was prepared according to the general-purpose coupling method of Example 93,
ADC-11
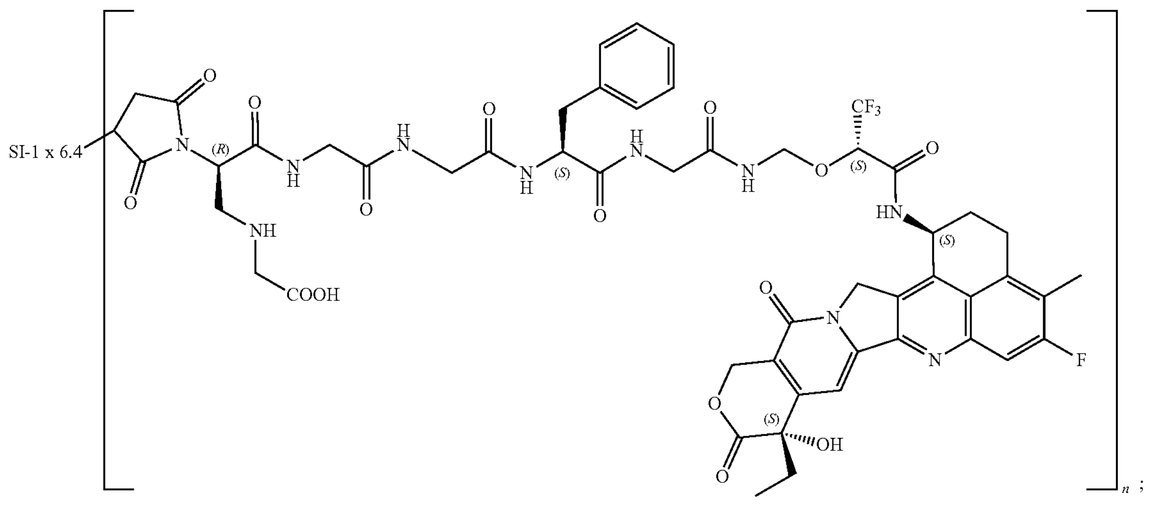
Example 106
ADC-12 was prepared according to the general-purpose coupling method of Example 93, ADC-12
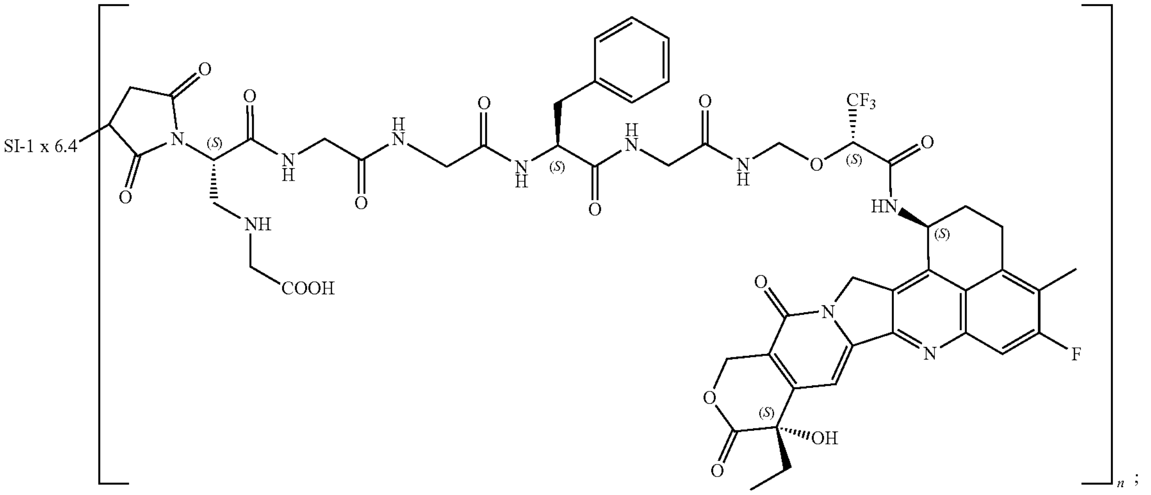
Example 107
ADC-13 was prepared according to the general-purpose coupling method of Example 93,
ADC-13
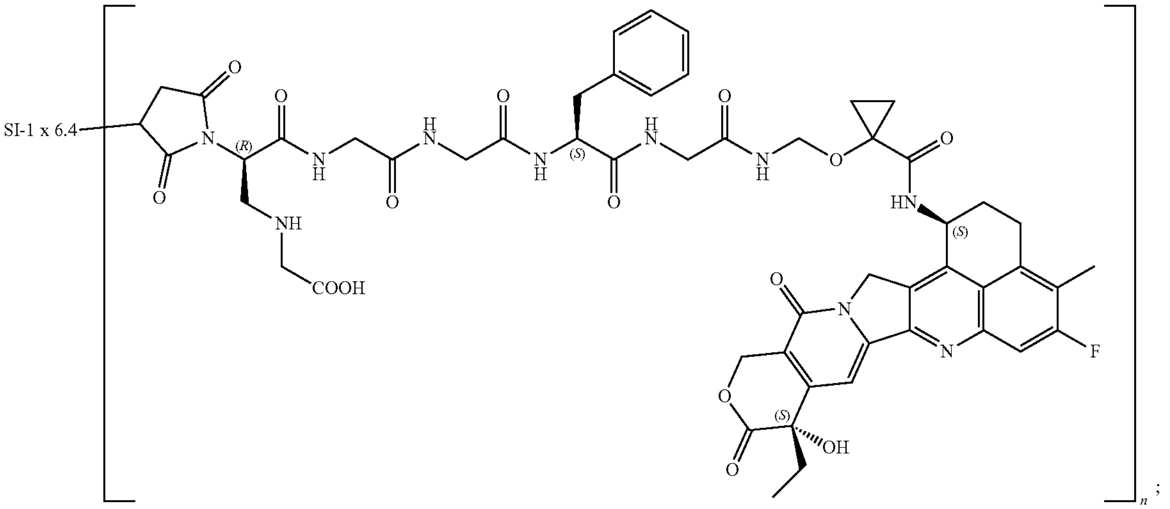
Example 108
ADC-14 was prepared according to the general-purpose coupling method of Example 93, ADC-14
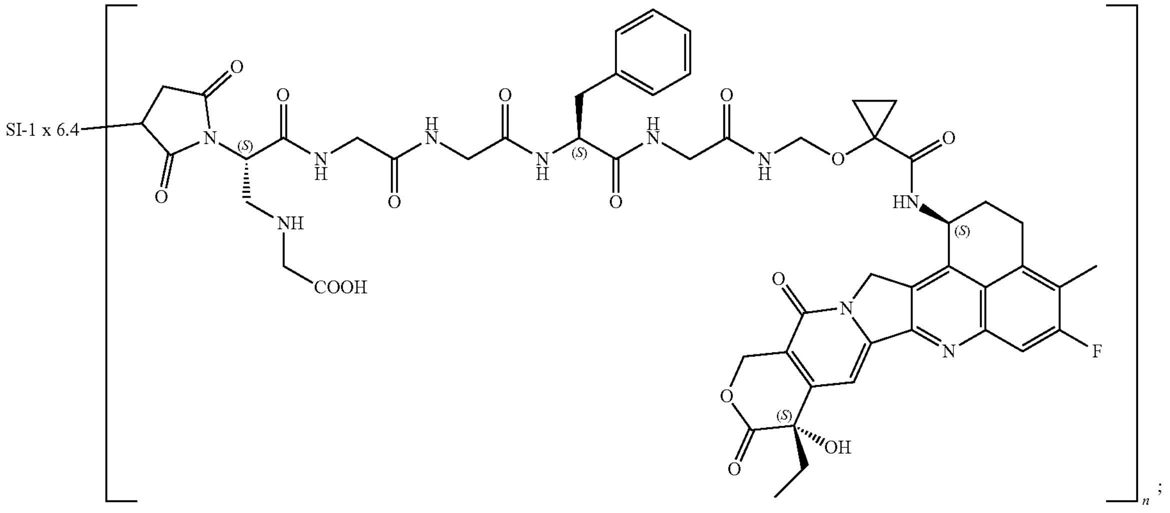
Example 109
ADC-15 was prepared according to the general-purpose coupling method of Example 93,
ADC-15
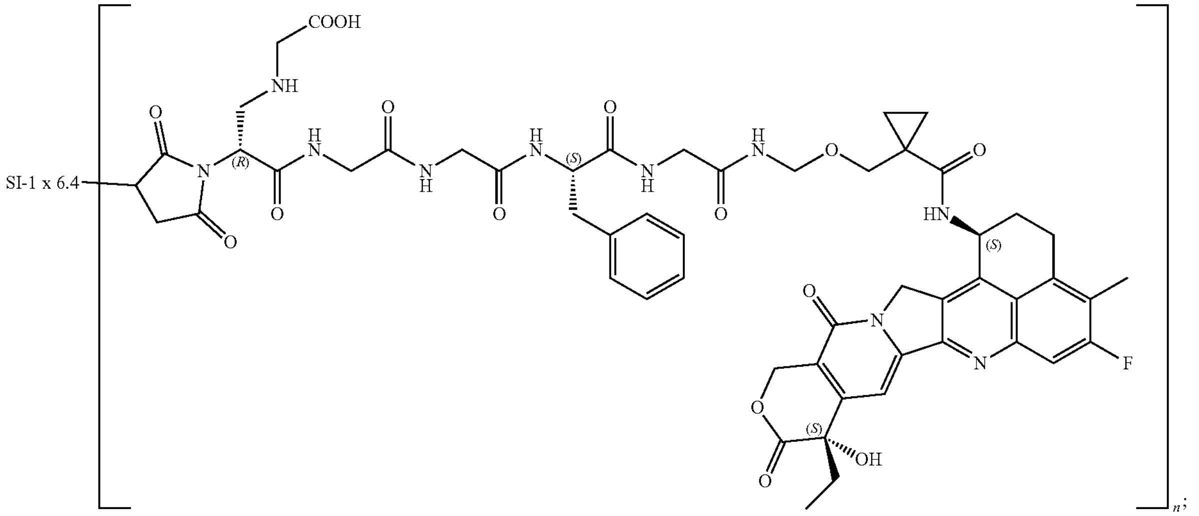
Example 110
ADC-16 was prepared according to the general-purpose coupling method of Example 93, ADC-16
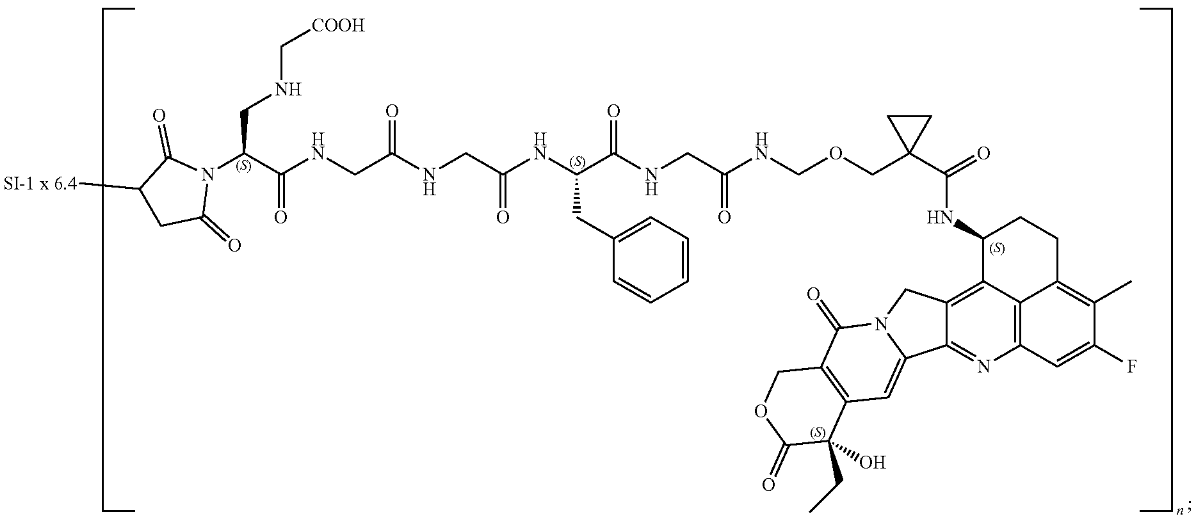
Example 111
ADC-17 was prepared according to the general-purpose coupling method of Example 93,
ADC-17
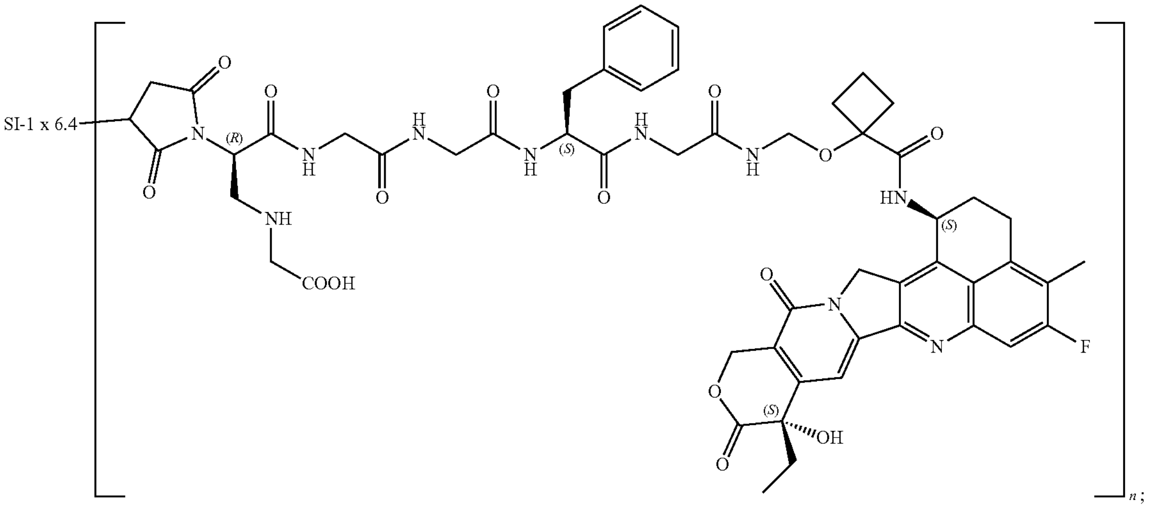
Example 112
ADC-18 was prepared according to the general-purpose coupling method of Example 93, ADC-18
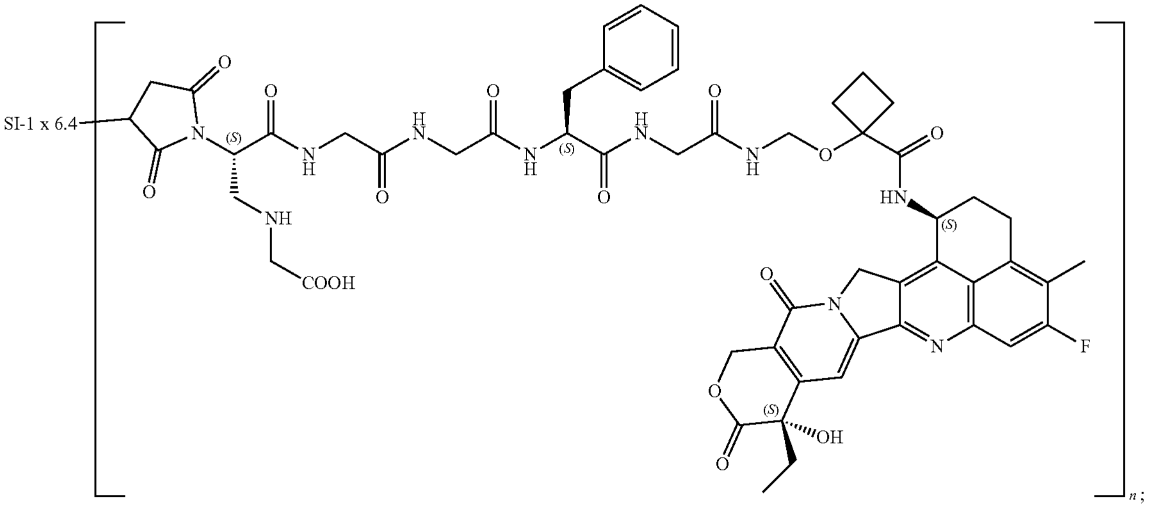
Example 113
ADC-19 was prepared according to the general-purpose coupling method of Example 93,
ADC-19
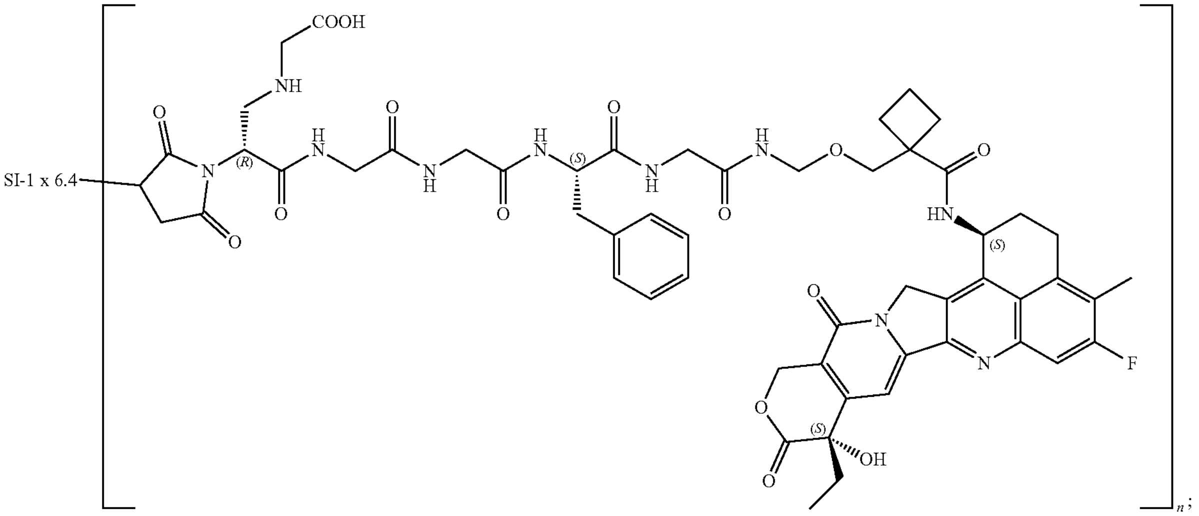
Example 114
ADC-20 was prepared according to the general-purpose coupling method of Example 93, ADC-20
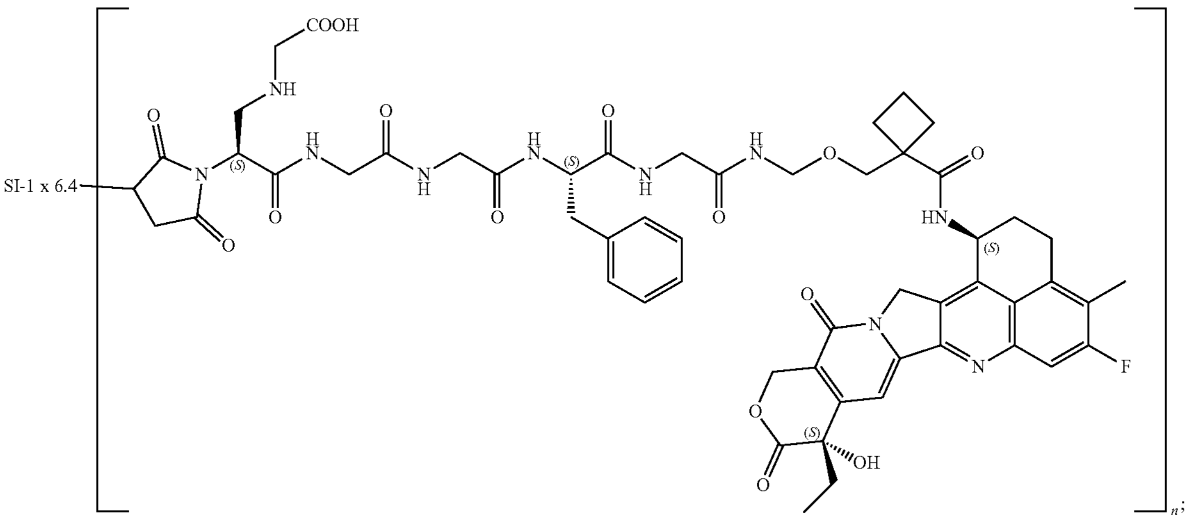
Example 115
ADC-21 was prepared according to the general-purpose coupling method of Example 93,
ADC-21
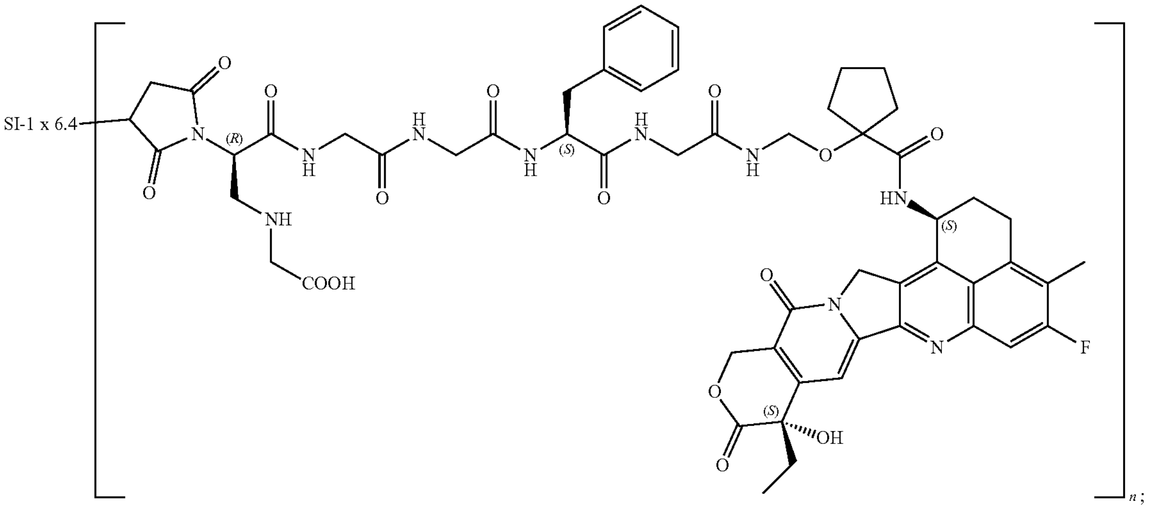
Example 116
ADC-22 was prepared according to the general-purpose coupling method of Example 93, ADC-22
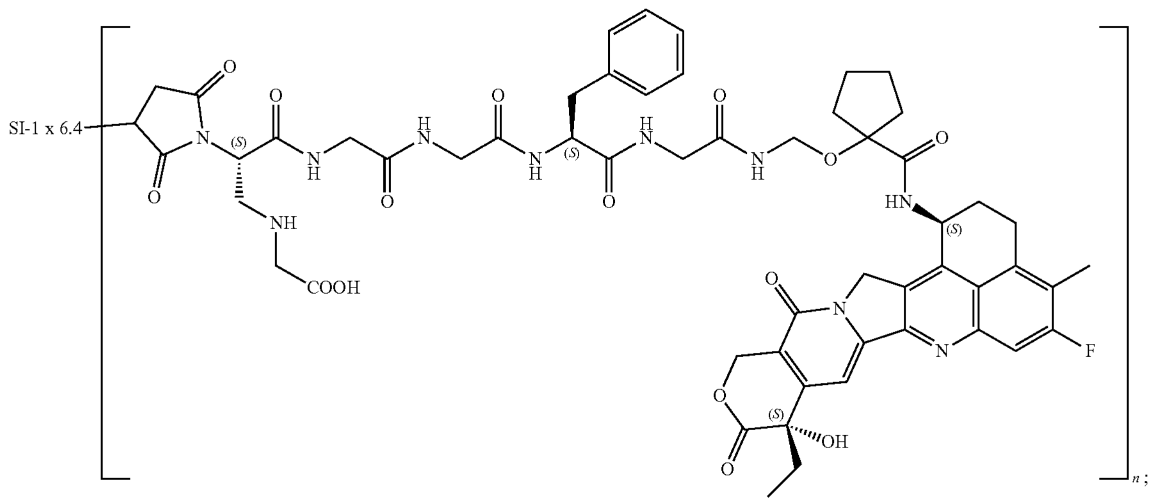
Example 117
ADC-23 was prepared according to the general-purpose coupling method of Example 93,
ADC-23
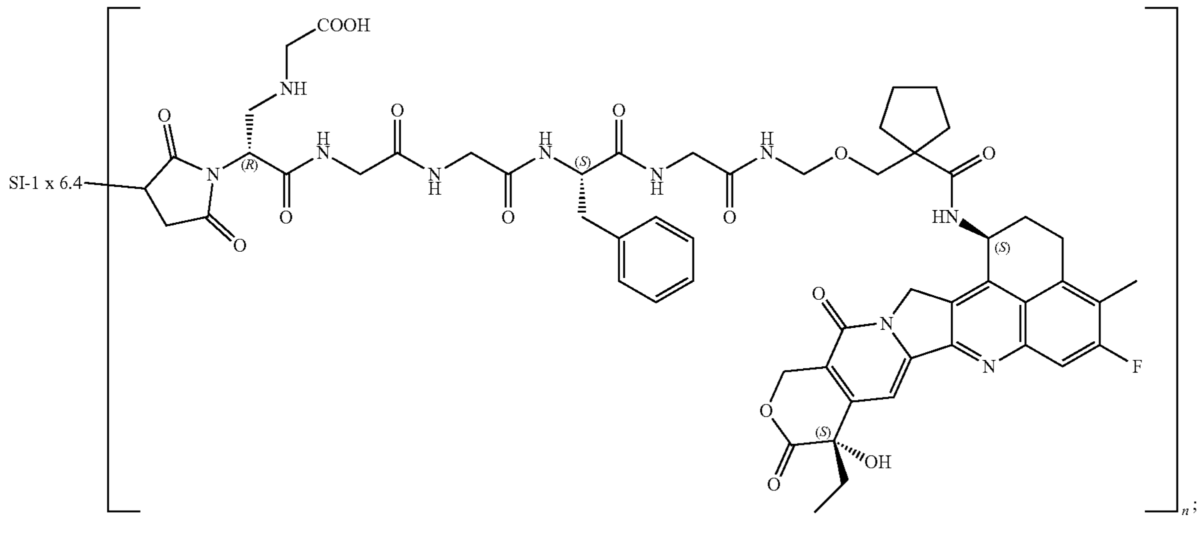
Example 118
ADC-24 was prepared according to the general-purpose coupling method of Example 93, ADC-24
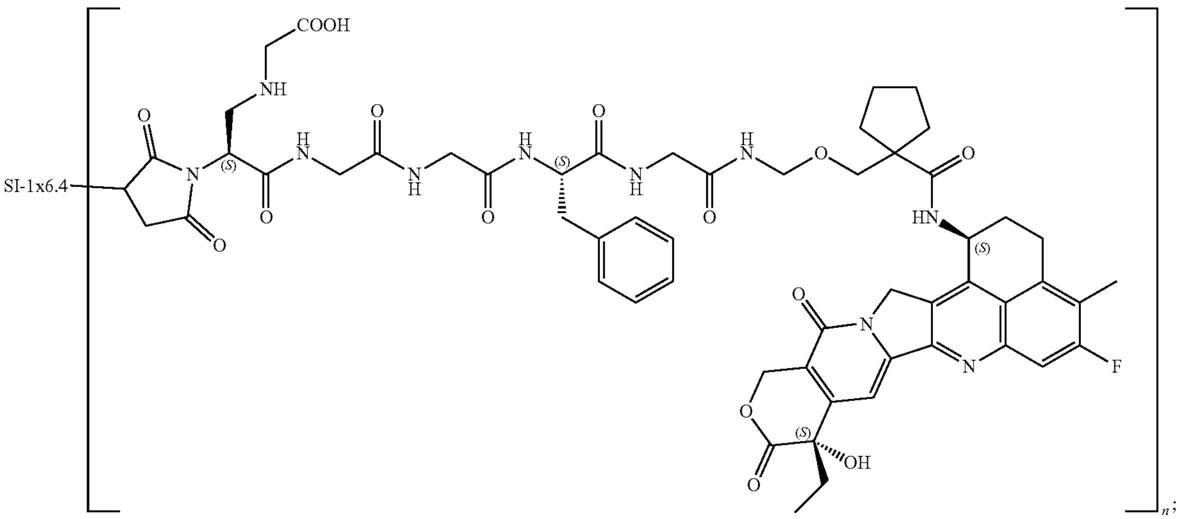
Example 119
ADC-25 was prepared according to the general-purpose coupling method of Example 93,
ADC-25
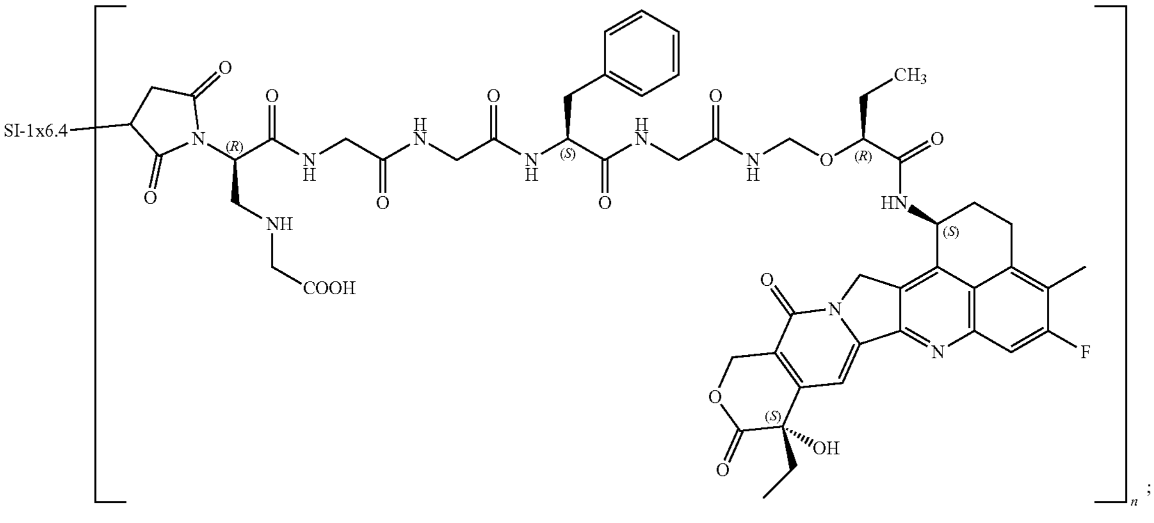
Example 120
ADC-26 was prepared according to the general-purpose coupling method of Example 93, ADC-26
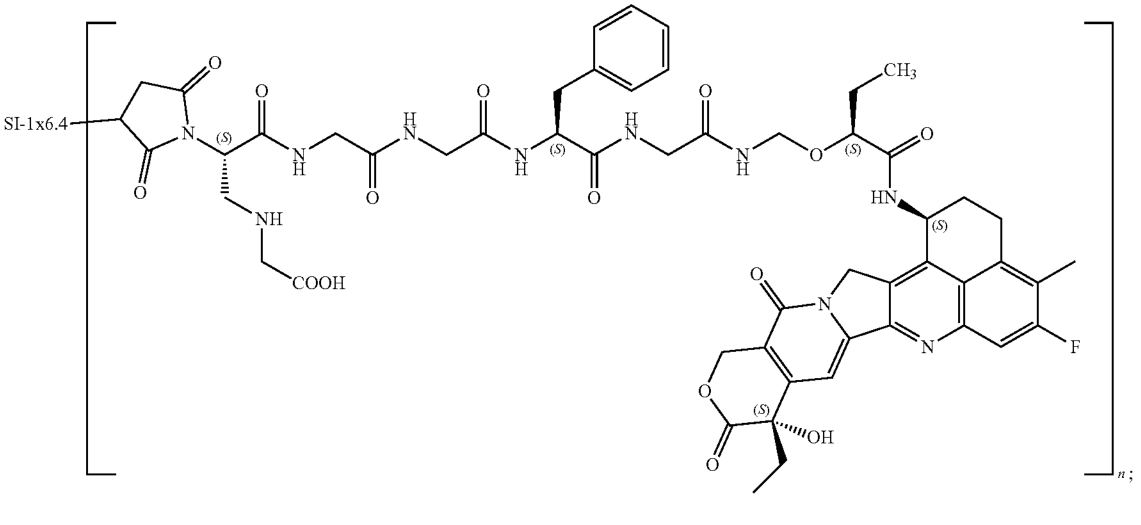
Example 121
ADC-27 was prepared according to the general-purpose coupling method of Example 93, v
ADC-27
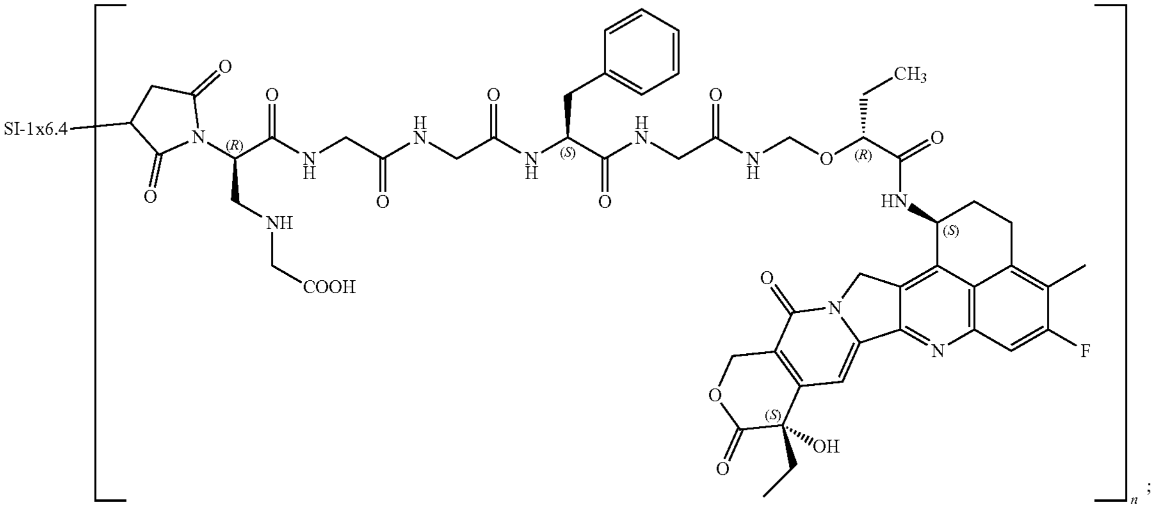
Example 122
ADC-28 was prepared according to the general-purpose coupling method of Example 93, ADC-28
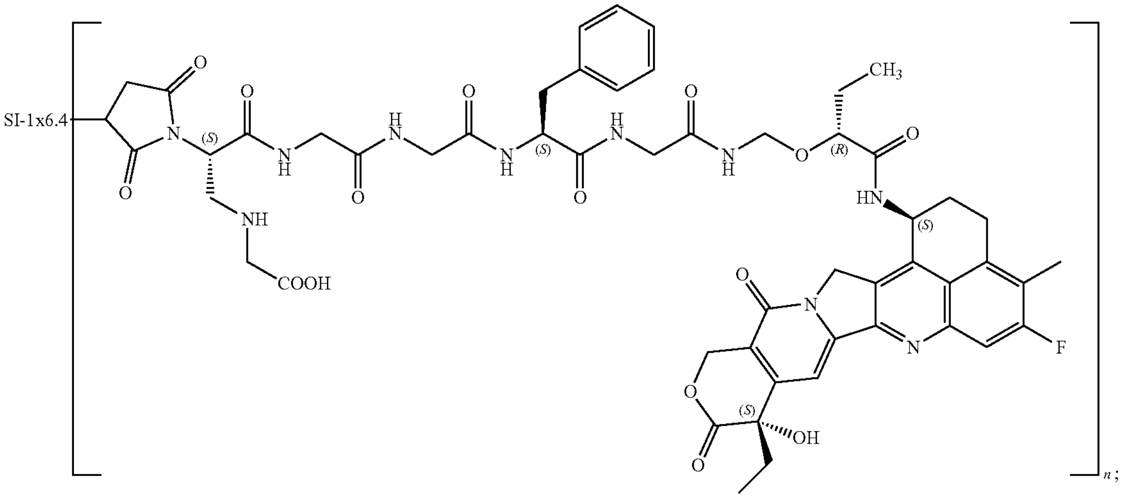
Example 123
ADC-29 was prepared according to the general-purpose coupling method of Example 93,
ADC-29
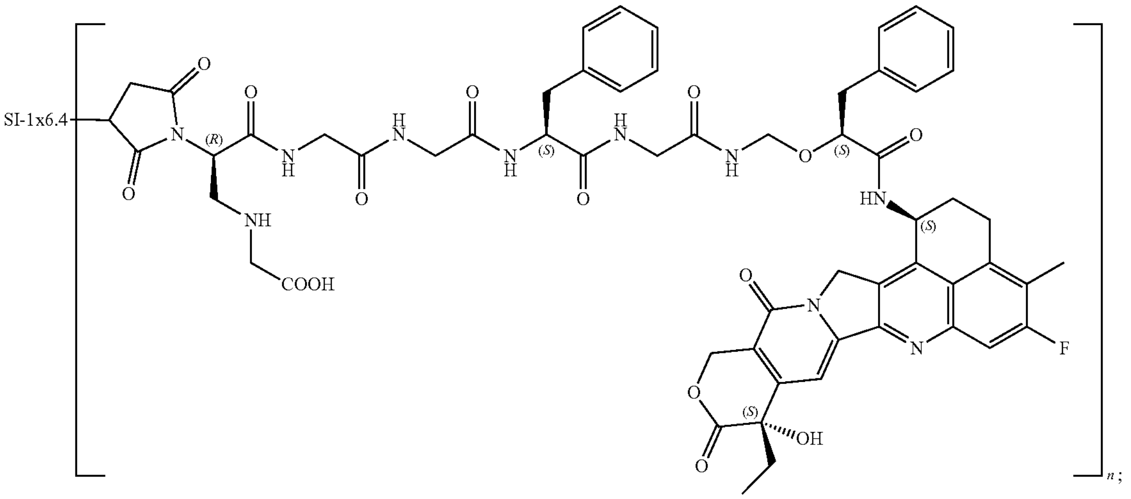
Example 124
ADC-30 was prepared according to the general-purpose coupling method of Example 93, ADC-30
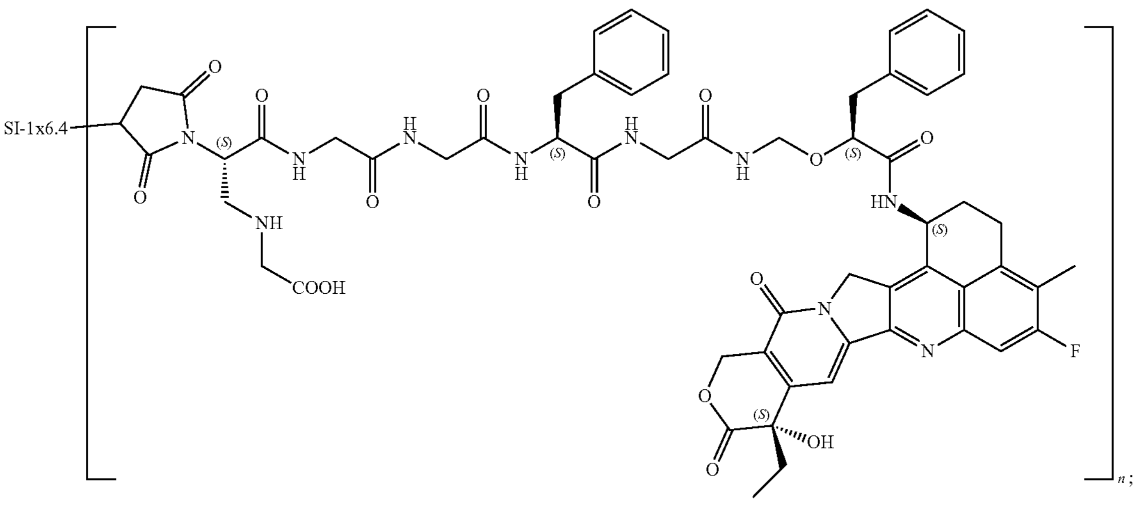
Example 125
ADC-31 was prepared according to the general-purpose coupling method of Example 93,
ADC-31
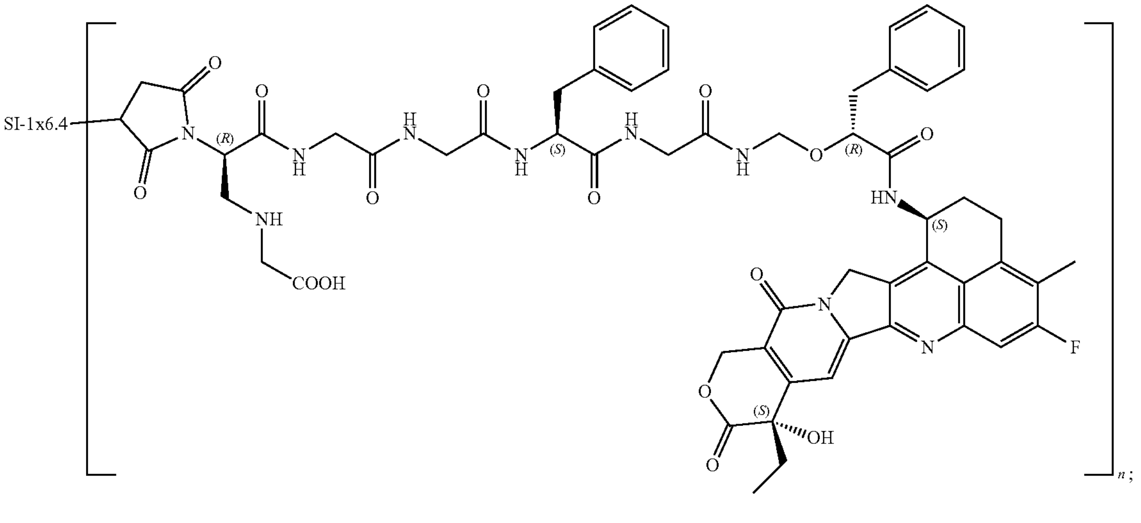
Example 126
ADC-32 was prepared according to the general-purpose coupling method of Example 93, ADC-32
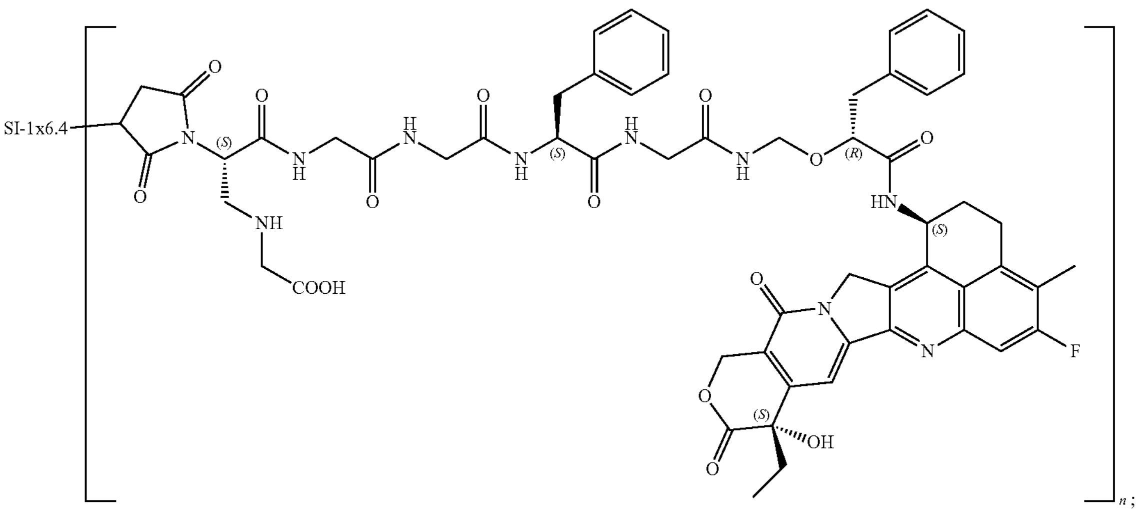
Example 127
ADC-33 was prepared according to the general-purpose coupling method of Example 93,
ADC-33
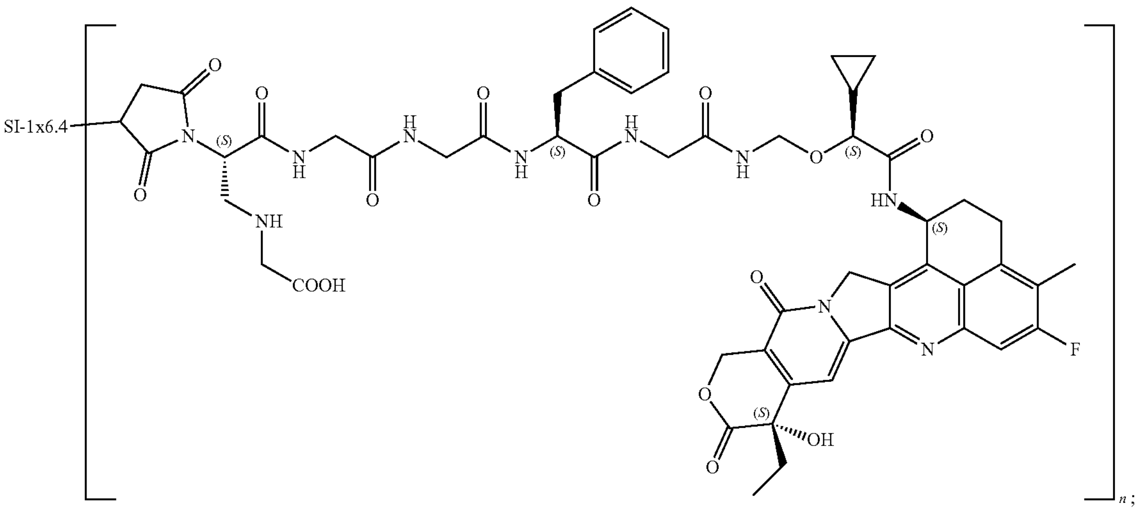
Example 128
ADC-34 was prepared according to the general-purpose coupling method of Example 93, ADC-34
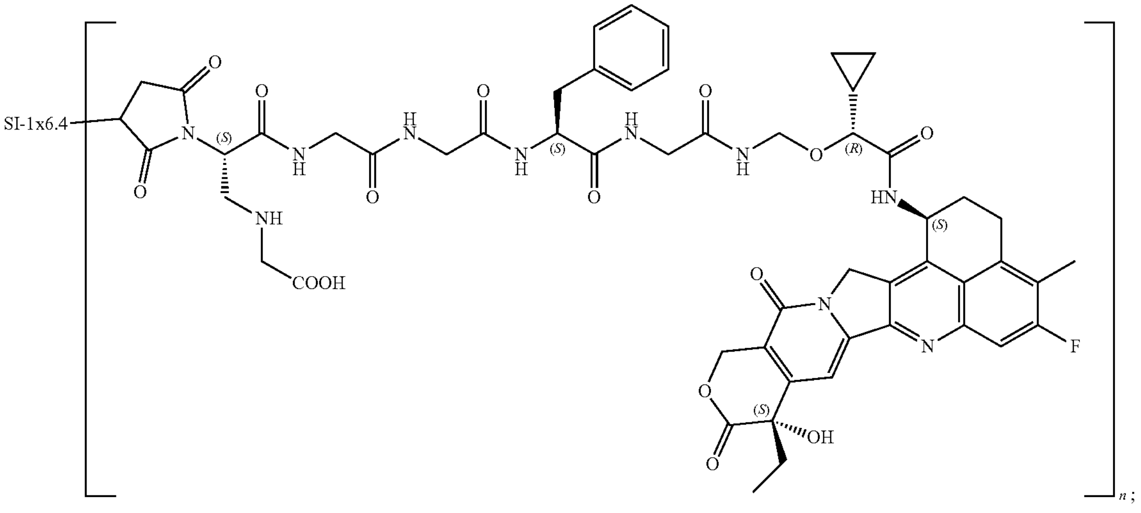
Example 129
ADC-35 was prepared according to the general-purpose coupling method of Example 93,
ADC-35
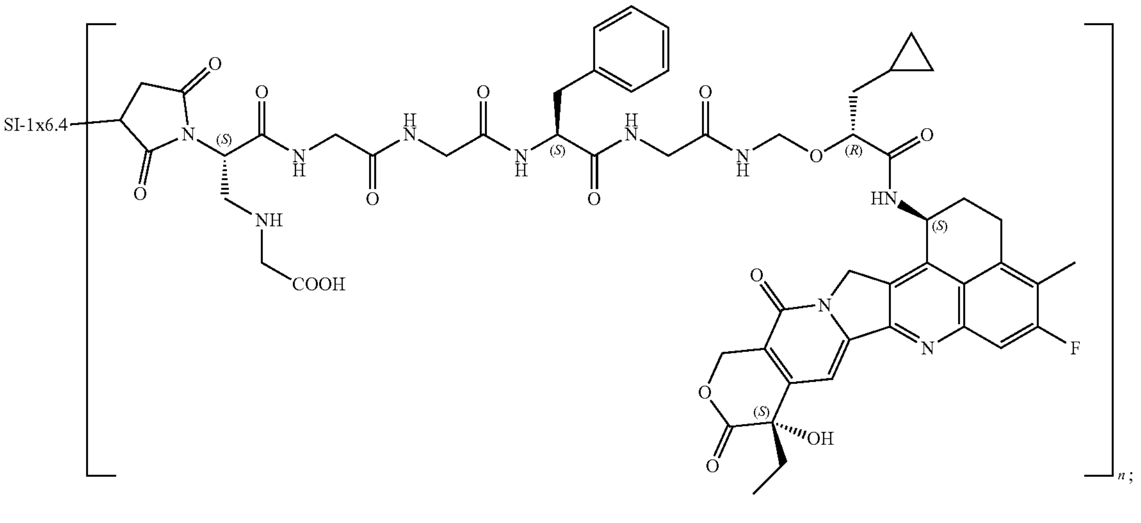
Example 130
ADC-36 was prepared according to the general-purpose coupling method of Example 93, ADC-36
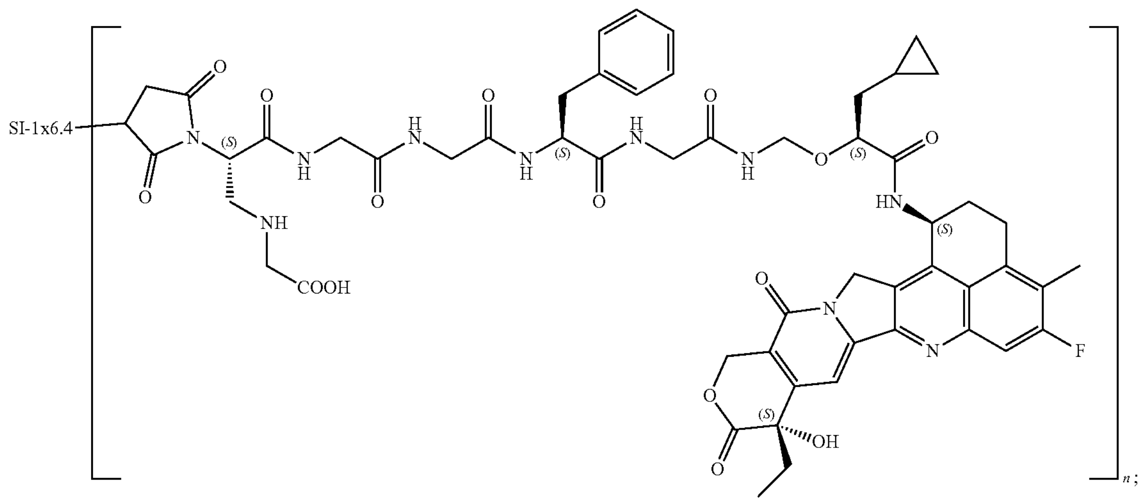
Example 131
ADC-37 was prepared according to the general-purpose coupling method of Example 93,
ADC-37
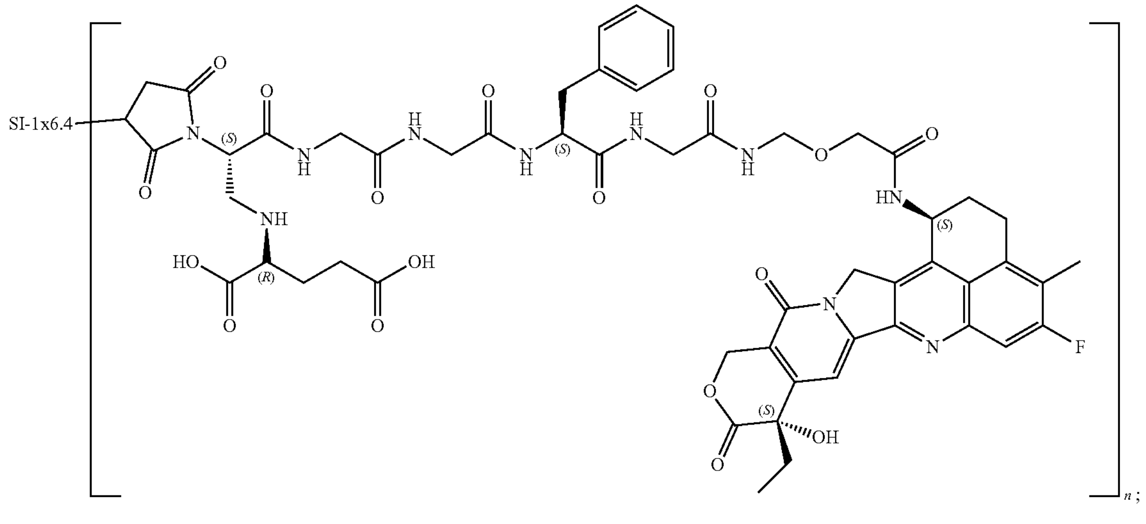
Example 132
ADC-38 was prepared according to the general-purpose coupling method of Example 93, ADC-38
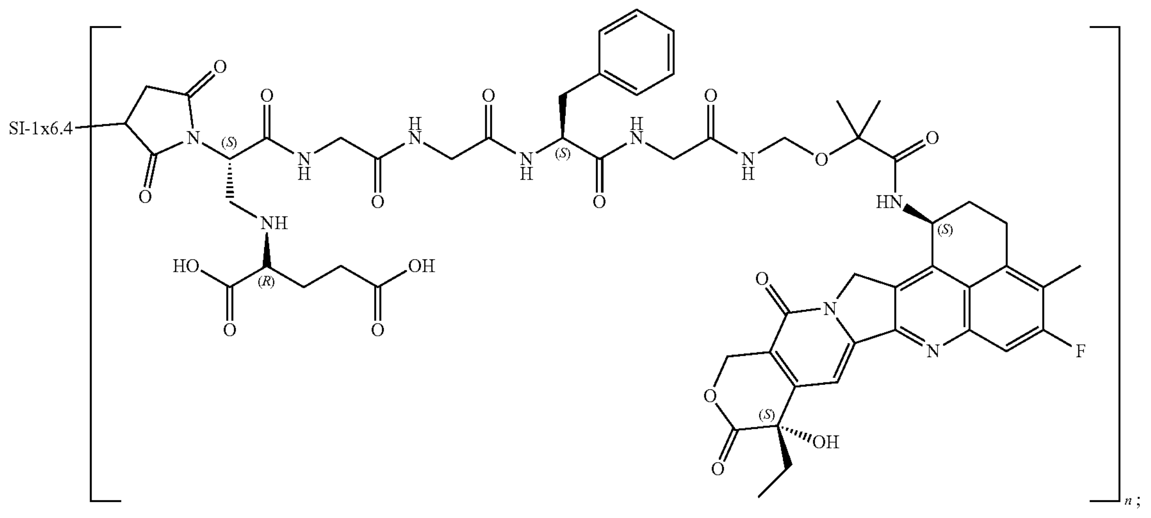
Example 133
ADC-39 was prepared according to the general-purpose coupling method of Example 93,
ADC-39
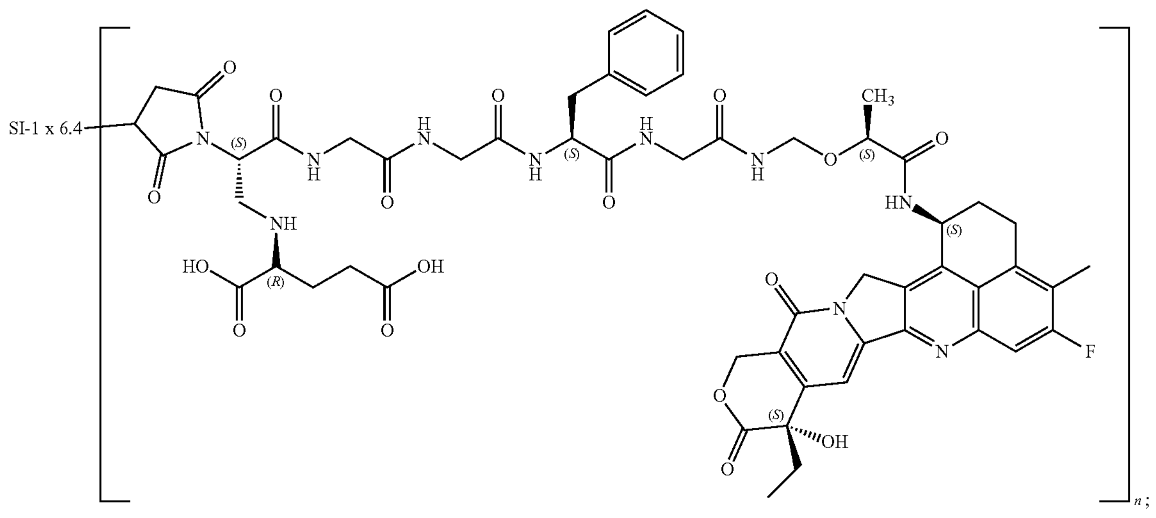
Example 134
ADC-40 was prepared according to the general-purpose coupling method of Example 93, ADC-40
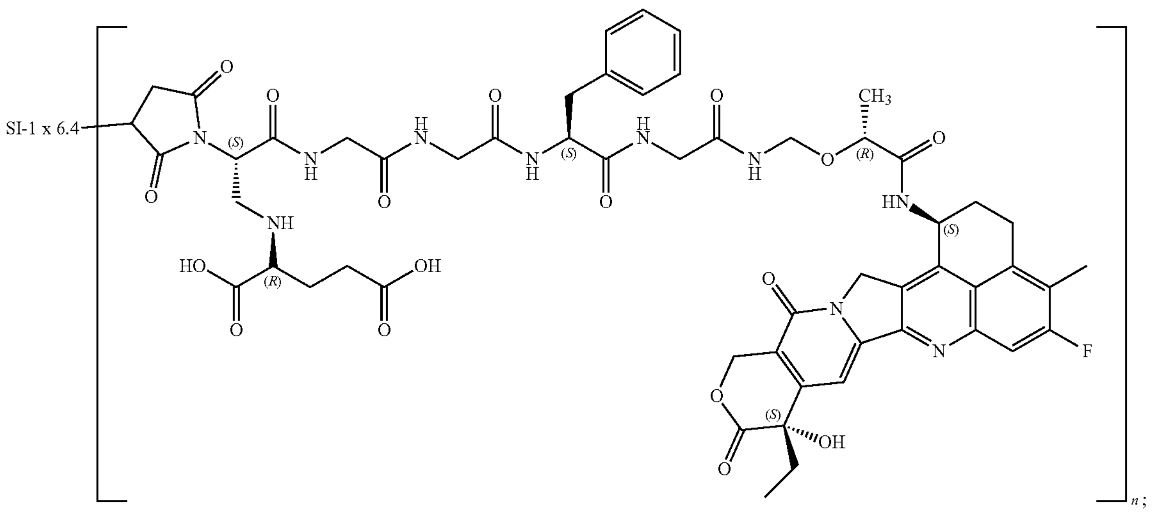
Example 135
ADC-41 was prepared according to the general-purpose coupling method of Example 93,
ADC-41
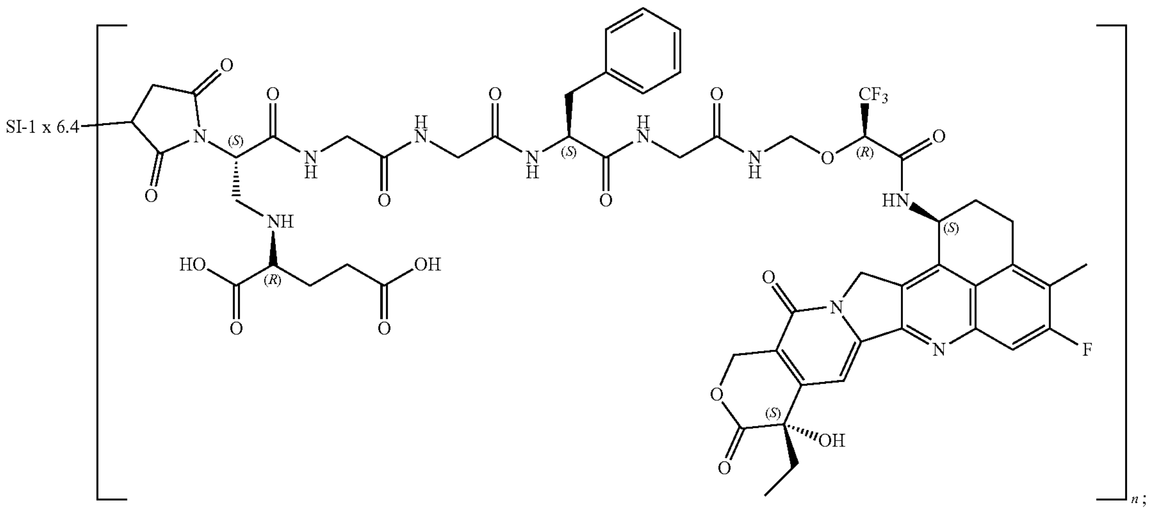
Example 136
ADC-42 was prepared according to the general-purpose coupling method of Example 93, ADC-42
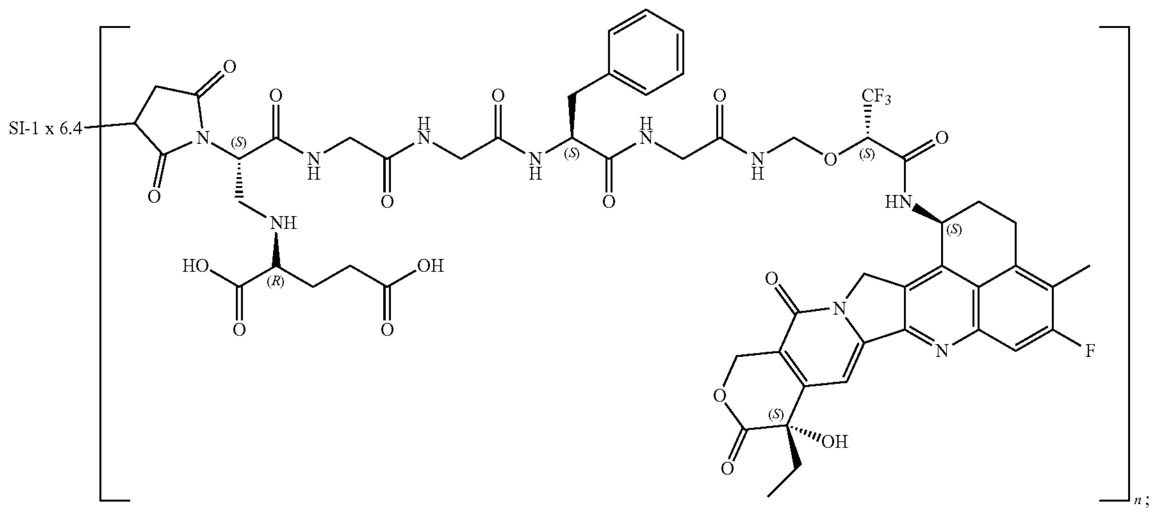
Example 137
ADC-43 was prepared according to the general-purpose coupling method of Example 93,
ADC-43
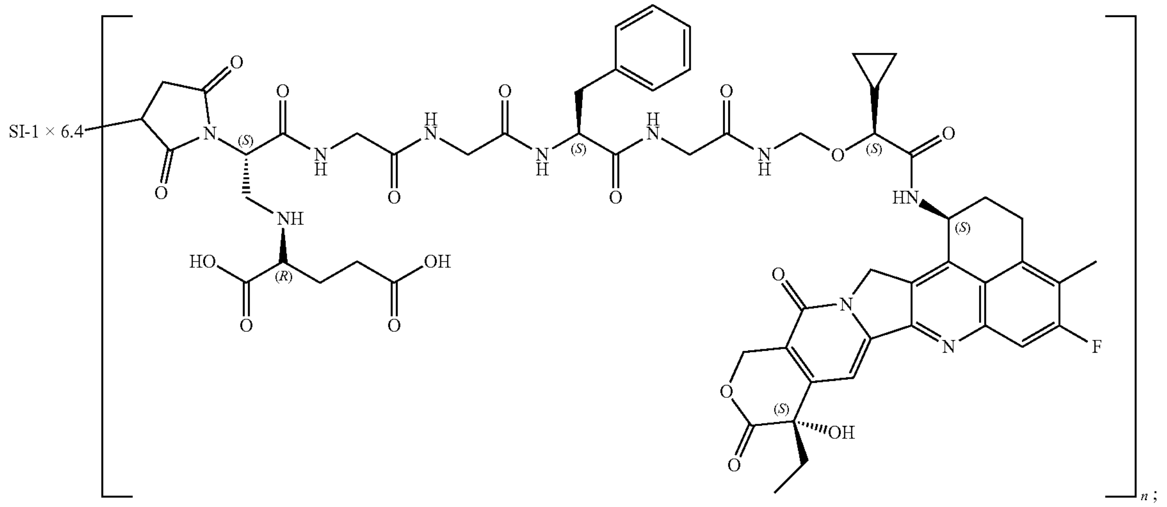
Example 138
ADC-44 was prepared according to the general-purpose coupling method of Example 93, ADC-44
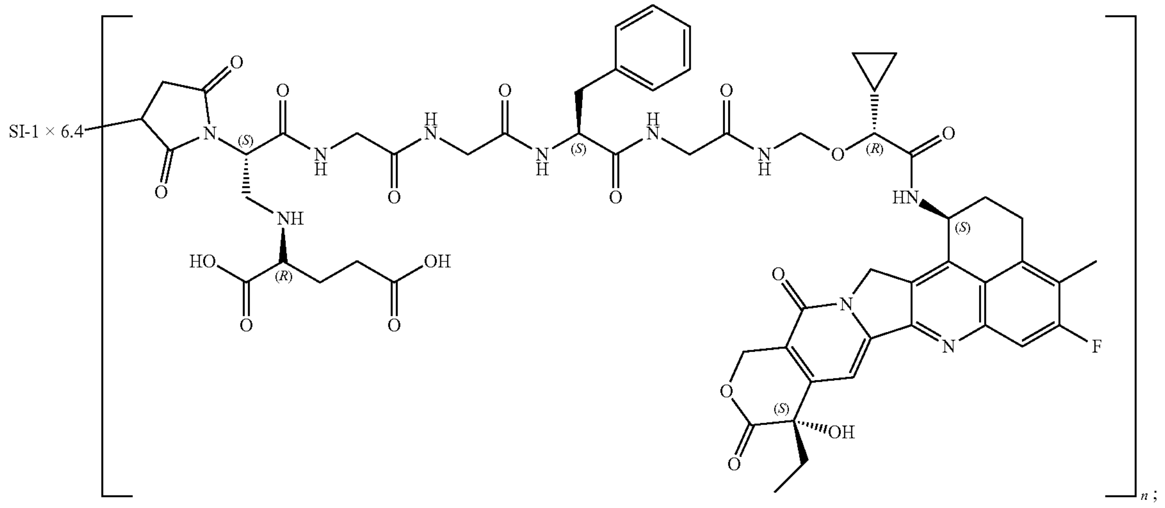
Example 139
ADC-45 was prepared according to the general-purpose coupling method of Example 93,
ADC-45
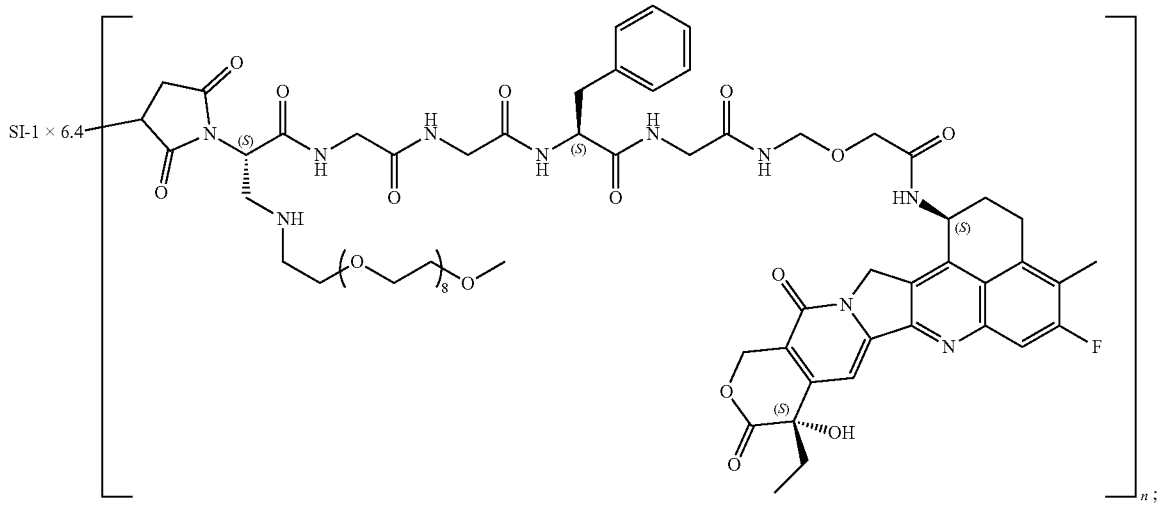
Example 140
ADC-46 was prepared according to the general-purpose coupling method of Example 93, ADC-46
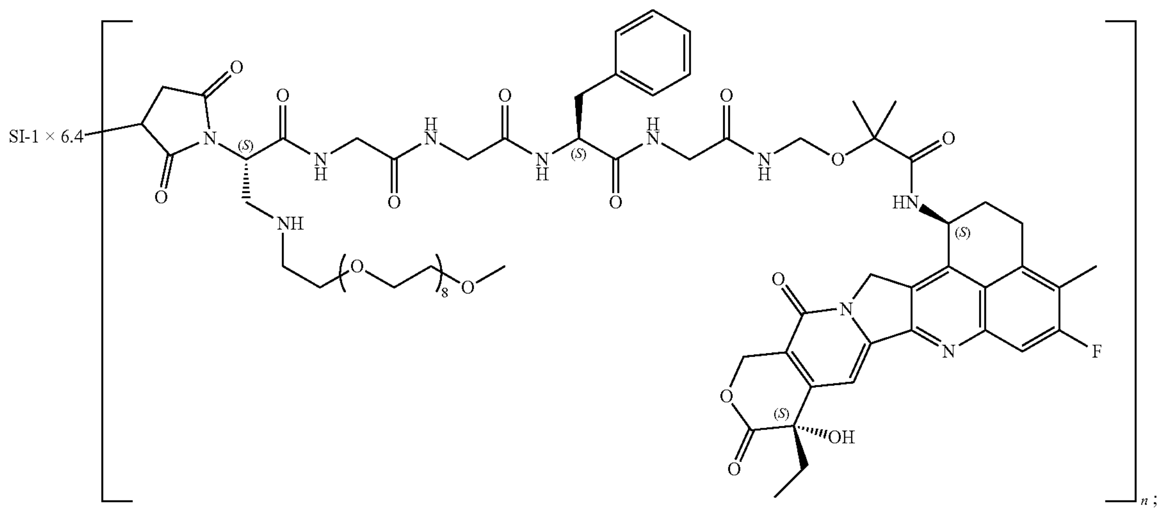
Example 141
ADC-47 was prepared according to the general-purpose coupling method of Example 93,
ADC-47
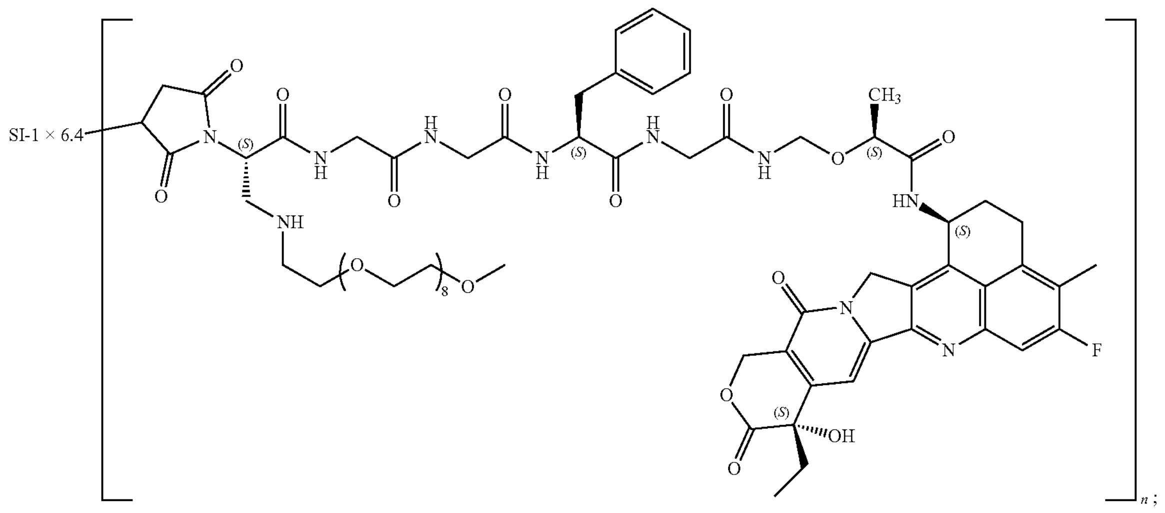
Example 142
ADC-48 was prepared according to the general-purpose coupling method of Example 93, ADC-48
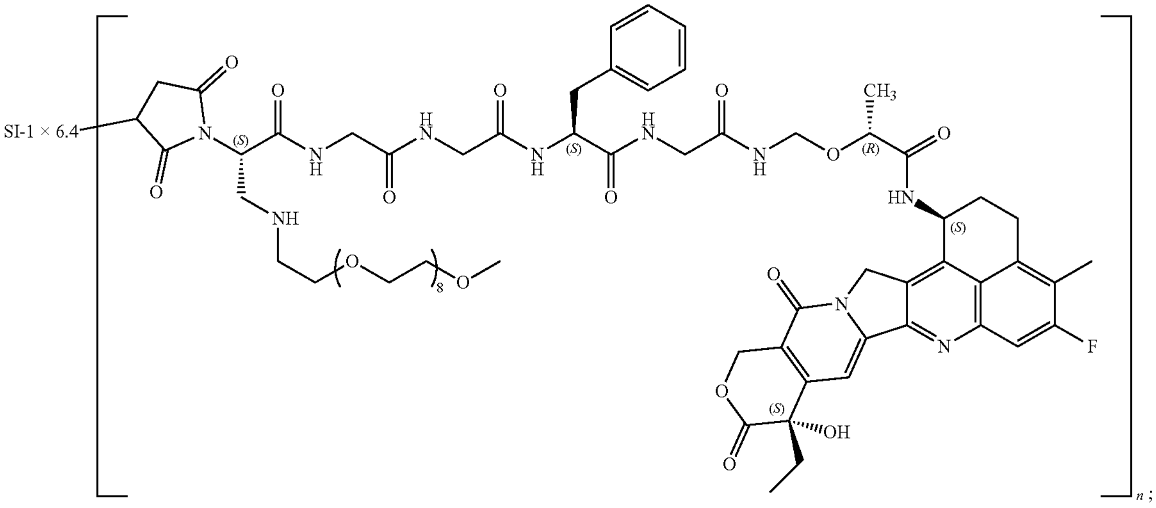
Example 143
ADC-49 was prepared according to the general-purpose coupling method of Example 93,
ADC-49
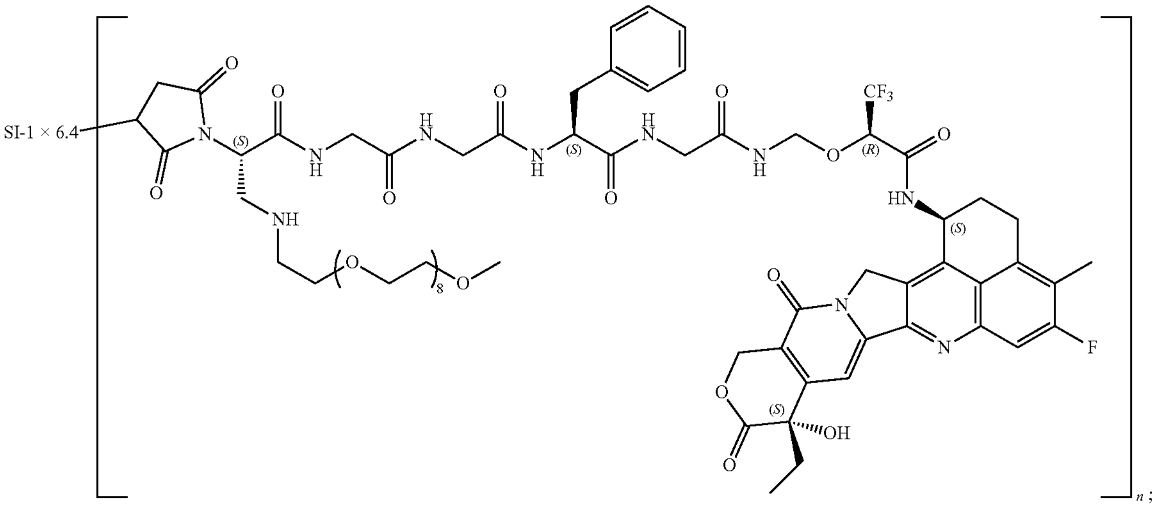
Example 144
ADC-50 was prepared according to the general-purpose coupling method of Example 93, ADC-50
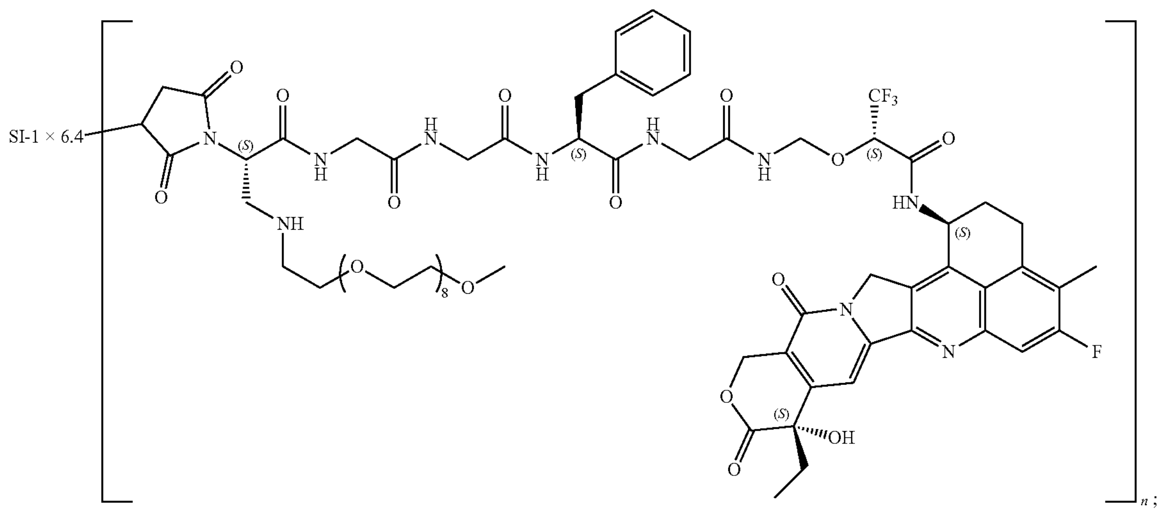
Example 145
ADC-51 was prepared according to the general-purpose coupling method of Example 93,
ADC-51
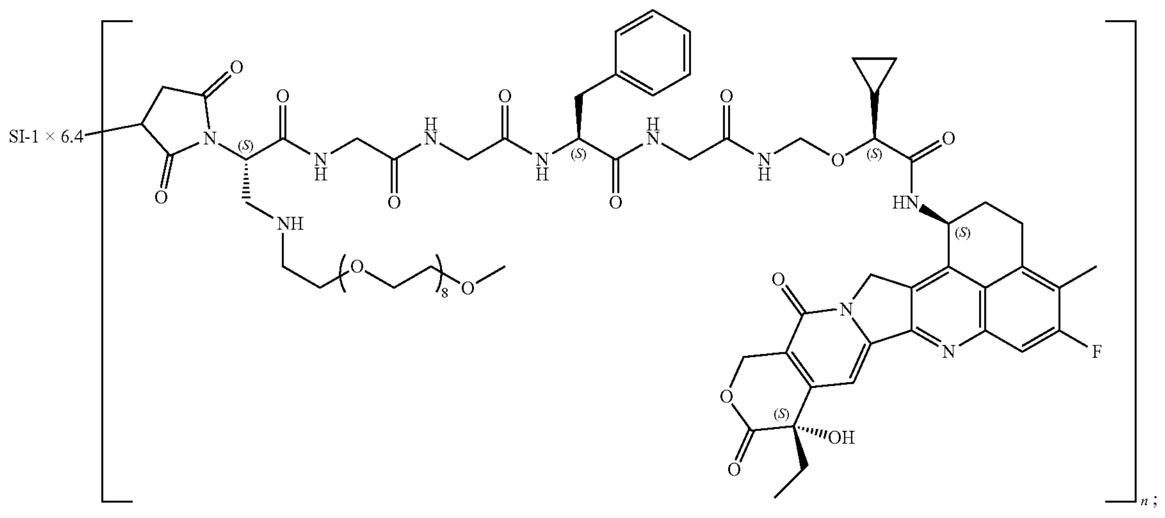
Example 146
ADC-52 was prepared according to the general-purpose coupling method of Example 93, ADC-52
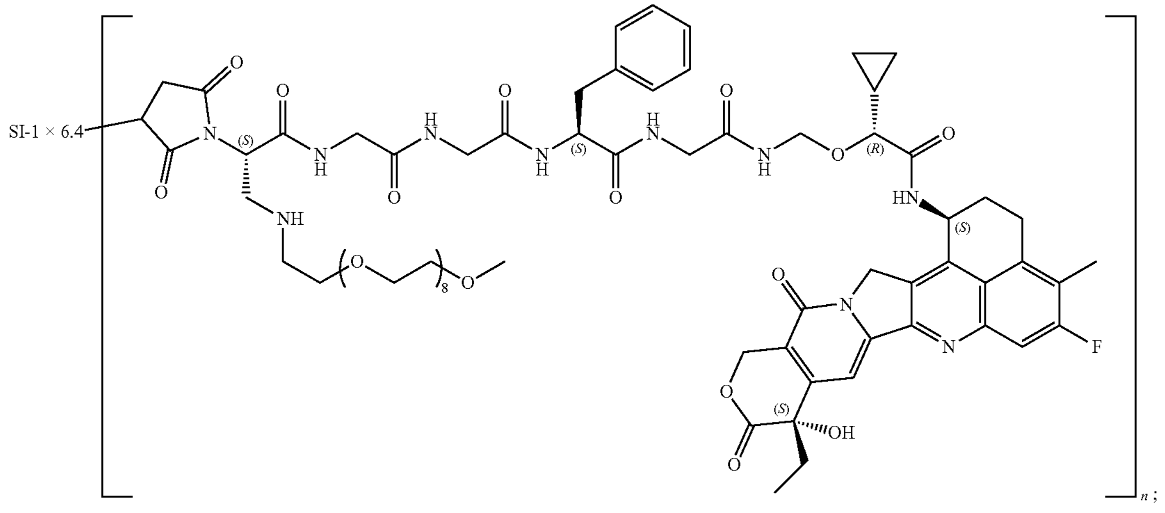
Example 147
ADC-53 was prepared according to the general-purpose coupling method of Example 93,
ADC-53
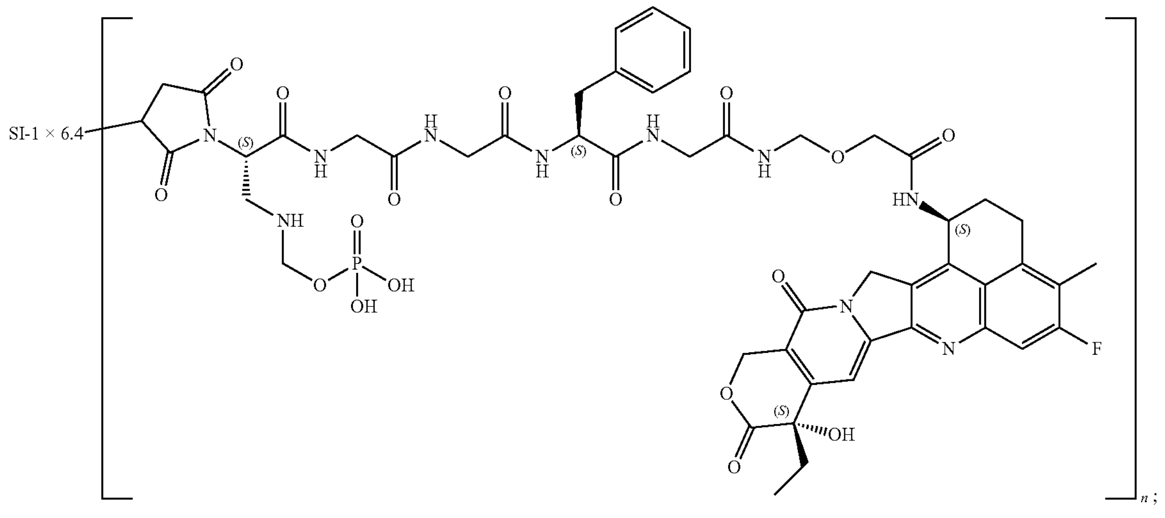
Example 148
ADC-54 was prepared according to the general-purpose coupling method of Example 93, ADC-54
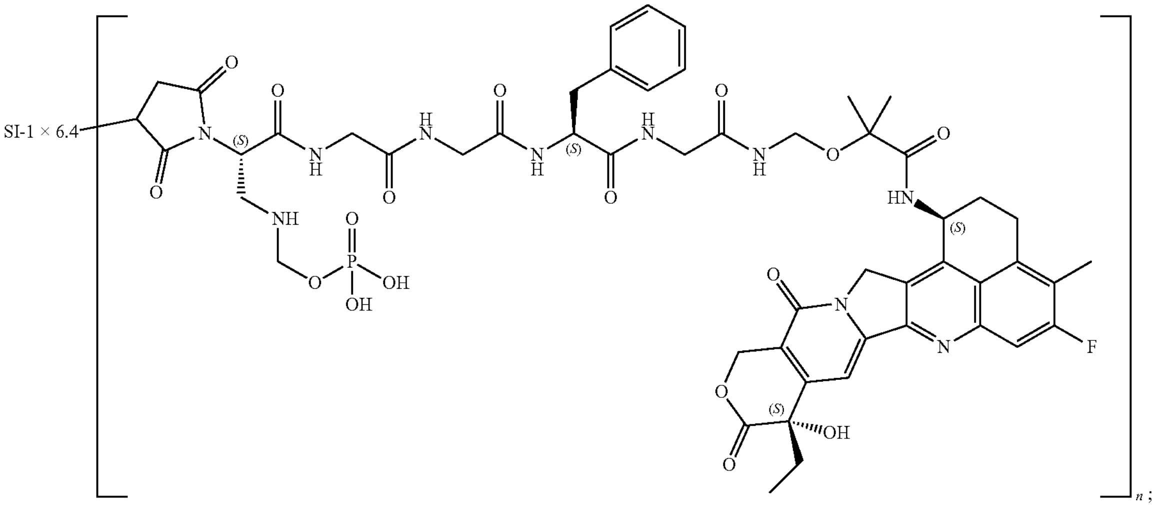
Example 149
ADC-55 was prepared according to the general-purpose coupling method of Example 93,
ADC-55
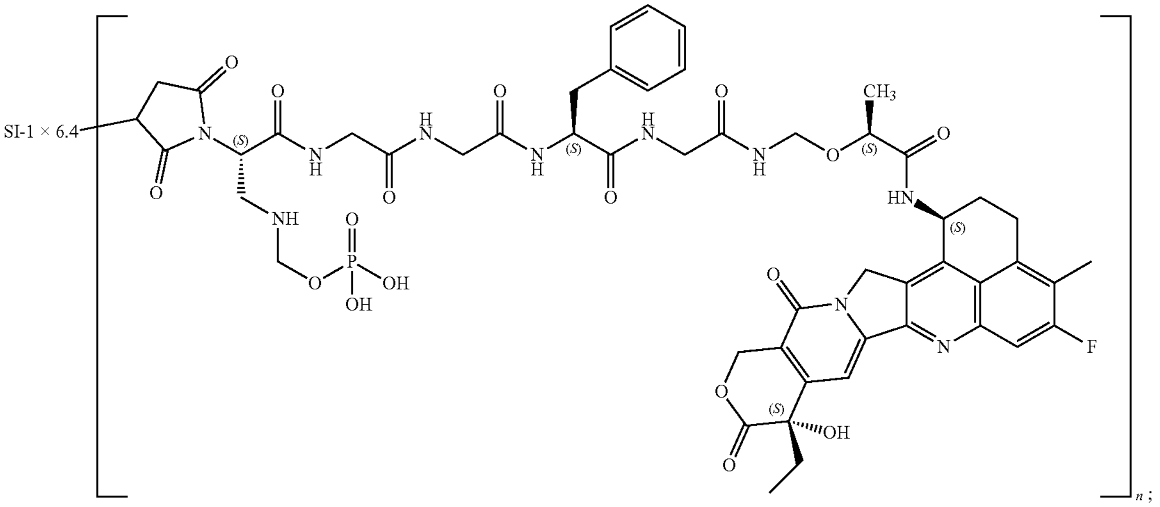
Example 150
ADC-56 was prepared according to the general-purpose coupling method of Example 93, ADC-56
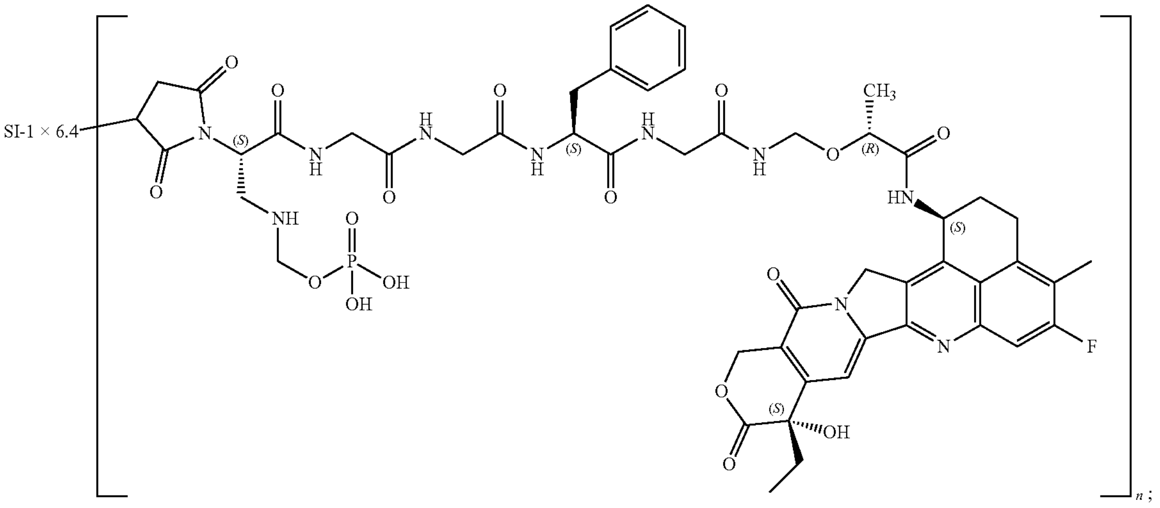
Example 151
ADC-57 was prepared according to the general-purpose coupling method of Example 93,
ADC-57
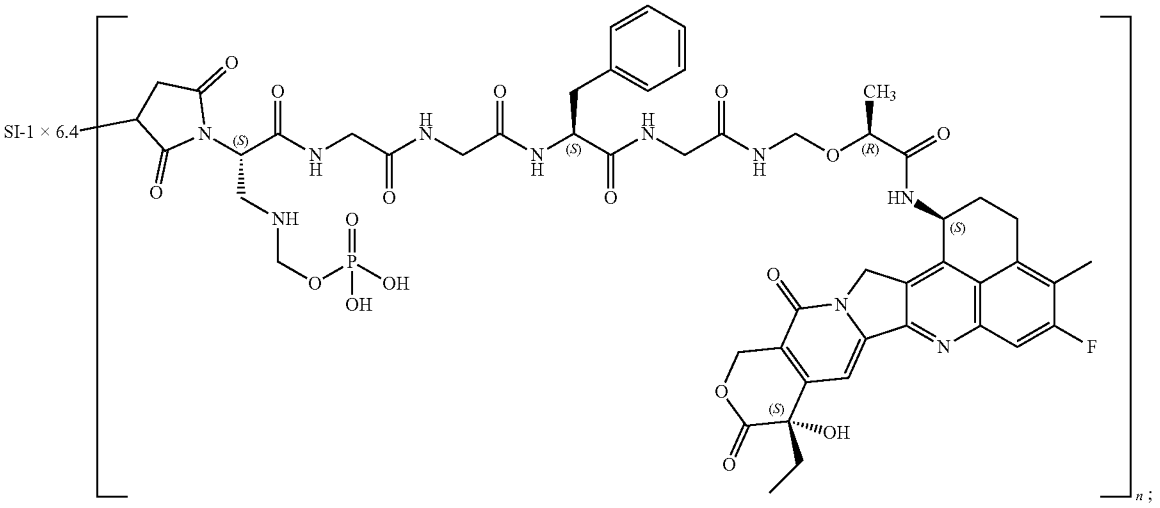
Example 152
ADC-58 was prepared according to the general-purpose coupling method of Example 93, ADC-58
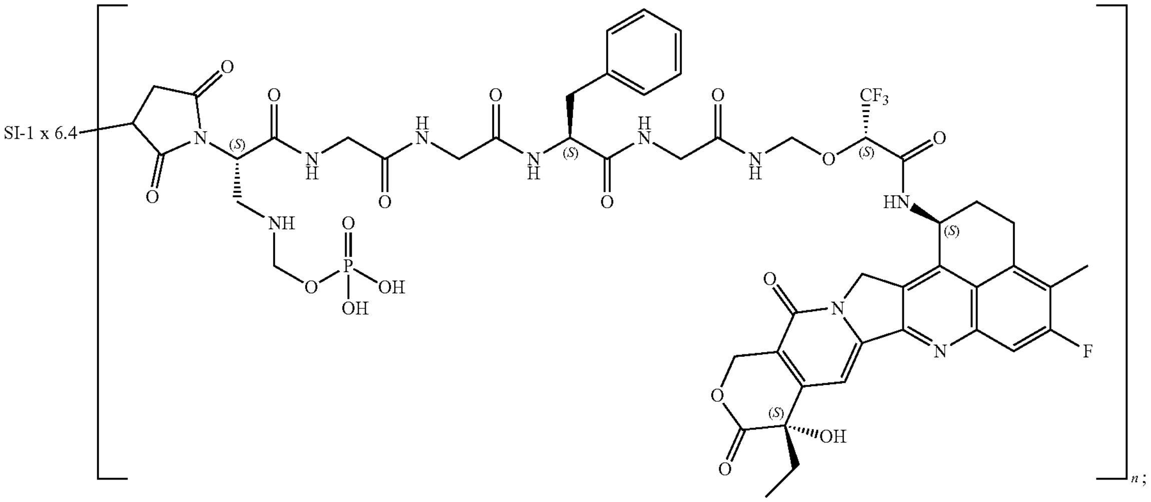
Example 153
ADC-59 was prepared according to the general-purpose coupling method of Example 93,
ADC-59
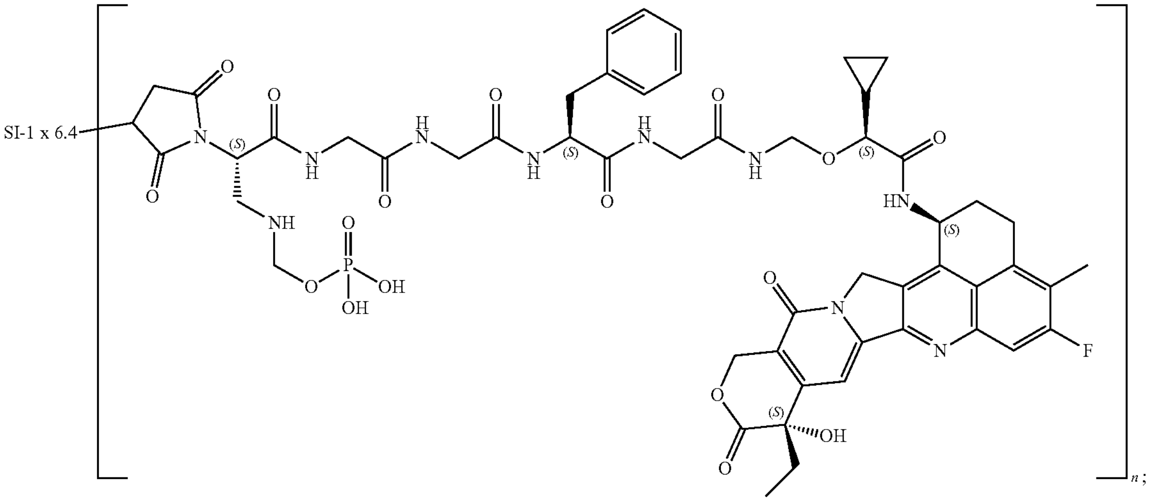
Example 154
ADC-60 was prepared according to the general-purpose coupling method of Example 93, ADC-60
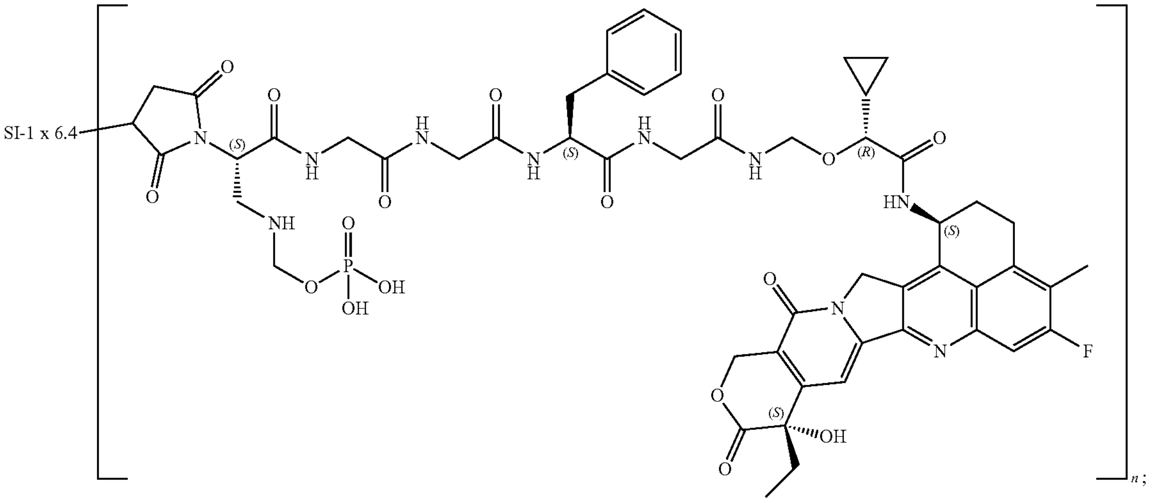
Example 155
ADC-61 was prepared according to the general-purpose coupling method of Example 93,
ADC-61
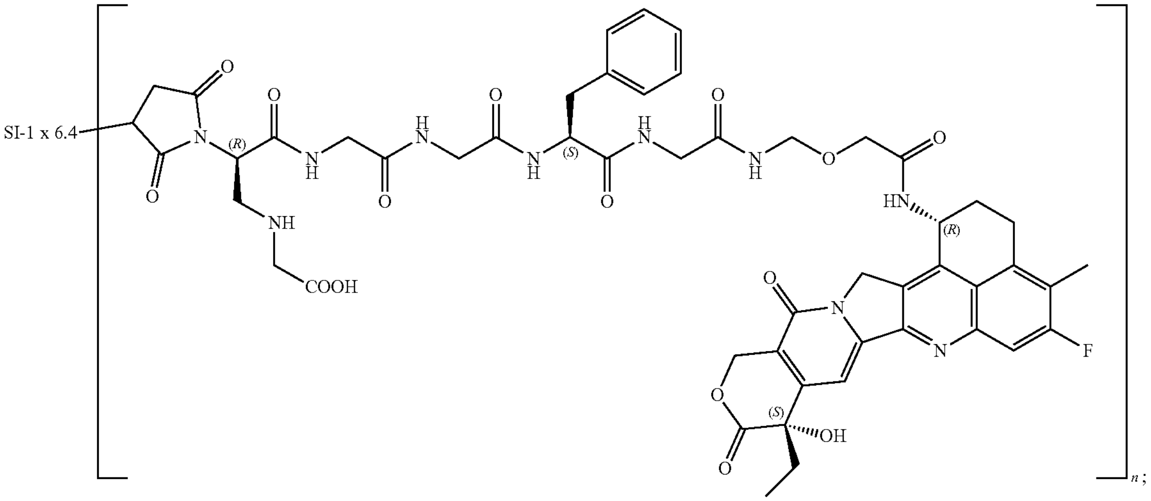
Example 156
ADC-62 was prepared according to the general-purpose coupling method of Example 93, ADC-62
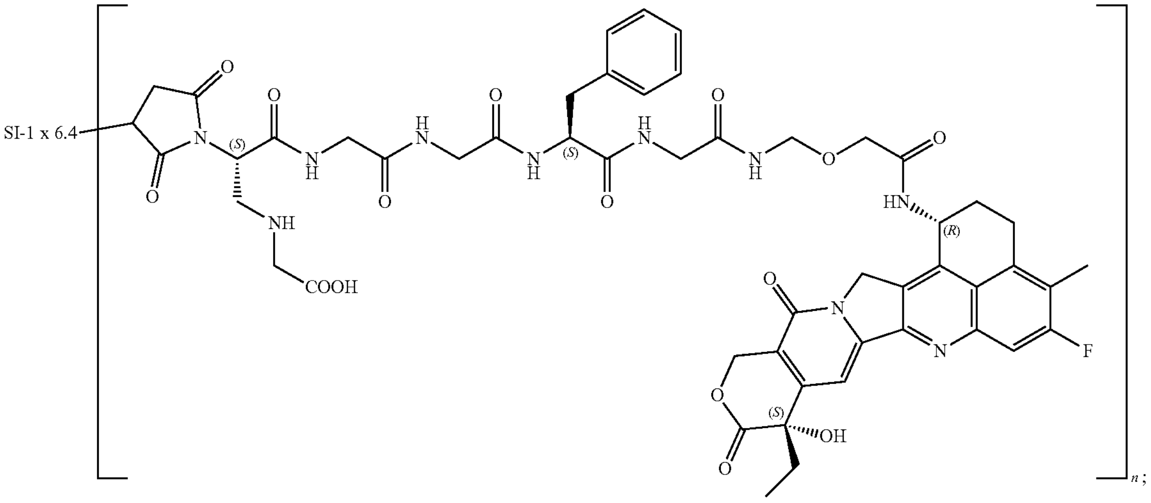
Example 157
ADC-63 was prepared according to the general-purpose coupling method of Example 93,
ADC-63
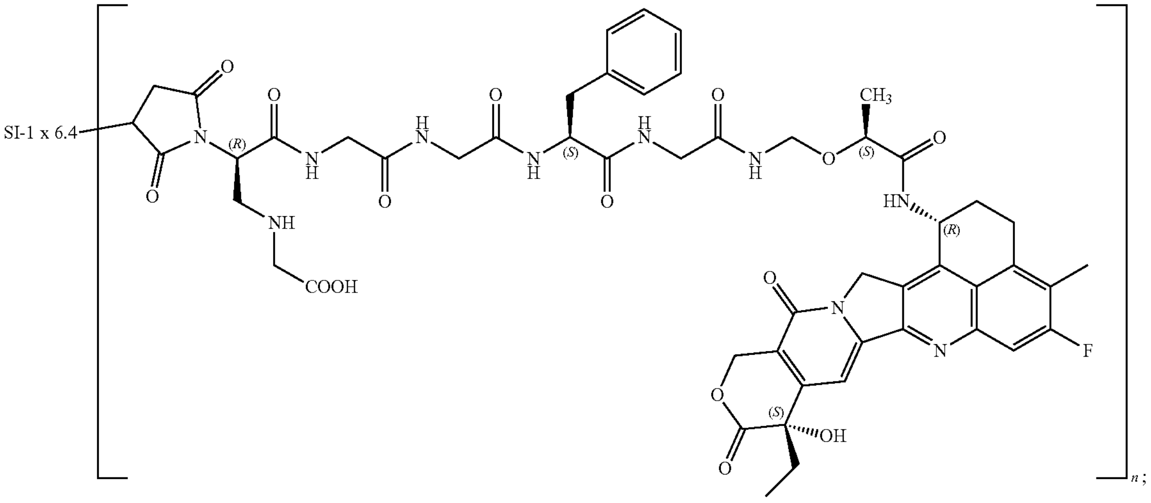
Example 158
ADC-64 was prepared according to the general-purpose coupling method of Example 93, ADC-64
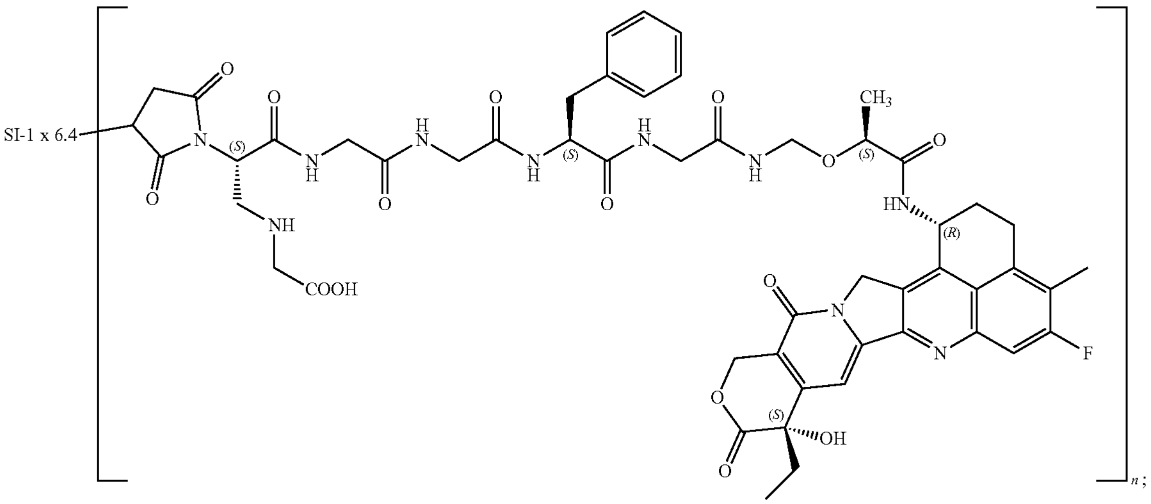
Example 159
ADC-65 was prepared according to the general-purpose coupling method of Example 93,
ADC-65
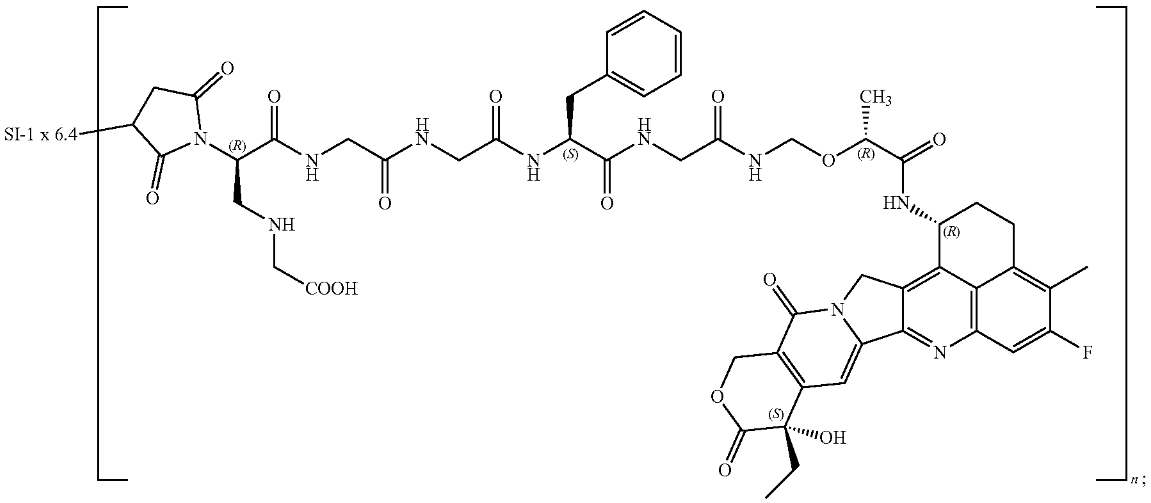
Example 160
ADC-66 was prepared according to the general-purpose coupling method of Example 93, ADC-66
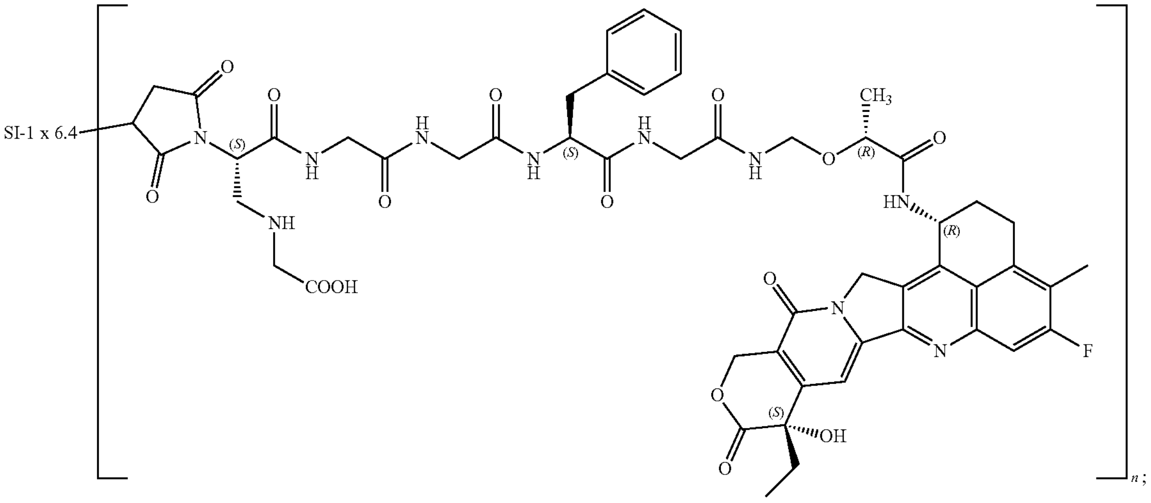
Example 161
ADC-67 was prepared according to the general-purpose coupling method of Example 93,
ADC-67
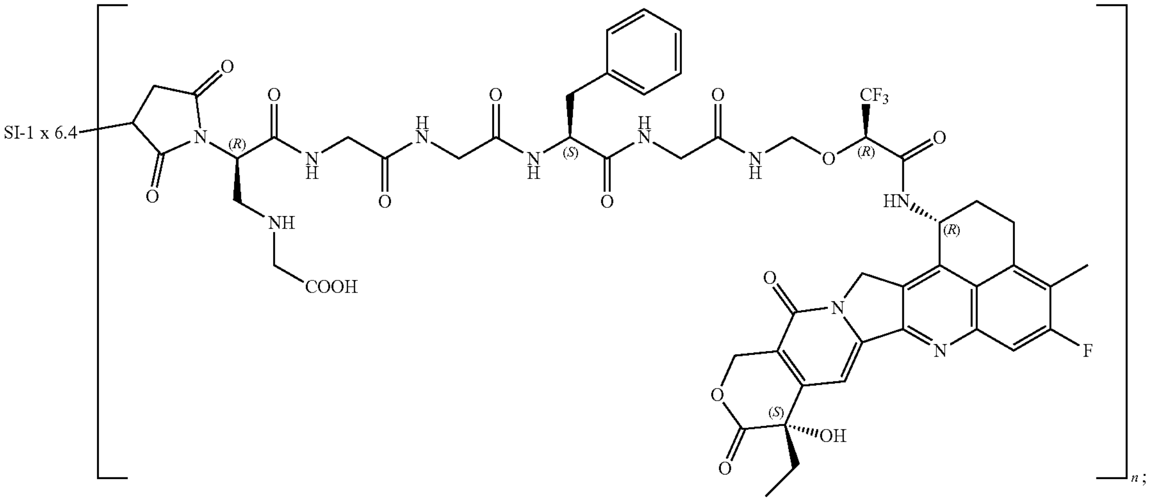
Example 162
ADC-68 was prepared according to the general-purpose coupling method of Example 93, ADC-68
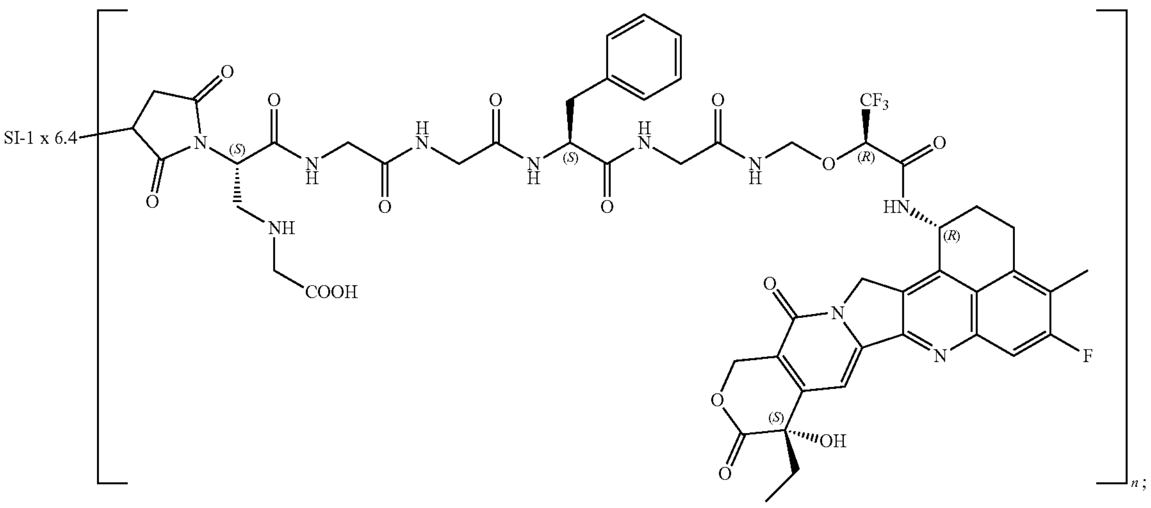
Example 163
ADC-69 was prepared according to the general-purpose coupling method of Example 93,
ADC-69
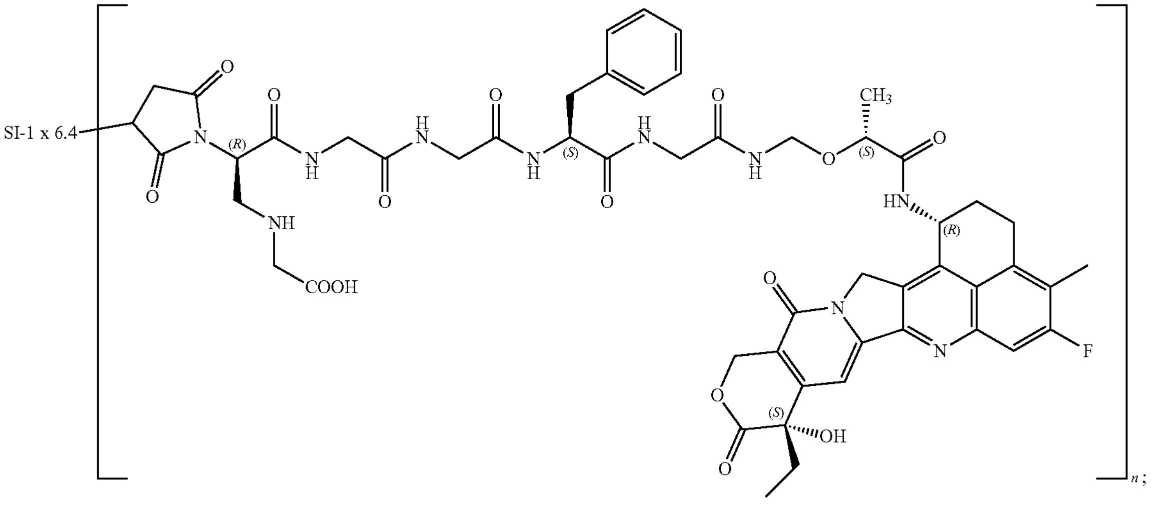
Example 164
ADC-70 was prepared according to the general-purpose coupling method of Example 93, ADC-70
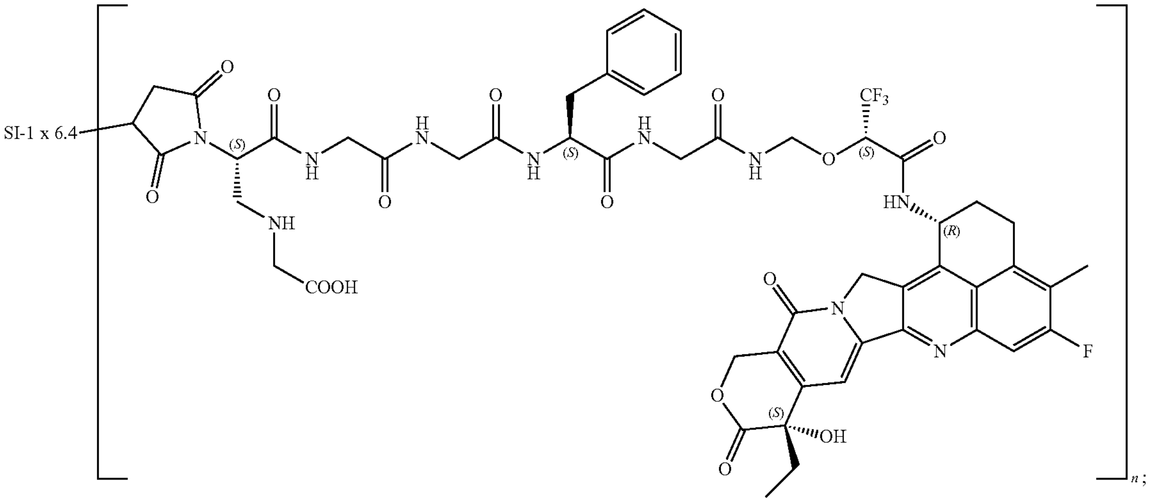
Example 165
ADC-71 was prepared according to the general-purpose coupling method of Example 93,
ADC-71
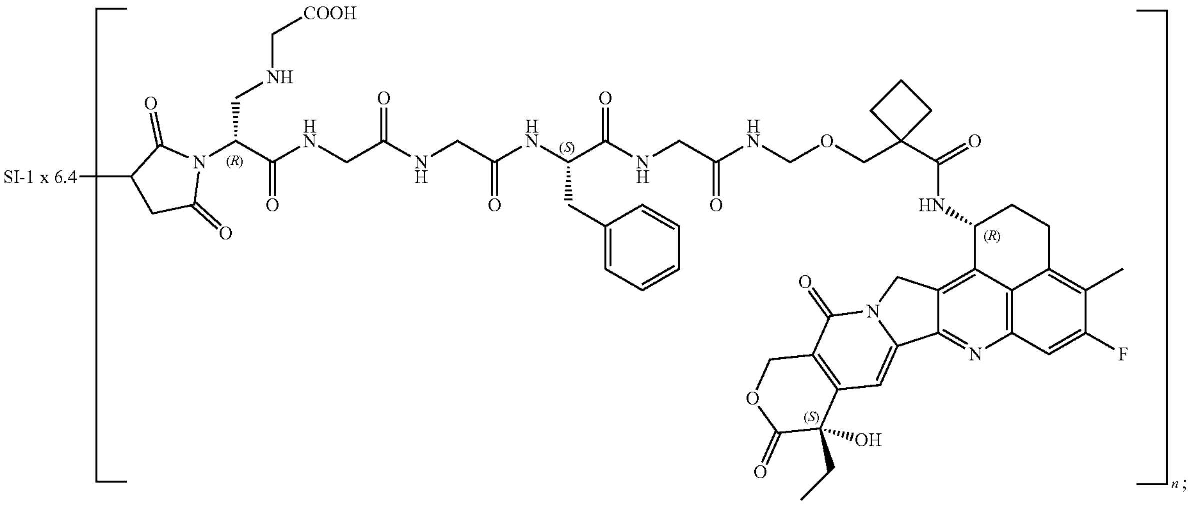
Example 166
ADC-72 was prepared according to the general-purpose coupling method of Example 93, ADC-72
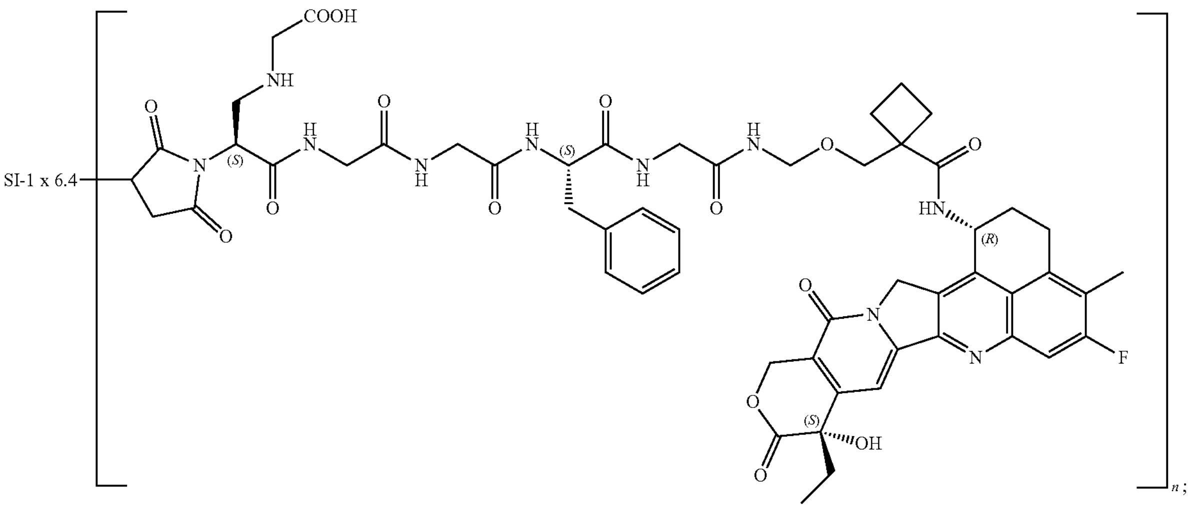
Example 167
ADC-73 was prepared according to the general-purpose coupling method of Example 93,
ADC-73
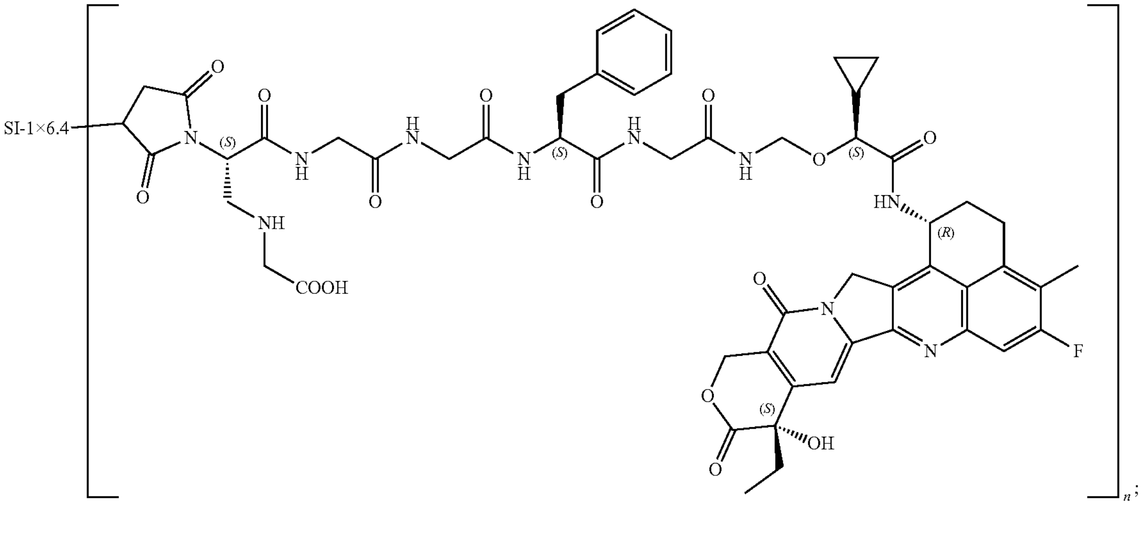
Example 168
ADC-74 was prepared according to the general-purpose coupling method of Example 93, ADC-74
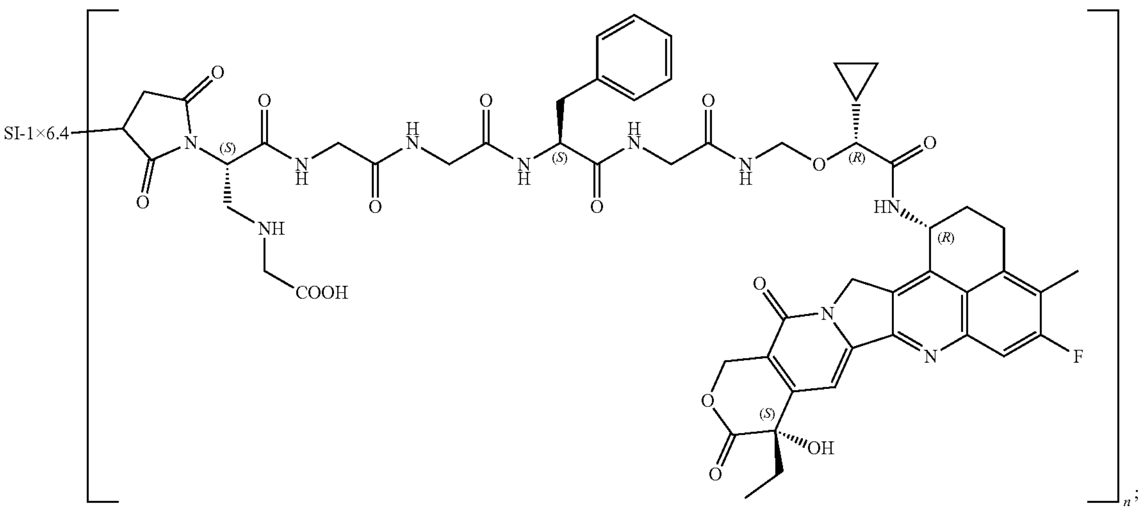
Example 169
ADC-75 was prepared according to the general-purpose coupling method of Example 93,
ADC-75
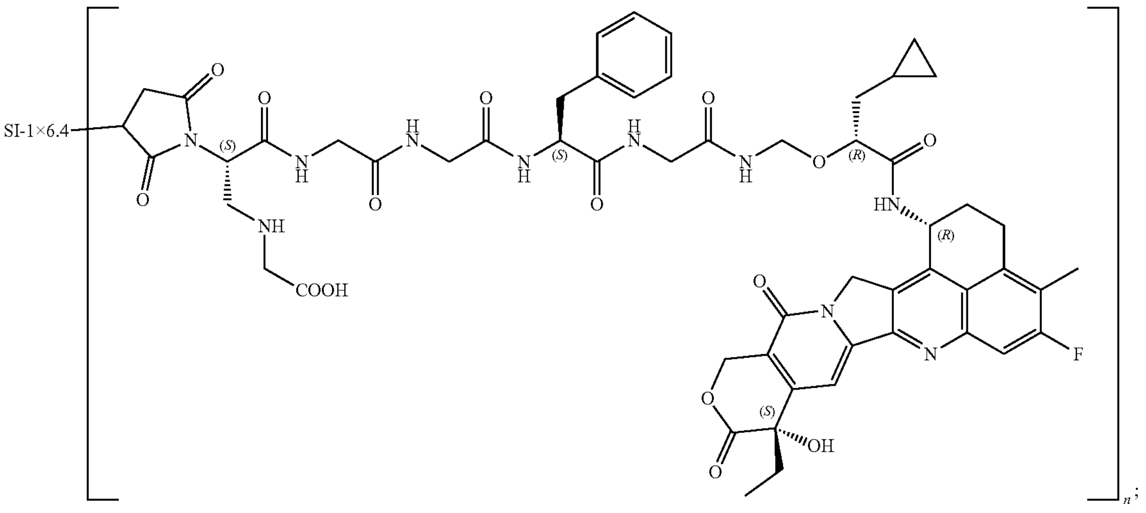
Example 170
ADC-76 was prepared according to the general-purpose coupling method of Example 93, ADC-76
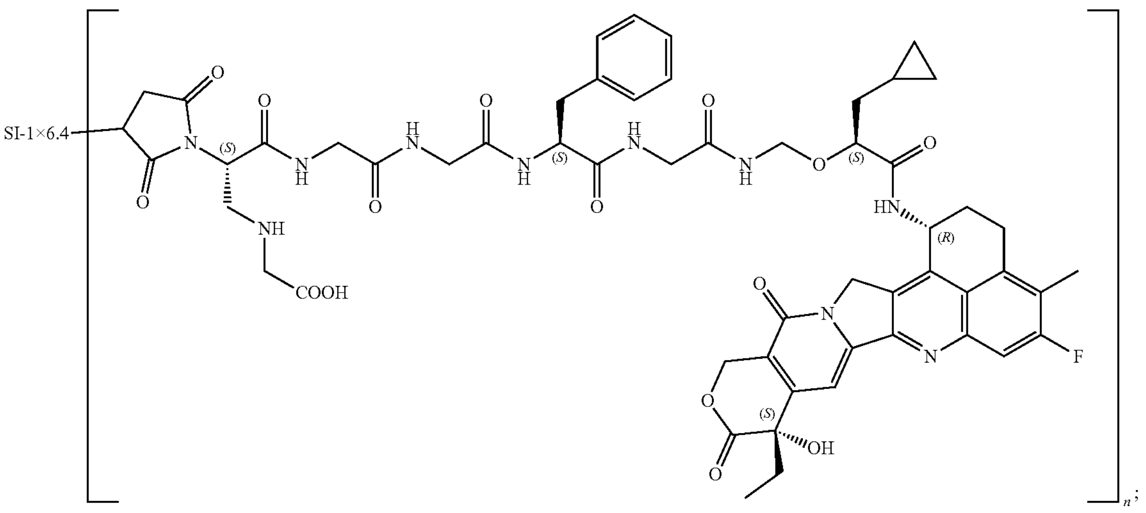
Example 171
ADC-77 was prepared according to the general-purpose coupling method of Example 93,
ADC-77
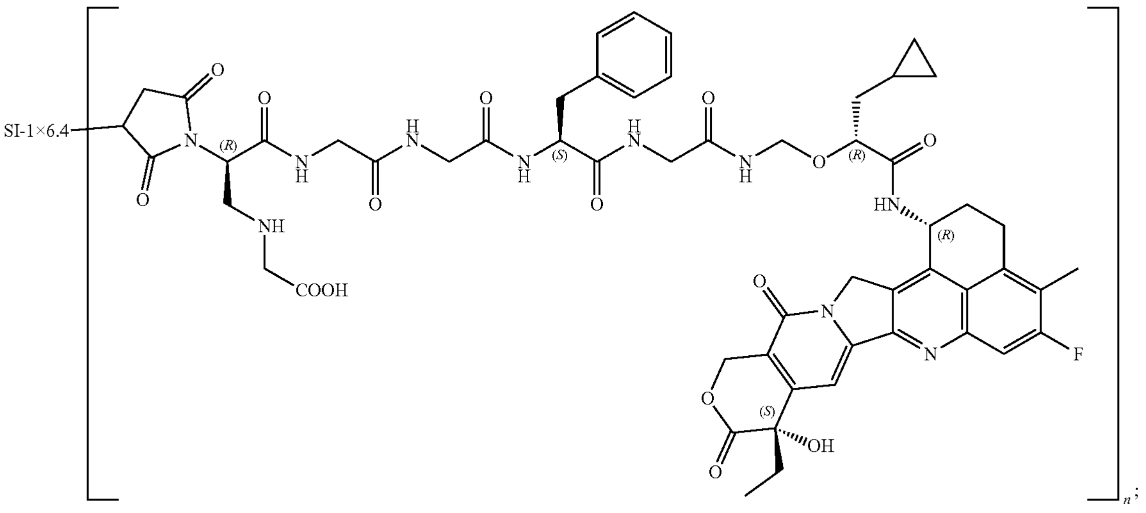
Example 172
ADC-78 was prepared according to the general-purpose coupling method of Example 93, ADC-78
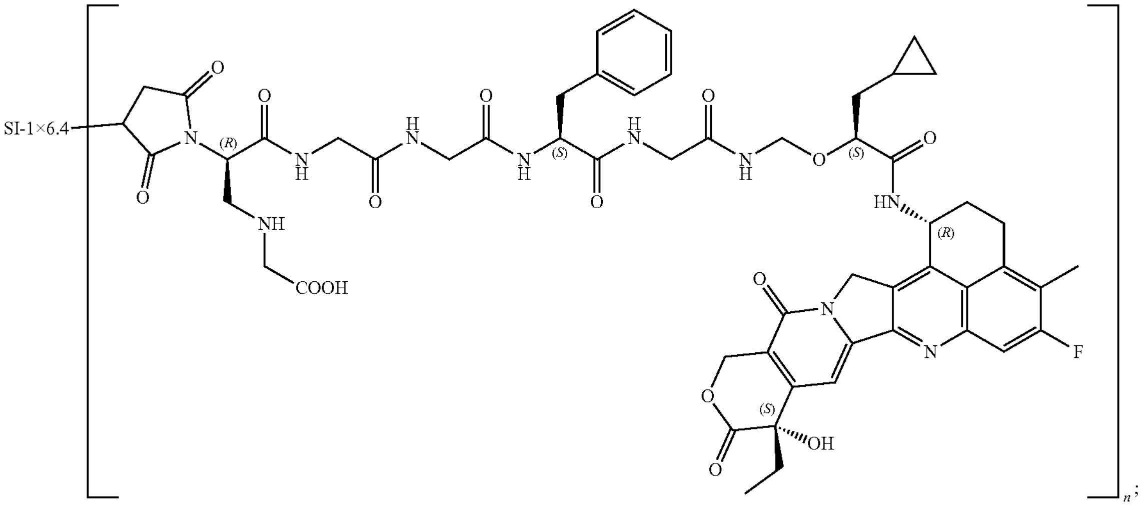
Example 173
ADC-79 was prepared according to the general-purpose coupling method of Example 93,
ADC-79
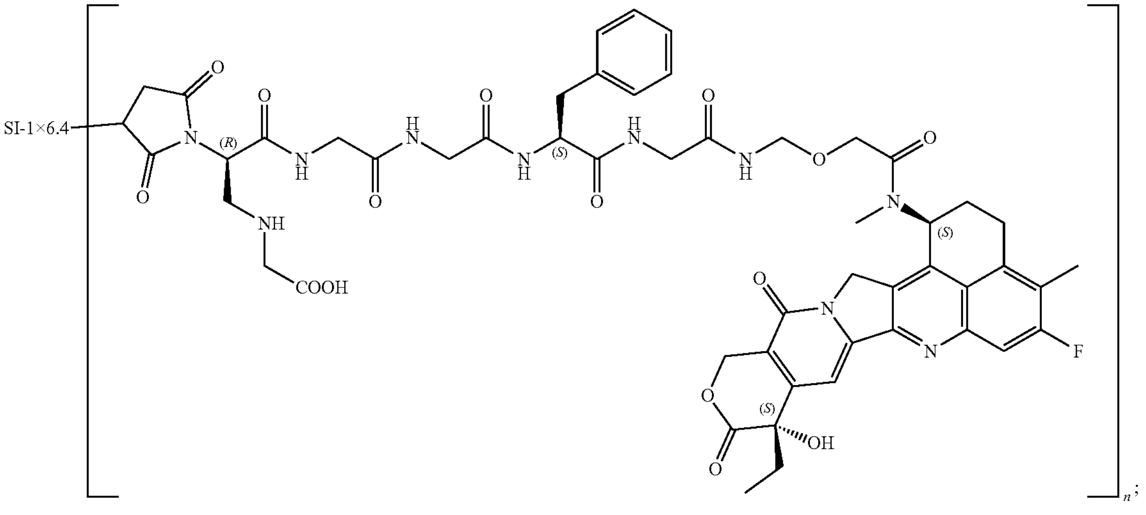
Example 174
ADC-80 was prepared according to the general-purpose coupling method of Example 93, ADC-80
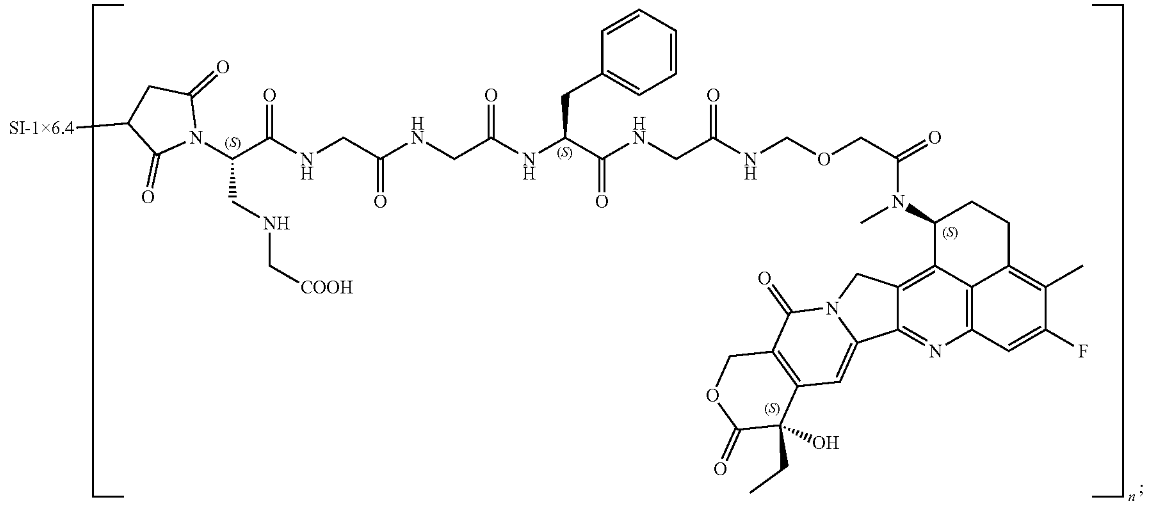
Example 175
ADC-81 was prepared according to the general-purpose coupling method of Example 93,
ADC-81
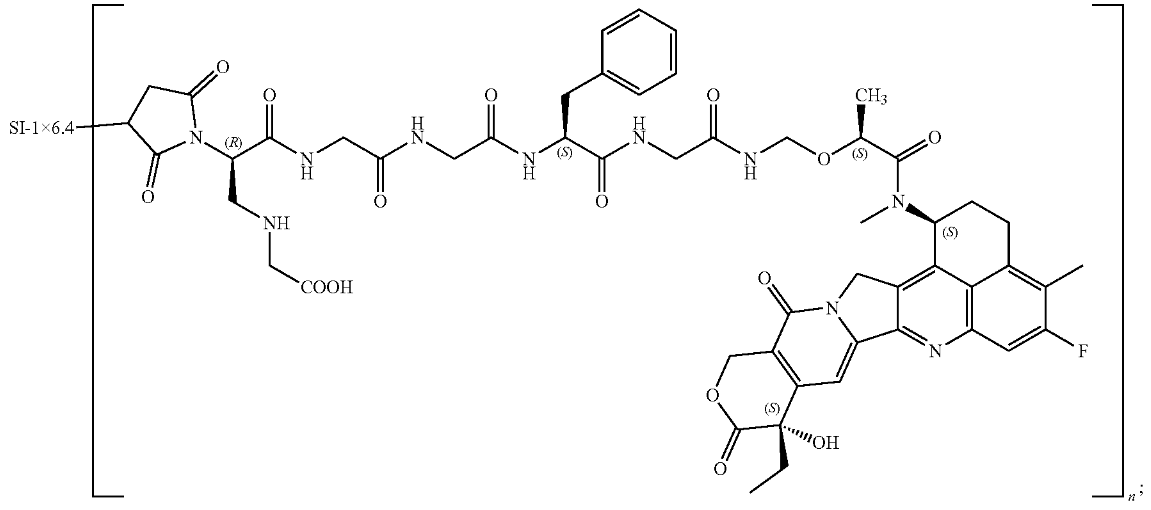
Example 176
ADC-82 was prepared according to the general-purpose coupling method of Example 93, ADC-82
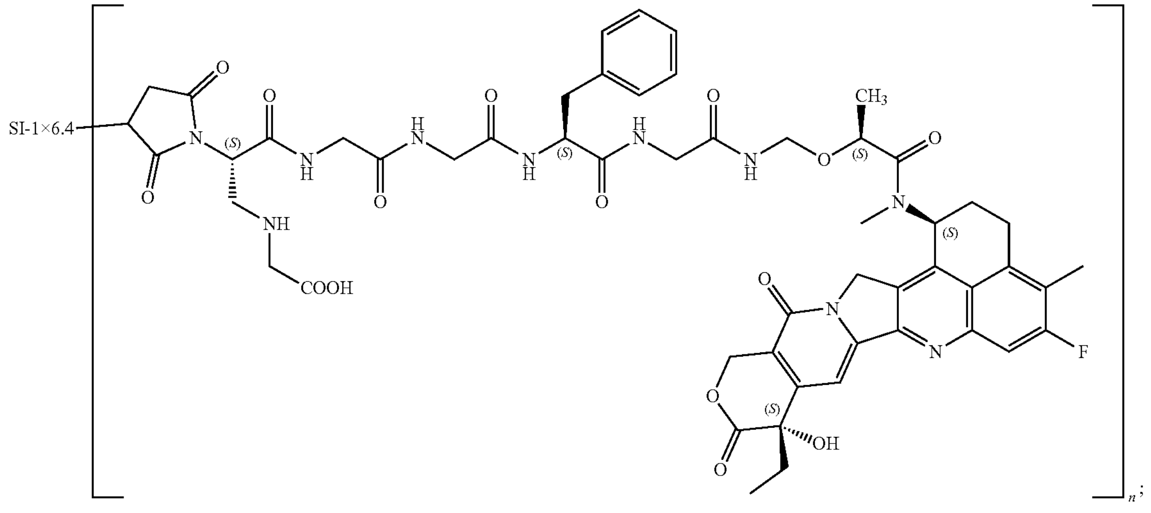
Example 177
ADC-83 was prepared according to the general-purpose coupling method of Example 93,
ADC-83
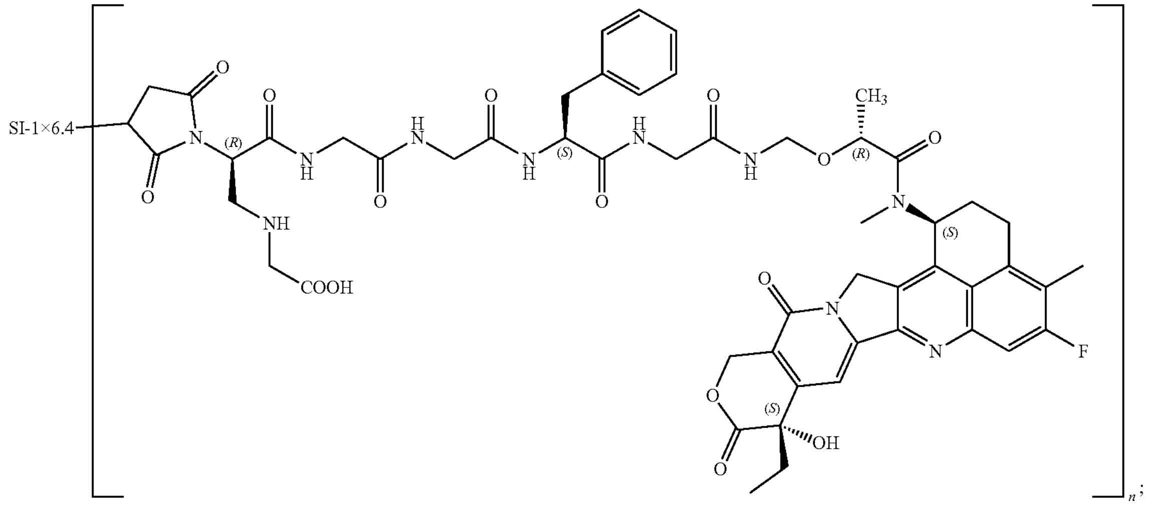
Example 178
ADC-84 was prepared according to the general-purpose coupling method of Example 93, ADC-84
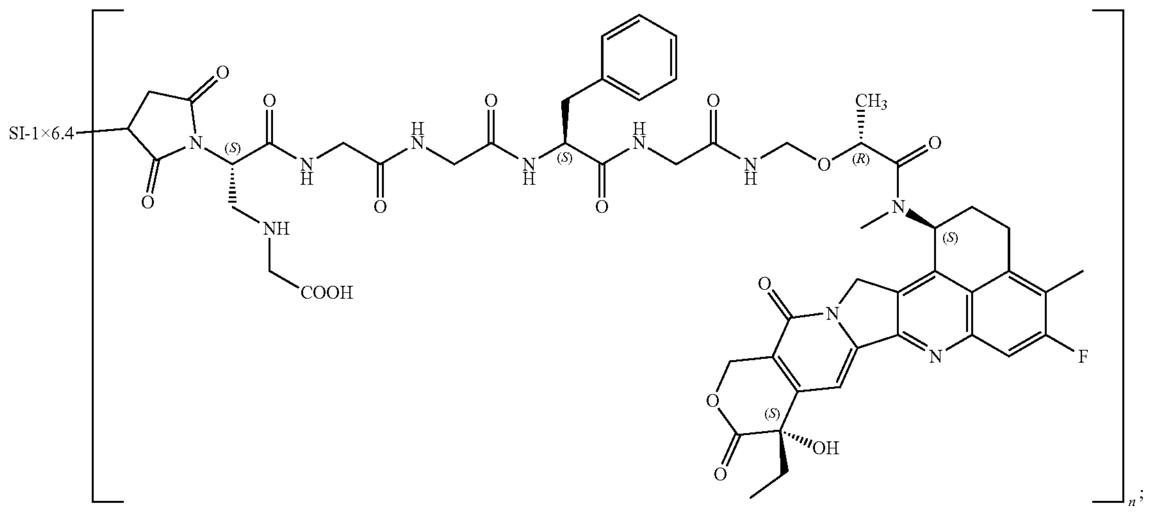
Example 179
ADC-85 was prepared according to the general-purpose coupling method of Example 93,
ADC-85
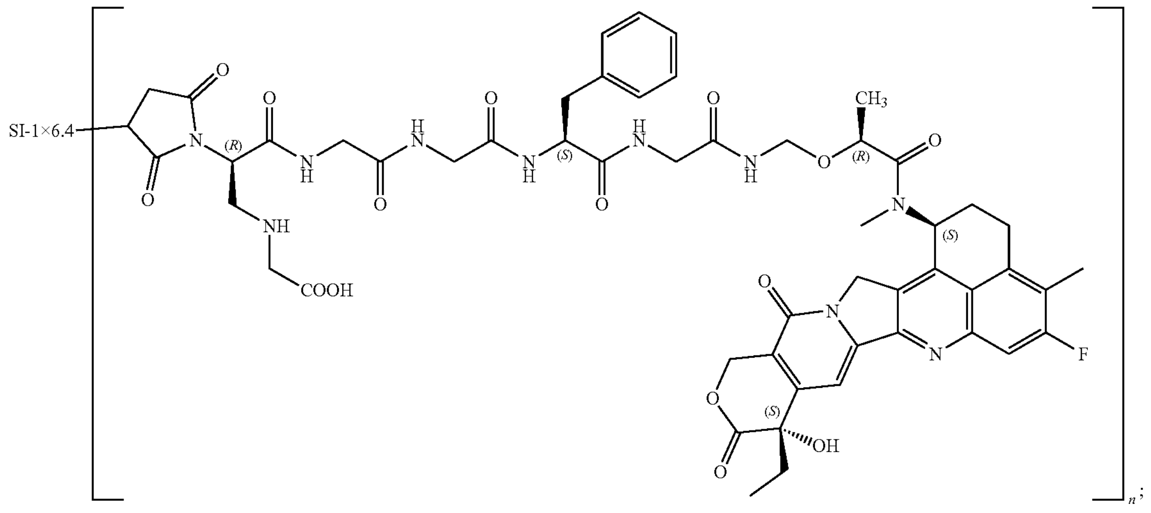
Example 180
ADC-86 was prepared according to the general-purpose coupling method of Example 93, ADC-86
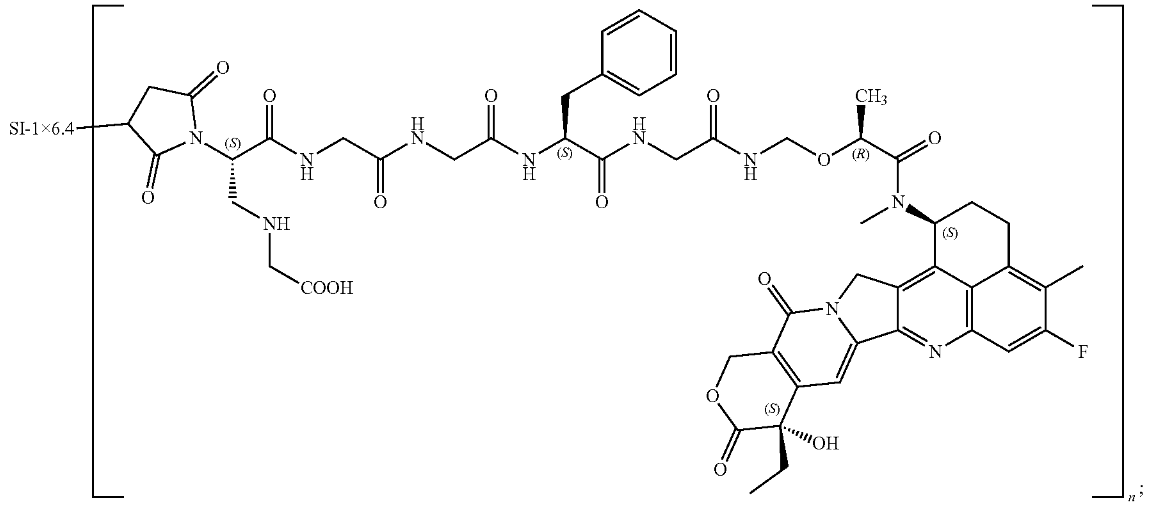
Example 181
ADC-87 was prepared according to the general-purpose coupling method of Example 93,
ADC-87
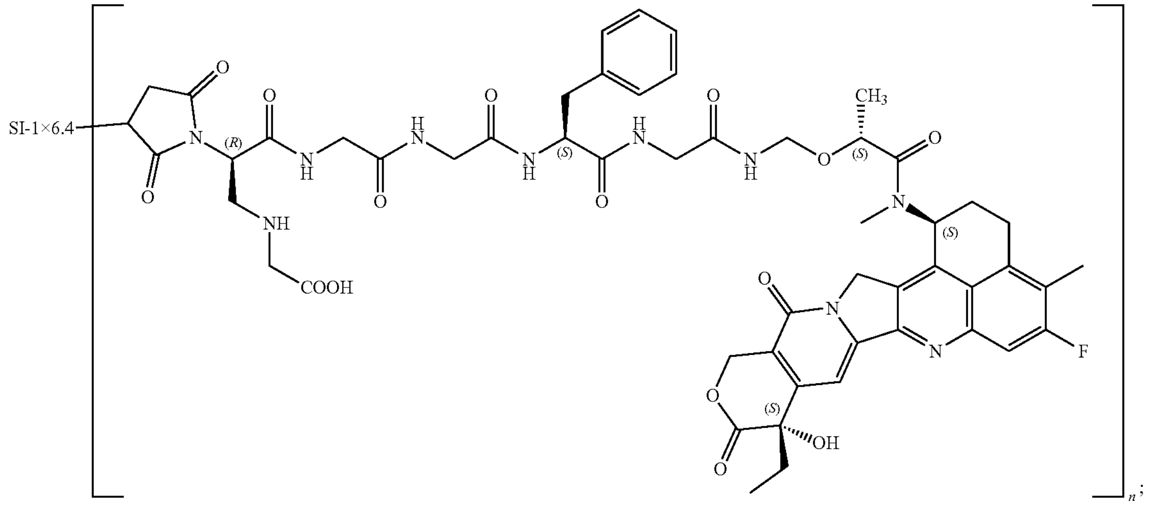
Example 182
ADC-88 was prepared according to the general-purpose coupling method of Example 93, ADC-88
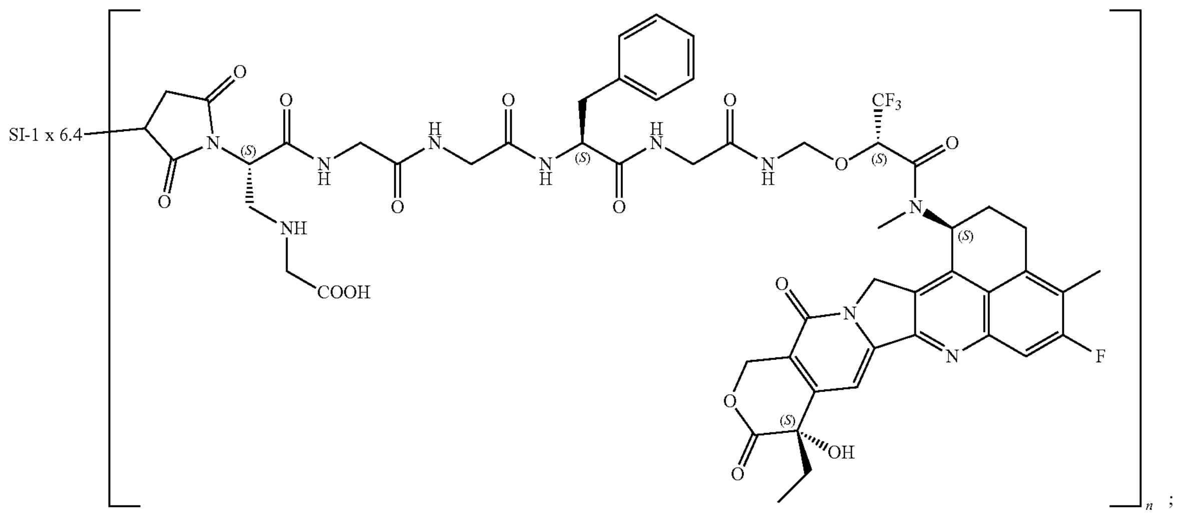
Example 183
ADC-89 was prepared according to the general-purpose coupling method of Example 93,
ADC-89
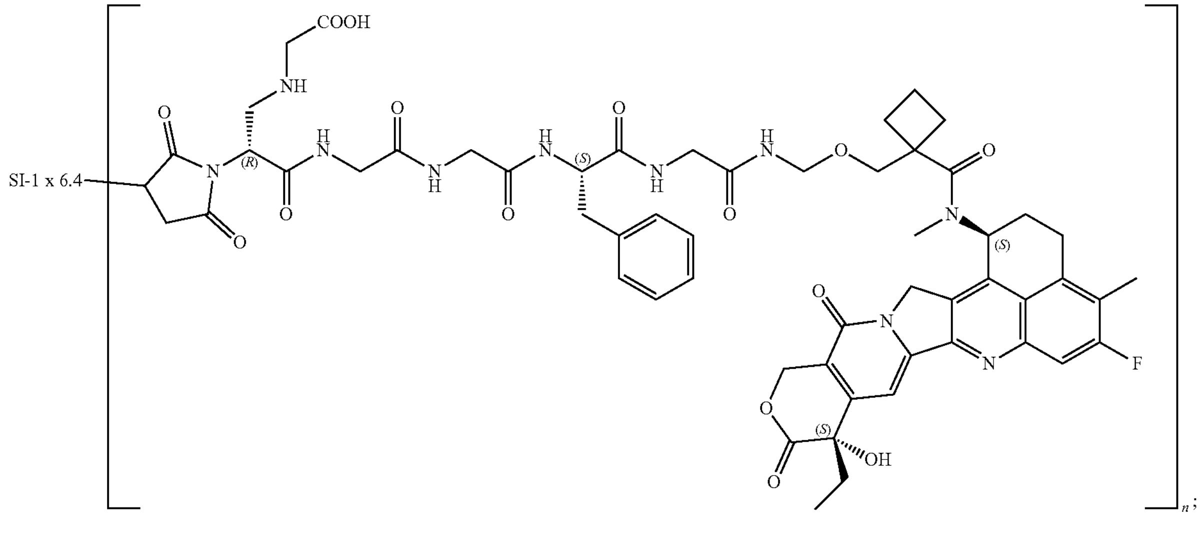
Example 184
ADC-90 was prepared according to the general-purpose coupling method of Example 93, ADC-90
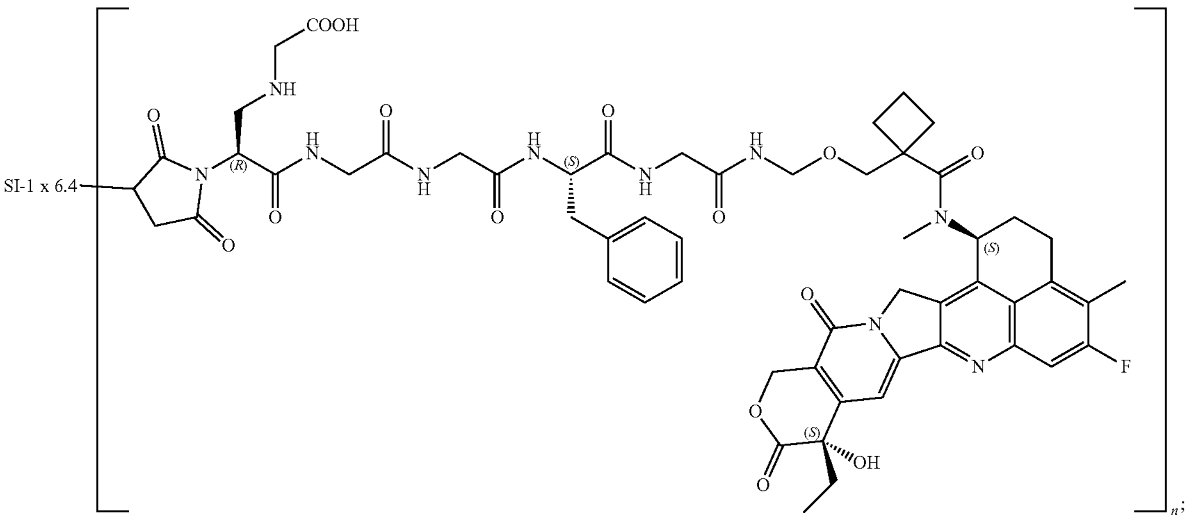
Example 185
ADC-91 was prepared according to the general-purpose coupling method of Example 93,
ADC-91
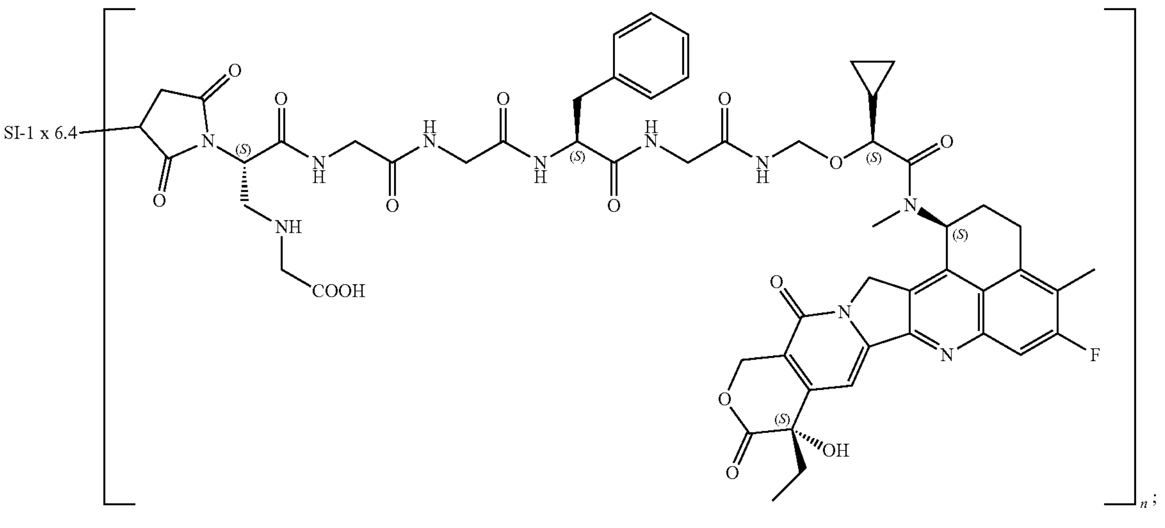
Example 186
ADC-92 was prepared according to the general-purpose coupling method of Example 93, ADC-92
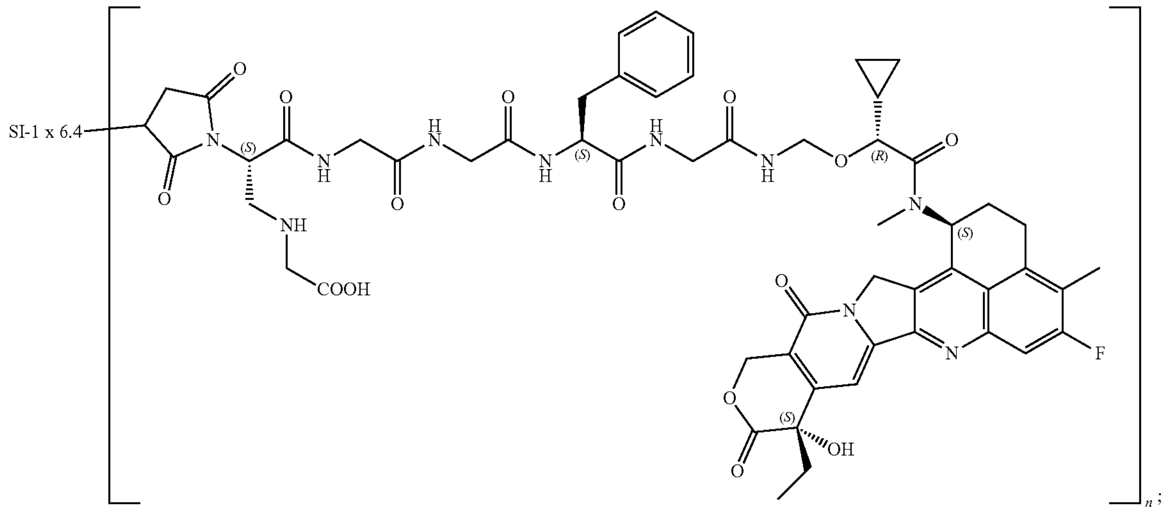
Example 187
ADC-93 was prepared according to the general-purpose coupling method of Example 93,
ADC-93
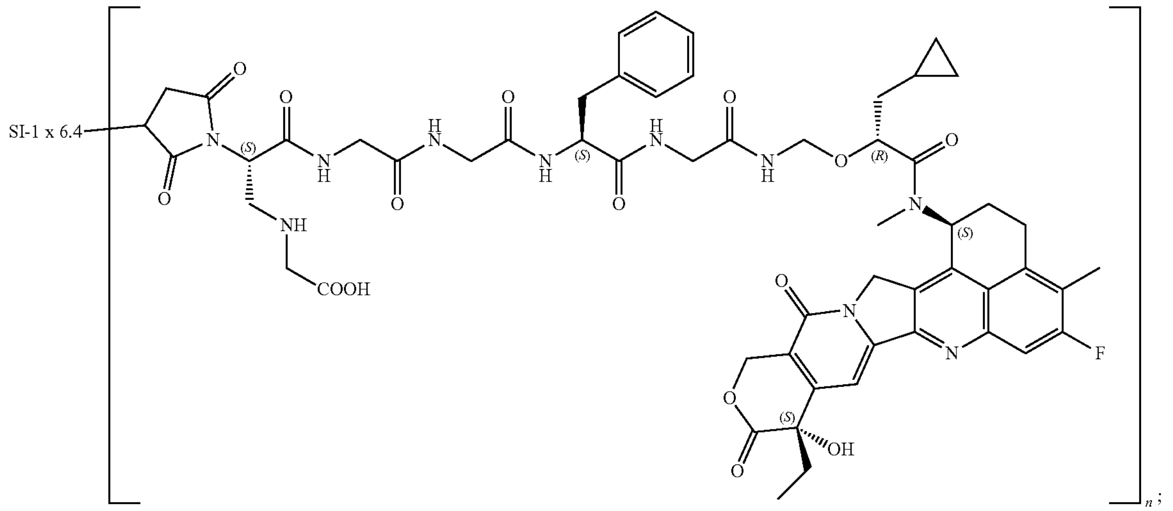
Example 188
ADC-94 was prepared according to the general-purpose coupling method of Example 93, ADC-94
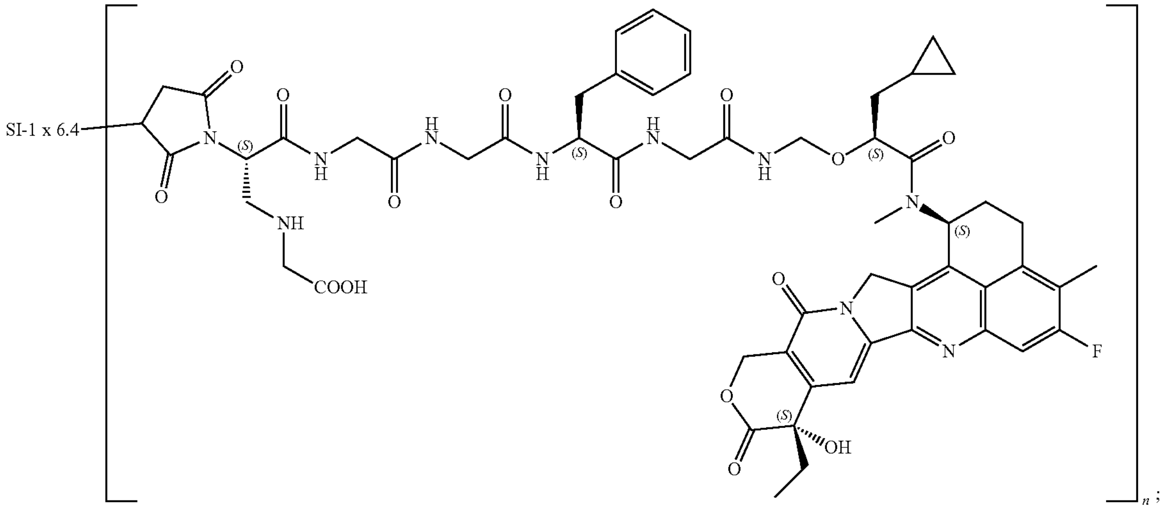
Example 189
ADC-95 was prepared according to the general-purpose coupling method of Example 93,
ADC-95
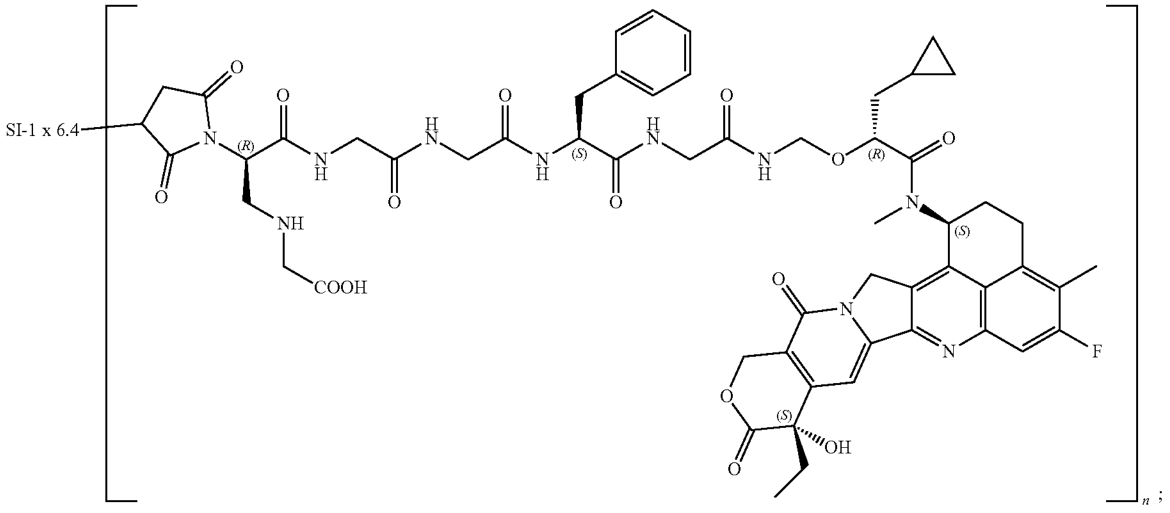
Example 190
ADC-96 was prepared according to the general-purpose coupling method of Example 93, ADC-96
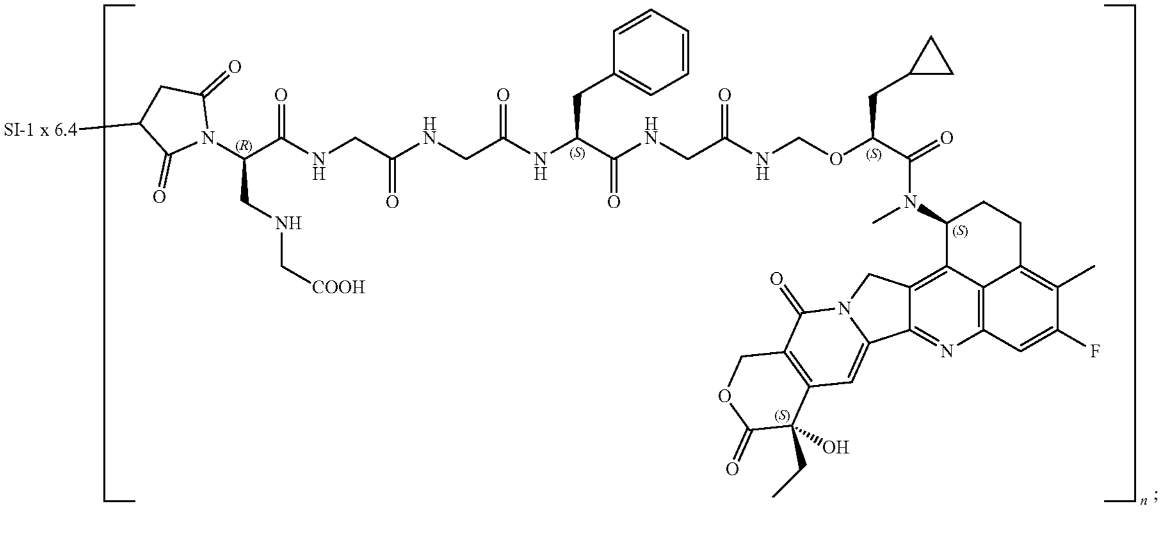
Example 191
ADC-97 was prepared according to the general-purpose coupling method of Example 93,
ADC-97
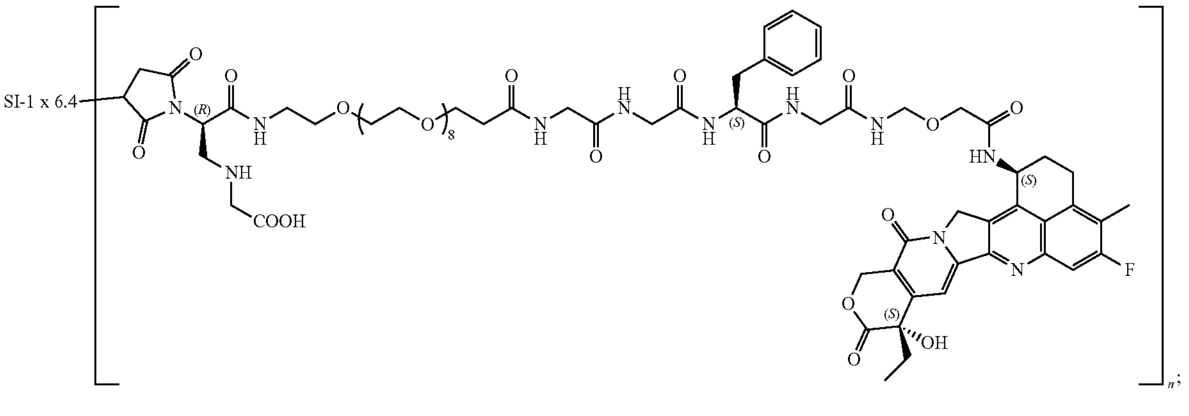
Example 192
ADC-98 was prepared according to the general-purpose coupling method of Example 93, ADC-98
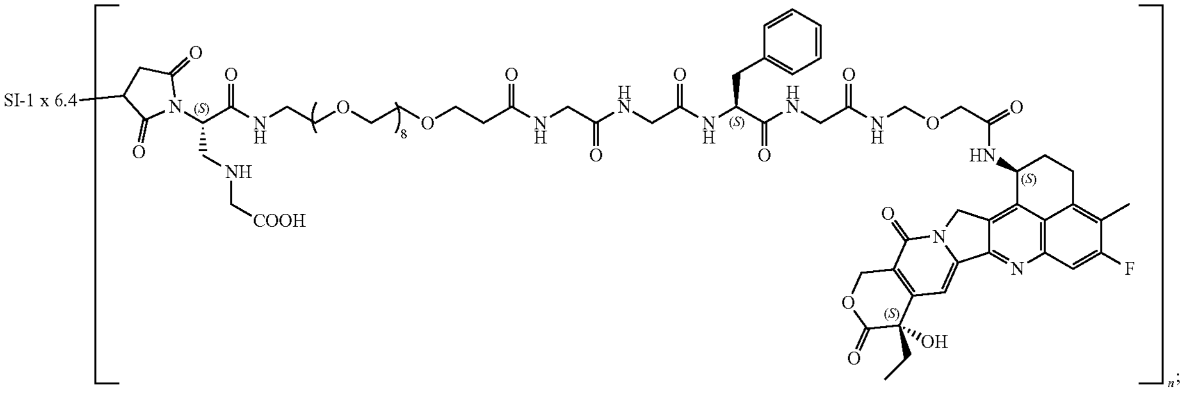
Example 193
ADC-99 was prepared according to the general-purpose coupling method of Example 93,
ADC-99
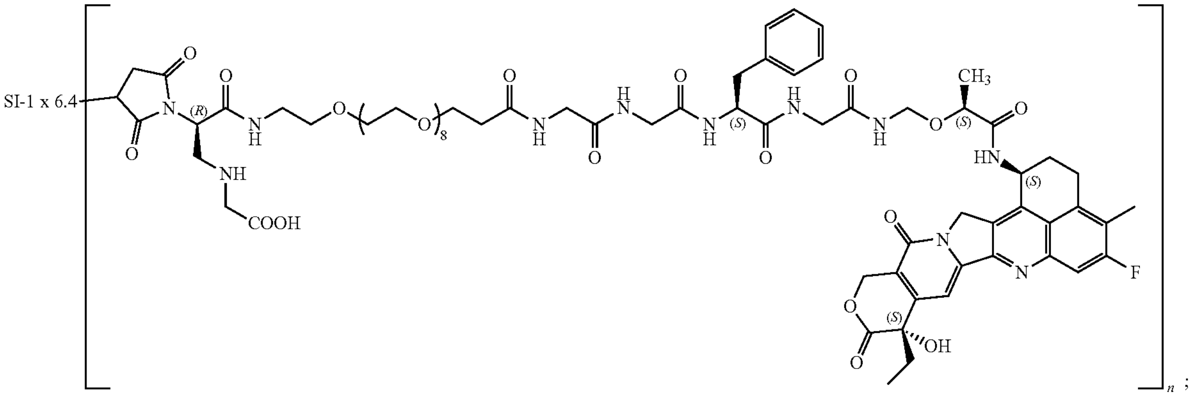
Example 194
ADC-100 was prepared according to the general-purpose coupling method of Example 93, ADC-100
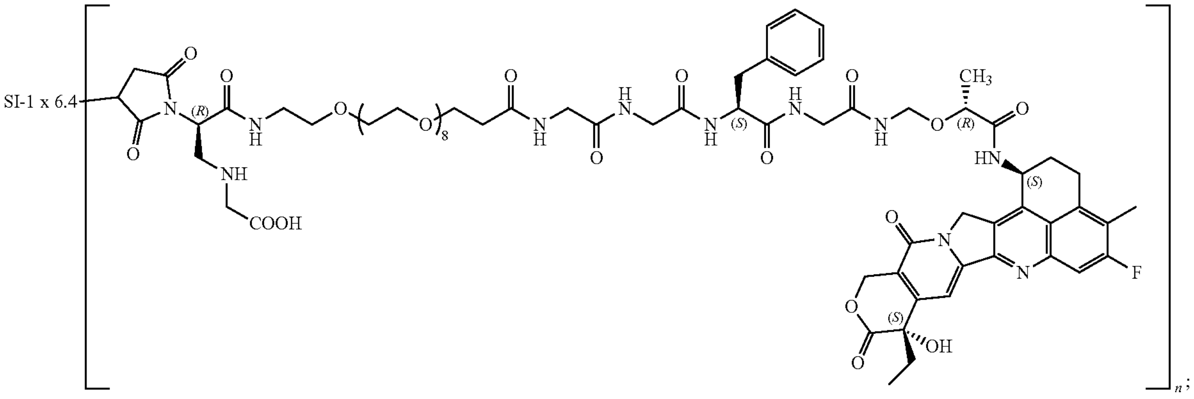
Example 195
ADC-101 was prepared according to the general-purpose coupling method of Example 93,
ADC-101
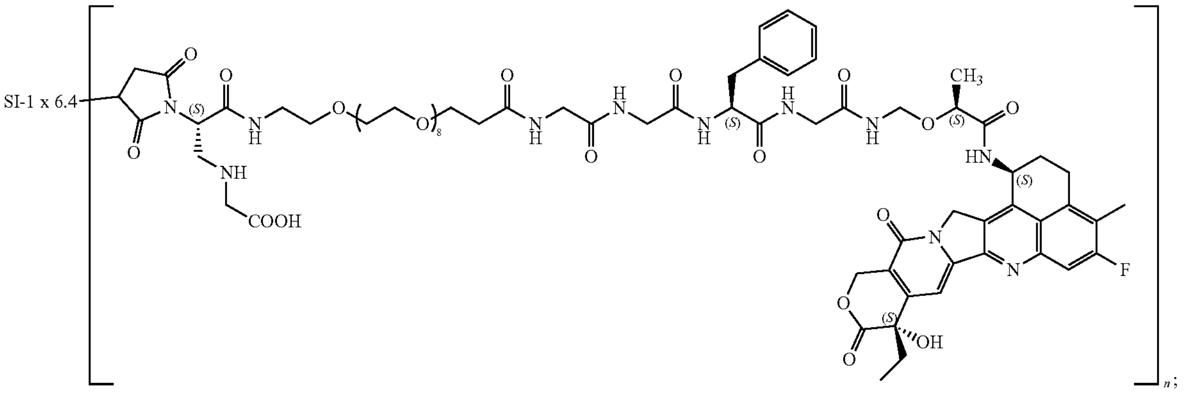
Example 196
ADC-102 was prepared according to the general-purpose coupling method of Example 93, ADC-102
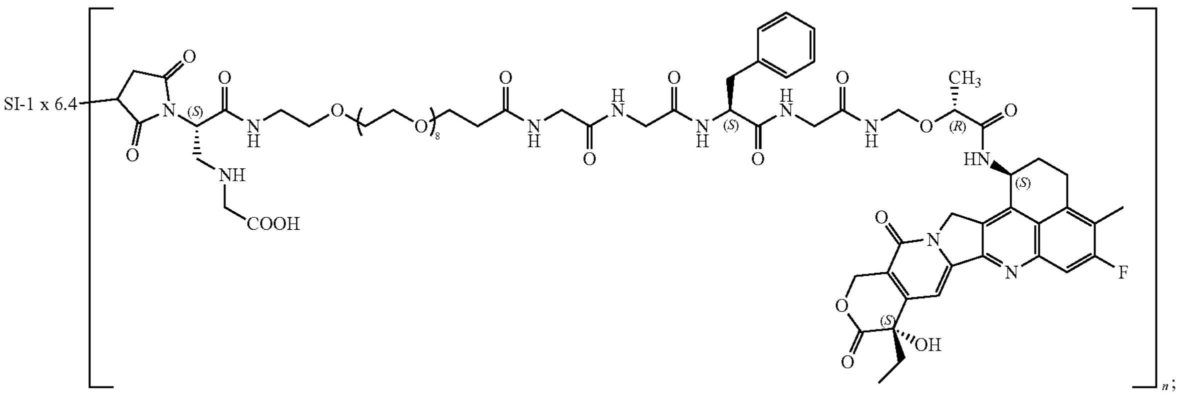
Example 197
ADC-103 was prepared according to the general-purpose coupling method of Example 93,
ADC-103
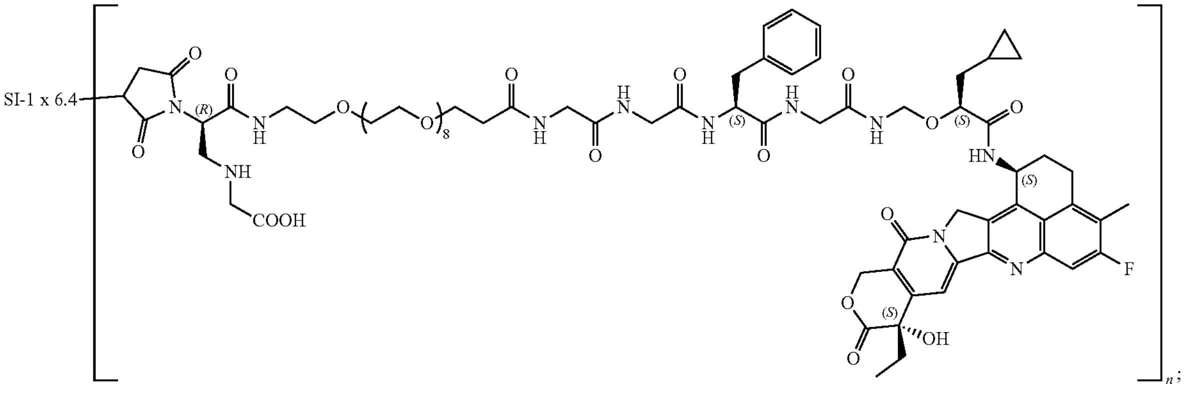
Example 198
ADC-104 was prepared according to the general-purpose coupling method of Example 93, ADC-104
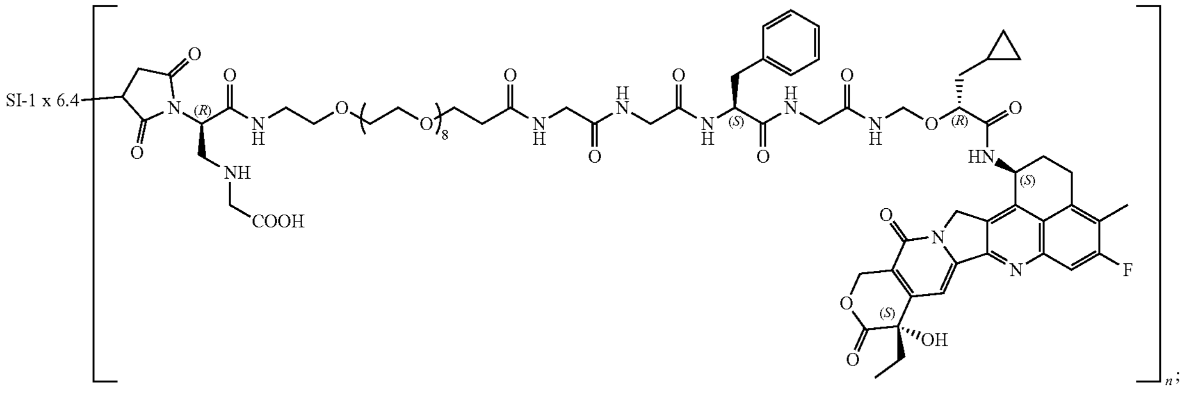
Example 199
ADC-105 was prepared according to the general-purpose coupling method of Example 93,
ADC-105
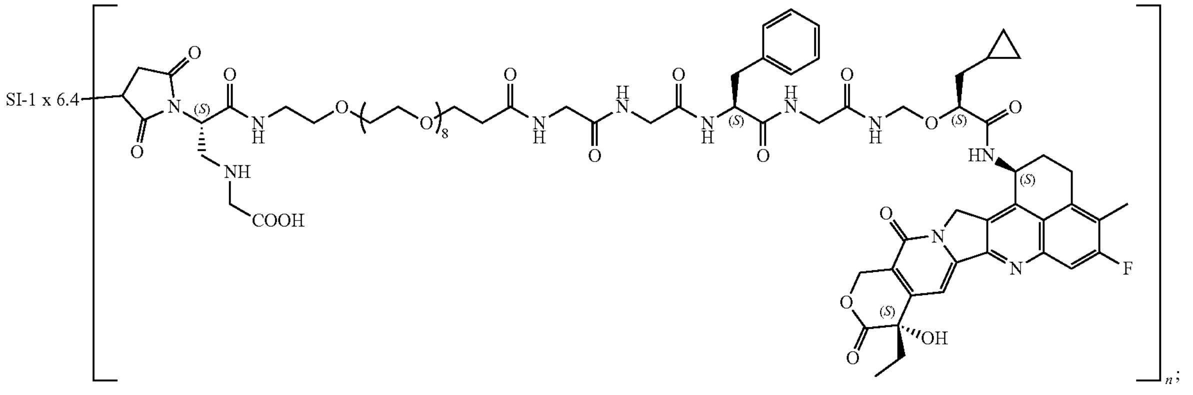
Example 200
ADC-106 was prepared according to the general-purpose coupling method of Example 93,
ADC-106
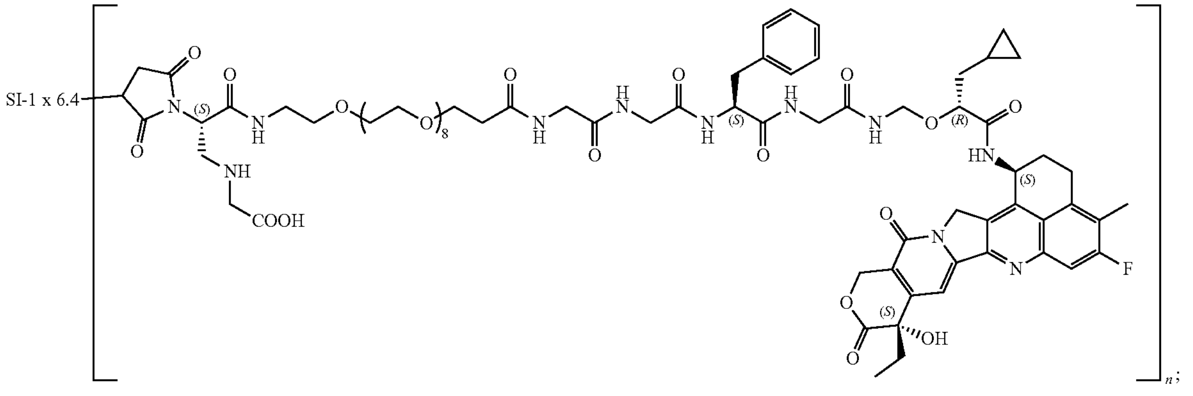

Example 201
ADC-DS was prepared from compound 45 according to the general-purpose coupling method of Example 93,
ADC-DS
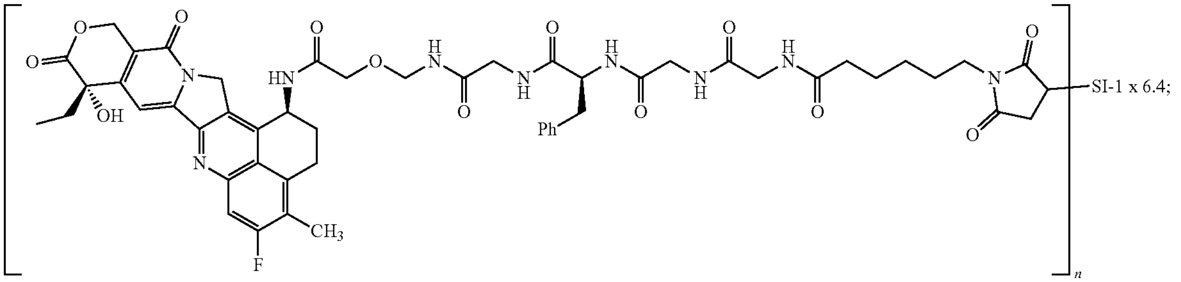
Example 202
ADC-107 was prepared according to the general-purpose coupling method of Example 94,
ADC-107
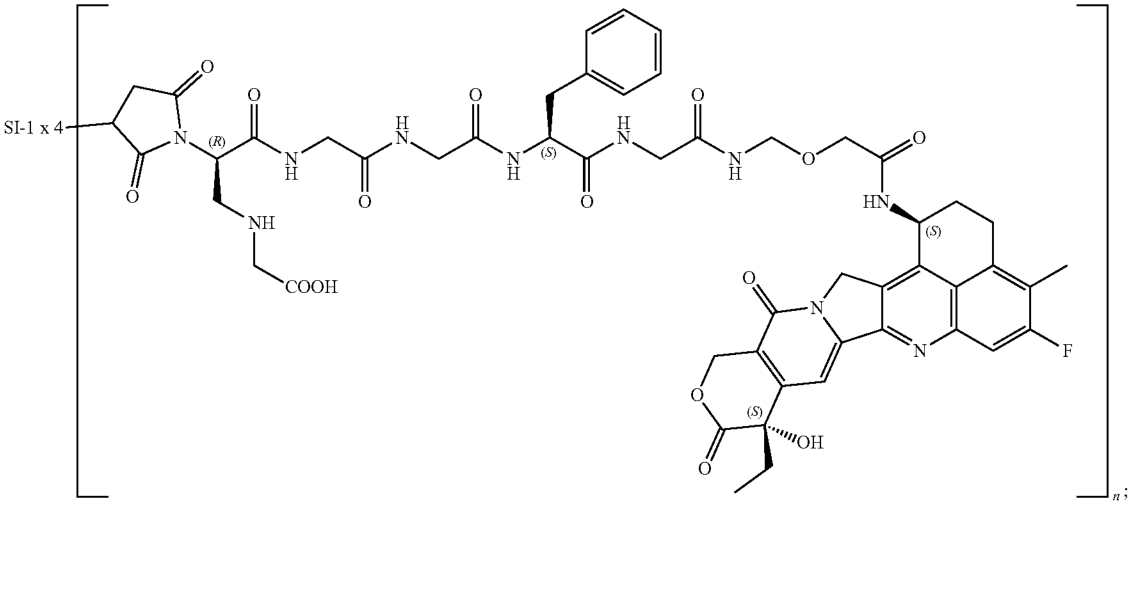
Example 203
ADC-108 was prepared according to the general-purpose coupling method of Example 94, ADC-108
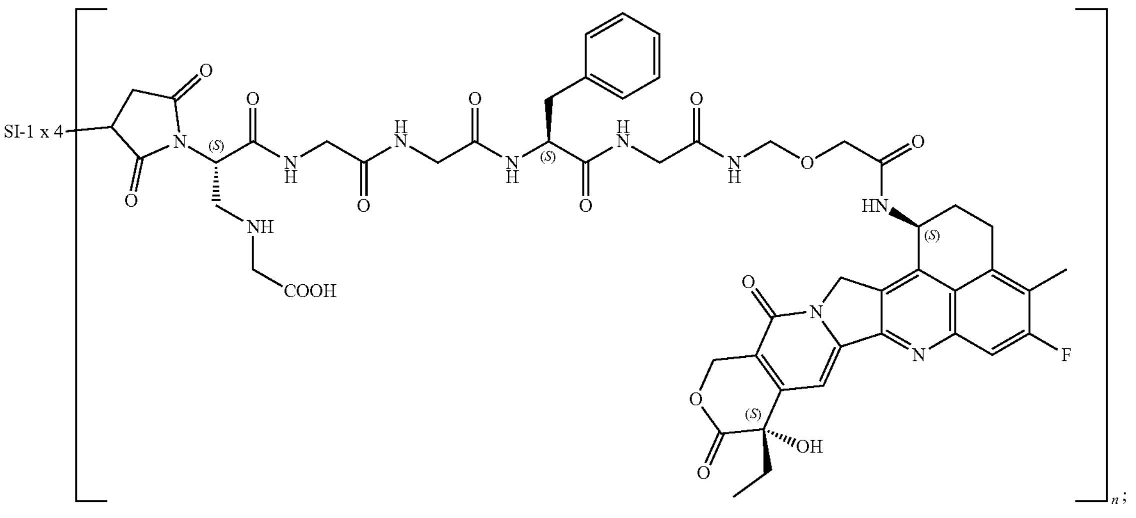
Example 204
ADC-109 was prepared according to the general-purpose coupling method of Example 94,
ADC-109
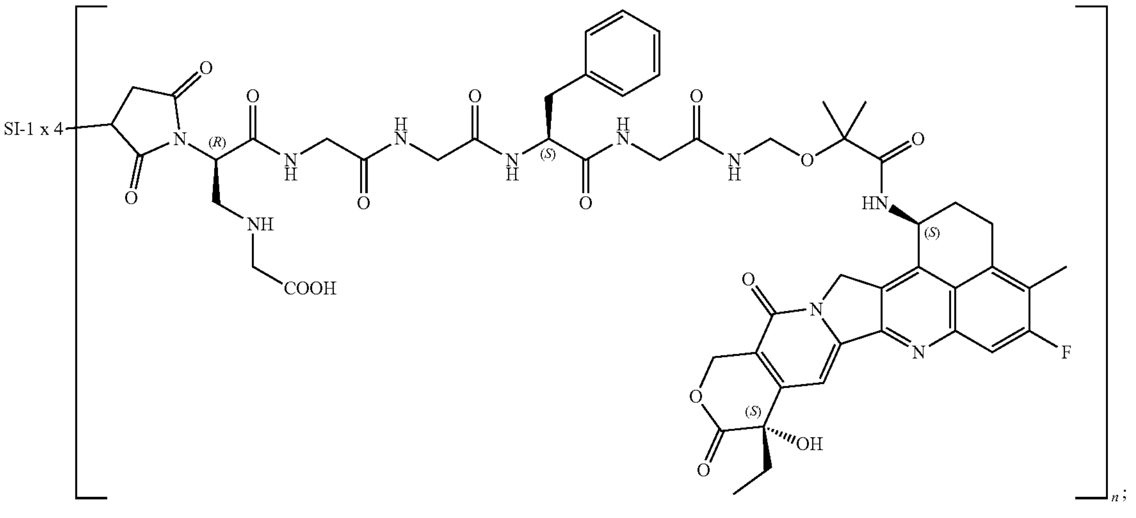
Example 205
ADC-110 was prepared according to the general-purpose coupling method of Example 94, ADC-110
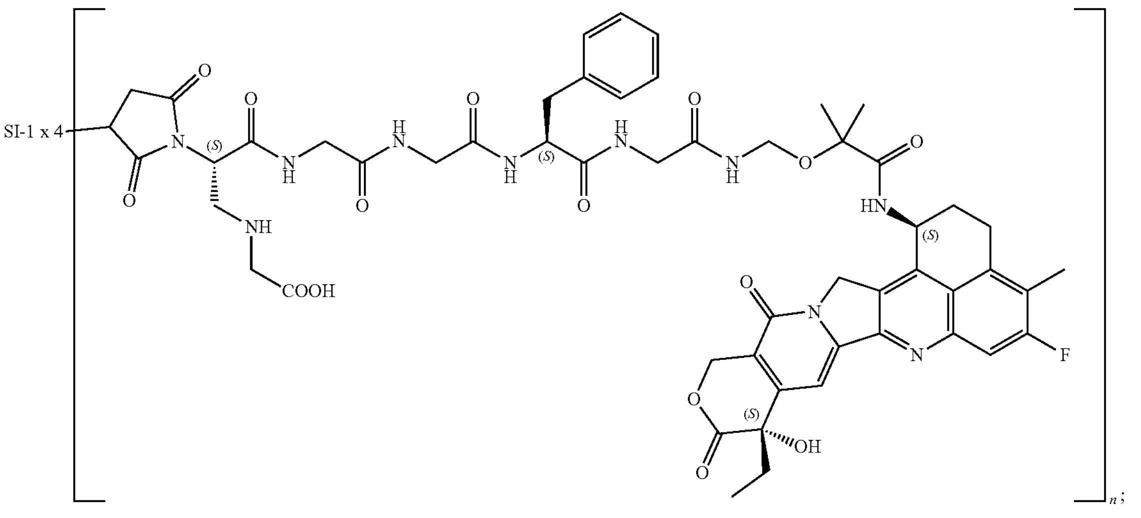
Example 206
ADC-111 was prepared according to the general-purpose coupling method of Example 94,
ADC-111
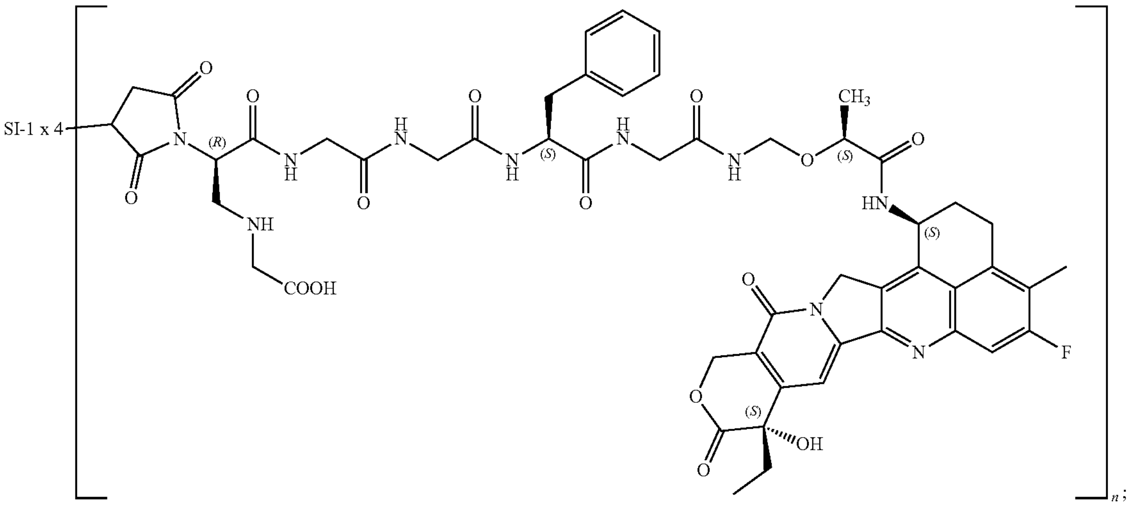
Example 207
ADC-112 was prepared according to the general-purpose coupling method of Example 94, ADC-112
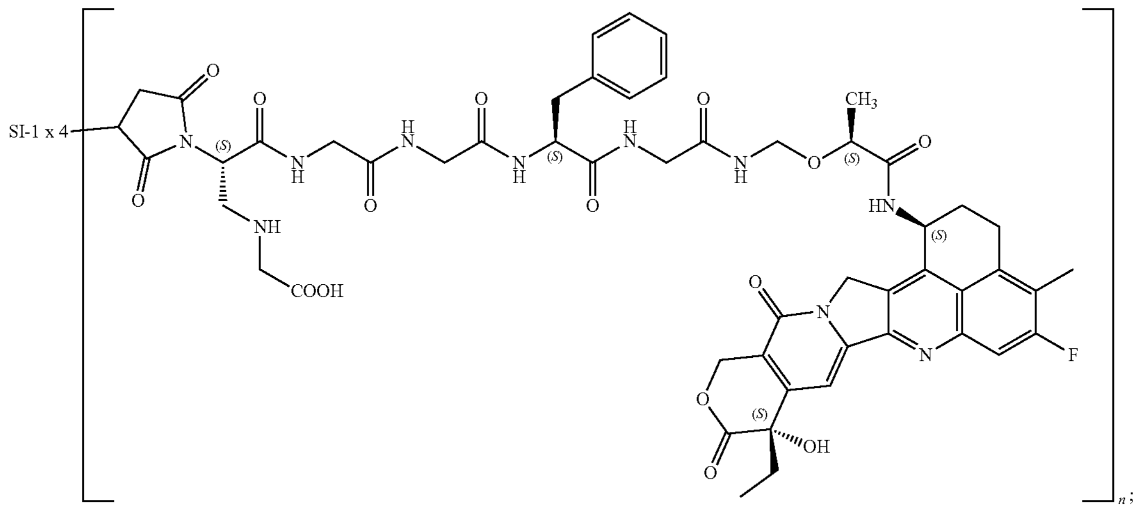
Example 208
ADC-113 was prepared according to the general-purpose coupling method of Example 94,
ADC-113
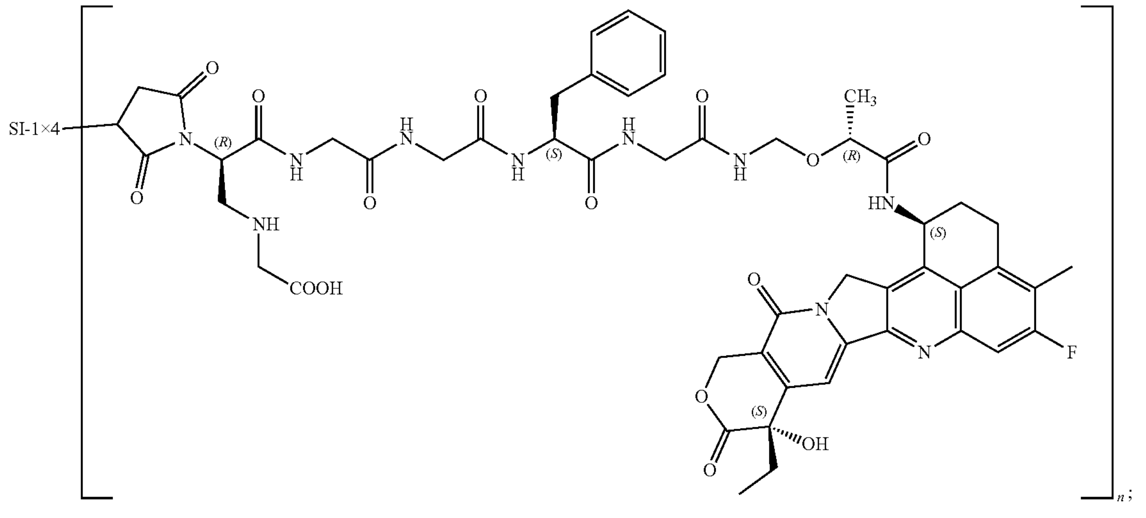
Example 209
ADC-114 was prepared according to the general-purpose coupling method of Example 94, ADC-114
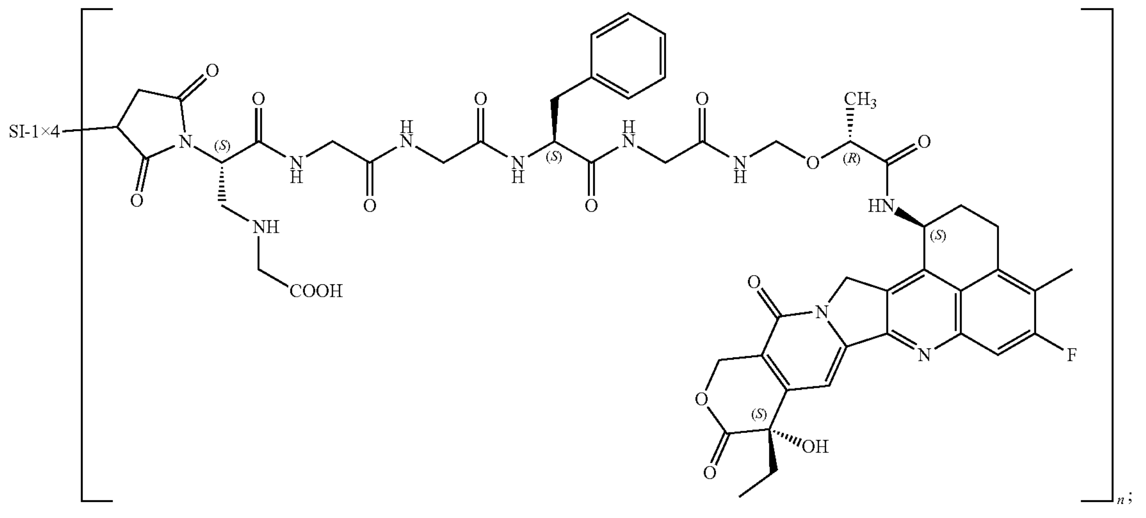
Example 210
ADC-115 was prepared according to the general-purpose coupling method of Example 94,
ADC-115
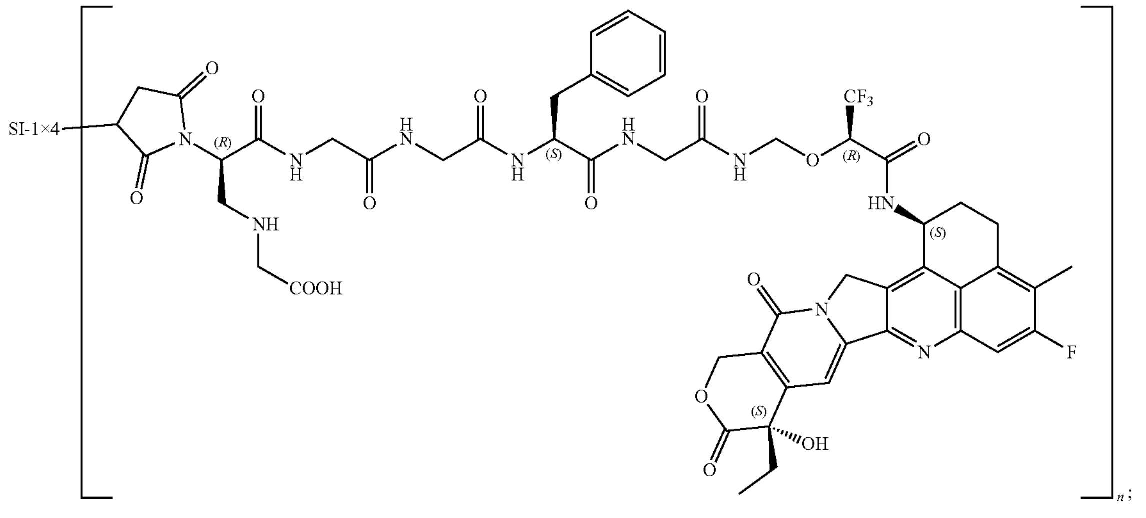
Example 211
ADC-116 was prepared according to the general-purpose coupling method of Example 94, ADC-116
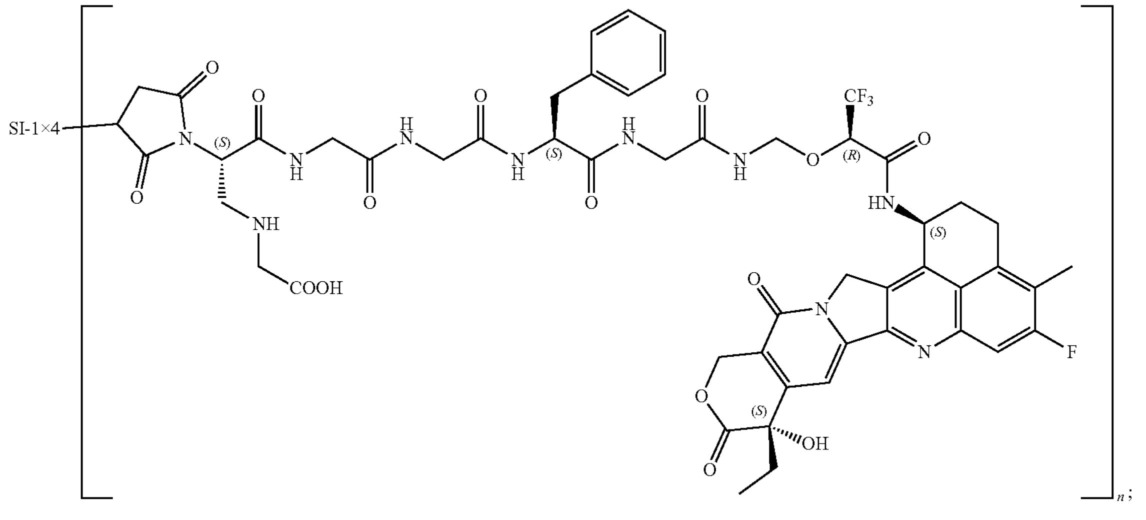
Example 212
ADC-117 was prepared according to the general-purpose coupling method of Example 94,
ADC-117
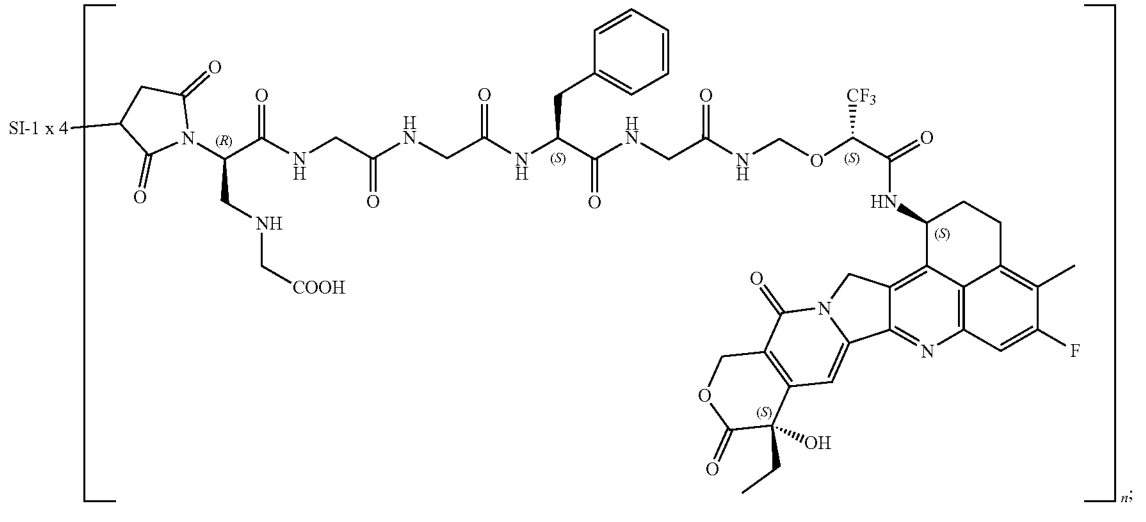
Example 213
ADC-118 was prepared according to the general-purpose coupling method of Example 94, ADC-118
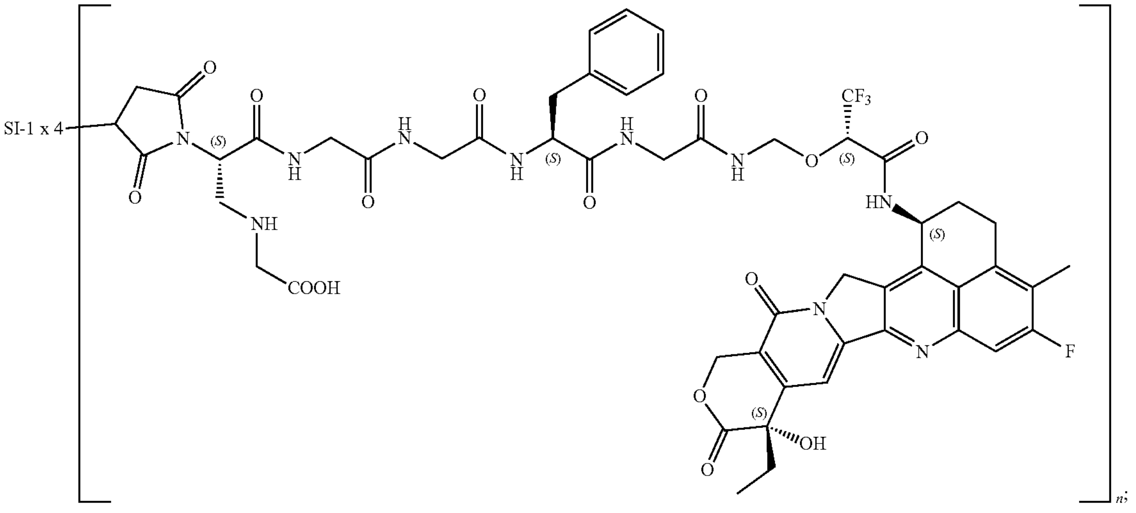
Example 214
ADC-119 was prepared according to the general-purpose coupling method of Example 94,
ADC-119
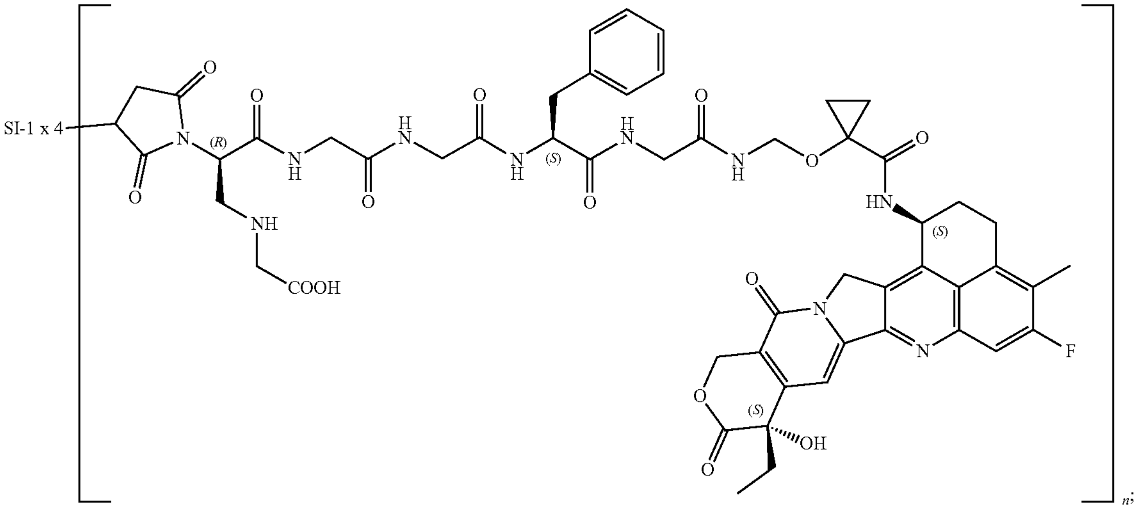
Example 215
ADC-120 was prepared according to the general-purpose coupling method of Example 94, ADC-120
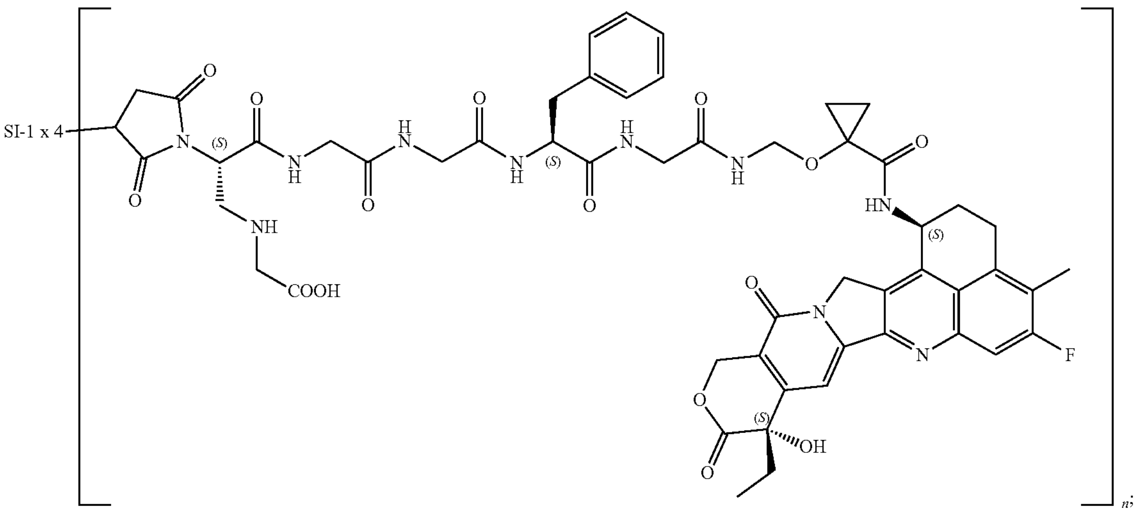
Example 216
ADC-121 was prepared according to the general-purpose coupling method of Example 94,
ADC-121
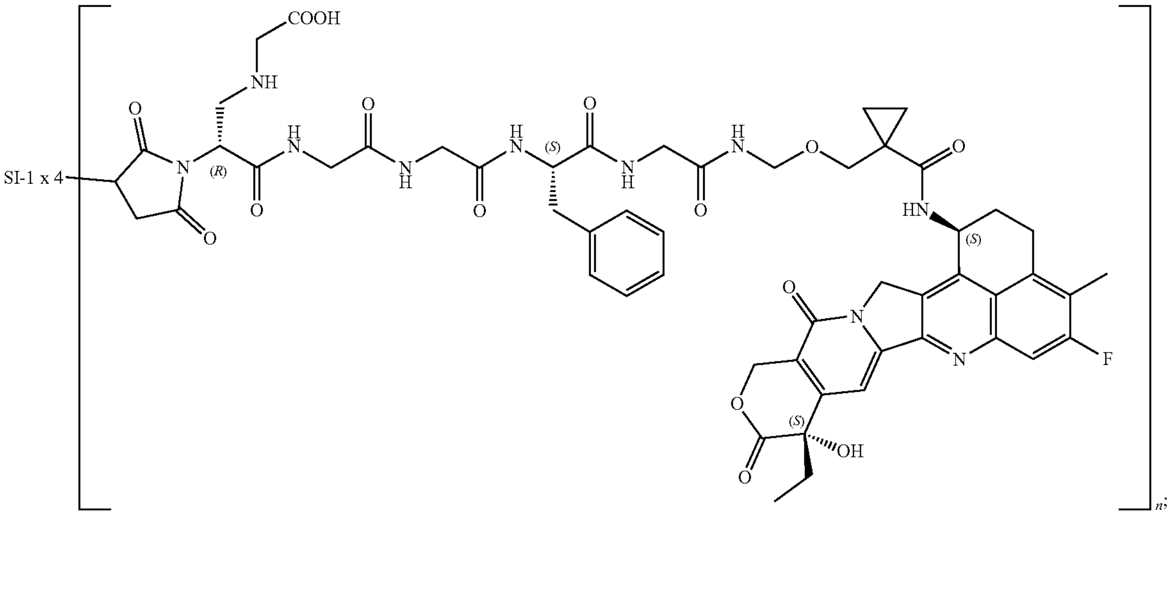
Example 217
ADC-122 was prepared according to the general-purpose coupling method of Example 94, ADC-122
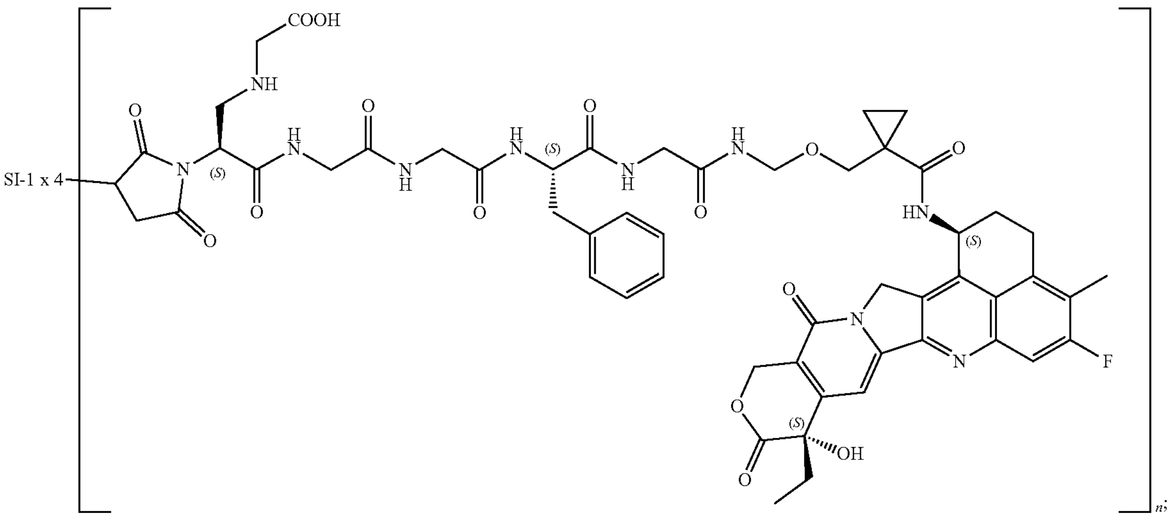
Example 218
ADC-123 was prepared according to the general-purpose coupling method of Example 94,
ADC-123
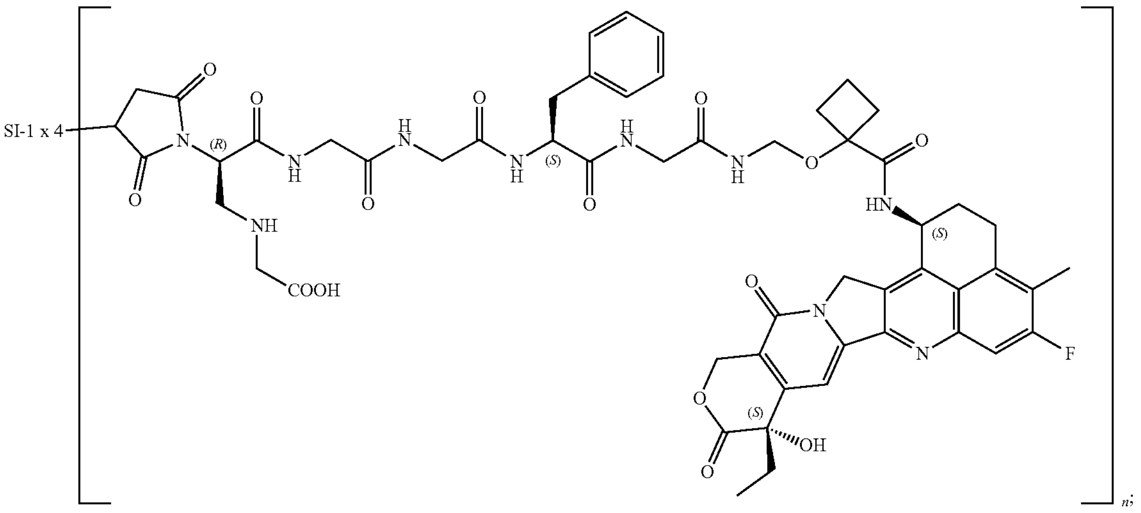
Example 219
ADC-124 was prepared according to the general-purpose coupling method of Example 94, ADC-124
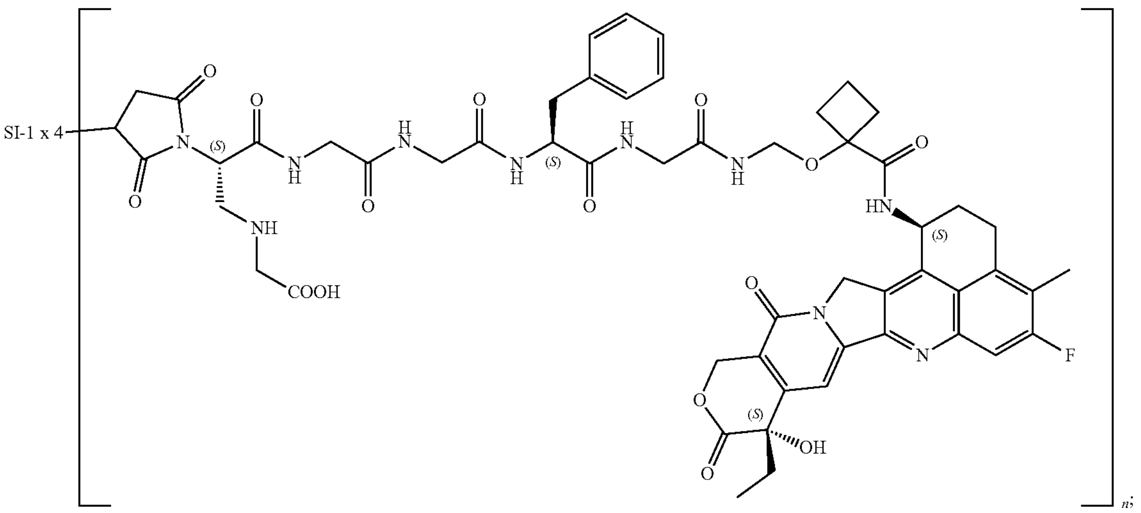
Example 220
ADC-125 was prepared according to the general-purpose coupling method of Example 94,
ADC-125
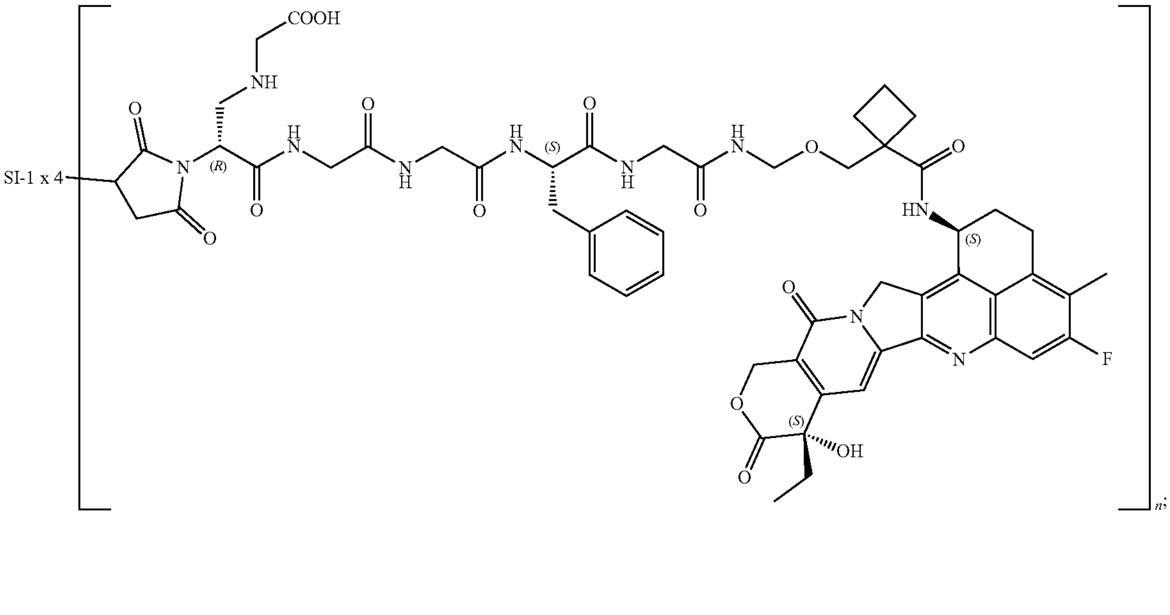
Example 221
ADC-126 was prepared according to the general-purpose coupling method of Example 94, ADC-126
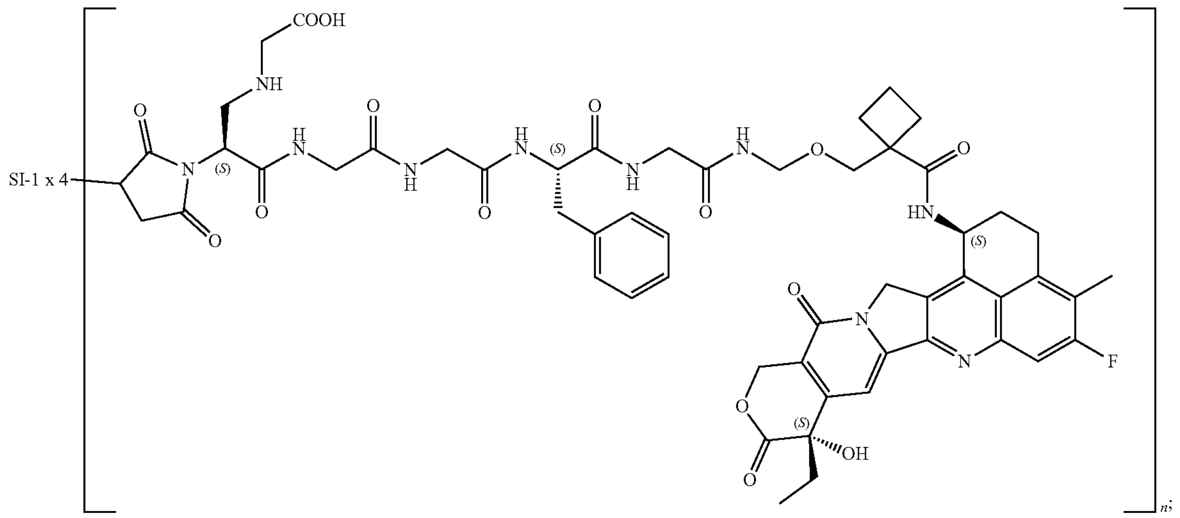
Example 222
ADC-127 was prepared according to the general-purpose coupling method of Example 94,
ADC-127
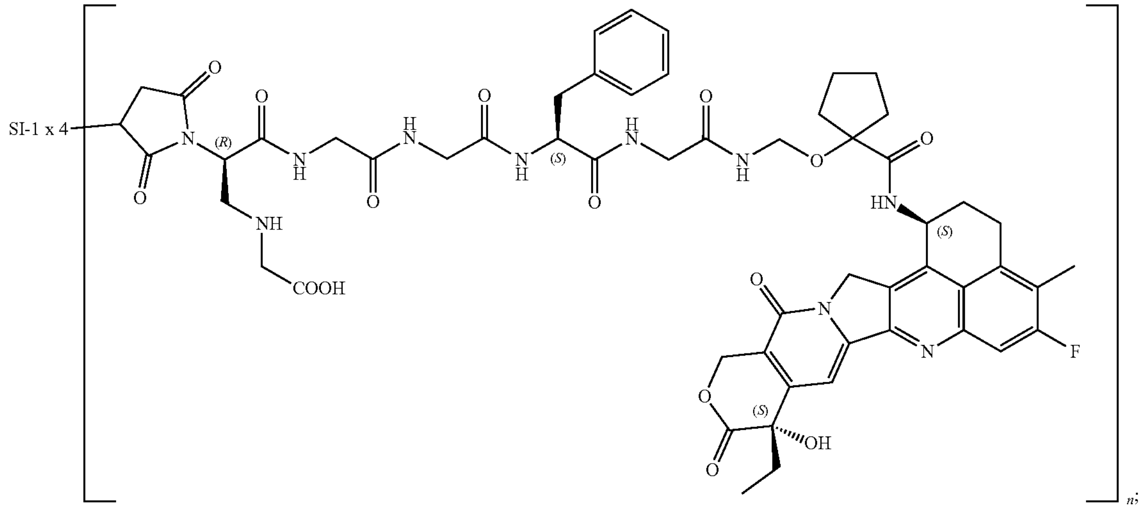
Example 223
ADC-128 was prepared according to the general-purpose coupling method of Example 94, ADC-128
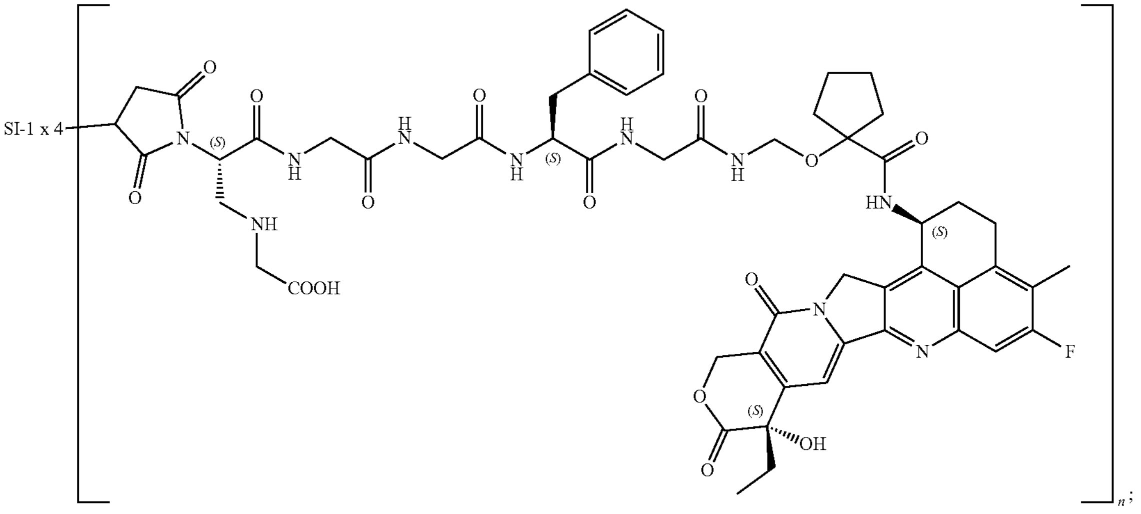
Example 224
ADC-129 was prepared according to the general-purpose coupling method of Example 94,
ADC-129
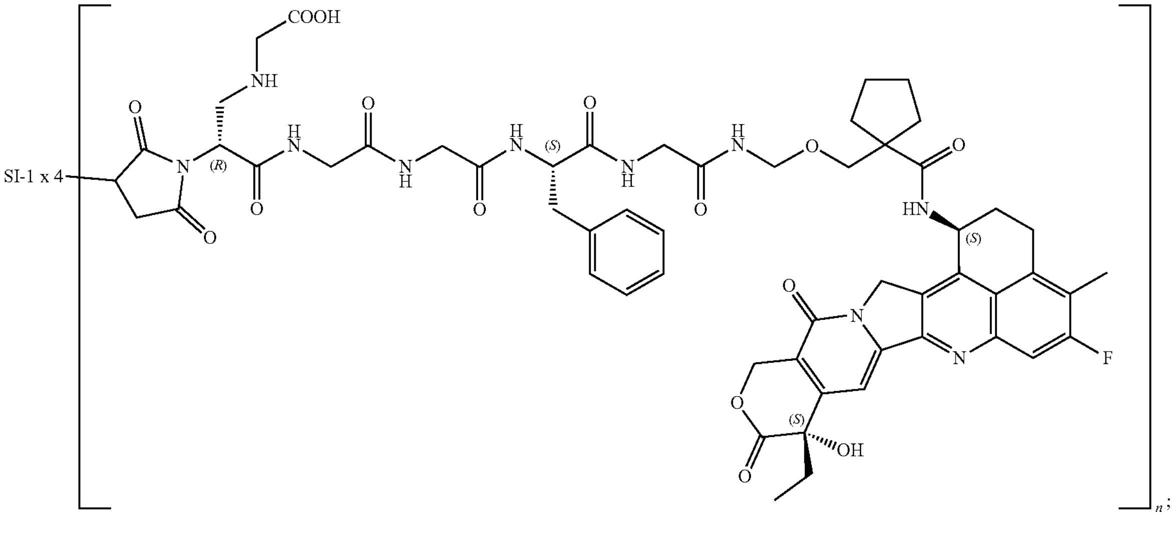
Example 225
ADC-130 was prepared according to the general-purpose coupling method of Example 94, ADC-130
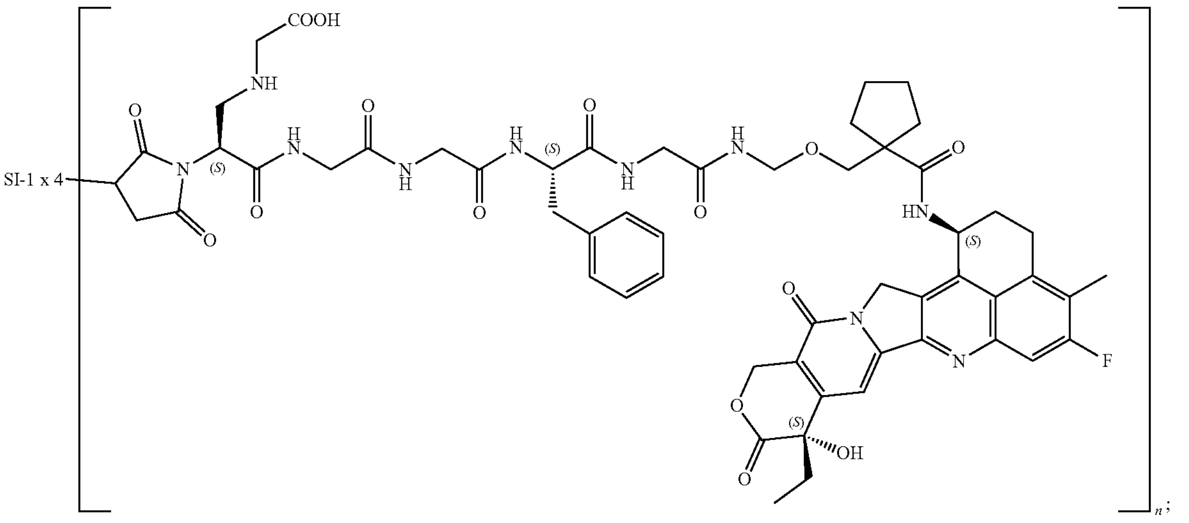
Example 226
ADC-131 was prepared according to the general-purpose coupling method of Example 94,
ADC-131
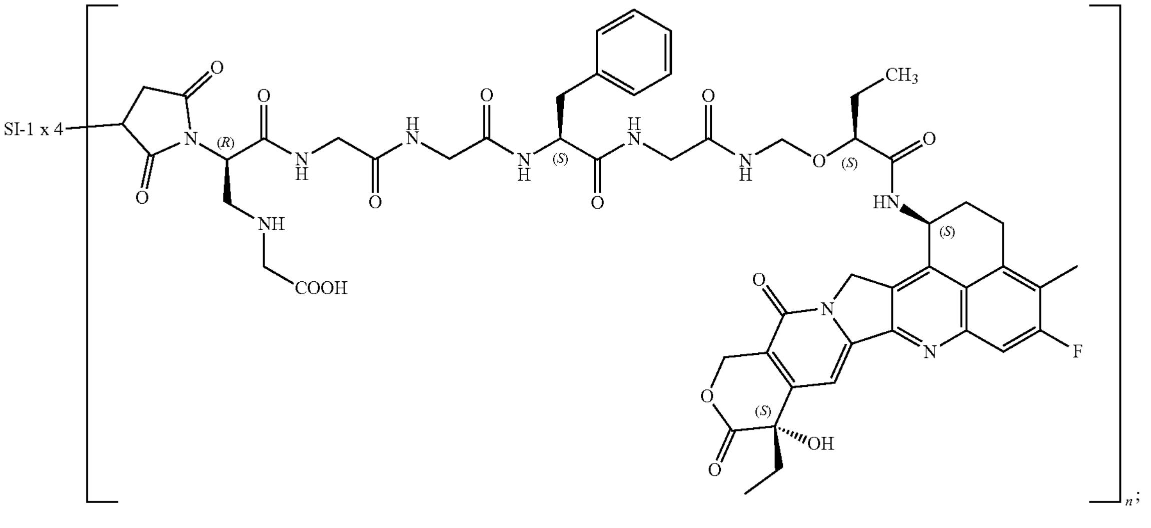
Example 227
ADC-132 was prepared according to the general-purpose coupling method of Example 94, ADC-132
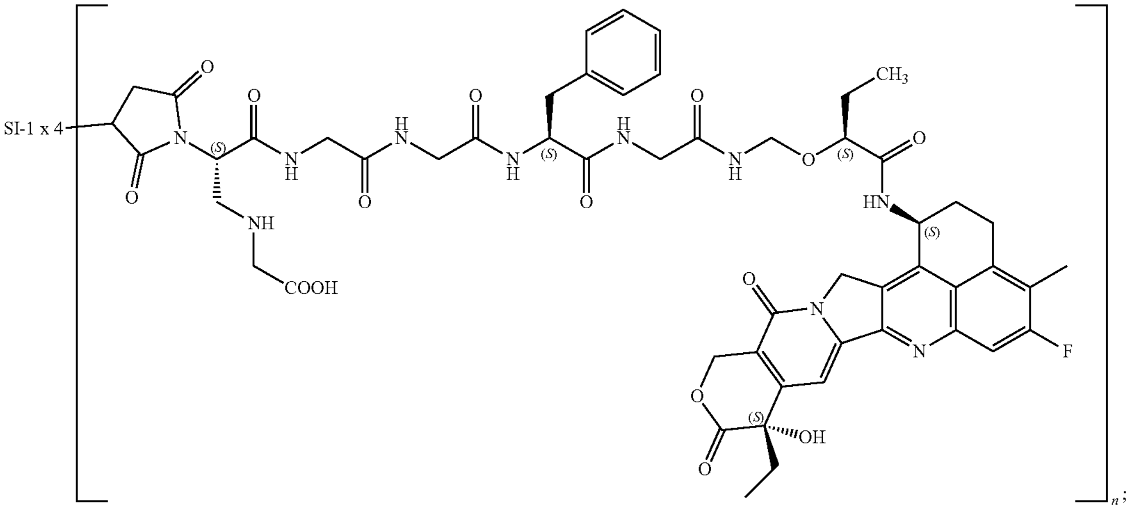
Example 228
ADC-133 was prepared according to the general-purpose coupling method of Example 94,
ADC-133
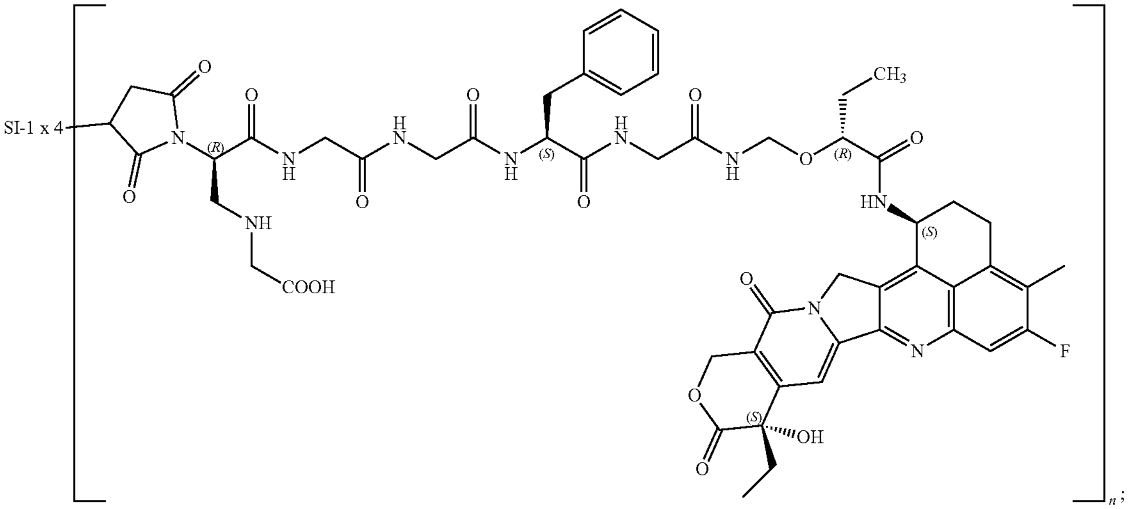
Example 229
ADC-134 was prepared according to the general-purpose coupling method of Example 94, ADC-134
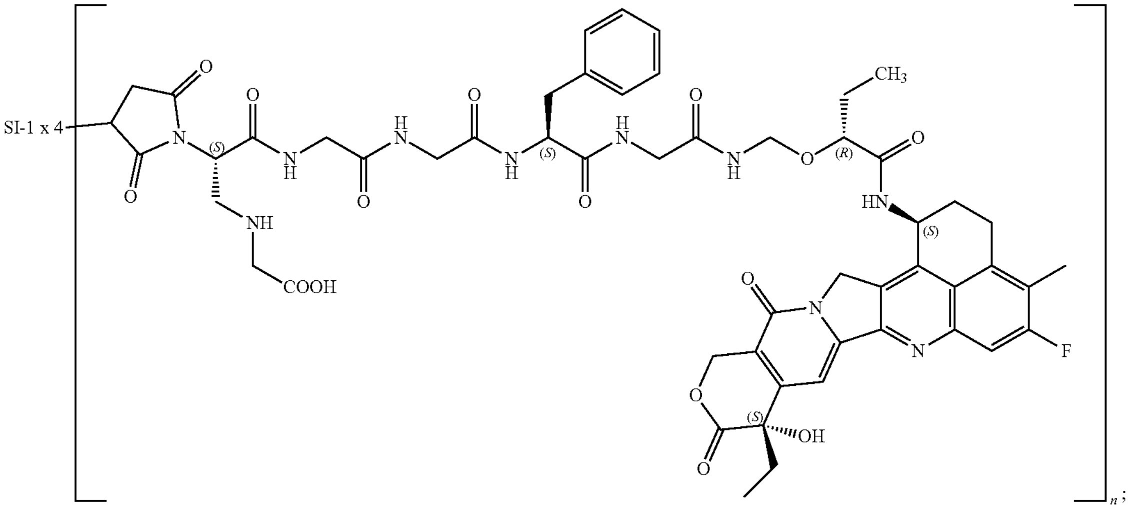
Example 230
ADC-135 was prepared according to the general-purpose coupling method of Example 94,
ADC-135
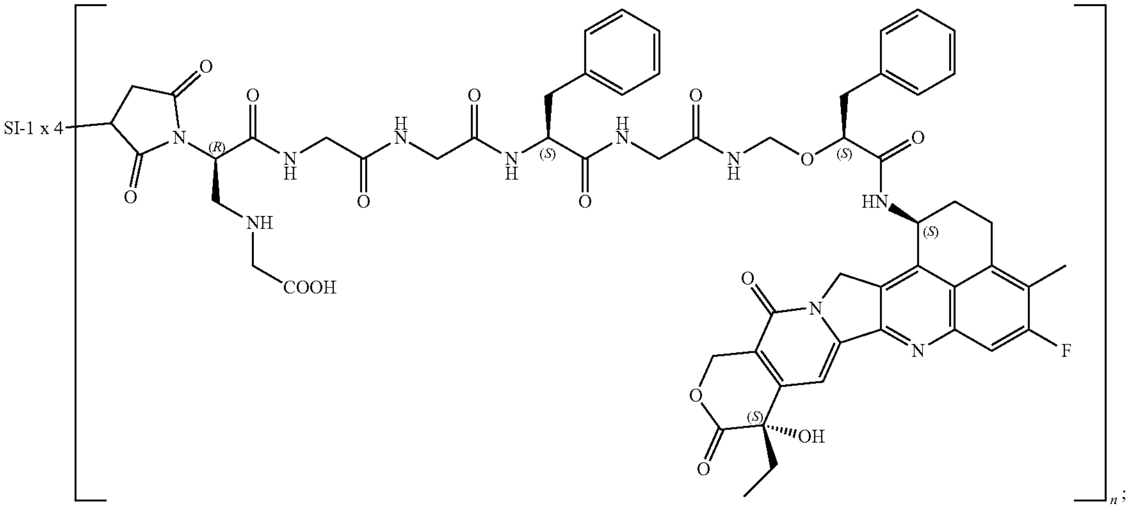
Example 231
ADC-136 was prepared according to the general-purpose coupling method of Example 94, ADC-136
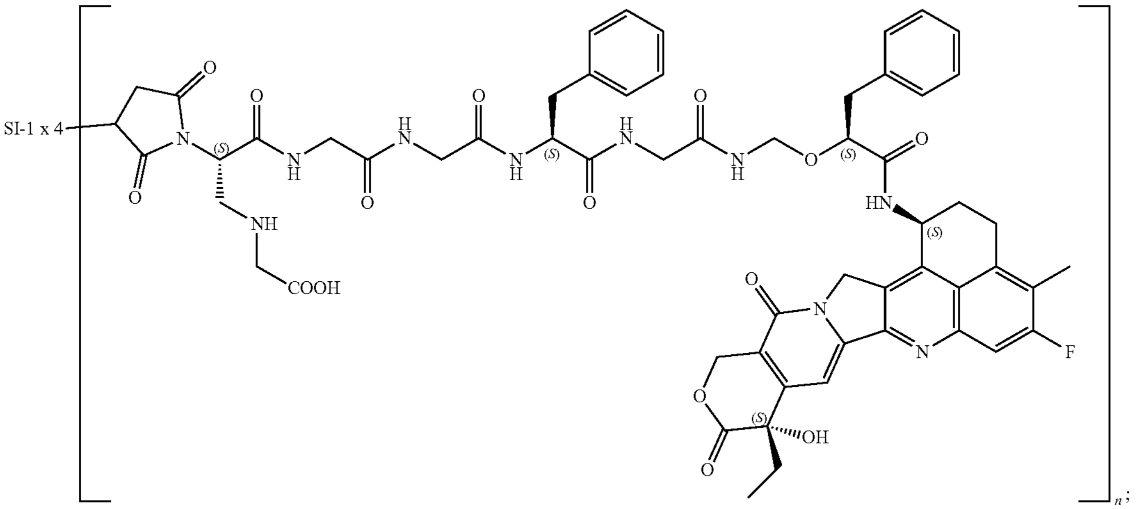
Example 232
ADC-137 was prepared according to the general-purpose coupling method of Example 94,
ADC-137
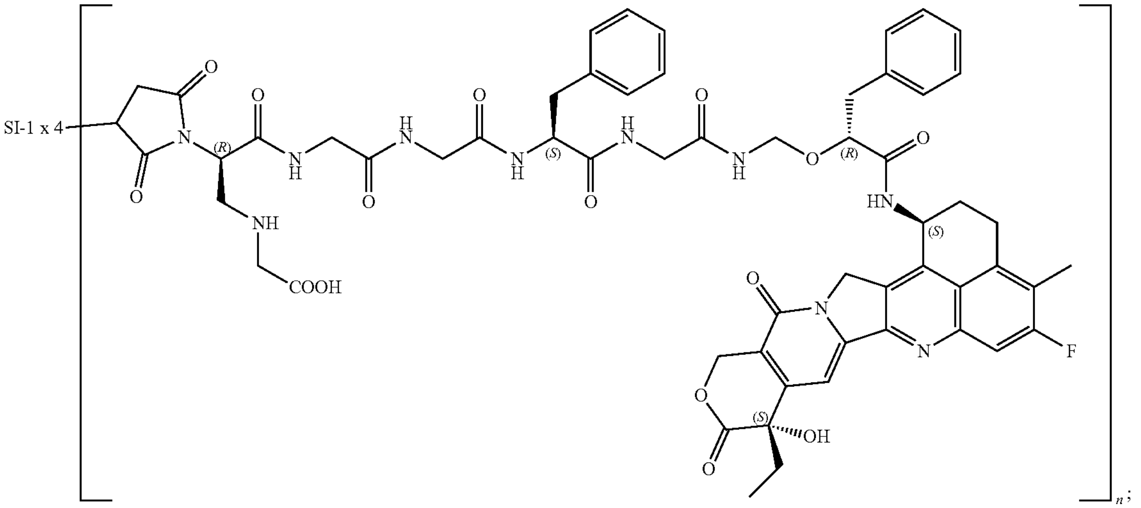
Example 233
ADC-138 was prepared according to the general-purpose coupling method of Example 94, ADC-138
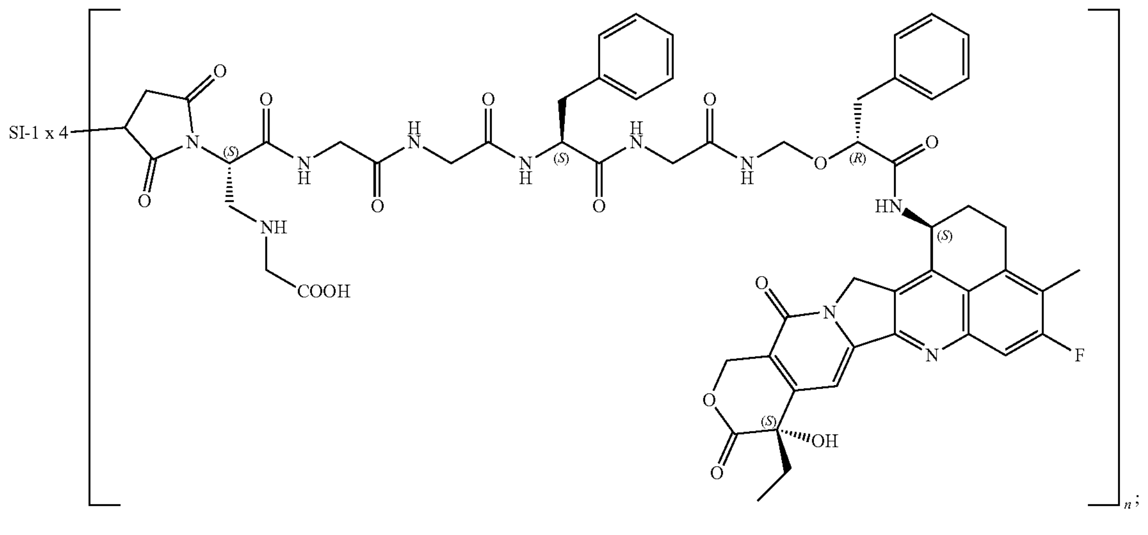
Example 234
ADC-139 was prepared according to the general-purpose coupling method of Example 94,
ADC-139
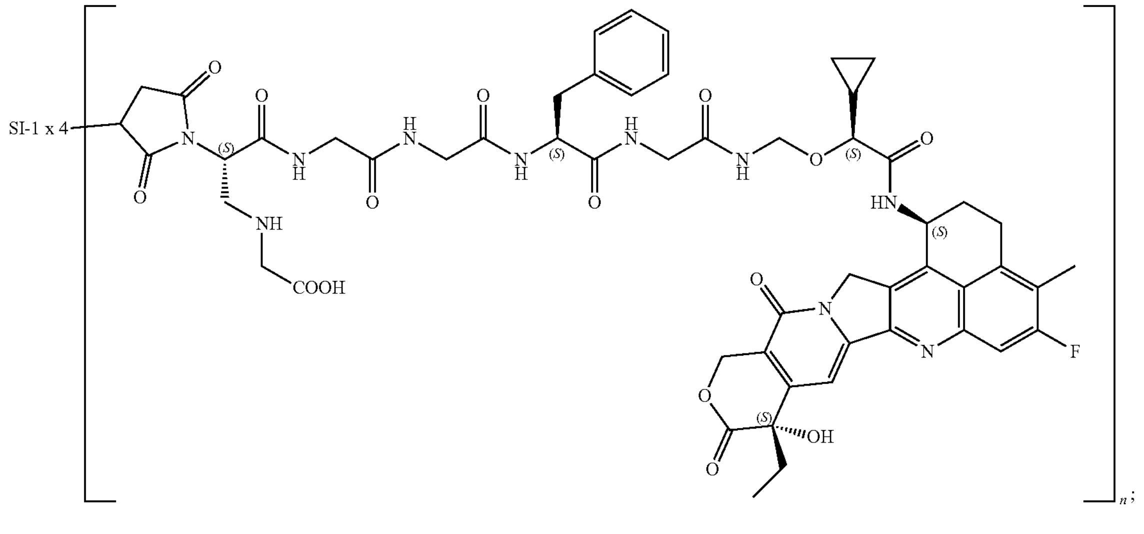
Example 235
ADC-140 was prepared according to the general-purpose coupling method of Example 94, ADC-140
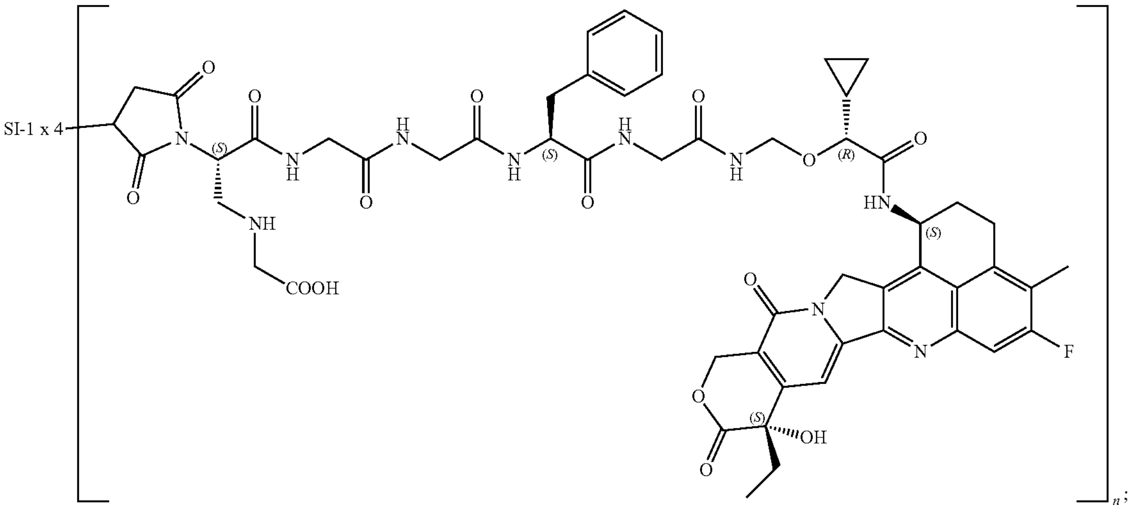
Example 236
ADC-141 was prepared according to the general-purpose coupling method of Example 94,
ADC-141
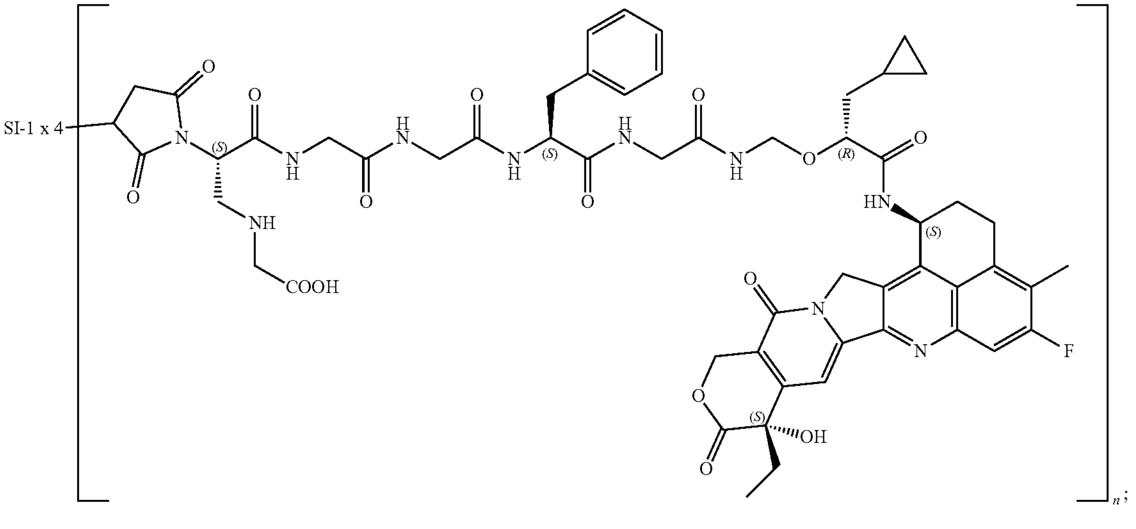
Example 237
ADC-142 was prepared according to the general-purpose coupling method of Example 94, ADC-142
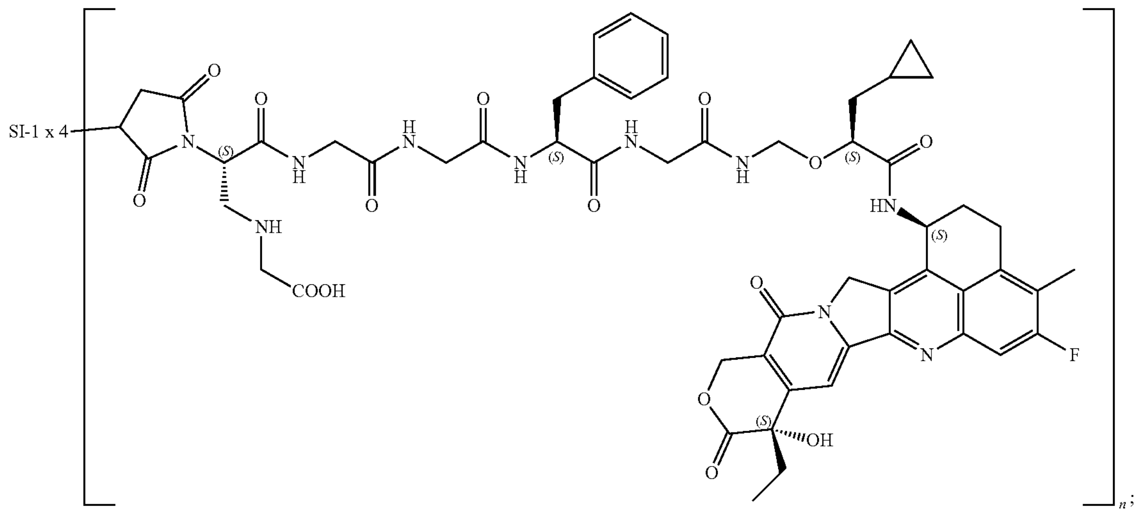
Example 238
ADC-143 was prepared according to the general-purpose coupling method of Example 94,
ADC-143
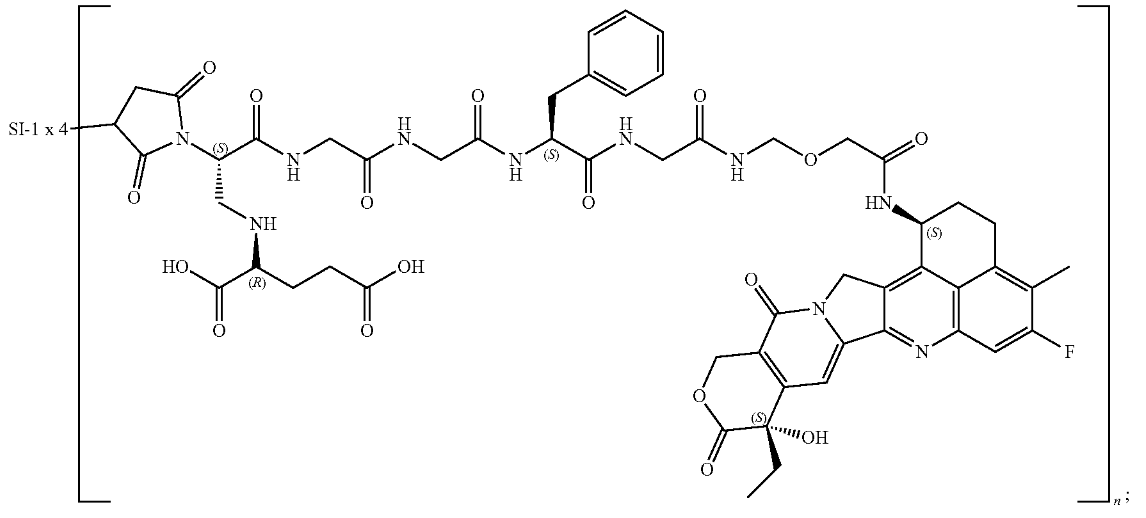
Example 239
ADC-144 was prepared according to the general-purpose coupling method of Example 94, ADC-144
SI-1 x 4
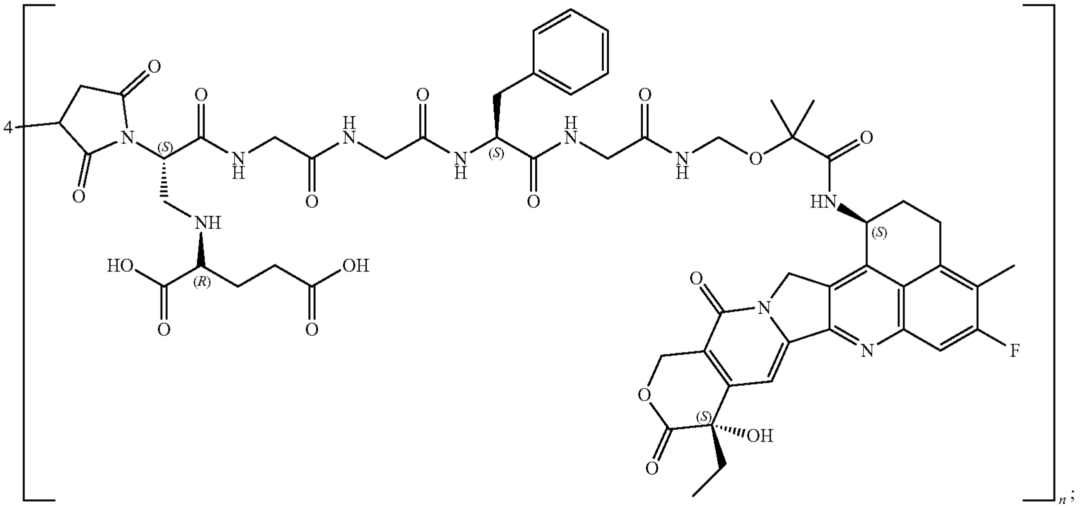
Example 240
ADC-145 was prepared according to the general-purpose coupling method of Example 94,
ADC-145
SI-1 x 4
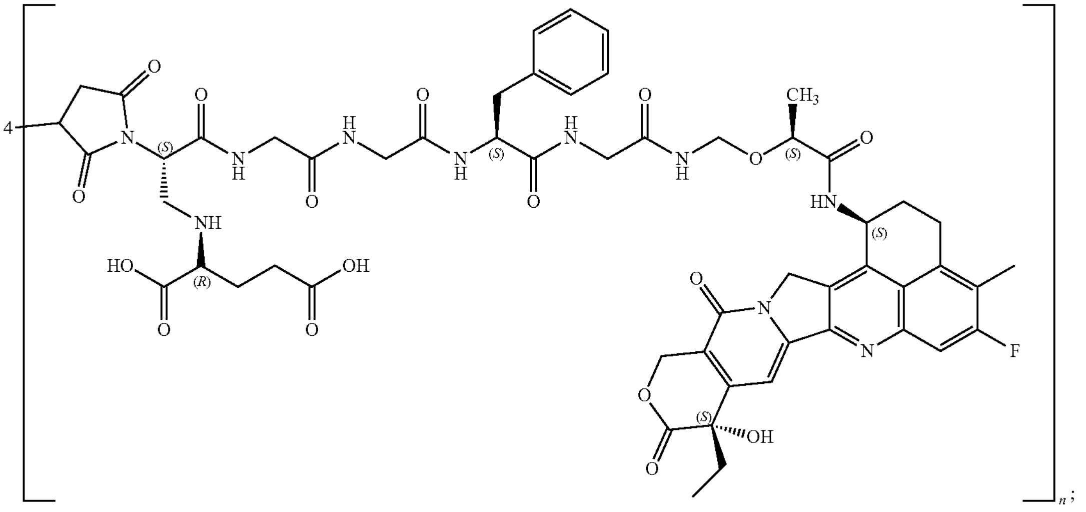
Example 241
ADC-146 was prepared according to the general-purpose coupling method of Example 94, ADC-146
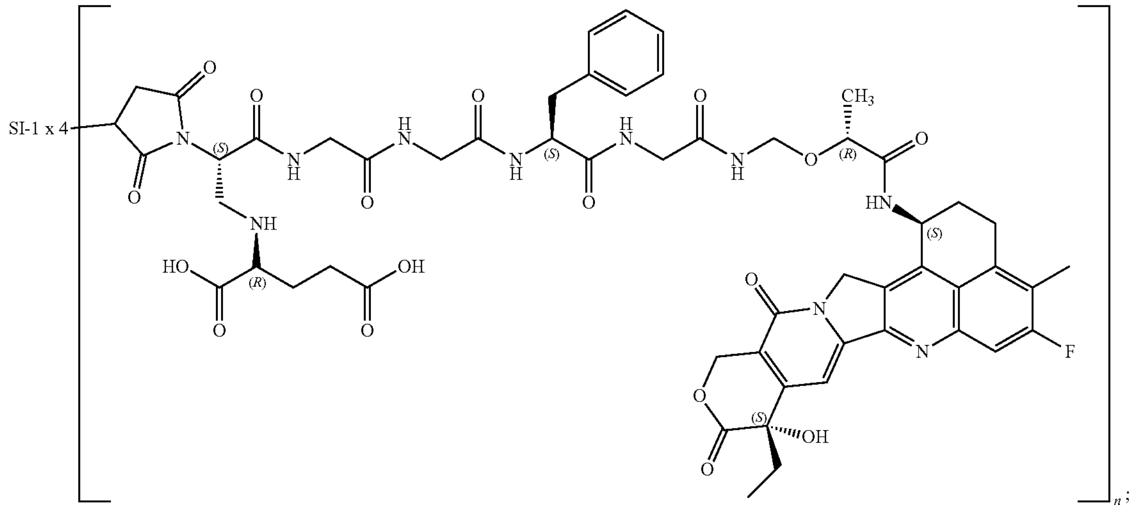
Example 242
ADC-147 was prepared according to the general-purpose coupling method of Example 94,
ADC-147
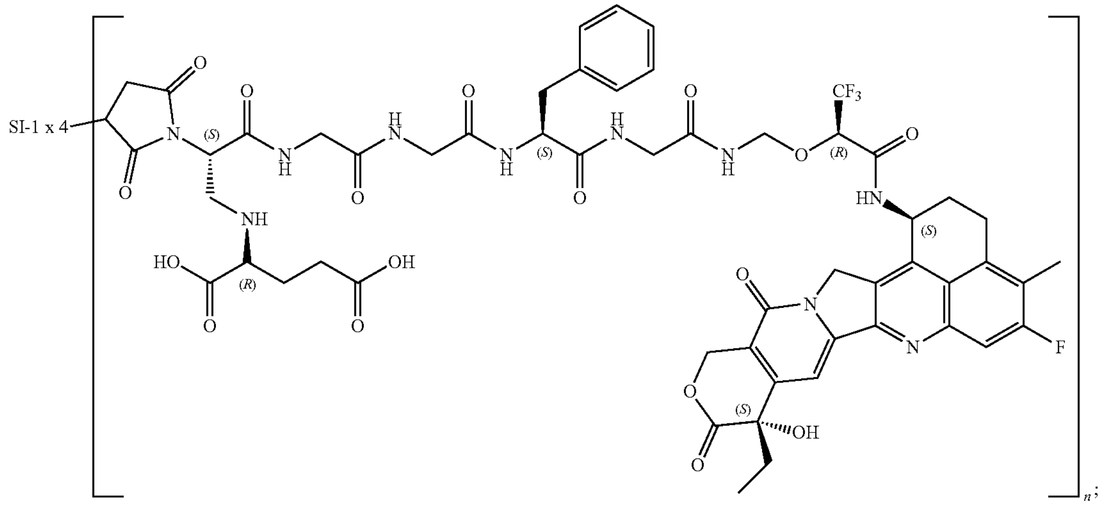
Example 243
ADC-148 was prepared according to the general-purpose coupling method of Example 94, ADC-148
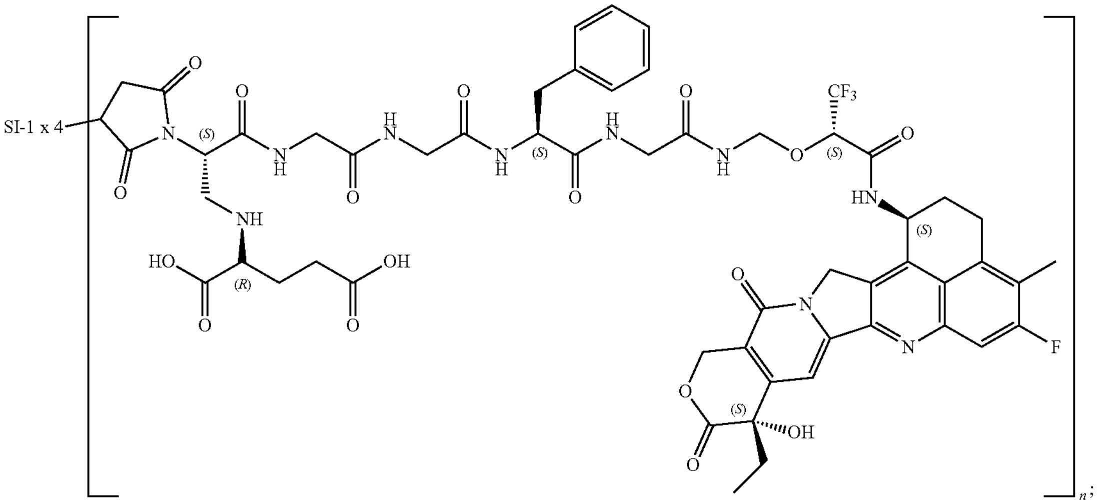
Example 244
ADC-149 was prepared according to the general-purpose coupling method of Example 94,
ADC-149
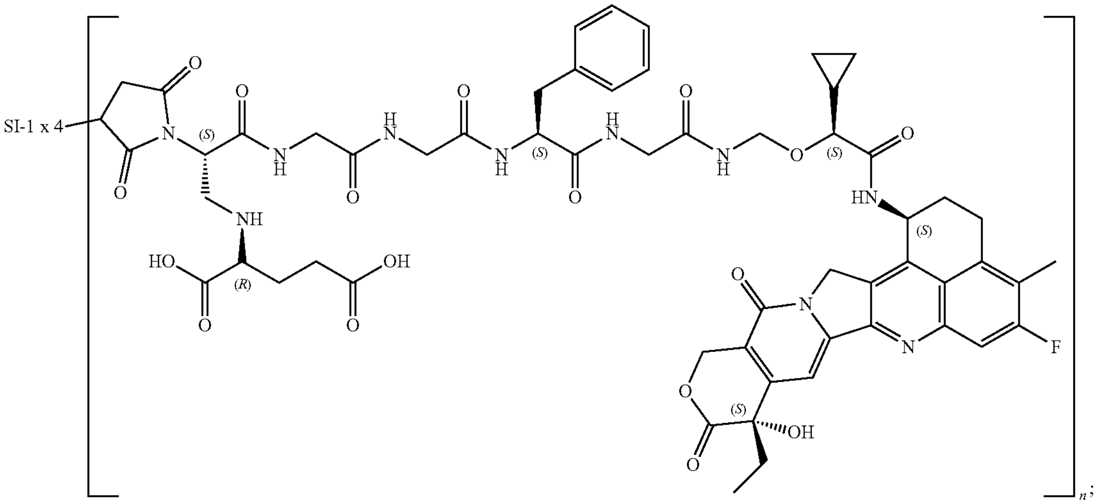
Example 245
ADC-150 was prepared according to the general-purpose coupling method of Example 94, ADC-150
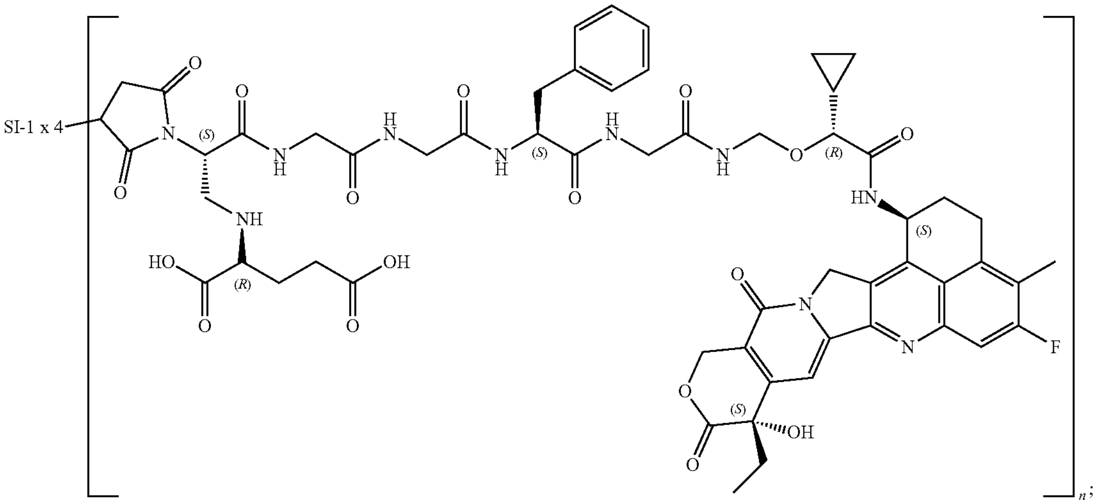
Example 246
ADC-151 was prepared according to the general-purpose coupling method of Example 94,
ADC-151
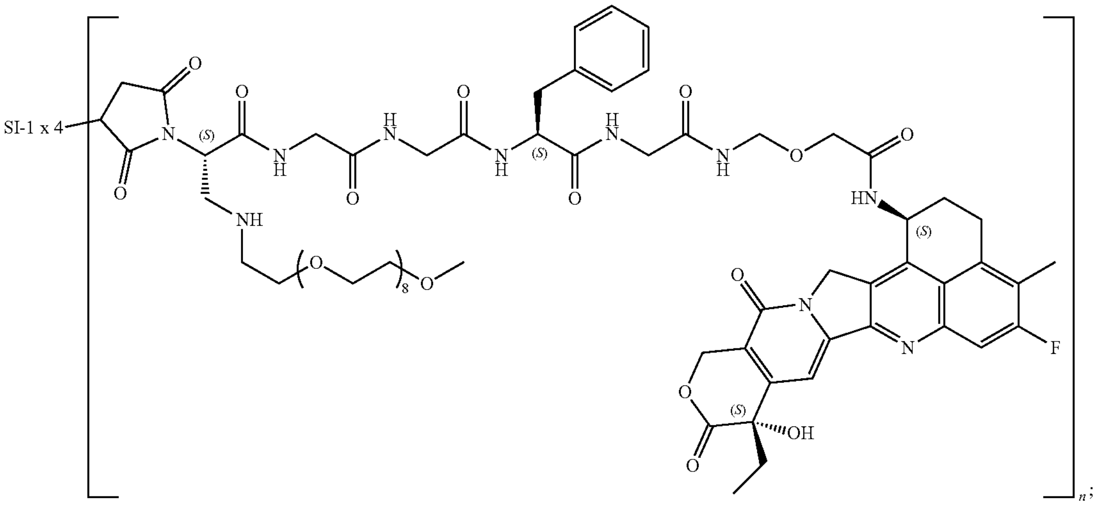
Example 247
ADC-152 was prepared according to the general-purpose coupling method of Example 94, ADC-152
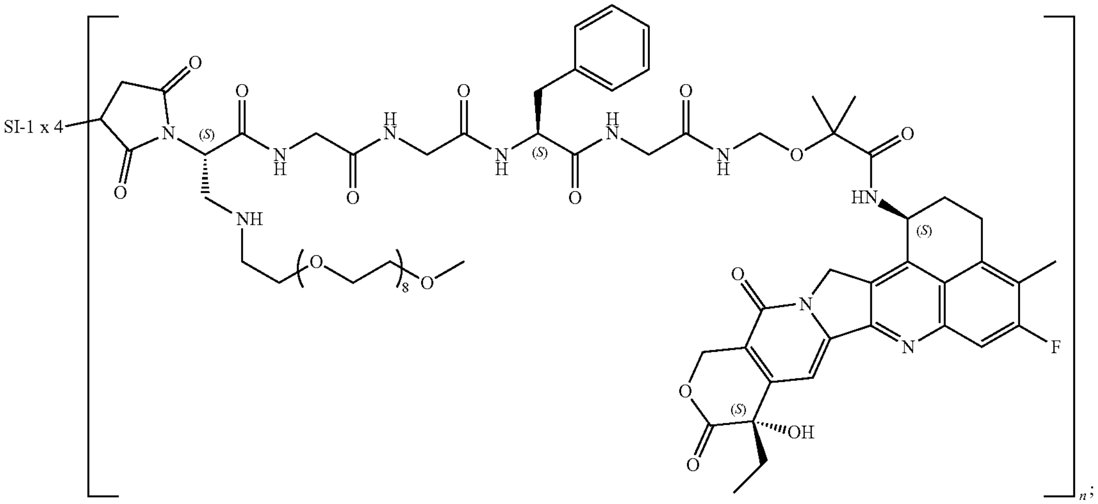
Example 248
ADC-153 was prepared according to the general-purpose coupling method of Example 94,
ADC-153
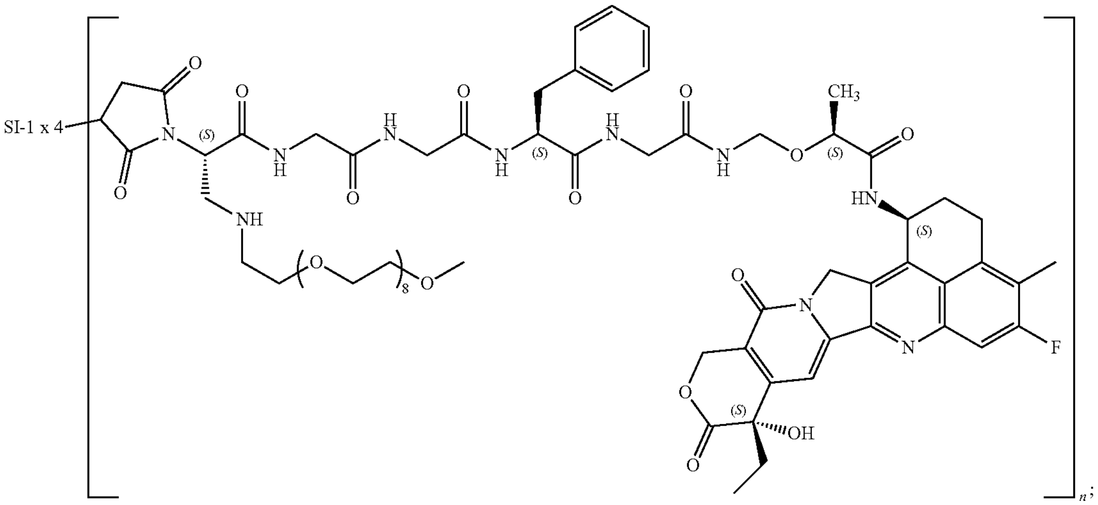
Example 249
ADC-154 was prepared according to the general-purpose coupling method of Example 94, ADC-154
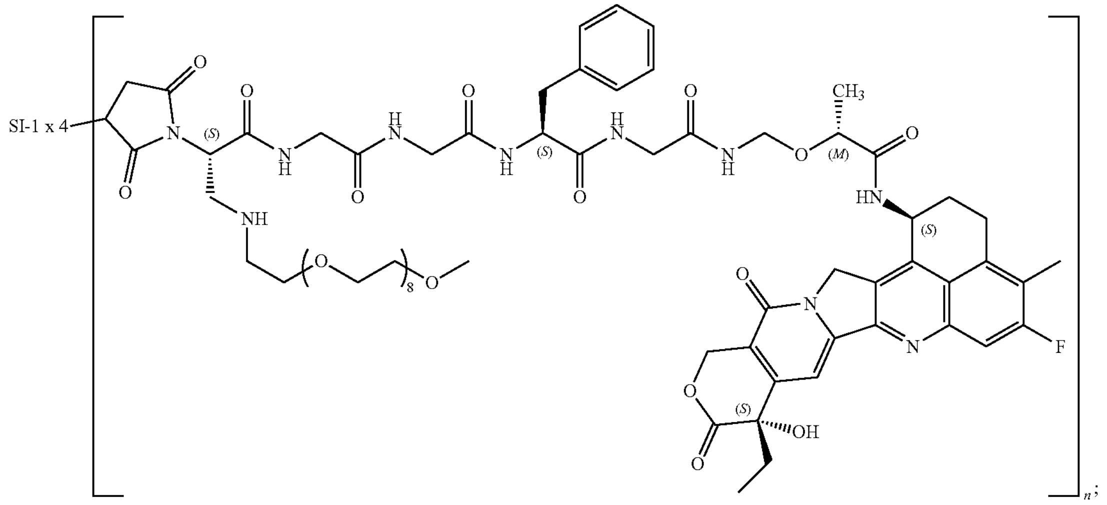
Example 250
ADC-155 was prepared according to the general-purpose coupling method of Example 94,
ADC-155
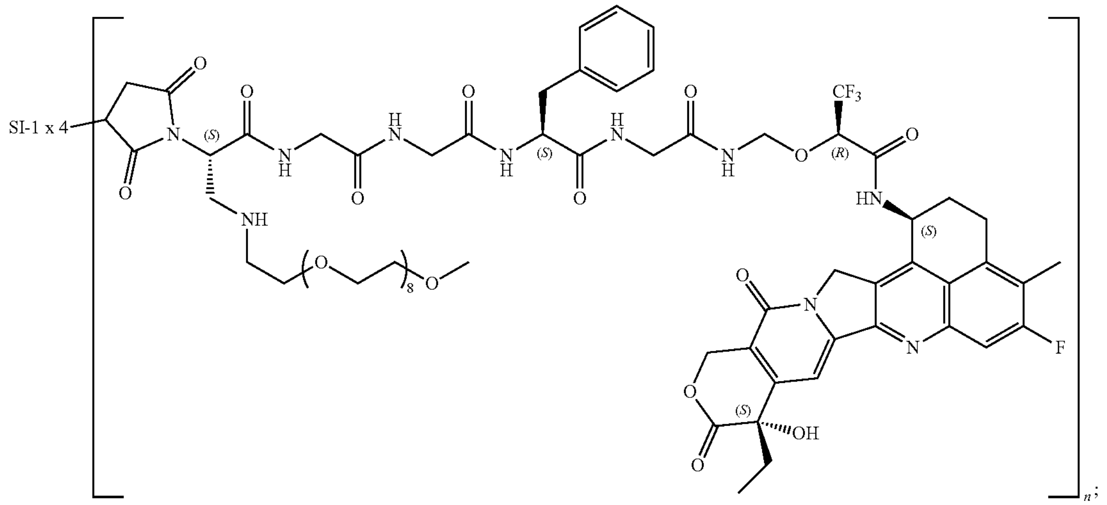
Example 251
ADC-156 was prepared according to the general-purpose coupling method of Example 94, ADC-156
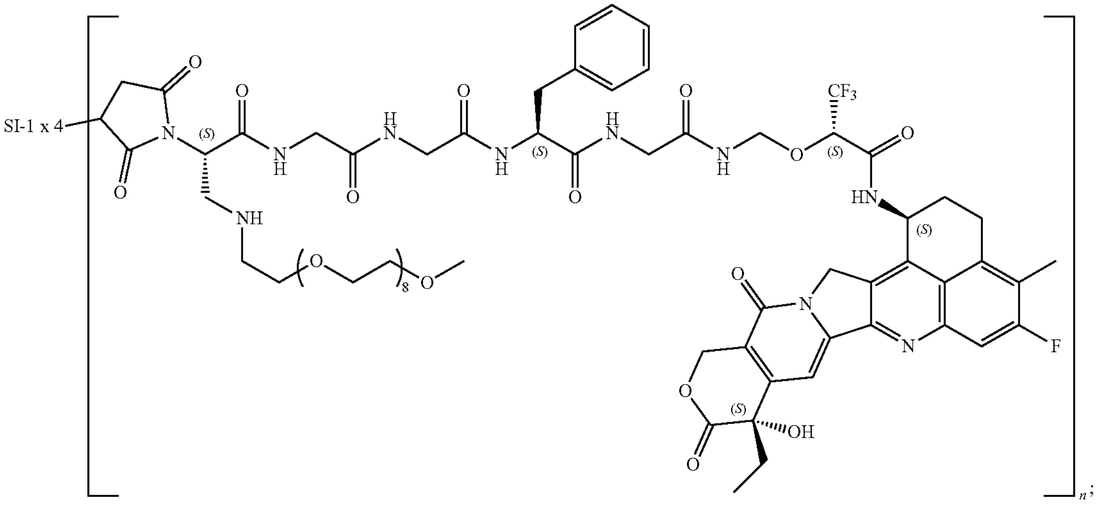
Example 252
ADC-157 was prepared according to the general-purpose coupling method of Example 94,
ADC-157
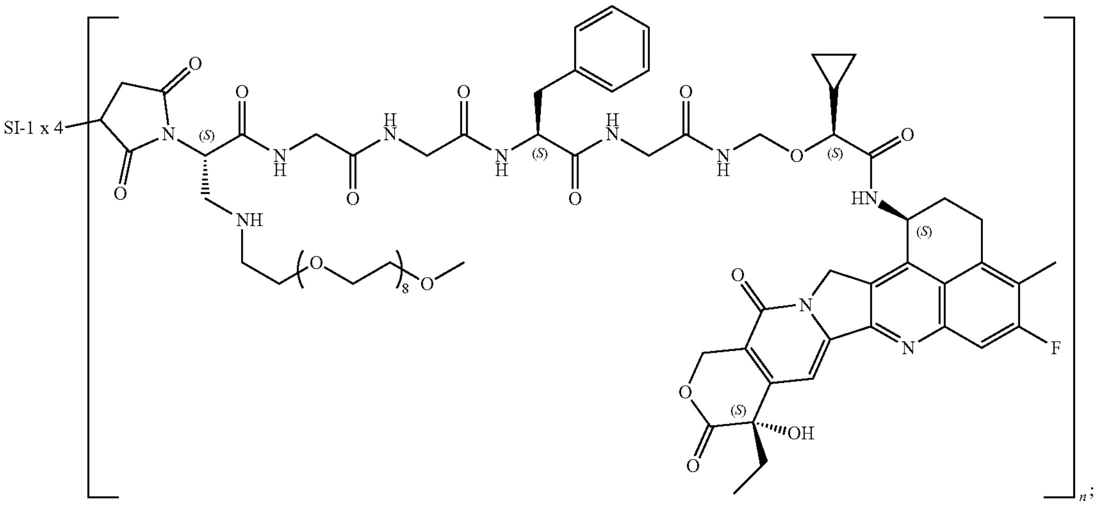
Example 253
ADC-158 was prepared according to the general-purpose coupling method of Example 94, ADC-158
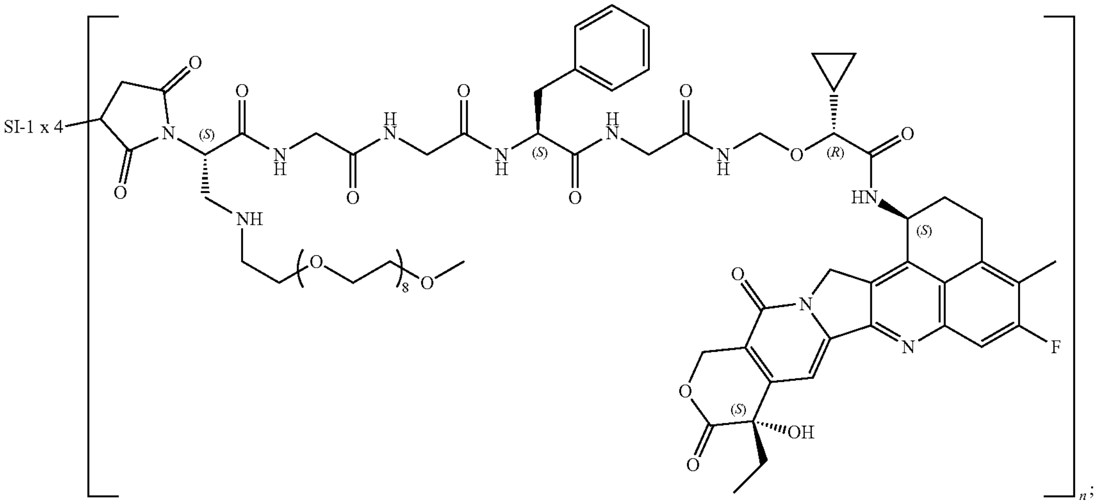
Example 254
ADC-159 was prepared according to the general-purpose coupling method of Example 94,
ADC-159
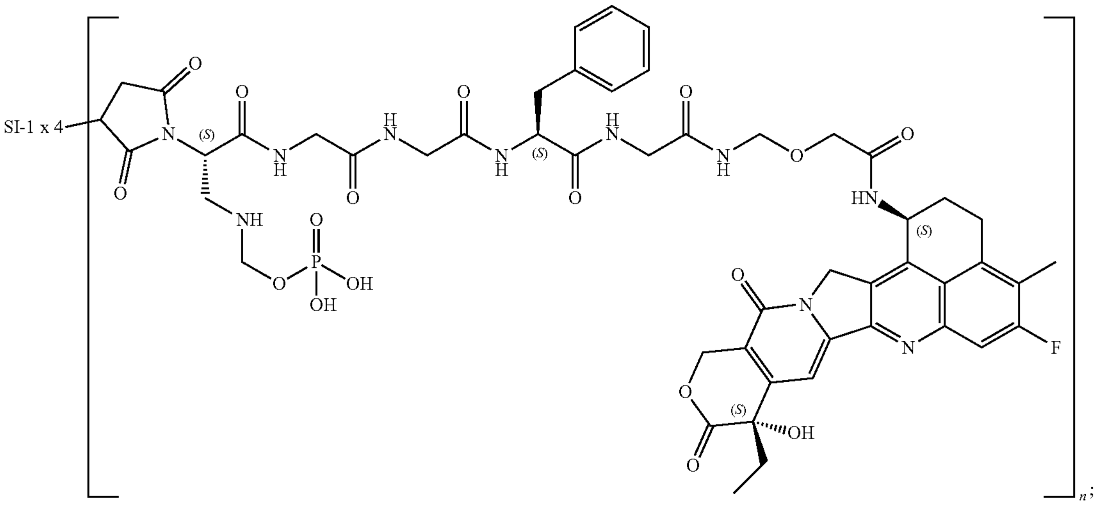
Example 255
ADC-160 was prepared according to the general-purpose coupling method of Example 94, ADC-160
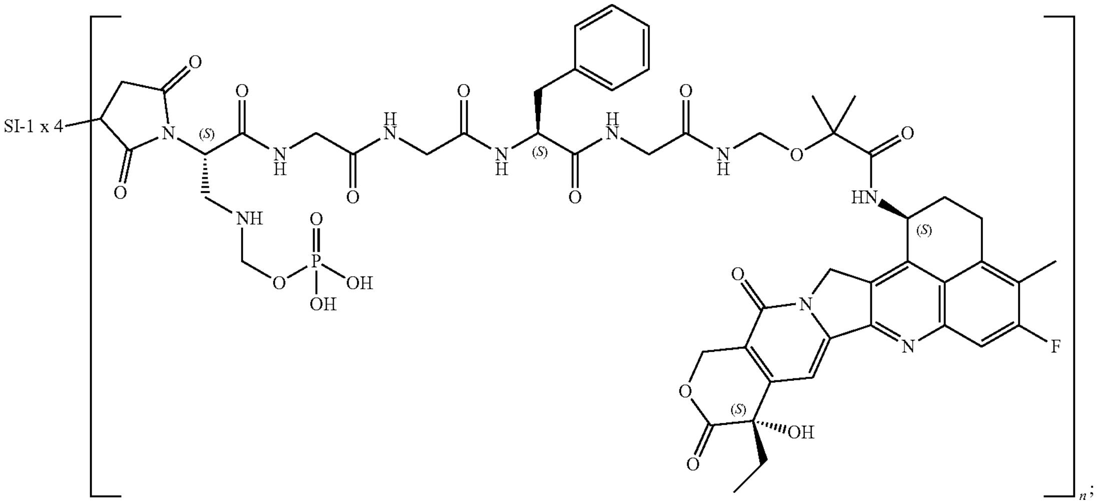
Example 256
ADC-161 was prepared according to the general-purpose coupling method of Example 94,
ADC-161
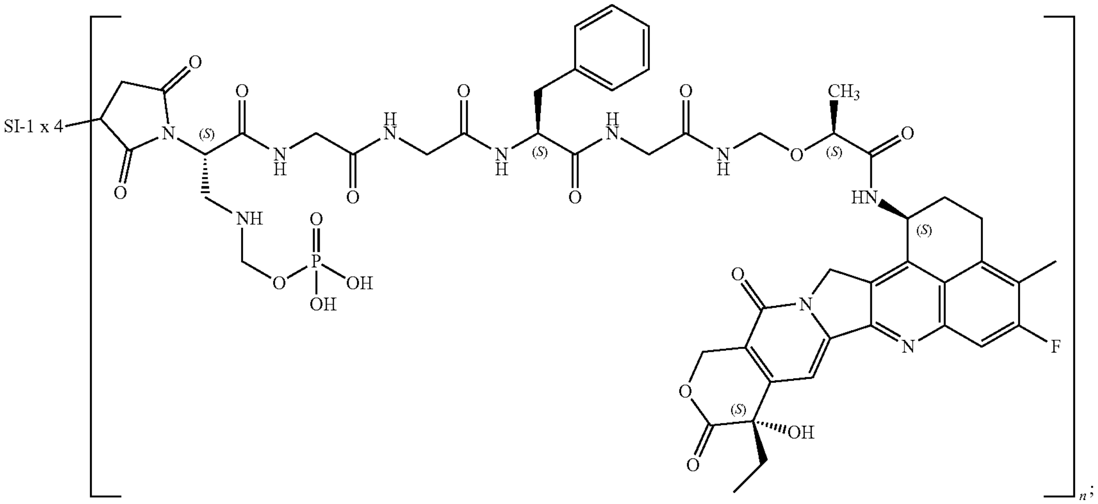
Example 257
ADC-162 was prepared according to the general-purpose coupling method of Example 94, ADC-162
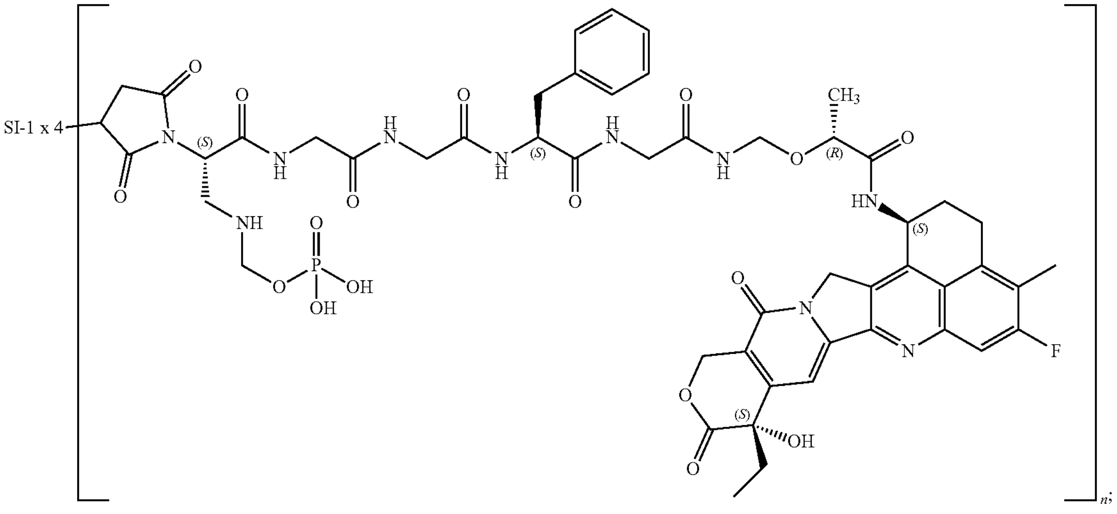
Example 258
ADC-163 was prepared according to the general-purpose coupling method of Example 94,
ADC-163
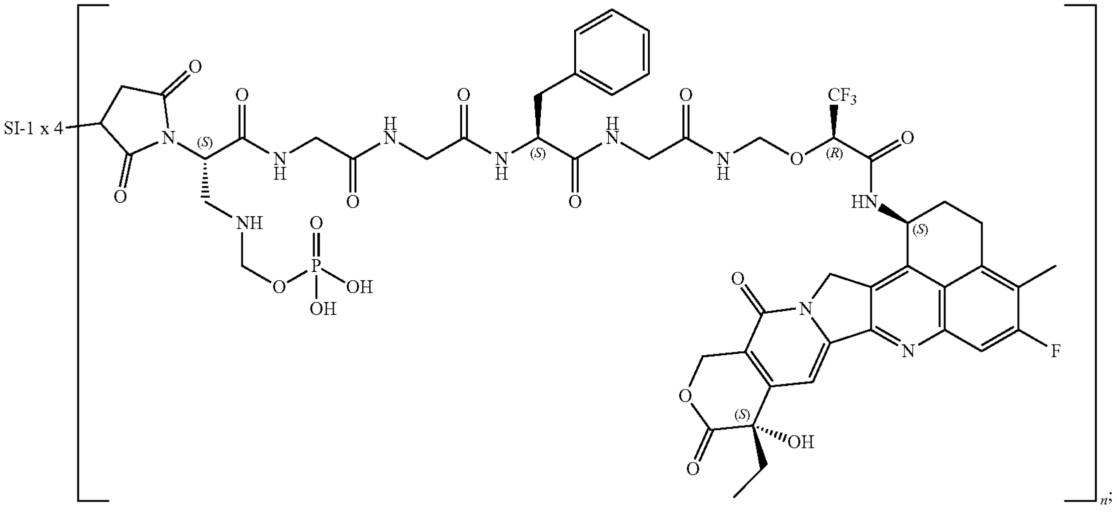
Example 259
ADC-164 was prepared according to the general-purpose coupling method of Example 94, ADC-164
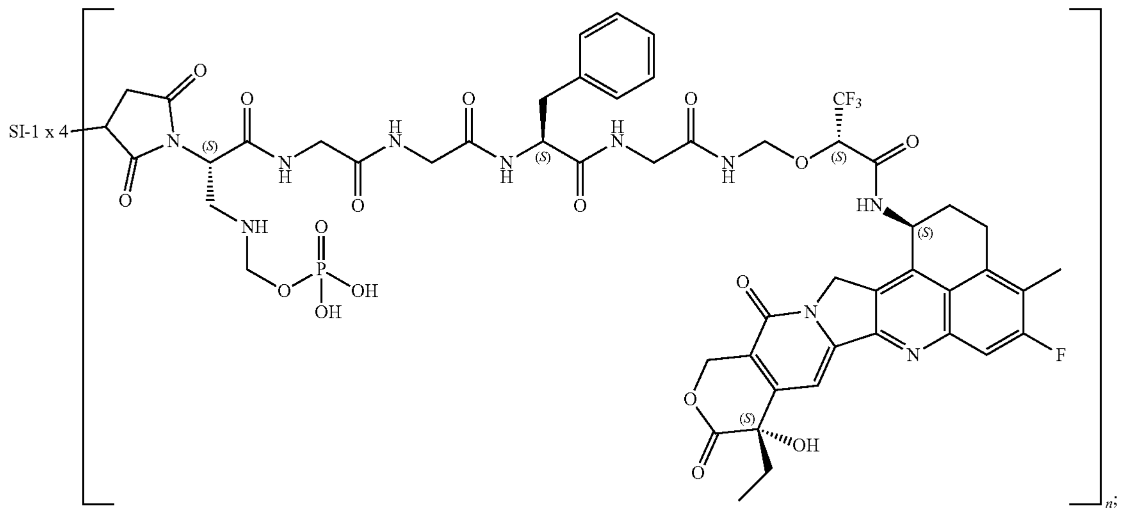
Example 260
ADC-165 was prepared according to the general-purpose coupling method of Example 94,
ADC-165
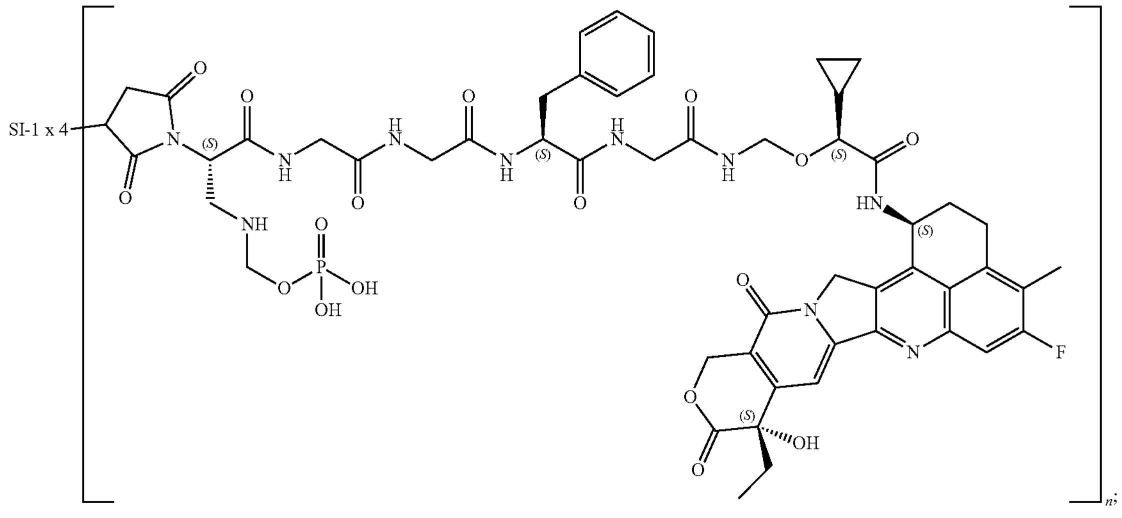
Example 261
ADC-166 was prepared according to the general-purpose coupling method of Example 94, ADC-166
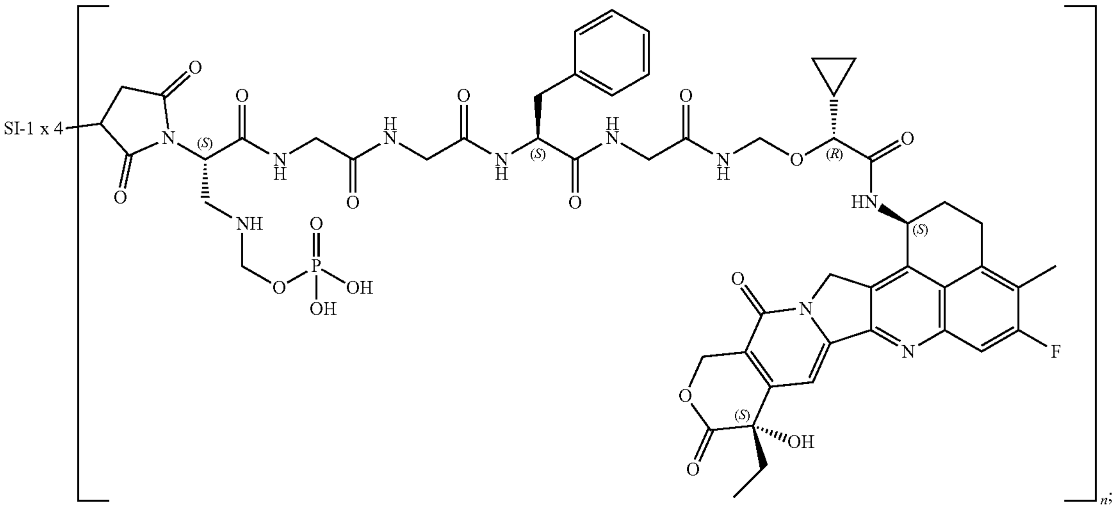
Example 262
ADC-167 was prepared according to the general-purpose coupling method of Example 94,
ADC-167
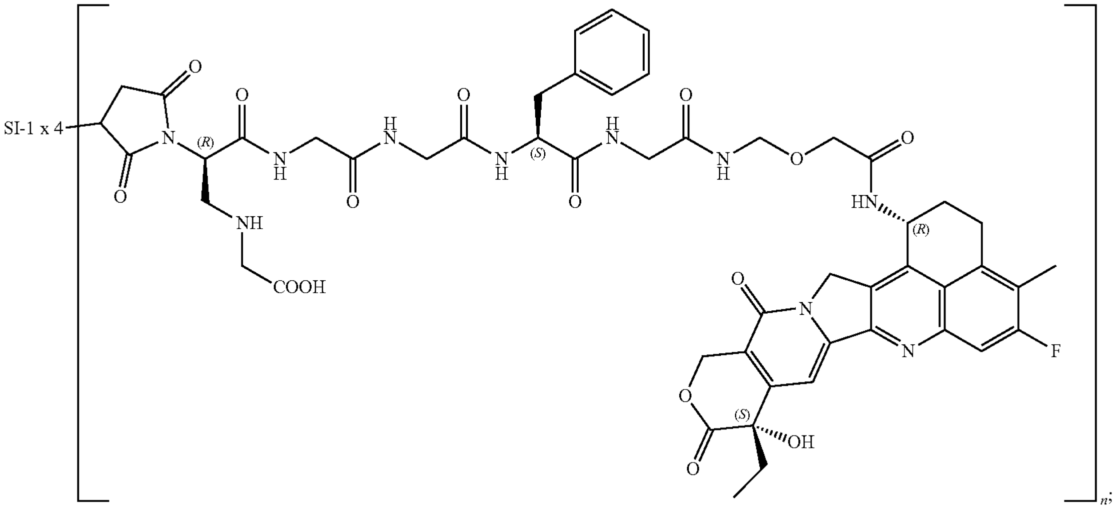
Example 263
ADC-168 was prepared according to the general-purpose coupling method of Example 94, ADC-168
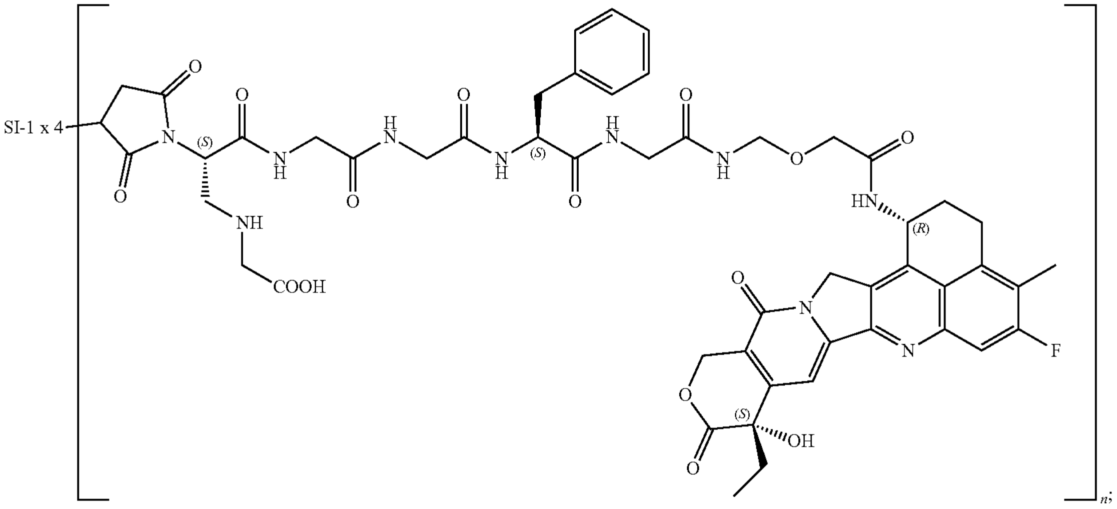
Example 264
ADC-169 was prepared according to the general-purpose coupling method of Example 94,
ADC-169
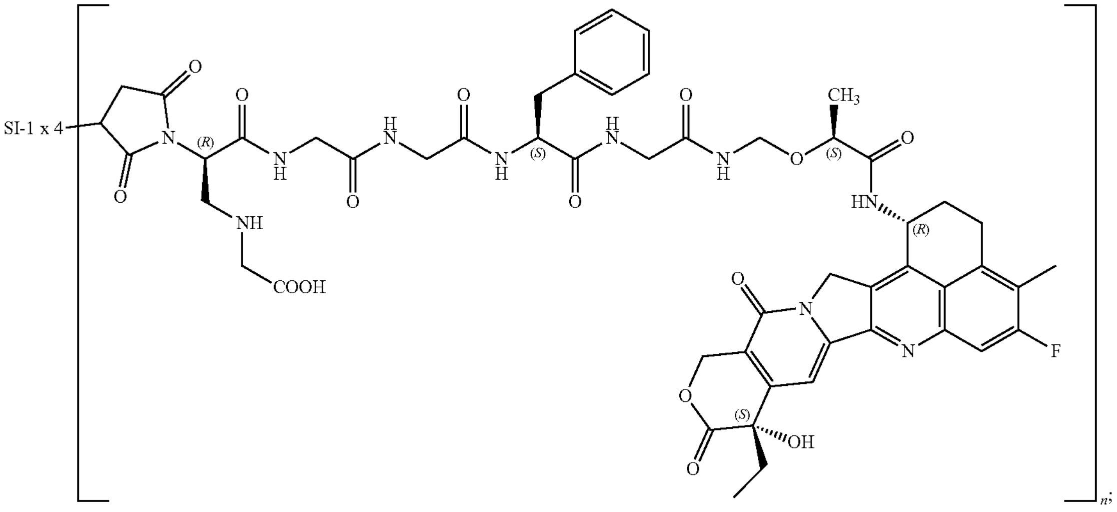
Example 265
ADC-170 was prepared according to the general-purpose coupling method of Example 94, ADC-170
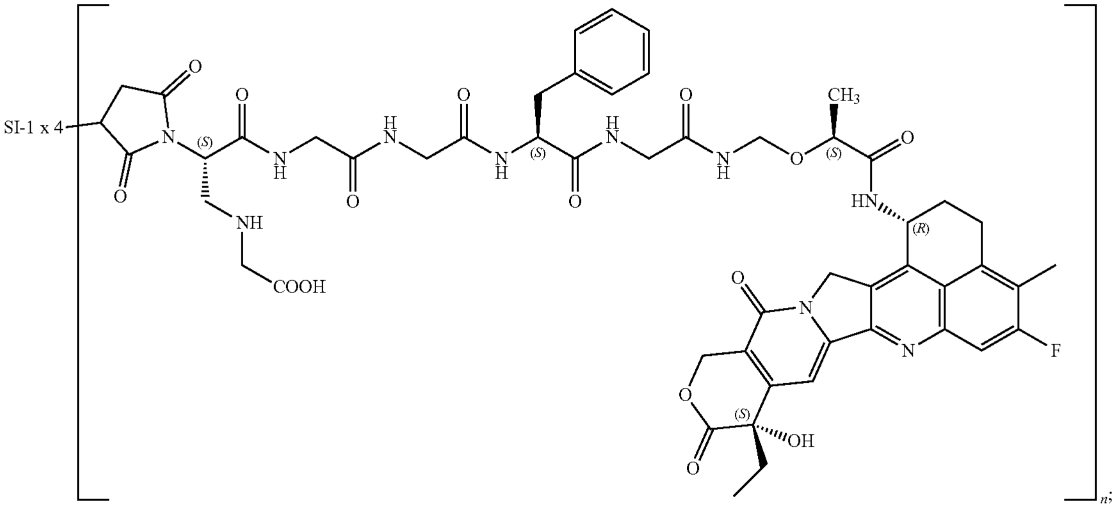
Example 266
ADC-171 was prepared according to the general-purpose coupling method of Example 94,
ADC-171
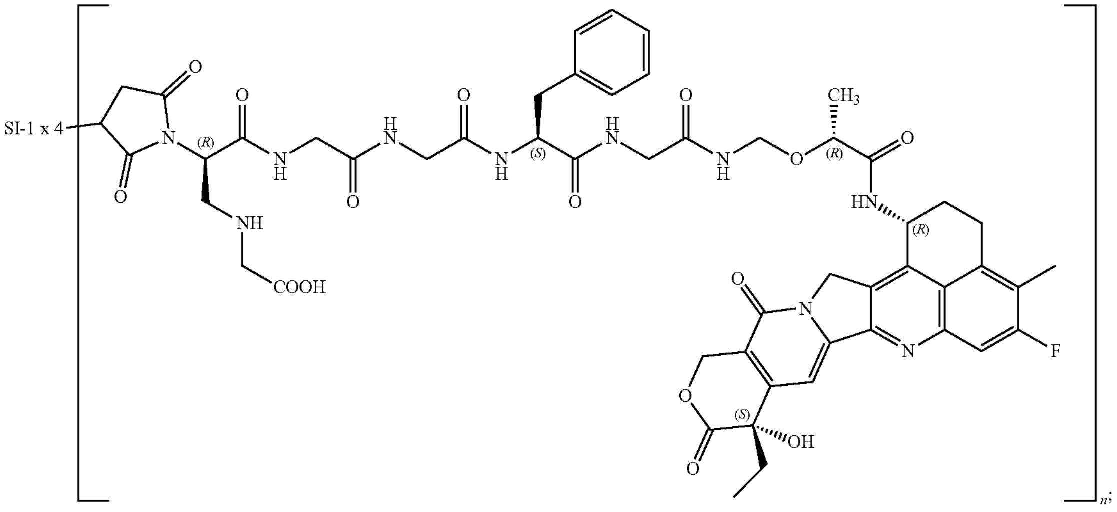
Example 267
ADC-172 was prepared according to the general-purpose coupling method of Example 94, ADC-172
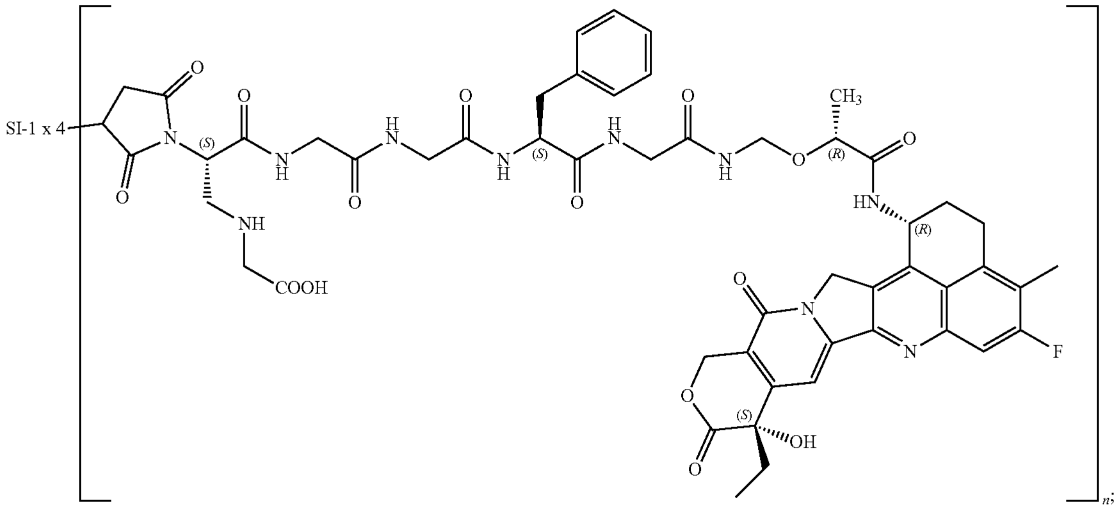
Example 268
ADC-173 was prepared according to the general-purpose coupling method of Example 94,
ADC-173
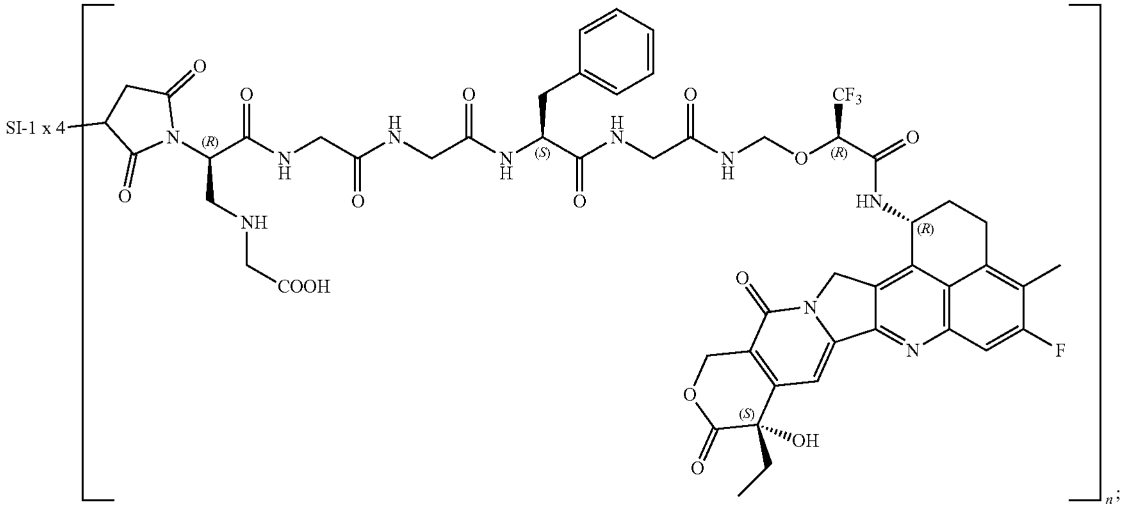
Example 269
ADC-174 was prepared according to the general-purpose coupling method of Example 94, ADC-174
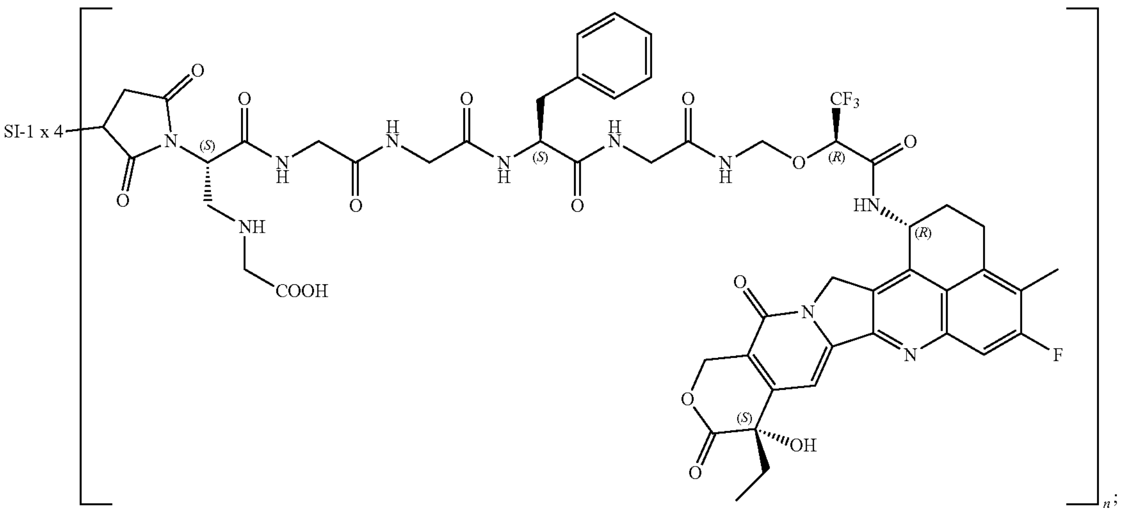
Example 270
ADC-175 was prepared according to the general-purpose coupling method of Example 94,
ADC-175
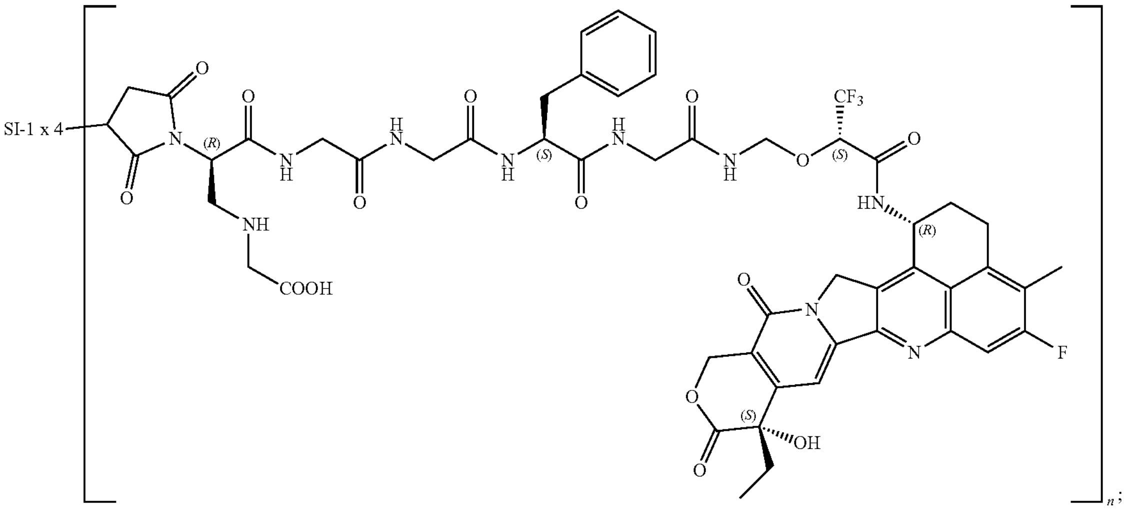
Example 271
ADC-176 was prepared according to the general-purpose coupling method of Example 94, ADC-176
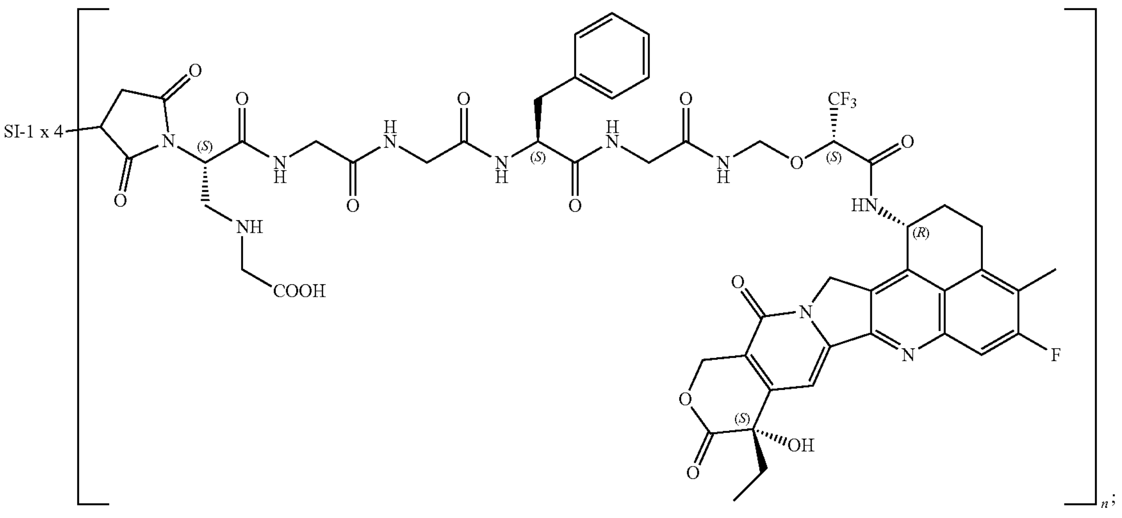
Example 272
ADC-177 was prepared according to the general-purpose coupling method of Example 94,
ADC-177
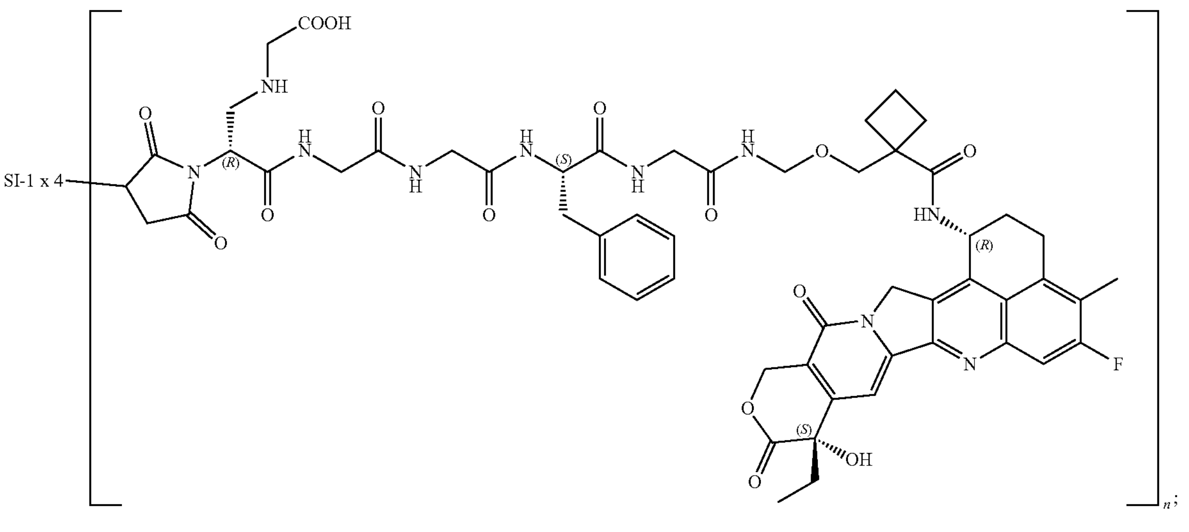
Example 273
ADC-178 was prepared according to the general-purpose coupling method of Example 94, ADC-178
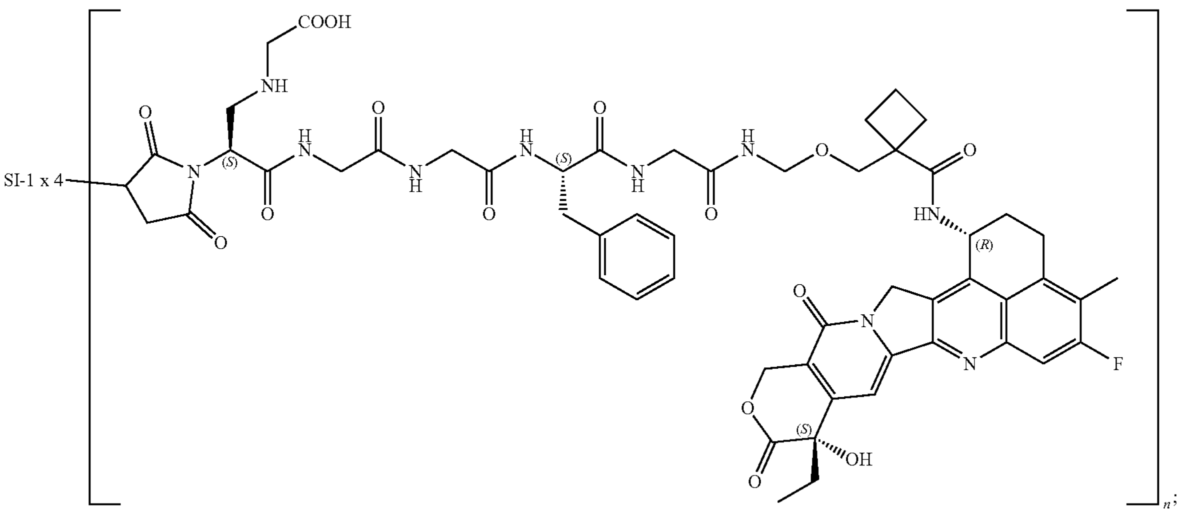
Example 274
ADC-179 was prepared according to the general-purpose coupling method of Example 94,
ADC-179
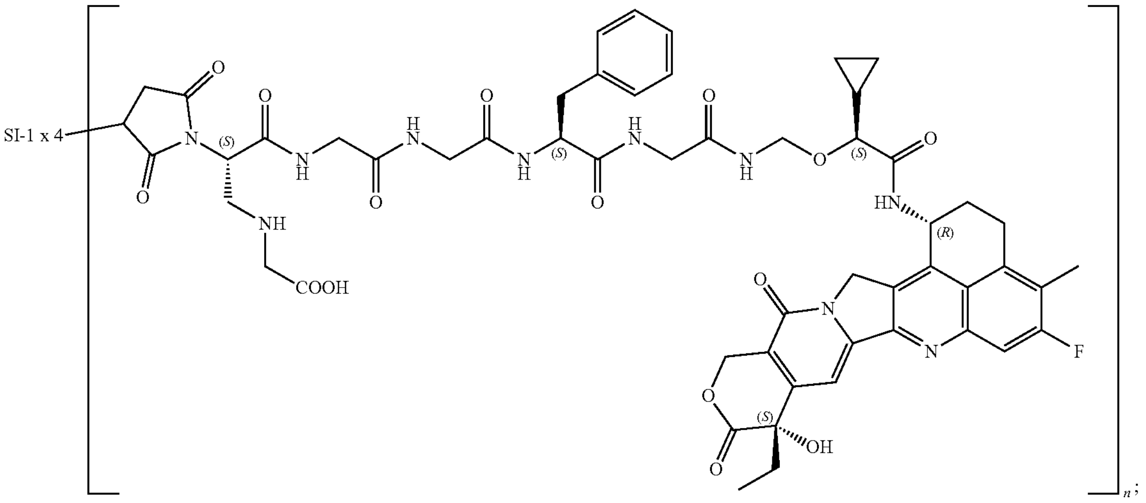
Example 275
ADC-180 was prepared according to the general-purpose coupling method of Example 94, ADC-180
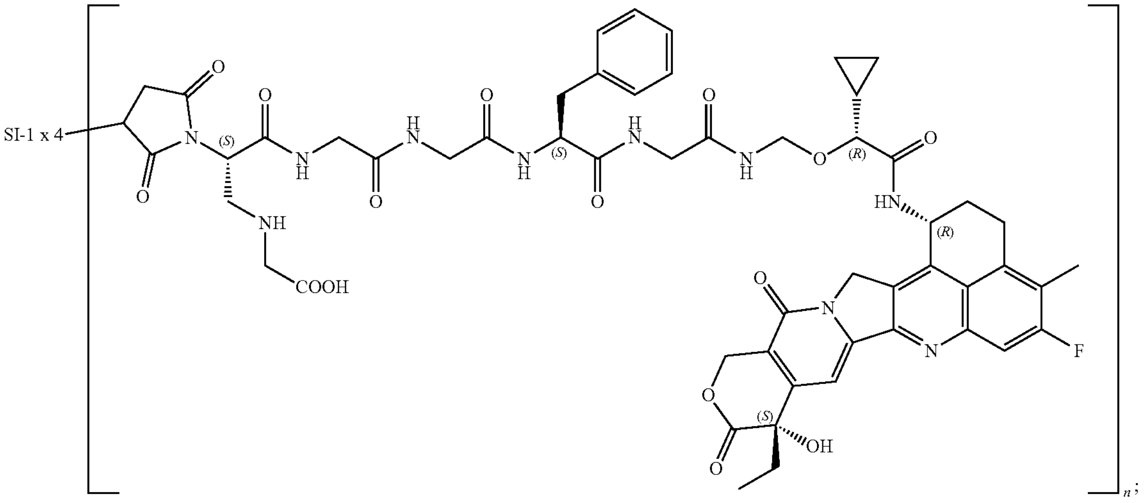
Example 276
ADC-181 was prepared according to the general-purpose coupling method of Example 94,
ADC-181
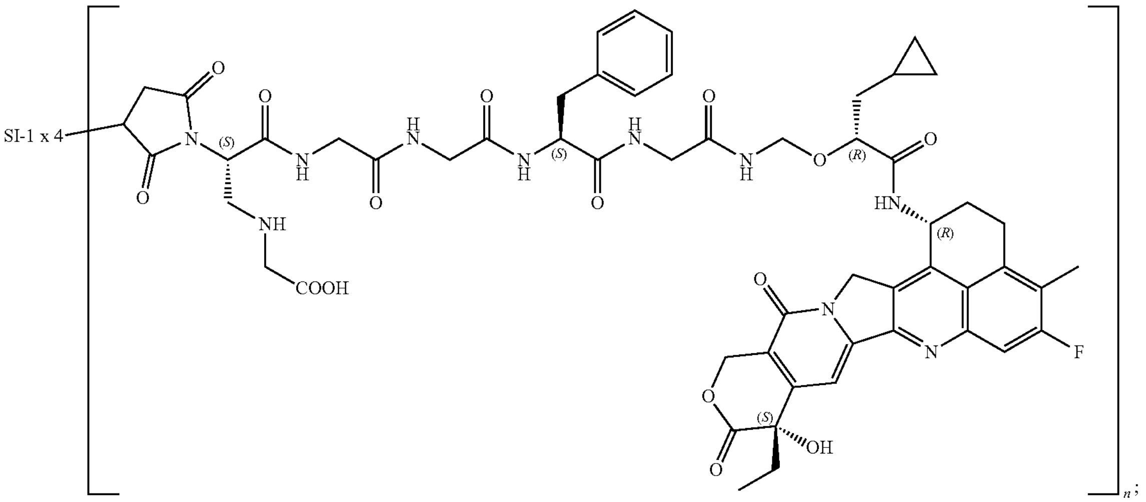
Example 277
ADC-182 was prepared according to the general-purpose coupling method of Example 94, ADC-182
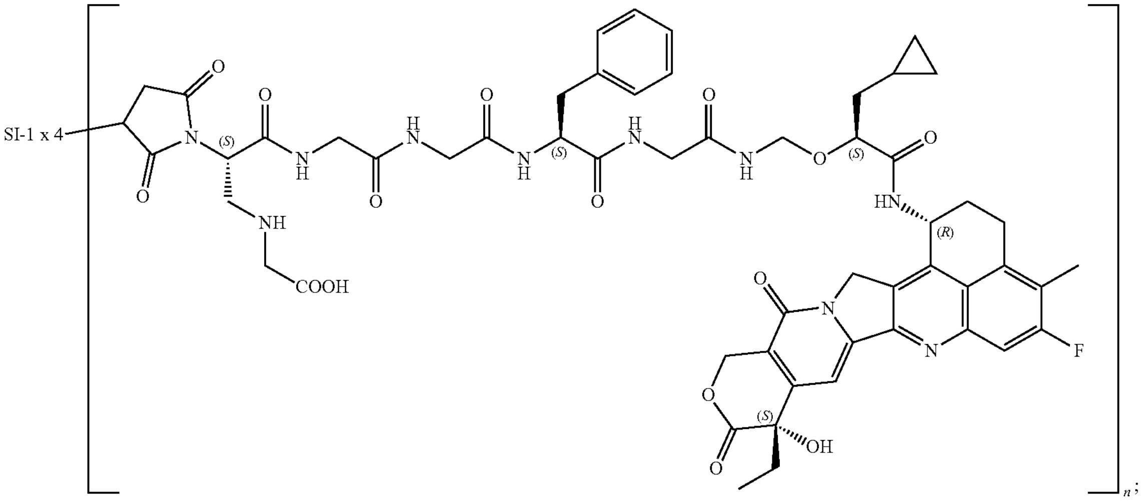
Example 278
ADC-183 was prepared according to the general-purpose coupling method of Example 94,
ADC-183
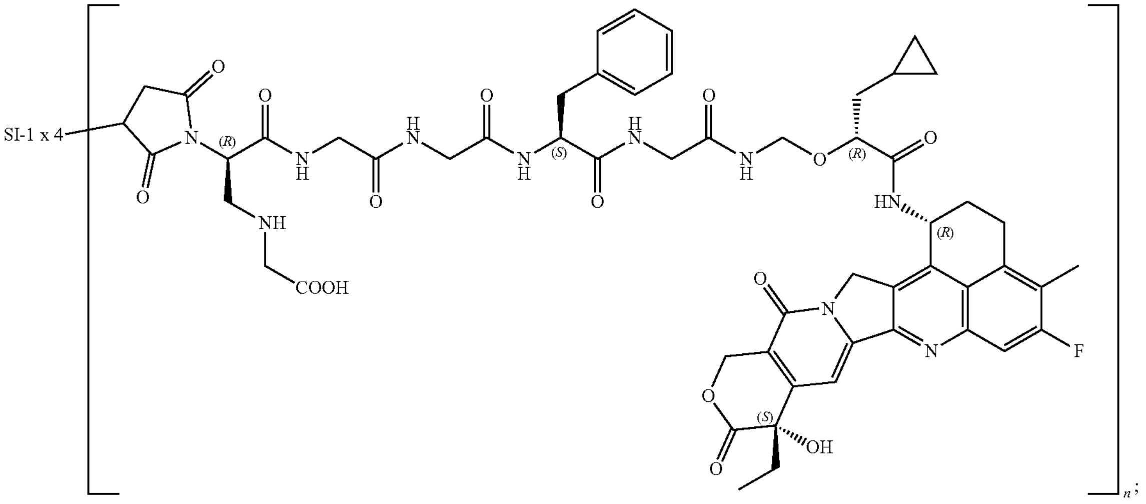
Example 279
ADC-184 was prepared according to the general-purpose coupling method of Example 94, ADC-184
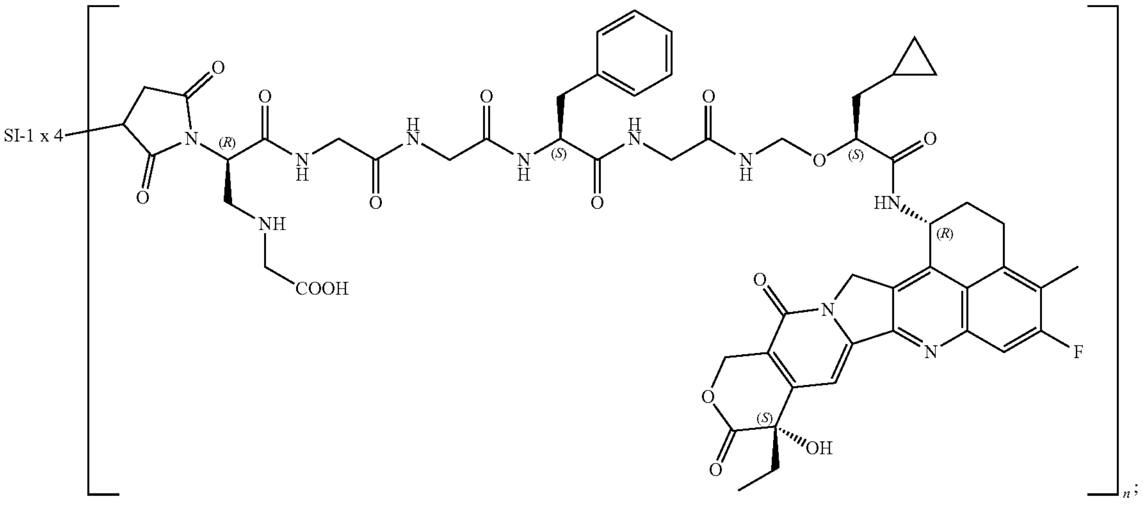
Example 280
ADC-185 was prepared according to the general-purpose coupling method of Example 94,
ADC-185
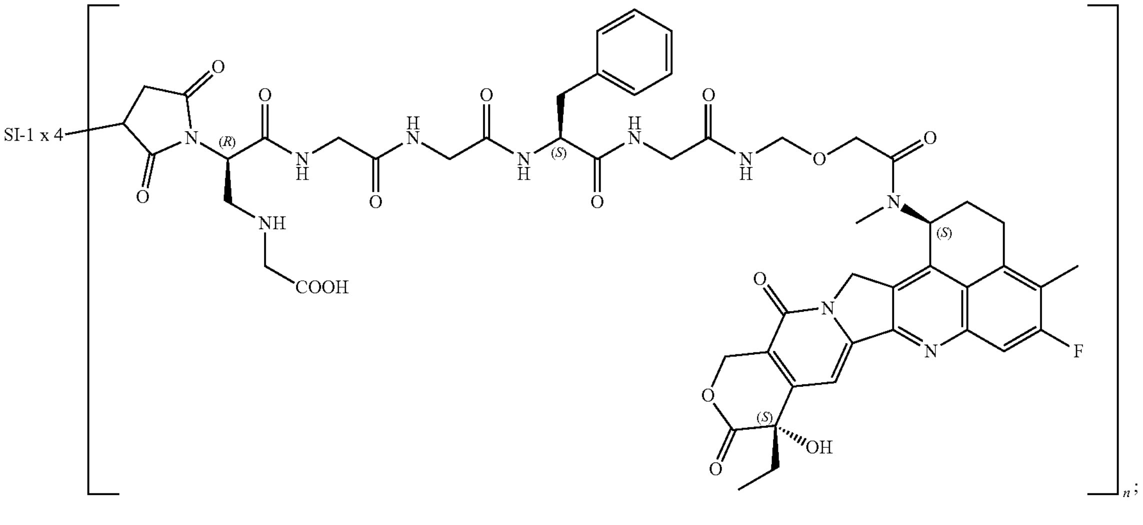
Example 281
ADC-186 was prepared according to the general-purpose coupling method of Example 94, ADC-186
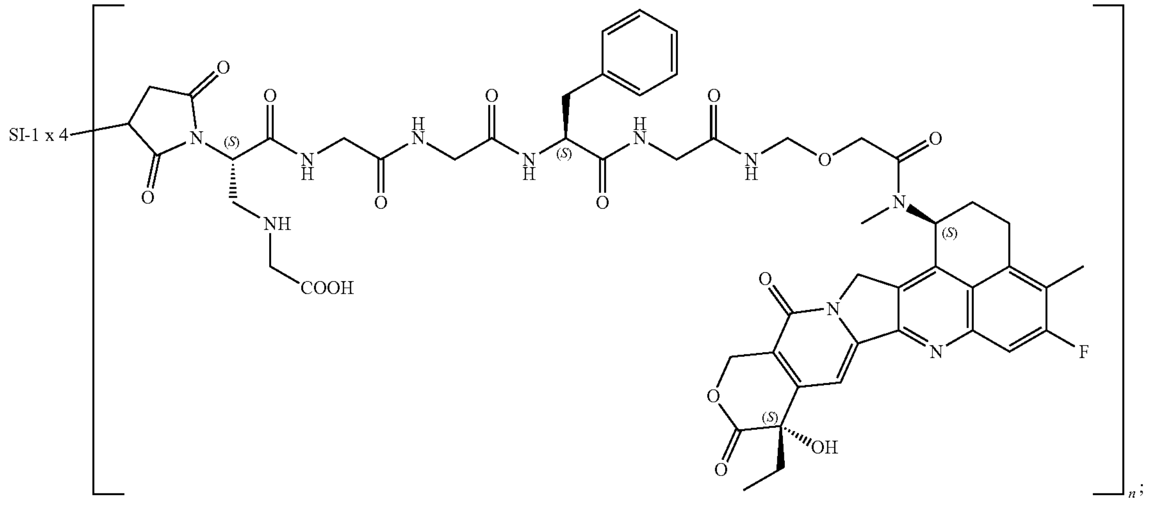
Example 282
ADC-187 was prepared according to the general-purpose coupling method of Example 94,
ADC-187
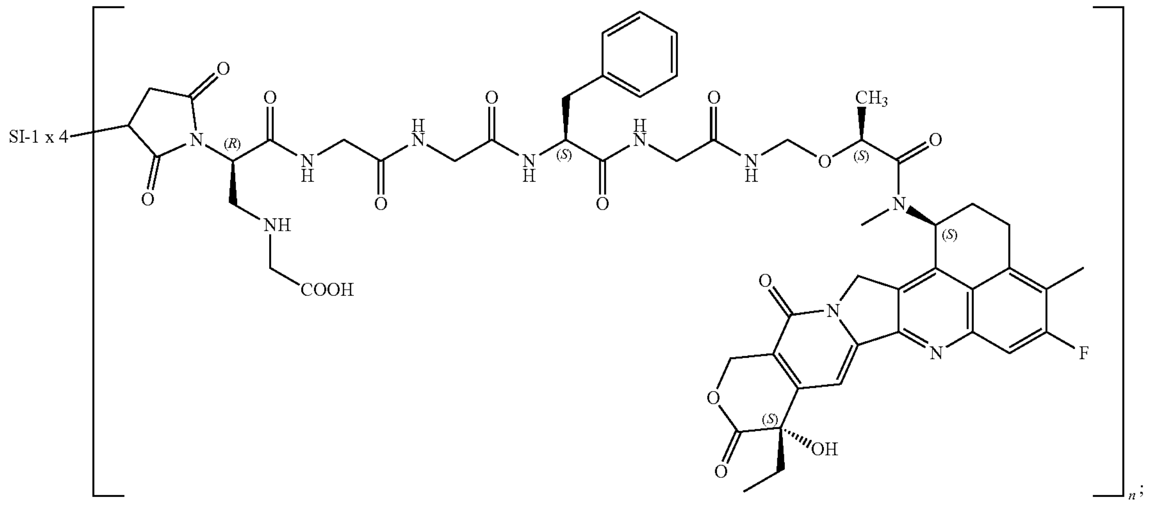
Example 283
ADC-188 was prepared according to the general-purpose coupling method of Example 94, ADC-188
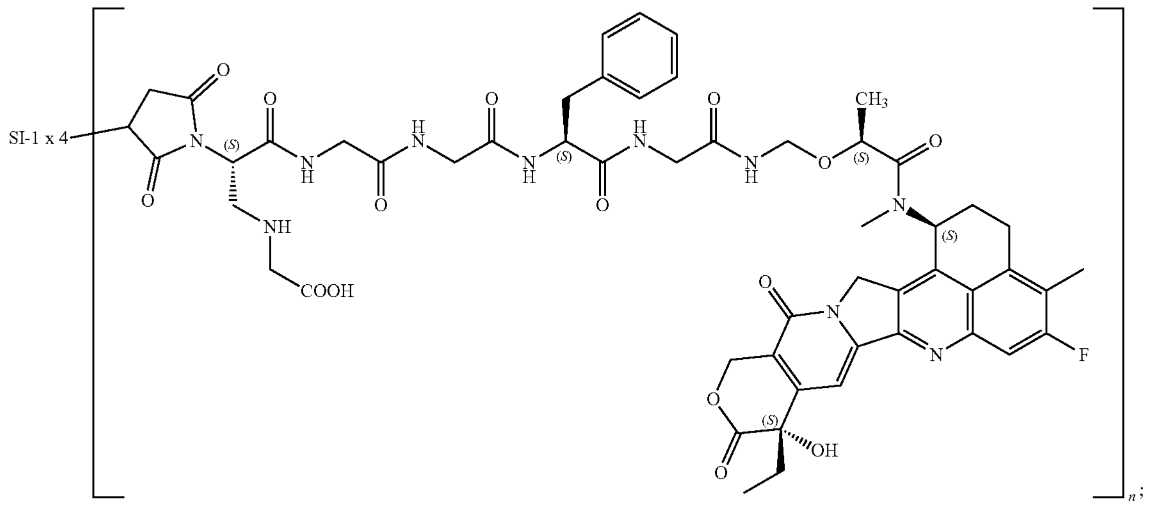
Example 284
ADC-189 was prepared according to the general-purpose coupling method of Example 94,
ADC-189
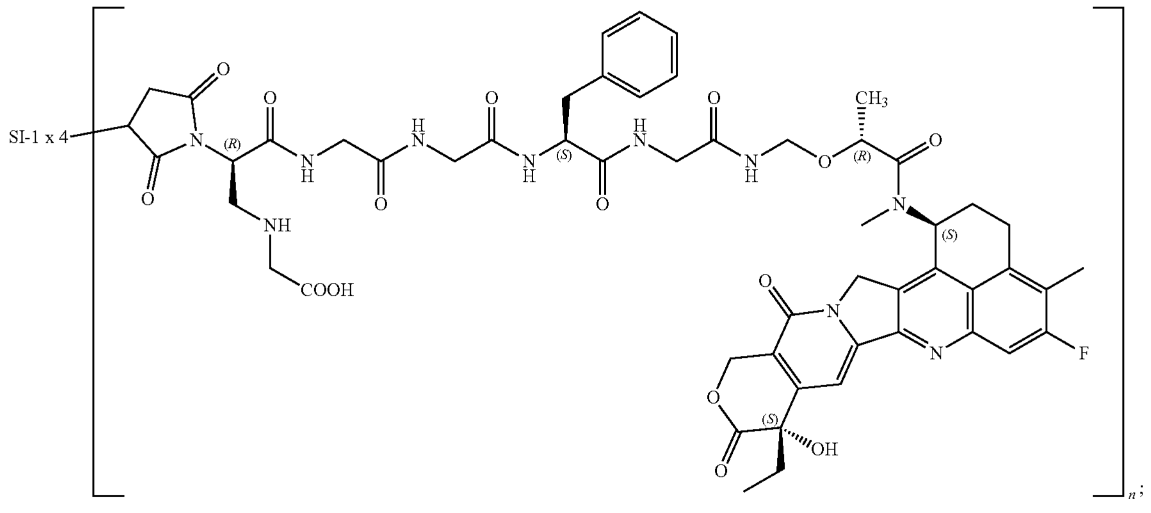
Example 285
ADC-190 was prepared according to the general-purpose coupling method of Example 94, ADC-190
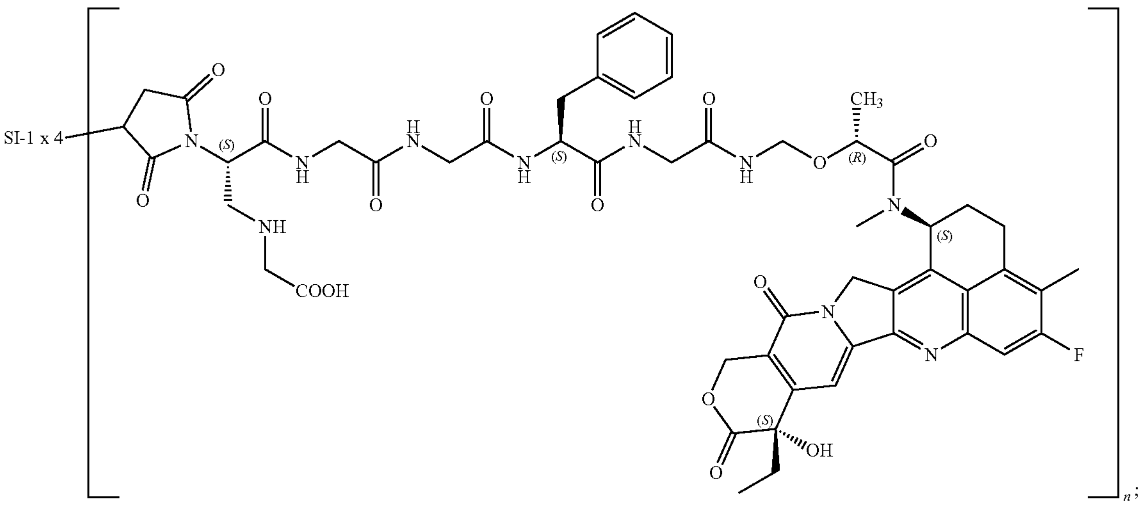
Example 286
ADC-191 was prepared according to the general-purpose coupling method of Example 94,
ADC-191
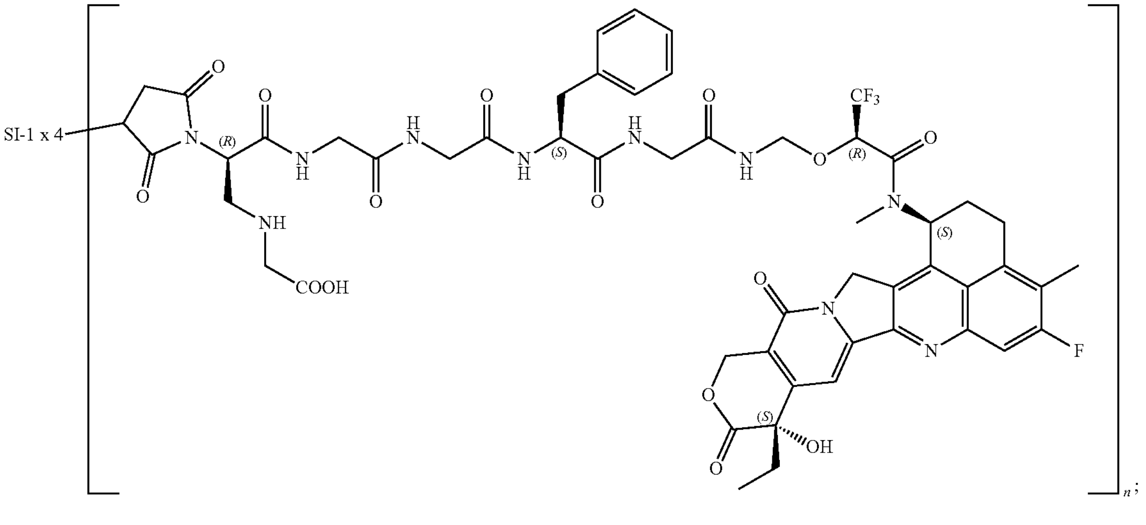
Example 287
ADC-192 was prepared according to the general-purpose coupling method of Example 94, ADC-192
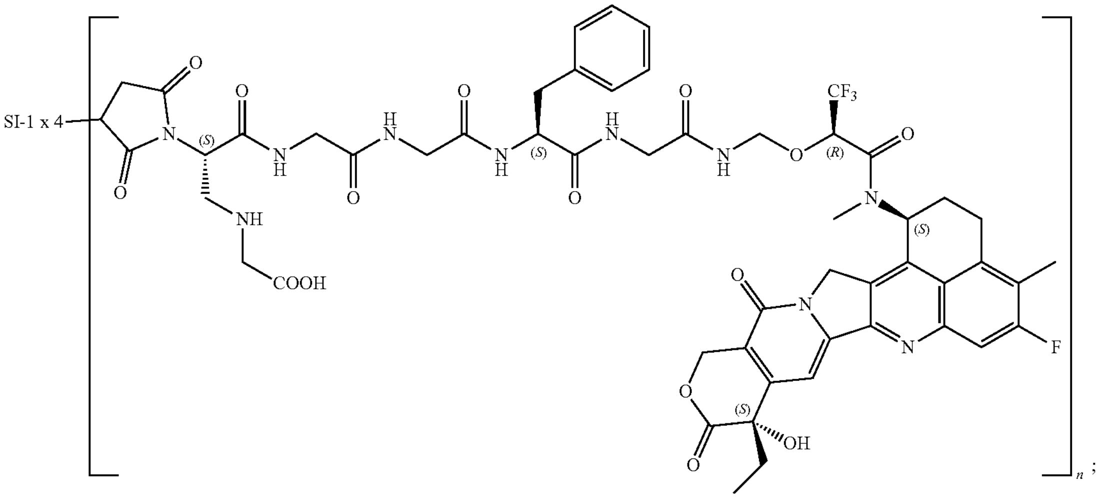
Example 288
ADC-193 was prepared according to the general-purpose coupling method of Example 94,
ADC-193
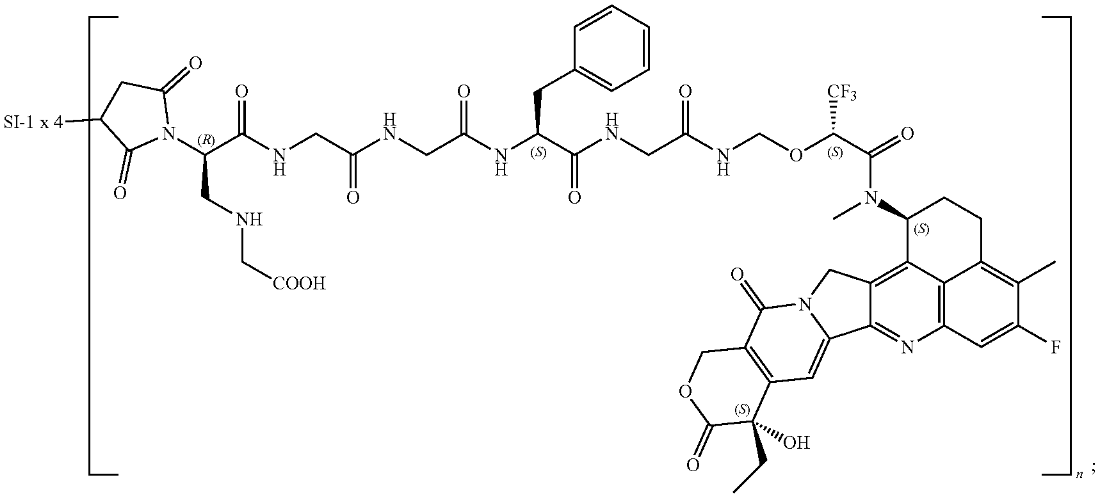
Example 289
ADC-194 was prepared according to the general-purpose coupling method of Example 94, ADC-194
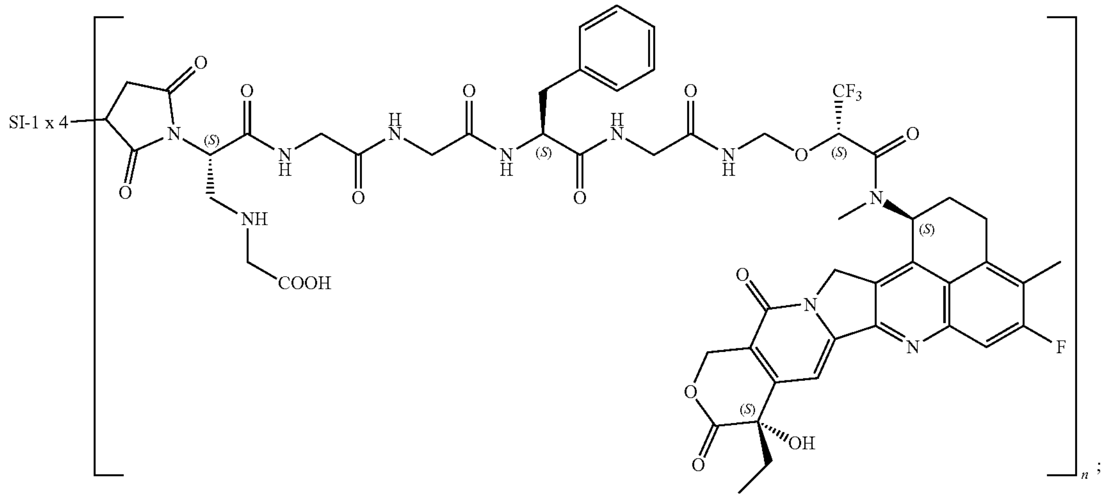
Example 290
ADC-195 was prepared according to the general-purpose coupling method of Example 94,
ADC-195
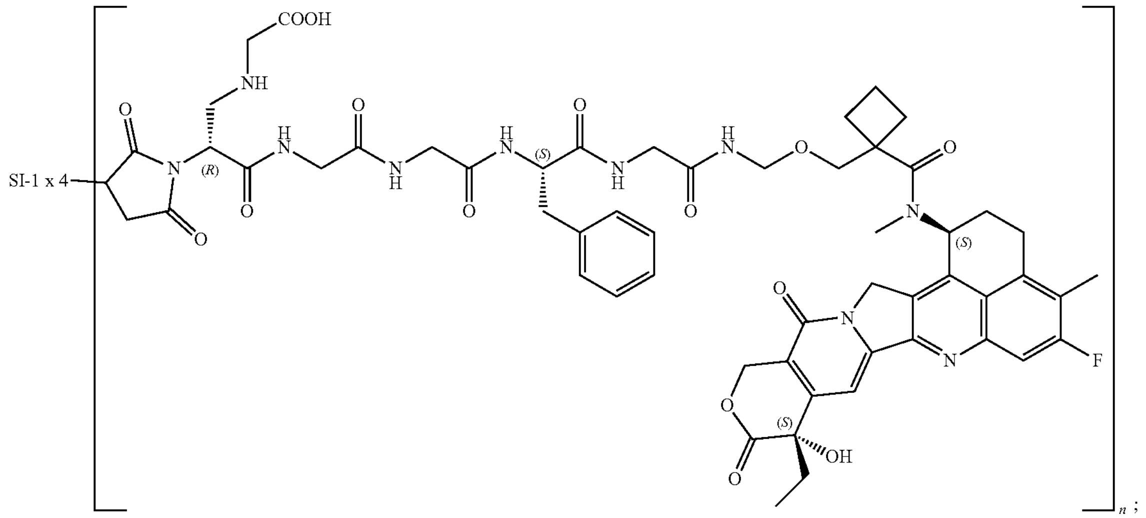
Example 291
ADC-196 was prepared according to the general-purpose coupling method of Example 94, ADC-196
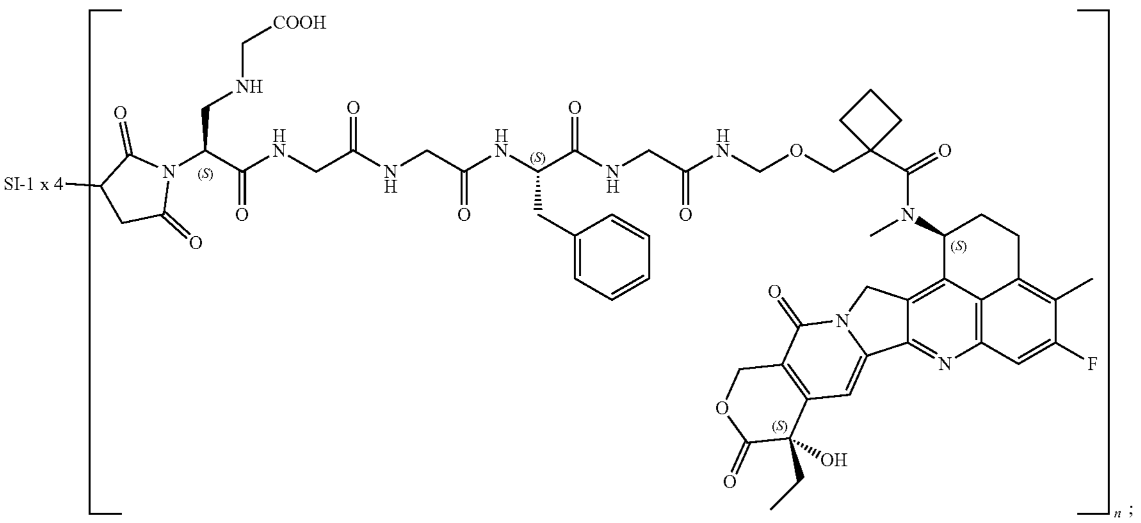
Example 292
ADC-197 was prepared according to the general-purpose coupling method of Example 94,
ADC-197
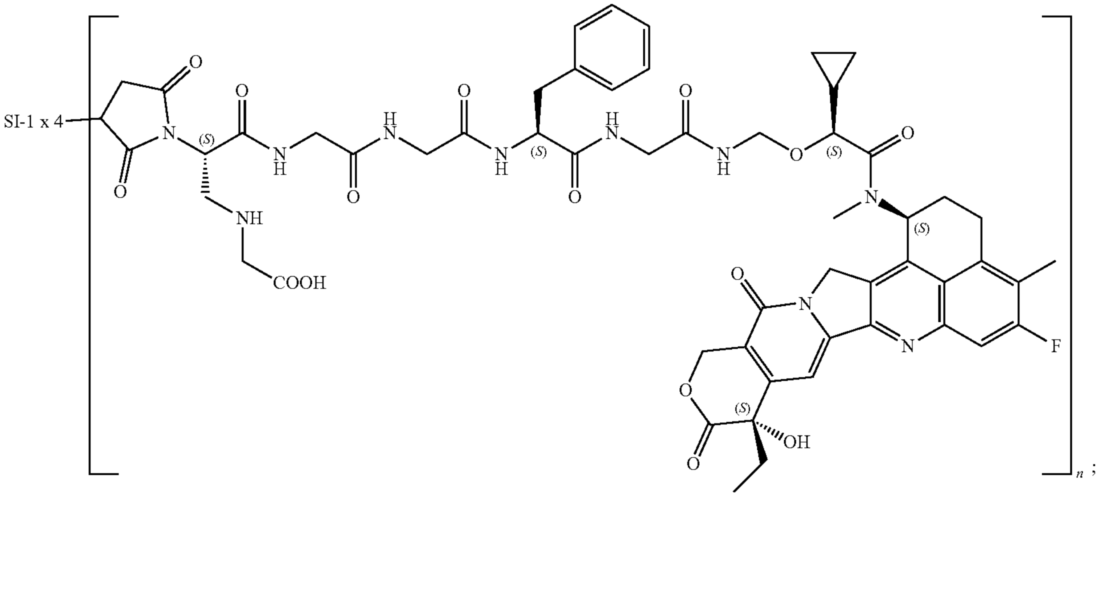
Example 293
ADC-198 was prepared according to the general-purpose coupling method of Example 94, ADC-198
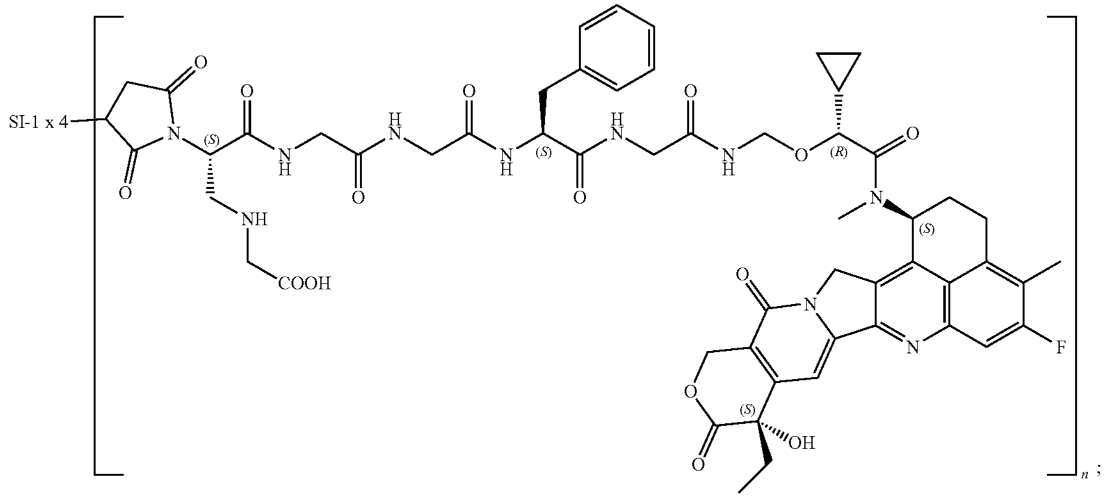
Example 294
ADC-199 was prepared according to the general-purpose coupling method of Example 94,
ADC-199
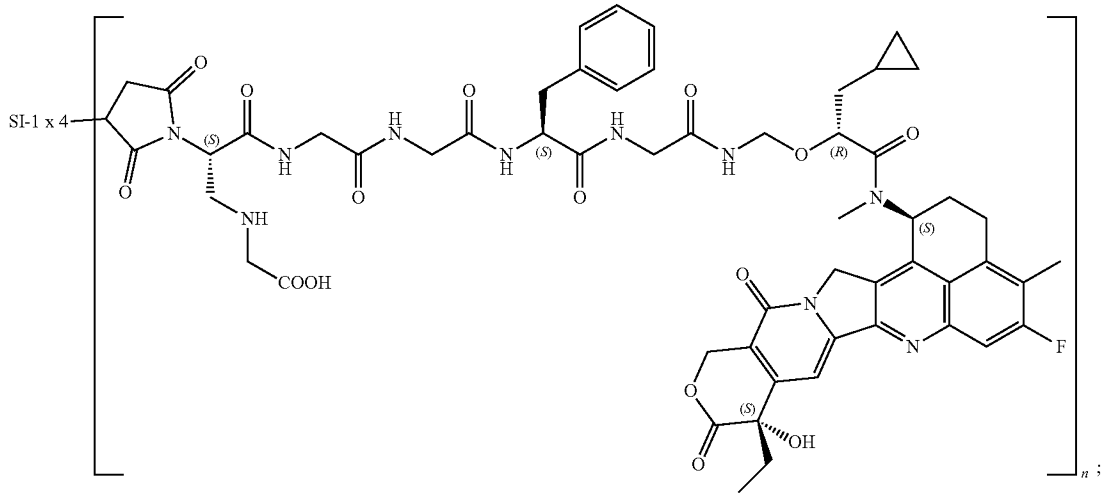
Example 295
ADC-200 was prepared according to the general-purpose coupling method of Example 94, ADC-200
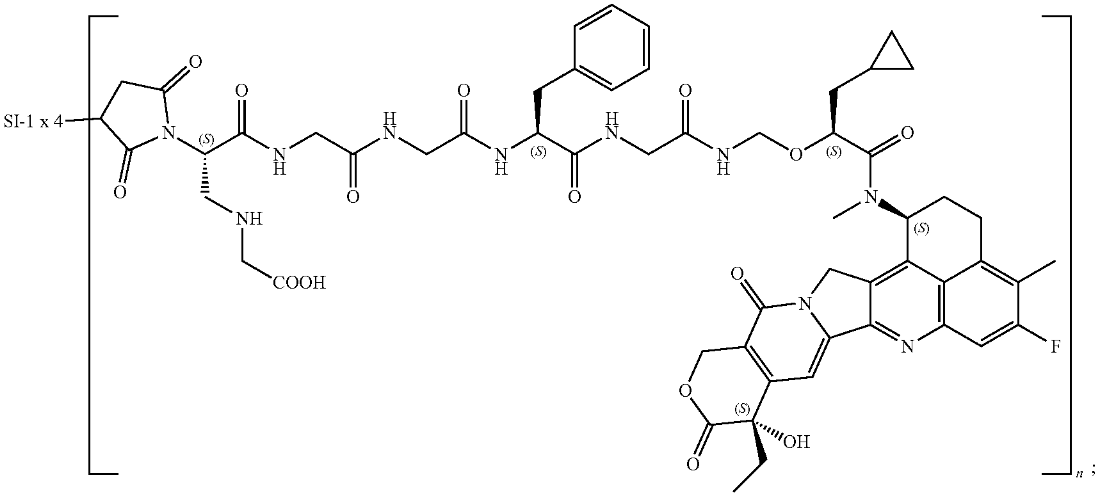
Example 296
ADC-201 was prepared according to the general-purpose coupling method of Example 94,
ADC-201
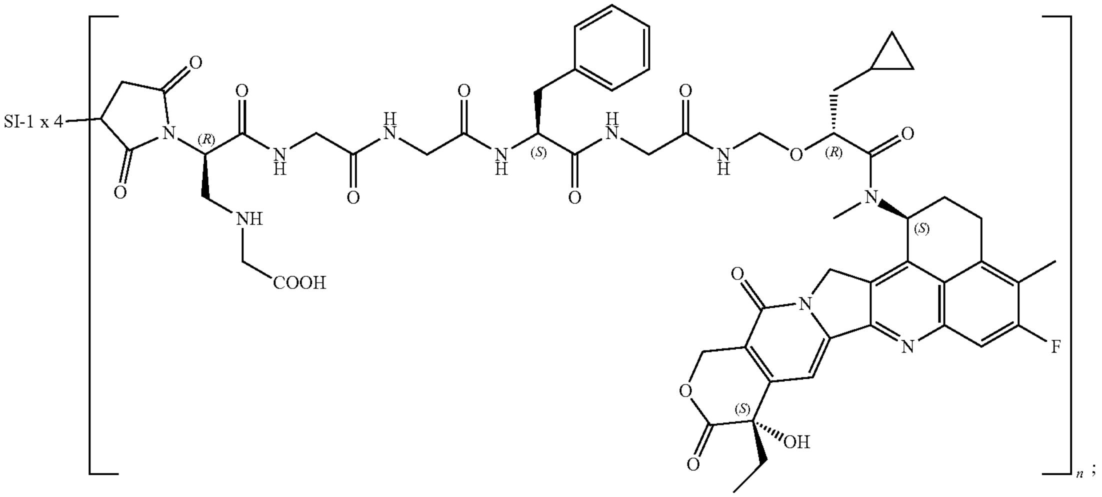
Example 297
ADC-202 was prepared according to the general-purpose coupling method of Example 94, ADC-202
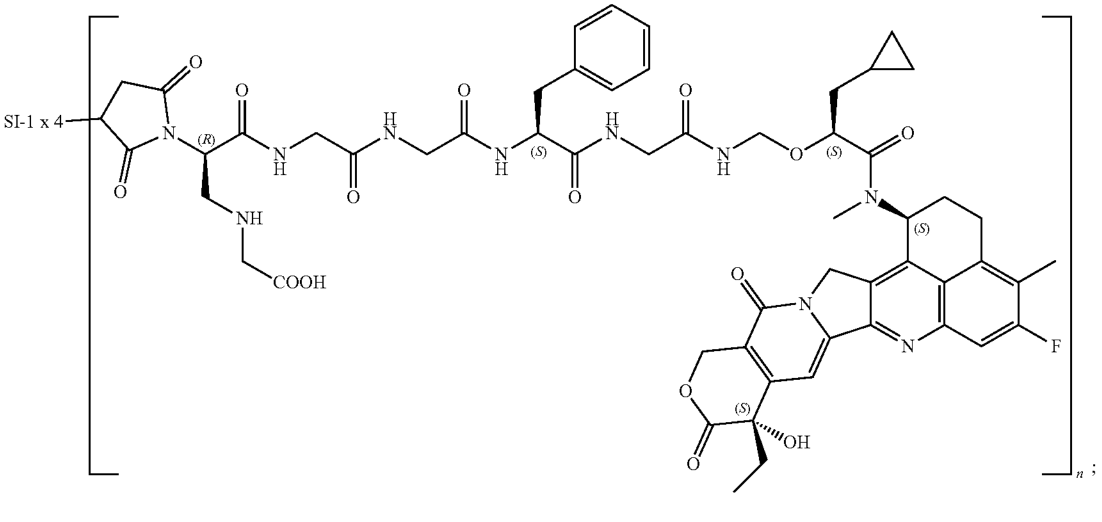
Example 298
ADC-203 was prepared according to the general-purpose coupling method of Example 94,
ADC-203
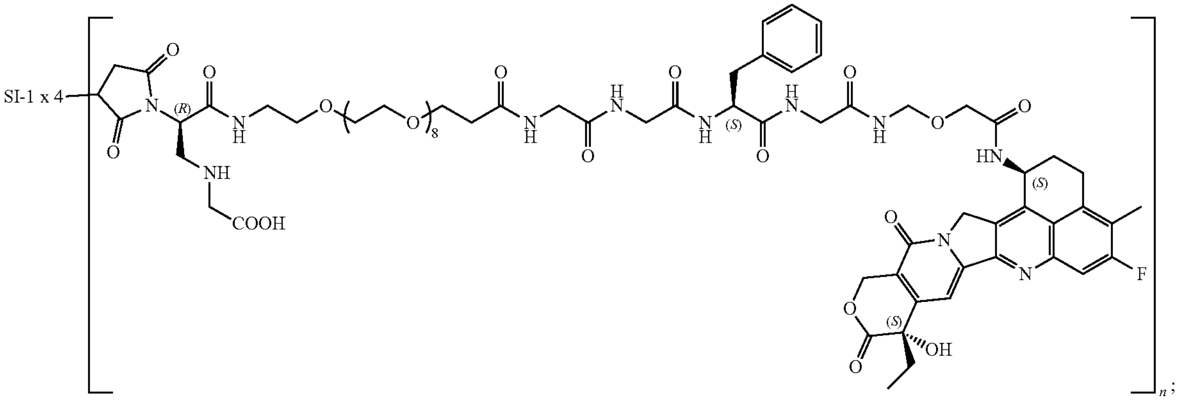
Example 299
ADC-204 was prepared according to the general-purpose coupling method of Example 94, ADC-204
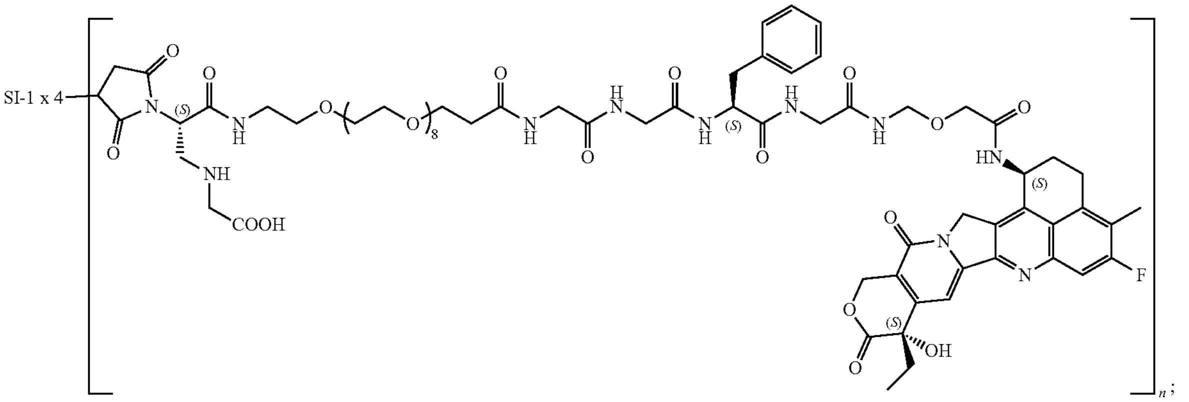
Example 300
ADC-205 was prepared according to the general-purpose coupling method of Example 94,
ADC-205
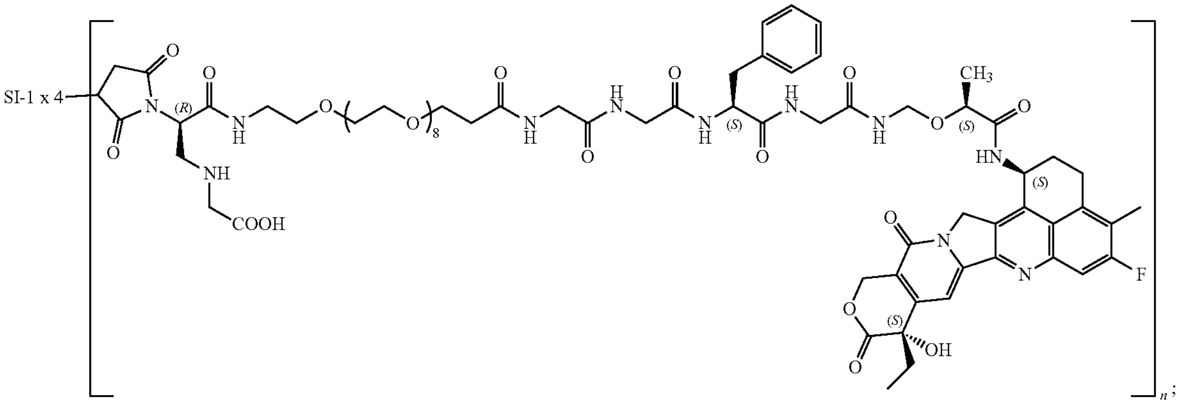
Example 301
ADC-206 was prepared according to the general-purpose coupling method of Example 94, ADC-206
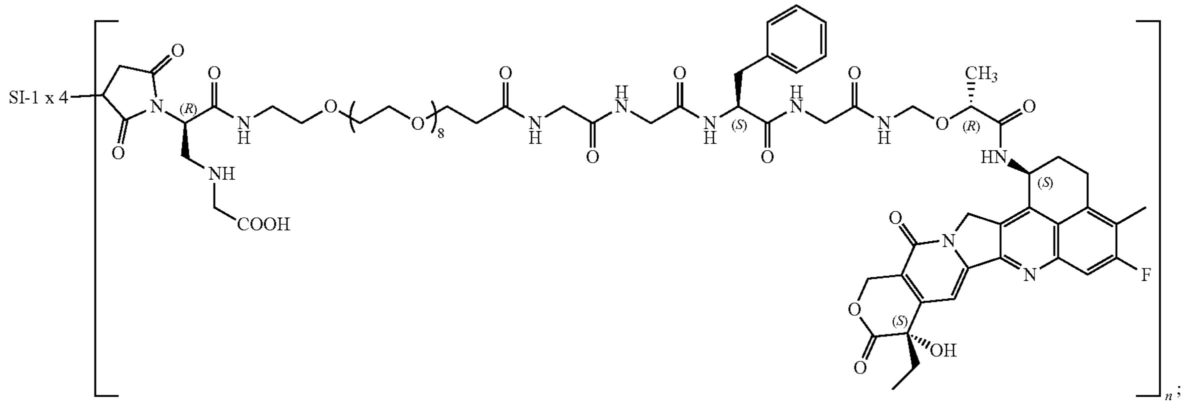
Example 302
ADC-207 was prepared according to the general-purpose coupling method of Example 94,
ADC-207
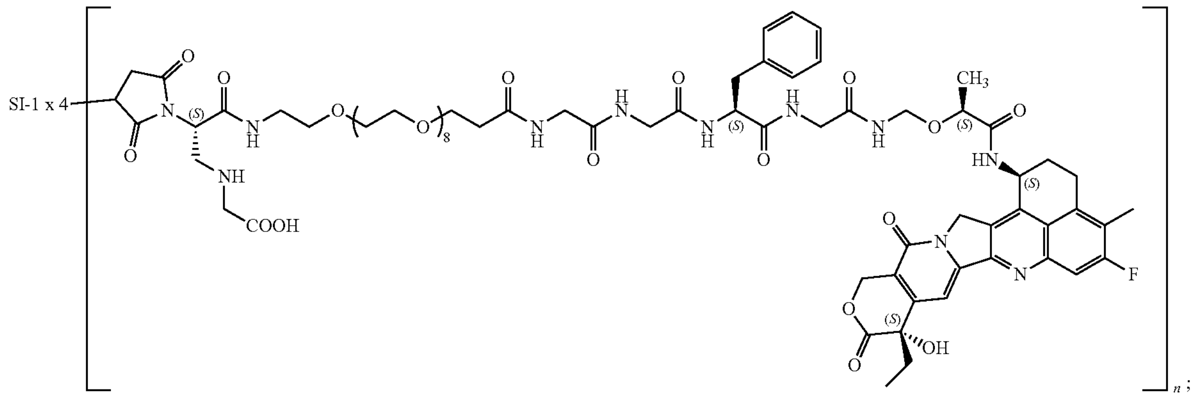
Example 303
ADC-208 was prepared according to the general-purpose coupling method of Example 94, ADC-208
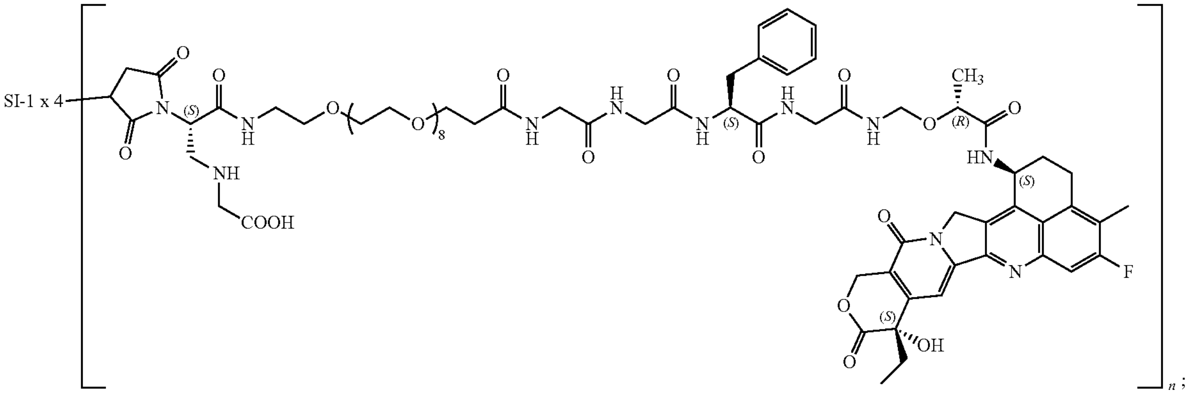
Example 304
ADC-209 was prepared according to the general-purpose coupling method of Example 94,
ADC-209
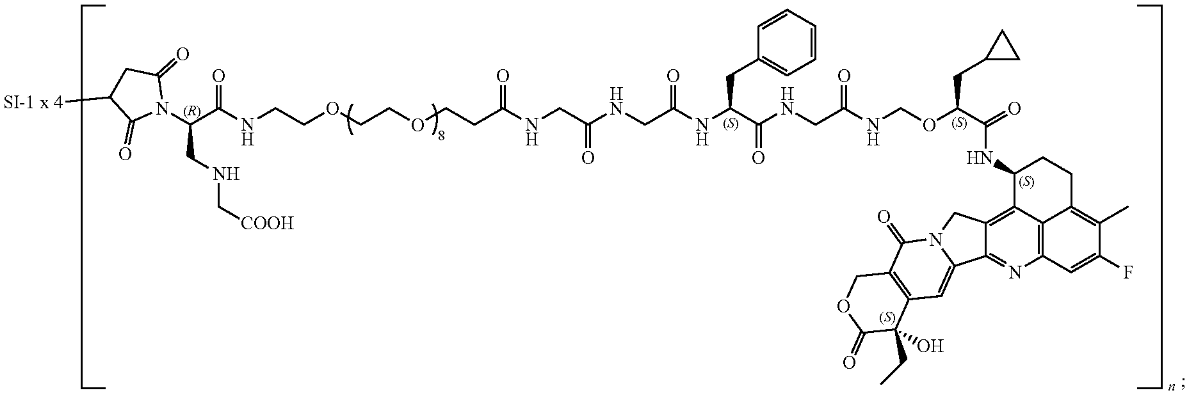
Example 305
ADC-210 was prepared according to the general-purpose coupling method of Example 94, ADC-210
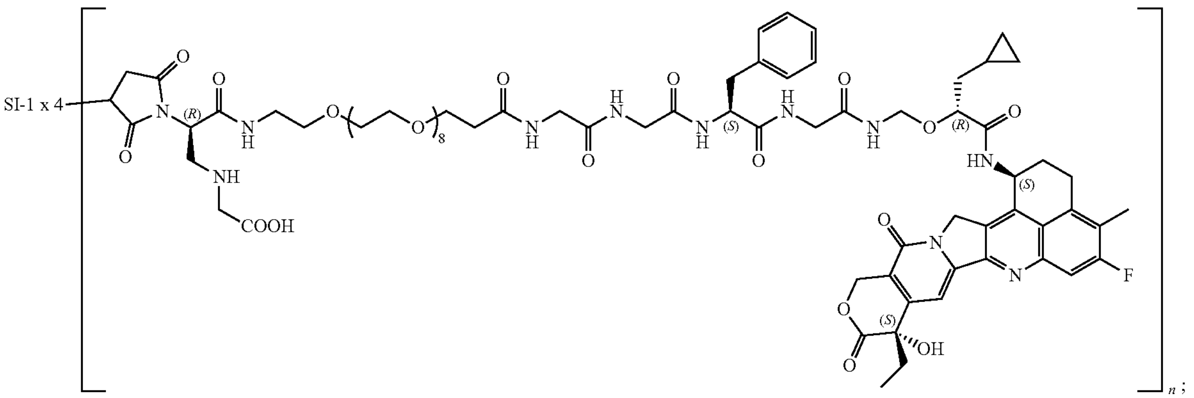
Example 306
ADC-211 was prepared according to the general-purpose coupling method of Example 94,
ADC-211
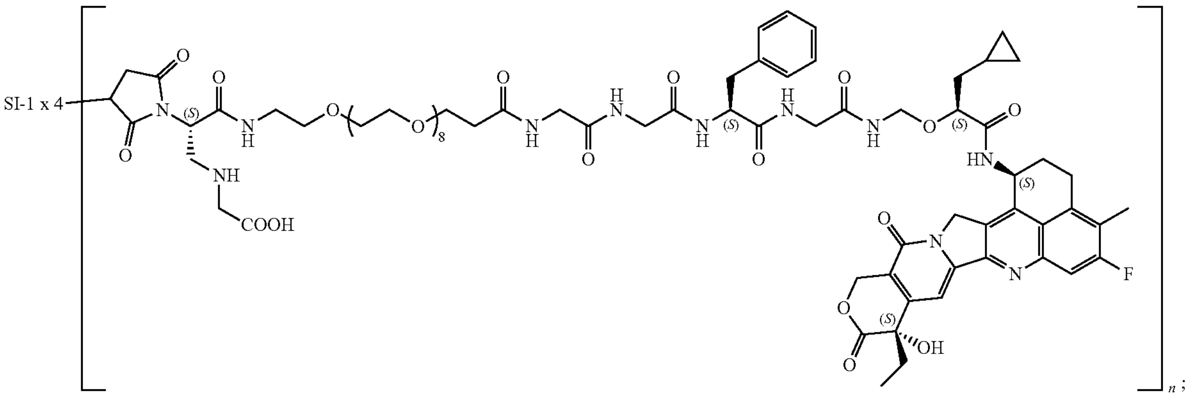
Example 307
ADC-212 was prepared according to the general-purpose coupling method of Example 94, ADC-212
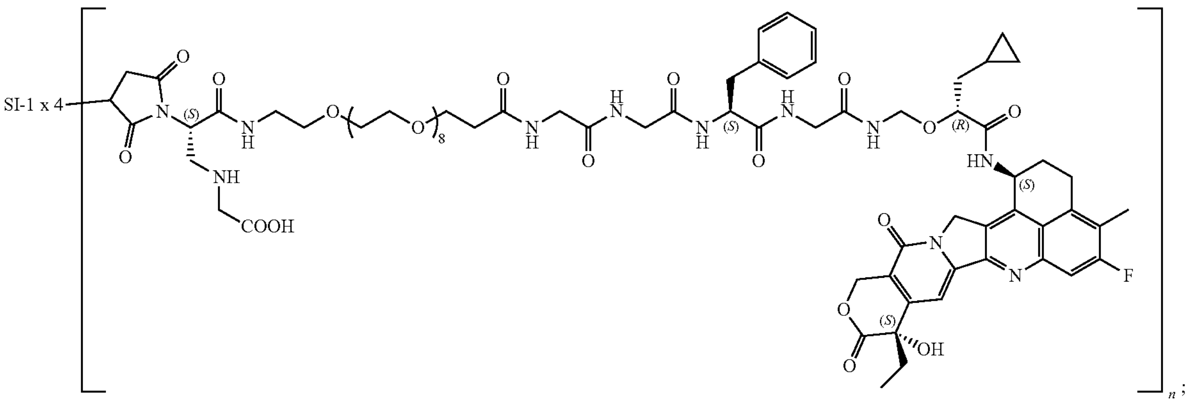
Example 308
ADC-213 was prepared from compound 45 according to the general-purpose coupling method of Example 94,
ADC-213
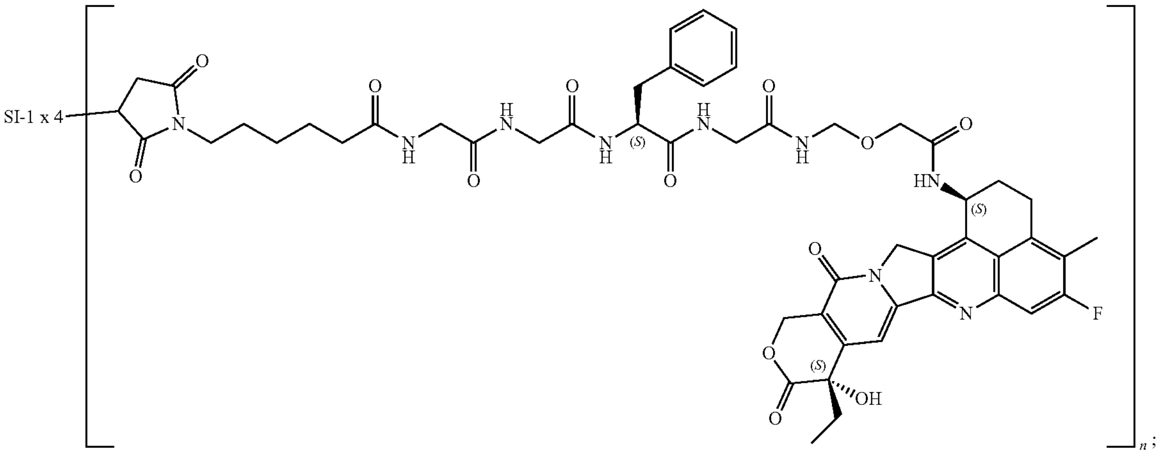
Example 309
ADC-214 was prepared from compound 5A according to the general-purpose coupling method of Example 93, ADC-214
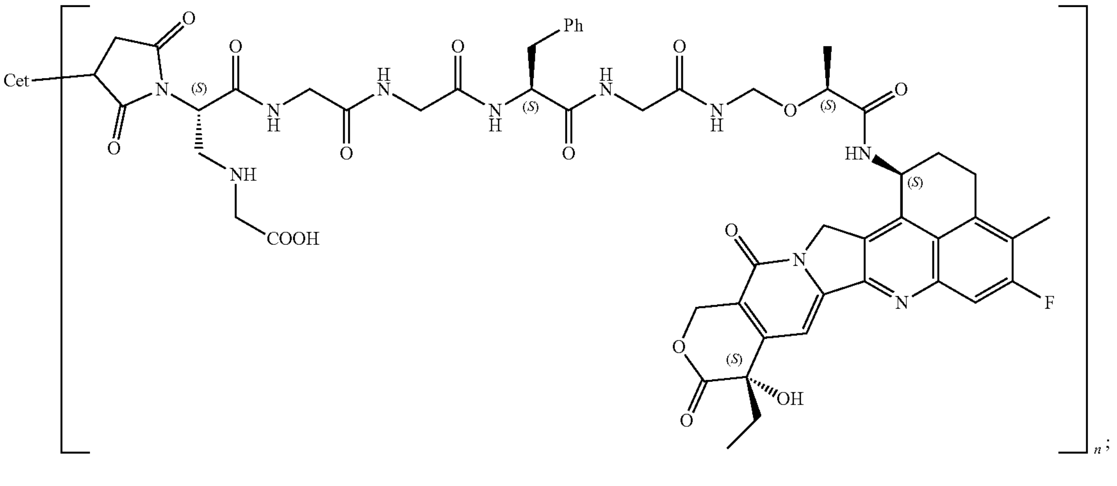
Example 310
ADC-215 of HER3 was prepared from compound 5A according to the general-purpose coupling method of Example 93,
ADC-215
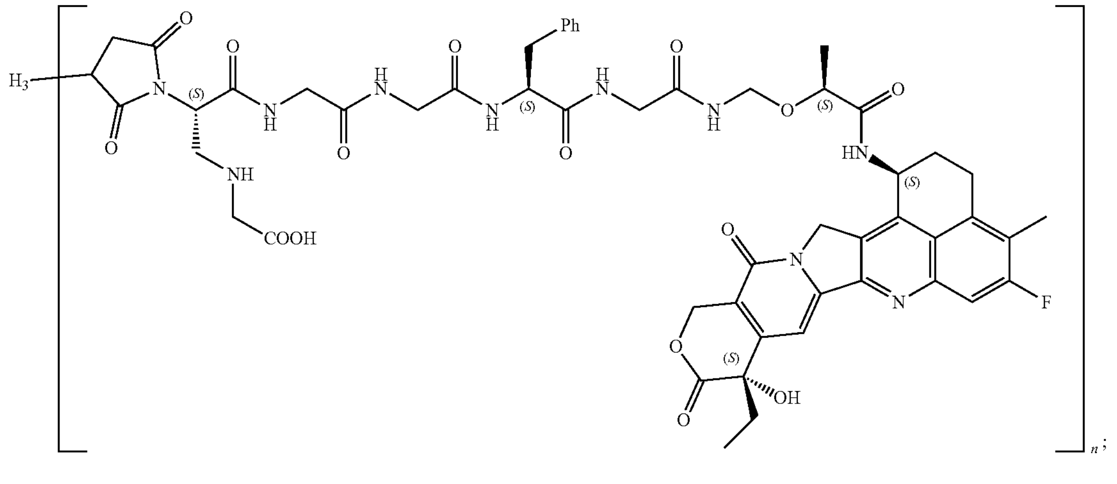
where the H3 antibody is the portion of the SI-1×6.4 antibody knockout targeting EGFR.
Example 311
ADC-216 to ADC-223 were prepared according to the general-purpose coupling method of Example 93, ADC-216
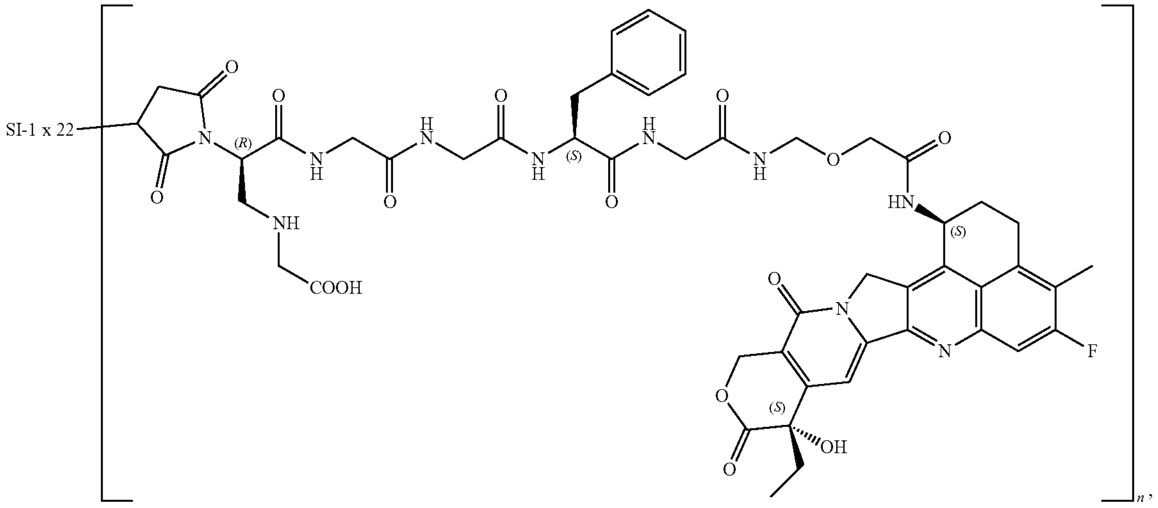
ADC-217
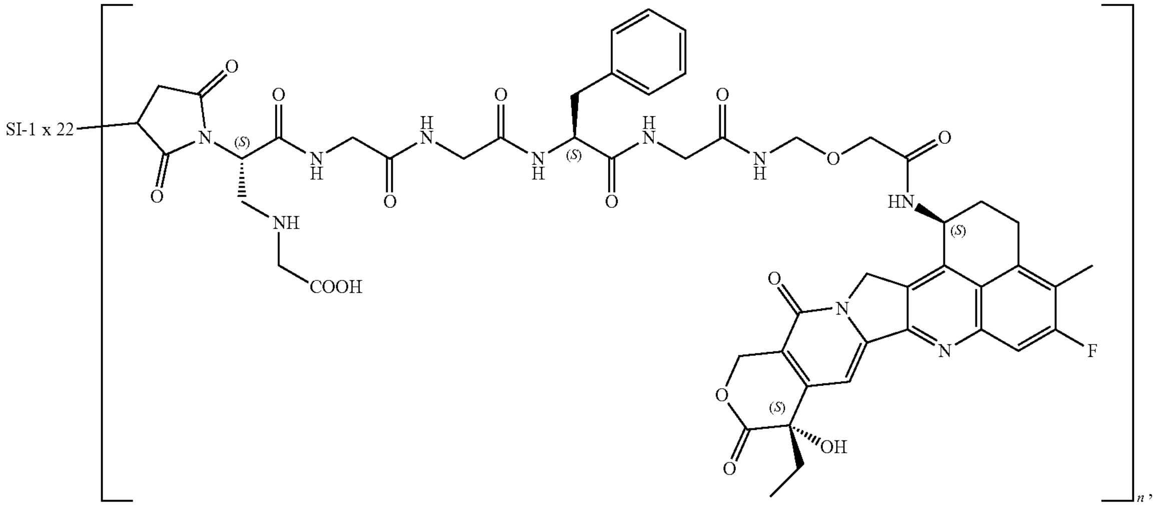
ADC-218
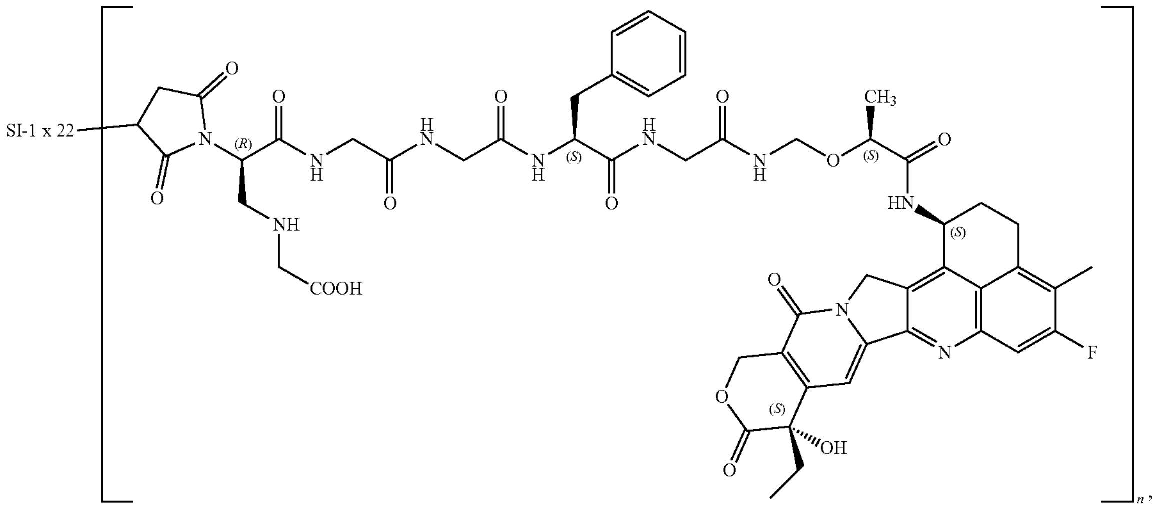

-continued
ADC-219
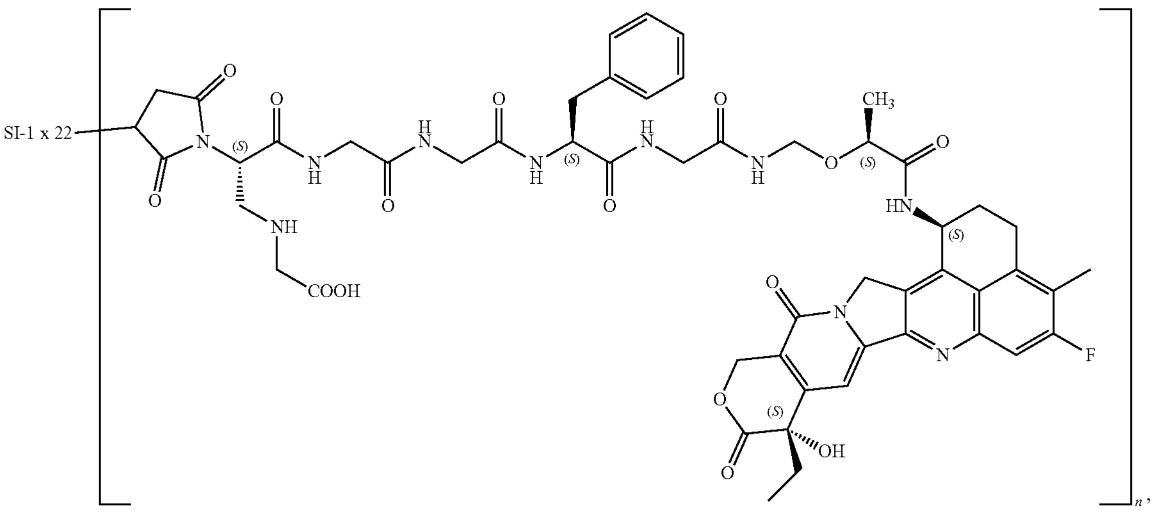
ADC-220
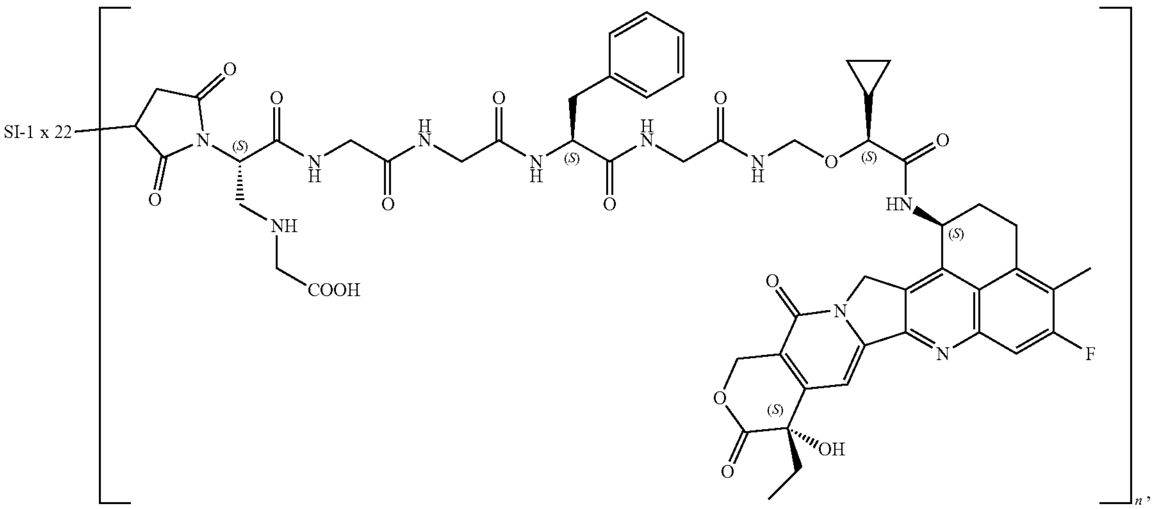
ADC-221
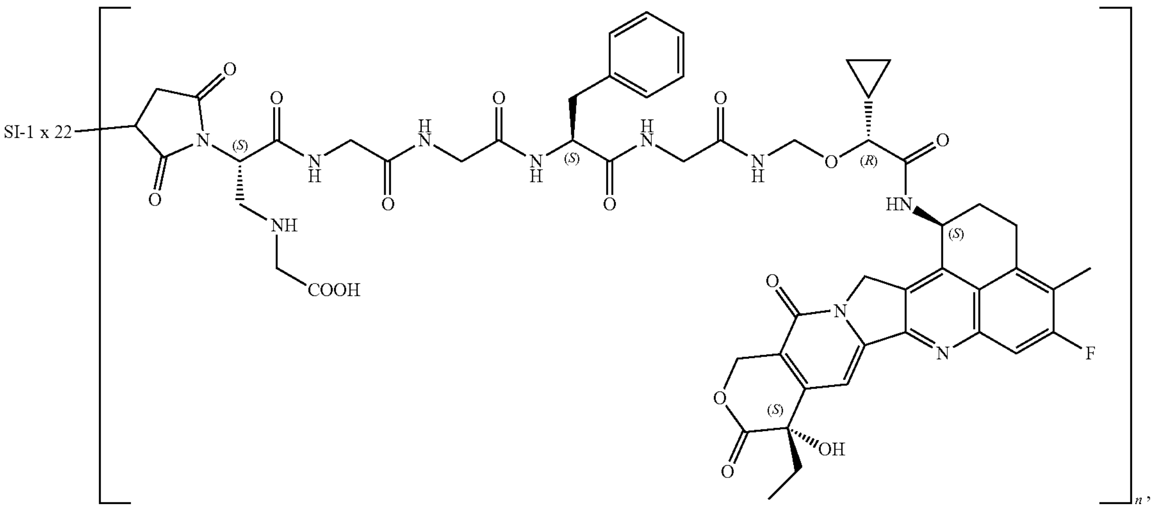

-continued
ADC-222
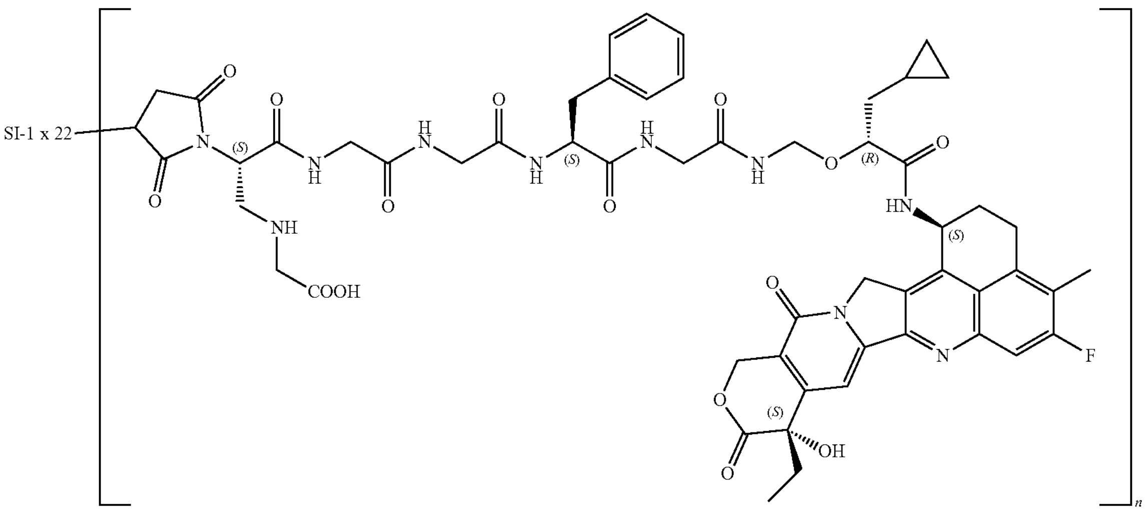
or
ADC-223
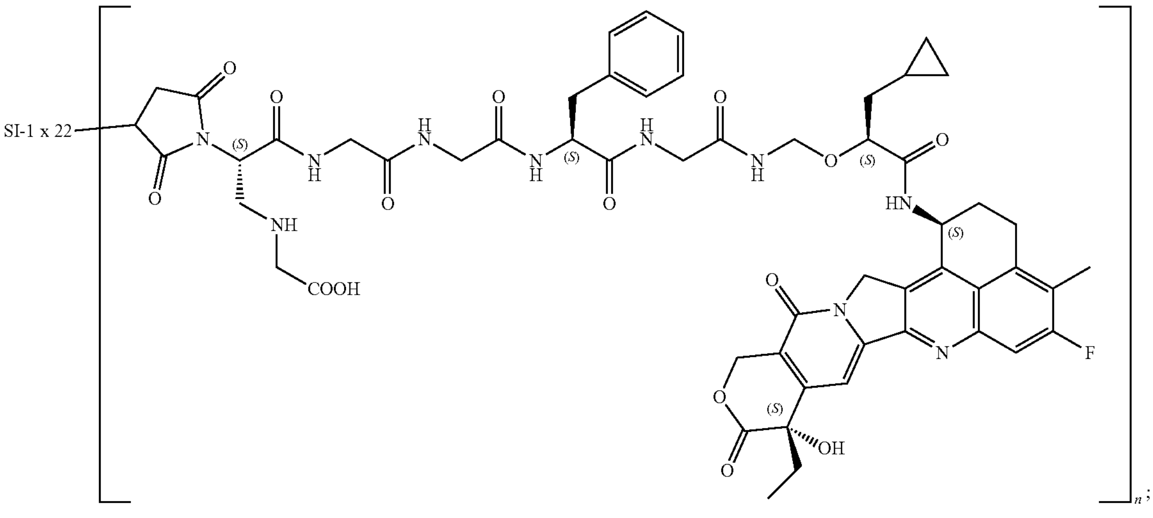
;
Example 312
ADC-224 to ADC-231 were prepared according to the general-purpose coupling method of Example 93, ADC-224
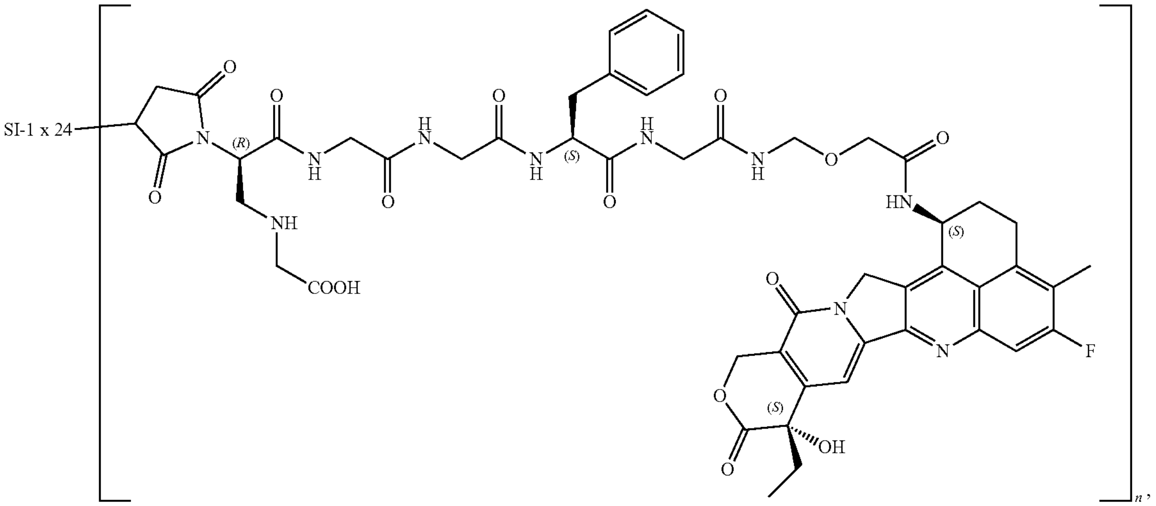
ADC-225
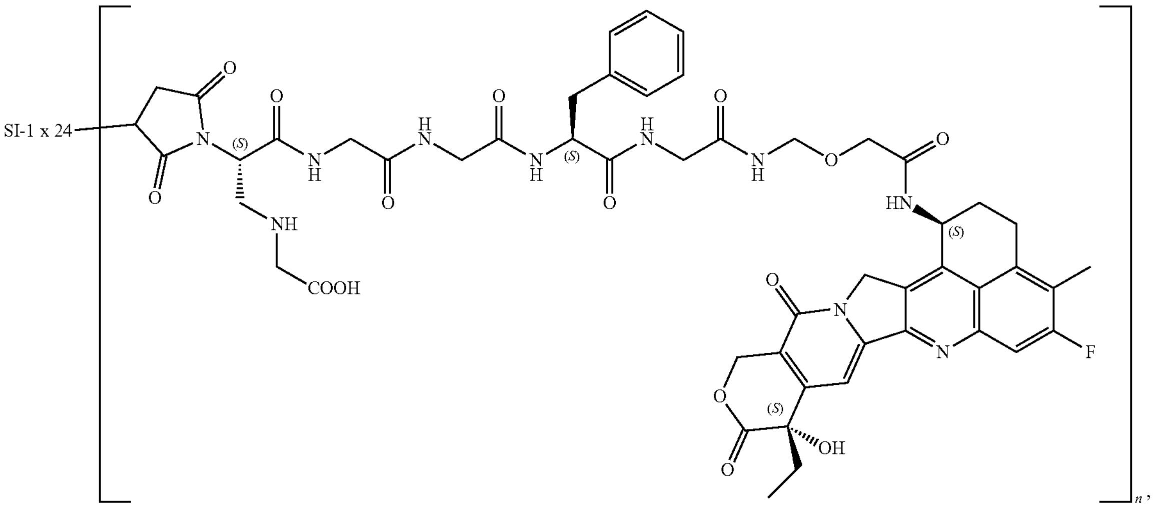
ADC-226
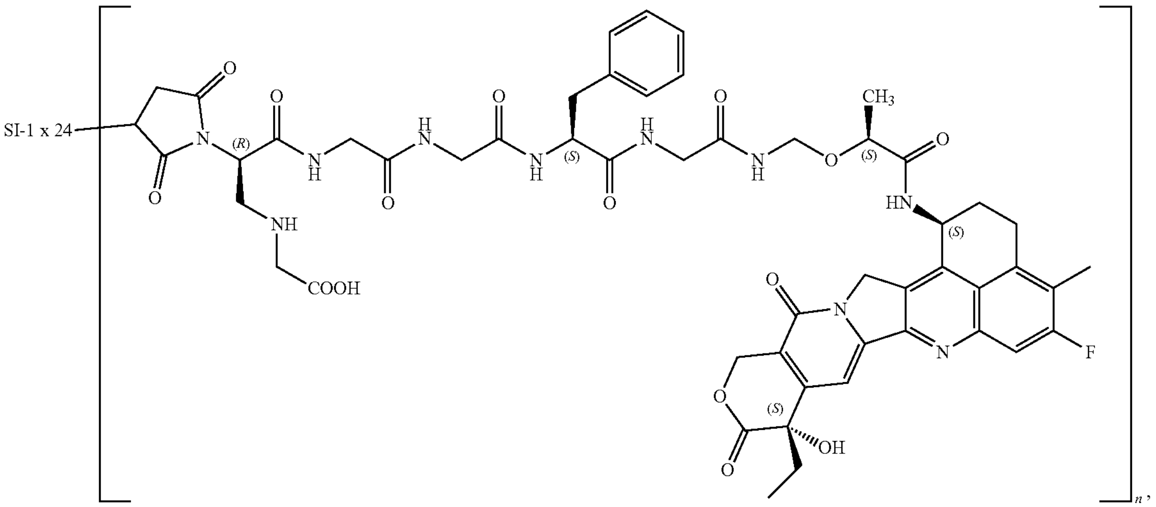

-continued
ADC-227
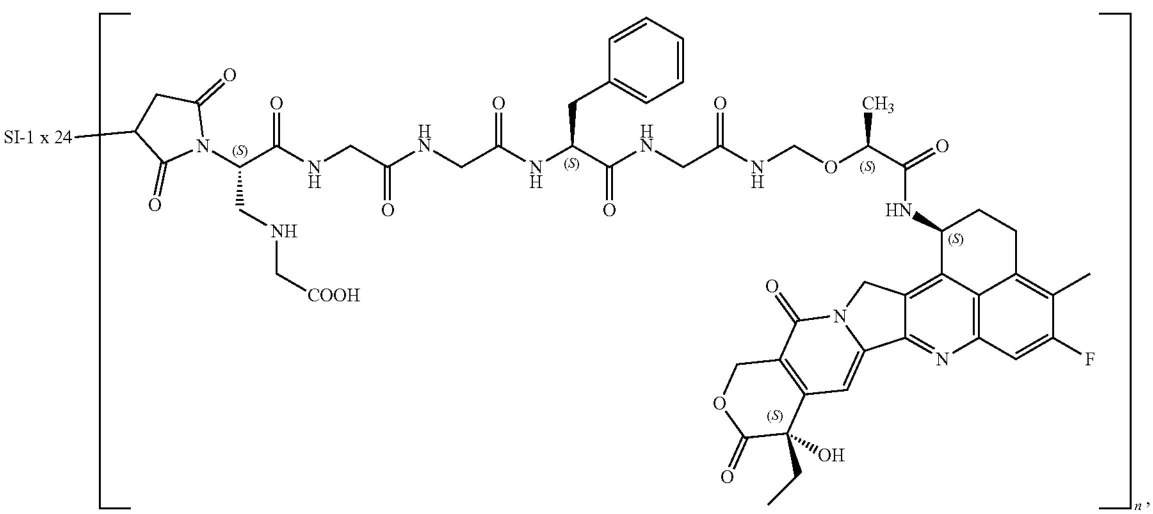
ADC-228
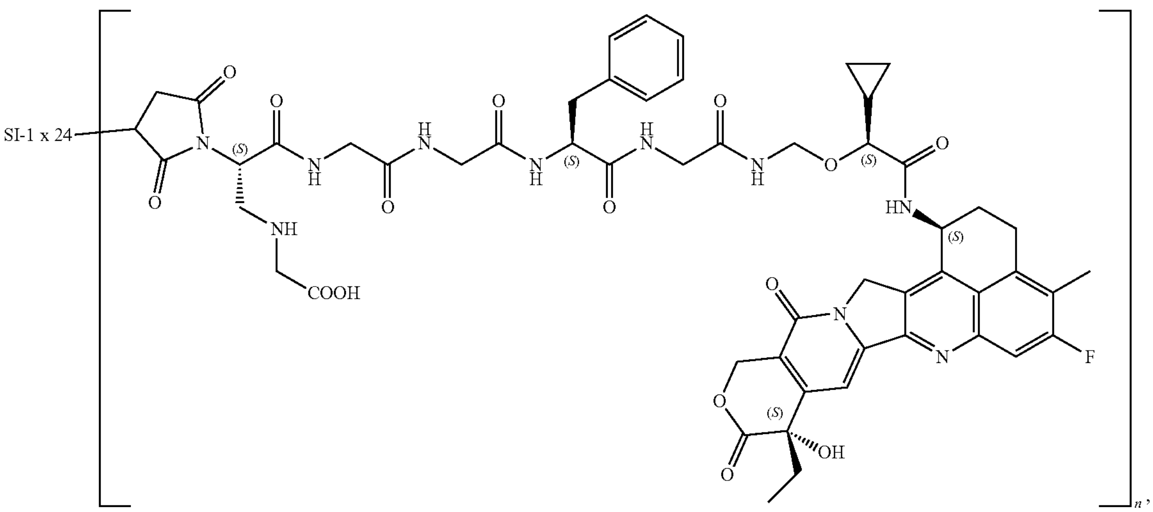
ADC-229
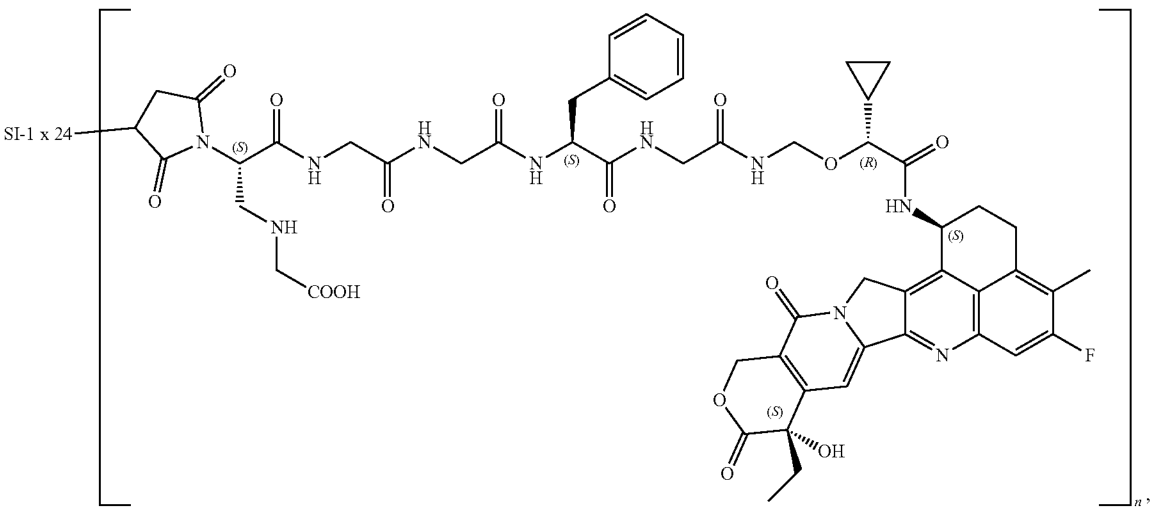

-continued
ADC-230
SI-1 x 24
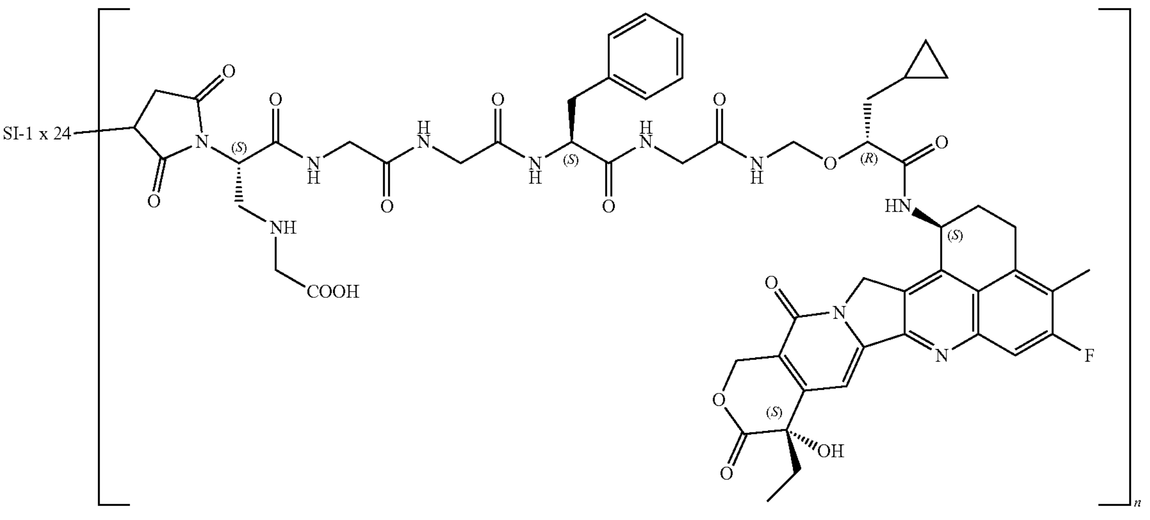
or
ADC-231
SI-1 x 24
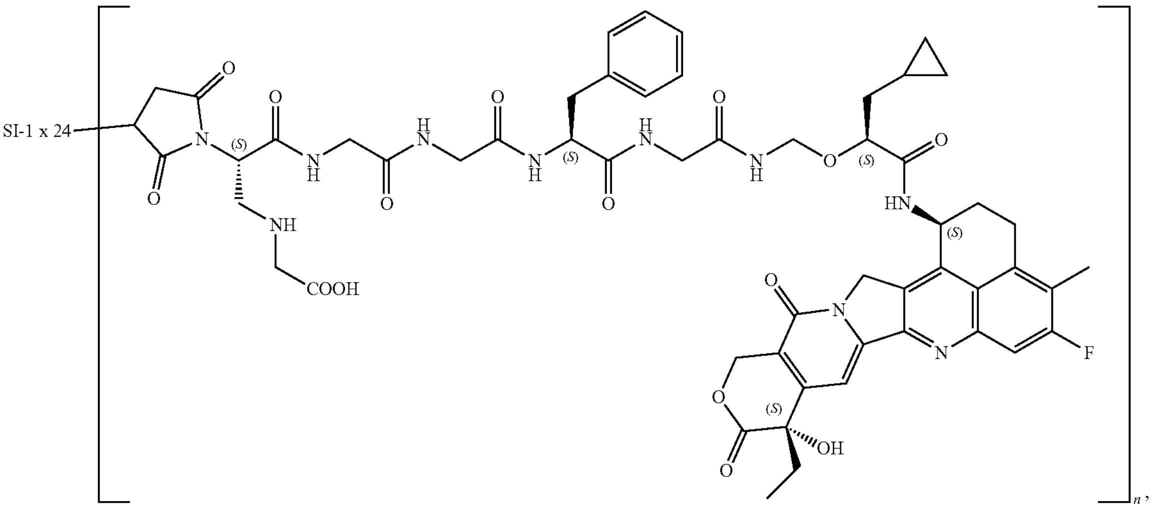
,
Example 313
ADC-232 to ADC-239 were prepared according to the general-purpose coupling method of Example 94, ADC-232
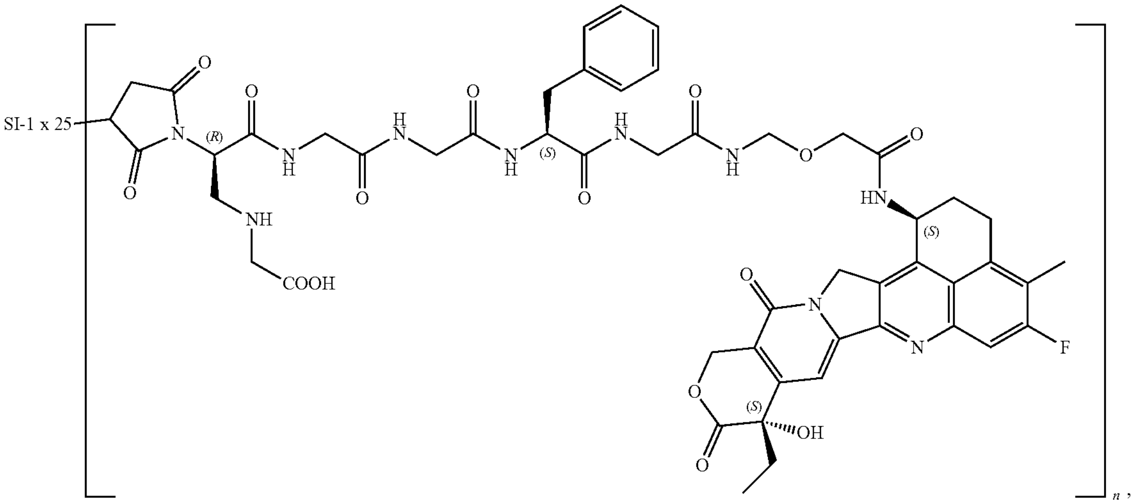
ADC-233
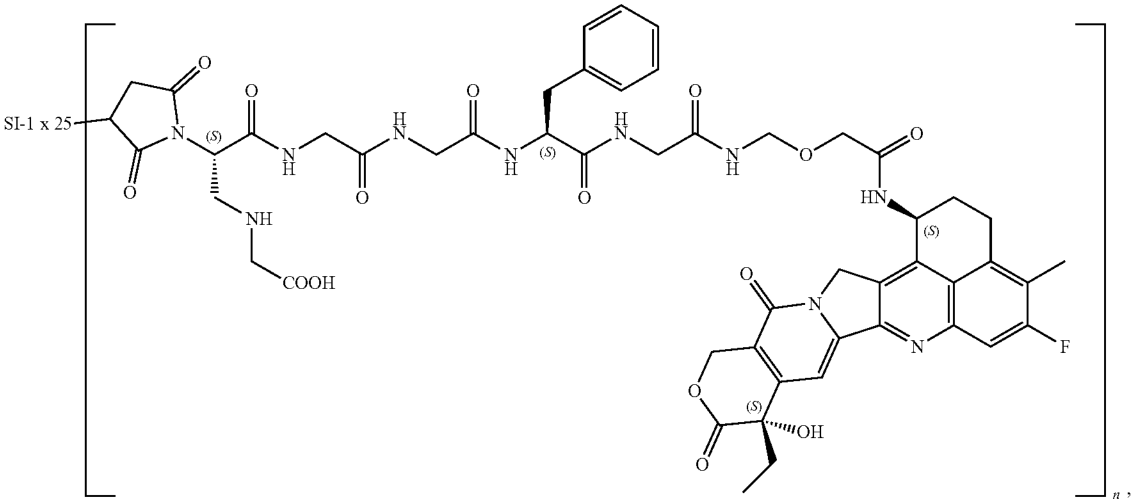
ADC-234
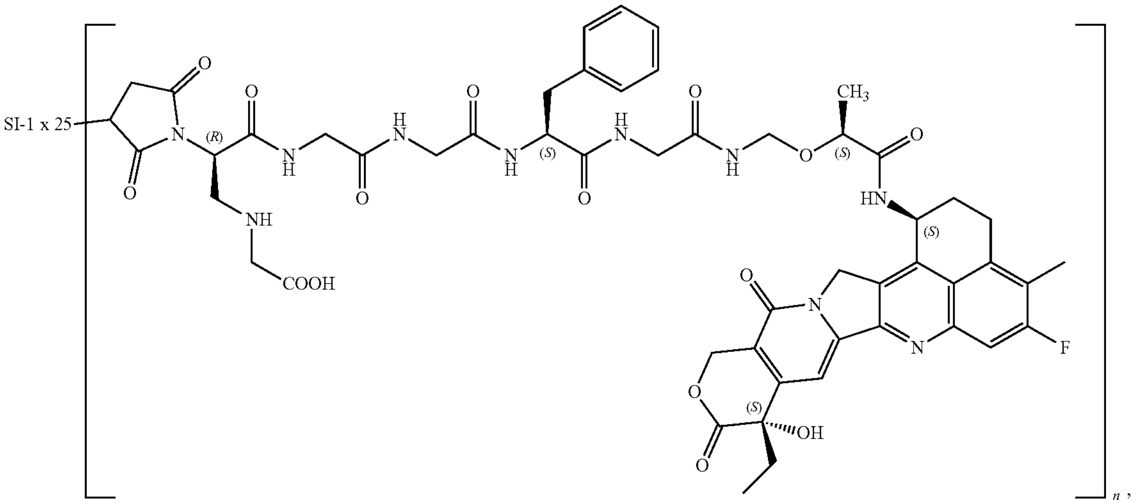

-continued
ADC-235
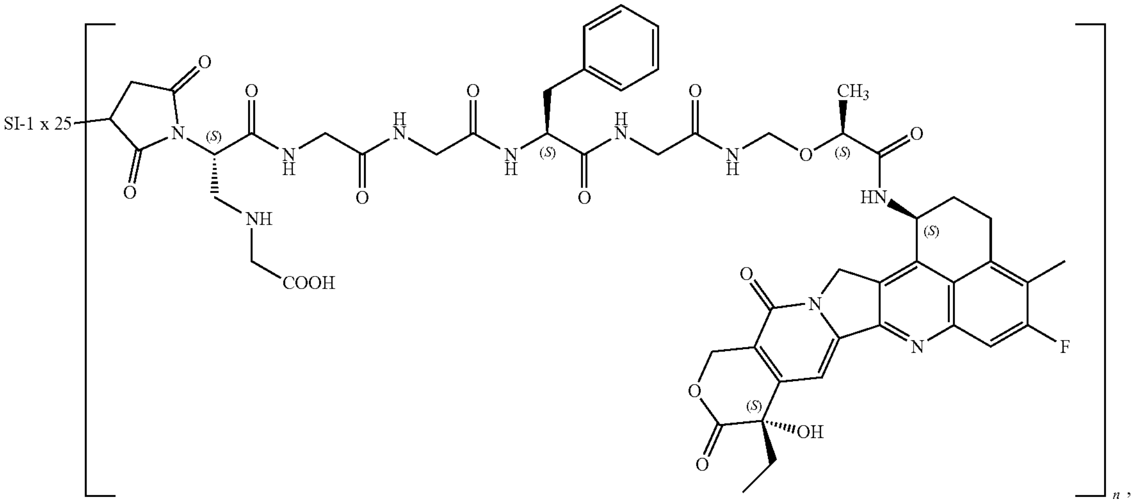
ADC-236
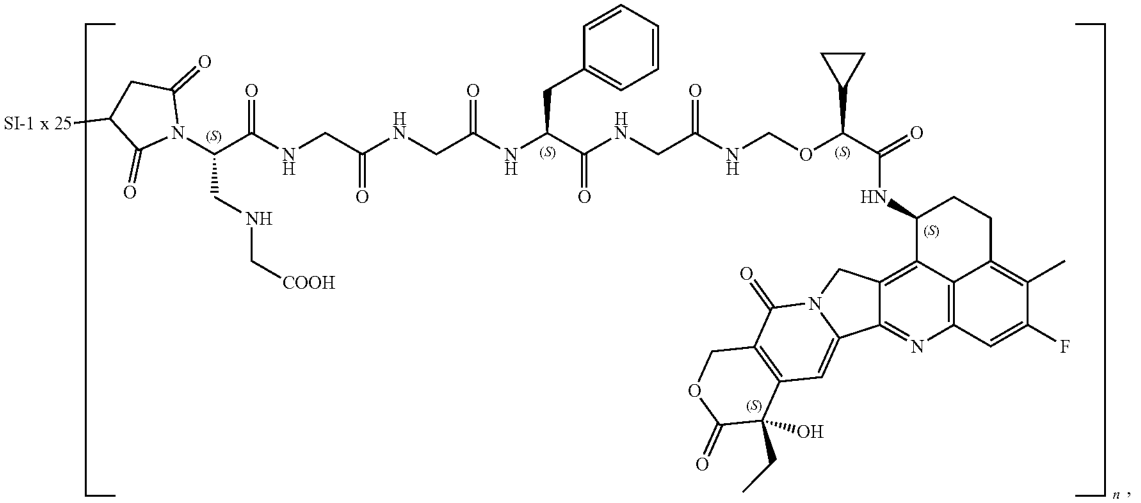
ADC-237
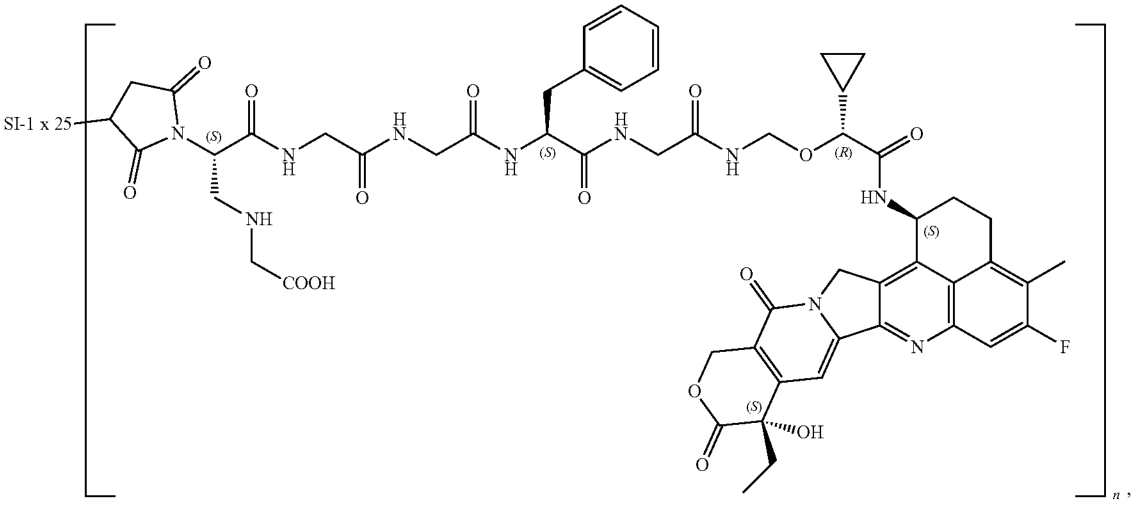

-continued
ADC-238
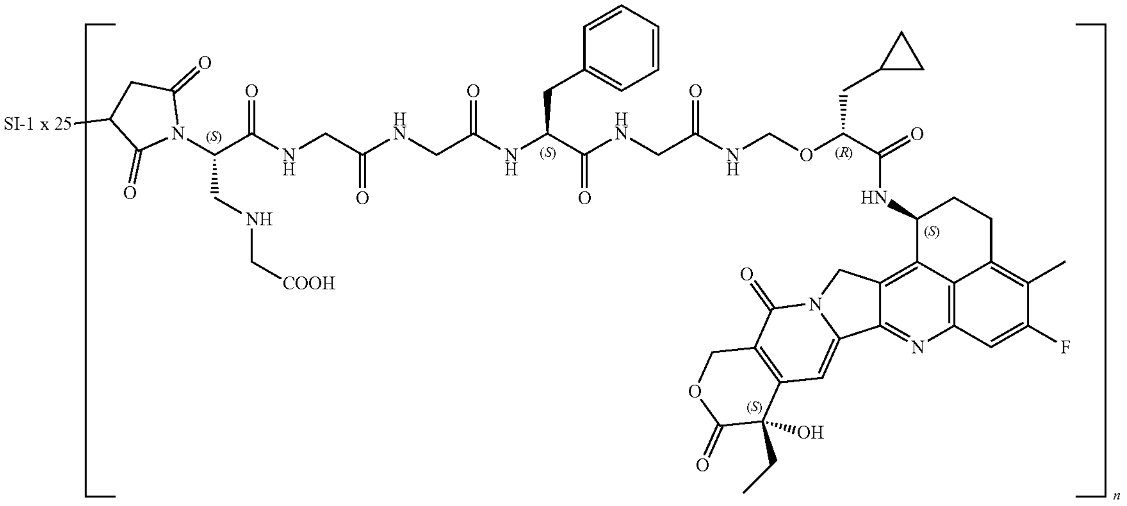
or
ADC-239
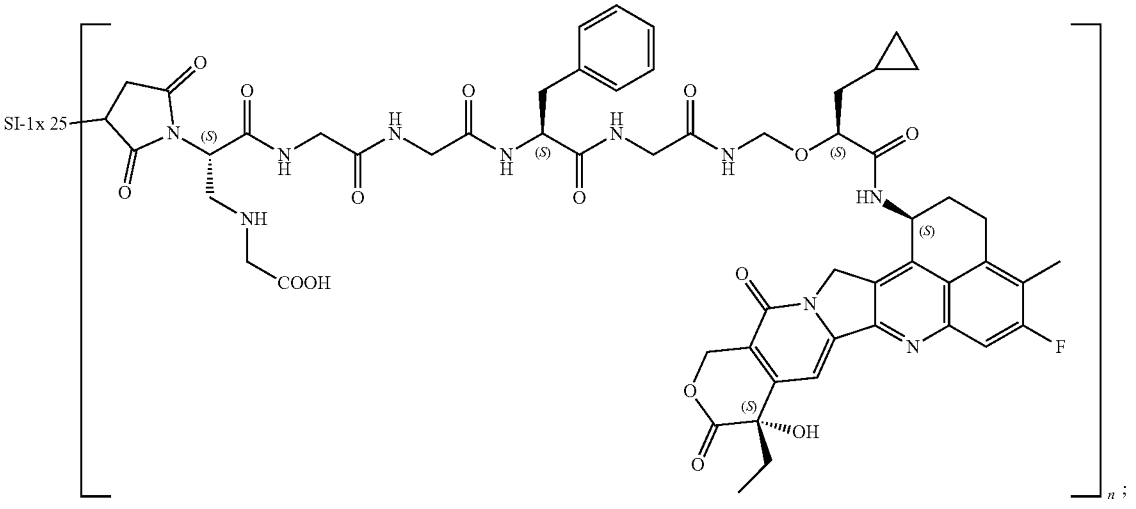
Example 314
ADC-240 to ADC-247 were prepared according to the general-purpose coupling method of Example 94, ADC-240
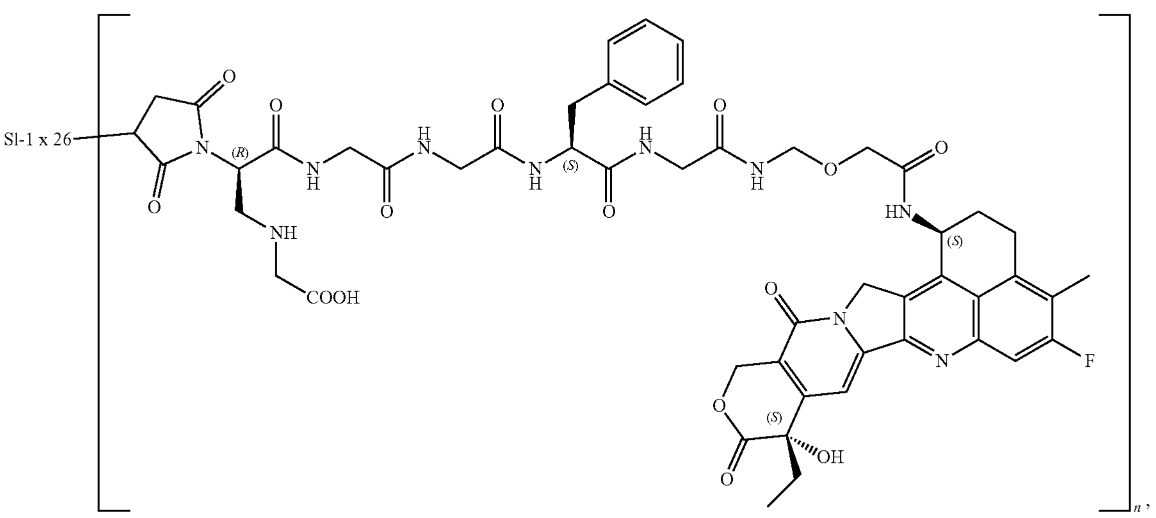
ADC-241
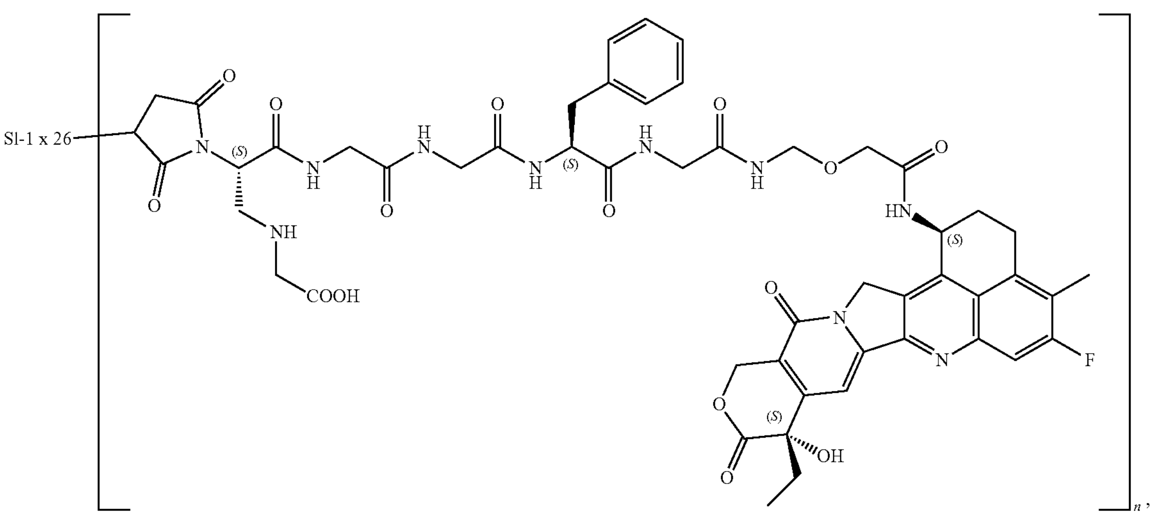
ADC-242
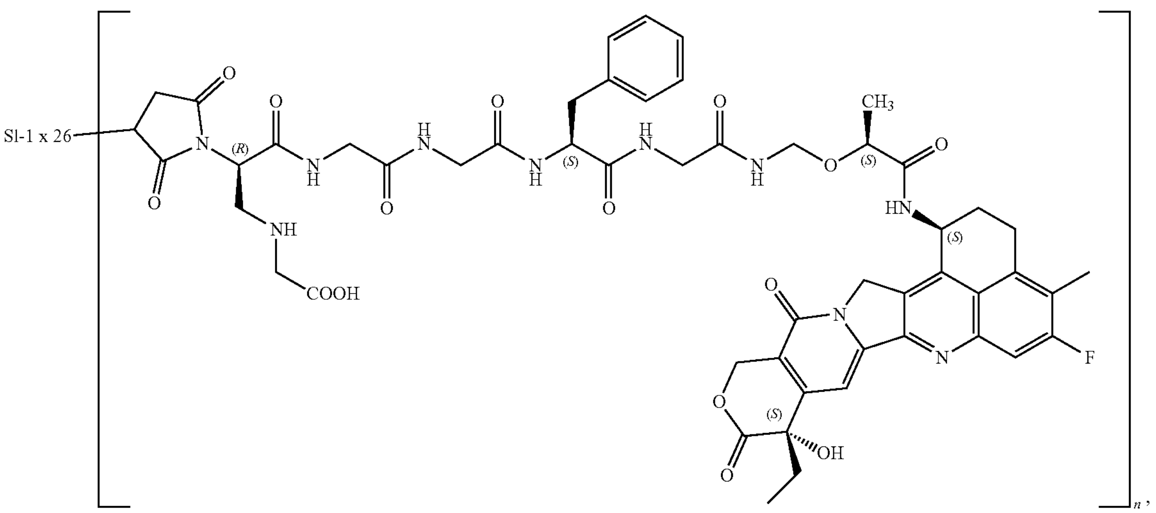

-continued
ADC-243
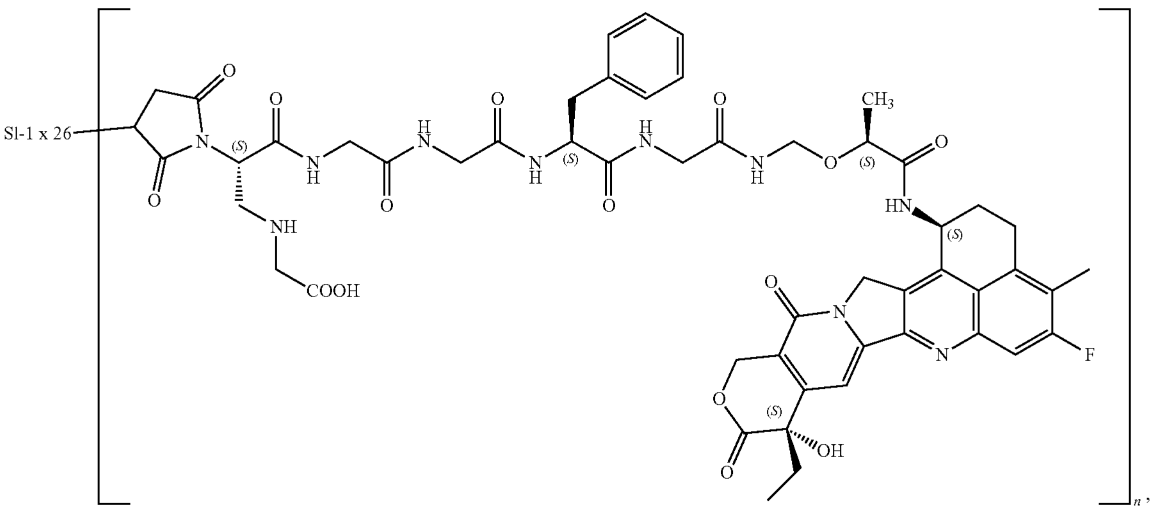
ADC-244
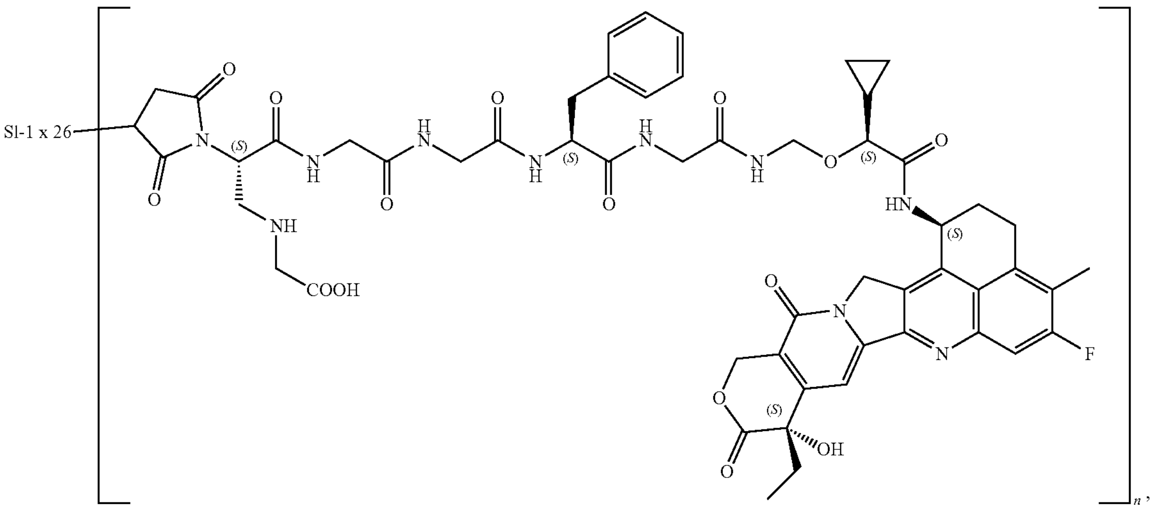
ADC-245
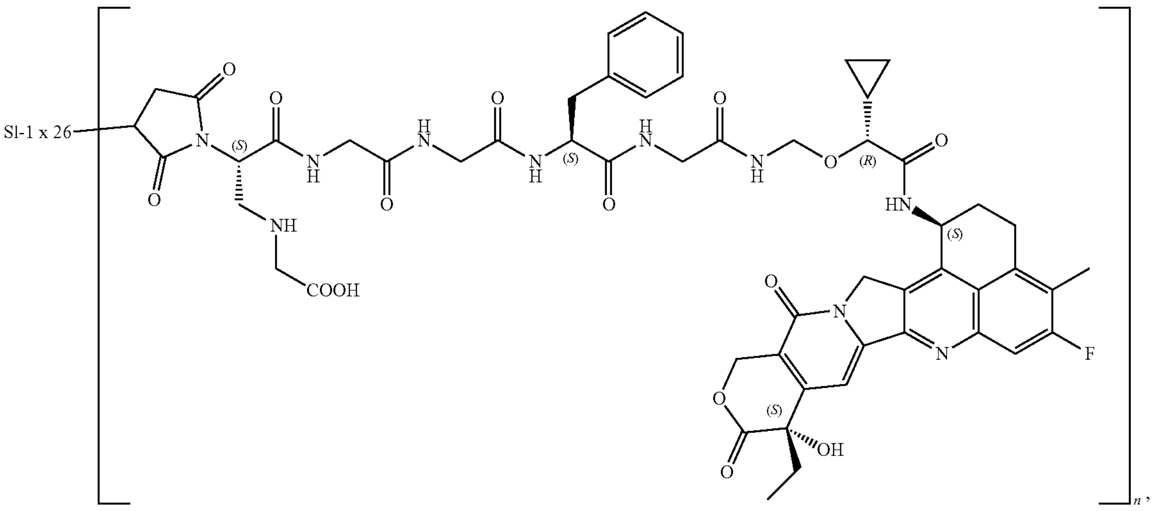

-continued

ADC-246

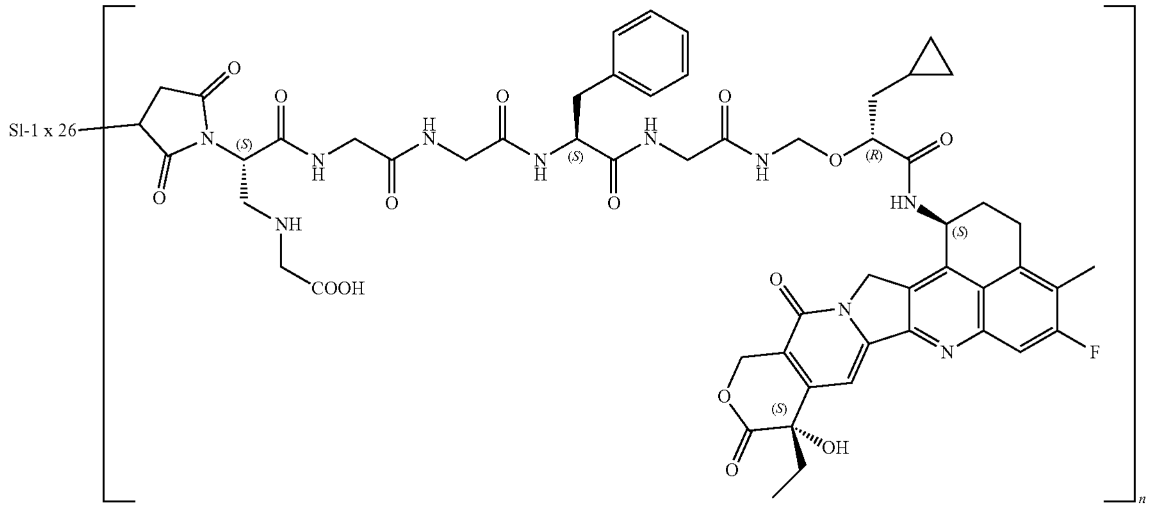

or

ADC-247

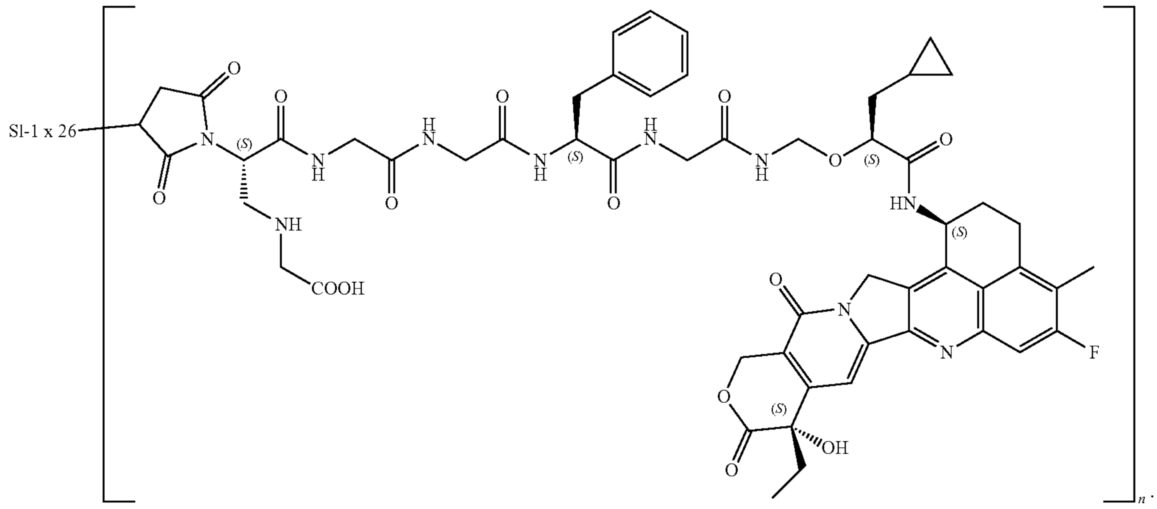

Example 315

The monomer rate was determined using the SEC-HPLC method:

- Chromatography column: Biocore SEC-300 5 μm, 4.6×300 mm
- Manufacturer: NanoChrom, Item No.: B213-050030-04630S
- Mobile phase: 50 mM PB+300 mM NaCl+200 mM Arg+5% IPA, pH=6.5

TABLE 1

| Methodological parameters | |
|---|---|
| Parameters | Settings |
| Flow rate | 0.3 mL/min |
| Wavelengths | 214 nm and 280 nm |
| Column temperature | 30° C. |
| Sample plate temperature | room temperature |
| Injection volume | 20 ug |
| Maximum pressure | 150 bar/15 MPa/2175 PSI |
| Gradient | isocratic |
| Operating time | 20 minutes |

TABLE 2

Monomer rate data for the disclosed ligand-drug conjugate (ADC) disclosed in the present application

| Molecule name | Degradation % | Aggregate % | Monomer rate % |
|---|---|---|---|
| ADC-1 | 0.01 | 1.60 | 98.39 |
| ADC-2 | 0.0 | 1.51 | 98.49 |
| ADC-5 | 0.0 | 2.43 | 97.57 |
| ADC-6 | 0.0 | 2.42 | 97.58 |
| ADC-7 | 0.12 | 2.16 | 97.72 |
| ADC-8 | 0.07 | 1.37 | 98.56 |

TABLE 2-continued

| Monomer rate data for the disclosed ligand-drug conjugate (ADC) disclosed in the present application | | | |
|---|---|---|---|
| Molecule name | Degradation % | Aggregate % | Monomer rate % |
| ADC-10 | 0.05 | 1.35 | 98.60 |
| ADC-11 | 0.11 | 1.51 | 98.38 |
| ADC-12 | 0.05 | 1.62 | 98.33 |
| ADC-13 | 0.08 | 1.30 | 98.62 |
| ADC-14 | 0.02 | 1.49 | 98.49 |
| ADC-48 | 0.06 | 1.71 | 98.23 |
| ADC-52 | 0.05 | 1.56 | 98.39 |
| ADC-DS | 0.0 | 2.82 | 97.18 |
| ADC-64 | 0.0 | 1.16 | 98.84 |
| ADC-68 | 0.01 | 0.44 | 98.55 |
| ADC-75 | 0.0 | 1.61 | 98.39 |
| ADC-81 | 0.2 | 1.59 | 98.39 |
| ADC-87 | 0.07 | 1.30 | 98.63 |
| ADC-96 | 0.08 | 1.32 | 98.60 |
| ADC-102 | 0.05 | 1.31 | 98.64 |
| ADC-108 | 0.0 | 6.36 | 93.64 |
| ADC-112 | 1.2 | 2.81 | 95.99 |
| ADC-113 | 0.03 | 1.22 | 98.75 |
| ADC-120 | 0.0 | 1.73 | 98.27 |
| ADC-122 | 0.01 | 1.44 | 98.55 |
| ADC-129 | 0.13 | 2.54 | 97.33 |
| ADC-130 | 0.37 | 2.18 | 97.45 |
| ADC-131 | 0.60 | 1.00 | 98.40 |
| ADC-132 | 0.03 | 2.22 | 97.75 |
| ADC-133 | 0.53 | 1.37 | 98.10 |
| ADC-145 | 0.11 | 1.24 | 98.65 |
| ADC-158 | 0.98 | 2.89 | 96.13 |
| ADC-160 | 0.10 | 1.45 | 98.45 |
| ADC-172 | 0.65 | 1.31 | 98.04 |
| ADC-179 | 0.1 | 1.06 | 98.84 |
| ADC-188 | 0.11 | 1.33 | 98.56 |
| ADC-193 | 0.11 | 1.51 | 98.38 |
| ADC-206 | 0.09 | 1.32 | 98.59 |
| ADC-214 | 0.03 | 1.18 | 98.79 |
| ADC-215 | 0.0 | 3.01 | 96.99 |
| ADC-219 | 0.0 | 7.35 | 92.65 |
| ADC-227 | 0.06 | 4.5 | 95.44 |
| ADC-235 | 0.1 | 6.83 | 93.07 |

CONCLUSION: The ADC disclosed in the present invention is characterized by a low degradation rate and a low aggregation rate, and has the excellent property of a high monomer rate.

Example 316

The drug antibody ratio DAR was determined using the RP-HPLC method:

Chromatography column name: Proteomix RP-1000 4.6×100 mm 5 μm 1000A Manufacturer: Sepax

TABLE 3

| Methodological parameters | |
|---|---|
| Parameters | Settings |
| Mobile phase | A: 0.1% TFA aqueous solution; B: 0.1% TFA acetonitrile solution |
| Flow rate | 0.5 mL/min |
| Wavelength | 214 nm and 280 nm |
| Column temperature | 65° C. |
| Sample plate temperature | room temperature |
| Injection volume | 25 ug |
| Maximum pressure | 100 bar/10 MPa/1450 PSI |

TABLE 3-continued

| Methodological parameters | | | | |
|---|---|---|---|---|
| | Time (min) | Flow rate (mL/min) | Mobile phase A (%) | Mobile phase B (%) |
| Gradient | 0.0 | 0.5 | 75 | 25 |
| | 3 | 0.5 | 75 | 25 |
| | 28 | 0.5 | 50 | 50 |
| | 30 | 0.5 | 5 | 95 |
| | 32 | 0.5 | 5 | 95 |
| | 33 | 0.5 | 75 | 25 |
| | 40 | 0.5 | 75 | 25 |

TABLE 4

| Detailed data on ADC drug-antibody coupling ratio (DAR) | | | | | |
|---|---|---|---|---|---|
| Sample Name | Batch number | RP-DAR | Sample Name | Batch number | RP-DAR |
| ADC-5 | 20201028 | 7.65 | ADC-120 | 20200708 | 7.83 |
| ADC-6 | 20200923 | 6.99 | ADC-122 | 20200708 | 6.97 |
| ADC-10 | 20200104 | 7.38 | ADC-137 | 20191125 | 7.44 |
| ADC-12 | 20191125 | 7.61 | ADC-140 | 20200708 | 7.52 |
| ADC-18 | 20201028 | 7.71 | ADC-142 | 20201028 | 7.50 |
| ADC-23 | 20200104 | 7.19 | ADC-143 | 20201028 | 7.61 |
| ADC-24 | 20200104 | 7.09 | ADC-159 | 20200708 | 7.28 |
| ADC-36 | 20200708 | 7.44 | ADC-160 | 20200708 | 7.89 |
| ADC-41 | 20201028 | 7.81 | ADC-168 | 20201028 | 7.24 |
| ADC-42 | 20201028 | 7.55 | ADC-169 | 20201028 | 7.89 |
| ADC-55 | 20200708 | 7.54 | ADC-170 | 20201028 | 7.55 |
| ADC-59 | 20200708 | 7.57 | ADC-171 | 20201028 | 6.91 |
| ADC-64 | 20201028 | 7.42 | ADC-176 | 20200708 | 7.32 |
| ADC-70 | 20200104 | 7.60 | ADC-183 | 20200708 | 7.18 |
| ADC-71 | 20200104 | 7.50 | ADC-184 | 20200708 | 7.49 |
| ADC-72 | 20200104 | 7.42 | ADC-185 | 20200708 | 7.30 |
| ADC-88 | 20200708 | 7.31 | ADC-186 | 20200708 | 7.77 |
| ADC-96 | 20191125 | 7.75 | ADC-190 | 20200708 | 7.26 |
| ADC-100 | 20200708 | 7.56 | ADC-199 | 20191125 | 7.42 |
| ADC-108 | 20200708 | 7.62 | ADC-214 | 20201028 | 7.85 |
| ADC-112 | 20201116 | 7.46 | ADC-215 | 20211013 | 7.38 |
| ADC-219 | 20211015 | 7.14 | ADC-227 | 20211013 | 7.46 |
| ADC-235 | 20211013 | 7.26 | ADC-243 | 20211027 | 7.38 |

CONCLUSION: The ADC disclosed in the present invention has the excellent property of high DAR value, which can significantly increase the concentration of the drug at the target site location at the same dose of ADC drug administered.

Example 317

ADC maintained the affinity of the corresponding original bispecific antibodies SI-1×6.4, SI-1×4, SI-1×22, SI-1×24, SI-1×25 and SI-1×26 for EGFR and HER3:

The relative affinities of SI-1×6.4 versus ADC-6 and SI-1×4 versus ADC-112 for EGFR and HER3 were compared by double-antigen sandwich ELISA. The specific steps were as follows:

Recombinant EGFR-His*6 antigen-coated plates were closed with 1% bovine serum protein; then SI-1×6.4, ADC-6, SI-1×4, and ADC-112 were diluted, respectively, and then diluted with a starting concentration of 5,000 ng/mL in successive 3-fold gradients, for a total of 11 concentrations; the samples were incubated on the coated ELISA plates for a certain period of time, followed by biotin-labeled HER3-Fc antigen incubation, followed by streptavidin HRP-labeled incubation; finally, TMB color development was performed, followed by sulfuric acid solution termination, and the absorbance value at 450 nm was detected on a microplate reader. The assay results were plotted against concentration for 0D450 nm.

Figure 3A:
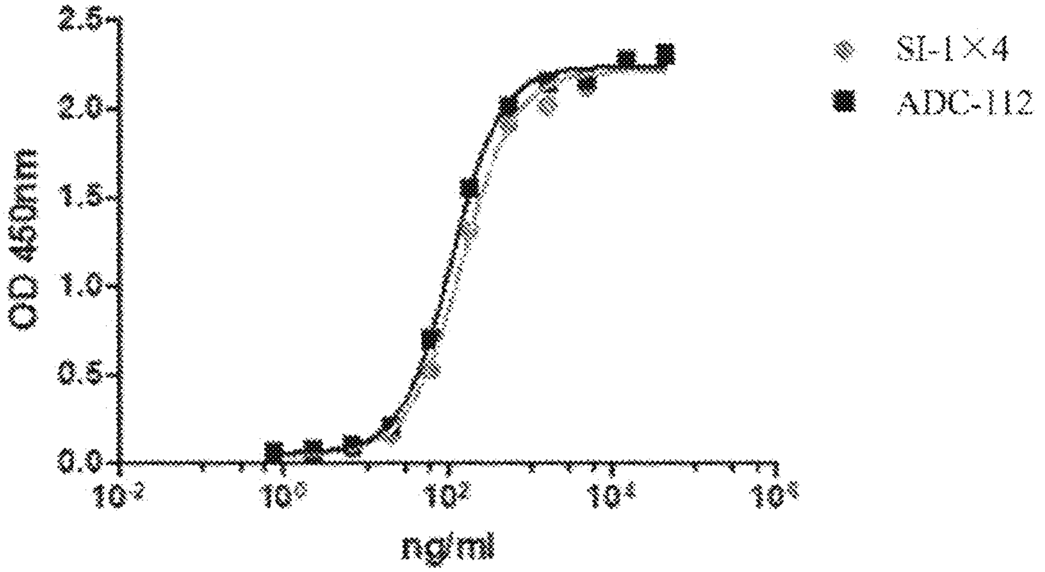
FIG. 3A illustrates that ADC-112 and the SI-1×4 antibody maintain affinity for both the antigens EGFR and HER3-Fc.
Figure 3B:
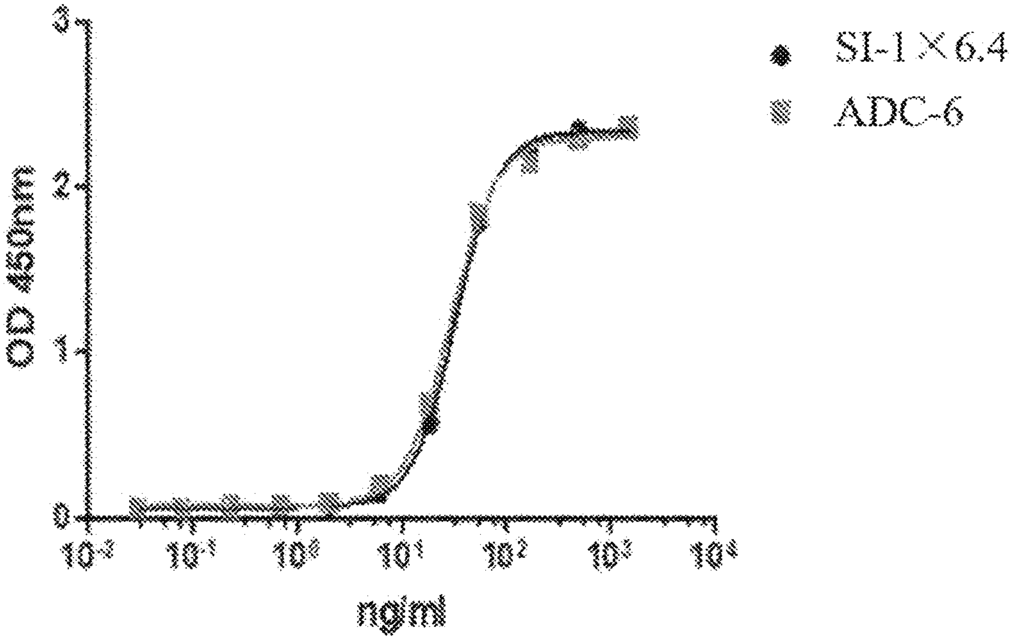
FIG. 3B illustrates that ADC-6 and the SI-1×6.4 antibody maintain affinity for both the antigens EGFR and HER3-Fc.
Figure 3C:
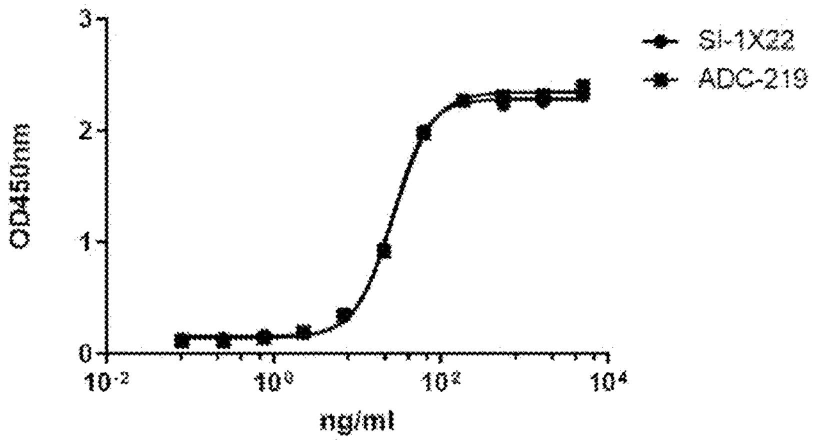
FIG. 3C illustrates that ADC-219 and the SI-1×22 antibody maintain affinity for both the antigens EGFR and HER3-Fc.
Figure 3D:
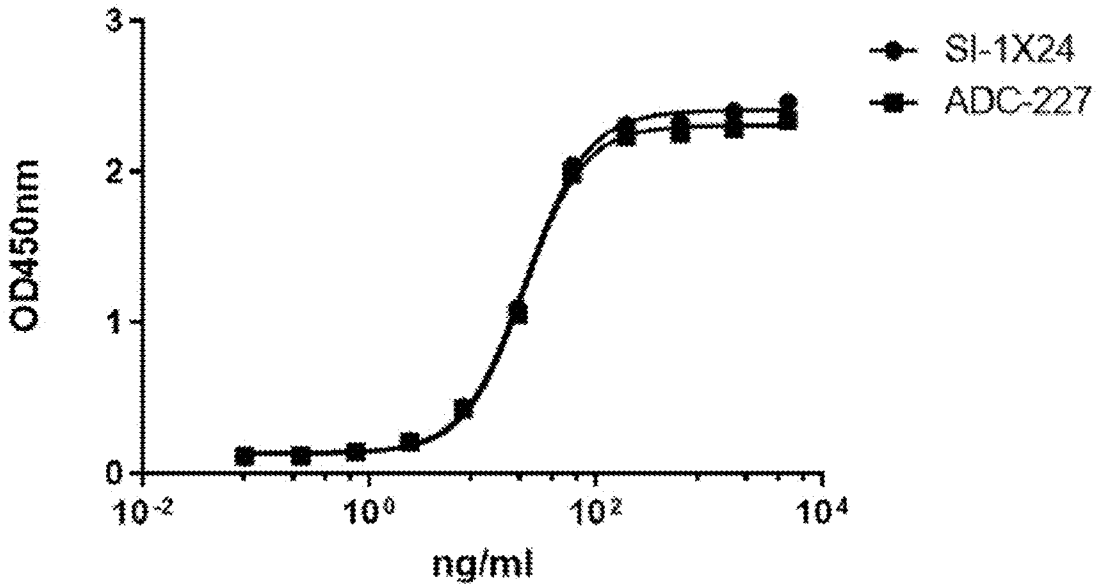
FIG. 3D illustrates that ADC-227 and the SI-1×24 antibody maintain affinity for both the antigens EGFR and HER3-Fc.
Figure 3E:
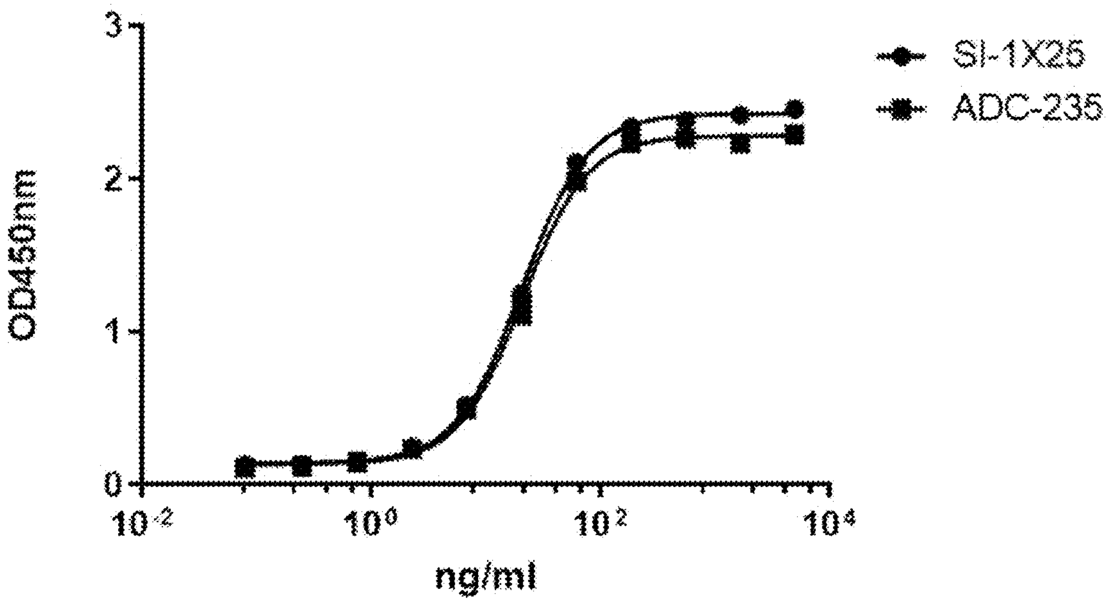
FIG. 3E illustrates that ADC-235 and the SI-1×25 antibody maintain affinity for both the antigens EGFR and HER3-Fc.
Figure 3F:
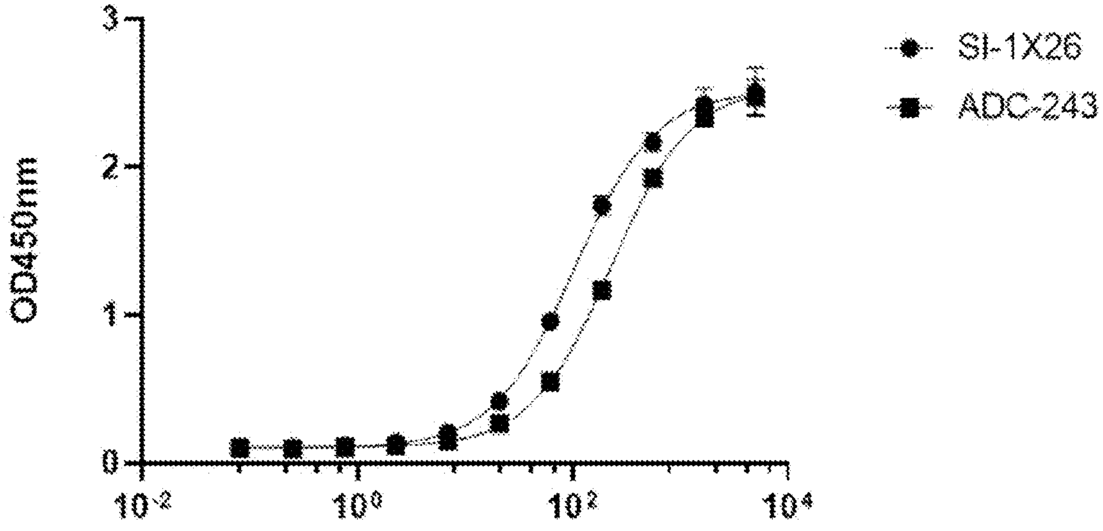
FIG. 3F illustrates that ADC-243 and the SI-1×26 antibody maintain affinity for both the antigens EGFR and HER3-Fc.
Figure 4A:
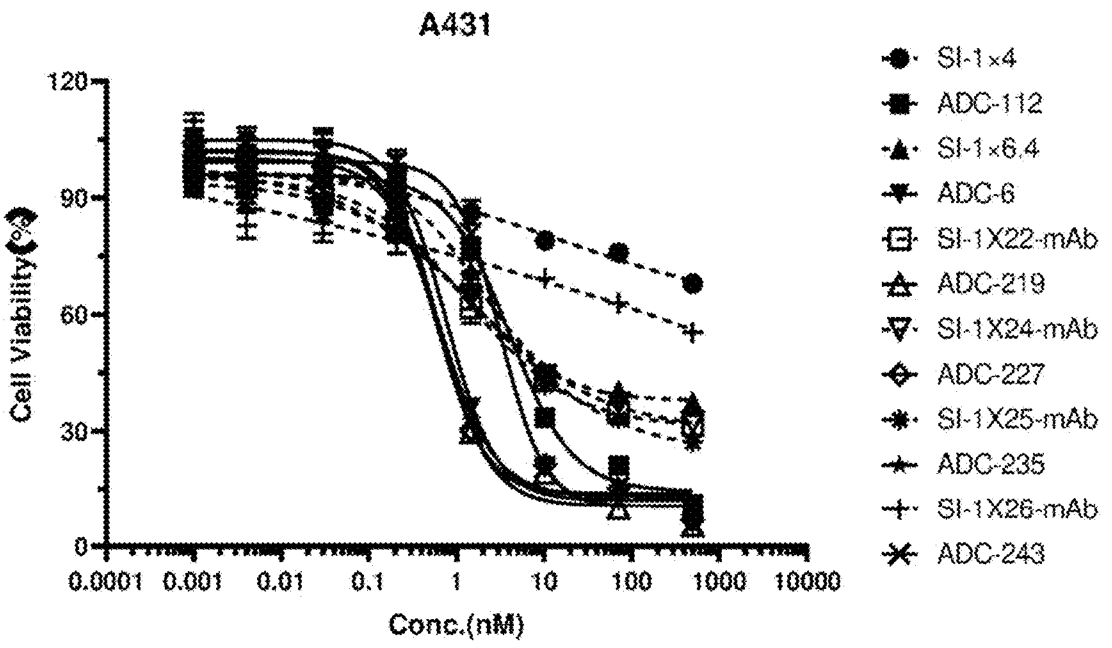
FIG. 4A illustrates the in vitro efficacy of six naked antibodies as well as six ADCs in A431.
Figure 4B:
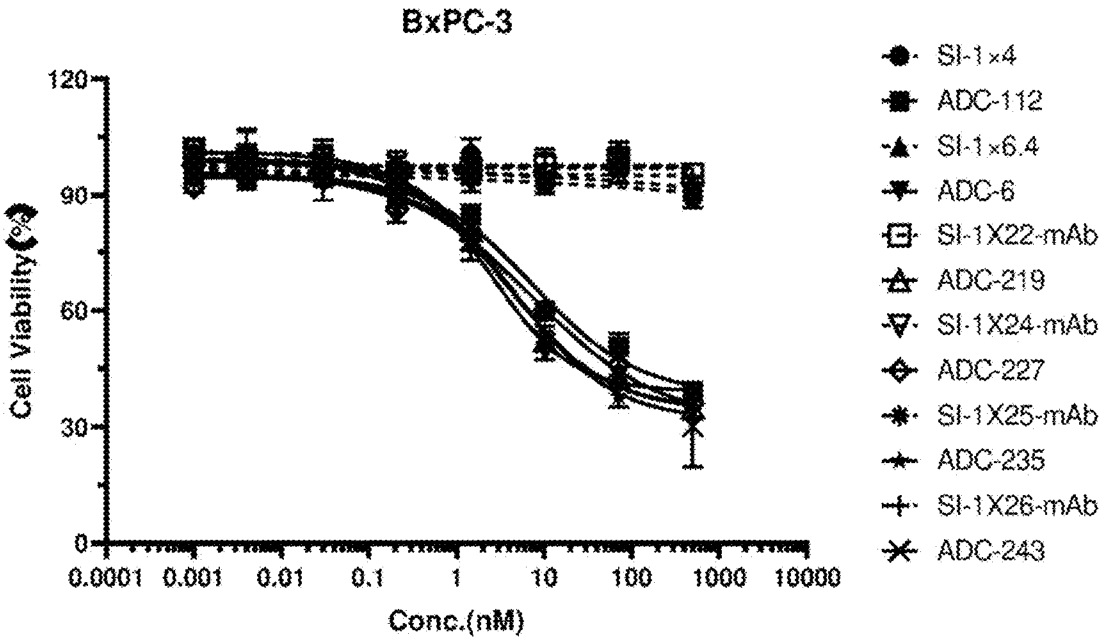
FIG. 4B illustrates the in vitro efficacy of six naked antibodies as well as six ADCs in BXPC-3.
Figure 4C:
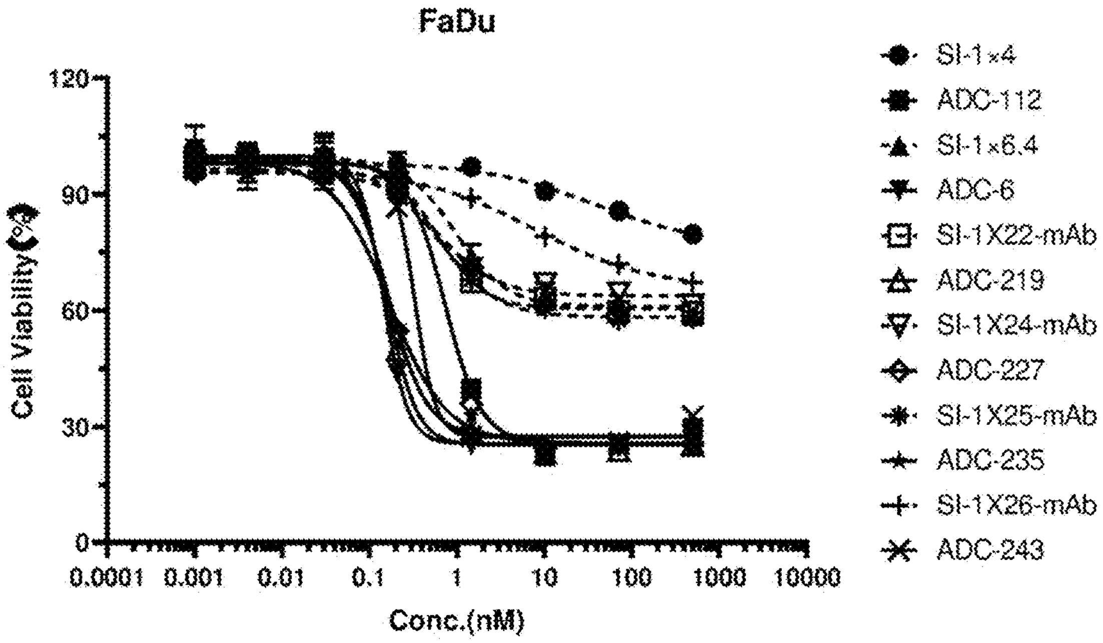
FIG. 4C illustrates the in vitro efficacy of six naked antibodies as well as six ADCs in FaDu.
Figure 4D:
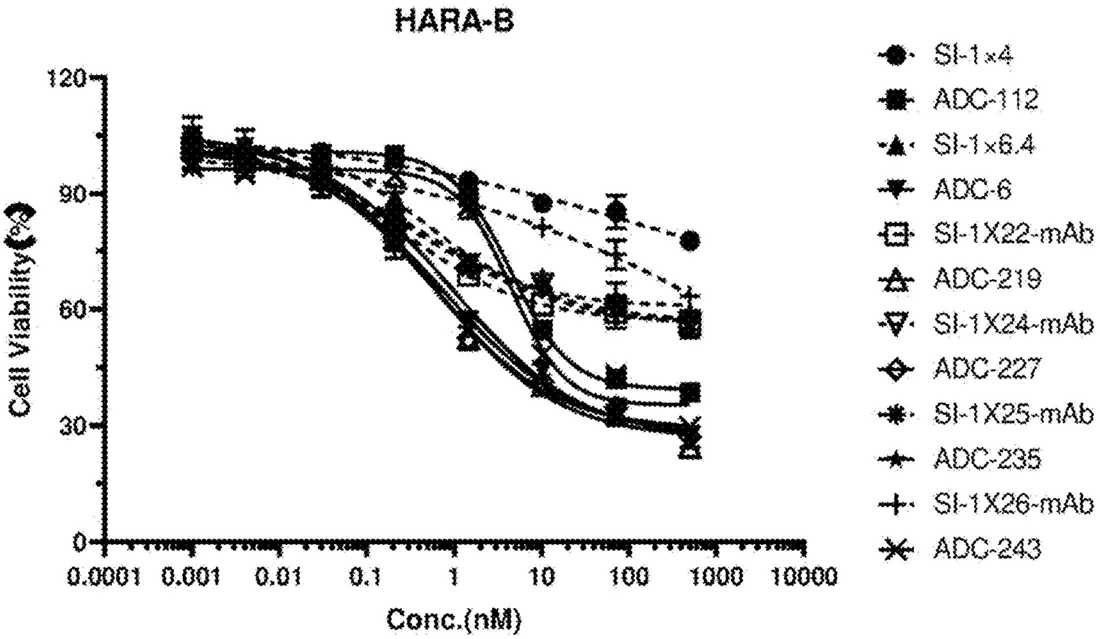
FIG. 4D illustrates the in vitro efficacy of six naked antibodies as well as six ADCs in HARA-B.
Figure 4E:
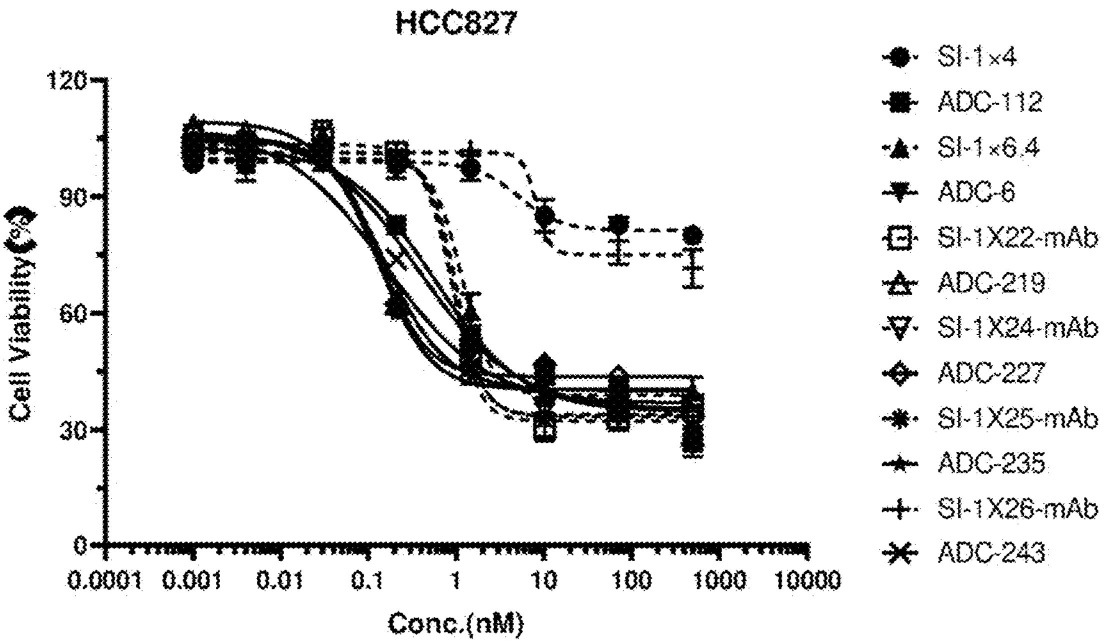
FIG. 4E illustrates the in vitro efficacy of six naked antibodies as well as six ADCs in HCC827.
Figure 4F:
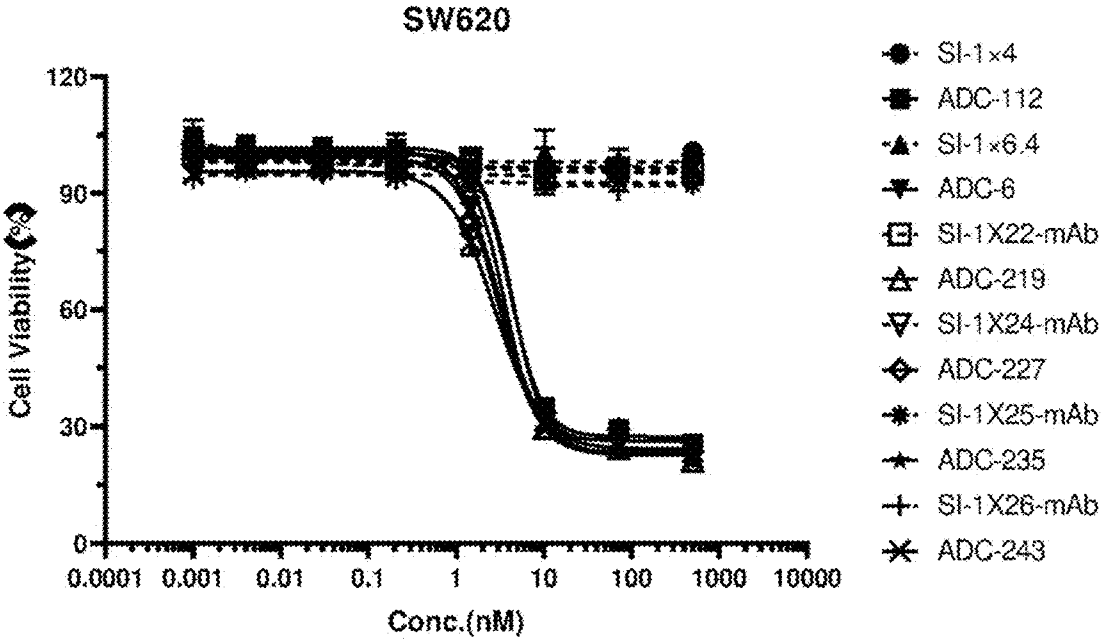
FIG. 4F illustrates the in vitro efficacy of the six naked antibodies as well as the six ADCs in SW620.

CONCLUSION: As shown in the accompanying FIGS. 3A and 3B, after coupling, ADC-6 and ADC-112 maintained similar affinities to those of SI-1×6.4 and SI-1×4, respectively, with no significant difference in EC50 values; indicating that coupling of toxins to SI-1×6.4 and SI-1×4 did not affect their affinity for the antigen.

Similarly, using a similar testing method to that described above, the results are shown in FIG. 3C, FIG. 3D, FIG. 3E, and FIG. 3F; after coupling, ADC-219, ADC-227, ADC-235, and ADC-243 retained similar affinities to those of SI-1×22, SI-1×24, SI-1×25, and SI-1×26, respectively, with no significant difference in the EC50 values; indicating that coupling of toxins to SI-1×22, SI-1×24, SI-1×25 and SI-1×26 did not affect their affinity for the antigen.

Example 318

In Vitro Pharmacodynamic Assays:

A variety of human-derived tumor cell lines (human epidermal cancer cells A431, human in situ pancreatic adenocarcinoma cells BXPC-3, human pharyngeal squamous cell carcinoma cells FaDu, human lung cancer squamous cell carcinoma cell line HARA-B, human non-small cell lung cancer cells HCC827, and human colon cancer cells SW620) were utilized as experimental models for evaluating in vitro efficacy of the ADC-coupled drug in the present invention. A certain number of tumor cells were inoculated in a 96-well plate, and the gradient-diluted test antibody and the corresponding ADC drug were added to the cells, followed by 5 days of treatment; the cell viability was measured using Alamar Blue or MTS, and the inhibitory effect of the test antibody and ADC on the tumor cell lines was evaluated by calculating the IC50. The starting concentration of the antibody drug was 500 nM, and the dilution was 7-fold, totaling 8 concentration points, and the treatment was carried out for 5 days. The final calculation method was survival rate=(experimental group−blank)/(control group−blank group)×10000, then Graph Pad Prism was used for curve fitting, to calculate the half inhibitory concentration (IC50) as well as Efficacy (0%).

TABLE 5

In vitro efficacy of six naked antibodies (SI-1 × 4, SI-1 × 6.4, SI-1 × 22, SI-1 × 24, SI-1 × 25, SI-1 × 26) and six ADCs (ADC-112, ADC-6, ADC-219, ADC-227, ADC-235, ADC-243) in A431

A431

| Groups | $IC_{50}$ (nM) | Groups | Efficacy (%) |
|---|---|---|---|
| ADC-112 | 4.95 | ADC-112 | 85.63 |
| ADC-6 | 0.98 | ADC-6 | 87.88 |
| ADC-219 | 0.75 | ADC-219 | 89.37 |
| ADC-227 | 0.77 | ADC-227 | 86.13 |
| ADC-235 | 0.81 | ADC-235 | 86.86 |
| ADC-243 | 3.61 | ADC-243 | 89.63 |
| SI-1 × 4 | >500 | SI-1 × 4 | 31.99 |
| SI-1 × 6.4 | 6.98 | SI-1 × 6.4 | 62.18 |
| SI-1 × 22 | 4.47 | SI-1 × 22 | 69.01 |
| SI-1 × 24 | 6.23 | SI-1 × 24 | 69.98 |
| SI-1 × 25 | 5.54 | SI-1 × 25 | 75.89 |
| SI-1 × 26 | >500 | SI-1 × 26 | 44.63 |

TABLE 6

In vitro efficacy of six naked antibodies (SI-1 × 4, SI-1 × 6.4, SI-1 × 22, SI-1 × 24, SI-1 × 25, SI-1 × 26) and six ADCs (ADC-112, ADC-6, ADC-219, ADC-227, ADC-235, ADC-243) in BXPC-3

BxPC-3

| Groups | $IC_{50}$ (nM) | Groups | Efficacy (%) |
|---|---|---|---|
| ADC-112 | 46.75 | ADC-112 | 61.96 |
| ADC-6 | 12.29 | ADC-6 | 61.02 |
| ADC-219 | 16.58 | ADC-219 | 65.64 |
| ADC-227 | 32.48 | ADC-227 | 68.85 |
| ADC-235 | 15.69 | ADC-235 | 68.24 |
| ADC-243 | 16.69 | ADC-243 | 65.96 |
| SI-1 × 4 | >500 | SI-1 × 4 | N/A |
| SI-1 × 6.4 | >500 | SI-1 × 6.4 | N/A |
| SI-1 × 22 | >500 | SI-1 × 22 | N/A |
| SI-1 × 24 | >500 | SI-1 × 24 | N/A |
| SI-1 × 25 | >500 | SI-1 × 25 | N/A |
| SI-1 × 26 | >500 | SI-1 × 26 | N/A |

TABLE 7

In vitro efficacy of six naked antibodies (SI-1 × 4, SI-1 × 6.4, SI-1 × 22, SI-1 × 24, SI-1 × 25, SI-1 × 26) and six ADCs (ADC-112, ADC-6, ADC-219, ADC-227, ADC-235, ADC-243) in FaDu FaDu

| Groups | $IC_{50}$ (nM) | Groups | Efficacy (%) |
|---|---|---|---|
| ADC-112 | 1.01 | ADC-112 | 74.09 |
| ADC-6 | 0.18 | ADC-6 | 74.31 |
| ADC-219 | 0.21 | ADC-219 | 74.68 |
| ADC-227 | 0.25 | ADC-227 | 72.44 |
| ADC-235 | 0.28 | ADC-235 | 74.09 |
| ADC-243 | 0.40 | ADC-243 | 72.63 |
| SI-1 × 4 | >500 | SI-1 × 4 | 23.34 |
| SI-1 × 6.4 | >500 | SI-1 × 6.4 | 38.92 |
| SI-1 × 22 | >500 | SI-1 × 22 | 39.45 |
| SI-1 × 24 | >500 | SI-1 × 24 | 36.18 |
| SI-1 × 25 | >500 | SI-1 × 25 | 41.65 |
| SI-1 × 26 | >500 | SI-1 × 26 | 34.43 |

TABLE 8

In vitro efficacy of six naked antibodies (SI-1 × 4, SI-1 × 6.4, SI-1 × 22, SI-1 × 24, SI-1 × 25, SI-1 × 26) as well as six ADCs (ADC-112, ADC-6, ADC-219, ADC-227, ADC-235, ADC-243) in HARA-B.

HARA-B

| Groups | $IC_{50}$ (nM) | Groups | Efficacy (%) |
|---|---|---|---|
| ADC-112 | 14.73 | ADC-112 | 60.67 |
| ADC-6 | 3.89 | ADC-6 | 73.43 |
| ADC-219 | 2.37 | ADC-219 | 73.4 |
| ADC-227 | 2.45 | ADC-227 | 71.07 |
| ADC-235 | 3.18 | ADC-235 | 73 |
| ADC-243 | 9.93 | ADC-243 | 64.77 |
| SI-1 × 6.4 | >500 | SI-1 × 6.4 | 39.27 |
| SI-1 × 22 | >500 | SI-1 × 22 | 43.36 |
| SI-1 × 24 | >500 | SI-1 × 24 | 43.65 |
| SI-1 × 25 | >500 | SI-1 × 25 | 44.73 |
| SI-1 × 26 | >500 | SI-1 × 26 | 36.55 |
| SI-1 × 4 | >500 | SI-1 × 4 | 44.32 |

TABLE 9

In vitro efficacy of six naked antibodies (SI-1 × 4, SI-1 × 6.4, SI-1 × 22, SI-1 × 24, SI-1 × 25, SI-1 × 26) and six ADCs (ADC-112, ADC-6, ADC-219, ADC-227, ADC-235, ADC-243) in HCC827.

HCC827

| Groups | $IC_{50}$ (nM) | Groups | Efficacy (%) |
|---|---|---|---|
| ADC-112 | 2.35 | ADC-112 | 73.10 |
| ADC-6 | 1.06 | ADC-6 | 71.31 |
| ADC-219 | 0.65 | ADC-219 | 71.21 |
| ADC-227 | 0.51 | ADC-227 | 66.61 |
| ADC-235 | 0.43 | ADC-235 | 68.22 |
| ADC-243 | 2.11 | ADC-243 | 69.56 |
| SI-1 × 4 | >500 | SI-1 × 4 | 18.52 |
| SI-1 × 6.4 | 2.08 | SI-1 × 6.4 | 60.02 |
| SI-1 × 22 | 1.42 | SI-1 × 22 | 63.69 |
| SI-1 × 24 | 1.48 | SI-1 × 24 | 66.70 |
| SI-1 × 25 | 1.32 | SI-1 × 25 | 69.43 |
| SI-1 × 26 | >500 | SI-1 × 26 | 28.44 |

TABLE 10

In vitro efficacy of six naked antibodies (SI-1 × 4, SI-1 × 6.4, SI-1 × 22, SI-1 × 24, SI-1 × 25, SI-1 × 26) and six ADCs (ADC-112, ADC-6, ADC-219, ADC-227, ADC-235, ADC-243) in SW620.

SW620

| Groups | $IC_{50}$ (nM) | Groups | Efficacy (%) |
|---|---|---|---|
| ADC-112 | 5.82 | ADC-112 | 70.72 |
| ADC-6 | 4.51 | ADC-6 | 75.35 |
| ADC-219 | 4.20 | ADC-219 | 75.56 |
| ADC-227 | 5.78 | ADC-227 | 70.76 |
| ADC-235 | 4.69 | ADC-235 | 73.94 |
| ADC-243 | 3.91 | ADC-243 | 69.68 |
| SI-1 × 4 | >500 | SI-1 × 4 | 4.02 |
| SI-1 × 6.4 | >500 | SI-1 × 6.4 | 0.24 |
| SI-1 × 22 | >500 | SI-1 × 22 | 3.45 |
| SI-1 × 24 | >500 | SI-1 × 24 | 5.61 |
| SI-1 × 25 | >500 | SI-1 × 25 | 5.92 |
| SI-1 × 26 | >500 | SI-1 × 26 | 6.47 |

CONCLUSION: In human epidermal cancer cells A431, human in situ pancreatic adenocarcinoma cells BXPC-3, human pharyngeal squamous cell carcinoma cells FaDu, human lung cancer squamous cell carcinoma cell line HARA-B, human non-small-cell lung cancer cells HCC827, and human colon cancer cells SW620, six ADCs (ADC-112, ADC-6, ADC-219, ADC-227, ADC-235, ADC-243) all showed more sensitive efficacy and stronger tumor cell growth inhibition relative to their respective corresponding naked antibodies (SI-1×4, SI-1×6.4, SI-1×22, SI-1×24, SI-1×25, SI-1×26) (FIG. 4A-FIG. 4F and Table 5-Table 10).

Example 319

In Vivo Efficacy Testing:

In the present invention, BALB/c nude mice were subcutaneously inoculated with a variety of human tumor cell lines (A431, SW620, A431+SW620) as experimental models to evaluate the in vivo efficacy of ADC-coupled drugs. A certain number of tumor cell lines were inoculated subcutaneously in BALB/c nude mice, and when the tumor volume grew to 150-300 $mm^3$, the antibodies and corresponding ADC drugs were injected into the tail vein; the drugs were administered once a week four times, with continuous observation, and tumor measurements were performed twice a week to evaluate the inhibitory effect of the test antibodies and ADCs on the tumor cell lines.

Conclusion

Figure 5A:
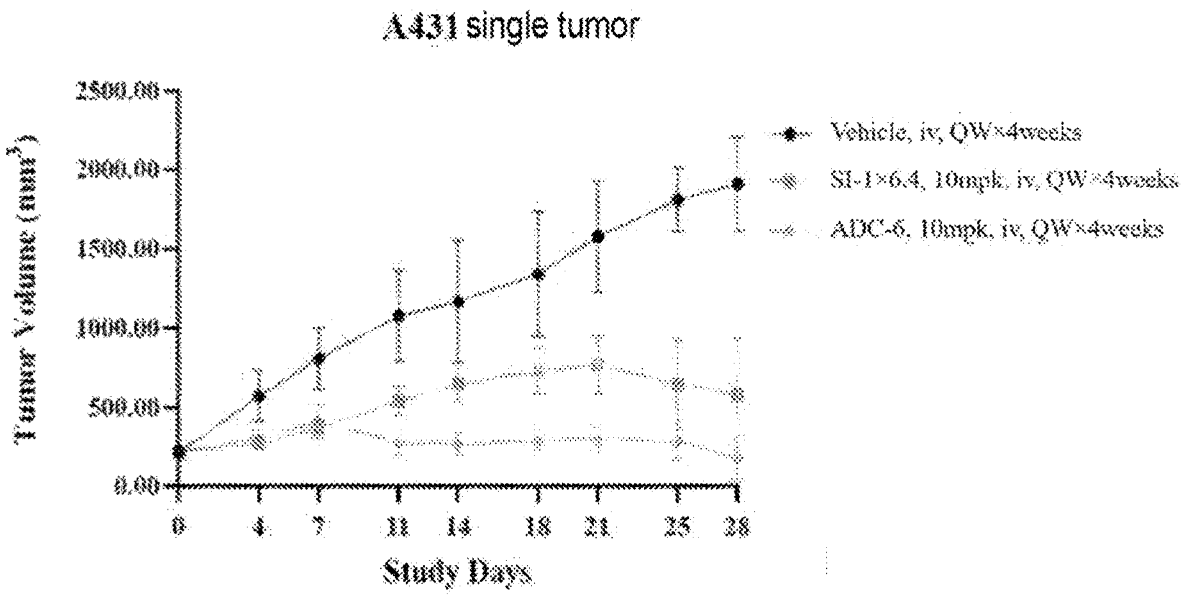
FIG. 5A illustrates the results of in vivo efficacy experiments of ADC-6 and SI-1×6.4 naked antibody in the A431 single-tumor model.

In the A431 single-tumor model with high expression of EGFR, 10 mg/kg of ADC-6 (DAR=8) exhibited stronger tumor inhibition relative to SI-1×6.4 naked antibody (FIG. 5A).

Figure 5B:
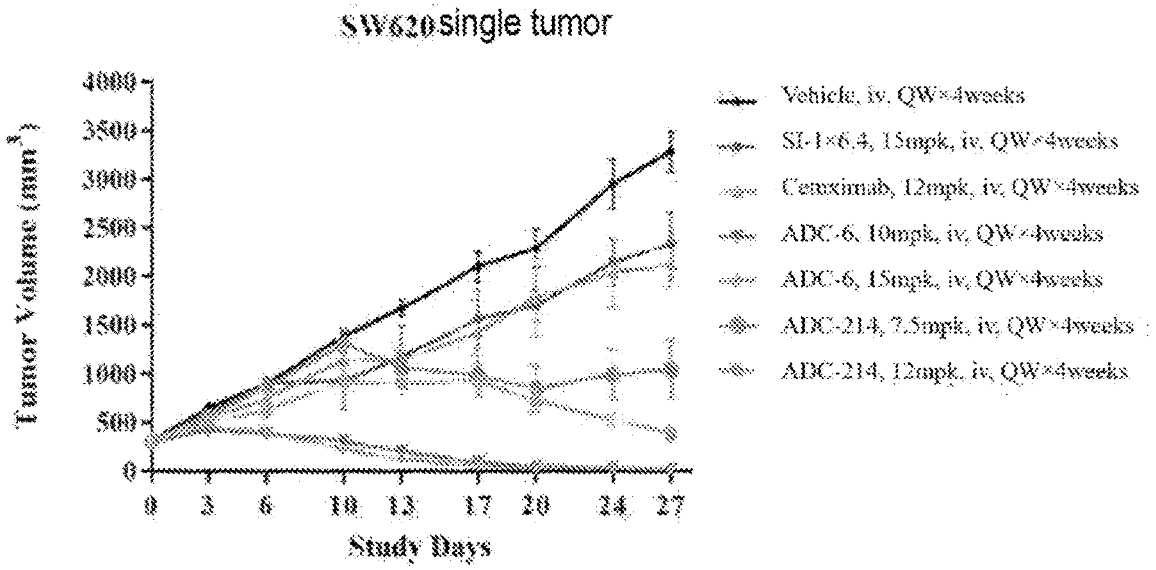
FIG. 5B illustrates the results of in vivo efficacy experiments of ADC-6, SI-1×6.4 naked antibody, Cetuximab (Cet) and ADC-214 in the SW620 single-tumor model.

In the SW620 single-tumor model with low EGFR expression, 10 and 15 mg/kg of ADC-6 also exhibited stronger tumor suppression relative to 15 mg/kg of SI-1×6.4 naked antibody; and was stronger than the tumor suppression of Cet-ADC (ADC-214, DAR=8) at a dose corresponding to the molecular molar concentration (FIG. 5B).

Figure 5C:
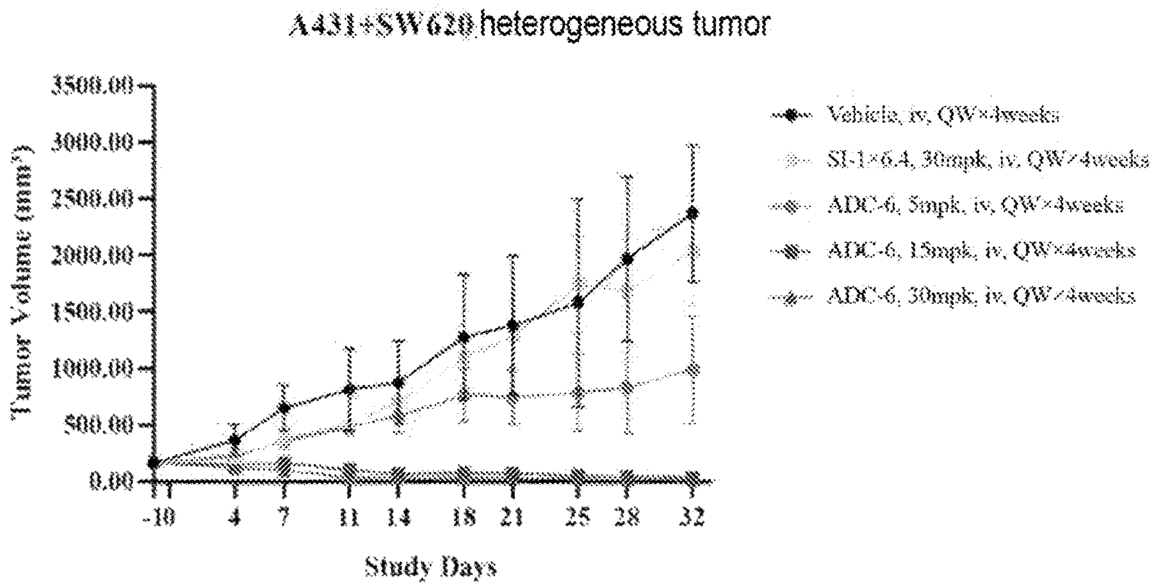
FIG. 5C illustrates the results of in vivo efficacy experiments of ADC-6 and SI-1×6.4 naked antibody in A431+SW620 heterogeneous tumors.

In A431+SW620 heterogeneous tumors, 5, 15, and 30 mg/kg of ADC-6 similarly demonstrated stronger tumor inhibition relative to 30 mg/kg of SI-1×6.4 naked antibody (FIG. 5C).

Example 320

In Vivo Efficacy Testing:

BALB/c Nude mice subcutaneously inoculated with human epidermal cancer cells A431 and human pancreatic cancer cells BxPC3 were utilized as experimental models in the present invention to evaluate the in vivo efficacy of ADC-coupled drugs. A certain number of tumor cell lines were inoculated subcutaneously on the right shoulder side of female BALB/c Nude mice, and when the average tumor volume grew to 180-250 $mm^3$, the corresponding ADC drugs were injected into the tail vein once a week for four consecutive administrations under continuous observation, and the tumor volume was measured twice a week to evaluate the inhibitory effect of the test ADC drugs on the growth of the tumors.

% change to D0=(Dn−D0)/DO*100;

% TGI=1−[changes of tumor volume in treatment group/changes of tumor volume in control group]×100.

Figure 6A:
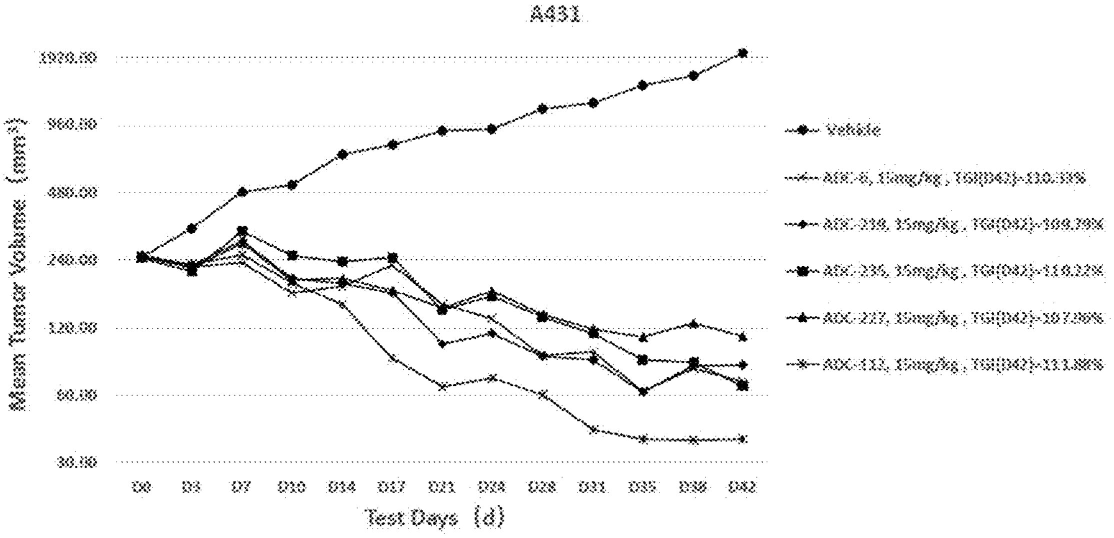
FIG. 6A illustrates the results of in vivo efficacy experiments of ADC-6, ADC-219, ADC-235, ADC-227 and ADC-112 in the A431 single-tumor model.

In the EGFR high-expressing A431 single-body tumor model, 42 days after the first administration, each test ADC drug caused significant tumor growth inhibition (P<0.05) in the BALB/c-Nude mouse subcutaneous graft tumor model of human epidermal cancer cells A431, wherein ADC-6, ADC-219, ADC-235, ADC-227 and ADC-112 had comparable tumor-suppressing effects, all of them showing strong tumor-suppressing effects (FIG. 6A).

Figure 6B:
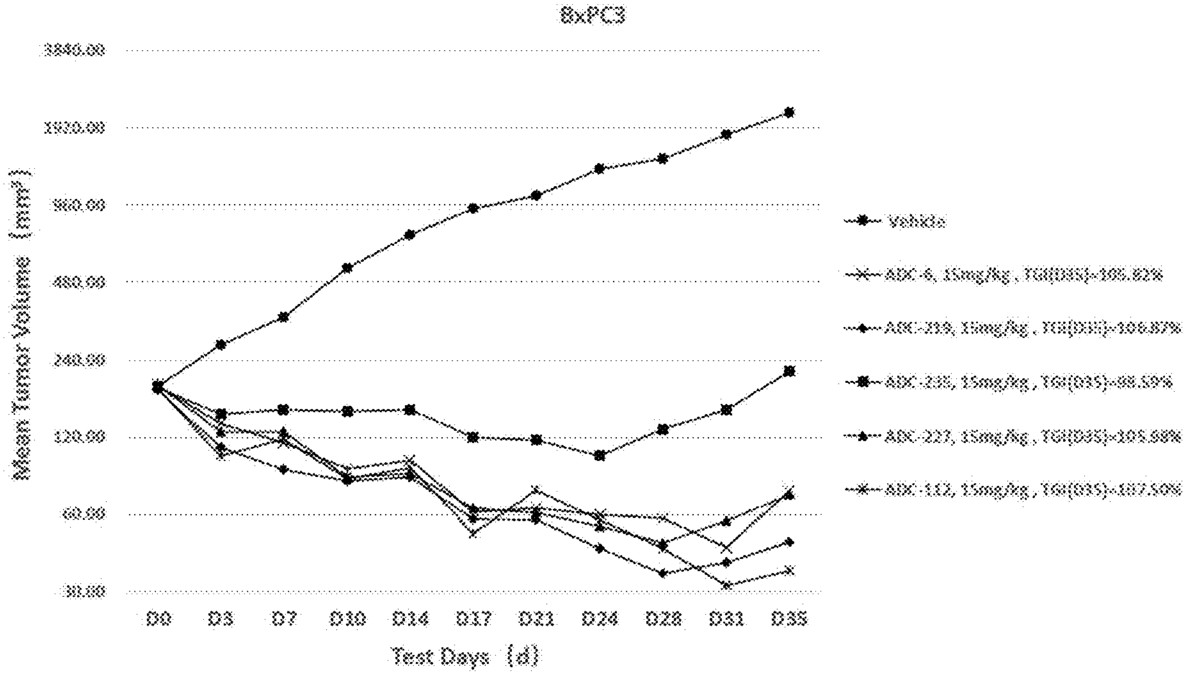
FIG. 6B illustrates the results of in vivo efficacy experiments of ADC-6, ADC-219, ADC-235, ADC-227 and ADC-112 in the BXPC-3 single-tumor model.

In the BxPC3 single-body tumor model with medium expression of EGFR, 35 days after the first administration, each test ADC drug caused significant tumor growth inhibition (P<0.05) in the human epidermal cancer cell BxPC3 BALB/c-Nude mouse subcutaneous graft tumor model, wherein ADC-6, ADC-219, ADC-235, ADC-227 and ADC-112 had comparable tumor-suppressing effects, all showing strong tumor-suppressing effects (FIG. 6B).

Example 321

In Vitro Efficacy of Payload Compound 5A:

1) Experimental Materials:

Cells: Cells for testing were obtained from the Cell Bank of the Chinese Academy of Sciences;

Cell culture medium DMEM: Gibco; FBS: BIOWEST.

2) Preparation of Culture Medium:

Growth medium (with 10% FBS, Penicillin/streptomycin (100 U/mL);

Detection medium (with 1% FBS, Penicillin/streptomycin (100 U/mL).

3) Operation:

Turn on the UV light of the biosafety cabinet 30 min in advance, and then turn on the ventilation for 3 min. Put the growth medium, detection medium, D-PBS and pancreatin into a 37° C. constant-temperature water bath to preheat, and then sterilize the surface with alcohol, and put into the biosafety cabinet. Place cells with about 80% confluence in the biosafety cabinet, draw off the old medium, rinse with D-PBS, draw and discard, digest with pancreatin for 2-3 min, and then the growth medium for neutralization, and centrifuge at 1200 rpm for 3 min. Draw off the centrifugation supernatant, mix evenly with 4 mL of detection medium, and collect 100 uL for counting (wherein 50 μL of cell fluid is taken out, 50 μL of Trypan Blue Stain is added and mixed evenly, followed by counting). Plate spreading was performed according to a pre-optimized cell spreading density; 80 ul/well was spread in a 96-well plate, with only 80 μL of detection medium being added to wells E11 and F11, and 150 μL of DPBS being added to the edge wells. 24 h after spreading the plate, diluted antibody was added, 20 uL per well, and a control was set up; only 20 μL of detection medium was added to the 11th column, and 2 duplicate wells were set up for each concentration; after addition, uniform mixing was performed on a cell vortex mixer, at 550 rpm for 3 min.

Dilution of solution: Use detection medium to prepare 300 μL of a test sample solution with a starting concentration of 5 uM in the first column of a V-shaped 96-well plate, add 240 μL of detection medium to the second to 10th columns respectively, take 60 uL from the evenly mixed first column and add it to the second column, mix uniformly up and down with a multi-channel pipette 10 times, discard the pipette tips, and perform operations for the next 7 concentrations in turn.

4) Detection:

After 4 days, take out the MTS reagent, thaw at room temperature in the dark, then mix thoroughly and evenly using a vortex mixer, then add 20 L of CellTiter One Solution Reagen MTS reagent per 100 L of cell culture volume along the side wall of the wells in the biosafety cabinet, gently tap the plate surface to mix the MTS solution evenly, and then put into a cell culture incubator and leave to incubate for 2 h in the dark. At the end of the reaction, take out the 96-well plate and measure the OD490 nm absorbance value in the microplate reader, and record, organize, analyze and store the data.

5) Results:

Table 11 illustrates that compound 5A (Payload) showed good inhibition of the following solid tumor cells and hematoma cells.

TABLE 11

In vitro inhibitory effect of compound 5A on human non-small cell lung adenocarcinoma cells H1975, human non-small cell lung cancer cells HCC827, human epidermal cancer cells A431, human gastric cancer cells NCI-N87, human in situ pancreatic adenocarcinoma cells BXPC-3, human epidermal cancer cells A431 + human colon cancer cells SW620, human breast cancer cells ZR-75-1, human plasma cell leukemia cells H929, human multiple myeloma cells RPMI8226, human leukemia cells JJN-3, human breast cancer cells MDA-MB-361 and human breast cancer cells SK-BR-3.

| Group | IC50 (nM) | Efficacy % |
|---|---|---|
| H1975 | 970.33 | 76.78 |
| HCC827 | 655.60 | 80.57 |
| A431 | 438.77 | 84.97 |
| NCI-N87 | 1023.92 | 63.93 |

TABLE 11-continued

In vitro inhibitory effect of compound 5A on human non-small cell lung adenocarcinoma cells H1975, human non-small cell lung cancer cells HCC827, human epidermal cancer cells A431, human gastric cancer cells NCI-N87, human in situ pancreatic adenocarcinoma cells BXPC-3, human epidermal cancer cells A431 + human colon cancer cells SW620, human breast cancer cells ZR-75-1, human plasma cell leukemia cells H929, human multiple myeloma cells RPMI8226, human leukemia cells JJN-3, human breast cancer cells MDA-MB-361 and human breast cancer cells SK-BR-3.

| Group | IC50 (nM) | Efficacy % |
|---|---|---|
| BxPC-3 | 320.09 | 64.4 |
| A431 + SW620 | 604.87 | 68.26 |
| ZR-75-1 | 557.95 | 54.79 |
| H929 | 23.94 | 99.03 |
| RPMI8226 | 147.00 | 93.61 |
| JJN-3 | 36.11 | 80.59 |
| MDA-MB-361 | 572.13 | 62.34 |
| SK-BR-3 | 732.43 | 70.9 |

Example 322: In Vitro Efficacy Data for ADC-6 and ADC-214

The in vitro efficacy of ADC-coupled drugs was evaluated using an experimental model of two human tumor cell lines (human poorly differentiated lung cancer squamous cell carcinoma cell line Oka-c-1, human lung squamous cell carcinoma cells SK-MES-1).

Figure 7A:
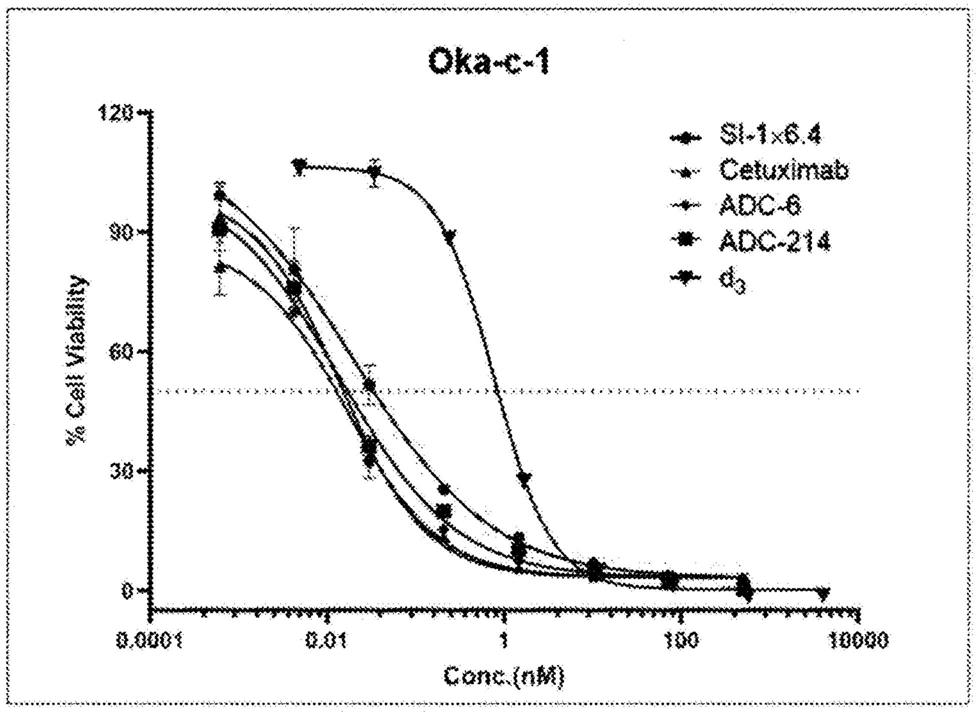
FIG. 7A illustrates the in vitro efficacy of SI-1×6.4, Cetuximab, ADC-6, ADC-214 and d3 on the human poorly differentiated lung cancer squamous cell carcinoma cell line Oka-c-1.
Figure 7B:
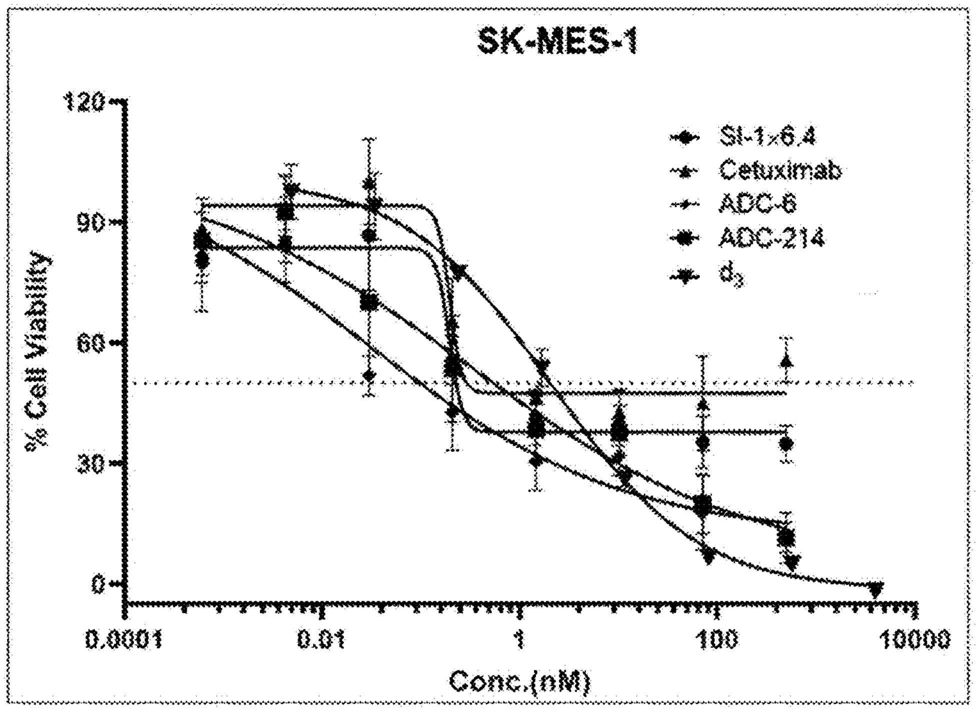
FIG. 7B illustrates the in vitro efficacy of SI-1×6.4, Cetuximab, ADC-6, ADC-214 and d3 on human lung squamous cell carcinoma cells SK-MES-1. Specific embodiments

Inoculate a certain number of tumor cells in a 96-well plate, add the gradient-diluted test antibody and the corresponding ADC drug to the cells, treat for 5 days, measure the cell viability using Alamar Blue or MTS, and evaluate the inhibitory effect of the test antibody, the ADC and the small molecule drug d3 on the tumor cell lines by calculating the IC50. The starting concentration of the antibody drug was 500 nM, and the dilution was 7-fold, totaling 7 concentration points, and the treatment was carried out for 5 days. The final calculation method was survival rate=(experimental group−blank)/(control group−blank group)×100%, followed by curve fitting using Graph Pad Prism, and calculation of the half inhibitory concentration (IC50). The results are shown in FIGS. 7A and 7B and Table 12.

TABLE 12

In vitro efficacy of SI-1 × 6.4, Cetuximab, ADC-6, ADC-214 and d3 on human poorly differentiated lung cancer squamous cell carcinoma cell line Oka-c-1 and human lung squamous cell carcinoma cells SK-MES-1.

| | IC50 (nM) | | | | |
|---|---|---|---|---|---|
| Group | SI-1 × 6.4 | Cetuximab | ADC-6 | ADC-214 | $d_3$ |
| Oka-c-1 | 0.033 | 0.015 | 0.013 | 0.017 | 0.846 |
| SK-MES-1 | 0.227 | 0.289 | 0.097 | 0.542 | 2.044 |

SEQUENCE LISTING

```
Sequence total quantity: 54
SEQ ID NO: 1            moltype = DNA  length = 645
FEATURE                 Location/Qualifiers
source                  1..645
                        mol_type = other DNA
                        organism = synthetic construct
SEQUENCE: 1
gacatcttgc tgactcagtc tccagtcatc ctgtctgtga gtccaggaga aagagtcagt  60
ttctcctgca gggccagtca gagtattggc acaaacatac actggtatca gcaaagaaca  120
aatggttctc caaggcttct cataaagtat gcttctgagt ctatctctgg gattccttcc  180
aggtttagtg gcagtggatc agggacagat tttactctta gcatcaacag tgtggagtct  240
gaagatattg cagattatta ctgtcaacaa aataataact ggccaaccac gttcggtgct  300
gggaccaagc tggagctgaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 2            moltype = AA  length = 214
FEATURE                 Location/Qualifiers
source                  1..214
                        mol_type = protein
                        organism = synthetic construct
SEQUENCE: 2
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3            moltype = DNA  length = 2109
FEATURE                 Location/Qualifiers
source                  1..2109
                        mol_type = other DNA
                        organism = synthetic construct
SEQUENCE: 3
caggtgcagc tgaagcagtc aggacctggc ctagtgcagc cctcacagag cctgtccatc  60
acctgcacag tctctggttt ctcattaact aactatggtg tacactgggt tcgccagtct  120
ccaggaaagg gtctggagtg gctgggagtg atatggagtg gtggaaacac agactataat  180
acacctttca catccagact gagcatcaac aaggacaatt ccaagagcca agttttcttt  240
aaaatgaaca gtctgcaatc taatgacaca gccatatatt actgtgccag agccctcacc  300
tactatgatt acgagtttgc ttactggggc caagggactc tggtcactgt ctctagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggtggcggt ggagggtccg gcggtggtgg atcacaggtg  1380
caattgcagg agtcgggggg aggcctggtc aagcctggag ggtccctgag actctcctgt  1440
gcagcctctg gattcacctt tagtagttat tggatgagct gggtccgcca ggctccaggg  1500
aaggggctgg agtgggtggc caacataaac cgcgatggaa gtgcgagtta ctatgtggac  1560
tctgtgaagg gccgattcac catctccaga gacgacgcca agaactcact gtatctgcaa  1620
atgaacagcc tgagagctga ggacacggct gtgtattact gtgcgagaga tcgtggggtg  1680
ggctacttcg atctctgggg ccgtggcacc ctggtcaccg tctcgagcgg tggaggcggt  1740
tcaggcggag gtggttccgg cggtggcggc tcccagtctg ccctgactca gcctgcctcc  1800
gtgtctgggt ctcctggaca gtcgatcacc atctcctgca ctggaaccag cagtgacgtt  1860
ggtggttata actttgtctc ctggtaccaa caacacccag gcaaagcccc caaactcatg  1920
atctatgatg tcagtgatcg gccctcaggg gtgtctgatc gcttctccgg ctccaagtct  1980
ggcaacacgg cctccctgat catctctggc ctccaggctg acgacgaggc tgattattac  2040
tgcagctcat atgggagcag cagcactcat gtgattttcg gcggagggac caaggtgacc  2100
gtcctataa                                                          2109

SEQ ID NO: 4            moltype = AA  length = 702
FEATURE                 Location/Qualifiers
source                  1..702
                        mol_type = protein
                        organism = synthetic construct
```

-continued

```
SEQUENCE: 4
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGGG GGSGGGGSQV QLQESGGGLV KPGGSLRLSC  480
AASGFTFSSY WMSWVRQAPG KGLEWVANIN RDGSASYYVD SVKGRFTISR DDAKNSLYLQ  540
MNSLRAEDTA VYYCARDRGV GYFDLWGRGT LVTVSSGGGG SGGGGSGGGG SQSALTQPAS  600
VSGSPGQSIT ISCTGTSSDV GGYNFVSWYQ QHPGKAPKLM IYDVSDRPSG VSDRFSGSKS  660
GNTASLIISG LQADDEADYY CSSYGSSSTH VIFGGGTKVT VL                    702

SEQ ID NO: 5            moltype = DNA  length = 660
FEATURE                 Location/Qualifiers
source                  1..660
                        mol_type = other DNA
                        organism = synthetic construct
SEQUENCE: 5
gatattcaaa tgactcaatc tccttcttct ctttctgctt ctgttggtga tcgtgttact  60
attacttgtc gttcttctca aaatattgtt cattctaatg gtaatactta tcttgattgg  120
tatcaacaaa ctcctggtaa agctcctaaa cttcttattt ataaagtttc taatcgtttt  180
tctggtgttc cttctcgttt ttctggttct ggttctggta ctgattttac ttttactatt  240
tcttctcttc aacctgaaga tattgctact tattattgtt ttcaatattc tcatgttcct  300
tggacttttg gtcaaggtac taaacttcaa attactcgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttag  660

SEQ ID NO: 6            moltype = AA  length = 219
FEATURE                 Location/Qualifiers
source                  1..219
                        mol_type = protein
                        organism = synthetic construct
SEQUENCE: 6
DIQMTQSPSS LSASVGDRVT ITCRSSQNIV HSNGNTYLDW YQQTPGKAPK LLIYKVSNRF  60
SGVPSRFSGS GSGTDFTFTI SSLQPEDIAT YYCFQYSHVP WTFGQGTKLQ ITRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 7            moltype = DNA  length = 2121
FEATURE                 Location/Qualifiers
source                  1..2121
                        mol_type = other DNA
                        organism = synthetic construct
SEQUENCE: 7
caggtgcagc tgcagcagag cggcgccgag gtgaagaagc ccggcagcag cgtgaaggtg  60
agctgcaagg ccagcggcta caccttcacc aactactaca tctactgggt gcggcaggcc  120
cccggccagg gcctggagtg gatcggcggc atcaacccca ccagcggcgg cagcaacttc  180
aacgagaagt tcaagacccg ggtgaccatc accgccgacg agagcagcac caccgcctac  240
atggagctga gcagcctgcg gagcgaggac accgccttct acttctgcac ccggcagggc  300
ctgtggttcg acagcgacgg ccggggcttc gacttctggg gccagggcac caccgtgacc  360
gtgagcagcg ctagcaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaga  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtggcg gtggagggtc cggcggtggt  1380
ggatcacagg tgcaattgca ggagtcgggg ggaggcctgg tcaagcctgg agggtccctg  1440
agactctcct gtgcagcctc tggattcacc tttagtagtt attggatgag ctgggtccgc  1500
caggctccag ggaaggggct ggagtgggtg gccaacataa accgcgatgg aagtgcgagt  1560
tactatgtgg actctgtgaa gggccgattc accatctcca gagacgacgc caagaactca  1620
ctgtatctgc aaatgaacag cctgagagct gaggacacgg ctgtgtatta ctgtgcgaga  1680
gatcgtgggg tgggctactt cgatctctgg ggccgtggca ccctggtcac cgtctcgagc  1740
ggtggaggcg gttcaggcgg aggtggttcc ggcggtggcg gctcccagtc tgccctgact  1800
```

-continued

```
cagcctgcct ccgtgtctgg gtctcctgga cagtcgatca ccatctcctg cactggaacc  1860
agcagtgacg ttggtggtta taactttgtc tcctggtacc aacaacaccc aggcaaagcc  1920
cccaaactca tgatctatga tgtcagtgat cggccctcag gggtgtctga tcgcttctcc  1980
ggctccaagt ctggcaacac ggcctccctg atcatctctg gcctccaggc tgacgacgag  2040
gctgattatt actgcagctc atatgggagc agcagcactc atgtgatttt cggcggaggg  2100
accaaggtga ccgtcctata a                                            2121

SEQ ID NO: 8            moltype = AA  length = 706
FEATURE                 Location/Qualifiers
source                  1..706
                        mol_type = protein
                        organism = synthetic construct
SEQUENCE: 8
QVQLQQSGAE VKKPGSSVKV SCKASGYTFT NYYIYWVRQA PGQGLEWIGG INPTSGGSNF  60
NEKFKTRVTI TADESSTTAY MELSSLRSED TAFYFCTRQG LWFDSDGRGF DFWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSQVQLQESG GGLVKPGGSL  480
RLSCAASGFT FSSYWMSWVR QAPGKGLEWV ANINRDGSAS YYVDSVKGRF TISRDDAKNS  540
LYLQMNSLRA EDTAVYYCAR DRGVGYFDLW GRGTLVTVSS GGGGSGGGGS GGGGSQSALT  600
QPASVSGSPG QSITISCTGT SSDVGGYNFV SWYQQHPGKA PKLMIYDVSD RPSGVSDRFS  660
GSKSGNTASL IISGLQADDE ADYYCSSYGS SSTHVIFGGG TKVTVL                 706

SEQ ID NO: 9            moltype = DNA  length = 1422
FEATURE                 Location/Qualifiers
source                  1..1422
                        mol_type = other DNA
                        organism = synthetic construct
SEQUENCE: 9
gacatcttgc tgactcagtc tccagtcatc ctgtctgtga gtccaggaga aagagtcagt  60
ttctcctgca gggccagtca gagtattggc acaaacatac actggtatca gcaaagaaca  120
aatggttctc caaggcttct cataaagtat gcttctgagt ctatctctgg gattccttcc  180
aggtttagtg gcagtggatc agggacagat tttactctta gcatcaacag tgtggagtct  240
gaagatattg cagattatta ctgtcaacaa aataataact ggccaaccac gttcggttgt  300
gggaccaagc tggagctgaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gtggtggcgg cggaagtggc  660
ggtggaggat ccggcggtgg tggatcacag gtgcagctgc aggagtcggg gggaggcctg  720
gtcaagcctg gagggtccct gagtctctcc tgtgcagcct ctggattcac ctttagtagt  780
tattggatga gctgggtccg ccaggctcca gggaaggggc tggagtgggt ggccaacata  840
aaccgcgatg gaagtgcgag ttactatgtg gactctgtga agggccgatt caccatctcc  900
agagacgacg ccaagaactc actgtatctg caaatgaaca gcctgagagc tgaggacacg  960
gctgtgtatt actgtgcgag agatcgtggg gtgggctact tcgatctctg gggccgtggc  1020
accctggtca ccgtctcgag cggtggaggc ggttcaggcg gaggtggttc cggcggtggc  1080
ggctcccagt ctgccctgac tcagcctgcc tccgtgtctg ggtctcctgg acagtcgatc  1140
accatctcct gcactggaac cagcagtgac gttggtggtt ataactttgt ctcctggtac  1200
caacaacacc caggcaaagc ccccaaactc atgatctatg atgtcagtga tcggccctca  1260
ggggtgtctg atcgcttctc cggctccaag tctggcaaca cggcctccct gatcatctct  1320
ggcctccagg ctgacgacga ggctgattat tactgcagct catatgggag cagcagcact  1380
catgtgattt tcggcggagg gaccaaggtg accgtcctat aa                     1422

SEQ ID NO: 10           moltype = AA  length = 473
FEATURE                 Location/Qualifiers
source                  1..473
                        mol_type = protein
                        organism = synthetic construct
SEQUENCE: 10
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGC GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGGGGSG GGGSGGGGSQ VQLQESGGGL  240
VKPGGSLSLS CAASGFTFSS YWMSWVRQAP GKGLEWVANI NRDGSASYYV DSVKGRFTIS  300
RDDAKNSLYL QMNSLRAEDT AVYYCARDRG VGYFDLWGRG TLVTVSSGGG GSGGGGSGGG  360
GSQSALTQPA SVSGSPGQSI TISCTGTSSD VGGYNFVSWY QQHPGKAPKL MIYDVSDRPS  420
GVSDRFSGSK SGNTASLIIS GLQADDEADY YCSSYGSSST HVIFGGGTKV TVL         473

SEQ ID NO: 11           moltype = DNA  length = 1347
FEATURE                 Location/Qualifiers
source                  1..1347
                        mol_type = other DNA
                        organism = synthetic construct
SEQUENCE: 11
caggtgcagc tgaagcagtc aggacctggc ctagtgcagc cctcacagag cctgtccatc  60
```

-continued

```
acctgcacag tctctggttt ctcattaact aactatggtg tacactgggt tcgccagtct  120
ccaggaaagt gcctggagtg gctgggagtg atatggagtg gtggaaacac agactataat  180
acacctttca catccagact gagcatcaac aaggacaatt ccaagagcca agttttcttt  240
aaaatgaaca gtctgcaatc taatgacaca gccatatatt actgtgccag agccctcacc  300
tactatgatt acgagtttgc ttactggggc caagggactc tggtcactgt ctctgctgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggttaa                                    1347

SEQ ID NO: 12          moltype = AA  length = 448
FEATURE                Location/Qualifiers
source                 1..448
                       mol_type = protein
                       organism = synthetic construct
SEQUENCE: 12
QVQLKQSGPG LVQPSQSLSI TCTVSGFSLT NYGVHWVRQS PGKCLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 13          moltype = DNA  length = 645
FEATURE                Location/Qualifiers
source                 1..645
                       mol_type = other DNA
                       organism = synthetic construct
SEQUENCE: 13
gacatcttgc tgactcagtc tccagtcatc ctgtctgtga gtccaggaga aagagtcagt  60
ttctcctgca gggccagtca gagtattggc acaaacatac actggtatca gcaaagaaca  120
aatggttctc caaggcttct cataaagtat gcttctgagt ctatctctgg gattccttcc  180
aggtttagtg gcagtggatc agggacagat tttactctta gcatcaacag tgtggagtct  240
gaagatattg cagattatta ctgtcaacaa aataataact ggccaaccac gttcggtgct  300
gggaccaagc tggagctgaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                645

SEQ ID NO: 14          moltype = AA  length = 214
FEATURE                Location/Qualifiers
source                 1..214
                       mol_type = protein
                       organism = synthetic construct
SEQUENCE: 14
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 15          moltype = DNA  length = 2109
FEATURE                Location/Qualifiers
source                 1..2109
                       mol_type = other DNA
                       organism = synthetic construct
SEQUENCE: 15
caggtgcagc tgcaggagtc gggggaggc ctggtcaagc ctggagggtc cctgagactc  60
tcctgtgcag cctctggatt cacctttagt agttattgga tgagctgggt ccgccaggct  120
ccagggaagg ggctggagtg ggtggccaac ataaaccgcg atggaagtgc gagttactat  180
gtggactctg tgaagggccg attcaccatc tccagagacg acgccaagaa ctcactgtat  240
ctgcaaatga acagcctgag agctgaggac acggctgtgt attactgtgc gagagatcgt  300
ggggtgggct acttcgatct ctggggccgt ggcaccctgg tcaccgtctc gagcggtgga  360
```

-continued

```
ggcggttcag gcggaggtgg ttccggcggt ggcggctccc agtctgccct gactcagcct  420
gcctccgtgt ctgggtctcc tggacagtcg atcaccatct cctgcactgg aaccagcagt  480
gacgttggtg gttataactt tgtctcctgg taccaacaac acccaggcaa agcccccaaa  540
ctcatgatct atgatgtcag tgatcggccc tcaggggtgt ctgatcgctt ctccggctcc  600
aagtctggca acacggcctc cctgatcatc tctggcctcc aggctgacga cgaggctgat  660
tattactgca gctcatatgg gagcagcagc actcatgtga ttttcggcgg agggaccaag  720
gtgaccgtcc taggcggtgg aggatccggc ggtggtggat cacaggtgca gctgaagcag  780
tcaggacctg gcctagtgca gccctcacag agcctgtcca tcacctgcac agtctctggt  840
ttctcattaa ctaactatgg tgtacactgg gttcgccagt ctccaggaaa gggtctggag  900
tggctgggag tgatatggag tggtggaaac acagactata atacaccttt cacatccaga  960
ctgagcatca acaaggacaa ttccaagagc caagttttct ttaaaatgaa cagtctgcaa  1020
tctaatgaca cagccatata ttactgtgcc agagccctca cctactatga ttacgagttt  1080
gcttactggg gccaagggac tctggtcact gtctctagcg ctagcaccaa gggcccatcg  1140
gtcttccccc tggcaccctc ctccaagagc acctctgggg gcacagcggc cctgggctgc  1200
ctggtcaagg actacttccc cgaaccggtg acggtgtcgt ggaactcagg cgccctgacc  1260
agcggcgtgc acaccttccc ggctgtccta cagtcctcag gactctactc cctcagcagc  1320
gtggtgaccg tgccctccag cagcttgggc acccagacct acatctgcaa cgtgaatcac  1380
aagcccagca acaccaaggt ggacaagaga gttgagccca aatcttgtga caaaactcac  1440
acatgcccac cgtgcccagc acctgaactc ctggggggac cgtcagtctt cctcttcccc  1500
ccaaaaccca aggacaccct catgatctcc cggacccctg aggtcacatg cgtggtggtg  1560
gacgtgagcc acgaagaccc tgaggtcaag ttcaactggt acgtggacgg cgtggaggtg  1620
cataatgcca agacaaagcc gcgggaggag cagtacaaca gcacgtaccg tgtggtcagc  1680
gtcctcaccg tcctgcacca ggactggctg aatggcaagg agtacaagtg caaggtctcc  1740
aacaaagccc tcccagcccc catcgagaaa accatctcca aagccaaagg gcagccccga  1800
gaaccacagg tgtacaccct gcccccatcc cgggatgagc tgaccaagaa ccaggtcagc  1860
ctgacctgcc tggtcaaagg cttctatccc agcgacatcg ccgtggagtg ggagagcaat  1920
gggcagccgg agaacaacta caagaccacg cctcccgtgc tggactccga cggctccttc  1980
ttcctctata gcaagctcac cgtggacaag agcaggtggc agcaggggaa cgtcttctca  2040
tgctccgtga tgcatgaggc tctgcacaac cactacacgc agaagagcct ctccctgtct  2100
ccgggttaa                                                          2109

SEQ ID NO: 16           moltype = AA  length = 702
FEATURE                 Location/Qualifiers
source                  1..702
                        mol_type = protein
                        organism = synthetic construct
SEQUENCE: 16
QVQLQESGGG LVKPGGSLRL SCAASGFTFS SYWMSWVRQA PGKGLEWVAN INRDGSASYY  60
VDSVKGRFTI SRDDAKNSLY LQMNSLRAED TAVYYCARDR GVGYFDLWGR GTLVTVSSGG  120
GGSGGGGSGG GGSQSALTQP ASVSGSPGQS ITISCTGTSS DVGGYNFVSW YQQHPGKAPK  180
LMIYDVSDRP SGVSDRFSGS KSGNTASLII SGLQADDEAD YYCSSYGSSS THVIFGGGTK  240
VTVLGGGGSG GGGSQVQLKQ SGPGLVQPSQ SLSITCTVSG FSLTNYGVHW VRQSPGKGLE  300
WLGVIWSGGN TDYNTPFTSR LSINKDNSKS QVFFKMNSLQ SNDTAIYYCA RALTYYDYEF  360
AYWGQGTLVT VSSASTKGPS VFPLAPSSKS TSGGTAALGC LVKDYFPEPV TVSWNSGALT  420
SGVHTFPAVL QSSGLYSLSS VVTVPSSSLG TQTYICNVNH KPSNTKVDKR VEPKSCDKTH  480
TCPPCPAPEL LGGPSVFLFP PKPKDTLMIS RTPEVTCVVV DVSHEDPEVK FNWYVDGVEV  540
HNAKTKPREE QYNSTYRVVS VLTVLHQDWL NGKEYKCKVS NKALPAPIEK TISKAKGQPR  600
EPQVYTLPPS RDELTKNQVS LTCLVKGFYP SDIAVEWESN GQPENNYKTT PPVLDSDGSF  660
FLYSKLTVDK SRWQQGNVFS CSVMHEALHN HYTQKSLSLS PG                     702

SEQ ID NO: 17           moltype = DNA  length = 1407
FEATURE                 Location/Qualifiers
source                  1..1407
                        mol_type = other DNA
                        organism = synthetic construct
SEQUENCE: 17
caggtgcagc tgcaggagtc gggggaggc ctggtcaagc ctggagggtc cctgagtctc  60
tcctgtgcag cctctggatt cacctttagt agttattgga tgagctgggt ccgccaggct  120
ccagggaagg ggctggagtg ggtggccaac ataaaccgcg atggaagtgc gagttactat  180
gtggactctg tgaagggccg attcaccatc tccagagacg acgccaagaa ctcactgtat  240
ctgcaaatga acagcctgag agctgaggac acggctgtgt attactgtgc gagagatcgt  300
ggggtgggct acttcgatct ctggggccgt ggcaccctgg tcaccgtctc gagcggtgga  360
ggcggttcag gcggaggtgg ttccggcggt ggcggctccc agtctgccct gactcagcct  420
gcctccgtgt ctgggtctcc tggacagtcg atcaccatct cctgcactgg aaccagcagt  480
gacgttggtg gttataactt tgtctcctgg taccaacaac acccaggcaa agcccccaaa  540
ctcatgatct atgatgtcag tgatcggccc tcaggggtgt ctgatcgctt ctccggctcc  600
aagtctggca acacggcctc cctgatcatc tctggcctcc aggctgacga cgaggctgat  660
tattactgca gctcatatgg gagcagcagc actcatgtga ttttcggcgg agggaccaag  720
gtgaccgtcc taggcggtgg aggatccggc ggtggtggat cagacatctt gctgactcag  780
tctccagtca tcctgtctgt gagtccagga gaaagagtca gtttctcctg cagggccagt  840
cagagtattg gcacaaacat acactggtat cagcaaagaa caaatggttc tccaaggctt  900
ctcataaagt atgcttctga gtctatctct gggattcctt ccaggtttag tggcagtgga  960
tcagggacag attttactct tagcatcaac agtgtggagt ctgaagatat tgcagattat  1020
tactgtcaac aaaataataa ctggccaacc acgttcggtt gtgggaccaa gctggagctg  1080
aaacgtacgg tggctgcacc atctgtcttc atcttcccgc catctgatga gcagttgaaa  1140
tctggaactg cctctgttgt gtgcctgctg aataacttct atcccagaga ggccaaagta  1200
cagtggaagg tggataacgc cctccaatcg ggtaactccc aggagagtgt cacagagcag  1260
gacagcaagg acagcaccta cagcctcagc agcaccctga cgctgagcaa agcagactac  1320
gagaaacaca aagtctacgc ctgcgaagtc acccatcagg gcctgagctc gcccgtcaca  1380
```

```
aagagcttca acaggggaga gtgttag                                1407

SEQ ID NO: 18          moltype = AA  length = 468
FEATURE                Location/Qualifiers
source                 1..468
                       mol_type = protein
                       organism = synthetic construct
SEQUENCE: 18
QVQLQESGGG LVKPGGSLSL SCAASGFTFS SYWMSWVRQA PGKGLEWVAN INRDGSASYY  60
VDSVKGRFTI SRDDAKNSLY LQMNSLRAED TAVYYCARDR GVGYFDLWGR GTLVTVSSGG  120
GGSGGGGSGG GGSQSALTQP ASVSGSPGQS ITISCTGTSS DVGGYNFVSW YQQHPGKAPK  180
LMIYDVSDRP SGVSDRFSGS KSGNTASLII SGLQADDEAD YYCSSYGSSS THVIFGGGTK  240
VTVLGGGGSG GGGSDILLTQ SPVILSVSPG ERVSFSCRAS QSIGTNIHWY QQRTNGSPRL  300
LIKYASESIS GIPSRFSGSG SGTDFTLSIN SVESEDIADY YCQQNNNWPT TFGCGTKLEL  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC          468

SEQ ID NO: 19          moltype = DNA  length = 1347
FEATURE                Location/Qualifiers
source                 1..1347
                       mol_type = other DNA
                       organism = synthetic construct
SEQUENCE: 19
caggtgcagc tgaagcagtc aggacctggc ctagtgcagc cctcacagag cctgtccatc  60
acctgcacag tctctggttt ctcattaact aactatggtg tacactgggt tcgccagtct  120
ccaggaaagt gcctggagtg gctgggagtg atatggagtg gtggaaacac agactataat  180
acacctttca catccagact gagcatcaac aaggacaatt ccaagagcca agttttcttt  240
aaaatgaaca gtctgcaatc taatgacaca gccatatatt actgtgccag agccctcacc  300
tactatgatt acgagtttgc ttactggggc caagggactc tggtcactgt ctctgctgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggttaa                                1347

SEQ ID NO: 20          moltype = AA  length = 448
FEATURE                Location/Qualifiers
source                 1..448
                       mol_type = protein
                       organism = synthetic construct
SEQUENCE: 20
QVQLKQSGPG LVQPSQSLSI TCTVSGFSLT NYGVHWVRQS PGKCLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                448

SEQ ID NO: 21          moltype = DNA  length = 1437
FEATURE                Location/Qualifiers
source                 1..1437
                       mol_type = other DNA
                       organism = synthetic construct
SEQUENCE: 21
gatattcaaa tgactcaatc tccttcttct ctttctgctt ctgttggtga tcgtgttact  60
attacttgtc gttcttctca aaatattgtt cattctaatg gtaatactta tcttgattgg  120
tatcaacaaa ctcctggtaa agctcctaaa cttcttattt ataaagtttc taatcgtttt  180
tctggtgttc cttctcgttt ttctggttct ggttctggta ctgattttac ttttactatt  240
tcttctcttc aacctgaaga tattgctact tattattgtt ttcaatattc tcatgttcct  300
tggacttttg gttgcggtac taaacttcaa attactcgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgtggt  660
```

```
ggcggcggaa gtggcggtgg aggatccggc ggtggtggat cacaggtgca gctgcaggag  720
tcgggggggag gcctggtcaa gcctggaggg tccctgagtc tctcctgtgc agcctctgga  780
ttcaccttta gtagttattg gatgagctgg gtccgccagg ctccagggaa ggggctggag  840
tgggtggcca acataaaccg cgatggaagt gcgagttact atgtggactc tgtgaagggc  900
cgattcacca tctccagaga cgacgccaag aactcactgt atctgcaaat gaacagcctg  960
agagctgagg acacggctgt gtattactgt gcgagagatc gtggggtggg ctacttcgat  1020
ctctggggcc gtggcaccct ggtcaccgtc tcgagcggtg gaggcggttc aggcggaggt  1080
ggttccggcg gtggcggctc ccagtctgcc ctgactcagc ctgcctccgt gtctgggtct  1140
cctggacagt cgatcaccat ctcctgcact ggaaccagca gtgacgttgg tggttataac  1200
tttgtctcct ggtaccaaca acacccaggc aaagccccca aactcatgat ctatgatgtc  1260
agtgatcggc cctcaggggt gtctgatcgc ttctccggct ccaagtctgg caacacggcc  1320
tccctgatca tctctggcct ccaggctgac gacgaggctg attattactg cagctcatat  1380
gggagcagca gcactcatgt gattttcggc ggagggacca aggtgaccgt cctataa     1437

SEQ ID NO: 22          moltype = AA  length = 478
FEATURE                Location/Qualifiers
source                 1..478
                       mol_type = protein
                       organism = synthetic construct
SEQUENCE: 22
DIQMTQSPSS LSASVGDRVT ITCRSSQNIV HSNGNTYLDW YQQTPGKAPK LLIYKVSNRF  60
SGVPSRFSGS GSGTDFTFTI SSLQPEDIAT YYCFQYSHVP WTFGCGTKLQ ITRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECG GGGSGGGGSG GGGSQVQLQE  240
SGGGLVKPGG SLSLSCAASG FTFSSYWMSW VRQAPGKGLE WVANINRDGS ASYYVDSVKG  300
RFTISRDDAK NSLYLQMNSL RAEDTAVYYC ARDRGVGYFD LWGRGTLVTV SSGGGGSGGG  360
GSGGGGSQSA LTQPASVSGS PGQSITISCT GTSSDVGGYN FVSWYQQHPG KAPKLMIYDV  420
SDRPSGVSDR FSGSKSGNTA SLIISGLQAD DEADYYCSSY GSSSTHVIFG GGTKVTVL    478

SEQ ID NO: 23          moltype = DNA  length = 1359
FEATURE                Location/Qualifiers
source                 1..1359
                       mol_type = other DNA
                       organism = synthetic construct
SEQUENCE: 23
caggtgcagc tgcagcagag cggcgccgag gtgaagaagc ccggcagcag cgtgaaggtg  60
agctgcaagg ccagcggcta caccttcacc aactactaca tctactgggt gcggcaggcc  120
cccggccagt gtctggagtg gatcggcggc atcaacccca ccagcggcgg cagcaacttc  180
aacgagaagt tcaagacccg ggtgaccatc accgccgacg agagcagcac caccgcctac  240
atggagctga gcagcctgcg gagcgaggac accgccttct acttctgcac ccggcagggc  300
ctgtggttcg acagcgacgg ccggggcttc gacttctggg gccagggcac caccgtgacc  360
gtgagcagcg ctagcaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaga  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggttaa                        1359

SEQ ID NO: 24          moltype = AA  length = 452
FEATURE                Location/Qualifiers
source                 1..452
                       mol_type = protein
                       organism = synthetic construct
SEQUENCE: 24
QVQLQQSGAE VKKPGSSVKV SCKASGYTFT NYYIYWVRQA PGQCLEWIGG INPTSGGSNF  60
NEKFKTRVTI TADESSTTAY MELSSLRSED TAFYFCTRQG LWFDSDGRGF DFWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PG                                452

SEQ ID NO: 25          moltype = AA  length = 11
FEATURE                Location/Qualifiers
source                 1..11
                       mol_type = protein
                       organism = synthetic construct
```

-continued

```
SEQUENCE: 25
RASQSIGTNI H                                                    11

SEQ ID NO: 26           moltype = AA  length = 7
FEATURE                 Location/Qualifiers
source                  1..7
                        mol_type = protein
                        organism = synthetic construct
SEQUENCE: 26
YASESIS                                                         7

SEQ ID NO: 27           moltype = AA  length = 9
FEATURE                 Location/Qualifiers
source                  1..9
                        mol_type = protein
                        organism = synthetic construct
SEQUENCE: 27
QQNNNWPTT                                                       9

SEQ ID NO: 28           moltype = AA  length = 107
FEATURE                 Location/Qualifiers
source                  1..107
                        mol_type = protein
                        organism = synthetic construct
SEQUENCE: 28
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELK             107

SEQ ID NO: 29           moltype = AA  length = 5
FEATURE                 Location/Qualifiers
source                  1..5
                        mol_type = protein
                        organism = synthetic construct
SEQUENCE: 29
NYGVH                                                           5

SEQ ID NO: 30           moltype = AA  length = 16
FEATURE                 Location/Qualifiers
source                  1..16
                        mol_type = protein
                        organism = synthetic construct
SEQUENCE: 30
VIWSGGNTDY NTPFTS                                               16

SEQ ID NO: 31           moltype = AA  length = 11
FEATURE                 Location/Qualifiers
source                  1..11
                        mol_type = protein
                        organism = synthetic construct
SEQUENCE: 31
ALTYYDYEFA Y                                                    11

SEQ ID NO: 32           moltype = AA  length = 5
FEATURE                 Location/Qualifiers
source                  1..5
                        mol_type = protein
                        organism = synthetic construct
SEQUENCE: 32
SYWMS                                                           5

SEQ ID NO: 33           moltype = AA  length = 17
FEATURE                 Location/Qualifiers
source                  1..17
                        mol_type = protein
                        organism = synthetic construct
SEQUENCE: 33
NINRDGSASY YVDSVKG                                              17

SEQ ID NO: 34           moltype = AA  length = 9
FEATURE                 Location/Qualifiers
source                  1..9
                        mol_type = protein
                        organism = synthetic construct
SEQUENCE: 34
DRGVGYFDL                                                       9

SEQ ID NO: 35           moltype = AA  length = 14
FEATURE                 Location/Qualifiers
source                  1..14
```

```
                         mol_type = protein
                         organism = synthetic construct
SEQUENCE: 35
TGTSSDVGGY NFVS                                              14

SEQ ID NO: 36            moltype = AA  length = 7
FEATURE                  Location/Qualifiers
source                   1..7
                         mol_type = protein
                         organism = synthetic construct
SEQUENCE: 36
DVSDRPS                                                      7

SEQ ID NO: 37            moltype = AA  length = 11
FEATURE                  Location/Qualifiers
source                   1..11
                         mol_type = protein
                         organism = synthetic construct
SEQUENCE: 37
SSYGSSSTHV I                                                 11

SEQ ID NO: 38            moltype = AA  length = 119
FEATURE                  Location/Qualifiers
source                   1..119
                         mol_type = protein
                         organism = synthetic construct
SEQUENCE: 38
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSS   119

SEQ ID NO: 39            moltype = AA  length = 118
FEATURE                  Location/Qualifiers
source                   1..118
                         mol_type = protein
                         organism = synthetic construct
SEQUENCE: 39
QVQLQESGGG LVKPGGSLRL SCAASGFTFS SYWMSWVRQA PGKGLEWVAN INRDGSASYY  60
VDSVKGRFTI SRDDAKNSLY LQMNSLRAED TAVYYCARDR GVGYFDLWGR GTLVTVSS    118

SEQ ID NO: 40            moltype = AA  length = 111
FEATURE                  Location/Qualifiers
source                   1..111
                         mol_type = protein
                         organism = synthetic construct
SEQUENCE: 40
QSALTQPASV SGSPGQSITI SCTGTSSDVG GYNFVSWYQQ HPGKAPKLMI YDVSDRPSGV  60
SDRFSGSKSG NTASLIISGL QADDEADYYC SSYGSSSTHV IFGGGTKVTV L           111

SEQ ID NO: 41            moltype = AA  length = 16
FEATURE                  Location/Qualifiers
source                   1..16
                         mol_type = protein
                         organism = synthetic construct
SEQUENCE: 41
RSSQNIVHSN GNTYLD                                            16

SEQ ID NO: 42            moltype = AA  length = 7
FEATURE                  Location/Qualifiers
source                   1..7
                         mol_type = protein
                         organism = synthetic construct
SEQUENCE: 42
KVSNRFS                                                      7

SEQ ID NO: 43            moltype = AA  length = 9
FEATURE                  Location/Qualifiers
source                   1..9
                         mol_type = protein
                         organism = synthetic construct
SEQUENCE: 43
FQYSHVPWT                                                    9

SEQ ID NO: 44            moltype = AA  length = 112
FEATURE                  Location/Qualifiers
source                   1..112
                         mol_type = protein
                         organism = synthetic construct
SEQUENCE: 44
DIQMTQSPSS LSASVGDRVT ITCRSSQNIV HSNGNTYLDW YQQTPGKAPK LLIYKVSNRF  60
```

-continued

```
SGVPSRFSGS GSGTDFTFTI SSLQPEDIAT YYCFQYSHVP WTFGQGTKLQ IT          112

SEQ ID NO: 45           moltype = AA  length = 5
FEATURE                 Location/Qualifiers
source                  1..5
                        mol_type = protein
                        organism = synthetic construct
SEQUENCE: 45
NYYIY                                                              5

SEQ ID NO: 46           moltype = AA  length = 17
FEATURE                 Location/Qualifiers
source                  1..17
                        mol_type = protein
                        organism = synthetic construct
SEQUENCE: 46
GINPTSGGSN FNEKFKT                                                 17

SEQ ID NO: 47           moltype = AA  length = 14
FEATURE                 Location/Qualifiers
source                  1..14
                        mol_type = protein
                        organism = synthetic construct
SEQUENCE: 47
QGLWFDSDGR GFDF                                                    14

SEQ ID NO: 48           moltype = AA  length = 123
FEATURE                 Location/Qualifiers
source                  1..123
                        mol_type = protein
                        organism = synthetic construct
SEQUENCE: 48
QVQLQQSGAE VKKPGSSVKV SCKASGYTFT NYYIYWVRQA PGQGLEWIGG INPTSGGSNF  60
NEKFKTRVTI TADESSTTAY MELSSLRSED TAFYFCTRQG LWFDSDGRGF DFWGQGTTVT  120
VSS                                                                123

SEQ ID NO: 49           moltype = AA  length = 107
FEATURE                 Location/Qualifiers
source                  1..107
                        mol_type = protein
                        organism = synthetic construct
SEQUENCE: 49
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGC GTKLELK                107

SEQ ID NO: 50           moltype = AA  length = 118
FEATURE                 Location/Qualifiers
source                  1..118
                        mol_type = protein
                        organism = synthetic construct
SEQUENCE: 50
QVQLQESGGG LVKPGGSLSL SCAASGFTFS SYWMSWVRQA PGKGLEWVAN INRDGSASYY  60
VDSVKGRFTI SRDDAKNSLY LQMNSLRAED TAVYYCARDR GVGYFDLWGR GTLVTVSS    118

SEQ ID NO: 51           moltype = AA  length = 111
FEATURE                 Location/Qualifiers
source                  1..111
                        mol_type = protein
                        organism = synthetic construct
SEQUENCE: 51
QSALTQPASV SGSPGQSITI SCTGTSSDVG GYNFVSWYQQ HPGKAPKLMI YDVSDRPSGV  60
SDRFSGSKSG NTASLIISGL QADDEADYYC SSYGSSSTHV IFGGGTKVTV L           111

SEQ ID NO: 52           moltype = AA  length = 119
FEATURE                 Location/Qualifiers
source                  1..119
                        mol_type = protein
                        organism = synthetic construct
SEQUENCE: 52
QVQLKQSGPG LVQPSQSLSI TCTVSGFSLT NYGVHWVRQS PGKCLEWLGV IWSGGNTDYN  60
TPFTSRLSIN KDNSKSQVFF KMNSLQSNDT AIYYCARALT YYDYEFAYWG QGTLVTVSA   119

SEQ ID NO: 53           moltype = AA  length = 112
FEATURE                 Location/Qualifiers
source                  1..112
                        mol_type = protein
                        organism = synthetic construct
SEQUENCE: 53
DIQMTQSPSS LSASVGDRVT ITCRSSQNIV HSNGNTYLDW YQQTPGKAPK LLIYKVSNRF  60
```

-continued

```
SGVPSRFSGS GSGTDFTFTI SSLQPEDIAT YYCFQYSHVP WTFGCGTKLQ IT         112

SEQ ID NO: 54          moltype = AA  length = 123
FEATURE                Location/Qualifiers
source                 1..123
                       mol_type = protein
                       organism = synthetic construct
SEQUENCE: 54
QVQLQQSGAE VKKPGSSVKV SCKASGYTFT NYYIYWVRQA PGQCLEWIGG INPTSGGSNF  60
NEKFKTRVTI TADESSTTAY MELSSLRSED TAFYFCTRQG LWFDSDGRGF DFWGQGTTVT  120
VSS                                                                123
```

The invention claimed is:

1. An antibody-drug conjugate, which is:

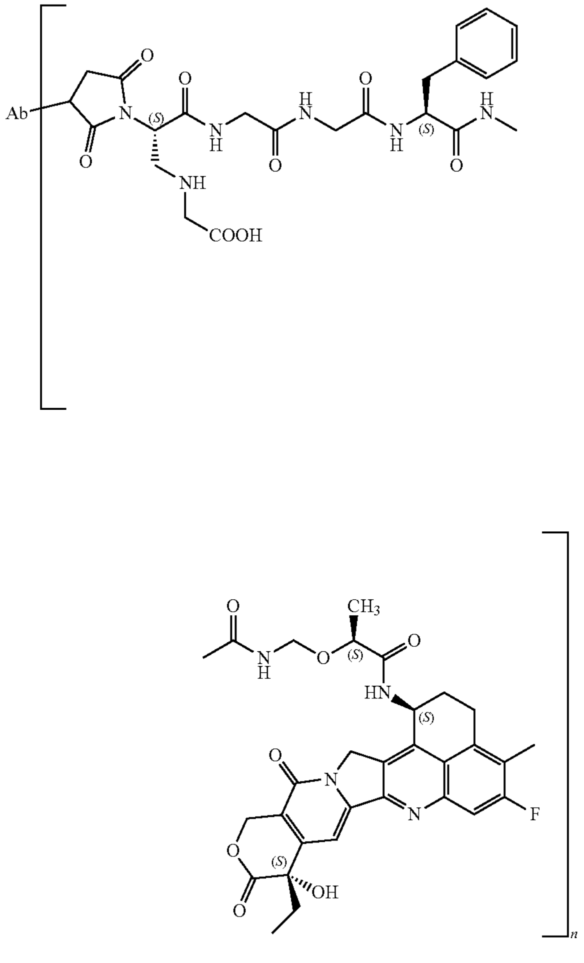

or as pharmaceutically acceptable salt thereof, wherein each instance of

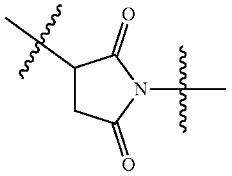 [SMILES: *C1CC(=O)N(*)C1=O]

is independently and optionally replaced by

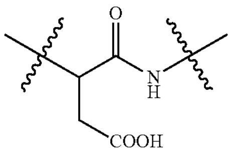

or

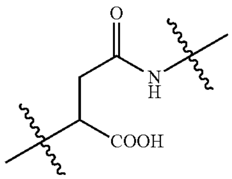

, wherein Ab is a bispecific antibody or antigen-binding fragment thereof, wherein the Ab comprises an IgG having binding specificity for EGFR and a single-chain Fv (scFv) having binding specificity for HER3, wherein the IgG comprises a heavy chain and a κ light chain, wherein the heavy chain of the IgG comprises a heavy chain CDR1 comprising the amino acid sequence of SEQ ID NO:29, a heavy chain CDR2 comprising the amino acid sequence of SEQ ID NO:30, and a heavy chain CDR3 comprising the amino acid sequence of SEQ ID NO:31, and wherein the κ light chain of the IgG comprises a light chain CDR1 comprising the amino acid sequence of SEQ ID NO:25, a light chain CDR2 comprising the amino acid sequence of SEQ ID NO:26, and a light chain CDR3 comprising the amino acid sequence of SEQ ID NO:27; and wherein the scFv comprises a heavy chain CDR1 comprising the amino acid sequence of SEQ ID NO:32, a heavy chain CDR2 comprising the amino acid sequence of SEQ ID NO:33, a heavy chain CDR3 comprising the amino acid sequence of SEQ ID NO:34, a light chain CDR1 comprising the amino acid sequence of SEQ ID NO:35, a light chain CDR2 comprising the amino acid sequence of SEQ ID NO:36, and a light chain CDR3 comprising the amino acid sequence of SEQ ID NO:37, and wherein n is 1, 2, 3, 4, 5, 6, 7, 8, 9, or 10.

2. The antibody-drug conjugate of claim 1, wherein the heavy chain of the IgG comprises a heavy chain variable region comprising the amino acid sequence of SEQ ID NO:38, and wherein the κ light chain of the IgG comprises a light chain variable region comprising the amino acid sequence of SEQ ID NO:28; and wherein the scFv comprises a heavy chain variable region comprising the amino acid sequence of SEQ ID NO:39; and a light chain variable region comprising the amino acid sequence of SEQ ID NO:40.

3. An antibody-drug conjugate, which is:

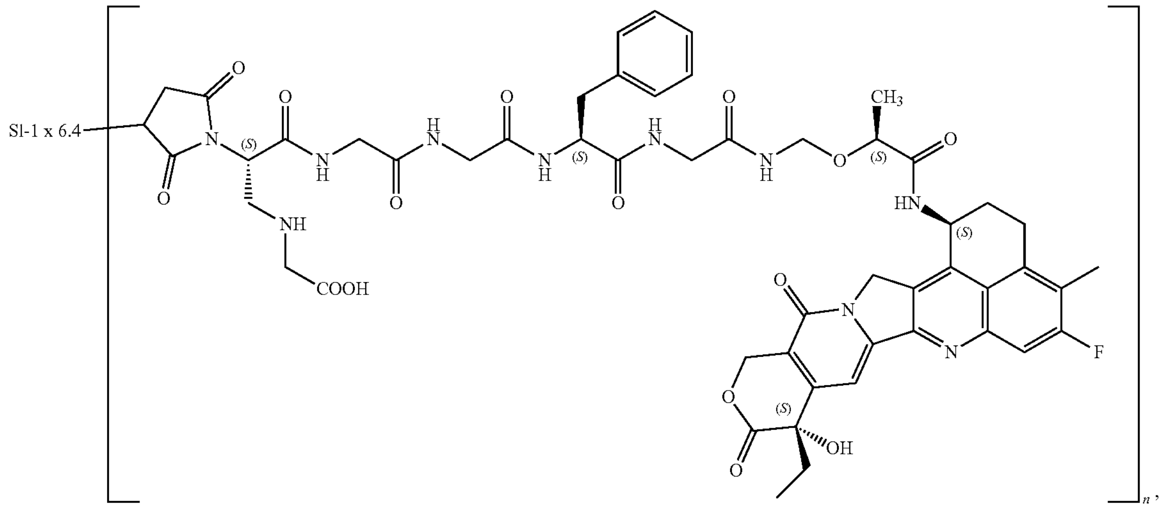

or a pharmaceutically acceptable salt thereof, wherein each instance of

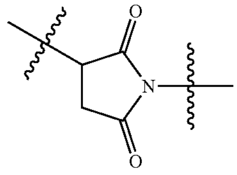 [SMILES: *C1CC(=O)N(*)C1=O]

is independently and optionally replaced

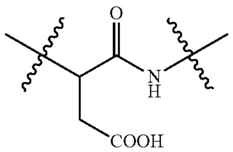

or

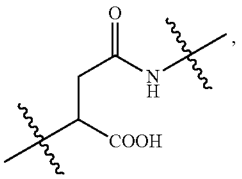

, wherein SI-1×6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 1, 2, 3, 4, 5, 6, 7, 8, 9, or 10.

4. An antibody-drug conjugate, which is:

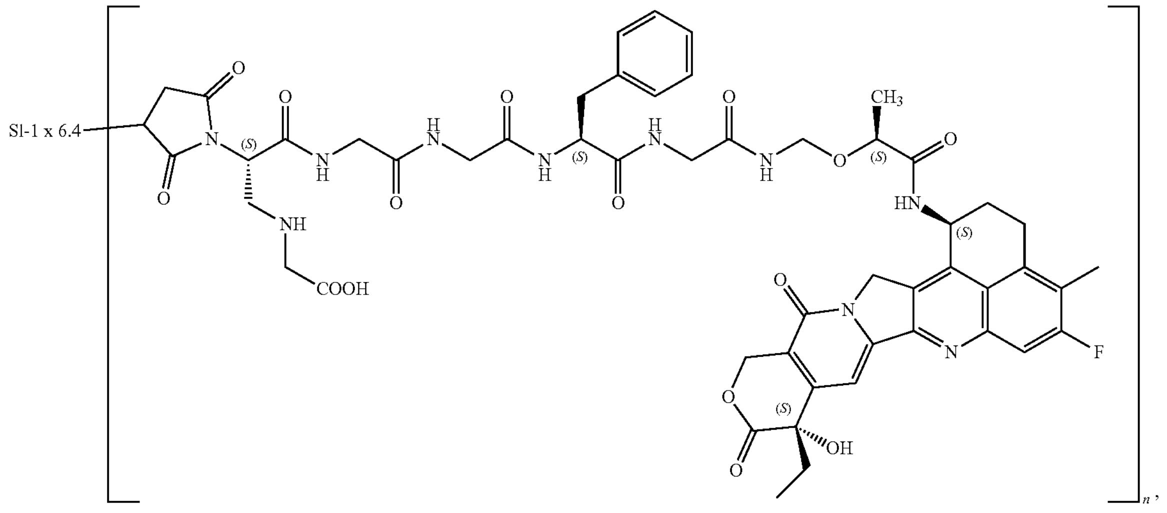

wherein each instance of

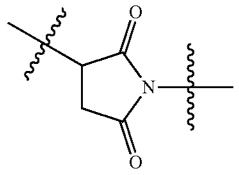 [SMILES: *C1CC(=O)N(*)C1=O]

is independently and optionally replaced by

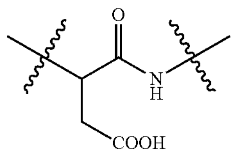

or

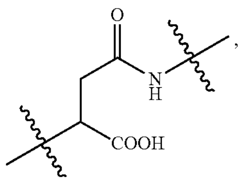

wherein SI-1×6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 5, 6, 7, or 8.

5. An antibody-drug conjugate, which is a pharmaceutically acceptable salt of:

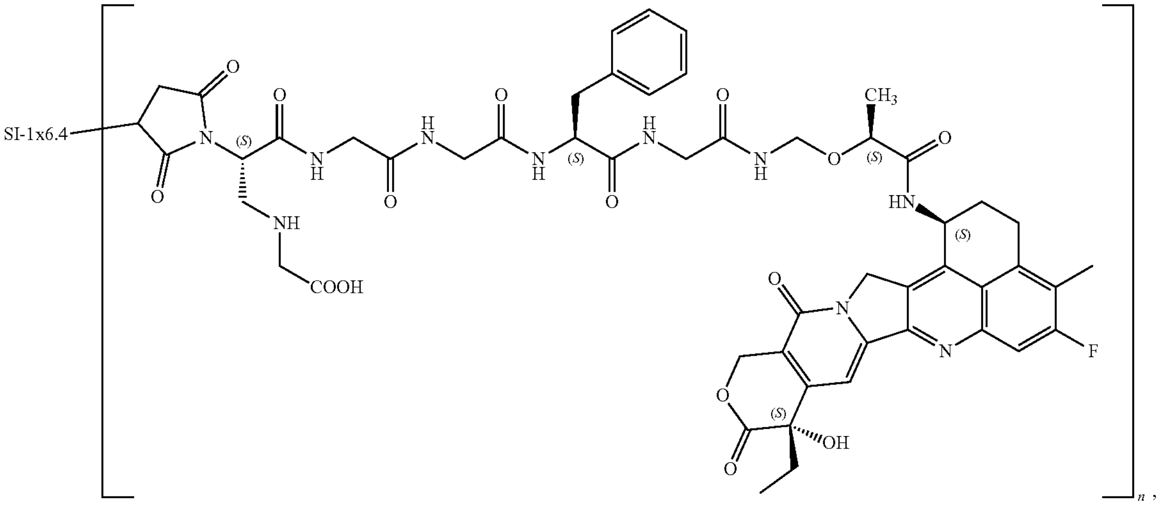

wherein each instance of

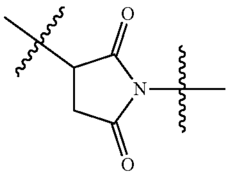 [SMILES: *C1CC(=O)N(*)C1=O]

is independently and optionally replaced by

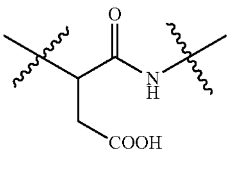

or

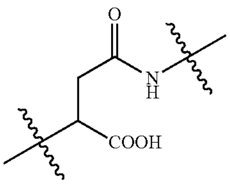

, wherein SI-1×6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 5, 6, 7, or 8.

6. The antibody-drug conjugate of claim 3, wherein n is 6, 7, or 8.

7. The antibody-drug conjugate of claim 3, wherein n is 8.

8. The antibody-drug conjugate of claim 3, wherein the moiety of

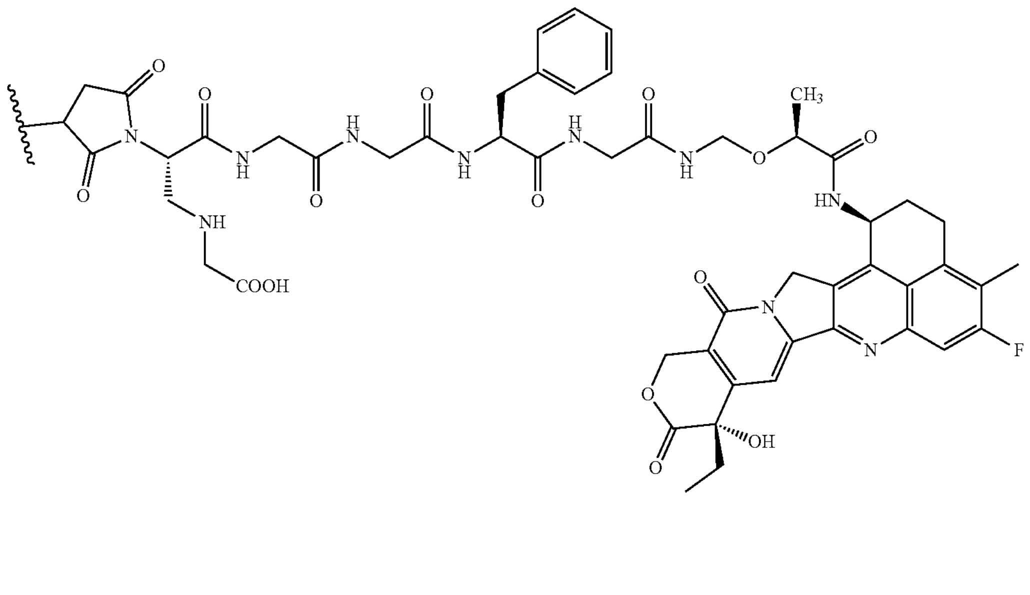 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]

is covalently attached to one or more sulfur atoms of one or more cysteine residues of SI-1×6.4, and wherein each instance of

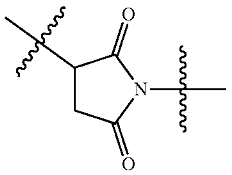

is independently and optionally replaced by

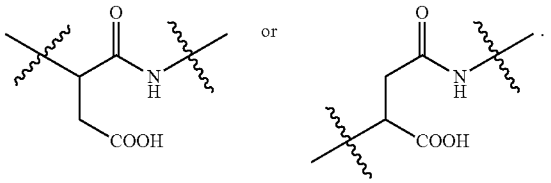 [SMILES: *NC(=O)C(*)CC(=O)O ; *NC(=O)CC(*)C(=O)O]

9. The antibody-drug conjugate of claim 8, wherein the one or more cysteine residues are derived from the opening of one or more interchain disulfide bonds of SI-1×6.4.

10. The antibody-drug conjugate of claim 3, wherein each light chain of SI-1×6.4 is conjugated to 0 to 1 of the moiety of

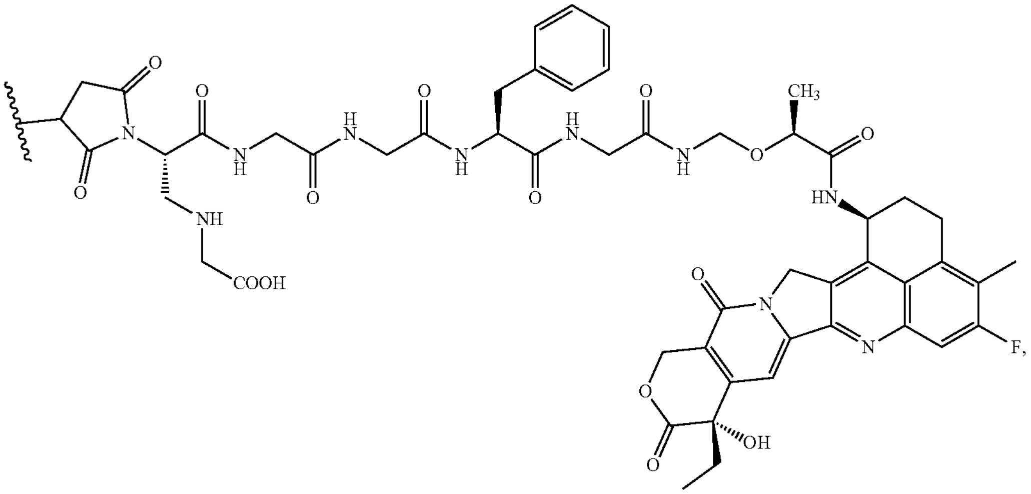 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]

and each heavy chain of SI-1×6.4 is conjugated to 0 to 3 of the moiety of
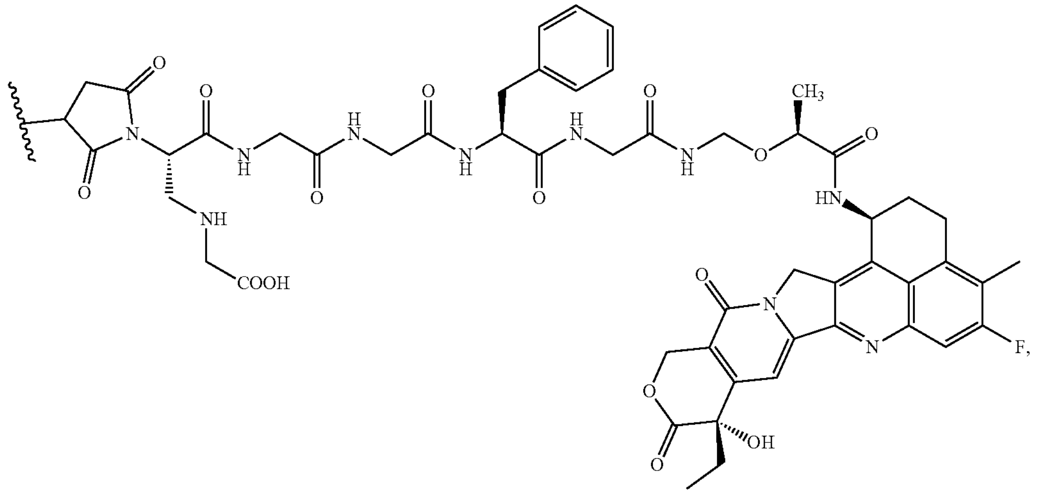 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]
wherein each instance of
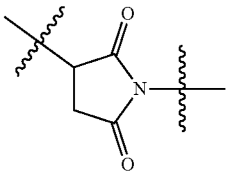 [SMILES: *C1CC(=O)N(*)C1=O]
is independently and optionally replaced by
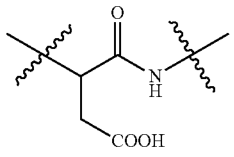
or
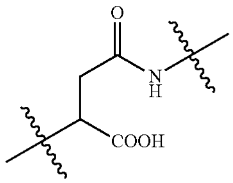
.
11. The antibody-drug conjugate of claim 3, which is:
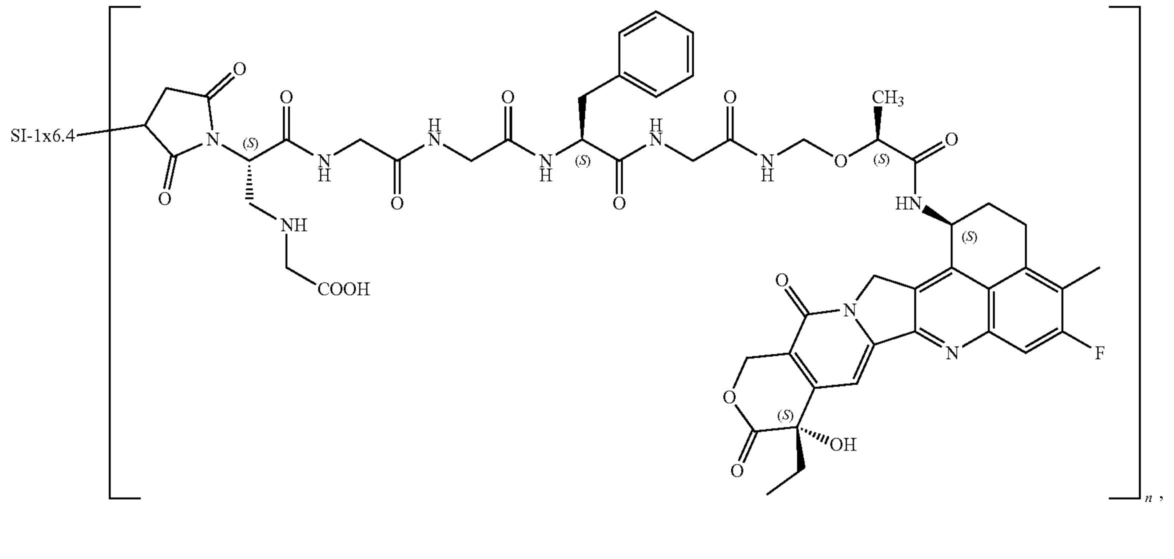
or a pharmaceutically acceptable salt thereof.

12. The antibody-drug conjugate of claim 3, which is:

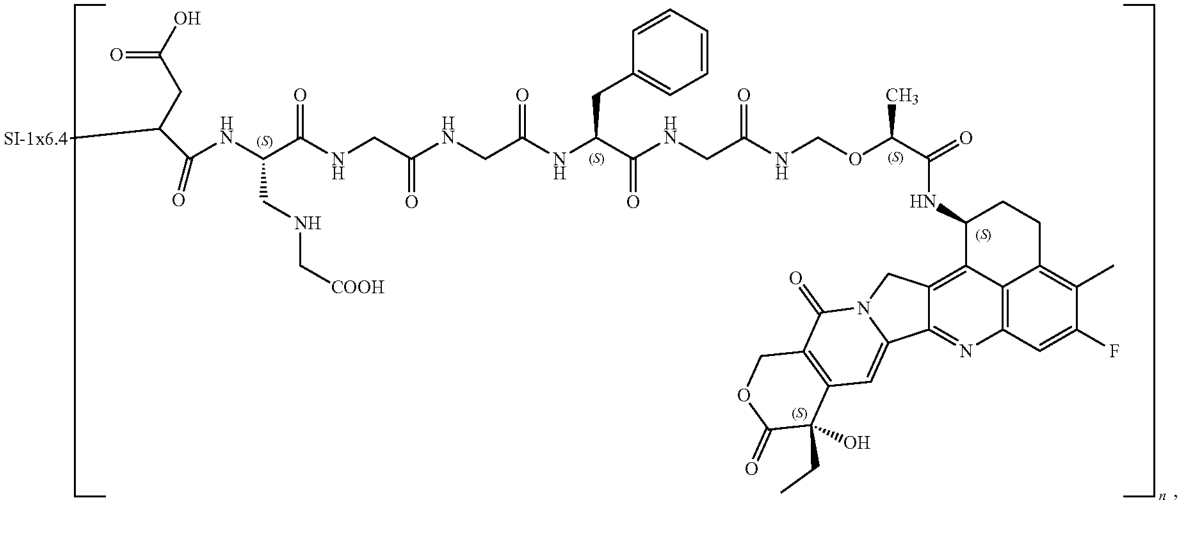

or a pharmaceutically acceptable salt thereof.

13. The antibody-drug conjugate of claim 3, which is:

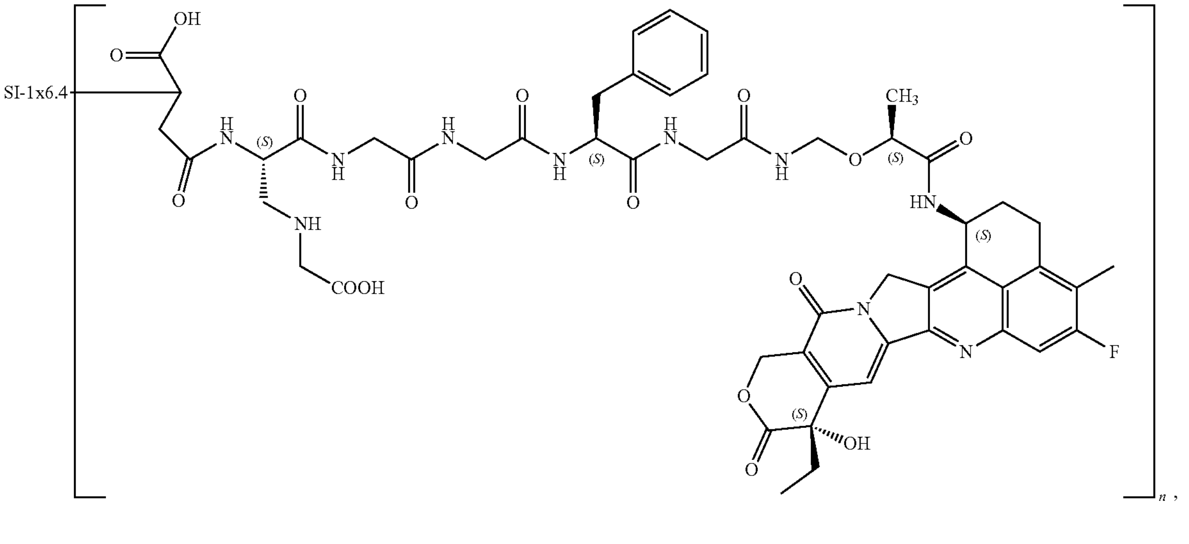

or a pharmaceutically acceptable salt thereof.

14. A pharmaceutical composition, comprising the antibody-drug conjugate of claim 1, and a pharmaceutically acceptable carrier.

15. A pharmaceutical composition, comprising the antibody-drug conjugate of claim 3, and a pharmaceutically acceptable carrier.

16. A pharmaceutical composition, comprising a multiplicity of antibody-drug conjugates of claim 3, and a pharmaceutically acceptable carrier, wherein the average drug-to-antibody ratio ("DAR") of the pharmaceutical composition is from 6 to 8.

17. The pharmaceutical composition of claim 16, wherein the average DAR of the pharmaceutical composition is about 6.99.

18. The pharmaceutical composition of claim 16, wherein the average DAR of the pharmaceutical composition is 8.

19. A pharmaceutical composition, comprising a multiplicity of antibody-drug conjugates of claim 1, and a pharmaceutically acceptable carrier, wherein the average drug-to-antibody ratio ("DAR") of the pharmaceutical composition is from 6 to 8.

20. The pharmaceutical composition of claim 19, wherein the average DAR of the pharmaceutical composition is about 6.99.

21. The pharmaceutical composition of claim 19, wherein the average DAR of the pharmaceutical composition is 8.

22. A pharmaceutical composition, comprising the antibody-drug conjugate of claim 4, and a pharmaceutically acceptable carrier.

23. A pharmaceutical composition, comprising the antibody-drug conjugate of claim 5, and a pharmaceutically acceptable carrier.

24. A pharmaceutical composition, comprising a multiplicity of antibody-drug conjugates of claim 4, and a pharmaceutically acceptable carrier, wherein the average drug-to-antibody ratio ("DAR") of the pharmaceutical composition is from 6 to 8.

25. The pharmaceutical composition of claim 24, wherein the average DAR of the pharmaceutical composition is about 6.99.

26. The pharmaceutical composition of claim 24, wherein the average DAR of the pharmaceutical composition is 8.

27. A pharmaceutical composition, comprising a multiplicity of antibody-drug conjugates of claim 5, and a pharmaceutically acceptable carrier, wherein the average drug-to-antibody ratio ("DAR") of the pharmaceutical composition is from 6 to 8.

28. The pharmaceutical composition of claim 27, wherein the average DAR of the pharmaceutical composition is about 6.99.

29. The pharmaceutical composition of claim 27, wherein the average DAR of the pharmaceutical composition is 8.

30. The pharmaceutical composition of claim 27, wherein the average DAR of the pharmaceutical composition is from 6.99 to 8.

31. The pharmaceutical composition of claim 24, wherein the average DAR of the pharmaceutical composition is from 6.99 to 8.

32. The antibody-drug conjugate of claim 4, wherein n is 6, 7, or 8.

33. The antibody-drug conjugate of claim 4, wherein n is 6.

34. The antibody-drug conjugate of claim 4, wherein n is 7.

35. The antibody-drug conjugate of claim 4, wherein n is 8.

36. The antibody-drug conjugate of claim 4, wherein the moiety of

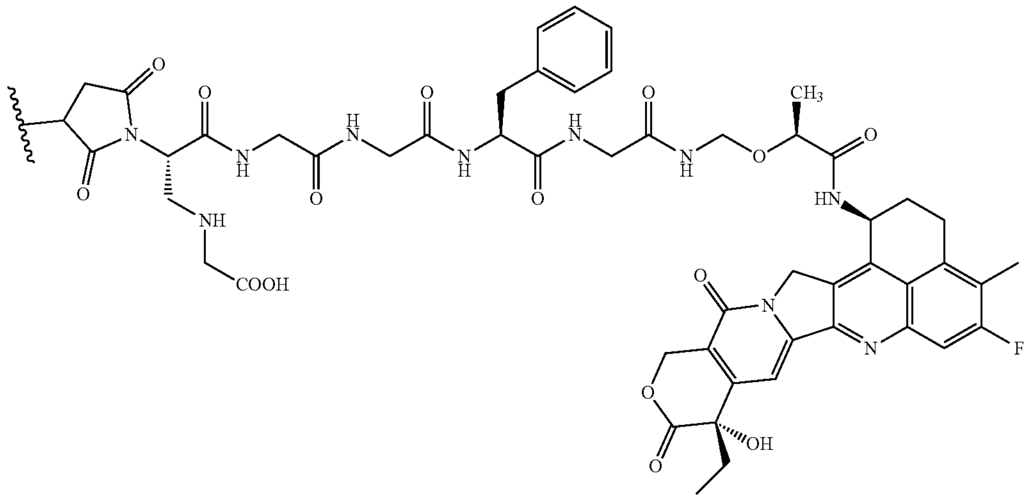 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]

is covalently attached to one or more sulfur atoms of one or more cysteine residues of SI-1×6.4, and wherein each instance of

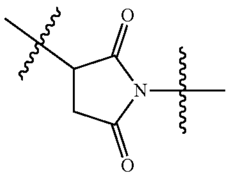 [SMILES: *C1CC(=O)N(*)C1=O]

is independently and optionally replaced by

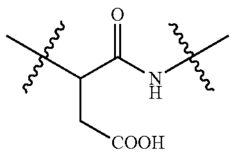

or

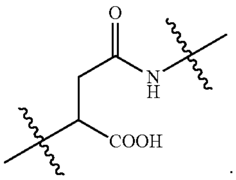

.

37. The antibody-drug conjugate of claim 36, wherein the one or more cysteine residues are derived from the opening of one or more interchain disulfide bonds of SI-1×6.4.

38. The antibody-drug conjugate of claim 4, wherein each light chain of SI-1×6.4 is conjugated to 0 to 1 of the moiety of

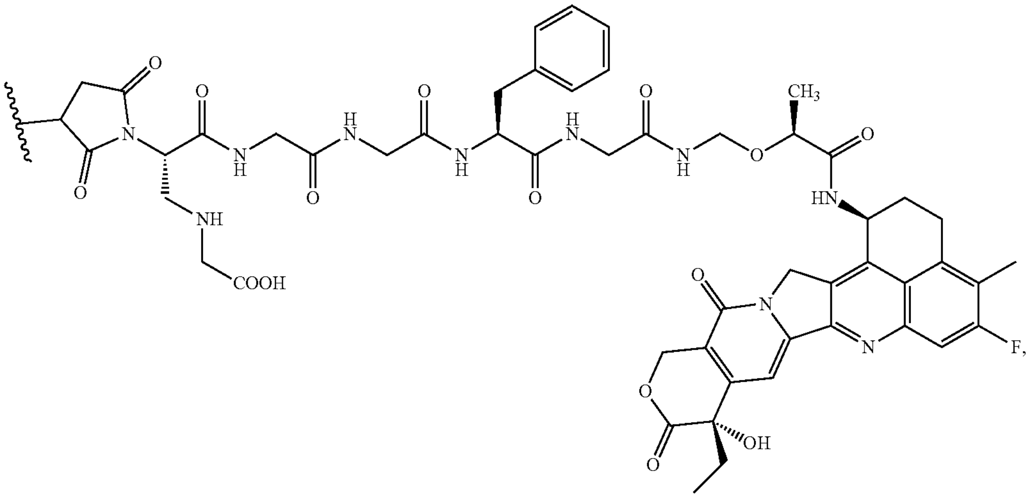 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]
and each heavy chain of SI-1×6.4 is conjugated to 0 to 3 of the moiety of
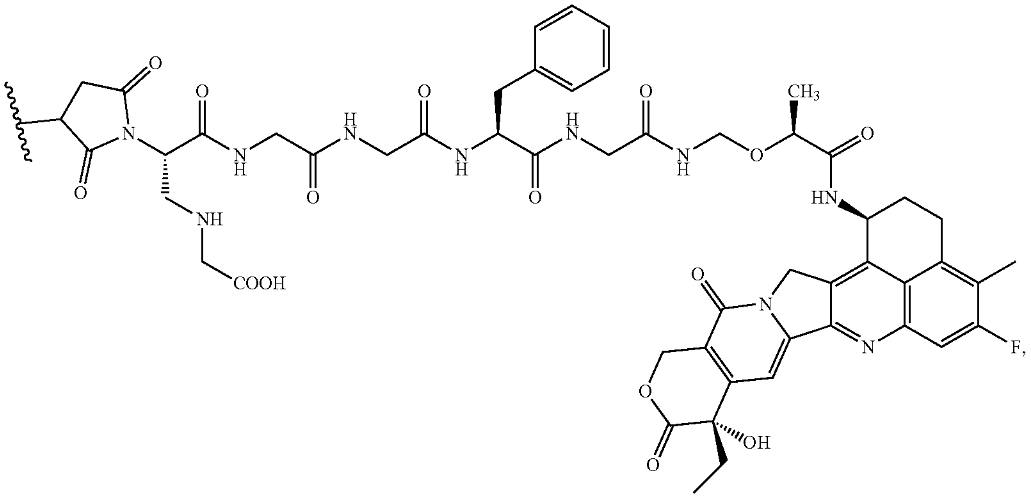 [SMILES: *C1CC(=O)N([C@@H](CNCC(=O)O)C(=O)NCC(=O)NCC(=O)N[C@@H](Cc2ccccc2)C(=O)NCC(=O)NCO[C@@H](C)C(=O)N[C@H]2CCc3c(C)c(F)cc4nc5c(c2c34)Cn2c-5cc3c(c2=O)COC(=O)[C@]3(O)CC)C1=O]
and wherein each instance of
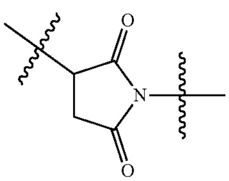 [SMILES: *C1CC(=O)N(*)C1=O]
is independently and optionally replaced by
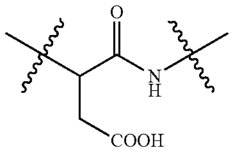 [SMILES: *NC(=O)C(*)CC(=O)O]
or
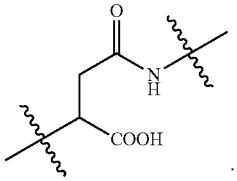 [SMILES: *NC(=O)CC(*)C(=O)O]
.

39. An antibody-drug conjugate, which is:

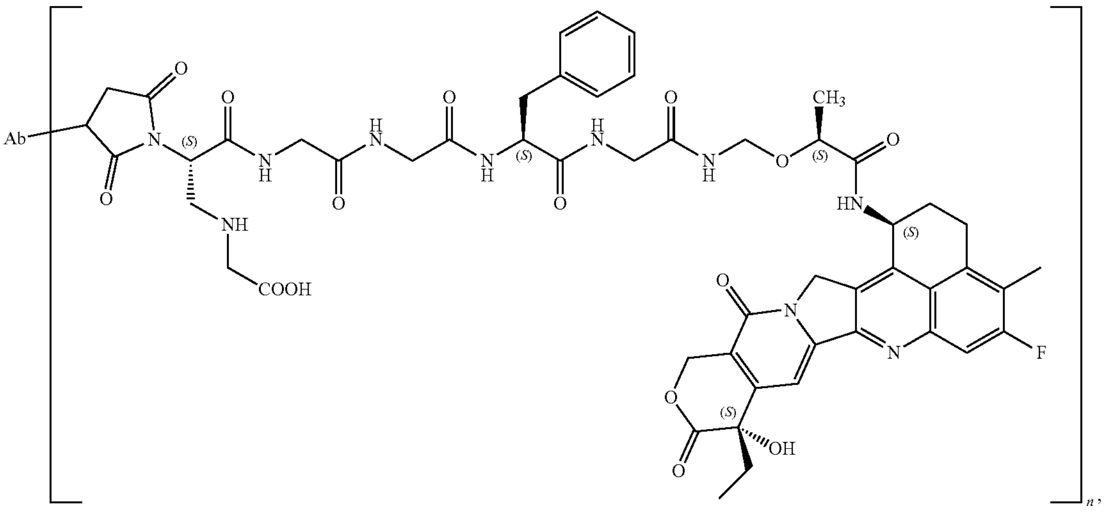

wherein each instance of

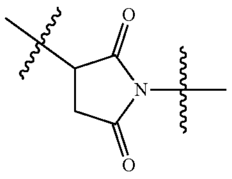 [SMILES: *C1CC(=O)N(*)C1=O]

is independently and optionally replaced by

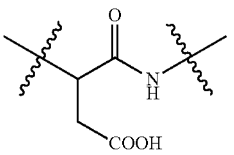

or

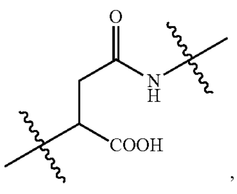

, wherein Ab is a bispecific antibody or antigen-binding fragment thereof, wherein the Ab comprises an IgG having binding specificity for EGFR and a single-chain Fv (scFv) having binding specificity for HER3, wherein the IgG comprises a heavy chain and a κ light chain, wherein the heavy chain of the IgG comprises a heavy chain CDR1 comprising the amino acid sequence of SEQ ID NO:29, a heavy chain CDR2 comprising the amino acid sequence of SEQ ID NO:30, and a heavy chain CDR3 comprising the amino acid sequence of SEQ ID NO:31, and wherein the κ light chain of the IgG comprises a light chain CDR1 comprising the amino acid sequence of SEQ ID NO:25, a light chain CDR2 comprising the amino acid sequence of SEQ ID NO:26, and a light chain CDR3 comprising the amino acid sequence of SEQ ID NO:27; and wherein the scFv comprises a heavy chain CDR1 comprising the amino acid sequence of SEQ ID NO:32, a heavy chain CDR2 comprising the amino acid sequence of SEQ ID NO:33, a heavy chain CDR3 comprising the amino acid sequence of SEQ ID NO:34, a light chain CDR1 comprising the amino acid sequence of SEQ ID NO:35, a light chain CDR2 comprising the amino acid sequence of SEQ ID NO:36, and a light chain CDR3 comprising the amino acid sequence of SEQ ID NO:37, and wherein n is 1, 2, 3, 4, 5, 6, 7, 8, 9, or 10.

40. The antibody-drug conjugate of claim 39, wherein the heavy chain of the IgG comprises a heavy chain variable region comprising the amino acid sequence of SEQ ID NO:38, and wherein the κ light chain of the IgG comprises a light chain variable region comprising the amino acid sequence of SEQ ID NO:28; and wherein the scFv comprises a heavy chain variable region comprising the amino acid sequence of SEQ ID NO:39; and a light chain variable region comprising the amino acid sequence of SEQ ID NO40.

41. An antibody-drug conjugate, which is:

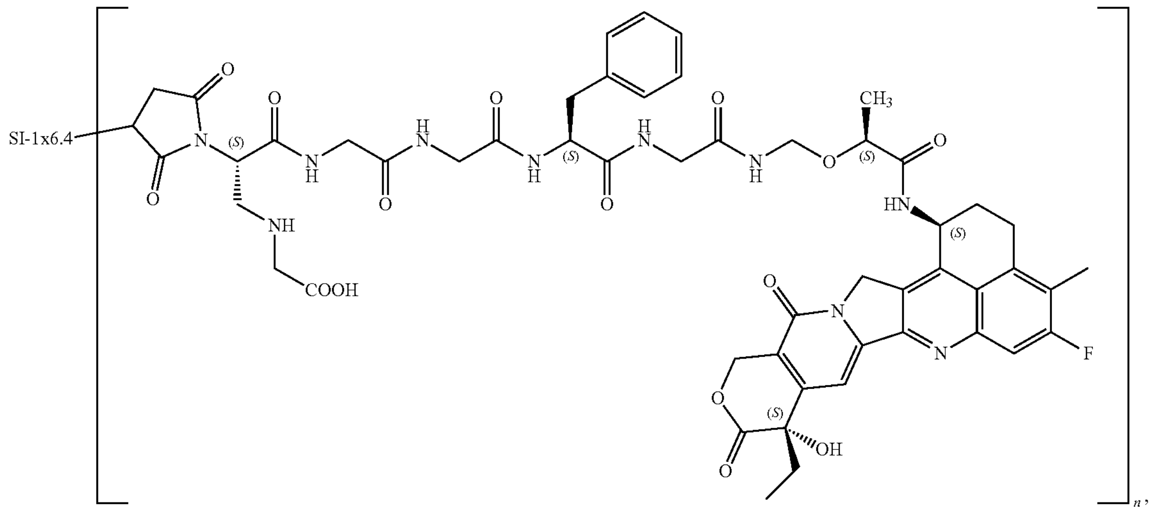

wherein SI-1×6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 8.

42. An antibody-drug conjugate, which is:

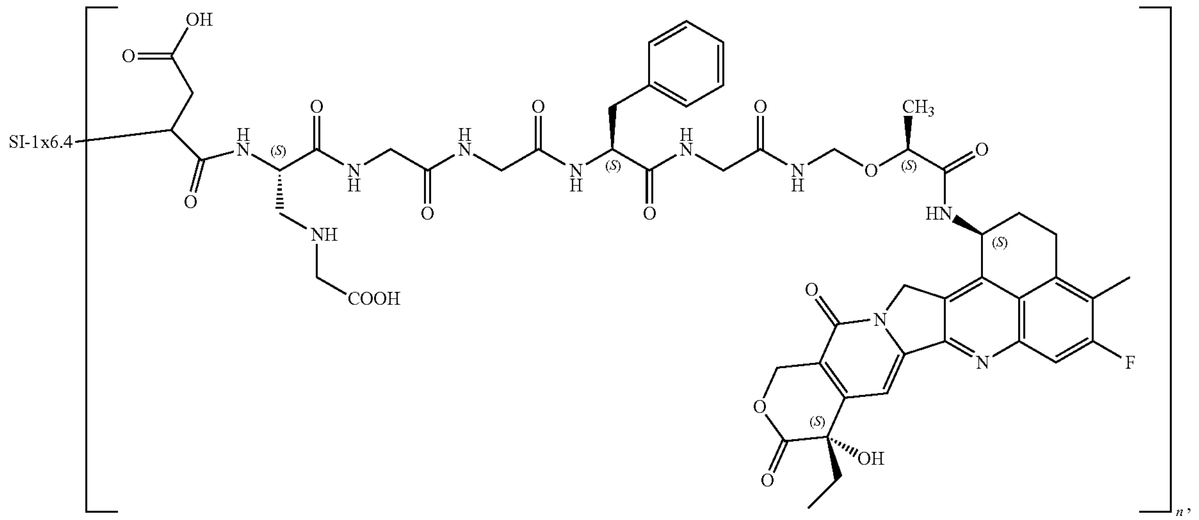

wherein SI-1×6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 8.

43. An antibody-drug conjugate, which is:

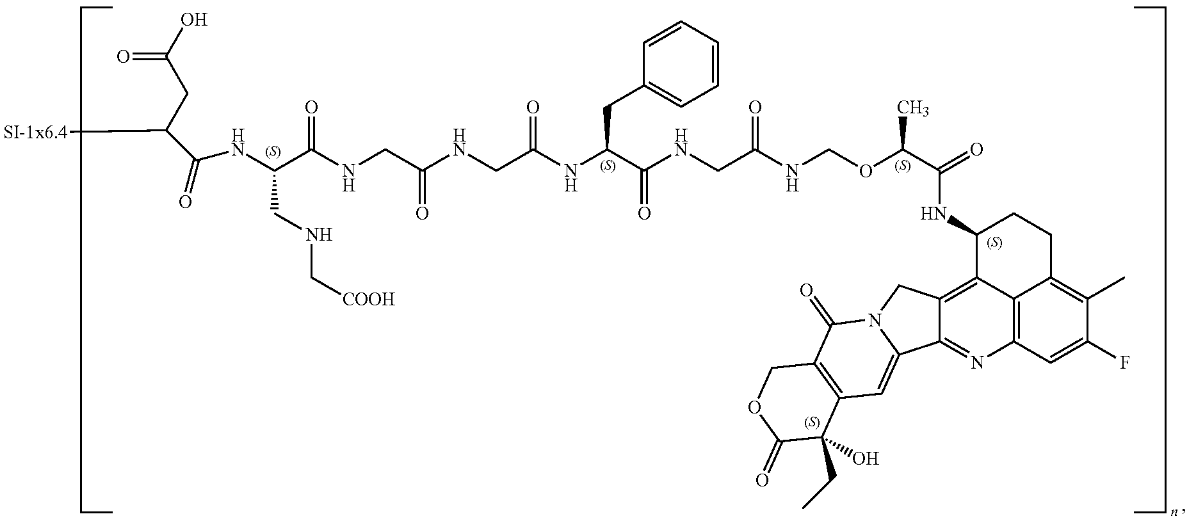

wherein SI-1x6.4 is a bispecific antibody comprising two IgG1 heavy chains, two κ light chains, and two scFvs, wherein the first IgG1 heavy chain and the first scFv form a construct comprising the amino acid sequence of SEQ ID NO: 4; the second IgG1 heavy chain and the second scFv form a construct comprising the amino acid sequence of SEQ ID NO: 4; the first κ light chain comprises the amino acid sequence of SEQ ID NO: 2; and the second κ light chain comprises the amino acid sequence of SEQ ID NO: 2, and wherein n is 8.

44. A pharmaceutical composition, comprising the antibody-drug conjugate of claim 41, and a pharmaceutically acceptable carrier.

45. A pharmaceutical composition, comprising the antibody-drug conjugate of claim 42, and a pharmaceutically acceptable carrier.

46. A pharmaceutical composition, comprising the antibody-drug conjugate of claim 43, and a pharmaceutically acceptable carrier.

* * * * *